US012807681B2

(12) United States Patent
Wong

(10) Patent No.: US 12,807,681 B2
(45) **Date of Patent: *Nov. 24, 2026**

(54) METHODS OF TREATING AGING-RELATED DISORDERS

(71) Applicant: ImmunityBio, Inc., San Diego, CA (US)

(72) Inventor: Hing Wong, Miramar, FL (US)

(73) Assignee: ImmunityBio, Inc., San Diego, CA (US)

( * ) Notice: Subject to any disclaimer, the term of this patent is extended or adjusted under 35 U.S.C. 154(b) by 859 days.

This patent is subject to a terminal disclaimer.

(21) Appl. No.: 18/308,894

(22) Filed: Apr. 28, 2023

(65) Prior Publication Data

US 2023/0372399 A1 Nov. 23, 2023

Related U.S. Application Data

(63) Continuation of application No. 16/557,875, filed on Aug. 30, 2019, now Pat. No. 11,672,826.

(60) Provisional application No. 62/881,039, filed on Jul. 31, 2019, provisional application No. 62/881,088, filed on Jul. 31, 2019, provisional application No. 62/817,244, filed on Mar. 12, 2019, provisional application No. 62/817,230, filed on Mar. 12, 2019, provisional application No. 62/817,241, filed on Mar. 12, 2019, provisional application No. 62/816,683, filed on Mar. 11, 2019, provisional application No. 62/749,506, filed on Oct. 23, 2018, provisional application No. 62/749,007, filed on Oct. 22, 2018, provisional application No. 62/746,832, filed on Oct. 17, 2018, provisional application No. 62/725,038, filed on Aug. 30, 2018, provisional application No. 62/725,010, filed on Aug. 30, 2018, provisional application No. 62/725,043, filed on Aug. 30, 2018, provisional application No. 62/724,969, filed on Aug. 30, 2018.

(51) Int. Cl.

| | |
|---|---|
| ***C07K 14/705*** | (2006.01) |
| ***A61K 40/10*** | (2025.01) |
| ***A61K 40/15*** | (2025.01) |
| ***A61K 40/42*** | (2025.01) |
| ***C07K 14/715*** | (2006.01) |
| ***C07K 16/22*** | (2006.01) |
| ***C07K 16/24*** | (2006.01) |
| ***C07K 16/28*** | (2006.01) |
| ***C07K 16/46*** | (2006.01) |

(52) U.S. Cl.

CPC .......... *C07K 14/7155* (2013.01); *A61K 40/10* (2025.01); *A61K 40/15* (2025.01); *A61K 40/4229* (2025.01); *C07K 14/70503* (2013.01); *C07K 16/22* (2013.01); *C07K 16/244* (2013.01); *C07K 16/2863* (2013.01); *C07K 16/468* (2013.01); *A61K 2239/31* (2023.05); *A61K 2239/48* (2023.05); *A61K 2239/57* (2023.05); *C07K 2317/24* (2013.01); *C07K 2317/52* (2013.01); *C07K 2317/569* (2013.01); *C07K 2317/622* (2013.01)

(58) Field of Classification Search

None

See application file for complete search history.

(56) References Cited

U.S. PATENT DOCUMENTS

| | | | |
|---|---|---|---|
| 6,117,980 | A | 9/2000 | Gonzalez et al. |
| 7,452,537 | B2 | 11/2008 | Bauer et al. |
| 7,482,436 | B2 | 1/2009 | Sugimura et al. |
| 7,488,802 | B2 | 2/2009 | Collins et al. |
| 7,521,051 | B2 | 4/2009 | Collins et al. |
| 7,612,181 | B2 | 11/2009 | Wu et al. |
| 7,691,380 | B2 | 4/2010 | Thorpe et al. |
| 7,723,482 | B2 | 5/2010 | Soulillou et al. |
| 7,968,094 | B2 | 6/2011 | Jiao et al. |
| 8,007,795 | B2 | 8/2011 | Jiao et al. |
| 8,133,485 | B2 | 3/2012 | Levi-Schaffer et al. |
| 8,217,149 | B2 | 7/2012 | Irving et al. |
| 8,258,268 | B2 | 9/2012 | Wu et al. |
| 8,552,156 | B2 | 10/2013 | Takayanagi et al. |
| 8,586,714 | B2 | 11/2013 | Ghayur et al. |
| 8,716,450 | B2 | 5/2014 | Ghayur et al. |
| 8,722,855 | B2 | 5/2014 | Ghayur et al. |
| 8,735,546 | B2 | 5/2014 | Ghayur et al. |

(Continued)

FOREIGN PATENT DOCUMENTS

| | | |
|---|---|---|
| CN | 1844150 | 10/2006 |
| CN | 101653603 | 2/2010 |

(Continued)

OTHER PUBLICATIONS

Kajdaniuk et al. (Endokrynol Pol 2013; 64 (5): 384-396). (Year: 2013).*

(Continued)

*Primary Examiner* — Zachary S Skelding

(74) *Attorney, Agent, or Firm* — Sheridan Ross P.C.

(57) ABSTRACT

Provided herein are methods of treating an aging-related disease or condition in a subject in need thereof, killing or reducing the number of senescent cells in a subject in need thereof, improving the texture and/or appearance of skin and/or hair in a subject in need thereof, and assisting in the treatment of obesity in a subject in need thereof, that include administering to the subject a therapeutically effective amount of one or more natural killer (NK) cell activating agent(s) and/or a therapeutically effective number of activated NK cells.

34 Claims, 150 Drawing Sheets

Specification includes a Sequence Listing.

(56) References Cited

U.S. PATENT DOCUMENTS

| | | | |
|---|---|---|---|
| 8,741,604 | B2 | 6/2014 | Campbell et al. |
| 8,753,640 | B2 | 6/2014 | Wu et al. |
| 8,759,494 | B2 | 6/2014 | Bachmann et al. |
| 8,822,645 | B2 | 9/2014 | Ghayur et al. |
| 9,035,026 | B2 | 5/2015 | Hoffmann et al. |
| 9,067,997 | B2 | 6/2015 | Romagne et al. |
| 9,085,623 | B2 | 7/2015 | Rother et al. |
| 9,090,684 | B2 | 7/2015 | Borras et al. |
| 9,226,962 | B2 | 1/2016 | Le Gall et al. |
| 9,238,084 | B2 | 1/2016 | Liu et al. |
| 9,273,136 | B2 | 3/2016 | Rader et al. |
| 9,371,395 | B2 | 6/2016 | Takahashi et al. |
| 9,441,034 | B2 | 9/2016 | Sivakumar et al. |
| 9,505,843 | B2 | 11/2016 | Kim et al. |
| 9,617,345 | B2 | 4/2017 | Berne et al. |
| 9,701,758 | B2 | 7/2017 | Cooper et al. |
| 11,672,826 | B2 | 6/2023 | Wong |
| 11,730,762 | B2 | 8/2023 | Wong |
| 11,738,052 | B2 | 8/2023 | Wong |
| 12,018,071 | B2 | 6/2024 | Wong |
| 12,024,545 | B2 | 7/2024 | Wong et al. |
| 2001/0044427 | A1 | 11/2001 | Mazel et al. |
| 2003/0124678 | A1 | 7/2003 | Epstein et al. |
| 2003/0219441 | A1 | 11/2003 | Thorpe et al. |
| 2005/0014224 | A1 | 1/2005 | Collins et al. |
| 2006/0159655 | A1 | 7/2006 | Collins et al. |
| 2007/0160579 | A1 | 7/2007 | Schmitz et al. |
| 2008/0025979 | A1 | 1/2008 | Honjo et al. |
| 2009/0148942 | A1 | 6/2009 | McDonagh et al. |
| 2012/0171197 | A1 | 7/2012 | Eriksson et al. |
| 2012/0264920 | A1 | 10/2012 | Wang et al. |
| 2013/0274446 | A1 | 10/2013 | Kumagai et al. |
| 2014/0242077 | A1 | 8/2014 | Choi |
| 2015/0218274 | A1 | 8/2015 | Sabatos-Peyton et al. |
| 2015/0259429 | A1 | 9/2015 | Benaroch et al. |
| 2016/0175397 | A1 | 6/2016 | Umana et al. |
| 2016/0340413 | A1 | 11/2016 | Duerner et al. |
| 2016/0367664 | A1 | 12/2016 | Wang et al. |
| 2017/0051063 | A1 | 2/2017 | Baum et al. |
| 2017/0198042 | A1 | 7/2017 | Williams et al. |
| 2017/0283499 | A1 | 10/2017 | Delhem et al. |
| 2018/0200366 | A1 | 7/2018 | Wong |
| 2019/0078082 | A1 | 3/2019 | Amorese et al. |
| 2019/0092846 | A1 | 3/2019 | Ibebunjo et al. |
| 2019/0177406 | A1 | 6/2019 | Ledbetter et al. |
| 2019/0315850 | A1 | 10/2019 | Bedinger et al. |
| 2020/0071374 | A1 | 3/2020 | Wong |
| 2020/0123607 | A1 | 4/2020 | Serrano Marugan et al. |
| 2020/0190174 | A1 | 6/2020 | Wong |
| 2020/0392221 | A1 | 12/2020 | Van Snick et al. |
| 2020/0399358 | A1 | 12/2020 | Shapiro et al. |
| 2021/0060064 | A1 | 3/2021 | Wong |
| 2021/0061897 | A1 | 3/2021 | Ledbetter et al. |
| 2021/0070825 | A1 | 3/2021 | Wong |
| 2021/0070826 | A1 | 3/2021 | Wong |
| 2021/0100840 | A1 | 4/2021 | Wong et al. |
| 2021/0137981 | A1 | 5/2021 | Wong |
| 2021/0268022 | A1 | 9/2021 | Wong et al. |
| 2021/0277054 | A1 | 9/2021 | Wong et al. |
| 2021/0338724 | A1 | 11/2021 | Wong |
| 2021/0355204 | A1 | 11/2021 | Bedinger et al. |
| 2021/0403545 | A1 | 12/2021 | Van Snick et al. |
| 2022/0073578 | A1 | 3/2022 | Wong et al. |
| 2023/0023389 | A1 | 1/2023 | Wong |
| 2023/0039157 | A1 | 2/2023 | Wong |
| 2023/0128292 | A1 | 4/2023 | Wong |
| 2023/0174666 | A1 | 6/2023 | Wong et al. |
| 2023/0272027 | A1 | 8/2023 | Wong |
| 2023/0372444 | A1 | 11/2023 | Wong et al. |
| 2023/0381238 | A1 | 11/2023 | Wong |
| 2023/0398151 | A1 | 12/2023 | Wong |
| 2024/0124543 | A1 | 4/2024 | Wong |
| 2024/0124544 | A1 | 4/2024 | Wong |
| 2024/0132561 | A1 | 4/2024 | Wong |

FOREIGN PATENT DOCUMENTS

| | | |
|---|---|---|
| CN | 101965364 | 2/2011 |
| CN | 102153653 | 8/2011 |
| CN | 106255703 | 12/2016 |
| CN | 109513003 | 3/2019 |
| EP | 1245676 | 10/2002 |
| EP | 1719528 | 11/2006 |
| EP | 2537933 | 12/2012 |
| EP | 3029069 | 6/2016 |
| EP | 3348276 | 7/2018 |
| JP | 2005-124568 | 5/2005 |
| JP | 2008-536487 | 9/2008 |
| JP | 2009-512433 | 3/2009 |
| JP | 4361133 | 8/2009 |
| KR | 2016/0127688 | 11/2016 |
| KR | 101778439 | 9/2017 |
| WO | WO 1995/015341 | 6/1995 |
| WO | WO 1996/001653 | 1/1996 |
| WO | WO 2001/083755 | 11/2001 |
| WO | WO 2002/083152 | 10/2002 |
| WO | WO 2003/037911 | 5/2003 |
| WO | WO 2003/104425 | 12/2003 |
| WO | WO 2004/076488 | 9/2004 |
| WO | WO 2006/096828 | 9/2006 |
| WO | WO 2006/097743 | 9/2006 |
| WO | WO 2006/119897 | 11/2006 |
| WO | WO 2008/096158 | 8/2008 |
| WO | WO 2009/042798 | 4/2009 |
| WO | WO 2011/127324 | 10/2011 |
| WO | WO 2012/040323 | 3/2012 |
| WO | WO 2012/120125 | 9/2012 |
| WO | WO 2012/170470 | 12/2012 |
| WO | WO 2012/175222 | 12/2012 |
| WO | WO 2012/175692 | 12/2012 |
| WO | WO 2013/068946 | 5/2013 |
| WO | WO 2014/007513 | 1/2014 |
| WO | WO 2014/026054 | 2/2014 |
| WO | WO 2014/095808 | 6/2014 |
| WO | WO 2014/130635 | 8/2014 |
| WO | WO 2014/159531 | 10/2014 |
| WO | WO 2015/089881 | 6/2015 |
| WO | WO 2016/106221 | 6/2016 |
| WO | WO 2016/154585 | 9/2016 |
| WO | WO 2016/166348 | 10/2016 |
| WO | WO 2017/053748 | 3/2017 |
| WO | WO 2017/083612 | 5/2017 |
| WO | WO 2017/149538 | 9/2017 |
| WO | WO 2017/189526 | 11/2017 |
| WO | WO 2018/067825 | 4/2018 |
| WO | WO 2018/075989 | 4/2018 |
| WO | WO 2018/129007 | 7/2018 |
| WO | WO 2018/158350 | 9/2018 |
| WO | WO 2018/183169 | 10/2018 |
| WO | WO 2018/165208 | 12/2018 |
| WO | WO 2019/046313 | 3/2019 |
| WO | WO 2020/0047299 | 3/2020 |
| WO | WO 2020/047333 | 3/2020 |
| WO | WO 2020/047462 | 3/2020 |
| WO | WO 2020/047473 | 3/2020 |
| WO | WO 2021/163369 | 8/2021 |

OTHER PUBLICATIONS

Chen et al. (Adv Drug Deliv Rev. Oct. 1, 20135; 65(10): 1357-1369). (Year: 2013).*

Goebel et al. (Experimental Biology and Medicine 2019; 244: 1530-1546). (Year: 2019).*

Radaev et al. (The Journal of Biological Chemistry vol. 285, No. 19, pp. 14806-14814, May 7, 2010). (Year: 2010).*

Prasad et al. (Phys.Chem. Chem.Phys., 2017, 19, 22230). (Year: 2017).*

Ring et al. (Nature immunology vol. 13,12 (2012): 1187-95). (Year: 2012).*

Zhang (Cold Spring Harb Perspect Biol. Apr. 3, 2017;9(4):a022145). (Year: 2017).*

Vadivel et al. (Frontiers in Bioscience 17, 2476-2494, Jun. 1, 2012). (Year: 2012).*

(56) References Cited

OTHER PUBLICATIONS

Zhou et al. (Biophysical Journal 112, 78-86, Jan. 10, 2017). (Year: 2017).*
U.S. Appl. No. 16/556,040, filed Aug. 29, 2019, Wong.
U.S. Appl. No. 16/557,822, filed Aug. 30, 2019, Wong.
[No Author Listed], "CN Br-activated Sepharose 4 Fast Flow," 1999, Affinity Chromatography, 4 pages.
Abbott et al., "Genomic organization, exact localization, and tissue expression of the human CD26 (dipeptidyl peptidase IV) gene," Immunogentics, Sep. 1994, 40(5):331-338.
Abdul-Aziz et al., "Acute myeloid leukemia induces protumoral p16INK4a-driven senescence in the bone marrow microenvironment," Blood, Jan. 31, 2019, 133(5):446-456.
Aertgeerts et al., "Crystal structure of human dipeptidyl peptidase IV in complex with a decapeptide reveals details on substrate specificity and tetrahedral intermediate formation," Protein Science, Feb. 2004, 13(2):412-421.
Ait-Oufella el al., "Natural regulatory T cells control the development of atherosclerosis in mice," Nature Medicine, Feb. 5, 2006, 12:178-180.
Akbari, et al., "Design, expression and evaluation of a novel humanized single chain antibody against epidermal growth factor receptor (EGFR)," Protein Expr. Purif, 2016, 127:8-15.
Ali et al., "Regulatory T cells in skin," Immunology, Jul. 12, 2017, 152(3):372-381.
Angevin et al., "First-in-human phase 1 of YS110, a monoclonal antibody directed against CD26 in advanced CD26-expressing cancers," British Journal of Cancer, Mar. 14, 2017, 116(9):1126-1134.
Bachelet et al., "Mast Cell Costimulation by CD226/CD112 (DNAM-1/Nectin-2) A Novel Interface in the Allergic Process," Journal of Biological Chemistry, Sep. 15, 2006, 281(37):27190-6.
Baker et al., "Chronic treatment with the beta(2)-adrenoceptor agonist prodrug BRL-47672 impairs rat skeletal muscle function by inducing a comprehensive shift to a faster muscle phenotype," J Pharmacol Exp Ther., Oct. 2006, 319(1):439-446.
Baker et al., "Effects of conjugated linoleic acid (CLA) on tissue composition parameters in a murine cachexia model," The FASEB Journal, Mar. 2006, 20(4), 2 pages (Abstract Only).
Baker, et al., "Clearance of p16Ink4a-positive senescent cells delays ageing-associated disorders," Nature, 2011, 479(7372): 232-236.
Bartscht et al., "Dasatinib blocks transcriptional and promigratory responses to transforming growth factor-beta in pancreatic adenocarcinoma cells through inhibition of Smad signalling: implications for in vivo mode of action," Molecular Cancer, Dec 2015, 14(199):1-12.
Bennett et al., "Erratum: Killing the old: cell senescence in atherosclerosis," Nature Reviews Cardiology, Jan. 12, 2017, 14(3):132.
Bennett et al., "Killing the old: cell senescence in atherosclerosis," Nature Reviews Cardiology, Dec 12, 2016, 14(1):8-9, 2 pages.
Bentebibel et al., "A First-in-Human Study and Biomarker Analysis of NKTR-214, a Novel IL2Raf Biased Cytokine, in Patients with Advanced or Metastatic Solid Tumors," Cancer Discovery, Jun. 2019, 9(6):711-721.
Berry et al., "Cancer Anorexia and Cachexia: Screening in an Ambulatory Infusion Service and Nutrition Consultation," Clin J Oncol Nurs., 2018, 22(1):63-68.
Bhat et al., "Astrocyte Senescence as a Component of Alzheimer's Disease," PLoS One, Sep. 12, 2012, 7(9):e45069, 10 pages.
Biran et al., "Senescent cells communicate via intercellular protein transfer," Genes & Development, Apr. 8, 2015, 29(8):791-802, 13 pages.
Bird et al., "TGFβ inhibition restores a regenerative response in acute liver injury by suppressing paracrine senescence," Science translational medicine, Aug. 15, 2018, 10(454):eaan1230, 15 pages.
Borea et al., "Pharmacology of Adenosine Receptors: The State of the Art," Physiological Reviews, May 30, 2018, 98(3):1591-1625.
Borgerding et al., "B-lymphoma cells escape rituximab-triggered elimination by NK cells through increased HLA class I expression," Experimental Hematology, Mar. 1, 2010, 38(3):213-21.
Bork, "Powers and Pitfalls in Sequence Analysis: The 70% Hurdle," Genome Research, 2000, 10:398-400.
Bourgeois et al., "Regulation of cellular senescence via the FOXO4-p53 axis, " FEBS Lett., 2018, 592(12): 2083-2097.
Bowie et al., "Deciphering the Message in Protein Sequences: Tolerance to Amino Acid Substitutions," Science, 1990, 247:1306-1310.
Boyman et al., "IL-7/Anti-IL-7 mAb Complexes Restore T Cell Development and Induce Homeostatic T Cell Expansion without Lymphopenia," The Journal of Immunology, Jun. 1, 2008, 180:7265-7275.
Boyman et al., "Selective Stimulation of T Cell Subsets with Antibody-Cytokine Immune Complexes," Science, Mar. 31, 2006, 311(5769):1924-1927.
Brämer et al., "Membrane adsorber for the fast purification of a monoclonal antibody using protein a chromatography," Membranes, Nov. 27, 2019, 9(12):159, 15 pages.
Brennan et al., "Structural determination of lipid antigens captured at the CD1d-T-cell receptor interface," PNAS, 2017, 114(31):8348-8353.
Brighton et al., "Clearance of senescent decidual cells by uterine natural killer cells in cycling human endometrium," Elife, Dec. 11, 2017, 6:e31274, 23 pages.
Brooks et al., "Combined inhibition of PD1 and CD96 checkpoints improves survival in a resectable murine model of pancreatic cancer," European Journal of Cancer, Jul. 1, 2016, 61:S189, 1 page.
Broxmeyer et al., "Modulation of Hematopoietic Chemokine Effects In Vitro and In Vivo by DPP-4/CD26," Stem Cells and Development, Mar. 4, 2016, 25(8):575-585.
Brunstein et al., "Infusion of Ex Vivo Expanded T Regulatory Cells in Adults Transplanted with Umbilical Cord Blood: Safety Profile and Detection Kinetics," Blood, Jan. 20, 2011, 117(3):1061-1070.
Brunstein et al., "Umbilical cord blood-derived T regulatory cells to prevent GVHD:kinetics, toxicity profile, and clinical effect," Blood, Feb. 25, 2016, 127(8):1044-1051.
Buhling et al., "Functional role of CD26 on human B lymphocytes," Immunology Letters, Feb. 1995, 45(1-2):47-51.
Burgess et al., "Possible Dissociation of the Heparin-binding and Mitogenic Activities of Heparin-binding (Acidic Fibroblast) GrowthFactor-1 from Its Receptor-binding Activities by Site-directed Mutagenesis of a Single Lysine Residue," J. Cell Biol., 1990, 111:2129-2138.
Bussian et al., "Clearance of senescent glial cells prevents tau-dependent pathology and cognitive decline," Nature, Sep. 19, 2018, 562(7728):578-582, 21 pages.
Cai et al., "Chibby suppresses aerobic glycolysis and proliferation of nasopharyngeal carcinoma via the Wnt/β-catenin-Lin28/let7-PDK1 cascade," Journal of Experimental & Clinical Cancer Research, Dec. 1, 2018, 37(1):104.
Cai et al., "Quercetin inhibits transforming growth factor β1-induced epithelial-mesenchymal transition in human retinal pigment epithelial cells via the Smad pathway," Drug design, development and therapy, Dec 6, 2018, 12:4149-4161.
Cao et al., "Expression and characterization of recombinant humanized anti-HER2 single-chain antibody in Pichia pastoris for targeted cancer therapy," Biotechnology Letters, Jul. 1, 2015, 37(7):1347-54.
Cao, "Self-regulation and cross-regulation of pattern-recognition receptor signaling in health and disease," Nature Reviews Immunology, Dec. 29, 2015, 16(1):35-50.
Carr et al., "NK Cell-Mediated Lysis of Autologous HCMV-Infected Skin Fibroblasts Is Highly Variable among NK Cell Clones and Polyclonal NK Cell Lines," Clinical Immunology, Nov. 2002, 105(2):126-140.
Catania et al., "The tumor-targeting immunocytokine F16-IL2 in combination with doxorubicin: dose escalation in patients with advanced solid tumors and expansion into patients with metastatic breast cancer," Cell Adhesion and Migration, Jan.-Apr. 2015, 9(1-2):14-21.
Cavinato et al., "Molecular mechanisms of UVB-induced senescence of dermal fibroblasts and its relevance for photoaging of the human skin," Experimental Gerontology. Aug. 2017, 94:78-82.
Chabannon et al., "Manufacturing natural killer cells as medicinal products," Frontiers in Immunology, Nov. 15, 2016, 7(504): 1-9.

(56) References Cited

OTHER PUBLICATIONS

Chalan et al., "Expression of Lectin-Like Transcript 1, the Ligand for CD161, in Rheumatoid Arthritis, " PLoS ONE, 2015, 10(7):e0132436.
Chambers et al., "Can blocking inflammation enhance immunity during aging?," Journal of Allergy and Clinical Immunology, May 2020, 145(5):1323-1331.
Chan et al., "Molecular mechanisms of natural killer cell activation in response to cellular stress," Cell Death & Differentiation, Jan. 2014, 21(1):5-14.
Chance et al., "A simple and rapid assay of oxidative phosphorylation," Nature, Jun. 1955, 175(4469):1120-1121.
Chandrudu et al., "Chemical methods for peptide and protein production," Molecules, 2013, 18(4):4373-4388.
Chang et al., "Association Between Sarcopenia and Cognitive Impairment: A Systematic Review and Meta-Analysis," J Am Med Dir Assoc, Dec 1, 2016, 17(12): 1164e7-1164e15, 9 pages.
Chang et al., "The dock and lock method: a novel platform technology for building multivalent, multifunctional structures of defined composition with retained bioactivity," Clinical cancer research, Sep. 15, 2007, 13(18):5586s-5591s.
Chattopadyhay et al., "Structural Basis of Inducible Costimulator Ligand Costimulatory Function: Determination of the Cell Surface Oligomeric State and Functional Mapping of the Receptor Binding Site of the Protein1," J Immunol., 2006, 3920-3929.
Chen et al., "Circulating levels of resistin and risk of type 2 diabetes in men and women: results from two prospective cohorts," Diabetes Care, Feb. 2009, 32(2):329-334.
Chen et al., "Sterile inflammation: sensing and reacting to damage," Nature Reviews Immunology, Nov. 19, 2010, 10(12):826-837.
Chichili et al., "Linkers in the structural biology of protein-protein interactions," Protein Science, Feb. 2013, 22(2):153-67.
Childs et al., "Senescent cells: an emerging target for diseases of ageing," Nature Reviews Drug Discovery, Jul. 21, 2017, 16(10):718-735, 18 pages.
Childs et al., "Senescent intimal foam cells are deleterious at all stages of atherosclerosis," Science, Oct. 28, 2016, 354(6311):472-477.
Chinta, et al., "Cellular senescence is induced by the environmental neurotoxin paraquat and contributes to neuropathology linked to Parkinson's Disease," Cell Rep., 2018, 22(4): 930-940.
Chong et al., "CD36 initiates the secretory phenotype during the establishment of cellular senescence, " EMBO Rep., May 18, 2018, 19(6):e45274, 13 pages.
Ciaglia et al., "Recognition by natural killer cells of N6-isopentenyladensoine-treated human glioma cell lines," Int. J. Cancer, 2018 142(1): 176-190.
Cichocki et al., "GSK3 inhibition drives maturation of NK cells and enhances their antitumor activity," Cancer Research, Oct. 15, 2017, 77(20):5664-75.
Cifaldi et al., "Boosting Natural Killer Cell-Based Immunotherapy with Anticancer Drugs: a Perspective," Trends Molecular Medicine, Dec 2017, 23(12):1156-1175, 20 pages.
Cipriani et al., "Hippocampal Radial Glial Subtypes and Their Neurogenic Potential in Human Fetuses and Healthy and Alzheimer's Disease Adults," Cerebral Cortex, May 2, 2018, 28(7):2458-2478, 21 pages.
Clayton et al.,"Soluble T Cell Immunoglobulin Mucin Domain 3 Is Shed from CD8 T Cells by the Sheddase ADAM10, Is Increased in Plasma during Untreated HIV Infection, and Correlates with HIV Disease Progression," J Viral., 2015, 89(7):3723-3736.
Collado et al., "Senescence in tumours: evidence from mice and humans," Nature Reviews Cancer, Jan. 2010, 10(1):51-57.
Conarello et al., "Mice lacking dipeptidyl peptidase IV are protected against obesity and insulin resistance," Proc. Natl. Acad. Sci. U.S.A., May 27, 2003, 100(11):6825-6830.
Conlon et al., "Abstract CT082: Phase (Ph) I/Ib study of NIZ985 with and without spartalizumab (PDR001) in patients (pts) with metastatic/unresectable solid tumors," Cancer Res. 79(13 Suppl.):CT082, Jul. 1, 2019, 2 pages.
Coppe et al., "Tumor Suppressor and Aging Biomarker p16INK4a Induces Cellular Senescence without the Associated Inflammatory Secretory Phenotype," Journal of Biological Chemistry, Oct. 21, 2011, 286(42): 36396-36403.
Cosgrove et al., "Usher protein functions in hair cells and photoreceptors," Int J Biochem Cell Biol., Jan. 2014, 46:80-89.
Cosman et al., "ULBPs, novel MHC class I-related molecules, bind to CMV glycoprotein UL16 and stimulate NK cytotoxicity through the NKG2D receptor," Immunity, Feb. 1, 2001, 14(2):123-33.
Costa et al., "Targeting the epidermal growth factor receptor can counteract the inhibition of natural killer cell function exerted by colorectal tumor-associated fibroblasts," Frontiers in Immunology, May 29, 2018, 9:1150, 14 pages.
Crews et al., "Molecular mechanisms of neurodegeneration in Alzheimer's disease," Human Molecular Genetics, Apr. 22, 2010, 19(R1):R12-R20, 9 pages.
Cromie et al., "Nanobodies and their use in GPCR drug discovery," Current Topics in Medicinal Chemistry, Dec. 1, 2015, 15(24):2543-57.
Czaja et al., "A comprehensive analysis of the binding of anti-KIR antibodies to activating KIRs," Genes and Immunity, Jan. 2014, 15(1), 15 pages.
Da Silva et al., "Dipeptidylpeptidase 4 inhibition enhances lymphocyte trafficking, improving both naturally occurring tumor immunity and immunotherapy," Nature Immunology, Jun. 15, 2015, 16(8):850-858, 11 pages.
Dall'Era et al., "Adoptive Regulatory T Cell Therapy in a Patient with Systemic Lupus Erythematosus," Arthritis Rheumatology, Mar. 2019, 71(3):431-440.
De Crescenzo et al., "Engineering TGF-β Traps: Artificially Dimerized Receptor Ectodomains as High-affinity Blockers of TGF-β Action," Transforming Growth Factor-β in Cancer Therapy, vol. II, 2008, Humana Press, 671-84.
De Genst et al., "Antibody repertoire development in camelids," Developmental & Comparative Immunology, Jan. 1, 2006, 30(1-2):187-98.
De Meyer et al., "Nanobody-based products as research and diagnostic tools," Trends in Biotechnology, May 1, 2014, 32(5):263-70.
De Stefano et al., "Establishing pathological cut-offs of brain atrophy rates in multiple sclerosis," Journal of Neurology, Neurosurgery, and Psychiatry, Jan. 2016, 87(1):93-99.
Deacon, "Physiology and Pharmacology of DPP-4 in Glucose Homeostasis and the Treatment of Type 2 Diabetes," Frontiers in Endocrinology, Feb. 2019, 10:80, 14 pages.
Deaglio et al., "Adenosine generation catalyzed by CD39 and CD73 expressed on regulatory T cells mediates immune suppression," Journal of Experimental Medicine, May 14, 2007, 204(6):1257-1265.
Demaria et al., "An Essential Role for Senescent Cellsin Optimal Wound Healing through Secretion of PDGF-AA," Developmental Cell, Dec. 22, 2014, 31(6):722-733.
Deyev et al., "Design of multivalent complexes using the barnase• barstar module," Nature Biotechnology, Dec. 2003, 21(12):1486-92.
Di Ianni et al., "Tregs prevent GVHD and promote immune reconstitution inHLA-haploidentical transplantation," Blood, Apr. 7, 2011, 117(14):3921-3928.
Dietel et al., "Decreased numbers of regulatory T cells are associated with human atherosclerotic lesion vulnerability and inversely correlate with infiltrated mature dendritic cells," Atherosclerosis, Sep. 2013, 230:92-99.
Digiammarino et al., "Design and generation of DVD-Ig™molecules for dual-specific targeting," Therapeutic Proteins: Methods and Protocols, Methods in Molecular Biology, 2012, Humana Press, Totowa, NJ., 899:145-516.
Dikov et al., "New fluorescent method for the histochemical detection of tripeptidyl peptidase I using glycyl-1-prolyl-1-met-2-anthraquinonyl hydrazide as substrate," Cellular and Molecular Biology, Jan. 1, 2004, 50 Online Pub: OL565-568, 1 page (Abstract Only).
Dimri et al., "A biomarker that identifies senescent human cells in culture and in aging skin in vivo," Proceedings of the National Academy of Sciences, Sep. 29, 1995, 92(20):9363-9367.

(56) References Cited

OTHER PUBLICATIONS

Dinarello, "Interleukin 1 and interleukin 18 as mediators of inflammation and the aging process," The American Journal of Clinical Nutrition, Feb. 1, 2006, 83(2):447S-455S.
Docagne et al., "A soluble transforming growth factor-β (TGF-β) type I receptor mimics TGF-β responses," Journal of Biological Chemistry, Dec. 7, 2001, 276(49):46243-50.
Dong et al., "Characterization of adenosine deaminase binding to human CD26 on T cells and its biologic role in immune response," Journal of Immunology, Feb. 15, 1996, 156(4):1349-1355.
Dong et al., "Determination of adenosine deaminase binding domain on CD26 and its immunoregulatory effect on T cell activation," Journal of Immunology, Dec. 15, 1997, 159(12):6070-6076.
Dong et al., "Loss of methylation at the IFNG promoter and CNS-1 is associated with the development of functional IFN-β memory in human CD4+T lymphocytes," European Journal of Immunology, 2013, 43(3), 793-804.
Dou et al., "Cytoplasmic chromatin triggers inflammation in senescence and cancer," Nature, Oct. 4, 2017, 550(7676):402-406, 21 pages.
Drees et al., "Soluble production of a biologically active single-chain antibody against murine PD-L1 in *Escherichia coli,*" Protein Express. Purif, 2014, 94:60-66.
Dubois et al., "Preassociation of IL-15 with IL-15Ra-IgG1-Fc Enhances Its Activity on Proliferation of NK and CD8+/CD44high T Cells and Its Antitumor Action," The Journal of Immunology, Feb. 15, 2008, 180:2099-2106.
Edwardraja et al., "Redesigning of anti-c-met single chain Fv antibody for the cytoplasmic folding and its structural analysis," Biotechnology and Bioengineering, Jun. 15, 2010, 106(3):367-75.
Eisenhut et al., "Ion Channels in Inflammation," Pflugers Archive, Jan. 29, 2011, 461(4):401-421.
Elgueta et al., "Molecular mechanism and function of CD40/CD40L engagement in the immune system," Immunological Reviews, 2009, 229(1):152-172 doi.org/10.1111/j.1600-065X.2009.00782.x.
Elpek et al., "Mature natural killer cells with phenotypic and functional alterations accumulate upon sustained stimulation with IL-15/IL-15Rα complexes," Proceedings of the National Academy of Science, Dec. 14, 2010, 107: 21647-21652.
Engel et al., "The crystal structure of dipeptidyl peptidase IV (CD26) reveals its functional regulation and enzymatic mechanism," Proc. Natl. Acad. Sci. U.S.A., Apr. 29, 2003, 100(9):5063-5068.
Epardaud et al., "Interleukin-15/Interleukin-15RA Complexes Promote Destruction of Established Tumors by Reviving Tumor-Resident CD8+ T Cells," Cancer Research 68: Apr. 15, 2008, 2972-2983.
Esensten et al., "Regulatory T-cell therapy for autoimmune and autoinflammatory diseases: The next frontier," The Journal of Allergy and Clinical Immunology, Dec. 1, 2018, 142(6):1710-1718.
Farr et al., "Targeting cellular senescence prevents age-related bone loss in mice," Nat. Med., 2017, 23(9): 1072-1079.
Fehniger et al., "A Phase 1 Trial of CNDO-109-Activated Natural Killer Cells in Patients with High-Risk Acute Myeloid Leukemia," Biology of Blood and Marrow Transplantation, Aug. 2018, 24(8):1581-1589.
Feng et al., "The yin and yang functions of extracellular ATP and adenosine in tumor immunity," Cancer Cell International, Apr. 7, 2020, 20:110, 11 pages.
Fernando et al., "Targeting tumor endothelial marker 8 in the tumor vasculature of colorectal carcinomas in mice," Cancer research, Jun. 15, 2009, 69(12):5126-5132.
Ferreira et al., "Next-generation regulatory T cell therapy," Nature Reviews Drug Discovery, Sep. 20, 2019, 18(10):749-769, 21 pages.
Ferrucci et al., "The origins of age-related proinflammatory state," Blood, Mar. 15, 2005, 105(6):2294-2299.
Finkelman et al., "Anti-cytokine antibodies as carrier proteins. Prolongation of in vivo effects of exogenous cytokines by injection of cytokine-anti-cytokine antibody complexes," The Journal of Immunology, Aug. 1, 1993, 151:1235-1244.
Finkelstein et al., "Obesity and Severe Obesity Forecasts Through 2030," American Journal of Preventative Medicine, Jun. 2012, 42(6):563-570.
Ford et al., "TREM and TREM-like receptors in inflammation and disease," Current Opinion in Immunology, Feb. 21, 2009, 21(1):38-46.
Franceschi et al., "Inflamm-aging. An evolutionary perspective on immunosenescence," Annals of the New York Academy of Sciences, Jun. 2000, 908:244-254.
Frutoso et al., "Emergence of NK Cell Hyporesponsiveness after Two IL-15 Stimulation Cycles," Journal of Immunology, May 30, 2018, 201: 493-506.
Ganesh et al., "TGF-β Inhibition and Immunotherapy: Checkmate," Immunity, Apr. 17, 2018, 48(4):626-628.
Garber, "Bispecific antibodies rise again," Nat. Rev. Drug Discov., 2014, 13:799-801.
Gaulton et al., "Characterization of a monoclonal rat anti-mouse interleukin 2 (IL-2) receptor antibody and its use in the biochemical characterization of the murine IL-2 receptor," Clinical Immunology and Immunopathology, Jul. 1, 1985, 36(1):18-29.
Gejima et al., "Human single-chain Fv (scFv) antibody specific to human IL-6 with the inhibitory activity on IL-6-signaling," Human Antibodies, Jan. 1, 2002, 11(4):121-9.
Geng et al., "A novel anti-TNF scFv constructed with human antibody frameworks and antagonistic peptides," Immunol. Res. 62(3):377-385, 2015.
Georgilis et al., "PTBP1-Mediated Alternative Splicing Regulates the Inflammatory Secretome and the Pro-tumorigenic Effects of Senescent Cells," Cancer Cell, Jul. 9, 2018, 34(1):85-102.
Ghosh et al., "The Senescence-Associated Secretory Phenotype: Critical Effector in SkinCancer and Aging," Journal of Investigative Dermatology, Nov. 2016, 136(11):2133-2139.
Gibbs et al., "Identification of the factor VIIa binding site on tissue factor by homologous loop swap and alanine scanning mutagenesis," Biochemistry, Nov. 1, 1994, 33(47):14003-10.
Gong et al., "DAMP-sensing receptors in sterile inflammation and inflammatory diseases," Nature Reviews Immunology, Sep. 26, 2019, 20(2):95-112.
Gorrell et al., "Expression of the rat CD26 Antigen (dipeptidyl peptidase IV) on subpopulations of rat lymphocytes," Cellular Immunology, Apr. 15, 1991, 134(1):205-215.
Greenspan et al., "Defining epitopes: Its not as easy as it seems," Nature Biotechnology, 1999, 17:936-937.
Grupp et al., "Chimeric Antigen Receptor-Modified T Cells for Acute Lymphoid Leukemia," The New England Journal of Medicine, Apr. 18, 2013, 368(16):1509-1518.
Gu et al., "Human CD39hi regulatory T cells present stronger stability and function under inflammatory conditions," Cellular and Molecular Immunology, Jul. 4, 2016, 14(6):521-528.
Guha et al., "Affinity purification of human tissue factor: interaction of factor VII and tissue factor in detergent micelles," Proceedings of the National Academy of Sciences, Jan. 1986, 83(2):299-302.
Guo et al., "Immunobiology of the IL-15-IL-15R complex as an antitumor and antiviral agent," 2017, Cytokine & Growth Factor Reviews, 38:10-21.
Gutschmidt et al., "A quantitative histochemical study of dipeptidyl peptidase IV (DPP IV)," Histochemistry, 1981, 73(2):285-304.
Haile et al., "Soluble CD80 Restores T Cell Activation and Overcomes Tumor Cell Programmed Death Ligand 1-Mediated Immune Suppression," J. Immunol., 2013, 191(5):2829-2836.
Hayflick et al., "The serial cultivation of human diploid cell strains," Experimental Cell Research, Dec. 1961, 25:585-621.
He et al., "Senescence in Health and Disease," Cell, Jun. 1, 2017, 169(6):1000-1011.
Hebbar et al., "Detection of circulating soluble CD28 in patients with systemic lupus erythematosus, primary Sjögren's syndrome and systemic sclerosis," Clinical & Experimental Immunology, May 2004, 136(2):388-92.
Helfrich et al., "A rapid and versatile method for harnessing scFv antibody fragments with varous biological effector functions," Journal of Immunological methods, 2000, 237(1-2):131-145.

(56) References Cited

OTHER PUBLICATIONS

Hélie et al., "Application of the Protein Maker as a platform purification system for therapeutic antibody research and development," Computational and Structural Biotechnology Journal, Jan. 1, 2016, 14:238-244.
Helman et al., "Effects of ageing and senescence on pancreatic β-cell function," Diabetes Obes Metab., Sep. 2016, 18(Suppl. 1):58-62.
Heneka et al., "Inflammasome signaling in brain function and neurodegenerative disease," Nature Reviews Neuroscience, Sep. 11, 2018, 19(10):610-621.
Heneka et al., "NLRP3 is activated in Alzheimer's disease and contributes to pathology in APP/PS1 mice," Nature, Jan. 31, 2013, 493(7434):674-678, 8 pages.
Heng et al., "G Protein-Coupled Receptors Revisited: Therapeutic Applications Inspired by Synthetic Biology," Annual Review of Pharmacology and Toxicology, Jan. 2014, 54:227-249.
Heng et al., "Multiple soluble TGF-β receptors in addition to soluble endoglin are elevated in preeclamptic serum and they synergistically inhibit TGF-β signaling." Placenta, 2017 57: 320 (1 page).
Highfill et al., "Overcoming Challenges in Process Development of Cellular Therapies," Current Hematologic Malignancy Reports, Jul. 6, 2019, 14(4):269-277, 9 pages.
Hoare et al., "The Power Behind the Throne: Senescence and the Hallmarks of Cancer," Annual Review of Cancer Biology, 2018, 2:175-194.
Hoffmann et al., "Large-scale in vitro expansion of polyclonal human CD4+CD25high regulatory T Cells," Blood, Aug. 2004, 104(3):895-903.
Hollande et al., "Inhibition of the dipeptidyl peptidase DPP4 (CD26) reveals IL-33-dependent eosinophil-mediated control of tumor growth," Nature Immunology, Feb. 18, 2019, 20(3):257-264.
Hombach et al., "Generation of the single chain antibody fragment conserves the idiotypic profile of the anti-CD30 monoclonal antibody HRS3," Scandinavian Journal of Immunology, Nov. 1998, 48(5):497-501.
Hu et al., "Discovery of a novel IL-15 based protein with improved developability and efficacy for cancer immunotherapy," Scientific Reports, 2018, 8:7675, 11 pages.
Huang et al., "Substrate recognition by tissue factor-factor VIIa Evidence for interaction of residues Lys165 and Lys166 of tissue factor with the 4-carboxyglutamate-rich domain of factor X," Journal of Biological Chemistry, Sep. 6, 1996, 271(36):21752-7.
Huang et al., "Targeting the vasculature of colorectal carcinoma with a fused protein of (RGD) 3-tTF" The Scientific World Journal, 2013(637086): 1-11, 2013.
Hudak et al., "Glycocalyx engineering reveals a Siglec-based mechanism for NK cell immunoevasion," Nature Chemical Biology, Jan. 2014, 10(1), 20 pages.
Hudson et al., "Targeting RAGE Signaling in Inflammatory Disease," Annual Review of Medicine, Jan. 2018, 69:349-364, 16 pages.
Huell et al., "Interleukin-6 is present in early stages of plaque formation and is restricted to the brains of Alzheimer's disease patients," Acta Neuropathologica, Nov. 1995, 89(6):544-551.
Hughes et al., "Transfer of a TCR gene derived from a patient with a marked antitumor response conveys highly active T-cell effector functions," Hum. Gene Ther., 2005, 16:457-72.
Hui et al., "Butyrate inhibit collagen-induced arthritis via Treg/IL-10/Th17 axis," International immunopharmacology, Mar. 1, 2019, 68: Abstract 1 page.
Hynes et al., "In vitro analysis of cell metabolism using a long-decay pH-sensitive lanthanide probe and extracellular acidification assay," Analytical biochemistry, Jul. 1, 2009, 390(1):21-28.
Iannello et al., "p53-dependent chemokine production by senescent tumor cells supports NKG2D-dependent tumor elimination by natural killer cells," Journal of Experimental Medicine, Sep. 23, 2013, 210(10):2057-69.
Iihoshi et al., "Aclarubicin, an anthracycline anti-cancer drug, fluorescently contrasts mitochondria and reduces the oxygen consumption rate in living human cells," Toxicology Letters, Aug. 5, 2017, 277:109-114, 22 pages.
info.gbiosciences.com [Online], "G-Biosciences, The Basics of Affinity Purification/Affinity Chromatography," Jul. 31, 2018, retrieved on Apr. 18, 2023, retrieved from URL<https://info.gbiosciences.com/blog/the-basics-of-affinity-purification/affinity-chromatography?utm_campaign=G-Bio+Search+Ads&utm_term=&utm_source=adwords&utm_medium=ppc&hsa_src=g&hsa_ver=3&hsa_cam=737902488&hsa kw=&hsa ad=621736020174&hsa_tgt=dsa-460355902483&hsa_mt=&hsa_acc-6752996364&hsa_grp-92226101427&hsa_net=adwords&gclid=CjwKCAjw_ihBhADEiwAXEazJvXifVFgeRGV_W99XbY72eRROhWnHtdd695ydPgyh8qdvTwd9ikGIRoCdecQAvD_BWE>, 5 pages.
International Preliminary Report on Patentability in International Appln. No. PCT/US2019/048881, dated Mar. 11, 2021, 7 pages.
International Preliminary Report on Patentability in International Appln. No. PCT/US2019/048930, dated Mar. 11, 2021, 9 pages.
International Preliminary Report on Patentability in International Appln. No. PCT/US2019/049142, dated Mar. 11, 2021, 11 pages.
International Preliminary Report on Patentability in International Appln. No. PCT/US2019/049158, dated Mar. 11, 2021, 8 pages.
International Preliminary Report on Patentability in International Appln. No. PCT/US2020/035598, mailed Dec. 6, 2022, 7 pages.
International Preliminary Report on Patentability in International Appln. No. PCT/US2020/038717, dated Dec. 30, 2021, 9 pages.
International Preliminary Report on Patentability in International Appln. No. PCT/US2021/017620, dated Aug. 25, 2022, 12 pages.
International Preliminary Report on Patentability in International Appln. No. PCT/US2021/017621, dated Aug. 25, 2022, 8 pages.
International Preliminary Report on Patentability in International Appln. No. PCT/US2021/017714, dated Aug. 25, 2022, 12 pages.
International Preliminary Report on Patentability in International Appln. No. PCT/US2021/029920, dated Nov. 10, 2022, 11 pages.
International Preliminary Report on Patentability in International Appln. No. PCT/US2021/035285, mailed Dec. 15, 2022, 7 pages.
International Search Report and Written Opinion in International Appln. No. PCT/US2019/048881, dated Nov. 9, 2019, 16 pages.
International Search Report and Written Opinion in International Appln. No. PCT/US2019/048930, dated Nov. 20, 2019, 18 pages.
International Search Report and Written Opinion in International Appln. No. PCT/US2019/049142, dated Jun. 23, 2020, 20 pages.
International Search Report and Written Opinion in International Appln. No. PCT/US2019/049158, dated Jan. 20, 2020, 17 pages.
International Search Report and Written Opinion in International Appln. No. PCT/US2020/035598, dated Feb. 18, 2021, 12 pages.
International Search Report and Written Opinion in International Appln. No. PCT/US2020/038717, dated Oct. 16, 2020, 17 pages.
International Search Report and Written Opinion in International Appln. No. PCT/US2021/017620, dated Aug. 6, 2021, 22 pages.
International Search Report and Written Opinion in International Appln. No. PCT/US2021/017621, dated Jun. 9, 2021, 15 pages.
International Search Report and Written Opinion in International Appln. No. PCT/US2021/017714, dated Aug. 27, 2021, 22 pages.
International Search Report and Written Opinion in International Appln. No. PCT/US2021/029920, dated Oct. 6, 2021, 21 pages.
International Search Report and Written Opinion in International Appln. No. PCT/US2021/035285, dated Oct. 18, 2021, 14 pages.
Inzucchi et al., "New Drugs for the Treatment of Diabetes, Part II: Incretin-Based Therapy and Beyond, " Circulation, Jan. 29, 2008, 117(4):574-584, 21 pages.
Jain et al., "Mitochondrial Reactive Oxygen Species Regulate Transforming Growth Factor-β Signaling," Journal of Biological Chemistry, Jan. 11, 2013, 288(2):770-777.
Jakob et al., "Structure reveals function of the dual variable domain immunoglobulin (DVD-Ig™) molecule," Mabs, May 1, 2013, Taylor & Francis, 5(3):358-63.
Janeway, "Approaching the Asymptote? Evolution and Revolution in Immunology," Cold Spring Harbor Symposia on Quantitative Biology, 1989, 54 Pt 1:1-13.

(56) References Cited

OTHER PUBLICATIONS

Jeannin et al., "Soluble CD86 Is a Costimulatory Molecule for Human T Lymphocytes, " Immunity, 2000, 13(3):303-312.
Jeon et al., "Local clearance of senescent cells attenuates the development of post-traumatic osteoarthritis and creates a pro-regenerative environment," Nat Med., Jun. 2017, 23(6):775-781.
Jin et al., "Novel Insights Into the NLRP3 Inflammasome in Atherosclerosis," Journal of the American Heart Association, Jun. 11, 2019, 8(12):e012219, 12 pages.
Justice et al., "Senolytics in idiopathic pulmonary fibrosis: Results from a first-in-human, open-label, pilot study," EBioMedicine, Feb. 2019, 40:554-563.
Kain et al., "The identification of the endogenous ligands of natural killer T cells reveals the presence of mammalian α-linked glycosylceramides," Immunity, Oct. 16, 2014, 41(4):543-54.
Karin et al., "Senescent cell turnover slows with age providing an explanation for the Gompertz law," Nature Communications, 10:5495, 9 pages.
Karkera et al., "The anti-interleukin-6 antibody siltuximab down-regulates genes implicated in tumorigenesis in prostate cancer patients from a phase I study," The Prostate, Feb. 14, 2011, 71(13):1455-1465.
Katsuumi et al., "Vascular Senescence in Cardiovascular and Metabolic Diseases," Frontiers in Cardiovascular Medicine, 5:18, 13 pages.
Kellner et al., "Enhancing natural killer cell-mediated lysis of lymphoma cells by combining therapeutic antibodies with CD20-specific immunoligands engaging NKG2D or NKp30," Oncoimmunology, Jan. 2, 2016, 5(1):e1058459, 12 pages.
Kijanka et al., "Nanobody-based cancer therapy of solid tumors," Nanomedicine, Jan. 2015, 10(1):161-74.
Kim et al., "Experimental malaria infection triggers early expansion of natural killer cells," Infection and Immunity, Dec 1, 2008, 76(12):5873-82.
Kim et al., "Identification of senescent cell surface targetable protein DPP4," Genes & Development, 2017, 31(15):1529-1534.
Kim et al., "Insulin resistance, inflammation, and nonalcoholic fatty liver disease in non-obese adults without metabolic syndrome components," Hepatol Int., Jun. 2013, 7(2):586-591.
Kim et al., "SCAMP4 enhances the senescent cell secretome," Genes & Development, 2018, 32(13-14):909-914.
Kirchhofer et al., "The tissue factor region that interacts with substrates factor IX and factor X," Biochemistry, Jun. 27, 2000, 39(25):7380-7.
Kirkland et al., "Cellular Senescence: A Translational Perspective," EBioMedicine, Jul. 2017, 21:21-28.
Klein et al., "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines," Oncoimmunology, 2017 6(3):e1277306, 15 pages.
Klein et al., "Design and characterization of structured protein linkers with differing flexibilities," Protein Engineering, Design & Selection, 2014, 27(10):325-30.
Klemann et al., "Cut to the chase: a review of CD26/dipeptidyl peptidase-4's (DPP4) entanglement in the immune system," Clinical and Experimental Immunology, Feb. 25, 2016, 185(1):1-21.
Klingemann et al., "Natural killer cells for immunotherapy-advantages of the NK-92 cell line over blood NK cells," Frontiers in immunology, Mar. 14, 2016, 7(91): 1-7.
Klingenberg et al., "Depletion of FOXP3+ regulatory T cells promotes hypercholesterolemia and atherosclerosis," The Journal of Clinical Investigation, Feb. 15, 2013, 123:1323-1334.
Kondo et al., "Requirements for the functional expression of OX40 ligand on human activated CD4+ and CD8+ T cells," Human Immunology, 2007, 68(7):563-571.
Kovaleva et al., "Shark variable new antigen receptor biologics—a novel technology platform for therapeutic drug development," Expert Opinion on Biological Therapy, Oct. 1, 2014, 14(10):1527-39.
Kozlowska et al., "Adoptive transfer of osteoclast-expanded natural killer cells for immunotherapy targeting cancer stem-like cells in humanized mice," Cancer Immunology, Immunotherapy, Jul. 2016, 65:835-845.
Krah et al., "Single-domain antibodies for biomedical applications," Immunopharmacology and Immunotoxicology, Jan. 2, 2016, 38(1):21-8.
Kritsilis et al., "Ageing, Cellular Senescence and Neurodegenerative Disease," International Journal of Molecular Sciences, Sep. 27, 2018, 19(10):2937, 37 pages.
Krizhanovsky et al., "Senescence of activated stellate cells limits liver fibrosis," Cell, Aug. 22, 2008, 134(4):657-67.
Kumagai et al., "Monitoring of glutamate-induced excitotoxicity by mitochondrial oxygen consumption," Synapse, Jan. 2019, 73(1):e22067, 24 Pages.
Kuyinu et al., "Animal models of osteoarthritis: classification, update, and measurement of outcomes," J Orthop Surg Res., Feb. 2, 2016, 11:19, 27 pages.
Lambeir et al., "Dipeptidyl-Peptidase IV from Bench to Bedside: An Update on Structural Properties, Functions, and Clinical Aspects of the Enzyme DPP IV," Critical Reviews in Clinical Laboratory Sciences, Sep. 29, 2003, 40(3):209-294.
Lamkanfi et al., "Mechanisms and Functions of Inflammasomes," Cell, May 22, 2014, 157(5):1013-1022.
Lansigan et al., "DI-Leu16-IL2, an Anti-CD20-Interleukin-2 Immunocytokine, Is Safe and Active in Patients with Relapsed and Refractory B-Cell Lymphoma: A Report of Maximum Tolerated Dose, Optimal Biologic Dose, and Recommended Phase 2 Dose," Blood, Dec 2, 2016, 128(22):620, 3 pages (Abstract Only).
Latz et al., "Activation and regulation of the inflammasomes," Nature Reviews Immunology, May 24, 2013, 13(6):397-411.
Latz et al., "NLRP3 inflammasome activation in inflammaging," Seminars in Immunology, Dec. 2018, 40:61-73, 13 pages.
Lau et al., "RNA-associated autoantigens activate B cells by combined B cell antigen receptor/Toll-like receptor 7 engagement," The Journal of Experimental Medicine, Oct. 31, 2005, 202(9):1171-1177.
Lazar et al., "Transforming Growth Factor Alpha: Mutation of Aspartic Acid 47 and Leucine 48 Results in Different Biological Activities," Mol. Cell. Biol., 1988, 8:1247-1252.
Li et al., "A Novel I L2-based Irrmunotherapeutic Protein Prevents the Development of Atherosclerosis in ApoE-/mice and LDLR-/-mice," Journal of Immunology, May 1, 2020, 204(1): Supplement (Abstract Only), 2 pages.
Li et al., "Adoptive transfer of natural killer cells in combination with chemotherapy improves outcomes of patients with locally advanced colon carcinoma," Cytotherapy, Jan. 2018, 20(1):134-148, 15 pages.
Li et al., "Lipid metabolism fuels cancer's spread," Cell metabolism, Feb. 7, 2017, 25(2):228-230.
Li et al., "The cGAS-cGAMP-STING pathway connects DNA damage to inflammation, senescence, and cancer," Journal of Experimental Medicine, Apr. 5, 2018, 215(5):1287-1299.
Li et al., "Transforming Growth Factor-β Regulation of Immune Responses," Annu. Rev. Immunol., 2006, 24:99-146.
Liton et al., "Cellular senescence in the glaucomatous outflow pathway," Experimental Gerontology, Aug.-Sep. 2005, 40(8-9):745-748.
Liu et al., "A Novel Fusion of ALT-803 (IL-15 Superagonist) with an Antibody Demonstrates Antigen-specific Antitumor Responses," Journal of Biological Chemistry, 2016, 291(46):23869-23881.
Liu et al., "Evaluation of the biological activities of the IL-15 superagonist complex, ALT-803, following intravenous versus subcutaneous administration in murine models," Cytokine, Jul. 2018, 107: 105-112, 8 pages.
Loster et al., "The Cysteine-Rich Region of Dipeptidyl Peptidase IV (CD 26) Is the Collagen Binding Site," Biochemical and Biophysical Research Communications, Dec. 5, 1995, 217(1):341-348.
Lu et al., "Molecular basis of binding between novel human coronavirus MERS-CoV and its receptor CD26," Nature, Jul. 7, 2013, 500(7461):227-231.
Lujambio et al., "Non-Cell-Autonomous Tumor Suppression by p53," Cell, Apr. 11, 2013, 153(2):449-460.

(56) References Cited

OTHER PUBLICATIONS

Maeda et al., "Original Ligand for LTBR Is LIGHT: Insight into Evolution of the LT/LTBR System," J Immunol., 2018, 201(1):202-214.
Maganto-García et al., "Dynamic Changes in Regulatory T Cells Are Linked to Levels of Diet-Induced Hypercholesterolemia," Circulation, Jun. 20, 2011, 124:185-195.
Mandelboim et al., "Recognition of haemagglutinins on virus-infected cells by NKp46 activates lysis by human NK cells," Nature, Feb. 2001, 409(6823):1055.
Marguet et al., "Enhanced insulin secretion and improved glucose tolerance in mice lacking CD26," Proc. Natl. Acad. Sci. U.S.A., Jun. 6, 2000, 97(12):6874-6879.
Martelli et al., "HLA-haploidentical transplantation with regulatory and conventionalT-cell adoptive immunotherapy prevents acute leukemia relapse," Blood, Jul. 24, 2014, 124(4):638-644.
Masoumi et al., "The role of hypoxia as the driving force for non-erythroid production of globin chains in preeclamptic placentas," Placenta. 2017;57:320.
Mccarron et al., "TGF-β prevents T follicular helper cell accumulation and B cell autoreactivity," J Clin Invest., 2014, 124(10):4375-4386.
McHugh et al., "Senescence and aging: Causes, consequences, and therapeutic avenues," Journal of Cellular Biology, Nov. 7, 2017, 217(1):65-77.
Mehta et al., "Why do trials for Alzheimer's disease drugs keep failing? A discontinued drug perspective for 2010-2015," Expert Opinion on Investigational Drugs, May 2017, 26(6):735-739.
Melk et al., "Expression of p16INK4a and other cell cycle regulator and senescence associated genes in aging human kidney," Kidney Int., Feb. 2004, 65(2):510-520.
Melk et al., "Senescence of renal cells: molecular basis and clinical implications," Nephrology Dialysis Transplantation, Dec 2003, 18(12):2474-2478.
Menshawy et al., "CD58; leucocyte function adhesion-3 (LFA-3) could be used as a differentiating marker between immune and non-immune thyroid disorders," Comparative Clinical Pathology, 2018, 27(3), 721-727.
Mentlein et al., "Dipeptidyl-peptidase IV (CD26)-role in the inactivation of regulatory peptides," Regulatory Peptides, Nov. 30, 1999, 85(1):9-24.
Miah et al., "KIR2DL4 differentially signals downstream functions in human NK cells through distinct structural modules," The Journal of Immunology, Mar. 1, 2008, 180(5):2922-32.
Michelet et al., "Metabolic reprogramming of natural killer cells in obesity limits antitumor responses," Nature Immunology, Nov. 12, 2018, 19(12):1330-1340.
Mikayama et al., "Molecular cloning and functional expression of a cDNA encoding glycosylation-inhibiting factor," Proc. Natl. Acad. Sci. USA, Nov. 1, 1993, 90(21):10056-10060.
Milanovic et al., "Senescence-associated reprogramming promotes cancer stemness," Nature, Dec 20, 2017, 553(7686):96-100.
Milanovic et al., "The Senescence-Stemness Alliance—A Cancer-Hijacked Regeneration Principle," Trends in Cellular Biology, Dec 2018, 28(12):1049-1061, 13 pages.
Miller et al., "Soluble CD70: a novel immunotherapeutic agent for experimental glioblastoma," J Neurosurg., 2010, 113(2):280-285.
Miller et al., "Successful adoptive transfer and in vivo expansion of human haploidentical NK cells in patients with cancer," Blood, Apr. 15, 2005, 105(8):3051-3057.
Minamino et al., "A crucial role for adipose tissue p53 in the regulation of insulin resistance," Nature Medicine, Aug. 30, 2009, 15(9):1082-1087.
Mitterberger et al., "Adipogenic Differentiation Is Impaired in Replicative Senescent Human Subcutaneous Adipose-Derived Stromal/Progenitor Cells," The Journals of Gerontology: Series A, Biological Sciences and Medical Sciences, Jan. 2014, 69(1):13-24.
Miyazaki et al., "Abstract 3265: NKTR-255, a polymer-conjugated IL-15 enhances anti-tumor NK cell responses and synergizes with monoclonal antibodies to provide long-term survival in human lymphoma model," Proceedings: AACR Annual Meeting 2019, Atlanta, GA, Mar. 29-Apr. 3, 2019, 1 page.
Moesta et al., "Targeting CD39 in cancer," Nature Reviews Immunology, Jul. 29, 2020, 20(12):739-755, 17 pages.
Moiseeva et al., "Metformin inhibits the senescence-associated secretory phenotype by interfering with IKK/NF-κb activation," Aging Cell, Mar. 23, 2013, 12(3):489-498.
Molema et al., "The use of bispecific antibodies in tumor cell and tumor vasculature directed immunotherapy," Journal of Controlled Release, 2000, 64(1-3):229-239.
Molgora et al., "Regulatory role of IL-1R8 in immunity and disease, " Frontiers in Immunology, Apr. 20, 2016, 7:149.
Mookerjee et al., "Measurement and Analysis of Extracellular Acid Production to Determine Glycolytic Rate," Journal of Visualized Experiments : Jove, Dec. 2015, (106):e53464, 9 Pages.
Moore et al., "Macrophages in atherosclerosis: a dynamic balance," Nature Reviews Immunology, Sep. 2, 2013, 13:709-721, 13 pages.
Moreno et al., "Molecular Evidence of Adenosine Deaminase Linking Adenosine A2A Receptor and CD26 Proteins," Frontiers in Pharmacology, Feb. 15, 2018, 9:106, 18 pages.
Moretta et al., "CD69-mediated pathway of lymphocyte activation: anti-CD69 monoclonal antibodies trigger the cytolytic activity of different lymphoid effector cells with the exception of cytolytic T lymphocytes expressing T cell receptor alpha/beta," Journal of Experimental Medicine, Dec. 1, 1991, 174(6):1393-8.
Mortier et al., "Soluble interleukin-15 receptor α (IL-15Rα)-sushi as a selective and potent agonist of IL-15 action through IL-15Rβ/γ: hyperagonist IL-15• IL-15Rα fusion proteins," Journal of Biological Chemistry, Jan. 20, 2006, 281(3):1612-1619.
Mujić-Delić et al., "GPCR-targeting nanobodies: attractive research tools, diagnostics, and therapeutics," Trends in Pharmacological Sciences, May 1, 2014, 35(5):247-55.
Muller et al., "Antibody fusions with immunomodulatory proteins for cancer therapy," Pharmacology and Therapeutics, 2015, 154:57-66.
Mulvihill et al., "Pharmacology, Physiology, and Mechanisms of Action of Dipeptidyl Peptidase-4 Inhibitors," Endocrine Reviews, Dec. 1, 2014, 35(6):992-1019.
Munoz-Espin et al., "Cellular senescence: from physiology to pathology," Nature Reviews Molecular Cellular Biology, Jun. 23, 2014, 15(7):482-496.
Munoz-Espin et al., "Programmed Cell Senescence during Mammalian Embryonic Development," Cell, Nov. 21, 2013, 155(5):1104-1118.
Musi et al., "Tau protein aggregation is associated with cellular senescence in the brain," Aging Cell, Aug. 20, 2018, 17(6):e12840, 13 pages.
Must et al., "The Disease Burden Associated with Overweight and Obesity," Endotext, Feingold et al. (eds.), South Dartmouth, MA, 2000, 35 pages.
Muyldermans et al., "Recognition of antigens by single-domain antibody fragments: the superfluous luxury of paired domains," Trends in Biochemical Sciences, Apr. 1, 2001, 26(4):230-5.
Muyldermans, "Nanobodies: natural single-domain antibodies," Annual Review of Biochemistry, Jun. 2, 2013, 82:775-97.
Muyldermans, "Single domain camel antibodies: current status," Reviews in Molecular Biotechnology, Jun. 1, 2001, 74(4):277-302.
Myung et al., "Evidence of DNA damage in Alzheimer disease: phosphorylation of histone H2AX in astrocytes," Age, Apr. 23, 2008, 30(4):209-215.
Nag et al., "Soluble MHC II-peptide complexes induce antigen-specific apoptosis in T cells," Cellular Immunology, May 25, 1996, 170(1):25-33.
Nayyar et al., "Overcoming Resistance to Natural Killer Cell Based Immunotherapies for Solid Tumors," Frontiers in Oncology, 2019, 9: 28 pages.
Nelson et al., "A senescent cell bystander effect: senescence-induced senescence," Aging Cell, Feb. 9, 2012, 11(2):345-349.
Nilsson et al., "Targeted delivery of tissue factor to the ED-B domain of fibronectin, a marker of angiogenesis, mediates the infarction of solid tumors in mice," Cancer Research, American Association for Cancer Researc, Proceedings: AACR 107th Annual Meeting, 2016, Apr. 16-20, 2016, New Orleans, LA 61(2):711-716.

(56) References Cited

OTHER PUBLICATIONS

Nishida et al., "CD26 is a potential therapeutic target by humanized monoclonal antibody for the treatment of multiple myeloma," Blood Cancer Journal, Oct. 22, 2018, 8(11):99, 17 pages.
O'Sullivan et al., "Natural Killer Cell Memory," Immunity, Oct. 20, 2015, 43(4):634-645.
Oberle et al., "Rapid Suppression of Cytokine Transcription in Human CD4+CD25− T Cells by CD4+Foxp3+ Regulatory T Cells: Independence of IL-2 Consumption, TGF-β, and Various Inhibitors of TCR Signaling," The Journal of Immunology, Sep. 15, 2007, 179(6):3578-3587.
Ogrodnik et al., "Cellular senescence drives age-dependent hepatic steatosis," Nat Commun. Jun. 13, 2017;8:15691, 12 pages.
Ogrodnik et al., "Obesity-Induced Cellular Senescence Drives Anxiety and Impairs Neurogenesis," Cell Metabolism, May 2019, 29(5):1061-1077, 25 pages.
Ohnuma et al., "Blockade of CD26-mediated T cell costimulation with soluble caveolin-1-Ig fusion protein induces anergy in CD4+T cells," Biochemical and Biophysics Research Communications, Aug. 21, 2009, 386(2):327-332.
Ohnuma et al., "CD26 Mediates Dissociation of Tollip and IRAK-1 from Caveolin-1 and Induces Upregulation of CD86 on Antigen-Presenting Cells," Molecular and Cellular Biology, Sep. 1, 2005, 25(17):7743-7757.
Ohnuma et al., "CD26 up-regulates expression of CD86 on antigen-presenting cells by means of caveolin-1," Proc. Natl. Acad. Sci. U.S.A., Sep. 28, 2004, 101(39):14186-14191.
Ohnuma et al., "Role of CD26/dipeptidyl peptidase IV in human T cell activation and function," Frontiers in Bioscience, Jan. 1, 2008, 13:2299-2310.
Ohnuma et al., "Soluble CD26/Dipeptidyl Peptidase IV Induces T Cell Proliferation Through CD86 Up-Regulation on APCs," Journal of Immunology, Dec 15, 2001, 167(12):6745-6755.
Ovadya et al., "Strategies targeting cellular senescence," The Journal of Clinical Investigation, Apr. 2, 2018, 128(4):1247-54.
Owicki et al., "Biosensors based on the energy metabolism of living cells: the physical chemistry and cell biology of extracellular acidification," Biosensors and Bioelectronics, Jan. 1, 1992, 7(4):255-272.
Padutsch et al., "Superior Treg-Expanding Properties of a Novel Dual-Acting Cytokine Fusion Protein," Frontiers in Pharmacology, Dec 18, 2019, 10:1490, 10 pages.
Palmer et al., "Cellular Senescence in Type 2 Diabetes: A Therapeutic Opportunity," Diabetes, Jul. 2015, 64(7):2289-2298.
Parker et al., "Design, production, and characterization of a single-chain variable fragment (ScFv) derived from the prostate specific membrane antigen (PSMA) monoclonal antibody J591," Protein Expression and Purification, Jun. 1, 2013, 89(2):136-45.
Peipp et al., "HER2-specific immunoligands engaging NKp30 or NKp80 trigger NK-cell-mediated lysis of tumor cells and enhance antibody-dependent cell-mediated cytotoxicity," Oncotarget, Oct. 13, 2015, 6(31):32075.
Pittayapruek et al., "Role of Matrix Metalloproteinases in Photoaging and Photocarcinogenesis," International Journal of Molecular Sciences, 2016, 17(6):868, 20 pages.
Price et al., "Comparison of collagenase-cleaved articular cartilage collagen in mice in the naturally occurring STR/ort model of osteoarthritis and in collagen-induced arthritis," Osteoarthritis Cartilage, Mar. 2002, 10(3):172-179.
Priyanka et al., "Linkers in the structural biology of protein-protein interactions," Protein Sci., 2013, 22(2):153-167.
Purohit et al., "Smad3-dependent regulation of type I collagen in human dermal fibroblasts: Impact on human skin connective tissue aging," Journal of Dermatological Science, Jul. 2016, 83(1):80-83.
Putnam et al., "Clinical grade manufacturing of human alloantigen-reactive regulatory T cells for use in transplantation," American journal of transplantation, Nov. 1, 2013, 13(11):3010-3020.
Qin et al., "Critical Role of P2Y12 Receptor in Regulation of Th17 Differentiation and Experimental Autoimmune Encephalomyelitis Pathogenesis," The Journal of Immunology, Jul. 1, 2017, 199(1):72-81.
Rafei et al., "Off-the-shelf virus specific T-cells for therapy of adenovirus disease in immunosuppressed patients," Journal of Clinical Oncology, May 26, 2019, 37(15 Suppl.):7008, 2 pages.
Rahbarizadeh et al., "Nanobody; an old concept and new vehicle for immunotargeting, " Immunological Investigations, Jan. 1, 2011, 40(3):299-338.
Raj et al., "Adenosine Deaminase Acts as a Natural Antagonist for Dipeptidyl Peptidase 4-Mediated Entry of the Middle East Respiratory Syndrome Coronavirus," Journal of Virology, Feb. 2014, 88(3):1834-1838, 7 pages.
Ranganathan et al., "Pinpointing the putative heparin/sialic acid-binding residues in the 'sushi' domain 7 of factor H: a molecular modeling study," Biocomputing 2000, 1999, 155-67.
Rao et al., "Purification and characterization of rabbit tissue factor," Thrombosis Research, Oct. 1, 1989, 56(1):109-118.
Rasmussen et al., "Crystal structure of human dipeptidyl peptidase IV/CD26 in complex with a substrate analog," Nature Structural and Molecular Biology, 2003, 10(1):19-25.
Raz et al., "Efficacy and safety of the dipeptidyl peptidase-4 inhibitor sitagliptin as monotherapy in patients with type 2 diabetes mellitus," Diabetologia, Sep. 26, 2006, 49(11):2564-2571.
Resta et al., "Ecto-enzyme and signaling functions of lymphocyte CD 7 3," Immunological Reviews, 1998, 161:95-109.
Rhein et al., "Characterization of Human and Murine T-Cell Immunoglobulin Mucin Domain 4 (TIM-4) IgV Domain Residues Critical for Ebola Virus Entry," J Viral., 2016, 90(13):6097-6111.
Rippmann et al., "Fusion of the Tissue Factor Extracellular Domain to a Tumor Stromaspecific Single-Chain Fragment Variable Antibody Results in an Antigen-Specific Coagulation-Promoting Molecule," Biochemical Journal, 2000, 349(3):805-812.
Rittie et al., "Natural and Sun-Induced Aging of Human Skin," Cold Spring Harbor Perspective in Medicine, 2015, 5(1):a015370, 15 pages.
Rocha et al., "A novel immunofluorescent assay to investigate oxidative phosphorylation deficiency in mitochondrial myopathy: understanding mechanisms and improving diagnosis," Scientific reports, Oct. 15, 2015, 5:15037, 17 Pages.
Rodier et al., "Persistent DNA damage signaling triggers senescence-associated inflammatory cytokine secretion," Nature Cell Biology, Jul. 13, 2009, 11(8): 15 pages.
Rogge et al., "Antibodies to the IL-12 receptor β2 chain mark human Th1 but not Th2 cells in vitro and in vivo," The Journal of Immunology, Apr. 1, 1999, 162(7):3926-32.
Roh et al., "Damage-Associated Molecular Patterns in Inflammatory Diseases," Immune Network, Aug. 2018, 18(4):e27, 14 pages.
Romano et al., "Past, Present, and Future of Regulatory T Cell Therapy in Transplantation and Autoimmunity," Frontiers in Immunology, Jan. 1, 2019, 10:43, 14 pages.
Romee et al., "Cytokine activation induces human memory-like NK cells," Blood, Dec 6, 2012, 120(24):4751-4760.
Rossi et al., "Complex and defined biostructures with the dock-and-lock method," Trends in Pharmacological Sciences, Sep. 1, 2012, 33(9):474-81.
Rossi et al., "Stably tethered multifunctional structures of defined composition made by the dock and lock method for use in cancer targeting," Proceedings of the National Academy of Sciences, May 2, 2006, 103(18):6841-6.
Rubinstein et al., "Converting IL-15 to a superagonist by binding to soluble IL-15Rα," Proceedings of the National Academy of Sciences U.S.A., Jun. 13, 2006, 103(24):9166-9171.
Ruf et al., "Cofactor residues lysine 165 and 166 are critical for protein substrate recognition by the tissue factor-factor VIIa protease complex," Journal of Biological Chemistry, Mar. 25, 1992, 267(9):6375-81.
Ruf et al., "Tissue factor residues 157-167 are required for efficient proteolytic activation of factor X and factor VII," Journal of Biological Chemistry, Nov. 5, 1992, 267(31):22206-10.

(56) References Cited

OTHER PUBLICATIONS

Ruscetti et al., "NK cell-mediated cytotoxicity contributes to tumor control by a cytostatic drug combination," Science, Dec 21, 2018, 362(6421):1416-1422, 8 pages.
Sagiv et al., "Granule exocytosis mediates immune surveillance of senescent cells," Oncogene, 2013, 32(15):1971-1977.
Sakaguchi et al., "Regulatory T Cells and Human Disease," Annual Review of Immunology, Apr. 26, 2020, 38:541-566.
Sakaguchi et al., "Regulatory T Cells and Immune Tolerance," Cell, May 30, 2008, 133(5):775-787.
Sakaguchi et al., "Regulatory T cells: how do they suppress immune responses?" International Immunology, Sep. 7, 2009, 21(10):1105-1111.
Sakamoto et al., "Phase I clinical trial of autologous NK cell therapy using novel expansion method in patients with advanced digestive cancer," Journal of Translational Medicine, Aug. 25, 2015, 13:277, 13 pages.
Sakamuri et al., "Measurement of respiratory function in isolated cardiac mitochondria using Seahorse XFe24 Analyzer: applications for aging research," Geroscience, Jun. 1, 2018, 40(3):347-356.
Salminen et al., "Emerging role of NF-KB signaling in the induction of senescence- associated secretory phenotype (SASP)," Cellular Signaling, Apr. 2012, 24(4):835-845.
Sandusky et al., "Regulation of 2B4 (CD244)-mediated NK cell activation by ligand-induced receptor modulation," European Journal of Immunology, Dec. 2006, 36(12):3268-76.
Sato et al., "Recombinant soluble murine IL-4 receptor can inhibit or enhance IgE responses in vivo," The Journal of Immunology, Apr. 1, 1993, 150:2717-2723.
Schafer et al., "Cellular senescence mediates fibrotic pulmonary disease," Nat Commun., Feb. 2017, 8:14532, 11 pages.
Schullek et al., "Key ligand interface residues in tissue factor contribute independently to factor VIIa binding," Journal of Biological Chemistry, Jul. 29, 1994, 269(30):19399-403.
Schwoppe et al., "Tissue-factor fusion proteins induce occlusion of tumor vessels," Thrombosis Research, Apr. 1, 2010, 125:S143-S150.
Seo et al., "Positive Feedback Loop between Plasminogen Activator Inhibitor-1 and Transforming Growth Factor-Betal during Renal Fibrosis in Diabetes," American Journal of Nephrology, Sep. 25, 2009, 30:481-490.
Sharkey et al., "Improved Therapeutic Results by Pretargeted Radioimmunotherapy of Non-Hodgkin's Lymphoma with a New Recombinant, Trivalent, Anti-CD20, Bispecific Antibody," Cancer Research, Jul. 1, 2008, 68(13):5282-90.
Sharma et al., "Regulatory T Cells License Macrophage Pro Resolving Functions During Atherosclerosis Regression," Circulation Research, Apr. 27, 2020, 127:335-353.
Smith et al., "Antigen Nature and Complexity Influence Human Antibody Light Chain Usage and Specificity," Vaccine, 2016, 34(25): 2813-2820.
Smith et al., "Development and evaluation of an optimal human single-chain variable fragment-derived BCMA-targeted Car T cell vector," Molecular Therapy, Jun. 6, 2018, 26(6):1447-56.
Soerensen et al., "Safety, PK/PD, and anti-tumor activity of RO6874281, an engineered variant of interleukin-2 (IL-2v) targeted to tumor-associated fibroblasts via binding to fibroblast activation protein (FAP)," Journal of Clinical Oncology, Jun. 1, 2018, 36(No. 15 Suppl.):e15155, 2 pages.
Sondel et al., "Combination Therapy with Interleukin-2 and Antitumor Monoclonal Antibodies," Cancer Journal from Scientific American, Jan. 1, 1997, 3(Suppl. 1):S121-S127.
Sone et al., "Pancreatic beta cell senescence contributes to the pathogenesis of type 2 diabetes in high-fat diet-induced diabetic mice," Diabetologia, 2005, 48(1):58-67.
Song et al., "IL-12/IL-18-preactivated donor NK cells enhance GVL effects and mitigate GvHD after allogeneic hematopoietic stem cell transplantation," European Journal of Immunology, Apr. 2018, 48(4):670-682.
Soriani et al., "ATM-ATR-dependent up-regulation of DNAM-1 and NKG2D ligands on multiple myeloma cells by therapeutic agents results in enhanced NK-cell susceptibility and is associated with a senescent phenotype," Blood, Apr. 9, 2009, 113(15):3503-11.
Sousa-Victor et al., "Geroconversion of aged muscle stem cells under regenerative pressure," Cell Cycle, Oct. 15, 2014, 13(20):3183-3190.
Spiess et al., "Alternative molecular formats and therapeutic applications for bispecific antibodies," Molecular Immunology, Oct. 1, 2015, 67(2):95-106.
Stoklasek et al., "Combined IL-15/IL-15Rα Immunotherapy Maximizes IL-15 Activity In Vivo," The Journal of Immunology, Nov. 1, 2006, 177(9):6072-6080.
Storer et al., "Senescence Is a Developmental Mechanism that Contributes to Embryonic Growth and Patterning," Cell, Nov. 21, 2013, 155(5):1119-1130.
Stryer, Biochemistry Fourth Edition, W. H. Freeman and Company, New York, 1995, pp. 18-23, 8 pages.
Swanson et al., "The NLRP3 inflammasome: molecular activation and regulation to therapeutics," Nature Reviews Immunology, Apr. 29, 2019, 19(8):477-489, 13 pages.
Szalay et al., "Cutting edge: anti-CD1 monoclonal antibody treatment reverses the production patterns of TGF-β2 and Th1 cytokines and ameliorates listeriosis in mice," The Journal of Immunology, Jun. 15, 1999, 162(12):6955-8.
Tahara-Hanaoka et al., "Functional characterization of DNAM-1 (CD226) interaction with its ligands PVR (CD155) and nectin-2 (PRR-2/CD112)," International Immunology, Apr. 1, 2004, 16(4):533-8.
Takahashi et al., "Downregulation of cytoplasmic DNases is implicated in cytoplasmic DNA accumulation and SASP in senescent cells," Nature Communications, Mar. 28, 2018, 9:1249, 12 pages.
Takahashi et al., "Simple and inexpensive technique for measuring oxygen consumption rate in adherent cultured cells," The Journal of Physiological Sciences, Nov. 2017, 67(6):731-737.
Takeda et al., "Phase I study of YS110, a recombinant humanized monoclonal antibody to CD26, in Japanese patients with advanced malignant pleural mesothelioma," Lung Cancer, Nov. 2019, 137:64-70.
Tam et al., "Methods and strategies of peptide ligation," Peptide Science: Original Research on Biomolecules, 2001, 60(3):194-205.
Tanaka et al., "Cloning and functional expression of the T cell activation antigen CD26," Journal of Immunology, Jul. 15, 1992, 149(2):481-486.
Tang et al., "The Foxp3+ regulatory T cell: a jack of all trades, master of regulation," Nature Immunology, Feb. 19, 2008, 9(3):239-244.
Teissier et al., "The receptor for advanced glycation end-products (RAGE) is an important pattern recognition receptor (PRR) for inflammaging," Biogerontology, Apr. 9, 2019, 20(3):279-301, 23 pages.
Teng et al., "Structural assessment of the effects of amino acid substitutions on protein stability and protein protein interaction," International journal of computational biology and drug design, Feb. 7, 2011, 3(4):334-349.
Theil et al., "Adoptive transfer of allogeneic regulatory T cells into patients with chronic graft-versus-host disease," Cytotherapy, Apr. 2015, 17(4):473-486, 14 pages.
ThermoFisher.com [Online], "Covalent Immobilization of Affinity Ligands," 2018, retrieved on Apr. 18, 2023, retrieved from <URLhttps://www.thermofisher.com/us/en/home/life-science/protein-biology/protein-biology-learning-center/protein-biology-resource-library/pierce-protein-methods/covalent-immobilization-affinity-ligands.html>, 13 pages.
Thonhoff et al., "Expanded autologous regulatory T-lymphocyte infusions in ALS," Neurology Neuroimmunology Neuroinflammation, May 18, 2018, 5(4):e465, 8 pages.
Tobin et al., "NK cells in childhood obesity are activated, metabolically stressed, and functionally deficient," JCI Insight, Dec. 21, 2017, 2(24):e94939, 9 pages.
Tomala et al., "In Vivo Expansion of Activated Naive CD8+ T Cells and NK Cells Driven by Complexes of IL-2 and Anti-IL-2 Mono-

(56) References Cited

OTHER PUBLICATIONS clonal Antibody As Novel Approach of Cancer Immunotherapy," The Journal of Immunology, Oct. 15, 2009, 183:4904-4912.
Tominaga et al., "TGF-β Signaling in Cellular Senescence and Aging-Related Pathology," International Journal of Molecular Sciences, Oct. 10, 2019, 20(20):5002, 18 pages.
Trevani et al., "Extracellular acidification induces human neutrophil activation," The Journal of Immunology, Apr. 15, 1999, 162(8):4849-4857.
Tse et al., "ABT-263: A Potent and Orally Bioavailable Bcl-2 Family Inhibitor," Cancer Research, May 2008, 68(9):3421-3428.
Uppendahl et al., "Natural killer cell-based immunotherapy in gynecologic malignancy: a review," Frontiers in immunology, Jan. 5, 2018, 8(1825): 1-15.
Urh et al., "Affinity chromatography: general methods," Methods in enzymology, Jan. 1, 2009, 463: 23 pages.
Uryga et al., "Ageing induced vascular smooth muscle cell senescence in atherosclerosis," Journal of Physiology, Apr. 15, 2016, 594(8):2115-2124.
Vaishampayan et al., "A phase I trial of ALKS 4230, an engineered cytokine activator of NK and effector T cells, in patients with advanced solid tumors," Journal of Clinical Oncology, 2017, 35(15 Suppl.):TPS3111, 4 pages (Abstract Only).
Van Audenhove et al., "Nanobodies as versatile tools to understand, diagnose, visualize and treat cancer," EBioMedicine, Jun. 1, 2016, 8:40-8.
Van den Bergh et al., "IL-15 receptor alpha as the magic wand to boost the success of IL-15 antitumor therapies: The upswing of IL-15 transpresentation," Pharmacology and Therapeutics, 2017, 170:73-79.
Van Deursen, "The role of senescent cells in ageing," Nature, May 21, 2014, 509(7501):439-446.
Vankadari et al., "Emerging COVID-19 coronavirus: glycan shield and structure prediction of spike glycoprotein and its interaction with human CD26," Emerging Microbes and Infection, Mar. 17, 2020, 9(1):601-604.
Veluchamy et al., "The rise of allogeneic natural killer cells as a platform for cancer immunotherapy: recent innovations and future developments," Frontiers in immunology, May 31, 2017, 8(631): 1-20.
Vidarsson et al., "IgG subclasses and allotypes: from structure to effector functions," Frontiers in immunology, Oct. 20, 2014, 5:520, 17 Pages.
Vincke et al., "Introduction to heavy chain antibodies and derived Nanobodies," Single Domain Antibodies, Humana Press, Totowa, NJ, 2012, pp. 15-26.
Voelker et al., "Anti-TGF-β1 Antibody Therapy in Patients with Diabetic Nephropathy," J Am Soc Nephrol., 2017, 28:953-962.
Voet et al., Biochemistry, John Wiley & Sons, Inc., 1990, pp. 126-128 and 228-234, 12 pages.
Von Kobbe, "Cellular senescence: a view throughout organismal life," Cellular and Molecular Life Sciences, Jul. 20, 2018, 75:3553-3567, 15 pages.
Waaijer et al., "Do senescence markers correlate in vitro and in situ within individual human donors?," Aging Feb. 2018, 10(2):278-289.
Wallace et al., "B lymphocytes confer immune tolerance via cell surface GARP-TGF-β complex," JCI Insight., 2018, 3(7):e99863, 19 pages.
Walsh et al., "Inflammasomes in the CNS," Nature Reviews Neuroscience, Jan. 8, 2014, 15(2):84-97, 14 pages.
Wang et al., A New Recombinant Single Chain Trispecific Antibody Recruits T Lymphocytes to Kill CEA (Carcinoma Embryonic Antigen) Positive Tumor Cells In Vitro Efficiently, Journal of Biochemisty, 2004, 135(4):555-565.
Wang et al., "Biomarkers of Cellular Senescence and Skin Aging," Frontiers in Genetics, Aug. 23, 2018, 9:247, 14 pages.
Wang et al., "Loss of lamin B1 is a biomarker to quantify cellular senescence in photoaged skin," Scientific Reports, Nov. 15, 2017, 7(1):15678, 8 pages.
Wang et al., "Recombinant human CD137L for cancer immunotherapy: effects of different fusions and linkers on its activity," Cancer Immunol Immunother., 2012, 61(4):489-495.
Washburn et al., "A potential role for shed soluble major histocompatibility class I molecules as modulators of neurite outgrowth," PLoS One, Mar. 31, 2011, 6(3):e18439.
Weber et al., "Specific low-affinity recognition of major histocompatibility complex plus peptide by soluble T-cell receptor," Nature, Apr. 1992, 356(6372):793.
Weihermann et al., "Elastin structure and its involvement in skin photoageing," International Journal of Cosmetic Science, Jun. 2017, 39(3):241-247.
Weihofen et al., "Crystal Structure of CD26/Dipeptidyl-peptidase IV in Complex with Adenosine Deaminase Reveals a Highly Amphiphilic Interface," Journal of Biological Chemistry, Oct. 2004, 279(41):43330-43335.
Weiner et al., "Antibody-based immunotherapy of cancer," Cell, Mar. 16, 2012, 148(6):1081-4.
Weiss et al., "Formyl-Peptide Receptors in Infection, Inflammation, and Cancer," Trends in Immunology, Oct. 2018, 39(10):815-829, 15 pages.
Wesolowski et al., "Single domain antibodies: promising experimental and therapeutic tools in infection and immunity," Medical Microbiology and Immunology. Aug. 1, 2009, 198(3):157-74.
Wiemann et al., "Hepatocyte telomere shortening and senescence are general markers of human liver cirrhosis, " The FASEB Journal, Jul. 2002, 16(9):935-942.
Wilchek et al., "Essentials of biorecognition: The (strept) avidin-biotin system as a model for protein-protein and protein-ligand interaction," Immunology letters, Feb. 28, 2006, 103(1): Abstract 2 pages.
Wiley et al., "Mitochondrial Dysfunction Induces Senescence with a Distinct Secretory Phenotype," Cell Metabolism, Feb. 9, 2016, 23(2):303-314.
Witkowsa et al., "Soluble intercellular adhesion molecule-1 (sICAM-1): an overview," Eur Cytokine Netw. 2004, 15(2):91-98.
Wong et al., "Interleukin-15: Interleukin-15 receptor a scaffold for creation of multivalent targeted immune molecules," Protein Engineering, Design & Selection, Apr. 1, 2011, 24(4):373-383.
Xiong et al., "Maternal uterine NK cell-activating receptor KIR2DS1 enhances placentation," The Journal of Clinical Investigation, Oct. 1, 2013, 123(10):4264-72.
Xu et al., "Celecoxib attenuates cachectic events in mice by modulating the expression of vascular endothelial growth factor," Mol Med Rep., Jan. 2015, 11(1):289-294.
Xu et al., "JAK inhibition alleviates the cellular senescence-associated secretory phenotype and frailty in old age," Proceedings of the National Academy of Sciences U.S.A., Nov. 17, 2015, 112(46):E6301-6310, 10 pages.
Xu et al., "Senolytics improve physical function and increase lifespan in old age," Nature Medicine, Aug. 2018, 24(8):1246, 15 pages.
Xu et al., "Transplanted senescent cells induce an osteoarthritis-like condition in mice," The Journals of Gerontology: Series A, Jun. 1, 2017, 72(6):780-5.
Yamamoto et al., "Measurement of glucose uptake in cultured cells," Curr Protoc Pharmacol, Dec. 2011, Chapter 12:12.14.1-12.14.22.
Yamazaki et al., "Vascular Cell Senescence Contributes to Blood-Brain Barrier Breakdown," Stroke, Feb. 16, 2016, 47(4):1068-1077, 15 pages.
Yan et al., "Obesity- and aging-induced excess of central transforming growth factor-β potentiates diabetic development via an RNA stress response," Nature Medicine, Aug. 3, 2014, 20:1001-1008, 9 pages.
Yanai et al., "Cellular senescence-like features of lung fibroblasts derived from idiopathic pulmonary fibrosis patients," Aging (Albany NY), Sep. 2015, 7(9):664-672.
Yigit et al., "A combination of an anti-SLAMF6 antibody and ibrutinib efficiently abrogates expansion of chronic lymphocytic leukemia cells," Oncotarget, May 3, 2016, 7(18):26346.

(56) References Cited

OTHER PUBLICATIONS

Yousefzadeh et al., "An aged immune system drives senescence and ageing of solid organs, " Nature, May 12, 2021, 594:100-105, 34 pages.
Yu et al., "Targeting the Senescence-Overriding Cooperative Activity of Structurally Unrelated H3K9 Demethylases in Melanoma," Cancer Cell, Feb. 12, 2018, 33(2):322-336, 23 pages.
Yu et al., "The dipeptidyl peptidase IV family in cancer and cell biology," FEBS Journal, Feb. 5, 2010, 277(5):1126-1144.
Yun et al., "Recurrent turnover of senescent cells during regeneration of a complex structure," Elife, May 5, 2015, 4:e05505, 16 pages.
Yung et al., "A selective transforming growth factor-β ligand trap attenuates pulmonary hypertension," American Journal of Respiratory and Critical Care Medicine, Nov. 1, 2016, 194(9):1140-51.
Zhang et al., "AAED1 modulates proliferation and glycolysis in gastric cancer," Oncology Reports, Aug. 1, 2018, 40(2):1156-1164.
Zhang et al., "Depletion of NK cells improves cognitive function in the Alzheimer disease mouse model," The Journal of Immunology, Jul. 15, 2020, 205(2): 10pages.
Zhang et al., "The bone anabolic effects of irisin are through preferential stimulation of aerobic glycolysis," Bone, Sep. 1, 2018, 114:150-160.
Zhao et al., "Histone Deacetylase-3 Modification of MicroRNA-31 Promotes Cell Proliferation and Aerobic Glycolysis in Breast Cancer and Is Predictive of Poor Prognosis," Journal of breast cancer, Jun. 1, 2018, 21(2):112-123.
Zheng et al., "Acquisition of Suppressive Function by Activated Human CD4+CD25-T Cells Is Associated with the Expression of CTLA-4 Not FoxP3," The Journal of Immunology, Aug. 1, 2008, 181(3):1683-1691.
Zhong et al., "A Potential Role for Dendritic Cell/Macrophage-Expressing DPP4 in Obesity-Induced Visceral Inflammation," Diabetes, Jan. 2013, 62(1):149-157.
Zhou et al., "A novel chimeric antigen receptor redirecting T-cell specificity towards CD26cancer cells," Leukemia, Apr. 2020, 35(1):119-129, 11 pages.
Zhou, "Emerging mechanisms and applications of low-dose IL-2 therapy in autoimmunity," Cytokine & Growth Factor Reviews, Jun. 30, 2022, 67: 80-88.
Zhu et al., "New agents that target senescent cells: the flavone, fisetin, and the BCL-XL inhibitors, A1331852 and A1155463," Aging (Albany NY), Mar. 2017, 9(3):955-963.
Zhu et al., "Novel Human Interleukin-15 Agonists," The Journal of Immunology, Sep. 15, 2009, 183(6):3598-3607.
Zou et al., "2-NBDG as a fluorescent indicator for direct glucose uptake measurement," Journal of biochemical and biophysical methods, Sep. 30, 2005, 64(3):207-215.
Zwaagstra et al., "Engineering and therapeutic application of single-chain bivalent TGF-β family traps," Molecular Cancer Therapeutics, Jul. 1, 2012, 11(7):1477-87.
Chen et al., "A novel idea for establishing Parkinson's disease mouse model by intranasal administration of paraquat," Neurological Research, 2021, 43(4):267-277.
Igarashi et al., "VEGF-C and TGF-β reciprocally regulate mesenchymal stem cell commitment to differentiation into lymphatic endothelial or osteoblastic phenotypes," International Journal of Molecular Medicine, Apr. 1, 2016, 37(4):1005-1013.
Infante-Duarte et al., "New developments in understanding and treating neuroinflammation," Journal of Molecular Medicine, Sep. 2008, 86:975-985.
International Search Report and Written Opinion in International Appln. No. PCT/US2023/065745, mailed on Jun. 26, 2023, 14 pages.
Janeway et al., "The interaction of the antibody molecule with specific antigen," In Immunobiology: The Immune System in Health and Disease, 5th edition, 5 pages, 2001.
Matsuura et al., "Pole test is a useful method for evaluating the mouse movement disorder caused by striatal dopamine depletion," Journal of Neuroscience Methods, 73(1):45-48, 1997.
Reddy et al., "Linkers in the structural biology of protein-protein interactions," Protein Science, 2013, 22(2):153-167.
Ross et al., "Signaling and function of interleukin-2 in T lymphocytes," Annual Review of Immunology, 2018, 36:411-433.
Van Bockstaele et al., "The development of nanobodies for therapeutic applications," Current Opinion in Investigational Drugs, 2009, 10(11):1212-1224.
Shen et al., "Engineering peptide linkers for scFv immunosensors," Anal Chem., Mar. 2008, 80(6):1910-1917.
Chen et al., "A novel idea for establishing Parkinson's disease mouse model by intranasal administration of paraquat" Neurological Research, 43(4):267-277, 2021.
Infante-Duarte et al., "New developments in understanding and treating neuroinflammation" Journal of Molecular Medicine, 86:975-985, Sep. 2008.
Reddy et al., "Linkers in the structural biology of protein-protein interactions" Protein science, 22(2):153-167, 2013.
Ross et al., "Signaling and function of interleukin-2 in T lymphocytes" Annual review of immunology, 36:411-433, 2018.
Van Bockstaele et al., "The development of nanobodies for therapeutic applications" Current opinion in investigational drugs, 10(11):1212-1224, 2009.
Gao et al., "Natural killer and natural killer T cells in liver fibrosis," Biochimica et Biophysica Acta, 2013, vol. 1832, pp. 1061-1069.

* cited by examiner

* Statistically significant from High Fat Diet untreated Group

* Statistically significant from High fat diet untreated Group

CD + PBS | WD + PBS | WD + TGFRt15-TGFRs | WD + 2t2 | WD + 21t15-TGFRs

* Statistically significant from Control Normal Diet Group

TGFRt15-16s21

SEQUENCE LISTING

```
Sequence total quantity: 334
SEQ ID NO: 1           moltype = AA  length = 251
FEATURE                Location/Qualifiers
REGION                 1..251
                       note = source = /note="CD25"
```

```
source                 1..251
                       mol_type = protein
                       organism = Homo sapiens
SEQUENCE: 1
ELCDDDPPEI PHATFKAMAY KEGTMLNCEC KRGFRRIKSG SLYMLCTGNS SHSSWDNQCQ  60
CTSSATRNTT KQVTPQPEEQ KERKTTEMQS PMQPVDQASL PGHCREPPPW ENEATERIYH  120
FVVGQMVYYQ CVQGYRALHR GPAESVCKMT HGKTRWTQPQ LICTGEMETS QFPGEEKPQA  180
SPEGRPESET SCLVTTTDFQ IQTEMAATME TSIFTTEYQV AVAGCVFLLI SVLLLSGLTW  240
QRRQRKSRRT I                                                       251

SEQ ID NO: 2           moltype = DNA  length = 753
FEATURE                Location/Qualifiers
source                 1..753
                       mol_type = genomic DNA
                       note = source=CD25
                       organism = Homo sapiens
SEQUENCE: 2
gagctctgtg acgatgaccc gccagagatc ccacacgcca cattcaaagc catggcctac  60
aaggaaggaa ccatgttgaa ctgtgaatgc aagagaggtt tccgcagaat aaaaagcggg  120
tcactctata tgctctgtac aggaaactct agccactcgt cctgggacaa ccaatgtcaa  180
tgcacaagct ctgccactcg gaacacaacg aaacaagtga cacctcaacc tgaagaacag  240
aaagaaagga aaaccacaga aatgcaaagt ccaatgcagc cagtggacca agcgagcctt  300
ccaggtcact gcagggaacc tccaccatgg gaaaatgaag ccacagagag aatttatcat  360
ttcgtggtgg ggcagatggt ttattatcag tgcgtccagg gatacagggc tctacacaga  420
ggtcctgctg agagcgtctg caaaatgacc cacgggaaga caaggtggac ccagccccag  480
ctcatatgca caggtgaaat ggagaccagt cagtttccag gtgaagagaa gcctcaggca  540
agccccgaag gccgtcctga gagtgagact tcctgcctcg tcacaacaac agattttcaa  600
atacagacag aaatggctgc aaccatggag acgtccatat ttacaacaga gtaccaggta  660
gcagtggccg gctgtgtttt cctgctgatc agcgtcctcc tcctgagtgg gctcacctgg  720
cagcggagac agaggaagag tagaagaaca atc                               753

SEQ ID NO: 3           moltype = AA  length = 199
FEATURE                Location/Qualifiers
REGION                 1..199
                       note = source = /note="CD69"
source                 1..199
                       mol_type = protein
                       organism = Homo sapiens
SEQUENCE: 3
MSSENCFVAE NSSLHPESGQ ENDATSPHFS TRHEGSFQVP VLCAVMNVVF ITILIIALIA  60
LSVGQYNCPG QYTFSMPSDS HVSSCSEDWV GYQRKCYFIS TVKRSWTSAQ NACSEHGATL  120
AVIDSEKDMN FLKRYAGREE HWVGLKKEPG HPWKWSNGKE FNNWFNVTGS DKCVFLKNTE  180
VSSMECEKNL YWICNKPYK                                               199

SEQ ID NO: 4           moltype = DNA  length = 600
FEATURE                Location/Qualifiers
source                 1..600
                       mol_type = genomic DNA
                       note = source = CD69
                       organism = Homo sapiens
SEQUENCE: 4
atgagctctg aaaattgttt cgtagcagag aacagctctt tgcatccgga gagtggacaa  60
gaaaatgatg ccaccagtcc ccatttctca acacgtcatg aagggtcctt ccaagttcct  120
gtcctgtgtg ctgtaatgaa tgtggtcttc atcaccattt taatcatagc tctcattgcc  180
ttatcagtgg gccaatacaa ttgtccaggc caatacacat tctcaatgcc atcagacagc  240
catgtttctt catgctctga ggactgggtt ggctaccaga ggaaatgcta ctttatttct  300
actgtgaaga ggagctggac ttcagcccaa aatgcttgtt ctgaacatgg tgctactctt  360
gctgtcattg attctgaaaa ggacatgaac tttctaaaac gatacgcagg tagagaggaa  420
cactgggttg gactgaaaaa ggaacctggt cacccatgga agtggtcaaa tggcaaagaa  480
tttaacaact ggttcaacgt tacagggtct gacaagtgtg tttttctgaa aaacacagag  540
gtcagcagca tggaatgtga gaagaattta tactggatat gtaacaaacc ttacaaataa  600

SEQ ID NO: 5           moltype = AA  length = 77
FEATURE                Location/Qualifiers
REGION                 1..77
                       note = source = /note="CD59"
source                 1..77
                       mol_type = protein
                       organism = Homo sapiens
SEQUENCE: 5
LQCYNCPNPT ADCKTAVNCS SDFDACLITK AGLQVYNKCW KFEHCNFNDV TTRLRENELT  60
YYCCKKDLCN FNEQLEN                                                 77

SEQ ID NO: 6           moltype = DNA  length = 387
FEATURE                Location/Qualifiers
source                 1..387
                       mol_type = genomic DNA
                       note = source = CD59
                       organism = Homo sapiens
```

```
SEQUENCE: 6
atgggaatcc aaggagggtc tgtcctgttc gggctgctgc tcgtcctggc tgtcttctgc  60
cattcaggtc atagcctgca gtgctacaac tgtcctaacc caactgctga ctgcaaaaca  120
gccgtcaatt gttcatctga ttttgatgcg tgtctcatta ccaaagctgg gttacaagtg  180
tataacaagt gttggaagtt tgagcattgc aatttcaacg acgtcacaac ccgcttgagg  240
gaaaatgagc taacgtacta ctgctgcaag aaggacctgt gtaactttaa cgaacagctt  300
gaaaatggtg ggacatcctt atcagagaaa acagttcttc tgctggtgac tccatttctg  360
gcagcagcct ggagccttca tccctaa                                      387

SEQ ID NO: 7           moltype = AA  length = 311
FEATURE                Location/Qualifiers
REGION                 1..311
                       note = source = /note="CD352"
source                 1..311
                       mol_type = protein
                       organism = Homo sapiens
SEQUENCE: 7
QSSLTPLMVN GILGESVTLP LEFPAGEKVN FITWLFNETS LAFIVPHETK SPEIHVTNPK  60
QGKRLNFTQS YSLQLSNLKM EDTGSYRAQI STKTSAKLSS YTLRILRQLR NIQVTNHSQL  120
FQNMTCELHL TCSVEDADDN VSFRWEALGN TLSSQPNLTV SWDPRISSEQ DYTCIAENAV  180
SNLSFSVSAQ KLCEDVKIQY TDTKMILFMV SGICIVFGFI ILLLLVLRKR RDSLSLSTQR  240
TQGPAESARN LEYVSVSPTN NTVYASVTHS NRETEIWTPR ENDTITIYST INHSKESKPT  300
FSRATALDNV V                                                       311

SEQ ID NO: 8           moltype = DNA  length = 996
FEATURE                Location/Qualifiers
source                 1..996
                       mol_type = genomic DNA
                       note = source = CD59
                       organism = Homo sapiens
SEQUENCE: 8
atgttgtggc tgttccaatc gctcctgttt gtcttctgct ttggcccagg gaatgtagtt  60
tcacaaagca gcttaacccc attgatggtg aacgggattc tgggggagtc agtaactctt  120
cccctggagt ttcctgcagg agagaaggtc aacttcatca cttggctttt caatgaaaca  180
tctcttgcct tcatagtacc ccatgaaacc aaaagtccag aaatccacgt gactaatccg  240
aaacagggaa agcgactgaa cttcacccag tcctactccc tgcaactcag caacctgaag  300
atggaagaca caggctctta cagagcccag atatccacaa agacctctgc aaagctgtcc  360
agttacactc tgaggatatt aagacaactg aggaacatac aagttaccaa tcacagtcag  420
ctatttcaga atatgacctg tgagctccat ctgacttgct ctgtggagga tgcagatgac  480
aatgtctcat tcagatggga ggccttggga aacacacttt caagtcagcc aaacctcact  540
gtctcctggg accccaggat ttccagtgaa caggactaca cctgcatagc agagaatgct  600
gtcagtaatt tatccttctc tgtctctgcc cagaagcttt gcgaagatgt taaaattcaa  660
tatacagata ccaaaatgat tctgtttatg gtttctggga tatgcatagt cttcggtttc  720
atcatactgc tgttacttgt tttgaggaaa agaagagatt ccctatcttt gtctactcag  780
cgaacacagg gccccgagtc cgcaaggaac ctagagtatg tttcagtgtc tccaacgaac  840
aacactgtgt atgcttcagt cactcattca aacagggaaa cagaaatctg gacacctaga  900
gaaaatgata ctatcacaat ttactccaca attaatcatt ccaaagagag taaacccact  960
ttttccaggg caactgccct tgacaatgtc gtgtaa                            996

SEQ ID NO: 9           moltype = AA  length = 231
FEATURE                Location/Qualifiers
REGION                 1..231
                       note = source = /note="NKp80"
source                 1..231
                       mol_type = protein
                       organism = Homo sapiens
SEQUENCE: 9
MQDEERYMTL NVQSKKRSSA QTSQLTFKDY SVTLHWYKIL LGISGTVNGI LTLTLISLIL  60
LVSQGVLLKC QKGSCSNATQ YEDTGDLKVN NGTRRNISNK DLCASRSADQ TVLCQSEWLK  120
YQGKCYWFSN EMKSWSDSYV YCLERKSHLL IIHDQLEMAF IQKNLRQLNY VWIGLNFTSL  180
KMTWTWVDGS PIDSKIFFIK GPAKENSCAA IKESKIFSET CSSVFKWICQ Y           231

SEQ ID NO: 10          moltype = DNA  length = 546
FEATURE                Location/Qualifiers
source                 1..546
                       mol_type = genomic DNA
                       note = source = Npk80
                       organism = Homo sapiens
SEQUENCE: 10
atgcaagatg aagaaagata catgacattg aatgtacagt caaagaaaag gagttctgcc  60
caaacatctc aacttacatt taaagattat tcagtgacgt tgcactggta taaaatctta  120
ctgggaatat ctggaaccgt gaatggtatt ctcactttga ctttgatctc cttgatcctg  180
ttggtactat gccaatcaga atggctcaaa taccaaggga agtgttattg gttctctaat  240
gagatgaaaa gctggagtga cagttatgtg tattgtttgg aaagaaaatc tcatctacta  300
atcatacatg accaacttga aatggctttt atacagaaaa acctaagaca attaaactac  360
gtatggattg ggcttaactt tacctccttg aaaatgacat ggacttgggt ggatggttct  420
ccaatagatt caaagatatt cttcataaag ggaccagcta aagaaaacag ctgtgctgcc  480
attaaggaaa gcaaaatttt ctctgaaacc tgcagcagtg ttttcaaatg gatttgtcag  540
tattag                                                             546
```

```
SEQ ID NO: 11          moltype = AA  length = 318
FEATURE                Location/Qualifiers
REGION                 1..318
                       note = source = /note="DNAM-1"
source                 1..318
                       mol_type = protein
                       organism = Homo sapiens
SEQUENCE: 11
EEVLWHTSVP FAENMSLECV YPSMGILTQV EWFKIGTQQD SIAIFSPTHG MVIRKPYAER  60
VYFLNSTMAS NNMTLFFRNA SEDDVGYYSC SLYTYPQGTW QKVIQVVQSD SFEAAVPSNS  120
HIVSEPGKNV TLTCQPQMTW PVQAVRWEKI QPRQIDLLTY CNLVHGRNFT SKFPRQIVSN  180
CSHGRWSVIV IPDVTVSDSG LYRCYLQASA GENETFVMRL TVAEGKTDNQ YTLFVAGGTV  240
LLLLFVISIT TIIVIFLNRR RRRERRDLFT ESWDTQKAPN NYRSPISTSQ PTNQSMDDTR  300
EDIYVNYPTF SRRPKTRV                                               318

SEQ ID NO: 12          moltype = DNA  length = 1011
FEATURE                Location/Qualifiers
source                 1..1011
                       mol_type = genomic DNA
                       note = source = DNAM-1
                       organism = Homo sapiens
SEQUENCE: 12
atggattatc ctactttact tttggctctt cttcatgtat acagagctct atgtgaagag  60
gtgctttggc atacatcagt tccctttgcc gagaacatgt ctctagaatg tgtgtatcca  120
tcaatgggca tcttaacaca ggtggagtgg ttcaagatcg ggacccagca ggattccata  180
gccattttca gccctactca tggcatggtc ataaggaagc cctatgctga gagggtttac  240
tttttgaatt caacgatggc ttccaataac atgactcttt tctttcggaa tgcctctgaa  300
gatgatgttg gctactattc ctgctctctt tacacttacc cacagggaac ttggcagaag  360
gtgatacagg tggttcagtc agatagtttt gaggcagctg tgccatcaaa tagccacatt  420
gtttcggaac ctggaaagaa tgtcacactc acttgtcagc ctcagatgac gtggcctgtg  480
caggcagtga ggtgggaaaa gatccagccc cgtcagatcg acctcttaac ttactgcaac  540
ttggtccatg gcagaaattt cacctccaag ttcccaagac aaatagtgag caactgcagc  600
cacggaaggt ggagcgtcat cgtcatcccc gatgtcacag tctcagactc ggggctttac  660
cgctgctact tgcaggccag cgcaggagaa aacgaaacct tcgtgatgag attgactgta  720
gccgagggta aaaccgataa ccaatatacc ctctttgtgg ctggagggac agttttattg  780
ttgttgtttg ttatctcaat taccaccatc attgtcattt tccttaacag aaggagaagg  840
agagagagaa gagatctatt tacagagtcc tgggatacac agaaggcacc caataactat  900
agaagtccca tctctaccag tcaacctacc aatcaatcca tggatgatac aagagaggat  960
atttatgtca actatccaac cttctctcgc agaccaaaga ctagagttta a          1011

SEQ ID NO: 13          moltype = AA  length = 347
FEATURE                Location/Qualifiers
REGION                 1..347
                       note = source = /note="HB4"
source                 1..347
                       mol_type = protein
                       organism = Homo sapiens
SEQUENCE: 13
GKGCQGSADH VVSISGVPLQ LQPNSIQTKV DSIAWKKLLP SQNGFHHILK WENGSLPSNT  60
SNDRFSFIVK NLSLLIKAAQ QQDSGLYCLE VTSISGKVQT ATFQVFVFDK VEKPRLQGQG  120
KILDRGRCQV ALSCLVSRDG NVSYAWYRGS KLIQTAGNLT YLDEEVDING THTYTCNVSN  180
PVSWESHTLN LTQDCQNAHQ EFRFWPFLVI IVILSALFLG TLACFCVWRR KRKEKQSETS  240
PKEFLTIYED VKDLKTRRNH EQEQTFPGGG STIYSMIQSQ SSAPTSQEPA YTLYSLIQPS  300
RKSGSRKRNH SPSFNSTIYE VIGKSQPKAQ NPARLSRKEL ENFDVYS                347

SEQ ID NO: 14          moltype = DNA  length = 1098
FEATURE                Location/Qualifiers
source                 1..1098
                       mol_type = genomic DNA
                       note = source = HB4
                       organism = Homo sapiens
SEQUENCE: 14
atgctggggc aagtggtcac cctcatactc ctcctgctcc tcaaggtgta tcagggcaaa  60
ggatgccagg gatcagctga ccatgtggtt agcatctcgg gagtgcctct tcagttacaa  120
ccaaacagca tacagacgaa ggttgacagc attgcatgga agaagttgct gccctcacaa  180
aatggatttc atcacatatt gaagtgggag aatggctctt tgccttccaa tacttccaat  240
gatagattca gttttatagt caagaacttg agtcttctca tcaaggcagc tcagcagcag  300
gacagtggcc tctactgcct ggaggtcacc agtatatctg gaaaagttca gacagccacg  360
ttccaggttt ttgtatttga taaagttgag aaaccccgcc tacaggggca ggggaagatc  420
ctggacagag ggagatgcca agtggctctg tcttgcttgg tctccaggga tggcaatgtg  480
tcctatgctt ggtacagagg gagcaagctg atccagacag cagggaacct cacctacctg  540
gacgaggagg ttgacattaa tggcactcac acatatacct gcaatgtcag caatcctgtt  600
agctgggaaa gccacaccct gaatctcact caggactgtc agaatgccca tcaggaattc  660
agattttggc cgtttttggt gatcatcgtg attctaagcg cactgttcct tggcaccctt  720
gcctgcttct gtgtgtggag gagaaagagg aaggagaagc agtcagagac cagtcccaag  780
gaatttttga caatttacga agatgtcaag gatctgaaaa ccaggagaaa tcacgagcag  840
gagcagactt ttcctggagg ggggagcacc atctactcta tgatccagtc ccagtcttct  900
gctcccacgt cacaagaacc tgcatataca ttatattcat taattcagcc ttccaggaag  960
```

```
tctggatcca ggaagaggaa ccacagccct tccttcaata gcactatcta tgaagtgatt  1020
ggaaagagtc aacctaaagc ccagaaccct gctcgattga gccgcaaaga gctggagaac  1080
tttgatgttt attcctag                                                1098

SEQ ID NO: 15          moltype = AA  length = 183
FEATURE                Location/Qualifiers
REGION                 1..183
                       note = source = /note="NK-p30"
source                 1..183
                       mol_type = protein
                       organism = Homo sapiens
SEQUENCE: 15
LWVSQPPEIR TLEGSSAFLP CSFNASQGRL AIGSVTWFRD EVVPGKEVRN GTPEFRGRLA  60
PLASSRFLHD HQAELHIRDV RGHDASIYVC RVEVLGLGVG TGNGTRLVVE KEHPQLGAGT  120
VLLLRAGFYA VSFLSVAVGS TVYYQGKCLT WKGPRRQLPA VVPAPLPPPC GSSAHLLPPV  180
PGG                                                                183

SEQ ID NO: 16          moltype = DNA  length = 573
FEATURE                Location/Qualifiers
source                 1..573
                       mol_type = genomic DNA
                       note = source = NKp30
                       organism = Homo sapiens
SEQUENCE: 16
atggcctgga tgctgttgct catcttgatc atggtccatc caggatcctg tgctctctgg  60
gtgtcccagc cccctgagat tcgtaccctg gaaggatcct ctgccttcct gccctgctcc  120
ttcaatgcca gccaagggag actggccatt ggctccgtca cgtggttccg agatgaggtg  180
gttccaggga aggaggtgag gaatggaacc ccagagttca ggggccgcct ggccccactt  240
gcttcttccc gtttcctcca tgaccaccag gctgagctgc acatccggga cgtgcgaggc  300
catgacgcca gcatctacgt gtgcagagtg gaggtgctgg gccttggtgt cgggacaggg  360
aatgggactc ggctggtggt ggagaaagaa catcctcagc taggggctgg tacagtcctc  420
ctccttcggg ctggattcta tgctgtcagc tttctctctg tggccgtggg cagcaccgtc  480
tattaccagg gcaaatgcca ctgtcacatg ggaacacact gccactcctc agatgggccc  540
cgaggagtga ttccagagcc cagatgtccc tag                              573

SEQ ID NO: 17          moltype = AA  length = 255
FEATURE                Location/Qualifiers
REGION                 1..255
                       note = source = /note="NKp44"
source                 1..255
                       mol_type = protein
                       organism = Homo sapiens
SEQUENCE: 17
QSKAQVLQSV AGQTLTVRCQ YPPTGSLYEK KGWCKEASAL VCIRLVTSSK PRTMAWTSRF  60
TIWDDPDAGF FTVTMTDLRE EDSGHYWCRI YRPSDNSVSK SVRFYLVVSP ASASTQTSWT  120
PRDLVSSQTQ TQSCVPPTAG ARQAPESPST IPVPSQPQNS TLRPGPAAPI ALVPVFCGLL  180
VAKSLVLSAL LVWWGDIWWK TMMELRSLDT QKATCHLQQV TDLPWTSVSS PVEREILYHT  240
VARTKISDDD DEHTL                                                   255

SEQ ID NO: 18          moltype = DNA  length = 777
FEATURE                Location/Qualifiers
source                 1..777
                       mol_type = genomic DNA
                       note = source = NKp44
                       organism = Homo sapiens
SEQUENCE: 18
atggcctggc gagccctaca cccactgcta ctgctgctgc tgctgttccc aggctctcag  60
gcacaatcca aggctcaggt acttcaaagt gtggcagggc agacgctaac cgtgagatgc  120
cagtaccccg ccacgggcag tctctacgag aagaaaggct ggtgtaagga ggcttcagca  180
cttgtgtgca tcaggttagt caccagctcc aagcccagga cgatggcttg gacctctcga  240
ttcacaatct gggacgaccc tgatgctggc ttcttcactg tcaccatgac tgatctgaga  300
gaggaagact caggacatta ctggtgtaga atctaccgcc cttctgacaa ctctgtctct  360
aagtccgtca gattctatct ggtggtatct ccagcctctg cctccacaca gacctcctgg  420
actccccgcg acctggtctc ttcacagacc cagacccaga gctgtgtgcc tcccactgca  480
ggagccagac aagcccctga gtctccatct accatccctg tcccttcaca gccacagaac  540
tccacgctcc gccctggccc tgcagccccc attgccctgg tgcctgtgtt ctgtggactc  600
ctcgtagcca agagcctggt gctgtcagcc ctgctcgtct ggtgggtttt aaggaatcgg  660
cacatgcagc atcaagggag gtctctgctg cacccagctc agcccaggcc ccaggcccat  720
agacacttcc cactgagcca cagggcacca ggggggacat atggtggaaa accatga     777

SEQ ID NO: 19          moltype = AA  length = 283
FEATURE                Location/Qualifiers
REGION                 1..283
                       note = source = /note="NKp46"
source                 1..283
                       mol_type = protein
                       organism = Homo sapiens
SEQUENCE: 19
QQQTLPKPFI WAEPHFMVPK EKQVTICCQG NYGAVEYQLH FEGSLFAVDR PKPPERINKV  60
```

```
QFYIPDMNSR MAGQYSCIYR VGELWSEPSN LLDLVVTEMY DTPTLSVHPG PEVISGEKVT  120
FYCRLDTATS MFLLLKEGRS SHVQRGYGKV QAEFPLGPVT TAHRGTYRCF GSYNNHAWSF  180
PSEPVKLLVT GDIENTSLAP EDPTFPADTW GTYLLTTETG LQKDHALWDH TAQNLLRMGL  240
AFLVLVALVW FLVEDWLSRK RTRERASRAS TWEGRRRLNT QTL                    283

SEQ ID NO: 20          moltype = DNA  length = 777
FEATURE                Location/Qualifiers
source                 1..777
                       mol_type = genomic DNA
                       note = source = NKp46
                       organism = Homo sapiens
SEQUENCE: 20
atggcctggc gagccctaca cccactgcta ctgctgctgc tgctgttccc aggctctcag  60
gcacaatcca aggctcaggt acttcaaagt gtggcagggc agacgctaac cgtgagatgc  120
cagtacccgc ccacgggcag tctctacgag aagaaaggct ggtgtaagga ggcttcagca  180
cttgtgtgca tcaggttagt caccagctcc aagcccagga cgatggcttg gacctctcga  240
ttcacaatct gggacgaccc tgatgctggc ttcttcactg tcaccatgac tgatctgaga  300
gaggaagact caggacatta ctggtgtaga atctaccgcc cttctgacaa ctctgtctct  360
aagtccgtca gattctatct ggtggtatct ccagcctctg cctccacaca gacctcctgg  420
actccccgcg acctggtctc ttcacagacc cagacccaga gctgtgtgcc tcccactgca  480
ggagccagac aagcccctga gtctccatct accatccctg tcccttcaca gccacagaac  540
tccacgctcc gccctggccc tgcagccccc attgccctgg tgcctgtgtt ctgtggactc  600
ctcgtagcca agagcctggt gctgtcagcc ctgctcgtct ggtgggtttt aaggaatcgg  660
cacatgcagc atcaagggag gtctctgctg cacccagctc agcccaggcc ccaggcccat  720
agacacttcc cactgagcca cagggcacca gggggggacat atggtggaaa accatga    777

SEQ ID NO: 21          moltype = AA  length = 216
FEATURE                Location/Qualifiers
REGION                 1..216
                       note = source = /note="NKG2D"
source                 1..216
                       mol_type = protein
                       organism = Homo sapiens
SEQUENCE: 21
MGWIRGRRSR HSWEMSEFHN YNLDLKKSDF STRWQKQRCP VVKSKCRENA SPFFFCCFIA  60
VAMGIRFIIM VAIWSAVFLN SLFNQEVQIP LTESYCGPCP KNWICYKNNC YQFFDESKNW  120
YESQASCMSQ NASLLKVYSK EDQDLLKLVK SYHWMGLVHI PTNGSWQWED GSILSPNLLT  180
IIEMQKGDCA LYASSFKGYI ENCSTPNTYI CMQRTV                            216

SEQ ID NO: 22          moltype = DNA  length = 651
FEATURE                Location/Qualifiers
source                 1..651
                       mol_type = genomic DNA
                       note = source = NKG2D
                       organism = Homo sapiens
SEQUENCE: 22
atggggtgga ttcgtggtcg gaggtctcga cacagctggg agatgagtga atttcataat  60
tataacttgg atctgaagaa gagtgatttt tcaacacgat ggcaaaagca aagatgtcca  120
gtagtcaaaa gcaaatgtag agaaaatgca tctccatttt ttttctgctg cttcatcgct  180
gtagccatgg gaatccgttt cattattatg gtaacaatat ggagtgctgt attcctaaac  240
tcattattca accaagaagt tcaaattccc ttgaccgaaa gttactgtgg cccatgtcct  300
aaaaactgga tatgttacaa aaataactgc taccaatttt ttgatgagag taaaaactgg  360
tatgagagcc aggcttcttg tatgtctcaa aatgccagcc ttctgaaagt atacagcaaa  420
gaggaccagg atttacttaa actggtgaag tcatatcatt ggatgggact agtacacatt  480
ccaacaaatg gatcttggca gtgggaagat ggctccattc tctcacccaa cctactaaca  540
ataattgaaa tgcagaaggg agactgtgca ctctatgcct cgagctttaa aggctatata  600
gaaaactgtt caactccaaa tacgtacatc tgcatgcaaa ggactgtgta a           651

SEQ ID NO: 23          moltype = AA  length = 359
FEATURE                Location/Qualifiers
REGION                 1..359
                       note = source = /note="CD16"
source                 1..359
                       mol_type = protein
                       organism = Homo sapiens
SEQUENCE: 23
MAEGTLWQIL CVSSDAQPQT FEGVKGADPP TLPPGSFLPG PVLWWGSLAR LQTEKSDEVS  60
RKGNWWVTEM GGGAGERLFT SSCLVGLVPL GLRISLVTCP LQCGIMWQLL LPTALLLLVS  120
AGMRTEDLPK AVVFLEPQWY RVLEKDSVTL KCQGAYSPED NSTQWFHNES LISSQASSYF  180
IDAATVDDSG EYRCQTNLST LSDPVQLEVH IGWLLLQAPR WVFKEEDPIH LRCHSWKNTA  240
LHKVTYLQNG KGRKYFHHNS DFYIPKATLK DSGSYFCRGL FGSKNVSSET VNITITQGLA  300
VSTISSFFPP GYQVSFCLVM VLLFAVDTGL YFSVKTNIRS STRDWKDHKF KWRKDPQDK   359

SEQ ID NO: 24          moltype = DNA  length = 1080
FEATURE                Location/Qualifiers
source                 1..1080
                       mol_type = genomic DNA
                       note = source = CD16
                       organism = Homo sapiens
```

SEQUENCE: 24
atggctgagg gcacactctg gcagattctg tgtgtgtcct cagatgctca gccacagacc 60
tttgagggag taaagggggc agacccaccc accttgcctc caggctcttt ccttcctggt 120
cctgttctat ggtggggctc ccttgccaga cttcagactg agaagtcaga tgaagtttca 180
agaaaaggaa attggtgggt gacagagatg ggtggagggg ctggggaaag gctgtttact 240
tcctcctgtc tagtcggttt ggtcccttta gggctccgga tatctttggt gacttgtcca 300
ctccagtgtg gcatcatgtg gcagctgctc ctcccaactg ctctgctact tctagtttca 360
gctggcatgc ggactgaaga tctcccaaag gctgtggtgt tcctggagcc tcaatggtac 420
agggtgctcg agaaggacag tgtgactctg aagtgccagg gagcctactc ccctgaggac 480
aattccacac agtggtttca caatgagagc ctcatctcaa gccaggcctc gagctacttc 540
attgacgctg ccacagtcga cgacagtgga gagtacaggt gccagacaaa cctctccacc 600
ctcagtgacc cggtgcagct agaagtccat atcggctggc tgttgctcca ggcccctcgg 660
tgggtgttca aggaggaaga ccctattcac ctgaggtgtc acagctggaa gaacactgct 720
ctgcataagg tcacatattt acagaatggc aaaggcagga agtattttca tcataattct 780
gacttctaca ttccaaaagc cacactcaaa gacagcggct cctacttctg caggggggctt 840
tttgggagta aaaatgtgtc ttcagagact gtgaacatca ccatcactca aggtttggca 900
gtgtcaacca tctcatcatt ctttccacct gggtaccaag tctctttctg cttggtgatg 960
gtactccttt ttgcagtgga cacaggacta tatttctctg tgaagacaaa cattcgaagc 1020
tcaacaagag actggaagga ccataaattt aaatggagaa aggaccctca agacaaatga 1080

SEQ ID NO: 25 moltype = AA length = 233
FEATURE Location/Qualifiers
REGION 1..233
note = source = /note="CD16"
source 1..233
mol_type = protein
organism = Homo sapiens
SEQUENCE: 25
MWQLLLPTAL LLLVSAGMRT EDLPKAVVFL EPQWYSVLEK DSVTLKCQGA YSPEDNSTQW 60
FHNESLISSQ ASSYFIDAAT VNDSGEYRCQ TNLSTLSDPV QLEVHIGWLL LQAPRWVFKE 120
EDPIHLRCHS WKNTALHKVT YLQNGKDRKY FHHNSDFHIP KATLKDSGSY FCRGLVGSKN 180
VSSETVNITI TQGLAVSTIS SFSPPGYQVS FCLVMVLLFA VDTGLYFSVK TNI 233

SEQ ID NO: 26 moltype = DNA length = 702
FEATURE Location/Qualifiers
source 1..702
mol_type = genomic DNA
note = source = CD16
organism = Homo sapiens
SEQUENCE: 26
atgtggcagc tgctcctccc aactgctctg ctacttctag tttcagctgg catgcggact 60
gaagatctcc caaaggctgt ggtgttcctg gagcctcaat ggtacagcgt gcttgagaag 120
gacagtgtga ctctgaagtg ccagggagcc tactcccctg aggacaattc cacacagtgg 180
tttcacaatg agaacctcat ctcaagccag gcctcgagct acttcattga cgctgccaca 240
gtcaacgaca gtggagagta caggtgccag acaaacctct ccaccctcag tgacccggtg 300
cagctagaag tccatatcgg ctggctgttg ctccaggccc ctcggtgggt gttcaaggag 360
gaagacccta ttcacctgag gtgtcacagc tggaagaaca ctgctctgca taaggtcaca 420
tatttacaga atggcaaaga caggaagtat tttcatcata attctgactt ccacattcca 480
aaagccacac tcaaagatag cggctcctac ttctgcaggg ggcttgttgg gagtaaaaat 540
gtgtcttcag agactgtgaa catcaccatc actcaaggtt tggcagtgtc aaccatctca 600
tcattctctc cacctgggta ccaagtctct ttctgcttgg tgatggtact cctttttgca 660
gtggacacag gactatattt ctctgtgaag acaaacattt ga 702

SEQ ID NO: 27 moltype = AA length = 304
FEATURE Location/Qualifiers
REGION 1..304
note = source = /note="KIR2DS1"
source 1..304
mol_type = protein
organism = Homo sapiens
SEQUENCE: 27
MSLTVVSMAC VGFFLLQGAW PHEGVHRKPS LLAHPGRLVK SEETVILQCW SDVMFEHFLL 60
HREGMFNDTL RLIGEHHDGV SKANFSISRM KQDLAGTYRC YGSVTHSPYQ VSAPSDPLDI 120
VIIGLYEKPS LSAQPGPTVL AGESVTLSCS SRSSYDMYHL SREGEAHERR LPAGTKVNGT 180
FQANFPLGPA THGGTYRCFG SFRDSPYEWS KSSDPLLVSV TGNPSNSWPS PTEPSSETGN 240
PRHLHVLIGT SVVKIPFTIL LFFLLHRWCS DKKNAAVMDQ EPAGNRTVNS EDSDEQDHQE 300
VSYA 304

SEQ ID NO: 28 moltype = DNA length = 915
FEATURE Location/Qualifiers
source 1..915
mol_type = genomic DNA
note = source = KIR2DS1
organism = Homo sapiens
SEQUENCE: 28
atgtcgctca cggtcgtcag catggcgtgt gttgggttct tcttgctgca gggggcctgg 60
ccacatgagg gagtccacag aaaaccttcc ctcctggccc acccaggtcg cctggtgaaa 120
tcagaagaga cagtcatcct gcaatgttgg tcagatgtca tgtttgaaca cttccttctg 180
cacagagagg ggatgtttaa cgacactttg cgcctcattg gagaacacca tgatggggtc 240

```
tccaaggcca acttctccat cagtcgcatg aagcaagacc tggcagggac ctacagatgc  300
tacggttctg ttactcactc cccctatcag ttgtcagctc ccagtgaccc tctggacatc  360
gtgatcatag gtctatatga gaaaccttct ctctcagccc agccgggccc cacggttctg  420
gcaggagaga atgtgacctt gtcctgcagc tcccggagct cctatgacat gtaccatcta  480
tccagggaag gggaggccca tgaacgtagg ctccctgcag ggaccaaggt caacggaaca  540
ttccaggcca actttcctct gggccctgcc acccatggag ggacctacag atgcttcggc  600
tctttccgtg actctccata cgagtggtca aagtcaagtg acccactgct tgtttctgtc  660
acaggaaacc cttcaaatag ttggccttca cccactgaac caagctccga aaccggtaac  720
cccagacacc tacatgttct gattgggacc tcagtggtca aaatcccttt caccatcctc  780
ctcttctttc tccttcatcg ctggtgctcc gacaaaaaaa atgctgctgt aatggaccaa  840
gagcctgcag ggaacagaac agtgaacagc gaggattctg atgaacaaga ccatcaggag  900
gtgtcatacg cataa                                                   915
```

```
SEQ ID NO: 29          moltype = AA  length = 304
FEATURE                Location/Qualifiers
REGION                 1..304
                       note = source = /note="KIR2DS2"
source                 1..304
                       mol_type = protein
                       organism = Homo sapiens
SEQUENCE: 29
MSLMVVSMVC VGFFLLQGAW PHEGVHRKPS LLAHPGPLVK SEETVILQCW SDVRFEHFLL  60
HREGKYKDTL HLIGEHHDGV SKANFSIGPM MQDLAGTYRC YGSVTHSPYQ LSAPSDPLDI  120
VITGLYEKPS LSAQPGPTVL AGESVTLSCS SRSSYDMYHL SREGEAHERR FSAGPKVNGT  180
FQADFPLGPA THGGTYRCFG SFRDSPYEWS NSSDPLLVSV TGNPSNSWPS PTEPSSKTGN  240
PRHLHVLIGT SVVKIPFTIL LFFLLHRWCS NKKNAAVMDQ EPAGNRTVNS EDSDEQDHQE  300
VSYA                                                               304
```

```
SEQ ID NO: 30          moltype = DNA  length = 1026
FEATURE                Location/Qualifiers
source                 1..1026
                       mol_type = genomic DNA
                       note = source = KIR2DS2
                       organism = Homo sapiens
SEQUENCE: 30
atgtcgctca tggtcgtcag catggcgtgt gttgggttct tcttgctgca gggggcctgg  60
ccacatgagg gagtccacag aaaaccttcc ctcctggccc acccaggtcc cctggtgaaa  120
tcagaagaga cagtcatcct gcaatgttgg tcagatgtca ggtttgagca cttccttctg  180
cacagagagg ggaagtataa ggacactttg cacctcattg gagagcacca tgatggggtc  240
tccaaggcca acttctccat cggtcccatg atgcaagacc ttgcagggac ctacagatgc  300
tacggttctg ttactcactc cccctatcag ttgtcagctc ccagtgaccc tctggacatc  360
gtcatcacag gtctatatga gaaaccttct ctctcagccc agccgggccc cacggttttg  420
gcaggagaga gcgtgacctt gtcctgcagc tcccggagct cctatgacat gtaccatcta  480
tccagggagg gggaggccca tgaacgtagg ttctctgcag ggcccaaggt caacggaaca  540
ttccaggccg actttcctct gggccctgcc acccacggag gaacctacag atgcttcggc  600
tctttccgtg actctcccta tgagtggtca aactcgagtg acccactgct tgtttctgtc  660
acaggaaacc cttcaaatag ttggccttca cccactgaac caagctccaa aaccggtaac  720
cccagacacc tgcatgttct gattgggacc tcagtggtca aaatcccttt caccatcctc  780
ctcttctttc tccttcatcg ctggtgctcc aacaaaaaaa atgctgctgt aatggaccaa  840
gagcctgcag ggaacagaac agtgaacagc gaggactctg atgaacaaga ccctcaggag  900
gtgacataca cacagttgaa tcactgcgtt ttcacacaga gaaaaatcac tcgcccttct  960
cagaggccca agacaccccc aacagatatc atcgtgtaca cggaacttcc aaatgctgag  1020
tccaga                                                             1026
```

```
SEQ ID NO: 31          moltype = AA  length = 304
FEATURE                Location/Qualifiers
REGION                 1..304
                       note = source = /note="KIR2DS3"
source                 1..304
                       mol_type = protein
                       organism = Homo sapiens
SEQUENCE: 31
MSLMVISMAC VGFFWLQGAW PHEGFRRKPS LLAHPGRLVK SEETVILQCW SDVMFEHFLL  60
HREGTFNDTL RLIGEHIDGV SKANFSIGRM RQDLAGTYRC YGSVPHSPYQ FSAPSDPLDI  120
VITGLYEKPS LSAQPGPTVL AGESVTLSCS SWSSYDMYHL STEGEAHERR FSAGPKVNGT  180
FQADFPLGPA TQGGTYRCFG SFHDSPYEWS KSSDPLLVSV TGNPSNSWPS PTEPSSKTGN  240
PRHLHVLIGT SVVKLPFTIL LFFLLHRWCS DKKNASVMDQ GPAGNRTVNR EDSDEQDHQE  300
VSYA                                                               304
```

```
SEQ ID NO: 32          moltype = DNA  length = 915
FEATURE                Location/Qualifiers
source                 1..915
                       mol_type = genomic DNA
                       note = source = KIR2DS3
                       organism = Homo sapiens
SEQUENCE: 32
atgtcgctca tggtcatcag catggcatgt gttgggttct tctggctgca gggggcctgg  60
ccacatgagg gattccgcag aaaaccttcc ctcctggccc acccaggtcg cctggtgaaa  120
tcagaagaga cagtcatcct gcaatgttgg tcagatgtca tgtttgagca cttccttctg  180
```

```
cacagagagg ggacgtttaa cgacactttg cgcctcattg gagagcacat tgatggggtc  240
tccaaggcca acttctccat cggtcgcatg aggcaagacc tggcagggac ctacagatgc  300
tacggttctg ttcctcactc cccctatcag ttttcagctc ccagtgaccc tctggacatc  360
gtgatcacag gtctatatga gaaaccttct ctctcagccc agccgggccc cacggttctg  420
gcaggagaga gcgtgacctt gtcctgcagc tcctggagct cctatgacat gtaccatcta  480
tccacggagg gggaggccca tgaacgtagg ttctctgcag ggcccaaggt caacggaaca  540
ttccaggccg actttcctct gggccctgcc acccaaggag gaacctacag atgcttcggc  600
tctttccatg actctcccta cgagtggtca aagtcaagtg acccactgct tgtttctgtc  660
acaggaaacc cttcaaatag ttggccttca cccactgaac caagctccaa aaccggtaac  720
cccagacacc tacacgttct gattgggacc tcagtggtca aactcccttt caccatcctc  780
ctcttctttc tccttcatcg ctggtgctcc gacaaaaaaa atgcatctgt aatggaccaa  840
gggcctgcgg ggaacagaac agtgaacagg gaggattctg atgaacagga ccatcaggag  900
gtgtcatacg cataa                                                    915
```

```
SEQ ID NO: 33           moltype = AA  length = 354
FEATURE                 Location/Qualifiers
REGION                  1..354
                        note = source = /note="KIR2DL4"
source                  1..354
                        mol_type = protein
                        organism = Homo sapiens
SEQUENCE: 33
HVGGQDKPFC SAWPSAVVPQ GGHATLRCHC RRGFNIFTLY KKDGVPVPEL YNRIFWNSFL  60
ISPVTPAHAG TYRCRGFHPH SPTEWSAPSN PLVIMVTGLY EKPSLTARPG PTVRAGENVT  120
LSCSSQSSFD IYHLSREGEA HELRLPAVPS INGTFQADFP LGPATHGETY RCFGSFHGSP  180
YEWSDPSDPL PVSVTGNPSS SWPSPTEPSF KTGIARHLHA VIRYSVAIIL FTILPFFLLH  240
RWCSKKKNAA VMNQEPAGHR TVNREDSDEQ DPQEVTYAQL DHCIFTQRKI TGPSQRSKRP  300
STDTSVCIEL PNAEPRALSP AHEHHSQALM GSSRETTALS QTQLASSNVP AAGI        354
```

```
SEQ ID NO: 34           moltype = DNA  length = 1251
FEATURE                 Location/Qualifiers
source                  1..1251
                        mol_type = genomic DNA
                        note = source = KIR2DL4
                        organism = Homo sapiens
SEQUENCE: 34
atgtcccctt cacatgttgt ggtcaatgtg tcaactgcac gatccgggcc cctcaccaca  60
tcctctgcac cggtcagtcg agccgagtca ctgcgtcctg gcagcagaag ctgcaccatg  120
tccatgtcac ccacggtcat catcctggca tgtcttgggt tcttcttgga ccagagtgtg  180
tgggcacacg tgggtggtca ggacaagccc ttctgctctg cctggcccag cgctgtggtg  240
cctcaaggag gacacgtgac tcttcggtgt cactatcgtc gtgggtttaa catcttcacg  300
ctgtacaaga aagatggggt ccctgtccct gagctctaca acagaatatt ctggaacagt  360
ttcctcatta gccctgtgac cccagcacac gcagggacct acagatgtcg aggttttcac  420
ccgcactccc ccactgagtg gtcggcaccc agcaaccccc tggtgatcat ggtcacaggt  480
ctatatgaga aaccttcgct tacagcccgg ccgggcccca cggttcgcgc aggagagaac  540
gtgaccttgt cctgcagctc ccagagctcc tttgacatct accatctatc cagggagggg  600
gaagcccatg aacttaggct ccctgcagtg cccagcatca atggaacatt ccaggccgac  660
ttccctctgg gtcctgccac ccacggagag acctacagat gcttcggctc tttccatgga  720
tctccctacg agtggtcaga cccgagtgac ccactgcctg tttctgtcac aggaaaccct  780
tctagtagtt ggccttcacc cactgaacca agcttcaaaa ctggtatcgc cagacacctg  840
catgctgtga ttaggtactc agtggccatc atcctcttta ccatccttcc cttctttctc  900
cttcatcgct ggtgctccaa aaaaaaagat gctgctgtaa tgaaccaaga gcctgcggga  960
cacagaacag tgaacaggga ggactctgat gaacaagacc ctcaggaggt gacatacgca  1020
cagttggatc actgcatttt cacacagaga aaaatcactg gcccttctca gaggagcaag  1080
agaccctcaa cagataccag cgtgtgtata gaacttccaa atgctgagcc cagagcgttg  1140
tctcctgccc atgagcacca cagtcaggcc ttgatgggat cttctaggga gacaacagcc  1200
ctgtctcaaa cccagcttgc cagctctaat gtaccagcag ctggaatctg a            1251
```

```
SEQ ID NO: 35           moltype = AA  length = 218
FEATURE                 Location/Qualifiers
REGION                  1..218
                        note = source = /note="KIR2DS4"
source                  1..218
                        mol_type = protein
                        organism = Homo sapiens
SEQUENCE: 35
QEGVHRKPSF LALPGHLVKS EETVILQCWS DVMFEHFLLH REGKFNNTLH LIGEHHDGVS  60
KANFSIGPMM PVLAGTYRCY SSVPHSPYQL SAPSDPLDMV IIGLYEKPSL SAQPGPTVQA  120
GENVSLSCSS IYPGRGRPMN VGSLQCAAST EHSRPTFLWA LPPTEGPTDA SALSVTLPTS  180
GQTRVIHCLF PSQETLQIVG LHPLNQAPKP VTPDTYMF                           218
```

```
SEQ ID NO: 36           moltype = DNA  length = 893
FEATURE                 Location/Qualifiers
source                  1..893
                        mol_type = genomic DNA
                        note = source = KIR2DS4
                        organism = Homo sapiens
SEQUENCE: 36
atgtcgctca tggtcatcat catggcgtgt gttgggttct tcttgctgca gggggcctgg  60
```

```
ccacaggagg gagtccacag aaaaccttcc ttcctggccc tcccaggtca cctggtgaaa  120
tcagaagaga cagtcatcct gcaatgttgg tcggatgtca tgtttgagca cttccttctg  180
cacagagagg ggaagtttaa caacactttg cacctcattg gagagcacca tgatggggtt  240
tccaaggcca acttctccat tggtcccatg atgcctgtcc ttgcaggaac ctacagatgc  300
tacggttctg ttcctcactc cccctatcag ttgtcagctc ccagtgaccc tctggacatg  360
gtgatcatag gtctatatga gaaaccttct ctctcagccc agccgggccc cacggttcag  420
gcaggagaga atgtgacctt gtcctgcagc tccatctatc cagggaaggg gaggcccatg  480
aacgtaggct ccctgcagtg cgcagcatca acggaacatt ccaggccgac tttcctctgg  540
gccctgccac ccacggaggg acctacagat gcttcggctc tttccgtgac gctccctacg  600
agtggtcaaa ctcgagtgat ccactgcttg tttccgtcac aggaaaccct tcaaatagtt  660
ggccttcacc cactgaacca agctccaaaa ccggtaaccc cagacaccta catgttctga  720
ttgggacctc agtggtcaaa atccctttca ccatcctcct cttctttctc cttcatcgct  780
ggtgctccga caaaaaaaat gctgctgtaa tggaccaaga gcctgcaggg aacagaacag  840
tgaacagcga ggattctgat gaacaagacc atcaggaggt gtcatacgca taa         893
```

```
SEQ ID NO: 37          moltype = AA  length = 283
FEATURE                Location/Qualifiers
REGION                 1..283
                       note = source = /note="KIR2DS5"
source                 1..283
                       mol_type = protein
                       organism = Homo sapiens
SEQUENCE: 37
HEGFRRKPSL LAHPGPLVKS EETVILQCWS DVMFEHFLLH REGTFNHTLR LIGEHIDGVS  60
KGNFSIGRMT QDLAGTYRCY GSVTHSPYQL SAPSDPLDIV ITGLYEKPSL SAQPGPTVLA  120
GESVTLSCSS RSSYDMYHLS REGEAHERRL PAGTKVNGTF QADFPLDPAT HGGTYRCFGS  180
FRDSPYEWSK SSDPLLVSVT GNTSNSWPSP TEPSSKTGNP RHLHVLIGTS VVKLPFTILL  240
FFLLHRWCSN KKNASVMDQG PAGNRTVNRE DSDEQDHQEV SYA                  283
```

```
SEQ ID NO: 38          moltype = DNA  length = 915
FEATURE                Location/Qualifiers
source                 1..915
                       mol_type = genomic DNA
                       note = source = KIR2DS
                       organism = Homo sapiens
SEQUENCE: 38
atgtcgctca tggtcatcag catggcgtgt gttgcgttct tcttgctgca gggggcctgg  60
ccacatgagg gattccgcag aaaaccttcc ctcctggccc acccaggtcc cctggtgaaa  120
tcagaagaga cagtcatcct gcaatgttgg tcagatgtca tgtttgagca cttccttctg  180
cacagagagg ggacgtttaa ccacactttg cgcctcattg gagagcacat tgatggggtc  240
tccaagggca acttctccat cggtcgcatg acacaagacc tggcagggac ctacagatgc  300
tacggttctg ttactcactc cccctatcag ttgtcagcgc ccagtgaccc tctggacatc  360
gtgatcacag gtctatatga gaaaccttct ctctcagccc agccgggccc cacggttctg  420
gcaggagaga gcgtgacctt gtcctgcagc tcccggagct cctatgacat gtaccatcta  480
tccagggaag gggaggccca tgaacgtagg ctccctgcag ggcccaaggt caacagaaca  540
ttccaggccg actttcctct ggaccctgcc acccacggag ggacctacag atgcttcggc  600
tctttccgtg actctccata cgagtggtca aagtcaagtg acccactgct tgtttctgtc  660
acaggaaact cttcaaatag ttggccttca cccactgaac caagctccga aaccggtaac  720
cccagacacc tacacgttct gattgggacc tcagtggtca aactcccttt caccatcctc  780
ctcttctttc tccttcatcg ctggtgctcc aacaaaaaaa atgcatctgt aatggaccaa  840
gggcctgcgg ggaacagaac agtgaacagg gaggattctg atgaacagga ccatcaggag  900
gtgtcatacg cataa                                                 915
```

```
SEQ ID NO: 39          moltype = AA  length = 361
FEATURE                Location/Qualifiers
REGION                 1..361
                       note = source = /note="KIR3DS1"
source                 1..361
                       mol_type = protein
                       organism = Homo sapiens
SEQUENCE: 39
HMGGQDKPFL SAWPSAVVPR GGHVTLRCHY RHRFNNFMLY KEDRIHVPIF HGRIFQEGFN  60
MSPVTTAHAG NYTCRGSHPH SPTGWSAPSN PMVIMVTGNH RKPSLLAHPG PLVKSGERVI  120
LQCWSDIMFE HFFLHKEGIS KDPSRLVGQI HDGVSKANFS IGSMMRALAG TYRCYGSVTH  180
TPYQLSAPSD PLDIVVTGLY EKPSLSAQPG PKVQAGESVT LSCSSRSSYD MYHLSREGGA  240
HERRLPAVRK VNRTFQADFP LGPATHGGTY RCFGSFRHSP YEWSDPSDPL LVSVTGNPSS  300
SWPSPTEPSS KSGNLRHLHI LIGTSVVKIP FTILLFFLLH RWCSNKKKCC CNGPRACREQ  360
K                                                                361
```

```
SEQ ID NO: 40          moltype = DNA  length = 1149
FEATURE                Location/Qualifiers
source                 1..1149
                       mol_type = genomic DNA
                       note = source = KIR3DS1
                       organism = Homo sapiens
SEQUENCE: 40
atgttgctca tggtcgtcag catggcgtgt gttgggttgt tcttggtcca gagggccggt  60
ccacacatgg gtggtcagga caagcccttc ctgtctgcct ggcccagcgc tgtggtgcct  120
cgcggaggac acgtgactct tcggtgtcac tatcgtcata ggtttaacaa tttcatgcta  180
```

```
tacaaagaag acagaatcca cgttcccatc ttccatggca gaatattcca ggagggcttc  240
aacatgagcc ctgtgaccac agcacatgca gggaactaca catgtcgggg ttcacaccca  300
cactccccca ctgggtggtc ggcacccagc aaccccatgg tgatcatggt cacaggaaac  360
cacagaaaac cttccctcct ggcccaccca ggtcccctgg tgaaatcagg agagagagtc  420
atcctgcaat gttggtcaga tatcatgttt gagcacttct ttctgcacaa agagtggatc  480
tctaaggacc cctcacgcct cgttggacag atccatgatg gggtctccaa ggccaatttc  540
tccatcggtt ccatgatgcg tgcccttgca gggacctaca gatgctacgg ttctgttact  600
cacaccccct atcagttgtc agctcccagt gatcccctgg acatcgtggt cacaggtcta  660
tatgagaaac cttctctctc agcccagccg ggccccaagg ttcaggcagg agagagcgtg  720
accttgtcct gtagctcccg gagctcctat gacatgtacc atctatccag ggaggggga   780
gcccatgaac gtaggctccc tgcagtgcgc aaggtcaaca gaacattcca ggcagatttc  840
cctctgggcc ctgccaccca cggagggacc tacagatgct tcggctcttt ccgtcactct  900
ccctacgagt ggtcagaccc gagtgaccca ctgcttgttt ctgtcacagg aaacccttca  960
agtagttggc cttcacccac agaaccaagc tccaaatctg gtaacctcag acacctgcac  1020
attctgattg ggacctcagt ggtcaaaatc cctttcacca tcctcctctt ctttctcctt  1080
catcgctggt gctccaacaa aaaaaaatgc tgctgtaatg gaccaagagc ctgcagggaa  1140
cagaagtga                                                         1149

SEQ ID NO: 41          moltype = AA  length = 231
FEATURE                Location/Qualifiers
REGION                 1..231
                       note = source = /note="NKG2C"
source                 1..231
                       mol_type = protein
                       organism = Homo sapiens
SEQUENCE: 41
MSKQRGTFSE VSLAQDPKRQ QRKPKGNKSS ISGTEQEIFQ VELNLQNPSL NHQGIDKIYD  60
CQGLLPPPEK LTAEVLGIIC IVLMATVLKT IVLIPFLEQN NSSPNTRTQK ARHCGHCPEE  120
WITYSNSCYY IGKERRTWEE SLLACTSKNS SLLSIDNEEE MKFLASILPS SWIGVFRNSS  180
HHPWVTINGL AFKHKIKDSD NAELNCAVLQ VNRLKSAQCG SSMIYHCKHK L           231

SEQ ID NO: 42          moltype = DNA  length = 696
FEATURE                Location/Qualifiers
source                 1..696
                       mol_type = genomic DNA
                       note = source = NKG2C
                       organism = Homo sapiens
SEQUENCE: 42
atgaataaac aaagaggaac cttctcagaa gtgagtctgg cccaggaccc aaagcggcag  60
caaaggaaac ctaaaggcaa taaaagctcc atttcaggaa ccgaacagga aatattccaa  120
gtagaattaa atcttcaaaa tccttccctg aatcatcaag ggattgataa aatatatgac  180
tgccaaggtt tactgccacc tccagagaag ctcactgccg aggtcctagg aatcatttgc  240
attgtcctga tggccactgt gttaaaaaca atagttctta ttcctttcct ggagcagaac  300
aatttttccc cgaatacaag aacgcagaaa gcacgtcatt gtggccattg tcctgaggag  360
tggattacat attccaacag ttgttattac attggtaagg aaagaagaac ttgggaagag  420
agtttgctgg cctgtacttc gaagaactcc agtctgcttt ctatagataa tgaagaagaa  480
atgaaatttc tggccagcat tttaccttcc tcatggattg gtgtgtttcg taacagcagt  540
catcatccat gggtgacaat aaatggtttg gctttcaaac ataagataaa agactcagat  600
aatgctgaac ttaactgtgc agtgctacaa gtaaatcgac ttaaatcagc ccagtgtgga  660
tcttcaatga tatatcattg taagcataag ctttag                           696

SEQ ID NO: 43          moltype = AA  length = 354
FEATURE                Location/Qualifiers
REGION                 1..354
                       note = source = /note="CCR7"
source                 1..354
                       mol_type = protein
                       organism = Homo sapiens
SEQUENCE: 43
QDEVTDDYIG DNTTVDYTLF ESLCSKKDVR NFKAWFLPIM YSIICFVGLL GNGLVVLTYI  60
YFKRLKTMTD TYLLNLAVAD ILFLLTLPFW AYSAAKSWVF GVHFCKLIFA IYKMSFFSGM  120
LLLLCISIDR YVAIVQAVSA HRHRARVLLI SKLSCVGIWI LATVLSIPEL LYSDLQRSSS  180
EQAMRCSLIT EHVEAFITIQ VAQMVIGFLV PLLAMSFCYL VIIRTLLQAR NFERNKAIKV  240
IIAVVVVFIV FQLPYNGVVL AQTVANFNIT SSTCELSKQL NIAYDVTYSL ACVRCCVNPF  300
LYAFIGVKFR NDLFKLFKDL GCLSQEQLRQ WSSCRHIRRS SMSVEAETTT TFSP        354

SEQ ID NO: 44          moltype = DNA  length = 1137
FEATURE                Location/Qualifiers
source                 1..1137
                       mol_type = genomic DNA
                       note = source = CCR7
                       organism = Homo sapiens
SEQUENCE: 44
atggacctgg ggaaaccaat gaaaagcgtg ctggtggtgg ctctccttgt cattttccag  60
gtatgcctgt gtcaagatga ggtcacggac gattacatcg gagacaacac cacagtggac  120
tacactttgt tcgagtcttt gtgctccaag aaggacgtgc ggaactttaa agcctggttc  180
ctccctatca tgtactccat catttgtttc gtgggcctac tgggcaatgg gctggtcgtg  240
ttgacctata tctatttcaa gaggctcaag accatgaccg atacctacct gctcaacctg  300
gcggtggcag acatcctctt cctcctgacc cttcccttct gggcctacag cgcggccaag  360
```

```
tcctgggtct tcggtgtcca cttttgcaag ctcatctttg ccatctacaa gatgagcttc  420
ttcagtggca tgctcctact tctttgcatc agcattgacc gctacgtggc catcgtccag  480
gctgtctcag ctcaccgcca ccgtgcccgc gtccttctca tcagcaagct gtcctgtgtg  540
ggcatctgga tactagccac agtgctctcc atcccagagc tcctgtacag tgacctccag  600
aggagcagca gtgagcaagc gatgcgatgc tctctcatca cagagcatgt ggaggccttt  660
atcaccatcc aggtggccca gatggtgatc ggctttctgg tcccccctgct ggccatgagc 720
ttctgttacc ttgtcatcat ccgcaccctg ctccaggcac gcaactttga gcgcaacaag  780
gccatcaagg tgatcatcgc tgtggtcgtg gtcttcatag tcttccagct gccctacaat  840
ggggtggtcc tggcccagac ggtggccaac ttcaacatca ccagtagcac ctgtgagctc  900
agtaagcaac tcaacatcgc ctacgacgtc acctacagcc tggcctgcgt ccgctgctgc  960
gtcaaccctt tcttgtacgc cttcatcggc gtcaagttcc gcaacgatct cttcaagctc  1020
ttcaaggacc tgggctgcct cagccaggag cagctccggc agtggtcttc ctgtcggcac  1080
atccggcgct cctccatgag tgtggaggcc gagaccacca ccaccttctc cccatag     1137

SEQ ID NO: 45          moltype = AA  length = 368
FEATURE                Location/Qualifiers
REGION                 1..368
                       note = source = /note="CXCR3"
source                 1..368
                       mol_type = protein
                       organism = Homo sapiens
SEQUENCE: 45
MVLEVSDHQV LNDAEVAALL ENFSSSYDYG ENESDSCCTS PPCPQDFSLN FDRAFLPALY  60
SLLFLLGLLG NGAVAAVLLS RRTALSSTDT FLLHLAVADT LLVLTLPLWA VDAAVQWVFG  120
SGLCKVAGAL FNINFYAGAL LLACISFDRY LNIVHATQLY RRGPPARVTL TCLAVWGLCL  180
LFALPDFIFL SAHHDERLNA THCQYNFPQV GRTALRVLQL VAGFLLPLLV MAYCYAHILA  240
VLLVSRGQRR LRAMRLVVVV VVAFALCWTP YHLVVLVDIL MDLGALARNC GRESRVDVAK  300
SVTSGLGYMH CCLNPLLYAF VGVKFRERMW MLLLRLGCPN QRGLQRQPSS SRRDSSWSET  360
SEASYSGL                                                           368

SEQ ID NO: 46          moltype = DNA  length = 1248
FEATURE                Location/Qualifiers
source                 1..1248
                       mol_type = genomic DNA
                       note = source = CXCR3
                       organism = Homo sapiens
SEQUENCE: 46
atggagttga ggaagtacgg ccctggaaga ctggcgggga cagttatagg aggagctgct  60
cagagtaaat cacagactaa atcagactca atcacaaaag agttcctgcc aggcctttac  120
acagcccctt cctccccgtt cccgccctca caggtgagtg accaccaagt gctaaatgac  180
gccgaggttg ccgccctcct ggagaacttc agctcttcct atgactatgg agaaaacgag  240
agtgactcgt gctgtacctc cccgccctgc ccacaggact tcagcctgaa cttcgaccgg  300
gccttcctgc cagccctcta cagcctcctc tttctgctgg ggctgctggg caacggcgcg  360
gtggcagccg tgctgctgag ccggcggaca gccctgagca gcaccgacac cttcctgctc  420
cacctagctg tagcagacac gctgctggtg ctgacactgc cgctctgggc agtggacgct  480
gccgtccagt gggtctttgg ctctggcctc tgcaaagtgg caggtgccct cttcaacatc  540
aacttctacg caggagccct cctgctggcc tgcatcagct ttgaccgcta cctgaacata  600
gttcatgcca cccagctcta ccgccggggg cccccggccc gcgtgaccct cacctgcctg  660
gctgtctggg ggctctgcct gcttttcgcc ctcccagact tcatcttcct gtcggcccac  720
cacgacgagc gcctcaacgc cacccactgc caatacaact tcccacaggt gggccgcacg  780
gctctgcggg tgctgcagct ggtggctggc tttctgctgc ccctgctggt catggcctac  840
tgctatgccc acatcctggc cgtgctgctg gtttccaggg gccagcggcg cctgcgggcc  900
atgcggctgg tggtggtggt cgtggtggcc tttgccctct gctggacccc ctatcacctg  960
gtggtgctgg tggacatcct catggacctg ggcgctttgg cccgcaactg tggccgagaa  1020
agcagggtag acgtggccaa gtcggtcacc tcaggcctgg gctacatgca ctgctgcctc  1080
aacccgctgc tctatgcctt tgtaggggtc aagttccggg agcggatgtg gatgctgctc  1140
ttgcgcctgg gctgccccaa ccagagaggg ctccagaggc agccatcgtc ttcccgccgg  1200
gattcatcct ggtctgagac ctcagaggcc tcctactcgg gcttgtga               1248

SEQ ID NO: 47          moltype = AA  length = 344
FEATURE                Location/Qualifiers
REGION                 1..344
                       note = source = /note="L-selectin"
source                 1..344
                       mol_type = protein
                       organism = Homo sapiens
SEQUENCE: 47
DFLAHHGTDC WTYHYSEKPM NWQRARRFCR DNYTDLVAIQ NKAEIEYLEK TLPFSRSYYW  60
IGIRKIGGIW TWVGTNKSLT EEAENWGDGE PNNKKNKEDC VEIYIKRNKD AGKWNDDACH  120
KLKAALCYTA SCQPWSCSGH GECVEIINNY TCNCDVGYYG PQCQFVIQCE PLEAPELGTM  180
DCTHPLGNFS FSSQCAFSCS EGTNLTGIEE TTCGPFGNWS SPEPTCQVIQ CEPLSAPDLG  240
IMNCSHPLAS FSFTSACTFI CSEGTELIGK KKTICESSGI WSNPSPICQK LDKSFSMIKE  300
GDYNPLFIPV AVMVTAFSGL AFIIWLARRL KKGKKSKRSM NDPY                   344

SEQ ID NO: 48          moltype = DNA  length = 1158
FEATURE                Location/Qualifiers
source                 1..1158
                       mol_type = genomic DNA
                       note = source = L-selectin
```

```
                         organism = Homo sapiens
SEQUENCE: 48
atgggctgca gaagaactag agaaggacca agcaaagcca tgatatttcc atggaaatgt  60
cagagcaccc agagggactt atggaacatc ttcaagttgt gggggtggac aatgctctgt  120
tgtgatttcc tggcacatca tggaaccgac tgctggactt accattattc tgaaaaaccc  180
atgaactggc aaagggctag aagattctgc cgagacaatt acacagattt agttgccata  240
caaaacaagg cggaaattga gtatctggag aagactctgc ctttcagtcg ttcttactac  300
tggataggaa tccggaagat aggaggaata tggacgtggg tgggaaccaa caaatctctt  360
actgaagaag cagagaactg gggagatggt gagcccaaca acaagaagaa caaggaggac  420
tgcgtggaga tctatatcaa gagaaacaaa gatgcaggca aatggaacga tgacgcctgc  480
cacaaactaa aggcagccct ctgttacaca gcttcttgcc agccctggtc atgcagtggc  540
catggagaat gtgtagaaat catcaataat tacacctgca actgtgatgt ggggtactat  600
gggccccagt gtcagtttgt gattcagtgt gagcctttgg aggccccaga gctgggtacc  660
atggactgta ctcacccttt gggaaacttc agcttcagct cacagtgtgc cttcagctgc  720
tctgaaggaa caaacttaac tgggattgaa gaaaccacct gtggaccatt tggaaactgg  780
tcatctccag aaccaacctg tcaagtgatt cagtgtgagc ctctatcagc accagatttg  840
gggatcatga actgtagcca tcccctggcc agcttcagct ttacctctgc atgtaccttc  900
atctgctcag aaggaactga gttaattggg aagaagaaaa ccatttgtga atcatctgga  960
atctggtcaa atcctagtcc aatatgtcaa aaattggaca aaagtttctc aatgattaag  1020
gagggtgatt ataacccccct cttcattcca gtggcagtca tggttactgc attctctggg  1080
ttggcattta tcatttggct ggcaaggaga ttaaaaaaag gcaagaaatc caagagaagt  1140
atgaatgacc catattaa                                               1158

SEQ ID NO: 49            moltype = AA  length = 350
FEATURE                  Location/Qualifiers
REGION                   1..350
                         note = source = /note="CXCR1"
source                   1..350
                         mol_type = protein
                         organism = Homo sapiens
SEQUENCE: 49
MSNITDPQMW DFDDLNFTGM PPADEDYSPC XLETETLNKY VVIIAYALVF LLSLLGNSLV  60
MLVILYSRVG RSVTDVYLLN LALADLLFAL TLPIWAASKV NGWIFGTFLC KVVSLLKEVN  120
FYSGILLLAC ISVDRYLAIV HATRTLTQKR HLVKFVCLGC WGLSMNLSLP FFLFRQAYHP  180
NNSSPVCYEV LGNDTAKWRM VLRILPHTFG FIVPLFVMLF CYGFTLRTLF KAHMGQKHRA  240
MRVIFAVVLI FLLCWLPYNL VLLADTLMRT QVIQESCERR NNIGRALDAT EILGFLHSCL  300
NPIIYAFIGQ NFRHGFLKIL AMHGLVSKEF LARHRVTSYT SSSVNVSSNL             350

SEQ ID NO: 50            moltype = DNA  length = 1053
FEATURE                  Location/Qualifiers
source                   1..1053
                         mol_type = genomic DNA
                         note = source = CXCR1
                         organism = Homo sapiens
SEQUENCE: 50
atgtcaaata ttacagatcc acagatgtgg gattttgatg atctaaattt cactggcatg  60
ccacctgcag atgaagatta cagcccctgt atgctagaaa ctgagacact caacaagtat  120
gttgtgatca tcgcctatgc cctagtgttc ctgctgagcc tgctgggaaa ctccctggtg  180
atgctggtca tcttatacag cagggtcggc cgctccgtca ctgatgtcta cctgctgaac  240
ctggccttgg ccgacctact ctttgccctg accttgccca tctgggccgc ctccaaggtg  300
aatggctgga tttttggcac attcctgtgc aaggtggtct cactcctgaa ggaagtcaac  360
ttctacagtg gcatcctgct gttggcctgc atcagtgtgg accgttacct ggccattgtc  420
catgccacac gcacactgac ccagaagcgt cacttggtca agtttgtttg tcttggctgc  480
tggggactgt ctatgaatct gtccctgccc ttcttccttt tccgccaggc ttaccatcca  540
aacaattcca gtccagtttg ctatgaggtc ctgggaaatg acacagcaaa atggcggatg  600
gtgttgcgga tcctgcctca cacctttggc ttcatcgtgc cgctgtttgt catgctgttc  660
tgctatggat tcaccctgcg tacactgttt aaggcccaca tggggcagaa gcaccgagcc  720
atgagggtca tctttgctgt cgtcctcatc ttcctgcttt gctggctgcc ctacaacctg  780
gtcctgctgg cagacaccct catgaggacc caggtgatcc aggagagctg tgagcgccgc  840
aacaacatcg gccgggccct ggatgccact gagattctgg gatttctcca tagctgcctc  900
aaccccatca tctacgcctt catcggccaa aattttcgcc atggattcct caagatcctg  960
gctatgcatg gcctggtcag caaggagttc ttggcacgtc atcgtgttac ctcctacact  1020
tcttcgtctg tcaatgtctc ttccaacctc tga                              1053

SEQ ID NO: 51            moltype = AA  length = 360
FEATURE                  Location/Qualifiers
REGION                   1..360
                         note = source = /note="CXCR2"
source                   1..360
                         mol_type = protein
                         organism = Homo sapiens
SEQUENCE: 51
MEDFNMESDS FEDFWKGEDL SNYSYSSTLP PFLLDAAPCE PESLEINKYF VVIIYALVFL  60
LSLLGNSLVM LVILYSRVGR SVTDVYLLNL ALADLLFALT LPIWAASKVN GWIFGTFLCK  120
VVSLLKEVNF YSGILLLACI SVDRYLAIVH ATRTLTQKRY LVKFICLSIW GLSLLLALPV  180
LLFRRTVYSS NVSPACYEDM GNNTANWRML LRILPQSFGF IVPLLIMLFC YGFTLRTLFK  240
AHMGQKHRAM RVIFAVVLIF LLCWLPYNLV LLADTLMRTQ VIQETCERRN HIDRALDATE  300
ILGILHSCLN PLIYAFIGQK FRHGLLKILA IHGLISKDSL PKDSRPSFVG SSSGHTSTTL  360
```

```
SEQ ID NO: 52           moltype = DNA  length = 1083
FEATURE                 Location/Qualifiers
source                  1..1083
                        mol_type = genomic DNA
                        note = source = CXCR2
                        organism = Homo sapiens
SEQUENCE: 52
atggaagatt ttaacatgga gagtgacagc tttgaagatt tctggaaagg tgaagatctt  60
agtaattaca gttacagctc taccctgccc ccttttctac tagatgccgc cccatgtgaa  120
ccagaatccc tggaaatcaa caagtatttt gtggtcatta tctatgccct ggtattcctg  180
ctgagcctgc tgggaaactc cctcgtgatg ctggtcatct tatacagcag ggtcggccgc  240
tccgtcactg atgtctacct gctgaaccta gccttggccg acctactctt tgccctgacc  300
ttgcccatct gggccgcctc caaggtgaat ggctggattt ttggcacatt cctgtgcaag  360
gtggtctcac tcctgaagga agtcaacttc tatagtggca tcctgctact ggcctgcatc  420
agtgtggacc gttacctggc cattgtccat gccacacgca cactgaccca gaagcgctac  480
ttggtcaaat tcatatgtct cagcatctgg ggtctgtcct tgctcctggc cctgcctgtc  540
ttactttttcc gaaggaccgt ctactcatcc aatgttagcc cagcctgcta tgaggacatg  600
ggcaacaata cagcaaactg gcggatgctg ttacggatcc tgccccagtc ctttggcttc  660
atcgtgccac tgctgatcat gctgttctgc tacggattca ccctgcgtac gctgtttaag  720
gcccacatgg ggcagaagca ccgggccatg cgggtcatct ttgctgtcgt cctcatcttc  780
ctgctctgct ggctgcccta caacctggtc ctgctggcag acaccctcat gaggacccag  840
gtgatccagg agacctgtga gcgccgcaat cacatcgacc gggctctgga tgccaccgag  900
attctgggca tccttcacag ctgcctcaac cccctcatct acgccttcat tggccagaag  960
tttcgccatg gactcctcaa gattctagct atacatggct tgatcagcaa ggactccctg  1020
cccaaagaca gcaggccttc ctttgttggc tcttcttcag ggcacacttc cactactctc  1080
taa                                                                1083

SEQ ID NO: 53           moltype = AA  length = 355
FEATURE                 Location/Qualifiers
REGION                  1..355
                        note = source = /note="CXC3CR1"
source                  1..355
                        mol_type = protein
                        organism = Homo sapiens
SEQUENCE: 53
MDQFPESVTE NFEYDDLAEA CYIGDIVVFG TVFLSIFYSV IFAIGLVGNL LVVFALTNSK  60
KPKSVTDIYL LNLALSDLLF VATLPFWTHY LINEKGLHNA MCKFTTAFFF IGFFGSIFFI  120
TVISIDRYLA IVLAANSMNN RTVQHGVTIS LGVWAAAILV AAPQFMFTKQ KENECLGDYP  180
EVLQEIWPVL RNVETNFLGF LLPLLIMSYC YFRIIQTLFS CKNHKKAKAI KLILLVVIVF  240
FLFWTPYNVM IFLETLKLYD FFPSCDMRKD LRLALSVTET VAFSHCCLNP LIYAFAGEKF  300
RRYLYHLYGK CLAVLCGRSV HVDFSSSESQ RSRHGSVLSS NFTYHTSDGD ALLLL       355

SEQ ID NO: 54           moltype = DNA  length = 1068
FEATURE                 Location/Qualifiers
source                  1..1068
                        mol_type = genomic DNA
                        note = source = CXC3CR1
                        organism = Homo sapiens
SEQUENCE: 54
atggatcagt tccctgaatc agtgacagaa aactttgagt acgatgattt ggctgaggcc  60
tgttatattg gggacatcgt ggtctttggg actgtgttcc tgtccatatt ctactccgtc  120
atctttgcca ttggcctggt gggaaatttg ttggtagtgt ttgccctcac caacagcaag  180
aagcccaaga gtgtcaccga catttacctc ctgaacctgg ccttgtctga tctgctgttt  240
gtagccactt tgcccttctg gactcactat ttgataaatg aaaagggcct ccacaatgcc  300
atgtgcaaat tcactaccgc cttcttcttc atcggctttt ttggaagcat attcttcatc  360
accgtcatca gcattgatag gtacctggcc atcgtcctgg ccgccaactc catgaacaac  420
cggaccgtgc agcatggcgt caccatcagc ctaggcgtct gggcagcagc cattttggtg  480
gcagcacccc agttcatgtt cacaaagcag aaagaaaatg aatgccttgg tgactacccc  540
gaggtcctcc aggaaatctg gcccgtgctc cgcaatgtgg aaacaaattt tcttggcttc  600
ctactccccc tgctcattat gagttattgc tacttcagaa tcatccagac gctgttttcc  660
tgcaagaacc acaagaaagc caaagccatt aaactgatcc ttctggtggt catcgtgttt  720
ttcctcttct ggacacccta caacgttatg attttcctgg agacgcttaa gctctatgac  780
ttctttccca gttgtgacat gaggaaggat ctgaggctgg ccctcagtgt gactgagacg  840
gttgcattta gccattgttg cctgaatcct ctcatctatg catttgctgg ggagaagttc  900
agaagatacc tttaccacct gtatgggaaa tgcctggctg tcctgtgtgg gcgctcagtc  960
cacgttgatt tctcctcatc tgaatcacaa aggagcaggc atggaagtgt tctgagcagc  1020
aattttactt accacacgag tgatggagat gcattgctcc ttctctga               1068

SEQ ID NO: 55           moltype = AA  length = 373
FEATURE                 Location/Qualifiers
REGION                  1..373
                        note = source = /note="ChemR23"
source                  1..373
                        mol_type = protein
                        organism = Homo sapiens
SEQUENCE: 55
MRMEDEDYNT SISYGDEYPD YLDSIVVLED LSPLEARVTR IFLVVVYSIV CFLGILGNGL  60
VIIIATFKMK KTVNMVWFLN LAVADFLFNV FLPIHITYAA MDYHWVFGTA MCKISNFLLI  120
HNMFTSVFLL TIISSDRCIS VLLPVWSQNH RSVRLAYMAC MVIWVLAFFL SSPSLVFRDT  180
```

-continued

```
ANLHGKISCF NNFSLSTPGS SSWPTHSQMD PVGYSRHMVV TVTRFLCGFL VPVLIITACY  240
LTIVCKLQRN RLAKTKKPFK IIVTIIITFF LCWCPYHTLN LLELHHTAMP GSVFSLGLPL  300
ATALAIANSC MNPILYVFMG QDFKKFKVAL FSRLVNALSE DTGHSSYPSH RSFTKMSSMN  360
ERTSMNERET GML                                                   373

SEQ ID NO: 56          moltype = DNA  length = 1122
FEATURE                Location/Qualifiers
source                 1..1122
                       mol_type = genomic DNA
                       note = source = ChemR23
                       organism = Homo sapiens
SEQUENCE: 56
atgagaatgg aggatgaaga ttacaacact tccatcagtt acggtgatga ataccctgat  60
tatttagact ccattgtggt tttggaggac ttatccccct tggaagccag ggtgaccagg  120
atcttcctgg tggtggtcta cagcatcgtc tgcttcctcg ggattctggg caatggtctg  180
gtgatcatca ttgccacctt caagatgaag aagacagtga acatggtctg gttcctcaac  240
ctggcagtgg cagatttcct gttcaacgtc ttcctcccaa tccatatcac ctatgccgcc  300
atggactacc actgggtttt cgggacagcc atgtgcaaga tcagcaactt ccttctcatc  360
cacaacatgt tcaccagcgt cttcctgctg accatcatca gctctgaccg ctgcatctct  420
gtgctcctcc ctgtctggtc ccagaaccac cgcagcgttc gcctggctta catggcctgc  480
atggtcatct gggtcctggc tttcttcttg agttccccat ctctcgtctt ccgggacaca  540
gccaacctgc atgggaaaat atcctgcttc aacaacttca gcctgtccac acctgggtct  600
tcctcgtggc ccactcactc ccaaatggac cctgtggggt atagccggca catggtggtg  660
actgtcaccc gcttcctctg tggcttcctg gtcccagtcc tcatcatcac agcttgctac  720
ctcaccatcg tgtgcaaact gcagcgcaac cgcctggcca agaccaagaa gcccttcaag  780
attattgtga ccatcatcat taccttcttc ctctgctggt gcccctacca cacactcaac  840
ctcctagagc tccaccacac tgccatgcct ggctctgtct tcagcctggg tttgcccctg  900
gccactgccc ttgccattgc caacagctgc atgaacccca ttctgtatgt tttcatgggt  960
caggacttca agaagttcaa ggtggccctc ttctctcgcc tggtcaatgc tctaagtgaa  1020
gatacaggcc actcttccta ccccagccat agaagcttta ccaagatgtc atcaatgaat  1080
gagaggactt ctatgaatga gagggagacc ggcatgcttt ga                   1122

SEQ ID NO: 57          moltype = AA  length = 352
FEATURE                Location/Qualifiers
REGION                 1..352
                       note = source = /note="CXCR4"
source                 1..352
                       mol_type = protein
                       organism = Homo sapiens
SEQUENCE: 57
MEGISIYTSD NYTEEMGSGD YDSMKEPCFR EENANFNKIF LPTIYSIIFL TGIVGNGLVI  60
LVMGYQKKLR SMTDKYRLHL SVADLLFVIT LPFWAVDAVA NWYFGNFLCK AVHVIYTVNL  120
YSSVLILAFI SLDRYLAIVH ATNSQRPRKL LAEKVVYVGV WIPALLLTIP DFIFANVSEA  180
DDRYICDRFY PNDLWVVVFQ FQHIMVGLIL PGIVILSCYC IIISKLSHSK GHQKRKALKT  240
TVILILAFFA CWLPYYIGIS IDSFILLEII KQGCEFENTV HKWISITEAL AFFHCCLNPI  300
LYAFLGAKFK TSAQHALTSV SRGSSLKILS KGKRGGHSSV STESESSSFH SS         352

SEQ ID NO: 58          moltype = DNA  length = 1071
FEATURE                Location/Qualifiers
source                 1..1071
                       mol_type = genomic DNA
                       note = source = CXCR4
                       organism = Homo sapiens
SEQUENCE: 58
atgtccattc ctttgcctct tttgcagata tacacttcag ataactacac cgaggaaatg  60
ggctcagggg actatgactc catgaaggaa ccctgtttcc gtgaagaaaa tgctaatttc  120
aataaaatct tcctgcccac catctactcc atcatcttct taactggcat tgtgggcaat  180
ggattggtca tcctggtcat gggttaccag aagaaactga gaagcatgac ggacaagtac  240
aggctgcacc tgtcagtggc cgacctcctc tttgtcatca cgcttccctt ctgggcagtt  300
gatgccgtgg caaactggta ctttgggaac ttcctatgca aggcagtcca tgtcatctac  360
acagtcaacc tctacagcag tgtcctcatc ctggccttca tcagtctgga ccgctacctg  420
gccatcgtcc acgccaccaa cagtcagagg ccaaggaagc tgttggctga aaaggtggtc  480
tatgttggcg tctggatccc tgccctcctg ctgactattc ccgacttcat ctttgccaac  540
gtcagtgagg cagatgacag atatatctgt gaccgcttct accccaatga cttgtgggtg  600
gttgtgttcc agtttcagca catcatggtt ggccttatcc tgcctggtat tgtcatcctg  660
tcctgctatt gcattatcat ctccaagctg tcacactcca agggccacca gaagcgcaag  720
gccctcaaga ccacagtcat cctcatcctg gctttcttcg cctgttggct gccttactac  780
attgggatca gcatcgactc cttcatcctc ctggaaatca tcaagcaagg gtgtgagttt  840
gagaacactg tgcacaagtg gatttccatc accgaggccc tagctttctt ccactgttgt  900
ctgaacccca tcctctatgc tttccttgga gccaaattta aaacctctgc ccagcacgca  960
ctcacctctg tgagcagagg gtccagcctc aagatcctct ccaaaggaaa gcgaggtgga  1020
cattcatctg tttccactga gtctgagtct tcaagttttc actccagcta a           1071

SEQ ID NO: 59          moltype = AA  length = 352
FEATURE                Location/Qualifiers
REGION                 1..352
                       note = source = /note="CCR5"
source                 1..352
                       mol_type = protein
```

```
                         organism = Homo sapiens
SEQUENCE: 59
MDYQVSSPIY DINYYTSEPC QKINVKQIAA RLLPPLYSLV FIFGFVGNML VILILINCKR  60
LKSMTDIYLL NLAISDLFFL LTVPFWAHYA AAQWDFGNTM CQLLTGLYFI GFFSGIFFII  120
LLTIDRYLAV VHAVFALKAR TVTFGVVTSV ITWVVAVFAS LPGIIFTRSQ KEGLHYTCSS  180
HFPYSQYQFW KNFQTLKIVI LGLVLPLLVM VICYSGILKT LLRCRNEKKR HRAVRLIFTI  240
MIVYFLFWAP YNIVLLLNTF QEFFGLNNCS SSNRLDQAMQ VTETLGMTHC CINPIIYAFV  300
GEKFRNYLLV FFQKHIAKRF CKCCSIFQQE APERASSVYT RSTGEQEISV GL          352

SEQ ID NO: 60            moltype = DNA  length = 1059
FEATURE                  Location/Qualifiers
source                   1..1059
                         mol_type = genomic DNA
                         note = source = CCR5
                         organism = Homo sapiens
SEQUENCE: 60
atggattatc aagtgtcaag tccaatctat gacatcaatt attatacatc ggagccctgc  60
caaaaaatca atgtgaagca aatcgcagcc cgcctcctgc ctccgctcta ctcactggtg  120
ttcatctttg gttttgtggg caacatgctg gtcatcctca tcctgataaa ctgcaaaagg  180
ctgaagagca tgactgacat ctacctgctc aacctggcca tctctgacct gtttttcctt  240
cttactgtcc ccttctgggc tcactatgct gccgcccagt gggactttgg aaatacaatg  300
tgtcaactct tgacagggct ctattttata ggcttcttct ctggaatctt cttcatcatc  360
ctcctgacaa tcgataggta cctggctgtc gtccatgctg tgtttgcttt aaaagccagg  420
acggtcacct ttggggtggt gacaagtgtg atcacttggg tggtggctgt gtttgcgtct  480
ctcccaggaa tcatctttac cagatctcaa aaagaaggtc ttcattacac ctgcagctct  540
cattttccat acagtcagta tcaattctgg aagaatttcc agacattaaa gatagtcatc  600
ttggggctgg tcctgccgct gcttgtcatg gtcatctgct actcgggaat cctaaaaact  660
ctgcttcggt gtcgaaatga gaagaagagg cacagggctg tgaggcttat cttcaccatc  720
atgattgttt attttctctt ctgggctccc tacaacattg tccttctcct gaacaccttc  780
caggaattct ttggcctgaa taattgcagt agctctaaca ggttggacca agctatgcag  840
gtgacagaga ctcttgggat gacgcactgc tgcatcaacc ccatcatcta tgcctttgtc  900
ggggagaagt tcagaaacta cctcttagtc ttcttccaaa agcacattgc caaacgcttc  960
tgcaaatgct gttctatttt ccagcaagag gctcccgagc gagcaagctc agtttacacc  1020
cgatccactg gggagcagga aatatctgtg ggcttgtga                        1059

SEQ ID NO: 61            moltype = AA  length = 398
FEATURE                  Location/Qualifiers
REGION                   1..398
                         note = source = /note="S1P5"
source                   1..398
                         mol_type = protein
                         organism = Homo sapiens
SEQUENCE: 61
MESGLLRPAP VSEVIVLHYN YTGKLRGARY QPGAGLRADA VVCLAVCAFI VLENLAVLLV  60
LGRHPRFHAP MFLLLGSLTL SDLLAGAAYA ANILLSGPLT LKLSPALWFA REGGVFVALT  120
ASVLSLLAIA LERSLTMARR GPAPVSSRGR TLAMAAAAWG VSLLLGLLPA LGWNCLGRLD  180
ACSTVLPLYA KAYVLFCVLA FVGILAAICA LYARIYCQVR ANARRLPARP GTAGTTSTRA  240
RRKPRSLALL RTLSVVLLAF VACWGPLFLL LLLDVACPAR TCPVLLQADP FLGLAMANSL  300
LNPIIYTLTN RDLRHALLRL VCCGRHSCGR DPSGSQQSAS AAEASGGLRR CLPPGLDGSF  360
SGSERSSPQR DGLDTSGSTG SPGAPTAART LVSEPAAD                          398

SEQ ID NO: 62            moltype = DNA  length = 1197
FEATURE                  Location/Qualifiers
source                   1..1197
                         mol_type = genomic DNA
                         note = source = S1P5
                         organism = Homo sapiens
SEQUENCE: 62
atggagtcgg ggctgctgcg gccggcgccg gtgagcgagg tcatcgtcct gcattacaac  60
tacaccggca agctccgcgg tgcgcgctac cagccgggtg ccggcctgcg cgccgacgcc  120
gtggtgtgcc tggcggtgtg cgccttcatc gtgctagaga atctagccgt gttgttggtg  180
ctcggacgcc acccgcgctt ccacgctccc atgttcctgc tcctgggcag cctcacgttg  240
tcggatctgc tggcaggcgc cgcctacgcc gccaacatcc tactgtcggg gccgctcacg  300
ctgaaactgt cccccgcgct ctggttcgca cgggagggag gcgtcttcgt ggcactcact  360
gcgtccgtgc tgagcctcct ggccatcgcg ctggagcgca gcctcaccat ggcgcgcagg  420
gggcccgcgc ccgtctccag tcgggggcgc acgctggcga tggcagccgc ggcctggggc  480
gtgtcgctgc tcctcgggct cctgccagcg ctgggctgga attgcctggg tcgcctggac  540
gcttgctcca ctgtcttgcc gctctacgcc aaggcctacg tgctcttctg cgtgctcgcc  600
ttcgtgggca tcctggccgc tatctgtgca ctctacgcgc gcatctactg ccaggtacgc  660
gccaacgcgc ggcgcctgcc ggcacggccc gggactgcgg ggaccacctc gacccgggcg  720
cgtcgcaagc cgcgctcgct ggccttgctg cgcacgctca gcgtggtgct cctggccttt  780
gtggcatgtt ggggcccccct cttcctgctg ctgttgctcg acgtggcgtg cccggcgcgc  840
acctgtcctg tactcctgca ggccgatccc ttcctgggac tggccatggc caactcactt  900
ctgaacccca tcatctacac gctcaccaac cgcgacctgc gccacgcgct cctgcgcctg  960
gtctgctgcg gacgccactc ctgcggcaga gacccgagtg gctcccagca gtcggcgagc  1020
gcggctgagg cttccggggg cctgcgccgc tgcctgcccc cgggccttga tgggagcttc  1080
agcggctcgg agcgctcatc gccccagcgc gacgggctgg acaccagcgg ctccacaggc  1140
agccccggtg cacccacagc cgcccggact ctggtatcag aaccggctgc agactga     1197
```

```
SEQ ID NO: 63           moltype = AA  length = 951
FEATURE                 Location/Qualifiers
REGION                  1..951
                        note = source = /note="cKit"
source                  1..951
                        mol_type = protein
                        organism = Homo sapiens
SEQUENCE: 63
QPSVSPGEPS PPSIHPGKSD LIVRVGDEIR LLCTDPGFVK WTFEILDETN ENKQNEWITE  60
KAEATNTGKY TCTNKHGLSN SIYVFVRDPA KLFLVDRSLY GKEDNDTLVR CPLTDPEVTN  120
YSLKGCQGKP LPKDLRFIPD PKAGIMIKSV KRAYHRLCLH CSVDQEGKSV LSEKFILKVR  180
PAFKAVPVVS VSKASYLLRE GEEFTVTCTI KDVSSSVYST WKRENSQTKL QEKYNSWHHG  240
DFNYERQATL TISSARVNDS GVFMCYANNT FGSANVTTTL EVVDKGFINI FPMINTTVFV  300
NDGENVDLIV EYEAFPKPEH QQWIYMNRTF TDKWEDYPKS ENESNIRYVS ELHLTRLKGT  360
EGGTYTFLVS NSDVNAAIAF NVYVNTKPEI LTYDRLVNGM LQCVAAGFPE PTIDWYFCPG  420
TEQRCSASVL PVDVQTLNSS GPPFGKLVVQ SSIDSSAFKH NGTVECKAYN DVGKTSAYFN  480
FAFKGNNKEQ IHPHTLFTPL LIGFVIVAGM MCIIVMILTY KYLQKPMYEV QWKVVEEING  540
NNYVYIDPTQ LPYDHKWEFP RNRLSFGKTL GAGAFGKVVE ATAYGLIKSD AAMTVAVKML  600
KPSAHLTERE ALMSELKVLS YLGNHMNIVN LLGACTIGGP TLVITEYCCY GDLLNFLRRK  660
RDSFICSKQE DHAEAALYKN LLHSKESSCS DSTNEYMDMK PGVSYVVPTK ADKRRSVRIG  720
SYIERDVTPA IMEDDELALD LEDLLSFSYQ VAKGMAFLAS KNCIHRDLAA RNILLTHGRI  780
TKICDFGLAR DIKNDSNYVV KGNARLPVKW MAPESIFNCV YTFESDVWSY GIFLWELFSL  840
GSSPYPGMPV DSKFYKMIKE GFRMLSPEHA PAEMYDIMKT CWDADPLKRP TFKQIVQLIE  900
KQISESTNHI YSNLANCSPN RQKPVVDHSV RINSVGSTAS SSQPLLVHDD V            951

SEQ ID NO: 64           moltype = DNA  length = 2931
FEATURE                 Location/Qualifiers
source                  1..2931
                        mol_type = genomic DNA
                        note = source = cKit
                        organism = Homo sapiens
SEQUENCE: 64
atgagaggcg ctcgcggcgc ctgggatttt ctctgcgttc tgctcctact gcttcgcgtc  60
cagacaggct cttctcaacc atctgtgagt ccaggggaac cgtctccacc atccatccat  120
ccaggaaaat cagacttaat agtccgcgtg ggcgacgaga ttaggctgtt atgcactgat  180
ccgggcttg tcaaatggac ttttgagatc ctggatgaaa cgaatgagaa taagcagaat  240
gaatggatca cggaaaaggc agaagccacc aacaccggca aatacacgtg caccaacaaa  300
cacggcttaa gcaattccat ttatgtgttt gttagagatc ctgccaagct tttccttgtt  360
gaccgctcct tgtatgggaa agaagacaac gacacgctgg tccgctgtcc tctcacagac  420
ccagaagtga ccaattattc cctcaagggg tgccagggga agcctcttcc caaggacttg  480
aggtttattc ctgaccccaa ggcgggcatc atgatcaaaa gtgtgaaacg cgcctaccat  540
cggctctgtc tgcattgttc tgtggaccag gagggcaagt cagtgctgtc ggaaaaattc  600
atcctgaaag tgaggccagc cttcaaagct gtgcctgttg tgtctgtgtc caaagcaagc  660
tatcttctta gggaagggga agaattcaca gtgacgtgca caataaaaga tgtgtctagt  720
tctgtgtact caacgtggaa aagagaaaac agtcagacta aactacagga gaaatataat  780
agctggcatc acggtgactt caattatgaa cgtcaggcaa cgttgactat cagttcagcg  840
agagttaatg attctggagt gttcatgtgt tatgccaata atacttttgg atcagcaaat  900
gtcacaacaa ccttggaagt agtagataaa ggattcatta atatcttccc catgataaac  960
actacagtat ttgtaaacga tggagaaaat gtagatttga ttgttgaata tgaagcattc  1020
cccaaacctg aacaccagca gtggatctat atgaacagaa ccttcactga taaatgggaa  1080
gattatccca agtctgagaa tgaaagtaat atcagatacg taagtgaact tcatctaacg  1140
agattaaaag gcaccgaagg aggcacttac acattcctag tgtccaattc tgacgtcaat  1200
gctgccatag catttaatgt ttatgtgaat acaaaaccag aaatcctgac ttacgacagg  1260
ctcgtgaatg gcatgctcca atgtgtggca gcaggattcc cagagcccac aatagattgg  1320
tatttttgtc caggaactga gcagagatgc tctgcttctg tactgccagt ggatgtgcag  1380
acactaaact catctgggcc accgtttgga aagctagtgg ttcagagttc tatagattct  1440
agtgcattca agcacaatgg cacggttgaa tgtaaggctt acaacgatgt gggcaagact  1500
tctgcctatt ttaactttgc atttaaaggt aacaacaaag agcaaatcca tccccacacc  1560
ctgttcactc ctttgctgat tggtttcgta atcgtagctg gcatgatgtg cattattgtg  1620
atgattctga cctacaaata tttacagaaa cccatgtatg aagtacagtg gaaggttgtt  1680
gaggagataa atggaaacaa ttatgtttac atagacccaa cacaacttcc ttatgatcac  1740
aaatgggagt ttcccagaaa caggctgagt tttgggaaaa ccctgggtgc tggagctttc  1800
gggaaggttg ttgaggcaac tgcttatggc ttaattaagt cagatgcggc catgactgtc  1860
gctgtaaaga tgctcaagcc gagtgcccat ttgacagaac gggaagccct catgtctgaa  1920
ctcaaagtcc tgagttacct tggtaatcac atgaatattg tgaatctact tggagcctgc  1980
accattggag ggcccaccct ggtcattaca gaatattgtt gctatggtga tcttttgaat  2040
tttttgagaa gaaaacgtga ttcatttatt tgttcaaagc aggaagatca tgcagaagct  2100
gcactttata agaatcttct gcattcaaag gagtcttcct gcagcgatag tactaatgag  2160
tacatggaca tgaaacctgg agtttcttat gttgtcccaa ccaaggccga caaaaggaga  2220
tctgtgagaa taggctcata catagaaaga gatgtgactc ccgccatcat ggaggatgac  2280
gagttggccc tagacttaga agacttgctg agcttttctt accaggtggc aaagggcatg  2340
gctttcctcg cctccaagaa ttgtattcac agagacttgg cagccagaaa tatcctcctt  2400
actcatggtc ggatcacaaa gatttgtgat tttggtctag ccagagacat caagaatgat  2460
tctaattatg tggttaaagg aaacgctcga ctacctgtga agtggatggc acctgaaagc  2520
attttcaact gtgtatacac gtttgaaagt gacgtctggt cctatgggat tttcctttgg  2580
gagctgttct ctttaggaag cagcccctat cctggaatgc cggtcgattc taagttctac  2640
aagatgatca aggaaggctt ccggatgctc agccctgaac acgcacctgc tgaaatgtat  2700
gacataatga agacttgctg ggatgcagat cccctaaaaa gaccaacatt caagcaaatt  2760
gttcagctaa ttgagaagca gatttcagag agcaccaatc atatttactc caacttagca  2820
```

```
aactgcagcc ccaaccgaca gaagcccgtg gtagaccatt ctgtgcggat caattctgtc  2880
ggcagcaccg cttcctcctc ccagcctctg cttgtgcacg acgatgtctg a           2931

SEQ ID NO: 65          moltype = AA  length = 2549
FEATURE                Location/Qualifiers
REGION                 1..2549
                       note = source = /note="mTor"
source                 1..2549
                       mol_type = protein
                       organism = Homo sapiens
SEQUENCE: 65
MLGTGPAAAT TAATTSSNVS VLQQFASGLK SRNEETRAKA AKELQHYVTM ELREMSQEES  60
TRFYDQLNHH IFELVSSSDA NERKGGILAI ASLIGVEGGN ATRIGRFANY LRNLLPSNDP  120
VVMEMASKAI GRLAMAGDTF TAEYVEFEVK RALEWLGADR NEGRRHAAVL VLRELAISVP  180
TFFFQQVQPF FDNIFVAVWD PKQAIREGAV AALRACLILT TQREPKEMQK PQWYRHTFEE  240
AEKGFDETLA KEKGMNRDDR IHGALLILNE LVRISSMEGE RLREEMEEIT QQQLVHDKYC  300
KDLMGFGTKP RHITPFTSFQ AVQPQQSNAL VGLLGYSSHQ GLMGFGTSPS PAKSTLVESR  360
CCRDLMEEKF DQVCQWVLKC RNSKNSLIQM TILNLLPRLA AFRPSAFTDT QYLQDTMNHV  420
LSCVKKEKER TAAFQALGLL SVAVRSEFKV YLPRVLDIIR AALPPKDFAH KRQKAMQVDA  480
TVFTCISMLA RAMGPGIQQD IKELLEPMLA VGLSPALTAV LYDLSRQIPQ LKKDIQDGLL  540
KMLSLVLMHK PLRHPGMPKG LAHQLASPGL TTLPEASDVG SITLALRTLG SFEFEGHSLT  600
QFVRHCADHF LNSEHKEIRM EAARTCSRLL TPSIHLISGH AHVVSQTAVQ VVADVLSKLL  660
VVGITDPDPD IRYCVLASLD ERFDAHLAQA ENLQALFVAL NDQVFEIREL AICTVGRLSS  720
MNPAFVMPFL RKMLIQILTE LEHSGIGRIK EQSARMLGHL VSNAPRLIRP YMEPILKALI  780
LKLKDPDPDP NPGVINNVLA TIGELAQVSG LEMRKWVDEL FIIIMDMLQD SSLLAKRQVA  840
LWTLGQLVAS TGYVVEPYRK YPTLLEVLLN FLKTEQNQGT RREAIRVLGL LGALDPYKHK  900
VNIGMIDQSR DASAVSLSES KSSQDSSDYS TSEMLVNMGN LPLDEFYPAV SMVALMRIFR  960
DQSLSHHHTM VVQAITFIFK SLGLKCVQFL PQVMPTFLNV IRVCDGAIRE FLFQQLGMLV  1020
SFVKSHIRPY MDEIVTLMRE FWVMNTSIQS TIILLIEQIV VALGGEFKLY LPQLIPHMLR  1080
VFMHDNSPGR IVSIKLLAAI QLFGANLDDY LHLLLPPIVK LFDAPEAPLP SRKAALETVD  1140
RLTESLDFTD YASRIIHPIV RTLDQSPELR STAMDTLSSL VFQLGKKYQI FIPMVNKVLV  1200
RHRINHQRYD VLICRIVKGY TLADEEEDPL IYQHRMLRSG QGDALASGPV ETGPMKKLHV  1260
STINLQKAWG AARRVSKDDW LEWLRRLSLE LLKDSSSPSL RSCWALAQAY NPMARDLFNA  1320
AFVSCWSELN EDQQDELIRS IELALTSQDI AEVTQTLLNL AEFMEHSDKG PLPLRDDNGI  1380
VLLGERAAKC RAYAKALHYK ELEFQKGPTP AILESLISIN NKLQQPEAAA GVLEYAMKHF  1440
GELEIQATWY EKLHEWEDAL VAYDKKMDTN KDDPELMLGR MRCLEALGEW GQLHQQCCEK  1500
WTLVNDETQA KMARMAAAAA WGLGQWDSME EYTCMIPRDT HDGAFYRAVL ALHQDLFSLA  1560
QQCIDKARDL LDAELTAMAG ESYSRAYGAM VSCHMLSELE EVIQYKLVPE RREIIRQIWW  1620
ERLQGCQRIV EDWQKILMVR SLVVSPHEDM RTWLKYASLC GKSGRLALAH KTLVLLLGVD  1680
PSRQLDHPLP TVHPQVTYAY MKNMWKSARK IDAFQHMQHF VQTMQQQAQH AIATEDQQHK  1740
QELHKLMARC FLKLGEWQLN LQGINESTIP KVLQYYSAAT EHDRSWYKAW HAWAVMNFEA  1800
VLHYKHQNQA RDEKKKLRHA SGANITNATT AATTAATATT TASTEGSNSE SEAESTENSP  1860
TPSPLQKKVT EDLSKTLLMY TVPAVQGFFR SISLSRGNNL QDTLRVLTLW FDYGHWPDVN  1920
EALVEGVKAI QIDTWLQVIP QLIARIDTPR PLVGRLIHQL LTDIGRYHPQ ALIYPLTVAS  1980
KSTTTARHNA ANKILKNMCE HSNTLVQQAM MVSEELIRVA ILWHEMWHEG LEEASRLYFG  2040
ERNVKGMFEV LEPLHAMMER GPQTLKETSF NQAYGRDLME AQEWCRKYMK SGNVKDLTQA  2100
WDLYYHVFRR ISKQLPQLTS LELQYVSPKL LMCRDLELAV PGTYDPNQPI IRIQSIAPSL  2160
QVITSKQRPR KLTLMGSNGH EFVFLLKGHE DLRQDERVMQ LFGLVNTLLA NDPTSLRKNL  2220
SIQRYAVIPL STNSGLIGWV PHCDTLHALI RDYREKKKIL LNIEHRIMLR MAPDYDHLTL  2280
MQKVEVFEHA VNNTAGDDLA KLLWLKSPSS EVWFDRRTNY TRSLAVMSMV GYILGLGDRH  2340
PSNLMLDRLS GKILHIDFGD CFEVAMTREK FPEKIPFRLT RMLTNAMEVT GLDGNYRITC  2400
HTVMEVLREH KDSVMAVLEA FVYDPLLNWR LMDTNTKGNK RSRTRTDSYS AGQSVEILDG  2460
VELGEPAHKK TGTTVPESIH SFIGDGLVKP EALNKKAIQI INRVRDKLTG RDFSHDDTLD  2520
VPTQVELLIK QATSHENLCQ CYIGWCPFW                                    2549

SEQ ID NO: 66          moltype = DNA  length = 7650
FEATURE                Location/Qualifiers
source                 1..7650
                       mol_type = genomic DNA
                       note = source = mTor
                       organism = Homo sapiens
SEQUENCE: 66
atgcttggaa ccggacctgc cgccgccacc accgctgcca ccacatctag caatgtgagc  60
gtcctgcagc agtttgccag tggcctaaag agccggaatg aggaaaccag ggccaaagcc  120
gccaaggagc tccagcacta tgtcaccatg gaactccgag agatgagtca agaggagtct  180
actcgcttct atgaccaact gaaccatcac atttttgaat tggtttccag ctcagatgcc  240
aatgagagga aaggtggcat cttggccata gctagcctca taggagtgga aggtgggaat  300
gccacccgaa ttggcagatt tgccaactat cttcggaacc tcctcccctc caatgaccca  360
gttgtcatgg aaatggcatc caaggccatt ggccgtcttg ccatggcagg ggacactttt  420
accgctgagt acgtggaatt tgaggtgaag cgagccctgg aatggctggg tgctgaccgc  480
aatgagggcc ggagacatgc agctgtcctg gttctccgtg agctggccat cagcgtccct  540
accttcttct tccagcaagt gcaacccttc tttgacaaca tttttgtggc cgtgtgggac  600
cccaaacagg ccatccgtga gggagctgta gccgcccttc gtgcctgtct gattctcaca  660
acccagcgtg agccgaagga gatgcagaag cctcagtggt acaggcacac atttgaagaa  720
gcagagaagg gatttgatga gaccttggcc aaagagaagg gcatgaatcg ggatgatcgg  780
atccatggag ccttgttgat ccttaacgag ctggtccgaa tcagcagcat ggagggagag  840
cgtctgagag aagaaatgga agaaatcaca cagcagcagc tggtacacga caagtactgc  900
aaagatctca tgggcttcgg aacaaaacct cgtcacatta ccccccttcac cagtttccag  960
gctgtacagc cccagcagtc aaatgccttg gtggggctgc tggggtacag ctctcaccaa  1020
```

```
ggcctcatgg gatttgggac ctcccccagt ccagctaagt ccaccctggt ggagagccgg  1080
tgttgcagag acttgatgga ggagaaattt gatcaggtgt gccagtgggt gctgaaatgc  1140
aggaatagca agaactcgct gatccaaatg acaatcctta atttgttgcc ccgcttggct  1200
gcattccgac cttctgcctt cacagatacc cagtatctcc aagataccat gaaccatgtc  1260
ctaagctgtg tcaagaagga gaaggaacgt acagcggcct tccaagccct ggggctactt  1320
tctgtggctg tgaggtctga gtttaaggtc tatttgcctc gcgtgctgga catcatccga  1380
gcggccctgc ccccaaagga cttcgcccat aagaggcaga aggcaatgca ggtggatgcc  1440
acagtcttca cttgcatcag catgctggct cgagcaatgg ggccaggcat ccagcaggat  1500
atcaaggagc tgctggagcc catgctggca gtgggactaa gccctgccct cactgcagtg  1560
ctctacgacc tgagccgtca gattccacag ctaaagaagg acattcaaga tgggctactg  1620
aaaatgctgt ccctggtcct tatgcacaaa ccccttcgcc acccaggcat gcccaagggc  1680
ctggcccatc agctggcctc tcctggcctc acgaccctcc ctgaggccag cgatgtgggc  1740
agcatcactc ttgccctccg aacgcttggc agctttgaat ttgaaggcca ctctctgacc  1800
caatttgttc gccactgtgc ggatcatttc ctgaacagtg agcacaagga gatccgcatg  1860
gaggctgccc gcacctgctc ccgcctgctc acaccctcca tccacctcat cagtggccat  1920
gctcatgtgg ttagccagac cgcagtgcaa gtggtggcag atgtgcttag caaactgctc  1980
gtagttggga taacagatcc tgaccctgac attcgctact gtgtcttggc gtccctggac  2040
gagcgctttg atgcacacct ggcccaggcg gagaacttgc aggccttgtt tgtggctctg  2100
aatgaccagg tgtttgagat ccgggagctg gccatctgca ctgtgggccg actcagtagc  2160
atgaaccctg cctttgtcat gcctttcctg cgcaagatgc tcatccagat tttgacagag  2220
ttggagcaca gtgggattgg aagaatcaaa gagcagagtg cccgcatgct ggggcacctg  2280
gtctccaatg ccccccgact catccgcccc tacatggagc ctattctgaa ggcattaatt  2340
ttgaaactga aagatccaga ccctgatcca aacccaggtg tgatcaataa tgtcctggca  2400
acaataggag aattggcaca ggttagtggc ctggaaatga ggaaatgggt tgatgaactt  2460
tttattatca tcatggacat gctccaggat tcctctttgt tggccaaaag gcaggtggct  2520
ctgtggaccc tgggacagtt ggtggccagc actggctatg tagtagagcc ctacaggaag  2580
taccctactt tgcttgaggt gctactgaat tttctgaaga ctgagcagaa ccagggtaca  2640
cgcagagagg ccatccgtgt gttagggctt ttaggggctt tggatcctta caagcacaaa  2700
gtgaacattg gcatgataga ccagtcccgg gatgcctctg ctgtcagcct gtcagaatcc  2760
aagtcaagtc aggattcctc tgactatagc actagtgaaa tgctggtcaa catgggaaac  2820
ttgcctctgg atgagttcta cccagctgtg tccatggtgg ccctgatgcg gatcttccga  2880
gaccagtcac tctctcatca tcacaccatg gttgtccagg ccatcacctt catcttcaag  2940
tccctgggac tcaaatgtgt gcagttcctg ccccaggtca tgcccacgtt ccttaacgtc  3000
attcgagtct gtgatggggc catccgggaa tttttgttcc agcagctggg aatgttggtg  3060
tcctttgtga agagccacat cagaccttat atggatgaaa tagtcaccct catgagagaa  3120
ttctgggtca tgaacacctc aattcagagc acgatcattc ttctcattga gcaaattgtg  3180
gtagctcttg gggggtgaatt taagctctac ctgccccagc tgatcccaca catgctgcgt  3240
gtcttcatgc atgacaacag cccaggccgc attgtctcta tcaagttact ggctgcaatc  3300
cagctgtttg gcgccaacct ggatgactac ctgcatttac tgctgcctcc tattgttaag  3360
ttgtttgatg cccctgaagc tccactgcca tctcgaaagg cagcgctaga gactgtggac  3420
cgcctgacgg agtccctgga tttcactgac tatgcctccc ggatcattca ccctattgtt  3480
cgaacactgg accagagccc agaactgcgc tccacagcca tggacacgct gtcttcactt  3540
gtttttcagc tggggaagaa gtaccaaatt ttcattccaa tggtgaataa agttctggtg  3600
cgacaccgaa tcaatcatca gcgctatgat gtgctcatct gcagaattgt caagggatac  3660
acacttgctg atgaagagga ggatcctttg atttaccagc atcggatgct taggagtggc  3720
caaggggatg cattggctag tggaccagtg gaaacaggac ccatgaagaa actgcacgtc  3780
agcaccatca acctccaaaa ggcctggggc gctgccagga gggtctccaa agatgactgg  3840
ctggaatggc tgagacggct gagcctggag ctgctgaagg actcatcatc gccctccctg  3900
cgctcctgct gggccctggc acaggcctac aacccgatgg ccagggatct cttcaatgct  3960
gcatttgtgt cctgctggtc tgaactgaat gaagatcaac aggatgagct catcagaagc  4020
atcgagttgg ccctcacctc acaagacatc gctgaagtca cacagaccct cttaaacttg  4080
gctgaattca tggaacacag tgacaagggc cccctgccac tgagagatga caatggcatt  4140
gttctgctgg gtgagagagc tgccaagtgc cgagcatatg ccaaagcact acactacaaa  4200
gaactggagt tccagaaagg ccccacccct gccattctag aatctctcat cagcattaat  4260
aataagctac agcagccgga ggcagcggcc ggagtgttag aatatgccat gaaacacttt  4320
ggagagctgg agatccaggc tacctggtat gagaaactgc acgagtggga ggatgccctt  4380
gtggcctatg acaagaaaat ggacaccaac aaggacgacc cagagctgat gctgggccgc  4440
atgcgctgcc tcgaggcctt gggggaatgg ggtcaactcc accagcagtg ctgtgaaaag  4500
tggaccctgg ttaatgatga gacccaagcc aagatggccc ggatggctgc tgcagctgca  4560
tggggtttag gtcagtggga cagcatggaa gaatacacct gtatgatccc tcgggacacc  4620
catgatgggg cattttatag agctgtgctg gcactgcatc aggacctctt ctccttggca  4680
caacagtgca ttgacaaggc cagggacctg ctggatgctg aattaactgc gatggcagga  4740
gagagttaca gtcgggcata tggggccatg gtttcttgcc acatgctgtc cgagctggag  4800
gaggttatcc agtacaaact tgtccccgag cgacgagaga tcatccgcca gatctggtgg  4860
gagagactgc agggctgcca gcgtatcgta gaggactggc agaaaatcct tatggtgcgg  4920
tcccttgtgg tcagccctca tgaagacatg agaacctggc tcaagtatgc aagcctgtgc  4980
ggcaagagtg gcaggctggc tcttgctcat aaaactttag tgttgctcct gggagttgat  5040
ccgtctcggc aacttgacca tcctctgcca acagttcacc ctcaggtgac ctatgcctac  5100
atgaaaaaca tgtggaagag tgcccgcaag atcgatgcct tccagcacat gcagcatttt  5160
gtccagacca tgcagcaaca ggcccagcat gccatcgcta ctgaggacca gcagcataag  5220
caggaactgc acaagctcat ggcccgatgc ttcctgaaac ttggagagtg gcagctgaat  5280
ctacagggca tcaatgagag cacaatcccc aaagtgctgc agtactacag cgccgccaca  5340
gagcacgacc gcagctggta caaggcctgg catgcgtggg cagtgatgaa cttcgaagct  5400
gtgctacact acaaacatca gaaccaagcc cgcgatgaga agaagaaact gcgtcatgcc  5460
agcggggcca acatcaccaa cgccaccact gccgccacca cggccgccac tgccaccacc  5520
actgccagca ccgagggcag caacagtgag agcgaggccg agagcaccga gaacagcccc  5580
accccatcgc cgctgcagaa gaaggtcact gaggatctgt ccaaaaccct cctgatgtac  5640
acggtgcctg ccgtccaggg cttcttccgt tccatctcct tgtcacgagg caacaacctc  5700
caggatacac tcagagttct caccttatgg tttgattatg gtcactggcc agatgtcaat  5760
```

```
gaggccttag tggagggggt gaaagccatc cagattgata cctggctaca ggttatacct  5820
cagctcattg caagaattga tacgcccaga cccttggtgg gacgtctcat tcaccagctt  5880
ctcacagaca ttggtcggta ccacccccag gccctcatct acccactgac agtggcttct  5940
aagtctacca cgacagcccg gcacaatgca gccaacaaga ttctgaagaa catgtgtgag  6000
cacagcaaca ccctggtcca gcaggccatg atggtgagcg aggagctgat ccgagtggcc  6060
atcctctggc atgagatgtg gcatgaaggc ctggaagagg catctcgttt gtactttggg  6120
gaaaggaacg tgaaaggcat gtttgaggtg ctggagccct tgcatgctat gatggaacgg  6180
ggcccccaga ctctgaagga aacatccttt aatcaggcct atggtcgaga tttaatggag  6240
gcccaagagt ggtgcaggaa gtacatgaaa tcagggaatg tcaaggacct cacccaagcc  6300
tgggacctct attatcatgt gttccgacga atctcaaagc agctgcctca gctcacatcc  6360
ttagagctgc aatatgtttc cccaaaactt ctgatgtgcc gggaccttga attggctgtg  6420
ccaggaacat atgaccccaa ccagccaatc attcgcattc agtccatagc accgtctttg  6480
caagtcatca catccaagca gaggccccgg aaattgacac ttatgggcag caacggacat  6540
gagtttgttt tccttctaaa aggccatgaa gatctgcgcc aggatgagcg tgtgatgcag  6600
ctcttcggcc tggttaacac ccttctggcc aatgacccaa catctcttcg gaaaaacctc  6660
agcatccaga gatacgctgt catcccttta tcgaccaact cgggcctcat tggctgggtt  6720
ccccactgtg acacactgca cgccctcatc cgggactaca gggagaagaa gaagatcctt  6780
ctcaacatcg agcatcgcat catgttgcgg atggctccgg actatgacca cttgactctg  6840
atgcagaagg tggaggtgtt tgagcatgcc gtcaataata cagctgggga cgacctggcc  6900
aagctgctgt ggctgaaaag ccccagctcc gaggtgtggt ttgaccgaag aaccaattat  6960
acccgttctt tagcggtcat gtcaatggtt gggtatattt taggcctggg agatagacac  7020
ccatccaacc tgatgctgga ccgtctgagt gggaagatcc tgcacattga ctttggggac  7080
tgctttgagg ttgctatgac ccgagagaag tttccagaga agattccatt tagactaaca  7140
agaatgttga ccaatgctat ggaggttaca ggcctggatg gcaactacag aatcacatgc  7200
cacacagtga tggaggtgct gcgagagcac aaggacagtg tcatggccgt gctggaagcc  7260
tttgtctatg accccttgct gaactggagg ctgatggaca caaataccaa aggcaacaag  7320
cgatcccgaa cgaggacgga ttcctactct gctggccagt cagtcgaaat tttggacggt  7380
gtggaacttg gagagccagc ccataagaaa acggggacca cagtgccaga atctattcat  7440
tctttcattg gagacggttt ggtgaaacca gaggccctaa ataagaaagc tatccagatt  7500
attaacaggg ttcgagataa gctcactggt cgggacttct ctcatgatga cactttggat  7560
gttccaacgc aagttgagct gctcatcaaa caagcgacat cccatgaaaa cctctgccag  7620
tgctatattg gctggtgccc tttctggtaa                                   7650
```

```
SEQ ID NO: 67          moltype = AA  length = 1147
FEATURE                Location/Qualifiers
REGION                 1..1147
                       note = source = /note="SREBP1"
source                 1..1147
                       mol_type = protein
                       organism = Homo sapiens
SEQUENCE: 67
MDEPPFSEAA LEQALGEPCD LDAALLTDIE DMLQLINNQD SDFPGLFDPP YAGSGAGGTD  60
PASPDTSSPG SLSPPPATLS SSLEAFLSGP QAAPSPLSPP QPAPTPLKMY PSMPAFSPGP  120
GIKEESVPLS ILQTPTPQPL PGALLPQSFP APAPPQFSST PVLGYPSPPG GFSTGSPPGN  180
TQQPLPGLPL ASPPGVPPVS LHTQVQSVVP QQLLTVTAAP TAAPVTTTVT SQIQQVPVLL  240
QPHFIKADSL LLTAMKTDGA TVKAAGLSPL VSGTTVQTGP LPTLVSGGTI LATVPLVVDA  300
EKLPINRLAA GSKAPASAQS RGEKRTAHNA IEKRYRSSIN DKIIELKDLV VGTEAKLNKS  360
AVLRKAIDYI RFLQHSNQKL KQENLSLRTA VHKSKSLKDL VSACGSGGNT DVLMEGVKTE  420
VEDTLTPPPS DAGSPFQSSP LSLGSRGSGS GGSGSDSEPD SPVFEDSKAK PEQRPSLHSR  480
GMLDRSRLAL CTLVFLCLSC NPLASLLGAR GLPSPSDTTS VYHSPGRNVL GTESRDGPGW  540
AQWLLPPVVW LLNGLLVLVS LVLLFVYGEP VTRPHSGPAV YFWRHRKQAD LDLARGDFAQ  600
AAQQLWLALR ALGRPLPTSH LDLACSLLWN LIRHLLQRLW VGRWLAGRAG GLQQDCALRV  660
DASASARDAA LVYHKLHQLH TMGKHTGGHL TATNLALSAL NLAECAGDAV SVATLAEIYV  720
AAALRVKTSL PRALHFLTRF FLSSARQACL AQSGSVPPAM QWLCHPVGHR FFVDGDWSVL  780
STPWESLYSL AGNPVDPLAQ VTQLFREHLL ERALNCVTQP NPSPGSADGD KEFSDALGYL  840
QLLNSCSDAA GAPAYSFSIS SSMATTTGVD PVAKWWASLT AVVIHWLRRD EEAAERLCPL  900
VEHLPRVLQE SERPLPRAAL HSFKAARALL GCAKAESGPA SLTICEKASG YLQDSLATTP  960
ASSSIDKAVQ LFLCDLLLVV RTSLWRQQQP PAPAPAAQGT SSRPQASALE LRGFQRDLSS  1020
LRRLAQSFRP AMRRVFLHEA TARLMAGASP TRTHQLLDRS LRRRAGPGGK GGAVAELEPR  1080
PTRREHAEAL LLASCYLPPG FLSAPGQRVG MLAEAARTLE KLGDRRLLHD CQQMLMRLGG  1140
GTTVTSS                                                            1147
```

```
SEQ ID NO: 68          moltype = DNA  length = 3444
FEATURE                Location/Qualifiers
source                 1..3444
                       mol_type = genomic DNA
                       note = source = SREBP1
                       organism = Homo sapiens
SEQUENCE: 68
atggacgagc cacccttcag cgaggcggct ttggagcagg cgctgggcga gccgtgcgat  60
ctggacgcgg cgctgctgac cgacatcgaa gacatgcttc agcttatcaa caaccaagac  120
agtgacttcc ctggcctatt tgacccaccc tatgctggga gtggggcagg gggcacagac  180
cctgccagcc ccgataccag ctccccaggc agcttgtctc cacctcctgc cacattgagc  240
tcctctcttg aagccttcct gagcgggccg caggcagcgc cctcacccct gtcccctccc  300
cagcctgcac ccactccatt gaagatgtac ccgtccatgc ccgctttctc ccctgggcct  360
ggtatcaagg aagagtcagt gccactgagc atcctgcaga cccccacccc acagcccctg  420
ccaggggccc tcctgccaca gagcttccca gccccagccc caccgcagtt cagctccacc  480
cctgtgttag gctaccccag ccctccggga ggcttctcta caggaagccc tcccgggaac  540
acccagcagc cgctgcctgg cctgccactg gcttccccgc caggggtccc gcccgtctcc  600
```

-continued

```
ttgcacaccc aggtccagag tgtggtcccc cagcagctac tgacagtcac agctgccccc  660
acggcagccc ctgtaacgac cactgtgacc tcgcagatcc agcaggtccc ggtcctgctg  720
cagccccact tcatcaaggc agactcgctg cttctgacag ccatgaagac agacggagcc  780
actgtgaagg cggcaggtct cagtcccctg gtctctggca ccactgtgca gacagggcct  840
ttgccgaccc tggtgagtgg cggaaccatc ttggcaacag tcccactggt cgtagatgcg  900
gagaagctgc ctatcaaccg gctcgcagct ggcagcaagg ccccggcctc tgcccagagc  960
cgtggagaga agcgcacagc ccacaacgcc attgagaagc gctaccgctc ctccatcaat  1020
gacaaaatca ttgagctcaa ggatctggtg gtgggcactg aggcaaagct gaataaatct  1080
gctgtcttgc gcaaggccat cgactacatt cgctttctgc aacacagcaa ccagaaactc  1140
aagcaggaga acctaagtct gcgcactgct gtccacaaaa gcaaatctct gaaggatctg  1200
gtgtcggcct gtggcagtgg agggaacaca gacgtgctca tggagggcgt gaagactgag  1260
gtggaggaca cactgacccc accccccctcg gatgctggct cacctttcca gagcagcccc  1320
ttgtcccttg gcagcagggg cagtggcagc ggtggcagtg gcagtgactc ggagcctgac  1380
agcccagtct ttgaggacag caaggcaaag ccagagcagc ggccgtctct gcacagccgg  1440
ggcatgctgg accgctcccg cctggccctg tgcacgctcg tcttcctctg cctgtcctgc  1500
aacccccttgg cctccttgct gggggcccgg gggcttccca gcccctcaga taccaccagc  1560
gtctaccata gccctgggcg caacgtgctg ggcaccgaga gcagagatgg ccctggctgg  1620
gcccagtggc tgctgccccc agtggtctgg ctgctcaatg ggctgttggt gctcgtctcc  1680
ttggtgcttc tctttgtcta cggtgagcca gtcacacggc cccactcagg ccccgccgtg  1740
tacttctgga ggcatcgcaa gcaggctgac ctggacctgg cccggggaga ctttgcccag  1800
gctgcccagc agctgtggct ggccctgcgg gcactgggcc ggcccctgcc cacctcccac  1860
ctggacctgg cttgtagcct cctctggaac ctcatccgtc acctgctgca gcgtctctgg  1920
gtgggccgct ggctggcagg ccgggcaggg ggcctgcagc aggactgtgc tctgcgagtg  1980
gatgctagcg ccagcgcccg agacgcagcc ctggtctacc ataagctgca ccagctgcac  2040
accatgggga agcacacagg cgggcacctc actgccacca acctggcgct gagtgccctg  2100
aacctggcag agtgtgcagg ggatgccgtg tctgtggcga cgctggccga gatctatgtg  2160
gcggctgcat tgagagtgaa gaccagtctc ccacgggcct tgcattttct gacacgcttc  2220
ttcctgagca gtgcccgcca ggcctgcctg gcacagagtg gctcagtgcc tcctgccatg  2280
cagtggctct gccaccccgt gggccaccgt ttcttcgtgg atggggactg gtccgtgctc  2340
agtaccccat gggagagcct gtacagcttg gccgggaacc cagtggaccc cctggcccag  2400
gtgactcagc tattccggga acatctctta gagcgagcac tgaactgtgt gacccagccc  2460
aaccccagcc ctgggtcagc tgatggggac aaggaattct cggatgccct cgggtacctg  2520
cagctgctga acagctgttc tgatgctgcg ggggctcctg cctacagctt ctccatcagt  2580
tccagcatgg ccaccaccac cggcgtagac ccggtggcca agtggtgggc ctctctgaca  2640
gctgtggtga tccactggct gcggcgggat gaggaggcgg ctgagcggct gtgcccgctg  2700
gtggagcacc tgccccgggt gctgcaggag tctgagagac ccctgcccag ggcagctctg  2760
cactccttca aggctgcccg ggccctgctg ggctgtgcca aggcagagtc tggtccagcc  2820
agcctgacca tctgtgagaa ggccagtggg tacctgcagg acagcctggc taccacacca  2880
gccagcagct ccattgacaa ggccgtgcag ctgttcctgt gtgacctgct tcttgtggtg  2940
cgcaccagcc tgtggcggca gcagcagccc ccggccccgg ccccagcagc ccagggcacc  3000
agcagcaggc cccaggcttc cgcccttgag ctgcgtggct tccaacggga cctgagcagc  3060
ctgaggcggc tggcacagag cttccggccc gccatgcgga gggtgttcct acatgaggcc  3120
acggcccggc tgatggcggg ggccagcccc acacggacac accagctcct cgaccgcagt  3180
ctgaggcggc gggcaggccc cggtggcaaa ggaggcgcgg tggcggagct ggagccgcgg  3240
cccacgcggc gggagcacgc ggaggccttg ctgctggcct cctgctacct gcccccggc  3300
ttcctgtcgg cgcccgggca gcgcgtgggc atgctggctg aggcggcgcg cacactcgag  3360
aagcttggcg atcgccggct gctgcacgac tgtcagcaga tgctcatgcg cctgggcggt  3420
gggaccactg tcacttccag ctag                                        3444
```

```
SEQ ID NO: 69          moltype = AA  length = 138
FEATURE                Location/Qualifiers
REGION                 1..138
                       note = source = /note="Interferon-gamma"
source                 1..138
                       mol_type = protein
                       organism = Homo sapiens
SEQUENCE: 69
QDPYVKEAEN LKKYFNAGHS DVADNGTLFL GILKNWKEES DRKIMQSQIV SFYFKLFKNF  60
KDDQSIQKSV ETIKEDMNVK FFNSNKKKRD DFEKLTNYSV TDLNVQRKAI HELIQVMAEL  120
SPAAKTGKRK RSQMLFRG                                                138
```

```
SEQ ID NO: 70          moltype = DNA  length = 414
FEATURE                Location/Qualifiers
source                 1..414
                       mol_type = genomic DNA
                       note = source = Interferon-gamma
                       organism = Homo sapiens
SEQUENCE: 70
caggacccat atgtaaaaga agcagaaaac cttaagaaat attttaatgc aggtcattca  60
gatgtagcgg ataatggaac tcttttctta ggcattttga agaattggaa agaggagagt  120
gacagaaaaa taatgcagag ccaaattgtc tccttttact tcaaactttt taaaaacttt  180
aaagatgacc agagcatcca aaagagtgtg gagaccatca aggaagacat gaatgtcaag  240
tttttcaata gcaacaaaaa gaaacgagat gacttcgaaa agctgactaa ttattcggta  300
actgacttga atgtccaacg caaagcaata catgaactca tccaagtgat ggctgaactg  360
tcgccagcag ctaaaacagg gaagcgaaaa aggagtcaga tgctgtttcg aggt        414
```

```
SEQ ID NO: 71          moltype = AA  length = 227
FEATURE                Location/Qualifiers
REGION                 1..227
```

```
                        note = source = /note="Granzyme B"
source                  1..227
                        mol_type = protein
                        organism = Homo sapiens
SEQUENCE: 71
IIGGHEAKPH SRPYMAYLMI WDQKSLKRCG GFLIRDDFVL TAAHCWGSSI NVTLGAHNIK  60
EQEPTQQFIP VKRPIPHPAY NPKNFSNDIM LLQLERKAKR TRAVQPLRLP SNKAQVKPGQ  120
TCSVAGWGQT APLGKHSHTL QEVKMTVQED RKCESDLRHY YDSTIELCVG DPEIKKTSFK  180
GDSGGPLVCN KVAQGIVSYG RNNGMPPRAC TKVSSFVHWI KKTMKRY                227

SEQ ID NO: 72           moltype = DNA  length = 681
FEATURE                 Location/Qualifiers
source                  1..681
                        mol_type = genomic DNA
                        note = source = Granzyme B
                        organism = Homo sapiens
SEQUENCE: 72
atcatcgggg gacatgaggc caagccccac tcccgcccct acatggctta tcttatgatc  60
tgggatcaga agtctctgaa gaggtgcggt ggcttcctga tacgagacga cttcgtgctg  120
acagctgctc actgttgggg aagctccata aatgtcacct tgggggccca caatatcaaa  180
gaacaggagc cgacccagca gtttatccct gtgaaaagac ccatccccca tccagcctat  240
aatcctaaga acttctccaa cgacatcatg ctactgcagc tggagagaaa ggccaagcgg  300
accagagctg tgcagcccct caggctacct agcaacaagg cccaggtgaa gccagggcag  360
acatgcagtg tggccggctg ggggcagacg gcccccctgg gaaaacactc acacacacta  420
caagaggtga agatgacagt gcaggaagat cgaaagtgcg aatctgactt acgccattat  480
tacgacagta ccattgagtt gtgcgtgggg gacccagaga ttaaaaagac ttcctttaag  540
ggggactctg gaggccctct tgtgtgtaac aaggtggccc agggcattgt ctcctatgga  600
cgaaacaatg gcatgcctcc acgagcctgc accaaagtct caagctttgt acactggata  660
aagaaaacca tgaaacgcta c                                            681

SEQ ID NO: 73           moltype = AA  length = 268
FEATURE                 Location/Qualifiers
REGION                  1..268
                        note = source = /note="PD-1"
source                  1..268
                        mol_type = protein
                        organism = Homo sapiens
SEQUENCE: 73
PGWFLDSPDR PWNPPTFSPA LLVVTEGDNA TFTCSFSNTS ESFVLNWYRM SPSNQTDKLA  60
AFPEDRSQPG QDCRFRVTQL PNGRDFHMSV VRARRNDSGT YLCGAISLAP KAQIKESLRA  120
ELRVTERRAE VPTAHPSPSP RPAGQFQTLV VGVVGGLLGS LVLLVWVLAV ICSRAARGTI  180
GARRTGQPLK EDPSAVPVFS VDYGELDFQW REKTPEPPVP CVPEQTEYAT IVFPSGMGTS  240
SPARRGSADG PRSAQPLRPE DGHCSWPL                                     268

SEQ ID NO: 74           moltype = AA  length = 272
FEATURE                 Location/Qualifiers
REGION                  1..272
                        note = source = /note="PD-L1"
source                  1..272
                        mol_type = protein
                        organism = Homo sapiens
SEQUENCE: 74
FTVTVPKDLY VVEYGSNMTI ECKFPVEKQL DLAALIVYWE MEDKNIIQFV HGEEDLKVQH  60
SSYRQRARLL KDQLSLGNAA LQITDVKLQD AGVYRCMISY GGADYKRITV KVNAPYNKIN  120
QRILVVDPVT SEHELTCQAE GYPKAEVIWT SSDHQVLSGK TTTTNSKREE KLFNVTSTLR  180
INTTTNEIFY CTFRRLDPEE NHTAELVIPE LPLAHPPNER THLVILGAIL LCLGVALTFI  240
FRLRKGRMMD VKKCGIQDTN SKKQSDTHLE ET                                272

SEQ ID NO: 75           moltype = AA  length = 223
FEATURE                 Location/Qualifiers
REGION                  1..223
                        note = source = /note="TIGIT"
source                  1..223
                        mol_type = protein
                        organism = Homo sapiens
SEQUENCE: 75
MMTGTIETTG NISAEKGGSI ILQCHLSSTT AQVTQVNWEQ QDQLLAICNA DLGWHISPSF  60
KDRVAPGPGL GLTLQSLTVN DTGEYFCIYH TYPDGTYTGR IFLEVLESSV AEHGARFQIP  120
LLGAMAATLV VICTAVIVVV ALTRKKKALR IHSVEGDLRR KSAGQEEWSP SAPSPPGSCV  180
QAEAAPAGLC GEQRGEDCAE LHDYFNVLSY RSLGNCSFFT ETG                    223

SEQ ID NO: 76           moltype = AA  length = 311
FEATURE                 Location/Qualifiers
REGION                  1..311
                        note = source = /note="CD1A"
source                  1..311
                        mol_type = protein
                        organism = Homo sapiens
SEQUENCE: 76
```

```
NADGLKEPLS FHVTWIASFY NHSWKQNLVS GWLSDLQTHT WDSNSSTIVF LCPWSRGNFS  60
NEEWKELETL FRIRTIRSFE GIRRYAHELQ FEYPFEIQVT GGCELHSGKV SGSFLQLAYQ  120
GSDFVSFQNN SWLPYPVAGN MAKHFCKVLN QNQHENDITH NLLSDTCPRF ILGLLDAGKA  180
HLQRQVKPEA WLSHGPSPGP GHLQLVCHVS GFYPKPVWVM WMRGEQEQQG TQRGDILPSA  240
DGTWYLRATL EVAAGEADL SCRVKHSSLE GQDIVLYWEH HSSVGFIILA VIVPLLLLIG  300
LALWFRKRCF C                                                       311

SEQ ID NO: 77           moltype = AA  length = 279
FEATURE                 Location/Qualifiers
REGION                  1..279
                        note = source = /note="TIM3"
source                  1..279
                        mol_type = protein
                        organism = Homo sapiens
SEQUENCE: 77
SEVEYRAEVG QNAYLPCFYT PAAPGNLVPV CWGKGACPVF ECGNVVLRTD ERDVNYWTSR  60
YWLNGDFRKG DVSLTIENVT LADSGIYCCR IQIPGIMNDE KFNLKLVIKP AKVTPAPTRQ  120
RDFTAAFPRM LTTRGHGPAE TQTLGSLPDI NLTQISTLAN ELRDSRLAND LRDSGATIRI  180
GIYIGAGICA GLALALIFGA LIFKWYSHSK EKIQNLSLIS LANLPPSGLA NAVAEGIRSE  240
ENIYTIEENV YEVEEPNEYY CYVSSRQQPS QPLGCRFAM                         279

SEQ ID NO: 78           moltype = AA  length = 133
FEATURE                 Location/Qualifiers
REGION                  1..133
                        note = source = /note="IL-2"
source                  1..133
                        mol_type = protein
                        organism = Homo sapiens
SEQUENCE: 78
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 79           moltype = AA  length = 152
FEATURE                 Location/Qualifiers
REGION                  1..152
                        note = source = /note="IL-7"
source                  1..152
                        mol_type = protein
                        organism = Homo sapiens
SEQUENCE: 79
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EH                                152

SEQ ID NO: 80           moltype = AA  length = 197
FEATURE                 Location/Qualifiers
REGION                  1..197
                        note = source = /note="IL-12alpha"
source                  1..197
                        mol_type = protein
                        organism = Homo sapiens
SEQUENCE: 80
RNLPVATPDP GMFPCLHHSQ NLLRAVSNML QKARQTLEFY PCTSEEIDHE DITKDKTSTV  60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNAS                                                 197

SEQ ID NO: 81           moltype = AA  length = 306
FEATURE                 Location/Qualifiers
REGION                  1..306
                        note = source = /note="IL-12beta"
source                  1..306
                        mol_type = protein
                        organism = Homo sapiens
SEQUENCE: 81
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCS                                                             306

SEQ ID NO: 82           moltype = AA  length = 114
FEATURE                 Location/Qualifiers
REGION                  1..114
                        note = source = /note="IL-15"
source                  1..114
                        mol_type = protein
```

```
                         organism = Homo sapiens
SEQUENCE: 82
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 83            moltype = AA  length = 133
FEATURE                  Location/Qualifiers
REGION                   1..133
                         note = source = /note="IL-21"
source                   1..133
                         mol_type = protein
                         organism = Homo sapiens
SEQUENCE: 83
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDS                                                    133

SEQ ID NO: 84            moltype = AA  length = 270
FEATURE                  Location/Qualifiers
REGION                   1..270
                         note = source = /note="IL-33"
source                   1..270
                         mol_type = protein
                         organism = Homo sapiens
SEQUENCE: 84
MKPKMKYSTN KISTAKWKNT ASKALCFKLG KSQQKAKEVC PMYFMKLRSG LMIKKEACYF  60
RRETTKRPSL KTGRKHKRHL VLAACQQQST VECFAFGISG VQKYTRALHD SSITGISPIT  120
EYLASLSTYN DQSITFALED ESYEIYVEDL KKDEKKDKVL LSYYESQHPS NESGDGVDGK  180
MLMVTLSPTK DFWLHANNKE HSVELHKCEK PLPDQAFFVL HNMHSNCVSF ECKTDPGVFI  240
GVKDNHLALI KVDSSENLCT ENILFKLSET                                  270

SEQ ID NO: 85            moltype = AA  length = 696
FEATURE                  Location/Qualifiers
source                   1..696
                         mol_type = protein
                         organism = synthetic construct
SEQUENCE: 85
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEINRGGG GSGGGGSGGG  120
GSQVQLQQSG AELARPGASV KMSCKASGYT FTRYTMHWVK QRPGQGLEWI GYINPSRGYT  180
NYNQKFKDKA TLTTDKSSST AYMQLSSLTS EDSAVYYCAR YYDDHYCLDY WGQGTTLTVS  240
SSGTTNTVAA YNLTWKSTNF KTILEWEPKP VNQVYTVQIS TKSGDWKSKC FYTTDTECDL  300
TDEIVKDVKQ TYLARVFSYP AGNVESTGSA GEPLYENSPE FTPYLETNLG QPTIQSFEQV  360
GTKVNVTVED ERTLVRRNNT FLSLRDVFGK DLIYTLYYWK SSSSGKKTAK TNTNEFLIDV  420
DKGENYCFSV QAVIPSRTVN RKSTDSPVEC MGQEKGEFRE VQLQQSGPEL VKPGASVKMS  480
CKASGYTFTS YVIQWVKQKP GQGLEWIGSI NPYNDYTKYN EKFKGKATLT SDKSSITAYM  540
EFSSLTSEDS ALYYCARWGD GNYWGRGTTL TVSSGGGGSG GGGSGGGGSD IEMTQSPAIM  600
SASLGERVTM TCTASSSVSS SYFHWYQQKP GSSPKLCIYS TSNLASGVPP RFSGSGSTSY  660
SLTISSMEAE DAATYFCHQY HRSPTFGGGT KLETKR                            696

SEQ ID NO: 86            moltype = DNA  length = 2088
FEATURE                  Location/Qualifiers
source                   1..2088
                         mol_type = other DNA
                         organism = synthetic construct
SEQUENCE: 86
cagatcgtgc tgacccaaag ccccgccatc atgagcgcta gccccggtga gaaggtgacc  60
atgacatgct ccgcttccag ctccgtgtcc tacatgaact ggtatcagca gaaaagcgga  120
accagcccca aaaggtggat ctacgacacc agcaagctgg cctccggagt gcccgctcat  180
ttccggggct ctggatccgg caccagctac tctttaacca tttccggcat ggaagctgaa  240
gacgctgcca cctactattg ccagcaatgg agcagcaacc ccttcacatt cggatctggc  300
accaagctcg aaatcaatcg tggaggaggt ggcagcggcg gcggtggatc cggcggagga  360
ggaagccaag ttcaactcca gcagagcggc gctgaactgg cccggcccgg cgcctccgtc  420
aagatgagct gcaaggcttc cggctataca tttactcgtt acacaatgca ttgggtcaag  480
cagaggcccg gtcaaggttt agagtggatc ggatatatca acccttcccg gggctacacc  540
aactataacc aaaagttcaa ggataaagcc actttaacca ctgacaagag ctcctccacc  600
gcctacatgc agctgtcctc tttaaccagc gaggactccg ctgtttacta ctgcgctagg  660
tattacgacg accactactg tttagactat tggggacaag gtaccacttt aaccgtcagc  720
agctccggca ccaccaatac cgtggccgct tataacctca catggaagag caccaacttc  780
aagacaattc tggaatggga acccaagccc gtcaatcaag tttacaccgt gcagatctcc  840
accaaatccg gagactggaa gagcaagtgc ttctacacaa cagacaccga gtgtgattta  900
accgacgaaa tcgtcaagga cgtcaagcaa acctatctgg ctcgggtctt ttcctacccc  960
gctggcaatg tcgagtccac cggctccgct ggcgagcctc tctacgagaa ttcccccgaa  1020
ttcacccctt atttagagac caatttaggc cagcctacca tccagagctt cgagcaagtt  1080
ggcaccaagg tgaacgtcac cgtcgaggat gaaaggactt tagtgcggcg gaataacaca  1140
tttttatccc tccgggatgt gttcggcaaa gacctcatct acacactgta ctattggaag  1200
tccagctcct ccggcaaaaa gaccgctaag accaacacca acgagttttt aattgacgtg  1260
gacaaaggcg agaactactg cttcagcgtg caagccgtga tcccttctcg taccgtcaac  1320
cggaagagca cagattcccc cgttgagtgc atgggccaag aaaagggcga gttccgggag  1380
```

```
gtccagctgc agcagagcgg acccgaactc gtgaaacccg gtgcttccgt gaaaatgtct  1440
tgtaaggcca gcggatacac cttcacctcc tatgtgatcc agtgggtcaa acagaagccc  1500
ggacaaggtc tcgagtggat cggcagcatc aacccttaca acgactatac caaatacaac  1560
gagaagttta agggaaaggc tactttaacc tccgacaaaa gctccatcac agcctacatg  1620
gagttcagct ctttaacatc cgaggacagc gctctgtact attgcgcccg gtggggcgac  1680
ggcaattact ggggacgggg cacaacactg accgtgagca gcggaggcgg aggctccggc  1740
ggaggcggat ctggcggtgg cggctccgac atcgagatga cccagtcccc cgctatcatg  1800
tccgcctctt taggcgagcg ggtcacaatg acttgtacag cctcctccag cgtctcctcc  1860
tcctacttcc attggtacca acagaaaccc ggaagctccc ctaaactgtg catctacagc  1920
accagcaatc tcgccagcgg cgtgccccct aggttttccg gaagcggaag caccagctac  1980
tctttaacca tctcctccat ggaggctgag gatgccgcca cctacttttg tcaccagtac  2040
caccggtccc ccaccttcgg aggcggcacc aaactggaga caaagagg              2088

SEQ ID NO: 87          moltype = AA  length = 714
FEATURE                Location/Qualifiers
source                 1..714
                       mol_type = protein
                       organism = synthetic construct
SEQUENCE: 87
MKWVTFISLL FLFSSAYSQI VLTQSPAIMS ASPGEKVTMT CSASSSVSYM NWYQQKSGTS  60
PKRWIYDTSK LASGVPAHFR GSGSGTSYSL TISGMEAEDA ATYYCQQWSS NPFTFGSGTK  120
LEINRGGGGS GGGGSGGGGS QVQLQQSGAE LARPGASVKM SCKASGYTFT RYTMHWVKQR  180
PGQGLEWIGY INPSRGYTNY NQKFKDKATL TTDKSSSTAY MQLSSLTSED SAVYYCARYY  240
DDHYCLDYWG QGTTLTVSSS GTTNTVAAYN LTWKSTNFKT ILEWEPKPVN QVYTVQISTK  300
SGDWKSKCFY TTDTECDLTD EIVKDVKQTY LARVFSYPAG NVESTGSAGE PLYENSPEFT  360
PYLETNLGQP TIQSFEQVGT KVNVTVEDER TLVRRNNTFL SLRDVFGKDL IYTLYYWKSS  420
SSGKKTAKTN TNEFLIDVDK GENYCFSVQA VIPSRTVNRK STDSPVECMG QEKGEFREVQ  480
LQQSGPELVK PGASVKMSCK ASGYTFTSYV IQWVKQKPGQ GLEWIGSINP YNDYTKYNEK  540
FKGKATLTSD KSSITAYMEF SSLTSEDSAL YYCARWGDGN YWGRGTTLTV SSGGGGSGGG  600
GSGGGGSDIE MTQSPAIMSA SLGERVTMTC TASSSVSSSY FHWYQQKPGS SPKLCIYSTS  660
NLASGVPPRF SGSGSTSYSL TISSMEAEDA ATYFCHQYHR SPTFGGGTKL ETKR        714

SEQ ID NO: 88          moltype = DNA  length = 2142
FEATURE                Location/Qualifiers
source                 1..2142
                       mol_type = other DNA
                       organism = synthetic construct
SEQUENCE: 88
atgaagtggg tgaccttcat cagcttatta tttttattca gctccgccta ttcccagatc  60
gtgctgaccc aaagccccgc catcatgagc gctagccccg gtgagaaggt gaccatgaca  120
tgctccgctt ccagctccgt gtcctacatg aactggtatc agcagaaaag cggaaccagc  180
cccaaaaggt ggatctacga caccagcaag ctggcctccg gagtgcccgc tcatttccgg  240
ggctctggat ccggcaccag ctactcttta accatttccg gcatggaagc tgaagacgct  300
gccacctact attgccagca atggagcagc aaccccttca cattcggatc tggcaccaag  360
ctcgaaatca atcgtggagg aggtggcagc ggcggcggtg gatccggcgg aggaggaagc  420
caagttcaac tccagcagag cggcgctgaa ctggcccggc ccggcgcctc cgtcaagatg  480
agctgcaagg cttccggcta tacatttact cgttacacaa tgcattgggt caagcagagg  540
cccggtcaag gtttagagtg gatcggatat atcaaccctt cccggggcta caccaactat  600
aaccaaaagt tcaaggataa agccacttta accactgaca agagctcctc caccgcctac  660
atgcagctgt cctctttaac cagcgaggac tccgctgttt actactgcgc taggtattac  720
gacgaccact actgtttaga ctattgggga caaggtacca ctttaaccgt cagcagctcc  780
ggcaccacca ataccgtggc cgcttataac ctcacatgga agagcaccaa cttcaagaca  840
attctggaat gggaacccaa gcccgtcaat caagtttaca ccgtgcagat ctccaccaaa  900
tccggagact ggaagagcaa gtgcttctac acaacagaca ccgagtgtga tttaaccgac  960
gaaatcgtca aggacgtcaa gcaaacctat ctggctcggg tcttttccta ccccgctggc  1020
aatgtcgagt ccaccggctc cgctggcgag cctctctacg agaattcccc cgaattcacc  1080
ccttatttag agaccaattt aggccagcct accatccaga gcttcgagca agttggcacc  1140
aaggtgaacg tcaccgtcga ggatgaaagg actttagtgc ggcggaataa cacattttta  1200
tccctccggg atgtgttcgg caaagacctc atctacacac tgtactattg gaagtccagc  1260
tcctccggca aaaagaccgc taagaccaac accaacgagt ttttaattga cgtggacaaa  1320
ggcgagaact actgcttcag cgtgcaagcc gtgatccctt ctcgtaccgt caaccggaag  1380
agcacagatt cccccgttga gtgcatgggc caagaaaagg gcgagttccg ggaggtccag  1440
ctgcagcaga gcggacccga actcgtgaaa cccggtgctt ccgtgaaaat gtcttgtaag  1500
gccagcggat acaccttcac ctcctatgtg atccagtggg tcaaacagaa gcccggacaa  1560
ggtctcgagt ggatcggcag catcaaccct tacaacgact ataccaaata caacgagaag  1620
tttaagggaa aggctacttt aacctccgac aaaagctcca tcacagccta catggagttc  1680
agctctttaa catccgagga cagcgctctg tactattgcg cccggtgggg cgacggcaat  1740
tactggggac ggggcacaac actgaccgtg agcagcggag gcggaggctc cggcggaggc  1800
ggatctggcg gtggcggctc cgacatcgag atgacccagt cccccgctat catgtccgcc  1860
tctttaggcg agcgggtcac aatgacttgt acagcctcct ccagcgtctc ctcctcctac  1920
ttccattggt accaacagaa acccggaagc tcccctaaac tgtgcatcta cagcaccagc  1980
aatctcgcca gcggcgtgcc ccctaggttt tccggaagcg gaagcaccag ctactcttta  2040
accatctcct ccatggaggc tgaggatgcc gccacctact tttgtcacca gtaccaccgg  2100
tcccccacct tcggaggcgg caccaaactg gagacaaaga gg                    2142

SEQ ID NO: 89          moltype = AA  length = 696
FEATURE                Location/Qualifiers
source                 1..696
                       mol_type = protein
```

```
                         organism = synthetic construct
SEQUENCE: 89
VQLQQSGPEL VKPGASVKMS CKASGYTFTS YVIQWVKQKP GQGLEWIGSI NPYNDYTKYN  60
EKFKGKATLT SDKSSITAYM EFSSLTSEDS ALYYCARWGD GNYWGRGTTL TVSSGGGGSG  120
GGGSGGGGSD IEMTQSPAIM SASLGERVTM TCTASSSVSS SYFHWYQQKP GSSPKLCIYS  180
TSNLASGVPP RFSGSGSTSY SLTISSMEAE DAATYFCHQY HRSPTFGGGT KLETKRSGTT  240
NTVAAYNLTW KSTNFKTILE WEPKPVNQVY TVQISTKSGD WKSKCFYTTD TECDLTDEIV  300
KDVKQTYLAR VFSYPAGNVE STGSAGEPLY ENSPEFTPYL ETNLGQPTIQ SFEQVGTKVN  360
VTVEDERTLV RRNNTFLSLR DVFGKDLIYT LYYWKSSSSG KKTAKTNTNE FLIDVDKGEN  420
YCFSVQAVIP SRTVNRKSTD SPVECMGQEK GEFREQIVLT QSPAIMSASP GEKVTMTCSA  480
SSSVSYMNWY QQKSGTSPKR WIYDTSKLAS GVPAHFRGSG SGTSYSLTIS GMEAEDAATY  540
YCQQWSSNPF TFGSGTKLEI NRGGGGSGGG GSGGGGSQVQ LQQSGAELAR PGASVKMSCK  600
ASGYTFTRYT MHWVKQRPGQ GLEWIGYINP SRGYTNYNQK FKDKATLTTD KSSSTAYMQL  660
SSLTSEDSAV YYCARYYDDH YCLDYWGQGT TLTVSS                          696

SEQ ID NO: 90            moltype = DNA  length = 2088
FEATURE                  Location/Qualifiers
source                   1..2088
                         mol_type = other DNA
                         organism = synthetic construct
SEQUENCE: 90
gtgcagctgc agcagtccgg acccgaactg gtcaagcccg gtgcctccgt gaaaatgtct  60
tgtaaggctt ctggctacac ctttacctcc tacgtcatcc aatgggtgaa gcagaagccc  120
ggtcaaggtc tcgagtggat cggcagcatc aatccctaca acgattacac caagtataac  180
gaaaagttta agggcaaggc cactctgaca agcgacaaga gctccattac cgcctacatg  240
gagttttcct ctttaacttc tgaggactcc gctttatact attgcgctcg ttggggcgat  300
ggcaattatt ggggccgggg aactacttta acagtgagct ccggcggcgg cggaagcgga  360
ggtggaggat ctggcggtgg aggcagcgac atcgagatga cacagtcccc cgctatcatg  420
agcgcctctt taggagaacg tgtgaccatg acttgtacag cttcctccag cgtgagcagc  480
tcctatttcc actggtacca gcagaaaccc ggctcctccc ctaaactgtg tatctactcc  540
acaagcaatt tagctagcgg cgtgcctcct cgttttagcg gctccggcag cacctcttac  600
tctttaacca ttagctctat ggaggccgaa gatgccgcca catacttttg ccatcagtac  660
caccggtccc ctacctttgg cggaggcaca aagctggaga ccaagcggag cggcaccacc  720
aacacagtgg ccgcctacaa tctgacttgg aaatccacca acttcaagac catcctcgag  780
tgggagccca agcccgttaa tcaagtttat accgtgcaga tttccaccaa gagcggcgac  840
tggaaatcca agtgcttcta taccacagac accgagtgcg atctcaccga cgagatcgtc  900
aaagacgtga agcagacata tttagctagg gtgttctcct accccgctgg aaacgtggag  960
agcaccggat ccgctggaga gcctttatac gagaactccc ccgaattcac cccctatctg  1020
gaaaccaatt taggccagcc caccatccag agcttcgaac aagttggcac aaaggtgaac  1080
gtcaccgtcg aagatgagag gactttagtg cggaggaaca atacattttt atccttacgt  1140
gacgtcttcg gcaaggattt aatctacaca ctgtattact ggaagtctag ctcctccggc  1200
aagaagaccg ccaagaccaa taccaacgaa tttttaattg acgtggacaa gggcgagaac  1260
tactgcttct ccgtgcaagc tgtgatcccc tcccggacag tgaaccggaa gtccaccgac  1320
tcccccgtgg agtgcatggg ccaagagaag ggagagtttc gtgagcagat cgtgctgacc  1380
cagtcccccg ctattatgag cgctagcccc ggtgaaaagg tgactatgac atgcagcgcc  1440
agctcttccg tgagctacat gaactggtat cagcagaagt ccggcaccag ccctaaaagg  1500
tggatctacg acaccagcaa gctggccagc ggcgtccccg ctcactttcg gggctccggc  1560
tccggaacaa gctactctct gaccatcagc ggcatggaag ccgaggatgc cgctacctat  1620
tactgtcagc agtggagctc caaccccttc acctttggat ccggcaccaa gctcgagatt  1680
aatcgtggag gcggaggtag cggaggaggc ggatccggcg gtggaggtag ccaagttcag  1740
ctccagcaaa gcggcgccga actcgctcgg cccggcgctt ccgtgaagat gtcttgtaag  1800
gcctccggct ataccttcac ccggtacaca atgcactggg tcaagcaacg gcccggtcaa  1860
ggtttagagt ggattggcta tatcaacccc tcccggggct ataccaacta caaccagaag  1920
ttcaaggaca aagccaccct caccaccgac aagtccagca gcaccgctta catgcagctg  1980
agctctttaa catccgagga ttccgccgtg tactactgcg ctcggtacta cgacgatcat  2040
tactgcctcg attactgggg ccaaggtacc accttaacag tctcctcc             2088

SEQ ID NO: 91            moltype = AA  length = 714
FEATURE                  Location/Qualifiers
source                   1..714
                         mol_type = protein
                         organism = synthetic construct
SEQUENCE: 91
MKWVTFISLL FLFSSAYSVQ LQQSGPELVK PGASVKMSCK ASGYTFTSYV IQWVKQKPGQ  60
GLEWIGSINP YNDYTKYNEK FKGKATLTSD KSSITAYMEF SSLTSEDSAL YYCARWGDGN  120
YWGRGTTLTV SSGGGGSGGG GSGGGGSDIE MTQSPAIMSA SLGERVTMTC TASSSVSSSY  180
FHWYQQKPGS SPKLCIYSTS NLASGVPPRF SGSGSTSYSL TISSMEAEDA ATYFCHQYHR  240
SPTFGGGTKL ETKRSGTTNT VAAYNLTWKS TNFKTILEWE PKPVNQVYTV QISTKSGDWK  300
SKCFYTTDTE CDLTDEIVKD VKQTYLARVF SYPAGNVEST GSAGEPLYEN SPEFTPYLET  360
NLGQPTIQSF EQVGTKVNVT VEDERTLVRR NNTFLSLRDV FGKDLIYTLY YWKSSSSGKK  420
TAKTNTNEFL IDVDKGENYC FSVQAVIPSR TVNRKSTDSP VECMGQEKGE FREQIVLTQS  480
PAIMSASPGE KVTMTCSASS SVSYMNWYQQ KSGTSPKRWI YDTSKLASGV PAHFRGSGSG  540
TSYSLTISGM EAEDAATYYC QQWSSNPFTF GSGTKLEINR GGGGSGGGGS GGGGSQVQLQ  600
QSGAELARPG ASVKMSCKAS GYTFTRYTMH WVKQRPGQGL EWIGYINPSR GYTNYNQKFK  660
DKATLTTDKS SSTAYMQLSS LTSEDSAVYY CARYYDDHYC LDYWGQGTTL TVSS        714

SEQ ID NO: 92            moltype = DNA  length = 2142
FEATURE                  Location/Qualifiers
source                   1..2142
```

```
                        mol_type = other DNA
                        organism = synthetic construct
SEQUENCE: 92
atgaaatggg tcaccttcat ctctttactg tttttattta gcagcgccta cagcgtgcag  60
ctgcagcagt ccggacccga actggtcaag cccggtgcct ccgtgaaaat gtcttgtaag  120
gcttctggct acacctttac ctcctacgtc atccaatggg tgaagcagaa gcccggtcaa  180
ggtctcgagt ggatcggcag catcaatccc tacaacgatt acaccaagta taacgaaaag  240
tttaagggca aggccactct gacaagcgac aagagctcca ttaccgccta catggagttt  300
tcctctttaa cttctgagga ctccgcttta tactattgcg ctcgttgggg cgatggcaat  360
tattggggcc ggggaactac tttaacagtg agctccggcg gcggcggaag cggaggtgga  420
ggatctggcg gtggaggcag cgacatcgag atgacacagt cccccgctat catgagcgcc  480
tctttaggag aacgtgtgac catgacttgt acagcttcct ccagcgtgag cagctcctat  540
ttccactggt accagcagaa acccggctcc tcccctaaac tgtgtatcta ctccacaagc  600
aatttagcta gcggcgtgcc tcctcgtttt agcggctccg gcagcacctc ttactcttta  660
accattagct ctatggaggc cgaagatgcc gccacatact tttgccatca gtaccaccgg  720
tcccctacct ttggcggagg cacaaagctg gagaccaagc ggagcggcac caccaacaca  780
gtggccgcct acaatctgac ttggaaatcc accaacttca agaccatcct cgagtgggag  840
cccaagcccg ttaatcaagt ttataccgtg cagatttcca ccaagagcgg cgactggaaa  900
tccaagtgct tctataccac agacaccgag tgcgatctca ccgacgagat cgtcaaagac  960
gtgaagcaga catatttagc tagggtgttc tcctaccccg ctggaaacgt ggagagcacc  1020
ggatccgctg gagagccttt atacgagaac tcccccgaat tcacccccta tctggaaacc  1080
aatttaggcc agcccaccat ccagagcttc gaacaagttg gcacaaaggt gaacgtcacc  1140
gtcgaagatg agaggacttt agtgcggagg aacaatacat tttatcctt acgtgacgtc  1200
ttcggcaagg atttaatcta cacactgtat tactggaagt ctagctcctc cggcaagaag  1260
accgccaaga ccaataccaa cgaattttta attgacgtgg acaagggcga gaactactgc  1320
ttctccgtgc aagctgtgat cccctcccgg acagtgaacc ggaagtccac cgactccccc  1380
gtggagtgca tgggccaaga gaagggagag tttcgtgagc agatcgtgct gacccagtcc  1440
cccgctatta tgagcgctag ccccggtgaa aaggtgacta tgacatgcag cgccagctct  1500
tccgtgagct acatgaactg gtatcagcag aagtccggca ccagccctaa aaggtggatc  1560
tacgacacca gcaagctggc cagcggcgtc cccgctcact ttcggggctc cggctccgga  1620
acaagctact ctctgaccat cagcggcatg gaagccgagg atgccgctac ctattactgt  1680
cagcagtgga gctccaaccc cttcaccttt ggatccggca ccaagctcga gattaatcgt  1740
ggaggcggag gtagcggagg aggcggatcc ggcggtggag gtagccaagt tcagctccag  1800
caaagcggcg ccgaactcgc tcggcccggc gcttccgtga agatgtcttg taaggcctcc  1860
ggctatacct tcacccggta cacaatgcac tgggtcaagc aacggcccgg tcaaggttta  1920
gagtggattg gctatatcaa cccctcccgg ggctatacca actacaacca gaagttcaag  1980
gacaaagcca ccctcaccac cgacaagtcc agcagcaccg cttacatgca gctgagctct  2040
ttaacatccg aggattccgc cgtgtactac tgcgctcggt actacgacga tcattactgc  2100
ctcgattact ggggccaagg taccacctta acagtctcct cc                    2142

SEQ ID NO: 93           moltype = AA  length = 219
FEATURE                 Location/Qualifiers
REGION                  1..219
                        note = source = /note="Tissue factor"
source                  1..219
                        mol_type = protein
                        organism = Homo sapiens
SEQUENCE: 93
SGTTNTVAAY NLTWKSTNFK TILEWEPKPV NQVYTVQIST KSGDWKSKCF YTTDTECDLT  60
DEIVKDVKQT YLARVFSYPA GNVESTGSAG EPLYENSPEF TPYLETNLGQ PTIQSFEQVG  120
TKVNVTVEDE RTLVRRNNTF LSLRDVFGKD LIYTLYYWKS SSSGKKTAKT NTNEFLIDVD  180
KGENYCFSVQ AVIPSRTVNR KSTDSPVECM GQEKGEFRE                        219

SEQ ID NO: 94           moltype = DNA  length = 657
FEATURE                 Location/Qualifiers
source                  1..657
                        mol_type = genomic DNA
                        note = source = Tissue factor
                        organism = Homo sapiens
SEQUENCE: 94
agcggcacaa ccaacacagt cgctgcctat aacctcactt ggaagagcac caacttcaaa  60
accatcctcg aatgggaacc caaacccgtt aaccaagttt acaccgtgca gatcagcacc  120
aagtccggcg actggaagtc caaatgtttc tataccaccg acaccgagtg cgatctcacc  180
gatgagatcg tgaaagatgt gaaacagacc tacctcgccc gggtgtttag ctaccccgcc  240
ggcaatgtgg agagcactgg ttccgctggc gagcctttat acgagaacag ccccgaattt  300
accccttacc tcgagaccaa tttaggacag cccaccatcc aaagctttga gcaagttggc  360
acaaaggtga atgtgacagt ggaggacgag cggactttag tgcggcggaa caacaccttt  420
ctcagcctcc gggatgtgtt cggcaaagat ttaatctaca cactgtatta ctggaagtcc  480
tcttcctccg gcaagaagac agctaaaacc aacacaaacg agtttttaat cgacgtggat  540
aaaggcgaaa actactgttt cagcgtgcaa gctgtgatcc cctcccggac cgtgaatagg  600
aaaagcaccg atagccccgt tgagtgcatg ggccaagaaa agggcgagtt ccgggag     657

SEQ ID NO: 95           moltype = AA  length = 223
FEATURE                 Location/Qualifiers
REGION                  1..223
                        note = source = /note="Tissue factor"
source                  1..223
                        mol_type = protein
                        organism = Mus musculus
```

```
SEQUENCE: 95
AGIPEKAFNL TWISTDFKTI LEWQPKPTNY TYTVQISDRS RNWKNKCFST TDTECDLTDE  60
IVKDVTWAYE AKVLSVPRRN SVHGDGDQLV IHGEEPPFTN APKFLPYRDT NLGQPVIQQF  120
EQDGRKLNVV VKDSLTLVRK NGTFLTLRQV FGKDLGYIIT YRKGSSTGKK TNITNTNEFS  180
IDVEEGVSYC FFVQAMIFSR KTNQNSPGSS TVCTEQWKSF LGE                   223

SEQ ID NO: 96          moltype = AA  length = 224
FEATURE                Location/Qualifiers
REGION                 1..224
                       note = source = /note="Tissue factor"
source                 1..224
                       mol_type = protein
                       organism = Rattus rattus
SEQUENCE: 96
AGTPPGKAFN LTWISTDFKT ILEWQPKPTN YTYTVQISDR SRNWKYKCTG TTDTECDLTD  60
EIVKDVNWTY EARVLSVPWR NSTHGKETLF GTHGEEPPFT NARKFLPYRD TKIGQPVIQK  120
YEQGGTKLKV TVKDSFTLVR KNGTFLTLRQ VFGNDLGYIL TYRKDSSTGR KTNTTHTNEF  180
LIDVEKGVSY CFFAQAVIFS RKTNHKSPES ITKCTEQWKS VLGE                  224

SEQ ID NO: 97          moltype = AA  length = 219
FEATURE                Location/Qualifiers
REGION                 1..219
                       note = source = /note="Tissue factor"
source                 1..219
                       mol_type = protein
                       organism = Homo sapiens
SEQUENCE: 97
SGTTNTVAAY NLTWKSTNFA TALEWEPKPV NQVYTVQIST KSGDWKSKCF YTTDTECALT  60
DEIVKDVKQT YLARVFSYPA GNVESTGSAG EPLYENSPEF TPYLETNLGQ PTIQSFEQVG  120
TKVNVTVEDE RTLVARNNTA LSLRDVFGKD LIYTLYYWKS SSSGKKTAKT NTNEFLIDVD  180
KGENYCFSVQ AVIPSRTVNR KSTDSPVECM GQEKGEFRE                        219

SEQ ID NO: 98          moltype = AA  length = 219
FEATURE                Location/Qualifiers
REGION                 1..219
                       note = source = /note="Tissue factor"
source                 1..219
                       mol_type = protein
                       organism = Homo sapiens
SEQUENCE: 98
SGTTNTVAAY NLTWKSTNFA TALEWEPKPV NQVYTVQIST KSGDAKSKCF YTTDTECALT  60
DEIVKDVKQT YLARVFSYPA GNVESTGSAG EPLAENSPEF TPYLETNLGQ PTIQSFEQVG  120
TKVNVTVEDE RTLVARNNTA LSLRDVFGKD LIYTLYYWKS SSSGKKTAKT NTNEFLIDVD  180
KGENYCFSVQ AVIPSRTVNR KSTDSPVECM GQEKGEFRE                        219

SEQ ID NO: 99          moltype = AA  length = 4
FEATURE                Location/Qualifiers
source                 1..4
                       mol_type = protein
                       organism = synthetic construct
SEQUENCE: 99
GGGS                                                              4

SEQ ID NO: 100         moltype = AA  length = 5
FEATURE                Location/Qualifiers
source                 1..5
                       mol_type = protein
                       organism = synthetic construct
SEQUENCE: 100
GGGGS                                                             5

SEQ ID NO: 101         moltype = AA  length = 4
FEATURE                Location/Qualifiers
source                 1..4
                       mol_type = protein
                       organism = synthetic construct
SEQUENCE: 101
GGSG                                                              4

SEQ ID NO: 102         moltype = AA  length = 15
FEATURE                Location/Qualifiers
source                 1..15
                       mol_type = protein
                       organism = synthetic construct
SEQUENCE: 102
GGGGSGGGGS GGGGS                                                  15

SEQ ID NO: 103         moltype = DNA  length = 45
FEATURE                Location/Qualifiers
```

```
source                  1..45
                        mol_type = other DNA
                        organism = synthetic construct
SEQUENCE: 103
ggcggtggag gatccggagg aggtggctcc ggcggcggag gatct                45

SEQ ID NO: 104          moltype = AA  length = 8
FEATURE                 Location/Qualifiers
source                  1..8
                        mol_type = protein
                        organism = synthetic construct
SEQUENCE: 104
GGGSGGGS                                                         8

SEQ ID NO: 105          moltype = AA  length = 133
FEATURE                 Location/Qualifiers
REGION                  1..133
                        note = source = /note="IL-3"
source                  1..133
                        mol_type = protein
                        organism = Homo sapiens
SEQUENCE: 105
APMTQTTPLK TSWVNCSNMI DEIITHLKQP PLPLLDFNNL NGEDQDILME NNLRRPNLEA  60
FNRAVKSLQN ASAIESILKN LLPCLPLATA APTRHPIHIK DGDWNEFRRK LTFYLKTLEN  120
AQAQQTTLSL AIF                                                   133

SEQ ID NO: 106          moltype = AA  length = 79
FEATURE                 Location/Qualifiers
REGION                  1..79
                        note = source = /note="IL-8"
source                  1..79
                        mol_type = protein
                        organism = Homo sapiens
SEQUENCE: 106
EGAVLPRSAK ELRCQCIKTY SKPFHPKFIK ELRVIESGPH CANTEIIVKL SDGRELCLDP  60
KENWVQRVVE KFLKRAENS                                             79

SEQ ID NO: 107          moltype = AA  length = 160
FEATURE                 Location/Qualifiers
REGION                  1..160
                        note = source = /note="IL-10"
source                  1..160
                        mol_type = protein
                        organism = Homo sapiens
SEQUENCE: 107
SPGQGTQSEN SCTHFPGNLP NMLRDLRDAF SRVKTFFQMK DQLDNLLLKE SLLEDFKGYL  60
GCQALSEMIQ FYLEEVMPQA ENQDPDIKAH VNSLGENLKT LRLRLRRCHR FLPCENKSKA  120
VEQVKNAFNK LQEKGIYKAM SEFDIFINYI EAYMTMKIRN                      160

SEQ ID NO: 108          moltype = AA  length = 132
FEATURE                 Location/Qualifiers
REGION                  1..132
                        note = source = /note="IL-17"
source                  1..132
                        mol_type = protein
                        organism = Homo sapiens
SEQUENCE: 108
GITIPRNPGC PNSEDKNFPR TVMVNLNIHN RNTNTNPKRS SDYYNRSTSP WNLHRNEDPE  60
RYPSVIWEAK CRHLGCINAD GNVDYHMNSV PIQQEILVLR REPPHCPNSF RLEKILVSVG  120
CTCVTPIVHH VA                                                    132

SEQ ID NO: 109          moltype = AA  length = 157
FEATURE                 Location/Qualifiers
REGION                  1..157
                        note = source = /note="IL-18"
source                  1..157
                        mol_type = protein
                        organism = Homo sapiens
SEQUENCE: 109
YFGKLESKLS VIRNLNDQVL FIDQGNRPLF EDMTDSDCRD NAPRTIFIIS MYKDSQPRGM  60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                         157

SEQ ID NO: 110          moltype = AA  length = 352
FEATURE                 Location/Qualifiers
REGION                  1..352
                        note = source = /note="PDGF-DD"
source                  1..352
                        mol_type = protein
```

```
                          organism = Homo sapiens
SEQUENCE: 110
RDTSATPQSA SIKALRNANL RRDESNHLTD LYRRDETIQV KGNGYVQSPR FPNSYPRNLL  60
LTWRLHSQEN TRIQLVFDNQ FGLEEAENDI CRYDFVEVED ISETSTIIRG RWCGHKEVPP  120
RIKSRTNQIK ITFKSDDYFV AKPGFKIYYS LLEDFQPAAA SETNWESVTS SISGVSYNSP  180
SVTDPTLIAD ALDKKIAEFD TVEDLLKYFN PESWQEDLEN MYLDTPRYRG RSYHDRKSKV  240
DLDRLNDDAK RYSCTPRNYS VNIREELKLA NVVFFPRCLL VQRCGGNCGC GTVNWRSCTC  300
NSGKTVKKYH EVLQFEPGHI KRRGRAKTMA LVDIQLDHHE RCDCICSSRP PR          352

SEQ ID NO: 111            moltype = AA  length = 248
FEATURE                   Location/Qualifiers
REGION                    1..248
                          note = source = /note="SCF"
source                    1..248
                          mol_type = protein
                          organism = Homo sapiens
SEQUENCE: 111
EGICRNRVTN NVKDVTKLVA NLPKDYMITL KYVPGMDVLP SHCWISEMVV QLSDSLTDLL  60
DKFSNISEGL SNYSIIDKLV NIVDDLVECV KENSSKDLKK SFKSPEPRLF TPEEFFRIFN  120
RSIDAFKDFV VASETSDCVV SSTLSPEKDS RVSVTKPFML PPVAASSLRN DSSSSNRKAK  180
NPPGDSSLHW AAMALPALFS LIIGFAFGAL YWKKRQPSLT RAVENIQINE EDNEISMLQE  240
KEREFQEV                                                           248

SEQ ID NO: 112            moltype = AA  length = 209
FEATURE                   Location/Qualifiers
REGION                    1..209
                          note = source = /note="FLT3L"
source                    1..209
                          mol_type = protein
                          organism = Homo sapiens
SEQUENCE: 112
TQDCSFQHSP ISSDFAVKIR ELSDYLLQDY PVTVASNLQD EELCGGLWRL VLAQRWMERL  60
KTVAGSKMQG LLERVNTEIH FVTKCAFQPP PSCLRFVQTN ISRLLQETSE QLVALKPWIT  120
RQNFSRCLEL QCQPDSSTLP PPWSPRPLEA TAPTAPQPPL LLLLLLPVGL LLLAAAWCLH  180
WQRTRRRTPR PGEQVPPVPS PQDLLLVEH                                    209

SEQ ID NO: 113            moltype = AA  length = 65
FEATURE                   Location/Qualifiers
REGION                    1..65
                          note = source = /note="IL15Ralpha"
source                    1..65
                          mol_type = protein
                          organism = Homo sapiens
SEQUENCE: 113
ITCPPPMSVE HADIWVKSYS LYSRERYICN SGFKRKAGTS SLTECVLNKA TNVAHWTTPS  60
LKCIR                                                              65

SEQ ID NO: 114            moltype = DNA  length = 195
FEATURE                   Location/Qualifiers
source                    1..195
                          mol_type = genomic DNA
                          note = source = IL15Ralpha
                          organism = Homo sapiens
SEQUENCE: 114
attacatgcc cccctcccat gagcgtggag cacgccgaca tctgggtgaa gagctatagc  60
ctctacagcc gggagaggta tatctgtaac agcggcttca agaggaaggc cggcaccagc  120
agcctcaccg agtgcgtgct gaataaggct accaacgtgg ctcactggac aacaccctct  180
ttaaagtgca tccgg                                                   195

SEQ ID NO: 115            moltype = AA  length = 114
FEATURE                   Location/Qualifiers
REGION                    1..114
                          note = source = /note="IL-15"
source                    1..114
                          mol_type = protein
                          organism = Homo sapiens
SEQUENCE: 115
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 116            moltype = DNA  length = 342
FEATURE                   Location/Qualifiers
source                    1..342
                          mol_type = genomic DNA
                          note = source = IL-15
                          organism = Homo sapiens
SEQUENCE: 116
aactgggtga acgtcatcag cgatttaaag aagatcgaag atttaattca gtccatgcat  60
atcgacgcca ctttatacac agaatccgac gtgcacccct cttgtaaggt gaccgccatg  120
```

```
aaatgttttt tactggagct gcaagttatc tctttagaga gcggagacgc tagcatccac  180
gacaccgtgg agaatttaat cattttagcc aataactctt tatccagcaa cggcaacgtg  240
acagagtccg gctgcaagga gtgcgaagag ctggaggaga agaacatcaa ggagtttctg  300
caatcctttg tgcacattgt ccagatgttc atcaatacct cc                      342

SEQ ID NO: 117          moltype = AA  length = 18
FEATURE                 Location/Qualifiers
source                  1..18
                        mol_type = protein
                        organism = synthetic construct
SEQUENCE: 117
MKWVTFISLL FLFSSAYS                                                 18

SEQ ID NO: 118          moltype = DNA  length = 54
FEATURE                 Location/Qualifiers
source                  1..54
                        mol_type = other DNA
                        organism = synthetic construct
SEQUENCE: 118
atgaaatggg tgacctttat ttctttactg ttcctcttta gcagcgccta ctcc         54

SEQ ID NO: 119          moltype = DNA  length = 54
FEATURE                 Location/Qualifiers
source                  1..54
                        mol_type = other DNA
                        organism = synthetic construct
SEQUENCE: 119
atgaagtggg tcacatttat ctctttactg ttcctcttct ccagcgccta cagc         54

SEQ ID NO: 120          moltype = DNA  length = 54
FEATURE                 Location/Qualifiers
source                  1..54
                        mol_type = other DNA
                        organism = synthetic construct
SEQUENCE: 120
atgaaatggg tgacctttat ttctttactg ttcctcttta gcagcgccta ctcc         54

SEQ ID NO: 121          moltype = AA  length = 16
FEATURE                 Location/Qualifiers
source                  1..16
                        mol_type = protein
                        organism = synthetic construct
SEQUENCE: 121
MKCLLYLAFL FLGVNC                                                   16

SEQ ID NO: 122          moltype = AA  length = 58
FEATURE                 Location/Qualifiers
source                  1..58
                        mol_type = protein
                        organism = synthetic construct
SEQUENCE: 122
MGQIVTMFEA LPHIIDEVIN IVIIVLIIIT SIKAVYNFAT CGILALVSFL FLAGRSCG     58

SEQ ID NO: 123          moltype = AA  length = 97
FEATURE                 Location/Qualifiers
source                  1..97
                        mol_type = protein
                        organism = synthetic construct
SEQUENCE: 123
MPNHQSGSPT GSSDLLLSGK KQRPHLALRR KRRREMRKIN RKVRRMNLAP IKEKTAWQHL  60
QALISEAEEV LKTSQTPQNS LTLFLALLSV LGPPVTG                            97

SEQ ID NO: 124          moltype = AA  length = 30
FEATURE                 Location/Qualifiers
source                  1..30
                        mol_type = protein
                        organism = synthetic construct
SEQUENCE: 124
MDSKGSSQKG SRLLLLLVVS NLLLCQGVVS                                    30

SEQ ID NO: 125          moltype = AA  length = 16
FEATURE                 Location/Qualifiers
source                  1..16
                        mol_type = protein
                        organism = synthetic construct
SEQUENCE: 125
MKCLLYLAFL FLGVNC                                                   16

SEQ ID NO: 126          moltype = AA  length = 15
```

```
FEATURE                Location/Qualifiers
source                 1..15
                       mol_type = protein
                       organism = synthetic construct
SEQUENCE: 126
GLNDIFEAQK IEWHE                                                    15

SEQ ID NO: 127         moltype = AA  length = 26
FEATURE                Location/Qualifiers
source                 1..26
                       mol_type = protein
                       organism = synthetic construct
SEQUENCE: 127
KRRWKKNFIA VSAANRFKKI SSSGAL                                        26

SEQ ID NO: 128         moltype = AA  length = 6
FEATURE                Location/Qualifiers
source                 1..6
                       mol_type = protein
                       organism = synthetic construct
SEQUENCE: 128
EEEEEE                                                              6

SEQ ID NO: 129         moltype = AA  length = 13
FEATURE                Location/Qualifiers
source                 1..13
                       mol_type = protein
                       organism = synthetic construct
SEQUENCE: 129
GAPVPYPDPL EPR                                                      13

SEQ ID NO: 130         moltype = AA  length = 8
FEATURE                Location/Qualifiers
source                 1..8
                       mol_type = protein
                       organism = synthetic construct
SEQUENCE: 130
DYKDDDDK                                                            8

SEQ ID NO: 131         moltype = AA  length = 9
FEATURE                Location/Qualifiers
source                 1..9
                       mol_type = protein
                       organism = synthetic construct
SEQUENCE: 131
YPYDVPDYA                                                           9

SEQ ID NO: 132         moltype = AA  length = 5
FEATURE                Location/Qualifiers
source                 1..5
                       mol_type = protein
                       organism = synthetic construct
SEQUENCE: 132
HHHHH                                                               5

SEQ ID NO: 133         moltype = AA  length = 6
FEATURE                Location/Qualifiers
source                 1..6
                       mol_type = protein
                       organism = synthetic construct
SEQUENCE: 133
HHHHHH                                                              6

SEQ ID NO: 134         moltype = AA  length = 7
FEATURE                Location/Qualifiers
source                 1..7
                       mol_type = protein
                       organism = synthetic construct
SEQUENCE: 134
HHHHHHH                                                             7

SEQ ID NO: 135         moltype = AA  length = 8
FEATURE                Location/Qualifiers
source                 1..8
                       mol_type = protein
                       organism = synthetic construct
SEQUENCE: 135
HHHHHHHH                                                            8
```

```
SEQ ID NO: 136          moltype = AA  length = 9
FEATURE                 Location/Qualifiers
source                  1..9
                        mol_type = protein
                        organism = synthetic construct
SEQUENCE: 136
HHHHHHHHH                                                          9

SEQ ID NO: 137          moltype = AA  length = 10
FEATURE                 Location/Qualifiers
source                  1..10
                        mol_type = protein
                        organism = synthetic construct
SEQUENCE: 137
HHHHHHHHHH                                                         10

SEQ ID NO: 138          moltype = AA  length = 10
FEATURE                 Location/Qualifiers
source                  1..10
                        mol_type = protein
                        organism = synthetic construct
SEQUENCE: 138
EQKLISEEDL                                                         10

SEQ ID NO: 139          moltype = AA  length = 18
FEATURE                 Location/Qualifiers
source                  1..18
                        mol_type = protein
                        organism = synthetic construct
SEQUENCE: 139
TKENPRSNQE ESYDDNES                                                18

SEQ ID NO: 140          moltype = AA  length = 15
FEATURE                 Location/Qualifiers
source                  1..15
                        mol_type = protein
                        organism = synthetic construct
SEQUENCE: 140
KETAAAKFER QHMDS                                                   15

SEQ ID NO: 141          moltype = AA  length = 38
FEATURE                 Location/Qualifiers
source                  1..38
                        mol_type = protein
                        organism = synthetic construct
SEQUENCE: 141
MDEKTTGWRG GHVVEGLAGE LEQLRARLEH HPQGQREP                          38

SEQ ID NO: 142          moltype = AA  length = 13
FEATURE                 Location/Qualifiers
source                  1..13
                        mol_type = protein
                        organism = synthetic construct
SEQUENCE: 142
SLAELLNAGL GGS                                                     13

SEQ ID NO: 143          moltype = AA  length = 8
FEATURE                 Location/Qualifiers
source                  1..8
                        mol_type = protein
                        organism = synthetic construct
SEQUENCE: 143
TQDPSRVG                                                           8

SEQ ID NO: 144          moltype = AA  length = 12
FEATURE                 Location/Qualifiers
source                  1..12
                        mol_type = protein
                        organism = synthetic construct
SEQUENCE: 144
PDRVRAVSHW SS                                                      12

SEQ ID NO: 145          moltype = AA  length = 8
FEATURE                 Location/Qualifiers
source                  1..8
                        mol_type = protein
                        organism = synthetic construct
SEQUENCE: 145
WSHPQFEK                                                           8
```

```
SEQ ID NO: 146          moltype = AA  length = 6
FEATURE                 Location/Qualifiers
source                  1..6
                        mol_type = protein
                        organism = synthetic construct
SEQUENCE: 146
CCPGCC                                                                  6

SEQ ID NO: 147          moltype = AA  length = 10
FEATURE                 Location/Qualifiers
source                  1..10
                        mol_type = protein
                        organism = synthetic construct
SEQUENCE: 147
EVHTNQDPLD                                                              10

SEQ ID NO: 148          moltype = AA  length = 14
FEATURE                 Location/Qualifiers
source                  1..14
                        mol_type = protein
                        organism = synthetic construct
SEQUENCE: 148
GKPIPNPLLG LDST                                                         14

SEQ ID NO: 149          moltype = AA  length = 11
FEATURE                 Location/Qualifiers
source                  1..11
                        mol_type = protein
                        organism = synthetic construct
SEQUENCE: 149
YTDIEMNRLG K                                                            11

SEQ ID NO: 150          moltype = AA  length = 8
FEATURE                 Location/Qualifiers
source                  1..8
                        mol_type = protein
                        organism = synthetic construct
SEQUENCE: 150
DLYDDDDK                                                                8

SEQ ID NO: 151          moltype = AA  length = 241
FEATURE                 Location/Qualifiers
REGION                  1..241
                        note = source = /note="CD3"
source                  1..241
                        mol_type = protein
                        organism = Homo sapiens
SEQUENCE: 151
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEINRGGG GSGGGGSGGG  120
GSQVQLQQSG AELARPGASV KMSCKASGYT FTRYTMHWVK QRPGQGLEWI GYINPSRGYT  180
NYNQKFKDKA TLTTDKSSST AYMQLSSLTS EDSAVYYCAR YYDDHYCLDY WGQGTTLTVS  240
S                                                                   241

SEQ ID NO: 152          moltype = DNA  length = 723
FEATURE                 Location/Qualifiers
source                  1..723
                        mol_type = genomic DNA
                        note = source = CD3
                        organism = Homo sapiens
SEQUENCE: 152
cagatcgtgc tgacccaaag ccccgccatc atgagcgcta gccccggtga gaaggtgacc  60
atgacatgct ccgcttccag ctccgtgtcc tacatgaact ggtatcagca gaaaagcgga  120
accagcccca aaaggtggat ctacgacacc agcaagctgg cctccggagt gcccgctcat  180
ttccggggct ctggatccgg caccagctac tctttaacca tttccggcat ggaagctgaa  240
gacgctgcca cctactattg ccagcaatgg agcagcaacc ccttcacatt cggatctggc  300
accaagctcg aaatcaatcg tggaggaggt ggcagcggcg gcggtggatc cggcggagga  360
ggaagccaag ttcaactcca gcagagcggc gctgaactgg cccggcccgg cgcctccgtc  420
aagatgagct gcaaggcttc cggctataca tttactcgtt acacaatgca ttgggtcaag  480
cagaggcccg gtcaaggttt agagtggatc ggatatatca acccttcccg gggctacacc  540
aactataacc aaaagttcaa ggataaagcc actttaacca ctgacaagag ctcctccacc  600
gcctacatgc agctgtcctc tttaaccagc gaggactccg ctgtttacta ctgcgctagg  660
tattacgacg accactactg tttagactat tggggacaag gtaccacttt aaccgtcagc  720
agc                                                                 723

SEQ ID NO: 153          moltype = AA  length = 236
FEATURE                 Location/Qualifiers
REGION                  1..236
```

```
                        note = source = /note="CD28"
source                  1..236
                        mol_type = protein
                        organism = Homo sapiens
SEQUENCE: 153
VQLQQSGPEL VKPGASVKMS CKASGYTFTS YVIQWVKQKP GQGLEWIGSI NPYNDYTKYN  60
EKFKGKATLT SDKSSITAYM EFSSLTSEDS ALYYCARWGD GNYWGRGTTL TVSSGGGGSG  120
GGGSGGGGSD IEMTQSPAIM SASLGERVTM TCTASSSVSS SYFHWYQQKP GSSPKLCIYS  180
TSNLASGVPP RFSGSGSTSY SLTISSMEAE DAATYFCHQY HRSPTFGGGT KLETKR      236

SEQ ID NO: 154          moltype = DNA  length = 708
FEATURE                 Location/Qualifiers
source                  1..708
                        mol_type = genomic DNA
                        note = source = CD28
                        organism = Homo sapiens
SEQUENCE: 154
gtccagctgc agcagagcgg acccgaactc gtgaaacccg gtgcttccgt gaaaatgtct  60
tgtaaggcca gcggatacac cttcacctcc tatgtgatcc agtgggtcaa acagaagccc  120
ggacaaggtc tcgagtggat cggcagcatc aacccttaca acgactatac caaatacaac  180
gagaagttta agggaaaggc tactttaacc tccgacaaaa gctccatcac agcctacatg  240
gagttcagct ctttaacatc cgaggacagc gctctgtact attgcgcccg gtggggcgac  300
ggcaattact ggggacgggg cacaacactg accgtgagca gcggaggcgg aggctccggc  360
ggaggcggat ctggcggtgg cggctccgac atcgagatga cccagtcccc cgctatcatg  420
tccgcctctt taggcgagcg ggtcacaatg acttgtacag cctcctccag cgtctcctcc  480
tcctacttcc attggtacca acagaaaccc ggaagctccc ctaaactgtg catctacagc  540
accagcaatc tcgccagcgg cgtgccccct aggttttccg gaagcggaag caccagctac  600
tctttaacca tctcctccat ggaggctgag gatgccgcca cctacttttg tcaccagtac  660
caccggtccc ccaccttcgg aggcggcacc aaactggaga caaagagg               708

SEQ ID NO: 155          moltype = AA  length = 696
FEATURE                 Location/Qualifiers
source                  1..696
                        mol_type = protein
                        organism = synthetic construct
SEQUENCE: 155
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEINRGGG GSGGGGSGGG  120
GSQVQLQQSG AELARPGASV KMSCKASGYT FTRYTMHWVK QRPGQGLEWI GYINPSRGYT  180
NYNQKFKDKA TLTTDKSSST AYMQLSSLTS EDSAVYYCAR YYDDHYCLDY WGQGTTLTVS  240
SSGTTNTVAA YNLTWKSTNF KTILEWEPKP VNQVYTVQIS TKSGDWKSKC FYTTDTECDL  300
TDEIVKDVKQ TYLARVFSYP AGNVESTGSA GEPLYENSPE FTPYLETNLG QPTIQSFEQV  360
GTKVNVTVED ERTLVRRNNT FLSLRDVFGK DLIYTLYYWK SSSSGKKTAK TNTNEFLIDV  420
DKGENYCFSV QAVIPSRTVN RKSTDSPVEC MGQEKGEFRE VQLQQSGPEL VKPGASVKMS  480
CKASGYTFTS YVIQWVKQKP GQGLEWIGSI NPYNDYTKYN EKFKGKATLT SDKSSITAYM  540
EFSSLTSEDS ALYYCARWGD GNYWGRGTTL TVSSGGGGSG GGGSGGGGSD IEMTQSPAIM  600
SASLGERVTM TCTASSSVSS SYFHWYQQKP GSSPKLCIYS TSNLASGVPP RFSGSGSTSY  660
SLTISSMEAE DAATYFCHQY HRSPTFGGGT KLETKR                            696

SEQ ID NO: 156          moltype = DNA  length = 2088
FEATURE                 Location/Qualifiers
source                  1..2088
                        mol_type = other DNA
                        organism = synthetic construct
SEQUENCE: 156
cagatcgtgc tgacccaaag ccccgccatc atgagcgcta gccccggtga gaaggtgacc  60
atgacatgct ccgcttccag ctccgtgtcc tacatgaact ggtatcagca gaaaagcgga  120
accagcccca aaaggtggat ctacgacacc agcaagctgg cctccggagt gcccgctcat  180
ttccggggct ctggatccgg caccagctac tctttaacca tttccggcat ggaagctgaa  240
gacgctgcca cctactattg ccagcaatgg agcagcaacc ccttcacatt cggatctggc  300
accaagctcg aaatcaatcg tggaggaggt ggcagcggcg gcggtggatc cggcggagga  360
ggaagccaag ttcaactcca gcagagcggc gctgaactgg cccggcccgg cgcctccgtc  420
aagatgagct gcaaggcttc cggctataca tttactcgtt acacaatgca ttgggtcaag  480
cagaggcccg gtcaaggttt agagtggatc ggatatatca acccttcccg gggctacacc  540
aactataacc aaaagttcaa ggataaagcc actttaacca ctgacaagag ctcctccacc  600
gcctacatgc agctgtcctc tttaaccagc gaggactccg ctgtttacta ctgcgctagg  660
tattacgacg accactactg tttagactat tggggacaag gtaccacttt aaccgtcagc  720
agctccggca ccaccaatac cgtggccgct tataacctca catggaagag caccaacttc  780
aagacaattc tggaatggga acccaagccc gtcaatcaag tttacaccgt gcagatctcc  840
accaaatccg gagactggaa gagcaagtgc ttctacacaa cagacaccga gtgtgattta  900
accgacgaaa tcgtcaagga cgtcaagcaa acctatctgg ctcgggtctt ttcctacccc  960
gctggcaatg tcgagtccac cggctccgct ggcgagcctc tctacgagaa ttcccccgaa  1020
ttcacccctt atttagagac caatttaggc cagcctacca tccagagctt cgagcaagtt  1080
ggcaccaagg tgaacgtcac cgtcgaggat gaaaggactt tagtgcggcg gaataacaca  1140
tttttatccc tccgggatgt gttcggcaaa gacctcatct acacactgta ctattggaag  1200
tccagctcct ccggcaaaaa gaccgctaag accaacacca acgagttttt aattgacgtg  1260
gacaaaggcg agaactactg cttcagcgtg caagccgtga tcccttctcg taccgtcaac  1320
cggaagagca cagattcccc cgttgagtgc atgggccaag aaaagggcga gttccgggag  1380
gtccagctgc agcagagcgg acccgaactc gtgaaacccg gtgcttccgt gaaaatgtct  1440
```

```
tgtaaggcca gcggatacac cttcacctcc tatgtgatcc agtgggtcaa acagaagccc  1500
ggacaaggtc tcgagtggat cggcagcatc aacccttaca acgactatac caaatacaac  1560
gagaagttta agggaaaggc tactttaacc tccgacaaaa gctccatcac agcctacatg  1620
gagttcagct ctttaacatc cgaggacagc gctctgtact attgcgcccg gtggggcgac  1680
ggcaattact ggggacgggg cacaacactg accgtgagca gcggaggcgg aggctccggc  1740
ggaggcggat ctggcggtgg cggctccgac atcgagatga cccagtcccc cgctatcatg  1800
tccgcctctt taggcgagcg ggtcacaatg acttgtacag cctcctccag cgtctcctcc  1860
tcctacttcc attggtacca acagaaaccc ggaagctccc ctaaactgtg catctacagc  1920
accagcaatc tcgccagcgg cgtgccccct aggttttccg gaagcggaag caccagctac  1980
tctttaacca tctcctccat ggaggctgag gatgccgcca cctactttg tcaccagtac  2040
caccggtccc ccaccttcgg aggcggcacc aaactggaga caaagagg              2088
```

```
SEQ ID NO: 157          moltype = AA  length = 714
FEATURE                 Location/Qualifiers
source                  1..714
                        mol_type = protein
                        organism = synthetic construct
SEQUENCE: 157
MKWVTFISLL FLFSSAYSQI VLTQSPAIMS ASPGEKVTMT CSASSSVSYM NWYQQKSGTS  60
PKRWIYDTSK LASGVPAHFR GSGSGTSYSL TISGMEAEDA ATYYCQQWSS NPFTFGSGTK  120
LEINRGGGGS GGGGSGGGGS QVQLQQSGAE LARPGASVKM SCKASGYTFT RYTMHWVKQR  180
PGQGLEWIGY INPSRGYTNY NQKFKDKATL TTDKSSSTAY MQLSSLTSED SAVYYCARYY  240
DDHYCLDYWG QGTTLTVSSS GTTNTVAAYN LTWKSTNFKT ILEWEPKPVN QVYTVQISTK  300
SGDWKSKCFY TTDTECDLTD EIVKDVKQTY LARVFSYPAG NVESTGSAGE PLYENSPEFT  360
PYLETNLGQP TIQSFEQVGT KVNVTVEDER TLVRRNNTFL SLRDVFGKDL IYTLYYWKSS  420
SSGKKTAKTN TNEFLIDVDK GENYCFSVQA VIPSRTVNRK STDSPVECMG QEKGEFREVQ  480
LQQSGPELVK PGASVKMSCK ASGYTFTSYV IQWVKQKPGQ GLEWIGSINP YNDYTKYNEK  540
FKGKATLTSD KSSITAYMEF SSLTSEDSAL YYCARWGDGN YWGRGTTLTV SSGGGGSGGG  600
GSGGGGSDIE MTQSPAIMSA SLGERVTMTC TASSSVSSSY FHWYQQKPGS SPKLCIYSTS  660
NLASGVPPRF SGSGSTSYSL TISSMEAEDA ATYFCHQYHR SPTFGGGTKL ETKR        714
```

```
SEQ ID NO: 158          moltype = DNA  length = 2142
FEATURE                 Location/Qualifiers
source                  1..2142
                        mol_type = other DNA
                        organism = synthetic construct
SEQUENCE: 158
atgaagtggg tgaccttcat cagcttatta tttttattca gctccgccta ttcccagatc  60
gtgctgaccc aaagccccgc catcatgagc gctagccccg gtgagaaggt gaccatgaca  120
tgctccgctt ccagctccgt gtcctacatg aactggtatc agcagaaaag cggaaccagc  180
cccaaaaggt ggatctacga caccagcaag ctggcctccg gagtgcccgc tcatttccgg  240
ggctctggat ccggcaccag ctactcttta accatttccg gcatggaagc tgaagacgct  300
gccacctact attgccagca atggagcagc aacccccttca cattcggatc tggcaccaag  360
ctcgaaatca atcgtggagg aggtggcagc ggcggcggtg gatccggcgg aggaggaagc  420
caagttcaac tccagcagag cggcgctgaa ctggcccggc ccggcgcctc cgtcaagatg  480
agctgcaagg cttccggcta tacatttact cgttacacaa tgcattgggt caagcagagg  540
cccggtcaag gtttagagtg gatcggatat atcaaccctt cccggggcta caccaactat  600
aaccaaaagt tcaaggataa agccacttta accactgaca agagctcctc caccgcctac  660
atgcagctgt cctctttaac cagcgaggac tccgctgttt actactgcgc taggtattac  720
gacgaccact actgtttaga ctattgggga caaggtacca ctttaaccgt cagcagctcc  780
ggcaccacca ataccgtggc cgcttataac ctcacatgga agagcaccaa cttcaagaca  840
attctggaat gggaacccaa gcccgtcaat caagtttaca ccgtgcagat ctccaccaaa  900
tccggagact ggaagagcaa gtgcttctac acaacagaca ccgagtgtga tttaaccgac  960
gaaatcgtca aggacgtcaa gcaaacctat ctggctcggg tcttttccta ccccgctggc  1020
aatgtcgagt ccaccggctc cgctggcgag cctctctacg agaattcccc cgaattcacc  1080
ccttatttag agaccaattt aggccagcct accatccaga gcttcgagca agttggcacc  1140
aaggtgaacg tcaccgtcga ggatgaaagg actttagtgc ggcggaataa cacattttta  1200
tccctccggg atgtgttcgg caaagacctc atctacacac tgtactattg gaagtccagc  1260
tcctccggca aaaagaccgc taagaccaac accaacgagt ttttaattga cgtggacaaa  1320
ggcgagaact actgcttcag cgtgcaagcc gtgatccctt ctcgtaccgt caaccggaag  1380
agcacagatt cccccgttga gtgcatgggc caagaaaagg gcgagttccg ggaggtccag  1440
ctgcagcaga gcggacccga actcgtgaaa cccggtgctt ccgtgaaaat gtcttgtaag  1500
gccagcggat acaccttcac ctcctatgtg atccagtggg tcaaacagaa gcccggacaa  1560
ggtctcgagt ggatcggcag catcaaccct tacaacgact ataccaaata caacgagaag  1620
tttaagggaa aggctacttt aacctccgac aaaagctcca tcacagccta catggagttc  1680
agctctttaa catccgagga cagcgctctg tactattgcg cccggtgggg cgacggcaat  1740
tactggggac ggggcacaac actgaccgtg agcagcggag gcggaggctc cggcggaggc  1800
ggatctggcg gtggcggctc cgacatcgag atgacccagt cccccgctat catgtccgcc  1860
tctttaggcg agcgggtcac aatgacttgt acagcctcct ccagcgtctc ctcctcctac  1920
ttccattggt accaacagaa acccggaagc tcccctaaac tgtgcatcta cagcaccagc  1980
aatctcgcca gcggcgtgcc ccctaggttt tccggaagcg gaagcaccag ctactcttta  2040
accatctcct ccatggaggc tgaggatgcc gccacctact tttgtcacca gtaccaccgg  2100
tcccccacct tcggaggcgg caccaaactg gagacaaaga gg                    2142
```

```
SEQ ID NO: 159          moltype = DNA  length = 399
FEATURE                 Location/Qualifiers
source                  1..399
                        mol_type = genomic DNA
                        note = source = IL-2
```

```
                         organism = Homo sapiens
SEQUENCE: 159
gcacctactt caagttctac aaagaaaaca cagctacaac tggagcattt actgctggat  60
ttacagatga ttttgaatgg aattaataat tacaagaatc ccaaactcac caggatgctc  120
acatttaagt tttacatgcc caagaaggcc acagaactga aacatcttca gtgtctagaa  180
gaagaactca aacctctgga ggaagtgcta aatttagctc aaagcaaaaa ctttcactta  240
agacccaggg acttaatcag caatatcaac gtaatagttc tggaactaaa gggatctgaa  300
acaacattca tgtgtgaata tgctgatgag acagcaacca ttgtagaatt tctgaacaga  360
tggattacct tttgtcaaag catcatctca acactaact                         399

SEQ ID NO: 160           moltype = DNA  length = 399
FEATURE                  Location/Qualifiers
source                   1..399
                         mol_type = genomic DNA
                         note = source = IL-2
                         organism = Homo sapiens
SEQUENCE: 160
gcccccacct cctcctccac caagaagacc cagctgcagc tggagcattt actgctggat  60
ttacagatga ttttaaacgg catcaacaac tacaagaacc ccaagctgac tcgtatgctg  120
accttcaagt tctacatgcc caagaaggcc accgagctga agcatttaca gtgtttagag  180
gaggagctga agcccctcga ggaggtgctg aatttagccc agtccaagaa tttccattta  240
aggccccggg atttaatcag caacatcaac gtgatcgttt tagagctgaa gggctccgag  300
accaccttca tgtgcgagta cgccgacgag accgccacca tcgtggagtt tttaaatcgt  360
tggatcacct tctgccagtc catcatctcc actttaacc                         399

SEQ ID NO: 161           moltype = AA  length = 485
FEATURE                  Location/Qualifiers
source                   1..485
                         mol_type = protein
                         organism = synthetic construct
SEQUENCE: 161
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGTTNTV AAYNLTWKST NFKTILEWEP KPVNQVYTVQ ISTKSGDWKS  180
KCFYTTDTEC DLTDEIVKDV KQTYLARVFS YPAGNVESTG SAGEPLYENS PEFTPYLETN  240
LGQPTIQSFE QVGTKVNVTV EDERTLVRRN NTFLSLRDVF GKDLIYTLYY WKSSSSGKKT  300
AKTNTNEFLI DVDKGENYCF SVQAVIPSRT VNRKSTDSPV ECMGQEKGEF REAPTSSSTK  360
KTQLQLEHLL LDLQMILNGI NNYKNPKLTR MLTFKFYMPK KATELKHLQC LEEELKPLEE  420
VLNLAQSKNF HLRPRDLISN INVIVLELKG SETTFMCEYA DETATIVEFL NRWITFCQSI  480
ISTLT                                                              485

SEQ ID NO: 162           moltype = DNA  length = 1455
FEATURE                  Location/Qualifiers
source                   1..1455
                         mol_type = other DNA
                         organism = synthetic construct
SEQUENCE: 162
gcccccacct cctcctccac caagaagacc cagctgcagc tggagcattt actgctggat  60
ttacagatga ttttaaacgg catcaacaac tacaagaacc ccaagctgac tcgtatgctg  120
accttcaagt tctacatgcc caagaaggcc accgagctga agcatttaca gtgtttagag  180
gaggagctga agcccctcga ggaggtgctg aatttagccc agtccaagaa tttccattta  240
aggccccggg atttaatcag caacatcaac gtgatcgttt tagagctgaa gggctccgag  300
accaccttca tgtgcgagta cgccgacgag accgccacca tcgtggagtt tttaaatcgt  360
tggatcacct tctgccagtc catcatctcc actttaacca gcggcacaac caacacagtc  420
gctgcctata acctcacttg gaagagcacc aacttcaaaa ccatcctcga atgggaaccc  480
aaacccgtta accaagttta caccgtgcag atcagcacca agtccggcga ctggaagtcc  540
aaatgtttct ataccaccga caccgagtgc gatctcaccg atgagatcgt gaaagatgtg  600
aaacagacct acctcgcccg ggtgtttagc taccccgccg gcaatgtgga gagcactggt  660
tccgctggcg agcctttata cgagaacagc cccgaattta ccccttacct cgagaccaat  720
ttaggacagc ccaccatcca aagctttgag caagttggca caaaggtgaa tgtgacagtg  780
gaggacgagc ggactttagt gcggcggaac aacacctttc tcagcctccg ggatgtgttc  840
ggcaaagatt taatctacac actgtattac tggaagtcct cttcctccgg caagaagaca  900
gctaaaacca acacaaacga gtttttaatc gacgtggata aaggcgaaaa ctactgtttc  960
agcgtgcaag ctgtgatccc ctcccggacc gtgaatagga aaagcaccga tagccccgtt  1020
gagtgcatgg gccaagaaaa gggcgagttc cgggaggcac ctacttcaag ttctacaaag  1080
aaaacacagc tacaactgga gcatttactg ctggatttac agatgatttt gaatggaatt  1140
aataattaca agaatcccaa actcaccagg atgctcacat ttaagtttta catgcccaag  1200
aaggccacag aactgaaaca tcttcagtgt ctagaagaag aactcaaacc tctggaggaa  1260
gtgctaaatt tagctcaaag caaaaacttt cacttaagac ccagggactt aatcagcaat  1320
atcaacgtaa tagttctgga actaaaggga tctgaaacaa cattcatgtg tgaatatgct  1380
gatgagacag caaccattgt agaatttctg aacagatgga ttaccttttg tcaaagcatc  1440
atctcaacac taact                                                   1455

SEQ ID NO: 163           moltype = AA  length = 503
FEATURE                  Location/Qualifiers
source                   1..503
                         mol_type = protein
                         organism = synthetic construct
SEQUENCE: 163
```

-continued

```
MKWVTFISLL FLFSSAYSAP TSSSTKKTQL QLEHLLLDLQ MILNGINNYK NPKLTRMLTF  60
KFYMPKKATE LKHLQCLEEE LKPLEEVLNL AQSKNFHLRP RDLISNINVI VLELKGSETT  120
FMCEYADETA TIVEFLNRWI TFCQSIISTL TSGTTNTVAA YNLTWKSTNF KTILEWEPKP  180
VNQVYTVQIS TKSGDWKSKC FYTTDTECDL TDEIVKDVKQ TYLARVFSYP AGNVESTGSA  240
GEPLYENSPE FTPYLETNLG QPTIQSFEQV GTKVNVTVED ERTLVRRNNT FLSLRDVFGK  300
DLIYTLYYWK SSSSGKKTAK TNTNEFLIDV DKGENYCFSV QAVIPSRTVN RKSTDSPVEC  360
MGQEKGEFRE APTSSSTKKT QLQLEHLLLD LQMILNGINN YKNPKLTRML TFKFYMPKKA  420
TELKHLQCLE EELKPLEEVL NLAQSKNFHL RPRDLISNIN VIVLELKGSE TTFMCEYADE  480
TATIVEFLNR WITFCQSIIS TLT                                       503

SEQ ID NO: 164         moltype = DNA  length = 1509
FEATURE                Location/Qualifiers
source                 1..1509
                       mol_type = other DNA
                       organism = synthetic construct
SEQUENCE: 164
atgaagtggg tgaccttcat cagcctgctg ttcctgttct ccagcgccta ctccgccccc  60
acctcctcct ccaccaagaa gacccagctg cagctggagc atttactgct ggatttacag  120
atgattttaa acggcatcaa caactacaag aaccccaagc tgactcgtat gctgaccttc  180
aagttctaca tgcccaagaa ggccaccgag ctgaagcatt tacagtgttt agaggaggag  240
ctgaagcccc tcgaggaggt gctgaattta gcccagtcca agaatttcca tttaaggccc  300
cgggatttaa tcagcaacat caacgtgatc gttttagagc tgaagggctc cgagaccacc  360
ttcatgtgcg agtacgccga cgagaccgcc accatcgtgg agtttttaaa tcgttggatc  420
accttctgcc agtccatcat ctccacttta accagcggca caaccaacac agtcgctgcc  480
tataacctca cttggaagag caccaacttc aaaaccatcc tcgaatggga acccaaaccc  540
gttaaccaag tttacaccgt gcagatcagc accaagtccg gcgactggaa gtccaaatgt  600
ttctatacca ccgacaccga gtgcgatctc accgatgaga tcgtgaaaga tgtgaaacag  660
acctacctcg cccgggtgtt tagctacccc gccggcaatg tggagagcac tggttccgct  720
ggcgagcctt tatacgagaa cagccccgaa tttacccctt acctcgagac caatttagga  780
cagcccacca tccaaagctt tgagcaagtt ggcacaaagg tgaatgtgac agtggaggac  840
gagcggactt tagtgcggcg gaacaacacc tttctcagcc tccgggatgt gttcggcaaa  900
gatttaatct acacactgta ttactggaag tcctcttcct ccggcaagaa gacagctaaa  960
accaacacaa acgagttttt aatcgacgtg gataaaggcg aaaactactg tttcagcgtg  1020
caagctgtga tcccctcccg gaccgtgaat aggaaaagca ccgatagccc cgttgagtgc  1080
atgggccaag aaaagggcga gttccgggag gcacctactt caagttctac aaagaaaaca  1140
cagctacaac tggagcattt actgctggat ttacagatga ttttgaatgg aattaataat  1200
tacaagaatc ccaaactcac caggatgctc acatttaagt tttacatgcc caagaaggcc  1260
acagaactga aacatcttca gtgtctagaa gaagaactca aacctctgga ggaagtgcta  1320
aatttagctc aaagcaaaaa ctttcactta agacccaggg acttaatcag caatatcaac  1380
gtaatagttc tggaactaaa gggatctgaa acaacattca tgtgtgaata tgctgatgag  1440
acagcaacca ttgtagaatt tctgaacaga tggattacct tttgtcaaag catcatctca  1500
acactaact                                                         1509

SEQ ID NO: 165         moltype = DNA  length = 342
FEATURE                Location/Qualifiers
source                 1..342
                       mol_type = genomic DNA
                       note = source = IL-15
                       organism = Homo sapiens
SEQUENCE: 165
aactgggtga acgtgatcag cgatttaaag aagatcgagg atttaatcca gagcatgcac  60
atcgacgcca ctctgtacac tgagagcgac gtgcacccta gctgcaaggt gactgccatg  120
aagtgctttt tactggagct gcaagttatc tctttagaga gcggcgatgc cagcatccac  180
gacactgtgg agaatttaat cattttagcc aacaactctt taagcagcaa cggcaacgtg  240
acagagagcg gctgcaagga gtgcgaggag ctggaggaga agaacatcaa ggagttttta  300
cagagcttcg tgcacatcgt gcagatgttc atcaacacta gc                     342

SEQ ID NO: 166         moltype = DNA  length = 342
FEATURE                Location/Qualifiers
source                 1..342
                       mol_type = genomic DNA
                       note = source = IL-15
                       organism = Homo sapiens
SEQUENCE: 166
aactgggtga acgtcatcag cgatttaaag aagatcgaag atttaattca gtccatgcat  60
atcgacgcca ctttatacac agaatccgac gtgcacccct cttgtaaggt gaccgccatg  120
aaatgttttt tactggagct gcaagttatc tctttagaga gcggagacgc tagcatccac  180
gacaccgtgg agaatttaat cattttagcc aataactctt tatccagcaa cggcaacgtg  240
acagagtccg gctgcaagga gtgcgaagag ctggaggaga agaacatcaa ggagtttctg  300
caatcctttg tgcacattgt ccagatgttc atcaatacct cc                     342

SEQ ID NO: 167         moltype = AA  length = 447
FEATURE                Location/Qualifiers
source                 1..447
                       mol_type = protein
                       organism = synthetic construct
SEQUENCE: 167
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTSSGTTNT  120
```

-continued

```
VAAYNLTWKS TNFKTILEWE PKPVNQVYTV QISTKSGDWK SKCFYTTDTE CDLTDEIVKD  180
VKQTYLARVF SYPAGNVEST GSAGEPLYEN SPEFTPYLET NLGQPTIQSF EQVGTKVNVT  240
VEDERTLVRR NNTFLSLRDV FGKDLIYTLY YWKSSSSGKK TAKTNTNEFL IDVDKGENYC  300
FSVQAVIPSR TVNRKSTDSP VECMGQEKGE FRENWVNVIS DLKKIEDLIQ SMHIDATLYT  360
ESDVHPSCKV TAMKCFLLEL QVISLESGDA SIHDTVENLI ILANNSLSSN GNVTESGCKE  420
CEELEEKNIK EFLQSFVHIV QMFINTS                                     447

SEQ ID NO: 168         moltype = DNA  length = 1341
FEATURE                Location/Qualifiers
source                 1..1341
                       mol_type = other DNA
                       organism = synthetic construct
SEQUENCE: 168
aactgggtga acgtgatcag cgatttaaag aagatcgagg atttaatcca gagcatgcac  60
atcgacgcca ctctgtacac tgagagcgac gtgcacccta gctgcaaggt gactgccatg  120
aagtgctttt tactggagct gcaagttatc tctttagaga gcggcgatgc cagcatccac  180
gacactgtgg agaatttaat cattttagcc aacaactctt taagcagcaa cggcaacgtg  240
acagagagcg gctgcaagga gtgcgaggag ctggaggaga agaacatcaa ggagttttta  300
cagagcttcg tgcacatcgt gcagatgttc atcaacacta gcagcggcac aaccaacaca  360
gtcgctgcct ataacctcac ttggaagagc accaacttca aaaccatcct cgaatgggaa  420
cccaaacccg ttaaccaagt ttacaccgtg cagatcagca ccaagtccgg cgactggaag  480
tccaaatgtt tctataccac cgacaccgag tgcgatctca ccgatgagat cgtgaaagat  540
gtgaaacaga cctacctcgc ccgggtgttt agctaccccg ccggcaatgt ggagagcact  600
ggttccgctg gcgagccttt atacgagaac agccccgaat ttaccccttta cctcgagacc  660
aatttaggac agcccaccat ccaaagcttt gagcaagttg gcacaaaggt gaatgtgaca  720
gtggaggacg agcggacttt agtgcggcgg aacaacacct ttctcagcct ccgggatgtg  780
ttcggcaaag atttaatcta cacactgtat tactggaagt cctcttcctc cggcaagaag  840
acagctaaaa ccaacacaaa cgagttttta atcgacgtgg ataaaggcga aaactactgt  900
ttcagcgtgc aagctgtgat cccctcccgg accgtgaata ggaaaagcac cgatagcccc  960
gttgagtgca tgggccaaga aaagggcgag ttccgggaga actgggtgaa cgtcatcagc  1020
gatttaaaga agatcgaaga tttaattcag tccatgcata tcgacgccac tttatacaca  1080
gaatccgacg tgcacccctc ttgtaaggtg accgccatga aatgtttttt actggagctg  1140
caagttatct ctttagagag cggagacgct agcatccacg acaccgtgga gaatttaatc  1200
attttagcca ataactcttt atccagcaac ggcaacgtga cagagtccgg ctgcaaggag  1260
tgcgaagagc tggaggagaa gaacatcaag gagtttctgc aatcctttgt gcacattgtc  1320
cagatgttca tcaatacctc c                                           1341

SEQ ID NO: 169         moltype = AA  length = 465
FEATURE                Location/Qualifiers
source                 1..465
                       mol_type = protein
                       organism = synthetic construct
SEQUENCE: 169
MKWVTFISLL FLFSSAYSNW VNVISDLKKI EDLIQSMHID ATLYTESDVH PSCKVTAMKC  60
FLLELQVISL ESGDASIHDT VENLIILANN SLSSNGNVTE SGCKECEELE EKNIKEFLQS  120
FVHIVQMFIN TSSGTTNTVA AYNLTWKSTN FKTILEWEPK PVNQVYTVQI STKSGDWKSK  180
CFYTTDTECD LTDEIVKDVK QTYLARVFSY PAGNVESTGS AGEPLYENSP EFTPYLETNL  240
GQPTIQSFEQ VGTKVNVTVE DERTLVRRNN TFLSLRDVFG KDLIYTLYYW KSSSSGKKTA  300
KTNTNEFLID VDKGENYCFS VQAVIPSRTV NRKSTDSPVE CMGQEKGEFR ENWVNVISDL  360
KKIEDLIQSM HIDATLYTES DVHPSCKVTA MKCFLLELQV ISLESGDASI HDTVENLIIL  420
ANNSLSSNGN VTESGCKECE ELEEKNIKEF LQSFVHIVQM FINTS                 465

SEQ ID NO: 170         moltype = DNA  length = 1395
FEATURE                Location/Qualifiers
source                 1..1395
                       mol_type = other DNA
                       organism = synthetic construct
SEQUENCE: 170
atgaagtggg tgaccttcat cagcctgctg ttcctgttct ccagcgccta ctccaactgg  60
gtgaacgtga tcagcgattt aaagaagatc gaggatttaa tccagagcat gcacatcgac  120
gccactctgt acactgagag cgacgtgcac cctagctgca aggtgactgc catgaagtgc  180
tttttactgg agctgcaagt tatctcttta gagagcggcg atgccagcat ccacgacact  240
gtggagaatt taatcatttt agccaacaac tctttaagca gcaacggcaa cgtgacagag  300
agcggctgca aggagtgcga ggagctggag gagaagaaca tcaaggagtt tttacagagc  360
ttcgtgcaca tcgtgcagat gttcatcaac actagcagcg gcacaaccaa cacagtcgct  420
gcctataacc tcacttggaa gagcaccaac ttcaaaacca tcctcgaatg ggaacccaaa  480
cccgttaacc aagtttacac cgtgcagatc agcaccaagt ccggcgactg gaagtccaaa  540
tgtttctata ccaccgacac cgagtgcgat ctcaccgatg agatcgtgaa agatgtgaaa  600
cagacctacc tcgcccgggt gtttagctac cccgccggca atgtggagag cactggttcc  660
gctggcgagc ctttatacga gaacagcccc gaatttaccc cttacctcga gaccaattta  720
ggacagccca ccatccaaag ctttgagcaa gttggcacaa aggtgaatgt gacagtggag  780
gacgagcgga ctttagtgcg gcggaacaac acctttctca gcctccggga tgtgttcggc  840
aaagatttaa tctacacact gtattactgg aagtcctctt cctccggcaa gaagacagct  900
aaaaccaaca caaacgagtt tttaatcgac gtggataaag gcgaaaacta ctgtttcagc  960
gtgcaagctg tgatcccctc ccggaccgtg aataggaaaa gcaccgatag ccccgttgag  1020
tgcatgggcc aagaaaaggg cgagttccgg gagaactggg tgaacgtcat cagcgattta  1080
aagaagatcg aagatttaat tcagtccatg catatcgacg ccactttata cacagaatcc  1140
gacgtgcacc cctcttgtaa ggtgaccgcc atgaaatgtt ttttactgga gctgcaagtt  1200
atctctttag agagcggaga cgctagcatc cacgacaccg tggagaattt aatcatttta  1260
```

```
gccaataact ctttatccag caacggcaac gtgacagagt ccggctgcaa ggagtgcgaa  1320
gagctggagg agaagaacat caaggagttt ctgcaatcct ttgtgcacat tgtccagatg  1380
ttcatcaata cctcc                                                   1395

SEQ ID NO: 171          moltype = DNA  length = 471
FEATURE                 Location/Qualifiers
source                  1..471
                        mol_type = genomic DNA
                        note = source = IL-18
                        organism = Homo sapiens
SEQUENCE: 171
tacttcggca aactggaatc caagctgagc gtgatccgga atttaaacga ccaagttctg  60
tttatcgatc aaggtaaccg gcctctgttc gaggacatga ccgactccga ttgccgggac  120
aatgcccccc ggaccatctt cattatctcc atgtacaagg acagccagcc ccggggcatg  180
gctgtgacaa ttagcgtgaa gtgtgagaaa atcagcactt tatcttgtga gaacaagatc  240
atctccttta aggaaatgaa cccccccgat aacatcaagg acaccaagtc cgatatcatc  300
ttcttccagc ggtccgtgcc cggtcacgat aacaagatgc agttcgaatc ctcctcctac  360
gagggctact ttttagcttg tgaaaaggag agggatttat tcaagctgat cctcaagaag  420
gaggacgagc tgggcgatcg ttccatcatg ttcaccgtcc aaaacgagga t           471

SEQ ID NO: 172          moltype = DNA  length = 918
FEATURE                 Location/Qualifiers
source                  1..918
                        mol_type = genomic DNA
                        note = source = IL12Beta
                        organism = Homo sapiens
SEQUENCE: 172
atttgggaac tgaagaagga cgtctacgtg gtcgaactgg actggtatcc cgatgctccc  60
ggcgaaatgg tggtgctcac ttgtgacacc cccgaagaag acggcatcac ttggaccctc  120
gatcagagca gcgaggtgct gggctccgga aagaccctca caatccaagt taaggagttc  180
ggagacgctg gccaatacac atgccacaag ggaggcgagg tgctcagcca ttccttatta  240
ttattacaca agaaggaaga cggaatctgg tccaccgaca ttttaaaaga tcagaaggag  300
cccaagaata agaccttttt aaggtgtgag gccaaaaact acagcggtcg tttcacttgt  360
tggtggctga ccaccatttc caccgattta accttctccg tgaaaagcag ccggggaagc  420
tccgaccctc aaggtgtgac atgtggagcc gctaccctca gcgctgagag ggttcgtggc  480
gataacaagg aatacgagta cagcgtggag tgccaagaag atagcgcttg tcccgctgcc  540
gaagaatctt tacccattga ggtgatggtg gacgccgtgc acaaactcaa gtacgagaac  600
tacacctcct ccttctttat ccgggacatc attaagcccg atcctcctaa gaatttacag  660
ctgaagcctc tcaaaaatag ccggcaagtt gaggtctctt gggaatatcc cgacacttgg  720
agcacaccccc acagctactt ctctttaacc ttttgtgtgc aagttcaagg taaaagcaag  780
cgggagaaga aagaccgggt gtttaccgac aaaaccagcg ccaccgtcat ctgtcggaag  840
aacgcctcca tcagcgtgag ggctcaagat cgttattact ccagcagctg gtccgagtgg  900
gccagcgtgc cttgttcc                                                918

SEQ ID NO: 173          moltype = DNA  length = 591
FEATURE                 Location/Qualifiers
source                  1..591
                        mol_type = genomic DNA
                        note = source = IL-12alpha
                        organism = Homo sapiens
SEQUENCE: 173
cgtaacctcc ccgtggctac ccccgatccc ggaatgttcc cttgtttaca ccacagccag  60
aatttactga gggccgtgag caacatgctg cagaaagcta ggcagacttt agaattttac  120
ccttgcacca gcgaggagat cgaccatgaa gatatcacca aggacaagac atccaccgtg  180
gaggcttgtt tacctctgga gctgacaaag aacgagtctt gtctcaactc tcgtgaaacc  240
agcttcatca caaatggctc ttgtttagct tcccggaaga cctcctttat gatggcttta  300
tgcctcagct ccatctacga ggatttaaag atgtaccaag tggagttcaa gaccatgaac  360
gccaagctgc tcatggaccc taaacggcag atctttttag accagaacat gctggctgtg  420
attgatgagc tgatgcaagc tttaaacttc aactccgaga ccgtccctca gaagtcctcc  480
ctcgaggagc ccgattttta caagacaaag atcaaactgt gcattttact ccacgccttt  540
aggatccggg ccgtgaccat tgaccgggtc atgagctatt taaacgccag c           591

SEQ ID NO: 174          moltype = AA  length = 490
FEATURE                 Location/Qualifiers
source                  1..490
                        mol_type = protein
                        organism = synthetic construct
SEQUENCE: 174
YFGKLESKLS VIRNLNDQVL FIDQGNRPLF EDMTDSDCRD NAPRTIFIIS MYKDSQPRGM  60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNEDSGT TNTVAAYNLT WKSTNFKTIL  180
EWEPKPVNQV YTVQISTKSG DWKSKCFYTT DTECDLTDEI VKDVKQTYLA RVFSYPAGNV  240
ESTGSAGEPL YENSPEFTPY LETNLGQPTI QSFEQVGTKV NVTVEDERTL VRRNNTFLSL  300
RDVFGKDLIY TLYYWKSSSS GKKTAKTNTN EFLIDVDKGE NYCFSVQAVI PSRTVNRKST  360
DSPVECMGQE KGEFRENWVN VISDLKKIED LIQSMHIDAT LYTESDVHPS CKVTAMKCFL  420
LELQVISLES GDASIHDTVE NLIILANNSL SSNGNVTESG CKECEELEEK NIKEFLQSFV  480
HIVQMFINTS                                                         490

SEQ ID NO: 175          moltype = DNA  length = 1470
```

```
FEATURE                Location/Qualifiers
source                 1..1470
                       mol_type = other DNA
                       organism = synthetic construct
SEQUENCE: 175
tacttcggca aactggaatc caagctgagc gtgatccgga atttaaacga ccaagttctg  60
tttatcgatc aaggtaaccg gcctctgttc gaggacatga ccgactccga ttgccgggac  120
aatgcccccc ggaccatctt cattatctcc atgtacaagg acagccagcc ccggggcatg  180
gctgtgacaa ttagcgtgaa gtgtgagaaa atcagcactt tatcttgtga gaacaagatc  240
atctccttta aggaaatgaa cccccccgat aacatcaagg acaccaagtc cgatatcatc  300
ttcttccagc ggtccgtgcc cggtcacgat aacaagatgc agttcgaatc ctcctcctac  360
gagggctact tttagcttg tgaaaaggag agggatttat tcaagctgat cctcaagaag  420
gaggacgagc tgggcgatcg ttccatcatg ttcaccgtcc aaaacgagga tagcggcaca  480
accaacacag tcgctgccta taacctcact tggaagagca ccaacttcaa aaccatcctc  540
gaatgggaac ccaaacccgt taaccaagtt tacaccgtgc agatcagcac caagtccggc  600
gactggaagt ccaaatgttt ctataccacc gacaccgagt gcgatctcac cgatgagatc  660
gtgaaagatg tgaaacagac ctacctcgcc cgggtgttta gctaccccgc cggcaatgtg  720
gagagcactg gttccgctgg cgagccttta tacgagaaca gccccgaatt taccccttac  780
ctcgagacca atttaggaca gcccaccatc caaagctttg agcaagttgg cacaaaggtg  840
aatgtgacag tggaggacga gcggacttta gtgcggcgga acaacacctt tctcagcctc  900
cgggatgtgt tcggcaaaga tttaatctac acactgtatt actggaagtc ctcttcctcc  960
ggcaagaaga cagctaaaac caacacaaac gagtttttaa tcgacgtgga taaaggcgaa  1020
aactactgtt tcagcgtgca agctgtgatc ccctcccgga ccgtgaatag gaaaagcacc  1080
gatagccccg ttgagtgcat gggccaagaa aagggcgagt tccgggagaa ctgggtgaac  1140
gtcatcagcg atttaaagaa gatcgaagat ttaattcagt ccatgcatat cgacgccact  1200
ttatacacag aatccgacgt gcacccctct tgtaaggtga ccgccatgaa atgtttttta  1260
ctggagctgc aagttatctc tttagagagc ggagacgcta gcatccacga caccgtggag  1320
aatttaatca ttttagccaa taactcttta tccagcaacg gcaacgtgac agagtccggc  1380
tgcaaggagt gcgaagagct ggaggagaag aacatcaagg agtttctgca atcctttgtg  1440
cacattgtcc agatgttcat caatacctcc                                   1470

SEQ ID NO: 176         moltype = AA  length = 508
FEATURE                Location/Qualifiers
source                 1..508
                       mol_type = protein
                       organism = synthetic construct
SEQUENCE: 176
MKWVTFISLL FLFSSAYSYF GKLESKLSVI RNLNDQVLFI DQGNRPLFED MTDSDCRDNA  60
PRTIFIISMY KDSQPRGMAV TISVKCEKIS TLSCENKIIS FKEMNPPDNI KDTKSDIIFF  120
QRSVPGHDNK MQFESSSYEG YFLACEKERD LFKLILKKED ELGDRSIMFT VQNEDSGTTN  180
TVAAYNLTWK STNFKTILEW EPKPVNQVYT VQISTKSGDW KSKCFYTTDT ECDLTDEIVK  240
DVKQTYLARV FSYPAGNVES TGSAGEPLYE NSPEFTPYLE TNLGQPTIQS FEQVGTKVNV  300
TVEDERTLVR RNNTFLSLRD VFGKDLIYTL YYWKSSSSGK KTAKTNTNEF LIDVDKGENY  360
CFSVQAVIPS RTVNRKSTDS PVECMGQEKG EFRENWVNVI SDLKKIEDLI QSMHIDATLY  420
TESDVHPSCK VTAMKCFLLE LQVISLESGD ASIHDTVENL IILANNSLSS NGNVTESGCK  480
ECEELEEKNI KEFLQSFVHI VQMFINTS                                     508

SEQ ID NO: 177         moltype = DNA  length = 1524
FEATURE                Location/Qualifiers
source                 1..1524
                       mol_type = other DNA
                       organism = synthetic construct
SEQUENCE: 177
atgaagtggg tcacatttat ctctttactg ttcctcttct ccagcgccta cagctacttc  60
ggcaaactgg aatccaagct gagcgtgatc cggaatttaa acgaccaagt tctgtttatc  120
gatcaaggta accggcctct gttcgaggac atgaccgact ccgattgccg ggacaatgcc  180
ccccggacca tcttcattat ctccatgtac aaggacagcc agccccgggg catggctgtg  240
acaattagcg tgaagtgtga gaaaatcagc actttatctt gtgagaacaa gatcatctcc  300
tttaaggaaa tgaacccccc cgataacatc aaggacacca agtccgatat catcttcttc  360
cagcggtccg tgcccggtca cgataacaag atgcagttcg aatcctcctc ctacgagggc  420
tacttttag cttgtgaaaa ggagagggat ttattcaagc tgatcctcaa gaaggaggac  480
gagctgggcg atcgttccat catgttcacc gtccaaaacg aggatagcgg cacaaccaac  540
acagtcgctg cctataacct cacttggaag agcaccaact tcaaaaccat cctcgaatgg  600
gaacccaaac ccgttaacca agtttacacc gtgcagatca gcaccaagtc cggcgactgg  660
aagtccaaat gtttctatac caccgacacc gagtgcgatc tcaccgatga gatcgtgaaa  720
gatgtgaaac agacctacct cgcccgggtg tttagctacc ccgccggcaa tgtggagagc  780
actggttccg ctggcgagcc tttatacgag aacagccccg aatttacccc ttacctcgag  840
accaatttag gacagcccac catccaaagc tttgagcaag ttggcacaaa ggtgaatgtg  900
acagtggagg acgagcggac tttagtgcgg cggaacaaca cctttctcag cctccgggat  960
gtgttcggca aagatttaat ctacacactg tattactgga agtcctcttc ctccggcaag  1020
aagacagcta aaaccaacac aaacgagttt ttaatcgacg tggataaagg cgaaaactac  1080
tgtttcagcg tgcaagctgt gatcccctcc cggaccgtga ataggaaaag caccgatagc  1140
cccgttgagt gcatgggcca agaaaagggc gagttccggg agaactgggt gaacgtcatc  1200
agcgatttaa agaagatcga agatttaatt cagtccatgc atatcgacgc cactttatac  1260
acagaatccg acgtgcaccc ctcttgtaag gtgaccgcca tgaaatgttt tttactggag  1320
ctgcaagtta tctctttaga gagcggagac gctagcatcc acgacaccgt ggagaattta  1380
atcattttag ccaataactc tttatccagc aacggcaacg tgacagagtc cggctgcaag  1440
gagtgcgaag agctggagga gaagaacatc aaggagtttc tgcaatcctt tgtgcacatt  1500
gtccagatgt tcatcaatac ctcc                                         1524
```

```
SEQ ID NO: 178         moltype = AA  length = 583
FEATURE                Location/Qualifiers
source                 1..583
                       mol_type = protein
                       organism = synthetic construct
SEQUENCE: 178
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASIT CPPPMSVEHA DIWVKSYSLY  540
SRERYICNSG FKRKAGTSSL TECVLNKATN VAHWTTPSLK CIR                  583

SEQ ID NO: 179         moltype = DNA  length = 1749
FEATURE                Location/Qualifiers
source                 1..1749
                       mol_type = other DNA
                       organism = synthetic construct
SEQUENCE: 179
atttgggaac tgaagaagga cgtctacgtg gtcgaactgg actggtatcc cgatgctccc  60
ggcgaaatgg tggtgctcac ttgtgacacc cccgaagaag acggcatcac ttggaccctc  120
gatcagagca gcgaggtgct gggctccgga aagaccctca caatccaagt taaggagttc  180
ggagacgctg gccaatacac atgccacaag ggaggcgagg tgctcagcca ttccttatta  240
ttattacaca agaaggaaga cggaatctgg tccaccgaca ttttaaaaga tcagaaggag  300
cccaagaata agaccttttt aaggtgtgag gccaaaaact acagcggtcg tttcacttgt  360
tggtggctga ccaccatttc caccgattta accttctccg tgaaaagcag ccggggaagc  420
tccgaccctc aaggtgtgac atgtggagcc gctaccctca gcgctgagag ggttcgtggc  480
gataacaagg aatacgagta cagcgtggag tgccaagaag atagcgcttg tcccgctgcc  540
gaagaatctt tacccattga ggtgatggtg gacgccgtgc acaaactcaa gtacgagaac  600
tacacctcct ccttctttat ccgggacatc attaagcccg atcctcctaa gaatttacag  660
ctgaagcctc tcaaaaatag ccggcaagtt gaggtctctt gggaatatcc cgacacttgg  720
agcacacccc acagctactt ctctttaacc ttttgtgtgc aagttcaagg taaaagcaag  780
cgggagaaga aagaccgggt gtttaccgac aaaaccagcg ccaccgtcat ctgtcggaag  840
aacgcctcca tcagcgtgag ggctcaagat cgttattact ccagcagctg gtccgagtgg  900
gccagcgtgc cttgttccgg cggtggagga tccggaggag gtggctccgg cggcggagga  960
tctcgtaacc tccccgtggc tacccccgat cccggaatgt tcccttgttt acaccacagc  1020
cagaatttac tgagggccgt gagcaacatg ctgcagaaag ctaggcagac tttagaattt  1080
tacccttgca ccagcgagga gatcgaccat gaagatatca ccaaggacaa gacatccacc  1140
gtggaggctt gtttacctct ggagctgaca aagaacgagt cttgtctcaa ctctcgtgaa  1200
accagcttca tcacaaatgg ctcttgttta gcttcccgga agacctcctt tatgatggct  1260
ttatgcctca gctccatcta cgaggattta aagatgtacc aagtggagtt caagaccatg  1320
aacgccaagc tgctcatgga ccctaaacgg cagatctttt tagaccagaa catgctggct  1380
gtgattgatg agctgatgca agctttaaac ttcaactccg agaccgtccc tcagaagtcc  1440
tccctcgagg agcccgattt ttacaagaca aagatcaaac tgtgcatttt actccacgcc  1500
tttaggatcc gggccgtgac cattgaccgg gtcatgagct atttaaacgc cagcattaca  1560
tgcccccctc ccatgagcgt ggagcacgcc gacatctggg tgaagagcta tagcctctac  1620
agccgggaga ggtatatctg taacagcggc ttcaagagga aggccggcac cagcagcctc  1680
accgagtgcg tgctgaataa ggctaccaac gtggctcact ggacaacacc ctctttaaag  1740
tgcatccgg                                                        1749

SEQ ID NO: 180         moltype = AA  length = 601
FEATURE                Location/Qualifiers
source                 1..601
                       mol_type = protein
                       organism = synthetic construct
SEQUENCE: 180
MKWVTFISLL FLFSSAYSIW ELKKDVYVVE LDWYPDAPGE MVVLTCDTPE EDGITWTLDQ  60
SSEVLGSGKT LTIQVKEFGD AGQYTCHKGG EVLSHSLLLL HKKEDGIWST DILKDQKEPK  120
NKTFLRCEAK NYSGRFTCWW LTTISTDLTF SVKSSRGSSD PQGVTCGAAT LSAERVRGDN  180
KEYEYSVECQ EDSACPAAEE SLPIEVMVDA VHKLKYENYT SSFFIRDIIK PDPPKNLQLK  240
PLKNSRQVEV SWEYPDTWST PHSYFSLTFC VQVQGKSKRE KKDRVFTDKT SATVICRKNA  300
SISVRAQDRY YSSSWSEWAS VPCSGGGGSG GGGSGGGGSR NLPVATPDPG MFPCLHHSQN  360
LLRAVSNMLQ KARQTLEFYP CTSEEIDHED ITKDKTSTVE ACLPLELTKN ESCLNSRETS  420
FITNGSCLAS RKTSFMMALC LSSIYEDLKM YQVEFKTMNA KLLMDPKRQI FLDQNMLAVI  480
DELMQALNFN SETVPQKSSL EEPDFYKTKI KLCILLHAFR IRAVTIDRVM SYLNASITCP  540
PPMSVEHADI WVKSYSLYSR ERYICNSGFK RKAGTSSLTE CVLNKATNVA HWTTPSLKCI  600
R                                                                601

SEQ ID NO: 181         moltype = DNA  length = 1803
FEATURE                Location/Qualifiers
source                 1..1803
                       mol_type = other DNA
                       organism = synthetic construct
SEQUENCE: 181
```

```
atgaaatggg tgacctttat ttctttactg ttcctcttta gcagcgccta ctccatttgg  60
gaactgaaga aggacgtcta cgtggtcgaa ctggactggt atcccgatgc tcccggcgaa  120
atggtggtgc tcacttgtga cacccccgaa gaagacggca tcacttggac cctcgatcag  180
agcagcgagg tgctgggctc cggaaagacc ctcacaatcc aagttaagga gttcggagac  240
gctggccaat acacatgcca caagggaggc gaggtgctca gccattcctt attattatta  300
cacaagaagg aagacggaat ctggtccacc gacattttaa aagatcagaa ggagcccaag  360
aataagacct ttttaaggtg tgaggccaaa aactacagcg gtcgtttcac ttgttggtgg  420
ctgaccacca tttccaccga tttaaccttc tccgtgaaaa gcagccgggg aagctccgac  480
cctcaaggtg tgacatgtgg agccgctacc ctcagcgctg agagggttcg tggcgataac  540
aaggaatacg agtacagcgt ggagtgccaa gaagatagcg cttgtcccgc tgccgaagaa  600
tctttaccca ttgaggtgat ggtggacgcc gtgcacaaac tcaagtacga gaactacacc  660
tcctccttct ttatccggga catcattaag cccgatcctc ctaagaattt acagctgaag  720
cctctcaaaa atagccggca agttgaggtc tcttgggaat atcccgacac ttggagcaca  780
ccccacagct acttctcttt aaccttttgt gtgcaagttc aaggtaaaag caagcgggag  840
aagaaagacc gggtgtttac cgacaaaacc agcgccaccg tcatctgtcg gaagaacgcc  900
tccatcagcg tgagggctca agatcgttat tactccagca gctggtccga gtgggccagc  960
gtgccttgtt ccggcggtgg aggatccgga ggaggtggct ccggcggcgg aggatctcgt  1020
aacctccccg tggctacccc cgatcccgga atgttccctt gtttacacca cagccagaat  1080
ttactgaggg ccgtgagcaa catgctgcag aaagctaggc agactttaga attttaccct  1140
tgcaccagcg aggagatcga ccatgaagat atcaccaagg acaagacatc caccgtggag  1200
gcttgtttac ctctggagct gacaaagaac gagtcttgtc tcaactctcg tgaaaccagc  1260
ttcatcacaa atggctcttg tttagcttcc cggaagacct cctttatgat ggctttatgc  1320
ctcagctcca tctacgagga tttaaagatg taccaagtgg agttcaagac catgaacgcc  1380
aagctgctca tggaccctaa acggcagatc tttttagacc agaacatgct ggctgtgatt  1440
gatgagctga tgcaagcttt aaacttcaac tccgagaccg tccctcagaa gtcctccctc  1500
gaggagcccg atttttacaa gacaaagatc aaactgtgca ttttactcca cgcctttagg  1560
atccgggccg tgaccattga ccgggtcatg agctatttaa acgccagcat tacatgcccc  1620
cctcccatga gcgtggagca cgccgacatc tgggtgaaga gctatagcct ctacagccgg  1680
gagaggtata tctgtaacag cggcttcaag aggaaggccg gcaccagcag cctcaccgag  1740
tgcgtgctga ataaggctac caacgtggct cactggacaa caccctcttt aaagtgcatc  1800
cgg                                                               1803
```

```
SEQ ID NO: 182         moltype = DNA  length = 399
FEATURE                Location/Qualifiers
source                 1..399
                       mol_type = genomic DNA
                       note = source = IL-21
                       organism = Homo sapiens
SEQUENCE: 182
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcc                        399
```

```
SEQ ID NO: 183         moltype = AA  length = 136
FEATURE                Location/Qualifiers
REGION                 1..136
                       note = source = /note="TGFRbetaRII"
source                 1..136
                       mol_type = protein
                       organism = Homo sapiens
SEQUENCE: 183
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPD                                                 136
```

```
SEQ ID NO: 184         moltype = AA  length = 136
FEATURE                Location/Qualifiers
REGION                 1..136
                       note = source = /note="TGFRbetaRII"
source                 1..136
                       mol_type = protein
                       organism = Homo sapiens
SEQUENCE: 184
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPD                                                 136
```

```
SEQ ID NO: 185         moltype = DNA  length = 408
FEATURE                Location/Qualifiers
source                 1..408
                       mol_type = genomic DNA
                       note = source = TGFRbetaRII
                       organism = Homo sapiens
SEQUENCE: 185
atcccccccc atgtgcaaaa gagcgtgaac aacgatatga tcgtgaccga caacaacggc  60
```

```
gccgtgaagt ttccccagct ctgcaagttc tgcgatgtca ggttcagcac ctgcgataat  120
cagaagtcct gcatgtccaa ctgcacgatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgat              408

SEQ ID NO: 186         moltype = DNA  length = 408
FEATURE                Location/Qualifiers
source                 1..408
                       mol_type = genomic DNA
                       note = source = TGFRbetaRII
                       organism = Homo sapiens
SEQUENCE: 186
attcctcccc acgtgcagaa gagcgtgaat aatgacatga tcgtgaccga taacaatggc  60
gccgtgaaat ttccccagct gtgcaaattc tgcgatgtga ggttttccac ctgcgacaac  120
cagaagtcct gtatgagcaa ctgcacaatc acctccatct gtgagaagcc tcaggaggtg  180
tgcgtggctg tctggcggaa gaatgacgag aatatcaccc tggaaaccgt ctgccacgat  240
cccaagctgc cctaccacga tttcatcctg gaagacgccg ccagccctaa gtgcatcatg  300
aaagagaaaa agaagcctgg cgagaccttt ttcatgtgct cctgcagcag cgacgaatgc  360
aacgacaata tcatctttag cgaggaatac aataccagca accccgac              408

SEQ ID NO: 187         moltype = DNA  length = 861
FEATURE                Location/Qualifiers
source                 1..861
                       mol_type = genomic DNA
                       note = source = TGFRbetaRII
                       organism = Homo sapiens
SEQUENCE: 187
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcacgatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgcaca  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga c                                           861

SEQ ID NO: 188         moltype = AA  length = 287
FEATURE                Location/Qualifiers
REGION                 1..287
                       note = source = /note="TGFRbetaRII"
source                 1..287
                       mol_type = protein
                       organism = Homo sapiens
SEQUENCE: 188
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPD                287

SEQ ID NO: 189         moltype = AA  length = 466
FEATURE                Location/Qualifiers
source                 1..466
                       mol_type = protein
                       organism = synthetic construct
SEQUENCE: 189
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSSGTTNTV AAYNLTWKST NFKTILEWEP KPVNQVYTVQ ISTKSGDWKS  180
KCFYTTDTEC DLTDEIVKDV KQTYLARVFS YPAGNVESTG SAGEPLYENS PEFTPYLETN  240
LGQPTIQSFE QVGTKVNVTV EDERTLVRRN NTFLSLRDVF GKDLIYTLYY WKSSSSGKKT  300
AKTNTNEFLI DVDKGENYCF SVQAVIPSRT VNRKSTDSPV ECMGQEKGEF RENWVNVISD  360
LKKIEDLIQS MHIDATLYTE SDVHPSCKVT AMKCFLLELQ VISLESGDAS IHDTVENLII  420
LANNSLSSNG NVTESGCKEC EELEEKNIKE FLQSFVHIVQ MFINTS                 466

SEQ ID NO: 190         moltype = DNA  length = 1398
FEATURE                Location/Qualifiers
source                 1..1398
                       mol_type = other DNA
                       organism = synthetic construct
```

```
SEQUENCE: 190
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcct ccggcaccac caataccgtg  420
gccgcttata acctcacatg gaagagcacc aacttcaaga caattctgga atgggaaccc  480
aagcccgtca atcaagttta caccgtgcag atctccacca aatccggaga ctggaagagc  540
aagtgcttct acacaacaga caccgagtgt gatttaaccg acgaaatcgt caaggacgtc  600
aagcaaacct atctggctcg ggtcttttcc taccccgctg gcaatgtcga gtccaccggc  660
tccgctggcg agcctctcta cgagaattcc cccgaattca ccccttattt agagaccaat  720
ttaggccagc ctaccatcca gagcttcgag caagttggca ccaaggtgaa cgtcaccgtc  780
gaggatgaaa ggactttagt gcggcggaat aacacatttt tatccctccg ggatgtgttc  840
ggcaaagacc tcatctacac actgtactat tggaagtcca gctcctccgg caaaaagacc  900
gctaagacca acaccaacga gtttttaatt gacgtggaca aaggcgagaa ctactgcttc  960
agcgtgcaag ccgtgatccc ttctcgtacc gtcaaccgga agagcacaga ttcccccgtt  1020
gagtgcatgg gccaagaaaa gggcgagttc cgggagaact gggtgaacgt catcagcgat  1080
ttaaagaaga tcgaagattt aattcagtcc atgcatatcg acgccacttt atacacagaa  1140
tccgacgtgc acccctcttg taaggtgacc gccatgaaat gtttttttact ggagctgcaa  1200
gttatctctt tagagagcgg agacgctagc atccacgaca ccgtggagaa tttaatcatt  1260
ttagccaata actctttatc cagcaacggc aacgtgacag agtccggctg caaggagtgc  1320
gaagagctgg aggagaagaa catcaaggag tttctgcaat cctttgtgca cattgtccag  1380
atgttcatca atacctcc                                                1398

SEQ ID NO: 191          moltype = AA  length = 484
FEATURE                 Location/Qualifiers
source                  1..484
                        mol_type = protein
                        organism = synthetic construct
SEQUENCE: 191
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SSGTTNTVAA YNLTWKSTNF KTILEWEPKP  180
VNQVYTVQIS TKSGDWKSKC FYTTDTECDL TDEIVKDVKQ TYLARVFSYP AGNVESTGSA  240
GEPLYENSPE FTPYLETNLG QPTIQSFEQV GTKVNVTVED ERTLVRRNNT FLSLRDVFGK  300
DLIYTLYYWK SSSSGKKTAK TNTNEFLIDV DKGENYCFSV QAVIPSRTVN RKSTDSPVEC  360
MGQEKGEFRE NWVNVISDLK KIEDLIQSMH IDATLYTESD VHPSCKVTAM KCFLLELQVI  420
SLESGDASIH DTVENLIILA NNSLSSNGNV TESGCKECEE LEEKNIKEFL QSFVHIVQMF  480
INTS                                                               484

SEQ ID NO: 192          moltype = DNA  length = 1452
FEATURE                 Location/Qualifiers
source                  1..1452
                        mol_type = other DNA
                        organism = synthetic construct
SEQUENCE: 192
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tcctccggca ccaccaatac cgtggccgct  480
tataacctca catggaagag caccaacttc aagacaattc tggaatggga acccaagccc  540
gtcaatcaag tttacaccgt gcagatctcc accaaatccg gagactggaa gagcaagtgc  600
ttctacacaa cagacaccga gtgtgattta accgacgaaa tcgtcaagga cgtcaagcaa  660
acctatctgg ctcgggtctt ttcctacccc gctggcaatg tcgagtccac cggctccgct  720
ggcgagcctc tctacgagaa ttcccccgaa ttcacccctt atttagagac caatttaggc  780
cagcctacca tccagagctt cgagcaagtt ggcaccaagg tgaacgtcac cgtcgaggat  840
gaaaggactt tagtgcggcg gaataacaca tttttatccc tccgggatgt gttcggcaaa  900
gacctcatct acacactgta ctattggaag tccagctcct ccggcaaaaa gaccgctaag  960
accaacacca acgagttttt aattgacgtg gacaaaggcg agaactactg cttcagcgtg  1020
caagccgtga tcccttctcg taccgtcaac cggaagagca cagattcccc cgttgagtgc  1080
atgggccaag aaaagggcga gttccgggag aactgggtga acgtcatcag cgatttaaag  1140
aagatcgaag atttaattca gtccatgcat atcgacgcca ctttatacac agaatccgac  1200
gtgcacccct cttgtaaggt gaccgccatg aaatgttttt tactggagct gcaagttatc  1260
tctttagaga gcggagacgc tagcatccac gacaccgtgg agaatttaat cattttagcc  1320
aataactctt tatccagcaa cggcaacgtg acagagtccg gctgcaagga gtgcgaagag  1380
ctggaggaga agaacatcaa ggagtttctg caatcctttg tgcacattgt ccagatgttc  1440
atcaatacct cc                                                      1452

SEQ ID NO: 193          moltype = AA  length = 352
FEATURE                 Location/Qualifiers
source                  1..352
                        mol_type = protein
                        organism = synthetic construct
```

```
SEQUENCE: 193
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDITC PPPMSVEHAD  300
IWVKSYSLYS RERYICNSGF KRKAGTSSLT ECVLNKATNV AHWTTPSLKC IR          352

SEQ ID NO: 194          moltype = DNA  length = 1056
FEATURE                 Location/Qualifiers
source                  1..1056
                        mol_type = other DNA
                        organism = synthetic construct
SEQUENCE: 194
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcacgatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgcaca  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga catcacgtgt cctcctccta tgtccgtgga acacgcagac  900
atctgggtca agagctacag cttgtactcc agggagcggt acatttgtaa ctctggtttc  960
aagcgtaaag ccggcacgtc cagcctgacg gagtgcgtgt tgaacaaggc cacgaatgtc  1020
gcccactgga caacccccag tctcaaatgt attaga                            1056

SEQ ID NO: 195          moltype = AA  length = 370
FEATURE                 Location/Qualifiers
source                  1..370
                        mol_type = protein
                        organism = synthetic construct
SEQUENCE: 195
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
WTTPSLKCIR                                                         370

SEQ ID NO: 196          moltype = DNA  length = 1110
FEATURE                 Location/Qualifiers
source                  1..1110
                        mol_type = other DNA
                        organism = synthetic construct
SEQUENCE: 196
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcac gatcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg cacaatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gacctttttc  840
atgtgctcct gcagcagcga cgaatgcaac gacaatatca tctttagcga ggaatacaat  900
accagcaacc ccgacatcac gtgtcctcct cctatgtccg tggaacacgc agacatctgg  960
gtcaagagct acagcttgta ctccagggag cggtacattt gtaactctgg tttcaagcgt  1020
aaagccggca cgtccagcct gacggagtgc gtgttgaaca aggccacgaa tgtcgcccac  1080
tggacaaccc ccagtctcaa atgtattaga                                   1110

SEQ ID NO: 197          moltype = DNA  length = 399
FEATURE                 Location/Qualifiers
source                  1..399
                        mol_type = genomic DNA
                        note = source = IL21
                        organism = Homo sapiens
```

```
SEQUENCE: 197
caaggtcaag atcgccacat gattagaatg cgtcaactta tagatattgt tgatcagctg  60
aaaaattatg tgaatgactt ggtccctgaa tttctgccag ctccagaaga tgtagagaca  120
aactgtgagt ggtcagcttt ttcctgtttt cagaaggccc aactaaagtc agcaaataca  180
ggaaacaatg aaaggataat caatgtatca attaaaaagc tgaagaggaa accaccttcc  240
acaaatgcag ggagaagaca gaaacacaga ctaacatgcc cttcatgtga ttcttatgag  300
aaaaaaccac ccaaagaatt cctagaaaga ttcaaatcac ttctccaaaa gatgattcat  360
cagcatctgt cctctagaac acacggaagt gaagattcc                         399

SEQ ID NO: 198         moltype = DNA  length = 456
FEATURE                Location/Qualifiers
source                 1..456
                       mol_type = genomic DNA
                       note = source = IL7
                       organism = Homo sapiens
SEQUENCE: 198
gattgtgata ttgaaggtaa agatggcaaa caatatgaga gtgttctaat ggtcagcatc  60
gatcaattat tggacagcat gaaagaaatt ggtagcaatt gcctgaataa tgaatttaac  120
ttttttaaaa gacatatctg tgatgctaat aaggaaggta tgtttttatt ccgtgctgct  180
cgcaagttga ggcaatttct taaaatgaat agcactggtg attttgatct ccacttatta  240
aaagtttcag aaggcacaac aatactgttg aactgcactg gccaggttaa aggaagaaaa  300
ccagctgccc tgggtgaagc ccaaccaaca aagagtttgg aagaaaataa atctttaaag  360
gaacagaaaa aactgaatga cttgtgtttc ctaaagagac tattacaaga gataaaaact  420
tgttggaata aaattttgat gggcactaaa gaacac                            456

SEQ ID NO: 199         moltype = AA  length = 466
FEATURE                Location/Qualifiers
source                 1..466
                       mol_type = protein
                       organism = synthetic construct
SEQUENCE: 199
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSSGTTNTV AAYNLTWKST NFKTILEWEP KPVNQVYTVQ ISTKSGDWKS  180
KCFYTTDTEC DLTDEIVKDV KQTYLARVFS YPAGNVESTG SAGEPLYENS PEFTPYLETN  240
LGQPTIQSFE QVGTKVNVTV EDERTLVRRN NTFLSLRDVF GKDLIYTLYY WKSSSSGKKT  300
AKTNTNEFLI DVDKGENYCF SVQAVIPSRT VNRKSTDSPV ECMGQEKGEF RENWVNVISD  360
LKKIEDLIQS MHIDATLYTE SDVHPSCKVT AMKCFLLELQ VISLESGDAS IHDTVENLII  420
LANNSLSSNG NVTESGCKEC EELEEKNIKE FLQSFVHIVQ MFINTS                 466

SEQ ID NO: 200         moltype = DNA  length = 1398
FEATURE                Location/Qualifiers
source                 1..1398
                       mol_type = other DNA
                       organism = synthetic construct
SEQUENCE: 200
caaggtcaag atcgccacat gattagaatg cgtcaactta tagatattgt tgatcagctg  60
aaaaattatg tgaatgactt ggtccctgaa tttctgccag ctccagaaga tgtagagaca  120
aactgtgagt ggtcagcttt ttcctgtttt cagaaggccc aactaaagtc agcaaataca  180
ggaaacaatg aaaggataat caatgtatca attaaaaagc tgaagaggaa accaccttcc  240
acaaatgcag ggagaagaca gaaacacaga ctaacatgcc cttcatgtga ttcttatgag  300
aaaaaaccac ccaaagaatt cctagaaaga ttcaaatcac ttctccaaaa gatgattcat  360
cagcatctgt cctctagaac acacggaagt gaagattcct caggcactac aaatactgtg  420
gcagcatata atttaacttg gaaatcaact aatttcaaga caattttgga gtgggaaccc  480
aaacccgtca atcaagtcta cactgttcaa ataagcacta agtcaggaga ttggaaaagc  540
aaatgctttt acacaacaga cacagagtgt gacctcaccg acgagattgt gaaggatgtg  600
aagcagacgt acttggcacg ggtcttctcc tacccggcag ggaatgtgga gagcaccggt  660
tctgctgggg agcctctgta tgagaactcc ccagagttca caccttacct ggagacaaac  720
ctcggacagc caacaattca gagttttgaa caggtgggaa caaaagtgaa tgtgaccgta  780
gaagatgaac ggactttagt cagaaggaac aacactttcc taagcctccg ggatgttttt  840
ggcaaggact taatttatac actttattat tggaaatctt caagttcagg aaagaaaaca  900
gccaaaacaa acactaatga gtttttgatt gatgtggata aaggagaaaa ctactgtttc  960
agtgttcaag cagtgattcc ctcccgaaca gttaaccgga agagtacaga cagcccggta  1020
gagtgtatgg gccaggagaa aggggaattc agagaaaact gggtgaacgt catcagcgat  1080
ttaaagaaga tcgaagattt aattcagtcc atgcatatcg acgccacttt atacacagaa  1140
tccgacgtgc accccttttg taaggtgacc gccatgaaat gttttttact ggagctgcaa  1200
gttatctctt tagagagcgg agacgctagc atccacgaca ccgtggagaa tttaatcatt  1260
ttagccaata actctttatc cagcaacggc aacgtgacag agtccggctg caaggagtgc  1320
gaagagctgg aggagaagaa catcaaggag tttctgcaat cctttgtgca cattgtccag  1380
atgttcatca atacctcc                                                1398

SEQ ID NO: 201         moltype = AA  length = 483
FEATURE                Location/Qualifiers
source                 1..483
                       mol_type = protein
                       organism = synthetic construct
SEQUENCE: 201
MGVKVLFALI CIAVAEAQGQ DRHMIRMRQL IDIVDQLKNY VNDLVPEFLP APEDVETNCE  60
WSAFSCFQKA QLKSANTGNN ERIINVSIKK LKRKPPSTNA GRRQKHRLTC PSCDSYEKKP  120
```

```
PKEFLERFKS LLQKMIHQHL SSRTHGSEDS SGTTNTVAAY NLTWKSTNFK TILEWEPKPV  180
NQVYTVQIST KSGDWKSKCF YTTDTECDLT DEIVKDVKQT YLARVFSYPA GNVESTGSAG  240
EPLYENSPEF TPYLETNLGQ PTIQSFEQVG TKVNVTVEDE RTLVRRNNTF LSLRDVFGKD  300
LIYTLYYWKS SSSGKKTAKT NTNEFLIDVD KGENYCFSVQ AVIPSRTVNR KSTDSPVECM  360
GQEKGEFREN WVNVISDLKK IEDLIQSMHI DATLYTESDV HPSCKVTAMK CFLLELQVIS  420
LESGDASIHD TVENLIILAN NSLSSNGNVT ESGCKECEEL EEKNIKEFLQ SFVHIVQMFI  480
NTS                                                                483

SEQ ID NO: 202          moltype = DNA  length = 1449
FEATURE                 Location/Qualifiers
source                  1..1449
                        mol_type = other DNA
                        organism = synthetic construct
SEQUENCE: 202
atgggagtga aagttctttt tgcccttatt tgtattgctg tggccgaggc ccaaggtcaa  60
gatcgccaca tgattagaat gcgtcaactt atagatattg ttgatcagct gaaaaattat  120
gtgaatgact tggtccctga atttctgcca gctccagaag atgtagagac aaactgtgag  180
tggtcagctt tttcctgttt tcagaaggcc caactaaagt cagcaaatac aggaaacaat  240
gaaaggataa tcaatgtatc aattaaaaag ctgaagagga aaccaccttc cacaaatgca  300
gggagaagac agaaacacag actaacatgc ccttcatgtg attcttatga gaaaaaacca  360
cccaaagaat tcctagaaag attcaaatca cttctccaaa agatgattca tcagcatctg  420
tcctctagaa cacacggaag tgaagattcc tcaggcacta caaatactgt ggcagcatat  480
aatttaactt ggaaatcaac taatttcaag acaattttgg agtgggaacc caaacccgtc  540
aatcaagtct acactgttca aataagcact aagtcaggag attggaaaag caaatgcttt  600
tacacaacag acacagagtg tgacctcacc gacgagattg tgaaggatgt gaagcagacg  660
tacttggcac gggtcttctc ctacccggca gggaatgtgg agagcaccgg ttctgctggg  720
gagcctctgt atgagaactc cccagagttc acaccttacc tggagacaaa cctcggacag  780
ccaacaattc agagttttga acaggtggga acaaaagtga atgtgaccgt agaagatgaa  840
cggactttag tcagaaggaa caacactttc ctaagcctcc gggatgtttt tggcaaggac  900
ttaatttata cactttatta ttggaaatct tcaagttcag gaaagaaaac agccaaaaca  960
aacactaatg agtttttgat tgatgtggat aaaggagaaa actactgttt cagtgttcaa  1020
gcagtgattc cctcccgaac agttaaccgg aagagtacag acagcccggt agagtgtatg  1080
ggccaggaga aaggggaatt cagagaaaac tgggtgaacg tcatcagcga tttaaagaag  1140
atcgaagatt taattcagtc catgcatatc gacgccactt tatacacaga atccgacgtg  1200
cacccctctt gtaaggtgac cgccatgaaa tgttttttac tggagctgca agttatctct  1260
ttagagagcg gagacgctag catccacgac accgtggaga atttaatcat tttagccaat  1320
aactctttat ccagcaacgg caacgtgaca gagtccggct gcaaggagtg cgaagagctg  1380
gaggagaaga acatcaagga gtttctgcaa tcctttgtgc acattgtcca gatgttcatc  1440
aatacctcc                                                          1449

SEQ ID NO: 203          moltype = AA  length = 217
FEATURE                 Location/Qualifiers
source                  1..217
                        mol_type = protein
                        organism = synthetic construct
SEQUENCE: 203
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EHITCPPPMS VEHADIWVKS YSLYSRERYI  180
CNSGFKRKAG TSSLTECVLN KATNVAHWTT PSLKCIR                           217

SEQ ID NO: 204          moltype = DNA  length = 651
FEATURE                 Location/Qualifiers
source                  1..651
                        mol_type = other DNA
                        organism = synthetic construct
SEQUENCE: 204
gattgtgata ttgaaggtaa agatggcaaa caatatgaga gtgttctaat ggtcagcatc  60
gatcaattat tggacagcat gaaagaaatt ggtagcaatt gcctgaataa tgaatttaac  120
ttttttaaaa gacatatctg tgatgctaat aaggaaggta tgtttttatt ccgtgctgct  180
cgcaagttga ggcaatttct taaaatgaat agcactggtg attttgatct ccacttatta  240
aaagtttcag aaggcacaac aatactgttg aactgcactg gccaggttaa aggaagaaaa  300
ccagctgccc tgggtgaagc ccaaccaaca aagagtttgg aagaaaataa atctttaaag  360
gaacagaaaa aactgaatga cttgtgtttc ctaaagagac tattacaaga gataaaaact  420
tgttggaata aaattttgat gggcactaaa gaacacatca cgtgccctcc ccccatgtcc  480
gtggaacacg cagacatctg ggtcaagagc tacagcttgt actccaggga gcggtacatt  540
tgtaactctg gtttcaagcg taaagccggc acgtccagcc tgacggagtg cgtgttgaac  600
aaggccacga atgtcgccca ctggacaacc cccagtctca aatgcattag a           651

SEQ ID NO: 205          moltype = AA  length = 234
FEATURE                 Location/Qualifiers
source                  1..234
                        mol_type = protein
                        organism = synthetic construct
SEQUENCE: 205
MGVKVLFALI CIAVAEADCD IEGKDGKQYE SVLMVSIDQL LDSMKEIGSN CLNNEFNFFK  60
RHICDANKEG MFLFRAARKL RQFLKMNSTG DFDLHLLKVS EGTTILLNCT GQVKGRKPAA  120
LGEAQPTKSL EENKSLKEQK KLNDLCFLKR LLQEIKTCWN KILMGTKEHI TCPPPMSVEH  180
ADIWVKSYSL YSRERYICNS GFKRKAGTSS LTECVLNKAT NVAHWTTPSL KCIR        234
```

```
SEQ ID NO: 206          moltype = DNA  length = 702
FEATURE                 Location/Qualifiers
source                  1..702
                        mol_type = other DNA
                        organism = synthetic construct
SEQUENCE: 206
atgggagtga aagttctttt tgcccttatt tgtattgctg tggccgaggc cgattgtgat  60
attgaaggta aagatggcaa acaatatgag agtgttctaa tggtcagcat cgatcaatta  120
ttggacagca tgaaagaaat tggtagcaat tgcctgaata atgaatttaa ctttttttaaa  180
agacatatct gtgatgctaa taaggaaggt atgtttttat tccgtgctgc tcgcaagttg  240
aggcaatttc ttaaaatgaa tagcactggt gattttgatc tccacttatt aaaagtttca  300
gaaggcacaa caatactgtt gaactgcact ggccaggtta aaggaagaaa accagctgcc  360
ctgggtgaag cccaaccaac aaagagtttg gaagaaaata aatctttaaa ggaacagaaa  420
aaactgaatg acttgtgttt cctaaagaga ctattacaag agataaaaac ttgttggaat  480
aaaattttga tgggcactaa agaacacatc acgtgccctc cccccatgtc cgtggaacac  540
gcagacatct gggtcaagag ctacagcttg tactccaggg agcggtacat ttgtaactct  600
ggtttcaagc gtaaagccgg cacgtccagc ctgacggagt gcgtgttgaa caaggccacg  660
aatgtcgccc actggacaac cccccagtctc aaatgcatta ga                    702

SEQ ID NO: 207          moltype = AA  length = 485
FEATURE                 Location/Qualifiers
source                  1..485
                        mol_type = protein
                        organism = synthetic construct
SEQUENCE: 207
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EHSGTTNTVA AYNLTWKSTN FKTILEWEPK  180
PVNQVYTVQI STKSGDWKSK CFYTTDTECD LTDEIVKDVK QTYLARVFSY PAGNVESTGS  240
AGEPLYENSP EFTPYLETNL GQPTIQSFEQ VGTKVNVTVE DERTLVRRNN TFLSLRDVFG  300
KDLIYTLYYW KSSSSGKKTA KTNTNEFLID VDKGENYCFS VQAVIPSRTV NRKSTDSPVE  360
CMGQEKGEFR ENWVNVISDL KKIEDLIQSM HIDATLYTES DVHPSCKVTA MKCFLLELQV  420
ISLESGDASI HDTVENLIIL ANNSLSSNGN VTESGCKECE ELEEKNIKEF LQSFVHIVQM  480
FINTS                                                              485

SEQ ID NO: 208          moltype = DNA  length = 1455
FEATURE                 Location/Qualifiers
source                  1..1455
                        mol_type = other DNA
                        organism = synthetic construct
SEQUENCE: 208
gattgcgaca tcgagggcaa ggacggcaag cagtacgaga gcgtgctgat ggtgtccatc  60
gaccagctgc tggacagcat gaaggagatc ggctccaact gcctcaacaa cgagttcaac  120
ttcttcaagc ggcacatctg cgacgccaac aaggagggca tgttcctgtt cagggccgcc  180
aggaaactgc ggcagttcct gaagatgaac tccaccggcg acttcgacct gcacctgctg  240
aaggtgtccg agggcaccac catcctgctg aactgcaccg gacaggtgaa gggccggaaa  300
cctgctgctc tgggagaggc ccaacccacc aagagcctgg aggagaacaa gtccctgaag  360
gagcagaaga agctgaacga cctgtgcttc ctgaagaggc tgctgcagga gatcaagacc  420
tgctggaaca agatcctgat gggcaccaag gagcatagcg gcacaaccaa cacagtcgct  480
gcctataacc tcacttggaa gagcaccaac ttcaaaacca tcctcgaatg ggaacccaaa  540
cccgttaacc aagtttacac cgtgcagatc agcaccaagt ccggcgactg gaagtccaaa  600
tgtttctata ccaccgacac cgagtgcgat ctcaccgatg agatcgtgaa agatgtgaaa  660
cagacctacc tcgcccgggt gtttagctac cccgccggca atgtggagag cactggttcc  720
gctggcgagc ctttatacga gaacagcccc gaatttaccc cttacctcga gaccaattta  780
ggacagccca ccatccaaag ctttgagcaa gttggcacaa aggtgaatgt gacagtggag  840
gacgagcgga ctttagtgcg gcggaacaac acctttctca gcctccggga tgtgttcggc  900
aaagatttaa tctacacact gtattactgg aagtcctctt cctccggcaa gaagacagct  960
aaaaccaaca caaacgagtt tttaatcgac gtggataaag gcgaaaacta ctgtttcagc  1020
gtgcaagctg tgatcccctc ccggaccgtg aataggaaaa gcaccgatag ccccgttgag  1080
tgcatgggcc aagaaaaggg cgagttccgg gagaactggg tgaacgtcat cagcgattta  1140
aagaagatcg aagatttaat tcagtccatg catatcgacg ccactttata cacagaatcc  1200
gacgtgcacc cctcttgtaa ggtgaccgcc atgaaatgtt ttttactgga gctgcaagtt  1260
atctctttag agagcggaga cgctagcatc cacgacaccg tggagaattt aatcatttta  1320
gccaataact ctttatccag caacggcaac gtgacagagt ccggctgcaa ggagtgcgaa  1380
gagctggagg agaagaacat caaggagttt ctgcaatcct ttgtgcacat tgtccagatg  1440
ttcatcaata cctcc                                                   1455

SEQ ID NO: 209          moltype = AA  length = 503
FEATURE                 Location/Qualifiers
source                  1..503
                        mol_type = protein
                        organism = synthetic construct
SEQUENCE: 209
MKWVTFISLL FLFSSAYSDC DIEGKDGKQY ESVLMVSIDQ LLDSMKEIGS NCLNNEFNFF  60
KRHICDANKE GMFLFRAARK LRQFLKMNST GDFDLHLLKV SEGTTILLNC TGQVKGRKPA  120
ALGEAQPTKS LEENKSLKEQ KKLNDLCFLK RLLQEIKTCW NKILMGTKEH SGTTNTVAAY  180
NLTWKSTNFK TILEWEPKPV NQVYTVQIST KSGDWKSKCF YTTDTECDLT DEIVKDVKQT  240
YLARVFSYPA GNVESTGSAG EPLYENSPEF TPYLETNLGQ PTIQSFEQVG TKVNVTVEDE  300
```

```
RTLVRRNNTF LSLRDVFGKD LIYTLYYWKS SSSGKKTAKT NTNEFLIDVD KGENYCFSVQ  360
AVIPSRTVNR KSTDSPVECM GQEKGEFREN WVNVISDLKK IEDLIQSMHI DATLYTESDV  420
HPSCKVTAMK CFLLELQVIS LESGDASIHD TVENLIILAN NSLSSNGNVT ESGCKECEEL  480
EEKNIKEFLQ SFVHIVQMFI NTS                                         503

SEQ ID NO: 210         moltype = DNA  length = 1509
FEATURE                Location/Qualifiers
source                 1..1509
                       mol_type = other DNA
                       organism = synthetic construct
SEQUENCE: 210
atgaagtggg tgaccttcat cagcctgctg ttcctgttct ccagcgccta ctccgattgc  60
gacatcgagg gcaaggacgg caagcagtac gagagcgtgc tgatggtgtc catcgaccag  120
ctgctggaca gcatgaagga gatcggctcc aactgcctca acaacgagtt caacttcttc  180
aagcggcaca tctgcgacgc caacaaggag ggcatgttcc tgttcagggc cgccaggaaa  240
ctgcggcagt tcctgaagat gaactccacc ggcgacttcg acctgcacct gctgaaggtg  300
tccgagggca ccaccatcct gctgaactgc accggacagg tgaagggccg gaaacctgct  360
gctctgggag aggcccaacc caccaagagc ctggaggaga acaagtccct gaaggagcag  420
aagaagctga acgacctgtg cttcctgaag aggctgctgc aggagatcaa gacctgctgg  480
aacaagatcc tgatgggcac caaggagcat agcggcacaa ccaacacagt cgctgcctat  540
aacctcactt ggaagagcac caacttcaaa accatcctcg aatgggaacc caaacccgtt  600
aaccaagttt acaccgtgca gatcagcacc aagtccggcg actggaagtc caaatgtttc  660
tataccaccg acaccgagtg cgatctcacc gatgagatcg tgaaagatgt gaaacagacc  720
tacctcgccc gggtgtttag ctaccccgcc ggcaatgtgg agagcactgg ttccgctggc  780
gagcctttat acgagaacag ccccgaattt accccttacc tcgagaccaa tttaggacag  840
cccaccatcc aaagctttga gcaagttggc acaaaggtga atgtgacagt ggaggacgag  900
cggactttag tgcggcggaa caacaccttt ctcagcctcc gggatgtgtt cggcaaagat  960
ttaatctaca cactgtatta ctggaagtcc tcttcctccg gcaagaagac agctaaaacc  1020
aacacaaacg agtttttaat cgacgtggat aaaggcgaaa actactgttt cagcgtgcaa  1080
gctgtgatcc cctcccggac cgtgaatagg aaaagcaccg atagccccgt tgagtgcatg  1140
ggccaagaaa agggcgagtt ccgggagaac tgggtgaacg tcatcagcga tttaaagaag  1200
atcgaagatt taattcagtc catgcatatc gacgccactt tatacacaga atccgacgtg  1260
cacccctctt gtaaggtgac cgccatgaaa tgtttttac tggagctgca agttatctct   1320
ttagagagcg gagacgctag catccacgac accgtggaga atttaatcat tttagccaat  1380
aactctttat ccagcaacgg caacgtgaca gagtccggct gcaaggagtg cgaagagctg  1440
gaggagaaga acatcaagga gtttctgcaa tcctttgtgc acattgtcca gatgttcatc  1500
aatacctcc                                                         1509

SEQ ID NO: 211         moltype = AA  length = 198
FEATURE                Location/Qualifiers
source                 1..198
                       mol_type = protein
                       organism = synthetic construct
SEQUENCE: 211
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSITCPPPM SVEHADIWVK SYSLYSRERY ICNSGFKRKA GTSSLTECVL  180
NKATNVAHWT TPSLKCIR                                               198

SEQ ID NO: 212         moltype = DNA  length = 594
FEATURE                Location/Qualifiers
source                 1..594
                       mol_type = other DNA
                       organism = synthetic construct
SEQUENCE: 212
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcca ttacatgccc ccctcccatg  420
agcgtggagc acgccgacat ctgggtgaag agctatagcc tctacagccg ggagaggtat  480
atctgtaaca gcggcttcaa gaggaaggcc ggcaccagca gcctcaccga gtgcgtgctg  540
aataaggcta ccaacgtggc tcactggaca acaccctctt taaagtgcat ccgg        594

SEQ ID NO: 213         moltype = AA  length = 216
FEATURE                Location/Qualifiers
source                 1..216
                       mol_type = protein
                       organism = synthetic construct
SEQUENCE: 213
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SITCPPPMSV EHADIWVKSY SLYSRERYIC  180
NSGFKRKAGT SSLTECVLNK ATNVAHWTTP SLKCIR                           216

SEQ ID NO: 214         moltype = DNA  length = 648
FEATURE                Location/Qualifiers
```

```
source                  1..648
                        mol_type = other DNA
                        organism = synthetic construct
SEQUENCE: 214
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tccattacat gcccccctcc catgagcgtg  480
gagcacgccg acatctgggt gaagagctat agcctctaca gccgggagag gtatatctgt  540
aacagcggct tcaagaggaa ggccggcacc agcagcctca ccgagtgcgt gctgaataag  600
gctaccaacg tggctcactg gacaacaccc tctttaaagt gcatccgg             648

SEQ ID NO: 215          moltype = AA  length = 108
FEATURE                 Location/Qualifiers
REGION                  1..108
                        note = source = /note="CD16"
source                  1..108
                        mol_type = protein
                        organism = Homo sapiens
SEQUENCE: 215
SELTQDPAVS VALGQTVRIT CQGDSLRSYY ASWYQQKPGQ APVLVIYGKN NRPSGIPDRF  60
SGSSSGNTAS LTITGAQAED EADYYCNSRD SSGNHVVFGG GTKLTVGH               108

SEQ ID NO: 216          moltype = DNA  length = 324
FEATURE                 Location/Qualifiers
source                  1..324
                        mol_type = genomic DNA
                        note = source = CD16
                        organism = Homo sapiens
SEQUENCE: 216
tccgagctga cccaggaccc tgctgtgtcc gtggctctgg gccagaccgt gaggatcacc  60
tgccagggcg actccctgag gtcctactac gcctcctggt accagcagaa gcccggccag  120
gctcctgtgc tggtgatcta cggcaagaac aacaggccct ccggcatccc tgacaggttc  180
tccggatcct cctccggcaa caccgcctcc ctgaccatca caggcgctca ggccgaggac  240
gaggctgact actactgcaa ctccagggac tcctccggca accatgtggt gttcggcggc  300
ggcaccaagc tgaccgtggg ccat                                        324

SEQ ID NO: 217          moltype = AA  length = 117
FEATURE                 Location/Qualifiers
REGION                  1..117
                        note = source = /note="CD16"
source                  1..117
                        mol_type = protein
                        organism = Homo sapiens
SEQUENCE: 217
EVQLVESGGG VVRPGGSLRL SCAASGFTFD DYGMSWVRQA PGKGLEWVSG INWNGGSTGY  60
ADSVKGRFTI SRDNAKNSLY LQMNSLRAED TAVYYCARGR SLLFDYWGQG TLVTVSR     117

SEQ ID NO: 218          moltype = DNA  length = 351
FEATURE                 Location/Qualifiers
source                  1..351
                        mol_type = genomic DNA
                        note = source = CD16
                        organism = Homo sapiens
SEQUENCE: 218
gaggtgcagc tggtggagtc cggaggagga gtggtgaggc ctggaggctc cctgaggctg  60
agctgtgctg cctccggctt caccttcgac gactacggca tgtcctgggt gaggcaggct  120
cctggaaagg gcctggagtg ggtgtccggc atcaactgga acggcggatc caccggctac  180
gccgattccg tgaagggcag gttcaccatc agcagggaca acgccaagaa ctccctgtac  240
ctgcagatga actccctgag ggccgaggac accgccgtgt actactgcgc caggggcagg  300
tccctgctgt tcgactactg gggacagggc accctggtga ccgtgtccag g           351

SEQ ID NO: 219          moltype =   length =
SEQUENCE: 219
000

SEQ ID NO: 220          moltype =   length =
SEQUENCE: 220
000

SEQ ID NO: 221          moltype =   length =
SEQUENCE: 221
000

SEQ ID NO: 222          moltype =   length =
```

SEQUENCE: 222
000

SEQ ID NO: 223 moltype = AA length = 823
FEATURE Location/Qualifiers
source 1..823
mol_type = protein
organism = synthetic construct
SEQUENCE: 223
IWELKKDVYV VELDWYPDAP GEMVVLTCDT PEEDGITWTL DQSSEVLGSG KTLTIQVKEF 60
GDAGQYTCHK GGEVLSHSLL LLHKKEDGIW STDILKDQKE PKNKTFLRCE AKNYSGRFTC 120
WWLTTISTDL TFSVKSSRGS SDPQGVTCGA ATLSAERVRG DNKEYEYSVE CQEDSACPAA 180
EESLPIEVMV DAVHKLKYEN YTSSFFIRDI IKPDPPKNLQ LKPLKNSRQV EVSWEYPDTW 240
STPHSYFSLT FCVQVQGKSK REKKDRVFTD KTSATVICRK NASISVRAQD RYYSSSWSEW 300
ASVPCSGGGG SGGGGSGGGG SRNLPVATPD PGMFPCLHHS QNLLRAVSNM LQKARQTLEF 360
YPCTSEEIDH EDITKDKTST VEACLPLELT KNESCLNSRE TSFITNGSCL ASRKTSFMMA 420
LCLSSIYEDL KMYQVEFKTM NAKLLMDPKR QIFLDQNMLA VIDELMQALN FNSETVPQKS 480
SLEEPDFYKT KIKLCILLHA FRIRAVTIDR VMSYLNASIT CPPPMSVEHA DIWVKSYSLY 540
SRERYICNSG FKRKAGTSSL TECVLNKATN VAHWTTPSLK CIRSELTQDP AVSVALGQTV 600
RITCQGDSLR SYYASWYQQK PGQAPVLVIY GKNNRPSGIP DRFSGSSSGN TASLTITGAQ 660
AEDEADYYCN SRDSSGNHVV FGGGTKLTVG HGGGGSGGGG SGGGGSEVQL VESGGGVVRP 720
GGSLRLSCAA SGFTFDDYGM SWVRQAPGKG LEWVSGINWN GGSTGYADSV KGRFTISRDN 780
AKNSLYLQMN SLRAEDTAVY YCARGRSLLF DYWGQGTLVT VSR 823

SEQ ID NO: 224 moltype = DNA length = 2469
FEATURE Location/Qualifiers
source 1..2469
mol_type = other DNA
organism = synthetic construct
SEQUENCE: 224
atttgggaac tgaagaagga cgtctacgtg gtcgaactgg actggtatcc cgatgctccc 60
ggcgaaatgg tggtgctcac ttgtgacacc cccgaagaag acggcatcac ttggaccctc 120
gatcagagca gcgaggtgct gggctccgga aagaccctca caatccaagt taaggagttc 180
ggagacgctg gccaatacac atgccacaag ggaggcgagg tgctcagcca ttccttatta 240
ttattacaca agaaggaaga cggaatctgg tccaccgaca ttttaaaaga tcagaaggag 300
cccaagaata agacctttt aaggtgtgag gccaaaaact acagcggtcg tttcacttgt 360
tggtggctga ccaccatttc caccgattta accttctccg tgaaaagcag ccggggaagc 420
tccgaccctc aaggtgtgac atgtggagcc gctaccctca gcgctgagag ggttcgtggc 480
gataacaagg aatacgagta cagcgtggag tgccaagaag atagcgcttg tcccgctgcc 540
gaagaatctt tacccattga ggtgatggtg gacgccgtgc acaaactcaa gtacgagaac 600
tacacctcct ccttctttat ccgggacatc attaagcccg atcctcctaa gaatttacag 660
ctgaagcctc tcaaaaatag ccggcaagtt gaggtctctt gggaatatcc cgacacttgg 720
agcacacccc acagctactt ctctttaacc ttttgtgtgc aagttcaagg taaaagcaag 780
cgggagaaga aagaccgggt gtttaccgac aaaaccagcg ccaccgtcat ctgtcggaag 840
aacgcctcca tcagcgtgag ggctcaagat cgttattact ccagcagctg gtccgagtgg 900
gccagcgtgc cttgttccgg cggtggagga tccggaggag gtggctccgg cggcggagga 960
tctcgtaacc tccccgtggc tacccccgat cccggaatgt tcccttgttt acaccacagc 1020
cagaatttac tgagggccgt gagcaacatg ctgcagaaag ctaggcagac tttagaattt 1080
tacccttgca ccagcgagga gatcgaccat gaagatatca ccaaggacaa gacatccacc 1140
gtggaggctt gtttacctct ggagctgaca aagaacgagt cttgtctcaa ctctcgtgaa 1200
accagcttca tcacaaatgg ctcttgttta gcttcccgga agacctcctt tatgatggct 1260
ttatgcctca gctccatcta cgaggattta aagatgtacc aagtggagtt caagaccatg 1320
aacgccaagc tgctcatgga ccctaaacgg cagatctttt tagaccagaa catgctggct 1380
gtgattgatg agctgatgca agctttaaac ttcaactccg agaccgtccc tcagaagtcc 1440
tccctcgagg agcccgattt ttacaagaca aagatcaaac tgtgcatttt actccacgcc 1500
tttaggatcc gggccgtgac cattgaccgg gtcatgagct atttaaacgc cagcattaca 1560
tgccccccctc ccatgagcgt ggagcacgcc gacatctggg tgaagagcta tagcctctac 1620
agccgggaga ggtatatctg taacagcggc ttcaagagga aggccggcac cagcagcctc 1680
accgagtgcg tgctgaataa ggctaccaac gtggctcact ggacaacacc ctctttaaag 1740
tgcatccggt ccgagctgac ccaggaccct gctgtgtccg tggctctggg ccagaccgtg 1800
aggatcacct gccagggcga ctccctgagg tcctactacg cctcctggta ccagcagaag 1860
cccggccagg ctcctgtgct ggtgatctac ggcaagaaca acaggccctc cggcatccct 1920
gacaggttct ccggatcctc ctccggcaac accgcctccc tgaccatcac aggcgctcag 1980
gccgaggacg aggctgacta ctactgcaac tccagggact cctccggcaa ccatgtggtg 2040
ttcggcggcg gcaccaagct gaccgtgggc catggcggcg gcggctccgg aggcggcggc 2100
agcggcggag gaggatccga ggtgcagctg gtggagtccg gaggaggagt ggtgaggcct 2160
ggaggctccc tgaggctgag ctgtgctgcc tccggcttca ccttcgacga ctacggcatg 2220
tcctgggtga ggcaggctcc tggaaagggc ctggagtggg tgtccggcat caactggaac 2280
ggcggatcca ccggctacgc cgattccgtg aagggcaggt tcaccatcag cagggacaac 2340
gccaagaact ccctgtacct gcagatgaac tccctgaggg ccgaggacac cgccgtgtac 2400
tactgcgcca ggggcaggtc cctgctgttc gactactggg gacagggcac cctggtgacc 2460
gtgtccagg 2469

SEQ ID NO: 225 moltype = AA length = 841
FEATURE Location/Qualifiers
source 1..841
mol_type = protein
organism = synthetic construct
SEQUENCE: 225

```
MKWVTFISLL FLFSSAYSIW ELKKDVYVVE LDWYPDAPGE MVVLTCDTPE EDGITWTLDQ  60
SSEVLGSGKT LTIQVKEFGD AGQYTCHKGG EVLSHSLLLL HKKEDGIWST DILKDQKEPK  120
NKTFLRCEAK NYSGRFTCWW LTTISTDLTF SVKSSRGSSD PQGVTCGAAT LSAERVRGDN  180
KEYEYSVECQ EDSACPAAEE SLPIEVMVDA VHKLKYENYT SSFFIRDIIK PDPPKNLQLK  240
PLKNSRQVEV SWEYPDTWST PHSYFSLTFC VQVQGKSKRE KKDRVFTDKT SATVICRKNA  300
SISVRAQDRY YSSSWSEWAS VPCSGGGGSG GGGSGGGGSR NLPVATPDPG MFPCLHHSQN  360
LLRAVSNMLQ KARQTLEFYP CTSEEIDHED ITKDKTSTVE ACLPLELTKN ESCLNSRETS  420
FITNGSCLAS RKTSFMMALC LSSIYEDLKM YQVEFKTMNA KLLMDPKRQI FLDQNMLAVI  480
DELMQALNFN SETVPQKSSL EEPDFYKTKI KLCILLHAFR IRAVTIDRVM SYLNASITCP  540
PPMSVEHADI WVKSYSLYSR ERYICNSGFK RKAGTSSLTE CVLNKATNVA HWTTPSLKCI  600
RSELTQDPAV SVALGQTVRI TCQGDSLRSY YASWYQQKPG QAPVLVIYGK NNRPSGIPDR  660
FSGSSSGNTA SLTITGAQAE DEADYYCNSR DSSGNHVVFG GGTKLTVGHG GGGSGGGGSG  720
GGGSEVQLVE SGGGVVRPGG SLRLSCAASG FTFDDYGMSW VRQAPGKGLE WVSGINWNGG  780
STGYADSVKG RFTISRDNAK NSLYLQMNSL RAEDTAVYYC ARGRSLLFDY WGQGTLVTVS  840
R                                                                 841

SEQ ID NO: 226         moltype = DNA  length = 2523
FEATURE                Location/Qualifiers
source                 1..2523
                       mol_type = other DNA
                       organism = synthetic construct
SEQUENCE: 226
atgaaatggg tgacctttat ttctttactg ttcctcttta gcagcgccta ctccatttgg  60
gaactgaaga aggacgtcta cgtggtcgaa ctggactggt atcccgatgc tcccggcgaa  120
atggtggtgc tcacttgtga cacccccgaa gaagacggca tcacttggac cctcgatcag  180
agcagcgagg tgctgggctc cggaaagacc ctcacaatcc aagttaagga gttcggagac  240
gctggccaat acacatgcca caagggaggc gaggtgctca gccattcctt attattatta  300
cacaagaagg aagacggaat ctggtccacc gacattttaa aagatcagaa ggagcccaag  360
aataagacct tttaaggtg tgaggccaaa aactacagcg gtcgtttcac ttgttggtgg  420
ctgaccacca tttccaccga tttaaccttc tccgtgaaaa gcagccgggg aagctccgac  480
cctcaaggtg tgacatgtgg agccgctacc ctcagcgctg agagggttcg tggcgataac  540
aaggaatacg agtacagcgt ggagtgccaa gaagatagcg cttgtcccgc tgccgaagaa  600
tctttaccca ttgaggtgat ggtggacgcc gtgcacaaac tcaagtacga gaactacacc  660
tcctccttct ttatccggga catcattaag cccgatcctc ctaagaattt acagctgaag  720
cctctcaaaa atagccggca agttgaggtc tcttgggaat atcccgacac ttggagcaca  780
ccccacagct acttctcttt aaccttttgt gtgcaagttc aaggtaaaag caagcgggag  840
aagaaagacc gggtgtttac cgacaaaacc agcgccaccg tcatctgtcg gaagaacgcc  900
tccatcagcg tgagggctca agatcgttat tactccagca gctggtccga gtgggccagc  960
gtgccttgtt ccggcggtgg aggatccgga ggaggtggct ccggcggcgg aggatctcgt  1020
aacctccccg tggctacccc cgatcccgga atgttccctt gtttacacca cagccagaat  1080
ttactgaggg ccgtgagcaa catgctgcag aaagctaggc agactttaga attttaccct  1140
tgcaccagcg aggagatcga ccatgaagat atcaccaagg acaagacatc caccgtggag  1200
gcttgtttac ctctggagct gacaaagaac gagtcttgtc tcaactctcg tgaaaccagc  1260
ttcatcacaa atggctcttg tttagcttcc cggaagacct cctttatgat ggctttatgc  1320
ctcagctcca tctacgagga tttaaagatg taccaagtgg agttcaagac catgaacgcc  1380
aagctgctca tggaccctaa acggcagatc tttttagacc agaacatgct ggctgtgatt  1440
gatgagctga tgcaagcttt aaacttcaac tccgagaccg tccctcagaa gtcctccctc  1500
gaggagcccg atttttacaa gacaaagatc aaactgtgca ttttactcca cgcctttagg  1560
atccgggccg tgaccattga ccgggtcatg agctatttaa acgccagcat tacatgcccc  1620
cctcccatga gcgtggagca cgccgacatc tgggtgaaga gctatagcct ctacagccgg  1680
gagaggtata tctgtaacag cggcttcaag aggaaggccg gcaccagcag cctcaccgag  1740
tgcgtgctga ataaggctac caacgtggct cactggacaa caccctcttt aaagtgcatc  1800
cggtccgagc tgacccagga ccctgctgtg tccgtggctc tgggccagac cgtgaggatc  1860
acctgccagg gcgactccct gaggtcctac tacgcctcct ggtaccagca gaagcccggc  1920
caggctcctg tgctggtgat ctacggcaag aacaacaggc cctccggcat ccctgacagg  1980
ttctccggat cctcctccgg caacaccgcc tccctgacca tcacaggcgc tcaggccgag  2040
gacgaggctg actactactg caactccagg gactcctccg gcaaccatgt ggtgttcggc  2100
ggcggcacca agctgaccgt gggccatggc ggcggcggct ccggaggcgg cggcagcggc  2160
ggaggaggat ccgaggtgca gctggtggag tccggaggag gagtggtgag gcctggaggc  2220
tccctgaggc tgagctgtgc tgcctccggc ttcaccttcg acgactacgg catgtcctgg  2280
gtgaggcagg ctcctggaaa gggcctggag tgggtgtccg gcatcaactg gaacggcgga  2340
tccaccggct acgccgattc cgtgaagggc aggttcacca tcagcaggga caacgccaag  2400
aactccctgt acctgcagat gaactccctg agggccgagg acaccgccgt gtactactgc  2460
gccaggggca ggtccctgct gttcgactac tggggacagg gcaccctggt gaccgtgtcc  2520
agg                                                               2523

SEQ ID NO: 227         moltype = DNA  length = 456
FEATURE                Location/Qualifiers
source                 1..456
                       mol_type = genomic DNA
                       note = source = IL7
                       organism = Homo sapiens
SEQUENCE: 227
gattgcgaca tcgagggcaa ggacggcaag cagtacgaga gcgtgctgat ggtgtccatc  60
gaccagctgc tggacagcat gaaggagatc ggctccaact gcctcaacaa cgagttcaac  120
ttcttcaagc ggcacatctg cgacgccaac aaggagggca tgttcctgtt cagggccgcc  180
aggaaactgc ggcagttcct gaagatgaac tccaccggcg acttcgacct gcacctgctg  240
aaggtgtccg agggcaccac catcctgctg aactgcaccg gacaggtgaa gggccggaaa  300
cctgctgctc tgggagaggc ccaacccacc aagagcctgg aggagaacaa gtccctgaag  360
```

```
gagcagaaga agctgaacga cctgtgcttc ctgaagaggc tgctgcagga gatcaagacc  420
tgctggaaca agatcctgat gggcaccaag gagcat                            456

SEQ ID NO: 228         moltype =   length =
SEQUENCE: 228
000

SEQ ID NO: 229         moltype =   length =
SEQUENCE: 229
000

SEQ ID NO: 230         moltype =   length =
SEQUENCE: 230
000

SEQ ID NO: 231         moltype =   length =
SEQUENCE: 231
000

SEQ ID NO: 232         moltype = AA  length = 438
FEATURE                Location/Qualifiers
source                 1..438
                       mol_type = protein
                       organism = synthetic construct
SEQUENCE: 232
SELTQDPAVS VALGQTVRIT CQGDSLRSYY ASWYQQKPGQ APVLVIYGKN NRPSGIPDRF  60
SGSSSGNTAS LTITGAQAED EADYYCNSRD SSGNHVVFGG GTKLTVGHGG GGSGGGGSGG  120
GGSEVQLVES GGGVVRPGGS LRLSCAASGF TFDDYGMSWV RQAPGKGLEW VSGINWNGGS  180
TGYADSVKGR FTISRDNAKN SLYLQMNSLR AEDTAVYYCA RGRSLLFDYW GQGTLVTVSR  240
ITCPPPMSVE HADIWVKSYS LYSRERYICN SGFKRKAGTS SLTECVLNKA TNVAHWTTPS  300
LKCIRQGQDR HMIRMRQLID IVDQLKNYVN DLVPEFLPAP EDVETNCEWS AFSCFQKAQL  360
KSANTGNNER IINVSIKKLK RKPPSTNAGR RQKHRLTCPS CDSYEKKPPK EFLERFKSLL  420
QKMIHQHLSS RTHGSEDS                                                438

SEQ ID NO: 233         moltype = DNA  length = 1314
FEATURE                Location/Qualifiers
source                 1..1314
                       mol_type = other DNA
                       organism = synthetic construct
SEQUENCE: 233
tccgagctga cccaggaccc tgctgtgtcc gtggctctgg gccagaccgt gaggatcacc  60
tgccagggcg actccctgag gtcctactac gcctcctggt accagcagaa gcccggccag  120
gctcctgtgc tggtgatcta cggcaagaac aacaggccct ccggcatccc tgacaggttc  180
tccggatcct cctccggcaa caccgcctcc ctgaccatca caggcgctca ggccgaggac  240
gaggctgact actactgcaa ctccagggac tcctccggca accatgtggt gttcggcggc  300
ggcaccaagc tgaccgtggg ccatggcggc ggcggctccg gaggcggcgg cagcggcgga  360
ggaggatccg aggtgcagct ggtggagtcc ggaggaggag tggtgaggcc tggaggctcc  420
ctgaggctga gctgtgctgc ctccggcttc accttcgacg actacggcat gtcctgggtg  480
aggcaggctc ctggaaaggg cctggagtgg gtgtccggca tcaactggaa cggcggatcc  540
accggctacg ccgattccgt gaagggcagg ttcaccatca gcagggacaa cgccaagaac  600
tccctgtacc tgcagatgaa ctccctgagg gccgaggaca ccgccgtgta ctactgcgcc  660
aggggcaggt ccctgctgtt cgactactgg ggacagggca ccctggtgac cgtgtccagg  720
attacatgcc cccctcccat gagcgtggag cacgccgaca tctgggtgaa gagctatagc  780
ctctacagcc gggagaggta tatctgtaac agcggcttca agaggaaggc cggcaccagc  840
agcctcaccg agtgcgtgct gaataaggct accaacgtgg ctcactggac aacaccctct  900
ttaaagtgca tccggcaggg ccaggacagg cacatgatcc ggatgaggca gctcatcgac  960
atcgtcgacc agctgaagaa ctacgtgaac gacctggtgc ccgagtttct gcctgccccc  1020
gaggacgtgg agaccaactg cgagtggtcc gccttctcct gctttcagaa ggcccagctg  1080
aagtccgcca acaccggcaa caacgagcgg atcatcaacg tgagcatcaa gaagctgaag  1140
cggaagcctc cctccacaaa cgccggcagg aggcagaagc acaggctgac ctgccccagc  1200
tgtgactcct acgagaagaa gccccccaag gagttcctgg agaggttcaa gtccctgctg  1260
cagaagatga tccatcagca cctgtcctcc aggacccacg gctccgagga ctcc        1314

SEQ ID NO: 234         moltype = AA  length = 456
FEATURE                Location/Qualifiers
source                 1..456
                       mol_type = protein
                       organism = synthetic construct
SEQUENCE: 234
MKWVTFISLL FLFSSAYSSE LTQDPAVSVA LGQTVRITCQ GDSLRSYYAS WYQQKPGQAP  60
VLVIYGKNNR PSGIPDRFSG SSSGNTASLT ITGAQAEDEA DYYCNSRDSS GNHVVFGGGT  120
KLTVGHGGGG SGGGGSGGGG SEVQLVESGG GVVRPGGSLR LSCAASGFTF DDYGMSWVRQ  180
APGKGLEWVS GINWNGGSTG YADSVKGRFT ISRDNAKNSL YLQMNSLRAE DTAVYYCARG  240
RSLLFDYWGQ GTLVTVSRIT CPPPMSVEHA DIWVKSYSLY SRERYICNSG FKRKAGTSSL  300
TECVLNKATN VAHWTTPSLK CIRQGQDRHM IRMRQLIDIV DQLKNYVNDL VPEFLPAPED  360
VETNCEWSAF SCFQKAQLKS ANTGNNERII NVSIKKLKRK PPSTNAGRRQ KHRLTCPSCD  420
SYEKKPPKEF LERFKSLLQK MIHQHLSSRT HGSEDS                            456

SEQ ID NO: 235         moltype = DNA  length = 1368
```

```
FEATURE                Location/Qualifiers
source                 1..1368
                       mol_type = other DNA
                       organism = synthetic construct
SEQUENCE: 235
atgaagtggg tgaccttcat cagcctgctg ttcctgttct ccagcgccta ctcctccgag  60
ctgacccagg accctgctgt gtccgtggct ctgggccaga ccgtgaggat cacctgccag  120
ggcgactccc tgaggtccta ctacgcctcc tggtaccagc agaagcccgg ccaggctcct  180
gtgctggtga tctacggcaa gaacaacagg ccctccggca tccctgacag gttctccgga  240
tcctcctccg gcaacaccgc ctccctgacc atcacaggcg ctcaggccga ggacgaggct  300
gactactact gcaactccag ggactcctcc ggcaaccatg tggtgttcgg cggcggcacc  360
aagctgaccg tgggccatgg cggcggcggc tccggaggcg gcggcagcgg cggaggagga  420
tccgaggtgc agctggtgga gtccggagga ggagtggtga ggcctggagg ctccctgagg  480
ctgagctgtg ctgcctccgg cttcaccttc gacgactacg gcatgtcctg ggtgaggcag  540
gctcctggaa agggcctgga gtgggtgtcc ggcatcaact ggaacggcgg atccaccggc  600
tacgccgatt ccgtgaaggg caggttcacc atcagcaggg acaacgccaa gaactccctg  660
tacctgcaga tgaactccct gagggccgag gacaccgccg tgtactactg cgccaggggc  720
aggtccctgc tgttcgacta ctggggacag ggcaccctgg tgaccgtgtc caggattaca  780
tgcccccctc ccatgagcgt ggagcacgcc gacatctggg tgaagagcta tagcctctac  840
agccgggaga ggtatatctg taacagcggc ttcaagagga aggccggcac cagcagcctc  900
accgagtgcg tgctgaataa ggctaccaac gtggctcact ggacaacacc ctctttaaag  960
tgcatccggc agggccagga caggcacatg atccggatga ggcagctcat cgacatcgtc  1020
gaccagctga agaactacgt gaacgacctg gtgcccgagt ttctgcctgc cccccgaggac  1080
gtggagacca actgcgagtg gtccgccttc tcctgctttc agaaggccca gctgaagtcc  1140
gccaacaccg gcaacaacga gcggatcatc aacgtgagca tcaagaagct gaagcggaag  1200
cctccctcca caaacgccgg caggaggcag aagcacaggc tgacctgccc cagctgtgac  1260
tcctacgaga agaagccccc caaggagttc ctggagaggt tcaagtccct gctgcagaag  1320
atgatccatc agcacctgtc ctccaggacc cacggctccg aggactcc               1368

SEQ ID NO: 236         moltype = AA  length = 620
FEATURE                Location/Qualifiers
source                 1..620
                       mol_type = protein
                       organism = synthetic construct
SEQUENCE: 236
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDSGT TNTVAAYNLT  300
WKSTNFKTIL EWEPKPVNQV YTVQISTKSG DWKSKCFYTT DTECDLTDEI VKDVKQTYLA  360
RVFSYPAGNV ESTGSAGEPL YENSPEFTPY LETNLGQPTI QSFEQVGTKV NVTVEDERTL  420
VRRNNTFLSL RDVFGKDLIY TLYYWKSSSS GKKTAKTNTN EFLIDVDKGE NYCFSVQAVI  480
PSRTVNRKST DSPVECMGQE KGEFRENWVN VISDLKKIED LIQSMHIDAT LYTESDVHPS  540
CKVTAMKCFL LELQVISLES GDASIHDTVE NLIILANNSL SSNGNVTESG CKECEELEEK  600
NIKEFLQSFV HIVQMFINTS                                              620

SEQ ID NO: 237         moltype = DNA  length = 1860
FEATURE                Location/Qualifiers
source                 1..1860
                       mol_type = other DNA
                       organism = synthetic construct
SEQUENCE: 237
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cagcggcaca accaacacag tcgctgccta taacctcact  900
tggaagagca ccaacttcaa aaccatcctc gaatgggaac ccaaacccgt taaccaagtt  960
tacaccgtgc agatcagcac caagtccggc gactggaagt ccaaatgttt ctataccacc  1020
gacaccgagt gcgatctcac cgatgagatc gtgaaagatg tgaaacagac ctacctcgcc  1080
cgggtgttta gctaccccgc cggcaatgtg gagagcactg gttccgctgg cgagccttta  1140
tacgagaaca gccccgaatt taccccttac ctcgagacca atttaggaca gcccaccatc  1200
caaagctttg agcaagttgg cacaaaggtg aatgtgacag tggaggacga gcggacttta  1260
gtgcggcgga acaacacctt tctcagcctc cgggatgtgt tcggcaaaga tttaatctac  1320
acactgtatt actggaagtc ctcttcctcc ggcaagaaga cagctaaaac caacacaaac  1380
gagtttttaa tcgacgtgga taaaggcgaa aactactgtt tcagcgtgca agctgtgatc  1440
ccctcccgga ccgtgaatag gaaaagcacc gatagccccg ttgagtgcat gggccaagaa  1500
aagggcgagt tccgggagaa ctgggtgaac gtcatcagcg atttaaagaa gatcgaagat  1560
```

```
ttaattcagt ccatgcatat cgacgccact ttatacacag aatccgacgt gcacccctct  1620
tgtaaggtga ccgccatgaa atgtttttta ctggagctgc aagttatctc tttagagagc  1680
ggagacgcta gcatccacga caccgtggag aatttaatca ttttagccaa taactcttta  1740
tccagcaacg gcaacgtgac agagtccggc tgcaaggagt gcgaagagct ggaggagaag  1800
aacatcaagg agtttctgca atcctttgtg cacattgtcc agatgttcat caatacctcc  1860

SEQ ID NO: 238         moltype = AA  length = 638
FEATURE                Location/Qualifiers
source                 1..638
                       mol_type = protein
                       organism = synthetic construct
SEQUENCE: 238
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDSGTTN TVAAYNLTWK STNFKTILEW EPKPVNQVYT VQISTKSGDW KSKCFYTTDT  360
ECDLTDEIVK DVKQTYLARV FSYPAGNVES TGSAGEPLYE NSPEFTPYLE TNLGQPTIQS  420
FEQVGTKVNV TVEDERTLVR RNNTFLSLRD VFGKDLIYTL YYWKSSSSGK KTAKTNTNEF  480
LIDVDKGENY CFSVQAVIPS RTVNRKSTDS PVECMGQEKG EFRENWVNVI SDLKKIEDLI  540
QSMHIDATLY TESDVHPSCK VTAMKCFLLE LQVISLESGD ASIHDTVENL IILANNSLSS  600
NGNVTESGCK ECEELEEKNI KEFLQSFVHI VQMFINTS                         638

SEQ ID NO: 239         moltype = DNA  length = 1914
FEATURE                Location/Qualifiers
source                 1..1914
                       mol_type = other DNA
                       organism = synthetic construct
SEQUENCE: 239
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt ttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gacctttttc  840
atgtgctcct gcagcagcga cgaatgcaac gacaatatca tctttagcga ggaatacaat  900
accagcaacc ccgacagcgg cacaaccaac acagtcgctg cctataacct cacttggaag  960
agcaccaact tcaaaaccat cctcgaatgg gaacccaaac ccgttaacca agtttacacc  1020
gtgcagatca gcaccaagtc cggcgactgg aagtccaaat gtttctatac caccgacacc  1080
gagtgcgatc tcaccgatga gatcgtgaaa gatgtgaaac agacctacct cgcccgggtg  1140
tttagctacc ccgccggcaa tgtggagagc actggttccg ctggcgagcc tttatacgag  1200
aacagccccg aatttacccc ttacctcgag accaatttag gacagcccac catccaaagc  1260
tttgagcaag ttggcacaaa ggtgaatgtg acagtggagg acgagcggac tttagtgcgg  1320
cggaacaaca cctttctcag cctccgggat gtgttcggca aagatttaat ctacacactg  1380
tattactgga agtcctcttc ctccggcaag aagacagcta aaaccaacac aaacgagttt  1440
ttaatcgacg tggataaagg cgaaaactac tgtttcagcg tgcaagctgt gatcccctcc  1500
cggaccgtga ataggaaaag caccgatagc cccgttgagt gcatgggcca agaaaagggc  1560
gagttccggg agaactgggt gaacgtcatc agcgatttaa agaagatcga agatttaatt  1620
cagtccatgc atatcgacgc cactttatac acagaatccg acgtgcaccc ctcttgtaag  1680
gtgaccgcca tgaaatgttt tttactggag ctgcaagtta tctctttaga gagcggagac  1740
gctagcatcc acgacaccgt ggagaattta atcattttag ccaataactc tttatccagc  1800
aacggcaacg tgacagagtc cggctgcaag gagtgcgaag agctggagga gaagaacatc  1860
aaggagtttc tgcaatcctt tgtgcacatt gtccagatgt tcatcaatac ctcc        1914

SEQ ID NO: 240         moltype =   length =
SEQUENCE: 240
000

SEQ ID NO: 241         moltype =   length =
SEQUENCE: 241
000

SEQ ID NO: 242         moltype =   length =
SEQUENCE: 242
000

SEQ ID NO: 243         moltype =   length =
SEQUENCE: 243
000
```

```
SEQ ID NO: 244         moltype =   length =
SEQUENCE: 244
000

SEQ ID NO: 245         moltype =   length =
SEQUENCE: 245
000

SEQ ID NO: 246         moltype =   length =
SEQUENCE: 246
000

SEQ ID NO: 247         moltype =   length =
SEQUENCE: 247
000

SEQ ID NO: 248         moltype =   length =
SEQUENCE: 248
000

SEQ ID NO: 249         moltype =   length =
SEQUENCE: 249
000

SEQ ID NO: 250         moltype = AA  length = 235
FEATURE                Location/Qualifiers
source                 1..235
                       mol_type = protein
                       organism = synthetic construct
SEQUENCE: 250
MKWVTFISLL FLFSSAYSDC DIEGKDGKQY ESVLMVSIDQ LLDSMKEIGS NCLNNEFNFF  60
KRHICDANKE GMFLFRAARK LRQFLKMNST GDFDLHLLKV SEGTTILLNC TGQVKGRKPA  120
ALGEAQPTKS LEENKSLKEQ KKLNDLCFLK RLLQEIKTCW NKILMGTKEH ITCPPPMSVE  180
HADIWVKSYS LYSRERYICN SGFKRKAGTS SLTECVLNKA TNVAHWTTPS LKCIR       235

SEQ ID NO: 251         moltype = DNA  length = 705
FEATURE                Location/Qualifiers
source                 1..705
                       mol_type = other DNA
                       organism = synthetic construct
SEQUENCE: 251
atgaagtggg tgaccttcat cagcctgctg ttcctgttct ccagcgccta ctccgattgc  60
gacatcgagg gcaaggacgg caagcagtac gagagcgtgc tgatggtgtc catcgaccag  120
ctgctggaca gcatgaagga gatcggctcc aactgcctca acaacgagtt caacttcttc  180
aagcggcaca tctgcgacgc caacaaggag ggcatgttcc tgttcagggc cgccaggaaa  240
ctgcggcagt tcctgaagat gaactccacc ggcgacttcg acctgcacct gctgaaggtg  300
tccgagggca ccaccatcct gctgaactgc accggacagg tgaagggccg gaaacctgct  360
gctctgggag aggcccaacc caccaagagc ctggaggaga acaagtccct gaaggagcag  420
aagaagctga acgacctgtg cttcctgaag aggctgctgc aggagatcaa gacctgctgg  480
aacaagatcc tgatgggcac caaggagcat attacatgcc cccctcccat gagcgtggag  540
cacgccgaca tctgggtgaa gagctatagc ctctacagcc gggagaggta tatctgtaac  600
agcggcttca agaggaaggc cggcaccagc agcctcaccg agtgcgtgct gaataaggct  660
accaacgtgg ctcactggac aacaccctct ttaaagtgca tccgg                 705

SEQ ID NO: 252         moltype =   length =
SEQUENCE: 252
000

SEQ ID NO: 253         moltype =   length =
SEQUENCE: 253
000

SEQ ID NO: 254         moltype =   length =
SEQUENCE: 254
000

SEQ ID NO: 255         moltype =   length =
SEQUENCE: 255
000

SEQ ID NO: 256         moltype =   length =
SEQUENCE: 256
000

SEQ ID NO: 257         moltype = DNA  length = 1056
FEATURE                Location/Qualifiers
source                 1..1056
                       mol_type = other DNA
                       organism = synthetic construct
```

```
SEQUENCE: 257
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cattacatgc ccccctccca tgagcgtgga gcacgccgac  900
atctgggtga agagctatag cctctacagc cgggagaggt atatctgtaa cagcggcttc  960
aagaggaagg ccggcaccag cagcctcacc gagtgcgtgc tgaataaggc taccaacgtg  1020
gctcactgga caacaccctc tttaaagtgc atccgg                           1056

SEQ ID NO: 258         moltype =   length =
SEQUENCE: 258
000

SEQ ID NO: 259         moltype = DNA  length = 1110
FEATURE                Location/Qualifiers
source                 1..1110
                       mol_type = other DNA
                       organism = synthetic construct
SEQUENCE: 259
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gacctttttc  840
atgtgctcct gcagcagcga cgaatgcaac gacaatatca tctttagcga ggaatacaat  900
accagcaacc ccgacattac atgccccccct cccatgagcg tggagcacgc cgacatctgg  960
gtgaagagct atagcctcta cagccgggag aggtatatct gtaacagcgg cttcaagagg  1020
aaggccggca ccagcagcct caccgagtgc gtgctgaata aggctaccaa cgtggctcac  1080
tggacaacac cctctttaaa gtgcatccgg                                  1110

SEQ ID NO: 260         moltype = AA  length = 184
FEATURE                Location/Qualifiers
REGION                 1..184
                       note = source = /note="CD137"
source                 1..184
                       mol_type = protein
                       organism = Homo sapiens
SEQUENCE: 260
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLPS  180
PRSE                                                              184

SEQ ID NO: 261         moltype = DNA  length = 552
FEATURE                Location/Qualifiers
source                 1..552
                       mol_type = genomic DNA
                       note = source = CD137
                       organism = Homo sapiens
SEQUENCE: 261
cgcgagggtc ccgagctttc gcccgacgat cccgccggcc tcttggacct gcggcagggc  60
atgtttgcgc agctggtggc ccaaaatgtt ctgctgatcg atgggcccct gagctggtac  120
agtgacccag gcctggcagg cgtgtccctg acgggggggcc tgagctacaa agaggacacg  180
aaggagctgg tggtggccaa ggctggagtc tactatgtct tctttcaact agagctgcgg  240
cgcgtggtgg ccggcgaggg ctcaggctcc gtttcacttg cgctgcacct gcagccactg  300
cgctctgctg ctggggccgc cgccctggct ttgaccgtgg acctgccacc cgcctcctcc  360
gaggctcgga actcggcctt cggtttccag ggccgcttgc tgcacctgag tgccggccag  420
cgcctgggcg tccatcttca cactgaggcc agggcacgcc atgcctggca gcttacccag  480
ggcgccacag tcttgggact cttccgggtg acccccgaaa tcccagccgg actcccttca  540
```

```
ccgaggtcgg aa                                                  552

SEQ ID NO: 262          moltype = AA  length = 165
FEATURE                 Location/Qualifiers
REGION                  1..165
                        note = source = /note="CD137"
source                  1..165
                        mol_type = protein
                        organism = Homo sapiens
SEQUENCE: 262
DPAGLLDLRQ GMFAQLVAQN VLLIDGPLSW YSDPGLAGVS LTGGLSYKED TKELVVAKAG  60
VYYVFFQLEL RRVVAGEGSG SVSLALHLQP LRSAAGAAAL ALTVDLPPAS SEARNSAFGF  120
QGRLLHLSAG QRLGVHLHTE ARARHAWQLT QGATVLGLFR VTPEI               165

SEQ ID NO: 263          moltype = DNA  length = 495
FEATURE                 Location/Qualifiers
source                  1..495
                        mol_type = genomic DNA
                        note = source = CD137
                        organism = Homo sapiens
SEQUENCE: 263
gatcccgccg gcctcttgga cctgcggcag ggcatgtttg cgcagctggt ggcccaaaat  60
gttctgctga tcgatgggcc cctgagctgg tacagtgacc caggcctggc aggcgtgtcc  120
ctgacggggg gcctgagcta caaagaggac acgaaggagc tggtggtggc caaggctgga  180
gtctactatg tcttctttca actagagctg cggcgcgtgg tggccggcga gggctcaggc  240
tccgtttcac ttgcgctgca cctgcagcca ctgcgctctg ctgctggggc cgccgccctg  300
gctttgaccg tggacctgcc acccgcctcc tccgaggctc ggaactcggc cttcggtttc  360
cagggccgct tgctgcacct gagtgccggc cagcgcctgg gcgtccatct tcacactgag  420
gccagggcac gccatgcctg gcagcttacc cagggcgcca cagtcttggg actcttccgg  480
gtgacccccg aaatc                                               495

SEQ ID NO: 264          moltype =   length =
SEQUENCE: 264
000

SEQ ID NO: 265          moltype =   length =
SEQUENCE: 265
000

SEQ ID NO: 266          moltype =   length =
SEQUENCE: 266
000

SEQ ID NO: 267          moltype =   length =
SEQUENCE: 267
000

SEQ ID NO: 268          moltype = AA  length = 397
FEATURE                 Location/Qualifiers
source                  1..397
                        mol_type = protein
                        organism = synthetic construct
SEQUENCE: 268
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSITCPPPM SVEHADIWVK SYSLYSRERY ICNSGFKRKA GTSSLTECVL  180
NKATNVAHWT TPSLKCIRGG GGSGGGGSGG GGSREGPELS PDDPAGLLDL RQGMFAQLVA  240
QNVLLIDGPL SWYSDPGLAG VSLTGGLSYK EDTKELVVAK AGVYYVFFQL ELRRVVAGEG  300
SGSVSLALHL QPLRSAAGAA ALALTVDLPP ASSEARNSAF GFQGRLLHLS AGQRLGVHLH  360
TEARARHAWQ LTQGATVLGL FRVTPEIPAG LPSPRSE                        397

SEQ ID NO: 269          moltype = DNA  length = 1191
FEATURE                 Location/Qualifiers
source                  1..1191
                        mol_type = other DNA
                        organism = synthetic construct
SEQUENCE: 269
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcca ttacatgccc ccctcccatg  420
agcgtggagc acgccgacat ctgggtgaag agctatagcc tctacagccg ggagaggtat  480
atctgtaaca gcggcttcaa gaggaaggcc ggcaccagca gcctcaccga gtgcgtgctg  540
aataaggcta ccaacgtggc tcactggaca acaccctctt taaagtgcat ccggggcggt  600
ggaggatccg gaggaggtgg ctccggcggc ggaggatctc gcgagggtcc cgagctttcg  660
cccgacgatc ccgccggcct cttggacctg cggcagggca tgtttgcgca gctggtggcc  720
```

```
caaaatgttc tgctgatcga tgggcccctg agctggtaca gtgacccagg cctggcaggc  780
gtgtccctga cggggggcct gagctacaaa gaggacacga aggagctggt ggtggccaag  840
gctggagtct actatgtctt ctttcaacta gagctgcggc gcgtggtggc cggcgagggc  900
tcaggctccg tttcacttgc gctgcacctg cagccactgc gctctgctgc tggggccgcc  960
gccctggctt tgaccgtgga cctgccaccc gcctcctccg aggctcggaa ctcggccttc  1020
ggtttccagg gccgcttgct gcacctgagt gccggccagc gcctgggcgt ccatcttcac  1080
actgaggcca gggcacgcca tgcctggcag cttacccagg gcgccacagt cttgggactc  1140
ttccgggtga cccccgaaat cccagccgga ctcccttcac cgaggtcgga a           1191

SEQ ID NO: 270         moltype = AA  length = 415
FEATURE                Location/Qualifiers
source                 1..415
                       mol_type = protein
                       organism = synthetic construct
SEQUENCE: 270
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SITCPPPMSV EHADIWVKSY SLYSRERYIC  180
NSGFKRKAGT SSLTECVLNK ATNVAHWTTP SLKCIRGGGG SGGGGSGGGG SREGPELSPD  240
DPAGLLDLRQ GMFAQLVAQN VLLIDGPLSW YSDPGLAGVS LTGGLSYKED TKELVVAKAG  300
VYYVFFQLEL RRVVAGEGSG SVSLALHLQP LRSAAGAAAL ALTVDLPPAS SEARNSAFGF  360
QGRLLHLSAG QRLGVHLHTE ARARHAWQLT QGATVLGLFR VTPEIPAGLP SPRSE       415

SEQ ID NO: 271         moltype = DNA  length = 1245
FEATURE                Location/Qualifiers
source                 1..1245
                       mol_type = other DNA
                       organism = synthetic construct
SEQUENCE: 271
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tccattacat gcccccctcc catgagcgtg  480
gagcacgccg acatctgggt gaagagctat agcctctaca gccgggagag gtatatctgt  540
aacagcggct tcaagaggaa ggccggcacc agcagcctca ccgagtgcgt gctgaataag  600
gctaccaacg tggctcactg gacaacaccc tctttaaagt gcatccgggg cggtggagga  660
tccggaggag gtggctccgg cggcggagga tctcgcgagg gtcccgagct ttcgccccgac  720
gatcccgccg gcctcttgga cctgcggcag ggcatgtttg cgcagctggt ggcccaaaat  780
gttctgctga tcgatgggcc cctgagctgg tacagtgacc caggcctggc aggcgtgtcc  840
ctgacggggg gcctgagcta caaagaggac acgaaggagc tggtggtggc caaggctgga  900
gtctactatg tcttctttca actagagctg cggcgcgtgg tggccggcga gggctcaggc  960
tccgtttcac ttgcgctgca cctgcagcca ctgcgctctg ctgctggggc cgccgccctg  1020
gctttgaccg tggacctgcc acccgcctcc tccgaggctc ggaactcggc cttcggtttc  1080
cagggccgct tgctgcacct gagtgccggc cagcgcctgg gcgtccatct tcacactgag  1140
gccagggcac gccatgcctg gcagcttacc cagggcgcca cagtcttggg actcttccgg  1200
gtgacccccg aaatcccagc cggactccct tcaccgaggt cggaa                  1245

SEQ ID NO: 272         moltype = AA  length = 378
FEATURE                Location/Qualifiers
source                 1..378
                       mol_type = protein
                       organism = synthetic construct
SEQUENCE: 272
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSITCPPPM SVEHADIWVK SYSLYSRERY ICNSGFKRKA GTSSLTECVL  180
NKATNVAHWT TPSLKCIRGG GGSGGGGSGG GGSDPAGLLD LRQGMFAQLV AQNVLLIDGP  240
LSWYSDPGLA GVSLTGGLSY KEDTKELVVA KAGVYYVFFQ LELRRVVAGE GSGSVSLALH  300
LQPLRSAAGA AALALTVDLP PASSEARNSA FGFQGRLLHL SAGQRLGVHL HTEARARHAW  360
QLTQGATVLG LFRVTPEI                                                378

SEQ ID NO: 273         moltype = DNA  length = 1134
FEATURE                Location/Qualifiers
source                 1..1134
                       mol_type = other DNA
                       organism = synthetic construct
SEQUENCE: 273
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcca ttacatgccc ccctcccatg  420
agcgtggagc acgccgacat ctgggtgaag agctatagcc tctacagccg ggagaggtat  480
```

```
atctgtaaca gcggcttcaa gaggaaggcc ggcaccagca gcctcaccga gtgcgtgctg  540
aataaggcta ccaacgtggc tcactggaca acaccctctt taaagtgcat ccggggcggt  600
ggaggatccg gaggaggtgg ctccggcggc ggaggatctg atcccgccgg cctcttggac  660
ctgcggcagg gcatgtttgc gcagctggtg gcccaaaatg ttctgctgat cgatgggccc  720
ctgagctggt acagtgaccc aggcctggca ggcgtgtccc tgacgggggg cctgagctac  780
aaagaggaca cgaaggagct ggtggtggcc aaggctggag tctactatgt cttctttcaa  840
ctagagctgc ggcgcgtggt ggccggcgag ggctcaggct ccgtttcact tgcgctgcac  900
ctgcagccac tgcgctctgc tgctggggcc gccgccctgg ctttgaccgt ggacctgcca  960
cccgcctcct ccgaggctcg gaactcggcc ttcggtttcc agggccgctt gctgcacctg  1020
agtgccggcc agcgcctggg cgtccatctt cacactgagg ccagggcacg ccatgcctgg  1080
cagcttaccc agggcgccac agtcttggga ctcttccggg tgacccccga aatc        1134

SEQ ID NO: 274         moltype = AA  length = 396
FEATURE                Location/Qualifiers
source                 1..396
                       mol_type = protein
                       organism = synthetic construct
SEQUENCE: 274
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SITCPPPMSV EHADIWVKSY SLYSRERYIC  180
NSGFKRKAGT SSLTECVLNK ATNVAHWTTP SLKCIRGGGG SGGGGSGGGG SDPAGLLDLR  240
QGMFAQLVAQ NVLLIDGPLS WYSDPGLAGV SLTGGLSYKE DTKELVVAKA GVYYVFFQLE  300
LRRVVAGEGS GSVSLALHLQ PLRSAAGAAA LALTVDLPPA SSEARNSAFG FQGRLLHLSA  360
GQRLGVHLHT EARARHAWQL TQGATVLGLF RVTPEI                           396

SEQ ID NO: 275         moltype = DNA  length = 1188
FEATURE                Location/Qualifiers
source                 1..1188
                       mol_type = other DNA
                       organism = synthetic construct
SEQUENCE: 275
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tccattacat gccccccctcc catgagcgtg  480
gagcacgccg acatctgggt gaagagctat agcctctaca gccgggagag gtatatctgt  540
aacagcggct tcaagaggaa ggccggcacc agcagcctca ccgagtgcgt gctgaataag  600
gctaccaacg tggctcactg gacaacaccc tctttaaagt gcatccgggg cggtggagga  660
tccggaggag gtggctccgg cggcggagga tctgatcccg ccggcctctt ggacctgcgg  720
cagggcatgt ttgcgcagct ggtggcccaa aatgttctgc tgatcgatgg gcccctgagc  780
tggtacagtg acccaggcct ggcaggcgtg tccctgacgg ggggcctgag ctacaaagag  840
gacacgaagg agctggtggt ggccaaggct ggagtctact atgtcttctt tcaactagag  900
ctgcggcgcg tggtggccgg cgagggctca ggctccgttt cacttgcgct gcacctgcag  960
ccactgcgct ctgctgctgg ggccgccgcc ctggctttga ccgtggacct gccacccgcc  1020
tcctccgagg ctcggaactc ggccttcggt ttccagggcc gcttgctgca cctgagtgcc  1080
ggccagcgcc tgggcgtcca tcttcacact gaggccaggg cacgccatgc ctggcagctt  1140
acccagggcg ccacagtctt gggactcttc cgggtgaccc ccgaaatc              1188

SEQ ID NO: 276         moltype =   length =
SEQUENCE: 276
000

SEQ ID NO: 277         moltype =   length =
SEQUENCE: 277
000

SEQ ID NO: 278         moltype =   length =
SEQUENCE: 278
000

SEQ ID NO: 279         moltype =   length =
SEQUENCE: 279
000

SEQ ID NO: 280         moltype =   length =
SEQUENCE: 280
000

SEQ ID NO: 281         moltype =   length =
SEQUENCE: 281
000

SEQ ID NO: 282         moltype =   length =
SEQUENCE: 282
```

```
000

SEQ ID NO: 283         moltype =   length =
SEQUENCE: 283
000

SEQ ID NO: 284         moltype =   length =
SEQUENCE: 284
000

SEQ ID NO: 285         moltype =   length =
SEQUENCE: 285
000

SEQ ID NO: 286         moltype =   length =
SEQUENCE: 286
000

SEQ ID NO: 287         moltype =   length =
SEQUENCE: 287
000

SEQ ID NO: 288         moltype =   length =
SEQUENCE: 288
000

SEQ ID NO: 289         moltype =   length =
SEQUENCE: 289
000

SEQ ID NO: 290         moltype =   length =
SEQUENCE: 290
000

SEQ ID NO: 291         moltype =   length =
SEQUENCE: 291
000

SEQ ID NO: 292         moltype =   length =
SEQUENCE: 292
000

SEQ ID NO: 293         moltype =   length =
SEQUENCE: 293
000

SEQ ID NO: 294         moltype =   length =
SEQUENCE: 294
000

SEQ ID NO: 295         moltype =   length =
SEQUENCE: 295
000

SEQ ID NO: 296         moltype =   length =
SEQUENCE: 296
000

SEQ ID NO: 297         moltype =   length =
SEQUENCE: 297
000

SEQ ID NO: 298         moltype =   length =
SEQUENCE: 298
000

SEQ ID NO: 299         moltype =   length =
SEQUENCE: 299
000

SEQ ID NO: 300         moltype = AA  length = 485
FEATURE                Location/Qualifiers
source                 1..485
                       mol_type = protein
                       organism = synthetic construct
SEQUENCE: 300
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
```

```
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDITC PPPMSVEHAD  300
IWVKSYSLYS RERYICNSGF KRKAGTSSLT ECVLNKATNV AHWTTPSLKC IRQGQDRHMI  360
RMRQLIDIVD QLKNYVNDLV PEFLPAPEDV ETNCEWSAFS CFQKAQLKSA NTGNNERIIN  420
VSIKKLKRKP PSTNAGRRQK HRLTCPSCDS YEKKPPKEFL ERFKSLLQKM IHQHLSSRTH  480
GSEDS                                                              485

SEQ ID NO: 301         moltype = DNA  length = 1455
FEATURE                Location/Qualifiers
source                 1..1455
                       mol_type = other DNA
                       organism = synthetic construct
SEQUENCE: 301
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cattacatgc ccccctccca tgagcgtgga gcacgccgac  900
atctgggtga agagctatag cctctacagc cgggagaggt atatctgtaa cagcggcttc  960
aagaggaagg ccggcaccag cagcctcacc gagtgcgtgc tgaataaggc taccaacgtg  1020
gctcactgga caacaccctc tttaaagtgc atccggcagg gccaggacag gcacatgatc  1080
cggatgaggc agctcatcga catcgtcgac cagctgaaga actacgtgaa cgacctggtg  1140
cccgagtttc tgcctgcccc cgaggacgtg gagaccaact gcgagtggtc cgccttctcc  1200
tgctttcaga aggcccagct gaagtccgcc aacaccggca acaacgagcg gatcatcaac  1260
gtgagcatca agaagctgaa gcggaagcct ccctccacaa acgccggcag gaggcagaag  1320
cacaggctga cctgccccag ctgtgactcc tacgagaaga agccccccaa ggagttcctg  1380
gagaggttca agtccctgct gcagaagatg atccatcagc acctgtcctc caggacccac  1440
ggctccgagg actcc                                                   1455

SEQ ID NO: 302         moltype = AA  length = 503
FEATURE                Location/Qualifiers
source                 1..503
                       mol_type = protein
                       organism = synthetic construct
SEQUENCE: 302
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
WTTPSLKCIR QGQDRHMIRM RQLIDIVDQL KNYVNDLVPE FLPAPEDVET NCEWSAFSCF  420
QKAQLKSANT GNNERIINVS IKKLKRKPPS TNAGRRQKHR LTCPSCDSYE KKPPKEFLER  480
FKSLLQKMIH QHLSSRTHGS EDS                                          503

SEQ ID NO: 303         moltype = DNA  length = 1509
FEATURE                Location/Qualifiers
source                 1..1509
                       mol_type = other DNA
                       organism = synthetic construct
SEQUENCE: 303
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gaccttttc  840
atgtgctcct gcagcagcga cgaatgcaac gacaatatca tctttagcga ggaatacaat  900
accagcaacc ccgacattac atgccccct cccatgagcg tggagcacgc cgacatctgg  960
gtgaagagct atagcctcta cagccgggag aggtatatct gtaacagcgg cttcaagagg  1020
aaggccggca ccagcagcct caccgagtgc gtgctgaata aggctaccaa cgtggctcac  1080
```

```
tggacaacac cctctttaaa gtgcatccgg cagggccagg acaggcacat gatccggatg  1140
aggcagctca tcgacatcgt cgaccagctg aagaactacg tgaacgacct ggtgcccgag  1200
tttctgcctg cccccgagga cgtggagacc aactgcgagt ggtccgcctt ctcctgcttt  1260
cagaaggccc agctgaagtc cgccaacacc ggcaacaacg agcggatcat caacgtgagc  1320
atcaagaagc tgaagcggaa gcctccctcc acaaacgccg gcaggaggca gaagcacagg  1380
ctgacctgcc ccagctgtga ctcctacgag aagaagcccc ccaaggagtt cctggagagg  1440
ttcaagtccc tgctgcagaa gatgatccat cagcacctgt cctccaggac ccacggctcc  1500
gaggactcc                                                          1509
```

```
SEQ ID NO: 304         moltype =   length =
SEQUENCE: 304
000

SEQ ID NO: 305         moltype =   length =
SEQUENCE: 305
000

SEQ ID NO: 306         moltype =   length =
SEQUENCE: 306
000

SEQ ID NO: 307         moltype =   length =
SEQUENCE: 307
000

SEQ ID NO: 308         moltype = AA  length = 592
FEATURE                Location/Qualifiers
source                 1..592
                       mol_type = protein
                       organism = synthetic construct
SEQUENCE: 308
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDITC PPPMSVEHAD  300
IWVKSYSLYS RERYICNSGF KRKAGTSSLT ECVLNKATNV AHWTTPSLKC IRSELTQDPA  360
VSVALGQTVR ITCQGDSLRS YYASWYQQKP GQAPVLVIYG KNNRPSGIPD RFSGSSSGNT  420
ASLTITGAQA EDEADYYCNS RDSSGNHVVF GGGTKLTVGH GGGGSGGGGS GGGGSEVQLV  480
ESGGGVVRPG GSLRLSCAAS GFTFDDYGMS WVRQAPGKGL EWVSGINWNG GSTGYADSVK  540
GRFTISRDNA KNSLYLQMNS LRAEDTAVYY CARGRSLLFD YWGQGTLVTV SR          592

SEQ ID NO: 309         moltype = DNA  length = 1776
FEATURE                Location/Qualifiers
source                 1..1776
                       mol_type = other DNA
                       organism = synthetic construct
SEQUENCE: 309
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cattacatgc ccccctccca tgagcgtgga gcacgccgac  900
atctgggtga agagctatag cctctacagc cgggagaggt atatctgtaa cagcggcttc  960
aagaggaagg ccggcaccag cagcctcacc gagtgcgtgc tgaataaggc taccaacgtg  1020
gctcactgga caacaccctc tttaaagtgc atccggtccg agctgaccca ggaccctgct  1080
gtgtccgtgg ctctgggcca gaccgtgagg atcacctgcc agggcgactc cctgaggtcc  1140
tactacgcct cctggtacca gcagaagccc ggccaggctc ctgtgctggt gatctacggc  1200
aagaacaaca ggccctccgg catccctgac aggttctccg gatcctcctc cggcaacacc  1260
gcctccctga ccatcacagg cgctcaggcc gaggacgagg ctgactacta ctgcaactcc  1320
agggactcct ccggcaacca tgtggtgttc ggcggcggca ccaagctgac cgtgggccat  1380
ggcggcggcg gctccggagg cggcggcagc ggcggaggag gatccgaggt gcagctggtg  1440
gagtccggag gaggagtggt gaggcctgga ggctccctga ggctgagctg tgctgcctcc  1500
ggcttcacct tcgacgacta cggcatgtcc tgggtgaggc aggctcctgg aaagggcctg  1560
gagtgggtgt ccggcatcaa ctggaacggc ggatccaccg gctacgccga ttccgtgaag  1620
ggcaggttca ccatcagcag ggacaacgcc aagaactccc tgtacctgca gatgaactcc  1680
ctgagggccg aggacaccgc cgtgtactac tgcgccaggg gcaggtccct gctgttcgac  1740
tactggggac agggcaccct ggtgaccgtg tccagg                            1776
```

```
SEQ ID NO: 310         moltype = AA  length = 610
FEATURE                Location/Qualifiers
source                 1..610
                       mol_type = protein
                       organism = synthetic construct
SEQUENCE: 310
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
WTTPSLKCIR SELTQDPAVS VALGQTVRIT CQGDSLRSYY ASWYQQKPGQ APVLVIYGKN  420
NRPSGIPDRF SGSSSGNTAS LTITGAQAED EADYYCNSRD SSGNHVVFGG GTKLTVGHGG  480
GGSGGGGSGG GGSEVQLVES GGGVVRPGGS LRLSCAASGF TFDDYGMSWV RQAPGKGLEW  540
VSGINWNGGS TGYADSVKGR FTISRDNAKN SLYLQMNSLR AEDTAVYYCA RGRSLLFDYW  600
GQGTLVTVSR                                                        610

SEQ ID NO: 311         moltype = DNA  length = 1830
FEATURE                Location/Qualifiers
source                 1..1830
                       mol_type = other DNA
                       organism = synthetic construct
SEQUENCE: 311
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gaccttttc  840
atgtgctcct gcagcagcga cgaatgcaac gacaatatca tctttagcga ggaatacaat  900
accagcaacc ccgacattac atgcccccct cccatgagcg tggagcacgc cgacatctgg  960
gtgaagagct atagcctcta cagccgggag aggtatatct gtaacagcgg cttcaagagg  1020
aaggccggca ccagcagcct caccgagtgc gtgctgaata aggctaccaa cgtggctcac  1080
tggacaacac cctctttaaa gtgcatccgg tccgagctga cccaggaccc tgctgtgtcc  1140
gtggctctgg gccagaccgt gaggatcacc tgccagggcg actccctgag gtcctactac  1200
gcctcctggt accagcagaa gcccggccag gctcctgtgc tggtgatcta cggcaagaac  1260
aacaggccct ccggcatccc tgacaggttc tccggatcct cctccggcaa caccgcctcc  1320
ctgaccatca caggcgctca ggccgaggac gaggctgact actactgcaa ctccagggac  1380
tcctccggca accatgtggt gttcggcggc ggcaccaagc tgaccgtggg ccatggcggc  1440
ggcggctccg gaggcggcgg cagcggcgga ggaggatccg aggtgcagct ggtggagtcc  1500
ggaggaggag tggtgaggcc tggaggctcc ctgaggctga gctgtgctgc ctccggcttc  1560
accttcgacg actacggcat gtcctgggtg aggcaggctc ctggaaaggg cctggagtgg  1620
gtgtccggca tcaactggaa cggcggatcc accggctacg ccgattccgt gaagggcagg  1680
ttcaccatca gcagggacaa cgccaagaac tccctgtacc tgcagatgaa ctccctgagg  1740
gccgaggaca ccgccgtgta ctactgcgcc aggggcaggt ccctgctgtt cgactactgg  1800
ggacagggca ccctggtgac cgtgtccagg                                  1830

SEQ ID NO: 312         moltype =   length =
SEQUENCE: 312
000

SEQ ID NO: 313         moltype =   length =
SEQUENCE: 313
000

SEQ ID NO: 314         moltype =   length =
SEQUENCE: 314
000

SEQ ID NO: 315         moltype =   length =
SEQUENCE: 315
000

SEQ ID NO: 316         moltype = AA  length = 551
FEATURE                Location/Qualifiers
source                 1..551
                       mol_type = protein
                       organism = synthetic construct
SEQUENCE: 316
IPPHVQKSVN NDMIVTDNNG AVKFPQLCKF CDVRFSTCDN QKSCMSNCSI TSICEKPQEV  60
```

```
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDITC PPPMSVEHAD  300
IWVKSYSLYS RERYICNSGF KRKAGTSSLT ECVLNKATNV AHWTTPSLKC IRGGGGSGGG  360
GSGGGGSREG PELSPDDPAG LLDLRQGMFA QLVAQNVLLI DGPLSWYSDP GLAGVSLTGG  420
LSYKEDTKEL VVAKAGVYYV FFQLELRRVV AGEGSGSVSL ALHLQPLRSA AGAAALALTV  480
DLPPASSEAR NSAFGFQGRL LHLSAGQRLG VHLHTEARAR HAWQLTQGAT VLGLFRVTPE  540
IPAGLPSPRS E                                                      551

SEQ ID NO: 317          moltype = DNA  length = 1653
FEATURE                 Location/Qualifiers
source                  1..1653
                        mol_type = other DNA
                        organism = synthetic construct
SEQUENCE: 317
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggtttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cattacatgc ccccctccca tgagcgtgga gcacgccgac  900
atctgggtga agagctatag cctctacagc cgggagaggt atatctgtaa cagcggcttc  960
aagaggaagg ccggcaccag cagcctcacc gagtgcgtgc tgaataaggc taccaacgtg  1020
gctcactgga caacaccctc tttaaagtgc atccggggcg gtggaggatc cggaggaggt  1080
ggctccggcg gcggaggatc tcgcgagggt cccgagcttt cgcccgacga tcccgccggc  1140
ctcttggacc tgcggcaggg catgtttgcg cagctggtgg cccaaaatgt tctgctgatc  1200
gatgggcccc tgagctggta cagtgaccca ggcctggcag gcgtgtccct gacgggggc  1260
ctgagctaca aagaggacac gaaggagctg gtggtggcca aggctggagt ctactatgtc  1320
ttctttcaac tagagctgcg gcgcgtggtg gccggcgagg gctcaggctc cgtttcactt  1380
gcgctgcacc tgcagccact gcgctctgct gctggggccg ccgccctggc tttgaccgtg  1440
gacctgccac ccgcctcctc cgaggctcgg aactcggcct tcggtttcca gggccgcttg  1500
ctgcacctga gtgccggcca gcgcctgggc gtccatcttc acactgaggc cagggcacgc  1560
catgcctggc agcttaccca gggcgccaca gtcttgggac tcttccgggt gacccccgaa  1620
atcccagccg gactcccttc accgaggtcg gaa                              1653

SEQ ID NO: 318          moltype = AA  length = 569
FEATURE                 Location/Qualifiers
source                  1..569
                        mol_type = protein
                        organism = synthetic construct
SEQUENCE: 318
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
WTTPSLKCIR GGGGSGGGGS GGGGSREGPE LSPDDPAGLL DLRQGMFAQL VAQNVLLIDG  420
PLSWYSDPGL AGVSLTGGLS YKEDTKELVV AKAGVYYVFF QLELRRVVAG EGSGSVSLAL  480
HLQPLRSAAG AAALALTVDL PPASSEARNS AFGFQGRLLH LSAGQRLGVH LHTEARARHA  540
WQLTQGATVL GLFRVTPEIP AGLPSPRSE                                   569

SEQ ID NO: 319          moltype = DNA  length = 1707
FEATURE                 Location/Qualifiers
source                  1..1707
                        mol_type = other DNA
                        organism = synthetic construct
SEQUENCE: 319
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
```

```
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gaccttttc   840
atgtgctcct gcagcagcga cgaatgcaac gacaatatca tctttagcga ggaatacaat  900
accagcaacc ccgacattac atgcccccct cccatgagcg tggagcacgc cgacatctgg  960
gtgaagagct atagcctcta cagccgggag aggtatatct gtaacagcgg cttcaagagg  1020
aaggccggca ccagcagcct caccgagtgc gtgctgaata aggctaccaa cgtggctcac  1080
tggacaacac cctctttaaa gtgcatccgg ggcggtggag gatccggagg aggtggctcc  1140
ggcggcggag gatctcgcga gggtcccgag ctttcgcccg acgatcccgc cggcctcttg  1200
gacctgcggc agggcatgtt tgcgcagctg gtggcccaaa atgttctgct gatcgatggg  1260
cccctgagct ggtacagtga cccaggcctg gcaggcgtgt ccctgacggg gggcctgagc  1320
tacaaagagg acacgaagga gctggtggtg gccaaggctg gagtctacta tgtcttcttt  1380
caactagagc tgcggcgcgt ggtggccggc gagggctcag gctccgtttc acttgcgctg  1440
cacctgcagc cactgcgctc tgctgctggg gccgccgccc tggctttgac cgtggacctg  1500
ccacccgcct cctccgaggc tcggaactcg gccttcggtt tccagggccg cttgctgcac  1560
ctgagtgccg gccagcgcct gggcgtccat cttcacactg aggccagggc acgccatgcc  1620
tggcagctta cccagggcgc cacagtcttg ggactcttcc gggtgacccc cgaaatccca  1680
gccggactcc cttcaccgag gtcggaa                                      1707
```

```
SEQ ID NO: 320          moltype = DNA  length = 720
FEATURE                 Location/Qualifiers
source                  1..720
                        mol_type = other DNA
                        organism = synthetic construct
SEQUENCE: 320
atgaagtggg tcacatttat ctctttactg ttcctcttct ccagcgccta cagctacttc  60
ggcaaactgg aatccaagct gagcgtgatc cggaatttaa acgaccaagt tctgtttatc  120
gatcaaggta accggcctct gttcgaggac atgaccgact ccgattgccg ggacaatgcc  180
ccccggacca tcttcattat ctccatgtac aaggacagcc agccccgggg catggctgtg  240
acaattagcg tgaagtgtga gaaaatcagc actttatctt gtgagaacaa gatcatctcc  300
tttaaggaaa tgaacccccc cgataacatc aaggacacca agtccgatat catcttcttc  360
cagcggtccg tgcccggtca cgataacaag atgcagttcg aatcctcctc ctacgagggc  420
tactttttag cttgtgaaaa ggagagggat ttattcaagc tgatcctcaa gaaggaggac  480
gagctgggcg atcgttccat catgttcacc gtccaaaacg aggatattac atgcccccct  540
cccatgagcg tggagcacgc cgacatctgg gtgaagagct atagcctcta cagccgggag  600
aggtatatct gtaacagcgg cttcaagagg aaggccggca ccagcagcct caccgagtgc  660
gtgctgaata aggctaccaa cgtggctcac tggacaacac cctctttaaa gtgcatccgg  720
```

```
SEQ ID NO: 321          moltype = DNA  length = 2607
FEATURE                 Location/Qualifiers
source                  1..2607
                        mol_type = other DNA
                        organism = synthetic construct
SEQUENCE: 321
atgaaatggg tgacctttat ttctttactg ttcctcttta gcagcgccta ctccatttgg  60
gaactgaaga aggacgtcta cgtggtcgaa ctggactggt atcccgatgc tcccggcgaa  120
atggtggtgc tcacttgtga cacccccgaa gaagacggca tcacttggac cctcgatcag  180
agcagcgagg tgctgggctc cggaaagacc ctcacaatcc aagttaagga gttcggagac  240
gctggccaat acacatgcca caagggaggc gaggtgctca gccattcctt attattatta  300
cacaagaagg aagacggaat ctggtccacc gacattttaa aagatcagaa ggagcccaag  360
aataagacct ttttaaggtg tgaggccaaa aactacagcg gtcgtttcac ttgttggtgg  420
ctgaccacca tttccaccga tttaaccttc tccgtgaaaa gcagccgggg aagctccgac  480
cctcaaggtg tgacatgtgg agccgctacc ctcagcgctg agagggttcg tggcgataac  540
aaggaatacg agtacagcgt ggagtgccaa gaagatagcg cttgtcccgc tgccgaagaa  600
tctttaccca ttgaggtgat ggtggacgcc gtgcacaaac tcaagtacga gaactacacc  660
tcctccttct ttatccggga catcattaag cccgatcctc ctaagaattt acagctgaag  720
cctctcaaaa atagccggca agttgaggtc tcttgggaat atcccgacac ttggagcaca  780
ccccacagct acttctcttt aaccttttgt gtgcaagttc aaggtaaaag caagcgggag  840
aagaaagacc gggtgtttac cgacaaaacc agcgccaccg tcatctgtcg gaagaacgcc  900
tccatcagcg tgagggctca agatcgttat tactccagca gctggtccga gtgggccagc  960
gtgccttgtt ccggcggtgg aggatccgga ggaggtggct ccggcggcgg aggatctcgt  1020
aacctccccg tggctacccc cgatcccgga atgttccctt gtttacacca cagccagaat  1080
ttactgaggg ccgtgagcaa catgctgcag aaagctaggc agactttaga attttaccct  1140
tgcaccagcg aggagatcga ccatgaagat atcaccaagg acaagacatc caccgtggag  1200
gcttgtttac ctctggagct gacaaagaac gagtcttgtc tcaactctcg tgaaaccagc  1260
ttcatcacaa atggctcttg tttagcttcc cggaagacct cctttatgat ggctttatgc  1320
ctcagctcca tctacgagga tttaaagatg taccaagtgg agttcaagac catgaacgcc  1380
aagctgctca tggaccctaa acggcagatc tttttagacc agaacatgct ggctgtgatt  1440
gatgagctga tgcaagcttt aaacttcaac tccgagaccg tccctcagaa gtcctccctc  1500
gaggagcccg atttttacaa gacaaagatc aaactgtgca ttttactcca cgcctttagg  1560
atccgggccg tgaccattga ccgggtcatg agctatttaa acgccagcag cggcacaacc  1620
aacacagtcg ctgcctataa cctcacttgg aagagcacca acttcaaaac catcctcgaa  1680
tgggaaccca aacccgttaa ccaagtttac accgtgcaga tcagcaccaa gtccggcgac  1740
tggaagtcca aatgtttcta taccaccgac accgagtgcg atctcaccga tgagatcgtg  1800
aaagatgtga aacagaccta cctcgcccgg gtgtttagct accccgccgg caatgtggag  1860
agcactggtt ccgctggcga gcctttatac gagaacagcc ccgaatttac cccttacctc  1920
gagaccaatt taggacagcc caccatccaa agctttgagc aagttggcac aaaggtgaat  1980
gtgacagtgg aggacgagcg gactttagtg cggcggaaca acacctttct cagcctccgg  2040
gatgtgttcg gcaaagattt aatctacaca ctgtattact ggaagtcctc ttcctccggc  2100
```

```
aagaagacag ctaaaaccaa cacaaacgag tttttaatcg acgtggataa aggcgaaaac  2160
tactgtttca gcgtgcaagc tgtgatcccc tcccggaccg tgaataggaa aagcaccgat  2220
agccccgttg agtgcatggg ccaagaaaag ggcgagttcc gggagaactg ggtgaacgtc  2280
atcagcgatt taaagaagat cgaagattta attcagtcca tgcatatcga cgccacttta  2340
tacacagaat ccgacgtgca cccctcttgt aaggtgaccg ccatgaaatg tttttactg   2400
gagctgcaag ttatctcttt agagagcgga gacgctagca tccacgacac cgtggagaat  2460
ttaatcattt tagccaataa ctctttatcc agcaacggca acgtgacaga gtccggctgc  2520
aaggagtgcg aagagctgga ggagaagaac atcaaggagt ttctgcaatc ctttgtgcac  2580
attgtccaga tgttcatcaa tacctcc                                     2607
```

```
SEQ ID NO: 322          moltype = AA  length = 240
FEATURE                 Location/Qualifiers
source                  1..240
                        mol_type = protein
                        organism = synthetic construct
SEQUENCE: 322
MKWVTFISLL FLFSSAYSYF GKLESKLSVI RNLNDQVLFI DQGNRPLFED MTDSDCRDNA  60
PRTIFIISMY KDSQPRGMAV TISVKCEKIS TLSCENKIIS FKEMNPPDNI KDTKSDIIFF  120
QRSVPGHDNK MQFESSSYEG YFLACEKERD LFKLILKKED ELGDRSIMFT VQNEDITCPP  180
PMSVEHADIW VKSYSLYSRE RYICNSGFKR KAGTSSLTEC VLNKATNVAH WTTPSLKCIR  240
```

```
SEQ ID NO: 323          moltype = AA  length = 869
FEATURE                 Location/Qualifiers
source                  1..869
                        mol_type = protein
                        organism = synthetic construct
SEQUENCE: 323
MKWVTFISLL FLFSSAYSIW ELKKDVYVVE LDWYPDAPGE MVVLTCDTPE EDGITWTLDQ  60
SSEVLGSGKT LTIQVKEFGD AGQYTCHKGG EVLSHSLLLL HKKEDGIWST DILKDQKEPK  120
NKTFLRCEAK NYSGRFTCWW LTTISTDLTF SVKSSRGSSD PQGVTCGAAT LSAERVRGDN  180
KEYEYSVECQ EDSACPAAEE SLPIEVMVDA VHKLKYENYT SSFFIRDIIK PDPPKNLQLK  240
PLKNSRQVEV SWEYPDTWST PHSYFSLTFC VQVQGKSKRE KKDRVFTDKT SATVICRKNA  300
SISVRAQDRY YSSSWSEWAS VPCSGGGGSG GGGSGGGGSR NLPVATPDPG MFPCLHHSQN  360
LLRAVSNMLQ KARQTLEFYP CTSEEIDHED ITKDKTSTVE ACLPLELTKN ESCLNSRETS  420
FITNGSCLAS RKTSFMMALC LSSIYEDLKM YQVEFKTMNA KLLMDPKRQI FLDQNMLAVI  480
DELMQALNFN SETVPQKSSL EEPDFYKTKI KLCILLHAFR IRAVTIDRVM SYLNASSGTT  540
NTVAAYNLTW KSTNFKTILE WEPKPVNQVY TVQISTKSGD WKSKCFYTTD TECDLTDEIV  600
KDVKQTYLAR VFSYPAGNVE STGSAGEPLY ENSPEFTPYL ETNLGQPTIQ SFEQVGTKVN  660
VTVEDERTLV RRNNTFLSLR DVFGKDLIYT LYYWKSSSSG KKTAKTNTNE FLIDVDKGEN  720
YCFSVQAVIP SRTVNRKSTD SPVECMGQEK GEFRENWVNV ISDLKKIEDL IQSMHIDATL  780
YTESDVHPSC KVTAMKCFLL ELQVISLESG DASIHDTVEN LIILANNSLS SNGNVTESGC  840
KECEELEEKN IKEFLQSFVH IVQMFINTS                                   869
```

```
SEQ ID NO: 324          moltype = DNA  length = 1452
FEATURE                 Location/Qualifiers
source                  1..1452
                        mol_type = other DNA
                        organism = synthetic construct
SEQUENCE: 324
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tcctccggca ccaccaatac cgtggccgct  480
tataacctca catggaagag caccaacttc gcgacagctc tggaatggga acccaagccc  540
gtcaatcaag tttacaccgt gcagatctcc accaaatccg gagactggaa gagcaagtgc  600
ttctacacaa cagacaccga gtgtgcttta accgacgaaa tcgtcaagga cgtcaagcaa  660
acctatctgg ctcgggtctt ttcctacccc gctggcaatg tcgagtccac cggctccgct  720
ggcgagcctc tctacgagaa ttcccccgaa ttcacccctt atttagagac caatttaggc  780
cagcctacca tccagagctt cgagcaagtt ggcaccaagg tgaacgtcac cgtcgaggat  840
gaaaggactt tagtggcgcg gaataacaca gctttatccc tccgggatgt gttcggcaaa  900
gacctcatct acacactgta ctattggaag tccagctcct ccggcaaaaa gaccgctaag  960
accaacacca acgagttttt aattgacgtg gacaaaggcg agaactactg cttcagcgtg  1020
caagccgtga tcccttctcg taccgtcaac cggaagagca cagattcccc cgttgagtgc  1080
atgggccaag aaaagggcga gttccgggag aactgggtga acgtcatcag cgatttaaag  1140
aagatcgaag atttaattca gtccatgcat atcgacgcca ctttatacac agaatccgac  1200
gtgcacccct cttgtaaggt gaccgccatg aaatgttttt tactggagct gcaagttatc  1260
tctttagaga gcggagacgc tagcatccac gacaccgtgg agaatttaat cattttagcc  1320
aataactctt tatccagcaa cggcaacgtg acagagtccg gctgcaagga gtgcgaagag  1380
ctggaggaga agaacatcaa ggagtttctg caatcctttg tgcacattgt ccagatgttc  1440
atcaatacct cc                                                     1452
```

```
SEQ ID NO: 325          moltype = AA  length = 484
FEATURE                 Location/Qualifiers
source                  1..484
                        mol_type = protein
```

```
                         organism = synthetic construct
SEQUENCE: 325
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SSGTTNTVAA YNLTWKSTNF ATALEWEPKP  180
VNQVYTVQIS TKSGDWKSKC FYTTDTECAL TDEIVKDVKQ TYLARVFSYP AGNVESTGSA  240
GEPLYENSPE FTPYLETNLG QPTIQSFEQV GTKVNVTVED ERTLVARNNT ALSLRDVFGK  300
DLIYTLYYWK SSSSGKKTAK TNTNEFLIDV DKGENYCFSV QAVIPSRTVN RKSTDSPVEC  360
MGQEKGEFRE NWVNVISDLK KIEDLIQSMH IDATLYTESD VHPSCKVTAM KCFLLELQVI  420
SLESGDASIH DTVENLIILA NNSLSSNGNV TESGCKECEE LEEKNIKEFL QSFVHIVQMF  480
INTS                                                               484

SEQ ID NO: 326           moltype = DNA  length = 2142
FEATURE                  Location/Qualifiers
source                   1..2142
                         mol_type = other DNA
                         organism = synthetic construct
SEQUENCE: 326
atgaaatggg tcaccttcat ctctttactg tttttattta gcagcgccta cagcgtgcag  60
ctgcagcagt ccggacccga actggtcaag cccggtgcct ccgtgaaaat gtcttgtaag  120
gcttctggct acacctttac ctcctacgtc atccaatggg tgaagcagaa gcccggtcaa  180
ggtctcgagt ggatcggcag catcaatccc tacaacgatt acaccaagta taacgaaaag  240
tttaagggca aggccactct gacaagcgac aagagctcca ttaccgccta catggagttt  300
tcctctttaa cttctgagga ctccgcttta tactattgcg ctcgttgggg cgatggcaat  360
tattggggcc ggggaactac tttaacagtg agctccggcg gcggcggaag cggaggtgga  420
ggatctggcg gtggaggcag cgacatcgag atgacacagt cccccgctat catgagcgcc  480
tctttaggag aacgtgtgac catgacttgt acagcttcct ccagcgtgag cagctcctat  540
ttccactggt accagcagaa acccggctcc tcccctaaac tgtgtatcta ctccacaagc  600
aatttagcta gcggcgtgcc tcctcgtttt agcggctccg gcagcacctc ttactcttta  660
accattagct ctatggaggc cgaagatgcc gccacatact tttgccatca gtaccaccgg  720
tcccctacct ttggcggagg cacaaagctg gagaccaagc ggagcggcac caccaacaca  780
gtggccgcct acaatctgac ttggaaatcc accaacttca agaccatcct cgagtgggag  840
cccaagcccg ttaatcaagt ttataccgtg cagatttcca ccaagagcgg cgactggaaa  900
tccaagtgct tctataccac agacaccgag tgcgatctca ccgacgagat cgtcaaagac  960
gtgaagcaga catatttagc tagggtgttc tcctaccccg ctggaaacgt ggagagcacc  1020
ggatccgctg gagagccttt atacgagaac tcccccgaat tcacccccta tctggaaacc  1080
aatttaggcc agcccaccat ccagagcttc gaacaagttg gcacaaaggt gaacgtcacc  1140
gtcgaagatg agaggacttt agtgcggagg aacaatacat ttttatcctt acgtgacgtc  1200
ttcggcaagg atttaatcta cacactgtat tactggaagt ctagctcctc cggcaagaag  1260
accgccaaga ccaataccaa cgaatttta attgacgtgg acaagggcga gaactactgc  1320
ttctccgtgc aagctgtgat cccctcccgg acagtgaacc ggaagtccac cgactccccc  1380
gtggagtgca tgggccaaga gaagggagag tttcgtgagc agatcgtgct gacccagtcc  1440
cccgctatta tgagcgctag ccccggtgaa aaggtgacta tgacatgcag cgccagctct  1500
tccgtgagct acatgaactg gtatcagcag aagtccggca ccagccctaa aaggtggatc  1560
tacgacacca gcaagctggc cagcggcgtc cccgctcact ttcggggctc cggctccgga  1620
acaagctact ctctgaccat cagcggcatg gaagccgagg atgccgctac ctattactgt  1680
cagcagtgga gctccaaccc cttcaccttt ggatccggca ccaagctcga gattaatcgt  1740
ggaggcggag gtagcggagg aggcggatcc ggcggtggag gtagccaagt tcagctccag  1800
caaagcggcg ccgaactcgc tcggcccggc gcttccgtga agatgtcttg taaggcctcc  1860
ggctatacct tcacccggta cacaatgcac tgggtcaagc aacggcccgg tcaaggttta  1920
gagtggattg gctatatcaa cccctcccgg ggctatacca actacaacca gaagttcaag  1980
gacaaagcca ccctcaccac cgacaagtcc agcagcaccg cttacatgca gctgagctct  2040
ttaacatccg aggattccgc cgtgtactac tgcgctcggt actacgacga tcattactgc  2100
ctcgattact ggggccaagg taccacctta acagtctcct cc                    2142

SEQ ID NO: 327           moltype = AA  length = 714
FEATURE                  Location/Qualifiers
source                   1..714
                         mol_type = protein
                         organism = synthetic construct
SEQUENCE: 327
MKWVTFISLL FLFSSAYSVQ LQQSGPELVK PGASVKMSCK ASGYTFTSYV IQWVKQKPGQ  60
GLEWIGSINP YNDYTKYNEK FKGKATLTSD KSSITAYMEF SSLTSEDSAL YYCARWGDGN  120
YWGRGTTLTV SSGGGGSGGG GSGGGGSDIE MTQSPAIMSA SLGERVTMTC TASSSVSSSY  180
FHWYQQKPGS SPKLCIYSTS NLASGVPPRF SGSGSTSYSL TISSMEAEDA ATYFCHQYHR  240
SPTFGGGTKL ETKRSGTTNT VAAYNLTWKS TNFKTILEWE PKPVNQVYTV QISTKSGDWK  300
SKCFYTTDTE CDLTDEIVKD VKQTYLARVF SYPAGNVEST GSAGEPLYEN SPEFTPYLET  360
NLGQPTIQSF EQVGTKVNVT VEDERTLVRR NNTFLSLRDV FGKDLIYTLY YWKSSSSGKK  420
TAKTNTNEFL IDVDKGENYC FSVQAVIPSR TVNRKSTDSP VECMGQEKGE FREQIVLTQS  480
PAIMSASPGE KVTMTCSASS SVSYMNWYQQ KSGTSPKRWI YDTSKLASGV PAHFRGSGSG  540
TSYSLTISGM EAEDAATYYC QQWSSNPFTF GSGTKLEINR GGGGSGGGGS GGGGSQVQLQ  600
QSGAELARPG ASVKMSCKAS GYTFTRYTMH WVKQRPGQGL EWIGYINPSR GYTNYNQKFK  660
DKATLTTDKS SSTAYMQLSS LTSEDSAVYY CARYYDDHYC LDYWGQGTTL TVSS        714

SEQ ID NO: 328           moltype = AA  length = 17
FEATURE                  Location/Qualifiers
source                   1..17
                         mol_type = protein
                         organism = synthetic construct
```

```
SEQUENCE: 328
MGVKVLFALI CIAVAEA                                           17

SEQ ID NO: 329          moltype = AA  length = 454
FEATURE                 Location/Qualifiers
REGION                  1..454
                        note = source = /note="Myc"
source                  1..454
                        mol_type = protein
                        organism = Homo sapiens
SEQUENCE: 329
MDFFRVVENQ QPPATMPLNV SFTNRNYDLD YDSVQPYFYC DEEENFYQQQ QQSELQPPAP  60
SEDIWKKFEL LPTPPLSPSR RSGLCSPSYV AVTPFSLRGD NDGGGGSFST ADQLEMVTEL  120
LGGDMVNQSF ICDPDDETFI KNIIIQDCMW SGFSAAAKLV SEKLASYQAA RKDSGSPNPA  180
RGHSVCSTSS LYLQDLSAAA SECIDPSVVF PYPLNDSSSP KSCASQDSSA FSPSSDSLLS  240
STESSPQGSP EPLVLHEETP PTTSSDSEEE QEDEEEIDVV SVEKRQAPGK RSESGSPSAG  300
GHSKPPHSPL VLKRCHVSTH QHNYAAPPST RKDYPAAKRV KLDSVRVLRQ ISNNRKCTSP  360
RSSDTEENVK RRTHNVLERQ RRNELKRSFF ALRDQIPELE NNEKAPKVVI LKKATAYILS  420
VQAEEQKLIS EEDLLRKRRE QLKHKLEQLR NSCA                            454

SEQ ID NO: 330          moltype = DNA  length = 1365
FEATURE                 Location/Qualifiers
source                  1..1365
                        mol_type = genomic DNA
                        note = source = Myc
                        organism = Homo sapiens
SEQUENCE: 330
ctggattttt ttcgggtagt ggaaaaccag cagcctcccg cgacgatgcc cctcaacgtt  60
agcttcacca acaggaacta tgacctcgac tacgactcgg tgcagccgta tttctactgc  120
gacgaggagg agaacttcta ccagcagcag cagcagagcg agctgcagcc cccggcgccc  180
agcgaggata tctggaagaa attcgagctg ctgcccaccc cgcccctgtc ccctagccgc  240
cgctccgggc tctgctcgcc ctcctacgtt gcggtcacac ccttctccct tcggggagac  300
aacgacggcg gtggcgggag cttctccacg gccgaccagc tggagatggt gaccgagctg  360
ctgggaggag acatggtgaa ccagagtttc atctgcgacc cggacgacga gaccttcatc  420
aaaaacatca tcatccagga ctgtatgtgg agcggcttct cggccgccgc caagctcgtc  480
tcagagaagc tggcctccta ccaggctgcg cgcaaagaca gcggcagccc gaaccccgcc  540
cgcggccaca gcgtctgctc cacctccagc ttgtacctgc aggatctgag cgccgccgcc  600
tcagagtgca tcgacccctc ggtggtcttc ccctaccctc tcaacgacag cagctcgccc  660
aagtcctgcg cctcgcaaga ctccagcgcc ttctctccgt cctcggattc tctgctctcc  720
tcgacggagt cctccccgca gggcagcccc gagcccctgg tgctccatga ggagacaccg  780
cccaccacca gcagcgactc tgaggaggaa caagaagatg aggaagaaat cgatgttgtt  840
tctgtggaaa agaggcaggc tcctggcaaa aggtcagagt ctggatcacc ttctgctgga  900
ggccacagca aacctcctca cagcccactg gtcctcaaga ggtgccacgt ctccacacat  960
cagcacaact acgcagcgcc tccctccact cggaaggact atcctgctgc caagagggtc  1020
aagttggaca gtgtcagagt cctgagacag atcagcaaca accgaaaatg caccagcccc  1080
aggtcctcgg acaccgagga gaatgtcaag aggcgaacac acaacgtctt ggagcgccag  1140
aggaggaacg agctaaaacg gagctttttt gccctgcgtg accagatccc ggagttggaa  1200
aacaatgaaa aggcccccaa ggtagttatc cttaaaaaag ccacagcata catcctgtcc  1260
gtccaagcag aggagcaaaa gctcatttct gaagaggact tgttgcggaa acgacgagaa  1320
cagttgaaac acaaacttga acagctacgg aactcttgtg cgtaa                1365

SEQ ID NO: 331          moltype = DNA  length = 1245
FEATURE                 Location/Qualifiers
source                  1..1245
                        mol_type = genomic DNA
                        note = source = 21s137L
                        organism = Homo sapiens
SEQUENCE: 331
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tccattacat gcccccctcc catgagcgtg  480
gagcacgccg acatctgggt gaagagctat agcctctaca gccgggagag gtatatctgt  540
aacagcggct tcaagaggaa ggccggcacc agcagcctca ccgagtgcgt gctgaataag  600
gctaccaacg tggctcactg gacaacaccc tctttaaagt gcatccgggg cggtggagga  660
tccggaggag gtggctccgg cggcggagga tctcgcgagg gtcccgagct ttcgcccgac  720
gatcccgccg gcctcttgga cctgcggcag ggcatgtttg cgcagctggt ggcccaaaat  780
gttctgctga tcgatgggcc cctgagctgg tacagtgacc caggcctggc aggcgtgtcc  840
ctgacggggg gcctgagcta caaagaggac acgaaggagc tggtggtggc caaggctgga  900
gtctactatg tcttctttca actagagctg cggcgcgtgg tggccggcga gggctcaggc  960
tccgtttcac ttgcgctgca cctgcagcca ctgcgctctg ctgctggggc cgccgccctg  1020
gctttgaccg tggacctgcc acccgcctcc tccgaggctc ggaactcggc cttcggtttc  1080
cagggccgct tgctgcacct gagtgccggc cagcgcctgg gcgtccatct tcacactgag  1140
gccagggcac gccatgcctg gcagcttacc cagggcgcca cagtcttggg actcttccgg  1200
gtgacccccg aaatcccagc cggactccct tcaccgaggt cggaa                 1245
```

-continued

```
SEQ ID NO: 332          moltype = AA  length = 415
FEATURE                 Location/Qualifiers
REGION                  1..415
                        note = source = /note="21s137L"
source                  1..415
                        mol_type = protein
                        organism = Homo sapiens
SEQUENCE: 332
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SITCPPPMSV EHADIWVKSY SLYSRERYIC  180
NSGFKRKAGT SSLTECVLNK ATNVAHWTTP SLKCIRGGGG SGGGGSGGGG SREGPELSPD  240
DPAGLLDLRQ GMFAQLVAQN VLLIDGPLSW YSDPGLAGVS LTGGLSYKED TKELVVAKAG  300
VYYVFFQLEL RRVVAGEGSG SVSLALHLQP LRSAAGAAAL ALTVDLPPAS SEARNSAFGF  360
QGRLLHLSAG QRLGVHLHTE ARARHAWQLT QGATVLGLFR VTPEIPAGLP SPRSE       415

SEQ ID NO: 333          moltype = DNA  length = 15
FEATURE                 Location/Qualifiers
source                  1..15
                        mol_type = other DNA
                        organism = synthetic construct
SEQUENCE: 333
ggtgggtata atggg                                                   15

SEQ ID NO: 334          moltype = DNA  length = 25
FEATURE                 Location/Qualifiers
source                  1..25
                        mol_type = other DNA
                        organism = synthetic construct
SEQUENCE: 334
attattttat tttaaaaaat ttgtg                                        25
```

METHODS OF TREATING AGING-RELATED DISORDERS

CROSS-REFERENCE TO RELATED APPLICATIONS

This application is a continuation application of U.S. patent application Ser. No. 16/557,875, filed Aug. 30, 2019, now U.S. Pat. No. 11,672,826, which claims priority to: U.S. Patent Application Ser. No. 62/816,683, filed Mar. 11, 2019; U.S. Patent Application Ser. No. 62/725,038, filed Aug. 30, 2018; U.S. Patent Application Ser. No. 62/817,244, filed Mar. 12, 2019; U.S. Patent Application Ser. No. 62/881,039, filed Jul. 31, 2019; U.S. Patent Application Ser. No. 62/724,969, filed Aug. 30, 2018; U.S. Patent Application Ser. No. 62/817,230, filed Mar. 12, 2019; U.S. Patent Application Ser. No. 62/725,043, filed Aug. 30, 2018; U.S. Patent Application Ser. No. 62/725,010, filed Aug. 30, 2018; U.S. Patent Application Ser. No. 62/749,007, filed Oct. 22, 2018; U.S. Patent Application Ser. No. 62/746,832, filed Oct. 17, 2018; U.S. Patent Application Ser. No. 62/749,506, filed Oct. 23, 2018; U.S. Patent Application Ser. No. 62/817,241, filed Mar. 12, 2019; and U.S. Patent Application Ser. No. 62/881,088, filed Jul. 31, 2019, each of which is incorporated hereby reference in its entirety.

SEQUENCE LISTING

This application contains a Sequence Listing that has been submitted electronically as an XML file named "47192-0013002_SL_ST26.XML." The XML file, created on Apr. 26, 2023, is 467,112 bytes in size. The material in the XML file is hereby incorporated by reference in its entirety.

TECHNICAL FIELD

The present disclosure relates to the field of immunology and cell biology.

BACKGROUND

Senescence is a form of irreversible growth arrest accompanied by phenotypic changes, resistance to apoptosis, and activation of damage-sensing signaling pathways. Cellular senescence was first described in cultured human fibroblast cells that lost their ability to proliferate, reaching permanent arrest after about 50 population doublings (referred to as the Hayflick limit). Senescence is considered a stress response that can be induced by a wide range of intrinsic and extrinsic insults, including oxidative and genotoxic stress, DNA damage, telomere attrition, oncogenic activation, mitochondrial dysfunction, or chemotherapeutic agents.

Senescent cells remain metabolically active and can influence tissue hemostasis, disease, and aging through their secretory phenotype. Senescence is considered as a physiologic process and is important in promoting wound healing, tissue homeostasis, regeneration, and regulation of fibrosis. For instance, transient induction of senescent cells is observed during would healing and contributes to wound resolution. Senescence also plays a role in tumor suppression. The accumulation of senescent cells also drives aging and aging-related diseases and conditions. The senescent phenotype also can trigger chronic inflammatory responses and consequently augment chronic inflammatory conditions to promote tumor growth. The connection between senescence and aging was initially based on the observation that senescent cells accumulate in aged tissue. The use of transgenic models has enabled the detection of senescent cells systematically in many aging-related disorders. Strategies to selectively eliminate senescent cells have demonstrated that senescent cells play a causal role in aging-related disorders.

SUMMARY

The present invention is based on the discovery that administration of NK cell activating agents to a mammal having a cancer resulted in a tumor inhibition and administration of NK cell activating agents to a diabetic animal model demonstrated improved skin and hair appearance and texture, and decreased blood glucose levels. In view of this discovery provided herein are methods of treating an aging-related disease or condition in a subject in need thereof that include administering to a subject identified as having an aging-related disease or condition a therapeutically effective amount of one or more natural killer (NK) cell activating agent (s) and/or a therapeutically effective number of activated NK cells. Also provided herein are methods of killing or reducing the number of senescent cells in a subject in need thereof that include administering to the subject a therapeutically effective amount of one or more NK cell activating agent(s) and/or or a therapeutically effective number of activated NK cells. Also provided herein are methods of improving the texture and/or appearance of skin and/or hair in a subject in need thereof over a period of time that include administering to the subject a therapeutically effective amount of one or more natural killer (NK) cell activating agent(s) and/or a therapeutically effective number of activated NK cells. Also provided herein are methods of assisting in the treatment of obesity in a subject in need thereof over a period of time that include administering to the subject a therapeutically effective amount of one or more natural killer (NK) cell activating agent(s) and/or a therapeutically effective number of activated NK cells.

Provided herein are methods of treating an aging-related disease or condition in a subject in need thereof that include administering to a subject identified as having an aging-related disease or condition a therapeutically effective amount of one or more natural killer (NK) cell activating agent(s).

Also provided herein are methods of killing or reducing the number of senescent cells in a subject in need thereof that include administering to the subject a therapeutically effective amount of one or more NK cell activating agent(s). In some embodiments of any of the methods described herein, the senescent cells are senescent cancer cells, senescent monocytes, senescent lymphocytes, senescent astrocytes, senescent microglia, senescent neurons, senescent tissue fibroblasts, senescent dermal fibroblasts, senescent keratinocytes, or other differentiated tissue-specific dividing functional cells. In some embodiments of any of the methods described herein, the senescent cancer cells are chemotherapy-induced senescent cells or radiation-induced senescent cells. In some embodiments of any of the methods described herein, the subject has been identified or diagnosed as having an aging-related disease or condition.

In some embodiments of any of the methods described herein, the aging-related disease or condition is selected from the group of: a cancer, an autoimmune disease, a metabolic disease, a neurodegenerative disease, a cardiovascular disease, a skin disease, a progeria disease, and a fragility disease. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the autoimmune disease is type-1 diabetes.

In some embodiments of any of the methods described herein, the metabolic disease is selected from the group of: obesity, a lipodystrophy, and type-2 diabetes mellitus.

In some embodiments of any of the methods described herein, the neurodegenerative disease is selected from the group of: Alzheimer's disease, Parkinson's disease, and dementia.

In some embodiments of any of the methods described herein, the cardiovascular disease is selected from the group of: coronary artery disease, atherosclerosis, and pulmonary arterial hypertension.

In some embodiments of any of the methods described herein, the skin disease is selected from the group of: wound healing, alopecia, wrinkles, senile lentigo, skin thinning, xeroderma pigmentosum, and dyskeratosis congenita.

In some embodiments of any of the methods described herein, the progeria disease is selected from the group of: progeria and Hutchinson-Gilford Progeria Syndrome.

In some embodiments of any of the methods described herein, the fragility disease is selected from the group of: frailty, responsiveness to vaccination, osteoporosis, and sarcopenia.

In some embodiments of any of the methods described herein, the aging-related disease or condition is selected from the group of: age-related macular degeneration, osteoarthritis, adipose atrophy, idiopathic pulmonary fibrosis, kidney transplant failure, liver fibrosis, loss of bone mass, sarcopenia, age-associated loss of lung tissue elasticity, osteoporosis, age-associated renal dysfunction, and chemical-induced renal dysfunction.

In some embodiments of any of the methods described herein, the aging-related disease or condition is type-2 diabetes or atherosclerosis.

In some embodiments of any of the methods described herein, the administering results in a decrease in the number of senescent cells in a target tissue in the subject. In some embodiments of any of the methods described herein, the target tissue is selected from the group of: adipose tissue, pancreatic tissue, liver tissue, lung tissue, vasculature, bone tissue, central nervous system (CNS) tissue, eye tissue, skin tissue, muscle tissue, and secondary lympho-organ tissue.

In some embodiments of any of the methods described herein, the administering results in an increase in the expression levels of CD25, CD69, mTORC1, SREBP1, IFN-γ, and granzyme B in activated NK cells.

Also provided herein are methods of treating an aging-related disease or condition in a subject in need thereof that include administering to a subject identified as having an aging-related disease or condition a therapeutically effective number of activated NK cells.

Also provided herein are methods of killing or reducing the number of senescent cells in a subject in need thereof that include administering to the subject a therapeutically effective number of activated NK cells. In some embodiments of any of the methods described herein, the senescent cells are senescent cancer cells, senescent monocytes, senescent lymphocytes, senescent astrocytes, senescent microglia, senescent neurons, senescent tissue fibroblasts, senescent dermal fibroblasts, senescent keratinocytes, or other differentiated tissue-specific dividing functional cells. In some embodiments of any of the methods described herein, the senescent cancer cells are chemotherapy-induced senescent cells or radiation-induced senescent cells. In some embodiments of any of the methods described herein, the subject has been identified or diagnosed as having an aging-related disease or condition.

In some embodiments of any of the methods described herein, the aging-related disease or condition is selected from the group of: a cancer, an autoimmune disease, a metabolic disease, a neurodegenerative disease, a cardiovascular disease, a skin disease, a progeria disease, and a fragility disease. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the autoimmune disease is type-1 diabetes.

In some embodiments of any of the methods described herein, the metabolic disease is selected from the group of: obesity, a lipodystrophy, and type-2 diabetes mellitus.

In some embodiments of any of the methods described herein, the neurodegenerative disease is selected from the group of: Alzheimer's disease, Parkinson's disease, and dementia.

In some embodiments of any of the methods described herein, the cardiovascular disease is selected from the group of: coronary artery disease, atherosclerosis, and pulmonary arterial hypertension.

In some embodiments of any of the methods described herein, the skin disease is selected from the group of: wound healing, alopecia, wrinkles, senile lentigo, skin thinning, xeroderma pigmentosum, and dyskeratosis congenita.

In some embodiments of any of the methods described herein, the progeria disease is selected from the group of: progeria and Hutchinson-Gilford Progeria Syndrome.

In some embodiments of any of the methods described herein, the fragility disease is selected from the group of: frailty, responsiveness to vaccination, osteoporosis, and sarcopenia.

In some embodiments of any of the methods described herein, the aging-related disease or condition is selected from the group of: age-related macular degeneration, osteoarthritis, adipose atrophy, idiopathic pulmonary fibrosis, kidney transplant failure, liver fibrosis, loss of bone mass, sarcopenia, age-associated loss of lung tissue elasticity, osteoporosis, age-associated renal dysfunction, and chemical-induced renal dysfunction.

Some embodiments of any of the methods described herein further include: obtaining a resting NK cell; and contacting the resting NK cell in vitro in a liquid culture medium including one or more NK cell activating agent(s), where the contacting results in the generation of the activated NK cells that are subsequently administered to the subject. In some embodiments of any of the methods described herein, the resting NK cell is an autologous NK cell obtained from the subject. In some embodiments of any of the methods described herein, the resting NK cell is an allogeneic resting NK cell. In some embodiments of any of the methods described herein, the resting NK cell is an artificial NK cell. In some embodiments of any of the methods described herein, the resting NK cell is a haploidentical resting NK cell. In some embodiments of any of the methods described herein, the resting NK cell is a genetically-engineered NK cell carrying a chimeric antigen receptor or recombinant T cell receptor. Some embodiments of any of the methods described herein further include isolating the activated NK cells before the activated NK cells are administered to the subject. Some embodiments of any of the methods described herein further include introducing a nucleic acid that encodes a chimeric antigen receptor or a recombinant T cell receptor into the resting NK cell or the activated NK cell prior to administration to the subject.

Also provided herein are methods of improving the texture and/or appearance of skin and/or hair in a subject in need thereof over a period of time that include administering to the subject a therapeutically effective amount of one or more natural killer (NK) cell activating agent(s).

Also provided herein are methods of improving the texture and/or appearance of skin and/or hair in a subject in need thereof over a period of time that include administering to the subject a therapeutically effective number of activated NK cells. Some embodiments of any of the methods described herein further include: obtaining a resting NK cell; and contacting the resting NK cell in vitro in a liquid culture medium including one or more NK cell activating agent(s), where the contacting results in the generation of the activated NK cells that are subsequently administered to the subject. In some embodiments of any of the methods described herein, the resting NK cell is an autologous NK cell obtained from the subject. In some embodiments of any of the methods described herein, the resting NK cell is an allogeneic resting NK cell. In some embodiments of any of the methods described herein, the resting NK cell is an artificial NK cell. In some embodiments of any of the methods described herein, the resting NK cell is a haploidentical resting NK cell. In some embodiments of any of the methods described herein, the resting NK cell is a genetically-engineered NK cell carrying a chimeric antigen receptor or recombinant T cell receptor. Some embodiments of any of the methods described herein further include isolating the activated NK cells before the activated NK cells are administered to the subject.

In some embodiments of any of the methods described herein, the method provides for an improvement in the texture and/or appearance of skin of the subject over the period of time. In some embodiments of any of the methods described herein, the method results in a decrease in the rate of formation of wrinkles in the skin of the subject over the period of time. In some embodiments of any of the methods described herein, the method results in an improvement in the coloration of skin of the subject over the period of time. In some embodiments of any of the methods described herein, the method results in an improvement in the texture of skin of the subject over the period of time. In some embodiments of any of the methods described herein, the method provides for an improvement in the texture and/or appearance of hair of the subject over the period of time. In some embodiments of any of the methods described herein, the method results in a decrease in the rate of formation of gray hair in the subject over the period of time. In some embodiments of any of the methods described herein, the method results in a decrease in the number of gray hairs of the subject over the period of time. In some embodiments of any of the methods described herein, the method results in a decrease in the rate of hair loss in the subject over time. In some embodiments of any of the methods described herein, the method results in an improvement in the texture of hair of the subject over the period of time.

In some embodiments of any of the methods described herein, the period of time is between about one month and about 10 years. In some embodiments of any of the methods described herein, the method results in a decrease in the number of senescent dermal fibroblasts in the skin of the subject over the period of time.

Also provided herein are methods of assisting in the treatment of obesity in a subject in need thereof over a period of time that include administering to the subject a therapeutically effective amount of one or more natural killer (NK) cell activating agent(s).

Also provided herein are methods of assisting in the treatment of obesity in a subject in need thereof over a period of time that include administering to the subject a therapeutically effective number of activated NK cells. Some embodiments of any of the methods described herein further include: obtaining a resting NK cell; and contacting the resting NK cell in vitro in a liquid culture medium including one or more NK cell activating agent(s), where the contacting results in the generation of the activated NK cells that are subsequently administered to the subject. In some embodiments of any of the methods described herein, the resting NK cell is an autologous NK cell obtained from the subject. In some embodiments of any of the methods described herein, the resting NK cell is an allogeneic resting NK cell. In some embodiments of any of the methods described herein, the resting NK cell is an artificial NK cell. In some embodiments of any of the methods described herein, the resting NK cell is a haploidentical resting NK cell. In some embodiments of any of the methods described herein, the resting NK cell is a genetically-engineered NK cell carrying a chimeric antigen receptor or recombinant T cell receptor. Some embodiments of any of the methods described herein further include isolating the activated NK cells before the activated NK cells are administered to the subject.

In some embodiments of any of the methods described herein, the method results in a decrease in the mass of the subject over the period of time. In some embodiments of any of the methods described herein, the method results in a decrease in the body mass index (BMI) of the subject over the period of time. In some embodiments of any of the methods described herein, the method results in a decrease in the rate of progression from pre-diabetes to type-2 diabetes in the subject. In some embodiments of any of the methods described herein, the method results in a decrease in fasting serum glucose level in the subject. In some embodiments of any of the methods described herein, the method results in an increase in insulin sensitivity in the subject. In some embodiments of any of the methods described herein, the method results in a decrease in the severity of atherosclerosis in the subject. In some embodiments of any of the methods described herein, the period of time is between about two weeks and about 10 years.

In some embodiments of any of the methods described herein, at least one of the one or more NK cell activating agent(s) results in activation of one or more of: a receptor for IL-2, a receptor for IL-7, a receptor for IL-12, a receptor for IL-15, a receptor for IL-18, a receptor for IL-21, a receptor for IL-33, CD16, CD69, CD25, CD59, CD352, NKp80, DNAM-1, 2B4, NKp30, NKp44, NKp46, NKG2D, KIR2DS1, KIR2Ds2/3, KIR2DL4, KIR2DS4, KIR2DS5, and KIR3DS1.

In some embodiments of any of the methods described herein, the at least one of the one or more NK cell activating agent(s) that results in activation of a receptor for IL-2 is a soluble IL-2 or an agonistic antibody that binds specifically to an IL-2 receptor.

In some embodiments of any of the methods described herein, the at least one of the one or more NK cell activating agent(s) that results in activation of a receptor for IL-7 is a soluble IL-7 or an agonistic antibody that binds specifically to an IL-7 receptor.

In some embodiments of any of the methods described herein, the at least one of the one or more NK cell activating agent(s) that results in activation of a receptor for IL-12 is a soluble IL-12 or an agonistic antibody that binds specifically to an IL-12 receptor.

In some embodiments of any of the methods described herein, the at least one of the one or more NK cell activating agent(s) that results in activation of a receptor for IL-15 is a soluble IL-15 or an agonistic antibody that binds specifically to an IL-15 receptor.

In some embodiments of any of the methods described herein, the at least one of the one or more NK cell activating agent(s) that results in activation of a receptor for IL-21 is a soluble IL-21 or an agonistic antibody that binds specifically to an IL-21 receptor.

In some embodiments of any of the methods described herein, the at least one of the one or more NK cell activating agent(s) that results in activation of a receptor for IL-33 is a soluble IL-33 or an agonistic antibody that binds specifically to an IL-33 receptor.

In some embodiments of any of the methods described herein, the at least one of the one or more NK cell activating agent(s) that results in activation of a receptor for CD16 is an agonistic antibody that binds specifically to a CD16.

In some embodiments of any of the methods described herein, the at least one of the one or more NK cell activating agent(s) that results in activation of a receptor for CD69 is an agonistic antibody that binds specifically to a CD69.

In some embodiments of any of the methods described herein, the at least one of the one or more NK cell activating agent(s) that results in activation of a receptor for CD25 or CD59 is an agonistic antibody that binds specifically to CD25 or CD59.

In some embodiments of any of the methods described herein, the at least one of the one or more NK cell activating agent(s) that results in activation of a receptor for CD352 is an agonistic antibody that binds specifically to a CD352.

In some embodiments of any of the methods described herein, the at least one of the one or more NK cell activating agent(s) that results in activation of a receptor for NKp80 is an agonistic antibody that binds specifically to an NKp80.

In some embodiments of any of the methods described herein, the at least one of the one or more NK cell activating agent(s) that results in activation of a receptor for DNAM-1 is an agonistic antibody that binds specifically to a DNAM-1.

In some embodiments of any of the methods described herein, the at least one of the one or more NK cell activating agent(s) that results in activation of a receptor for 2B4 is an agonistic antibody that binds specifically to a 2B4.

In some embodiments of any of the methods described herein, the at least one of the one or more NK cell activating agent(s) that results in activation of a receptor for NKp30 is an agonistic antibody that binds specifically to an NKp30.

In some embodiments of any of the methods described herein, the at least one of the one or more NK cell activating agent(s) that results in activation of a receptor for NKp44 is an agonistic antibody that binds specifically to an NKp44.

In some embodiments of any of the methods described herein, the at least one of the one or more NK cell activating agent(s) that results in activation of a receptor for NKp46 is an agonistic antibody that binds specifically to an NKp46.

In some embodiments of any of the methods described herein, the at least one of the one or more NK cell activating agent(s) that results in activation of a receptor for NKG2D is an agonistic antibody that binds specifically to an NKG2D.

In some embodiments of any of the methods described herein, the at least one of the one or more NK cell activating agent(s) that results in activation of a receptor for KIR2DS1 is an agonistic antibody that binds specifically to a KIR2DS1.

In some embodiments of any of the methods described herein, the at least one of the one or more NK cell activating agent(s) that results in activation of a receptor for KIR2DS2/3 is an agonistic antibody that binds specifically to a KIR2DS2/3.

In some embodiments of any of the methods described herein, the at least one of the one or more NK cell activating agent(s) that results in activation of a receptor for KIR2DL4 is an agonistic antibody that binds specifically to a KIR2DL4.

In some embodiments of any of the methods described herein, the at least one of the one or more NK cell activating agent(s) that results in activation of a receptor for KIR2DS4 is an agonistic antibody that binds specifically to a KIR2DS4.

In some embodiments of any of the methods described herein, the at least one of the one or more NK cell activating agent(s) that results in activation of a receptor for KIR2DS5 is an agonistic antibody that binds specifically to a KIR2DS5.

In some embodiments of any of the methods described herein, the at least one of the one or more NK cell activating agent(s) that results in activation of a receptor for KIR3DS1 is an agonistic antibody that binds specifically to a KIR3DS1.

In some embodiments of any of the methods described herein, at least one of the one or more NK cell activating agent(s) results in a decrease in the activation of one or more of: PD-1, a TGF-β receptor, TIGIT, CD1, TIM-3, Siglec-7, IRP60, Tactile, IL1R8, NKG2A/KLRD1, KIR2DL1, KIR2DL2/3, KIR2DL5, KIR3DL1, KIR3DL2, ILT2/LIR-1, and LAG-2. In some embodiments of any of the methods described herein, the at least one of the one or more NK cell activating agent(s) that results in a decrease in the activation of PD-1 is an antagonistic antibody that binds specifically to PD-1, a soluble PD-1, a soluble PD-L1, or an antibody that binds specifically to PD-L1. In some embodiments of any of the methods described herein, at least one of the one or more NK cell activating agent(s) that results in a decrease in the activation of a TGF-β receptor is a soluble TGF-β receptor, an antibody that binds specifically to TGF-β, or an antagonistic antibody that binds specifically to a TGF-β receptor.

In some embodiments of any of the methods described herein, at least one of the one or more NK cell activating agent(s) that results in a decrease in the activation of TIGIT is an antagonistic antibody that binds specifically to TIGIT, a soluble TIGIT, or an antibody that binds specifically to a ligand of TIGIT.

In some embodiments of any of the methods described herein, at least one of the one or more NK cell activating agent(s) that results in a decrease in the activation of CD1 is an antagonistic antibody that binds specifically to CD1, a soluble CD1, or an antibody that binds specifically to a ligand of CD1.

In some embodiments of any of the methods described herein, at least one of the one or more NK cell activating agent(s) that results in a decrease in the activation of TIM-3 is an antagonistic antibody that binds specifically to TIM-3, a soluble TIM-3, or an antibody that binds specifically to a ligand of TIM-3.

In some embodiments of any of the methods described herein, at least one of the one or more NK cell activating agent(s) that results in a decrease in the activation of Siglec-7 is an antagonistic antibody that binds specifically to Siglec-7 or an antibody that binds specifically to a ligand of Siglec-7.

In some embodiments of any of the methods described herein, at least one of the one or more NK cell activating agent(s) that results in a decrease in the activation of IRP60 is an antagonistic antibody that binds specifically to IRP60 or an antibody that binds specifically to a ligand of IRP60.

In some embodiments of any of the methods described herein, at least one of the one or more NK cell activating agent(s) that results in a decrease in the activation of Tactile is an antagonistic antibody that binds specifically to Tactile or an antibody that binds specifically to a ligand of Tactile.

In some embodiments of any of the methods described herein, at least one of the one or more NK cell activating agent(s) that results in a decrease in the activation of IL1R8 is an antagonistic antibody that binds specifically to IL1R8 or an antibody that binds specifically to a ligand of IL1R8.

In some embodiments of any of the methods described herein, at least one of the one or more NK cell activating agent(s) that results in a decrease in the activation of NKG2A/KLRD1 is an antagonistic antibody that binds specifically to NKG2A/KLRD1 or an antibody that binds specifically to a ligand of NKG2A/KLRD1.

In some embodiments of any of the methods described herein, at least one of the one or more NK cell activating agent(s) that results in a decrease in the activation of KIR2DL1 is an antagonistic antibody that binds specifically to KIR2DL1 or an antibody that binds specifically to a ligand of KIR2DL1.

In some embodiments of any of the methods described herein, at least one of the one or more NK cell activating agent(s) that results in a decrease in the activation of KIR2DL2/3 is an antagonistic antibody that binds specifically to KIR2DL2/3 or an antibody that binds specifically to a ligand of KIR2DL2/3.

In some embodiments of any of the methods described herein, at least one of the one or more NK cell activating agent(s) that results in a decrease in the activation of KIR2DL5 is an antagonistic antibody that binds specifically to KIR2DL5 or an antibody that binds specifically to a ligand of KIR2DL5.

In some embodiments of any of the methods described herein, at least one of the one or more NK cell activating agent(s) that results in a decrease in the activation of KIR3DL1 is an antagonistic antibody that binds specifically to KIR3DL1 or an antibody that binds specifically to a ligand of KIR3DL1.

In some embodiments of any of the methods described herein, at least one of the one or more NK cell activating agent(s) that results in a decrease in the activation of KIR3DL2 is an antagonistic antibody that binds specifically to KIR3DL2 or an antibody that binds specifically to a ligand of KIR3DL2.

In some embodiments of any of the methods described herein, at least one of the one or more NK cell activating agent(s) that results in a decrease in the activation of ILT2/LIR-1 is an antagonistic antibody that binds specifically to ILT2/LIR-1 or an antibody that binds specifically to a ligand of ILT2/LIR-1.

In some embodiments of any of the methods described herein, at least one of the one or more NK cell activating agent(s) that results in a decrease in the activation of LAG-2 is an antagonistic antibody that binds specifically to LAG-2 or an antibody that binds specifically to a ligand of LAG-2.

In some embodiments of any of the methods described herein, at least one of the one or more NK cell activating agent(s) is a single-chain chimeric polypeptide that includes: (i) a first target-binding domain; (ii) a soluble tissue factor domain; and (iii) a second target-binding domain. In some embodiments of any of the methods described herein, the first target-binding domain and the soluble tissue factor domain directly abut each other. In some embodiments of any of the methods described herein, the single-chain chimeric polypeptide further includes a linker sequence between the first target-binding domain and the soluble tissue factor domain. In some embodiments of any of the methods described herein, the soluble tissue factor domain and the second target-binding domain directly abut each other. In some embodiments of any of the methods described herein, the single-chain chimeric polypeptide further includes a linker sequence between the soluble tissue factor domain and the second target-binding domain. In some embodiments of any of the methods described herein, the first target-binding domain and the second target-binding domain directly abut each other. In some embodiments of any of the methods described herein, the single-chain chimeric polypeptide further includes a linker sequence between the first target-binding domain and the second target-binding domain. In some embodiments of any of the methods described herein, the second target-binding domain and the soluble tissue factor domain directly abut each other. In some embodiments of any of the methods described herein, the single-chain chimeric polypeptide further includes a linker sequence between the second target-binding domain and the soluble tissue factor domain.

In some embodiments of any of the methods described herein, the first target-binding domain and the second target-binding domain bind specifically to the same antigen. In some embodiments of any of the methods described herein, the first target-binding domain and the second target-binding domain bind specifically to the same epitope. In some embodiments of any of the methods described herein, the first target-binding domain and the second target-binding domain include the same amino acid sequence.

In some embodiments of any of the methods described herein, the first target-binding domain and the second target-binding domain bind specifically to different antigens.

In some embodiments of any of the methods described herein, one or both of the first target-binding domain and the second target-binding domain is an antigen-binding domain. In some embodiments of any of the methods described herein, the first target-binding domain and the second target-binding domain are each an antigen-binding domain. In some embodiments of any of the methods described herein, the antigen-binding domain includes a scFv or a single domain antibody.

In some embodiments of any of the methods described herein, one or both of the first target-binding domain and the second target-binding domain bind to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the methods described herein, one or both of the first target-binding domain and the second target-binding domain is a soluble interleukin or cytokine protein. In some embodiments of any of the methods described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the methods described herein, one or both of the first target-binding domain and the second target-binding domain is a soluble interleukin or cytokine receptor. In some embodiments of any of the methods described herein, the soluble interleukin or cytokine receptor is a soluble TGF-β receptor II (TGF-βRII) a soluble TGF-βRIII, a soluble receptor for TNFα, a soluble receptor for IL-4, or a soluble receptor for IL-10.

In some embodiments of any of the methods described herein, the soluble tissue factor domain is a soluble human tissue factor domain. In some embodiments of any of the methods described herein, the soluble human tissue factor domain includes a sequence that is at least 80% identical to SEQ ID NO: 93. In some embodiments of any of the methods described herein, the soluble human tissue factor domain includes a sequence that is at least 90% identical to SEQ ID NO: 93. In some embodiments of any of the methods described herein, the soluble human tissue factor domain includes a sequence that is at least 95% identical to SEQ ID NO: 93. In some embodiments of any of the methods described herein, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the soluble tissue factor domain is not capable of binding Factor VIIa. In some embodiments of any of the methods described herein, the soluble tissue factor domain does not convert inactive Factor X into Factor Xa. In some embodiments of any of the methods described herein, the single-chain chimeric polypeptide does not blood stimulate coagulation in a mammal. In some embodiments of any of the methods described herein, the single-chain chimeric polypeptide further includes one or more additional target-binding domains at its N- and/or C-terminus.

In some embodiments of any of the methods described herein, the single-chain chimeric polypeptide includes one or more additional target-binding domains at its N-terminus. In some embodiments of any of the methods described herein, one or more additional target-binding domains directly abuts the first target-binding domain, the second target-binding domain, or the soluble tissue factor domain. In some embodiments of any of the methods described herein, the single-chain chimeric polypeptide further includes a linker sequence between one of the at least one additional target-binding domains and the first target-binding domain, the second target-binding domain, or the soluble tissue factor domain.

In some embodiments of any of the methods described herein, the single-chain chimeric polypeptide includes one or more additional target-binding domains at its C-terminus. In some embodiments of any of the methods described herein, one of the one or more additional target-binding domains directly abuts the first target-binding domain, the second target-binding domain, or the soluble tissue factor domain. In some embodiments of any of the methods described herein, the single-chain chimeric polypeptide further includes a linker sequence between one of the at least one additional target-binding domains and the first target-binding domain, the second target-binding domain, or the soluble tissue factor domain.

In some embodiments of any of the methods described herein, the single-chain chimeric polypeptide includes one or more additional target binding domains at its N-terminus and the C-terminus. In some embodiments of any of the methods described herein, one of the one or more additional antigen binding domains at the N-terminus directly abuts the first target-binding domain, the second target-binding domain, or the soluble tissue factor domain. In some embodiments of any of the methods described herein, the single-chain chimeric polypeptide further includes a linker sequence between one of the one or more additional antigen-binding domains at the N-terminus and the first target-binding domain, the second target-binding domain, or the soluble tissue factor domain. In some embodiments of any of the methods described herein, one of the one or more additional antigen binding domains at the C-terminus directly abuts the first target-binding domain, the second target-binding domain, or the soluble tissue factor domain. In some embodiments of any of the methods described herein, the single-chain chimeric polypeptide further includes a linker sequence between one of the one or more additional antigen-binding domains at the C-terminus and the first target-binding domain, the second target-binding domain, or the soluble tissue factor domain.

In some embodiments of any of the methods described herein, two or more of the first target-binding domain, the second target-binding domain, and the one or more additional target-binding domains bind specifically to the same antigen. In some embodiments of any of the methods described herein, two or more of the first target-binding domain, the second target-binding domain, and the one or more additional target-binding domains bind specifically to the same epitope. In some embodiments of any of the methods described herein, two or more of the first target-binding domain, the second target-binding domain, and the one or more additional target-binding domains include the same amino acid sequence. In some embodiments of any of the methods described herein, the first target-binding domain, the second target-binding domain, and the one or more additional target-binding domains each bind specifically to the same antigen. In some embodiments of any of the methods described herein, the first target-binding domain, the second target-binding domain, and the one or more additional target-binding domains each bind specifically to the same epitope. In some embodiments of any of the methods described herein, the first target-binding domain, the second target-binding domain, and the one or more additional target-binding domains each include the same amino acid sequence.

In some embodiments of any of the methods described herein, the first target-binding domain, the second target-binding domain, and the one or more additional target-binding domains bind specifically to different antigens.

In some embodiments of any of the methods described herein, one or more of the first target-binding domain, the second target-binding domain, and the one or more target-binding domains is an antigen-binding domain. In some embodiments of any of the methods described herein, the first target-binding domain, the second target-binding domain, and the one or more additional target-binding domains are each an antigen-binding domain. In some embodiments of any of the methods described herein, the antigen-binding domain includes a scFv or a single domain antibody.

In some embodiments of any of the methods described herein, one or more of the first target-binding domain, the second target-binding domain, and the one or more target-binding domains bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the methods described herein, one or more of the first target-binding domain, the second target-binding domain, and the one or more additional target-binding domains is a soluble interleukin or cytokine protein. In some embodiments of any of the methods described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the methods described herein, one or more of the first target-binding domain, the second target-binding domain, and the one or more additional target-binding domains is a soluble interleukin or cytokine receptor. In some embodiments of any of the methods described herein, the soluble receptor is a soluble TGF-β receptor II (TGF-βRII) a soluble TGF-βRIII, a soluble receptor for TNFα, a soluble receptor for IL-4, or a soluble receptor for IL-10.

In some embodiments of any of the methods described herein, at least one of the one or more NK cell activating agent(s) is a multi-chain chimeric polypeptide that includes: (a) a first chimeric polypeptide including: (i) a first target-binding domain; (ii) a soluble tissue factor domain; and (iii) a first domain of a pair of affinity domains; and (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains.

In some embodiments of any of the methods described herein, the first target-binding domain and the soluble tissue factor domain directly abut each other in the first chimeric polypeptide. In some embodiments of any of the methods described herein, the first chimeric polypeptide further includes a linker sequence between the first target-binding domain and the soluble tissue factor domain in the first chimeric polypeptide. In some embodiments of any of the methods described herein, the soluble tissue factor domain and the first domain of the pair of affinity domains directly abut each other in the first chimeric polypeptide. In some embodiments of any of the methods described herein, the first chimeric polypeptide further includes a linker sequence between the soluble tissue factor domain and the first domain of the pair of affinity domains in the first chimeric polypeptide. In some embodiments of any of the methods described herein, the second domain of the pair of affinity domains and the second target-binding domain directly abut each other in the second chimeric polypeptide. In some embodiments of any of the methods described herein, the second chimeric polypeptide further includes a linker sequence between the second domain of the pair of affinity domains and the second target-binding domain in the second chimeric polypeptide.

In some embodiments of any of the methods described herein, the first target-binding domain and the second target-binding domain bind specifically to the same antigen. In some embodiments of any of the methods described herein, the first target-binding domain and the second target-binding domain bind specifically to the same epitope. In some embodiments of any of the methods described herein, the first target-binding domain and the second target-binding domain include the same amino acid sequence.

In some embodiments of any of the methods described herein, the first target-binding domain and the second target-binding domain bind specifically to different antigens.

In some embodiments of any of the methods described herein, one or both of the first target-binding domain and the second target-binding domain is an antigen-binding domain. In some embodiments of any of the methods described herein, the first target-binding domain and the second target-binding domain are each antigen-binding domains. In some embodiments of any of the methods described herein, the antigen-binding domain includes a scFv or a single domain antibody.

In some embodiments of any of the methods described herein, one or both of the first target-binding domain and the second target-binding domain bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the methods described herein, one or both of the first target-binding domain and the second target-binding domain is a soluble interleukin or cytokine protein. In some embodiments of any of the methods described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the methods described herein, one or both of the first target-binding domain and the second target-binding domain is a soluble interleukin or cytokine receptor. In some embodiments of any of the methods described herein, the soluble receptor is a soluble TGF-β receptor II (TGF-βRII) a soluble TGF-βRIII, a soluble receptor for TNFα, a soluble receptor for IL-4, or a soluble receptor for IL-10.

In some embodiments of any of the methods described herein, the first chimeric polypeptide further includes one or more additional target-binding domain(s), where at least one of the one or more additional antigen-binding domain(s) is positioned between the soluble tissue factor domain and the first domain of the pair of affinity domains. In some embodiments of any of the methods described herein, the first chimeric polypeptide further includes a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

In some embodiments of any of the methods described herein, the first chimeric polypeptide further includes one or more additional target-binding domains at the N-terminal and/or C-terminal end of the first chimeric polypeptide. In some embodiments of any of the methods described herein, at least one of the one or more additional target-binding domains directly abuts the first domain of the pair of affinity domains in the first chimeric polypeptide. In some embodiments of any of the methods described herein, the first chimeric polypeptide further includes a linker sequence between the at least one of the one or more additional target-binding domains and the first domain of the pair of affinity domains. In some embodiments of any of the methods described herein, the at least one of the one or more additional target-binding domains directly abuts the first target-binding domain in the first chimeric polypeptide. In some embodiments of any of the methods described herein, the first chimeric polypeptide further includes a linker sequence between the at least one of the one or more additional target-binding domains and the first target-binding domain.

In some embodiments of any of the methods described herein, at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide. In some embodiments of any of the methods described herein, the at least one additional target-binding domain of the one or more additional target-binding domains disposed at the N-terminus directly abuts the first target-binding domain or the first domain of the pair of affinity domains in the first chimeric polypeptide. In some embodiments of any of the methods described herein, the first chimeric polypeptide further includes a linker sequence disposed between the at least one additional target-binding domain and the first target-binding domain or the first domain of the pair of affinity domains in the first chimeric polypeptide. In some embodiments of any of the methods described herein, the at least one additional target-binding domain of the one or more additional target-binding domains disposed at the C-terminus directly abuts the first target-binding domain or the first domain of the pair of affinity domains in the first chimeric polypeptide. In some embodiments of any of the methods described herein, the first chimeric polypeptide further includes a linker sequence disposed between the at least one additional target-binding domain and the first target-binding domain or the first domain of the pair of affinity domains in the first chimeric polypeptide. In some embodiments of any of the methods described herein, the at least one of the one or more additional target-binding domains positioned between the soluble tissue factor domain and the first domain of the pair of affinity domains, directly abuts the soluble tissue factor domain and/or the first domain of the pair of affinity domains. In some embodiments of any of the methods described herein, the first chimeric polypeptide further includes a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

In some embodiments of any of the methods described herein, the second chimeric polypeptide further includes one or more additional target-binding domains at the N-terminal end or the C-terminal end of the second chimeric polypeptide. In some embodiments of any of the methods described herein, at least one of the one or more additional target-binding domains directly abuts the second domain of the pair of affinity domains in the second chimeric polypeptide. In some embodiments of any of the methods described herein, the second chimeric polypeptide further includes a linker sequence between at least one of the one or more additional target-binding domains and the second domain of the pair of affinity domains in the second chimeric polypeptide. In some embodiments of any of the methods described herein, at least one of the one or more additional target-binding domains directly abuts the second target-binding domain in the second chimeric polypeptide. In some embodiments of any of the methods described herein, the second chimeric polypeptide further includes a linker sequence between at least one of the one or more additional target-binding domains and the second target-binding domain in the second chimeric polypeptide.

In some embodiments of any of the methods described herein, two or more of the first target-binding domain, the second target-binding domain, and the one or more additional target-binding domains bind specifically to the same antigen. In some embodiments of any of the methods described herein, two or more of the first target-binding domain, the second target-binding domain, and the one or more additional target-binding domains bind specifically to the same epitope. In some embodiments of any of the methods described herein, two or more of the first target-binding domain, the second target-binding domain, and the one or more additional target-binding domains include the same amino acid sequence. In some embodiments of any of the methods described herein, the first target-binding domain, the second target-binding domain, and the one or more additional target-binding domains each bind specifically to the same antigen. In some embodiments of any of the methods described herein, the first target-binding domain, the second target-binding domain, and the one or more additional target-binding domains each bind specifically to the same epitope. In some embodiments of any of the methods described herein, the first target-binding domain, the second target-binding domain, and the one or more additional target-binding domains each include the same amino acid sequence.

In some embodiments of any of the methods described herein, the first target-binding domain, the second target-binding domain, and the one or more additional target-binding domains bind specifically to different antigens. In some embodiments of any of the methods described herein, one or more of the first target-binding domain, the second target-binding domain, and the one or more target-binding domains is an antigen-binding domain. In some embodiments of any of the methods described herein, the first target-binding domain, the second target-binding domain, and the one or more additional target-binding domains are each an antigen-binding domain. In some embodiments of any of the methods described herein, the antigen-binding domain includes a scFv.

In some embodiments of any of the methods described herein, one or more of the first target-binding domain, the second target-binding domain, and the one or more target-binding domains bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the methods described herein, one or more of the first target-binding domain, the second target-binding domain, and the one or more additional target-binding domains is a soluble interleukin or cytokine protein. In some embodiments of any of the methods described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the methods described herein, one or more of the first target-binding domain, the second target-binding domain, and the one or more additional target-binding domains is a soluble interleukin or cytokine receptor. In some embodiments of any of the methods described herein, the soluble receptor a soluble TGF-β receptor II (TGF-βRII) a soluble TGF-βRIII, a soluble receptor for TNFα, a soluble receptor for IL-4, or a soluble receptor for IL-10.

In some embodiments of any of the methods described herein, the soluble tissue factor domain is a soluble human tissue factor domain. In some embodiments of any of the methods described herein, the soluble human tissue factor domain includes a sequence that is at least 80% identical to SEQ ID NO: 93. In some embodiments of any of the methods described herein, the soluble human tissue factor domain includes a sequence that is at least 90% identical to SEQ ID NO: 93. In some embodiments of any of the methods described herein, the soluble human tissue factor domain includes a sequence that is at least 95% identical to SEQ ID NO: 93.

In some embodiments of any of the methods described herein, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the soluble tissue factor domain is not capable of binding to Factor VIIa. In some embodiments of any of the methods described herein, the soluble tissue factor domain does not convert inactive Factor X into Factor Xa. In some embodiments of any of the methods described herein, the multi-chain chimeric polypeptide does not stimulate blood coagulation in a mammal. In some embodiments of any of the methods described herein, the pair of affinity domains is a sushi domain from an alpha chain of human IL-15 receptor (IL-15Rα) and a soluble IL-15. In some embodiments of any of the methods described herein, the soluble IL-15 has a D8N or D8A amino acid substitution. In some embodiments of any of the methods described herein, the human IL-15Rα is a mature full-length IL-15Rα.

In some embodiments of any of the methods described herein, the pair of affinity domains is selected from the group of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

In some embodiments of any of the methods described herein, at least one of the one or more NK cell activating agent(s) is a multi-chain chimeric polypeptide that includes: (a) a first and second chimeric polypeptides, where each includes: (i) a first target-binding domain; (ii) a Fc domain; and (iii) a first domain of a pair of affinity domains; and (b) a third and fourth chimeric polypeptide, where each includes: (i) a second domain of a pair of affinity domains; and (ii) a second target-binding domain, where the first and second chimeric polypeptides and the third and fourth chimeric polypeptides associate through the binding of the first domain and the second domain of the pair of affinity domains, and the first and second chimeric polypeptides associate through their Fc domains.

In some embodiments of any of the methods described herein, the first target-binding domain and the Fc domain directly abut each other in the first and second chimeric polypeptides. In some embodiments of any of the methods described herein, the first and second chimeric polypeptides further include a linker sequence between the first target-binding domain and the Fc domain in the first and second chimeric polypeptides. In some embodiments of any of the methods described herein, the Fc domain and the first domain of the pair of affinity domains directly abut each other in the first and second chimeric polypeptides. In some embodiments of any of the methods described herein, the first chimeric polypeptide further includes a linker sequence between the Fc domain and the first domain of the pair of affinity domains in the first and second chimeric polypeptides.

In some embodiments of any of the methods described herein, the second domain of the pair of affinity domains and the second target-binding domain directly abut each other in the third and fourth chimeric polypeptides. In some embodiments of any of the methods described herein, the third and fourth chimeric polypeptides further include a linker sequence between the second domain of the pair of affinity domains and the second target-binding domain in the third and fourth chimeric polypeptides.

In some embodiments of any of the methods described herein, the first target-binding domain and the second target-binding domain bind specifically to the same antigen. In some embodiments of any of the methods described herein, the first target-binding domain and the second target-binding domain bind specifically to the same epitope. In some embodiments of any of the methods described herein, the first target-binding domain and the second target-binding domain include the same amino acid sequence.

In some embodiments of any of the methods described herein, the first target-binding domain and the second target-binding domain bind specifically to different antigens. In some embodiments of any of the methods described herein, one or both of the first target-binding domain and the second target-binding domain is an antigen-binding domain. In some embodiments of any of the methods described herein, the first target-binding domain and the second target-binding domain are each antigen-binding domains. In some embodiments of any of the methods described herein, the antigen-binding domain includes a scFv or a single domain antibody.

In some embodiments of any of the methods described herein, one or both of the first target-binding domain and the second target-binding domain bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the methods described herein, one or both of the first target-binding domain and the second target-binding domain is a soluble interleukin or cytokine protein. In some embodiments of any of the methods described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the methods described herein, one or both of the first target-binding domain and the second target-binding domain is a soluble interleukin or cytokine receptor. In some embodiments of any of the methods described herein, the soluble receptor is a soluble TGF-β receptor II (TGF-βRII) a soluble TGF-βRIII, a soluble receptor for TNFα, a soluble receptor for IL-4, or a soluble receptor for IL-10.

In some embodiments of any of the methods described herein, the soluble tissue factor domain is a soluble human tissue factor domain that does not stimulate blood coagulation. In some embodiments of any of the methods described herein, the soluble tissue factor domain comprises or consists of a sequence from a wildtype soluble human tissue factor.

As used herein, the term "chimeric" refers to a polypeptide that includes amino acid sequences (e.g., domains) originally derived from two different sources (e.g., two different naturally-occurring proteins, e.g., from the same or different species). For example, a chimeric polypeptide can include domains from at least two different naturally occurring human proteins. In some examples, a chimeric polypeptide can include a domain that is a synthetic sequence (e.g., a scFv) and a domain that is derived from a naturally-occurring protein (e.g., a naturally-occurring human protein). In some embodiments, a chimeric polypeptide can include at least two different domains that are synthetic sequences (e.g., two different scFvs).

An "activated NK cell" is a NK cell demonstrating increased expression levels of two or more (e.g., three, four, five, or six) of CD25, CD69, MTOR-C1, SREBP, IFN-γ, and a granzyme (e.g., granzyme B), e.g., as compared to a resting NK cell. Exemplary methods for identifying the expression levels of CD25, CD69, MTOR-C1, SREBP, IFN-γ, and a granzyme (e.g., granzyme B) are described herein.

A "resting NK cell" is a NK cell that has a reduced expression of two or more (e.g., three, four, five, or six) of CD25, CD69, MTOR-C1, SREBP, IFN-γ, and a granzyme (e.g., granzyme B), e.g., as compared to an activated NK cell.

An "NK cell activating agent" is an agent that induces or promotes (alone or in combination with additional NK cell activating agents) a resting NK cell to develop into an activated NK cell. Non-limiting examples and aspects of NK cell activating agents are described herein.

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigen(s). In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art.

A "soluble tissue factor domain" refers to a polypeptide having at least 70% identity (e.g., at least 75% identity, at least 80% identity, at least 85% identity, at least 90% identity, at least 95% identity, at least 99% identity, or 100% identical) to a segment of a wildtype mammalian tissue factor protein (e.g., a wildtype human tissue factor protein) that lacks the transmembrane domain and the intracellular domain. Non-limiting examples of soluble tissue factor domains are described herein.

The term "soluble interleukin protein" is used herein to refer to a mature and secreted interleukin protein or a biologically active fragment thereof. In some examples, a soluble interleukin protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble interleukin proteins are described herein.

The term "soluble cytokine protein" is used herein to refer to a mature and secreted cytokine protein or a biologically active fragment thereof. In some examples, a soluble cytokine protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble cytokine proteins are described herein.

The term "soluble interleukin receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble interleukin receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype interleukin receptor and retains its ability to specifically bind to one or more of its natural ligands, but lacks its transmembrane domain (and optionally, further lacks its intracellular domain). Non-limiting examples of soluble interleukin receptors are described herein.

The term "soluble cytokine receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble cytokine receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype cytokine receptor and retains its ability to specifically bind to one or more of its natural ligands, but lacks its transmembrane domain (and optionally, further lacks its intracellular domain). Non-limiting examples of soluble cytokine receptors are described herein.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins), antibody fragments, and multi-specific antibodies. One example of an antigen-binding domain is an antigen-binding domain formed by a VH-VL dimer. Additional examples of an antibody are described herein. Additional examples of an antibody are known in the art.

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an antigen-binding domain and its corresponding antigen or epitope are known in the art.

A "single-chain polypeptide" as used herein to refers to a single protein chain.

A "multi-chain polypeptide" as used herein to refers to a polypeptide comprising two or more (e.g., three, four, five, six, seven, eight, nine, or ten) protein chains (e.g., at least a first chimeric polypeptide and a second polypeptide), where the two or more proteins chains associate through non-covalent bonds to form a quaternary structure.

The term "pair of affinity domains" is two different protein domain(s) that bind specifically to each other with a $K_D$ of less than of less than $1\times10^{-7}$ M (e.g., less than $1\times10^{-8}$ M, less than $1\times10^{-9}$ M, less than $1\times10^{-10}$ M, or less than $1\times10^{-11}$ M). In some examples, a pair of affinity domains can be a pair of naturally-occurring proteins. In some embodiments, a pair of affinity domains can be a pair of synthetic proteins. Non-limiting examples of pairs of affinity domains are described herein.

The term "epitope" means a portion of an antigen that specifically binds to an antigen-binding domain. Epitopes can, e.g., consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. Methods for identifying an epitope to which an antigen-binding domain binds are known in the art.

The term "treatment" means to ameliorate at least one symptom of a disorder. In some examples, the disorder being treated is cancer and to ameliorate at least one symptom of cancer includes reducing aberrant proliferation, gene expression, signaling, translation, and/or secretion of factors. Generally, the methods of treatment include administering a therapeutically effective amount of a composition that reduces at least one symptom of a disorder to a subject who is in need of, or who has been determined to be in need of such treatment.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 1A shows the spleen weight of mice treated with increasing dosage of the exemplary multi-chain polypeptide as compared to mice treated with the control solution. FIG. 1B shows the percentages of immune cell types present in the spleen of mice treated with increasing dosage of the exemplary multi-chain polypeptide as compared to mice treated with the control solution.

FIG. 2A shows the spleen weight over a period of 92 hours in mice treated with 3 mg/kg of the exemplary multi-chain polypeptide. FIG. 2B shows the percentages of immune cell types present in the spleen over a period of 92 hours in mice treated with 3 mg/kg of the exemplary multi-chain polypeptide.

FIG. 3A shows the expression of Ki67 in $CD4^+$ T cells, $CD8^+$ T cells, natural killer (NK) cells, and $CD19^+$ B cells at various time points post-treatment with the multi-chain polypeptide. FIG. 3B shows the expression of Granzyme B in $CD4^+$ T cells, $CD8^+$ T cells, natural killer (NK) cells, and $CD19^+$ B cells at various time points post-treatment with the multi-chain polypeptide.

FIG. 5A shows the percentages of the different cell types in each control and experimental group. FIG. 5B shows the proliferation rate of the of the different cell types in each control and experimental group.

FIG. 9A shows chemotherapy induction of senescent B16F10 cells visualized using SA β-gal staining. FIGS. 9B-9F show expression of p21, IL6, DPP4, RATE1E, and ULBP1 over time in the chemotherapy-induced senescent B16F10 cells.

FIG. 10A shows colony formation by chemotherapy-induced senescent B16F10 cells. FIGS. 10B and 10C show expression of Oct4 mRNA and Notch4 mRNA by chemotherapy-induced senescent B16F10 cells as compared to control B16F10 cells. FIGS. 10D-10F show percentage of chemotherapy-induced senescent B16F10 cells double-positive for two out of the three stem cell markers including CD44, CD24, and CD133.

FIG. 11A shows the results of a migration assay comparing chemotherapy-induced senescent cells with stem cell properties (B16F10-SNC-CSC) with control B16F10 cells. FIGS. 11B and 11C show the results of an invasion assay comparing chemotherapy-induced senescent cells with stem cell properties (B16F10-SNC-CSC) with control B16F10 cells.

FIG. 12A shows an exemplary schematic of a process of obtaining in vitro expanded NK cells. FIG. 12B shows cytotoxicity of the expanded NK cells against chemotherapy-induced senescent cells with stem cell properties (B16F10-SNC-CSC) or control B16F10 cells.

FIG. 13A shows an exemplary schematic for treating melanoma in a mouse model. FIGS. 13B and 13C show the change in tumor volume over time with combination treatments including TGFRt15-TGFRs as compared to chemotherapy or TA99 treatment alone.

FIG. 84A shows binding affinity of TGFRT15-16S21 with CHO cells expressing human CD16b. FIG. 84B shows binding affinity of 7t15-21s with CHO cells expressing human CD16b.

FIG. 94A shows spleen weight in mice treated with 7t15-7s as compared to PBS control. FIG. 94B shows the percentage of $CD4^+$ T cells, $CD8^+$ T cells, and NK cells in mice treated with 7t15-7s as compared to PBS control.

FIG. 103A shows spleen weight in mice treated with TGFRt15-TGFRs as compared to PBS control. FIG. 103B shows the percentage of $CD4^+$ T cells, $CD8^+$ T cells, and NK cells in mice treated with TGFRt15-TGFRs as compared to PBS control.

FIG. 104A shows spleen weight of mice treated with TGFRt15-TGFRs at 16, 24, 48, 72, and 92 hours after treatment. FIG. 104B shows the percentages of immune cells in mice treated with TGFRt15-TGFRs at 16, 24, 48, 72, and 92 hours after treatment.

FIG. 114A shows detection of IL-15 in 7t15-21s137L (short version) with ELISA. FIG. 114B shows detection of IL21 in 7t15-21s137L (short version) with ELISA. FIG. 114C shows detection of IL7 in 7t15-21s137L (short version) with ELISA.

FIG. 121 shows results of a 32Dβ cell proliferation assay with 7t15-TGFRs or recombinant IL-15.

FIG. 122 is a line graph showing the chromatographic profile of 7t15-TGFRs protein containing cell culture supernatant following binding and elution on anti-TF antibody resin.

FIG. 123 shows 7t15-TGFRs before and after deglycosylation as analyzed using reduced SDS-PAGE.

FIG. 124 shows ELISA detection of IL-7, IL-15 and TGFβRII in the 7t15-TGFRs protein.

Figure 125A:
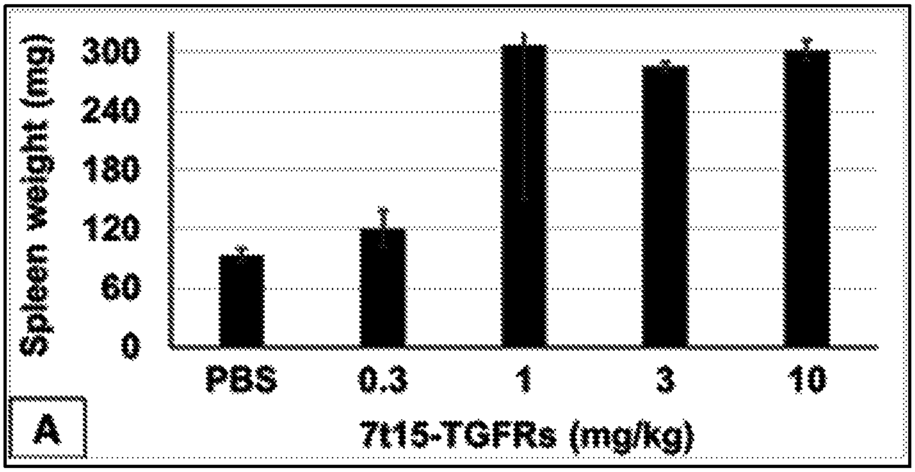
Figure 125B:
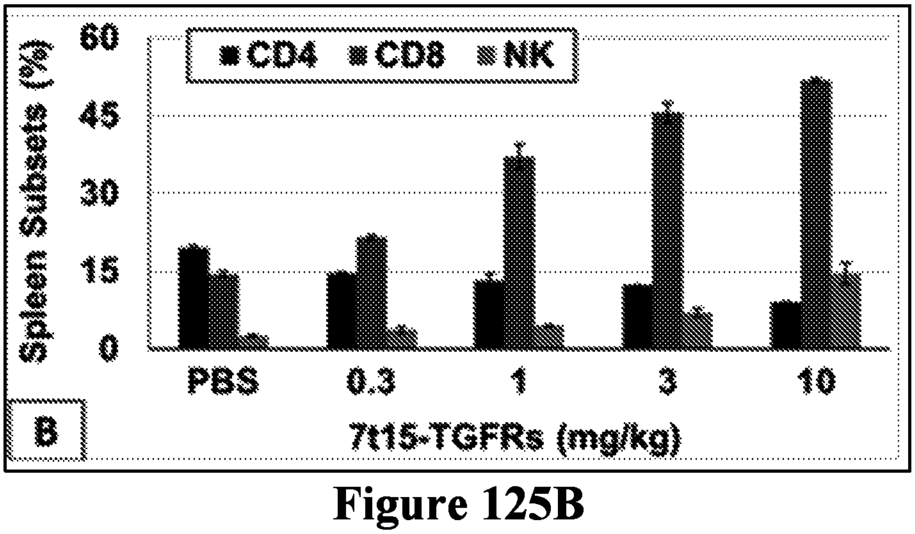

FIGS. 125A and 125B show spleen weight and the percentages of immune cell types in 7t15-TGFRs-treated and control-treated mice. FIG. 125A shows spleen weight in mice treated with 7t15-TGFRs at various dosages, as compared to PBS control. FIG. 125B shows the percentage of $CD4^+$ T cells, $CD8^+$ T cells, and NK cells in mice treated with 7t15-TGFRs at various dosages, as compared to PBS control.

Figure 126A:
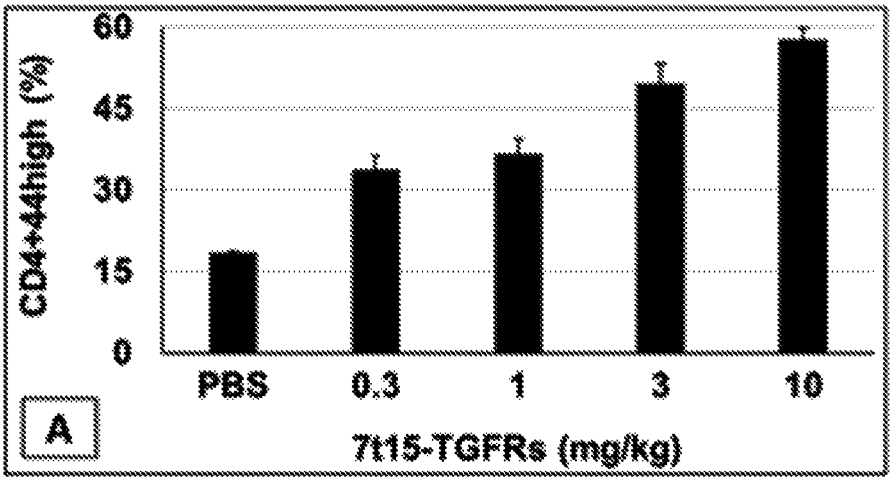
Figure 126B:
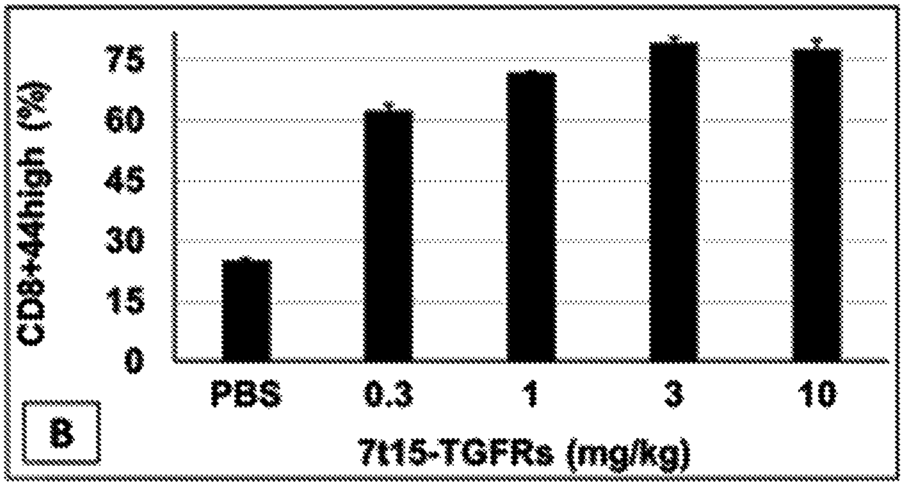

FIGS. 126A and 126B show upregulation of CD44 expression of $CD4^+$ and $CD8^+$ T cells by 7t15-TGFRs in C57BL/6 mice.

Figure 127A:
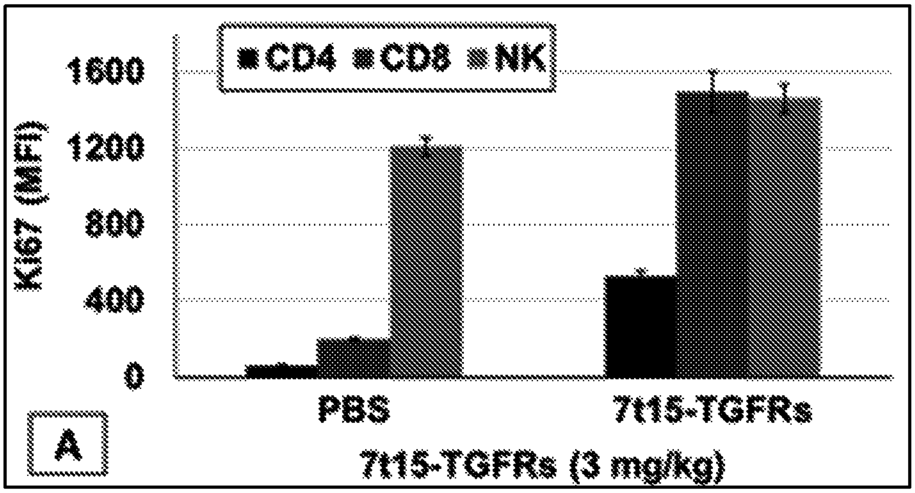
Figure 127B:
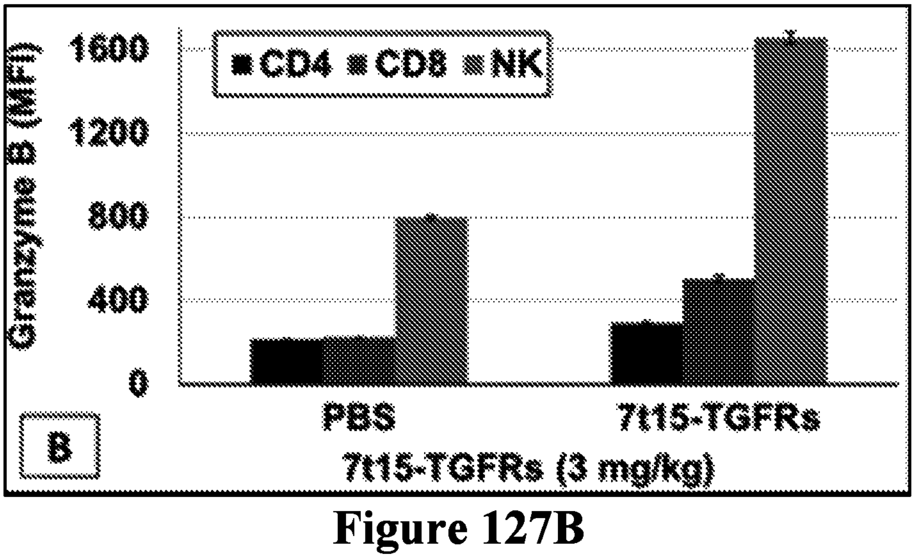

FIGS. 127A and 127B show upregulation of Ki67 expression and Granzyme B expression of $CD8^+$ T cells and NK Cells by 7t15-TGFRs in C57BL/6 mice.

Figure 128:
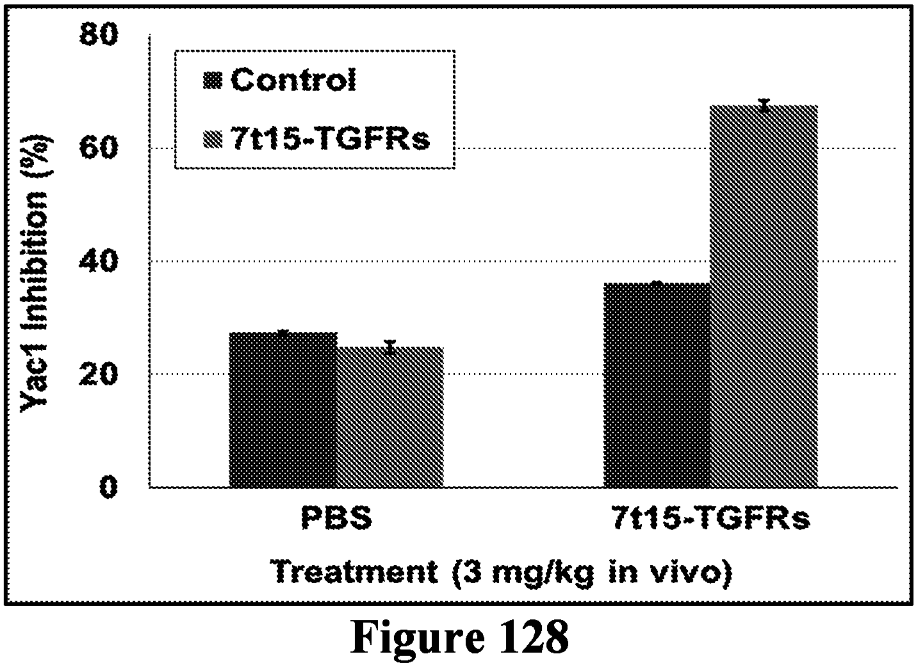

FIG. 128 shows enhancement of cytotoxicity of splenocytes by 7t15-TGFRs in C57BL/6 mice.

Figure 129:
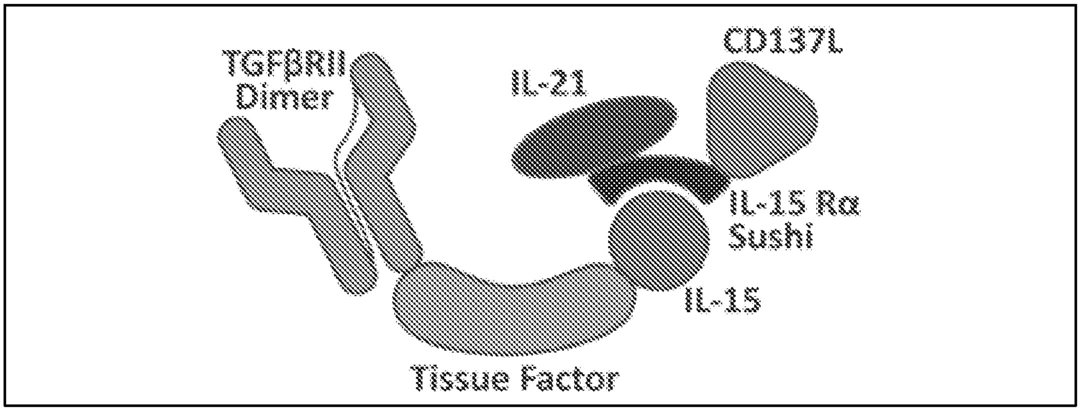

FIG. 129 shows a schematic of the TGFRt15-21s137L construct.

Figure 130:
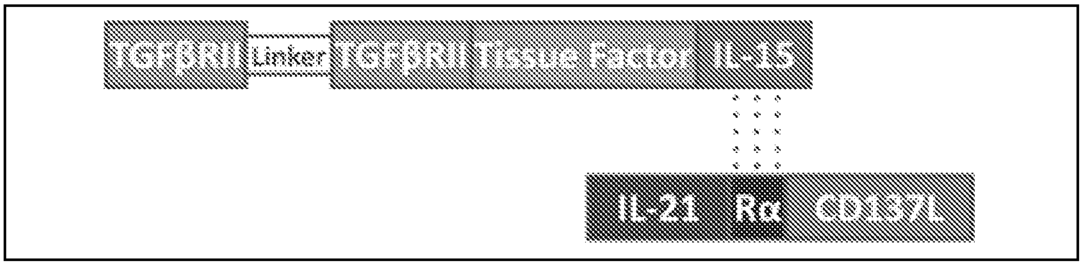

FIG. 130 shows an additional schematic of the TGFRt15-21s137L construct.

Figure 131:
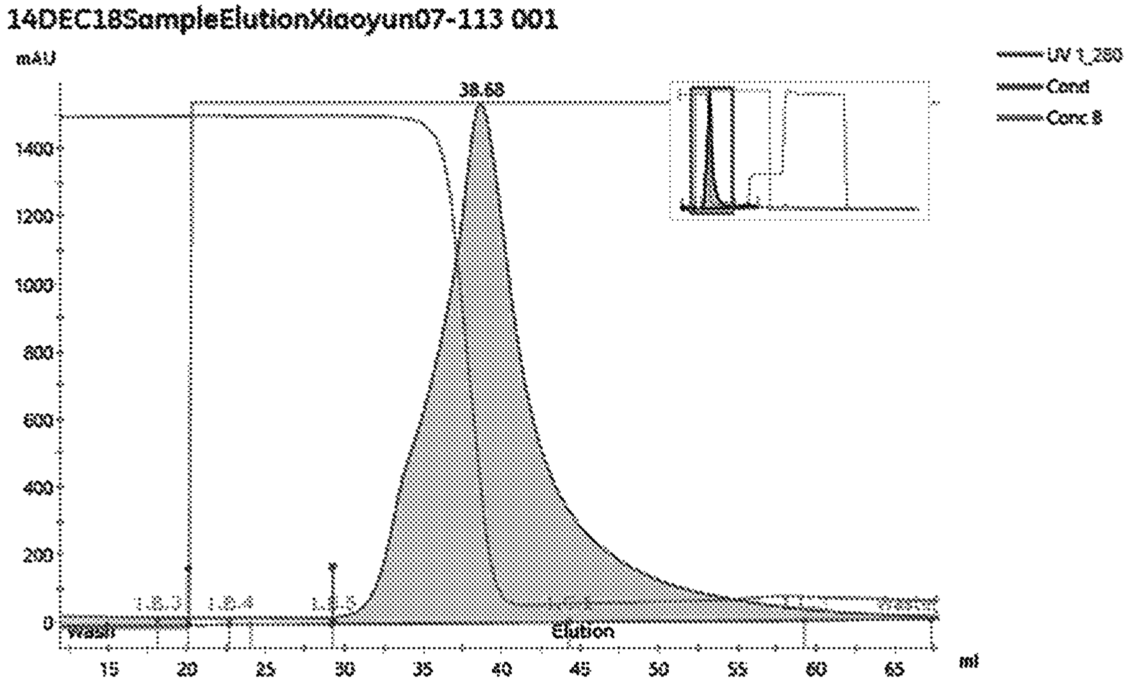

FIG. 131 is a line graph showing the chromatographic profile of TGFRt15-21s137L protein containing cell culture supernatant following binding and elution on anti-TF antibody resin.

Figure 132:
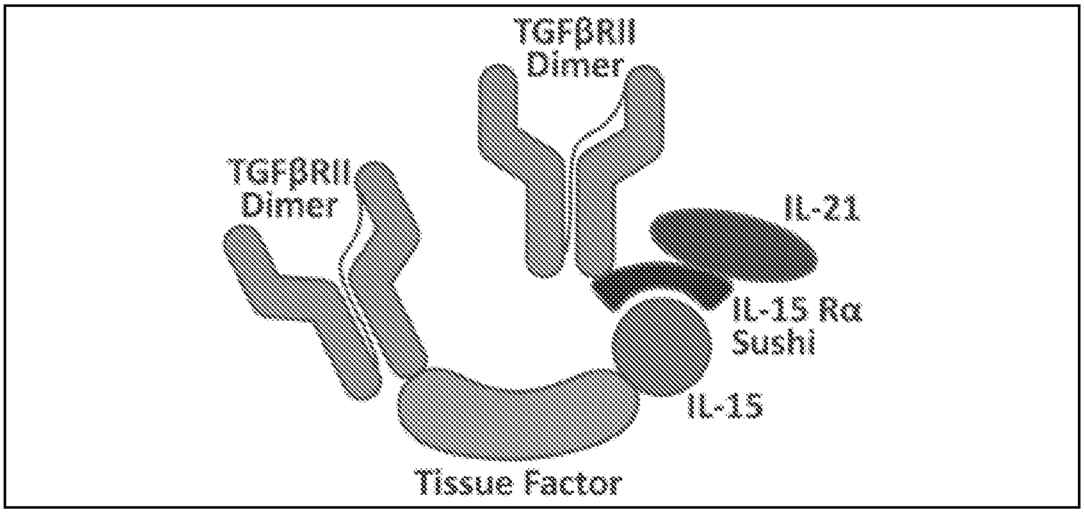

FIG. 132 shows a schematic of the TGFRt15-TGFRs21 construct.

Figure 133:
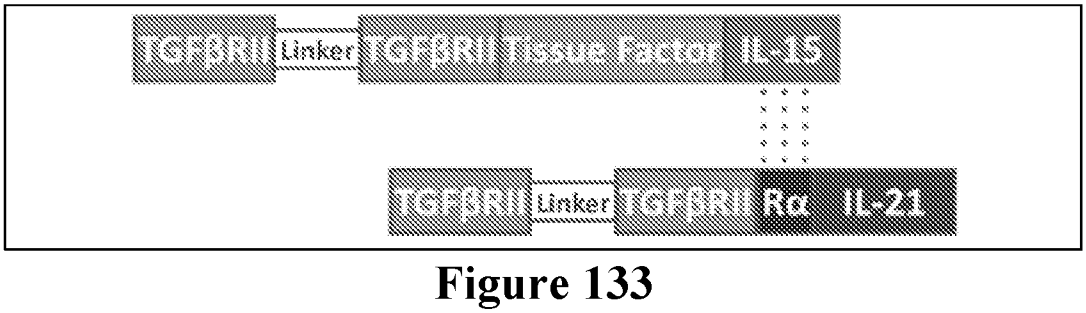

FIG. 133 shows an additional schematic of the TGFRt15-TGFRs21 construct.

Figure 134:
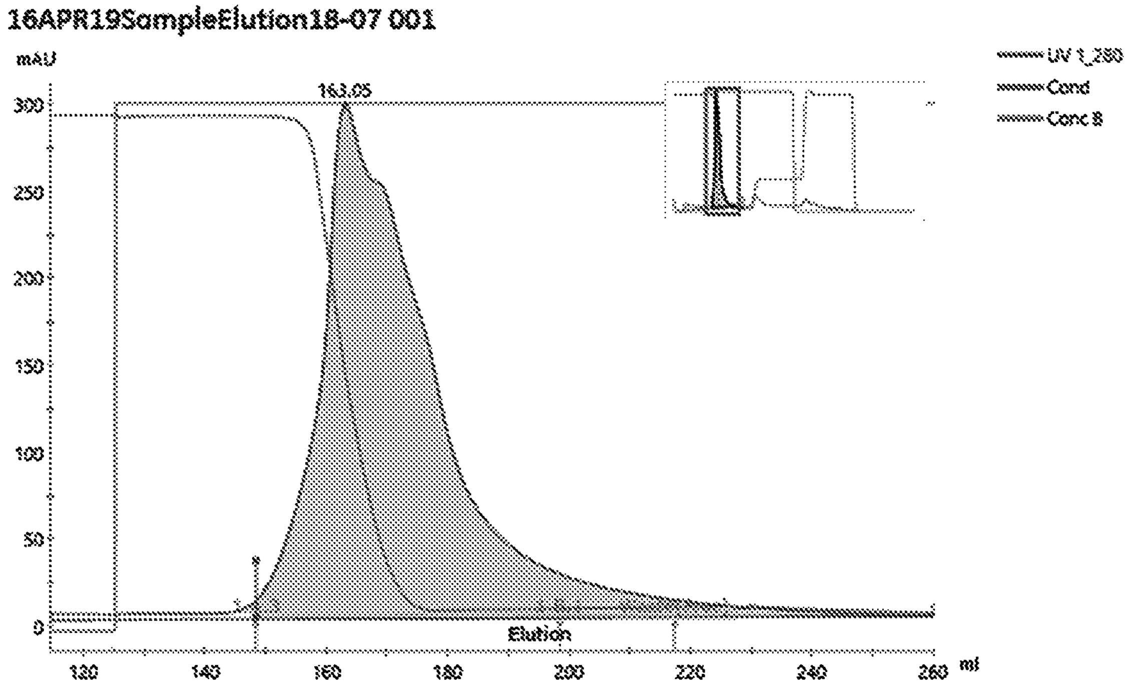

FIG. 134 is a line graph showing the chromatographic profile of TGFRt15-TGFRs21 protein containing cell culture supernatant following binding and elution on anti-TF antibody resin.

Figure 135:
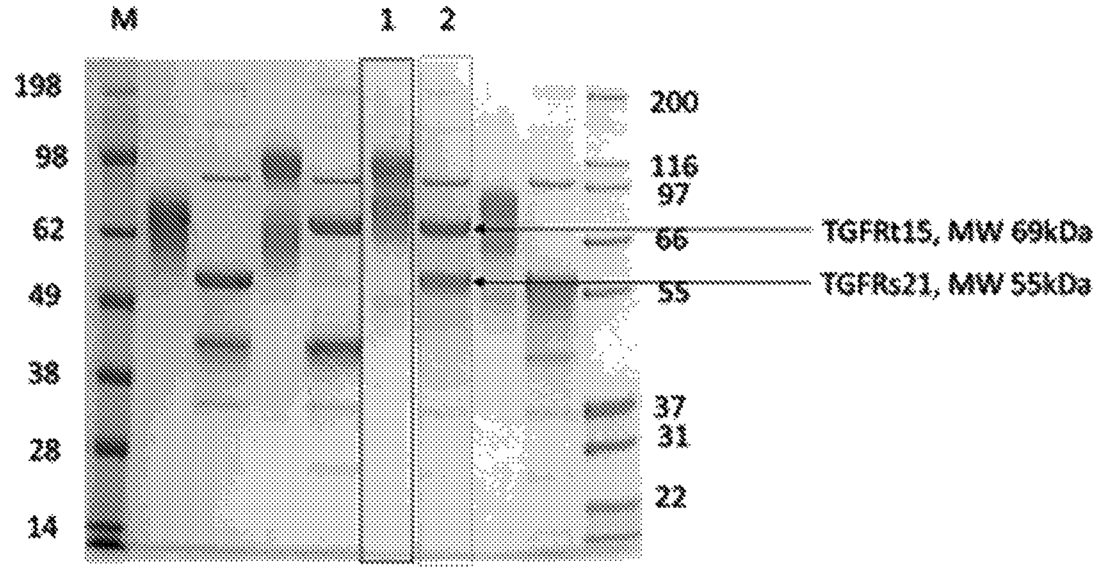

FIG. 135 shows TGFRt15-TGFRs21 before and after deglycosylation as analyzed by reduced SDS-PAGE.

Figure 136A:
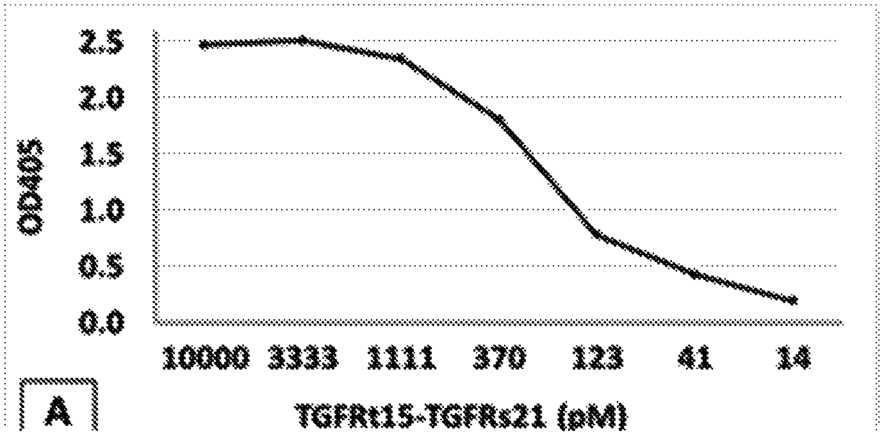
Figure 136B:
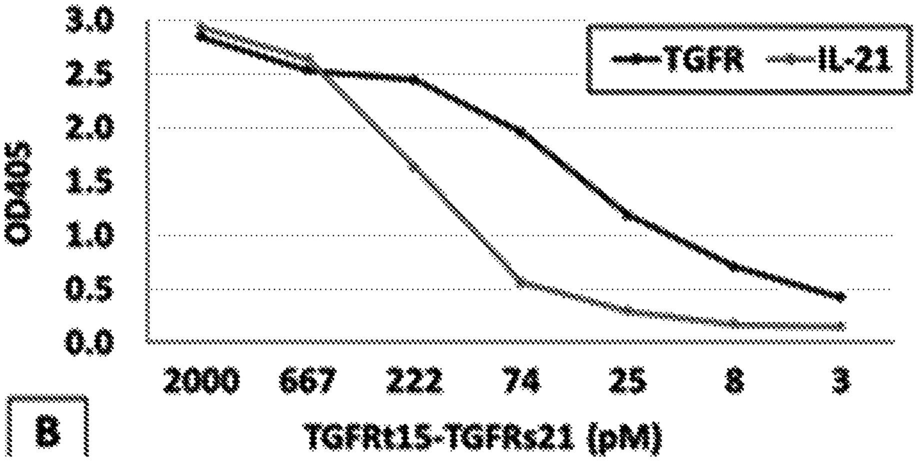

FIGS. 136A and 136B show detection of components of TGFRt15-TGFRs21 using ELISA.

Figure 137A:
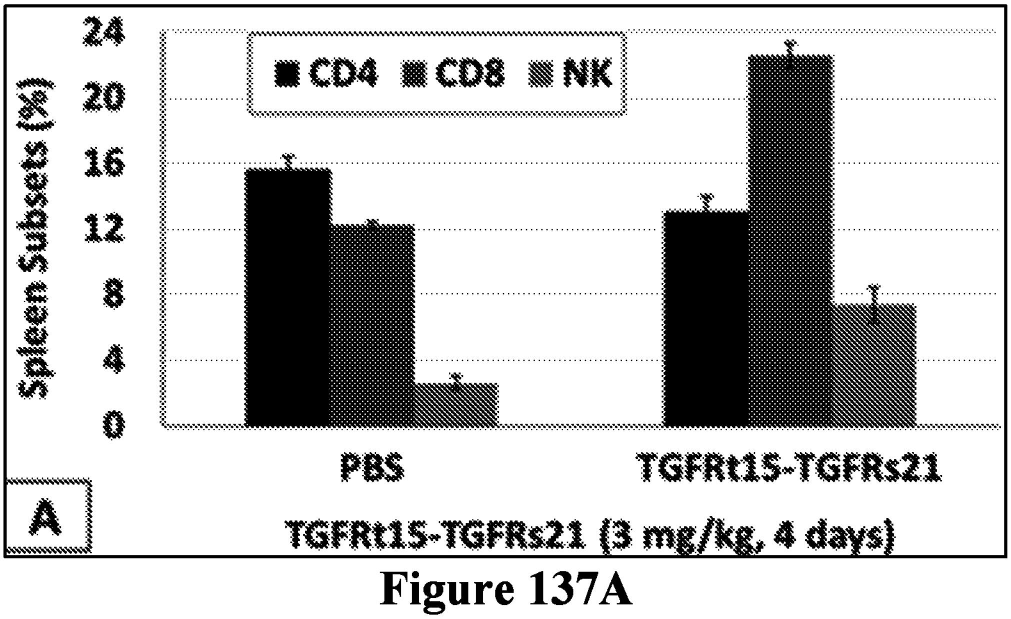
Figure 137B:
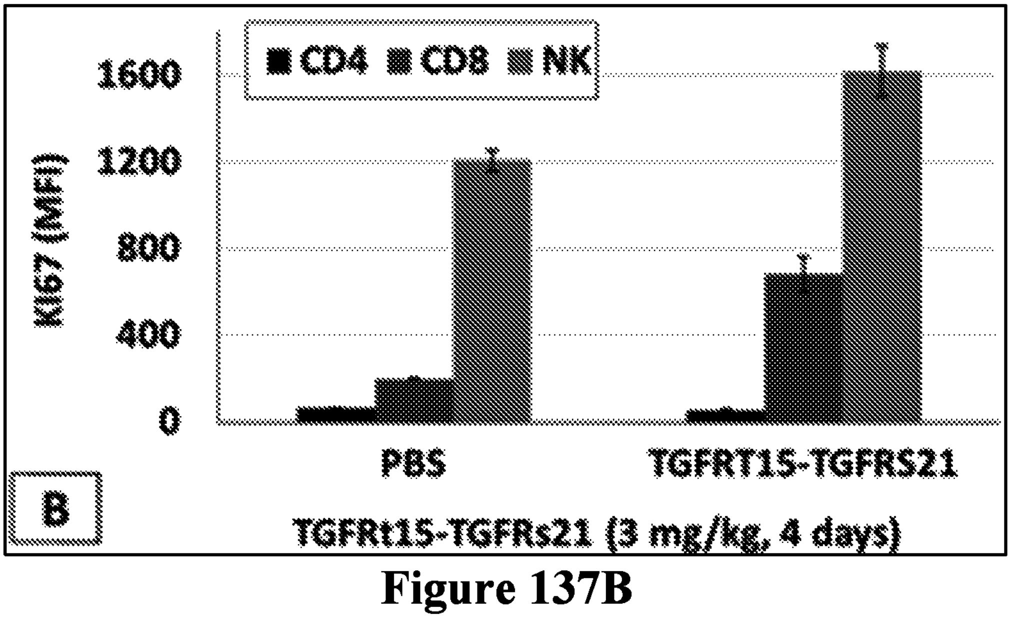

FIGS. 137A and 137B show the percentages and proliferation of CD4$^+$ T cells, CD8$^+$ T cells, and natural killer (NK) cells present in the spleen of control-treated and TGFRt15-TGFRs21-treated mice.

Figure 138:
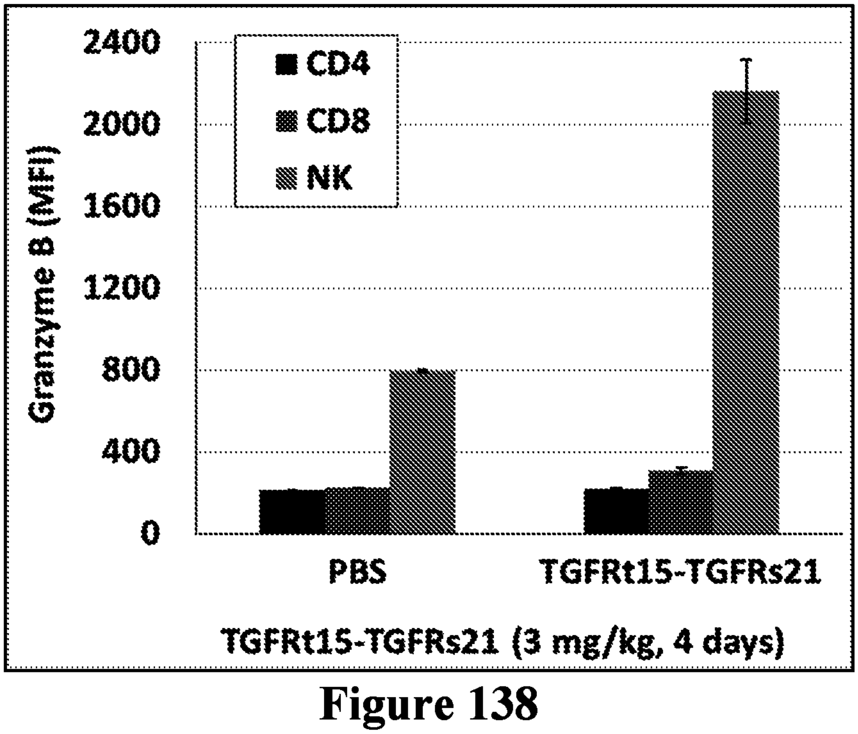

FIG. 138 shows upregulation of Granzyme B expression of splenocytes in mice treated with TGFRt15-TGFRs21.

Figure 139:
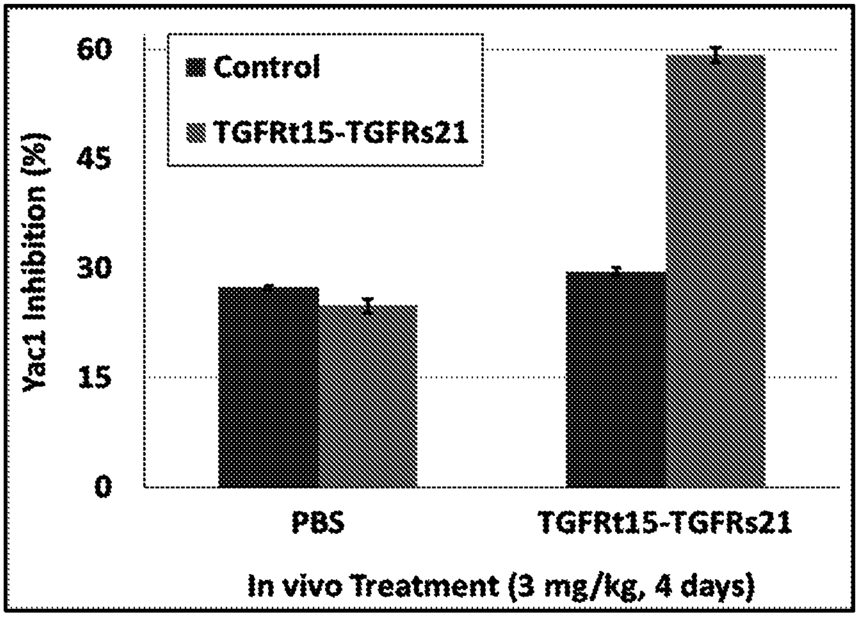

FIG. 139 shows enhancement of cytotoxicity of splenocytes by TGFRt15-TGFRs21 in C57BL/6 Mice.

Figure 140:
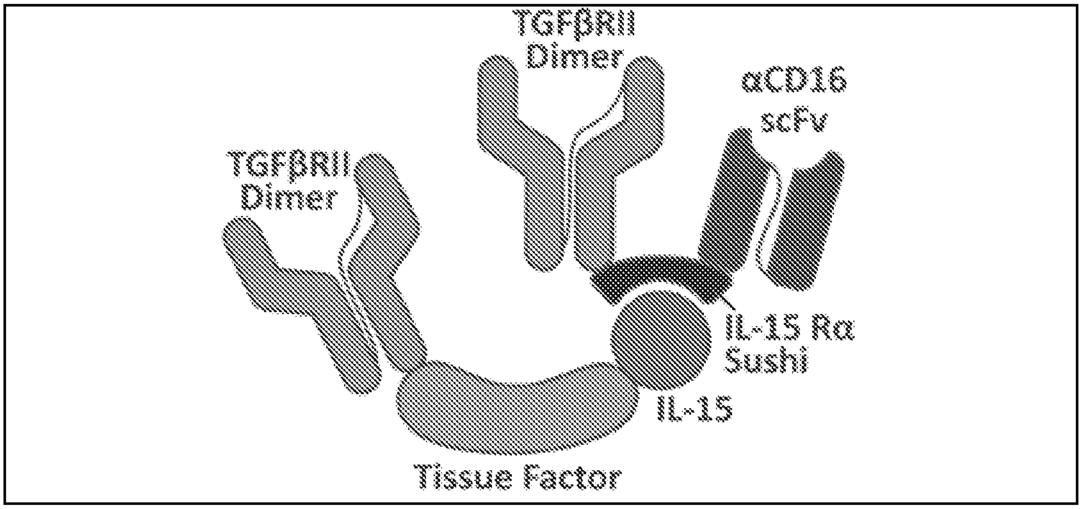

FIG. 140 shows a schematic of the TGFRt15-TGFRs16 construct.

Figure 141:
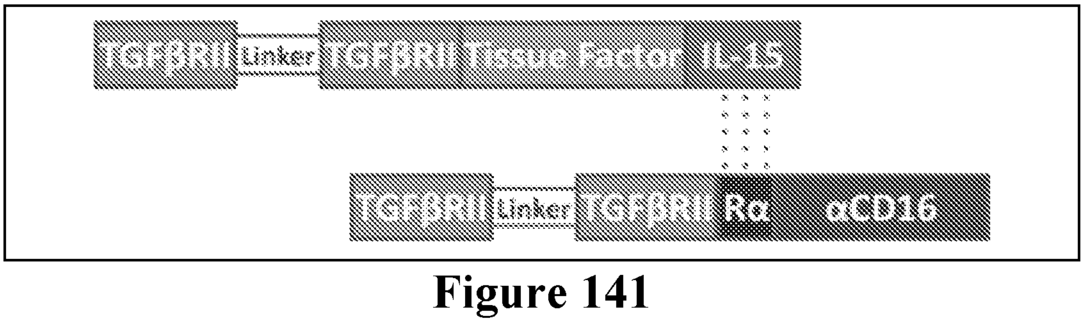

FIG. 141 shows an additional schematic of the TGFRt15-TGFRs16 construct.

Figure 142:
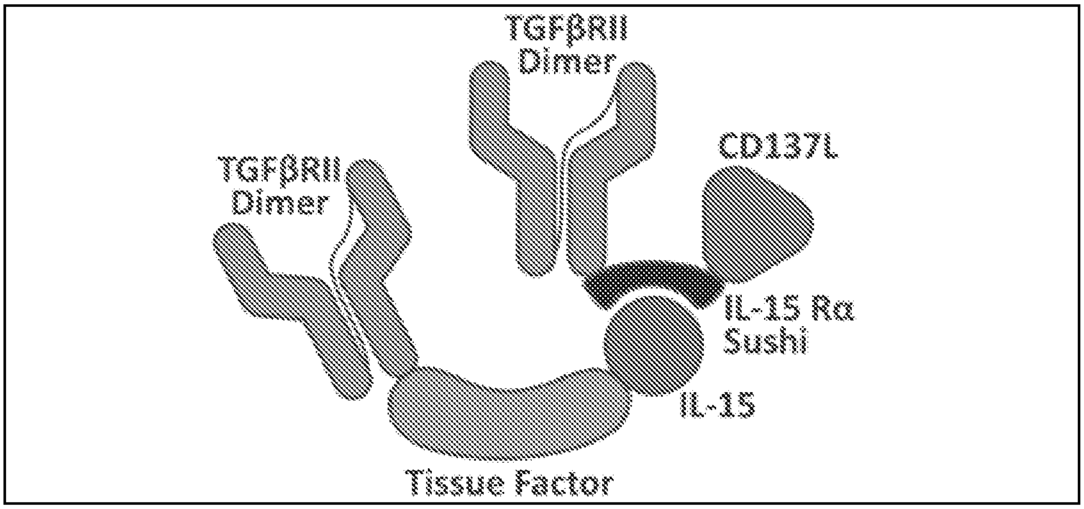

FIG. 142 shows a schematic of the TGFRt15-TGFRs137L construct.

Figure 143:
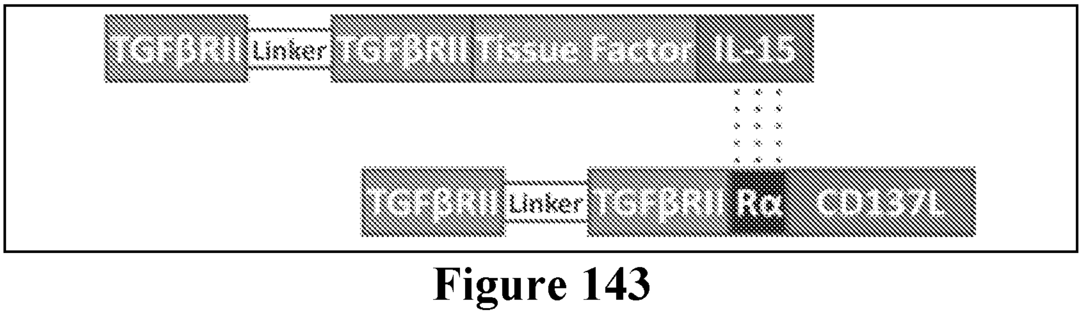

FIG. 143 shows an additional schematic of the TGFRt15-TGFRs137L construct.

Figure 144:
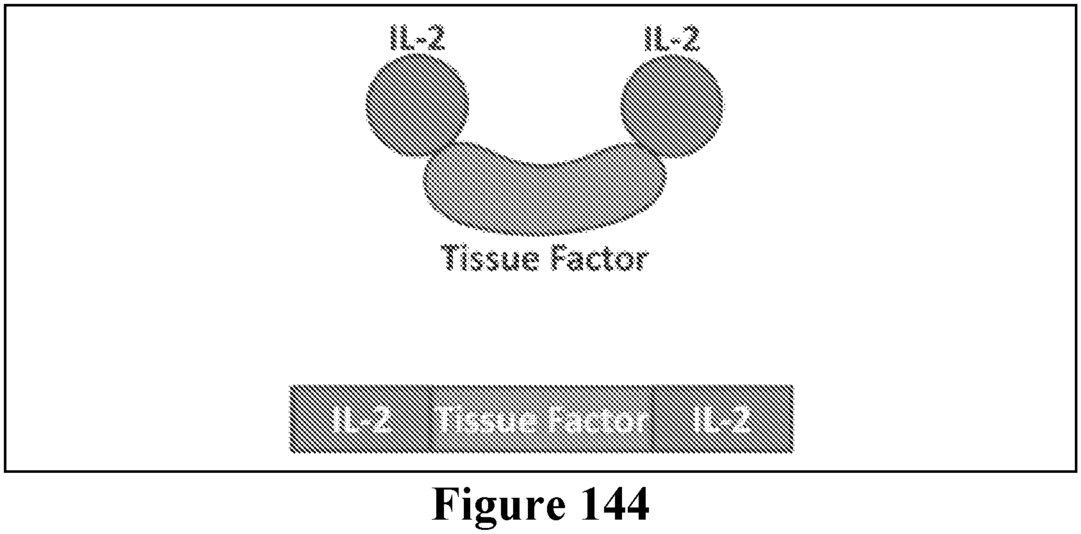

FIG. 144 are schematic diagrams of an exemplary 2t2 single-chain chimeric polypeptide.

Figure 145:
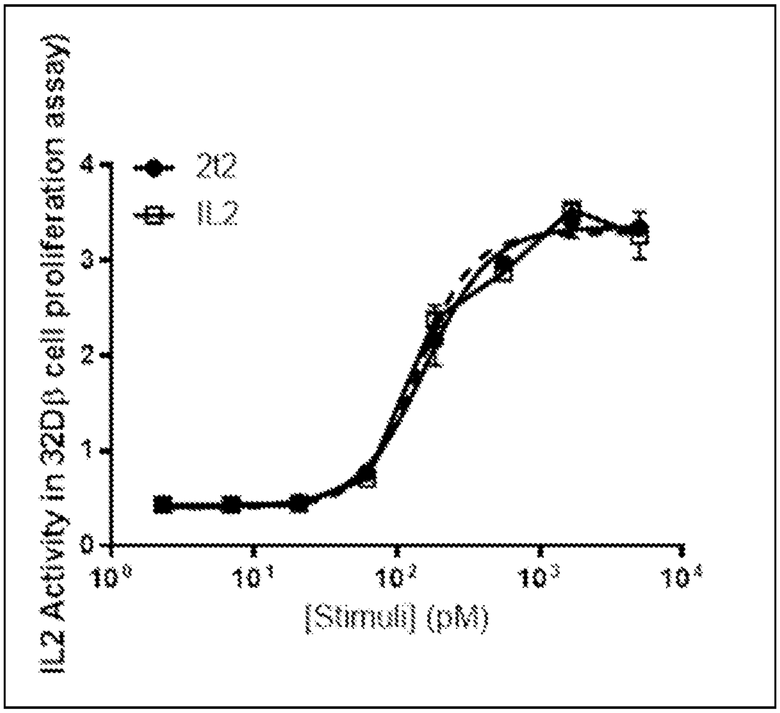

FIG. 145 shows IL-2 activity in 2t2 as compared to recombinant IL-2 using a 32Dβ cell proliferation assay.

Figure 146:
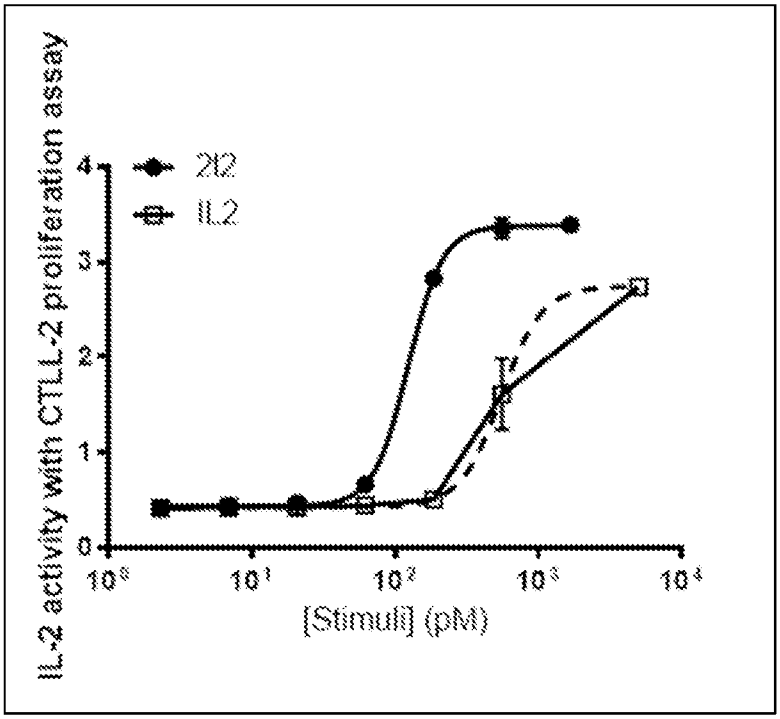

FIG. 146 shows IL-2 activity in 2t2 as compared to recombinant IL-2 using a CTLL-2 cell proliferation assay.

Figure 147:
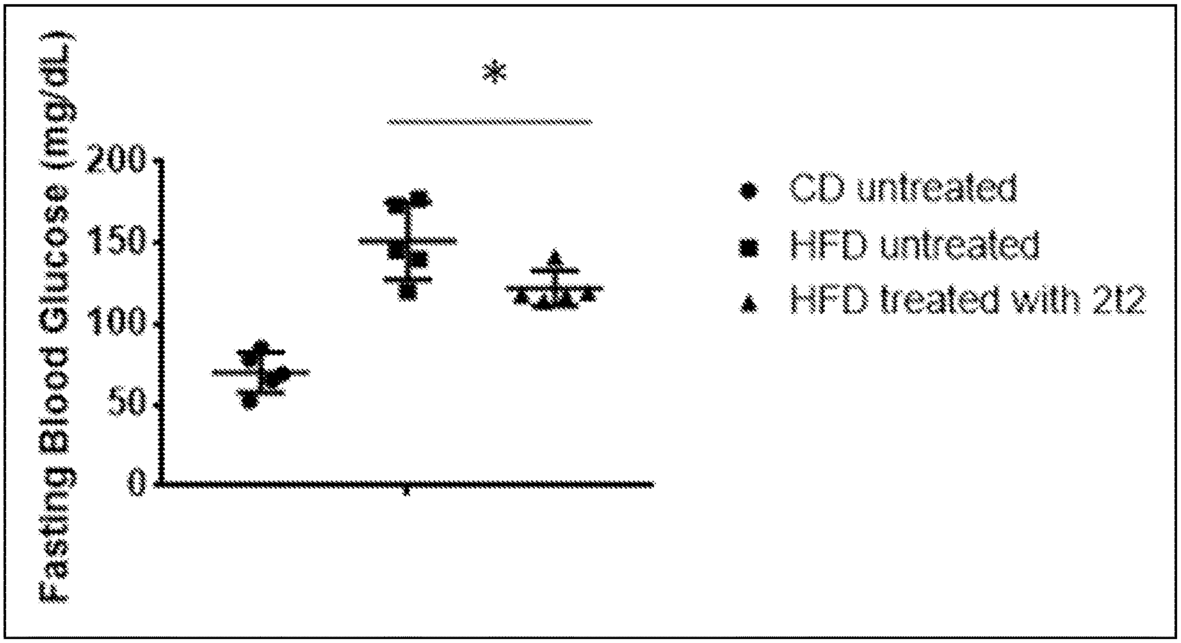

FIG. 147 shows the fasting blood glucose levels in ApoE$^{-/-}$ mice fed with standard chow or a high fat diet and treated with a PBS control (untreated) or with 2t2.

Figure 148:
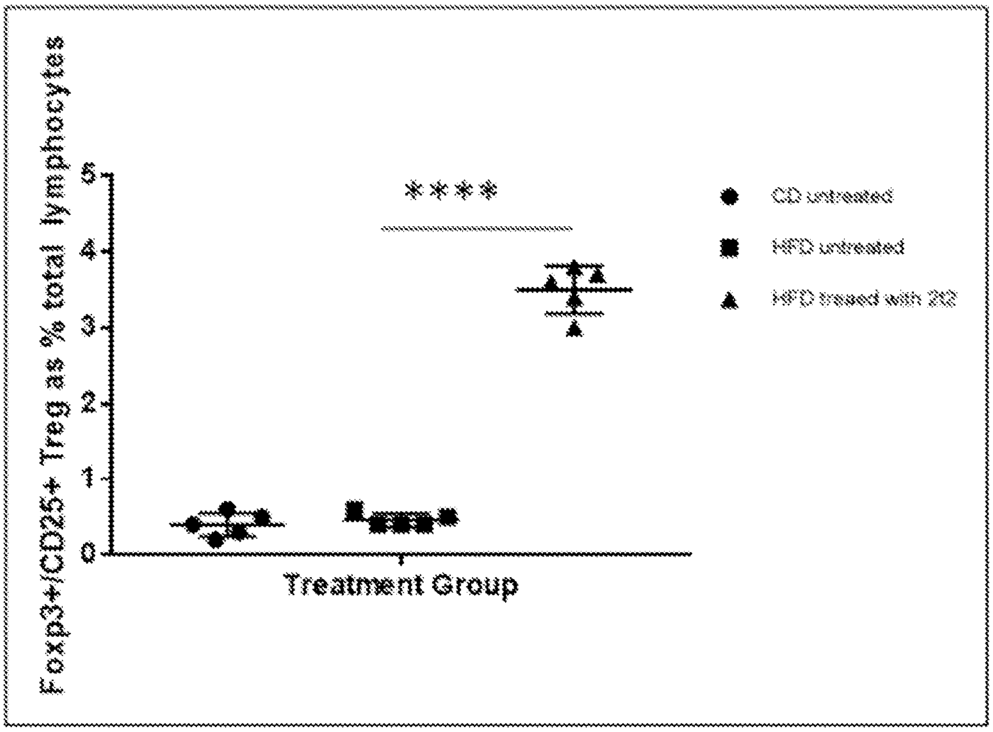

FIG. 148 shows the ratio of CD4$^+$CD25$^+$FoxP3$^+$ T regulatory cells in blood lymphocytes from ApoE$^{-/-}$ mice fed with standard chow or a high fat diet and treated with a PBS control (untreated) or with 2t2.

Figure 149:
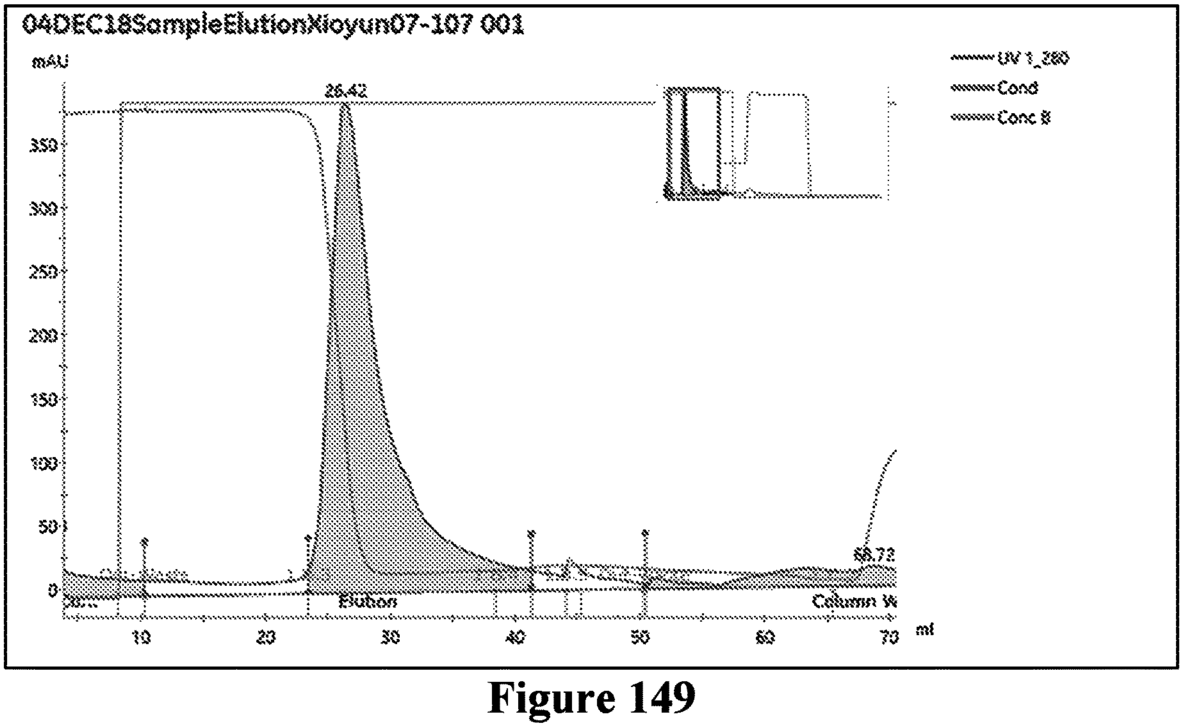

FIG. 149 is a line graph showing the chromatographic profile of 2t2 protein containing cell culture supernatant following binding and elution on anti-TF antibody resin.

Figure 150:
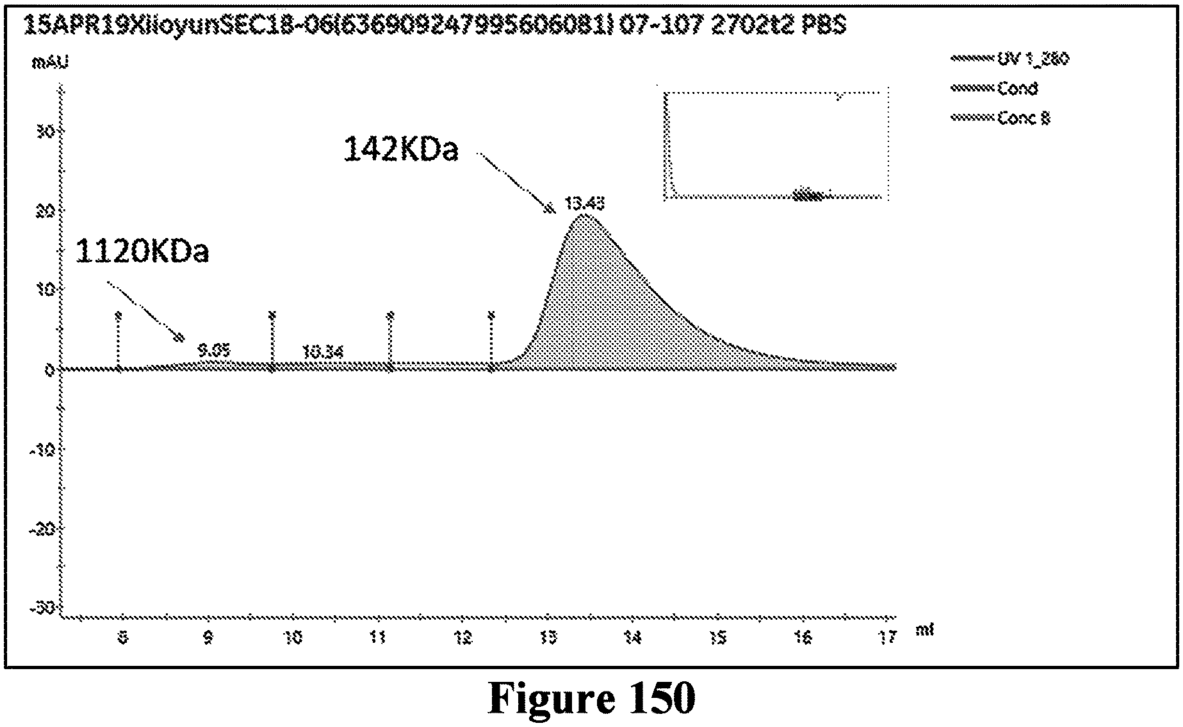

FIG. 150 shows an analytical SEC profile of 2t2.

Figure 151A:
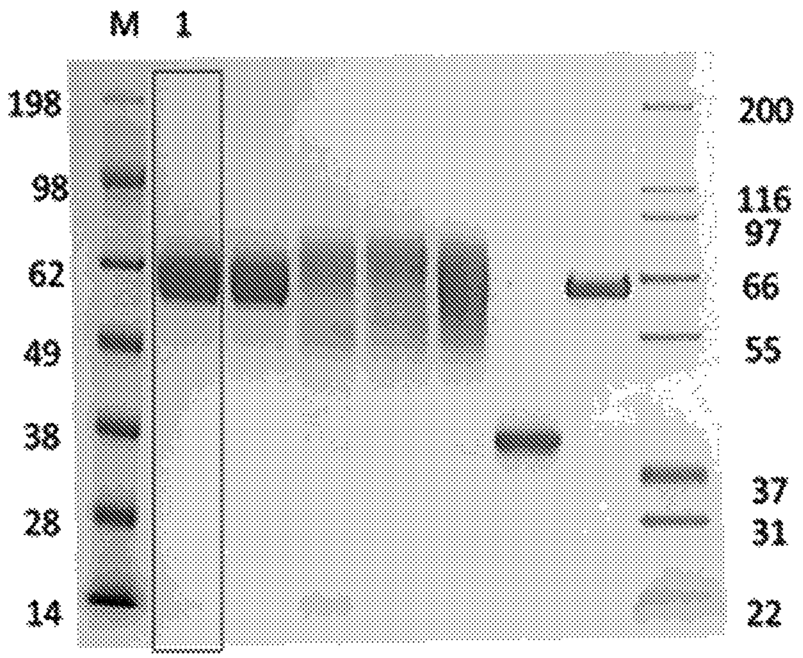
Figure 151B:
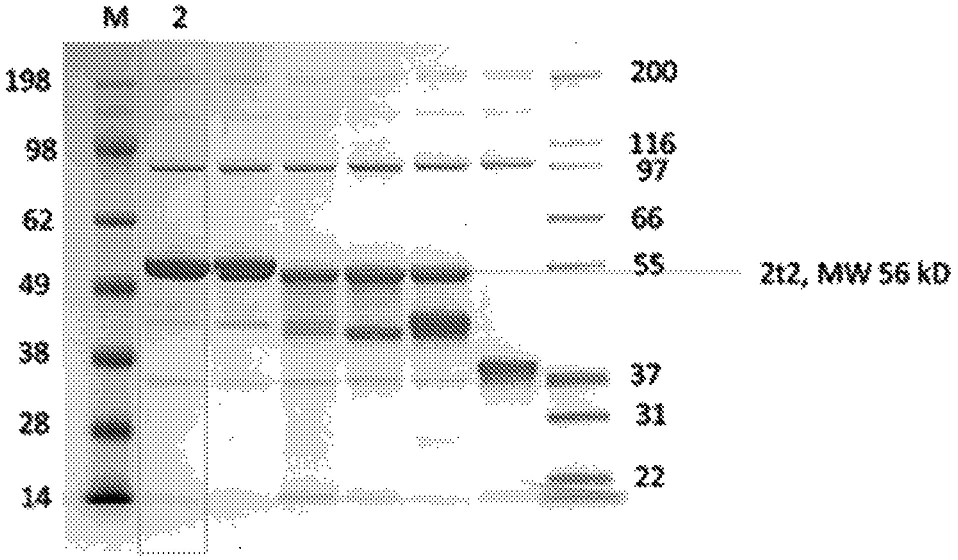

FIGS. 151A and 151B show reduced SDS-PAGE analysis of 2t2 before and after deglycosylation. FIG. 151A shows reduced SDS-PAGE analysis of 2t2 before deglycosylation. FIG. 151B shows reduced SDS-PAGE analysis of 2t2 after deglycosylation.

Figure 152A:
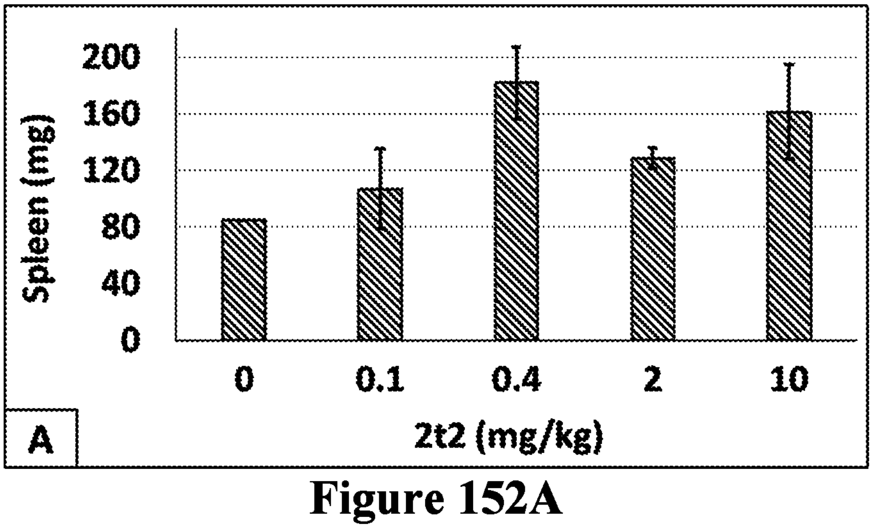
Figure 152B:
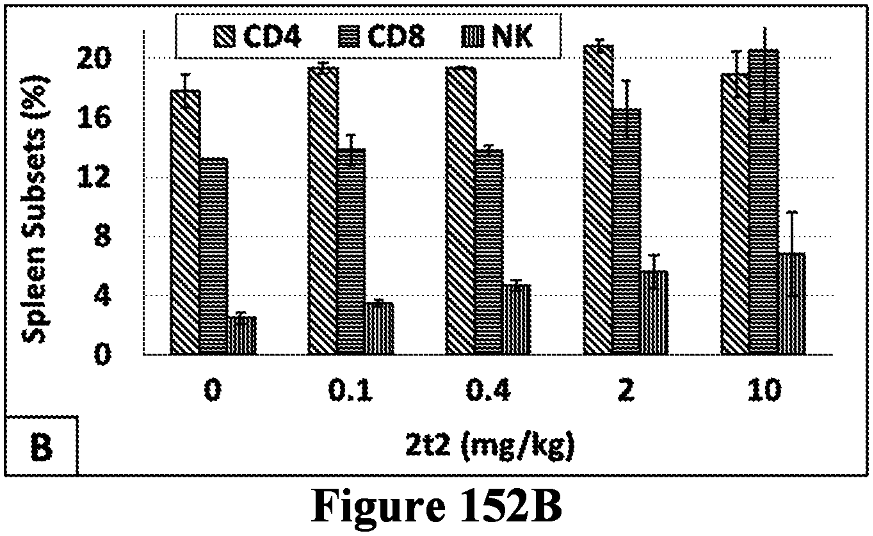

FIGS. 152A and 152B show results of immunostimulation in C57BL/6 mice using 2t2. FIG. 152A shows spleen weight following treatment with 2t2. FIG. 152B shows the percentages of immune cell types following 2t2 treatment.

Figure 153:
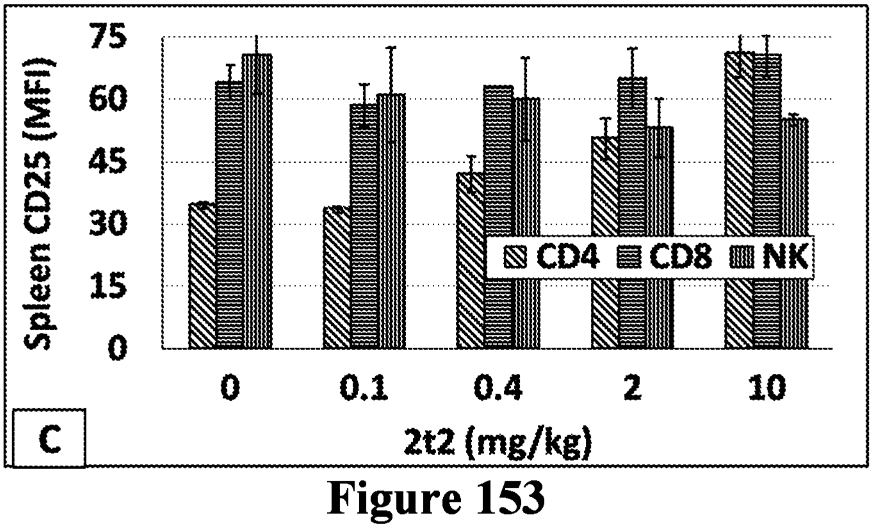

FIG. 153 shows upregulation of CD25 expression of CD4$^+$ T cells in mice treated with 2t2.

Figure 154:
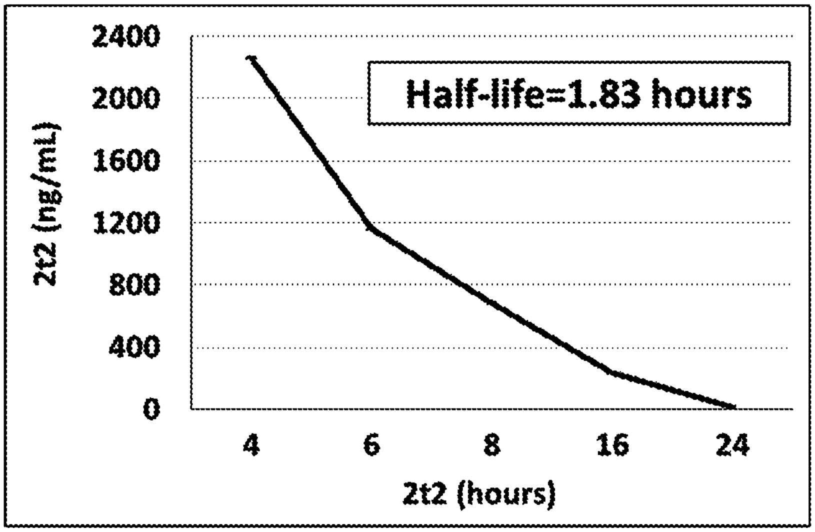

FIG. 154 shows the pharmacokinetics of 2t2 in C57BL/6 mice.

Figure 155A:
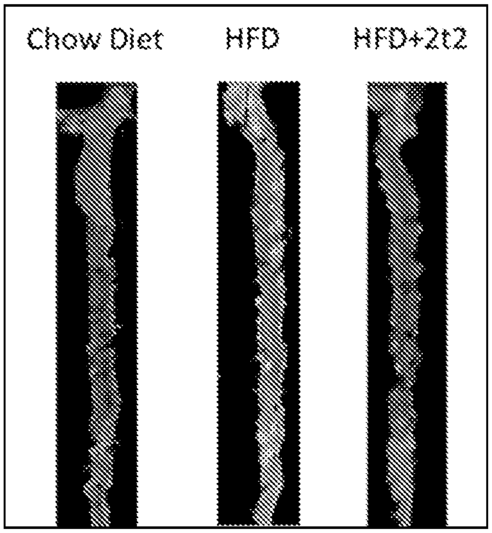
Figure 155B:
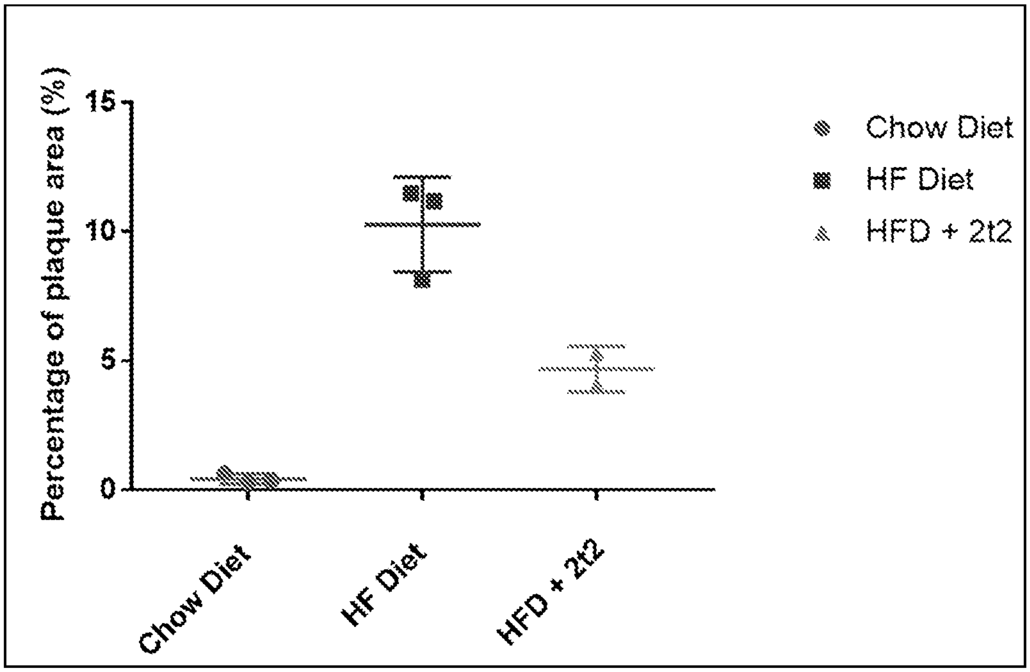

FIGS. 155A and 155B show effects of 2t2 in attenuating the formation of high fat-induced atherosclerotic plaques in ApoE$^{-/-}$ mice. FIG. 155A shows a representative view of atherosclerotic plaques from ApoE$^{-/-}$ mice fed with standard chow or a high fat diet and treated with either PBS control or 2t2. FIG. 155B shows the results of quantitative analysis of atherosclerotic plaques of each group.

Figure 156:
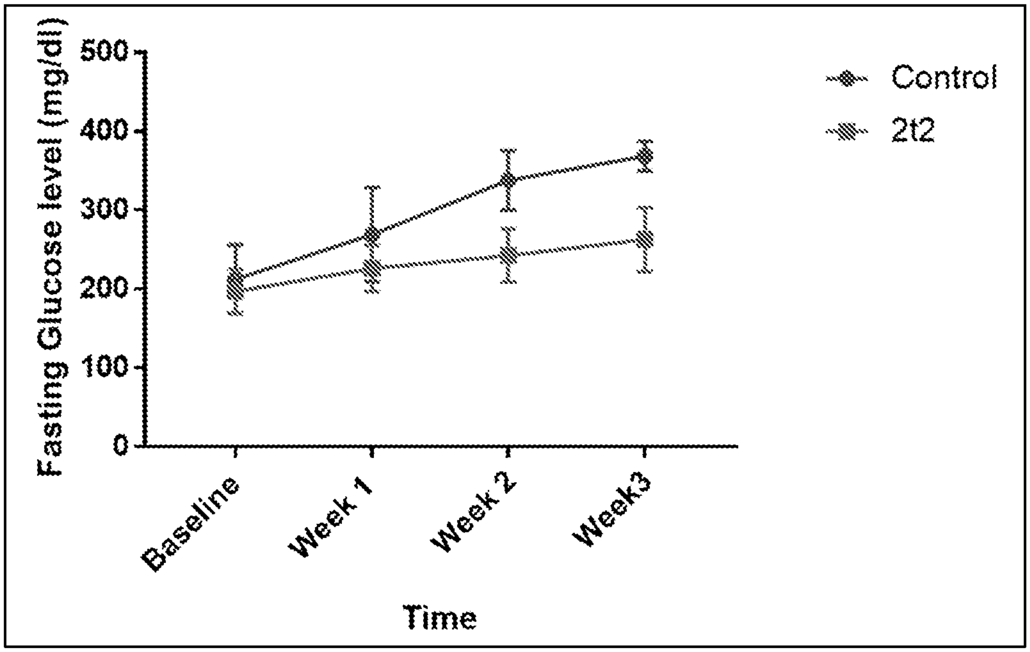

FIG. 156 shows fasting glucose levels in 2t2 treated-mice as compared to control-treated mice.

Figure 157:
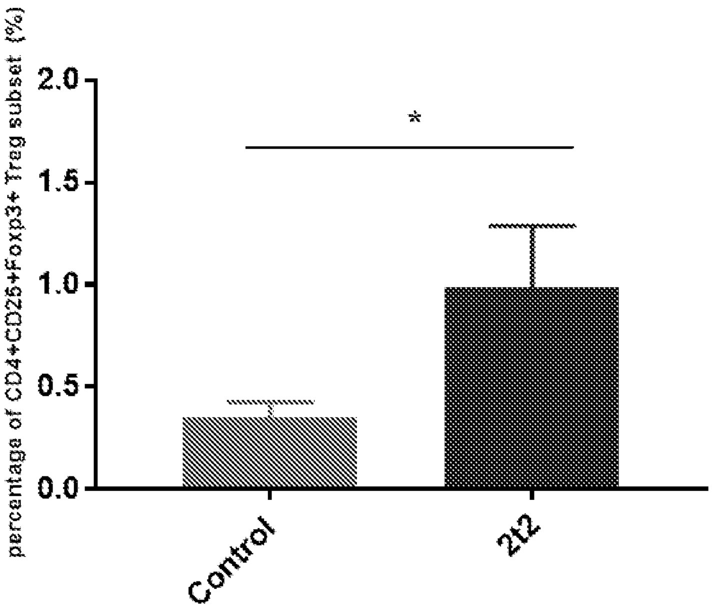

FIG. 157 shows the percentage of CD4$^+$CD25$^+$FoxP3$^+$ Tregs in blood lymphocytes from mice treated with 2t2 and control-treated mice.

Figure 158:
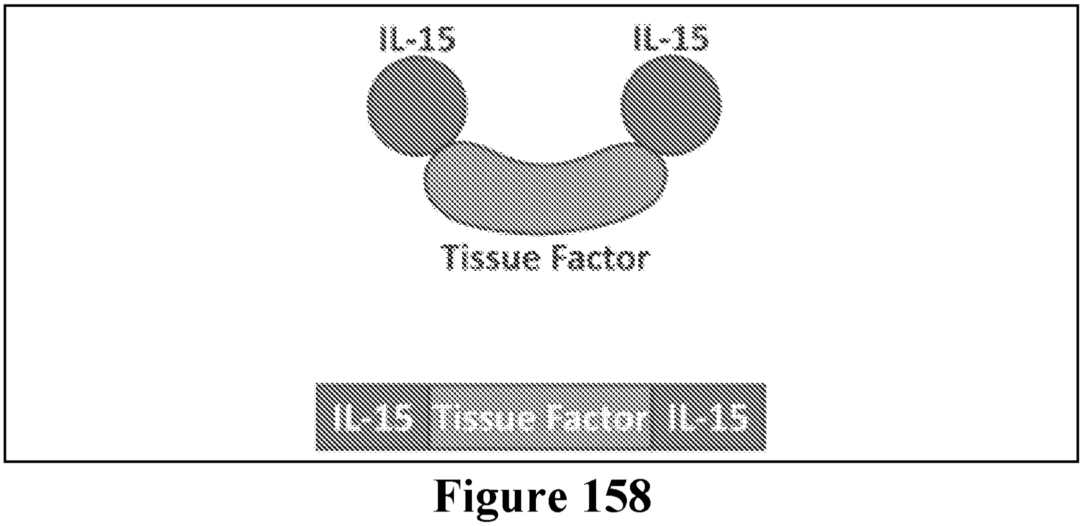

FIG. 158 are schematic diagrams of an exemplary 15t15 single-chain chimeric polypeptide.

Figure 159:
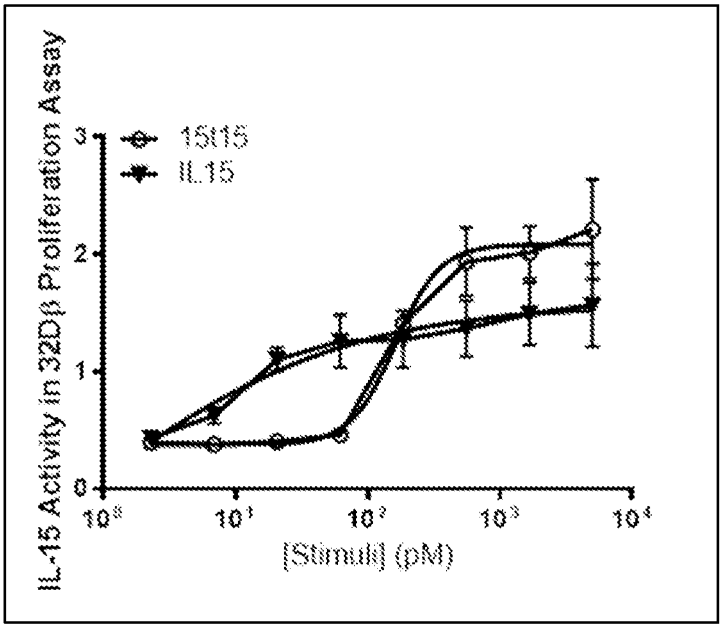

FIG. 159 shows the IL-15 activity of 15t15 as compared to recombinant IL-15 in a 32Dβ cell proliferation assay.

Figure 160:
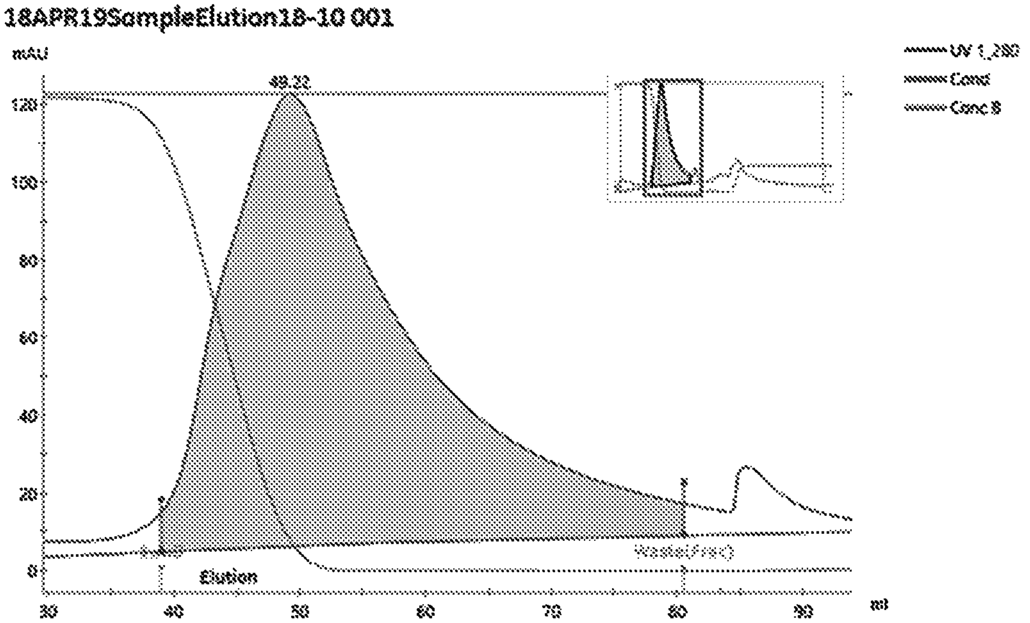

FIG. 160 is a line graph showing the chromatographic profile of 15t15 protein containing cell culture supernatant following binding and elution on anti-TF antibody resin.

Figure 161A:
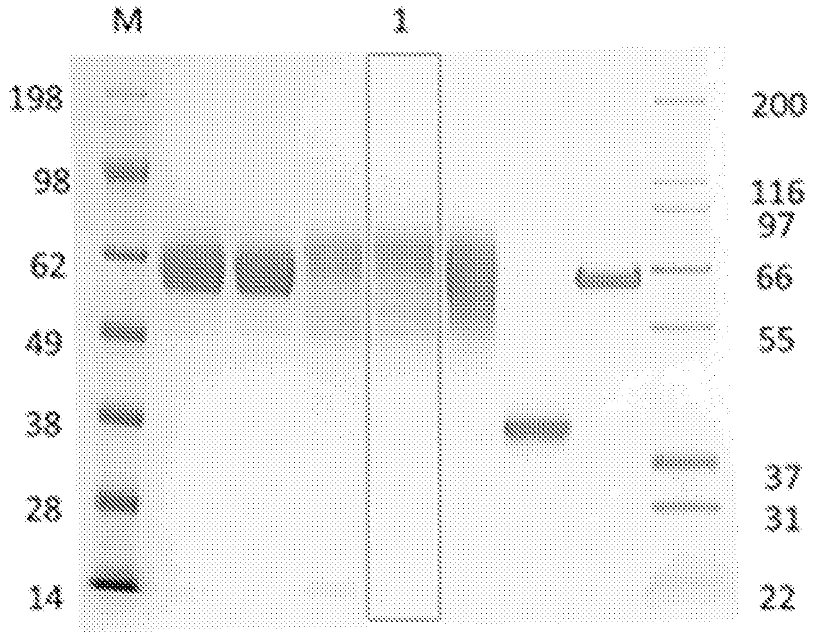
Figure 161B:
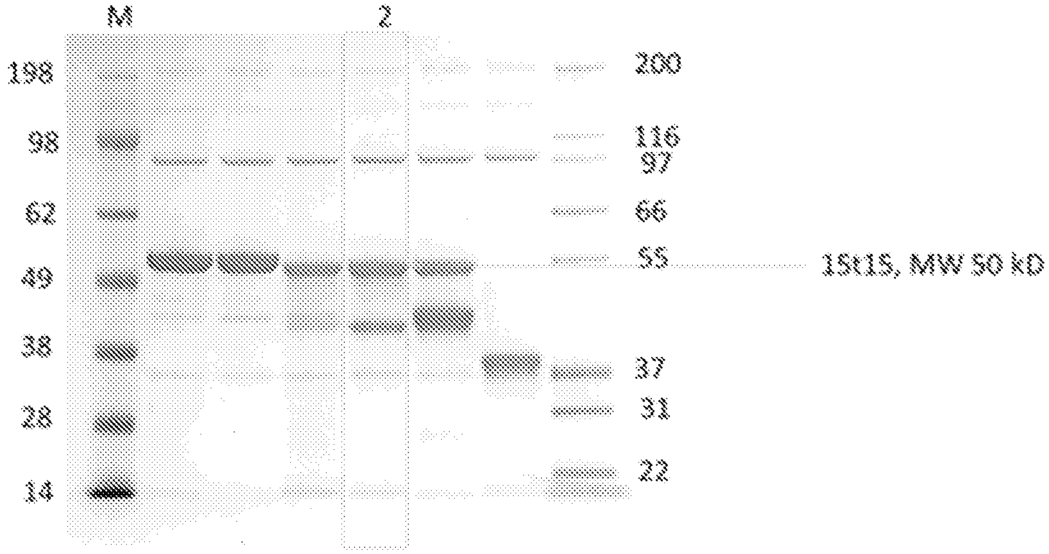

FIGS. 161A and 161B show reduced SDS-PAGE analysis of 15t15 before and after deglycosylation. FIG. 161A shows reduced SDS-PAGE analysis of 15t15 before deglycosylation. FIG. 161B shows reduced SDS-PAGE analysis of 15t15 after deglycosylation.

Figure 162A:
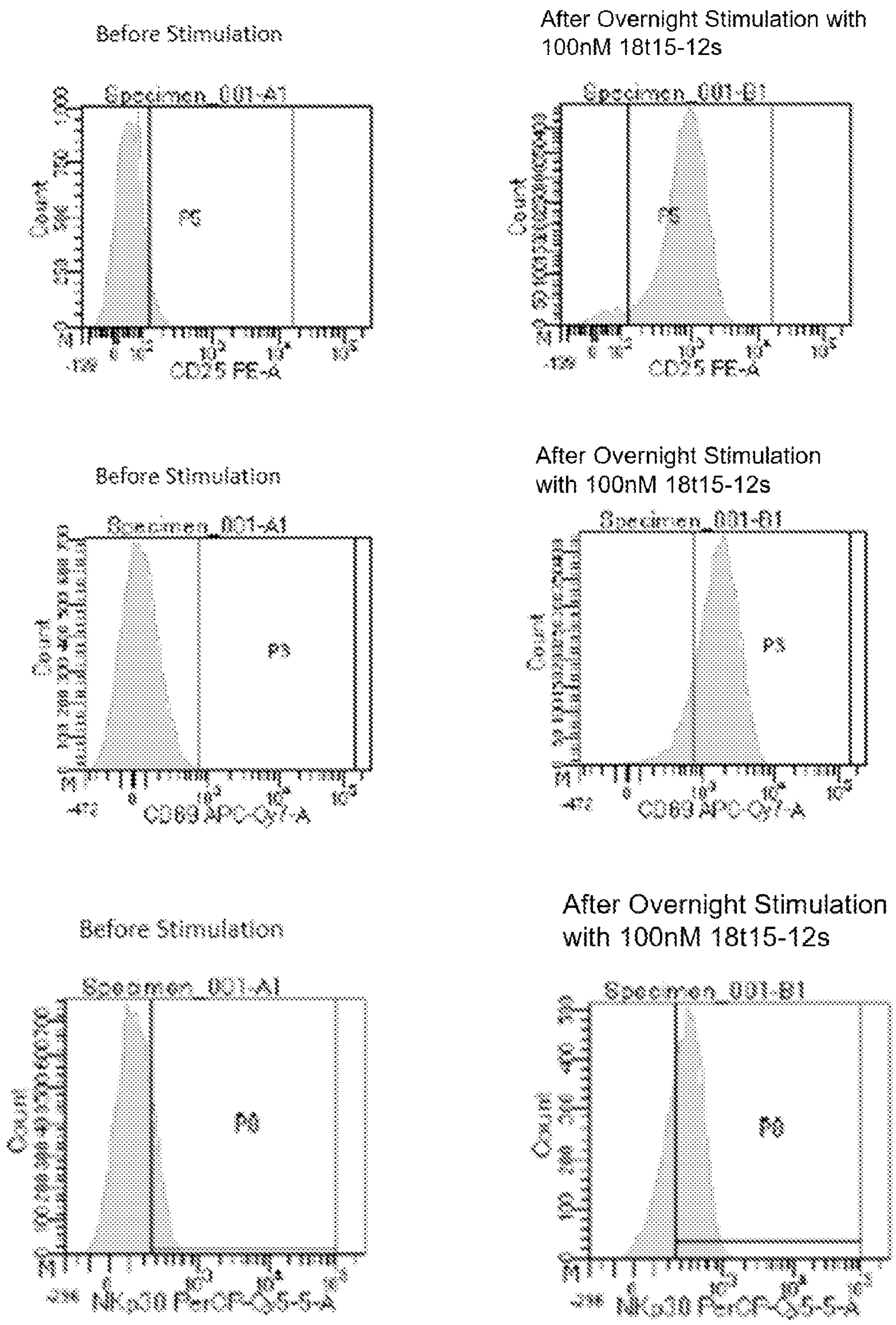
Figure 162B:
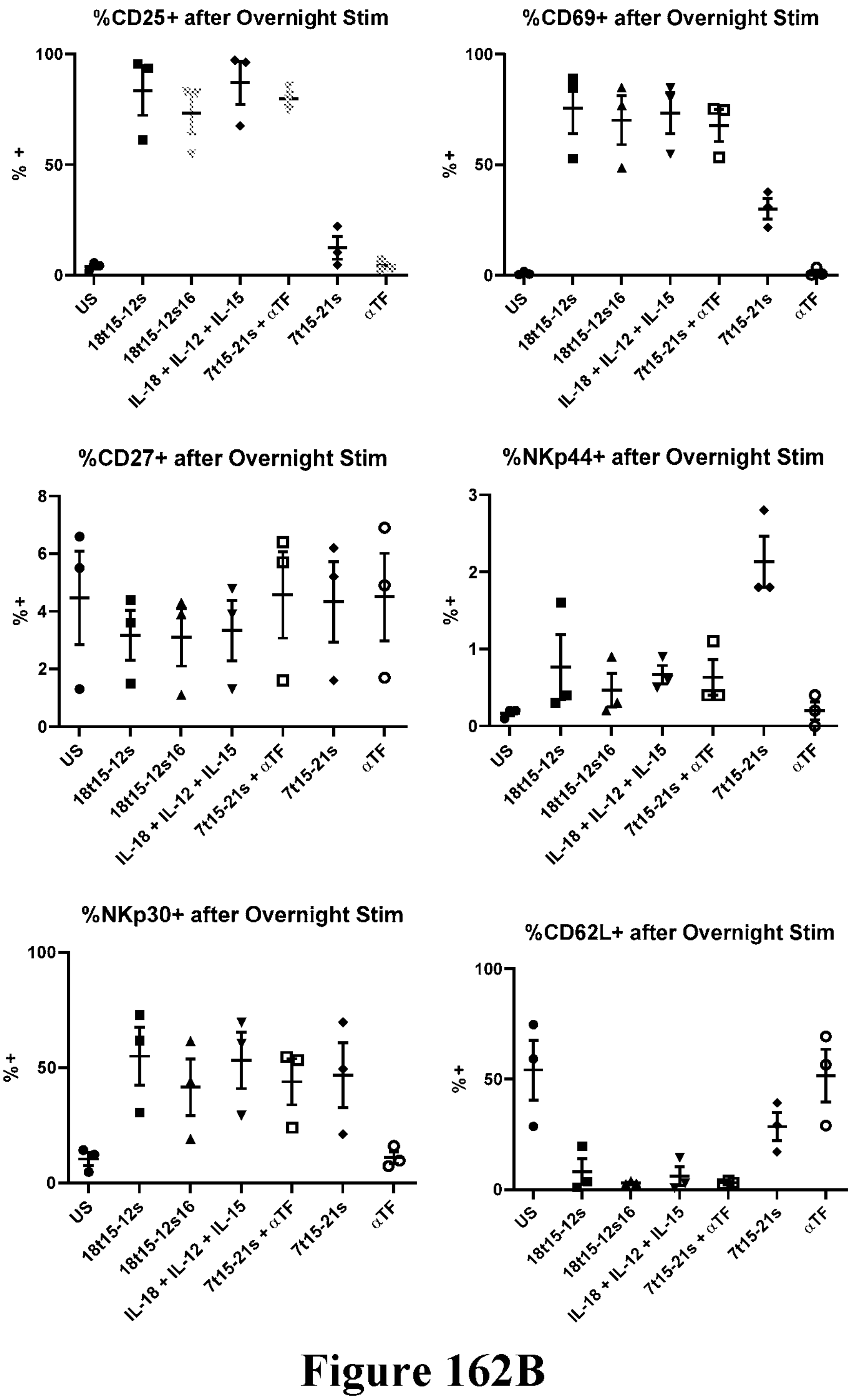

FIGS. 162A and 162B is a set of histograms (FIG. 162A) and a set of graphs (FIG. 162B) showing the change in the surface phenotype of NK cells after stimulation with 18t15-12s, 18t15-12s16, and 7t15-21s+anti-TF antibody.

Figure 163:
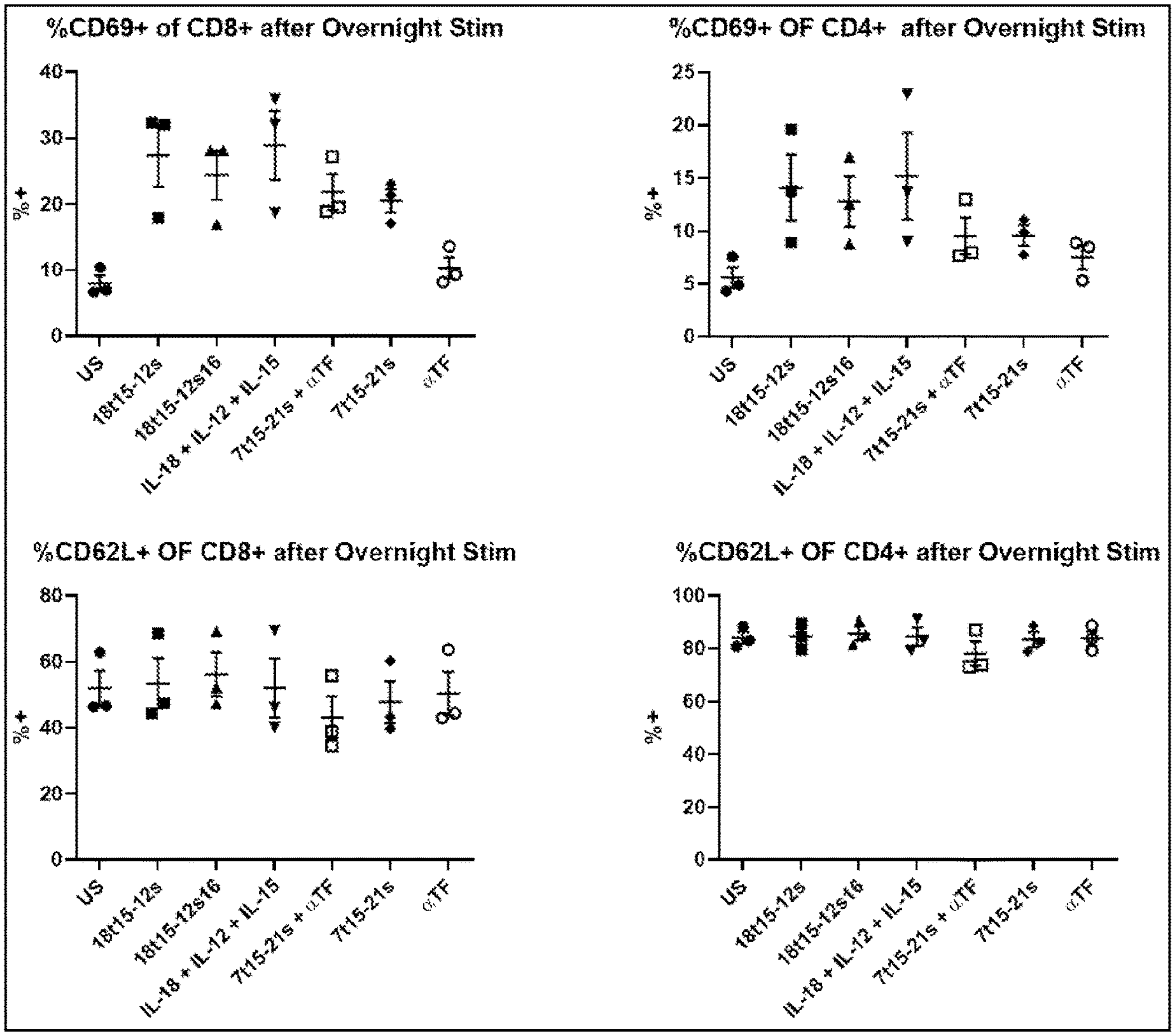

FIG. 163 is a set of graphs showing changes in the surface phenotype of lymphocyte populations after stimulation with 18t15-12s, 18t15-12s16, and 7t15-21s.

Figure 164:
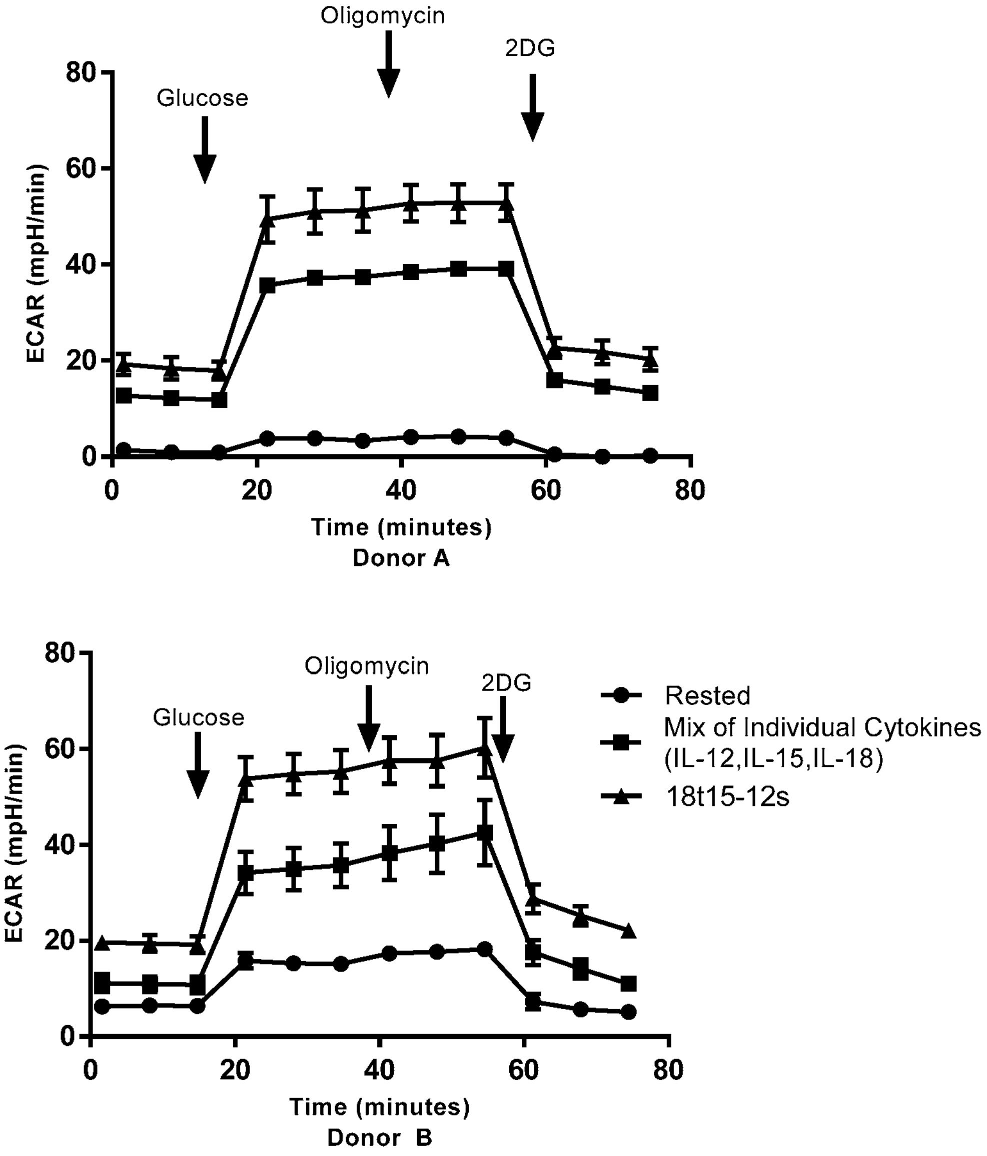

FIG. 164 is a set of graphs showing an increase in glycolysis in NK cells following treatment with 18t15-12s.

Figure 165:
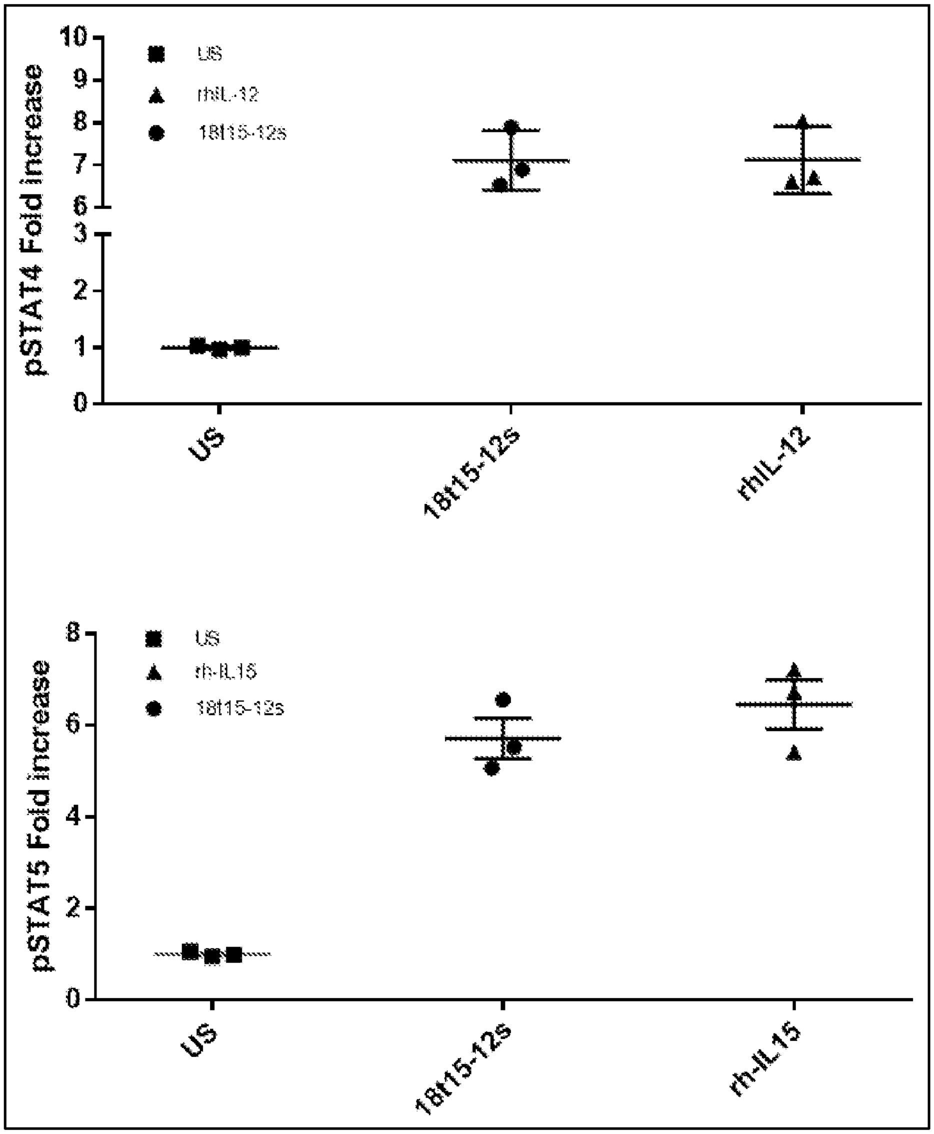

FIG. 165 is a set of graphs showing an increase in phospho-STAT4 and phospho-STAT5 levels in NK cells after stimulation with 18t15-12s.

Figure 166:
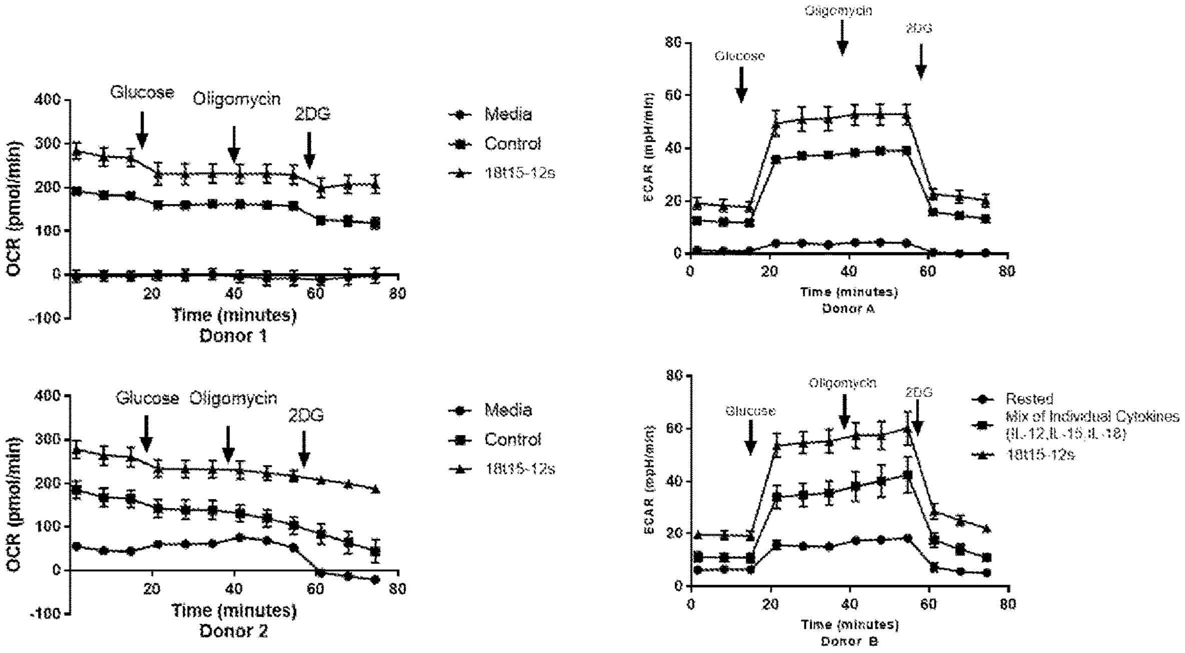

FIG. 166 is a set of graphs showing that overnight stimulation of NK cells with 18t15-12s enhances cell metabolism.

Figure 167A:
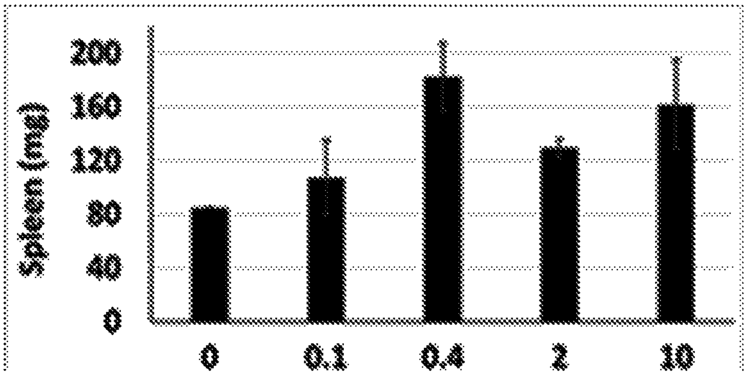
Figure 167B:
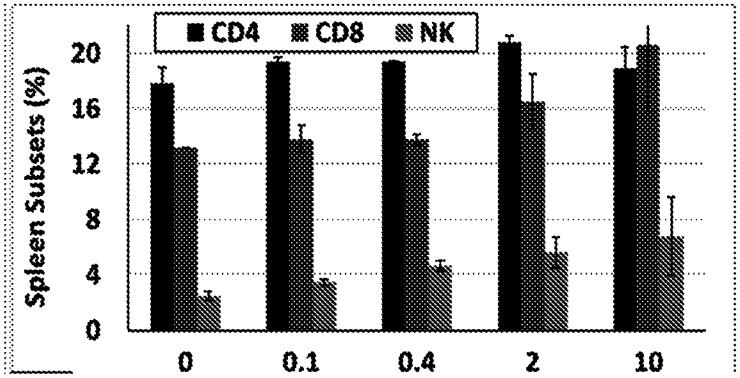
Figure 167C:
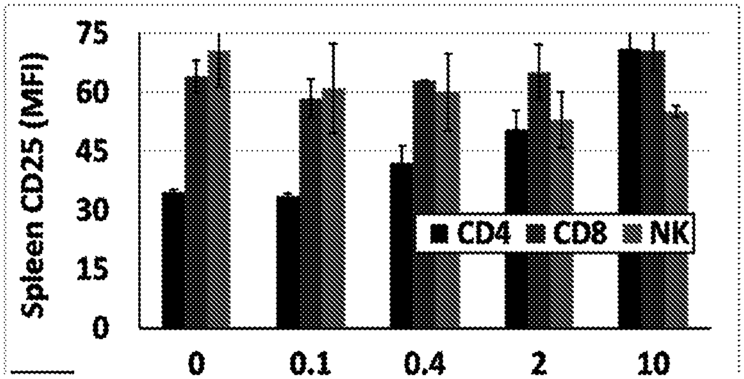

FIG. 167A-C is a set of graphs showing immunostimulation in C57BL/6 mice following treatment with 2t2.

Figure 168A:
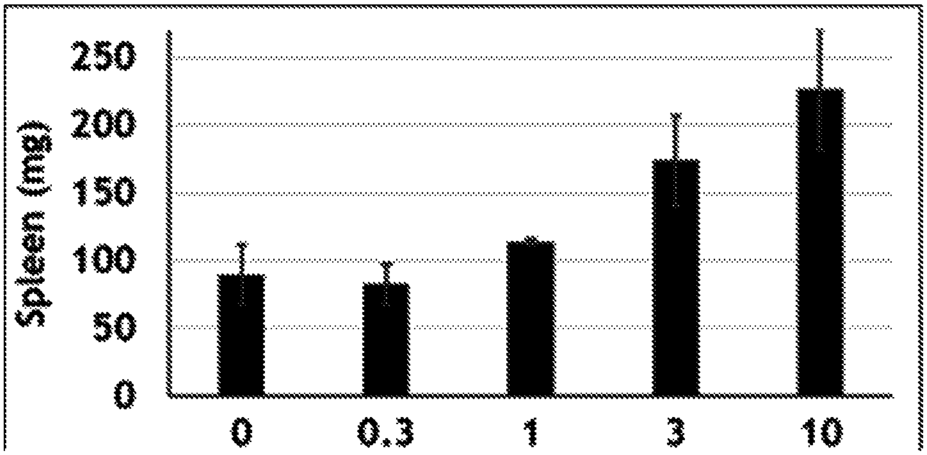
Figure 168B:
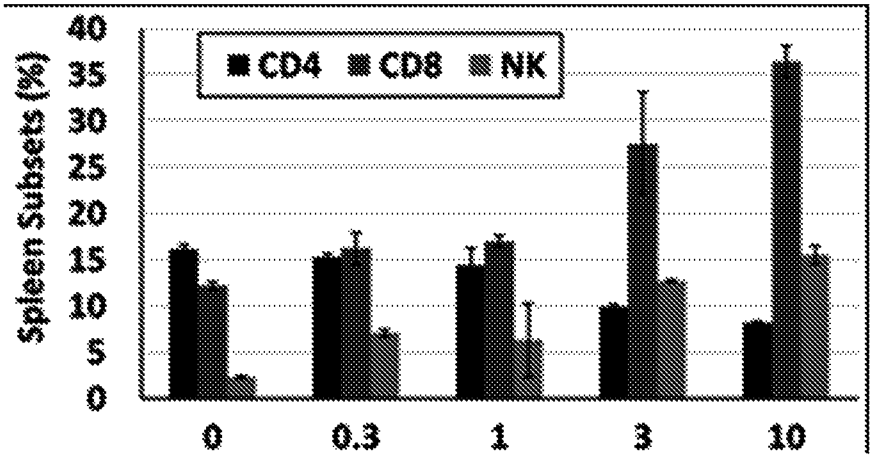

FIG. 168A-B is a set of graphs showing immunostimulation in C57BL/6 mice following treatment with TGFRt15-TGFRs.

Figure 169A:
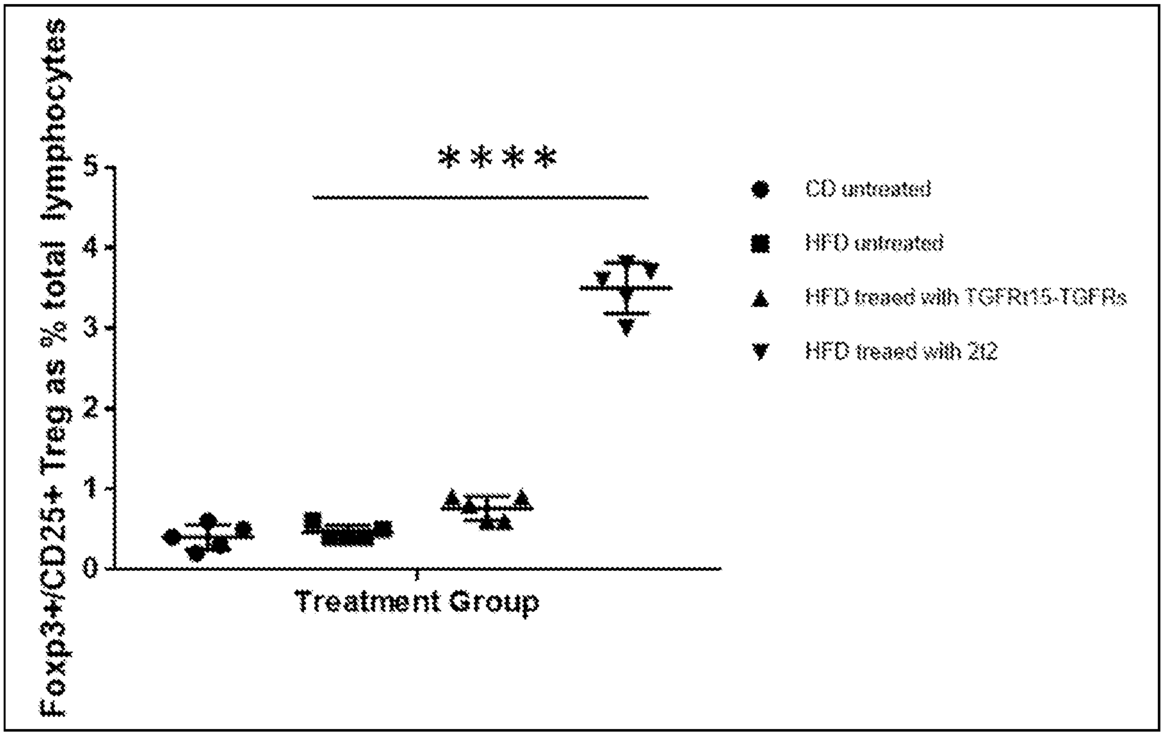
Figure 169B:
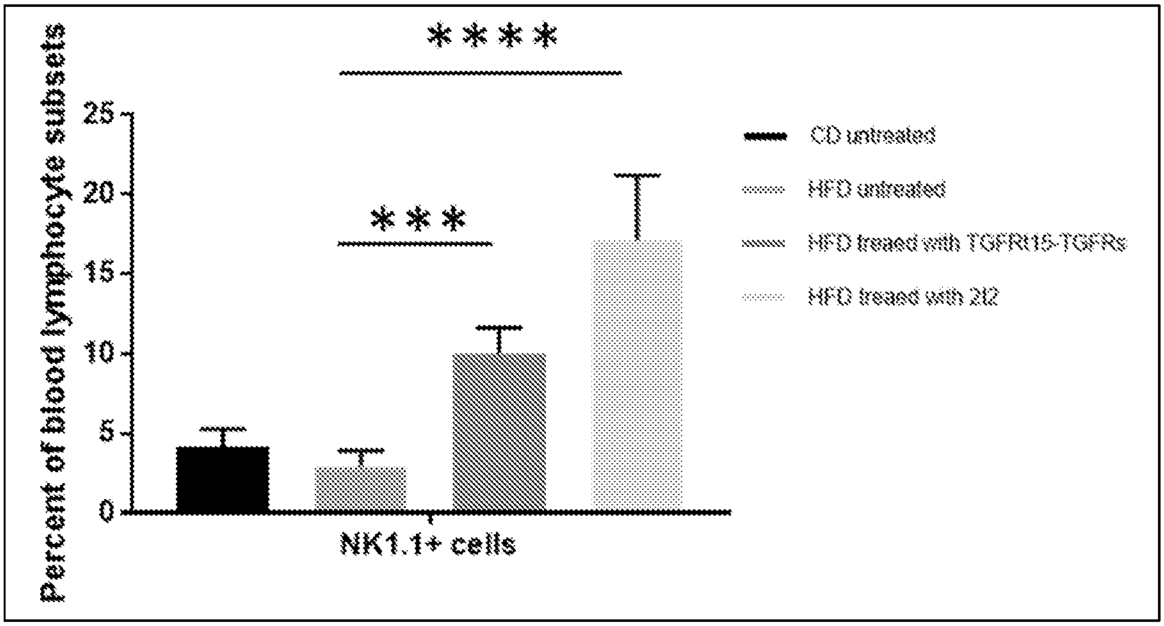
Figure 169C:
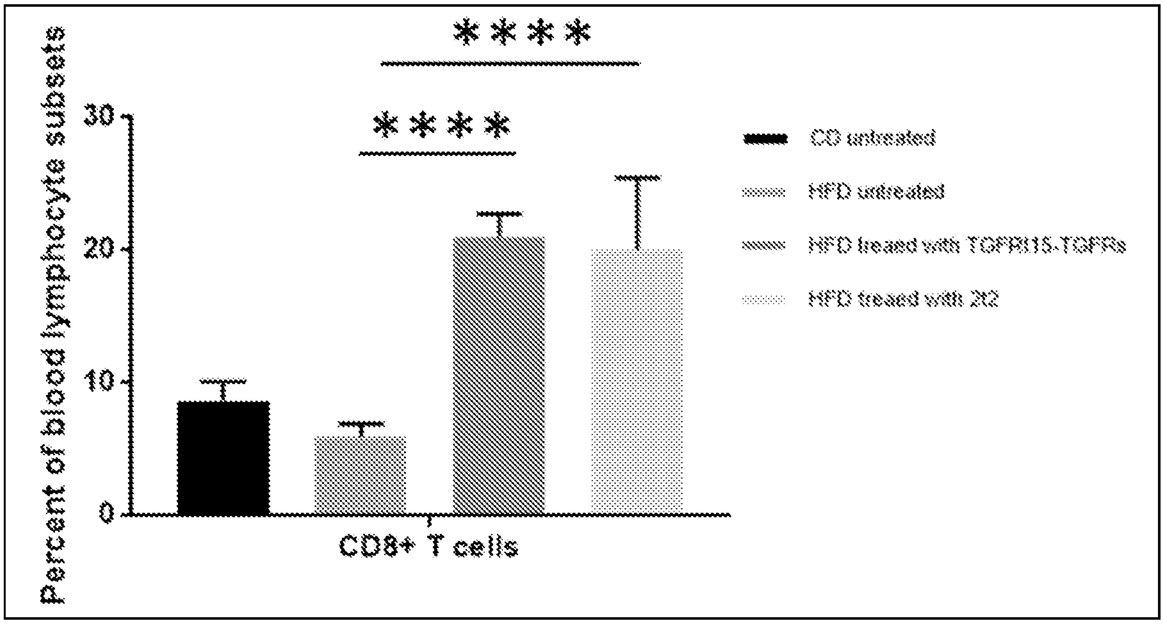

FIG. 169A-C is a set of graphs showing in vivo stimulation of Tregs, NK cells, and CD8$^+$ T cells in ApoE$^{-/-}$ mice fed with a Western diet and treated with TGFRt15-TGFRs or 2t2.

Figure 170A:
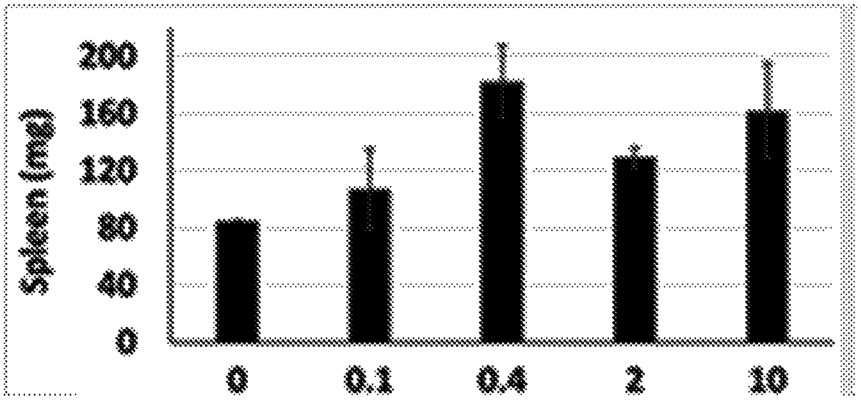
Figure 170B:
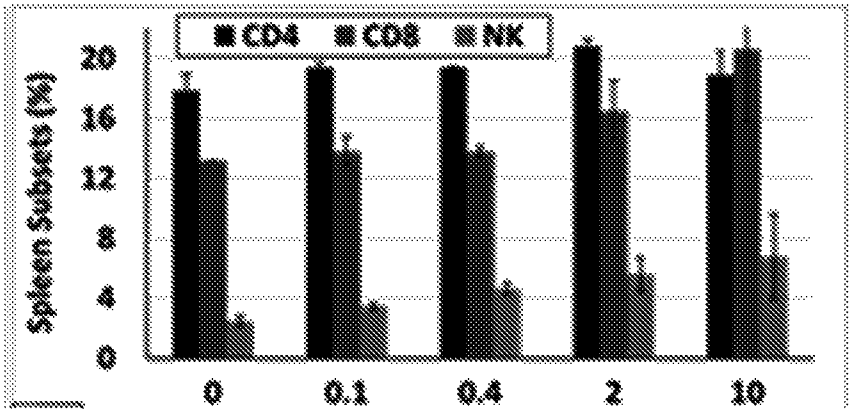

FIG. 170A-B is a set of graphs showing induction of splenocyte proliferation by 2t2 in C57BL/6 mice.

Figure 171A:
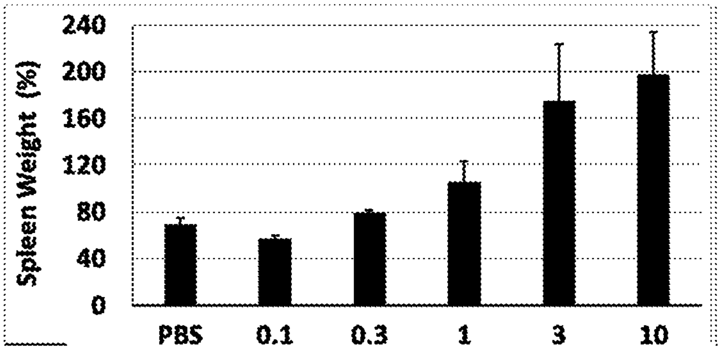
Figure 171B:
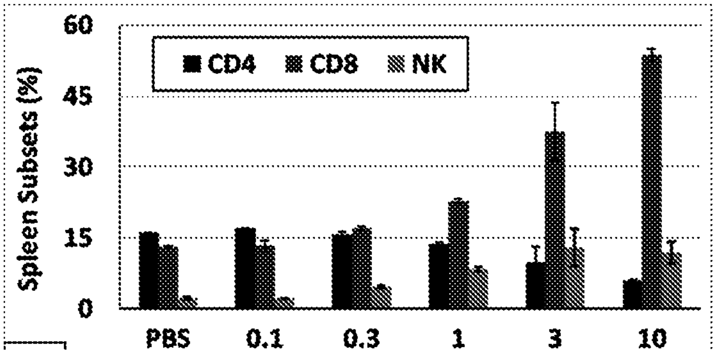
Figure 171C:
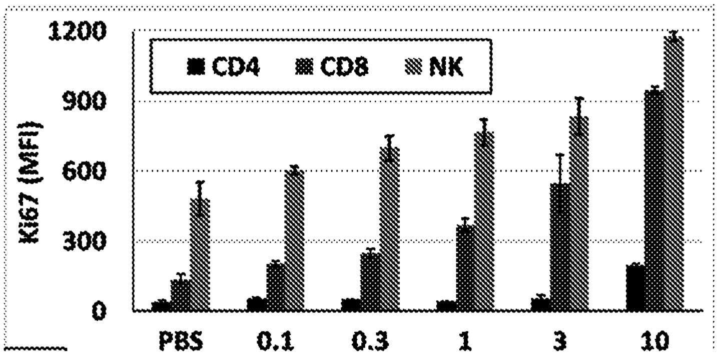

FIG. 171A-C is a set of graphs showing immunostimulation in C57BL/6 mice following treatment with TGFRt15-TGFRs.

Figure 172A:
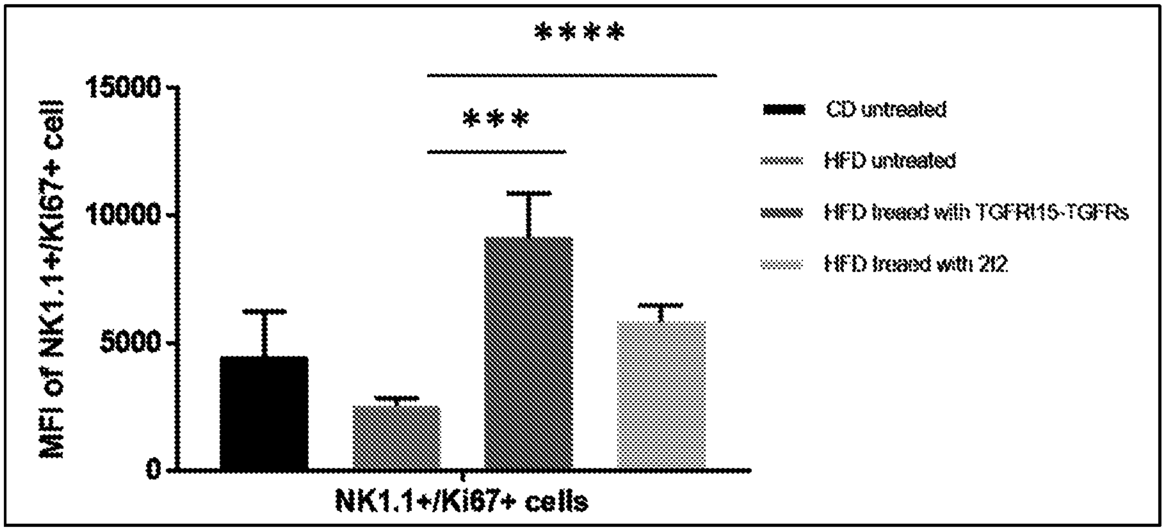
Figure 172B:
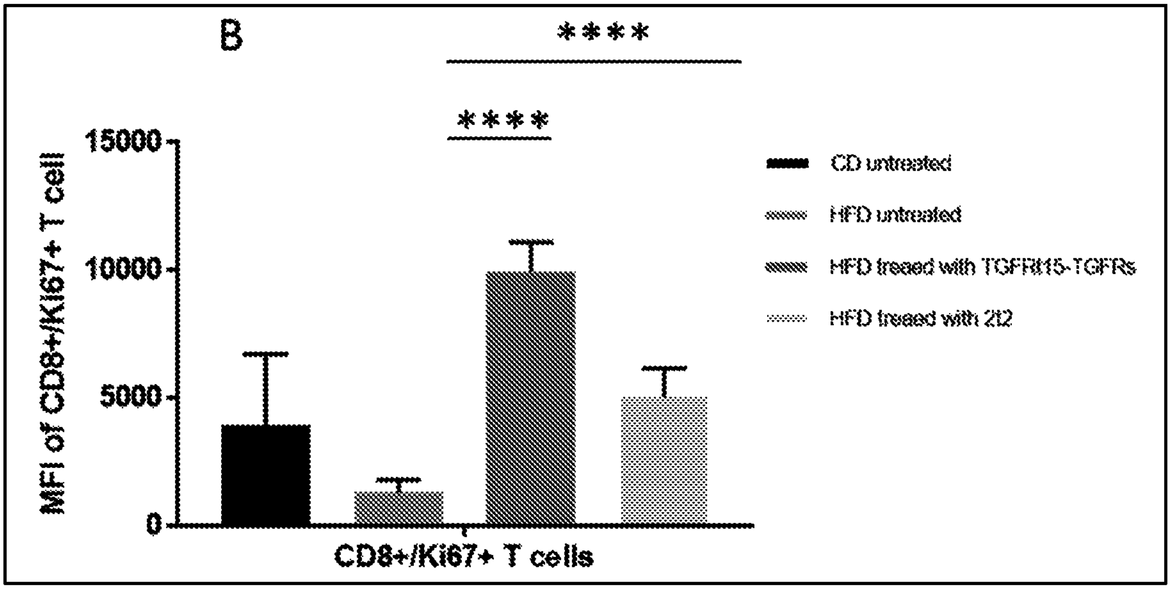

FIG. 172A-B is a set of graphs showing in vivo induction of proliferation of NK cells and CD8$^+$ T cells in ApoE$^{-/-}$ mice fed with a Western diet and treated with TGFRt15-TGFRs or 2t2.

Figure 173:
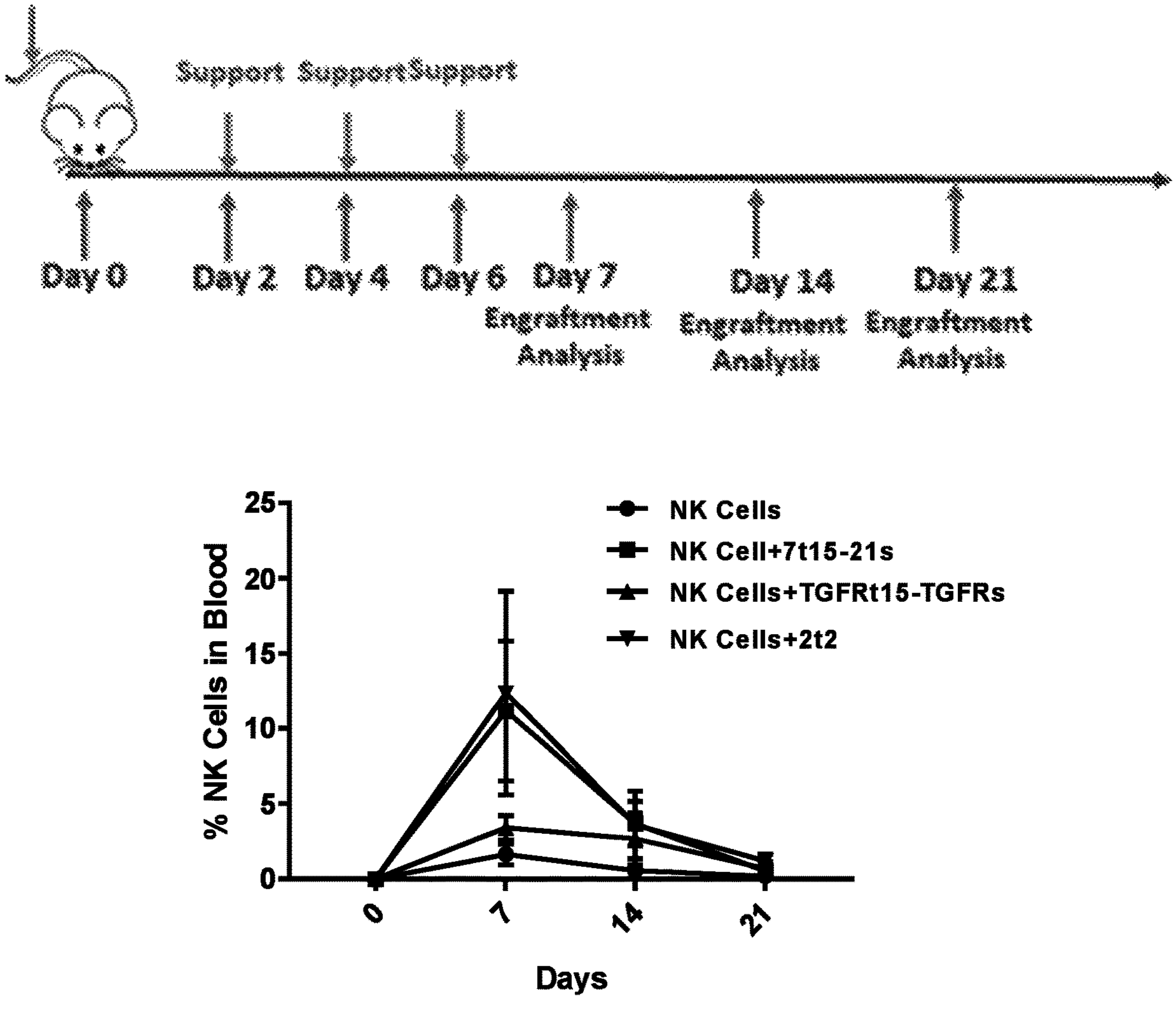

FIG. 173 is a schematic and a set of graphs showing the persistence of 7t15-21s and anti-TF antibody-expanded NK cells in NSG mice following treatment with 7t15-21, TGFRt15-TGFRs or 2t2.

Figure 174A:
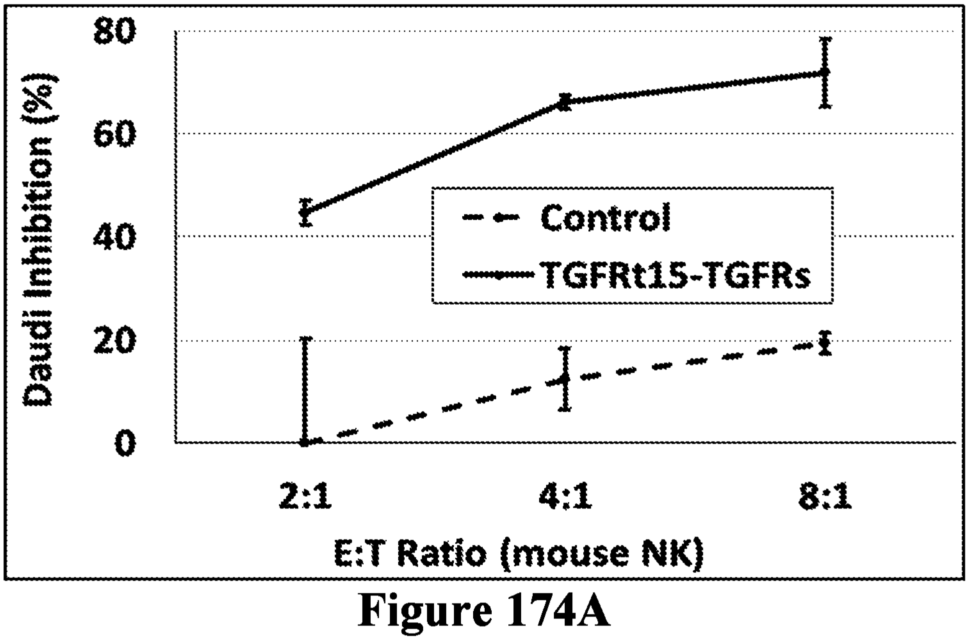
Figure 174B:
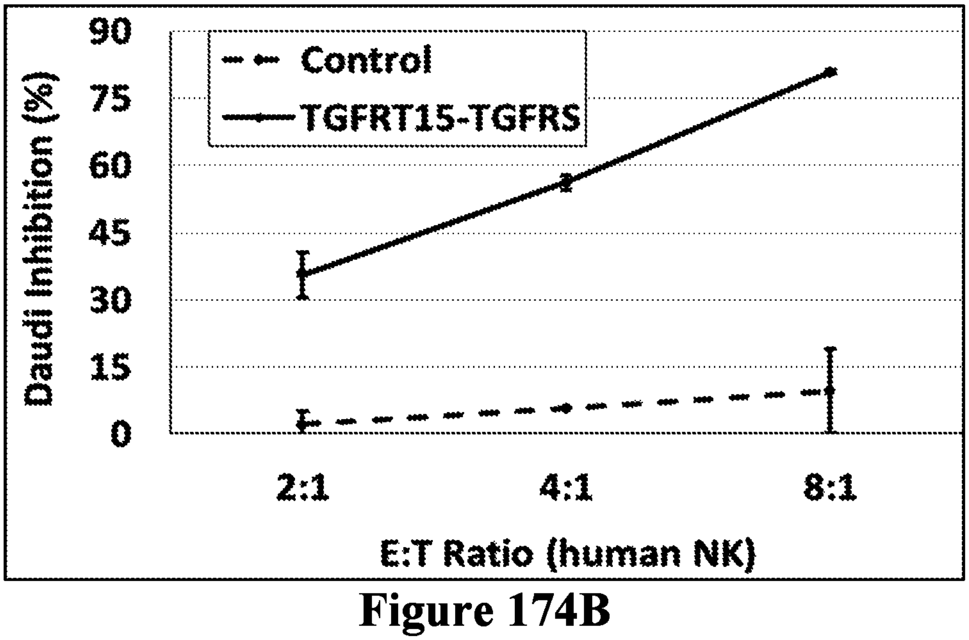

FIG. 174A-B is a set of graphs showing enhancement of cytotoxicity of NK cells following treatment of NK cells with TGFRt15-TGFRs.

Figure 175A:
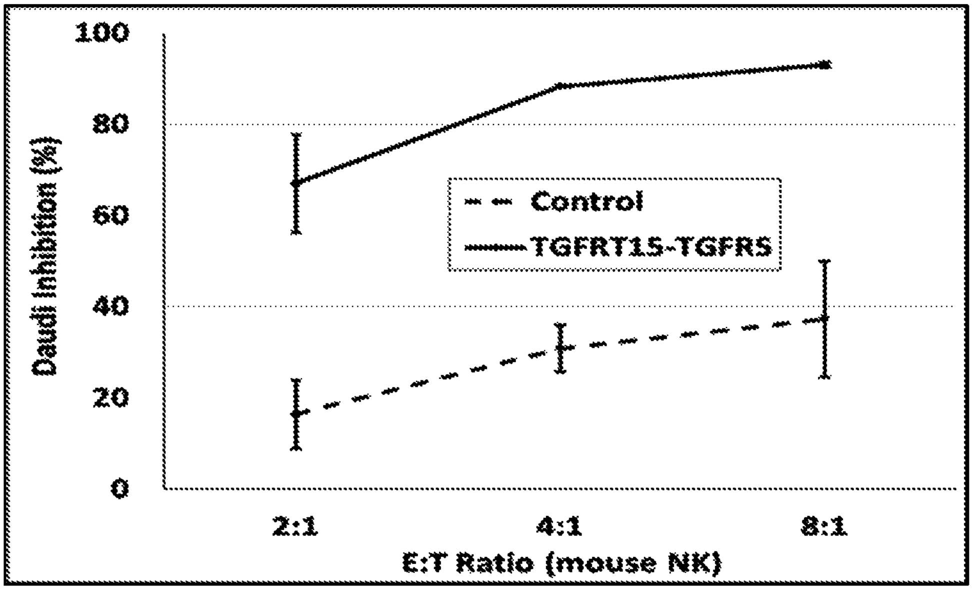
Figure 175B:
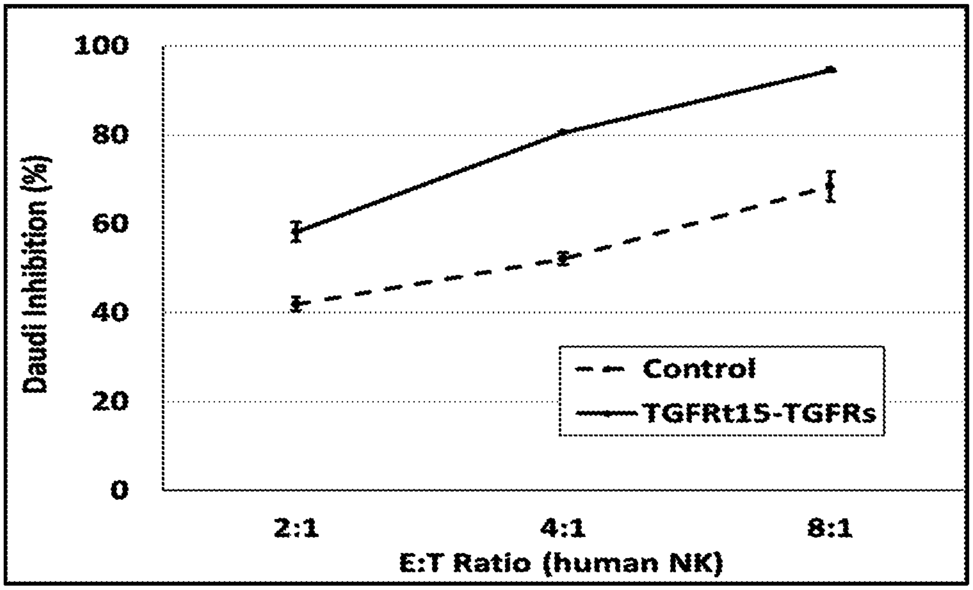

FIG. 175A-B is a set of graphs showing enhancement of ADCC activity of NK cells following treatment of NK cells with TGFRt15-TGFRs.

Figure 176:
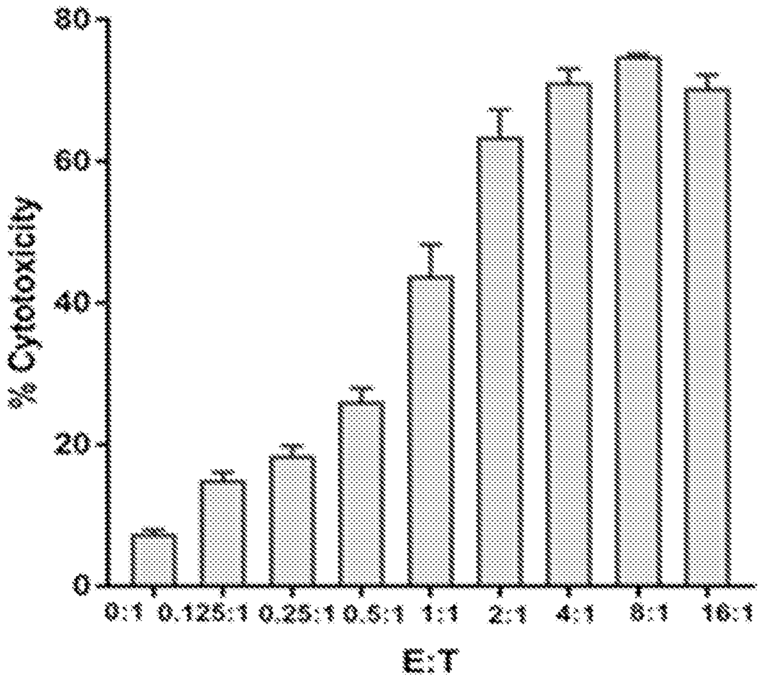

FIG. 176 is a graph of in vitro killing of senescent B16F10 melanoma cells by TGFRt15-TGFRs/2t2-activated mouse NK cells.

FIG. 177A-H is a set of graphs showing antitumor activity of TGFRt15-TGFRs plus anti-TRP1 antibody (TA99) in combination with chemotherapy in a melanoma mouse model.

Figure 178A:
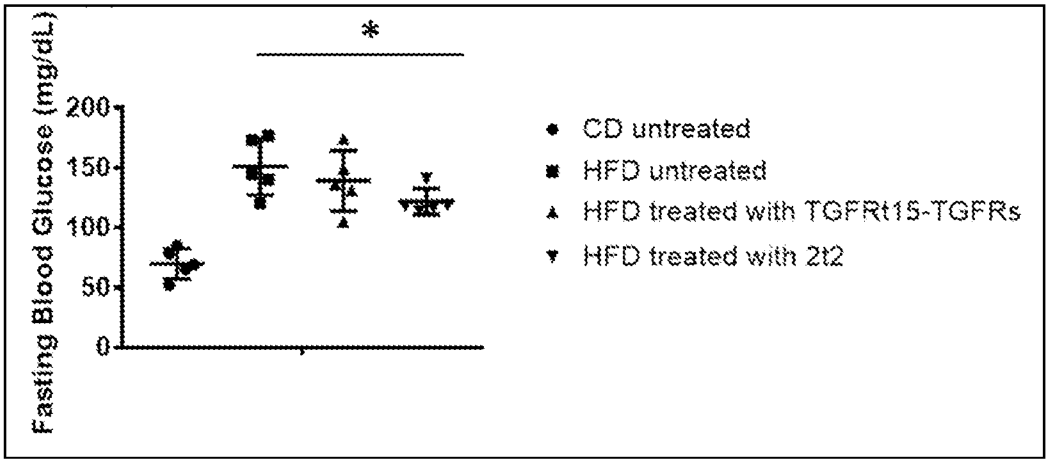
Figure 178B:
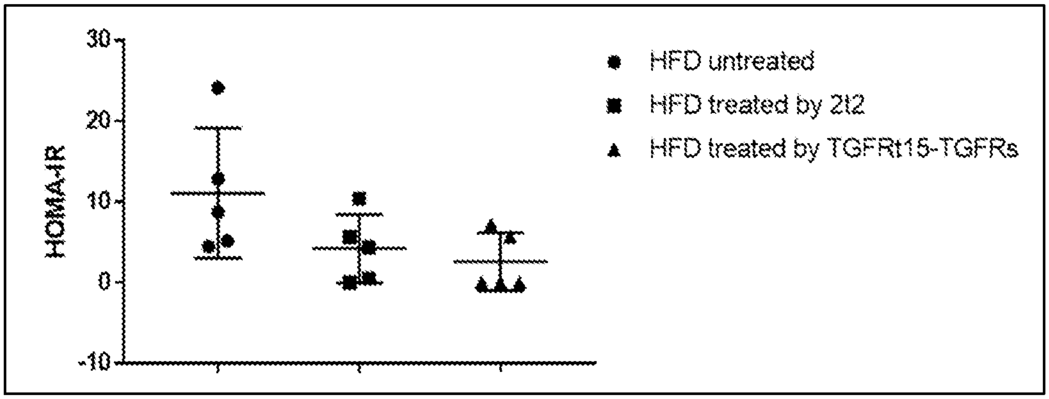
Figure 178C:
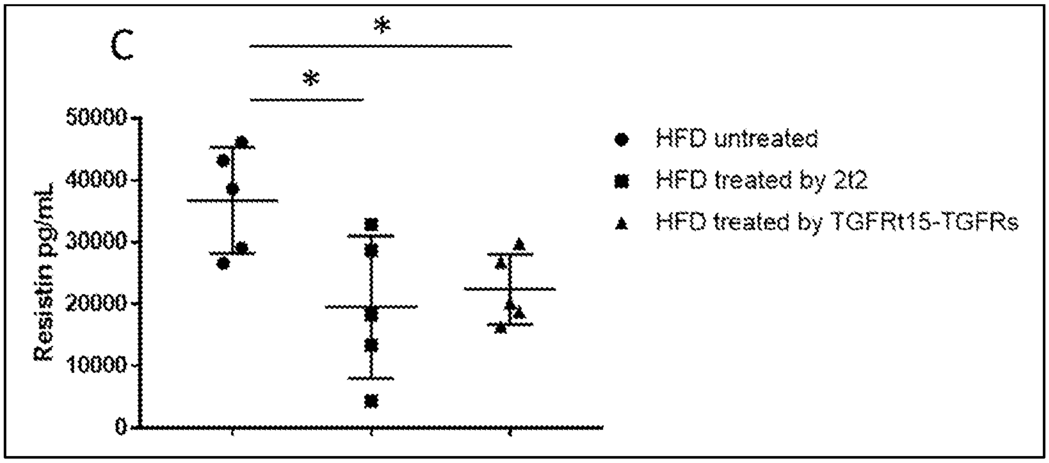

FIG. 178A-C is a set of graphs showing amelioration of the Western diet-induced hyperglycemia in ApoE$^{-/-}$ mice by 2t2.

Figure 179:
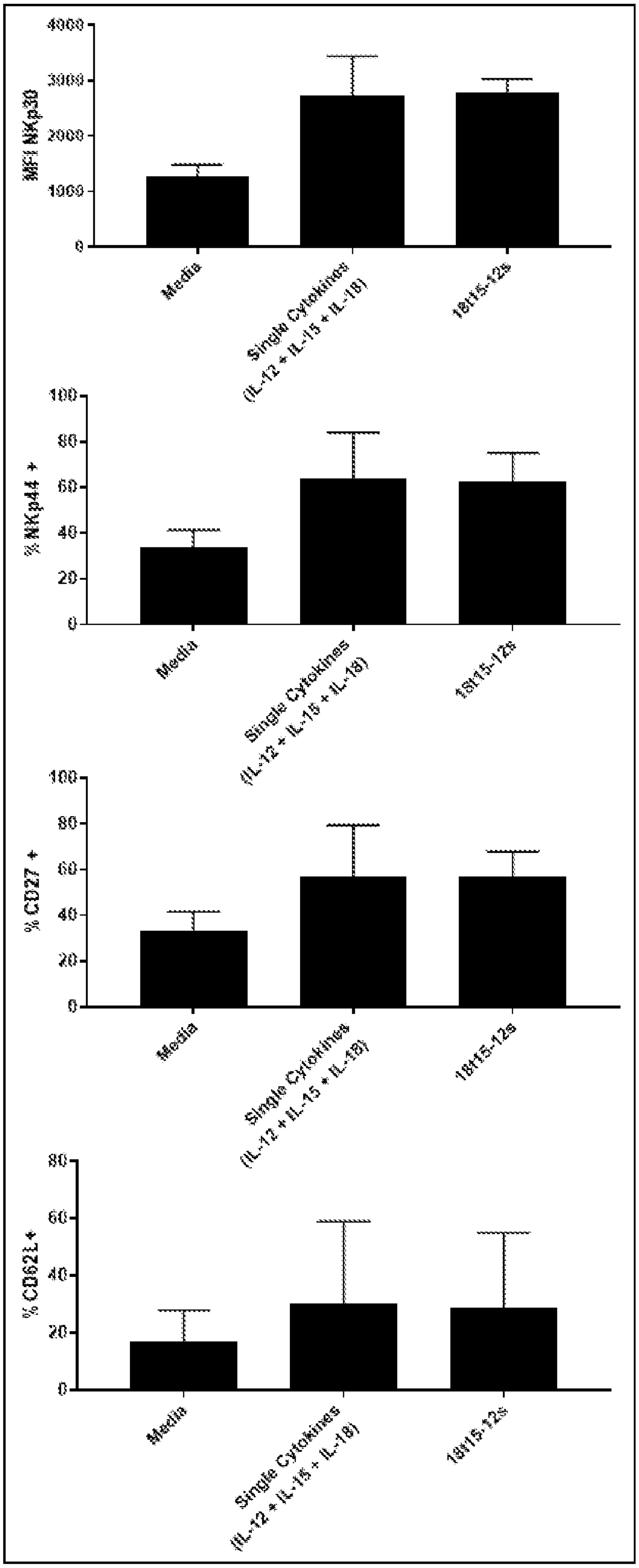

FIG. 179 is a set of graphs showing cell surface staining summarizing the differentiation of NK cells into cytokine-induced memory like NK cells (CIML-NK Cells) after stimulation with 18t15-12s and cultured in rhIL-15.

Figure 180:
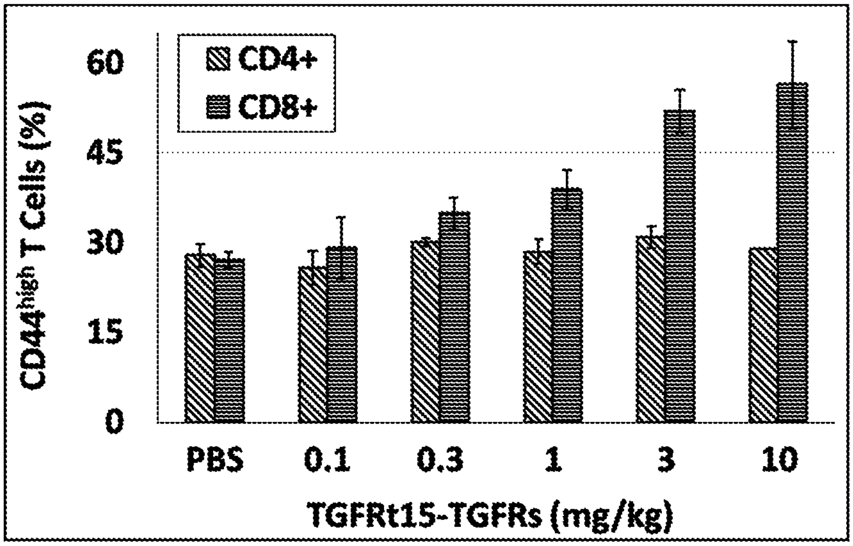
Figure 180:
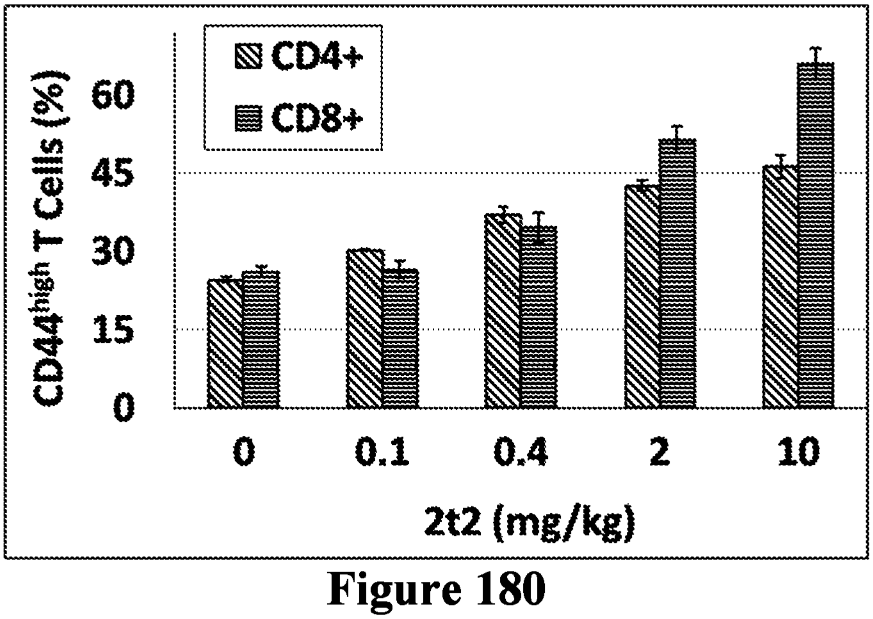

FIG. 180 shows upregulation of CD44 memory T cells. The upper panel shows upregulation of CD44 memory T cells upon treatment with TGFRt15-TGFRs. The lower panel shows upregulation of CD44 memory T cells upon treatment with 2t2.

Figure 181A:
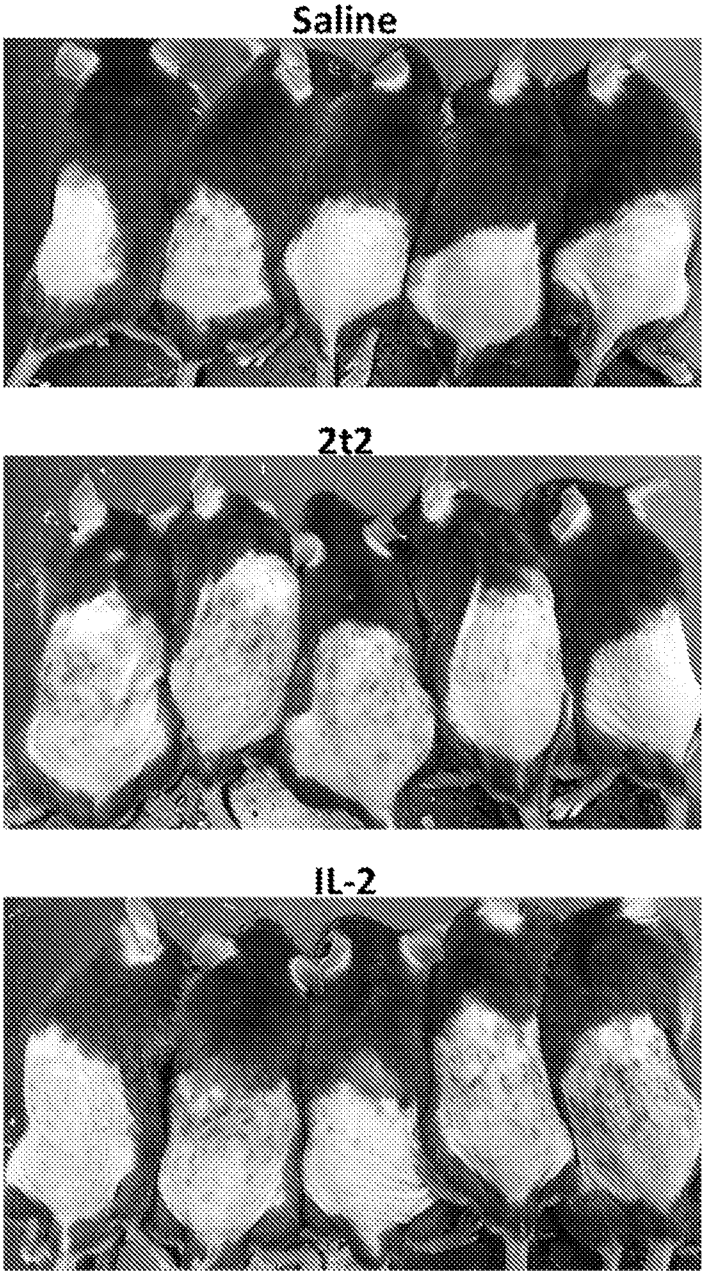
Figure 181B:
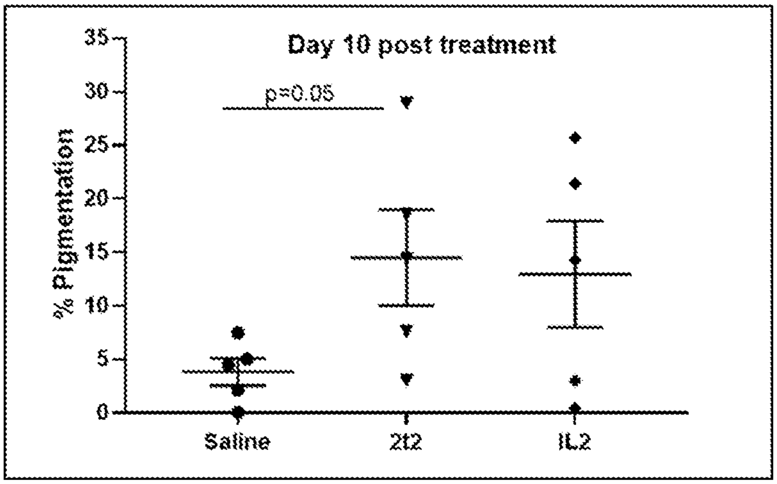

FIGS. 181A and 181B show improvement in hair regrowth following depilation in mice treated with 2t2 or IL-2. FIG. 181A shows skin pigmentation 10 days after depilation in PBS-, 2t2-, or IL-2-treated mice. FIG. 181B shows percent pigmentation in PBS-, 2t2-, or IL-2-treated mice as analyzed using the ImageJ software.

Figure 182:
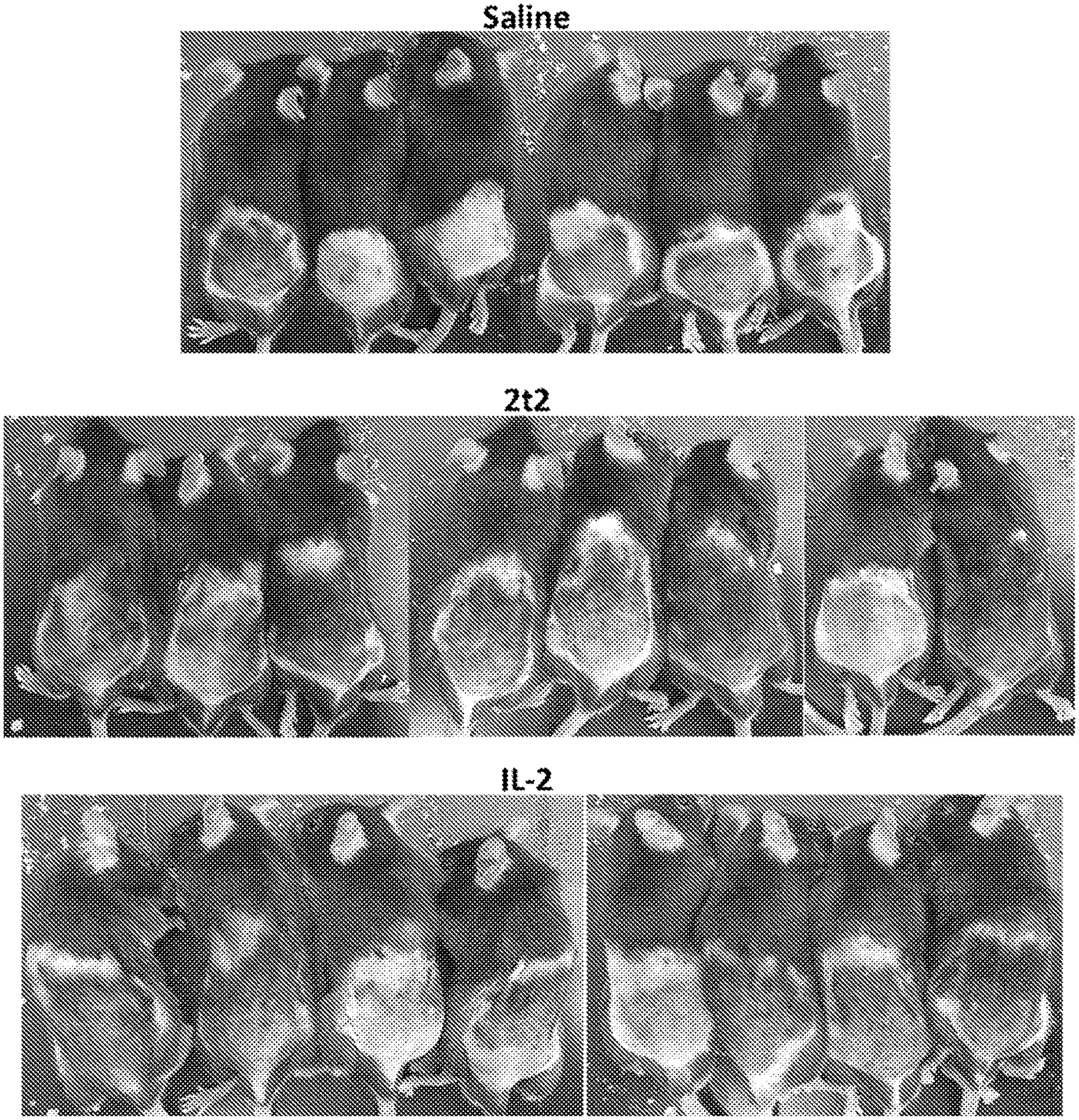

FIG. 182 shows skin pigmentation 14 days after depilation in PBS-, 2t2-, or IL-2-treated mice.

Figure 183:
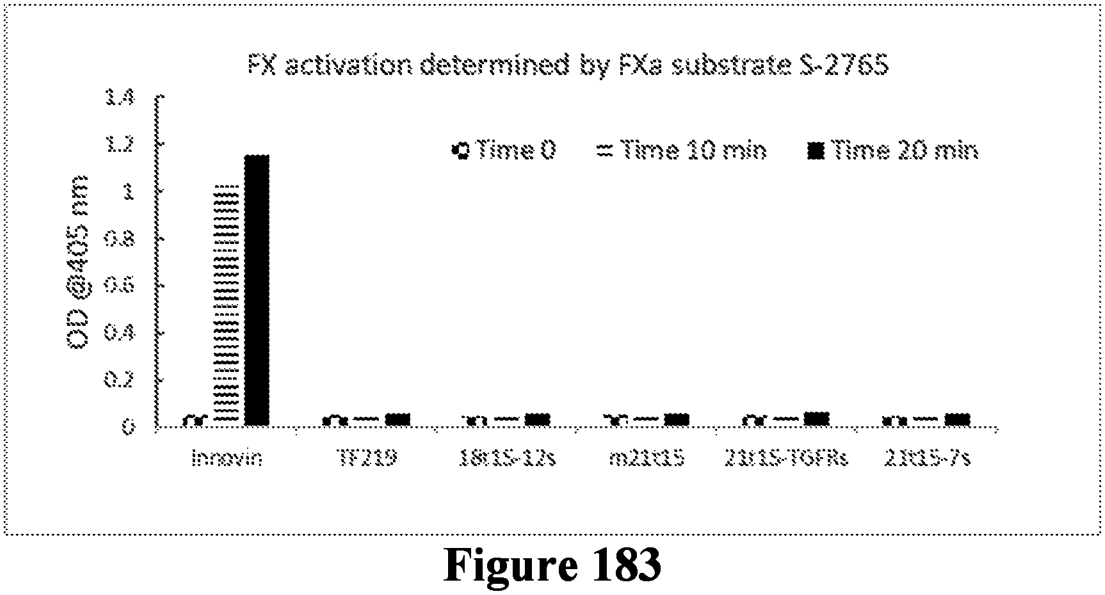

FIG. 183 shows a graph of Factor X (FX) activation following treatment with single-chain or multi-chain chimeric polypeptides.

Figure 184:
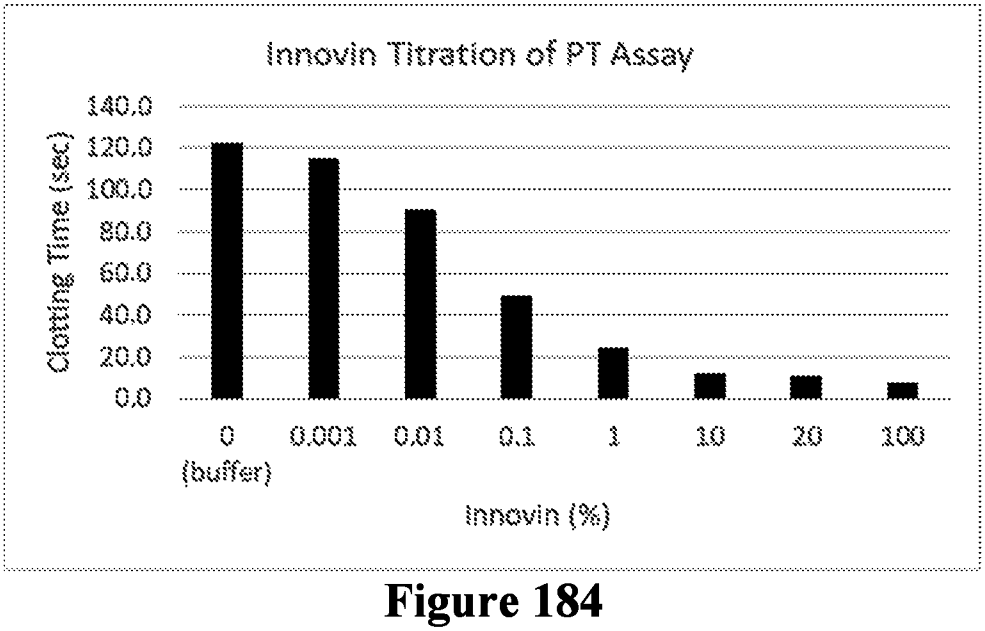

FIG. 184 shows clotting time for a buffer with varying concentrations of Innovin in a prothrombin time (PT) test.

Figure 185:
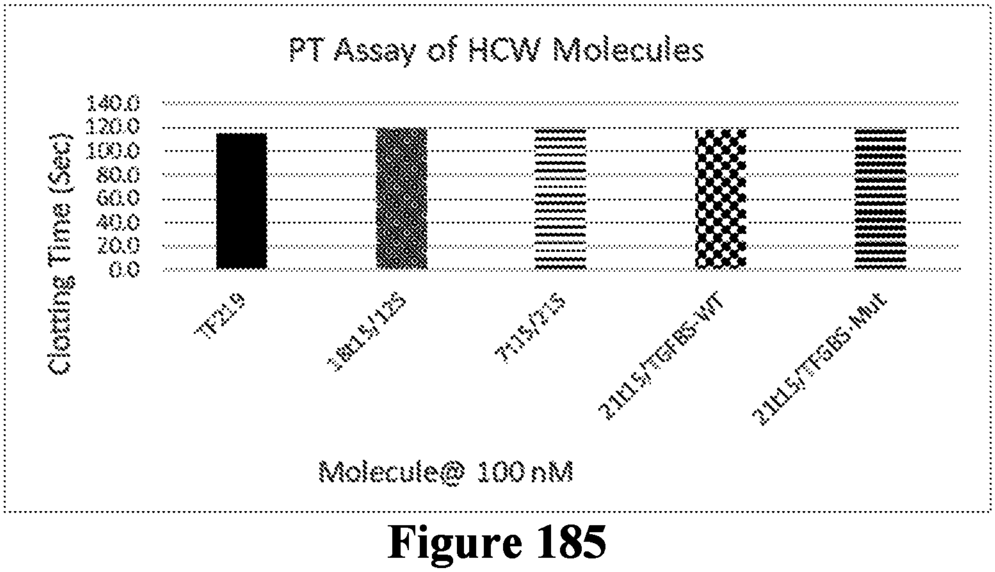

FIG. 185 shows clotting time for multi-chain chimeric polypeptides in a PT Assay.

Figure 186:
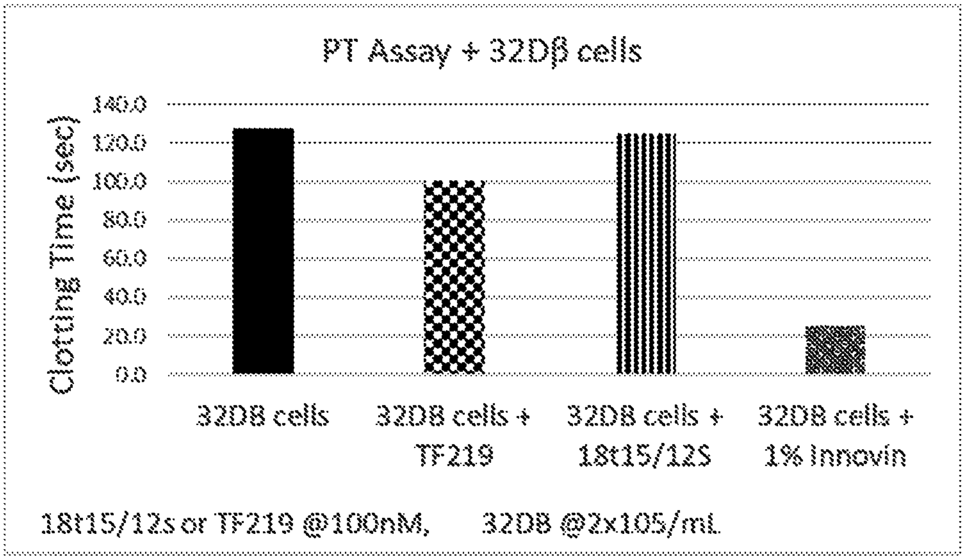

FIG. 186 shows clotting time of the multi-chain chimeric polypeptides in a PT assay when mixed with 32DB cells.

Figure 187:
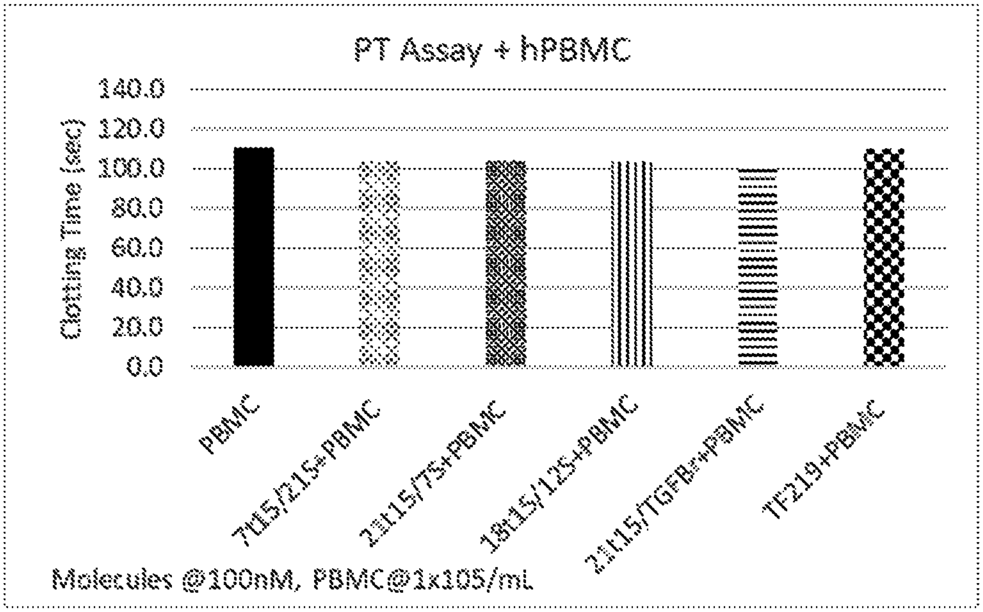

FIG. 187 shows clotting time of multi-chain chimeric polypeptides in a PT assay when mixed with human PBMC.

Figure 188:
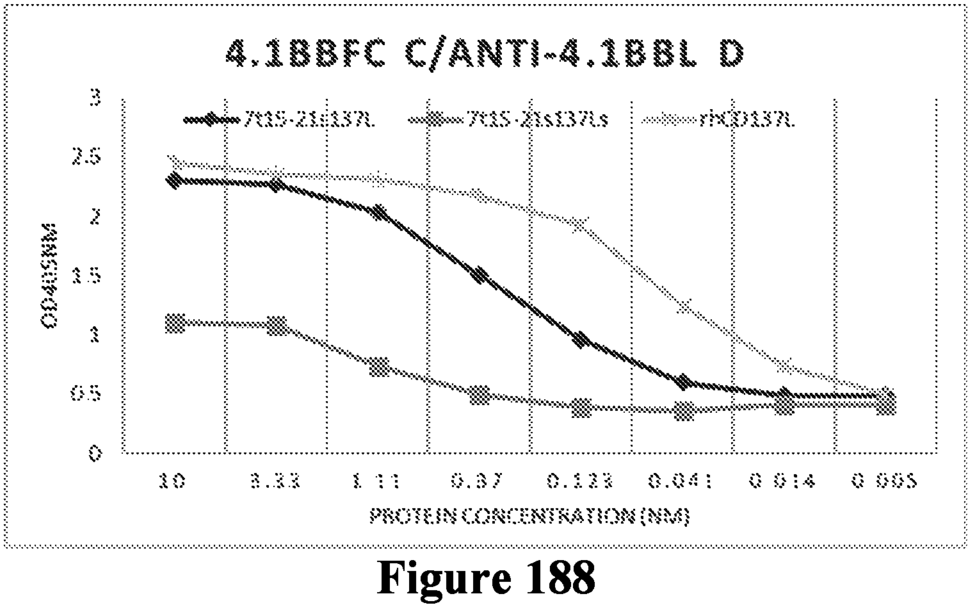
Figure 189A:
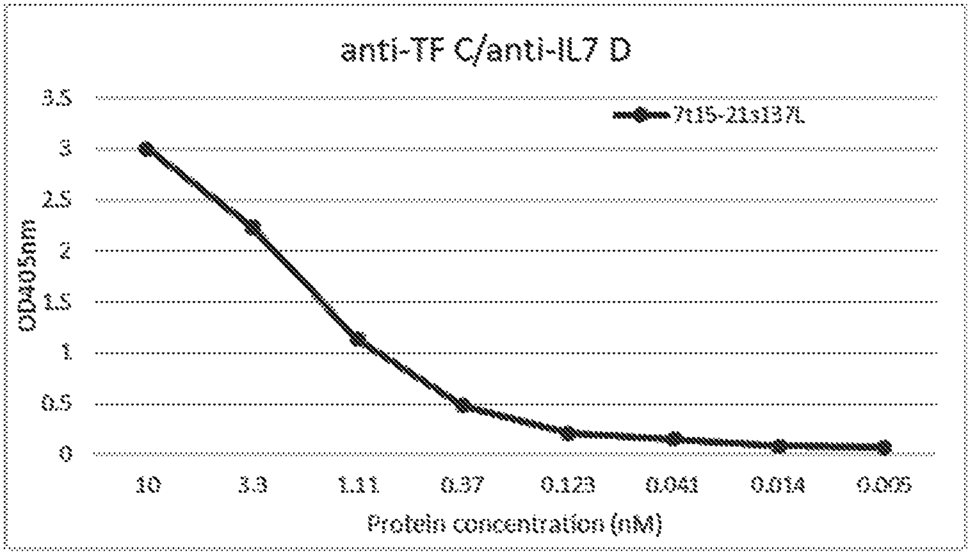
Figure 189B:
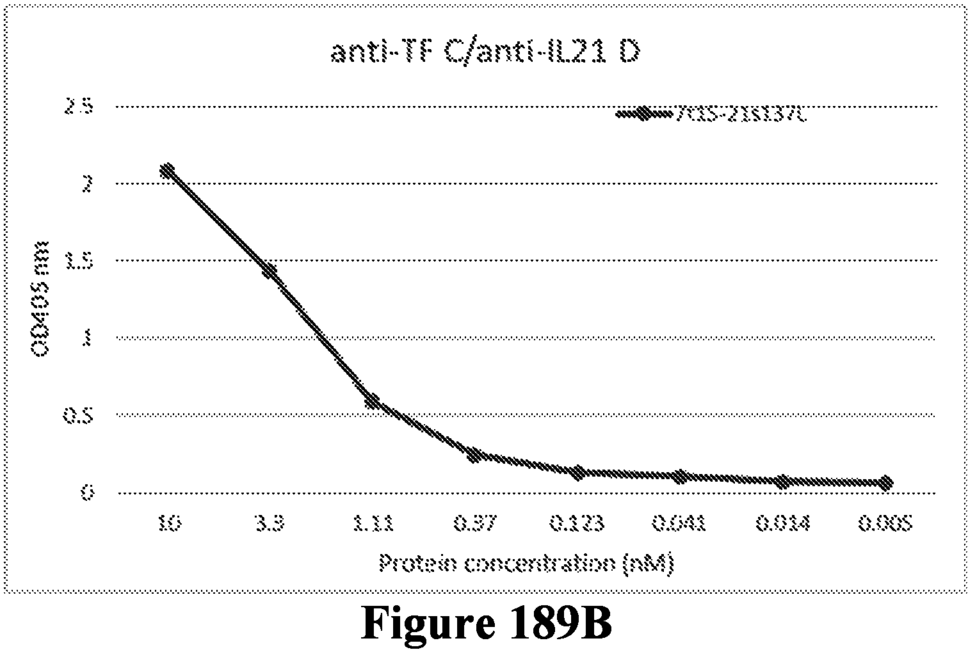
Figure 189C:
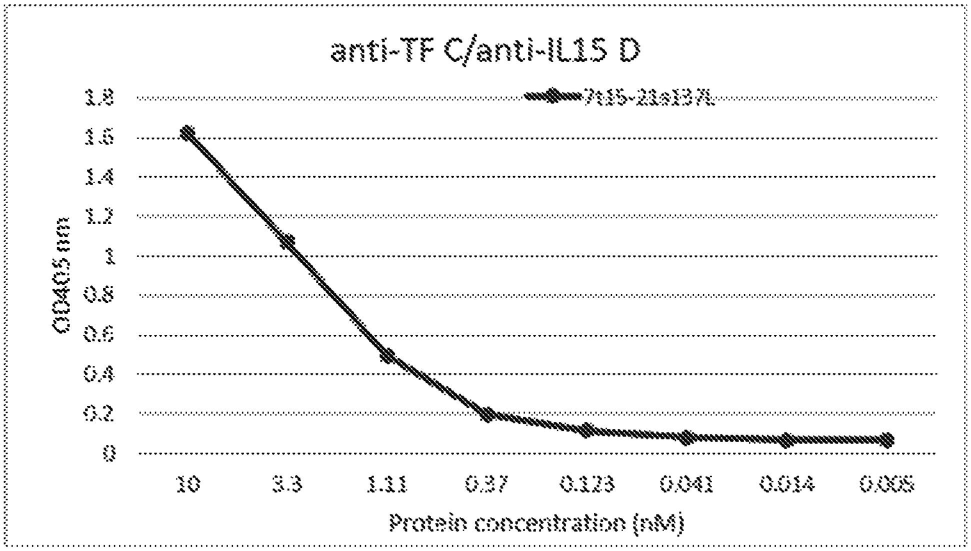
Figure 189D:
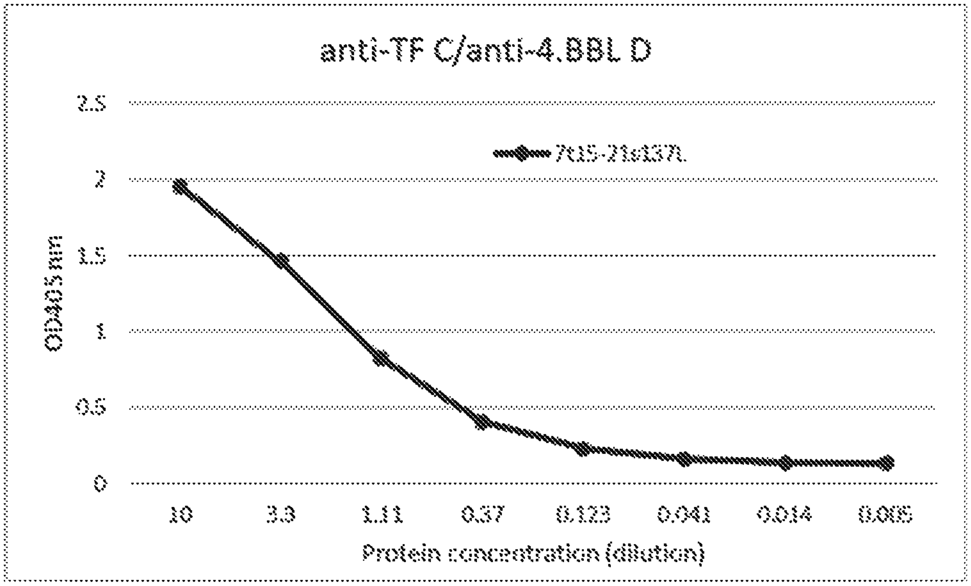

FIG. 188 shows binding of 7t15-21s137L (long version) and 7t15-21s137L (short version) to CD137 (4.1BB).

FIG. 189A-189D show detection of IL7, IL21, IL15, and 4.1BBL in 7t15-21s137L (long version) by the respective antibodies using ELISA.

Figure 190:
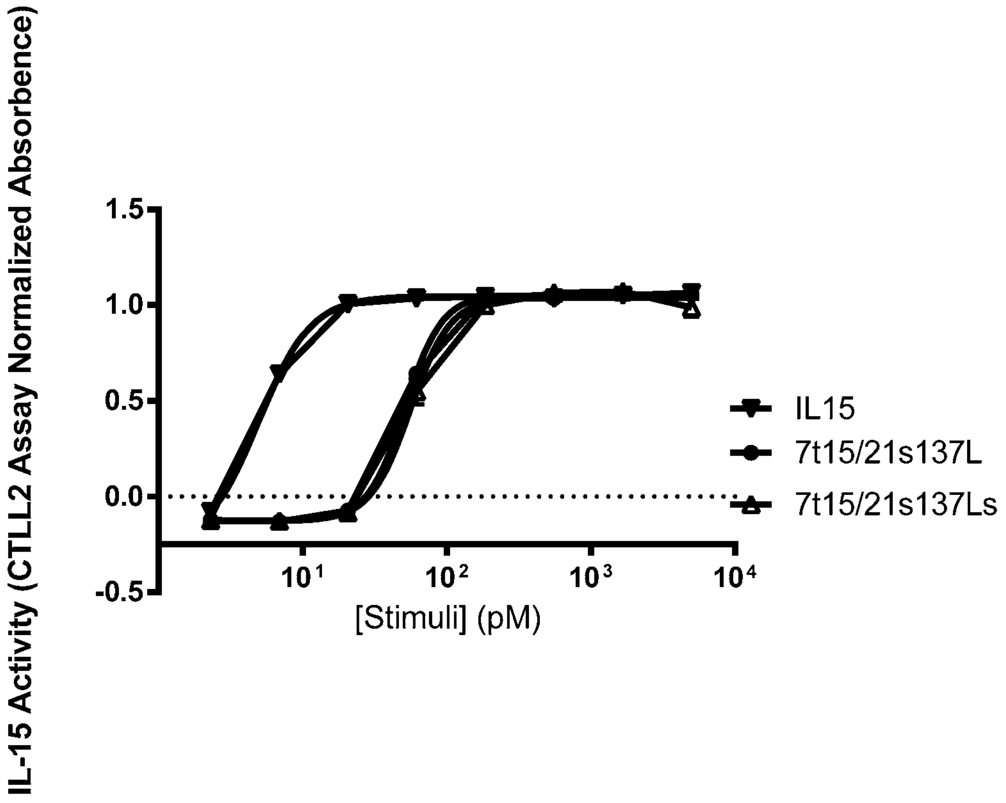

FIG. 190 shows IL-15 activity of 7t15-21s137L (long version) and 7t15-21s137L (short version) as evaluated by a IL2Rαβγ-containing CTLL2 cell proliferation assay.

Figure 191A:
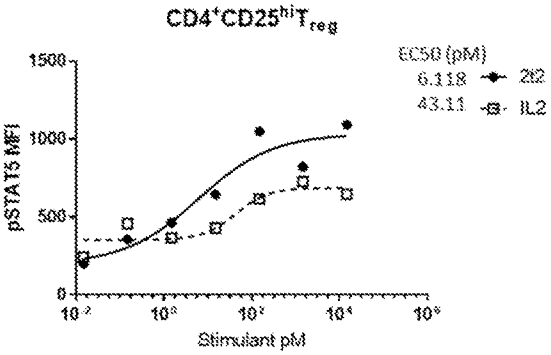
Figure 191B:
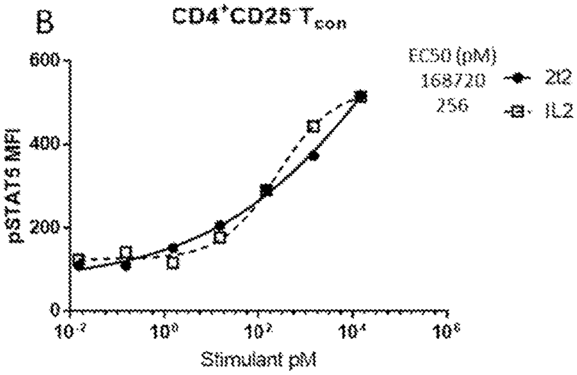
Figure 191C:
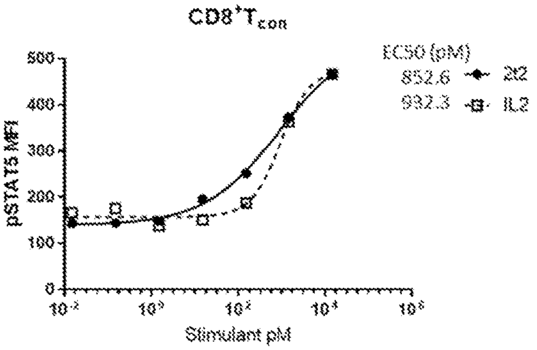

FIGS. 191A-191C show human blood lymphocyte pStat5a responses in $CD4^{+}CD25^{hi}T_{reg}$ cells, $CD4^{+}CD25^{-}$ $T_{con}$ cells, or in $CD8^{+}$ $T_{con}$ cells in response to 2t2 or IL2 treatment. FIG. 191A shows pSTAT5 responses in $CD4^{+}$ $CD25^{hi}T_{reg}$ cells. FIG. C191B shows pSTAT5 responses in $CD4^{+}CD25^{-}T_{con}$ cells. FIG. 191C shows pSTAT5 responses in $CD8^{+}$ $T_{con}$ cells.

Figure 192A:
Figure 192B:
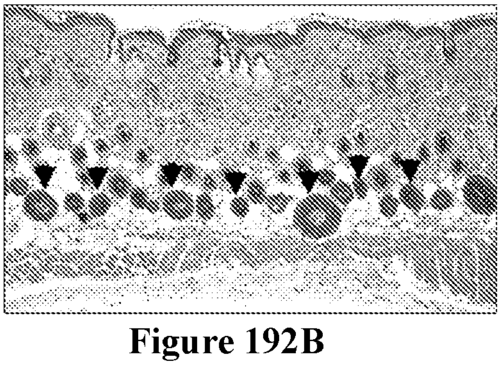
Figure 192C:
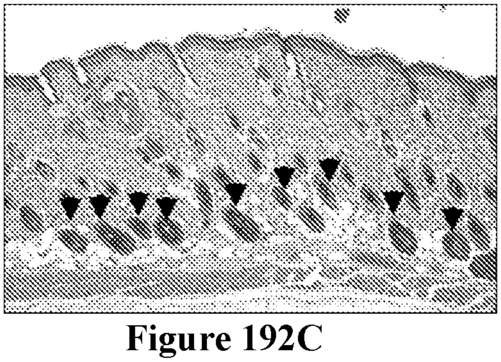
Figure 192D:
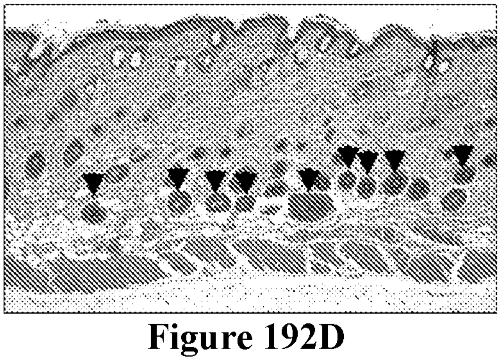
Figure 192E:
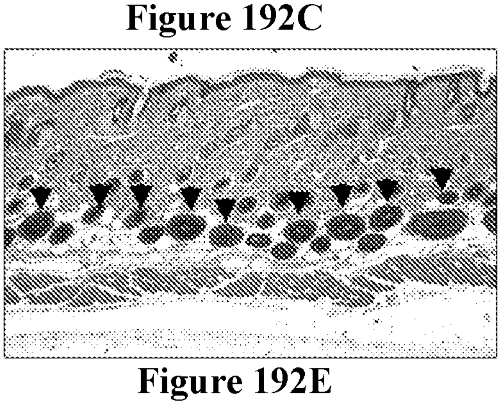

FIGS. 192A-192E is a set of imaging showing that treatment with an IL-2 based molecule (2t2) can induce formation of hair follicles following depilation in mouse model. FIG. 192A is an image from a control mouse—only depilation done after hair was shaved, FIG. 192B is an image from a mouse where depilation was followed by low dose IL-2 (1 mg/kg) administration, and FIGS. 192C-192E show images from mice where depilation was followed by 2t2 at 0.3 mg/kg, (FIG. 192C), 1 mg/kg (FIG. 192D), and (FIG. 192E) 3 mg/kg. Black arrows indicate anagen-phase hair follicles that will later extend into dermis and facilitate hair growth.

Figure 193:
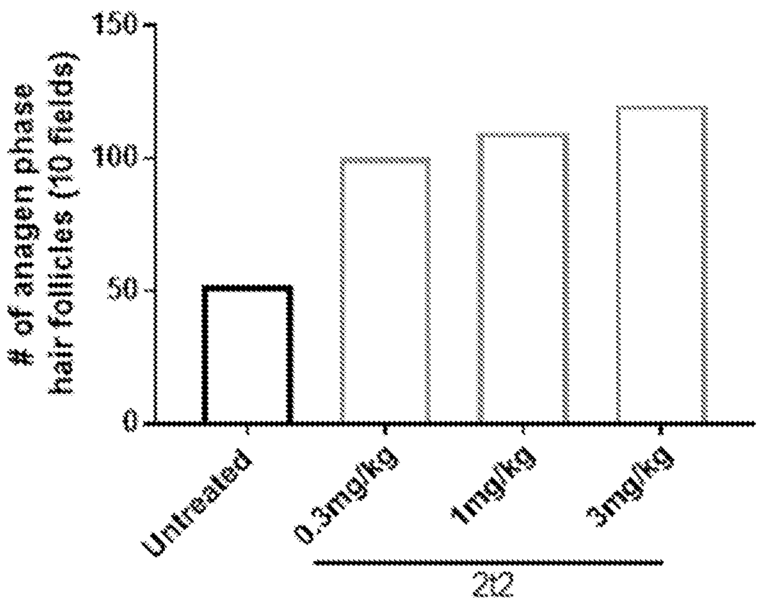

FIG. 193 shows the total number of anagen phase hair follicles counted per 10 fields for each treatment group.

Figure 194:
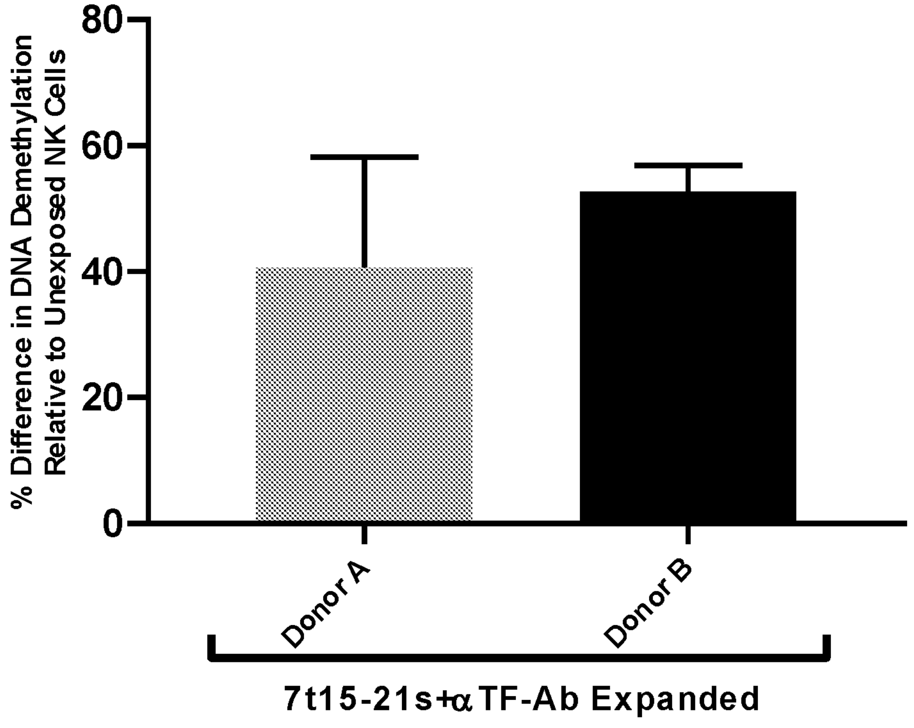

FIG. 194 is a graph showing the percentage different in DNA demethylation in NK cells (relative to unexposed NK cells) from two different donors following expansion with 7t15-21s+ anti-tissue factor (TF)-antibody (IgG1) (50 nM).

DETAILED DESCRIPTION

Provided herein are methods of treating an aging-related disease or condition in a subject in need thereof that include administering to a subject identified as having an aging-related disease or condition a therapeutically effective amount of one or more natural killer (NK) cell activating agent(s) and/or a therapeutically effective number of activated NK cells. Also provided herein are methods of killing or reducing the number of senescent cells in a subject in need thereof that include administering to the subject a therapeutically effective amount of one or more NK cell activating agent(s) and/or a therapeutically effective number of activated NK cells. Also provided herein are methods of improving the texture and/or appearance of skin and/or hair in a subject in need thereof over a period of time that include administering to the subject a therapeutically effective amount of one or more natural killer (NK) cell activating agent(s) and/or a therapeutically effective number of activated NK cells. Also provided herein are methods of assisting in the treatment of obesity in a subject in need thereof over a period of time that include administering to the subject a therapeutically effective amount of one or more natural killer (NK) cell activating agent(s) and/or a therapeutically effective number of activated NK cells.

Activated NK Cells

Some embodiments of any of the methods described herein can include administering to a subject (e.g., any of the exemplary subjects described herein) a therapeutically effective number of activated NK cells (e.g., human activated NK cells). An activated NK cell is an NK cell (e.g., a human NK cell) that has increased expression levels of two or more (e.g., three, four, five, or six) of CD25, CD69, MTOR-C1, SREBP1, IFN-γ, and a granzyme (e.g., granzyme B), e.g., as compared to a resting NK cell (e.g., a human resting NK cell). For example, an activated NK cell can have at least a 10% increase (e.g., at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, at least a 100% increase, at least a 120% increase, at least a 140% increase, at least a 160% increase, at least a 180% increase, at least a 200% increase, at least a 220% increase, at least a 240% increase, at least a 260% increase, at least a 280% increase, or at least a 300% increase) in the expression levels of two of more (e.g., three, four, five, or six) of CD25, CD69, MTOR-C1, SREBP1, IFN-γ, and a granzyme (e.g., granzyme B), e.g., as compared to a resting NK cell (e.g., a human activated NK cell).

In some embodiments, an activated NK cell can optionally further can have at least a 10% increase (e.g., at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, at least a 100% increase, at least a 120% increase, at least a 140% increase, at least a 160% increase, at least a 180% increase, at least a 200% increase, at least a 220% increase, at least a 240% increase, at least a 260% increase, at least a 280% increase, or at least a 300% increase) in the expression levels of two of more (e.g., 3, 4, 5, 6, 7, 8, 9, 10, 11, 12, 13, 14, 15, 16, 17, 18, 19, 20, 21, 22, 23, 24, 25, 26, 27, 28, or 29) of CD25, CD59, CD352, NKp80, DNAM-1, 2B4, NKp30, NKp44, NKp46, NKG2D, CD16, KIR2DS1, KIR2Ds2/3, KIR2DL4, KIR2DS4, KIR2DS5, KIR3DS1, NKG2C, CCR7, CXCR3, L-Selectin, CXCR1, CXCR2, CX3CR1, ChemR23, CXCR4, CCR5, S1P5, c-Kit, mTORC1, e.g., as compared to a resting NK cell (e.g., a human activated NK cell).

For example, an activated NK cell (e.g., a human activated NK cell) can have about a 10% increase to about a 500% increase, about a 10% increase to about a 450% increase, about a 10% increase to about a 400% increase, about a 10% increase to about a 350% increase, about a 10% increase to about a 300% increase, about a 10% increase to about a 280% increase, about a 10% increase to about a 260% increase, about a 10% increase to about a 240% increase, about a 10% increase to about a 220% increase, about a 10% increase to about a 200% increase, about a 10% increase to about a 180% increase, about a 10% increase to about a 160% increase, about a 10% increase to about a 140% increase, about a 10% increase to about a 120% increase, about a 10% increase to about a 100% increase, about a 10% increase to about a 80% increase, about a 10% increase to about a 60% increase, about a 10% increase to about a 40% increase, about a 10% increase to about a 20% increase, a 20% increase to about a 500% increase, about a 20% increase to about a 450% increase, about a 20% increase to about a 400% increase, about a 20% increase to about a 350% increase, about a 20% increase to about a 300% increase, about a 20% increase to about a 280% increase, about a 20% increase to about a 260% increase, about a 20% increase to about a 240% increase, about a 20% increase to about a 220% increase, about a 20% increase to about a 200% increase, about a 20% increase to about a 180% increase, about a 20% increase to about a 160% increase, about a 20% increase to about a 140% increase, about a 20% increase to about a 120% increase, about a 20% increase to about a 100% increase, about a 20% increase to about a 80% increase, about a 20% increase to about a 60% increase, about a 20% increase to about a 40% increase, a 40% increase to about a 500% increase, about a 40% increase to about a 450% increase, about a 40% increase to about a 400% increase, about a 40% increase to about a 350% increase, about a 40% increase to about a 300% increase, about a 40% increase to about a 280% increase, about a 40% increase to about a 260% increase, about a 40% increase to about a 240% increase, about a 40% increase to about a 220% increase, about a 40% increase to about a 200% increase, about a 40% increase to about a 180% increase, about a 40% increase to about a 160% increase, about a 40% increase to about a 140% increase, about a 40% increase to about a 120% increase, about a 40% increase to about a 100% increase, about a 40% increase to about a 80% increase, about a 40% increase to about a 60% increase, a 60% increase to about a 500% increase, about a 60% increase to about a 450% increase, about a 60% increase to about a 400% increase, about a 60% increase to about a 350% increase, about a 60% increase to about a 300% increase, about a 60% increase to about a 280% increase, about a 60% increase to about a 260% increase, about a 60% increase to about a 240% increase, about a 60% increase to about a 220% increase, about a 60% increase to about a 200% increase, about a 60% increase to about a 180% increase, about a 60% increase to about a 160% increase, about a 60% increase to about a 140% increase, about a 60% increase to about a 120% increase, about a 60% increase to about a 100% increase, about a 60% increase to about a 80% increase, a 80% increase to about a 500% increase, about a 80% increase to about a 450% increase, about a 80% increase to about a 400% increase, about a 80% increase to about a 350% increase, about a 80% increase to about a 300% increase, about a 80% increase to about a 280% increase, about a 80% increase to about a 260% increase, about a 80% increase to about a 240% increase, about a 80% increase to about a 220% increase, about a 80% increase to about a 200% increase, about a 80% increase to about a 180% increase, about a 80% increase to about a 160% increase, about a 80% increase to about a 140% increase, about a 80% increase to about a 120% increase, about a 80% increase to about a 100% increase, a 100% increase to about a 500% increase, about a 100% increase to about a 450% increase, about a 100% increase to about a 400% increase, about a 100% increase to about a 350% increase, about a 100% increase to about a 300% increase, about a 100% increase to about a 280% increase, about a 100% increase to about a 260% increase, about a 100% increase to about a 240% increase, about a 100% increase to about a 220% increase, about a 100% increase to about a 200% increase, about a 100% increase to about a 180% increase, about a 100% increase to about a 160% increase, about a 100% increase to about a 140% increase, about a 100% increase to about a 120% increase, a 120% increase to about a 500% increase, about a 120% increase to about a 450% increase, about a 120% increase to about a 400% increase, about a 120% increase to about a 350% increase, about a 120% increase to about a 300% increase, about a 120% increase to about a 280% increase, about a 120% increase to about a 260% increase, about a 120% increase to about a 240% increase, about a 120% increase to about a 220% increase, about a 120% increase to about a 200% increase, about a 120% increase to about a 180% increase, about a 120% increase to about a 160% increase, about a 120% increase to about a 140% increase, a 140% increase to about a 500% increase, about a 140% increase to about a 450% increase, about a 140% increase to about a 400% increase, about a 140% increase to about a 350% increase, about a 140% increase to about a 300% increase, about a 140% increase to about a 280% increase, about a 140% increase to about a 260% increase, about a 140% increase to about a 240% increase, about a 140% increase to about a 220% increase, about a 140% increase to about a 200% increase, about a 140% increase to about a 180% increase, about a 140% increase to about a 160% increase, a 160% increase to about a 500% increase, about a 160% increase to about a 450% increase, about a 160% increase to about a 400% increase, about a 160% increase to about a 350% increase, about a 160% increase to about a 300% increase, about a 160% increase to about a 280% increase, about a 160% increase to about a 260% increase, about a 160% increase to about a 240% increase, about a 160% increase to about a 220% increase, about a 160% increase to about a 200% increase, about a 160% increase to about a 180% increase, a 180% increase to about a 500% increase, about a 180% increase to about a 450% increase, about a 180% increase to about a 400% increase, about a 180% increase to about a 350% increase, about a 180% increase to about a 300% increase, about a 180% increase to about a 280% increase, about a 180% increase to about a 260% increase, about a 180% increase to about a 240% increase, about a 180% increase to about a 220% increase, about a 180% increase to about a 200% increase, a 200% increase to about a 500% increase, about a 200% increase to about a 450% increase, about a 200% increase to about a 400% increase, about a 200% increase to about a 350% increase, about a 200% increase to about a 300% increase, about a 200% increase to about a 280% increase, about a 200% increase to about a 260% increase, about a 200% increase to about a 240% increase, about a 200% increase to about a 220% increase, a 220% increase to about a 500% increase, about a 220% increase to about a 450% increase, about a 220% increase to about a 400% increase, about a 220% increase to about a 350% increase, about a 220% increase to about a 300% increase, about a 220% increase to about a 280% increase, about a 220% increase to about a 260% increase, about a 220% increase to about a 240% increase, a 240% increase to about a 500% increase, about a 240% increase to about a 450% increase, about a 240% increase to about a 400% increase, about a 240% increase to about a 350% increase, about a 240% increase to about a 300% increase, about a 240% increase to about a 280% increase, about a 240% increase to about a 260% increase, a 260% increase to about a 500% increase, about a 260% increase to about a 450% increase, about a 260% increase to about a 400% increase, about a 260% increase to about a 350% increase, about a 260% increase to about a 300% increase, about a 260% increase to about a 280% increase, a 280% increase to about a 500% increase, about a 280% increase to about a 450% increase, about a 280% increase to about a 400% increase, about a 280% increase to about a 350% increase, about a 280% increase to about a 300% increase, a 300% increase to about a 500% increase, about a 300% increase to about a 450% increase, about a 300% increase to about a 400% increase, about a 300% increase to about a 350% increase, a 350% increase to about a 500% increase, about a 350% increase to about a 450% increase, about a 350% increase to about a 400% increase, a 400% increase to about a 500% increase, about a 400% increase to about a 450% increase, or a 400% increase to about a 500% increase, in the expression levels of two of more (e.g., three, four, five, or six) of CD25, CD69, mTORC1, SREBP1, IFN-γ, and a granzyme (e.g., granzyme B), e.g., as compared to a resting NK cell (e.g., a human resting NK cell).

In some embodiments, an activated NK cell can further have about a 10% increase to about a 500% increase (e.g., or any of the subranges of this range described herein) in the expression levels of two of more (e.g., 3, 4, 5, 6, 7, 8, 9, 10, 11, 12, 13, 14, 15, 16, 17, 18, 19, 20, 21, 22, 23, 24, 25, 26, 27, 28, or 29) of CD25, CD59, CD352, NKp80, DNAM-1, 2B4, NKp30, NKp44, NKp46, NKG2D, CD16, KIR2DS1, KIR2Ds2/3, KIR2DL4, KIR2DS4, KIR2DS5, KIR3DS1, NKG2C, CCR7, CXCR3, L-Selectin, CXCR1, CXCR2, CX3CR1, ChemR23, CXCR4, CCR5, S1P5, c-Kit, mTORC1, e.g., as compared to a resting NK cell (e.g., a human activated NK cell).

Non-limiting examples of assays that can be used to determining the expression level of CD25, CD69, CD59, CD352, NKp80, DNAM-1, 2B4, NKp30, NKp44, NKp46, NKG2D, CD16, KIR2DS1, KIR2Ds2/3, KIR2DL4, KIR2DS4, KIR2DS5, KIR3DS1, NKG2C, CCR7, CXCR3, L-Selectin, CXCR1, CXCR2, CX3CR1, ChemR23, CXCR4, CCR5, S1P5, c-Kit, mTORC1, MYC, SREBP1, IFN-γ, and a granzyme (e.g., granzyme B) include, e.g., immunoblotting, fluorescence-assisted cell sorting, enzyme-linked immunosorbent assays, and RT-PCR.

Non-limiting examples of commercial ELISA assays that can be used to determine the expression level of CD25 are available from Diaclone, Covalab Biotechnology, and Caltag Medsystems. The protein and cDNA sequences for mature human CD25 are shown below.

```
Mature Human CD25 Protein
                                        (SEQ ID NO: 1)
elcdddppe iphatfkama ykegtmlnce ckrgfrriks

gslymlctgn sshsswdnqc qctssatrnt tkqvtpqpee

qkerkttemq spmqpvdqas lpghcreppp weneateriy

hfvvgqmvyy qcvqgyralh rgpaesvckm thgktrwtqp

qlictgemet sqfpgeekpq aspegrpese tsclvtttdf

qiqtemaatm etsiftteyq vavagcvfll isvlllsglt

wqrrqrksrr ti
```

-continued

```
Human CD25 cDNA
                                        (SEQ ID NO: 2)
gagctctg tgacgatgac ccgccagaga tcccacacgc

cacattcaaa gccatggcct acaaggaagg aaccatgttg

aactgtgaat gcaagagagg tttccgcaga ataaaaagcg

ggtcactcta tatgctctgt acaggaaact ctagccactc

gtcctgggac aaccaatgtc aatgcacaag ctctgccact

cggaacacaa cgaaacaagt gacacctcaa cctgaagaac

agaaagaaag gaaaaccaca gaaatgcaaa gtccaatgca

gccagtggac caagcgagcc ttccaggtca ctgcagggaa

cctccaccat gggaaaatga agccacagag agaatttatc

atttcgtggt ggggcagatg gtttattatc agtgcgtcca

gggatacagg gctctacaca gaggtcctgc tgagagcgtc

tgcaaaatga cccacgggaa gacaaggtgg acccagcccc

agctcatatg cacaggtgaa atggagacca gtcagtttcc

aggtgaagag aagcctcagg caagccccga aggccgtcct

gagagtgaga cttcctgcct cgtcacaaca acagattttc

aaatacagac agaaatggct gcaaccatgg agacgtccat

atttacaaca gagtaccagg tagcagtggc cggctgtgtt

ttcctgctga tcagcgtcct cctcctgagt gggctcacct

ggcagcggag acagaggaag agtagaagaa caatc
```

Non-limiting examples of commercial ELISA assays that can be used to determine the expression level of CD69 are available from RayBiotech, Novus Biologicals, and Aviscera Bioscience. The protein and cDNA sequences for mature human CD69 are shown below.

```
Mature Human CD69 Protein
                                        (SEQ ID NO: 3)
mssencfvae nsslhpesgq endatsphfs trhegsfqvp

vlcavmnvvf itiliialia lsvgqyncpg qytfsmpsds

hvsscsedwv gyqrkcyfis tvkrswtsaq nacsehgatl

avidsekdmn flkryagree hwvglkkepg hpwkwsngke

fnnwfnvtgs dkcvflknte vssmeceknl ywicnkpyk

Human CD69 cDNA
                                        (SEQ ID NO: 4)
atgagctctg aaaattgttt cgtagcagag aacagctctt

tgcatccgga gagtggacaa gaaaatgatg ccaccagtcc

ccatttctca acacgtcatg aagggtcctt ccaagttcct

gtcctgtgtg ctgtaatgaa tgtggtcttc atcaccattt

taatcatagc tctcattgcc ttatcagtgg gccaatacaa

ttgtccaggc caatacacat tctcaatgcc atcagacagc

catgtttctt catgctctga ggactgggtt ggctaccaga

ggaaatgcta ctttatttct actgtgaaga ggagctggac

ttcagcccaa aatgcttgtt ctgaacatgg tgctactctt
```

-continued gctgtcattg attctgaaaa ggacatgaac tttctaaaac gatacgcagg tagagaggaa cactgggttg gactgaaaaa ggaacctggt cacccatgga agtggtcaaa tggcaaagaa tttaacaact ggttcaacgt tacagggtct gacaagtgtg tttttctgaa aaacacagag gtcagcagca tggaatgtga gaagaattta tactggatat gtaacaaacc ttacaaataa The protein and cDNA sequences for mature human CD59 are shown below.

Mature Human CD59 Protein (SEQ ID NO: 5)

lqcyncpnptadckt avncssdfda clitkaglqv ynkcwkfehc nfndvttrlr eneltyycck kdlcnfneql en Human CD59 cDNA (SEQ ID NO: 6)

atgggaatcc aaggagggtc tgtcctgttc gggctgctgc tcgtcctggc tgtcttctgc cattcaggtc atagcctgca gtgctacaac tgtcctaacc caactgctga ctgcaaaaca gccgtcaatt gttcatctga ttttgatgcg tgtctcatta ccaaagctgg gttacaagtg tataacaagt gttggaagtt tgagcattgc aatttcaacg acgtcacaac ccgcttgagg gaaaatgagc taacgtacta ctgctgcaag aaggacctgt gtaactttaa cgaacagctt gaaaatggtg ggacatcctt atcagagaaa acagttcttc tgctggtgac tccatttctg gcagcagcct ggagccttca tccctaa The protein and cDNA sequences for mature human CD352 are shown below.

Mature Human CD352 Protein (SEQ ID NO: 7)

qssltplmv ngilgesvtl plefpagekv nfitwlfnet slafivphet kspeihvtnp kqgkrinftq syslqlsnlk medtgsyraq istktsakls sytlrilrql rniqvtnhsq lfqnmtcelh ltcsvedadd nvsfrwealg ntlssqpnlt vswdprisse qdytciaena vsnlsfsysa qklcedvkiq ytdtkmilfm vsgicivfgf iillllvlrk rrdslslstq rtqgpaesar nleyvsyspt nntvyasvth snreteiwtp rendtitiys tinhskeskp tfsrataldn vv Human CD352 cDNA (SEQ ID NO: 8)

atgttgtggc tgttccaatc gctcctgttt gtcttctgct ttggcccagg gaatgtagtt tcacaaagca gcttaacccc attgatggtg aacgggattc tgggggagtc agtaactctt cccctggagt ttcctgcagg agagaaggtc aacttcatca cttggctttt caatgaaaca tctcttgcct tcatagtacc -continued ccatgaaacc aaaagtccag aaatccacgt gactaatccg aaacagggaa agcgactgaa cttcacccag tcctactccc tgcaactcag caacctgaag atggaagaca caggctctta cagagcccag atatccacaa agacctctgc aaagctgtcc agttacactc tgaggatatt aagacaactg aggaacatac aagttaccaa tcacagtcag ctatttcaga atatgacctg tgagctccat ctgacttgct ctgtggagga tgcagatgac aatgtctcat tcagatggga ggccttggga aacacacttt caagtcagcc aaacctcact gtctcctggg accccaggat ttccagtgaa caggactaca cctgcatagc agagaatgct gtcagtaatt tatccttctc tgtctctgcc cagaagcttt gcgaagatgt taaaattcaa tatacagata ccaaaatgat tctgtttatg gtttctggga tatgcatagt cttcggtttc atcatactgc tgttacttgt tttgaggaaa agaagagatt ccctatcttt gtctactcag cgaacacagg gccccgagtc cgcaaggaac ctagagtatg tttcagtgtc tccaacgaac aacactgtgt atgcttcagt cactcattca aacagggaaa cagaaatctg gacacctaga gaaaatgata ctatcacaat ttactccaca attaatcatt ccaaagagag taaacccact ttttccaggg caactgccct tgacaatgtc gtgtaa The protein and cDNA sequences for mature human NKp80 are shown below.

Mature Human NKp80 Protein (SEQ ID NO: 9)

mqdeerymtl nvqskkrssa qtsqltfkdy svtlhwykil lgisgtvngi ltltlislil lvsqgvllkc qkgscsnatq yedtgdlkvn ngtrrnisnk dlcasrsadq tvlcqsewlk yqgkcywfsn emkswsdsyv yclerkshll iihdqlemaf iqknlrqlny vwiglnftsl kmtwtwvdgs pidskiffik gpakenscaa ikeskifset cssvfkwicq y Human NKp80 cDNA (SEQ ID NO: 10)

atgcaagatg aagaaagata catgacattg aatgtacagt caaagaaaag gagttctgcc caaacatctc aacttacatt taaagattat tcagtgacgt tgcactggta taaaatctta ctgggaatat ctggaaccgt gaatggtatt ctcactttga ctttgatctc cttgatcctg ttggtactat gccaatcaga atggctcaaa taccaaggga agtgttattg gttctctaat gagatgaaaa gctggagtga cagttatgtg tattgtttgg aaagaaaatc tcatctacta atcatacatg accaacttga aatggctttt atacagaaaa acctaagaca attaaactac gtatggattg ggcttaactt tacctccttg aaaatgacat -continued ggacttgggt ggatggttct ccaatagatt caaagatatt cttcataaag ggaccagcta aagaaaacag ctgtgctgcc attaaggaaa gcaaaatttt ctctgaaacc tgcagcagtg ttttcaaatg gatttgtcag tattag The protein and cDNA sequences for mature human DNAM-1 are shown below.

Mature Human DNAM-1 Protein
(SEQ ID NO: 11)

ee vlwhtsvpfa enmslecvyp smgiltqvew fkigtqqdsi aifspthgmv irkpyaervy flnstmasnn mtlffrnase ddvgyyscsl ytypqgtwqk viqvvqsdsf eaavpsnshi vsepgknvtl tcqpqmtwpv qavrwekiqp rqidlltycn lvhgrnftsk fprqivsncs hgrwsvivip dvtvsdsgly rcylqasage netfvmrltv aegktdnqyt lfvaggtvll llfvisitti iviflnrrrr rerrdlftes wdtqkapnny rspistsgpt nqsmddtred iyvnyptfsr rpktrv Human DNAM-1 cDNA
(SEQ ID NO: 12)

atggattatc ctactttact tttggctctt cttcatgtat acagagctct atgtgaagag gtgctttggc atacatcagt tccctttgcc gagaacatgt ctctagaatg tgtgtatcca tcaatgggca tcttaacaca ggtggagtgg ttcaagatcg ggacccagca ggattccata gccattttca gccctactca tggcatggtc ataaggaagc cctatgctga gagggtttac tttttgaatt caacgatggc ttccaataac atgactcttt tctttcggaa tgcctctgaa gatgatgttg gctactattc ctgctctctt tacacttacc cacagggaac ttggcagaag gtgatacagg tggttcagtc agatagtttt gaggcagctg tgccatcaaa tagccacatt gtttcggaac ctggaaagaa tgtcacactc acttgtcagc ctcagatgac gtggcctgtg caggcagtga ggtgggaaaa gatccagccc cgtcagatcg acctcttaac ttactgcaac ttggtccatg gcagaaattt cacctccaag ttcccaagac aaatagtgag caactgcagc cacggaaggt ggagcgtcat cgtcatcccc gatgtcacag tctcagactc ggggctttac cgctgctact tgcaggccag cgcaggagaa aacgaaacct tcgtgatgag attgactgta gccgagggta aaaccgataa ccaatatacc ctctttgtgg ctggagggac agttttattg ttgttgtttg ttatctcaat taccaccatc attgtcattt tccttaacag aaggagaagg agagagagaa gagatctatt tacagagtcc tgggatacac agaaggcacc caataactat agaagtccca tctctaccag tcaacctacc aatcaatcca tggatgatac aagagaggat -continued atttatgtca actatccaac cttctctcgc agaccaaaga ctagagttta a The protein and cDNA sequences for mature human 2B4 are shown below.

Mature Human 2B4 Protein
(SEQ ID NO: 13)

gk gcqgsadhvv sisgvplqlq pnsiqtkvds iawkkllpsq ngfhhilkwe ngslpsntsn drfsfivknl sllikaaqqq dsglyclevt sisgkvqtat fqvfvfdkve kprlqgqgki ldrgrcqval sclvsrdgnv syawyrgskl iqtagnltyl deevdingth tytcnvsnpv sweshtlnlt qdcqnahqef rfwpflviiv ilsalflgtl acfcvwrrkr kekqsetspk efltiyedvk dlktrrnheq eqtfpgggst iysmiqsqss aptsqepayt lysliqpsrk sgsrkrnhsp sfnstiyevi gksqpkaqnp arlsrkelen fdvys Human 2B4 cDNA
(SEQ ID NO: 14)

atgctggggc aagtggtcac cctcatactc ctcctgctcc tcaaggtgta tcagggcaaa ggatgccagg gatcagctga ccatgtggtt agcatctcgg gagtgcctct tcagttacaa ccaaacagca tacagacgaa ggttgacagc attgcatgga agaagttgct gccctcacaa aatggatttc atcacatatt gaagtgggag aatggctctt tgccttccaa tacttccaat gatagattca gttttatagt caagaacttg agtcttctca tcaaggcagc tcagcagcag gacagtggcc tctactgcct ggaggtcacc agtatatctg gaaaagttca gacagccacg ttccaggttt ttgtatttga taaagttgag aaaccccgcc tacaggggca ggggaagatc ctggacagag ggagatgcca agtggctctg tcttgcttgg tctccaggga tggcaatgtg tcctatgctt ggtacagagg gagcaagctg atccagacag cagggaacct cacctacctg gacgaggagg ttgacattaa tggcactcac acatatacct gcaatgtcag caatcctgtt agctgggaaa gccacaccct gaatctcact caggactgtc agaatgccca tcaggaattc agattttggc cgtttttggt gatcatcgtg attctaagcg cactgttcct tggcaccctt gcctgcttct gtgtgtggag gagaaagagg aaggagaagc agtcagagac cagtcccaag gaatttttga caatttacga agatgtcaag gatctgaaaa ccaggagaaa tcacgagcag gagcagactt ttcctggagg ggggagcacc atctactcta tgatccagtc ccagtcttct gctcccacgt cacaagaacc tgcatataca ttatattcat taattcagcc ttccaggaag tctggatcca ggaagaggaa ccacagccct tccttcaata -continued

```
gcactatcta tgaagtgatt ggaaagagtc aacctaaagc
ccagaaccct gctcgattga gccgcaaaga gctggagaac
tttgatgttt attcctag
```

The protein and cDNA sequences for mature human NKp30 are shown below.

Mature Human NKp30 Protein (SEQ ID NO: 15)

```
lw vsqppeirtl egssaflpcs fnasqgrlai gsvtwfrdev
vpgkevrngt pefrgrlapl assrflhdhq aelhirdvrg
hdasiyvcrv evlglgvgtg ngtrlvveke hpqlgagtvl
llragfyavs flsvavgstv yyqgkcltwk gprrqlpavv
paplpppcgs sahllppvpg g
```

Human NKp30 cDNA (SEQ ID NO: 16)

```
atggcctgga tgctgttgct catcttgatc atggtccatc
caggatcctg tgctctctgg gtgtcccagc cccctgagat
tcgtaccctg gaaggatcct ctgccttcct gccctgctcc
ttcaatgcca gccaagggag actggccatt ggctccgtca
cgtggttccg agatgaggtg gttccaggga aggaggtgag
gaatggaacc ccagagttca ggggccgcct ggccccactt
gcttcttccc gtttcctcca tgaccaccag gctgagctgc
acatccggga cgtgcgaggc catgacgcca gcatctacgt
gtgcagagtg gaggtgctgg gccttggtgt cgggacaggg
aatgggactc ggctggtggt ggagaaagaa catcctcagc
taggggctgg tacagtcctc ctccttcggg ctggattcta
tgctgtcagc tttctctctg tggccgtggg cagcaccgtc
tattaccagg gcaaatgcca ctgtcacatg ggaacacact
gccactcctc agatgggccc cgaggagtga ttccagagcc
cagatgtccc tag
```

The protein and cDNA sequences for mature human NKp44 are shown below.

Mature Human NKp44 Protein (SEQ ID NO: 17)

```
qskaqvlqs vagqtltvrc qypptgslye kkgwckeasa
lvcirlvtss kprtmawtsr ftiwddpdag fftvtmtdlr
eedsghywcr iyrpsdnsvs ksvrfylvvs pasastqtsw
tprdlvssqt qtqscvppta garqapesps tipvpsqpqn
stlrpgpaap ialvpvfcgl lvakslvlsa llvwwgdiww
ktmmelrsld tqkatchlqg vtdlpwtsvs spvereilyh
tvartkisdd ddehtl
```

Human NKp44 cDNA (SEQ ID NO: 18)

```
atggcctggc gagccctaca cccactgcta ctgctgctgc
tgctgttccc aggctctcag gcacaatcca aggctcaggt
```

-continued

```
acttcaaagt gtggcagggc agacgctaac cgtgagatgc
cagtacccgc ccacgggcag tctctacgag aagaaaggct
ggtgtaagga ggcttcagca cttgtgtgca tcaggttagt
caccagctcc aagcccagga cgatggcttg gacctctcga
ttcacaatct gggacgaccc tgatgctggc ttcttcactg
tcaccatgac tgatctgaga gaggaagact caggacatta
ctggtgtaga atctaccgcc cttctgacaa ctctgtctct
aagtccgtca gattctatct ggtggtatct ccagcctctg
cctccacaca gacctcctgg actccccgcg acctggtctc
ttcacagacc cagacccaga gctgtgtgcc tcccactgca
ggagccagac aagcccctga gtctccatct accatccctg
tcccttcaca gccacagaac tccacgctcc gccctggccc
tgcagccccc attgccctgg tgcctgtgtt ctgtggactc
ctcgtagcca agagcctggt gctgtcagcc ctgctcgtct
ggtgggtttt aaggaatcgg cacatgcagc atcaagggag
gtctctgctg cacccagctc agcccaggcc ccaggcccat
agacacttcc cactgagcca cagggcacca ggggggacat
atggtggaaa accatga
```

The protein and cDNA sequences for mature human NKp46 are shown below.

Mature Human NKp46 Protein (SEQ ID NO: 19)

```
qqqtlpkpf iwaephfmvp kekqvticcq gnygaveyql
hfegslfavd rpkpperink vqfyipdmns rmagqysciy
rvgelwseps nlldlvvtem ydtptlsvhp gpevisgekv
tfycrldtat smflllkegr sshvqrgygk vqaefplgpv
ttahrgtyrc fgsynnhaws fpsepvkllv tgdientsla
pedptfpadt wgtyllttet glqkdhalwd htagnllrmg
laflvlvalv wflvedwlsr krtrerasra stwegrrrln
tqtl
```

Human NKp46 cDNA (SEQ ID NO: 20)

```
atggcctggc gagccctaca cccactgcta ctgctgctgc
tgctgttccc aggctctcag gcacaatcca aggctcaggt
acttcaaagt gtggcagggc agacgctaac cgtgagatgc
cagtacccgc ccacgggcag tctctacgag aagaaaggct
ggtgtaagga ggcttcagca cttgtgtgca tcaggttagt
caccagctcc aagcccagga cgatggcttg gacctctcga
ttcacaatct gggacgaccc tgatgctggc ttcttcactg
tcaccatgac tgatctgaga gaggaagact caggacatta
ctggtgtaga atctaccgcc cttctgacaa ctctgtctct
aagtccgtca gattctatct ggtggtatct ccagcctctg
```

-continued cctccacaca gacctcctgg actccccgcg acctggtctc
ttcacagacc cagacccaga gctgtgtgcc tcccactgca
ggagccagac aagcccctga gtctccatct accatccctg
tcccttcaca gccacagaac tccacgctcc gccctggccc
tgcagccccc attgccctgg tgcctgtgtt ctgtggactc
ctcgtagcca agagcctggt gctgtcagcc ctgctcgtct
ggtgggtttt aaggaatcgg cacatgcagc atcaagggag
gtctctgctg cacccagctc agcccaggcc ccaggcccat
agacacttcc cactgagcca cagggcacca ggggggacat
atggtggaaa accatga The protein and cDNA sequences for mature human NKG2D are shown below.

Mature Human NKG2D Protein
(SEQ ID NO: 21)
mgwirgrrsr hswemsefhn ynldlkksdf strwqkqrcp
vvkskcrena spfffccfia vamgirfiim vaiwsavfln
slfnqevqip ltesycgpcp knwicyknnc yqffdesknw
yesqascmsq nasllkvysk edqdllklvk syhwmglvhi
ptngswqwed gsilspnllt iiemqkgdca lyassfkgyi
encstpntyi cmqrtv Human NKG2D cDNA
(SEQ ID NO: 22)
atggggtgga ttcgtggtcg gaggtctcga cacagctggg
agatgagtga atttcataat tataacttgg atctgaagaa
gagtgatttt tcaacacgat ggcaaaagca aagatgtcca
gtagtcaaaa gcaaatgtag agaaaatgca tctccatttt
ttttctgctg cttcatcgct gtagccatgg gaatccgttt
cattattatg gtaacaatat ggagtgctgt attcctaaac
tcattattca accaagaagt tcaaattccc ttgaccgaaa
gttactgtgg cccatgtcct aaaaactgga tatgttacaa
aaataactgc taccaatttt ttgatgagag taaaaactgg
tatgagagcc aggcttcttg tatgtctcaa aatgccagcc
ttctgaaagt atacagcaaa gaggaccagg atttacttaa
actggtgaag tcatatcatt ggatgggact agtacacatt
ccaacaaatg gatcttggca gtgggaagat ggctccattc
tctcacccaa cctactaaca ataattgaaa tgcagaaggg
agactgtgca ctctatgcct cgagctttaa aggctatata
gaaaactgtt caactccaaa tacgtacatc tgcatgcaaa
ggactgtgta a The protein and cDNA sequences for mature human CD16a are shown below.

Mature Human CD16a Protein
(SEQ ID NO: 23)
maegtlwqil cvssdaqpqt fegvkgadpp tlppgsflpg
pvlwwgslar lqteksdevs rkgnwwvtem gggagerlft
ssclvglvpl glrislvtcp lqcgimwqll lptallllvs
agmrtedlpk avvflepqwy rvlekdsvtl kcqgaysped
nstqwfhnes lissqassyf idaatvddsg eyrcqtnlst
lsdpvglevh igwlllqapr wvfkeedpih lrchswknta
lhkvtylqng kgrkyfhhns dfyipkatlk dsgsyfcrgl
fgsknvsset vnititqgla vstissffpp gyqvsfclvm
vllfavdtgl yfsvktnirs strdwkdhkf kwrkdpqdk Human CD16a cDNA
(SEQ ID NO: 24)
atggctgagggcacactctggcagattctgtgtgtgtcctcagatgctca
gccacagacctttgagggagtaaagggggcagacccacccaccttgcctc
caggctctttccttcctggtcctgttctatggtggggctcccttgccaga
cttcagactgagaagtcagatgaagtttcaagaaaaggaaattggtgggt
gacagagatgggtggaggggctggggaaaggctgtttacttcctcctgtc
tagtcggtttggtccctttagggctccggatatctttggtgacttgtcca
ctccagtgtggcatcatgtggcagctgctcctcccaactgctctgctact
tctagtttcagctggcatgcggactgaagatctcccaaaggctgtggtgt
tcctggagcctcaatggtacagggtgctcgagaaggacagtgtgactctg
aagtgccagggagcctactcccctgaggacaattccacacagtggtttca
caatgagagcctcatctcaagccaggcctcgagctacttcattgacgctg
ccacagtcgacgacagtggagagtacaggtgccagacaaacctctccacc
ctcagtgacccggtgcagctagaagtccatatcggctggctgttgctcca
ggcccctcggtgggtgttcaaggaggaagaccctattcacctgaggtgtc
acagctggaagaacactgctctgcataaggtcacatatttacagaatggc
aaaggcaggaagtattttcatcataattctgacttctacattccaaaagc
cacactcaaagacagcggctcctacttctgcagggggctttttgggagta
aaaatgtgtcttcagagactgtgaacatcaccatcactcaaggtttggca
gtgtcaaccatctcatcattctttccacctgggtaccaagtctctttctg
cttggtgatggtactcctttttgcagtggacacaggactatatttctctg
tgaagacaaacattcgaagctcaacaagagactggaaggaccataaattt
aaatggagaaaggaccctcaagacaaatga The protein and cDNA sequences for mature human CD16b are shown below.

Mature Human CD16b Protein
(SEQ ID NO: 25)
mwqlllptal lllvsagmrt edlpkavvfl epqwysvlek
dsvtlkcqga yspednstqw fhneslissq assyfidaat
vndsgeyrcq tnlstlsdpv qlevhigwll lqaprwvfke
edpihlrchs wkntalhkvt ylqngkdrky fhhnsdfhip -continued katlkdsgsy fcrglvgskn vssetvniti tqglaystis sfsppgyqvs fclvmvllfa vdtglyfsvk tni Human CD16b cDNA (SEQ ID NO: 26)

atgtggcagctgctcctcccaactgctctgctacttctagtttcagctgg catgcggactgaagatctcccaaaggctgtggtgttcctggagcctcaat ggtacagcgtgcttgagaaggacagtgtgactctgaagtgccagggagcc tactcccctgaggacaattccacacagtggtttcacaatgagaacctcat ctcaagccaggcctcgagctacttcattgacgctgccacagtcaacgaca gtggagagtacaggtgccagacaaacctctccaccctcagtgacccggtg cagctagaagtccatatcggctggctgttgctccaggcccctcggtgggt gttcaaggaggaagaccctattcacctgaggtgtcacagctggaagaaca ctgctctgcataaggtcacatatttacagaatggcaaagacaggaagtat tttcatcataattctgacttccacattccaaaagccacactcaaagatag cggctcctacttctgcaggggggcttgttgggagtaaaaatgtgtcttcag agactgtgaacatcaccatcactcaaggtttggcagtgtcaaccatctca tcattctctccacctgggtaccaagtctctttctgcttggtgatggtact cctttttgcagtggacacaggactatatttctctgtgaagacaaacattt ga The protein and cDNA sequences for mature human KIR2DS1 are shown below.

Human KIR2DS1 Protein (SEQ ID NO: 27)

msltvvsmac vgfflllqgaw phegvhrkps llahpgrlvk seetvilqcw sdvmfehfll hregmfndtl rligehhdgv skanfsisrm kqdlagtyrc ygsvthspyq vsapsdpldi viiglyekps lsaqpgptvl agesvtlscs srssydmyhl sregeaherr lpagtkvngt fqanfplgpa thggtyrcfg sfrdspyews kssdpllvsv tgnpsnswps ptepssetgn prhlhvligt svvkipftil lfflllhrwcs dkknaavmdq epagnrtvns edsdeqdhqe vsya Human KIR2DS1 cDNA (SEQ ID NO: 28)

atgtcgctcacggtcgtcagcatggcgtgtgttgggttcttcttgctgca gggggcctggccacatgagggagtccacagaaaaccttccctcctggccc acccaggtcgcctggtgaaatcagaagagacagtcatcctgcaatgttgg tcagatgtcatgtttgaacacttccttctgcacagagaggggatgtttaa cgacactttgcgcctcattggagaacaccatgatggggtctccaaggcca acttctccatcagtcgcatgaagcaagacctggcagggacctacagatgc tacggttctgttactcactcccccctatcagttgtcagctcccagtgaccc tctggacatcgtgatcataggtctatatgagaaaccttctctctcagccc agccgggccccacggttctggcaggagagaatgtgaccttgtcctgcagc tcccggagctcctatgacatgtaccatctatccagggaaggggaggccca tgaacgtaggctccctgcagggaccaaggtcaacggaacattccaggcca actttcctctgggccctgccacccatggagggacctacagatgcttcggc tctttccgtgactctccatacgagtggtcaaagtcaagtgacccactgct tgtttctgtcacaggaaacccttcaaatagttggccttcacccactgaac caagctccgaaaccggtaaccccagacacctacatgttctgattgggacc tcagtggtcaaaatccctttcaccatcctcctcttctttctccttcatcg ctggtgctccgacaaaaaaaatgctgctgtaatggaccaagagcctgcag ggaacagaacagtgaacagcgaggattctgatgaacaagaccatcaggag gtgtcatacgcataa The protein and cDNA sequences for mature human KIR2DS2 are shown below.

Human KIR2DS2 Protein (SEQ ID NO: 29)

mslmvvsmvc vgffllqgaw phegvhrkps llahpgplvk seetvilqcw sdvrfehfll hregkykdtl hligehhdgv skanfsigpm mqdlagtyrc ygsvthspyq lsapsdpldi vitglyekps lsaqpgptvl agesvtlscs srssydmyhl sregeaherr fsagpkvngt fqadfplgpa thggtyrcfg sfrdspyews nssdpllvsv tgnpsnswps ptepssktgn prhlhvligt svvkipftil lfflllhrwcs nkknaavmdq epagnrtvns edsdeqdhqe vsya Human KIR2DS2 cDNA (SEQ ID NO: 30)

atgtcgctcatggtcgtcagcatggcgtgtgttgggttcttcttgctgca gggggcctggccacatgagggagtccacagaaaaccttccctcctggccc acccaggtcccctggtgaaatcagaagagacagtcatcctgcaatgttgg tcagatgtcaggtttgagcacttccttctgcacagagaggggaagtataa ggacactttgcacctcattggagagcaccatgatggggtctccaaggcca acttctccatcggtcccatgatgcaagaccttgcagggacctacagatgc tacggttctgttactcactcccccctatcagttgtcagctcccagtgaccc tctggacatcgtcatcacaggtctatatgagaaaccttctctctcagccc agccgggccccacggttttggcaggagagagcgtgaccttgtcctgcagc tcccggagctcctatgacatgtaccatctatccagggagggggaggccca tgaacgtaggttctctgcagggcccaaggtcaacggaacattccaggccg actttcctctgggccctgccacccacggaggaacctacagatgcttcggc tctttccgtgactctccctatgagtggtcaaactcgagtgacccactgct tgtttctgtcacaggaaacccttcaaatagttggccttcacccactgaac caagctccaaaaccggtaaccccagacacctgcatgttctgattgggacc tcagtggtcaaaatccctttcaccatcctcctcttctttctccttcatcg ctggtgctccaacaaaaaaaatgctgctgtaatggaccaagagcctgcag ggaacagaacagtgaacagcgaggactctgatgaacaagaccctcaggag gtgacatacacacagttgaatcactgcgttttcacacagagaaaaatcac -continued tcgcccttctcagaggcccaagacacccccaacagatatcatcgtgtaca cggaacttccaaatgctgagtccaga The protein and cDNA sequences for mature human KIR2DS3 are shown below.

Mature Human KIR2DS3 Protein
(SEQ ID NO: 31)
mslmvismac vgffwlqgaw phegfrrkps llahpgrlvk seetvilqcw sdvmfehfll hregtfndtl rligehidgv skanfsigrm rqdlagtyrc ygsvphspyq fsapsdpldi vitglyekps lsaqpgptvl agesvtlscs swssydmyhl stegeaherr fsagpkvngt fqadfplgpa tqggtyrcfg sfhdspyews kssdpllvsv tgnpsnswps ptepssktgn prhlhvligt svvklpftil lffllhrwcs dkknasvmdq gpagnrtvnr edsdeqdhqe vsya Human KIR2DS3 cDNA
(SEQ ID NO: 32)
atgtcgctcatggtcatcagcatggcatgtgttgggttcttctggctgca gggggcctggccacatgagggattccgcagaaaaccttccctcctggccc acccaggtcgcctggtgaaatcagaagagacagtcatcctgcaatgttgg tcagatgtcatgtttgagcacttccttctgcacagagaggggacgtttaa cgacactttgcgcctcattggagagcacattgatggggtctccaaggcca acttctccatcggtcgcatgaggcaagacctggcagggacctacagatgc tacggttctgttcctcactcccccctatcagttttcagctcccagtgaccc tctggacatcgtgatcacaggtctatatgagaaaccttctctctcagccc agccgggccccacggttctggcaggagagagcgtgaccttgtcctgcagc tcctggagctcctatgacatgtaccatctatccacggagggggaggccca tgaacgtaggttctctgcagggcccaaggtcaacggaacattccaggccg actttcctctgggccctgccacccaaggaggaacctacagatgcttcggc tctttccatgactctccctacgagtggtcaaagtcaagtgacccactgct tgtttctgtcacaggaaacccttcaaatagttggccttcacccactgaac caagctccaaaaccggtaaccccagacacctacacgttctgattgggacc tcagtggtcaaactccctttcaccatcctcctcttctttctccttcatcg ctggtgctccgacaaaaaaaaatgcatctgtaatggaccaagggcctgcgg ggaacagaacagtgaacagggaggattctgatgaacaggaccatcaggag gtgtcatacgcataa The protein and cDNA sequences for mature human KIR2DL4 are shown below.

Mature Human KIR2DL4 Protein
(SEQ ID NO: 33)
hvggqdk pfcsawpsav vpqgghatlr chcrrgfnif tlykkdgvpv pelynrifwn sflispvtpa hagtyrcrgf hphsptewsa psnplvimvt glyekpslta rpgptvrage nvtlscssqs sfdiyhlsre geahelrlpa vpsingtfqa -continued dfplgpathg etyrcfgsfh gspyewsdps dplpvsvtgn pssswpspte psfktgiarh lhavirysva iilftilpff llhrwcskkk naavmnqepa ghrtvnreds deqdpqevty aqldhciftq rkitgpsqrs krpstdtsvc ielpnaepra lspahehhsq almgssrett alsqtqlass nvpaagi Human KIR2DL4 cDNA
(SEQ ID NO: 34)
atgtccccttcacatgttgtggtcaatgtgtcaactgcacgatccgggcc cctcaccacatcctctgcaccggtcagtcgagccgagtcactgcgtcctg gcagcagaagctgcaccatgtccatgtcacccacggtcatcatcctggca tgtcttgggttcttcttggaccagagtgtgtgggcacacgtgggtggtca ggacaagcccttctgctctgcctggcccagcgctgtggtgcctcaaggag gacacgtgactcttcggtgtcactatcgtcgtgggtttaacatcttcacg ctgtacaagaaagatggggtccctgtccctgagctctacaacagaatatt ctggaacagtttcctcattagccctgtgaccccagcacacgcagggacct acagatgtcgaggttttcacccgcactcccccactgagtggtcggcaccc agcaacccccctggtgatcatggtcacaggtctatatgagaaaccttcgct tacagcccggccgggccccacggttcgcgcaggagagaacgtgaccttgt cctgcagctcccagagctcctttgacatctaccatctatccagggagggg gaagcccatgaacttaggctccctgcagtgcccagcatcaatggaacatt ccaggccgacttccctctgggtcctgccacccacggagagacctacagat gcttcggctctttccatggatctccctacgagtggtcagacccgagtgac ccactgcctgtttctgtcacaggaaacccttctagtagttggccttcacc cactgaaccaagcttcaaaactggtatcgccagacacctgcatgctgtga ttaggtactcagtggccatcatcctctttaccatccttcccttctttctc cttcatcgctggtgctccaaaaaaaaagatgctgctgtaatgaaccaaga gcctgcgggacacagaacagtgaacagggaggactctgatgaacaagacc ctcaggaggtgacatacgcacagttggatcactgcattttcacacagaga aaaatcactggcccttctcagaggagcaagagaccctcaacagataccag cgtgtgtatagaacttccaaatgctgagcccagagcgttgtctcctgccc atgagcaccacagtcaggccttgatgggatcttctagggagacaacagcc ctgtctcaaacccagcttgccagctctaatgtaccagcagctggaatctg a The protein and cDNA sequences for mature human KIR2DS4 are shown below.

Mature Human KIR2DS4 Protein
(SEQ ID NO: 35)
qegvhrkps flalpghlvk seetvilqcw sdvmfehfll hregkfnntl hligehhdgv skanfsigpm mpvlagtyrc yssvphspyq lsapsdpldm viiglyekps lsaqpgptvq -continued agenvslscs siypgrgrpm nvgslqcaas tehsrptflw alpptegptd asalsvtlpt sgqtrvihcl fpsqetlqiv glhpinqapk pvtpdtymf Human KIR2DS4 cDNA (SEQ ID NO: 36)

atgtcgctcatggtcatcatcatggcgtgtgttgggttcttcttgctgca gggggcctggccacaggagggagtccacagaaaaccttccttcctggccc tcccaggtcacctggtgaaatcagaagagacagtcatcctgcaatgttgg tcggatgtcatgtttgagcacttccttctgcacagagaggggaagtttaa caacactttgcacctcattggagagcaccatgatggggtttccaaggcca acttctccattggtcccatgatgcctgtccttgcaggaacctacagatgc tacggttctgttcctcactcccccctatcagttgtcagctcccagtgaccc tctggacatggtgatcataggtctatatgagaaaccttctctctcagccc agccgggccccacggttcaggcaggagagaatgtgaccttgtcctgcagc tccatctatccagggaaggggaggcccatgaacgtaggctccctgcagtg cgcagcatcaacggaacattccaggccgactttcctctgggccctgccac ccacggagggacctacagatgcttcggctctttccgtgacgctccctacg agtggtcaaactcgagtgatccactgcttgtttccgtcacaggaaaccct tcaaatagttggccttcacccactgaaccaagctccaaaaccggtaaccc cagacacctacatgttctgattgggacctcagtggtcaaaatccctttca ccatcctcctcttctttctccttcatcgctggtgctccgacaaaaaaaat gctgctgtaatggaccaagagcctgcagggaacagaacagtgaacagcga ggattctgatgaacaagaccatcaggaggtgtcatacgcataa The protein and cDNA sequences for mature human KIR2DS5 are shown below.

Mature Human KIR2DS5

(SEQ ID NO: 37)

hegfrrkps llahpgplvk seetvilqcw sdvmfehfll hregtfnhtl rligehidgv skgnfsigrm tqdlagtyrc ygsvthspyq lsapsdpldi vitglyekps lsaqpgptvl agesvtlscs srssydmyhl sregeaherr lpagtkvngt fqadfpldpa thggtyrcfg sfrdspyews kssdpllvsv tgntsnswps ptepssktgn prhlhvligt svvklpftil lffllhrwcs nkknasvmdq gpagnrtvnr edsdeqdhqe vsya Human KIR2DS5 cDNA (SEQ ID NO: 38)

atgtcgctcatggtcatcagcatggcgtgtgttgcgttcttcttgctgca gggggcctggccacatgagggattccgcagaaaaccttccctcctggccc acccaggtcccctggtgaaatcagaagagacagtcatcctgcaatgttgg tcagatgtcatgtttgagcacttccttctgcacagagaggggacgtttaa ccacactttgcgcctcattggagagcacattgatggggtctccaagggca acttctccatcggtcgcatgacacaagacctggcagggacctacagatgc tacggttctgttactcactcccccctatcagttgtcagcgcccagtgaccc tctggacatcgtgatcacaggtctatatgagaaaccttctctctcagccc agccgggccccacggttctggcaggagagagcgtgaccttgtcctgcagc tcccggagctcctatgacatgtaccatctatccagggaaggggaggccca tgaacgtaggctccctgcagggcccaaggtcaacagaacattccaggccg actttcctctggaccctgccacccacggagggacctacagatgcttcggc tctttccgtgactctccatacgagtggtcaaagtcaagtgacccactgct tgtttctgtcacaggaaactcttcaaatagttggccttcacccactgaac caagctccgaaaccggtaaccccagacacctacacgttctgattgggacc tcagtggtcaaactccctttcaccatcctcctcttctttctccttcatcg ctggtgctccaacaaaaaaaatgcatctgtaatggaccaagggcctgcgg ggaacagaacagtgaacagggaggattctgatgaacaggaccatcaggag gtgtcatacgcataa The protein and cDNA sequences for mature human KIR3DS1 are shown below.

Mature Human KIR3DS1 cDNA (SEQ ID NO: 39)

hmggqdkpf lsawpsavvp rgghvtlrch yrhrfnnfml ykedrihvpi fhgrifqegf nmspvttaha gnytcrgshp hsptgwsaps npmvimvtgn hrkpsllahp gplvksgerv ilqcwsdimf ehfflhkegi skdpsrlvgq ihdgvskanf sigsmmrala gtyrcygsvt htpyqlsaps dpldivvtgl yekpslsaqp gpkvqagesv tlscssrssy dmyhlsregg aherrlpavr kvnrtfqadf plgpathggt yrcfgsfrhs pyewsdpsdp llvsvtgnps sswpspteps sksgnlrhlh iligtsvvki pftillffll hrwcsnkkkc ccngpracre qk Human KIR3DS1 cDNA (SEQ ID NO: 40)

atgttgctcatggtcgtcagcatggcgtgtgttgggttgttcttggtcca gagggccggtccacacatgggtggtcaggacaagcccttcctgtctgcct ggcccagcgctgtggtgcctcgcggaggacacgtgactcttcggtgtcac tatcgtcataggtttaacaatttcatgctatacaaagaagacagaatcca cgttcccatcttccatggcagaatattccaggagggcttcaacatgagcc ctgtgaccacagcacatgcagggaactacacatgtcggggttcacaccca cactcccccactgggtggtcggcacccagcaaccccatggtgatcatggt cacaggaaaccacagaaaaccttccctcctggcccacccaggtcccctgg tgaaatcaggagagagagtcatcctgcaatgttggtcagatatcatgttt gagcacttctttctgcacaaagagtggatctctaaggacccctcacgcct cgttggacagatccatgatggggtctccaaggccaatttctccatcggtt ccatgatgcgtgcccttgcagggacctacagatgctacggttctgttact cacacccccctatcagttgtcagctcccagtgatcccctggacatcgtggt -continued cacaggtctatatgagaaaccttctctctcagcccagccgggccccaagg ttcaggcaggagagagcgtgaccttgtcctgtagctcccggagctcctat gacatgtaccatctatccagggagggggggagcccatgaacgtaggctccc tgcagtgcgcaaggtcaacagaacattccaggcagatttccctctgggcc ctgccacccacggagggacctacagatgcttcggctctttccgtcactct ccctacgagtggtcagacccgagtgacccactgcttgtttctgtcacagg aaacccttcaagtagttggccttcacccacagaaccaagctccaaatctg gtaacctcagacacctgcacattctgattgggacctcagtggtcaaaatc cctttcaccatcctcctcttctttctccttcatcgctggtgctccaacaa aaaaaaatgctgctgtaatggaccaagagcctgcagggaacagaagtga The protein and cDNA sequences for mature human NKG2C are shown below.

Mature Human NKG2C Protein
(SEQ ID NO: 41)

mskqrgtfse vslaqdpkrq qrkpkgnkss isgteqeifq velnlqnpsl nhqgidkiyd cqgllpppek ltaevlgiic ivlmatvlkt ivlipfleqn nsspntrtqk arhcghcpee witysnscyy igkerrtwee sllactskns sllsidneee mkflasilps swigvfrnss hhpwvtingl afkhkikdsd naelncavlq vnrlksaqcg ssmiyhckhk l Human NKG2C cDNA
(SEQ ID NO: 42)

atgaataaacaaagaggaaccttctcagaagtgagtctggcccaggaccc aaagcggcagcaaaggaaacctaaaggcaataaaagctccatttcaggaa ccgaacaggaaatattccaagtagaattaaatcttcaaaatccttccctg aatcatcaagggattgataaaatatatgactgccaaggtttactgccacc tccagagaagctcactgccgaggtcctaggaatcatttgcattgtcctga tggccactgtgttaaaaacaatagttcttattcctttcctggagcagaac aatttttccccgaatacaagaacgcagaaagcacgtcattgtggccattg tcctgaggagtggattacatattccaacagttgttattacattggtaagg aaagaagaacttgggaagagagtttgctggcctgtacttcgaagaactcc agtctgctttctatagataatgaagaagaaatgaaatttctggccagcat tttaccttcctcatggattggtgtgtttcgtaacagcagtcatcatccat gggtgacaataaatggtttggctttcaaacataagataaaagactcagat aatgctgaacttaactgtgcagtgctacaagtaaatcgacttaaatcagc ccagtgtggatcttcaatgatatatcattgtaagcataagctttag The protein and cDNA sequences for mature human CCR7 are shown below.

Mature Human CCR7 Protein
(SEQ ID NO: 43)

qdevtd dyigdnttvd ytlfeslcsk kdvrnfkawf lpimysiicf vgllgnglvv ltyiyfkrlk tmtdtyllnl -continued avadilfllt lpfwaysaak swvfgvhfck lifaiykmsf fsgmllllci sidryvaivq avsahrhrar vllisklscv giwilatvls ipellysdlq rssseqamrc slitehveaf itiqvaqmvi gflvpllams fcylviirtl lqarnfernk aikviiavvv vfivfqlpyn gvvlaqtvan fnitsstcel skqlniaydv tyslacvrcc vnpflyafig vkfrndlfkl fkdlgclsqe qlrqwsscrh irrssmsvea ettttfsp Human CCR7 cDNA
(SEQ ID NO: 44)

atggacctggggaaaccaatgaaaagcgtgctggtggtggctctccttgt cattttccaggtatgcctgtgtcaagatgaggtcacggacgattacatcg gagacaacaccacagtggactacactttgttcgagtctttgtgctccaag aaggacgtgcggaactttaaagcctggttcctccctatcatgtactccat catttgtttcgtgggcctactgggcaatgggctggtcgtgttgacctata tctatttcaagaggctcaagaccatgaccgatacctacctgctcaacctg gcggtggcagacatcctcttcctcctgacccttcccttctgggcctacag cgcggccaagtcctgggtcttcggtgtccacttttgcaagctcatctttg ccatctacaagatgagcttcttcagtggcatgctcctacttctttgcatc agcattgaccgctacgtggccatcgtccaggctgtctcagctcaccgcca ccgtgcccgcgtccttctcatcagcaagctgtcctgtgtgggcatctgga tactagccacagtgctctccatcccagagctcctgtacagtgacctccag aggagcagcagtgagcaagcgatgcgatgctctctcatcacagagcatgt ggaggcctttatcaccatccaggtggcccagatggtgatcggctttctgg tcccccctgctggccatgagcttctgttaccttgtcatcatccgcaccctg ctccaggcacgcaactttgagcgcaacaaggccatcaaggtgatcatcgc tgtggtcgtggtcttcatagtcttccagctgccctacaatggggtggtcc tggcccagacggtggccaacttcaacatcaccagtagcacctgtgagctc agtaagcaactcaacatcgcctacgacgtcacctacagcctggcctgcgt ccgctgctgcgtcaaccctttcttgtacgccttcatcggcgtcaagttcc gcaacgatctcttcaagctcttcaaggacctgggctgcctcagccaggag cagctccggcagtggtcttcctgtcggcacatccggcgctcctccatgag tgtggaggccgagaccaccaccaccttctccccatag The protein and cDNA sequences for mature human CXCR3 are shown below.

Mature Human CXCR3 Protein
(SEQ ID NO: 45)

mvlevsdhqv lndaevaall enfsssydyg enesdsccts ppcpqdfsln fdraflpaly sllfllgllg ngavaavlls rrtalsstdt fllhlavadt llvltlplwa vdaavqwvfg sglckvagal fninfyagal llacisfdry lnivhatqly rrgpparvtl tclavwglcl lfalpdfifl sahhderlna thcqynfpqv grtalrvlql vagfllpllv maycyahila -continued vllvsrgqrr lramrlvvvv vvafalcwtp yhlvvlvdil mdlgalarnc gresrvdvak svtsglgymh cclnpllyaf vgvkfrermw mlllrlgcpn qrglqrqpss srrdsswset seasysgl Human CXCR3 cDNA (SEQ ID NO: 46)

atggagttgaggaagtacggccctggaagactggcggggacagttatagg aggagctgctcagagtaaatcacagactaaatcagactcaatcacaaaag agttcctgccaggcctttacacagccccttcctccccgttcccgccctca caggtgagtgaccaccaagtgctaaatgacgccgaggttgccgccctcct ggagaacttcagctcttcctatgactatggagaaaacgagagtgactcgt gctgtacctccccgccctgcccacaggacttcagcctgaacttcgaccgg gccttcctgccagccctctacagcctcctctttctgctggggctgctggg caacggcgcggtggcagccgtgctgctgagccggcggacagccctgagca gcaccgacaccttcctgctccacctagctgtagcagacacgctgctggtg ctgacactgccgctctgggcagtggacgctgccgtccagtgggtctttgg ctctggcctctgcaaagtggcaggtgccctcttcaacatcaacttctacg caggagccctcctgctggcctgcatcagctttgaccgctacctgaacata gttcatgccacccagctctaccgccgggggcccccggcccgcgtgaccct cacctgcctggctgtctggggggctctgcctgcttttcgccctcccagact tcatcttcctgtcggcccaccacgacgagcgcctcaacgccacccactgc caatacaacttcccacaggtgggccgcacggctctgcgggtgctgcagct ggtggctggctttctgctgcccctgctggtcatggcctactgctatgccc acatcctggccgtgctgctggtttccaggggccagcggcgcctgcgggcc atgcggctggtggtggtggtcgtggtggcctttgccctctgctggacccc ctatcacctggtggtgctggtggacatcctcatggacctgggcgctttgg cccgcaactgtggccgagaaagcagggtagacgtggccaagtcggtcacc tcaggcctgggctacatgcactgctgcctcaacccgctgctctatgcctt tgtaggggtcaagttccgggagcggatgtggatgctgctcttgcgcctgg gctgccccaaccagagagggctccagaggcagccatcgtcttcccgccgg gattcatcctggtctgagacctcagaggcctcctactcgggcttgtga The protein and cDNA sequences for mature human L-selectin are shown below.

Mature Human L-Selectin Protein (SEQ ID NO: 47)

df lahhgtdcwt yhysekpmnw qrarrfcrdn ytdlvaiqnk aeieylektl pfsrsyywig irkiggiwtw vgtnksltee aenwgdgepn nkknkedcve iyikrnkdag kwnddachkl kaalcytasc qpwscsghge cveiinnytc ncdvgyygpq cqfviqcepl eapelgtmdc thplgnfsfs sqcafscseg tnltgieett cgpfgnwssp eptcqviqce plsapdlgim ncshplasfs ftsactfics egteligkkk ticessgiws -continued npspicqkld ksfsmikegd ynplfipvav mvtafsglaf iiwlarrlkk gkkskrsmnd py Human L-Selectin cDNA (SEQ ID NO: 48)

atgggctgcagaagaactagagaaggaccaagcaaagccatgatatttcc atggaaatgtcagagcacccagagggacttatggaacatcttcaagttgt gggggtggacaatgctctgttgtgatttcctggcacatcatggaaccgac tgctggacttaccattattctgaaaaacccatgaactggcaaagggctag aagattctgccgagacaattacacagatttagttgccatacaaaacaagg cggaaattgagtatctggagaagactctgcctttcagtcgttcttactac tggataggaatccggaagataggaggaatatggacgtgggtgggaaccaa caaatctcttactgaagaagcagagaactggggagatggtgagcccaaca acaagaagaacaaggaggactgcgtggagatctatatcaagagaaacaaa gatgcaggcaaatggaacgatgacgcctgccacaaactaaaggcagccct ctgttacacagcttcttgccagccctggtcatgcagtggccatggagaat gtgtagaaatcatcaataattacacctgcaactgtgatgtggggtactat gggccccagtgtcagtttgtgattcagtgtgagcctttggaggccccaga gctgggtaccatggactgtactcaccctttgggaaacttcagcttcagct cacagtgtgccttcagctgctctgaaggaacaaacttaactgggattgaa gaaaccacctgtggaccatttggaaactggtcatctccagaaccaacctg tcaagtgattcagtgtgagcctctatcagcaccagatttggggatcatga actgtagccatcccctggccagcttcagctttacctctgcatgtaccttc atctgctcagaaggaactgagttaattgggaagaagaaaaccatttgtga atcatctggaatctggtcaaatcctagtccaatatgtcaaaaattggaca aaagtttctcaatgattaaggagggtgattataacccccctcttcattcca gtggcagtcatggttactgcattctctgggttggcatttatcatttggct ggcaaggagattaaaaaaaggcaagaaatccaagagaagtatgaatgacc catattaa The protein and cDNA sequences for mature human CXCR1 are shown below.

Mature Human CXCR1 Protein (SEQ ID NO: 49)

msnitdpqmw dfddlnftgm ppadedyspc xletetlnky vviiayalvf llsllgnslv mlvilysrvg rsvtdvylln laladllfal tlpiwaaskv ngwifgtflc kvvsllkevn fysgilllac isvdrylaiv hatrtltqkr hlvkfvclgc wglsmnlslp fflfrqayhp nnsspvcyev lgndtakwrm vlrilphtfg fivplfvmlf cygftlrtlf kahmgqkhra mrvifavvli fllcwlpynl vlladtlmrt qviqescerr nnigraldat eilgflhscl npiiyafigq nfrhgflkil amhglvskef larhrvtsyt sssvnvssnl Human CXCR1 cDNA
(SEQ ID NO: 50)
atgtcaaatattacagatccacagatgtgggattttgatgatctaaattt
cactggcatgccacctgcagatgaagattacagccctgtatgctagaaa
ctgagacactcaacaagtatgttgtgatcatcgcctatgccctagtgttc
ctgctgagcctgctgggaaactccctggtgatgctggtcatcttatacag
cagggtcggccgctccgtcactgatgtctacctgctgaacctggccttgg
ccgacctactctttgccctgaccttgcccatctgggccgcctccaaggtg
aatggctggatttttggcacattcctgtgcaaggtggtctcactcctgaa
ggaagtcaacttctacagtggcatcctgctgttggcctgcatcagtgtgg
accgttacctggccattgtccatgccacacgcacactgacccagaagcgt
cacttggtcaagtttgtttgtcttggctgctggggactgtctatgaatct
gtccctgcccttcttccttttccgccaggcttaccatccaaacaattcca
gtccagtttgctatgaggtcctgggaaatgacacagcaaaatggcggatg
gtgttgcggatcctgcctcacacctttggcttcatcgtgccgctgtttgt
catgctgttctgctatggattcaccctgcgtacactgtttaaggcccaca
tggggcagaagcaccgagccatgagggtcatctttgctgtcgtcctcatc
ttcctgctttgctggctgccctacaacctggtcctgctggcagacaccct
catgaggacccaggtgatccaggagagctgtgagcgccgcaacaacatcg
gccgggccctggatgccactgagattctgggatttctccatagctgcctc
aaccccatcatctacgccttcatcggccaaaattttcgccatggattcct
caagatcctggctatgcatggcctggtcagcaaggagttcttggcacgtc
atcgtgttacctcctacacttcttcgtctgtcaatgtctcttccaacctc
tga The protein and cDNA sequences for mature human CXCR2 are shown below.

Mature Human CXCR2 Protein
(SEQ ID NO: 51)
medfnmesds fedfwkgedl snysysstlp pflldaapce
pesleinkyf vviiyalvfl lsllgnslvm lvilysrvgr
svtdvyllnl aladllfalt lpiwaaskvn gwifgtflck
vvsllkevnf ysgilllaci svdrylaivh atrtltqkry
lvkficlsiw glslllalpv llfrrtvyss nvspacyedm
gnntanwrml lrilpqsfgf ivpllimlfc ygftlrtlfk
ahmgqkhram rvifavvlif llcwlpynlv lladtlmrtq
viqetcerrn hidraldate ilgilhscln pliyafigqk
frhgllkila ihgliskdsl pkdsrpsfvg sssghtsttl Human CXCR2 cDNA
(SEQ ID NO: 52)
atggaagattttaacatggagagtgacagctttgaagatttctggaaagg
tgaagatcttagtaattacagttacagctctaccctgcccccttttctac
tagatgccgccccatgtgaaccagaatccctggaaatcaacaagtatttt
gtggtcattatctatgccctggtattcctgctgagcctgctgggaaactc
cctcgtgatgctggtcatcttatacagcagggtcggccgctccgtcactg
atgtctacctgctgaacctagccttggccgacctactctttgccctgacc
ttgcccatctgggccgcctccaaggtgaatggctggatttttggcacatt
cctgtgcaaggtggtctcactcctgaaggaagtcaacttctatagtggca
tcctgctactggcctgcatcagtgtggaccgttacctggccattgtccat
gccacacgcacactgacccagaagcgctacttggtcaaattcatatgtct
cagcatctggggtctgtccttgctcctggccctgcctgtcttacttttcc
gaaggaccgtctactcatccaatgttagcccagcctgctatgaggacatg
ggcaacaatacagcaaactggcggatgctgttacggatcctgccccagtc
ctttggcttcatcgtgccactgctgatcatgctgttctgctacggattca
ccctgcgtacgctgtttaaggcccacatggggcagaagcaccgggccatg
cgggtcatctttgctgtcgtcctcatcttcctgctctgctggctgcccta
caacctggtcctgctggcagacaccctcatgaggacccaggtgatccagg
agacctgtgagcgccgcaatcacatcgaccgggctctggatgccaccgag
attctgggcatccttcacagctgcctcaaccccctcatctacgccttcat
tggccagaagtttcgccatggactcctcaagattctagctatacatggct
tgatcagcaaggactccctgcccaaagacagcaggccttcctttgttggc
tcttcttcagggcacacttccactactctctaa The protein and cDNA sequences for mature human CX3CR1 are shown below.

Mature Human CX3CR1 Protein
(SEQ ID NO: 53)
mdqfpesvte nfeyddlaea cyigdivvfg tvflsifysv
ifaiglvgnl lvvfaltnsk kpksvtdiyl lnlalsdllf
vatlpfwthy linekglhna mckfttafff igffgsiffi
tvisidryla ivlaansmnn rtvqhgvtis lgvwaaailv
aapqfmftkq keneclgdyp evlqeiwpvl rnvetnflgf
llpllimsyc yfriiqtlfs cknhkkakai klillvvivf
flfwtpynvm ifletlklyd ffpscdmrkd lrlalsvtet
vafshcclnp liyafagekf rrylyhlygk clavlcgrsv
hvdfsssesq rsrhgsvlss nftyhtsdgd allll Human CX3CR1 cDNA
(SEQ ID NO: 54)
atggatcagttccctgaatcagtgacagaaaactttgagtacgatgattt
ggctgaggcctgttatattggggacatcgtggtctttgggactgtgttcc
tgtccatattctactccgtcatctttgccattggcctggtgggaaatttg
ttggtagtgtttgccctcaccaacagcaagaagcccaagagtgtcaccga
catttacctcctgaacctggccttgtctgatctgctgtttgtagccactt
tgcccttctggactcactatttgataaatgaaaagggcctccacaatgcc
atgtgcaaattcactaccgccttcttcttcatcggctttttttggaagcat
attcttcatcaccgtcatcagcattgataggtacctggccatcgtcctgg
ccgccaactccatgaacaaccggaccgtgcagcatggcgtcaccatcagc -continued ctaggcgtctgggcagcagccattttggtggcagcaccccagttcatgtt cacaaagcagaaagaaaatgaatgccttggtgactaccccgaggtcctcc aggaaatctggcccgtgctccgcaatgtggaaacaaattttcttggcttc ctactccccctgctcattatgagttattgctacttcagaatcatccagac gctgttttcctgcaagaaccacaagaaagccaaagccattaaactgatcc ttctggtggtcatcgtgtttttcctcttctggacaccctacaacgttatg attttcctggagacgcttaagctctatgacttctttcccagttgtgacat gaggaaggatctgaggctggccctcagtgtgactgagacggttgcattta gccattgttgcctgaatcctctcatctatgcatttgctggggagaagttc agaagatacctttaccacctgtatgggaaatgcctggctgtcctgtgtgg gcgctcagtccacgttgatttctcctcatctgaatcacaaaggagcaggc atggaagtgttctgagcagcaattttacttaccacacgagtgatggagat gcattgctccttctctga The protein and cDNA sequences for mature human ChemR23 are shown below.

Mature Human ChemR23 Protein (SEQ ID NO: 55)

mrmededynt sisygdeypd yldsivvled lsplearvtr iflvvvysiv cflgilgngl viiiatfkmk ktvnmvwfln lavadflfnv flpihityaa mdyhwvfgta mckisnflli hnmftsvfll tiissdrcis vllpvwsqnh rsvrlaymac mviwvlaffl sspslvfrdt anlhgkiscf nnfslstpgs sswpthsqmd pvgysrhmvv tvtrflcgfl vpvliitacy ltivcklqrn rlaktkkpfk iivtiiitff lcwcpyhtln llelhhtamp gsvfslglpl atalaiansc mnpilyvfmg qdfkkfkval fsrlvnalse dtghssypsh rsftkmssmn ertsmneret gml Human ChemR23 cDNA (SEQ ID NO: 56)

atgagaatggaggatgaagattacaacacttccatcagttacggtgatga ataccctgattatttagactccattgtggttttggaggacttatccccct tggaagccagggtgaccaggatcttcctggtggtggtctacagcatcgtc tgcttcctcgggattctgggcaatggtctggtgatcatcattgccacctt caagatgaagaagacagtgaacatggtctggttcctcaacctggcagtgg cagatttcctgttcaacgtcttcctcccaatccatatcacctatgccgcc atggactaccactgggttttcgggacagccatgtgcaagatcagcaactt ccttctcatccacaacatgttcaccagcgtcttcctgctgaccatcatca gctctgaccgctgcatctctgtgctcctccctgtctggtcccagaaccac cgcagcgttcgcctggcttacatggcctgcatggtcatctgggtcctggc tttcttcttgagttccccatctctcgtcttccgggacacagccaacctgc atgggaaaatatcctgcttcaacaacttcagcctgtccacacctgggtct tcctcgtggcccactcactcccaaatggaccctgtggggtatagccggca catggtggtgactgtcacccgcttcctctgtggcttcctggtcccagtcc tcatcatcacagcttgctacctcaccatcgtgtgcaaactgcagcgcaac cgcctggccaagaccaagaagcccttcaagattattgtgaccatcatcat taccttcttcctctgctggtgcccctaccacacactcaacctcctagagc tccaccacactgccatgcctggctctgtcttcagcctgggtttgcccctg gccactgcccttgccattgccaacagctgcatgaaccccattctgtatgt tttcatgggtcaggacttcaagaagttcaaggtggccctcttctctcgcc tggtcaatgctctaagtgaagatacaggccactcttcctaccccagccat agaagctttaccaagatgtcatcaatgaatgagaggacttctatgaatga gagggagaccggcatgctttga The protein and cDNA sequences for mature human CXCR4 are shown below.

Mature Human CXCR4 Protein (SEQ ID NO: 57)

megisiytsd nyteemgsgd ydsmkepcfr eenanfnkif lptiysiifl tgivgnglvi lvmgyqkklr smtdkyrlhl svadllfvit lpfwavdava nwyfgnflck avhviytvnl yssvlilafi sldrylaivh atnsgrprkl laekvvyvgv wipallltip dfifanvsea ddryicdrfy pndlwvvvfq fqhimvglil pgivilscyc iiisklshsk ghqkrkalkt tvililaffa cwlpyyigis idsfilleii kqgcefentv hkwisiteal affhcclnpi lyaflgakfk tsaqhaltsv srgsslkils kgkrgghssv stesesssfh ss Human CXCR4 cDNA (SEQ ID NO: 58)

atgtccattcctttgcctcttttgcagatatacacttcagataactacac cgaggaaatgggctcaggggactatgactccatgaaggaaccctgtttcc gtgaagaaaatgctaatttcaataaaatcttcctgcccaccatctactcc atcatcttcttaactggcattgtgggcaatggattggtcatcctggtcat gggttaccagaagaaactgagaagcatgacggacaagtacaggctgcacc tgtcagtggccgacctcctctttgtcatcacgcttcccttctgggcagtt gatgccgtggcaaactggtactttgggaacttcctatgcaaggcagtcca tgtcatctacacagtcaacctctacagcagtgtcctcatcctggccttca tcagtctggaccgctacctggccatcgtccacgccaccaacagtcagagg ccaaggaagctgttggctgaaaaggtggtctatgttggcgtctggatccc tgccctcctgctgactattcccgacttcatctttgccaacgtcagtgagg cagatgacagatatatctgtgaccgcttctaccccaatgacttgtgggtg gttgtgttccagtttcagcacatcatggttggccttatcctgcctggtat tgtcatcctgtcctgctattgcattatcatctccaagctgtcacactcca agggccaccagaagcgcaaggccctcaagaccacagtcatcctcatcctg gctttcttcgcctgttggctgccttactacattgggatcagcatcgactc cttcatcctcctggaaatcatcaagcaagggtgtgagtttgagaacactg -continued tgcacaagtggatttccatcaccgaggccctagctttcttccactgttgt ctgaaccccatcctctatgctttccttggagccaaatttaaaacctctgc ccagcacgcactcacctctgtgagcagagggtccagcctcaagatcctct ccaaaggaaagcgaggtggacattcatctgtttccactgagtctgagtct tcaagttttcactccagctaa The protein and cDNA sequences for mature human CCR5 are shown below.

Mature Human CCR5 Protein (SEQ ID NO: 59)

mdyqvsspiy dinyytsepc qkinvkqiaa rllpplyslv fifgfvgnml vililinckr lksmtdiyll nlaisdlffl ltvpfwahya aaqwdfgntm cqlltglyfi gffsgiffii lltidrylav vhavfalkar tvtfgvvtsv itwvvavfas lpgiiftrsq keglhytcss hfpysqyqfw knfqtlkivi lglvlpllvm vicysgilkt llrcrnekkr hravrlifti mivyflfwap ynivlllntf qeffglnncs ssnrldqamq vtetlgmthc cinpiiyafv gekfrnyllv ffqkhiakrf ckccsifqqe aperassvyt rstgeqeisv gl Human CCR5 cDNA (SEQ ID NO: 60)

atggattatcaagtgtcaagtccaatctatgacatcaattattatacatc ggagccctgccaaaaaatcaatgtgaagcaaatcgcagcccgcctcctgc ctccgctctactcactggtgttcatctttggttttgtgggcaacatgctg gtcatcctcatcctgataaactgcaaaaggctgaagagcatgactgacat ctacctgctcaacctggccatctctgacctgtttttccttcttactgtcc ccttctgggctcactatgctgccgcccagtgggactttggaaatacaatg tgtcaactcttgacagggctctattttataggcttcttctctggaatctt cttcatcatcctcctgacaatcgataggtacctggctgtcgtccatgctg tgtttgctttaaaagccaggacggtcacctttggggtggtgacaagtgtg atcacttgggtggtggctgtgtttgcgtctctcccaggaatcatctttac cagatctcaaaaagaaggtcttcattacacctgcagctctcattttccat acagtcagtatcaattctggaagaatttccagacattaaagatagtcatc ttggggctggtcctgccgctgcttgtcatggtcatctgctactcgggaat cctaaaaactctgcttcggtgtcgaaatgagaagaagaggcacagggctg tgaggcttatcttcaccatcatgattgtttattttctcttctgggctccc tacaacattgtccttctcctgaacaccttccaggaattctttggcctgaa taattgcagtagctctaacaggttggaccaagctatgcaggtgacagaga ctcttgggatgacgcactgctgcatcaaccccatcatctatgcctttgtc ggggagaagttcagaaactacctcttagtcttcttccaaaagcacattgc caaacgcttctgcaaatgctgttctattttccagcaagaggctcccgagc gagcaagctcagtttacacccgatccactggggagcaggaaatatctgtg ggcttgtga The protein and cDNA sequences for mature human S1P5 are shown below.

Mature Human S1P5 Protein (SEQ ID NO: 61)

mesgllrpap vsevivlhyn ytgklrgary qpgaglrada vvclavcafi vlenlavllv lgrhprfhap mflllgsltl sdllagaaya anillsgplt lklspalwfa reggvfvalt asvlsllaia lersltmarr gpapvssrgr tlamaaaawg vslllgllpa lgwnclgrld acstvlplya kayvlfcvla fvgilaaica lyariycqvr anarrlparp gtagttstra rrkprslall rtlsvvllaf vacwgplfll lldvacpar tcpvllqadp flglamansl lnpiiytltn rdlrhallrl vccgrhscgr dpsgsqqsas aaeasgglrr clppgldgsf sgsersspqr dgldtsgstg spgaptaart lvsepaad Human S1P5 cDNA (SEQ ID NO: 62)

atggagtcggggctgctgcggccggcgccggtgagcgaggtcatcgtcct gcattacaactacaccggcaagctccgcggtgcgcgctaccagccgggtg ccggcctgcgcgccgacgccgtggtgtgcctggcggtgtgcgccttcatc gtgctagagaatctagccgtgttgttggtgctcggacgccacccgcgctt ccacgctcccatgttcctgctcctgggcagcctcacgttgtcggatctgc tggcaggcgccgcctacgccgccaacatcctactgtcggggccgctcacg ctgaaactgtcccccgcgctctggttcgcacgggagggaggcgtcttcgt ggcactcactgcgtccgtgctgagcctcctggccatcgcgctggagcgca gcctcaccatggcgcgcaggggggcccgcgcccgtctccagtcgggggcgc acgctggcgatggcagccgcggcctggggcgtgtcgctgctcctcgggct cctgccagcgctgggctggaattgcctgggtcgcctggacgcttgctcca ctgtcttgccgctctacgccaaggcctacgtgctcttctgcgtgctcgcc ttcgtgggcatcctggccgctatctgtgcactctacgcgcgcatctactg ccaggtacgcgccaacgcgcggcgcctgccggcacggcccgggactgcgg ggaccacctcgacccgggcgcgtcgcaagccgcgctcgctggccttgctg cgcacgctcagcgtggtgctcctggcctttgtggcatgttggggcccccct cttcctgctgctgttgctcgacgtggcgtgcccggcgcgcacctgtcctg tactcctgcaggccgatcccttcctgggactggccatggccaactcactt ctgaaccccatcatctacacgctcaccaaccgcgacctgcgccacgcgct cctgcgcctggtctgctgcggacgccactcctgcggcagagacccgagtg gctcccagcagtcggcgagcgcggctgaggcttccgggggcctgcgccgc tgcctgcccccgggccttgatgggagcttcagcggctcggagcgctcatc gccccagcgcgacgggctggacaccagcggctccacaggcagccccggtg cacccacagccgcccggactctggtatcagaaccggctgcagactga The protein and cDNA sequences for mature human C-kit are shown below.

Mature Human C-kit Protein (SEQ ID NO: 63)

qpsvs pgepsppsih pgksdlivrv gdeirllctd pgfvkwtfei ldetnenkqn ewitekaeat ntgkytctnk hglsnsiyvf vrdpaklflv drslygkedn dtlvrcpltd pevtnyslkg cqgkplpkdl rfipdpkagi miksvkrayh rlclhcsvdq egksvlsekf ilkvrpafka vpvvsvskas yllregeeft vtctikdvss svystwkren sqtklqekyn swhhgdfnye rqatltissa rvndsgvfmc yanntfgsan vtttlevvdk gfinifpmin ttvfvndgen vdliveyeaf pkpehqqwiy mnrtftdkwe dypksenesn iryvselhlt rlkgteggty tflvsnsdvn aaiafnvyvn tkpeiltydr lvngmlqcva agfpeptidw yfcpgteqrc sasvlpvdvq tlnssgppfg klvvqssids safkhngtve ckayndvgkt sayfnfafkg nnkeqihpht lftplligfv ivagmmciiv miltykylqk pmyevqwkvv eeingnnyvy idptqlpydh kwefprnrls fgktlgagaf gkvveatayg liksdaamtv avkmlkpsah lterealmse lkvlsylgnh mnivnllgac tiggptlvit eyccygdlln flrrkrdsfi cskqedhaea alyknllhsk esscsdstne ymdmkpgvsy vvptkadkrr svrigsyier dvtpaimedd elaldledll sfsyqvakgm aflaskncih rdlaarnill thgritkicd fglardiknd snyvvkgnar lpvkwmapes ifncvytfes dvwsygiflw elfslgsspy pgmpvdskfy kmikegfrml spehapaemy dimktcwdad plkrptfkqi vqliekqise stnhiysnla ncspnrqkpv vdhsvrinsv gstasssqpl lvhddv Human C-kit cDNA (SEQ ID NO: 64)

atgagaggcgctcgcggcgcctgggattttctctgcgttctgctcctact gcttcgcgtccagacaggctcttctcaaccatctgtgagtccaggggaac cgtctccaccatccatccatccaggaaaatcagacttaatagtccgcgtg ggcgacgagattaggctgttatgcactgatccgggctttgtcaaatggac ttttgagatcctggatgaaacgaatgagaataagcagaatgaatggatca cggaaaaggcagaagccaccaacaccggcaaatacacgtgcaccaacaaa cacggcttaagcaattccatttatgtgtttgttagagatcctgccaagct tttccttgttgaccgctccttgtatgggaaagaagacaacgacacgctgg tccgctgtcctctcacagacccagaagtgaccaattattccctcaagggg tgccaggggaagcctcttcccaaggacttgaggtttattcctgaccccaa ggcgggcatcatgatcaaaagtgtgaaacgcgcctaccatcggctctgtc tgcattgttctgtggaccaggagggcaagtcagtgctgtcggaaaaattc atcctgaaagtgaggccagccttcaaagctgtgcctgttgtgtctgtgtc caaagcaagctatcttcttagggaaggggaagaattcacagtgacgtgca caataaaagatgtgtctagttctgtgtactcaacgtggaaaagagaaaac -continued agtcagactaaactacaggagaaatataatagctggcatcacggtgactt caattatgaacgtcaggcaacgttgactatcagttcagcgagagttaatg attctggagtgttcatgtgttatgccaataatacttttggatcagcaaat gtcacaacaaccttggaagtagtagataaaggattcattaatatcttccc catgataaacactacagtatttgtaaacgatggagaaaatgtagatttga ttgttgaatatgaagcattccccaaacctgaacaccagcagtggatctat atgaacagaaccttcactgataaatgggaagattatcccaagtctgagaa tgaaagtaatatcagatacgtaagtgaacttcatctaacgagattaaaag gcaccgaaggaggcacttacacattcctagtgtccaattctgacgtcaat gctgccatagcatttaatgtttatgtgaatacaaaaccagaaatcctgac ttacgacaggctcgtgaatggcatgctccaatgtgtggcagcaggattcc cagagcccacaatagattggtattttttgtccaggaactgagcagagatgc tctgcttctgtactgccagtggatgtgcagacactaaactcatctgggcc accgtttggaaagctagtggttcagagttctatagattctagtgcattca agcacaatggcacggttgaatgtaaggcttacaacgatgtgggcaagact tctgcctattttaactttgcatttaaaggtaacaacaaagagcaaatcca tccccacaccctgttcactcctttgctgattggtttcgtaatcgtagctg gcatgatgtgcattattgtgatgattctgacctacaaatatttacagaaa cccatgtatgaagtacagtggaaggttgttgaggagataaatggaaacaa ttatgtttacatagacccaacacaacttccttatgatcacaaatgggagt ttcccagaaacaggctgagttttgggaaaaccctgggtgctggagctttc gggaaggttgttgaggcaactgcttatggcttaattaagtcagatgcggc catgactgtcgctgtaaagatgctcaagccgagtgcccatttgacagaac gggaagccctcatgtctgaactcaaagtcctgagttaccttggtaatcac atgaatattgtgaatctacttggagcctgcaccattggagggcccaccct ggtcattacagaatattgttgctatggtgatcttttgaatttttttgagaa gaaaacgtgattcatttatttgttcaaagcaggaagatcatgcagaagct gcactttataagaatcttctgcattcaaaggagtcttcctgcagcgatag tactaatgagtacatggacatgaaacctggagtttcttatgttgtcccaa ccaaggccgacaaaaggagatctgtgagaataggctcatacatagaaaga gatgtgactcccgccatcatggaggatgacgagttggccctagacttaga agacttgctgagcttttcttaccaggtggcaaagggcatggctttcctcg cctccaagaattgtattcacagagacttggcagccagaaatatcctcctt actcatggtcggatcacaaagatttgtgattttggtctagccagagacat caagaatgattctaattatgtggttaaaggaaacgctcgactacctgtga agtggatggcacctgaaagcattttcaactgtgtatacacgtttgaaagt gacgtctggtcctatgggatttttctttgggagctgttctctttaggaag cagcccctatcctggaatgccggtcgattctaagttctacaagatgatca aggaaggcttccggatgctcagccctgaacacgcacctgctgaaatgtat gacataatgaagacttgctgggatgcagatcccctaaaaagaccaacatt -continued caagcaaattgttcagctaattgagaagcagatttcagagagcaccaatc atatttactccaacttagcaaactgcagccccaaccgacagaagcccgtg gtagaccattctgtgcggatcaattctgtcggcagcaccgcttcctcctc ccagcctctgcttgtgcacgacgatgtctga The protein and cDNA sequences for mature human mTOR are shown below.

Mature Human mTOR Protein (SEQ ID NO: 65)

mlgtgpaaat taattssnvs vlqqfasglk srneetraka akelqhyvtm elremsqees trfydqlnhh ifelvsssda nerkggilai asligveggn atrigrfany lrnllpsndp vvmemaskai grlamagdtf taeyvefevk ralewlgadr negrrhaavl vlrelaisvp tfffqqvqpf fdnifvavwd pkqairegav aalraclilt tqrepkemqk pqwyrhtfee aekgfdetla kekgmnrddr ihgallilne lvrissmege rlreemeeit qqqlvhdkyc kdlmgfgtkp rhitpftsfq avqpqqsnal vgllgysshq glmgfgtsps pakstlvesr ccrdlmeekf dqvcqwvlkc rnsknsliqm tilnllprla afrpsaftdt qylqdtmnhv lscvkkeker taafqalgll svavrsefkv ylprvldiir aalppkdfah krqkamqvda tvftcismla ramgpgiqqd ikellepmla vglspaltav lydlsrqipq lkkdiqdgll kmlslvlmhk plrhpgmpkg lahglaspgl ttlpeasdvg sitlalrtlg sfefeghslt qfvrhcadhf lnsehkeirm eaartcsrll tpsihlisgh ahvvsqtavq vvadvlskll vvgitdpdpd irycvlasld erfdahlaqa enlqalfval ndqvfeirel aictvgrlss mnpafvmpfl rkmliqilte lehsgigrik eqsarmlghl vsnaprlirp ymepilkali lklkdpdpdp npgvinnvla tigelaqvsg lemrkwvdel fiiimdmlqd ssllakrqva lwtlgqlvas tgyvvepyrk yptllevlln flkteqnqgt rreairvlgl lgaldpykhk vnigmidqsr dasavslses kssqdssdys tsemlvnmgn lpldefypav smvalmrifr dqslshhhtm vvqaitfifk slglkcvqfl pqvmptflnv irvcdgaire flfqqlgmlv sfvkshirpy mdeivtlmre fwvmntsiqs tiillieqiv valggefkly lpqliphmlr vfmhdnspgr ivsikllaai qlfganlddy lhlllppivk lfdapeaplp srkaaletvd rltesldftd yasriihpiv rtldqspelr stamdtlssl vfqlgkkyqi fipmvnkvlv rhrinhqryd vlicrivkgy tladeeedpl iyqhrmlrsg qgdalasgpv etgpmkklhv stinlqkawg aarrvskddw lewlrrlsle llkdssspsl rscwalaqay npmardlfna -continued afvscwseln edqqdelirs ielaltsqdi aevtqtllnl aefmehsdkg plplrddngi vllgeraakc rayakalhyk elefqkgptp aileslisin nklqqpeaaa gvleyamkhf geleiqatwy eklhewedal vaydkkmdtn kddpelmlgr mrclealgew gqlhqqccek wtlvndetqa kmarmaaaaa wglgqwdsme eytcmiprdt hdgafyravl alhqdlfsla qqcidkardl ldaeltamag esysraygam vschmlsele eviqyklype rreiirqiww erlqgcqriv edwqkilmvr slvvsphedm rtwlkyaslc gksgrlalah ktlvlllgvd psrqldhplp tvhpqvtyay mknmwksark idafqhmqhf vqtmqqqaqh aiatedqqhk qelhklmarc flklgewqln lqginestip kvlqyysaat ehdrswykaw hawavmnfea vlhykhqnqa rdekkklrha sganitnatt aattaatatt tastegsnse seaestensp tpsplqkkvt edlsktllmy tvpavqgffr sislsrgnnl qdtlrvltlw fdyghwpdvn ealvegvkai qidtwlqvip qliaridtpr plvgrlihql ltdigryhpq aliypltvas kstttarhna ankilknmce hsntlvqqam mvseelirva ilwhemwheg leeasrlyfg ernvkgmfev leplhammer gpqtlketsf nqaygrdlme aqewcrkymk sgnvkdltqa wdlyyhvfrr iskqlpqlts lelgyvspkl lmcrdlelav pgtydpnqpi iriqsiapsl qvitskqrpr kltlmgsngh efvfllkghe dlrqdervmq lfglvntlla ndptslrknl siqryavipl stnsgligwv phcdtlhali rdyrekkkil lniehrimlr mapdydhltl mqkvevfeha vnntagddla kllwlkspss evwfdrrtny trslavmsmv gyilglgdrh psnlmldrls gkilhidfgd cfevamtrek fpekipfrlt rmltnamevt gldgnyritc htvmevlreh kdsvmavlea fvydpllnwr lmdtntkgnk rsrtrtdsys agqsveildg velgepahkk tgttvpesih sfigdglvkp ealnkkaiqi inrvrdkltg rdfshddtld vptqvellik qatshenlcq cyigwcpfw Human mTOR cDNA (SEQ ID NO: 66)

atgcttgga accggacctg ccgccgccac caccgctgcc accacatcta gcaatgtgag cgtcctgcag cagtttgcca gtggcctaaa gagccggaat gaggaaacca gggccaaagc cgccaaggag ctccagcact atgtcaccat ggaactccga gagatgagtc aagaggagtc tactcgcttc tatgaccaac tgaaccatca catttttgaa ttggtttcca gctcagatgc caatgagagg aaaggtggca tcttggccat agctagcctc ataggagtgg aaggtgggaa tgccacccga attggcagat ttgccaacta tcttcggaac ctcctcccct ccaatgaccc agttgtcatg gaaatggcat ccaaggccat tggccgtctt
gccatggcag gggacacttt taccgctgag tacgtggaat
ttgaggtgaa gcgagccctg gaatggctgg gtgctgaccg
caatgagggc cggagacatg cagctgtcct ggttctccgt
gagctggcca tcagcgtccc taccttcttc ttccagcaag
tgcaaccctt ctttgacaac atttttgtgg ccgtgtggga
ccccaaacag gccatccgtg agggagctgt agccgccctt
cgtgcctgtc tgattctcac aacccagcgt gagccgaagg
agatgcagaa gcctcagtgg tacaggcaca catttgaaga
agcagagaag ggatttgatg agaccttggc caaagagaag
ggcatgaatc gggatgatcg gatccatgga gccttgttga
tccttaacga gctggtccga atcagcagca tggagggaga
gcgtctgaga gaagaaatgg aagaaatcac acagcagcag
ctggtacacg acaagtactg caaagatctc atgggcttcg
gaacaaaacc tcgtcacatt accccttca ccagtttcca
ggctgtacag ccccagcagt caaatgcctt ggtggggctg
ctggggtaca gctctcacca aggcctcatg ggatttggga
cctcccccag tccagctaag tccaccctgg tggagagccg
gtgttgcaga gacttgatgg aggagaaatt tgatcaggtg
tgccagtggg tgctgaaatg caggaatagc aagaactcgc
tgatccaaat gacaatcctt aatttgttgc cccgcttggc
tgcattccga ccttctgcct tcacagatac ccagtatctc
caagatacca tgaaccatgt cctaagctgt gtcaagaagg
agaaggaacg tacagcggcc ttccaagccc tggggctact
ttctgtggct gtgaggtctg agtttaaggt ctatttgcct
cgcgtgctgg acatcatccg agcggccctg cccccaaagg
acttcgccca taagaggcag aaggcaatgc aggtggatgc
cacagtcttc acttgcatca gcatgctggc tcgagcaatg
gggccaggca tccagcagga tatcaaggag ctgctggagc
ccatgctggc agtgggacta agccctgccc tcactgcagt
gctctacgac ctgagccgtc agattccaca gctaaagaag
gacattcaag atgggctact gaaaatgctg tccctggtcc
ttatgcacaa accccttcgc cacccaggca tgcccaaggg
cctggcccat cagctggcct ctcctggcct cacgaccctc
cctgaggcca gcgatgtggg cagcatcact cttgccctcc
gaacgcttgg cagctttgaa tttgaaggcc actctctgac
ccaatttgtt cgccactgtg cggatcattt cctgaacagt
gagcacaagg agatccgcat ggaggctgcc cgcacctgct
cccgcctgct cacaccctcc atccacctca tcagtggcca
tgctcatgtg gttagccaga ccgcagtgca agtggtggca gatgtgctta gcaaactgct cgtagttggg ataacagatc
ctgaccctga cattcgctac tgtgtcttgg cgtccctgga
cgagcgcttt gatgcacacc tggcccaggc ggagaacttg
caggccttgt ttgtggctct gaatgaccag gtgtttgaga
tccgggagct ggccatctgc actgtgggcc gactcagtag
catgaaccct gcctttgtca tgcctttcct gcgcaagatg
ctcatccaga ttttgacaga gttggagcac agtgggattg
gaagaatcaa agagcagagt gcccgcatgc tggggcacct
ggtctccaat gcccccgac tcatccgccc ctacatggag
cctattctga aggcattaat tttgaaactg aaagatccag
accctgatcc aaacccaggt gtgatcaata atgtcctggc
aacaatagga gaattggcac aggttagtgg cctggaaatg
aggaaatggg ttgatgaact tttattatc atcatggaca
tgctccagga ttcctctttg ttggccaaaa ggcaggtggc
tctgtggacc ctgggacagt tggtggccag cactggctat
gtagtagagc cctacaggaa gtaccctact ttgcttgagg
tgctactgaa ttttctgaag actgagcaga accagggtac
acgcagagag gccatccgtg tgttagggct tttaggggct
ttggatcctt acaagcacaa agtgaacatt ggcatgatag
accagtcccg ggatgcctct gctgtcagcc tgtcagaatc
caagtcaagt caggattcct ctgactatag cactagtgaa
atgctggtca acatgggaaa cttgcctctg gatgagttct
acccagctgt gtccatggtg gccctgatgc ggatcttccg
agaccagtca ctctctcatc atcacaccat ggttgtccag
gccatcacct tcatcttcaa gtccctggga ctcaaatgtg
tgcagttcct gccccaggtc atgcccacgt tccttaacgt
cattcgagtc tgtgatgggg ccatccggga atttttgttc
cagcagctgg gaatgttggt gtcctttgtg aagagccaca
tcagacctta tatggatgaa atagtcaccc tcatgagaga
attctgggtc atgaacacct caattcagag cacgatcatt
cttctcattg agcaaattgt ggtagctctt gggggtgaat
ttaagctcta cctgccccag ctgatcccac acatgctgcg
tgtcttcatg catgacaaca gcccaggccg cattgtctct
atcaagttac tggctgcaat ccagctgttt ggcgccaacc
tggatgacta cctgcattta ctgctgcctc ctattgttaa
gttgtttgat gcccctgaag ctccactgcc atctcgaaag
gcagcgctag agactgtgga ccgcctgacg gagtccctgg
atttcactga ctatgcctcc cggatcattc accctattgt
tcgaacactg gaccagagcc cagaactgcg ctccacagcc
atggacacgc tgtcttcact tgtttttcag ctggggaaga
agtaccaaat tttcattcca atggtgaata aagttctggt -continued gcgacaccga atcaatcatc agcgctatga tgtgctcatc
tgcagaattg tcaagggata cacacttgct gatgaagagg
aggatccttt gatttaccag catcggatgc ttaggagtgg
ccaaggggat gcattggcta gtggaccagt ggaaacagga
cccatgaaga aactgcacgt cagcaccatc aacctccaaa
aggcctgggg cgctgccagg agggtctcca aagatgactg
gctggaatgg ctgagacggc tgagcctgga gctgctgaag
gactcatcat cgccctccct gcgctcctgc tgggccctgg
cacaggccta caacccgatg gccagggatc tcttcaatgc
tgcatttgtg tcctgctggt ctgaactgaa tgaagatcaa
caggatgagc tcatcagaag catcgagttg gccctcacct
cacaagacat cgctgaagtc acacagaccc tcttaaactt
ggctgaattc atggaacaca gtgacaaggg ccccctgcca
ctgagagatg acaatggcat tgttctgctg ggtgagagag
ctgccaagtg ccgagcatat gccaaagcac tacactacaa
agaactggag ttccagaaag gccccacccc tgccattcta
gaatctctca tcagcattaa taataagcta cagcagccgg
aggcagcggc cggagtgtta gaatatgcca tgaaacactt
tggagagctg gagatccagg ctacctggta tgagaaactg
cacgagtggg aggatgccct tgtggcctat gacaagaaaa
tggacaccaa caaggacgac ccagagctga tgctgggccg
catgcgctgc ctcgaggcct tgggggaatg gggtcaactc
caccagcagt gctgtgaaaa gtggaccctg gttaatgatg
agacccaagc caagatggcc cggatggctg ctgcagctgc
atggggttta ggtcagtggg acagcatgga agaatacacc
tgtatgatcc ctcgggacac ccatgatggg gcattttata
gagctgtgct ggcactgcat caggacctct tctccttggc
acaacagtgc attgacaagg ccagggacct gctggatgct
gaattaactg cgatggcagg agagagttac agtcgggcat
atggggccat ggtttcttgc cacatgctgt ccgagctgga
ggaggttatc cagtacaaac ttgtccccga gcgacgagag
atcatccgcc agatctggtg ggagagactg cagggctgcc
agcgtatcgt agaggactgg cagaaaatcc ttatggtgcg
gtcccttgtg gtcagccctc atgaagacat gagaacctgg
ctcaagtatg caagcctgtg cggcaagagt ggcaggctgg
ctcttgctca taaaacttta gtgttgctcc tgggagttga
tccgtctcgg caacttgacc atcctctgcc aacagttcac
cctcaggtga cctatgccta catgaaaaac atgtggaaga
gtgcccgcaa gatcgatgcc ttccagcaca tgcagcattt
tgtccagacc atgcagcaac aggcccagca tgccatcgct -continued actgaggacc agcagcataa gcaggaactg cacaagctca
tggcccgatg cttcctgaaa cttggagagt ggcagctgaa
tctacagggc atcaatgaga gcacaatccc caaagtgctg
cagtactaca gcgccgccac agagcacgac cgcagctggt
acaaggcctg gcatgcgtgg gcagtgatga acttcgaagc
tgtgctacac tacaaacatc agaaccaagc ccgcgatgag
aagaagaaac tgcgtcatgc cagcggggcc aacatcacca
acgccaccac tgccgccacc acggccgcca ctgccaccac
cactgccagc accgagggca gcaacagtga gagcgaggcc
gagagcaccg agaacagccc caccccatcg ccgctgcaga
agaaggtcac tgaggatctg tccaaaaccc tcctgatgta
cacggtgcct gccgtccagg gcttcttccg ttccatctcc
ttgtcacgag gcaacaacct ccaggataca ctcagagttc
tcaccttatg gtttgattat ggtcactggc cagatgtcaa
tgaggcctta gtggaggggg tgaaagccat ccagattgat
acctggctac aggttatacc tcagctcatt gcaagaattg
atacgcccag acccttggtg ggacgtctca ttcaccagct
tctcacagac attggtcggt accaccccca ggccctcatc
tacccactga cagtggcttc taagtctacc acgacagccc
ggcacaatgc agccaacaag attctgaaga acatgtgtga
gcacagcaac accctggtcc agcaggccat gatggtgagc
gaggagctga tccgagtggc catcctctgg catgagatgt
ggcatgaagg cctggaagag gcatctcgtt tgtactttgg
ggaaaggaac gtgaaaggca tgtttgaggt gctggagccc
ttgcatgcta tgatggaacg gggcccccag actctgaagg
aaacatcctt taatcaggcc tatggtcgag atttaatgga
ggcccaagag tggtgcagga agtacatgaa atcagggaat
gtcaaggacc tcacccaagc ctgggacctc tattatcatg
tgttccgacg aatctcaaag cagctgcctc agctcacatc
cttagagctg caatatgttt ccccaaaact tctgatgtgc
cgggaccttg aattggctgt gccaggaaca tatgacccca
accagccaat cattcgcatt cagtccatag caccgtcttt
gcaagtcatc acatccaagc agaggccccg gaaattgaca
cttatgggca gcaacggaca tgagtttgtt ttccttctaa
aaggccatga agatctgcgc caggatgagc gtgtgatgca
gctcttcggc ctggttaaca cccttctggc caatgaccca
acatctcttc ggaaaaacct cagcatccag agatacgctg
tcatcccttt atcgaccaac tcgggcctca ttggctgggt
tccccactgt gacacactgc acgccctcat ccgggactac
agggagaaga agaagatcct tctcaacatc gagcatcgca
tcatgttgcg gatggctccg gactatgacc acttgactct

```
gatgcagaag gtggaggtgt ttgagcatgc cgtcaataat
acagctgggg acgacctggc caagctgctg tggctgaaaa
gccccagctc cgaggtgtgg tttgaccgaa gaaccaatta
tacccgttct ttagcggtca tgtcaatggt tgggtatatt
ttaggcctgg gagatagaca cccatccaac ctgatgctgg
accgtctgag tgggaagatc ctgcacattg actttgggga
ctgctttgag gttgctatga cccgagagaa gtttccagag
aagattccat ttagactaac aagaatgttg accaatgcta
tggaggttac aggcctggat ggcaactaca gaatcacatg
ccacacagtg atggaggtgc tgcgagagca caaggacagt
gtcatggccg tgctggaagc ctttgtctat gaccccttgc
tgaactggag gctgatggac acaaatacca aaggcaacaa
gcgatcccga acgaggacgg attcctactc tgctggccag
tcagtcgaaa ttttggacgg tgtggaactt ggagagccag
cccataagaa aacggggacc acagtgccag aatctattca
ttctttcatt ggagacggtt tggtgaaacc agaggcccta
aataagaaag ctatccagat tattaacagg gttcgagata
agctcactgg tcgggacttc tctcatgatg acactttgga
tgttccaacg caagttgagc tgctcatcaa acaagcgaca
tcccatgaaa acctctgcca gtgctatatt ggctggtgcc
ctttctggta a
```

Non-limiting examples of commercial ELISA assays that can be used to determine the expression level of SREBP1 are available from Novus Biologicals and Abcam. The protein and cDNA sequences for mature human SREBP1 are shown below.

```
Mature Human SREBP1 Protein
                                   (SEQ ID NO: 67)
MDEPPFSEAALEQALGEPCDLDAALLTDIEDMLQLINNQDSDFPGLFDPP
YAGSGAGGTDPASPDTSSPGSLSPPPATLSSSLEAFLSGPQAAPSPLSPP
QPAPTPLKMYPSMPAFSPGPGIKEESVPLSILQTPTPQPLPGALLPQSFP
APAPPQFSSTPVLGYPSPPGGFSTGSPPGNTQQPLPGLPLASPPGVPPVS
LHTQVQSVVPQQLLTVTAAPTAAPVTTTVTSQIQQVPVLLQPHFIKADSL
LLTAMKTDGATVKAAGLSPLVSGTTVQTGPLPTLVSGGTILATVPLVVDA
EKLPINRLAAGSKAPASAQSRGEKRTAHNAIEKRYRSSINDKIIELKDLV
VGTEAKLNKSAVLRKAIDYIRFLQHSNQKLKQENLSLRTAVHKSKSLKDL
VSACGSGGNTDVLMEGVKTEVEDTLTPPPSDAGSPFQSSPLSLGSRGSGS
GGSGSDSEPDSPVFEDSKAKPEQRPSLHSRGMLDRSRLALCTLVFLCLSC
NPLASLLGARGLPSPSDTTSVYHSPGRNVLGTESRDGPGWAQWLLPPVVW
LLNGLLVLVSLVLLFVYGEPVTRPHSGPAVYFWRHRKQADLDLARGDFAQ
AAQQLWLALRALGRPLPTSHLDLACSLLWNLIRHLLQRLWVGRWLAGRAG
GLQQDCALRVDASASARDAALVYHKLHQLHTMGKHTGGHLTATNLALSAL
```

```
NLAECAGDAVSVATLAEIYVAAALRVKTSLPRALHFLTRFFLSSARQACL
AQSGSVPPAMQWLCHPVGHRFFVDGDWSVLSTPWESLYSLAGNPVDPLAQ
VTQLFREHLLERALNCVTQPNPSPGSADGDKEFSDALGYLQLLNSCSDAA
GAPAYSFSISSSMATTTGVDPVAKWWASLTAVVIHWLRRDEEAAERLCPL
VEHLPRVLQESERPLPRAALHSFKAARALLGCAKAESGPASLTICEKASG
YLQDSLATTPASSSIDKAVQLFLCDLLLVVRTSLWRQQQPPAPAPAAQGT
SSRPQASALELRGFQRDLSSLRRLAQSFRPAMRRVFLHEATARLMAGASP
TRTHQLLDRSLRRRAGPGGKGGAVAELEPRPTRREHAEALLLASCYLPPG
FLSAPGQRVGMLAEAARTLEKLGDRRLLHDCQQMLMRLGGGTTVTSS
```

```
Human SREBP1 cDNA
                                   (SEQ ID NO: 68)
atggacgagccacccttcagcgaggcggctttggagcaggcgctgggcga
gccgtgcgatctggacgcggcgctgctgaccgacatcgaagacatgcttc
agcttatcaacaaccaagacagtgacttccctggcctatttgacccaccc
tatgctgggagtggggcaggggcacagaccctgccagccccgataccag
ctccccaggcagcttgtctccacctcctgccacattgagctcctctcttg
aagccttcctgagcgggccgcaggcagcgccctcacccctgtcccctccc
cagcctgcacccactccattgaagatgtacccgtccatgcccgctttctc
ccctgggcctggtatcaaggaagagtcagtgccactgagcatcctgcaga
cccccaccccacagcccctgccaggggccctcctgccacagagcttccca
gccccagccccaccgcagttcagctccacccctgtgttaggctaccccag
ccctccgggaggcttctctacaggaagccctcccgggaacacccagcagc
cgctgcctggcctgccactggcttccccgccaggggtcccgcccgtctcc
ttgcacacccaggtccagagtgtggtcccccagcagctactgacagtcac
agctgcccccacggcagcccctgtaacgaccactgtgacctcgcagatcc
agcaggtcccggtcctgctgcagccccacttcatcaaggcagactcgctg
cttctgacagccatgaagacagacggagccactgtgaaggcggcaggtct
cagtcccctggtctctggcaccactgtgcagacagggcctttgccgaccc
tggtgagtggcggaaccatcttggcaacagtcccactggtcgtagatgcg
gagaagctgcctatcaaccggctcgcagctggcagcaaggccccggcctc
tgcccagagccgtggagagaagcgcacagcccacaacgccattgagaagc
gctaccgctcctccatcaatgacaaaatcattgagctcaaggatctggtg
gtgggcactgaggcaaagctgaataaatctgctgtcttgcgcaaggccat
cgactacattcgctttctgcaacacagcaaccagaaactcaagcaggaga
acctaagtctgcgcactgctgtccacaaaagcaaatctctgaaggatctg
gtgtcggcctgtggcagtggagggaacacagacgtgctcatggagggcgt
gaagactgaggtggaggacacactgaccccacccccctcggatgctggct
cacctttccagagcagccccttgtcccttggcagcaggggcagtggcagc
ggtggcagtggcagtgactcggagcctgacagcccagtctttgaggacag
caaggcaaagccagagcagcggccgtctctgcacagccggggcatgctgg
accgctcccgcctggccctgtgcacgctcgtcttcctctgcctgtcctgc
```

-continued

```
aaccccttggcctccttgctgggggcccgggggcttcccagcccctcaga
taccaccagcgtctaccatagccctgggcgcaacgtgctgggcaccgaga
gcagagatggccctggctgggcccagtggctgctgcccccagtggtctgg
ctgctcaatgggctgttggtgctcgtctccttggtgcttctctttgtcta
cggtgagccagtcacacggccccactcaggccccgccgtgtacttctgga
ggcatcgcaagcaggctgacctggacctggcccggggagactttgcccag
gctgcccagcagctgtggctggccctgcgggcactgggccggcccctgcc
cacctcccacctggacctggcttgtagcctcctctggaacctcatccgtc
acctgctgcagcgtctctgggtgggccgctggctggcaggccgggcaggg
ggcctgcagcaggactgtgctctgcgagtggatgctagcgccagcgcccg
agacgcagccctggtctaccataagctgcaccagctgcacaccatgggga
agcacacaggcgggcacctcactgccaccaacctggcgctgagtgccctg
aacctggcagagtgtgcaggggatgccgtgtctgtggcgacgctggccga
gatctatgtggcggctgcattgagagtgaagaccagtctcccacgggcct
tgcattttctgacacgcttcttcctgagcagtgcccgccaggcctgcctg
gcacagagtggctcagtgcctcctgccatgcagtggctctgccaccccgt
gggccaccgtttcttcgtggatggggactggtccgtgctcagtaccccat
gggagagcctgtacagcttggccgggaacccagtggacccccctggcccag
gtgactcagctattccgggaacatctcttagagcgagcactgaactgtgt
gacccagcccaaccccagccctgggtcagctgatggggacaaggaattct
cggatgccctcgggtacctgcagctgctgaacagctgttctgatgctgcg
ggggctcctgcctacagcttctccatcagttccagcatggccaccaccac
cggcgtagacccggtggccaagtggtgggcctctctgacagctgtggtga
tccactggctgcggcgggatgaggaggcggctgagcggctgtgcccgctg
gtggagcacctgccccgggtgctgcaggagtctgagagacccctgcccag
ggcagctctgcactccttcaaggctgcccgggccctgctgggctgtgcca
aggcagagtctggtccagccagcctgaccatctgtgagaaggccagtggg
tacctgcaggacagcctggctaccacaccagccagcagctccattgacaa
ggccgtgcagctgttcctgtgtgacctgcttcttgtggtgcgcaccagcc
tgtggcggcagcagcagccccggccccggccccagcagcccagggcacc
agcagcaggccccaggcttccgcccttgagctgcgtggcttccaacggga
cctgagcagcctgaggcggctggcacagagcttccggcccgccatgcgga
gggtgttcctacatgaggccacggcccggctgatggcgggggccagcccc
acacggacacaccagctcctcgaccgcagtctgaggcggcgggcaggccc
cggtggcaaaggaggcgcggtggcggagctggagccgcggcccacgcggc
gggagcacgcggaggccttgctgctggcctcctgctacctgccccccggc
ttcctgtcggcgcccgggcagcgcgtgggcatgctggctgaggcggcgcg
cacactcgagaagcttggcgatcgccggctgctgcacgactgtcagcaga
tgctcatgcgcctgggcggtgggaccactgtcacttccagctag
```

Non-limiting examples of commercial ELISA assays that can be used to determine the expression level of IFN-γ are available from R&D Systems, Thermo Fisher Scientific, Abcam, Enzo Life Sciences, and RayBiotech. The protein and cDNA sequences for mature human IFN-γ are shown below.

```
Mature Human IFN-γ
                                        (SEQ ID NO: 69)
qdpyvke aenlkkyfna ghsdvadngt lflgilknwk
eesdrkimqs qivsfyfklf knfkddqsiq ksvetikedm
nvkffnsnkk krddfekltn ysvtdlnvqr kaiheliqvm
aelspaaktg krkrsqmlfr g

Human IFN-γ cDNA
                                        (SEQ ID NO: 70)
caggac ccatatgtaa aagaagcaga aaaccttaag
aaatatttta atgcaggtca ttcagatgta gcggataatg
gaactctttt cttaggcatt ttgaagaatt ggaaagagga
gagtgacaga aaaataatgc agagccaaat tgtctccttt
tacttcaaac tttttaaaaa ctttaaagat gaccagagca
tccaaaagag tgtggagacc atcaaggaag acatgaatgt
caagtttttc aatagcaaca aaaagaaacg agatgacttc
gaaaagctga ctaattattc ggtaactgac ttgaatgtcc
aacgcaaagc aatacatgaa ctcatccaag tgatggctga
actgtcgcca gcagctaaaa cagggaagcg aaaaaggagt
cagatgctgt ttcgaggt
```

Non-limiting examples of commercial ELISA assays that can be used to determine the expression level of granzyme B are available from RayBiotech, Thermo Fisher Scientific, and R&D Systems. The protein and cDNA sequences for mature human granzyme B are shown below.

```
Mature Human Granzyme B
                                        (SEQ ID NO: 71)
iiggheakph srpymaylmi wdqkslkrcg gflirddfvl
taahcwgssi nvtlgahnik eqeptqqfip vkrpiphpay
npknfsndim llqlerkakr travqplrlp snkaqvkpgq
tcsvagwgqt aplgkhshtl gevkmtvqed rkcesdlrhy
ydstielcvg dpeikktsfk gdsggplvcn kvaqgivsyg
rnngmpprac tkvssfvhwi kktmkry

Human Granzyme B cDNA
                                        (SEQ ID NO: 72)
atcatcgggg gacatgaggc caagccccac tcccgcccct
acatggctta tcttatgatc tgggatcaga agtctctgaa
gaggtgcggt ggcttcctga tacgagacga cttcgtgctg
acagctgctc actgttgggg aagctccata aatgtcacct
tgggggccca caatatcaaa gaacaggagc cgacccagca
gtttatccct gtgaaaagac ccatccccca tccagcctat
aatcctaaga acttctccaa cgacatcatg ctactgcagc
tggagagaaa ggccaagcgg accagagctg tgcagcccct
caggctacct agcaacaagg cccaggtgaa gccagggcag
```

-continued

```
acatgcagtg tggccggctg ggggcagacg gccccccctgg
gaaaacactc acacacacta caagaggtga agatgacagt
gcaggaagat cgaaagtgcg aatctgactt acgccattat
tacgacagta ccattgagtt gtgcgtgggg gacccagaga
ttaaaaagac ttcctttaag gggactctg gaggccctct
tgtgtgtaac aaggtggccc agggcattgt ctcctatgga
cgaaacaatg gcatgcctcc acgagcctgc accaaagtct
caagctttgt acactggata aagaaaacca tgaaacgcta
c
```

Non-limiting examples of commercial ELISA assays that can be used to determine the expression level of MYC are available from Invitrogen, LSBio, Biocodon Technologies, and Elisa Genie. The protein and cDNA sequences for mature human MYC are shown below.

```
Human Myc Protien
                                        (SEQ ID NO: 329)
mdffrvvenq qppatmplnv sftnrnydld ydsvqpyfyc
deeenfyqqq qqselqppap sediwkkfel lptpplspsr
rsglcspsyv avtpfslrgd ndggggsfst adqlemvtel
lggdmvngsf icdpddetfi kniiiqdcmw sgfsaaaklv
seklasyqaa rkdsgspnpa rghsvcstss lylqdlsaaa
secidpsvvf pyplndsssp kscasqdssa fspssdslls
stesspqgsp eplvlheetp pttssdseee qedeeeidvv
svekrqapgk rsesgspsag ghskpphspl vlkrchvsth
qhnyaappst rkdypaakrv kldsvrvlrq isnnrkctsp
rssdteenvk rrthnvlerq rrnelkrsff alrdqipele
nnekapkvvi lkkatayils vqaeeqklis eedllrkrre
qlkhkleqlr nsca
Human Myc cDNA
                                        (SEQ ID NO: 330)
ctggatt tttttcgggt agtggaaaac cagcagcctc
ccgcgacgat gcccctcaac gttagcttca ccaacaggaa
ctatgacctc gactacgact cggtgcagcc gtatttctac
tgcgacgagg aggagaactt ctaccagcag cagcagcaga
gcgagctgca gcccccggcg cccagcgagg atatctggaa
gaaattcgag ctgctgccca ccccgcccct gtcccctagc
cgccgctccg ggctctgctc gccctcctac gttgcggtca
cacccttctc ccttcgggga gacaacgacg gcggtggcgg
gagcttctcc acggccgacc agctggagat ggtgaccgag
ctgctgggag gagacatggt gaaccagagt ttcatctgcg
acccggacga cgagaccttc atcaaaaaca tcatcatcca
ggactgtatg tggagcggct tctcggccgc cgccaagctc
gtctcagaga agctggcctc ctaccaggct gcgcgcaaag
acagcggcag cccgaacccc gcccgcggcc acagcgtctg
ctccacctcc agcttgtacc tgcaggatct gagcgccgcc
gcctcagagt gcatcgaccc ctcggtggtc ttcccctacc
ctctcaacga cagcagctcg cccaagtcct gcgcctcgca
agactccagc gccttctctc cgtcctcgga ttctctgctc
tcctcgacgg agtcctcccc gcagggcagc cccgagcccc
tggtgctcca tgaggagaca ccgcccacca ccagcagcga
ctctgaggag gaacaagaag atgaggaaga aatcgatgtt
gtttctgtgg aaaagaggca ggctcctggc aaaaggtcag
agtctggatc accttctgct ggaggccaca gcaaacctcc
tcacagccca ctggtcctca agaggtgcca cgtctccaca
catcagcaca actacgcagc gcctccctcc actcggaagg
actatcctgc tgccaagagg gtcaagttgg acagtgtcag
agtcctgaga cagatcagca acaaccgaaa atgcaccagc
cccaggtcct cggacaccga ggagaatgtc aagaggcgaa
cacacaacgt cttggagcgc cagaggagga acgagctaaa
acggagcttt tttgccctgc gtgaccagat cccggagttg
gaaaacaatg aaaaggcccc caaggtagtt atccttaaaa
aagccacagc atacatcctg tccgtccaag cagaggagca
aaagctcatt tctgaagagg acttgttgcg gaaacgacga
gaacagttga aacacaaact tgaacagcta cggaactctt
gtgcgtaa
```

In some embodiments, activated NK cells (e.g., human activated NK cells) can show increased (e.g., at least a 10% increase, at least a 20% increase, at least a 30% increase, at least a 40% increase, at least a 50% increase, at least a 60% increase, at least a 70% increase, at least 80% increase, at least a 90% increase, at least a 100% increase, at least a 120% increase, at least a 140% increase, at least a 160% increase, at least a 180% increase, at least a 200% increase, at least a 220% increase, at least a 240% increase, at least a 260% increase, at least a 280% increase, or at least a 300% increase) ability to kill senescent cells (e.g., any of the senescent cells described herein) in a subject (e.g., any of the subjects described herein) or in vitro as compared to resting NK cells (e.g., human resting NK cells).

In some embodiments, activated NK cells (e.g., human activated NK cells) can show about a 10% increase to about a 500% increase (or any of the subranges of this range described herein) ability to kill senescent cells (e.g., any of the senescent cells described herein) in a subject (e.g., any of the subjects described herein) or in vivo as compared to resting NK cells (e.g., human resting NK cells).

In some embodiments, activated NK cells (e.g., human activated NK cells) can show increased (e.g., at least a 10% increase, at least a 20% increase, at least a 30% increase, at least a 40% increase, at least a 50% increase, at least a 60% increase, at least a 70% increase, at least 80% increase, at least a 90% increase, at least a 100% increase, at least a 120% increase, at least a 140% increase, at least a 160% increase, at least a 180% increase, at least a 200% increase, at least a 220% increase, at least a 240% increase, at least a 260% increase, at least a 280% increase, or at least a 300% increase) cytotoxic activity in a contact-cytotoxicity assay in the presence of an antibody that binds specifically to an antigen present on a senescent or target cell, e.g., as compared to a resting NK cell (e.g., human resting NK cells).

In some embodiments, activated NK cells (e.g., human activated NK cells) can show increased (e.g., about a 10% increase to about a 500% increase, or any of the subranges of this range described herein) cytotoxic activity in a contact-cytotoxicity assay in the presence of an antibody that binds specifically to an antigen present on a senescent or target cell, e.g., as compared to a resting NK cell (e.g., human resting NK cells).

In some embodiments, an activated NK cell can be produced by a method that includes obtaining a resting NK cell; and contacting the resting NK cell in vitro in a liquid culture medium including one or more NK cell activating agent(s), where the contacting results in the generation of the activated NK cells that are subsequently administered to the subject. In some examples of these methods, the resting NK cell is an autologous NK cell obtained from the subject. In some examples of these methods, the resting NK cell is an autologous NK cell obtained from the subject. In some examples of these methods, the resting NK cell is an haploidentical resting NK cells. In some examples of these methods, the resting NK cell is an allogeneic resting NK cell. In some examples of these methods, the resting NK cell is an artificial NK cell. In some examples of any of these methods, the resting NK cell is a genetically-engineered NK cell carrying a chimeric antigen receptor or recombinant T cell receptor.

In some examples of these methods, the liquid culture medium is a serum-free liquid culture medium. In some embodiments of any of the methods described herein, the liquid culture medium is a chemically-defined liquid culture medium. Some examples of these methods further include isolating the activated NK cells (and optionally further administering a therapeutically effective amount of the activated NK cells to a subject, e.g., any of the subjects described herein).

In some embodiments of these methods, the contacting step is performed for a period of about 2 hours to about 20 days (e.g., about 2 hours to about 18 days, about 2 hours to about 16 days, about 2 hours to about 14 days, about 2 hours to about 12 days, about 2 hours to about 10 days, about 2 hours to about 8 days, about 2 hours to about 7 days, about 2 hours to about 6 days, about 2 hours to about 5 days, about 2 hours to about 4 days, about 2 hours to about 3 days, about 2 hours to about 2 days, about 2 hours to about 1 day, about 6 hours to about 18 days, about 6 hours to about 16 days, about 6 hours to about 14 days, about 6 hours to about 12 days, about 6 hours to about 10 days, about 6 hours to about 8 days, about 6 hours to about 7 days, about 6 hours to about 6 days, about 6 hours to about 5 days, about 6 hours to about 4 days, about 6 hours to about 3 days, about 6 hours to about 2 days, about 6 hours to about 1 day, about 12 hours to about 18 days, about 12 hours to about 16 days, about 12 hours to about 14 days, about 12 hours to about 12 days, about 12 hours to about 10 days, about 12 hours to about 8 days, about 12 hours to about 7 days, about 12 hours to about 6 days, about 12 hours to about 5 days, about 12 hours to about 4 days, about 12 hours to about 3 days, about 12 hours to about 2 days, about 12 hours to about 1 day, about 1 day to about 18 days, about 1 day to about 16 days, about 1 day to about 15 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 18 days, about 7 days to about 16 days, about 7 days to about 14 days, about 7 days to about 12 days, about 7 days to about 10 days, about 7 days to about 8 days, about 8 days to about 18 days, about 8 days to about 16 days, about 8 days to about 14 days, about 8 days to about 12 days, about 8 days to about 10 days, about 9 days to about 18 days, about 9 days to about 16 days, about 9 days to about 14 days, about 9 days to about 12 days, about 12 days to about 18 days, about 12 days to about 16 days, about 12 days to about 14 days, about 14 days to about 18 days, about 14 days to about 16 days, or about 16 days to about 18 days.

NK Cell Activating Agents

Provided herein are methods that include the use or administration of one or more NK cell activating agents. In some embodiments, an NK cell activating agent can be a protein. In some embodiments, an NK cell activating agent can be a single-chain chimeric polypeptide (e.g. any of the single-chain chimeric polypeptides described herein), a multi-chain chimeric polypeptide (e.g. any of the multi-chain chimeric polypeptides described herein, e.g., the exemplary type A and type B multi-chain chimeric polypeptides described herein), an antibody, a recombinant cytokine or an interleukin (e.g. any of the recombinant cytokines or interleukins described herein), and a soluble interleukin or cytokine receptor (e.g. any of the soluble interleukin or cytokine receptors described herein). In some embodiments, the NK cell activating agent can be a small molecule (e.g., a glycogen synthase kinase-3 (GSK3) inhibitor, e.g., CHIR99021 as described in Cichocki et al., *Cancer Res.* 77:5664-5675, 2017) or an aptamer.

In some embodiments of any of the one or more NK cell activating agents provided herein, at least one of the one or more NK cell activating agent(s) results in activation of one or more (e.g., two, three, four, five, six, seven, or eight) of: a receptor for IL-2, a receptor for IL-7, a receptor for IL-12, a receptor for IL-15, a receptor for IL-18, a receptor for IL-21, a receptor for IL-33, CD16, CD69, CD25, CD59, CD352, NKp80, DNAM-1, 2B4, NKp30, NKp44, NKp46, NKG2D, KIR2DS1, KIR2Ds2/3, KIR2DL4, KIR2DS4, KIR2DS5, and KIR3DS1 (e.g., in an immune cell, e.g., a human immune cell, e.g., a human NK cell) as compared to the level of activation in the absence of the one or more NK cell activating agent(s).

In some embodiments, the at least one of the one or more NK cell activating agent(s) that results in activation of a receptor for IL-2 is a soluble IL-2 or an agonistic antibody that binds specifically to an IL-2 receptor.

In some embodiments, the at least one of the one or more NK cell activating agent(s) that results in activation of a receptor for IL-7 is a soluble IL-7 or an agonistic antibody that binds specifically to an IL-7 receptor.

In some embodiments, the at least one of the one or more NK cell activating agent(s) that results in activation of a receptor for IL-12 is a soluble IL-12 or an agonistic antibody that binds specifically to an IL-12 receptor.

In some embodiments, the at least one of the one or more NK cell activating agent(s) that results in activation of a receptor for IL-15 is a soluble IL-15 or an agonistic antibody that binds specifically to an IL-15 receptor.

In some embodiments, the at least one of the one or more NK cell activating agent(s) that results in activation of a receptor for IL-21 is a soluble IL-21 or an agonistic antibody that binds specifically to an IL-21 receptor.

In some embodiments, the at least one of the one or more NK cell activating agent(s) that results in activation of a receptor for IL-33 is a soluble IL-33 or an agonistic antibody that binds specifically to an IL-33 receptor.

In some embodiments, the at least one of the one or more NK cell activating agent(s) that results in activation of CD16 is an agonistic antibody that binds specifically to CD16.

In some embodiments, the at least one of the one or more NK cell activating agent(s) that results in activation of CD69 is an agonistic antibody that binds specifically to CD69.

In some embodiments, the at least one of the one or more NK cell activating agent(s) that results in activation of CD25, CD59 is an agonistic antibody that binds specifically to CD25, CD59.

In some embodiments, the at least one of the one or more NK cell activating agent(s) that results in activation of CD352 is an agonistic antibody that binds specifically to CD352.

In some embodiments, the at least one of the one or more NK cell activating agent(s) that results in activation of NKp80 is an agonistic antibody that binds specifically to NKp80.

In some embodiments, the at least one of the one or more NK cell activating agent(s) that results in activation of DNAM-1 is an agonistic antibody that binds specifically to DNAM-1.

In some embodiments, the at least one of the one or more NK cell activating agent(s) that results in activation of 2B4 is an agonistic antibody that binds specifically to 2B4.

In some embodiments, the at least one of the one or more NK cell activating agent(s) that results in activation of NKp30 is an agonistic antibody that binds specifically to NKp30.

In some embodiments, the at least one of the one or more NK cell activating agent(s) that results in activation of NKp44 is an agonistic antibody that binds specifically to NKp44.

In some embodiments, the at least one of the one or more NK cell activating agent(s) that results in activation of NKp46 is an agonistic antibody that binds specifically to NKp46.

In some embodiments, the at least one of the one or more NK cell activating agent(s) that results in activation of NKG2D is an agonistic antibody that binds specifically to NKG2D.

In some embodiments, the at least one of the one or more NK cell activating agent(s) that results in activation of KIR2DS1 is an agonistic antibody that binds specifically to KIT2DS1.

In some embodiments, the at least one of the one or more NK cell activating agent(s) that results in activation of KIR2DS2/3 is an agonistic antibody that binds specifically to KIT2DS2/3.

In some embodiments, the at least one of the one or more NK cell activating agent(s) that results in activation of KIR2DL4 is an agonistic antibody that binds specifically to KIT2DL4.

In some embodiments, the at least one of the one or more NK cell activating agent(s) that results in activation of KIR2DS4 is an agonistic antibody that binds specifically to KIT2DS4.

In some embodiments, the at least one of the one or more NK cell activating agent(s) that results in activation of KIR2DS5 is an agonistic antibody that binds specifically to KIT2DS5.

In some embodiments, the at least one of the one or more NK cell activating agent(s) that results in activation of KIR3DS1 is an agonistic antibody that binds specifically to KIT3DS1.

In some embodiments of any of the one or more NK cell activating agents provided herein, at least one (e.g., two, three, four, or five) of the one or more NK cell activating agent(s) results in a decrease in the activation of one or more of: PD-1, a TGF-β receptor, TIGIT, CD1, TIM-3, Siglec-7, IRP60, Tactile, IL1R8, NKG2A/KLRD1, KIR2DL1, KIR2DL2/3, KIR2DL5, KIR3DL1, KIR3DL2, ILT2/LIR-1, and LAG-2 (e.g., in an immune cell, e.g., a human immune cell, e.g., a human NK cell) as compared to the level of activation in the absence of the one or more NK cell activating agent(s).

In some embodiments, the at least one of the one or more NK cell activating agent(s) that results in a decrease in the activation of a TGF-β receptor is a soluble TGF-β receptor, an antibody that binds specifically to TGF-β, or an antagonistic antibody that binds specifically to a TGF-β receptor.

In some embodiments, the at least one of the one or more NK cell activating agent(s) that results in a decrease in the activation of TIGIT is an antagonistic antibody that binds specifically to TIGIT, a soluble TIGIT, or an antibody that binds specifically to a ligand of TIGIT.

In some embodiments, the at least one of the one or more NK cell activating agent(s) that results in a decrease in the activation of CD1 is an antagonistic antibody that binds specifically to CD1, a soluble CD1, or an antibody that binds specifically to a ligand of CD1.

In some embodiments, the at least one of the one or more NK cell activating agent(s) that results in a decrease in the activation of TIM-3 is an antagonistic antibody that binds specifically to TIM-3, a soluble TIM-3, or an antibody that binds specifically to a ligand of TIM-3.

In some embodiments, the at least one of the one or more NK cell activating agent(s) that results in a decrease in the activation of Siglec-7 is an antagonistic antibody that binds specifically to Siglec-7, a soluble Siglec-7, or an antibody that binds specifically to a ligand of Siglec-7.

In some embodiments, the at least one of the one or more NK cell activating agent(s) that results in a decrease in the activation of IRP-60 is an antagonistic antibody that binds specifically to IRP-60, a soluble IRP-60, or an antibody that binds specifically to a ligand of IRP-60.

In some embodiments, the at least one of the one or more NK cell activating agent(s) that results in a decrease in the activation of Tactile is an antagonistic antibody that binds specifically to Tactile, a soluble Tactile, or an antibody that binds specifically to a ligand of Tactile.

In some embodiments, the at least one of the one or more NK cell activating agent(s) that results in a decrease in the activation of IL1R8 is an antagonistic antibody that binds specifically to IL1R8, a soluble IL1R8, or an antibody that binds specifically to a ligand of IL1R8.

In some embodiments, the at least one of the one or more NK cell activating agent(s) that results in a decrease in the activation of NKG2A/KLRD1 is an antagonistic antibody that binds specifically to NKG2A/KLRD1, a soluble NKG2A/KLRD1, or an antibody that binds specifically to a ligand of NKG2A/KLRD1.

In some embodiments, the at least one of the one or more NK cell activating agent(s) that results in a decrease in the activation of KIR2DL1 is an antagonistic antibody that binds specifically to KIR2DL1, a soluble KIR2DL1, or an antibody that binds specifically to a ligand of KIR2DL1.

In some embodiments, the at least one of the one or more NK cell activating agent(s) that results in a decrease in the activation of KIR2DL2/3 is an antagonistic antibody that binds specifically to KIR2DL2/3, a soluble KIR2DL2/3, or an antibody that binds specifically to a ligand of KIR2DL2/3.

In some embodiments, the at least one of the one or more NK cell activating agent(s) that results in a decrease in the activation of KIR2DL5 is an antagonistic antibody that binds specifically to KIR2DL5, a soluble KIR2DL5, or an antibody that binds specifically to a ligand of KIR2DL5.

In some embodiments, the at least one of the one or more NK cell activating agent(s) that results in a decrease in the activation of KIR3DL1 is an antagonistic antibody that binds specifically to KIR3DL1, a soluble KIR3DL1, or an antibody that binds specifically to a ligand of KIR3DL1.

In some embodiments, the at least one of the one or more NK cell activating agent(s) that results in a decrease in the activation of KIR3DL2 is an antagonistic antibody that binds specifically to KIR3DL2, a soluble KIR3DL2, or an antibody that binds specifically to a ligand of KIR3DL2.

In some embodiments, the at least one of the one or more NK cell activating agent(s) that results in a decrease in the activation of ILT2/LIR-1 is an antagonistic antibody that binds specifically to ILT2/LIR-1, a soluble ILT2/LIR-1, or an antibody that binds specifically to a ligand of ILT2/LIR-1.

In some embodiments, the at least one of the one or more NK cell activating agent(s) that results in a decrease in the activation of LAG2 is an antagonistic antibody that binds specifically to LAG2, a soluble LAG2, or an antibody that binds specifically to a ligand of LAG2.

Non-limiting examples of NK cell activating agents are described below and can be used in any combination.

In some examples, an NK cell activating agents can be a soluble PD-1, a soluble PD-L1, a soluble TIGIT, a soluble CD1, or a soluble TIM-3. Non-limiting examples of soluble PD-1, PD-L1, TIGIT, CD1, and TIM-3 are provided below.

```
Human Soluble PD-1
                                          (SEQ ID NO: 73)
pgwfldspdr pwnpptfspa llvvtegdna tftcsfsnts

esfvlnwyrm spsnqtdkla afpedrsqpg qdcrfrvtql
```

-continued

```
pngrdfhmsv vrarrndsgt ylcgaislap kaqikeslra

elrvterrae vptahpspsp rpagqfqtlv vgvvggllgs

lvllvwvlav icsraargti garrtgqplk edpsavpvfs

vdygeldfqw rektpeppvp cvpeqteyat ivfpsgmgts

sparrgsadg prsaqplrpe dghcswpl

Human Soluble PD-L1
                                          (SEQ ID NO: 74)
ftvtvpkdlyvv eygsnmtiec kfpvekqldl aalivyweme

dkniiqfvhg eedlkvqhss yrqrarllkd qlslgnaalq

itdvklqdag vyrcmisygg adykritvkv napynkinqr

ilvvdpvtse heltcqaegy pkaeviwtss dhqvlsgktt

ttnskreekl fnvtstlrin tttneifyct frrldpeenh

taelvipelp lahppnerth lvilgaillc lgvaltfifr

lrkgrmmdvk kcgiqdtnsk kqsdthleet

Human Soluble TIGIT
                                          (SEQ ID NO: 75)
mmtgtiett gnisaekggs iilqchlsst taqvtqvnwe

qqdqllaicn adlgwhisps fkdrvapgpg lgltlqsltv

ndtgeyfciy htypdgtytg riflevless vaehgarfqi

pllgamaatl vvictavivv valtrkkkal rihsvegdlr

rksagqeews psapsppgsc vqaeaapagl cgeqrgedca

elhdyfnvls yrslgncsff tetg

Human Soluble CD1A
                                          (SEQ ID NO: 76)
nadglkeplsfhvt wiasfynhsw kqnlvsgwls dlqthtwdsn

sstivflcpw srgnfsneew keletlfrir tirsfegirr

yahelqfeyp feiqvtggce lhsgkvsgsf lqlayqgsdf

vsfqnnswlp ypvagnmakh fckvlnqnqh endithnlls

dtcprfilgl ldagkahlqr qvkpeawlsh gpspgpghlq

lvchvsgfyp kpvwvmwmrg eqeqqgtqrg dilpsadgtw

ylratlevaa geaadlscrv khsslegqdi vlywehhssv

gfiilavivp lllliglalw frkrcfc

Human Soluble TIM3
                                          (SEQ ID NO: 77)
seveyraev gqnaylpcfy tpaapgnlvp vcwgkgacpv

fecgnvvlrt derdvnywts rywlngdfrk gdvsltienv

tladsgiycc riqipgimnd ekfnlklvik pakvtpaptr

qrdftaafpr mlttrghgpa etqtlgslpd inltqistla

nelrdsrlan dlrdsgatir igiyigagic aglalalifg

alifkwyshs kekiqnlsli slanlppsgl anavaegirs

eeniytieen vyeveepney ycyvssrqqp sqplgcrfam
```

In some embodiments, a soluble PD-1 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 73.

In some embodiments, a soluble PD-L1 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 74.

In some embodiments, a soluble TIGIT protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 75.

In some embodiments, a soluble CD1A protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 76.

In some embodiments, a soluble TIM3 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 77.

Recombinant Antibodies

In some examples, NK activating agent can be: an agonistic antibody that binds specifically to an IL-2 receptor (see, e.g., those described in Gaulton et al., *Clinical Immunology and Immunopathology* 36(1):18-29, 1985), an agonistic antibody that binds specifically to an IL-7 receptor, an agonistic antibody that binds specifically to IL-12 receptor (see, e.g., those described in Rogge et al., *J. Immunol.* 162(7): 3926-3932, 1999), an agonistic antibody that binds specifically to IL-15 receptor, an agonistic antibody that binds specifically to IL-21 receptor (see, e.g., those described in U.S. Patent Application Publication No. 2006/159655), an agonistic antibody that binds specifically to IL-33 receptor (see, e.g., those described in U.S. Patent Application Publication No. 2007/160579), an antagonistic antibody that binds specifically to PD-1 (see, e.g., those described in U.S. Pat. No. 7,521,051), an antibody that binds specifically to PD-L1 (see, e.g., those described in U.S. Pat. No. 8,217,149), an antibody that binds specifically to TGF-β, an antagonistic antibody that binds specifically to TGF-β receptor (see, e.g., those described in European Patent Application Publication No. 1245676 A1), an antagonistic antibody that binds specifically to TIGIT (see, e.g., those described in WO 2017/053748), an antibody that binds specifically to a ligand of TIGIT (see, e.g., those described in WO 2011/127324), an antagonistic antibody that binds specifically to CD1 (see, e.g., those described in Szalay et al., *J. Immunol.* 162(12):6955-6958, 1999), an antibody that binds specifically to a ligand of CD1 (see, e.g., those described in Kain et al., *Immunity* 41(4):543-554, 2014), an antagonistic antibody that binds specifically to TIM-3 (see, e.g., those described in U.S. Patent Application Publication No. 2015/218274), an antibody that binds specifically to a ligand of TIM-3 (see, e.g., those described in U.S. Patent Application Publication No. 2017/283499), an agonistic antibody that binds specifically to CD69 (see, e.g., those described in Moretta et al., *Journal of Experimental Medicine* 174:1393, 1991), an agonistic antibody that binds specifically to CD25, CD59, an agonistic antibody that binds specifically to CD352 (see, e.g., those described in Yigit et al., *Oncotarget* 7:26346-26360, 2016), an agonistic antibody that binds specifically to NKp80 (see, e.g., those described in Peipp et al., Oncotarget 6:32075-32088, 2015), an agonistic antibody that binds specifically to DNAM-1, an agonistic antibody that binds specifically to 2B4 (see, e.g., those described in Sandusky et al., *European J. Immunol.* 36:3268-3276, 2006), an agonistic antibody that binds specifically to NKp30 (see, e.g., those described in Kellner et al., *OncoImmunology* 5:1-12, 2016), an agonistic antibody that binds specifically to NKp44, an agonistic antibody that binds specifically to NKp46 (see, e.g., those described in Xiong et al., *J. Clin. Invest.* 123:4264-4272, 2013), an agonistic antibody that binds specifically to NKG2D (see, e.g., those described in Kellner et al., *OncoImmunology* 5:1-12, 2016), an agonistic antibody that binds specifically to KIR2DS1 (see, e.g., those described in Xiong et al., *J. Clin. Invest.* 123:4264-4272, 2013), an agonistic antibody that binds specifically to KIR2Ds2/3 (see, e.g., those described in Borgerding et al., *Exp. Hematology* 38:213-221, 2010), an agonistic antibody that binds specifically to KIR2DL4 (see, e.g., those described in Miah et al., *J. Immunol.* 180:2922-32, 2008), an agonistic antibody that binds specifically to KIR2DS4 (see, e.g., those described in Czaja et al., *Genes and Immunity* 15:33-37, 2014), an agonistic antibody that binds specifically to KIR2DS5 (see, e.g., those described in Czaja et al., *Genes and Immunity* 15:33-37, 2014), an agonistic antibody that binds specifically to KIR3DS1 (see, e.g., those described in Czaja et al., *Genes and Immunity* 15:33-37, 2014), an antagonistic antibody that binds specifically to Siglec-7 (see, e.g., those described in Hudak et al., *Nature Chemical Biology* 10:69-75, 2014), an antagonistic antibody that binds specifically to IRP60 (see, e.g., those described in Bachelet et al., *J. Biol. Chem.* 281:27190-27196, 2006), an antagonistic antibody that binds specifically to Tactile (see, e.g., those described in Brooks et al., *Eur. J. Cancer* 61 (Suppl. 1):S189, 2016), an antagonistic antibody that binds specifically to IL1R8 (see, e.g., those described in Molgora et al., *Frontiers Immunol.* 7:1, 2016), an antagonistic antibody that binds specifically to NKG2A/KLRD1 (see, e.g., those described in Kim et al., *Infection Immunity* 76:5873-5882, 2008), an antagonistic antibody that binds specifically to KIR2DL1 (see, e.g., those described in Weiner et al., *Cell* 148:1081-1084, 2012), an antagonistic antibody that binds specifically to KIR2DL2/3 (see, e.g., those described in Weiner et al., *Cell* 148:1081-1084, 2012), an antagonistic antibody that binds specifically to KIR2DL5 (see, e.g., those described in U.S. Pat. No. 9,067,997), and an antagonistic antibody that binds specifically KIR3DL1 (see, e.g., those described in U.S. Pat. No. 9,067,997), an antagonistic antibody that binds specifically to KIR3DL2 (see, e.g., those described in U.S. Pat. No. 9,067,997), an antagonistic antibody that binds specifically to ILT2/LIR-1 (see, e.g., those described in U.S. Pat. No. 8,133,485), and an antagonistic antibody that binds specifically to LAG-2.

A recombinant antibody that is an NK cell activating agent can be any of exemplary types of antibodies (e.g., a human or humanized antibody) or any of the exemplary antibody fragments described herein. A recombinant antibody that is an NK cell activating agent can include, e.g., any of the antigen-binding domains described herein.

Recombinant Interleukins or Cytokines

In some examples, NK activating agents can be, e.g., a soluble IL-2, a soluble IL-7, a soluble IL-12, a soluble IL-15, a soluble IL-21, and a soluble IL-33. Non-limiting examples of soluble IL-12, IL-15, IL-21, and IL-33. are provided below.

```
Human Soluble IL-2
                                        (SEQ ID NO: 78)
aptssstkkt qlqlehllld lqmilnginn yknpkltrml

tfkfympkka telkhlqcle eelkpleevl nlaqsknfhl

rprdlisnin vivlelkgse ttfmceyade tativeflnr

witfcgsiis tlt

Human Soluble IL-7
                                        (SEQ ID NO: 79)
dcdiegkdgkqyesv lmvsidqlld smkeigsncl

nnefnffkrh icdankegmf lfraarklrq flkmnstgdf

dlhllkvseg ttillnctgq vkgrkpaalg eaqptkslee

nkslkeqkkl ndlcflkrll qeiktcwnki lmgtkeh

Human Soluble IL-12 subunit alpha
                                        (SEQ ID NO: 80)
rnlpvatp dpgmfpclhh sqnllravsn mlqkarqtle

fypctseeid heditkdkts tveaclplel tknesclnsr

etsfitngsc lasrktsfmm alclssiyed lkmyqvefkt

mnakllmdpk rqifldqnml avidelmqal nfnsetvpqk

ssleepdfyk tkiklcillh afriravtid rvmsylnas

Human Soluble IL-12 subunit beta
                                        (SEQ ID NO: 81)
iwelkkdv yvveldwypd apgemvvltc dtpeedgitw

tldqssevlg sgktltiqvk efgdagqytc hkggevlshs

llllhkkedg iwstdilkdq kepknktflr ceaknysgrf

tcwwlttist dltfsvkssr gssdpqgvtc gaatlsaerv

rgdnkeyeys vecqedsacp aaeeslpiev mvdavhklky

enytssffir diikpdppkn lqlkplknsr qvevsweypd

twstphsyfs ltfcvqvqgk skrekkdrvf tdktsatvic

rknasisvra qdryysssws ewasvpcs

Human Soluble IL-15
                                        (SEQ ID NO: 82)
Nwvnvisdlkki edliqsmhid atlytesdvh psckvtamkc

fllelqvisl esgdasihdt venliilann slssngnvte

sgckeceele eknikeflqs fvhivqmfin ts

Human Soluble IL-21
                                        (SEQ ID NO: 83)
qgqdrhmi rmrqlidivd qlknyvndlv peflpapedv

etncewsafs cfqkaqlksa ntgnneriin vsikklkrkp

pstnagrrqk hrltcpscds yekkppkefl erfksllqkm

ihqhlssrth gseds
```

-continued

```
Human Soluble IL-33
                                        (SEQ ID NO: 84)
mkpkmkystn kistakwknt askalcfklg ksqqkakevc

pmyfmklrsg lmikkeacyf rrettkrpsl ktgrkhkrhl

vlaacqqqst vecfafgisg vqkytralhd ssitgispit

eylaslstyn dqsitfaled esyeiyvedl kkdekkdkvl

lsyyesqhps nesgdgvdgk mlmvtlsptk dfwlhannke

hsvelhkcek plpdqaffvl hnmhsncvsf ecktdpgvfi

gvkdnhlali kvdssenlct enilfklset
```

In some embodiments, a soluble IL-2 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 78.

In some embodiments, a soluble IL-7 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 79.

In some embodiments, a soluble IL-2 protein includes a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 80 and a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 81.

In some embodiments, a soluble IL-15 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 82.

In some embodiments, a soluble IL-21 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 83.

In some embodiments, a soluble IL-33 protein can include a sequence that is at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 84.

Soluble Cytokine or Interleukin Receptors

In some examples of any of the soluble cytokine or interleukin receptors described herein, the soluble cytokine or interleukin receptors can be a soluble TGF-β receptor. In some examples, the soluble TGF-β receptor is a soluble TGF-β receptor I (TGF-βRI) (see, e.g., those described in Docagne et al., *Journal of Biological Chemistry* 276(49): 46243-46250, 2001), a soluble TGF-β receptor II (TGF-βRII) (see, e.g., those described in Yung et al., *Am. J. Resp. Crit. Care Med.* 194(9):1140-1151, 2016), a soluble TGF-βRIII (see, e.g., those described in Heng et al., *Placenta* 57:320, 2017). In some examples, the soluble TGF-β receptor is a receptor "trap" for TGF-β (see, e.g., those described in Zwaagstra et al., *Mol. Cancer Ther.* 11(7):1477-1487, 2012, and those described in De Crescenzo et al. Transforming Growth Factor β in Cancer Therapy, Volume II, pp 671-684).

Additional examples of soluble cytokine or soluble interleukin receptors are known in the art.

Single Chain Chimeric Polypeptides

Non-limiting examples of NK cell activating agents are single-chain chimeric polypeptides that include: (i) a first target-binding domain (e.g., any of the target-binding domains described herein or known in the art), (ii) a soluble tissue factor domain (e.g., any of the exemplary soluble tissue factor domains described herein or known in the art), and (iii) as second target-binding domain (e.g., any of the target-binding domains described herein or known in the art).

In some examples of any of the single-chain chimeric polypeptides described herein, the single-chain chimeric polypeptide can have a total length of about 50 amino acids to about 3000 amino acids, about 50 amino acids to about 2500 amino acids, about 50 amino acids to about 2000 amino acids, about 50 amino acids to about 1500 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 480 amino acids, about 50 amino acids to about 460 amino acids, about 50 amino acids to about 440 amino acids, about 50 amino acids to about 420 amino acids, about 50 amino acids to about 400 amino acids, about 50 amino acids to about 380 amino acids, about 50 amino acids to about 360 amino acids, about 50 amino acids to about 340 amino acids, about 50 amino acids to about 320 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 150 amino acids, about 50 amino acids to about 100 amino acids, about 100 amino acids to about 3000 amino acids, about 100 amino acids to about 2500 amino acids, about 100 amino acids to about 2000 amino acids, about 100 amino acids to about 1500 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 480 amino acids, about 100 amino acids to about 460 amino acids, about 100 amino acids to about 440 amino acids, about 100 amino acids to about 420 amino acids, about 100 amino acids to about 400 amino acids, about 100 amino acids to about 380 amino acids, about 100 amino acids to about 360 amino acids, about 100 amino acids to about 340 amino acids, about 100 amino acids to about 320 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 150 amino acids, about 150 amino acids to about 3000 amino acids, about 150 amino acids to about 2500 amino acids, about 150 amino acids to about 2000 amino acids, about 150 amino acids to about 1500 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 480 amino acids, about 150 amino acids to about 460 amino acids, about 150 amino acids to about 440 amino acids, about 150 amino acids to about 420 amino acids, about 150 amino acids to about 400 amino acids, about 150 amino acids to about 380 amino acids, about 150 amino acids to about 360 amino acids, about 150 amino acids to about 340 amino acids, about 150 amino acids to about 320 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 200 amino acids to about 3000 amino acids, about 200 amino acids to about 2500 amino acids, about 200 amino acids to about 2000 amino acids, about 200 amino acids to about 1500 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 480 amino acids, about 200 amino acids to about 460 amino acids, about 200 amino acids to about 440 amino acids, about 200 amino acids to about 420 amino acids, about 200 amino acids to about 400 amino acids, about 200 amino acids to about 380 amino acids, about 200 amino acids to about 360 amino acids, about 200 amino acids to about 340 amino acids, about 200 amino acids to about 320 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 3000 amino acids, about 220 amino acids to about 2500 amino acids, about 220 amino acids to about 2000 amino acids, about 220 amino acids to about 1500 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 3000 amino acids, about 240 amino acids to about 2500 amino acids, about 240 amino acids to about 2000 amino acids, about 240 amino acids to about 1500 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 3000 amino acids, about 260 amino acids to about 2500 amino acids, about 260 amino acids to about 2000 amino acids, about 260 amino acids to about 1500 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 3000 amino acids, about 280 amino acids to about 2500 amino acids, about 280 amino acids to about 2000 amino acids, about 280 amino acids to about 1500 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 3000 amino acids, about 300 amino acids to about 2500 amino acids, about 300 amino acids to about 2000 amino acids, about 300 amino acids to about 1500 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 3000 amino acids, about 320 amino acids to about 2500 amino acids, about 320 amino acids to about 2000 amino acids, about 320 amino acids to about 1500 amino acids, about 320 amino acids to about 1000 amino acids, about 320 amino acids to about 950 amino acids, about 320 amino acids to about 900 amino acids, about 320 amino acids to about 850 amino acids, about 320 amino acids to about 800 amino acids, about 320 amino acids to about 750 amino acids, about 320 amino acids to about 700 amino acids, about 320 amino acids to about 650 amino acids, about 320 amino acids to about 600 amino acids, about 320 amino acids to about 550 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 3000 amino acids, about 340 amino acids to about 2500 amino acids, about 340 amino acids to about 2000 amino acids, about 340 amino acids to about 1500 amino acids, about 340 amino acids to about 1000 amino acids, about 340 amino acids to about 950 amino acids, about 340 amino acids to about 900 amino acids, about 340 amino acids to about 850 amino acids, about 340 amino acids to about 800 amino acids, about 340 amino acids to about 750 amino acids, about 340 amino acids to about 700 amino acids, about 340 amino acids to about 650 amino acids, about 340 amino acids to about 600 amino acids, about 340 amino acids to about 550 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 3000 amino acids, about 360 amino acids to about 2500 amino acids, about 360 amino acids to about 2000 amino acids, about 360 amino acids to about 1500 amino acids, about 360 amino acids to about 1000 amino acids, about 360 amino acids to about 950 amino acids, about 360 amino acids to about 900 amino acids, about 360 amino acids to about 850 amino acids, about 360 amino acids to about 800 amino acids, about 360 amino acids to about 750 amino acids, about 360 amino acids to about 700 amino acids, about 360 amino acids to about 650 amino acids, about 360 amino acids to about 600 amino acids, about 360 amino acids to about 550 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 3000 amino acids, about 380 amino acids to about 2500 amino acids, about 380 amino acids to about 2000 amino acids, about 380 amino acids to about 1500 amino acids, about 380 amino acids to about 1000 amino acids, about 380 amino acids to about 950 amino acids, about 380 amino acids to about 900 amino acids, about 380 amino acids to about 850 amino acids, about 380 amino acids to about 800 amino acids, about 380 amino acids to about 750 amino acids, about 380 amino acids to about 700 amino acids, about 380 amino acids to about 650 amino acids, about 380 amino acids to about 600 amino acids, about 380 amino acids to about 550 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 3000 amino acids, about 400 amino acids to about 2500 amino acids, about 400 amino acids to about 2000 amino acids, about 400 amino acids to about 1500 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 3000 amino acids, about 420 amino acids to about 2500 amino acids, about 420 amino acids to about 2000 amino acids, about 420 amino acids to about 1500 amino acids, about 420 amino acids to about 1000 amino acids, about 420 amino acids to about 950 amino acids, about 420 amino acids to about 900 amino acids, about 420 amino acids to about 850 amino acids, about 420 amino acids to about 800 amino acids, about 420 amino acids to about 750 amino acids, about 420 amino acids to about 700 amino acids, about 420 amino acids to about 650 amino acids, about 420 amino acids to about 600 amino acids, about 420 amino acids to about 550 amino acids, about 420 amino acids to about 500 amino acids, about 420 amino acids to about 480 amino acids, about 420 amino acids to about 460 amino acids, about 420 amino acids to about 440 amino acids, about 440 amino acids to about 3000 amino acids, about 440 amino acids to about 2500 amino acids, about 440 amino acids to about 2000 amino acids, about 440 amino acids to about 1500 amino acids, about 440 amino acids to about 1000 amino acids, about 440 amino acids to about 950 amino acids, about 440 amino acids to about 900 amino acids, about 440 amino acids to about 850 amino acids, about 440 amino acids to about 800 amino acids, about 440 amino acids to about 750 amino acids, about 440 amino acids to about 700 amino acids, about 440 amino acids to about 650 amino acids, about 440 amino acids to about 600 amino acids, about 440 amino acids to about 550 amino acids, about 440 amino acids to about 500 amino acids, about 440 amino acids to about 480 amino acids, about 440 amino acids to about 460 amino acids, about 460 amino acids to about 3000 amino acids, about 460 amino acids to about 2500 amino acids, about 460 amino acids to about 2000 amino acids, about 460 amino acids to about 1500 amino acids, about 460 amino acids to about 1000 amino acids, about 460 amino acids to about 950 amino acids, about 460 amino acids to about 900 amino acids, about 460 amino acids to about 850 amino acids, about 460 amino acids to about 800 amino acids, about 460 amino acids to about 750 amino acids, about 460 amino acids to about 700 amino acids, about 460 amino acids to about 650 amino acids, about 460 amino acids to about 600 amino acids, about 460 amino acids to about 550 amino acids, about 460 amino acids to about 500 amino acids, about 460 amino acids to about 480 amino acids, about 480 amino acids to about 3000 amino acids, about 480 amino acids to about 2500 amino acids, about 480 amino acids to about 2000 amino acids, about 480 amino acids to about 1500 amino acids, about 480 amino acids to about 1000 amino acids, about 480 amino acids to about 950 amino acids, about 480 amino acids to about 900 amino acids, about 480 amino acids to about 850 amino acids, about 480 amino acids to about 800 amino acids, about 480 amino acids to about 750 amino acids, about 480 amino acids to about 700 amino acids, about 480 amino acids to about 650 amino acids, about 480 amino acids to about 600 amino acids, about 480 amino acids to about 550 amino acids, about 480 amino acids to about 500 amino acids, about 500 amino acids to about 3000 amino acids, about 500 amino acids to about 2500 amino acids, about 500 amino acids to about 2000 amino acids, about 500 amino acids to about 1500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 3000 amino acids, about 550 amino acids to about 2500 amino acids, about 550 amino acids to about 2000 amino acids, about 550 amino acids to about 1500 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 3000 amino acids, about 600 amino acids to about 2500 amino acids, about 600 amino acids to about 2000 amino acids, about 600 amino acids to about 1500 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 3000 amino acids, about 650 amino acids to about 2500 amino acids, about 650 amino acids to about 2000 amino acids, about 650 amino acids to about 1500 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 3000 amino acids, about 700 amino acids to about 2500 amino acids, about 700 amino acids to about 2000 amino acids, about 700 amino acids to about 1500 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 3000 amino acids, about 750 amino acids to about 2500 amino acids, about 750 amino acids to about 2000 amino acids, about 750 amino acids to about 1500 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 3000 amino acids, about 800 amino acids to about 2500 amino acids, about 800 amino acids to about 2000 amino acids, about 800 amino acids to about 1500 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 3000 amino acids, about 850 amino acids to about 2500 amino acids, about 850 amino acids to about 2000 amino acids, about 850 amino acids to about 1500 amino acids, about 850 amino acids to about 1000 amino acids, about 850 amino acids to about 950 amino acids, about 850 amino acids to about 900 amino acids, about 900 amino acids to about 3000 amino acids, about 900 amino acids to about 2500 amino acids, about 900 amino acids to about 2000 amino acids, about 900 amino acids to about 1500 amino acids, about 900 amino acids to about 1000 amino acids, about 900 amino acids to about 950 amino acids, about 950 amino acids to about 3000 amino acids, about 950 amino acids to about 2500 amino acids, about 950 amino acids to about 2000 amino acids, about 950 amino acids to about 1500 amino acids, about 950 amino acids to about 1000 amino acids, about 1000 amino acids to about 3000 amino acids, about 1000 amino acids to about 2500 amino acids, about 1000 amino acids to about 2000 amino acids, about 1000 amino acids to about 1500 amino acids, about 1500 amino acids to about 3000 amino acids, about 1500 amino acids to about 2500 amino acids, about 1500 amino acids to about 2000 amino acids, about 2000 amino acids to about 3000 amino acids, about 2000 amino acids to about 2500 amino acids, or about 2500 amino acids to about 3000 amino acids.

In some embodiments of any of the single-chain chimeric polypeptides described herein, the first target-binding domain (e.g., any of the exemplary target-binding domains described herein or known in the art) and the soluble tissue factor domain (e.g., any of the exemplary soluble tissue factor domains described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the soluble tissue factor domain (e.g., any of the exemplary soluble tissue factor domains described herein). In some embodiments of any of the single-chain chimeric polypeptides described herein, the soluble tissue factor domain (e.g., any of the exemplary soluble tissue factor domains described herein) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the soluble tissue factor domain (e.g., any of the exemplary soluble tissue factor domains described herein) and the second target-binding domain (e.g., any of the exemplary target-binding domains described herein or known in the art).

In some embodiments of any of the single-chain chimeric polypeptides described herein, the first target-binding domain (e.g., any of the exemplary target-binding domains described herein or known in the art) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the second target-binding domain (e.g., any of the exemplary target-binding domains described herein or known in the art). In some embodiments of any of the single-chain chimeric polypeptides described herein, the second target-binding domain (e.g., any of the exemplary target-binding domains described herein or known in the art) and the soluble tissue factor domain (e.g., any of the exemplary soluble tissue factor domains described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the second target-binding domain (e.g., any of the exemplary target-binding domains described herein or known in the art) and the soluble tissue factor domain (e.g., any of the exemplary soluble tissue factor domains described herein or known in the art).

In some embodiments, a single-chain chimeric polypeptide can include a sequence that is at least 70% identical (e.g., at least 75% identical, at least 80% identical, at least 85% identical, at least 90% identical, at least 95% identical, at least 99% identical, or 100% identical) to (SEQ ID NO: 85)

QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINRGGGGSGGGGSGGGGSQVQLQQSGAELARPGASVKMSCKASGYT

FTRYTMHWVKQRPGQGLEWIGYINPSRGYTNYNQKFKDKATLTTDKSSST

AYMQLSSLTSEDSAVYYCARYYDDHYCLDYWGQGTTLTVSSSGTTNTVAA

YNLTWKSTNFKTILEWEPKPVNQVYTVQISTKSGDWKSKCFYTTDTECDL

TDEIVKDVKQTYLARVFSYPAGNVESTGSAGEPLYENSPEFTPYLETNLG

QPTIQSFEQVGTKVNVTVEDERTLVRRNNTFLSLRDVFGKDLIYTLYYWK

SSSSGKKTAKTNTNEFLIDVDKGENYCFSVQAVIPSRTVNRKSTDSPVEC

MGQEKGEFREVQLQQSGPELVKPGASVKMSCKASGYTFTSYVIQWVKQKP

GQGLEWIGSINPYNDYTKYNEKFKGKATLTSDKSSITAYMEFSSLTSEDS

ALYYCARWGDGNYWGRGTTLTVSSGGGGSGGGGSGGGGSDIEMTQSPAIM

SASLGERVTMTCTASSSVSSSYFHWYQQKPGSSPKLCIYSTSNLASGVPP

RFSGSGSTSYSLTISSMEAEDAATYFCHQYHRSPTFGGGTKLETKR.

In some embodiments, a single-chain chimeric polypeptide is encoded by a nucleic acid that includes a sequence that is at least 70% identical (e.g., at least 75% identical, at least 80% identical, at least 85% identical, at least 90% identical, at least 95% identical, at least 99% identical, or 100% identical) to (SEQ ID NO: 86)

CAGATCGTGCTGACCCAAAGCCCCGCCATCATGAGCGCTAGCCCCGGTGA

GAAGGTGACCATGACATGCTCCGCTTCCAGCTCCGTGTCCTACATGAACT

GGTATCAGCAGAAAAGCGGAACCAGCCCCAAAAGGTGGATCTACGACACC

AGCAAGCTGGCCTCCGGAGTGCCCGCTCATTTCCGGGGCTCTGGATCCGG

CACCAGCTACTCTTTAACCATTTCCGGCATGGAAGCTGAAGACGCTGCCA

CCTACTATTGCCAGCAATGGAGCAGCAACCCCTTCACATTCGGATCTGGC

ACCAAGCTCGAAATCAATCGTGGAGGAGGTGGCAGCGGCGGCGGTGGATC

CGGCGGAGGAGGAAGCCAAGTTCAACTCCAGCAGAGCGGCGCTGAACTGG

CCCGGCCCGGCGCCTCCGTCAAGATGAGCTGCAAGGCTTCCGGCTATACA

TTTACTCGTTACACAATGCATTGGGTCAAGCAGAGGCCCGGTCAAGGTTT

AGAGTGGATCGGATATATCAACCCTTCCCGGGGCTACACCAACTATAACC

AAAAGTTCAAGGATAAAGCCACTTTAACCACTGACAAGAGCTCCTCCACC

GCCTACATGCAGCTGTCCTCTTTAACCAGCGAGGACTCCGCTGTTTACTA

CTGCGCTAGGTATTACGACGACCACTACTGTTTAGACTATTGGGGACAAG

-continued

GTACCACTTTAACCGTCAGCAGCTCCGGCACCACCAATACCGTGGCCGCT

TATAACCTCACATGGAAGAGCACCAACTTCAAGACAATTCTGGAATGGGA

ACCCAAGCCCGTCAATCAAGTTTACACCGTGCAGATCTCCACCAAATCCG

GAGACTGGAAGAGCAAGTGCTTCTACACAACAGACACCGAGTGTGATTTA

ACCGACGAAATCGTCAAGGACGTCAAGCAAACCTATCTGGCTCGGGTCTT

TTCCTACCCCGCTGGCAATGTCGAGTCCACCGGCTCCGCTGGCGAGCCTC

TCTACGAGAATTCCCCCGAATTCACCCCTTATTTAGAGACCAATTTAGGC

CAGCCTACCATCCAGAGCTTCGAGCAAGTTGGCACCAAGGTGAACGTCAC

CGTCGAGGATGAAAGGACTTTAGTGCGGCGGAATAACACATTTTTATCCC

TCCGGGATGTGTTCGGCAAAGACCTCATCTACACACTGTACTATTGGAAG

TCCAGCTCCTCCGGCAAAAAGACCGCTAAGACCAACACCAACGAGTTTTT

AATTGACGTGGACAAAGGCGAGAACTACTGCTTCAGCGTGCAAGCCGTGA

TCCCTTCTCGTACCGTCAACCGGAAGAGCACAGATTCCCCCGTTGAGTGC

ATGGGCCAAGAAAAGGGCGAGTTCCGGGAGGTCCAGCTGCAGCAGAGCGG

ACCCGAACTCGTGAAACCCGGTGCTTCCGTGAAAATGTCTTGTAAGGCCA

GCGGATACACCTTCACCTCCTATGTGATCCAGTGGGTCAAACAGAAGCCC

GGACAAGGTCTCGAGTGGATCGGCAGCATCAACCCTTACAACGACTATAC

CAAATACAACGAGAAGTTTAAGGGAAAGGCTACTTTAACCTCCGACAAAA

GCTCCATCACAGCCTACATGGAGTTCAGCTCTTTAACATCCGAGGACAGC

GCTCTGTACTATTGCGCCCGGTGGGGCGACGGCAATTACTGGGGACGGGG

CACAACACTGACCGTGAGCAGCGGAGGCGGAGGCTCCGGCGGAGGCGGAT

CTGGCGGTGGCGGCTCCGACATCGAGATGACCCAGTCCCCCGCTATCATG

TCCGCCTCTTTAGGCGAGCGGGTCACAATGACTTGTACAGCCTCCTCCAG

CGTCTCCTCCTCCTACTTCCATTGGTACCAACAGAAACCCGGAAGCTCCC

CTAAACTGTGCATCTACAGCACCAGCAATCTCGCCAGCGGCGTGCCCCCT

AGGTTTTCCGGAAGCGGAAGCACCAGCTACTCTTTAACCATCTCCTCCAT

GGAGGCTGAGGATGCCGCCACCTACTTTTGTCACCAGTACCACCGGTCCC

CCACCTTCGGAGGCGGCACCAAACTGGAGACAAAGAGG.

In some embodiments, a single-chain chimeric polypeptide can include a sequence that is at least 70% identical (e.g., at least 75% identical, at least 80% identical, at least 85% identical, at least 90% identical, at least 95% identical, at least 99% identical, or 100% identical) to (SEQ ID NO: 87)

MKWVTFISLLFLFSSAYSQIVLTQSPAIMSASPGEKVTMTCSASSSVSYM

NWYQQKSGTSPKRWIYDTSKLASGVPAHFRGSGSGTSYSLTISGMEAEDA

ATYYCQQWSSNPFTFGSGTKLEINRGGGGSGGGGSGGGGSQVQLQQSGAE

LARPGASVKMSCKASGYTFTRYTMHWVKQRPGQGLEWIGYINPSRGYTNY

NQKFKDKATLTTDKSSSTAYMQLSSLTSEDSAVYYCARYYDDHYCLDYWG

QGTTLTVSSSGTTNTVAAYNLTWKSTNFKTILEWEPKPVNQVYTVQISTK

SGDWKSKCFYTTDTECDLTDEIVKDVKQTYLARVFSYPAGNVESTGSAGE

-continued

```
PLYENSPEFTPYLETNLGQPTIQSFEQVGTKVNVTVEDERTLVRRNNTFL
SLRDVFGKDLIYTLYYWKSSSSGKKTAKTNTNEFLIDVDKGENYCFSVQA
VIPSRTVNRKSTDSPVECMGQEKGEFREVQLQQSGPELVKPGASVKMSCK
ASGYTFTSYVIQWVKQKPGQGLEWIGSINPYNDYTKYNEKFKGKATLTSD
KSSITAYMEFSSLTSEDSALYYCARWGDGNYWGRGTTLTVSSGGGGSGGG
GSGGGGSDIEMTQSPAIMSASLGERVTMTCTASSSVSSSYFHWYQQKPGS
SPKLCIYSTSNLASGVPPRFSGSGSTSYSLTISSMEAEDAATYFCHQYHR
SPTFGGGTKLETKR.
```

In some embodiments, a single-chain chimeric polypeptide is encoded by a nucleic acid that includes a sequence that is at least 70% identical (e.g., at least 75% identical, at least 80% identical, at least 85% identical, at least 90% identical, at least 95% identical, at least 99% identical, or 100% identical) to

```
(SEQ ID NO: 88)
ATGAAGTGGGTGACCTTCATCAGCTTATTATTTTTATTCAGCTCCGCCTA
TTCCCAGATCGTGCTGACCCAAAGCCCCGCCATCATGAGCGCTAGCCCCG
GTGAGAAGGTGACCATGACATGCTCCGCTTCCAGCTCCGTGTCCTACATG
AACTGGTATCAGCAGAAAAGCGGAACCAGCCCCAAAAGGTGGATCTACGA
CACCAGCAAGCTGGCCTCCGGAGTGCCCGCTCATTTCCGGGGCTCTGGAT
CCGGCACCAGCTACTCTTTAACCATTTCCGGCATGGAAGCTGAAGACGCT
GCCACCTACTATTGCCAGCAATGGAGCAGCAACCCCTTCACATTCGGATC
TGGCACCAAGCTCGAAATCAATCGTGGAGGAGGTGGCAGCGGCGGCGGTG
GATCCGGCGGAGGAGGAAGCCAAGTTCAACTCCAGCAGAGCGGCGCTGAA
CTGGCCCGGCCCGGCGCCTCCGTCAAGATGAGCTGCAAGGCTTCCGGCTA
TACATTTACTCGTTACACAATGCATTGGGTCAAGCAGAGGCCCGGTCAAG
GTTTAGAGTGGATCGGATATATCAACCCTTCCCGGGGCTACACCAACTAT
AACCAAAAGTTCAAGGATAAAGCCACTTTAACCACTGACAAGAGCTCCTC
CACCGCCTACATGCAGCTGTCCTCTTTAACCAGCGAGGACTCCGCTGTTT
ACTACTGCGCTAGGTATTACGACGACCACTACTGTTTAGACTATTGGGGA
CAAGGTACCACTTTAACCGTCAGCAGCTCCGGCACCACCAATACCGTGGC
CGCTTATAACCTCACATGGAAGAGCACCAACTTCAAGACAATTCTGGAAT
GGGAACCCAAGCCCGTCAATCAAGTTTACACCGTGCAGATCTCCACCAAA
TCCGGAGACTGGAAGAGCAAGTGCTTCTACACAACAGACACCGAGTGTGA
TTTAACCGACGAAATCGTCAAGGACGTCAAGCAAACCTATCTGGCTCGGG
TCTTTTCCTACCCCGCTGGCAATGTCGAGTCCACCGGCTCCGCTGGCGAG
CCTCTCTACGAGAATTCCCCCGAATTCACCCCTTATTTAGAGACCAATTT
AGGCCAGCCTACCATCCAGAGCTTCGAGCAAGTTGGCACCAAGGTGAACG
TCACCGTCGAGGATGAAAGGACTTTAGTGCGGCGGAATAACACATTTTTA
TCCCTCCGGGATGTGTTCGGCAAAGACCTCATCTACACACTGTACTATTG
GAAGTCCAGCTCCTCCGGCAAAAAGACCGCTAAGACCAACACCAACGAGT
TTTTAATTGACGTGGACAAAGGCGAGAACTACTGCTTCAGCGTGCAAGCC
```

-continued

```
GTGATCCCTTCTCGTACCGTCAACCGGAAGAGCACAGATTCCCCCGTTGA
GTGCATGGGCCAAGAAAAGGGCGAGTTCCGGGAGGTCCAGCTGCAGCAGA
GCGGACCCGAACTCGTGAAACCCGGTGCTTCCGTGAAAATGTCTTGTAAG
GCCAGCGGATACACCTTCACCTCCTATGTGATCCAGTGGGTCAAACAGAA
GCCCGGACAAGGTCTCGAGTGGATCGGCAGCATCAACCCTTACAACGACT
ATACCAAATACAACGAGAAGTTTAAGGGAAAGGCTACTTTAACCTCCGAC
AAAAGCTCCATCACAGCCTACATGGAGTTCAGCTCTTTAACATCCGAGGA
CAGCGCTCTGTACTATTGCGCCCGGTGGGGCGACGGCAATTACTGGGGAC
GGGGCACAACACTGACCGTGAGCAGCGGAGGCGGAGGCTCCGGCGGAGGC
GGATCTGGCGGTGGCGGCTCCGACATCGAGATGACCCAGTCCCCCGCTAT
CATGTCCGCCTCTTTAGGCGAGCGGGTCACAATGACTTGTACAGCCTCCT
CCAGCGTCTCCTCCTCCTACTTCCATTGGTACCAACAGAAACCCGGAAGC
TCCCCTAAACTGTGCATCTACAGCACCAGCAATCTCGCCAGCGGCGTGCC
CCCTAGGTTTTCCGGAAGCGGAAGCACCAGCTACTCTTTAACCATCTCCT
CCATGGAGGCTGAGGATGCCGCCACCTACTTTTGTCACCAGTACCACCGG
TCCCCCACCTTCGGAGGCGGCACCAAACTGGAGACAAAGAGG.
```

In some embodiments, a single-chain chimeric polypeptide can include a sequence that is at least 70% identical (e.g., at least 75% identical, at least 80% identical, at least 85% identical, at least 90% identical, at least 95% identical, at least 99% identical, or 100% identical) to

```
(SEQ ID NO: 89)
VQLQQSGPELVKPGASVKMSCKASGYTFTSYVIQWVKQKPGQGLEWIGSI
NPYNDYTKYNEKFKGKATLTSDKSSITAYMEFSSLTSEDSALYYCARWGD
GNYWGRGTTLTVSSGGGGSGGGGSGGGGSDIEMTQSPAIMSASLGERVTM
TCTASSSVSSSYFHWYQQKPGSSPKLCIYSTSNLASGVPPRFSGSGSTSY
SLTISSMEAEDAATYFCHQYHRSPTFGGGTKLETKRSGTTNTVAAYNLTW
KSTNFKTILEWEPKPVNQVYTVQISTKSGDWKSKCFYTTDTECDLTDEIV
KDVKQTYLARVFSYPAGNVESTGSAGEPLYENSPEFTPYLETNLGQPTIQ
SFEQVGTKVNVTVEDERTLVRRNNTFLSLRDVFGKDLIYTLYYWKSSSSG
KKTAKTNTNEFLIDVDKGENYCFSVQAVIPSRTVNRKSTDSPVECMGQEK
GEFREQIVLTQSPAIMSASPGEKVTMTCSASSSVSYMNWYQQKSGTSPKR
WIYDTSKLASGVPAHFRGSGSGTSYSLTISGMEAEDAATYYCQQWSSNPF
TFGSGTKLEINRGGGGSGGGGSGGGGSQVQLQQSGAELARPGASVKMSCK
ASGYTFTRYTMHWVKQRPGQGLEWIGYINPSRGYTNYNQKFKDKATLTTD
KSSSTAYMQLSSLTSEDSAVYYCARYYDDHYCLDYWGQGTTLTVSS.
```

In some embodiments, a single-chain chimeric polypeptide is encoded by a nucleic acid that includes a sequence that is at least 70% identical (e.g., at least 75% identical, at least 80% identical, at least 85% identical, at least 90% identical, at least 95% identical, at least 99% identical, or 100% identical) to (SEQ ID NO: 90)
GTGCAGCTGCAGCAGTCCGGACCCGAACTGGTCAAGCCCGGTGCCTCCGT
GAAAATGTCTTGTAAGGCTTCTGGCTACACCTTTACCTCCTACGTCATCC
AATGGGTGAAGCAGAAGCCCGGTCAAGGTCTCGAGTGGATCGGCAGCATC
AATCCCTACAACGATTACACCAAGTATAACGAAAAGTTTAAGGGCAAGGC
CACTCTGACAAGCGACAAGAGCTCCATTACCGCCTACATGGAGTTTTCCT
CTTTAACTTCTGAGGACTCCGCTTTATACTATTGCGCTCGTTGGGGCGAT
GGCAATTATTGGGGCCGGGGAACTACTTTAACAGTGAGCTCCGGCGGCGG
CGGAAGCGGAGGTGGAGGATCTGGCGGTGGAGGCAGCGACATCGAGATGA
CACAGTCCCCCGCTATCATGAGCGCCTCTTTAGGAGAACGTGTGACCATG
ACTTGTACAGCTTCCTCCAGCGTGAGCAGCTCCTATTTCCACTGGTACCA
GCAGAAACCCGGCTCCTCCCCTAAACTGTGTATCTACTCCACAAGCAATT
TAGCTAGCGGCGTGCCTCCTCGTTTTAGCGGCTCCGGCAGCACCTCTTAC
TCTTTAACCATTAGCTCTATGGAGGCCGAAGATGCCGCCACATACTTTTG
CCATCAGTACCACCGGTCCCCTACCTTTGGCGGAGGCACAAAGCTGGAGA
CCAAGCGGAGCGGCACCACCAACACAGTGGCCGCCTACAATCTGACTTGG
AAATCCACCAACTTCAAGACCATCCTCGAGTGGGAGCCCAAGCCCGTTAA
TCAAGTTTATACCGTGCAGATTTCCACCAAGAGCGGCGACTGGAAATCCA
AGTGCTTCTATACCACAGACACCGAGTGCGATCTCACCGACGAGATCGTC
AAAGACGTGAAGCAGACATATTTAGCTAGGGTGTTCTCCTACCCCGCTGG
AAACGTGGAGAGCACCGGATCCGCTGGAGAGCCTTTATACGAGAACTCCC
CCGAATTCACCCCCTATCTGGAAACCAATTTAGGCCAGCCCACCATCCAG
AGCTTCGAACAAGTTGGCACAAAGGTGAACGTCACCGTCGAAGATGAGAG
GACTTTAGTGCGGAGGAACAATACATTTTTATCCTTACGTGACGTCTTCG
GCAAGGATTTAATCTACACACTGTATTACTGGAAGTCTAGCTCCTCCGGC
AAGAAGACCGCCAAGACCAATACCAACGAATTTTTAATTGACGTGGACAA
GGGCGAGAACTACTGCTTCTCCGTGCAAGCTGTGATCCCCTCCCGGACAG
TGAACCGGAAGTCCACCGACTCCCCCGTGGAGTGCATGGGCCAAGAGAAG
GGAGAGTTTCGTGAGCAGATCGTGCTGACCCAGTCCCCCGCTATTATGAG
CGCTAGCCCCGGTGAAAAGGTGACTATGACATGCAGCGCCAGCTCTTCCG
TGAGCTACATGAACTGGTATCAGCAGAAGTCCGGCACCAGCCCTAAAAGG
TGGATCTACGACACCAGCAAGCTGGCCAGCGGCGTCCCCGCTCACTTTCG
GGGCTCCGGCTCCGGAACAAGCTACTCTCTGACCATCAGCGGCATGGAAG
CCGAGGATGCCGCTACCTATTACTGTCAGCAGTGGAGCTCCAACCCCTTC
ACCTTTGGATCCGGCACCAAGCTCGAGATTAATCGTGGAGGCGGAGGTAG
CGGAGGAGGCGGATCCGGCGGTGGAGGTAGCCAAGTTCAGCTCCAGCAAA
GCGGCGCCGAACTCGCTCGGCCCGGCGCTTCCGTGAAGATGTCTTGTAAG
GCCTCCGGCTATACCTTCACCCGGTACACAATGCACTGGGTCAAGCAACG
GCCCGGTCAAGGTTTAGAGTGGATTGGCTATATCAACCCCTCCCGGGGCT
ATACCAACTACAACCAGAAGTTCAAGGACAAAGCCACCCTCACCACCGAC
AAGTCCAGCAGCACCGCTTACATGCAGCTGAGCTCTTTAACATCCGAGGA -continued
TTCCGCCGTGTACTACTGCGCTCGGTACTACGACGATCATTACTGCCTCG
ATTACTGGGGCCAAGGTACCACCTTAACAGTCTCCTCC.

In some embodiments, a single-chain chimeric polypeptide can include a sequence that is at least 70% identical (e.g., at least 75% identical, at least 80% identical, at least 85% identical, at least 90% identical, at least 95% identical, at least 99% identical, or 100% identical) to (SEQ ID NO: 91)
MKWVTFISLLFLFSSAYSVQLQQSGPELVKPGASVKMSCKASGYTFTSYV
IQWVKQKPGQGLEWIGSINPYNDYTKYNEKFKGKATLTSDKSSITAYMEF
SSLTSEDSALYYCARWGDGNYWGRGTTLTVSSGGGGSGGGGSGGGGSDIE
MTQSPAIMSASLGERVTMTCTASSSVSSSYFHWYQQKPGSSPKLCIYSTS
NLASGVPPRFSGSGSTSYSLTISSMEAEDAATYFCHQYHRSPTFGGGTKL
ETKRSGTTNTVAAYNLTWKSTNFKTILEWEPKPVNQVYTVQISTKSGDWK
SKCFYTTDTECDLTDEIVKDVKQTYLARVFSYPAGNVESTGSAGEPLYEN
SPEFTPYLETNLGQPTIQSFEQVGTKVNVTVEDERTLVRRNNTFLSLRDV
FGKDLIYTLYYWKSSSSGKKTAKTNTNEFLIDVDKGENYCFSVQAVIPSR
TVNRKSTDSPVECMGQEKGEFREQIVLTQSPAIMSASPGEKVTMTCSASS
SVSYMNWYQQKSGTSPKRWIYDTSKLASGVPAHFRGSGSGTSYSLTISGM
EAEDAATYYCQQWSSNPFTFGSGTKLEINRGGGGSGGGGSGGGGSQVQLQ
QSGAELARPGASVKMSCKASGYTFTRYTMHWVKQRPGQGLEWIGYINPSR
GYTNYNQKFKDKATLTTDKSSSTAYMQLSSLTSEDSAVYYCARYYDDHYC
LDYWGQGTTLTVSS.

In some embodiments, a single-chain chimeric polypeptide is encoded by a nucleic acid that includes a sequence that is at least 70% identical (e.g., at least 75% identical, at least 80% identical, at least 85% identical, at least 90% identical, at least 95% identical, at least 99% identical, or 100% identical) to (SEQ ID NO: 92)
ATGAAATGGGTCACCTTCATCTCTTTACTGTTTTTATTTAGCAGCGCCTA
CAGCGTGCAGCTGCAGCAGTCCGGACCCGAACTGGTCAAGCCCGGTGCCT
CCGTGAAAATGTCTTGTAAGGCTTCTGGCTACACCTTTACCTCCTACGTC
ATCCAATGGGTGAAGCAGAAGCCCGGTCAAGGTCTCGAGTGGATCGGCAG
CATCAATCCCTACAACGATTACACCAAGTATAACGAAAAGTTTAAGGGCA
AGGCCACTCTGACAAGCGACAAGAGCTCCATTACCGCCTACATGGAGTTT
TCCTCTTTAACTTCTGAGGACTCCGCTTTATACTATTGCGCTCGTTGGGG
CGATGGCAATTATTGGGGCCGGGGAACTACTTTAACAGTGAGCTCCGGCG
GCGGCGGAAGCGGAGGTGGAGGATCTGGCGGTGGAGGCAGCGACATCGAG
ATGACACAGTCCCCCGCTATCATGAGCGCCTCTTTAGGAGAACGTGTGAC
CATGACTTGTACAGCTTCCTCCAGCGTGAGCAGCTCCTATTTCCACTGGT
ACCAGCAGAAACCCGGCTCCTCCCCTAAACTGTGTATCTACTCCACAAGC
AATTTAGCTAGCGGCGTGCCTCCTCGTTTTAGCGGCTCCGGCAGCACCTC
TTACTCTTTAACCATTAGCTCTATGGAGGCCGAAGATGCCGCCACATACT -continued

```
TTTGCCATCAGTACCACCGGTCCCCTACCTTTGGCGGAGGCACAAAGCTG

GAGACCAAGCGGAGCGGCACCACCAACACAGTGGCCGCCTACAATCTGAC

TTGGAAATCCACCAACTTCAAGACCATCCTCGAGTGGGAGCCCAAGCCCG

TTAATCAAGTTTATACCGTGCAGATTTCCACCAAGAGCGGCGACTGGAAA

TCCAAGTGCTTCTATACCACAGACACCGAGTGCGATCTCACCGACGAGAT

CGTCAAAGACGTGAAGCAGACATATTTAGCTAGGGTGTTCTCCTACCCCG

CTGGAAACGTGGAGAGCACCGGATCCGCTGGAGAGCCTTTATACGAGAAC

TCCCCCGAATTCACCCCCTATCTGGAAACCAATTTAGGCCAGCCCACCAT

CCAGAGCTTCGAACAAGTTGGCACAAAGGTGAACGTCACCGTCGAAGATG

AGAGGACTTTAGTGCGGAGGAACAATACATTTTTATCCTTACGTGACGTC

TTCGGCAAGGATTTAATCTACACACTGTATTACTGGAAGTCTAGCTCCTC

CGGCAAGAAGACCGCCAAGACCAATACCAACGAATTTTTAATTGACGTGG

ACAAGGGCGAGAACTACTGCTTCTCCGTGCAAGCTGTGATCCCCTCCCGG

ACAGTGAACCGGAAGTCCACCGACTCCCCCGTGGAGTGCATGGGCCAAGA

GAAGGGAGAGTTTCGTGAGCAGATCGTGCTGACCCAGTCCCCCGCTATTA

TGAGCGCTAGCCCCGGTGAAAAGGTGACTATGACATGCAGCGCCAGCTCT

TCCGTGAGCTACATGAACTGGTATCAGCAGAAGTCCGGCACCAGCCCTAA

AAGGTGGATCTACGACACCAGCAAGCTGGCCAGCGGCGTCCCCGCTCACT

TTCGGGGCTCCGGCTCCGGAACAAGCTACTCTCTGACCATCAGCGGCATG

GAAGCCGAGGATGCCGCTACCTATTACTGTCAGCAGTGGAGCTCCAACCC

CTTCACCTTTGGATCCGGCACCAAGCTCGAGATTAATCGTGGAGGCGGAG

GTAGCGGAGGAGGCGGATCCGGCGGTGGAGGTAGCCAAGTTCAGCTCCAG

CAAAGCGGCGCCGAACTCGCTCGGCCCGGCGCTTCCGTGAAGATGTCTTG

TAAGGCCTCCGGCTATACCTTCACCCGGTACACAATGCACTGGGTCAAGC

AACGGCCCGGTCAAGGTTTAGAGTGGATTGGCTATATCAACCCCTCCCGG

GGCTATACCAACTACAACCAGAAGTTCAAGGACAAAGCCACCCTCACCAC

CGACAAGTCCAGCAGCACCGCTTACATGCAGCTGAGCTCTTTAACATCCG

AGGATTCCGCCGTGTACTACTGCGCTCGGTACTACGACGATCATTACTGC

CTCGATTACTGGGGCCAAGGTACCACCTTAACAGTCTCCTCC.
```

Some embodiments of any of the single-chain chimeric polypeptides described herein can further include one or more (e.g., two, three, four, five, six, seven, eight, nine, or ten) additional target-binding domains (e.g., any of the exemplary target-binding domains described herein or known in the art) at its N- and/or C-terminus.

In some embodiments, the single-chain chimeric polypeptides can include one or more (e.g., two, three, four, five, six, seven, eight, nine, or ten) additional target-binding domains (e.g., any of the exemplary target-binding domains described herein or known in the art) at its N-terminus. In some embodiments, one of the one or more additional target-binding domains (e.g., any of the exemplary target-binding domains described herein or known in the art) at the N-terminus of the single-chain chimeric polypeptide can directly abut the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein). In some embodiments, the single-chain chimeric polypeptide further includes a linker sequence (e.g., any of the exemplary linker sequences described herein or known in the art) between one of the at least one additional target-binding domains (e.g., any of the exemplary target-binding domains described herein or known in the art) at the N-terminus of the single-chain chimeric polypeptide and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, the single-chain chimeric polypeptide includes one or more (e.g., two, three, four, five, six, seven, eight, nine, or ten) additional target-binding domains (e.g., any of the exemplary target-binding domains described herein or known in the art) at its C-terminus. In some embodiments, one of the one or more additional target-binding domains (e.g., any of the exemplary target-binding domains described herein or known in the art) at the C-terminus of the single-chain chimeric polypeptide directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein or known in the art). In some embodiments, the single-chain chimeric polypeptide further comprises a linker sequence (e.g., any of the exemplary linker sequences described herein or known in the art) between one of the at least one additional target-binding domains (e.g., any of the exemplary target-binding domains described herein or known in the art) at the C-terminus of the single-chain chimeric polypeptide and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, the single-chain chimeric polypeptide comprises one or more (e.g., two, three, four, five, six, seven, eight, nine, or ten) additional target binding domains (e.g., any of the exemplary target-binding domains described herein or known in the art) at its N-terminus and its C-terminus. In some embodiments, one of the one or more additional antigen binding domains (e.g., any of the exemplary target-binding domains described herein or known in the art) at the N-terminus of the single-chain chimeric polypeptide directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein). In some embodiments, the single-chain chimeric polypeptide further includes a linker sequence (e.g., any of the exemplary linker sequences described herein or known in the art) between one of the one or more additional antigen-binding domains (e.g., any of the exemplary target-binding domains described herein or known in the art) at the N-terminus and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains). In some embodiments, one of the one or more additional antigen binding domains (e.g., any of the exemplary target-binding domains described herein or known in the art) at the C-terminus directly abuts the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains). In some embodiments, the single-chain chimeric polypeptide further includes a linker sequence (e.g., any of the exemplary linker sequences described herein or known in the art) between one of the one or more additional antigen-binding domains (e.g., any of the exemplary target-binding domains described herein or known in the art) at the C-terminus and the first target-binding domain (e.g., any of the exemplary target-binding domains described herein or known in the art), the second target-binding domain (e.g., any of the exemplary target-binding domains described herein or known in the art), or the soluble tissue factor domain (e.g., any of the exemplary soluble tissue factor domains described herein).

In some embodiments of any of the single-chain chimeric polypeptides described herein, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to the same antigen. In some embodiments, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to the same epitope. In some embodiments, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) include the same amino acid sequence.

In some embodiments of any of the single-chain chimeric polypeptides described herein, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) each bind specifically to the same antigen. In some embodiments, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) each bind specifically to the same epitope. In some embodiments, the first target-binding domain, the second target-binding domain, and the one or more (e.g., two, three, four, five, six, seven, eight, nine, or ten) additional target-binding domains each comprise the same amino acid sequence.

In some embodiments of any of the single-chain chimeric polypeptides described herein, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) bind specifically to different antigens.

In some embodiments of any of the single-chain chimeric polypeptides, one or more of the first target-binding domain, the second target-binding domain, and the one or more target-binding domains is an antigen-binding domain (e.g., any of the exemplary antigen-binding domains described herein or known in the art). In some embodiments of any of the single-chain chimeric polypeptides described herein, the first target-binding domain, the second target-binding domain, and the one or more additional target-binding domains are each an antigen-binding domain (e.g., any of the exemplary antigen-binding domains described herein or known in the art). In some embodiments, the antigen-binding domain can include a scFv or a single domain antibody.

In some embodiments of any of the single-chain chimeric polypeptides described herein, one or more (e.g., two, three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine protein. Non-limiting examples of soluble interleukin proteins and soluble cytokine proteins include: IL-1, IL-2, IL-3, IL-7, IL-8, IL-10, IL-12, IL-15, IL-17, IL-18, IL-21, PDGF-DD, and SCF.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine receptor. Non-limiting examples of soluble interleukin receptors and soluble cytokine receptors include: a soluble TGF-β receptor II (TGF-βRII), a soluble TGF-βRIII, a soluble NKG2D, a soluble NKP30, a soluble NKp44, a soluble NKp46, a soluble DNAM1, a scMHCI, a scMHCII, a scTCR, a soluble CD155, a soluble CD122, a soluble CD3, or a soluble CD28.

In some embodiments of any of the single-chain chimeric polypeptides described herein, the first target-binding domain (e.g., any of the target-binding domains described herein), the second target-binding domain (e.g., any of the target-binding domains described herein), and the one or more additional target-binding domains (e.g., any of the target-binding domains described herein) can each, independently, bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKP30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine protein. In some embodiments of any of the multi-chain chimeric polypeptides described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the single-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine receptor. In some embodiments of any of the multi-chain chimeric polypeptides described herein, the soluble receptor is a soluble TGF-β receptor II (TGF-βRII) a soluble TGF-βRIII, a soluble receptor for TNFα, a soluble receptor for IL-4, or a soluble receptor for IL-10.

Multi-Chain Chimeric Polypeptides—Type A

Non-limiting examples of NK cell activating agents are multi-chain chimeric polypeptides that include: (a) a first chimeric polypeptide including: (i) a first target-binding domain; (ii) a soluble tissue factor domain; and (iii) a first domain of a pair of affinity domains; and (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains.

In some examples of any of the multi-chain chimeric polypeptides described herein the total length of first chimeric polypeptide and/or the second chimeric polypeptide can each independently be about 50 amino acids to about 3000 amino acids, about 50 amino acids to about 2500 amino acids, about 50 amino acids to about 2000 amino acids, about 50 amino acids to about 1500 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 480 amino acids, about 50 amino acids to about 460 amino acids, about 50 amino acids to about 440 amino acids, about 50 amino acids to about 420 amino acids, about 50 amino acids to about 400 amino acids, about 50 amino acids to about 380 amino acids, about 50 amino acids to about 360 amino acids, about 50 amino acids to about 340 amino acids, about 50 amino acids to about 320 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 150 amino acids, about 50 amino acids to about 100 amino acids, about 100 amino acids to about 3000 amino acids, about 100 amino acids to about 2500 amino acids, about 100 amino acids to about 2000 amino acids, about 100 amino acids to about 1500 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 480 amino acids, about 100 amino acids to about 460 amino acids, about 100 amino acids to about 440 amino acids, about 100 amino acids to about 420 amino acids, about 100 amino acids to about 400 amino acids, about 100 amino acids to about 380 amino acids, about 100 amino acids to about 360 amino acids, about 100 amino acids to about 340 amino acids, about 100 amino acids to about 320 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 150 amino acids, about 150 amino acids to about 3000 amino acids, about 150 amino acids to about 2500 amino acids, about 150 amino acids to about 2000 amino acids, about 150 amino acids to about 1500 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 480 amino acids, about 150 amino acids to about 460 amino acids, about 150 amino acids to about 440 amino acids, about 150 amino acids to about 420 amino acids, about 150 amino acids to about 400 amino acids, about 150 amino acids to about 380 amino acids, about 150 amino acids to about 360 amino acids, about 150 amino acids to about 340 amino acids, about 150 amino acids to about 320 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 200 amino acids to about 3000 amino acids, about 200 amino acids to about 2500 amino acids, about 200 amino acids to about 2000 amino acids, about 200 amino acids to about 1500 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 480 amino acids, about 200 amino acids to about 460 amino acids, about 200 amino acids to about 440 amino acids, about 200 amino acids to about 420 amino acids, about 200 amino acids to about 400 amino acids, about 200 amino acids to about 380 amino acids, about 200 amino acids to about 360 amino acids, about 200 amino acids to about 340 amino acids, about 200 amino acids to about 320 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 3000 amino acids, about 220 amino acids to about 2500 amino acids, about 220 amino acids to about 2000 amino acids, about 220 amino acids to about 1500 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 3000 amino acids, about 240 amino acids to about 2500 amino acids, about 240 amino acids to about 2000 amino acids, about 240 amino acids to about 1500 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 3000 amino acids, about 260 amino acids to about 2500 amino acids, about 260 amino acids to about 2000 amino acids, about 260 amino acids to about 1500 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 3000 amino acids, about 280 amino acids to about 2500 amino acids, about 280 amino acids to about 2000 amino acids, about 280 amino acids to about 1500 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 3000 amino acids, about 300 amino acids to about 2500 amino acids, about 300 amino acids to about 2000 amino acids, about 300 amino acids to about 1500 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 3000 amino acids, about 320 amino acids to about 2500 amino acids, about 320 amino acids to about 2000 amino acids, about 320 amino acids to about 1500 amino acids, about 320 amino acids to about 1000 amino acids, about 320 amino acids to about 950 amino acids, about 320 amino acids to about 900 amino acids, about 320 amino acids to about 850 amino acids, about 320 amino acids to about 800 amino acids, about 320 amino acids to about 750 amino acids, about 320 amino acids to about 700 amino acids, about 320 amino acids to about 650 amino acids, about 320 amino acids to about 600 amino acids, about 320 amino acids to about 550 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 3000 amino acids, about 340 amino acids to about 2500 amino acids, about 340 amino acids to about 2000 amino acids, about 340 amino acids to about 1500 amino acids, about 340 amino acids to about 1000 amino acids, about 340 amino acids to about 950 amino acids, about 340 amino acids to about 900 amino acids, about 340 amino acids to about 850 amino acids, about 340 amino acids to about 800 amino acids, about 340 amino acids to about 750 amino acids, about 340 amino acids to about 700 amino acids, about 340 amino acids to about 650 amino acids, about 340 amino acids to about 600 amino acids, about 340 amino acids to about 550 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 3000 amino acids, about 360 amino acids to about 2500 amino acids, about 360 amino acids to about 2000 amino acids, about 360 amino acids to about 1500 amino acids, about 360 amino acids to about 1000 amino acids, about 360 amino acids to about 950 amino acids, about 360 amino acids to about 900 amino acids, about 360 amino acids to about 850 amino acids, about 360 amino acids to about 800 amino acids, about 360 amino acids to about 750 amino acids, about 360 amino acids to about 700 amino acids, about 360 amino acids to about 650 amino acids, about 360 amino acids to about 600 amino acids, about 360 amino acids to about 550 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 3000 amino acids, about 380 amino acids to about 2500 amino acids, about 380 amino acids to about 2000 amino acids, about 380 amino acids to about 1500 amino acids, about 380 amino acids to about 1000 amino acids, about 380 amino acids to about 950 amino acids, about 380 amino acids to about 900 amino acids, about 380 amino acids to about 850 amino acids, about 380 amino acids to about 800 amino acids, about 380 amino acids to about 750 amino acids, about 380 amino acids to about 700 amino acids, about 380 amino acids to about 650 amino acids, about 380 amino acids to about 600 amino acids, about 380 amino acids to about 550 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 3000 amino acids, about 400 amino acids to about 2500 amino acids, about 400 amino acids to about 2000 amino acids, about 400 amino acids to about 1500 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 3000 amino acids, about 420 amino acids to about 2500 amino acids, about 420 amino acids to about 2000 amino acids, about 420 amino acids to about 1500 amino acids, about 420 amino acids to about 1000 amino acids, about 420 amino acids to about 950 amino acids, about 420 amino acids to about 900 amino acids, about 420 amino acids to about 850 amino acids, about 420 amino acids to about 800 amino acids, about 420 amino acids to about 750 amino acids, about 420 amino acids to about 700 amino acids, about 420 amino acids to about 650 amino acids, about 420 amino acids to about 600 amino acids, about 420 amino acids to about 550 amino acids, about 420 amino acids to about 500 amino acids, about 420 amino acids to about 480 amino acids, about 420 amino acids to about 460 amino acids, about 420 amino acids to about 440 amino acids, about 440 amino acids to about 3000 amino acids, about 440 amino acids to about 2500 amino acids, about 440 amino acids to about 2000 amino acids, about 440 amino acids to about 1500 amino acids, about 440 amino acids to about 1000 amino acids, about 440 amino acids to about 950 amino acids, about 440 amino acids to about 900 amino acids, about 440 amino acids to about 850 amino acids, about 440 amino acids to about 800 amino acids, about 440 amino acids to about 750 amino acids, about 440 amino acids to about 700 amino acids, about 440 amino acids to about 650 amino acids, about 440 amino acids to about 600 amino acids, about 440 amino acids to about 550 amino acids, about 440 amino acids to about 500 amino acids, about 440 amino acids to about 480 amino acids, about 440 amino acids to about 460 amino acids, about 460 amino acids to about 3000 amino acids, about 460 amino acids to about 2500 amino acids, about 460 amino acids to about 2000 amino acids, about 460 amino acids to about 1500 amino acids, about 460 amino acids to about 1000 amino acids, about 460 amino acids to about 950 amino acids, about 460 amino acids to about 900 amino acids, about 460 amino acids to about 850 amino acids, about 460 amino acids to about 800 amino acids, about 460 amino acids to about 750 amino acids, about 460 amino acids to about 700 amino acids, about 460 amino acids to about 650 amino acids, about 460 amino acids to about 600 amino acids, about 460 amino acids to about 550 amino acids, about 460 amino acids to about 500 amino acids, about 460 amino acids to about 480 amino acids, about 480 amino acids to about 3000 amino acids, about 480 amino acids to about 2500 amino acids, about 480 amino acids to about 2000 amino acids, about 480 amino acids to about 1500 amino acids, about 480 amino acids to about 1000 amino acids, about 480 amino acids to about 950 amino acids, about 480 amino acids to about 900 amino acids, about 480 amino acids to about 850 amino acids, about 480 amino acids to about 800 amino acids, about 480 amino acids to about 750 amino acids, about 480 amino acids to about 700 amino acids, about 480 amino acids to about 650 amino acids, about 480 amino acids to about 600 amino acids, about 480 amino acids to about 550 amino acids, about 480 amino acids to about 500 amino acids, about 500 amino acids to about 3000 amino acids, about 500 amino acids to about 2500 amino acids, about 500 amino acids to about 2000 amino acids, about 500 amino acids to about 1500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 3000 amino acids, about 550 amino acids to about 2500 amino acids, about 550 amino acids to about 2000 amino acids, about 550 amino acids to about 1500 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 3000 amino acids, about 600 amino acids to about 2500 amino acids, about 600 amino acids to about 2000 amino acids, about 600 amino acids to about 1500 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 3000 amino acids, about 650 amino acids to about 2500 amino acids, about 650 amino acids to about 2000 amino acids, about 650 amino acids to about 1500 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 3000 amino acids, about 700 amino acids to about 2500 amino acids, about 700 amino acids to about 2000 amino acids, about 700 amino acids to about 1500 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 3000 amino acids, about 750 amino acids to about 2500 amino acids, about 750 amino acids to about 2000 amino acids, about 750 amino acids to about 1500 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 3000 amino acids, about 800 amino acids to about 2500 amino acids, about 800 amino acids to about 2000 amino acids, about 800 amino acids to about 1500 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 3000 amino acids, about 850 amino acids to about 2500 amino acids, about 850 amino acids to about 2000 amino acids, about 850 amino acids to about 1500 amino acids, about 850 amino acids to about 1000 amino acids, about 850 amino acids to about 950 amino acids, about 850 amino acids to about 900 amino acids, about 900 amino acids to about 3000 amino acids, about 900 amino acids to about 2500 amino acids, about 900 amino acids to about 2000 amino acids, about 900 amino acids to about 1500 amino acids, about 900 amino acids to about 1000 amino acids, about 900 amino acids to about 950 amino acids, about 950 amino acids to about 3000 amino acids, about 950 amino acids to about 2500 amino acids, about 950 amino acids to about 2000 amino acids, about 950 amino acids to about 1500 amino acids, about 950 amino acids to about 1000 amino acids, about 1000 amino acids to about 3000 amino acids, about 1000 amino acids to about 2500 amino acids, about 1000 amino acids to about 2000 amino acids, about 1000 amino acids to about 1500 amino acids, about 1500 amino acids to about 3000 amino acids, about 1500 amino acids to about 2500 amino acids, about 1500 amino acids to about 2000 amino acids, about 2000 amino acids to about 3000 amino acids, about 2000 amino acids to about 2500 amino acids, or about 2500 amino acids to about 3000 amino acids.

In some embodiments of any of the multi-chain chimeric polypeptides described herein, the first target-binding domain (e.g., any of the first target-binding domains described herein) and the soluble tissue factor domain (e.g., any of the exemplary soluble tissue factor domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the first target-binding domain (e.g., any of the exemplary first target-binding domains described herein) and the soluble tissue factor domain (e.g., any of the exemplary soluble tissue factor domains described herein) in the first chimeric polypeptide.

In some embodiments of any of the multi-chain chimeric polypeptides described herein, the soluble tissue factor domain (e.g., any of the exemplary soluble tissue factor domains described herein) and the first domain of the pair of affinity domains (e.g., any of the exemplary first domains of any of the exemplary pairs of affinity domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the soluble tissue factor domain (e.g., any of the exemplary soluble tissue factor domains described herein) and the first domain of the pair of affinity domains (e.g., any of the exemplary first domains of any of the exemplary pairs of affinity domains described herein) in the first chimeric polypeptide.

In some embodiments of any of the multi-chain chimeric polypeptides described herein, the second domain of the pair of affinity domains (e.g., any of the exemplary second domains of any of the exemplary pairs of affinity domains described herein) and the second target-binding domain (e.g., any of the exemplary second target-binding domains described herein) directly abut each other in the second chimeric polypeptide. In some embodiments of any of the multi-chain chimeric polypeptides described herein, the second chimeric polypeptide further comprises a linker sequence (e.g., any of the exemplary linker sequences described herein or known in the art) between the second domain of the pair of affinity domains (e.g., any of the exemplary second domains of any of the exemplary pairs of affinity domains described herein) and the second target-binding domain (e.g., any of the exemplary second target-binding domains described herein) in the second chimeric polypeptide.

In some embodiments of any of the multi-chain chimeric polypeptides, the first chimeric polypeptide further includes one or more (e.g., two, three, four, five, six, seven, eight, nine, or ten) additional target-binding domain(s) (e.g., any of the exemplary target-binding domains described herein or known in the art), where at least one of the one or more additional antigen-binding domain(s) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein). In some embodiments, the first chimeric polypeptide can further include a linker sequence (e.g., any of the exemplary linker sequences described herein or known in the art) between the soluble tissue factor domain (e.g., any of the exemplary soluble tissue factor domains described herein) and the at least one of the one or more additional target-binding domain(s) (e.g., any of the exemplary target-binding domains described herein or known in the art), and/or a linker sequence (e.g., any of the exemplary linker sequences described herein or known in the art) between the at least one of the one or more additional target-binding domain(s) (e.g., any of the exemplary target-binding domains described herein or known in the art) and the first domain of the pair of affinity domains (e.g., any of the exemplary first domains described herein of any of the exemplary pairs of affinity domains described herein).

In some embodiments of any of the multi-chain chimeric polypeptides described herein, the first chimeric polypeptide further includes one or more (e.g., two, three, four, five, six, seven, eight, nine, or ten) additional target-binding domains at the N-terminal and/or C-terminal end of the first chimeric polypeptide. In some embodiments, at least one of the one or more additional target-binding domains (e.g., any of the exemplary target-binding domains described herein or known in the art) directly abuts the first domain of the pair of affinity domains (e.g., any of the exemplary first domains described herein of any of the exemplary pairs of affinity domains described herein) in the first chimeric polypeptide. In some embodiments, the first chimeric polypeptide further includes a linker sequence (e.g., any of the exemplary linker sequences described herein or known in the art) between the at least one of the one or more additional target-binding domains (e.g., any of the exemplary target-binding domains described herein or known in the art) and the first domain of the pair of affinity domains (e.g., any of the exemplary first domains described herein of any of the exemplary pairs of affinity domains described herein). In some embodiments, the at least one of the one or more additional target-binding domains (e.g., any of the exemplary target-binding domains described herein or known in the art) directly abuts the first target-binding domain (e.g., any of the exemplary target-binding domains described herein or known in the art) in the first chimeric polypeptide. In some embodiments, the first chimeric polypeptide further comprises a linker sequence (e.g., any of the exemplary linker sequences described herein or known in the art) between the at least one of the one or more additional target-binding domains (e.g., any of the exemplary target-binding domains described herein or known in the art) and the first target-binding domain (e.g., any of the exemplary target-binding domains described herein or known in the art).

In some embodiments of any of the multi-chain chimeric polypeptides described herein, at least one of the one or more additional target-binding domains (e.g., any of the exemplary target-binding domains described herein or known in the art) is disposed at the N- and/or C-terminus of the first chimeric polypeptide, and at least one of the one or more additional target-binding domains (e.g., any of the exemplary target-binding domains described herein or known in the art) is positioned between the soluble tissue factor domain (e.g., any of the exemplary soluble tissue factor domains described herein or known in the art) and the first domain of the pair of affinity domains (e.g., any of the exemplary first domains of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the N-terminus directly abuts the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the first chimeric polypeptide further comprises a linker sequence (e.g., any of the linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the C-terminus directly abuts the first target-binding domain (e.g., any of the exemplary target-binding domains described herein or known in the art) or the first domain of the pair of affinity domains (e.g., any of the exemplary first domains of any of the exemplary pairs of affinity domains described herein) in the first chimeric polypeptide. In some embodiments, the first chimeric polypeptide further includes a linker sequence (e.g., any of the exemplary linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the first domains described herein or any of the exemplary pairs of affinity domains described herein), directly abuts the soluble tissue factor domain and/or the first domain of the pair of affinity domains. In some embodiments, the first chimeric polypeptide further comprises a linker sequence (e.g., any of the exemplary linker sequences described herein or known in the art) disposed (i) between the soluble tissue factor domain (e.g., any of the exemplary soluble tissue factor domains described herein) and the at least one of the one or more additional target-binding domains (e.g., any of the exemplary target-binding domains described herein or known in the art) positioned between the soluble tissue factor domain (e.g., any of the exemplary soluble tissue factor domains described herein) and the first domain of the pair of affinity domains (e.g., any of the exemplary first domains of any of the exemplary pairs of affinity domains described herein), and/or (ii) between the first domain of the pair of affinity domains and the at least one of the one or more additional target-binding domains positioned between the soluble tissue factor domain and the first domain of the pair of affinity domains.

In some embodiments of any of the multi-chain chimeric polypeptides described herein, the second chimeric polypeptide further includes one or more (e.g., two, three, four, five, six, seven, eight, nine, or ten) additional target-binding domains (e.g., any of the exemplary target-binding domains described herein or known in the art) at the N-terminal end and/or the C-terminal end of the second chimeric polypeptide. In some embodiments, at least one of the one or more additional target-binding domains (e.g., any of the exemplary target-binding domains described herein or known in the art) directly abuts the second domain of the pair of affinity domains (e.g., any of the exemplary second domains of any of the exemplary pairs of affinity domains described herein) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target-binding domains described herein or known in the art) and the second domain of the pair of affinity domains (e.g., any of the second domains described herein of any of the exemplary pairs of affinity domains described herein) in the second chimeric polypeptide. In some embodiments, at least one of the one or more additional target-binding domains (e.g., any of the exemplary target-binding domains described herein or known in the art) directly abuts the second target-binding domain (e.g., any of the target-binding domains described herein or known in the art) in the second chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target binding domains described herein or known in the art) and the second target-binding domain (e.g., any of the exemplary target binding domains described herein or known in the art) in the second chimeric polypeptide.

In some embodiments of any of the multi-chain chimeric polypeptides described herein, two or more (e.g., three or more, four or more, five or more, six or more, seven or more, eight or more, nine or more, or ten or more) of the first target-binding domain, the second target-binding domain, and the one or more additional target-binding domains bind specifically to the same antigen. In some embodiments, two or more (e.g., three or more, four or more, five or more, six or more, seven or more, eight or more, nine or more, or ten or more) of the first target-binding domain, the second target-binding domain, and the one or more additional target-binding domains bind specifically to the same epitope. In some embodiments, two or more (e.g., three or more, four or more, five or more, six or more, seven or more, eight or more, nine or more, or ten or more) of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence.

In some embodiments of any of the multi-chain chimeric polypeptides described herein, the first target-binding domain, the second target-binding domain, and the one or more additional target-binding domains bind specifically to different antigens. In some embodiments of any of the multi-chain chimeric polypeptides described herein, one or more (e.g., two or more, three or more, four or more, five or more, six or more, seven or more, eight or more, nine or more, or ten or more) of the first target-binding domain, the second target-binding domain, and the one or more additional target-binding domains is an antigen-binding domain. In some embodiments, the first target-binding domain, the second target-binding domain, and the one or more additional target-binding domains are each an antigen-binding domain (e.g., a scFv or a single-domain antibody).

In some embodiments of any of the multi-chain chimeric polypeptides described herein, one or more (e.g., two, three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKP30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the multi-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine protein. Non-limiting examples of soluble interleukin proteins and soluble cytokine proteins include: IL-1, IL-2, IL-3, IL-7, IL-8, IL-10, IL-12, IL-15, IL-17, IL-18, IL-21, PDGF-DD, and SCF.

In some embodiments of any of the multi-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine receptor. Non-limiting examples of soluble interleukin receptors and soluble cytokine receptors include: a soluble TGF-β receptor II (TGF-βRII), a soluble TGF-βRIII, a soluble NKG2D, a soluble NKP30, a soluble NKp44, a soluble NKp46, a soluble DNAM1, a scMHCI, a scMHCII, a scTCR, a soluble CD155, a soluble CD122, a soluble CD3, or a soluble CD28.

In some embodiments of any of the multi-chain chimeric polypeptides described herein, the first target-binding domain (e.g., any of the target-binding domains described herein, the second target-binding domain (e.g., any of the target-binding domains described herein), and the one or more additional target-binding domains (e.g., any of the target-binding domains described herein) can each, independently, bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the multi-chain chimeric polypeptides described herein, one or both of the first target-binding domain (e.g., any of the target-binding domains described herein), the second target-binding domain (e.g., any of the target-binding domains described herein), and the one or more additional binding domains (e.g., any of the target-binding described herein) is a soluble interleukin or cytokine protein. In some embodiments of any of the multi-chain chimeric polypeptides described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the multi-chain chimeric polypeptides described herein, one or both of the first target-binding domain and the second target-binding domain is a soluble interleukin or cytokine receptor. In some embodiments of any of the multi-chain chimeric polypeptides described herein, the soluble receptor is a soluble TGF-β receptor II (TGF-βRII) a soluble TGF-βRIII, a soluble receptor for TNFα, a soluble receptor for IL-4, or a soluble receptor for IL-10.

Multi-Chain Chimeric Polypeptides—Type B

Non-limiting examples of NK cell activating agents are multi-chain chimeric polypeptides that include: (a) a first and second chimeric polypeptide each including: (i) a first target-binding domain; (ii) a Fc domain; and (iii) a first domain of a pair of affinity domains; and (b) a third and fourth chimeric polypeptide each including: (i) a second domain of a pair of affinity domains; and (ii) a second target-binding domain, where the first and second chimeric polypeptides and the third and fourth chimeric polypeptides associate through the binding of the first domain and the second domain of the pair of affinity domains, and the first and second chimeric polypeptides associate through their Fc domains.

In some embodiments of any of the multi-chain chimeric polypeptides described herein, the first target-binding domain (e.g., any of the first target-binding domains described herein) and the Fc domain (e.g., any of the exemplary Fc domains described herein) directly abut each other in the first and second chimeric polypeptides. In some embodiments of any of the multi-chain chimeric polypeptides described herein, the first and second chimeric polypeptides further comprise a linker sequence (e.g., any of the exemplary linker sequences described herein or known in the art) between the first target-binding domain (e.g., any of the exemplary first target-binding domains described herein) and the Fc domain (e.g., any of the exemplary Fc domains described herein) in the first and second chimeric polypeptides.

In some embodiments of any of the multi-chain chimeric polypeptides described herein, the Fc domain (e.g., any of the exemplary Fc domains described herein) and the first domain of the pair of affinity domains (e.g., any of the exemplary first domains of any of the exemplary pairs of affinity domains described herein) directly abut each other in the first and second chimeric polypeptide. In some embodiments of any of the multi-chain chimeric polypeptides described herein, the first and second chimeric polypeptide further comprises a linker sequence (e.g., any of the exemplary linker sequences described herein or known in the art) between the Fc domain (e.g., any of the exemplary Fc domains described herein) and the first domain of the pair of affinity domains (e.g., any of the exemplary first domains of any of the exemplary pairs of affinity domains described herein) in the first and second chimeric polypeptide.

In some embodiments of any of the multi-chain chimeric polypeptides described herein, the second domain of the pair of affinity domains (e.g., any of the exemplary second domains of any of the exemplary pairs of affinity domains described herein) and the second target-binding domain (e.g., any of the exemplary second target-binding domains described herein) directly abut each other in the third and fourth chimeric polypeptide. In some embodiments of any of the multi-chain chimeric polypeptides described herein, the third and fourth chimeric polypeptide further comprise a linker sequence (e.g., any of the exemplary linker sequences described herein or known in the art) between the second domain of the pair of affinity domains (e.g., any of the exemplary second domains of any of the exemplary pairs of affinity domains described herein) and the second target-binding domain (e.g., any of the exemplary second target-binding domains described herein) in the third and fourth chimeric polypeptide.

In some embodiments of any of the multi-chain chimeric polypeptides described herein, the first target-binding domain and the second target-binding domain bind specifically to the same antigen. In some embodiments of any of the multi-chain chimeric polypeptides described herein, the first target-binding domain and the second target-binding domain bind specifically to the same epitope. In some embodiments of any of the multi-chain chimeric polypeptides described herein, the first target-binding domain and the second target-binding domain include the same amino acid sequence. In some embodiments of any of the multi-chain chimeric polypeptides described herein, the first target-binding domain and the second target-binding domain bind specifically to different antigens. In some embodiments of any of the multi-chain chimeric polypeptides described herein, one or both of the first target-binding domain and the second target-binding domain is an antigen-binding domain (e.g., any of the exemplary second target-binding domains described herein). In some embodiments of any of the multi-chain chimeric polypeptides described herein, the first target-binding domain and the second target-binding domain are each antigen-binding domains (e.g., any of the exemplary second target-binding domains described herein). In some embodiments of any of the multi-chain chimeric polypeptides described herein, the antigen-binding domain (e.g., any of the exemplary second target-binding domains described herein) includes a scFv or a single domain antibody.

In some embodiments of any of the multi-chain chimeric polypeptides described herein, one or both of the first target-binding domain (e.g., any of the exemplary target-binding domains described herein or known in the art) and the second target-binding domain (e.g., any of the exemplary target-binding domains described herein or known in the art) bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the multi-chain chimeric polypeptides described herein, one or both of the first target-binding domain (e.g., any of the exemplary target-binding domains described herein or known in the art) and the second target-binding domain (e.g., any of the exemplary target-binding domains described herein or known in the art) is a soluble interleukin or cytokine protein. Non-limiting examples of soluble interleukin proteins and soluble cytokine proteins include: IL-1, IL-2, IL-3, IL-7, IL-8, IL-10, IL-12, IL-15, IL-17, IL-18, IL-21, PDGF-DD, and SCF.

In some embodiments of any of the multi-chain chimeric polypeptides described herein, one or both of the first target-binding domain and the second target-binding domain (e.g., any of the exemplary target-binding domains described herein or known in the art) is a soluble interleukin or cytokine receptor. Non-limiting examples of soluble interleukin receptors and soluble cytokine receptors include: a soluble TGF-β receptor II (TGF-βRII), a soluble TGF-βRIII, a soluble NKG2D, a soluble NKp30, a soluble NKp44, a soluble NKp46, a soluble DNAM1, a scMHCI, a scMHCII, a scTCR, a soluble CD155, a soluble CD122, a soluble CD3, or a soluble CD28.

In some embodiments of any of the multi-chain chimeric polypeptides described herein, the first target-binding domain and the second target-binding domain can each, independently, bind specifically to a target selected from the group of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

In some embodiments of any of the multi-chain chimeric polypeptides described herein, one or both of the first target-binding domain and the second target-binding domain is a soluble interleukin or cytokine protein. In some embodiments of any of the multi-chain chimeric polypeptides described herein, the soluble interleukin or cytokine protein is selected from the group of: IL-1, IL-2, IL-3, IL-7, IL-8, IL-10, IL-12, IL-15, IL-17, IL-18, IL-21, PDGF-DD, and SCF.

In some embodiments of any of the multi-chain chimeric polypeptides described herein, one or both of the first target-binding domain and the second target-binding domain is a soluble interleukin or cytokine receptor. In some embodiments of any of the multi-chain chimeric polypeptides described herein, the soluble receptor is a soluble TGF-β receptor II (TGF-βRII) a soluble TGF-βRIII, a soluble receptor for TNFα, a soluble receptor for IL-4, or a soluble receptor for IL-10.

Tissue Factor

Human tissue factor is a 263 amino-acid transmembrane protein containing three domains: (1) a 219-amino acid N-terminal extracellular domain (residues 1-219); (2) a 22-amino acid transmembrane domain (residues 220-242); and (3) a 21-amino acid cytoplasmic C-terminal tail (residues 242-263) ((UniProtKB Identifier Number: P13726). The cytoplasmic tail contains two phosphorylation sites at Ser253 and Ser258, and one S-palmitoylation site at Cys245. Deletion or mutation of the cytoplasmic domain was not found to affect tissue factor coagulation activity. Tissue factor has one S-palmitoylation site in the intracellular domain of the protein at Cys245. The Cys245 is located at the amino acid terminus of the intracellular domain and close to the membrane surface. The tissue factor transmembrane domain is composed of a single-spanning α-helix.

The extracellular domain of tissue factor, composed of two fibronectin type III domains, is connected to the transmembrane domain through a six-amino acid linker. This linker provides conformational flexibility to decouple the tissue factor extracellular domain from its transmembrane and cytoplasmic domains. Each tissue factor fibronectin type III module is composed of two overlapping β sheets with the top sheet domain containing three antiparallel β-strands and the bottom sheet containing four β-strands. The β-strands are connected by β-loops between strand PA and βB, βC and βD, and βE and βF, all of which are conserved in conformation in the two modules. There are three short α-helix segments connecting the β-strands. A unique feature of tissue factor is a 17-amino acid β-hairpin between strand β10 and strand β11, which is not a common element of the fibronectin superfamily. The N-terminal domain also contains a 12 amino acid loop between β6F and β7G that is not present in the C-terminal domain and is unique to tissue factor. Such a fibronectin type III domain structure is a feature of the immunoglobulin-like family of protein folds and is conserved among a wide variety of extracellular proteins.

The zymogen FVII is rapidly converted to FVIIa by limited proteolysis once it binds to tissue to form the active tissue factor-FVIIa complex. The FVIIa, which circulates as an enzyme at a concentration of approximately 0.1 nM (1% of plasma FVII), can also bind directly to tissue factor. The allosteric interaction between tissue factor and FVIIa on the tissue factor-FVIIa complex greatly increases the enzymatic activity of FVIIa: an approximate 20- to 100-fold increase in the rate of hydrolysis of small, chromogenic peptidyl substrates, and nearly a million-fold increase in the rate of activation of the natural macromolecular substrates FIX and FX. In concert with allosteric activation of the active site of FVIIa upon binding to tissue factor, the formation of tissue factor-FVIIa complex on phospholipid bilayer (i.e., upon exposure of phosphatidyl-L-serine on membrane surfaces) increases the rate of FIX or FX activation, in a $Ca^{2+}$-dependent manner, an additional 1,000-fold. The roughly million-fold overall increase in FX activation by tissue factor-FVIIa-phospholipid complex relative to free FVIIa is a critical regulatory point for the coagulation cascade.

FVII is a ~50 kDa, single-chain polypeptide consisting of 406 amino acid residues, with an N-terminal γ-carboxyglutamate-rich (GLA) domain, two epidermal growth factor-like domains (EGF1 and EFG2), and a C-terminal serine protease domain. FVII is activated to FVIIa by a specific proteolytic cleavage of the Ile-$^{154}$-Arg$^{152}$ bond in the short linker region between the EGF2 and the protease domain. This cleavage results in the light and heavy chains being held together by a single disulfide bond of Cys$^{135}$ and Cys$^{262}$. FVIIa binds phospholipid membrane in a $Ca^{2+}$-dependent manner through its N-terminal GLA-domain. Immediately C-terminal to the GLA domain is an aromatic stack and two EGF domains. The aromatic stack connects the GLA to EGF1 domain which binds a single $Ca^{2+}$ ion. Occupancy of this $Ca^{2+}$-binding site increases FVIIa amidolytic activity and tissue factor association. The catalytic triad consist of His$^{193}$, Asp$^{242}$, and Ser$^{344}$, and binding of a single $Ca^{2+}$ ion within the FVIIa protease domain is critical for its catalytic activity. Proteolytic activation of FVII to FVIIa frees the newly formed amino terminus at Ile$^{153}$ to fold back and be inserted into the activation pocket forming a salt bridge with the carboxylate of Asp$^{343}$ to generate the oxyanion hole. Formation of this salt bridge is critical for FVIIa activity. However, oxyanion hole formation does not occur in free FVIIa upon proteolytic activation. As a result, FVIIa circulates in a zymogen-like state that is poorly recognized by plasma protease inhibitors, allowing it to circulate with a half-life of approximately 90 minutes.

Tissue factor-mediated positioning of the FVIIa active site above the membrane surface is important for FVIIa towards cognate substrates. Free FVIIa adopts a stable, extended structure when bound to the membrane with its active site positioned ~80 Å above the membrane surface. Upon FVIIa binding to tissue factor, the FVa active site is repositioned ~6 Å closer to the membrane. This modulation may aid in a proper alignment of the FVIIa catalytic triad with the target substrate cleavage site. Using GLA-domainless FVIIa, it has been shown that the active site was still positioned a similar distance above the membrane, demonstrating that tissue factor is able to fully support FVIIa active site positioning even in the absence of FVIIa-membrane interaction. Additional data showed that tissue factor supported full FVIIa proteolytic activity as long as the tissue factor extracellular domain was tethered in some way to the membrane surface. However, raising the active site of FVIIa greater than 80 Å above the membrane surface greatly reduced the ability of the tissue factor-FVIIa complex to activate FX but did not diminish tissue factor-FVIIa amidolytic activity.

Alanine scanning mutagenesis has been used to assess the role of specific amino acid side chains in the tissue factor extracellular domain for interaction with FVIIa (Gibbs et al., *Biochemistry* 33(47): 14003-14010, 1994; Schullek et al., *J Biol Chem* 269(30): 19399-19403, 1994). Alanine substitution identified a limited number of residue positions at which alanine replacements cause 5- to 10-fold lower affinity for FVIIa binding. Most of these residue side chains were found to be well-exposed to solvent in the crystal structure, concordant with macromolecular ligand interaction. The FVIIa ligand-binding site is located over an extensive region at the boundary between the two modules. In the C-module, residues Arg$^{135}$ and Phe$^{140}$ located on the protruding B-C loop provide an independent contact with FVIIa. Leu$^{133}$ is located at the base of the fingerlike structure and packed into the cleft between the two modules. This provides continuity to a major cluster of important binding residues consisting of Lys$^{20}$, Thr$^{60}$, Asp$^{58}$, and Ile$^{22}$. Thr$^{60}$ is only partially solvent-exposed and may play a local structural role rather than making a significant contact with ligand. The binding site extends onto the concave side of the intermodule angle involving Glu$^{24}$ and Gln$^{110}$, and potentially the more distant residue Val$^{207}$. The binding region extends from Asp58 onto a convex surface area formed by Lys$^{48}$, Lys$^{46}$, Gln$^{37}$, Asp$^{44}$, and Trp$^{45}$. Trp$^{45}$ and Asp$^{44}$ do not interact independently with FVIIa, indicating that the mutational effect at the Trp$^{45}$ position may reflect a structural importance of this side chain for the local packing of the adjacent Asp$^{44}$ and Gln$^{37}$ side chain. The interactive area further includes two surface-exposed aromatic residues, Phe$^{76}$ and Tyr$^{78}$, which form part of the hydrophobic cluster in the N-module.

The known physiologic substrates of tissue factor-FVIIa are FVII, FIX, and FX and certain proteinase-activated receptors. Mutational analysis has identified a number of residues that, when mutated, support full FVIIa amidolytic activity towards small peptidyl substrates but are deficient in their ability to support macromolecular substrate (i.e., FVII, FIX, and FX) activation (Ruf et al., *J Biol Chem* 267(31): 22206-22210, 1992; Ruf et al., *J Biol Chem* 267(9): 6375-6381, 1992; Huang et al., *J Biol Chem* 271(36): 21752-21757, 1996; Kirchhofer et al., *Biochemistry* 39(25): 7380-7387, 2000). The tissue factor loop region at residues 159-165, and residues in or adjacent to this flexible loop have been shown to be critical for the proteolytic activity of the tissue factor-FVIIa complex. This defines the proposed substrate-binding exosite region of tissue factor that is quite distant from the FVIIa active site. A substitution of the glycine residue by a marginally bulkier residue alanine, significantly impairs tissue factor-FVIIa proteolytic activity. This suggests that the flexibility afforded by glycine is critical for the loop of residues 159-165 for tissue factor macromolecular substrate recognition.

The residues Lys$^{165}$ and Lys$^{166}$ have also been demonstrated to be important for substrate recognition and binding. Mutation of either of these residues to alanine results in a significant decrease in the tissue factor co-factor function. Lys$^{165}$ and Lys$^{166}$ face away from each other, with Lys$^{165}$ pointing towards FVIIa in most tissue factor-FVIIa structures, and Lys$^{166}$ pointing into the substrate binding exosite region in the crystal structure. Putative salt bridge formation between Lys$^{165}$ of and Gla$^{35}$ of FVIIa would support the notion that tissue factor interaction with the GLA domain of FVIIa modulates substrate recognition. These results suggest that the C-terminal portion of the tissue factor ectodomain directly interacts with the GLA-domain, the possible adjacent EGF1 domains, of FIX and FX, and that the presence of the FVIIa GLA-domain may modulate these interactions either directly or indirectly.

Soluble Tissue Factor Domain

In some embodiments of any of the polypeptides, compositions, or methods described herein, the soluble tissue factor domain can be a wildtype tissue factor polypeptide lacking the signal sequence, the transmembrane domain, and the intracellular domain. In some examples, the soluble tissue factor domain can be a tissue factor mutant, wherein a wildtype tissue factor polypeptide lacking the signal sequence, the transmembrane domain, and the intracellular domain, and has been further modified at selected amino acids. In some examples, the soluble tissue factor domain can be a soluble human tissue factor domain. In some examples, the soluble tissue factor domain can be a soluble mouse tissue factor domain. In some examples, the soluble tissue factor domain can be a soluble rat tissue factor domain. Non-limiting examples of soluble human tissue factor domains, a mouse soluble tissue factor domain, a rat soluble tissue factor domain, and mutant soluble tissue factor domains are shown below.

```
Exemplary Soluble Human Tissue Factor Domain
                                      (SEQ ID NO: 93)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE

Exemplary Nucleic Acid Encoding Soluble Human
Tissue Factor Domain
                                      (SEQ ID NO: 94)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT
```

-continued

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG

Exemplary Soluble Mouse Tissue Factor Domain (SEQ ID NO: 95)

agipekafnltwistdfktilewqpkptnytytvqisdrsrnwknkcfst tdtecdltdeivkdvtwayeakvlsvprrnsvhgdgdqlvihgeeppftn apkflpyrdtnlggpviqqfeqdgrklnvvvkdsltlvrkngtfltlrqv fgkdlgyiityrkgsstgkktnitntnefsidveegvsycffvqamifsr ktnqnspgsstvcteqwksflge Exemplary Soluble Rat Tissue Factor Domain (SEQ ID NO: 96)

Agtppgkafnltwistdfktilewqpkptnytytvqisdrsrnwkykctg ttdtecdltdeivkdvnwtyearvlsvpwrnsthgketlfgthgeeppft narkflpyrdtkigqpviqkyeqggtklkvtvkdsftlvrkngtfltlrq vfgndlgyiltyrkdsstgrktntthtneflidvekgvsycffaqavifs rktnhkspesitkcteqwksvlge Exemplary Mutant Soluble Human Tissue Factor Domain (SEQ ID NO: 97)

SGTTNTVAAYNLTWKSTNFATALEWEPKPVNQVYTVQISTKSGDWKSKCF

YTTDTECALTDEIVKDVKQTYLARVFSYPAGNVESTGSAGEPLYENSPEF

TPYLETNLGQPTIQSFEQVGTKVNVTVEDERTLVARNNTALSLRDVFGKD

LIYTLYYWKSSSSGKKTAKTNTNEFLIDVDKGENYCFSVQAVIPSRTVNR

KSTDSPVECMGQEKGEFRE

Exemplary Mutant Soluble Human Tissue Factor Domain (SEQ ID NO: 98)

SGTTNTVAAYNLTWKSTNFATALEWEPKPVNQVYTVQISTKSGDAKSKCF

YTTDTECALTDEIVKDVKQTYLARVFSYPAGNVESTGSAGEPLAENSPEF

TPYLETNLGQPTIQSFEQVGTKVNVTVEDERTLVARNNTALSLRDVFGKD

LIYTLYYWKSSSSGKKTAKTNTNEFLIDVDKGENYCFSVQAVIPSRTVNR

KSTDSPVECMGQEKGEFRE

In some embodiments, a soluble tissue factor domain can include a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 93, 95, 96, 97 or 98. In some embodiments, a soluble tissue factor domain can include a sequence of SEQ ID NO: 93, 95, 96, 97, or 98, with one to twenty amino acids (e.g., 2, 3, 4, 5, 6, 7, 8, 9, 10, 11, 12, 13, 14, 15, 16, 17, 18, 19, or 20) amino acids removed from its N-terminus and/or one to twenty amino acids (e.g., 2, 3, 4, 5, 6, 7, 8, 9, 10, 11, 12, 13, 14, 15, 16, 17, 18, 19, or 20) amino acids removed from its C-terminus.

As can be appreciated in the art, one skilled in the art would understand that mutation of amino acids that are conserved between different mammalian species is more likely to decrease the activity and/or structural stability of the protein, while mutation of amino acids that are not conserved between different mammalian species is less likely to decrease the activity and/or structural stability of the protein.

In some examples of any of the multi-chain chimeric polypeptides described herein, the soluble tissue factor domain is not capable of binding to Factor VIIa. In some examples of any of the multi-chain chimeric polypeptides described herein, the soluble tissue factor domain does not convert inactive Factor X into Factor Xa. In some embodiments of any of the multi-chain chimeric polypeptides described herein, the multi-chain chimeric polypeptide does not stimulate blood coagulation in a mammal.

In some examples, the soluble tissue factor domain can be a soluble human tissue factor domain. In some embodiments, the soluble tissue factor domain can be a soluble mouse tissue factor domain. In some embodiments, the soluble tissue factor domain can be a soluble rat tissue factor domain.

In some examples, the soluble tissue factor domain does not include one or more (e.g., two, three, four, five, six, or seven) of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the mutant soluble tissue factor possesses the amino acid sequence of SEQ ID NO: 97 or SEQ ID NO: 98.

In some examples, the soluble tissue factor domain can be encoded by a nucleic acid including a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 94.

In some embodiments, the soluble tissue factor domain can have a total length of about 20 amino acids to about 220 amino acids, about 20 amino acids to about 215 amino acids, about 20 amino acids to about 210 amino acids, about 20 amino acids to about 205 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 60 amino acids, about 20 amino acids to about 50 amino acids, about 20 amino acids to about 40 amino acids, about 20 amino acids to about 30 amino acids, about 30 amino acids to about 220 amino acids, about 30 amino acids to about 215 amino acids, about 30 amino acids to about 210 amino acids, about 30 amino acids to about 205 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 60 amino acids, about 30 amino acids to about 50 amino acids, about 30 amino acids to about 40 amino acids, about 40 amino acids to about 220 amino acids, about 40 amino acids to about 215 amino acids, about 40 amino acids to about 210 amino acids, about 40 amino acids to about 205 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 60 amino acids, about 40 amino acids to about 50 amino acids, about 50 amino acids to about 220 amino acids, about 50 amino acids to about 215 amino acids, about 50 amino acids to about 210 amino acids, about 50 amino acids to about 205 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 60 amino acids, about 60 amino acids to about 220 amino acids, about 60 amino acids to about 215 amino acids, about 60 amino acids to about 210 amino acids, about 60 amino acids to about 205 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 70 amino acids to about 220 amino acids, about 70 amino acids to about 215 amino acids, about 70 amino acids to about 210 amino acids, about 70 amino acids to about 205 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 80 amino acids to about 220 amino acids, about 80 amino acids to about 215 amino acids, about 80 amino acids to about 210 amino acids, about 80 amino acids to about 205 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 90 amino acids to about 220 amino acids, about 90 amino acids to about 215 amino acids, about 90 amino acids to about 210 amino acids, about 90 amino acids to about 205 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 100 amino acids to about 220 amino acids, about 100 amino acids to about 215 amino acids, about 100 amino acids to about 210 amino acids, about 100 amino acids to about 205 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 110 amino acids to about 220 amino acids, about 110 amino acids to about 215 amino acids, about 110 amino acids to about 210 amino acids, about 110 amino acids to about 205 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 220 amino acids, about 115 amino acids to about 215 amino acids, about 115 amino acids to about 210 amino acids, about 115 amino acids to about 205 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 220 amino acids, about 120 amino acids to about 215 amino acids, about 120 amino acids to about 210 amino acids, about 120 amino acids to about 205 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 220 amino acids, about 125 amino acids to about 215 amino acids, about 125 amino acids to about 210 amino acids, about 125 amino acids to about 205 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 220 amino acids, about 130 amino acids to about 215 amino acids, about 130 amino acids to about 210 amino acids, about 130 amino acids to about 205 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 220 amino acids, about 135 amino acids to about 215 amino acids, about 135 amino acids to about 210 amino acids, about 135 amino acids to about 205 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 220 amino acids, about 140 amino acids to about 215 amino acids, about 140 amino acids to about 210 amino acids, about 140 amino acids to about 205 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 220 amino acids, about 145 amino acids to about 215 amino acids, about 145 amino acids to about 210 amino acids, about 145 amino acids to about 205 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 220 amino acids, about 150 amino acids to about 215 amino acids, about 150 amino acids to about 210 amino acids, about 150 amino acids to about 205 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 220 amino acids, about 155 amino acids to about 215 amino acids, about 155 amino acids to about 210 amino acids, about 155 amino acids to about 205 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 220 amino acids, about 160 amino acids to about 215 amino acids, about 160 amino acids to about 210 amino acids, about 160 amino acids to about 205 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 220 amino acids, about 165 amino acids to about 215 amino acids, about 165 amino acids to about 210 amino acids, about 165 amino acids to about 205 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 220 amino acids, about 170 amino acids to about 215 amino acids, about 170 amino acids to about 210 amino acids, about 170 amino acids to about 205 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 220 amino acids, about 175 amino acids to about 215 amino acids, about 175 amino acids to about 210 amino acids, about 175 amino acids to about 205 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 220 amino acids, about 180 amino acids to about 215 amino acids, about 180 amino acids to about 210 amino acids, about 180 amino acids to about 205 amino acids, about 180 amino acids to about 200 amino acids, about 180 amino acids to about 195 amino acids, about 180 amino acids to about 190 amino acids, about 180 amino acids to about 185 amino acids, about 185 amino acids to about 220 amino acids, about 185 amino acids to about 215 amino acids, about 185 amino acids to about 210 amino acids, about 185 amino acids to about 205 amino acids, about 185 amino acids to about 200 amino acids, about 185 amino acids to about 195 amino acids, about 185 amino acids to about 190 amino acids, about 190 amino acids to about 220 amino acids, about 190 amino acids to about 215 amino acids, about 190 amino acids to about 210 amino acids, about 190 amino acids to about 205 amino acids, about 190 amino acids to about 200 amino acids, about 190 amino acids to about 195 amino acids, about 195 amino acids to about 220 amino acids, about 195 amino acids to about 215 amino acids, about 195 amino acids to about 210 amino acids, about 195 amino acids to about 205 amino acids, about 195 amino acids to about 200 amino acids, about 200 amino acids to about 220 amino acids, about 200 amino acids to about 215 amino acids, about 200 amino acids to about 210 amino acids, about 200 amino acids to about 205 amino acids, about 205 amino acids to about 220 amino acids, about 205 amino acids to about 215 amino acids, about 205 amino acids to about 210 amino acids, about 210 amino acids to about 220 amino acids, about 210 amino acids to about 215 amino acids, or about 215 amino acids to about 220 amino acids.

Linker Sequences

In some embodiments, the linker sequence can be a flexible linker sequence. Non-limiting examples of linker sequences that can be used are described in Klein et al., *Protein Engineering, Design & Selection* 27(10):325-330, 2014; Priyanka et al., *Protein Sci.* 22(2):153-167, 2013. In some examples, the linker sequence is a synthetic linker sequence.

In some embodiments of any of the single-chain chimeric polypeptides described herein can include one, two, three, four, five, six, seven, eight, nine, or ten linker sequence(s) (e.g., the same or different linker sequences, e.g., any of the exemplary linker sequences described herein or known in the art). In some embodiments of any of the single-chain chimeric polypeptides described herein can include one, two, three, four, five, six, seven, eight, nine, or ten linker sequence(s) (e.g., the same or different linker sequences, e.g., any of the exemplary linker sequences described herein or known in the art).

In some embodiments of any of the multi-chain chimeric polypeptides described herein, the first chimeric polypeptide can include one, two, three, four, five, six, seven, eight, nine, or ten linker sequence(s) (e.g., the same or different linker sequences, e.g., any of the exemplary linker sequences described herein or known in the art). In some embodiments of any of the multi-chain chimeric polypeptides described herein, the second chimeric polypeptide can include one, two, three, four, five, six, seven, eight, nine, or ten linker sequence(s) (e.g., the same or different linker sequences, e.g., any of the exemplary linker sequences described herein or known in the art).

In some embodiments, a linker sequence can have a total length of 1 amino acid to about 100 amino acids, 1 amino acid to about 90 amino acids, 1 amino acid to about 80 amino acids, 1 amino acid to about 70 amino acids, 1 amino acid to about 60 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about 25 amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, about 2 amino acids to about 100 amino acids, about 2 amino acids to about 90 amino acids, about 2 amino acids to about 80 amino acids, about 2 amino acids to about 70 amino acids, about 2 amino acids to about 60 amino acids, about 2 amino acids to about 50 amino acids, about 2 amino acids to about 45 amino acids, about 2 amino acids to about 40 amino acids, about 2 amino acids to about 35 amino acids, about 2 amino acids to about 30 amino acids, about 2 amino acids to about 25 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 100 amino acids, about 4 amino acids to about 90 amino acids, about 4 amino acids to about 80 amino acids, about 4 amino acids to about 70 amino acids, about 4 amino acids to about 60 amino acids, about 4 amino acids to about 50 amino acids, about 4 amino acids to about 45 amino acids, about 4 amino acids to about 40 amino acids, about 4 amino acids to about 35 amino acids, about 4 amino acids to about 30 amino acids, about 4 amino acids to about 25 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about amino acids, about 4 amino acids to about 8 amino acids, about 4 amino acids to about 6 amino acids, about 6 amino acids to about 100 amino acids, about 6 amino acids to about 90 amino acids, about 6 amino acids to about 80 amino acids, about 6 amino acids to about 70 amino acids, about 6 amino acids to about 60 amino acids, about 6 amino acids to about 50 amino acids, about 6 amino acids to about 45 amino acids, about 6 amino acids to about 40 amino acids, about 6 amino acids to about 35 amino acids, about 6 amino acids to about 30 amino acids, about 6 amino acids to about 25 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 100 amino acids, about 8 amino acids to about 90 amino acids, about 8 amino acids to about 80 amino acids, about 8 amino acids to about 70 amino acids, about 8 amino acids to about 60 amino acids, about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 100 amino acids, about 10 amino acids to about 90 amino acids, about 10 amino acids to about 80 amino acids, about 10 amino acids to about 70 amino acids, about 10 amino acids to about 60 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 100 amino acids, about 12 amino acids to about 90 amino acids, about 12 amino acids to about 80 amino acids, about 12 amino acids to about 70 amino acids, about 12 amino acids to about 60 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 100 amino acids, about 14 amino acids to about 90 amino acids, about 14 amino acids to about 80 amino acids, about 14 amino acids to about 70 amino acids, about 14 amino acids to about 60 amino acids, about 14 amino acids to about 50 amino acids, about 14 amino acids to about 45 amino acids, about 14 amino acids to about 40 amino acids, about 14 amino acids to about 35 amino acids, about 14 amino acids to about 30 amino acids, about 14 amino acids to about 25 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 100 amino acids, about 16 amino acids to about 90 amino acids, about 16 amino acids to about 80 amino acids, about 16 amino acids to about 70 amino acids, about 16 amino acids to about 60 amino acids, about 16 amino acids to about 50 amino acids, about 16 amino acids to about 45 amino acids, about 16 amino acids to about 40 amino acids, about 16 amino acids to about 35 amino acids, about 16 amino acids to about 30 amino acids, about 16 amino acids to about 25 amino acids, about 16 amino acids to about 24 amino acids, about 16 amino acids to about 22 amino acids, about 16 amino acids to about 20 amino acids, about 16 amino acids to about 18 amino acids, about 18 amino acids to about 100 amino acids, about 18 amino acids to about 90 amino acids, about 18 amino acids to about 80 amino acids, about 18 amino acids to about 70 amino acids, about 18 amino acids to about 60 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 24 amino acids, about 18 amino acids to about 22 amino acids, about 18 amino acids to about 20 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 24 amino acids, about 20 amino acids to about 22 amino acids, about 22 amino acids to about 100 amino acids, about 22 amino acids to about 90 amino acids, about 22 amino acids to about 80 amino acids, about 22 amino acids to about 70 amino acids, about 22 amino acids to about 60 amino acids, about 22 amino acids to about 50 amino acids, about 22 amino acids to about 45 amino acids, about 22 amino acids to about 40 amino acids, about 22 amino acids to about 35 amino acids, about 22 amino acids to about 30 amino acids, about 22 amino acids to about 25 amino acids, about 22 amino acids to about 24 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 100 amino acids, about 60 amino acids to about 90 amino acids, about 60 amino acids to about 80 amino acids, about 60 amino acids to about 70 amino acids, about 70 amino acids to about 100 amino acids, about 70 amino acids to about 90 amino acids, about 70 amino acids to about 80 amino acids, about 80 amino acids to about 100 amino acids, about 80 amino acids to about 90 amino acids, or about 90 amino acids to about 100 amino acids.

In some embodiments, the linker is rich in glycine (Gly or G) residues. In some embodiments, the linker is rich in serine (Ser or S) residues. In some embodiments, the linker is rich in glycine and serine residues. In some embodiments, the linker has one or more glycine-serine residue pairs (GS), e.g., 1, 2, 3, 4, 5, 6, 7, 8, 9, or 10 or more GS pairs. In some embodiments, the linker has one or more Gly-Gly-Gly-Ser (GGGS) (SEQ ID NO: 99) sequences, e.g., 1, 2, 3, 4, 5, 6, 7, 8, 9, or 10 or more GGGS (SEQ ID NO: 99) sequences.

In some embodiments, the linker has one or more Gly-Gly-Gly-Gly-Ser (GGGGS) sequences, e.g., 1, 2, 3, 4, 5, 6, 7, 8, 9, or 10 or more GGGGS (SEQ ID NO: 100) sequences. In some embodiments, the linker has one or more Gly-Gly-Ser-Gly (GGSG) (SEQ ID NO: 101) sequences, e.g., 1, 2, 3, 4, 5, 6, 7, 8, 9, or 10 or more GGSG (SEQ ID NO: 101) sequences.

In some embodiments, the linker sequence can comprise or consist of GGGGSGGGGSGGGGS (SEQ ID NO: 102). In some embodiments, the linker sequence can be encoded by a nucleic acid comprising or consisting of: GGCGGTG-GAGGATCCGGAGGAGGTGGCTCCGGCGGCGGAG-GATCT (SEQ ID NO: 103). In some embodiments, the linker sequence can comprise or consist of: GGGSGGGS (SEQ ID NO: 104), Target-Binding Domains In some embodiments of any of the multi-chain chimeric polypeptides described herein, the first target-binding domain, the second target-binding domain, and/or the additional one or more target-binding domains can be an antigen-binding domain (e.g., any of the exemplary antigen-binding domains described herein or known in the art), a soluble interleukin or cytokine protein (e.g., any of the exemplary soluble interleukin proteins or soluble cytokine proteins described herein), and a soluble interleukin or cytokine receptor (e.g., any of the exemplary soluble interleukin receptors or soluble cytokine receptors described herein).

In some embodiments of any of the multi-chain chimeric polypeptides described herein, the first target-binding domain, the second target-binding domain, and/or the one or more additional target-binding domains can each independent have a total number of amino acids of about 5 amino acids to about 1000 amino acids, about 5 amino acids to about 950 amino acids, about 5 amino acids to about 900 amino acids, about 5 amino acids to about 850 amino acids, about 5 amino acids to about 800 amino acids, about 5 amino acids to about 750 amino acids, about 5 amino acids to about 700 amino acids, about 5 amino acids to about 650 amino acids, about 5 amino acids to about 600 amino acids, about 5 amino acids to about 550 amino acids, about 5 amino acids to about 500 amino acids, about 5 amino acids to about 450 amino acids, about 5 amino acids to about 400 amino acids, about 5 amino acids to about 350 amino acids, about 5 amino acids to about 300 amino acids, about 5 amino acids to about 280 amino acids, about 5 amino acids to about 260 amino acids, about 5 amino acids to about 240 amino acids, about 5 amino acids to about 220 amino acids, about 5 amino acids to about 200 amino acids, about 5 amino acids to about 195 amino acids, about 5 amino acids to about 190 amino acids, about 5 amino acids to about 185 amino acids, about 5 amino acids to about 180 amino acids, about 5 amino acids to about 175 amino acids, about 5 amino acids to about 170 amino acids, about 5 amino acids to about 165 amino acids, about 5 amino acids to about 160 amino acids, about 5 amino acids to about 155 amino acids, about 5 amino acids to about 150 amino acids, about 5 amino acids to about 145 amino acids, about 5 amino acids to about 140 amino acids, about 5 amino acids to about 135 amino acids, about 5 amino acids to about 130 amino acids, about 5 amino acids to about 125 amino acids, about 5 amino acids to about 120 amino acids, about 5 amino acids to about 115 amino acids, about 5 amino acids to about 110 amino acids, about 5 amino acids to about 105 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about 5 amino acids to about 70 amino acids, about 5 amino acids to about 65 amino acids, about 5 amino acids to about 60 amino acids, about amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about amino acids, about 5 amino acids to about 15 amino acids, about 5 amino acids to about 10 amino acids, about 10 amino acids to about 1000 amino acids, about 10 amino acids to about 950 amino acids, about 10 amino acids to about 900 amino acids, about 10 amino acids to about 850 amino acids, about 10 amino acids to about 800 amino acids, about 10 amino acids to about 750 amino acids, about 10 amino acids to about 700 amino acids, about 10 amino acids to about 650 amino acids, about 10 amino acids to about 600 amino acids, about 10 amino acids to about 550 amino acids, about 10 amino acids to about 500 amino acids, about 10 amino acids to about 450 amino acids, about 10 amino acids to about 400 amino acids, about 10 amino acids to about 350 amino acids, about 10 amino acids to about 300 amino acids, about 10 amino acids to about 280 amino acids, about 10 amino acids to about 260 amino acids, about 10 amino acids to about 240 amino acids, about 10 amino acids to about 220 amino acids, about 10 amino acids to about 200 amino acids, about 10 amino acids to about 195 amino acids, about 10 amino acids to about 190 amino acids, about 10 amino acids to about 185 amino acids, about 10 amino acids to about 180 amino acids, about 10 amino acids to about 175 amino acids, about 10 amino acids to about 170 amino acids, about 10 amino acids to about 165 amino acids, about 10 amino acids to about 160 amino acids, about 10 amino acids to about 155 amino acids, about 10 amino acids to about 150 amino acids, about 10 amino acids to about 145 amino acids, about 10 amino acids to about 140 amino acids, about 10 amino acids to about 135 amino acids, about 10 amino acids to about 130 amino acids, about 10 amino acids to about 125 amino acids, about 10 amino acids to about 120 amino acids, about 10 amino acids to about 115 amino acids, about 10 amino acids to about 110 amino acids, about 10 amino acids to about 105 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 15 amino acids to about 1000 amino acids, about 15 amino acids to about 950 amino acids, about 15 amino acids to about 900 amino acids, about 15 amino acids to about 850 amino acids, about 15 amino acids to about 800 amino acids, about 15 amino acids to about 750 amino acids, about 15 amino acids to about 700 amino acids, about 15 amino acids to about 650 amino acids, about 15 amino acids to about 600 amino acids, about 15 amino acids to about 550 amino acids, about 15 amino acids to about 500 amino acids, about 15 amino acids to about 450 amino acids, about 15 amino acids to about 400 amino acids, about 15 amino acids to about 350 amino acids, about 15 amino acids to about 300 amino acids, about 15 amino acids to about 280 amino acids, about 15 amino acids to about 260 amino acids, about 15 amino acids to about 240 amino acids, about 15 amino acids to about 220 amino acids, about 15 amino acids to about 200 amino acids, about 15 amino acids to about 195 amino acids, about 15 amino acids to about 190 amino acids, about 15 amino acids to about 185 amino acids, about 15 amino acids to about 180 amino acids, about 15 amino acids to about 175 amino acids, about 15 amino acids to about 170 amino acids, about 15 amino acids to about 165 amino acids, about 15 amino acids to about 160 amino acids, about 15 amino acids to about 155 amino acids, about 15 amino acids to about 150 amino acids, about 15 amino acids to about 145 amino acids, about 15 amino acids to about 140 amino acids, about 15 amino acids to about 135 amino acids, about 15 amino acids to about 130 amino acids, about 15 amino acids to about 125 amino acids, about 15 amino acids to about 120 amino acids, about 15 amino acids to about 115 amino acids, about 15 amino acids to about 110 amino acids, about 15 amino acids to about 105 amino acids, about 15 amino acids to about 100 amino acids, about 15 amino acids to about 95 amino acids, about 15 amino acids to about 90 amino acids, about 15 amino acids to about 85 amino acids, about 15 amino acids to about 80 amino acids, about 15 amino acids to about 75 amino acids, about 15 amino acids to about 70 amino acids, about 15 amino acids to about 65 amino acids, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 1000 amino acids, about 20 amino acids to about 950 amino acids, about 20 amino acids to about 900 amino acids, about 20 amino acids to about 850 amino acids, about 20 amino acids to about 800 amino acids, about 20 amino acids to about 750 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 280 amino acids, about 20 amino acids to about 260 amino acids, about 20 amino acids to about 240 amino acids, about 20 amino acids to about 220 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 1000 amino acids, about 25 amino acids to about 950 amino acids, about 25 amino acids to about 900 amino acids, about 25 amino acids to about 850 amino acids, about 25 amino acids to about 800 amino acids, about 25 amino acids to about 750 amino acids, about 25 amino acids to about 700 amino acids, about 25 amino acids to about 650 amino acids, about 25 amino acids to about 600 amino acids, about 25 amino acids to about 550 amino acids, about 25 amino acids to about 500 amino acids, about 25 amino acids to about 450 amino acids, about 25 amino acids to about 400 amino acids, about 25 amino acids to about 350 amino acids, about 25 amino acids to about 300 amino acids, about 25 amino acids to about 280 amino acids, about 25 amino acids to about 260 amino acids, about 25 amino acids to about 240 amino acids, about 25 amino acids to about 220 amino acids, about 25 amino acids to about 200 amino acids, about 25 amino acids to about 195 amino acids, about 25 amino acids to about 190 amino acids, about 25 amino acids to about 185 amino acids, about 25 amino acids to about 180 amino acids, about 25 amino acids to about 175 amino acids, about 25 amino acids to about 170 amino acids, about 25 amino acids to about 165 amino acids, about 25 amino acids to about 160 amino acids, about 25 amino acids to about 155 amino acids, about 25 amino acids to about 150 amino acids, about 25 amino acids to about 145 amino acids, about 25 amino acids to about 140 amino acids, about 25 amino acids to about 135 amino acids, about 25 amino acids to about 130 amino acids, about 25 amino acids to about 125 amino acids, about 25 amino acids to about 120 amino acids, about 25 amino acids to about 115 amino acids, about 25 amino acids to about 110 amino acids, about 25 amino acids to about 105 amino acids, about 25 amino acids to about 100 amino acids, about 25 amino acids to about 95 amino acids, about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 280 amino acids, about 30 amino acids to about 260 amino acids, about 30 amino acids to about 240 amino acids, about 30 amino acids to about 220 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 1000 amino acids, about 35 amino acids to about 950 amino acids, about 35 amino acids to about 900 amino acids, about 35 amino acids to about 850 amino acids, about 35 amino acids to about 800 amino acids, about 35 amino acids to about 750 amino acids, about 35 amino acids to about 700 amino acids, about 35 amino acids to about 650 amino acids, about 35 amino acids to about 600 amino acids, about 35 amino acids to about 550 amino acids, about 35 amino acids to about 500 amino acids, about 35 amino acids to about 450 amino acids, about 35 amino acids to about 400 amino acids, about 35 amino acids to about 350 amino acids, about 35 amino acids to about 300 amino acids, about 35 amino acids to about 280 amino acids, about 35 amino acids to about 260 amino acids, about 35 amino acids to about 240 amino acids, about 35 amino acids to about 220 amino acids, about 35 amino acids to about 200 amino acids, about 35 amino acids to about 195 amino acids, about 35 amino acids to about 190 amino acids, about 35 amino acids to about 185 amino acids, about 35 amino acids to about 180 amino acids, about 35 amino acids to about 175 amino acids, about 35 amino acids to about 170 amino acids, about 35 amino acids to about 165 amino acids, about 35 amino acids to about 160 amino acids, about 35 amino acids to about 155 amino acids, about 35 amino acids to about 150 amino acids, about 35 amino acids to about 145 amino acids, about 35 amino acids to about 140 amino acids, about 35 amino acids to about 135 amino acids, about 35 amino acids to about 130 amino acids, about 35 amino acids to about 125 amino acids, about 35 amino acids to about 120 amino acids, about 35 amino acids to about 115 amino acids, about 35 amino acids to about 110 amino acids, about 35 amino acids to about 105 amino acids, about 35 amino acids to about 100 amino acids, about 35 amino acids to about 95 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 1000 amino acids, about 40 amino acids to about 950 amino acids, about 40 amino acids to about 900 amino acids, about 40 amino acids to about 850 amino acids, about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 280 amino acids, about 40 amino acids to about 260 amino acids, about 40 amino acids to about 240 amino acids, about 40 amino acids to about 220 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 1000 amino acids, about 45 amino acids to about 950 amino acids, about 45 amino acids to about 900 amino acids, about 45 amino acids to about 850 amino acids, about 45 amino acids to about 800 amino acids, about 45 amino acids to about 750 amino acids, about 45 amino acids to about 700 amino acids, about 45 amino acids to about 650 amino acids, about 45 amino acids to about 600 amino acids, about 45 amino acids to about 550 amino acids, about 45 amino acids to about 500 amino acids, about 45 amino acids to about 450 amino acids, about 45 amino acids to about 400 amino acids, about 45 amino acids to about 350 amino acids, about 45 amino acids to about 300 amino acids, about 45 amino acids to about 280 amino acids, about 45 amino acids to about 260 amino acids, about 45 amino acids to about 240 amino acids, about 45 amino acids to about 220 amino acids, about 45 amino acids to about 200 amino acids, about 45 amino acids to about 195 amino acids, about 45 amino acids to about 190 amino acids, about 45 amino acids to about 185 amino acids, about 45 amino acids to about 180 amino acids, about 45 amino acids to about 175 amino acids, about 45 amino acids to about 170 amino acids, about 45 amino acids to about 165 amino acids, about 45 amino acids to about 160 amino acids, about 45 amino acids to about 155 amino acids, about 45 amino acids to about 150 amino acids, about 45 amino acids to about 145 amino acids, about 45 amino acids to about 140 amino acids, about 45 amino acids to about 135 amino acids, about 45 amino acids to about 130 amino acids, about 45 amino acids to about 125 amino acids, about 45 amino acids to about 120 amino acids, about 45 amino acids to about 115 amino acids, about 45 amino acids to about 110 amino acids, about 45 amino acids to about 105 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 1000 amino acids, about 55 amino acids to about 950 amino acids, about 55 amino acids to about 900 amino acids, about 55 amino acids to about 850 amino acids, about 55 amino acids to about 800 amino acids, about 55 amino acids to about 750 amino acids, about 55 amino acids to about 700 amino acids, about 55 amino acids to about 650 amino acids, about 55 amino acids to about 600 amino acids, about 55 amino acids to about 550 amino acids, about 55 amino acids to about 500 amino acids, about 55 amino acids to about 450 amino acids, about 55 amino acids to about 400 amino acids, about 55 amino acids to about 350 amino acids, about 55 amino acids to about 300 amino acids, about 55 amino acids to about 280 amino acids, about 55 amino acids to about 260 amino acids, about 55 amino acids to about 240 amino acids, about 55 amino acids to about 220 amino acids, about 55 amino acids to about 200 amino acids, about 55 amino acids to about 195 amino acids, about 55 amino acids to about 190 amino acids, about 55 amino acids to about 185 amino acids, about 55 amino acids to about 180 amino acids, about 55 amino acids to about 175 amino acids, about 55 amino acids to about 170 amino acids, about 55 amino acids to about 165 amino acids, about 55 amino acids to about 160 amino acids, about 55 amino acids to about 155 amino acids, about 55 amino acids to about 150 amino acids, about 55 amino acids to about 145 amino acids, about 55 amino acids to about 140 amino acids, about 55 amino acids to about 135 amino acids, about 55 amino acids to about 130 amino acids, about 55 amino acids to about 125 amino acids, about 55 amino acids to about 120 amino acids, about 55 amino acids to about 115 amino acids, about 55 amino acids to about 110 amino acids, about 55 amino acids to about 105 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 1000 amino acids, about 60 amino acids to about 950 amino acids, about 60 amino acids to about 900 amino acids, about 60 amino acids to about 850 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 280 amino acids, about 60 amino acids to about 260 amino acids, about 60 amino acids to about 240 amino acids, about 60 amino acids to about 220 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 1000 amino acids, about 65 amino acids to about 950 amino acids, about 65 amino acids to about 900 amino acids, about 65 amino acids to about 850 amino acids, about 65 amino acids to about 800 amino acids, about 65 amino acids to about 750 amino acids, about 65 amino acids to about 700 amino acids, about 65 amino acids to about 650 amino acids, about 65 amino acids to about 600 amino acids, about 65 amino acids to about 550 amino acids, about 65 amino acids to about 500 amino acids, about 65 amino acids to about 450 amino acids, about 65 amino acids to about 400 amino acids, about 65 amino acids to about 350 amino acids, about 65 amino acids to about 300 amino acids, about 65 amino acids to about 280 amino acids, about 65 amino acids to about 260 amino acids, about 65 amino acids to about 240 amino acids, about 65 amino acids to about 220 amino acids, about 65 amino acids to about 200 amino acids, about 65 amino acids to about 195 amino acids, about 65 amino acids to about 190 amino acids, about 65 amino acids to about 185 amino acids, about 65 amino acids to about 180 amino acids, about 65 amino acids to about 175 amino acids, about 65 amino acids to about 170 amino acids, about 65 amino acids to about 165 amino acids, about 65 amino acids to about 160 amino acids, about 65 amino acids to about 155 amino acids, about 65 amino acids to about 150 amino acids, about 65 amino acids to about 145 amino acids, about 65 amino acids to about 140 amino acids, about 65 amino acids to about 135 amino acids, about 65 amino acids to about 130 amino acids, about 65 amino acids to about 125 amino acids, about 65 amino acids to about 120 amino acids, about 65 amino acids to about 115 amino acids, about 65 amino acids to about 110 amino acids, about 65 amino acids to about 105 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 1000 amino acids, about 70 amino acids to about 950 amino acids, about 70 amino acids to about 900 amino acids, about 70 amino acids to about 850 amino acids, about 70 amino acids to about 800 amino acids, about 70 amino acids to about 750 amino acids, about 70 amino acids to about 700 amino acids, about 70 amino acids to about 650 amino acids, about 70 amino acids to about 600 amino acids, about 70 amino acids to about 550 amino acids, about 70 amino acids to about 500 amino acids, about 70 amino acids to about 450 amino acids, about 70 amino acids to about 400 amino acids, about 70 amino acids to about 350 amino acids, about 70 amino acids to about 300 amino acids, about 70 amino acids to about 280 amino acids, about 70 amino acids to about 260 amino acids, about 70 amino acids to about 240 amino acids, about 70 amino acids to about 220 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 1000 amino acids, about 75 amino acids to about 950 amino acids, about 75 amino acids to about 900 amino acids, about 75 amino acids to about 850 amino acids, about 75 amino acids to about 800 amino acids, about 75 amino acids to about 750 amino acids, about 75 amino acids to about 700 amino acids, about 75 amino acids to about 650 amino acids, about 75 amino acids to about 600 amino acids, about 75 amino acids to about 550 amino acids, about 75 amino acids to about 500 amino acids, about 75 amino acids to about 450 amino acids, about 75 amino acids to about 400 amino acids, about 75 amino acids to about 350 amino acids, about 75 amino acids to about 300 amino acids, about 75 amino acids to about 280 amino acids, about 75 amino acids to about 260 amino acids, about 75 amino acids to about 240 amino acids, about 75 amino acids to about 220 amino acids, about 75 amino acids to about 200 amino acids, about 75 amino acids to about 195 amino acids, about 75 amino acids to about 190 amino acids, about 75 amino acids to about 185 amino acids, about 75 amino acids to about 180 amino acids, about 75 amino acids to about 175 amino acids, about 75 amino acids to about 170 amino acids, about 75 amino acids to about 165 amino acids, about 75 amino acids to about 160 amino acids, about 75 amino acids to about 155 amino acids, about 75 amino acids to about 150 amino acids, about 75 amino acids to about 145 amino acids, about 75 amino acids to about 140 amino acids, about 75 amino acids to about 135 amino acids, about 75 amino acids to about 130 amino acids, about 75 amino acids to about 125 amino acids, about 75 amino acids to about 120 amino acids, about 75 amino acids to about 115 amino acids, about 75 amino acids to about 110 amino acids, about 75 amino acids to about 105 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 1000 amino acids, about 80 amino acids to about 950 amino acids, about 80 amino acids to about 900 amino acids, about 80 amino acids to about 850 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 280 amino acids, about 80 amino acids to about 260 amino acids, about 80 amino acids to about 240 amino acids, about 80 amino acids to about 220 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 80 amino acids to about 85 amino acids, about 85 amino acids to about 1000 amino acids, about 85 amino acids to about 950 amino acids, about 85 amino acids to about 900 amino acids, about 85 amino acids to about 850 amino acids, about 85 amino acids to about 800 amino acids, about 85 amino acids to about 750 amino acids, about 85 amino acids to about 700 amino acids, about 85 amino acids to about 650 amino acids, about 85 amino acids to about 600 amino acids, about 85 amino acids to about 550 amino acids, about 85 amino acids to about 500 amino acids, about 85 amino acids to about 450 amino acids, about 85 amino acids to about 400 amino acids, about 85 amino acids to about 350 amino acids, about 85 amino acids to about 300 amino acids, about 85 amino acids to about 280 amino acids, about 85 amino acids to about 260 amino acids, about 85 amino acids to about 240 amino acids, about 85 amino acids to about 220 amino acids, about 85 amino acids to about 200 amino acids, about 85 amino acids to about 195 amino acids, about 85 amino acids to about 190 amino acids, about 85 amino acids to about 185 amino acids, about 85 amino acids to about 180 amino acids, about 85 amino acids to about 175 amino acids, about 85 amino acids to about 170 amino acids, about 85 amino acids to about 165 amino acids, about 85 amino acids to about 160 amino acids, about 85 amino acids to about 155 amino acids, about 85 amino acids to about 150 amino acids, about 85 amino acids to about 145 amino acids, about 85 amino acids to about 140 amino acids, about 85 amino acids to about 135 amino acids, about 85 amino acids to about 130 amino acids, about 85 amino acids to about 125 amino acids, about 85 amino acids to about 120 amino acids, about 85 amino acids to about 115 amino acids, about 85 amino acids to about 110 amino acids, about 85 amino acids to about 105 amino acids, about 85 amino acids to about 100 amino acids, about 85 amino acids to about 95 amino acids, about 85 amino acids to about 90 amino acids, about 90 amino acids to about 1000 amino acids, about 90 amino acids to about 950 amino acids, about 90 amino acids to about 900 amino acids, about 90 amino acids to about 850 amino acids, about 90 amino acids to about 800 amino acids, about 90 amino acids to about 750 amino acids, about 90 amino acids to about 700 amino acids, about 90 amino acids to about 650 amino acids, about 90 amino acids to about 600 amino acids, about 90 amino acids to about 550 amino acids, about 90 amino acids to about 500 amino acids, about 90 amino acids to about 450 amino acids, about 90 amino acids to about 400 amino acids, about 90 amino acids to about 350 amino acids, about 90 amino acids to about 300 amino acids, about 90 amino acids to about 280 amino acids, about 90 amino acids to about 260 amino acids, about 90 amino acids to about 240 amino acids, about 90 amino acids to about 220 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 90 amino acids to about 95 amino acids, about 95 amino acids to about 1000 amino acids, about 95 amino acids to about 950 amino acids, about 95 amino acids to about 900 amino acids, about 95 amino acids to about 850 amino acids, about 95 amino acids to about 800 amino acids, about 95 amino acids to about 750 amino acids, about 95 amino acids to about 700 amino acids, about 95 amino acids to about 650 amino acids, about 95 amino acids to about 600 amino acids, about 95 amino acids to about 550 amino acids, about 95 amino acids to about 500 amino acids, about 95 amino acids to about 450 amino acids, about 95 amino acids to about 400 amino acids, about 95 amino acids to about 350 amino acids, about 95 amino acids to about 300 amino acids, about 95 amino acids to about 280 amino acids, about 95 amino acids to about 260 amino acids, about 95 amino acids to about 240 amino acids, about 95 amino acids to about 220 amino acids, about 95 amino acids to about 200 amino acids, about 95 amino acids to about 195 amino acids, about 95 amino acids to about 190 amino acids, about 95 amino acids to about 185 amino acids, about 95 amino acids to about 180 amino acids, about 95 amino acids to about 175 amino acids, about 95 amino acids to about 170 amino acids, about 95 amino acids to about 165 amino acids, about 95 amino acids to about 160 amino acids, about 95 amino acids to about 155 amino acids, about 95 amino acids to about 150 amino acids, about 95 amino acids to about 145 amino acids, about 95 amino acids to about 140 amino acids, about 95 amino acids to about 135 amino acids, about 95 amino acids to about 130 amino acids, about 95 amino acids to about 125 amino acids, about 95 amino acids to about 120 amino acids, about 95 amino acids to about 115 amino acids, about 95 amino acids to about 110 amino acids, about 95 amino acids to about 105 amino acids, about 95 amino acids to about 100 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 100 amino acids to about 105 amino acids, about 105 amino acids to about 1000 amino acids, about 105 amino acids to about 950 amino acids, about 105 amino acids to about 900 amino acids, about 105 amino acids to about 850 amino acids, about 105 amino acids to about 800 amino acids, about 105 amino acids to about 750 amino acids, about 105 amino acids to about 700 amino acids, about 105 amino acids to about 650 amino acids, about 105 amino acids to about 600 amino acids, about 105 amino acids to about 550 amino acids, about 105 amino acids to about 500 amino acids, about 105 amino acids to about 450 amino acids, about 105 amino acids to about 400 amino acids, about 105 amino acids to about 350 amino acids, about 105 amino acids to about 300 amino acids, about 105 amino acids to about 280 amino acids, about 105 amino acids to about 260 amino acids, about 105 amino acids to about 240 amino acids, about 105 amino acids to about 220 amino acids, about 105 amino acids to about 200 amino acids, about 105 amino acids to about 195 amino acids, about 105 amino acids to about 190 amino acids, about 105 amino acids to about 185 amino acids, about 105 amino acids to about 180 amino acids, about 105 amino acids to about 175 amino acids, about 105 amino acids to about 170 amino acids, about 105 amino acids to about 165 amino acids, about 105 amino acids to about 160 amino acids, about 105 amino acids to about 155 amino acids, about 105 amino acids to about 150 amino acids, about 105 amino acids to about 145 amino acids, about 105 amino acids to about 140 amino acids, about 105 amino acids to about 135 amino acids, about 105 amino acids to about 130 amino acids, about 105 amino acids to about 125 amino acids, about 105 amino acids to about 120 amino acids, about 105 amino acids to about 115 amino acids, about 105 amino acids to about 110 amino acids, about 110 amino acids to about 1000 amino acids, about 110 amino acids to about 950 amino acids, about 110 amino acids to about 900 amino acids, about 110 amino acids to about 850 amino acids, about 110 amino acids to about 800 amino acids, about 110 amino acids to about 750 amino acids, about 110 amino acids to about 700 amino acids, about 110 amino acids to about 650 amino acids, about 110 amino acids to about 600 amino acids, about 110 amino acids to about 550 amino acids, about 110 amino acids to about 500 amino acids, about 110 amino acids to about 450 amino acids, about 110 amino acids to about 400 amino acids, about 110 amino acids to about 350 amino acids, about 110 amino acids to about 300 amino acids, about 110 amino acids to about 280 amino acids, about 110 amino acids to about 260 amino acids, about 110 amino acids to about 240 amino acids, about 110 amino acids to about 220 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 1000 amino acids, about 115 amino acids to about 950 amino acids, about 115 amino acids to about 900 amino acids, about 115 amino acids to about 850 amino acids, about 115 amino acids to about 800 amino acids, about 115 amino acids to about 750 amino acids, about 115 amino acids to about 700 amino acids, about 115 amino acids to about 650 amino acids, about 115 amino acids to about 600 amino acids, about 115 amino acids to about 550 amino acids, about 115 amino acids to about 500 amino acids, about 115 amino acids to about 450 amino acids, about 115 amino acids to about 400 amino acids, about 115 amino acids to about 350 amino acids, about 115 amino acids to about 300 amino acids, about 115 amino acids to about 280 amino acids, about 115 amino acids to about 260 amino acids, about 115 amino acids to about 240 amino acids, about 115 amino acids to about 220 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 1000 amino acids, about 120 amino acids to about 950 amino acids, about 120 amino acids to about 900 amino acids, about 120 amino acids to about 850 amino acids, about 120 amino acids to about 800 amino acids, about 120 amino acids to about 750 amino acids, about 120 amino acids to about 700 amino acids, about 120 amino acids to about 650 amino acids, about 120 amino acids to about 600 amino acids, about 120 amino acids to about 550 amino acids, about 120 amino acids to about 500 amino acids, about 120 amino acids to about 450 amino acids, about 120 amino acids to about 400 amino acids, about 120 amino acids to about 350 amino acids, about 120 amino acids to about 300 amino acids, about 120 amino acids to about 280 amino acids, about 120 amino acids to about 260 amino acids, about 120 amino acids to about 240 amino acids, about 120 amino acids to about 220 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 1000 amino acids, about 125 amino acids to about 950 amino acids, about 125 amino acids to about 900 amino acids, about 125 amino acids to about 850 amino acids, about 125 amino acids to about 800 amino acids, about 125 amino acids to about 750 amino acids, about 125 amino acids to about 700 amino acids, about 125 amino acids to about 650 amino acids, about 125 amino acids to about 600 amino acids, about 125 amino acids to about 550 amino acids, about 125 amino acids to about 500 amino acids, about 125 amino acids to about 450 amino acids, about 125 amino acids to about 400 amino acids, about 125 amino acids to about 350 amino acids, about 125 amino acids to about 300 amino acids, about 125 amino acids to about 280 amino acids, about 125 amino acids to about 260 amino acids, about 125 amino acids to about 240 amino acids, about 125 amino acids to about 220 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 1000 amino acids, about 130 amino acids to about 950 amino acids, about 130 amino acids to about 900 amino acids, about 130 amino acids to about 850 amino acids, about 130 amino acids to about 800 amino acids, about 130 amino acids to about 750 amino acids, about 130 amino acids to about 700 amino acids, about 130 amino acids to about 650 amino acids, about 130 amino acids to about 600 amino acids, about 130 amino acids to about 550 amino acids, about 130 amino acids to about 500 amino acids, about 130 amino acids to about 450 amino acids, about 130 amino acids to about 400 amino acids, about 130 amino acids to about 350 amino acids, about 130 amino acids to about 300 amino acids, about 130 amino acids to about 280 amino acids, about 130 amino acids to about 260 amino acids, about 130 amino acids to about 240 amino acids, about 130 amino acids to about 220 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 1000 amino acids, about 135 amino acids to about 950 amino acids, about 135 amino acids to about 900 amino acids, about 135 amino acids to about 850 amino acids, about 135 amino acids to about 800 amino acids, about 135 amino acids to about 750 amino acids, about 135 amino acids to about 700 amino acids, about 135 amino acids to about 650 amino acids, about 135 amino acids to about 600 amino acids, about 135 amino acids to about 550 amino acids, about 135 amino acids to about 500 amino acids, about 135 amino acids to about 450 amino acids, about 135 amino acids to about 400 amino acids, about 135 amino acids to about 350 amino acids, about 135 amino acids to about 300 amino acids, about 135 amino acids to about 280 amino acids, about 135 amino acids to about 260 amino acids, about 135 amino acids to about 240 amino acids, about 135 amino acids to about 220 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 1000 amino acids, about 140 amino acids to about 950 amino acids, about 140 amino acids to about 900 amino acids, about 140 amino acids to about 850 amino acids, about 140 amino acids to about 800 amino acids, about 140 amino acids to about 750 amino acids, about 140 amino acids to about 700 amino acids, about 140 amino acids to about 650 amino acids, about 140 amino acids to about 600 amino acids, about 140 amino acids to about 550 amino acids, about 140 amino acids to about 500 amino acids, about 140 amino acids to about 450 amino acids, about 140 amino acids to about 400 amino acids, about 140 amino acids to about 350 amino acids, about 140 amino acids to about 300 amino acids, about 140 amino acids to about 280 amino acids, about 140 amino acids to about 260 amino acids, about 140 amino acids to about 240 amino acids, about 140 amino acids to about 220 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 1000 amino acids, about 145 amino acids to about 950 amino acids, about 145 amino acids to about 900 amino acids, about 145 amino acids to about 850 amino acids, about 145 amino acids to about 800 amino acids, about 145 amino acids to about 750 amino acids, about 145 amino acids to about 700 amino acids, about 145 amino acids to about 650 amino acids, about 145 amino acids to about 600 amino acids, about 145 amino acids to about 550 amino acids, about 145 amino acids to about 500 amino acids, about 145 amino acids to about 450 amino acids, about 145 amino acids to about 400 amino acids, about 145 amino acids to about 350 amino acids, about 145 amino acids to about 300 amino acids, about 145 amino acids to about 280 amino acids, about 145 amino acids to about 260 amino acids, about 145 amino acids to about 240 amino acids, about 145 amino acids to about 220 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 1000 amino acids, about 155 amino acids to about 950 amino acids, about 155 amino acids to about 900 amino acids, about 155 amino acids to about 850 amino acids, about 155 amino acids to about 800 amino acids, about 155 amino acids to about 750 amino acids, about 155 amino acids to about 700 amino acids, about 155 amino acids to about 650 amino acids, about 155 amino acids to about 600 amino acids, about 155 amino acids to about 550 amino acids, about 155 amino acids to about 500 amino acids, about 155 amino acids to about 450 amino acids, about 155 amino acids to about 400 amino acids, about 155 amino acids to about 350 amino acids, about 155 amino acids to about 300 amino acids, about 155 amino acids to about 280 amino acids, about 155 amino acids to about 260 amino acids, about 155 amino acids to about 240 amino acids, about 155 amino acids to about 220 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 1000 amino acids, about 160 amino acids to about 950 amino acids, about 160 amino acids to about 900 amino acids, about 160 amino acids to about 850 amino acids, about 160 amino acids to about 800 amino acids, about 160 amino acids to about 750 amino acids, about 160 amino acids to about 700 amino acids, about 160 amino acids to about 650 amino acids, about 160 amino acids to about 600 amino acids, about 160 amino acids to about 550 amino acids, about 160 amino acids to about 500 amino acids, about 160 amino acids to about 450 amino acids, about 160 amino acids to about 400 amino acids, about 160 amino acids to about 350 amino acids, about 160 amino acids to about 300 amino acids, about 160 amino acids to about 280 amino acids, about 160 amino acids to about 260 amino acids, about 160 amino acids to about 240 amino acids, about 160 amino acids to about 220 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 1000 amino acids, about 165 amino acids to about 950 amino acids, about 165 amino acids to about 900 amino acids, about 165 amino acids to about 850 amino acids, about 165 amino acids to about 800 amino acids, about 165 amino acids to about 750 amino acids, about 165 amino acids to about 700 amino acids, about 165 amino acids to about 650 amino acids, about 165 amino acids to about 600 amino acids, about 165 amino acids to about 550 amino acids, about 165 amino acids to about 500 amino acids, about 165 amino acids to about 450 amino acids, about 165 amino acids to about 400 amino acids, about 165 amino acids to about 350 amino acids, about 165 amino acids to about 300 amino acids, about 165 amino acids to about 280 amino acids, about 165 amino acids to about 260 amino acids, about 165 amino acids to about 240 amino acids, about 165 amino acids to about 220 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 1000 amino acids, about 170 amino acids to about 950 amino acids, about 170 amino acids to about 900 amino acids, about 170 amino acids to about 850 amino acids, about 170 amino acids to about 800 amino acids, about 170 amino acids to about 750 amino acids, about 170 amino acids to about 700 amino acids, about 170 amino acids to about 650 amino acids, about 170 amino acids to about 600 amino acids, about 170 amino acids to about 550 amino acids, about 170 amino acids to about 500 amino acids, about 170 amino acids to about 450 amino acids, about 170 amino acids to about 400 amino acids, about 170 amino acids to about 350 amino acids, about 170 amino acids to about 300 amino acids, about 170 amino acids to about 280 amino acids, about 170 amino acids to about 260 amino acids, about 170 amino acids to about 240 amino acids, about 170 amino acids to about 220 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 1000 amino acids, about 175 amino acids to about 950 amino acids, about 175 amino acids to about 900 amino acids, about 175 amino acids to about 850 amino acids, about 175 amino acids to about 800 amino acids, about 175 amino acids to about 750 amino acids, about 175 amino acids to about 700 amino acids, about 175 amino acids to about 650 amino acids, about 175 amino acids to about 600 amino acids, about 175 amino acids to about 550 amino acids, about 175 amino acids to about 500 amino acids, about 175 amino acids to about 450 amino acids, about 175 amino acids to about 400 amino acids, about 175 amino acids to about 350 amino acids, about 175 amino acids to about 300 amino acids, about 175 amino acids to about 280 amino acids, about 175 amino acids to about 260 amino acids, about 175 amino acids to about 240 amino acids, about 175 amino acids to about 220 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 1000 amino acids, about 180 amino acids to about 950 amino acids, about 180 amino acids to about 900 amino acids, about 180 amino acids to about 850 amino acids, about 180 amino acids to about 800 amino acids, about 180 amino acids to about 750 amino acids, about 180 amino acids to about 700 amino acids, about 180 amino acids to about 650 amino acids, about 180 amino acids to about 600 amino acids, about 180 amino acids to about 550 amino acids, about 180 amino acids to about 500 amino acids, about 180 amino acids to about 450 amino acids, about 180 amino acids to about 400 amino acids, about 180 amino acids to about 350 amino acids, about 180 amino acids to about 300 amino acids, about 180 amino acids to about 280 amino acids, about 180 amino acids to about 260 amino acids, about 180 amino acids to about 240 amino acids, about 180 amino acids to about 220 amino acids, about 180 amino acids to about 200 amino acids, about 180 amino acids to about 195 amino acids, about 180 amino acids to about 190 amino acids, about 180 amino acids to about 185 amino acids, about 185 amino acids to about 1000 amino acids, about 185 amino acids to about 950 amino acids, about 185 amino acids to about 900 amino acids, about 185 amino acids to about 850 amino acids, about 185 amino acids to about 800 amino acids, about 185 amino acids to about 750 amino acids, about 185 amino acids to about 700 amino acids, about 185 amino acids to about 650 amino acids, about 185 amino acids to about 600 amino acids, about 185 amino acids to about 550 amino acids, about 185 amino acids to about 500 amino acids, about 185 amino acids to about 450 amino acids, about 185 amino acids to about 400 amino acids, about 185 amino acids to about 350 amino acids, about 185 amino acids to about 300 amino acids, about 185 amino acids to about 280 amino acids, about 185 amino acids to about 260 amino acids, about 185 amino acids to about 240 amino acids, about 185 amino acids to about 220 amino acids, about 185 amino acids to about 200 amino acids, about 185 amino acids to about 195 amino acids, about 185 amino acids to about 190 amino acids, about 190 amino acids to about 1000 amino acids, about 190 amino acids to about 950 amino acids, about 190 amino acids to about 900 amino acids, about 190 amino acids to about 850 amino acids, about 190 amino acids to about 800 amino acids, about 190 amino acids to about 750 amino acids, about 190 amino acids to about 700 amino acids, about 190 amino acids to about 650 amino acids, about 190 amino acids to about 600 amino acids, about 190 amino acids to about 550 amino acids, about 190 amino acids to about 500 amino acids, about 190 amino acids to about 450 amino acids, about 190 amino acids to about 400 amino acids, about 190 amino acids to about 350 amino acids, about 190 amino acids to about 300 amino acids, about 190 amino acids to about 280 amino acids, about 190 amino acids to about 260 amino acids, about 190 amino acids to about 240 amino acids, about 190 amino acids to about 220 amino acids, about 190 amino acids to about 200 amino acids, about 190 amino acids to about 195 amino acids, about 195 amino acids to about 1000 amino acids, about 195 amino acids to about 950 amino acids, about 195 amino acids to about 900 amino acids, about 195 amino acids to about 850 amino acids, about 195 amino acids to about 800 amino acids, about 195 amino acids to about 750 amino acids, about 195 amino acids to about 700 amino acids, about 195 amino acids to about 650 amino acids, about 195 amino acids to about 600 amino acids, about 195 amino acids to about 550 amino acids, about 195 amino acids to about 500 amino acids, about 195 amino acids to about 450 amino acids, about 195 amino acids to about 400 amino acids, about 195 amino acids to about 350 amino acids, about 195 amino acids to about 300 amino acids, about 195 amino acids to about 280 amino acids, about 195 amino acids to about 260 amino acids, about 195 amino acids to about 240 amino acids, about 195 amino acids to about 220 amino acids, about 195 amino acids to about 200 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 450 amino acids, about 220 amino acids to about 400 amino acids, about 220 amino acids to about 350 amino acids, about 220 amino acids to about 300 amino acids, about 220 amino acids to about 280 amino acids, about 220 amino acids to about 260 amino acids, about 220 amino acids to about 240 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 450 amino acids, about 240 amino acids to about 400 amino acids, about 240 amino acids to about 350 amino acids, about 240 amino acids to about 300 amino acids, about 240 amino acids to about 280 amino acids, about 240 amino acids to about 260 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 450 amino acids, about 260 amino acids to about 400 amino acids, about 260 amino acids to about 350 amino acids, about 260 amino acids to about 300 amino acids, about 260 amino acids to about 280 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 450 amino acids, about 280 amino acids to about 400 amino acids, about 280 amino acids to about 350 amino acids, about 280 amino acids to about 300 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1000 amino acids, about 850 amino acids to about 950 amino acids, about 850 amino acids to about 900 amino acids, about 900 amino acids to about 1000 amino acids, about 900 amino acids to about 950 amino acids, or about 950 amino acids to about 1000 amino acids.

Any of the target-binding domains described herein can bind to its target with a dissociation equilibrium constant ($K_D$) of less than $1\times10^{-7}$ M, less than $1\times10^{-8}$ M, less than $1\times10^{-9}$ M, less than $1\times10^{-10}$ M less than $1\times10^{-11}$ M, less than $1\times10^{-12}$ M, or less than $1\times10^{-13}$ M. In some embodiments, the antigen-binding protein construct provided herein can bind to an identifying antigen with a $K_D$ of about $1\times10^{-3}$ M to about $1\times10^{-5}$ M, about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, or about $1\times10^{-9}$ M to about $1\times10^{-11}$ M (inclusive).

Any of the target-binding domains described herein can bind to its target with a $K_D$ of between about 1 pM to about 30 nM (e.g., about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 90 pM, about 2 pM to about 80 pM, about 2 pM to about 70 pM, about 2 pM to about 60 pM, about 2 pM to about 50 pM, about 2 pM to about 40 pM, about 2 pM to about 30 pM, about 2 pM to about 20 pM, about 2 pM to about 10 pM, about 2 pM to about 5 pM, about 2 pM to about 4 pM, about 2 pM to about 3 pM, about 5 pM to about 30 nM, about 5 pM to about nM, about 5 pM to about 20 nM, about 5 pM to about 15 nM, about 5 pM to about 10 nM, about 5 pM to about 5 nM, about 5 pM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 90 pM, about 5 pM to about 80 pM, about 5 pM to about 70 pM, about 5 pM to about 60 pM, about 5 pM to about 50 pM, about 5 pM to about 40 pM, about 5 pM to about 30 pM, about 5 pM to about 20 pM, about 5 pM to about 10 pM, about 10 pM to about 30 nM, about 10 pM to about 25 nM, about 10 pM to about 20 nM, about 10 pM to about 15 nM, about 10 pM to about 10 nM, about 10 pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about pM to about 200 pM, about 10 pM to about 150 pM, about 10 pM to about 100 pM, about 10 pM to about 90 pM, about 10 pM to about 80 pM, about 10 pM to about 70 pM, about 10 pM to about 60 pM, about 10 pM to about 50 pM, about 10 pM to about 40 pM, about 10 pM to about 30 pM, about 10 pM to about 20 pM, about 15 pM to about 30 nM, about 15 pM to about 25 nM, about 15 pM to about 20 nM, about 15 pM to about 15 nM, about 15 pM to about 10 nM, about 15 pM to about 5 nM, about 15 pM to about 2 nM, about 15 pM to about 1 nM, about 15 pM to about 950 pM, about 15 pM to about 900 pM, about 15 pM to about 850 pM, about 15 pM to about 800 pM, about 15 pM to about 750 pM, about 15 pM to about 700 pM, about 15 pM to about 650 pM, about 15 pM to about 600 pM, about 15 pM to about 550 pM, about 15 pM to about 500 pM, about 15 pM to about 450 pM, about 15 pM to about 400 pM, about 15 pM to about 350 pM, about pM to about 300 pM, about 15 pM to about 250 pM, about 15 pM to about 200 pM, about 15 pM to about 150 pM, about 15 pM to about 100 pM, about 15 pM to about 90 pM, about 15 pM to about 80 pM, about 15 pM to about 70 pM, about 15 pM to about 60 pM, about 15 pM to about 50 pM, about 15 pM to about 40 pM, about 15 pM to about 30 pM, about 15 pM to about 20 pM, about 20 pM to about 30 nM, about 20 pM to about 25 nM, about 20 pM to about 20 nM, about 20 pM to about 15 nM, about 20 pM to about 10 nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about pM to about 400 pM, about 20 pM to about 350 pM, about 20 pM to about 300 pM, about 20 pM to about 250 pM, about 20 pM to about 20 pM, about 200 pM to about 150 pM, about 20 pM to about 100 pM, about 20 pM to about 90 pM, about 20 pM to about 80 pM, about 20 pM to about 70 pM, about 20 pM to about 60 pM, about 20 pM to about 50 pM, about 20 pM to about 40 pM, about 20 pM to about 30 pM, about 30 pM to about nM, about 30 pM to about 25 nM, about 30 pM to about 30 nM, about 30 pM to about nM, about 30 pM to about 10 nM, about 30 pM to about 5 nM, about 30 pM to about 2 nM, about 30 pM to about 1 nM, about 30 pM to about 950 pM, about 30 pM to about 900 pM, about 30 pM to about 850 pM, about 30 pM to about 800 pM, about 30 pM to about 750 pM, about 30 pM to about 700 pM, about 30 pM to about 650 pM, about 30 pM to about 600 pM, about 30 pM to about 550 pM, about 30 pM to about 500 pM, about pM to about 450 pM, about 30 pM to about 400 pM, about 30 pM to about 350 pM, about 30 pM to about 300 pM, about 30 pM to about 250 pM, about 30 pM to about 200 pM, about 30 pM to about 150 pM, about 30 pM to about 100 pM, about 30 pM to about 90 pM, about 30 pM to about 80 pM, about 30 pM to about 70 pM, about 30 pM to about 60 pM, about 30 pM to about 50 pM, about 30 pM to about 40 pM, about 40 pM to about nM, about 40 pM to about 25 nM, about 40 pM to about 30 nM, about 40 pM to about nM, about 40 pM to about 10 nM, about 40 pM to about 5 nM, about 40 pM to about 2 nM, about 40 pM to about 1 nM, about 40 pM to about 950 pM, about 40 pM to about 900 pM, about 40 pM to about 850 pM, about 40 pM to about 800 pM, about 40 pM to about 750 pM, about 40 pM to about 700 pM, about 40 pM to about 650 pM, about 40 pM to about 600 pM, about 40 pM to about 550 pM, about 40 pM to about 500 pM, about pM to about 450 pM, about 40 pM to about 400 pM, about 40 pM to about 350 pM, about 40 pM to about 300 pM, about 40 pM to about 250 pM, about 40 pM to about 200 pM, about 40 pM to about 150 pM, about 40 pM to about 100 pM, about 40 pM to about 90 pM, about 40 pM to about 80 pM, about 40 pM to about 70 pM, about 40 pM to about 60 pM, about 40 pM to about 50 pM, about 50 pM to about 30 nM, about 50 pM to about nM, about 50 pM to about 30 nM, about 50 pM to about 15 nM, about 50 pM to about nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about 50 pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 90 pM, about 50 pM to about 80 pM, about 50 pM to about 70 pM, about 50 pM to about 60 pM, about 60 pM to about nM, about 60 pM to about 25 nM, about 60 pM to about 30 nM, about 60 pM to about nM, about 60 pM to about 10 nM, about 60 pM to about 5 nM, about 60 pM to about 2 nM, about 60 pM to about 1 nM, about 60 pM to about 950 pM, about 60 pM to about 900 pM, about 60 pM to about 850 pM, about 60 pM to about 800 pM, about 60 pM to about 750 pM, about 60 pM to about 700 pM, about 60 pM to about 650 pM, about 60 pM to about 600 pM, about 60 pM to about 550 pM, about 60 pM to about 500 pM, about 60 pM to about 450 pM, about 60 pM to about 400 pM, about 60 pM to about 350 pM, about 60 pM to about 300 pM, about 60 pM to about 250 pM, about 60 pM to about 200 pM, about 60 pM to about 150 pM, about 60 pM to about 100 pM, about 60 pM to about 90 pM, about 60 pM to about 80 pM, about 60 pM to about 70 pM, about 70 pM to about nM, about 70 pM to about 25 nM, about 70 pM to about 30 nM, about 70 pM to about nM, about 70 pM to about 10 nM, about 70 pM to about 5 nM, about 70 pM to about 2 nM, about 70 pM to about 1 nM, about 70 pM to about 950 pM, about 70 pM to about 900 pM, about 70 pM to about 850 pM, about 70 pM to about 800 pM, about 70 pM to about 750 pM, about 70 pM to about 700 pM, about 70 pM to about 650 pM, about 70 pM to about 600 pM, about 70 pM to about 550 pM, about 70 pM to about 500 pM, about 70 pM to about 450 pM, about 70 pM to about 400 pM, about 70 pM to about 350 pM, about 70 pM to about 300 pM, about 70 pM to about 250 pM, about 70 pM to about 200 pM, about 70 pM to about 150 pM, about 70 pM to about 100 pM, about 70 pM to about 90 pM, about 70 pM to about 80 pM, about 80 pM to about 30 nM, about 80 pM to about nM, about 80 pM to about 30 nM, about 80 pM to about 15 nM, about 80 pM to about nM, about 80 pM to about 5 nM, about 80 pM to about 2 nM, about 80 pM to about 1 nM, about 80 pM to about 950 pM, about 80 pM to about 900 pM, about 80 pM to about 850 pM, about 80 pM to about 800 pM, about 80 pM to about 750 pM, about 80 pM to about 700 pM, about 80 pM to about 650 pM, about 80 pM to about 600 pM, about 80 pM to about 550 pM, about 80 pM to about 500 pM, about 80 pM to about 450 pM, about 80 pM to about 400 pM, about 80 pM to about 350 pM, about 80 pM to about 300 pM, about 80 pM to about 250 pM, about 80 pM to about 200 pM, about 80 pM to about 150 pM, about 80 pM to about 100 pM, about 80 pM to about 90 pM, about 90 pM to about nM, about 90 pM to about 25 nM, about 90 pM to about 30 nM, about 90 pM to about nM, about 90 pM to about 10 nM, about 90 pM to about 5 nM, about 90 pM to about 2 nM, about 90 pM to about 1 nM, about 90 pM to about 950 pM, about 90 pM to about 900 pM, about 90 pM to about 850 pM, about 90 pM to about 800 pM, about 90 pM to about 750 pM, about 90 pM to about 700 pM, about 90 pM to about 650 pM, about 90 pM to about 600 pM, about 90 pM to about 550 pM, about 90 pM to about 500 pM, about 90 pM to about 450 pM, about 90 pM to about 400 pM, about 90 pM to about 350 pM, about 90 pM to about 300 pM, about 90 pM to about 250 pM, about 90 pM to about 200 pM, about 90 pM to about 150 pM, about 90 pM to about 100 pM, about 100 pM to about 30 nM, about 100 pM to about 25 nM, about 100 pM to about 30 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 150 pM to about 30 nM, about 150 pM to about 25 nM, about 150 pM to about 30 nM, about 150 pM to about 15 nM, about 150 pM to about 10 nM, about 150 pM to about 5 nM, about 150 pM to about 2 nM, about 150 pM to about 1 nM, about 150 pM to about 950 pM, about 150 pM to about 900 pM, about 150 pM to about 850 pM, about 150 pM to about 800 pM, about 150 pM to about 750 pM, about 150 pM to about 700 pM, about 150 pM to about 650 pM, about 150 pM to about 600 pM, about 150 pM to about 550 pM, about 150 pM to about 500 pM, about 150 pM to about 450 pM, about 150 pM to about 400 pM, about 150 pM to about 350 pM, about 150 pM to about 300 pM, about 150 pM to about 250 pM, about 150 pM to about 200 pM, about 200 pM to about 30 nM, about 200 pM to about 25 nM, about 200 pM to about 30 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 30 nM, about 300 pM to about 25 nM, about 300 pM to about 30 nM, about 300 pM to about 15 nM, about 300 pM to about 10 nM, about 300 pM to about 5 nM, about 300 pM to about 2 nM, about 300 pM to about 1 nM, about 300 pM to about 950 pM, about 300 pM to about 900 pM, about 300 pM to about 850 pM, about 300 pM to about 800 pM, about 300 pM to about 750 pM, about 300 pM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 30 nM, about 400 pM to about 25 nM, about 400 pM to about 30 nM, about 400 pM to about nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 500 pM to about 30 nM, about 500 pM to about 25 nM, about 500 pM to about 30 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 30 nM, about 600 pM to about 25 nM, about 600 pM to about 30 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 30 nM, about 700 pM to about 25 nM, about 700 pM to about 30 nM, about 700 pM to about nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 30 nM, about 800 pM to about 25 nM, about 800 pM to about 30 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 30 nM, about 900 pM to about 25 nM, about 900 pM to about 30 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 30 nM, about 1 nM to about 25 nM, about 1 nM to about 20 nM, about 1 nM to about 15 nM, about 1 nM to about 10 nM, about 1 nM to about 5 nM, about 2 nM to about 30 nM, about 2 nM to about 25 nM, about 2 nM to about 20 nM, about 2 nM to about 15 nM, about 2 nM to about 10 nM, about 2 nM to about 5 nM, about 4 nM to about 30 nM, about 4 nM to about 25 nM, about 4 nM to about 20 nM, about 4 nM to about 15 nM, about 4 nM to about 10 nM, about 4 nM to about 5 nM, about 5 nM to about 30 nM, about 5 nM to about 25 nM, about 5 nM to about 20 nM, about 5 nM to about 15 nM, about 5 nM to about 10 nM, about 10 nM to about 30 nM, about 10 nM to about 25 nM, about 10 nM to about 20 nM, about 10 nM to about 15 nM, about 15 nM to about 30 nM, about 15 nM to about 25 nM, about 15 nM to about 20 nM, about 20 nM to about 30 nM, and about 20 nM to about 25 nM).

Any of the target-binding domains described herein can bind to its target with a $K_D$ of between about 1 nM to about 10 nM (e.g., about 1 nM to about 9 nM, about 1 nM to about 8 nM, about 1 nM to about 7 nM, about 1 nM to about 6 nM, about 1 nM to about 5 nM, about 1 nM to about 4 nM, about 1 nM to about 3 nM, about 1 nM to about 2 nM, about 2 nM to about 10 nM, about 2 nM to about 9 nM, about 2 nM to about 8 nM, about 2 nM to about 7 nM, about 2 nM to about 6 nM, about 2 nM to about 5 nM, about 2 nM to about 4 nM, about 2 nM to about 3 nM, about 3 nM to about 10 nM, about 3 nM to about 9 nM, about 3 nM to about 8 nM, about 3 nM to about 7 nM, about 3 nM to about 6 nM, about 3 nM to about 5 nM, about 3 nM to about 4 nM, about 4 nM to about 10 nM, about 4 nM to about 9 nM, about 4 nM to about 8 nM, about 4 nM to about 7 nM, about 4 nM to about 6 nM, about 4 nM to about 5 nM, about 5 nM to about 10 nM, about 5 nM to about 9 nM, about 5 nM to about 8 nM, about 5 nM to about 7 nM, about 5 nM to about 6 nM, about 6 nM to about 10 nM, about 6 nM to about 9 nM, about 6 nM to about 8 nM, about 6 nM to about 7 nM, about 7 nM to about 10 nM, about 7 nM to about 9 nM, about 7 nM to about 8 nM, about 8 nM to about 10 nM, about 8 nM to about 9 nM, and about 9 nM to about 10 nM).

A variety of different methods known in the art can be used to determine the $K_D$ values of any of the antigen-binding protein constructs described herein (e.g., an electrophoretic mobility shift assay, a filter binding assay, surface plasmon resonance, and a biomolecular binding kinetics assay, etc.).

Antigen-Binding Domains

In some embodiments of any of the single-chain or multi-chain chimeric polypeptides described herein, the first target-binding domain and the second target-binding domain bind specifically to the same antigen. In some embodiments of these single-chain or multi-chain chimeric polypeptides, the first target-binding domain and the second target-binding domain bind specifically to the same epitope. In some embodiments of these single-chain or multi-chain chimeric polypeptides, the first target-binding domain and the second target-binding domain include the same amino acid sequence.

In some embodiments of any of the single-chain or multi-chain chimeric polypeptides described herein, the first target-binding domain and the second target-binding domain bind specifically to different antigens.

In some embodiments of any of the single-chain or multi-chain chimeric polypeptides described herein, one or both of the first target-binding domain and the second target-binding domain is an antigen-binding domain. In some embodiments of any of the single-chain or multi-chain chimeric polypeptides described herein, the first target-binding domain and the second target-binding domain are each antigen-binding domains. In some embodiments of any of the single-chain or multi-chain chimeric polypeptides described herein, the antigen-binding domain includes or is a scFv or a single domain antibody (e.g., a $V_{aH}H$ or a $V_{NAR}$ domain).

In some examples, an antigen-binding domain (e.g., any of the antigen-binding domains described herein) can bind specifically to any one of CD16a (see, e.g., those described in U.S. Pat. No. 9,035,026), CD28 (see, e.g., those described in U.S. Pat. No. 7,723,482), CD3 (see, e.g., those described in U.S. Pat. No. 9,226,962), CD33 (see, e.g., those described in U.S. Pat. No. 8,759,494), CD20 (see, e.g., those described in WO 2014/026054), CD19 (see, e.g., those described in U.S. Pat. No. 9,701,758), CD22 (see, e.g., those described in WO 2003/104425), CD123 (see, e.g., those described in WO 2014/130635), IL-1R (see, e.g., those described in U.S. Pat. No. 8,741,604), IL-1 (see, e.g., those described in WO 2014/095808), VEGF (see, e.g., those described in U.S. Pat. No. 9,090,684), IL-6R (see, e.g., those described in U.S. Pat. No. 7,482,436), IL-4 (see, e.g., those described in U.S. Patent Application Publication No. 2012/0171197), IL-10 (see, e.g., those described in U.S. Patent Application Publication No. 2016/0340413), PDL-1 (see, e.g., those described in Drees et al., *Protein Express. Purif.* 94:60-66, 2014), TIGIT (see, e.g., those described in U.S. Patent Application Publication No. 2017/0198042), PD-1 (see, e.g., those described in U.S. Pat. No. 7,488,802), TIM3 (see, e.g., those described in U.S. Pat. No. 8,552,156), CTLA4 (see, e.g., those described in WO 2012/120125), MICA (see, e.g., those described in WO 2016/154585), MICB (see, e.g., those described in U.S. Pat. No. 8,753,640), IL-6 (see, e.g., those described in Gejima et al., *Human Antibodies* 11(4): 121-129, 2002), IL-8 (see, e.g., those described in U.S. Pat. No. 6,117,980), TNFα (see, e.g., those described in Geng et al., *Immunol. Res.* 62(3):377-385, 2015), CD26 (see, e.g., those described in WO 2017/189526), CD36 (see, e.g., those described in U.S. Patent Application Publication No. 2015/0259429), ULBP2 (see, e.g., those described in U.S. Pat. No. 9,273,136), CD30 (see, e.g., those described in Homach et al., *Scand. J. Immunol.* 48(5):497-501, 1998), CD200 (see, e.g., those described in U.S. Pat. No. 9,085,623), IGF-1R (see, e.g., those described in U.S. Patent Application Publication No. 2017/0051063), MUC4AC (see, e.g., those described in WO 2012/170470), MUC5AC (see, e.g., those described in U.S. Pat. No. 9,238,084), Trop-2 (see, e.g., those described in WO 2013/068946), CMET (see, e.g., those described in Edwardraja et al., *Biotechnol. Bioeng.* 106(3):367-375, 2010), EGFR (see, e.g., those described in Akbari et al., *Protein Expr. Purif.* 127:8-15, 2016), HER1 (see, e.g., those described in U.S. Patent Application Publication No. 2013/0274446), HER2 (see, e.g., those described in Cao et al., *Biotechnol. Lett.* 37(7):1347-1354, 2015), HER3 (see, e.g., those described in U.S. Pat. No. 9,505,843), PSMA (see, e.g., those described in Parker et al., *Protein Expr. Purif.* 89(2):136-145, 2013), CEA (see, e.g., those described in WO 1995/015341), B7H3 (see, e.g., those described in U.S. Pat. No. 9,371,395), EPCAM (see, e.g., those described in WO 2014/159531), BCMA (see, e.g., those described in Smith et al., *Mol. Ther.* 26(6):1447-1456, 2018), P-cadherin (see, e.g., those described in U.S. Pat. No. 7,452,537), CEACAM5 (see, e.g., those described in U.S. Pat. No. 9,617,345), a UL16-binding protein (see, e.g., those described in WO 2017/083612), HLA-DR (see, e.g., Pistillo et al., *Exp. Clin. Immunogenet.* 14(2):123-130, 1997), DLL4 (see, e.g., those described in WO 2014/007513), TYRO3 (see, e.g., those described in WO 2016/166348), AXL (see, e.g., those described in WO 2012/175692), MER (see, e.g., those described in WO 2016/106221), CD122 (see, e.g., those described in U.S. Patent Application Publication No. 2016/0367664), CD155 (see, e.g., those described in WO 2017/149538), or PDGF-DD (see, e.g., those described in U.S. Pat. No. 9,441,034).

The antigen-binding domains present in any of the single-chain or multi-chain chimeric polypeptides described herein are each independently selected from the group consisting of: a VHH domain, a VNAR domain, and a scFv. In some embodiments, any of the antigen-binding domains described herein is a BiTe, a $(scFv)_2$, a nanobody, a nanobody-HSA, a DART, a TandAb, a scDiabody, a scDiabody-CH3, scFv-CH-CL-scFv, a HSAbody, scDiabody-HAS, or a tandem-scFv. Additional examples of antigen-binding domains that can be used in any of the single-chain or multi-chain chimeric polypeptide are known in the art.

A VHH domain is a single monomeric variable antibody domain that can be found in camelids. A VNAR domain is a single monomeric variable antibody domain that can be found in cartilaginous fish. Non-limiting aspects of VHH domains and $V_{NAR}$ domains are described in, e.g., Cromie et al., *Curr. Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther.* 14:1527-1539, 2014; Krah et al., *Immunopharmacol. Immunotoxicol.* 38:21-28, 2016; Mujic-Delic et al., *Trends Pharmacol. Sci.* 35:247-255, 2014; *Muyldermans, J. Biotechnol.* 74:277-302, 2001; Muyldermans et al., *Trends Biochem*. Sci. 26:230-235, 2001*; Muyldermans, Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr. Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

In some embodiments, each of the antigen-binding domains in the single-chain or multi-chain chimeric polypeptides described herein are both VHH domains, or at least one antigen-binding domain is a VHH domain. In some embodiments, each of the antigen-binding domains in the single-chain or multi-chain chimeric polypeptides described herein are both VNAR domains, or at least one antigen-binding domain is a VNAR domain. In some embodiments, each of the antigen-binding domains in the single-chain or multi-chain chimeric polypeptides described herein are both scFv domains, or at least one antigen-binding domain is a scFv domain.

In some embodiments, two or more of polypeptides present in the single-chain or multi-chain chimeric polypeptide can assemble (e.g., non-covalently assemble) to form any of the antigen-binding domains described herein, e.g., an antigen-binding fragment of an antibody (e.g., any of the antigen-binding fragments of an antibody described herein), a VHH-scAb, a VHH-Fab, a Dual scFab, a F(ab')2, a diabody, a crossMab, a DAF (two-in-one), a DAF (four-in-one), a DutaMab, a DT-IgG, a knobs-in-holes common light chain, a knobs-in-holes assembly, a charge pair, a Fab-arm exchange, a SEEDbody, a LUZ-Y, a Fcab, a κλ-body, an orthogonal Fab, a DVD-IgG, a IgG(H)-scFv, a scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, Zybody, DVI-IgG, Diabody-CH3, a triple body, a miniantibody, a minibody, a TriBi minibody, scFv-CH3 KIH, Fab-scFv, a F(ab')2-scFv2, a scFv-KIH, a Fab-scFv-Fc, a tetravalent HCAb, a scDiabody-Fc, a Diabody-Fc, a tandem scFv-Fc, an Intrabody, a dock and lock, a 1 mmTAC, an IgG-IgG conjugate, a Cov-X-Body, and a scFv1-PEG-scFv2. See, e.g., Spiess et al., *Mol. Immunol.* 67:95-106, 2015, incorporated in its entirety herewith, for a description of these elements. Non-limiting examples of an antigen-binding fragment of an antibody include an Fv fragment, a Fab fragment, a $F(ab')_2$ fragment, and a Fab' fragment. Additional examples of an antigen-binding fragment of an antibody is an antigen-binding fragment of an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); or an antigen-binding fragment of an IgM (e.g., an antigen-binding fragment of a human or humanized IgM).

An "Fv" fragment includes a non-covalently-linked dimer of one heavy chain variable domain and one light chain variable domain.

A "Fab" fragment includes, the constant domain of the light chain and the first constant domain ($C_{H1}$) of the heavy chain, in addition to the heavy and light chain variable domains of the Fv fragment.

A "$F(ab')_2$" fragment includes two Fab fragments joined, near the hinge region, by disulfide bonds.

A "dual variable domain immunoglobulin" or "DVD-Ig" refers to multivalent and multispecific binding proteins as described, e.g., in DiGiammarino et al., *Methods Mol. Biol.* 899:145-156, 2012; Jakob et al., MABs 5:358-363, 2013; and U.S. Pat. Nos. 7,612,181; 8,258,268; 8,586,714; 8,716,450; 8,722,855; 8,735,546; and 8,822,645, each of which is incorporated by reference in its entirety.

DARTs are described in, e.g., Garber, Nature Reviews Drug Discovery 13:799-801, 2014.

In some embodiments of any of the antigen-binding domains described herein can bind to an antigen selected from the group consisting of: a protein, a carbohydrate, a lipid, and a combination thereof.

Additional examples and aspects of antigen-binding domains are known in the art.

Soluble Interleukin or Cytokine Protein

In some embodiments of any of the single-chain or multi-chain chimeric polypeptides described herein, one or both of the first target-binding domain and the second target-binding domain can be a soluble interleukin protein or soluble cytokine protein. In some embodiments, the soluble interleukin or soluble cytokine protein is selected from the group of: IL-2, IL-3, IL-7, IL-8, IL-10, IL-12, IL-15, IL-17, IL-18, IL-21, PDGF-DD, and SCF. Non-limiting examples of soluble IL-2, IL-3, IL-7, IL-8, IL-10, IL-15, IL-17, IL-18, IL-21, PDGF-DD, and SCF are provided below.

```
Human Soluble IL-3
                                    (SEQ ID NO: 105)
apmtqttplkt swvncsnmid eiithlkqpp lplldfnnln

gedqdilmen nlrrpnleaf nravkslqna saiesilknl

lpclplataa ptrhpihikd gdwnefrrkl tfylktlena

qaqqttlsla if

Human Soluble IL-8
                                    (SEQ ID NO: 106)
egavlprsak elrcqcikty skpfhpkfik elrviesgph

canteiivkl sdgrelcldp kenwvqrvve kflkraens

Human Soluble IL-10
                                    (SEQ ID NO: 107)
spgqgtqsensc thfpgnlpnm lrdlrdafsr vktffqmkdq

ldnlllkesl ledfkgylgc qalsemiqfy leevmpqaen

qdpdikahvn slgenlktlr lrlrrchrfl pcenkskave

qvknafnklq ekgiykamse fdifinyiea ymtmkirn

Human Soluble IL-17
                                    (SEQ ID NO: 108)
gitiprn pgcpnsedkn fprtvmvnln ihnrntntnp

krssdyynrs tspwnlhrne dperypsviw eakcrhlgci

nadgnvdyhm nsvpiqqeil vlrrepphcp nsfrlekilv

svgctcvtpi vhhva

Human Soluble IL-18
                                    (SEQ ID NO: 109)
yfgklesklsvirn lndqvlfidq gnrplfedmt dsdcrdnapr

tifiismykd sqprgmavti svkcekistl scenkiisfk

emnppdnikd tksdiiffqr svpghdnkmq fesssyegyf

lacekerdlf klilkkedel gdrsimftvq ned

Human Soluble PDGF-DD
                                    (SEQ ID NO: 110)
rdtsatpqsasi kalrnanlrr desnhltdly rrdetiqvkg

ngyvqsprfp nsyprnlllt wrlhsqentr iqlvfdnqfg

leeaendicr ydfvevedis etstiirgrw cghkevppri

ksrtnqikit fksddyfvak pgfkiyysll edfqpaaase

tnwesvtssi sgvsynspsv tdptliadal dkkiaefdtv
```

-continued

```
edllkyfnpe swqedlenmy ldtpryrgrs yhdrkskvdl

drlnddakry sctprnysvn ireelklanv vffprcllvq

rcggncgcgt vnwrsctcns gktvkkyhev lqfepghikr

rgraktmalv diqldhherc dcicssrppr

Human Soluble SCF
                                    (SEQ ID NO: 111)
egicrnrvtnnvkdv tklvanlpkd ymitlkyvpg mdvlpshcwi

semvvqlsds ltdlldkfsn iseglsnysi idklvnivdd

lvecvkenss kdlkksfksp eprlftpeef frifnrsida

fkdfvvaset sdcvvsstls pekdsrvsvt kpfmlppvaa

sslrndssss nrkaknppgd sslhwaamal palfsliigf

afgalywkkr qpsltraven iqineednei smlqekeref

qev

Human Soluble FLT3L
                                    (SEQ ID NO: 112)
tqdcsfqhspissd favkirelsd yllqdypvtv asnlqdeelc

gglwrlvlaq rwmerlktva gskmqgller vnteihfvtk

cafqpppscl rfvqtnisrl lqetseqlva lkpwitrqnf

srclelqcqp dsstlpppws prpleatapt apqpplllll

llpvgllllla aawclhwqrt rrrtprpgeq vppvpspqdl

llveh
```

Additional examples of soluble interleukin proteins and soluble cytokine proteins are known in the art.

Soluble Receptor

In some embodiments of any of the single-chain or multi-chain chimeric polypeptides described herein, one or both of the first target-binding domain and the second target-binding domain is a soluble interleukin receptor or a soluble cytokine receptor. In some embodiments, the soluble receptor is a soluble TGF-β receptor II (TGF-β RII) (see, e.g., those described in Yung et al., *Am. J. Resp. Crit. Care Med.* 194(9):1140-1151, 2016), a soluble TGF-βRIII (see, e.g., those described in Heng et al., *Placenta* 57:320, 2017), a soluble NKG2D (see, e.g., Cosman et al., *Immunity* 14(2):123-133, 2001; Costa et al., *Front. Immunol.*, Vol. 9, Article 1150, May 29, 2018; doi: 10.3389/fimmu.2018.01150), a soluble NKp30 (see, e.g., Costa et al., *Front. Immunol.*, Vol. 9, Article 1150, May 29, 2018; doi: 10.3389/fimmu.2018.01150), a soluble NKp44 (see, e.g., those described in Costa et al., *Front. Immunol.*, Vol. 9, Article 1150, May 29, 2018; doi: 10.3389/fimmu.2018.01150), a soluble NKp46 (see, e.g., Mandelboim et al., *Nature* 409:1055-1060, 2001; Costa et al., *Front. Immunol.*, Vol. 9, Article 1150, May 29, 2018; doi: 10.3389/fimmu.2018.01150), a soluble DNAM1 (see, e.g., those described in Costa et al., *Front. Immunol.*, Vol. 9, Article 1150, May 29, 2018; doi: 10.3389/fimmu.2018.01150), a scMHCI (see, e.g., those described in Washburn et al., *PLoS One* 6(3):e18439, 2011), a scMHCII (see, e.g., those described in Bishwajit et al., *Cellular Immunol.* 170(1):25-33, 1996), a scTCR (see, e.g., those described in Weber et al., *Nature* 356(6372):793-796, 1992), a soluble CD155 (see, e.g., those described in Tahara-Hanaoka et al., *Int. Immunol.* 16(4):533-538, 2004), or a soluble CD28 (see, e.g., Hebbar et al., *Clin. Exp. Immunol.* 136:388-392, 2004).

Additional examples of soluble interleukin receptors and soluble cytokine receptors are known in the art.

Pairs of Affinity Domains

In some embodiments, a multi-chain chimeric polypeptide includes: 1) a first chimeric polypeptide that includes a first domain of a pair of affinity domains, and 2) a second chimeric polypeptide that includes a second domain of a pair of affinity domains such that the first chimeric polypeptide and the second chimeric polypeptide associate through the binding of the first domain and the second domain of the pair of affinity domains. In some embodiments, the pair of affinity domains is a sushi domain from an alpha chain of human IL-15 receptor (IL-15Rα) and a soluble IL-15. A sushi domain, also known as a short consensus repeat or type 1 glycoprotein motif, is a common motif in protein-protein interaction. Sushi domains have been identified on a number of protein-binding molecules, including complement components C1r, C1s, factor H, and C2m, as well as the nonimmunologic molecules factor XIII and β2-glycoprotein. A typical Sushi domain has approximately 60 amino acid residues and contains four cysteines (Ranganathan, Pac. Symp Biocomput. 2000:155-67). The first cysteine can form a disulfide bond with the third cysteine, and the second cysteine can form a disulfide bridge with the fourth cysteine. In some embodiments in which one member of the pair of affinity domains is a soluble IL-15, the soluble IL-15 has a D8N or D8A amino acid substitution. In some embodiments in which one member of the pair of affinity domains is an alpha chain of human IL-15 receptor (IL-15Rα), the human IL-15Rα is a mature full-length IL-15Rα. In some embodiments, the pair of affinity domains is barnase and barnstar. In some embodiments, the pair of affinity domains is a PKA and an AKAP. In some embodiments, the pair of affinity domains is an adapter/docking tag module based on mutated RNase I fragments (Rossi, *Proc Natl Acad Sci USA.* 103: 6841-6846, 2006; Sharkey et al., *Cancer Res.* 68:5282-5290, 2008; Rossi et al., *Trends Pharmacol Sci.* 33:474-481, 2012) or SNARE modules based on interactions of the proteins syntaxin, synaptotagmin, synaptobrevin, and SNAP25 (Deyev et al., *Nat Biotechnol.* 1486-1492, 2003).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains and the second domain of the pair of affinity domains bind to each other with a dissociation equilibrium constant ($K_D$) of less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In some embodiments, the first domain of the pair of affinity domains and the second domain of the pair of affinity domains bind to each other with a $K_D$ of about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, about $1\times10^{-9}$ M to about $1\times10^{-11}$ M, about $1\times10^{-10}$ M to about $1\times10^{-12}$ M, about $1\times10^{-11}$ M to about $1\times10^{-13}$ M, about $1\times10^{-4}$ M to about $1\times10^{-5}$ M, about $1\times10^{-5}$ M to about $1\times10^{-6}$ M, about $1\times10^{-6}$ M to about $1\times10^{-7}$ M, about $1\times10^{-7}$ M to about $1\times10^{-8}$ M, about $1\times10^{-8}$ M to about $1\times10^{-9}$ M, about $1\times10^{-9}$ M to about $1\times10^{-10}$ M, about $1\times10^{-10}$ M to about $1\times10^{-11}$ M, about $1\times10^{-11}$ M to about $1\times10^{-12}$ M, or about $1\times10^{-12}$ M to about $1\times10^{-13}$ M (inclusive). Any of a variety of different methods known in the art can be used to determine the $K_D$ value of the binding of the first domain of the pair of affinity domains and the second domain of the pair of affinity domains (e.g., an electrophoretic mobility shift assay, a filter binding assay, surface plasmon resonance, and a biomolecular binding kinetics assay, etc.).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains, the second domain of the pair of affinity domains, or both is about 10 to 100 amino acids in length. For example, a first domain of a pair of affinity domains, a second domain of a pair of affinity domains, or both can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about to 65 amino acids in length, about 10 to 60 amino acids in length, about 10 to 55 amino acids in length, about 10 to 50 amino acids in length, about 10 to 45 amino acids in length, about 10 to 40 amino acids in length, about 10 to 35 amino acids in length, about to 30 amino acids in length, about 10 to 25 amino acids in length, about 10 to 20 amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a first domain of a pair of affinity domains, a second domain of a pair of affinity domains, or both is about 10, 15, 20, 25, 30, 35, 40, 45, 50, 55, 60, 65, 70, 75, 80, 85, 90, 95, or 100 amino acids in length.

In some embodiments, any of the first and/or second domains of a pair of affinity domains disclosed herein can include one or more additional amino acids (e.g., 1, 2, 3, 5, 6, 7, 8, 9, 10, or more amino acids) at its N-terminus and/or C-terminus, so long as the function of the first and/or second domains of a pair of affinity domains remains intact. For example, a sushi domain from an alpha chain of human IL-15 receptor (IL-15Rα) can include one or more additional amino acids at the N-terminus and/or the C-terminus, while still retaining the ability to bind to a soluble IL-15. Additionally or alternatively, a soluble IL-15 can include one or more additional amino acids at the N-terminus and/or the C-terminus, while still retaining the ability to bind to a sushi domain from an alpha chain of human IL-15 receptor (IL-15Rα).

A non-limiting example of a sushi domain from an alpha chain of IL-15 receptor alpha (IL-15Rα) can include a sequence that is at least 70% identical, at least 75% identical, at least 80% identical, at least 85% identical, at least 90% identical, at least 95% identical, at least 99% identical, or 100% identical to ITCPPPMSVEHADIWVKSYSLYSRERYICNSGFKRKAGTSSLTECVLNKATNVAH WTTPSLKCIR (SEQ ID NO: 113). In some embodiments, a sushi domain from an alpha chain of IL-15Rα can be encoded by a nucleic acid including (SEQ ID NO: 114)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG.

In some embodiments, a soluble IL-15 can include a sequence that is at least 70% identical, at least 75% identical, at least 80% identical, at least 85% identical, at least 90% identical, at least 95% identical, at least 99% identical, or 100% identical to NWVNVISDLKKIEDLIQSMHIDATLYTESDVHPSCKVTAMKCFLLELQVISLESGD ASIHDTVENLIILANNSLSSNGNVTESGCKECEELEEKNIKEFLQSFVHIVQIVIFINT S (SEQ ID NO: 115). In some embodiments, a soluble IL-15 can be encoded by a nucleic acid including the sequence of (SEQ ID NO: 116)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC.

Signal Sequence

In some embodiments, a single-chain chimeric polypeptide comprises a signal sequence at its N-terminal end. In some embodiments, a multi-chain chimeric polypeptide includes a first chimeric polypeptide that includes a signal sequence at its N-terminal end. In some embodiments, a multi-chain chimeric polypeptide includes a second chimeric polypeptide that includes a signal sequence at its N-terminal end. In some embodiments, both the first chimeric polypeptide of a multi-chain chimeric polypeptide and a second chimeric polypeptide of the multi-chain chimeric polypeptide include a signal sequence. As will be understood by those of ordinary skill in the art, a signal sequence is an amino acid sequence that is present at the N-terminus of a number of endogenously produced proteins that directs the protein to the secretory pathway (e.g., the protein is directed to reside in certain intracellular organelles, to reside in the cell membrane, or to be secreted from the cell). Signal sequences are heterogeneous and differ greatly in their primary amino acid sequences. However, signal sequences are typically 16 to 30 amino acids in length and include a hydrophilic, usually positively charged N-terminal region, a central hydrophobic domain, and a C-terminal region that contains the cleavage site for signal peptidase.

In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence having an amino acid sequence MKWVTFISLLFLFSSAYS (SEQ ID NO: 117). In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence encoded by the nucleic acid sequence (SEQ ID NO: 118)
ATGAAATGGGTGACCTTTATTTCTTTACTGTTCCTCTTTAGCAGCGCCTA

CTCC, (SEQ ID NO: 119)
ATGAAGTGGGTCACATTTATCTCTTTACTGTTCCTCTTCTCCAGCGCCTA

CAGC,
or (SEQ ID NO: 120)
ATGAAATGGGTGACCTTTATTTCTTTACTGTTCCTCTTTAGCAGCGCCTA

CTCC.

In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence having an amino acid sequence MKCLLYLAFLFLGVNC (SEQ ID NO: 121). In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence having an amino acid sequence MGQIVTMFEALPHIIDEVINIVIIVLIIITSIKAVYNFATCGILALVSFLFLAGRSCG (SEQ ID NO: 122). In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence having an amino acid sequence:

(SEQ ID NO: 123)
MPNHQSGSPTGSSDLLLSGKKQRPHLALRRKRRREMRKINRKVRRMNLAP

IKEKTAWQHLQALISEAEEVLKTSQTPQNSLTLFLALLSVLGPPVTG.

In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence having an amino acid sequence MDSKGSSQKGSRLLLLLVVSNLLLCQGVVS (SEQ ID NO: 124). Those of ordinary skill in the art will be aware of other appropriate signal sequences for use in a first chimeric polypeptide and/or a second chimeric polypeptide of multi-chain chimeric polypeptides, or single-chain chimeric polypeptides described herein.

In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence that is about 10 to 100 amino acids in length. For example, a signal sequence can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about to 80 amino acids in length, about 40 to 70 amino acids in length, about 50 to 60 amino acids in length, or any range in between. In some embodiments, a signal sequence is about 10, 15, 20, 25, 30, 35, 40, 45, 50, 55, 60, 65, 70, 75, 80, 85, 90, 95, or 100 amino acids in length.

In some embodiments, any of the signal sequences disclosed herein can include one or more additional amino acids (e.g., 1, 2, 3, 5, 6, 7, 8, 9, 10, or more amino acids) at its N-terminus and/or C-terminus, so long as the function of the signal sequence remains intact. For example, a signal sequence having the amino acid sequence MKCLLYLAFLFLGVNC (SEQ ID NO: 125) can include one or more additional amino acids at the N-terminus or C-terminus, while still retaining the ability to direct the a first chimeric polypeptide of a multi-chain chimeric polypeptide, a second chimeric polypeptide of the multi-chain chimeric polypeptide, or both, or a single-chain chimeric polypeptide, to the secretory pathway.

In some embodiments, a first chimeric polypeptide of a multi-chain chimeric polypeptide, a second chimeric polypeptide of the multi-chain chimeric polypeptide, or both, or a single-chain chimeric polypeptide, includes a signal sequence that directs the multi-chain chimeric polypeptide into the extracellular space. Such embodiments are useful in producing single-chain or multi-chain chimeric polypeptides that are relatively easy to be isolated and/or purified.

Peptide Tags

In some embodiments, a single-chain chimeric polypeptide includes a peptide tag (e.g., at the N-terminal end or the C-terminal end of the chimeric polypeptide). In some embodiments, a multi-chain chimeric polypeptide includes a first chimeric polypeptide that includes a peptide tag (e.g., at the N-terminal end or the C-terminal end of the first chimeric polypeptide). In some embodiments, a multi-chain chimeric polypeptide includes a second chimeric polypeptide that includes a peptide tag (e.g., at the N-terminal end or the C-terminal end of the second chimeric polypeptide). In some embodiments, both the first chimeric polypeptide of a multi-chain chimeric polypeptide and a second chimeric polypeptide of the multi-chain chimeric polypeptide include a peptide tag. In some embodiments, a first chimeric polypeptide of a multi-chain chimeric polypeptide, a second chimeric polypeptide of the multi-chain chimeric polypeptide, or both, or a single-chain chimeric polypeptide, includes two or more peptide tags.

Exemplary peptide tags that can be included in a first chimeric polypeptide of a multi-chain chimeric polypeptide, a second chimeric polypeptide of the multi-chain chimeric polypeptide, or both, or a single-chain chimeric polypeptide include, without limitation, AviTag (GLNDIFEAQKIEWHE; SEQ ID NO: 126), a calmodulin-tag (KRRWKKNFIAVSAANRFKKISSSGAL; SEQ ID NO: 127), a polyglutamate tag (EEEEEE; SEQ ID NO: 128), an E-tag (GAPVPYPDPLEPR; SEQ ID NO: 129), a FLAG-tag (DYKDDDDK; SEQ ID NO: 130), an HA-tag, a peptide from hemagglutinin (YPYDVPDYA; SEQ ID NO: 131), a his-tag (HHHHH (SEQ ID NO: 132); HHHHHH (SEQ ID NO: 133); HHHHHHH (SEQ ID NO: 134); HHHHHHHH (SEQ ID NO: 135); HHHHHHHHH (SEQ ID NO: 136); or HHHHHHHHHH (SEQ ID NO: 137)), a myc-tag (EQKLISEEDL; SEQ ID NO: 138), NE-tag (TKENPRSNQEESYDDNES; SEQ ID NO: 139), S-tag, (KETAAAKFERQHMDS; SEQ ID NO: 140), SBP-tag (MDEKTTGWRGGHVVEGLAGELEQLRARLEHHPQGQREP; SEQ ID NO: 141), Softag 1 (SLAELLNAGLGGS; SEQ ID NO: 142), Softag 3 (TQDPSRVG; SEQ ID NO: 143), Spot-tag (PDRVRAVSHWSS; SEQ ID NO: 144), Strep-tag (WSHPQFEK; SEQ ID NO: 145), TC tag (CCPGCC; SEQ ID NO: 146), Ty tag (EVHTNQDPLD; SEQ ID NO: 147), V5 tag (GKPIPNPLLGLDST; SEQ ID NO: 148), VSV-tag (YTDIEMNRLGK; SEQ ID NO: 149), and Xpress tag (DLYDDDDK; SEQ ID NO: 150). In some embodiments, tissue factor protein is a peptide tag.

Peptide tags that can be included in a first chimeric polypeptide of a multi-chain chimeric polypeptide, a second chimeric polypeptide of the multi-chain chimeric polypeptide, or both, or a single-chain chimeric polypeptide can be used in any of a variety of applications related to the multi-chain or single-chain chimeric polypeptide, respectively. For example, a peptide tag can be used in the purification of a multi-chain or single-chain chimeric polypeptide. As one non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both, or a single-chain chimeric polypeptide, can include a myc tag; the multi-chain chimeric polypeptide that includes the myc-tagged first chimeric polypeptide, the myc-tagged second chimeric polypeptide, or both, or the myc-tagged single-chain chimeric polypeptide can be purified using an antibody that recognizes the myc tag(s). One non-limiting example of an antibody that recognizes a myc tag is 9E10, available from the non-commercial Developmental Studies Hybridoma Bank. As another non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both, or a single-chain chimeric polypeptide, can include a histidine tag; the multi-chain chimeric polypeptide that includes the histidine-tagged first chimeric polypeptide, the histidine-tagged second chimeric polypeptide, or both, or the histidine-tagged single-chain chimeric polypeptide can be purified using a nickel or cobalt chelate. Those of ordinary skill in the art will be aware of other suitable tags and agents that bind those tags for use in purifying a single-chain or multi-chain chimeric polypeptide. In some embodiments, a peptide tag is removed from the first chimeric polypeptide and/or the second chimeric polypeptide of the multi-chain chimeric polypeptide, or the single-chain chimeric polypeptide after purification. In some embodiments, a peptide tag is not removed from the first chimeric polypeptide and/or the second chimeric polypeptide of the multi-chain chimeric polypeptide, or the single-chain chimeric polypeptide, after purification.

Peptide tags that can be included in a first chimeric polypeptide of a multi-chain chimeric polypeptide, a second chimeric polypeptide of the multi-chain chimeric polypeptide, or both, or a single-chain chimeric polypeptide, can be used, for example, in immunoprecipitation of the multi-chain chimeric polypeptide or single-chain chimeric polypeptide, respectively, imaging of the multi-chain chimeric polypeptide or single-chain chimeric polypeptide, respectively (e.g., via Western blotting, ELISA, flow cytometry, and/or immunocytochemistry), and/or solubilization of the multi-chain chimeric polypeptide or single-chain chimeric polypeptide, respectively.

In some embodiments, a first chimeric polypeptide of a multi-chain chimeric polypeptide, a second chimeric polypeptide of the multi-chain chimeric polypeptide, or both, or a single-chain chimeric polypeptide, includes a peptide tag that is about 10 to 100 amino acids in length. For example, a peptide tag can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about to 35 amino acids in length, about 10 to 30 amino acids in length, about 10 to 25 amino acids in length, about 10 to 20 amino acids in length, about 10 to 15 amino acids in length, about 20 to 30 amino acids in length, about 30 to 40 amino acids in length, about to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about to 80 amino acids in length, about 40 to 70 amino acids in length, about 50 to 60 amino acids in length, or any range in between. In some embodiments, a peptide tag is about 10, 15, 20, 25, 30, 35, 40, 45, 50, 55, 60, 65, 70, 75, 80, 85, 90, 95, or 100 amino acids in length.

Peptide tags included in a first chimeric polypeptide of a multi-chain chimeric polypeptide, a second chimeric polypeptide of the multi-chain chimeric polypeptide, or both, or a single-chain chimeric polypeptide, can be of any suitable length. For example, peptide tags can be 5, 6, 7, 8, 9, 10, 11, 12, 13, 14, 15, 16, 17, 18, 19, 20, or more amino acids in length. In embodiments in which a single-chain or multi-chain chimeric polypeptide includes two or more peptide tags, the two or more peptide tags can be of the same or different lengths. In some embodiments, any of the peptide tags disclosed herein may include one or more additional amino acids (e.g., 1, 2, 3, 5, 6, 7, 8, 9, 10, or more amino acids) at the N-terminus and/or C-terminus, so long as the function of the peptide tag remains intact. For example, a myc tag having the amino acid sequence EQKLISEEDL (SEQ ID NO: 138) can include one or more additional amino acids (e.g., at the N-terminus and/or the C-terminus of the peptide tag), while still retaining the ability to be bound by an antibody (e.g., 9E10).

Exemplary Embodiments of Single-Chain Chimeric Polypeptides—Type A

In some embodiments of any of the single-chain chimeric polypeptides described herein, the first target-binding domain and/or the second target-binding domain can independently bind specifically to CD3 (e.g., human CD3) or CD28 (e.g., human CD28). In some embodiments, the first target-binding domain binds specifically to CD3 (e.g., human CD3) and the second target-binding domain binds specifically to CD28 (e.g., human CD28). In some embodiments, the first target-binding domain binds specifically to CD28 (e.g., human CD28) and the second target-binding domain binds specifically to CD3 (e.g., human CD3).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, one or both of the first target-binding domain and the second target-binding domain is an antigen-binding domain. In some embodiments of these single-chain chimeric polypeptides, the first target-binding domain and the second target-binding domain are each an antigen-binding domain (e.g., any of the exemplary antigen-binding domains described herein). In some embodiments of these single-chain chimeric polypeptides, the antigen-binding domain includes a scFv or a single domain antibody.

A non-limiting example of an scFv that binds specifically to CD3 can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 151)

QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINRGGGGSGGGGSGGGGSQVQLQQSGAELARPGASVKMSCKASGYT

-continued

FTRYTMHWVKQRPGQGLEWIGYINPSRGYTNYNQKFKDKATLTTDKSSST

AYMQLSSLTSEDSAVYYCARYYDDHYCLDYWGQGTTLTVSS.

In some embodiments, an scFv that binds specifically to CD3 can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 152)
CAGATCGTGCTGACCCAAAGCCCCGCCATCATGAGCGCTAGCCCCGGTGA

GAAGGTGACCATGACATGCTCCGCTTCCAGCTCCGTGTCCTACATGAACT

GGTATCAGCAGAAAAGCGGAACCAGCCCCAAAAGGTGGATCTACGACACC

AGCAAGCTGGCCTCCGGAGTGCCCGCTCATTTCCGGGGCTCTGGATCCGG

CACCAGCTACTCTTTAACCATTTCCGGCATGGAAGCTGAAGACGCTGCCA

CCTACTATTGCCAGCAATGGAGCAGCAACCCCTTCACATTCGGATCTGGC

ACCAAGCTCGAAATCAATCGTGGAGGAGGTGGCAGCGGCGGCGGTGGATC

CGGCGGAGGAGGAAGCCAAGTTCAACTCCAGCAGAGCGGCGCTGAACTGG

CCCGGCCCGGCGCCTCCGTCAAGATGAGCTGCAAGGCTTCCGGCTATACA

TTTACTCGTTACACAATGCATTGGGTCAAGCAGAGGCCCGGTCAAGGTTT

AGAGTGGATCGGATATATCAACCCTTCCCGGGGCTACACCAACTATAACC

AAAAGTTCAAGGATAAAGCCACTTTAACCACTGACAAGAGCTCCTCCACC

GCCTACATGCAGCTGTCCTCTTTAACCAGCGAGGACTCCGCTGTTTACTA

CTGCGCTAGGTATTACGACGACCACTACTGTTTAGACTATTGGGGACAAG

GTACCACTTTAACCGTCAGCAGC.

A non-limiting example of an scFv that binds specifically to CD28 can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 153)
VQLQQSGPELVKPGASVKMSCKASGYTFTSYVIQWVKQKPGQGLEWIGSI

NPYNDYTKYNEKFKGKATLTSDKSSITAYMEFSSLTSEDSALYYCARWGD

GNYWGRGTTLTVSSGGGGSGGGGSGGGGSDIEMTQSPAIMSASLGERVTM

TCTASSSVSSSYFHWYQQKPGSSPKLCIYSTSNLASGVPPRFSGSGSTSY

SLTISSMEAEDAATYFCHQYHRSPTFGGGTKLETKR.

In some embodiments, an scFv that binds specifically to CD28 can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 154)
GTCCAGCTGCAGCAGAGCGGACCCGAACTCGTGAAACCCGGTGCTTCCGT

GAAAATGTCTTGTAAGGCCAGCGGATACACCTTCACCTCCTATGTGATCC

AGTGGGTCAAACAGAAGCCCGGACAAGGTCTCGAGTGGATCGGCAGCATC

AACCCTTACAACGACTATACCAAATACAACGAGAAGTTTAAGGGAAAGGC

TACTTTAACCTCCGACAAAAGCTCCATCACAGCCTACATGGAGTTCAGCT

CTTTAACATCCGAGGACAGCGCTCTGTACTATTGCGCCCGGTGGGGCGAC

GGCAATTACTGGGGACGGGGCACAACACTGACCGTGAGCAGCGGAGGCGG

AGGCTCCGGCGGAGGCGGATCTGGCGGTGGCGGCTCCGACATCGAGATGA

CCCAGTCCCCCGCTATCATGTCCGCCTCTTTAGGCGAGCGGGTCACAATG

ACTTGTACAGCCTCCTCCAGCGTCTCCTCCTCCTACTTCCATTGGTACCA

ACAGAAACCCGGAAGCTCCCCTAAACTGTGCATCTACAGCACCAGCAATC

TCGCCAGCGGCGTGCCCCCTAGGTTTTCCGGAAGCGGAAGCACCAGCTAC

TCTTTAACCATCTCCTCCATGGAGGCTGAGGATGCCGCCACCTACTTTTG

TCACCAGTACCACCGGTCCCCCACCTTCGGAGGCGGCACCAAACTGGAGA

CAAAGAGG.

In some embodiments of these single-chain chimeric polypeptides, the first target-binding domain and/or the second target-binding domain is a soluble receptor (e.g., a soluble CD28 receptor or a soluble CD3 receptor). In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 155)
QIVLTQSPAIMSASPGEKVTMTCSASSSVSYMNWYQQKSGTSPKRWIYDT

SKLASGVPAHFRGSGSGTSYSLTISGMEAEDAATYYCQQWSSNPFTFGSG

TKLEINRGGGGSGGGGSGGGGSQVQLQQSGAELARPGASVKMSCKASGYT

FTRYTMHWVKQRPGQGLEWIGYINPSRGYTNYNQKFKDKATLTTDKSSST

AYMQLSSLTSEDSAVYYCARYYDDHYCLDYWGQGTTLTVSSSGTTNTVAA

YNLTWKSTNFKTILEWEPKPVNQVYTVQISTKSGDWKSKCFYTTDTECDL

TDEIVKDVKQTYLARVFSYPAGNVESTGSAGEPLYENSPEFTPYLETNLG

QPTIQSFEQVGTKVNVTVEDERTLVRRNNTFLSLRDVFGKDLIYTLYYWK

SSSSGKKTAKTNTNEFLIDVDKGENYCFSVQAVIPSRTVNRKSTDSPVEC

MGQEKGEFREVQLQQSGPELVKPGASVKMSCKASGYTFTSYVIQWVKQKP

GQGLEWIGSINPYNDYTKYNEKFKGKATLTSDKSSITAYMEFSSLTSEDS

ALYYCARWGDGNYWGRGTTLTVSSGGGGSGGGGSGGGGSDIEMTQSPAIM

SASLGERVTMTCTASSSVSSSYFHWYQQKPGSSPKLCIYSTSNLASGVPP

RFSGSGSTSYSLTISSMEAEDAATYFCHQYHRSPTFGGGTKLETKR.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 156)

```
CAGATCGTGCTGACCCAAAGCCCCGCCATCATGAGCGCTAGCCCCGGTGA
GAAGGTGACCATGACATGCTCCGCTTCCAGCTCCGTGTCCTACATGAACT
GGTATCAGCAGAAAAGCGGAACCAGCCCCAAAAGGTGGATCTACGACACC
AGCAAGCTGGCCTCCGGAGTGCCCGCTCATTTCCGGGGCTCTGGATCCGG
CACCAGCTACTCTTTAACCATTTCCGGCATGGAAGCTGAAGACGCTGCCA
CCTACTATTGCCAGCAATGGAGCAGCAACCCCTTCACATTCGGATCTGGC
ACCAAGCTCGAAATCAATCGTGGAGGAGGTGGCAGCGGCGGCGGTGGATC
CGGCGGAGGAGGAAGCCAAGTTCAACTCCAGCAGAGCGGCGCTGAACTGG
CCCGGCCCGGCGCCTCCGTCAAGATGAGCTGCAAGGCTTCCGGCTATACA
TTTACTCGTTACACAATGCATTGGGTCAAGCAGAGGCCCGGTCAAGGTTT
AGAGTGGATCGGATATATCAACCCTTCCCGGGGCTACACCAACTATAACC
AAAAGTTCAAGGATAAAGCCACTTTAACCACTGACAAGAGCTCCTCCACC
GCCTACATGCAGCTGTCCTCTTTAACCAGCGAGGACTCCGCTGTTTACTA
CTGCGCTAGGTATTACGACGACCACTACTGTTTAGACTATTGGGGACAAG
GTACCACTTTAACCGTCAGCAGCTCCGGCACCACCAATACCGTGGCCGCT
TATAACCTCACATGGAAGAGCACCAACTTCAAGACAATTCTGGAATGGGA
ACCCAAGCCCGTCAATCAAGTTTACACCGTGCAGATCTCCACCAAATCCG
GAGACTGGAAGAGCAAGTGCTTCTACACAACAGACACCGAGTGTGATTTA
ACCGACGAAATCGTCAAGGACGTCAAGCAAACCTATCTGGCTCGGGTCTT
TTCCTACCCCGCTGGCAATGTCGAGTCCACCGGCTCCGCTGGCGAGCCTC
TCTACGAGAATTCCCCCGAATTCACCCCTTATTTAGAGACCAATTTAGGC
CAGCCTACCATCCAGAGCTTCGAGCAAGTTGGCACCAAGGTGAACGTCAC
CGTCGAGGATGAAAGGACTTTAGTGCGGCGGAATAACACATTTTTATCCC
TCCGGGATGTGTTCGGCAAAGACCTCATCTACACACTGTACTATTGGAAG
TCCAGCTCCTCCGGCAAAAAGACCGCTAAGACCAACACCAACGAGTTTTT
AATTGACGTGGACAAAGGCGAGAACTACTGCTTCAGCGTGCAAGCCGTGA
TCCCTTCTCGTACCGTCAACCGGAAGAGCACAGATTCCCCCGTTGAGTGC
ATGGGCCAAGAAAAGGGCGAGTTCCGGGAGGTCCAGCTGCAGCAGAGCGG
ACCCGAACTCGTGAAACCCGGTGCTTCCGTGAAAATGTCTTGTAAGGCCA
GCGGATACACCTTCACCTCCTATGTGATCCAGTGGGTCAAACAGAAGCCC
GGACAAGGTCTCGAGTGGATCGGCAGCATCAACCCTTACAACGACTATAC
CAAATACAACGAGAAGTTTAAGGGAAAGGCTACTTTAACCTCCGACAAAA
GCTCCATCACAGCCTACATGGAGTTCAGCTCTTTAACATCCGAGGACAGC
GCTCTGTACTATTGCGCCCGGTGGGGCGACGGCAATTACTGGGGACGGGG
CACAACACTGACCGTGAGCAGCGGAGGCGGAGGCTCCGGCGGAGGCGGAT
CTGGCGGTGGCGGCTCCGACATCGAGATGACCCAGTCCCCCGCTATCATG
TCCGCCTCTTTAGGCGAGCGGGTCACAATGACTTGTACAGCCTCCTCCAG
```

-continued

```
CGTCTCCTCCTCCTACTTCCATTGGTACCAACAGAAACCCGGAAGCTCCC
CTAAACTGTGCATCTACAGCACCAGCAATCTCGCCAGCGGCGTGCCCCCT
AGGTTTTCCGGAAGCGGAAGCACCAGCTACTCTTTAACCATCTCCTCCAT
GGAGGCTGAGGATGCCGCCACCTACTTTTGTCACCAGTACCACCGGTCCC
CCACCTTCGGAGGCGGCACCAAACTGGAGACAAAGAGG.
```

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 157)

```
MKWVTFISLLFLFSSAYSQIVLTQSPAIMSASPGEKVTMTCSASSSVSYM
NWYQQKSGTSPKRWIYDTSKLASGVPAHFRGSGSGTSYSLTISGMEAEDA
ATYYCQQWSSNPFTFGSGTKLEINRGGGGSGGGGSGGGGSQVQLQQSGAE
LARPGASVKMSCKASGYTFTRYTMHWVKQRPGQGLEWIGYINPSRGYTNY
NQKFKDKATLTTDKSSSTAYMQLSSLTSEDSAVYYCARYYDDHYCLDYWG
QGTTLTVSSSGTTNTVAAYNLTWKSTNFKTILEWEPKPVNQVYTVQISTK
SGDWKSKCFYTTDTECDLTDEIVKDVKQTYLARVFSYPAGNVESTGSAGE
PLYENSPEFTPYLETNLGQPTIQSFEQVGTKVNVTVEDERTLVRRNNTFL
SLRDVFGKDLIYTLYYWKSSSSGKKTAKTNTNEFLIDVDKGENYCFSVQA
VIPSRTVNRKSTDSPVECMGQEKGEFREVQLQQSGPELVKPGASVKMSCK
ASGYTFTSYVIQWVKQKPGQGLEWIGSINPYNDYTKYNEKFKGKATLTSD
KSSITAYMEFSSLTSEDSALYYCARWGDGNYWGRGTTLTVSSGGGGSGGG
GSGGGGSDIEMTQSPAIMSASLGERVTMTCTASSSVSSSYFHWYQQKPGS
SPKLCIYSTSNLASGVPPRFSGSGSGTSYSLTISSMEAEDAATYFCHQYHR
SPTFGGGTKLETKR.
```

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 158)

```
ATGAAGTGGGTGACCTTCATCAGCTTATTATTTTTATTCAGCTCCGCCTA
TTCCCAGATCGTGCTGACCCAAAGCCCCGCCATCATGAGCGCTAGCCCCG
GTGAGAAGGTGACCATGACATGCTCCGCTTCCAGCTCCGTGTCCTACATG
AACTGGTATCAGCAGAAAAGCGGAACCAGCCCCAAAAGGTGGATCTACGA
CACCAGCAAGCTGGCCTCCGGAGTGCCCGCTCATTTCCGGGGCTCTGGAT
CCGGCACCAGCTACTCTTTAACCATTTCCGGCATGGAAGCTGAAGACGCT
GCCACCTACTATTGCCAGCAATGGAGCAGCAACCCCTTCACATTCGGATC
TGGCACCAAGCTCGAAATCAATCGTGGAGGAGGTGGCAGCGGCGGCGGTG
```

-continued

GATCCGGCGGAGGAGGAAGCCAAGTTCAACTCCAGCAGAGCGGCGCTGAA

CTGGCCCGGCCCGGCGCCTCCGTCAAGATGAGCTGCAAGGCTTCCGGCTA

TACATTTACTCGTTACACAATGCATTGGGTCAAGCAGAGGCCCGGTCAAG

GTTTAGAGTGGATCGGATATATCAACCCTTCCCGGGGCTACACCAACTAT

AACCAAAAGTTCAAGGATAAAGCCACTTTAACCACTGACAAGAGCTCCTC

CACCGCCTACATGCAGCTGTCCTCTTTAACCAGCGAGGACTCCGCTGTTT

ACTACTGCGCTAGGTATTACGACGACCACTACTGTTTAGACTATTGGGGA

CAAGGTACCACTTTAACCGTCAGCAGCTCCGGCACCACCAATACCGTGGC

CGCTTATAACCTCACATGGAAGAGCACCAACTTCAAGACAATTCTGGAAT

GGGAACCCAAGCCCGTCAATCAAGTTTACACCGTGCAGATCTCCACCAAA

TCCGGAGACTGGAAGAGCAAGTGCTTCTACACAACAGACACCGAGTGTGA

TTTAACCGACGAAATCGTCAAGGACGTCAAGCAAACCTATCTGGCTCGGG

TCTTTTCCTACCCCGCTGGCAATGTCGAGTCCACCGGCTCCGCTGGCGAG

CCTCTCTACGAGAATTCCCCCGAATTCACCCCTTATTTAGAGACCAATTT

AGGCCAGCCTACCATCCAGAGCTTCGAGCAAGTTGGCACCAAGGTGAACG

TCACCGTCGAGGATGAAAGGACTTTAGTGCGGCGGAATAACACATTTTTA

TCCCTCCGGGATGTGTTCGGCAAAGACCTCATCTACACACTGTACTATTG

GAAGTCCAGCTCCTCCGGCAAAAAGACCGCTAAGACCAACACCAACGAGT

TTTTAATTGACGTGGACAAAGGCGAGAACTACTGCTTCAGCGTGCAAGCC

GTGATCCCTTCTCGTACCGTCAACCGGAAGAGCACAGATTCCCCCGTTGA

GTGCATGGGCCAAGAAAAGGGCGAGTTCCGGGAGGTCCAGCTGCAGCAGA

GCGGACCCGAACTCGTGAAACCCGGTGCTTCCGTGAAAATGTCTTGTAAG

GCCAGCGGATACACCTTCACCTCCTATGTGATCCAGTGGGTCAAACAGAA

GCCCGGACAAGGTCTCGAGTGGATCGGCAGCATCAACCCTTACAACGACT

ATACCAAATACAACGAGAAGTTTAAGGGAAAGGCTACTTTAACCTCCGAC

AAAAGCTCCATCACAGCCTACATGGAGTTCAGCTCTTTAACATCCGAGGA

CAGCGCTCTGTACTATTGCGCCCGGTGGGGCGACGGCAATTACTGGGGAC

GGGGCACAACACTGACCGTGAGCAGCGGAGGCGGAGGCTCCGGCGGAGGC

GGATCTGGCGGTGGCGGCTCCGACATCGAGATGACCCAGTCCCCCGCTAT

CATGTCCGCCTCTTTAGGCGAGCGGGTCACAATGACTTGTACAGCCTCCT

CCAGCGTCTCCTCCTCCTACTTCCATTGGTACCAACAGAAACCCGGAAGC

TCCCCTAAACTGTGCATCTACAGCACCAGCAATCTCGCCAGCGGCGTGCC

CCCTAGGTTTTCCGGAAGCGGAAGCACCAGCTACTCTTTAACCATCTCCT

CCATGGAGGCTGAGGATGCCGCCACCTACTTTTGTCACCAGTACCACCGG

TCCCCCACCTTCGGAGGCGGCACCAAACTGGAGACAAAGAGG.

Exemplary Embodiments of Single-Chain Chimeric Polypeptides—Type B

In some embodiments of any of the single-chain chimeric polypeptides described herein, the first target-binding domain and/or the second target-binding domain can independently bind specifically to an IL-2 receptor (e.g., human IL-2 receptor).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, the first target-binding domain and the second target-binding domain is a soluble human IL-2 protein. A non-limiting example of an IL-2 protein that binds specifically to an IL-2 receptor can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 78)

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLT.

In some embodiments, an IL-2 protein that binds specifically to an IL-2 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 159)

GCACCTACTTCAAGTTCTACAAAGAAAACACAGCTACAACTGGAGCATTT

ACTGCTGGATTTACAGATGATTTTGAATGGAATTAATAATTACAAGAATC

CCAAACTCACCAGGATGCTCACATTTAAGTTTTACATGCCCAAGAAGGCC

ACAGAACTGAAACATCTTCAGTGTCTAGAAGAAGAACTCAAACCTCTGGA

GGAAGTGCTAAATTTAGCTCAAAGCAAAAACTTTCACTTAAGACCCAGGG

ACTTAATCAGCAATATCAACGTAATAGTTCTGGAACTAAAGGGATCTGAA

ACAACATTCATGTGTGAATATGCTGATGAGACAGCAACCATTGTAGAATT

TCTGAACAGATGGATTACCTTTTGTCAAAGCATCATCTCAACACTAACT.

In some embodiments, an IL-2 protein that binds specifically to an IL-2 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 160)

GCCCCCACCTCCTCCTCCACCAAGAAGACCCAGCTGCAGCTGGAGCATTT

ACTGCTGGATTTACAGATGATTTTAAACGGCATCAACAACTACAAGAACC

-continued

CCAAGCTGACTCGTATGCTGACCTTCAAGTTCTACATGCCCAAGAAGGCC

ACCGAGCTGAAGCATTTACAGTGTTTAGAGGAGGAGCTGAAGCCCCTCGA

GGAGGTGCTGAATTTAGCCCAGTCCAAGAATTTCCATTTAAGGCCCCGGG

ATTTAATCAGCAACATCAACGTGATCGTTTTAGAGCTGAAGGGCTCCGAG

ACCACCTTCATGTGCGAGTACGCCGACGAGACCGCCACCATCGTGGAGTT

TTTAAATCGTTGGATCACCTTCTGCCAGTCCATCATCTCCACTTTAACC.

In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 161)

APTSSSTKKTQLQLEHLLLDLQMILNGINNYKNPKLTRMLTFKFYMPKKA

TELKHLQCLEEELKPLEEVLNLAQSKNFHLRPRDLISNINVIVLELKGSE

TTFMCEYADETATIVEFLNRWITFCQSIISTLTSGTTNTVAAYNLTWKST

NFKTILEWEPKPVNQVYTVQISTKSGDWKSKCFYTTDTECDLTDEIVKDV

KQTYLARVFSYPAGNVESTGSAGEPLYENSPEFTPYLETNLGQPTIQSFE

QVGTKVNVTVEDERTLVRRNNTFLSLRDVFGKDLIYTLYYWKSSSSGKKT

AKTNTNEFLIDVDKGENYCFSVQAVIPSRTVNRKSTDSPVECMGQEKGEF

REAPTSSSTKKTQLQLEHLLLDLQMILNGINNYKNPKLTRMLTFKFYMPK

KATELKHLQCLEEELKPLEEVLNLAQSKNFHLRPRDLISNINVIVLELKG

SETTFMCEYADETATIVEFLNRWITFCQSIISTLT.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)

GCCCCCACCTCCTCCTCCACCAAGAAGACCCAGCTGCAGCTGGAGCATTT

ACTGCTGGATTTACAGATGATTTTAAACGGCATCAACAACTACAAGAACC

CCAAGCTGACTCGTATGCTGACCTTCAAGTTCTACATGCCCAAGAAGGCC

ACCGAGCTGAAGCATTTACAGTGTTTAGAGGAGGAGCTGAAGCCCCTCGA

GGAGGTGCTGAATTTAGCCCAGTCCAAGAATTTCCATTTAAGGCCCCGGG

ATTTAATCAGCAACATCAACGTGATCGTTTTAGAGCTGAAGGGCTCCGAG

ACCACCTTCATGTGCGAGTACGCCGACGAGACCGCCACCATCGTGGAGTT

TTTAAATCGTTGGATCACCTTCTGCCAGTCCATCATCTCCACTTTAACCA

GCGGCACAACCAACACAGTCGCTGCCTATAACCTCACTTGGAAGAGCACC

AACTTCAAAACCATCCTCGAATGGGAACCCAAACCCGTTAACCAAGTTTA

-continued

CACCGTGCAGATCAGCACCAAGTCCGGCGACTGGAAGTCCAAATGTTTCT

ATACCACCGACACCGAGTGCGATCTCACCGATGAGATCGTGAAAGATGTG

AAACAGACCTACCTCGCCCGGGTGTTTAGCTACCCCGCCGGCAATGTGGA

GAGCACTGGTTCCGCTGGCGAGCCTTTATACGAGAACAGCCCCGAATTTA

CCCCTTACCTCGAGACCAATTTAGGACAGCCCACCATCCAAAGCTTTGAG

CAAGTTGGCACAAAGGTGAATGTGACAGTGGAGGACGAGCGGACTTTAGT

GCGGCGGAACAACACCTTTCTCAGCCTCCGGGATGTGTTCGGCAAAGATT

TAATCTACACACTGTATTACTGGAAGTCCTCTTCCTCCGGCAAGAAGACA

GCTAAAACCAACACAAACGAGTTTTTAATCGACGTGGATAAAGGCGAAAA

CTACTGTTTCAGCGTGCAAGCTGTGATCCCCTCCCGGACCGTGAATAGGA

AAAGCACCGATAGCCCCGTTGAGTGCATGGGCCAAGAAAAGGGCGAGTTC

CGGGAGGCACCTACTTCAAGTTCTACAAAGAAAACACAGCTACAACTGGA

GCATTTACTGCTGGATTTACAGATGATTTTGAATGGAATTAATAATTACA

AGAATCCCAAACTCACCAGGATGCTCACATTTAAGTTTTACATGCCCAAG

AAGGCCACAGAACTGAAACATCTTCAGTGTCTAGAAGAAGAACTCAAACC

TCTGGAGGAAGTGCTAAATTTAGCTCAAAGCAAAAACTTTCACTTAAGAC

CCAGGGACTTAATCAGCAATATCAACGTAATAGTTCTGGAACTAAAGGGA

TCTGAAACAACATTCATGTGTGAATATGCTGATGAGACAGCAACCATTGT

AGAATTTCTGAACAGATGGATTACCTTTTGTCAAAGCATCATCTCAACAC

TAACT.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)

MKWVTFISLLFLFSSAYSAPTSSSTKKTQLQLEHLLLDLQMILNGINNYK

NPKLTRMLTFKFYMPKKATELKHLQCLEEELKPLEEVLNLAQSKNFHLRP

RDLISNINVIVLELKGSETTFMCEYADETATIVEFLNRWITFCQSIISTL

TSGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSPE

FTPYLETNLGQPTIQSFEQVGTKVNVTVEDERTLVRRNNTFLSLRDVFGK

DLIYTLYYWKSSSSGKKTAKTNTNEFLIDVDKGENYCFSVQAVIPSRTVN

RKSTDSPVECMGQEKGEFREAPTSSSTKKTQLQLEHLLLDLQMILNGINN

YKNPKLTRMLTFKFYMPKKATELKHLQCLEEELKPLEEVLNLAQSKNFHL

RPRDLISNINVIVLELKGSETTFMCEYADETATIVEFLNRWITFCQSIIS

TLT.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)

ATGAAGTGGGTGACCTTCATCAGCCTGCTGTTCCTGTTCTCCAGCGCCTA

CTCCGCCCCCACCTCCTCCTCCACCAAGAAGACCCAGCTGCAGCTGGAGC

ATTTACTGCTGGATTTACAGATGATTTTAAACGGCATCAACAACTACAAG

AACCCCAAGCTGACTCGTATGCTGACCTTCAAGTTCTACATGCCCAAGAA

GGCCACCGAGCTGAAGCATTTACAGTGTTTAGAGGAGGAGCTGAAGCCCC

TCGAGGAGGTGCTGAATTTAGCCCAGTCCAAGAATTTCCATTTAAGGCCC

CGGGATTTAATCAGCAACATCAACGTGATCGTTTTAGAGCTGAAGGGCTC

CGAGACCACCTTCATGTGCGAGTACGCCGACGAGACCGCCACCATCGTGG

AGTTTTTAAATCGTTGGATCACCTTCTGCCAGTCCATCATCTCCACTTTA

ACCAGCGGCACAACCAACACAGTCGCTGCCTATAACCTCACTTGGAAGAG

CACCAACTTCAAAACCATCCTCGAATGGGAACCCAAACCCGTTAACCAAG

TTTACACCGTGCAGATCAGCACCAAGTCCGGCGACTGGAAGTCCAAATGT

TTCTATACCACCGACACCGAGTGCGATCTCACCGATGAGATCGTGAAAGA

TGTGAAACAGACCTACCTCGCCCGGGTGTTTAGCTACCCCGCCGGCAATG

TGGAGAGCACTGGTTCCGCTGGCGAGCCTTTATACGAGAACAGCCCCGAA

TTTACCCCTTACCTCGAGACCAATTTAGGACAGCCCACCATCCAAAGCTT

TGAGCAAGTTGGCACAAAGGTGAATGTGACAGTGGAGGACGAGCGGACTT

TAGTGCGGCGGAACAACACCTTTCTCAGCCTCCGGGATGTGTTCGGCAAA

GATTTAATCTACACACTGTATTACTGGAAGTCCTCTTCCTCCGGCAAGAA

GACAGCTAAAACCAACACAAACGAGTTTTTAATCGACGTGGATAAAGGCG

AAAACTACTGTTTCAGCGTGCAAGCTGTGATCCCCTCCCGGACCGTGAAT

AGGAAAAGCACCGATAGCCCCGTTGAGTGCATGGGCCAAGAAAAGGGCGA

GTTCCGGGAGGCACCTACTTCAAGTTCTACAAAGAAAACACAGCTACAAC

TGGAGCATTTACTGCTGGATTTACAGATGATTTTGAATGGAATTAATAAT

TACAAGAATCCCAAACTCACCAGGATGCTCACATTTAAGTTTTACATGCC

CAAGAAGGCCACAGAACTGAAACATCTTCAGTGTCTAGAAGAAGAACTCA

AACCTCTGGAGGAAGTGCTAAATTTAGCTCAAAGCAAAAACTTTCACTTA

AGACCCAGGGACTTAATCAGCAATATCAACGTAATAGTTCTGGAACTAAA

GGGATCTGAAACAACATTCATGTGTGAATATGCTGATGAGACAGCAACCA

TTGTAGAATTTCTGAACAGATGGATTACCTTTTGTCAAAGCATCATCTCA

ACACTAACT.

Exemplary Embodiments of Single-Chain Chimeric Polypeptides—Type C

In some embodiments of any of the single-chain chimeric polypeptides described herein, the first target-binding domain and/or the second target-binding domain can independently bind specifically to an IL-15 receptor (e.g., a human IL-15 receptor).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, the first target-binding domain and the second target-binding domain is a soluble human IL-15 protein. A non-limiting example of an IL-15 protein that binds specifically to an IL-15 receptor can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 82)

NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS.

In some embodiments, an IL-15 protein that binds specifically to an IL-15 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 165)

AACTGGGTGAACGTGATCAGCGATTTAAAGAAGATCGAGGATTTAATCCA

GAGCATGCACATCGACGCCACTCTGTACACTGAGAGCGACGTGCACCCTA

GCTGCAAGGTGACTGCCATGAAGTGCTTTTTACTGGAGCTGCAAGTTATC

TCTTTAGAGAGCGGCGATGCCAGCATCCACGACACTGTGGAGAATTTAAT

CATTTTAGCCAACAACTCTTTAAGCAGCAACGGCAACGTGACAGAGAGCG

GCTGCAAGGAGTGCGAGGAGCTGGAGGAGAAGAACATCAAGGAGTTTTTA

CAGAGCTTCGTGCACATCGTGCAGATGTTCATCAACACTAGC.

In some embodiments, an IL-15 protein that binds specifically to an IL-15 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 166)

AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

-continued

GCTGCAAGGAGTGCGAAGAGCTGGAGGAGAAGAACATCAAGGAGTTTCTG

CAATCCTTTGTGCACATTGTCCAGATGTTCATCAATACCTCC.

In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 167)

NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTSSGTTNTVAAYNLTWKSTNFKTILEWEPKPVNQVYTV

QISTKSGDWKSKCFYTTDTECDLTDEIVKDVKQTYLARVFSYPAGNVEST

GSAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENYC

FSVQAVIPSRTVNRKSTDSPVECMGQEKGEFRENWVNVISDLKKIEDLIQ

SMHIDATLYTESDVHPSCKVTAMKCFLLELQVISLESGDASIHDTVENLI

ILANNSLSSNGNVTESGCKECEELEEKNIKEFLQSFVHIVQMFINTS.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 168)

AACTGGGTGAACGTGATCAGCGATTTAAAGAAGATCGAGGATTTAATCCA

GAGCATGCACATCGACGCCACTCTGTACACTGAGAGCGACGTGCACCCTA

GCTGCAAGGTGACTGCCATGAAGTGCTTTTTACTGGAGCTGCAAGTTATC

TCTTTAGAGAGCGGCGATGCCAGCATCCACGACACTGTGGAGAATTTAAT

CATTTTAGCCAACAACTCTTTAAGCAGCAACGGCAACGTGACAGAGAGCG

GCTGCAAGGAGTGCGAGGAGCTGGAGGAGAAGAACATCAAGGAGTTTTTA

CAGAGCTTCGTGCACATCGTGCAGATGTTCATCAACACTAGCAGCGGCAC

AACCAACACAGTCGCTGCCTATAACCTCACTTGGAAGAGCACCAACTTCA

AAACCATCCTCGAATGGGAACCCAAACCCGTTAACCAAGTTTACACCGTG

CAGATCAGCACCAAGTCCGGCGACTGGAAGTCCAAATGTTTCTATACCAC

CGACACCGAGTGCGATCTCACCGATGAGATCGTGAAAGATGTGAAACAGA

CCTACCTCGCCCGGGTGTTTAGCTACCCCGCCGGCAATGTGGAGAGCACT

GGTTCCGCTGGCGAGCCTTTATACGAGAACAGCCCCGAATTTACCCCTTA

CCTCGAGACCAATTTAGGACAGCCCACCATCCAAAGCTTTGAGCAAGTTG

GCACAAAGGTGAATGTGACAGTGGAGGACGAGCGGACTTTAGTGCGGCGG

-continued

AACAACACCTTTCTCAGCCTCCGGGATGTGTTCGGCAAAGATTTAATCTA

CACACTGTATTACTGGAAGTCCTCTTCCTCCGGCAAGAAGACAGCTAAAA

CCAACACAAACGAGTTTTTAATCGACGTGGATAAAGGCGAAAACTACTGT

TTCAGCGTGCAAGCTGTGATCCCCTCCCGGACCGTGAATAGGAAAAGCAC

CGATAGCCCCGTTGAGTGCATGGGCCAAGAAAAGGGCGAGTTCCGGGAGA

ACTGGGTGAACGTCATCAGCGATTTAAAGAAGATCGAAGATTTAATTCAG

TCCATGCATATCGACGCCACTTTATACACAGAATCCGACGTGCACCCCTC

TTGTAAGGTGACCGCCATGAAATGTTTTTACTGGAGCTGCAAGTTATCT

CTTTAGAGAGCGGAGACGCTAGCATCCACGACACCGTGGAGAATTTAATC

ATTTTAGCCAATAACTCTTTATCCAGCAACGGCAACGTGACAGAGTCCGG

CTGCAAGGAGTGCGAAGAGCTGGAGGAGAAGAACATCAAGGAGTTTCTGC

AATCCTTTGTGCACATTGTCCAGATGTTCATCAATACCTCC.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 169)

MKWVTFISLLFLFSSAYSNWVNVISDLKKIEDLIQSMHIDATLYTESDVH

PSCKVTAMKCFLLELQVISLESGDASIHDTVENLIILANNSLSSNGNVTE

SGCKECEELEEKNIKEFLQSFVHIVQMFINTSSGTTNTVAAYNLTWKSTN

FKTILEWEPKPVNQVYTVQISTKSGDWKSKCFYTTDTECDLTDEIVKDVK

QTYLARVFSYPAGNVESTGSAGEPLYENSPEFTPYLETNLGQPTIQSFEQ

VGTKVNVTVEDERTLVRRNNTFLSLRDVFGKDLIYTLYYWKSSSSGKKTA

KTNTNEFLIDVDKGENYCFSVQAVIPSRTVNRKSTDSPVECMGQEKGEFR

ENWVNVISDLKKIEDLIQSMIIIDATLYTESDVHPSCKVTAMKCFLLELQ

VISLESGDASIHDTVENLIILANNSLSSNGNVTESGCKECEELEEKNIKE

FLQSFVHIVQMFINTS.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 170)

ATGAAGTGGGTGACCTTCATCAGCCTGCTGTTCCTGTTCTCCAGCGCCTA

CTCCAACTGGGTGAACGTGATCAGCGATTTAAAGAAGATCGAGGATTTAA

TCCAGAGCATGCACATCGACGCCACTCTGTACACTGAGAGCGACGTGCAC

CCTAGCTGCAAGGTGACTGCCATGAAGTGCTTTTTACTGGAGCTGCAAGT

TATCTCTTTAGAGAGCGGCGATGCCAGCATCCACGACACTGTGGAGAATT

TAATCATTTTAGCCAACAACTCTTTAAGCAGCAACGGCAACGTGACAGAG

-continued

AGCGGCTGCAAGGAGTGCGAGGAGCTGGAGGAGAAGAACATCAAGGAGTT

TTTACAGAGCTTCGTGCACATCGTGCAGATGTTCATCAACACTAGCAGCG

GCACAACCAACACAGTCGCTGCCTATAACCTCACTTGGAAGAGCACCAAC

TTCAAAACCATCCTCGAATGGGAACCCAAACCCGTTAACCAAGTTTACAC

CGTGCAGATCAGCACCAAGTCCGGCGACTGGAAGTCCAAATGTTTCTATA

CCACCGACACCGAGTGCGATCTCACCGATGAGATCGTGAAAGATGTGAAA

CAGACCTACCTCGCCCGGGTGTTTAGCTACCCCGCCGGCAATGTGGAGAG

CACTGGTTCCGCTGGCGAGCCTTTATACGAGAACAGCCCCGAATTTACCC

CTTACCTCGAGACCAATTTAGGACAGCCCACCATCCAAAGCTTTGAGCAA

GTTGGCACAAAGGTGAATGTGACAGTGGAGGACGAGCGGACTTTAGTGCG

GCGGAACAACACCTTTCTCAGCCTCCGGGATGTGTTCGGCAAAGATTTAA

TCTACACACTGTATTACTGGAAGTCCTCTTCCTCCGGCAAGAAGACAGCT

AAAACCAACACAAACGAGTTTTTAATCGACGTGGATAAAGGCGAAAACTA

CTGTTTCAGCGTGCAAGCTGTGATCCCCTCCCGGACCGTGAATAGGAAAA

GCACCGATAGCCCCGTTGAGTGCATGGGCCAAGAAAAGGGCGAGTTCCGG

GAGAACTGGGTGAACGTCATCAGCGATTTAAAGAAGATCGAAGATTTAAT

TCAGTCCATGCATATCGACGCCACTTTATACACAGAATCCGACGTGCACC

CCTCTTGTAAGGTGACCGCCATGAAATGTTTTTACTGGAGCTGCAAGTT

ATCTCTTTAGAGAGCGGAGACGCTAGCATCCACGACACCGTGGAGAATTT

AATCATTTTAGCCAATAACTCTTTATCCAGCAACGGCAACGTGACAGAGT

CCGGCTGCAAGGAGTGCGAAGAGCTGGAGGAGAAGAACATCAAGGAGTTT

CTGCAATCCTTTGTGCACATTGTCCAGATGTTCATCAATACCTCC.

Exemplary Multi-Chain Chimeric Polypeptides—Type A

In some embodiments of any of the multi-chain chimeric polypeptides described herein, the first target-binding domain and the second targeting-binding domain each independently bind specifically to a receptor of IL-18 or a receptor of IL-12. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is an agonistic antigen-binding domain. In some embodiments of these multi-chain chimeric polypeptides, the first target-binding domain and the second target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12.

In some embodiments of these multi-chain chimeric polypeptides, the first target-binding domain includes a soluble IL-18 (e.g., a soluble human IL-18).

In some embodiments of these multi-chain chimeric polypeptides, the soluble human IL-18 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 109)

YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

FFQRSVPGHDNKMQFESSSYEGYFLACEKERDLFKLILKKEDELGDRSIM

FTVQNED.

In some embodiments of these multi-chain chimeric polypeptides, the soluble human IL-18 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 171)

TACTTCGGCAAACTGGAATCCAAGCTGAGCGTGATCCGGAATTTAAACGA

CCAAGTTCTGTTTATCGATCAAGGTAACCGGCCTCTGTTCGAGGACATGA

-continued

CCGACTCCGATTGCCGGGACAATGCCCCCCGGACCATCTTCATTATCTCC

ATGTACAAGGACAGCCAGCCCCGGGGCATGGCTGTGACAATTAGCGTGAA

GTGTGAGAAAATCAGCACTTTATCTTGTGAGAACAAGATCATCTCCTTTA

AGGAAATGAACCCCCCCGATAACATCAAGGACACCAAGTCCGATATCATC

TTCTTCCAGCGGTCCGTGCCCGGTCACGATAACAAGATGCAGTTCGAATC

CTCCTCCTACGAGGGCTACTTTTTAGCTTGTGAAAAGGAGAGGGATTTAT

TCAAGCTGATCCTCAAGAAGGAGGACGAGCTGGGCGATCGTTCCATCATG

TTCACCGTCCAAAACGAGGAT.

In some embodiments of these multi-chain chimeric polypeptides, the second target-binding domain includes a soluble IL-12 (e.g., a soluble human IL-12). In some embodiments of these multi-chain chimeric polypeptides, the soluble human IL-15 includes a sequence of soluble human IL-12β (p40) and a sequence of soluble human IL-12α (p35). In some embodiments of these multi-chain chimeric polypeptides, the soluble IL-15 human IL-15 further includes a linker sequence (e.g., any of the exemplary linker sequences described herein) between the sequence of soluble IL-12β (p40) and the sequence of soluble human IL-12α (p35). In some examples of these multi-chain chimeric polypeptides, the linker sequence comprises GGGGSGGGGSGGGGS (SEQ ID NO: 102).

In some embodiments of these multi-chain chimeric polypeptides, the sequence of soluble human IL-12β (p40) comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 81)

IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS.

In some embodiments of these multi-chain chimeric polypeptides, the soluble human IL-12β (p40) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 172)

ATTTGGGAACTGAAGAAGGACGTCTACGTGGTCGAACTGGACTGGTATCC

CGATGCTCCCGGCGAAATGGTGGTGCTCACTTGTGACACCCCCGAAGAAG

ACGGCATCACTTGGACCCTCGATCAGAGCAGCGAGGTGCTGGGCTCCGGA

AAGACCCTCACAATCCAAGTTAAGGAGTTCGGAGACGCTGGCCAATACAC

-continued

ATGCCACAAGGGAGGCGAGGTGCTCAGCCATTCCTTATTATTATTACACA

AGAAGGAAGACGGAATCTGGTCCACCGACATTTTAAAAGATCAGAAGGAG

CCCAAGAATAAGACCTTTTTAAGGTGTGAGGCCAAAAACTACAGCGGTCG

TTTCACTTGTTGGTGGCTGACCACCATTTCCACCGATTTAACCTTCTCCG

TGAAAAGCAGCCGGGGAAGCTCCGACCCTCAAGGTGTGACATGTGGAGCC

GCTACCCTCAGCGCTGAGAGGGTTCGTGGCGATAACAAGGAATACGAGTA

CAGCGTGGAGTGCCAAGAAGATAGCGCTTGTCCCGCTGCCGAAGAATCTT

TACCCATTGAGGTGATGGTGGACGCCGTGCACAAACTCAAGTACGAGAAC

TACACCTCCTCCTTCTTTATCCGGGACATCATTAAGCCCGATCCTCCTAA

GAATTTACAGCTGAAGCCTCTCAAAAATAGCCGGCAAGTTGAGGTCTCTT

GGGAATATCCCGACACTTGGAGCACACCCCACAGCTACTTCTCTTTAACC

TTTTGTGTGCAAGTTCAAGGTAAAAGCAAGCGGGAGAAGAAAGACCGGGT

GTTTACCGACAAAACCAGCGCCACCGTCATCTGTCGGAAGAACGCCTCCA

TCAGCGTGAGGGCTCAAGATCGTTATTACTCCAGCAGCTGGTCCGAGTGG

GCCAGCGTGCCTTGTTCC.

In some embodiments of these multi-chain chimeric polypeptides, the soluble human IL-12α (p35) includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 80)

RNLPVATPDPGMFPCLHHSQNLLRAVSNMLQKARQTLEFYPCTSEEIDHED

ITKDKTSTVEACLPLELTKNESCLNSRETSFITNGSCLASRKTSFMMALCL

SSIYEDLKMYQVEFKTMNAKLLMDPKRQIFLDQNMLAVIDELMQALNFNSE

TVPQKSSLEEPDFYKTKIKLCILLHAFRIRAVTIDRVMSYLNAS.

In some embodiments of these multi-chain chimeric polypeptides, the soluble human IL-12α (p35) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 173)

CGTAACCTCCCCGTGGCTACCCCCGATCCCGGAATGTTCCCTTGTTTACAC

CACAGCCAGAATTTACTGAGGGCCGTGAGCAACATGCTGCAGAAAGCTAGG

CAGACTTTAGAATTTTACCCTTGCACCAGCGAGGAGATCGACCATGAAGAT

ATCACCAAGGACAAGACATCCACCGTGGAGGCTTGTTTACCTCTGGAGCTG

ACAAAGAACGAGTCTTGTCTCAACTCTCGTGAAACCAGCTTCATCACAAAT

GGCTCTTGTTTAGCTTCCCGGAAGACCTCCTTTATGATGGCTTTATGCCTC

AGCTCCATCTACGAGGATTTAAAGATGTACCAAGTGGAGTTCAAGACCATG

AACGCCAAGCTGCTCATGGACCCTAAACGGCAGATCTTTTTAGACCAGAAC

-continued

ATGCTGGCTGTGATTGATGAGCTGATGCAAGCTTTAAACTTCAACTCCGAG

ACCGTCCCTCAGAAGTCCTCCCTCGAGGAGCCCGATTTTTACAAGACAAAG

ATCAAACTGTGCATTTTACTCCACGCCTTTAGGATCCGGGCCGTGACCATT

GACCGGGTCATGAGCTATTTAAACGCCAGC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 174)
YFGKLESKLSVIRNLNDQVLFIDQGNRPLFEDMTDSDCRDNAPRTIFIISM

YKDSQPRGMAVTISVKCEKISTLSCENKIISFKEMNPPDNIKDTKSDIIFF

QRSVPGHDNKMQFESSSYEGYFLACEKERDLFKLILKKEDELGDRSIMFTV

QNEDSGTTNTVAAYNLTWKSTNFKTILEWEPKPVNQVYTVQISTKSGDWKS

KCFYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVFGK

DLIYTLYYWKSSSSGKKTAKTNTNEFLIDVDKGENYCFSVQAVIPSRTVNR

KSTDSPVECMGQEKGEFRENWVNVISDLKKIEDLIQSMHIDATLYTESDVH

PSCKVTAMKCFLLELQVISLESGDASIHDTVENLIILANNSLSSNGNVTES

GCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 175)
TACTTCGGCAAACTGGAATCCAAGCTGAGCGTGATCCGGAATTTAAACGAC

CAAGTTCTGTTTATCGATCAAGGTAACCGGCCTCTGTTCGAGGACATGACC

GACTCCGATTGCCGGGACAATGCCCCCCGGACCATCTTCATTATCTCCATG

TACAAGGACAGCCAGCCCCGGGGCATGGCTGTGACAATTAGCGTGAAGTGT

GAGAAAATCAGCACTTTATCTTGTGAGAACAAGATCATCTCCTTTAAGGAA

ATGAACCCCCCCGATAACATCAAGGACACCAAGTCCGATATCATCTTCTTC

CAGCGGTCCGTGCCCGGTCACGATAACAAGATGCAGTTCGAATCCTCCTCC

TACGAGGGCTACTTTTTAGCTTGTGAAAAGGAGAGGGATTTATTCAAGCTG

ATCCTCAAGAAGGAGGACGAGCTGGGCGATCGTTCCATCATGTTCACCGTC

CAAAACGAGGATAGCGGCACAACCAACACAGTCGCTGCCTATAACCTCACT

TGGAAGAGCACCAACTTCAAAACCATCCTCGAATGGGAACCCAAACCCGTT

AACCAAGTTTACACCGTGCAGATCAGCACCAAGTCCGGCGACTGGAAGTCC

AAATGTTTCTATACCACCGACACCGAGTGCGATCTCACCGATGAGATCGTG

AAAGATGTGAAACAGACCTACCTCGCCCGGGTGTTTAGCTACCCCGCCGGC

-continued

AATGTGGAGAGCACTGGTTCCGCTGGCGAGCCTTTATACGAGAACAGCCCC

GAATTTACCCCTTACCTCGAGACCAATTTAGGACAGCCCACCATCCAAAGC

TTTGAGCAAGTTGGCACAAAGGTGAATGTGACAGTGGAGGACGAGCGGACT

TTAGTGCGGCGGAACAACACCTTTCTCAGCCTCCGGGATGTGTTCGGCAAA

GATTTAATCTACACACTGTATTACTGGAAGTCCTCTTCCTCCGGCAAGAAG

ACAGCTAAAACCAACACAAACGAGTTTTTAATCGACGTGGATAAAGGCGAA

AACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTTC

CGGGAGAACTGGGTGAACGTCATCAGCGATTTAAAGAAGATCGAAGATTTA

ATTCAGTCCATGCATATCGACGCCACTTTATACACAGAATCCGACGTGCAC

CCCTCTTGTAAGGTGACCGCCATGAAATGTTTTTTACTGGAGCTGCAAGTT

ATCTCTTTAGAGAGCGGAGACGCTAGCATCCACGACACCGTGGAGAATTTA

ATCATTTTAGCCAATAACTCTTTATCCAGCAACGGCAACGTGACAGAGTCC

GGCTGCAAGGAGTGCGAAGAGCTGGAGGAGAAGAACATCAAGGAGTTTCTG

CAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 176)
MKWVTFISLLFLFSSAYSYFGKLESKLSVIRNLNDQVLFIDQGNRPLFEDM

TDSDCRDNAPRTIFIISMYKDSQPRGMAVTISVKCEKISTLSCENKIISFK

EMNPPDNIKDTKSDIIFFQRSVPGHDNKMQFESSSYEGYFLACEKERDLFK

LILKKEDELGDRSIMFTVQNEDSGTTNTVAAYNLTWKSTNFKTILEWEPKP

VNQVYTVQISTKSGDWKSKCFYTTDTECDLTDEIVKDVKQTYLARVFSYPA

GNVESTGSAGEPLYENSPEFTPYLETNLGQPTIQSFEQVGTKVNVTVEDER

TLVRRNNTFLSLRDVFGKDLIYTLYYWKSSSSGKKTAKTNTNEFLIDVDKG

ENYCFSVQAVIPSRTVNRKSTDSPVECMGQEKGEFRENWVNVISDLKKIED

LIQSMHIDATLYTESDVHPSCKVTAMKCFLLELQVISLESGDASIHDTVEN

LIILANNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 177)
ATGAAGTGGGTCACATTTATCTCTTTACTGTTCCTCTTCTCCAGCGCCTAC

AGCTACTTCGGCAAACTGGAATCCAAGCTGAGCGTGATCCGGAATTTAAAC

GACCAAGTTCTGTTTATCGATCAAGGTAACCGGCCTCTGTTCGAGGACATG

ACCGACTCCGATTGCCGGGACAATGCCCCCCGGACCATCTTCATTATCTCC

-continued

ATGTACAAGGACAGCCAGCCCCGGGGCATGGCTGTGACAATTAGCGTGAAG
TGTGAGAAAATCAGCACTTTATCTTGTGAGAACAAGATCATCTCCTTTAAG
GAAATGAACCCCCCCGATAACATCAAGGACACCAAGTCCGATATCATCTTC
TTCCAGCGGTCCGTGCCCGGTCACGATAACAAGATGCAGTTCGAATCCTCC
TCCTACGAGGGCTACTTTTTAGCTTGTGAAAAGGAGAGGGATTTATTCAAG
CTGATCCTCAAGAAGGAGGACGAGCTGGGCGATCGTTCCATCATGTTCACC
GTCCAAAACGAGGATAGCGGCACAACCAACACAGTCGCTGCCTATAACCTC
ACTTGGAAGAGCACCAACTTCAAAACCATCCTCGAATGGGAACCCAAACCC
GTTAACCAAGTTTACACCGTGCAGATCAGCACCAAGTCCGGCGACTGGAAG
TCCAAATGTTTCTATACCACCGACACCGAGTGCGATCTCACCGATGAGATC
GTGAAAGATGTGAAACAGACCTACCTCGCCCGGGTGTTTAGCTACCCCGCC
GGCAATGTGGAGAGCACTGGTTCCGCTGGCGAGCCTTTATACGAGAACAGC
CCCGAATTTACCCCTTACCTCGAGACCAATTTAGGACAGCCCACCATCCAA
AGCTTTGAGCAAGTTGGCACAAAGGTGAATGTGACAGTGGAGGACGAGCGG
ACTTTAGTGCGGCGGAACAACACCTTTCTCAGCCTCCGGGATGTGTTCGGC
AAAGATTTAATCTACACACTGTATTACTGGAAGTCCTCTTCCTCCGGCAAG
AAGACAGCTAAAACCAACACAAACGAGTTTTTAATCGACGTGGATAAAGGC
GAAAACTACTGTTTCAGCGTGCAAGCTGTGATCCCCTCCCGGACCGTGAAT
AGGAAAAGCACCGATAGCCCCGTTGAGTGCATGGGCCAAGAAAAGGGCGAG
TTCCGGGAGAACTGGGTGAACGTCATCAGCGATTTAAAGAAGATCGAAGAT
TTAATTCAGTCCATGCATATCGACGCCACTTTATACACAGAATCCGACGTG
CACCCCTCTTGTAAGGTGACCGCCATGAAATGTTTTTTACTGGAGCTGCAA
GTTATCTCTTTAGAGAGCGGAGACGCTAGCATCCACGACACCGTGGAGAAT
TTAATCATTTTAGCCAATAACTCTTTATCCAGCAACGGCAACGTGACAGAG
TCCGGCTGCAAGGAGTGCGAAGAGCTGGAGGAGAAGAACATCAAGGAGTTT
CTGCAATCCTTTGTGCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 178)
IWELKKDVYVVELDWYPDAPGEMVVLTCDTPEEDGITWTLDQSSEVLGSGK
TLTIQVKEFGDAGQYTCHKGGEVLSHSLLLLHKKEDGIWSTDILKDQKEPK
NKTFLRCEAKNYSGRFTCWWLTTISTDLTFSVKSSRGSSDPQGVTCGAATL
SAERVRGDNKEYEYSVECQEDSACPAAEESLPIEVMVDAVHKLKYENYTSS
FFIRDIIKPDPPKNLQLKPLKNSRQVEVSWEYPDTWSTPHSYFSLTFCVQV
QGKSKREKKDRVFTDKTSATVICRKNASISVRAQDRYYSSSWSEWASVPCS
GGGGSGGGGSGGGGSRNLPVATPDPGMFPCLHEISQNLLRAVSNMLQKARQ
TLEFYPCTSEEIDHEDITKDKTSTVEACLPLELTKNESCLNSRETSFITNG

-continued

SCLASRKTSFMMALCLSSIYEDLKMYQVEFKTMNAKLLMDPKRQIFLDQNM
LAVIDELMQALNFNSETVPQKSSLEEPDFYKTKIKLCILLHAFRIRAVTID
RVMSYLNASITCPPPMSVEHADIWVKSYSLYSRERYICNSGFKRKAGTSSL
TECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 179)
ATTTGGGAACTGAAGAAGGACGTCTACGTGGTCGAACTGGACTGGTATCCC
GATGCTCCCGGCGAAATGGTGGTGCTCACTTGTGACACCCCCGAAGAAGAC
GGCATCACTTGGACCCTCGATCAGAGCAGCGAGGTGCTGGGCTCCGGAAAG
ACCCTCACAATCCAAGTTAAGGAGTTCGGAGACGCTGGCCAATACACATGC
CACAAGGGAGGCGAGGTGCTCAGCCATTCCTTATTATTATTACACAAGAAG
GAAGACGGAATCTGGTCCACCGACATTTTAAAAGATCAGAAGGAGCCCAAG
AATAAGACCTTTTTAAGGTGTGAGGCCAAAAACTACAGCGGTCGTTTCACT
TGTTGGTGGCTGACCACCATTTCCACCGATTTAACCTTCTCCGTGAAAAGC
AGCCGGGGAAGCTCCGACCCTCAAGGTGTGACATGTGGAGCCGCTACCCTC
AGCGCTGAGAGGGTTCGTGGCGATAACAAGGAATACGAGTACAGCGTGGAG
TGCCAAGAAGATAGCGCTTGTCCCGCTGCCGAAGAATCTTTACCCATTGAG
GTGATGGTGGACGCCGTGCACAAACTCAAGTACGAGAACTACACCTCCTCC
TTCTTTATCCGGGACATCATTAAGCCCGATCCTCCTAAGAATTTACAGCTG
AAGCCTCTCAAAAATAGCCGGCAAGTTGAGGTCTCTTGGGAATATCCCGAC
ACTTGGAGCACACCCCACAGCTACTTCTCTTTAACCTTTTGTGTGCAAGTT
CAAGGTAAAAGCAAGCGGGAGAAGAAAGACCGGGTGTTTACCGACAAAACC
AGCGCCACCGTCATCTGTCGGAAGAACGCCTCCATCAGCGTGAGGGCTCAA
GATCGTTATTACTCCAGCAGCTGGTCCGAGTGGGCCAGCGTGCCTTGTTCC
GGCGGTGGAGGATCCGGAGGAGGTGGCTCCGGCGGCGGAGGATCTCGTAAC
CTCCCCGTGGCTACCCCCGATCCCGGAATGTTCCCTTGTTTACACCACAGC
CAGAATTTACTGAGGGCCGTGAGCAACATGCTGCAGAAAGCTAGGCAGACT
TTAGAATTTTACCCTTGCACCAGCGAGGAGATCGACCATGAAGATATCACC
AAGGACAAGACATCCACCGTGGAGGCTTGTTTACCTCTGGAGCTGACAAAG
AACGAGTCTTGTCTCAACTCTCGTGAAACCAGCTTCATCACAAATGGCTCT
TGTTTAGCTTCCCGGAAGACCTCCTTTATGATGGCTTTATGCCTCAGCTCC
ATCTACGAGGATTTAAAGATGTACCAAGTGGAGTTCAAGACCATGAACGCC
AAGCTGCTCATGGACCCTAAACGGCAGATCTTTTTAGACCAGAACATGCTG
GCTGTGATTGATGAGCTGATGCAAGCTTTAAACTTCAACTCCGAGACCGTC
CCTCAGAAGTCCTCCCTCGAGGAGCCCGATTTTTACAAGACAAAGATCAAA
CTGTGCATTTTACTCCACGCCTTTAGGATCCGGGCCGTGACCATTGACCGG
GTCATGAGCTATTTAAACGCCAGCATTACATGCCCCCCTCCCATGAGCGTG

-continued

```
GAGCACGCCGACATCTGGGTGAAGAGCTATAGCCTCTACAGCCGGGAGAGG

TATATCTGTAACAGCGGCTTCAAGAGGAAGGCCGGCACCAGCAGCCTCACC

GAGTGCGTGCTGAATAAGGCTACCAACGTGGCTCACTGGACAACACCCTCT

TTAAAGTGCATCCGG.
```

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 180)
MKWVTFISLLFLFSSAYSIWELKKDVYVVELDWYPDAPGEMVVLTCDTPEE

DGITWTLDQSSEVLGSGKTLTIQVKEFGDAGQYTCHKGGEVLSHSLLLLHK

KEDGIWSTDILKDQKEPKNKTFLRCEAKNYSGRFTCWWLTTISTDLTFSVK

SSRGSSDPQGVTCGAATLSAERVRGDNKEYEYSVECQEDSACPAAEESLPI

EVMVDAVHKLKYENYTSSFFIRDIIKPDPPKNLQLKPLKNSRQVEVSWEYP

DTWSTPHSYFSLTFCVQVQGKSKREKKDRVFTDKTSATVICRKNASISVRA

QDRYYSSSWSEWASVPCSGGGGSGGGGSGGGGSRNLPVATPDPGMFPCLHH

SQNLLRAVSNMLQKARQTLEFYPCTSEEIDHEDITKDKTSTVEACLPLELT

KNESCLNSRETSFITNGSCLASRKTSFMMALCLSSIYEDLKMYQVEFKTMN

AKLLMDPKRQIFLDQNMLAVIDELMQALNFNSETVPQKSSLEEPDFYKTKI

KLCILLHAFRIRAVTIDRVMSYLNASITCPPPMSVEHADIWVKSYSLYSRE

RYICNSGFKRKAGTSSLTECVLNKATNVAHWTTPSLKCIR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 181)
ATGAAATGGGTGACCTTTATTTCTTTACTGTTCCTCTTTAGCAGCGCCTAC

TCCATTTGGGAACTGAAGAAGGACGTCTACGTGGTCGAACTGGACTGGTAT

CCCGATGCTCCCGGCGAAATGGTGGTGCTCACTTGTGACACCCCCGAAGAA

GACGGCATCACTTGGACCCTCGATCAGAGCAGCGAGGTGCTGGGCTCCGGA

AAGACCCTCACAATCCAAGTTAAGGAGTTCGGAGACGCTGGCCAATACACA

TGCCACAAGGGAGGCGAGGTGCTCAGCCATTCCTTATTATTATTACACAAG

AAGGAAGACGGAATCTGGTCCACCGACATTTTAAAAGATCAGAAGGAGCCC

AAGAATAAGACCTTTTTAAGGTGTGAGGCCAAAAACTACAGCGGTCGTTTC

ACTTGTTGGTGGCTGACCACCATTTCCACCGATTTAACCTTCTCCGTGAAA

AGCAGCCGGGGAAGCTCCGACCCTCAAGGTGTGACATGTGGAGCCGCTACC

CTCAGCGCTGAGAGGGTTCGTGGCGATAACAAGGAATACGAGTACAGCGTG

GAGTGCCAAGAAGATAGCGCTTGTCCCGCTGCCGAAGAATCTTTACCCATT
```

-continued

```
GAGGTGATGGTGGACGCCGTGCACAAACTCAAGTACGAGAACTACACCTCC

TCCTTCTTTATCCGGGACATCATTAAGCCCGATCCTCCTAAGAATTTACAG

CTGAAGCCTCTCAAAAATAGCCGGCAAGTTGAGGTCTCTTGGGAATATCCC

GACACTTGGAGCACACCCCACAGCTACTTCTCTTTAACCTTTTGTGTGCAA

GTTCAAGGTAAAAGCAAGCGGGAGAAGAAAGACCGGGTGTTTACCGACAAA

ACCAGCGCCACCGTCATCTGTCGGAAGAACGCCTCCATCAGCGTGAGGGCT

CAAGATCGTTATTACTCCAGCAGCTGGTCCGAGTGGGCCAGCGTGCCTTGT

TCCGGCGGTGGAGGATCCGGAGGAGGTGGCTCCGGCGGCGGAGGATCTCGT

AACCTCCCCGTGGCTACCCCCGATCCCGGAATGTTCCCTTGTTTACACCAC

AGCCAGAATTTACTGAGGGCCGTGAGCAACATGCTGCAGAAAGCTAGGCAG

ACTTTAGAATTTTACCCTTGCACCAGCGAGGAGATCGACCATGAAGATATC

ACCAAGGACAAGACATCCACCGTGGAGGCTTGTTTACCTCTGGAGCTGACA

AAGAACGAGTCTTGTCTCAACTCTCGTGAAACCAGCTTCATCACAAATGGC

TCTTGTTTAGCTTCCCGGAAGACCTCCTTTATGATGGCTTTATGCCTCAGC

TCCATCTACGAGGATTTAAAGATGTACCAAGTGGAGTTCAAGACCATGAAC

GCCAAGCTGCTCATGGACCCTAAACGGCAGATCTTTTTAGACCAGAACATG

CTGGCTGTGATTGATGAGCTGATGCAAGCTTTAAACTTCAACTCCGAGACC

GTCCCTCAGAAGTCCTCCCTCGAGGAGCCCGATTTTTACAAGACAAAGATC

AAACTGTGCATTTTACTCCACGCCTTTAGGATCCGGGCCGTGACCATTGAC

CGGGTCATGAGCTATTTAAACGCCAGCATTACATGCCCCCCTCCCATGAGC

GTGGAGCACGCCGACATCTGGGTGAAGAGCTATAGCCTCTACAGCCGGGAG

AGGTATATCTGTAACAGCGGCTTCAAGAGGAAGGCCGGCACCAGCAGCCTC

ACCGAGTGCGTGCTGAATAAGGCTACCAACGTGGCTCACTGGACAACACCC

TCTTTAAAGTGCATCCGG.
```

Exemplary Multi-Chain Chimeric Polypeptides—Type B

In some embodiments of any of the multi-chain chimeric polypeptides described herein, the first target-binding domain and the second targeting-binding domain each independently bind specifically to a receptor of IL-21 or to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble TGF-β receptor (e.g., a soluble TGFRβRII receptor). In some embodiments of these multi-chain chimeric polypeptides, the first target-binding domain and the second target-binding domain are each independently a soluble IL-21 or a soluble TGF-β receptor (e.g., a soluble TGFRβRII receptor). In some embodiments of these multi-chain chimeric polypeptides, the first target-binding domain and the second target-binding domain both bind specifically to a receptor of IL-21 or to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to TGF-β. In some embodiments of these multi-chain chimeric polypeptides, the first target-binding domain binds specifically to TGF-β, and the second target-binding domain bind specifically to a receptor for IL-21.

In some embodiments of these multi-chain chimeric polypeptides, the first target-binding domain includes a soluble IL-21 (e.g., a soluble human IL-21). In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 83)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS.
```

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 182)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC.
```

In some embodiments of these multi-chain chimeric polypeptides, the second target-binding domain includes a soluble TGF-β receptor (e.g., a soluble TGFRβRII receptor (e.g., a soluble human TGFRβRII receptor)). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 183)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 184)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.
```

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCACG
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)
ATTCCTCCCCACGTGCAGAAGAGCGTGAATAATGACATGATCGTGACCG
ATAACAATGGCGCCGTGAAATTTCCCCAGCTGTGCAAATTCTGCGATGT
GAGGTTTTCCACCTGCGACAACCAGAAGTCCTGTATGAGCAACTGCACA
ATCACCTCCATCTGTGAGAAGCCTCAGGAGGTGTGCGTGGCTGTCTGGC
GGAAGAATGACGAGAATATCACCCTGGAAACCGTCTGCCACGATCCCAA
GCTGCCCTACCACGATTTCATCCTGGAAGACGCCGCCAGCCCTAAGTGC
ATCATGAAAGAGAAAAAGAAGCCTGGCGAGACCTTTTTCATGTGCTCCT
GCAGCAGCGACGAATGCAACGACAATATCATCTTTAGCGAGGAATACAA
TACCAGCAACCCCGAC.

In some embodiments of these multi-chain chimeric polypeptides, the soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCACG
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCCCCCCAAATGCA
TCATGAAGGAGAAGAAGAAGCCCGGAGAGACCTTCTTTATGTGTTCCTG
TAGCAGCGACGAGTGTAACGACAACATCATCTTCAGCGAAGAGTACAAC
ACCAGCAACCCTGATGGAGGTGGCGGATCCGGAGGTGGAGGTTCTGGTG

-continued

GAGGTGGGAGTATTCCTCCCCACGTGCAGAAGAGCGTGAATAATGACAT
GATCGTGACCGATAACAATGGCGCCGTGAAATTTCCCCAGCTGTGCAAA
TTCTGCGATGTGAGGTTTTCCACCTGCGACAACCAGAAGTCCTGTATGA
GCAACTGCACAATCACCTCCATCTGTGAGAAGCCTCAGGAGGTGTGCGT
GGCTGTCTGGCGGAAGAATGACGAGAATATCACCCTGGAAACCGTCTGC
CACGATCCCAAGCTGCCCTACCACGATTTCATCCTGGAAGACGCCGCCA
GCCCTAAGTGCATCATGAAAGAGAAAAAGAAGCCTGGCGAGACCTTTTT
CATGTGCTCCTGCAGCAGCGACGAATGCAACGACAATATCATCTTTAGC
GAGGAATACAATACCAGCAACCCCGAC.

In some embodiments of these multi-chain chimeric polypeptides, the human TGFβRII receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHFILEDAAS
PKCIMKEKKKPGETFFMCSCSSDECNDNIIFSEEYNTSNPD.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 189)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDSSGTTNTVAAYNLTW
KSTNFKTILEWEPKPVNQVYTVQISTKSGDWKSKCFYTTDTECDLTDEI
VKDVKQTYLARVFSYPAGNVESTGSAGEPLYENSPEFTPYETNLGQPTI
QSFEQVGTKVNVTVEDERTLVRRNNTFLSLRDVFGKDLIYTLYYWKSSS
SGKKTAKTNTNEFLIDVDKGENYCFSVQAVIPSRTVNRKSTDSPVECMG
QEKGEFRENWVNVISDLKKIEDLIQSMHIDATLYTESDVHPSCKVTAMK
CFLLELQVISLESGDASIHDTVENLIILANNSLSSNGNVTESGCKECEE
LEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 190)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCCTCCGGCACCACCAATACCGTGGCCGCTTATAACCTCACATGG
AAGAGCACCAACTTCAAGACAATTCTGGAATGGGAACCCAAGCCCGTCA
ATCAAGTTTACACCGTGCAGATCTCCACCAAATCCGGAGACTGGAAGAG
CAAGTGCTTCTACACAACAGACACCGAGTGTGATTTAACCGACGAAATC
GTCAAGGACGTCAAGCAAACCTATCTGGCTCGGGTCTTTTCCTACCCCG
CTGGCAATGTCGAGTCCACCGGCTCCGCTGGCGAGCCTCTCTACGAGAA
TTCCCCCGAATTCACCCCTTATTTAGAGACCAATTTAGGCCAGCCTACC
ATCCAGAGCTTCGAGCAAGTTGGCACCAAGGTGAACGTCACCGTCGAGG
ATGAAAGGACTTTAGTGCGGCGGAATAACACATTTTTATCCCTCCGGGA
TGTGTTCGGCAAAGACCTCATCTACACACTGTACTATTGGAAGTCCAGC
TCCTCCGGCAAAAAGACCGCTAAGACCAACACCAACGAGTTTTTAATTG
ACGTGGACAAAGGCGAGAACTACTGCTTCAGCGTGCAAGCCGTGATCCC
TTCTCGTACCGTCAACCGGAAGAGCACAGATTCCCCCGTTGAGTGCATG
GGCCAAGAAAAGGGCGAGTTCCGGGAGAACTGGGTGAACGTCATCAGCG
ATTTAAAGAAGATCGAAGATTTAATTCAGTCCATGCATATCGACGCCAC
TTTATACACAGAATCCGACGTGCACCCCTCTTGTAAGGTGACCGCCATG
AAATGTTTTTTACTGGAGCTGCAAGTTATCTCTTTAGAGAGCGGAGACG
CTAGCATCCACGACACCGTGGAGAATTTAATCATTTTAGCCAATAACTC
TTTATCCAGCAACGGCAACGTGACAGAGTCCGGCTGCAAGGAGTGCGAA
GAGCTGGAGGAGAAGAACATCAAGGAGTTTCTGCAATCCTTTGTGCACA
TTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 191)
MKWVTFISLLFLFSSAYSQGQDRHMIRMRQLIDIVDQLKNYVNDLVPEF
LPAPEDVETNCEWSAFSCFQKAQLKSANTGNNERIINVSIKKLKRKPPS
TNAGRRQKHRLTCPSCDSYEKKPPKEFLERFKSLLQKMIHQHLSSRTHG
SEDSSGTTNTVAAYNLTWKSTNFKTILEWEPKPVNQVYTVQISTKSGDW
KSKCFYTTDTECDLTDEIVKDVKQTYLARVFSYPAGNVESTGSAGEPLY

-continued

ENSPEFTPYLETNLGQPTIQSFEQVGTKVNVTVEDERTLVRRNNTFLSL
RDVFGKDLIYTLYYWKSSSSGKKTAKTNTNEFLIDVDKGENYCFSVQAV
IPSRTVNRKSTDSPVECMGQEKGEFRENWVNVISDLKKIEDLIQSMHID
ATLYTESDVHPSCKVTAMKCFLLELQVISLESGDASIHDTVENLIILAN
NSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 192)
ATGAAGTGGGTGACCTTCATCAGCCTGCTGTTCCTGTTCTCCAGCGCCT
ACTCCCAGGGCCAGGACAGGCACATGATCCGGATGAGGCAGCTCATCGA
CATCGTCGACCAGCTGAAGAACTACGTGAACGACCTGGTGCCCGAGTTT
CTGCCTGCCCCCGAGGACGTGGAGACCAACTGCGAGTGGTCCGCCTTCT
CCTGCTTTCAGAAGGCCCAGCTGAAGTCCGCCAACACCGGCAACAACGA
GCGGATCATCAACGTGAGCATCAAGAAGCTGAAGCGGAAGCCTCCCTCC
ACAAACGCCGGCAGGAGGCAGAAGCACAGGCTGACCTGCCCCAGCTGTG
ACTCCTACGAGAAGAAGCCCCCCAAGGAGTTCCTGGAGAGGTTCAAGTC
CCTGCTGCAGAAGATGATCCATCAGCACCTGTCCTCCAGGACCCACGGC
TCCGAGGACTCCTCCGGCACCACCAATACCGTGGCCGCTTATAACCTCA
CATGGAAGAGCACCAACTTCAAGACAATTCTGGAATGGGAACCCAAGCC
CGTCAATCAAGTTTACACCGTGCAGATCTCCACCAAATCCGGAGACTGG
AAGAGCAAGTGCTTCTACACAACAGACACCGAGTGTGATTTAACCGACG
AAATCGTCAAGGACGTCAAGCAAACCTATCTGGCTCGGGTCTTTTCCTA
CCCCGCTGGCAATGTCGAGTCCACCGGCTCCGCTGGCGAGCCTCTCTAC
GAGAATTCCCCCGAATTCACCCCTTATTTAGAGACCAATTTAGGCCAGC
CTACCATCCAGAGCTTCGAGCAAGTTGGCACCAAGGTGAACGTCACCGT
CGAGGATGAAAGGACTTTAGTGCGGCGGAATAACACATTTTTATCCCTC
CGGGATGTGTTCGGCAAAGACCTCATCTACACACTGTACTATTGGAAGT
CCAGCTCCTCCGGCAAAAAGACCGCTAAGACCAACACCAACGAGTTTTT
AATTGACGTGGACAAAGGCGAGAACTACTGCTTCAGCGTGCAAGCCGTG
ATCCCTTCTCGTACCGTCAACCGGAAGAGCACAGATTCCCCCGTTGAGT
GCATGGGCCAAGAAAAGGGCGAGTTCCGGGAGAACTGGGTGAACGTCAT
CAGCGATTTAAAGAAGATCGAAGATTTAATTCAGTCCATGCATATCGAC
GCCACTTTATACACAGAATCCGACGTGCACCCCTCTTGTAAGGTGACCG
CCATGAAATGTTTTTTACTGGAGCTGCAAGTTATCTCTTTAGAGAGCGG
AGACGCTAGCATCCACGACACCGTGGAGAATTTAATCATTTTAGCCAAT
AACTCTTTATCCAGCAACGGCAACGTGACAGAGTCCGGCTGCAAGGAGT
GCGAAGAGCTGGAGGAGAAGAACATCAAGGAGTTTCTGCAATCCTTTGT
GCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 193)

IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDITCPPPM

SVEHADIWVKSYSLYSRERYICNSGFKRKAGTSSLTECVLNKATNVAHW

TTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 194)

ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

ACGATCACCTCCATCTGCGAGAAGCCCCAAGAAGTGTGCGTGGCCGTG

TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

GGTTCTGGTGGAGGTGGGAGTATTCCTCCCCACGTGCAGAAGAGCGTG

AATAATGACATGATCGTGACCGATAACAATGGCGCCGTGAAATTTCCC

CAGCTGTGCAAATTCTGCGATGTGAGGTTTTCCACCTGCGACAACCAG

AAGTCCTGTATGAGCAACTGCACAATCACCTCCATCTGTGAGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGACATC

ACGTGTCCTCCTCCTATGTCCGTGGAACACGCAGACATCTGGGTCAAG

AGCTACAGCTTGTACTCCAGGGAGCGGTACATTTGTAACTCTGGTTTC

-continued

AAGCGTAAAGCCGGCACGTCCAGCCTGACGGAGTGCGTGTTGAACAAG

GCCACGAATGTCGCCCACTGGACAACCCCCAGTCTCAAATGTATTAGA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 195)

MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDITCPPPMSVEHADIWVKSYSLYSRERYICNSGFKRKAG

TSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 196)

ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCACGATCACCTCCATCTGCGAGAAGCCCCAAGAAGTGTGCGTGGCCGT

GTGGCGGAAAAATGACGAGAACATCACCCTGGAGACCGTGTGTCACGAC

CCCAAGCTCCCTTATCACGACTTCATTCTGGAGGACGCTGCCTCCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

TGCAAATTCTGCGATGTGAGGTTTTCCACCTGCGACAACCAGAAGTCCT

GTATGAGCAACTGCACAATCACCTCCATCTGTGAGAAGCCTCAGGAGGT

GTGCGTGGCTGTCTGGCGGAAGAATGACGAGAATATCACCCTGGAAACC

GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

-continued

TTTAGCGAGGAATACAATACCAGCAACCCCGACATCACGTGTCCTCCTC

CTATGTCCGTGGAACACGCAGACATCTGGGTCAAGAGCTACAGCTTGTA

CTCCAGGGAGCGGTACATTTGTAACTCTGGTTTCAAGCGTAAAGCCGGC

ACGTCCAGCCTGACGGAGTGCGTGTTGAACAAGGCCACGAATGTCGCCC

ACTGGACAACCCCCAGTCTCAAATGTATTAGA.

Exemplary Multi-Chain Chimeric Polypeptides—Type C

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the first target-binding domain includes a soluble IL-21 (e.g., a soluble human IL-21).

In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)

QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)

CAAGGTCAAGATCGCCACATGATTAGAATGCGTCAACTTATAGATAT

TGTTGATCAGCTGAAAAATTATGTGAATGACTTGGTCCCTGAATTTC

TGCCAGCTCCAGAAGATGTAGAGACAAACTGTGAGTGGTCAGCTTTT

TCCTGTTTTCAGAAGGCCCAACTAAAGTCAGCAAATACAGGAAACAA

TGAAAGGATAATCAATGTATCAATTAAAAAGCTGAAGAGGAAACCAC

CTTCCACAAATGCAGGGAGAAGACAGAAACACAGACTAACATGCCCT

TCATGTGATTCTTATGAGAAAAAACCACCCAAAGAATTCCTAGAAAG

ATTCAAATCACTTCTCCAAAAGATGATTCATCAGCATCTGTCCTCTA

GAACACACGGAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)

CAGGGCCAGGACAGGCACATGATCCGGATGAGGCAGCTCATCGA

CATCGTCGACCAGCTGAAGAACTACGTGAACGACCTGGTGCCCG

AGTTTCTGCCTGCCCCCGAGGACGTGGAGACCAACTGCGAGTGG

TCCGCCTTCTCCTGCTTTCAGAAGGCCCAGCTGAAGTCCGCCAA

-continued

```
CACCGGCAACAACGAGCGGATCATCAACGTGAGCATCAAGAAGC

TGAAGCGGAAGCCTCCCTCCACAAACGCCGGCAGGAGGCAGAAG

CACAGGCTGACCTGCCCCAGCTGTGACTCCTACGAGAAGAAGCC

CCCCAAGGAGTTCCTGGAGAGGTTCAAGTCCCTGCTGCAGAAGA

TGATCCATCAGCACCTGTCCTCCAGGACCCACGGCTCCGAGGAC

TCC.
```

In some embodiments of these multi-chain chimeric polypeptides, the sequence of soluble human IL-7 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
(SEQ ID NO: 79)
DCDIEGKDGKQYESVLMVSIDQLLDSMKEIGSNCLNNEFNFFK

RHICDANKEGMFLFRAARKLRQFLKMNSTGDFDLHLLKVSEGT

TILLNCTGQVKGRKPAALGEAQPTKSLEENKSLKEQKKLNDLC

FLKRLLQEIKTCWNKILMGTKEH.
```

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
(SEQ ID NO: 198)
GATTGTGATATTGAAGGTAAAGATGGCAAACAATATGAGAGTGT

TCTAATGGTCAGCATCGATCAATTATTGGACAGCATGAAAGAAA

TTGGTAGCAATTGCCTGAATAATGAATTTAACTTTTTTAAAAGA

CATATCTGTGATGCTAATAAGGAAGGTATGTTTTTATTCCGTGC

TGCTCGCAAGTTGAGGCAATTTCTTAAAATGAATAGCACTGGTG

ATTTTGATCTCCACTTATTAAAAGTTTCAGAAGGCACAACAATA

CTGTTGAACTGCACTGGCCAGGTTAAAGGAAGAAAACCAGCTGC

CCTGGGTGAAGCCCAACCAACAAAGAGTTTGGAAGAAAATAAAT

CTTTAAAGGAACAGAAAAAACTGAATGACTTGTGTTTCCTAAAG

AGACTATTACAAGAGATAAAAACTTGTTGGAATAAAATTTTGAT

GGGCACTAAAGAACAC.
```

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
(SEQ ID NO: 199)
QGQDRHMIRMRQLIDIVDQLKNYVNDLVPEFLPAPEDVETNCE

WSAFSCFQKAQLKSANTGNNERIINVSIKKLKRKPPSTNAGRR

QKHRLTCPSCDSYEKKPPKEFLERFKSLLQKMIHQHLSSRTHG

SEDSSGTTNTVAAYNLTWKSTNFKTILEWEPKPVNQVYTVQIS

TKSGDWKSKCFYTTDTECDLTDEIVKDVKQTYLARVFSYPAGN

VESTESTGSAGEPLYENSPEFTPYLETNLGQPTIQSFEQVGTK

VNVTVEDERTLVRRNNTFLSLRDVFGKDLIYTLYYWKSSSSGK

KTAKTNTNEFLIDVDKGENYCFSVQAVIPSRTVNRKSTDSPVE

CMGQEKGEFRENWVNVISDLKKIEDLIQSMHIDATLYTESDVH

PSCKVTAMKCFLLELQVISLESGDASIHDTVENLIILLANNSL

SSNGNVTESGCKECEELEEKNIKEFLQSFVHIVQMFINTS.
```

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
(SEQ ID NO: 200)
CAAGGTCAAGATCGCCACATGATTAGAATGCGTCAACTTATAGAT

ATTGTTGATCAGCTGAAAAATTATGTGAATGACTTGGTCCCTGAA

TTTCTGCCAGCTCCAGAAGATGTAGAGACAAACTGTGAGTGGTCA

GCTTTTTCCTGTTTTCAGAAGGCCCAACTAAAGTCAGCAAATACA

GGAAACAATGAAAGGATAATCAATGTATCAATTAAAAAGCTGAAG

AGGAAACCACCTTCCACAAATGCAGGGAGAAGACAGAAACACAGA

CTAACATGCCCTTCATGTGATTCTTATGAGAAAAAACCACCCAAA

GAATTCCTAGAAAGATTCAAATCACTTCTCCAAAAGATGATTCAT

CAGCATCTGTCCTCTAGAACACACGGAAGTGAAGATTCCTCAGGC

ACTACAAATACTGTGGCAGCATATAATTTAACTTGGAAATCAACT

AATTTCAAGACAATTTTGGAGTGGGAACCCAAACCCGTCAATCAA

GTCTACACTGTTCAAATAAGCACTAAGTCAGGAGATTGGAAAAGC

AAATGCTTTTACACAACAGACACAGAGTGTGACCTCACCGACGAG

ATTGTGAAGGATGTGAAGCAGACGTACTTGGCACGGGTCTTCTCC

TACCCGGCAGGGAATGTGGAGAGCACCGGTTCTGCTGGGGAGCCT

CTGTATGAGAACTCCCCAGAGTTCACACCTTACCTGGAGACAAAC

CTCGGACAGCCAACAATTCAGAGTTTTGAACAGGTGGGAACAAAA

GTGAATGTGACCGTAGAAGATGAACGGACTTTAGTCAGAAGGAAC

AACACTTTCCTAAGCCTCCGGGATGTTTTTGGCAAGGACTTAATT

TATACACTTTATTATTGGAAATCTTCAAGTTCAGGAAAGAAAACA

GCCAAAACAAACACTAATGAGTTTTTGATTGATGTGGATAAAGGA

GAAAACTACTGTTTCAGTGTTCAAGCAGTGATTCCCTCCCGAACA

GTTAACCGGAAGAGTACAGACAGCCCGGTAGAGTGTATGGGCCAG
```

-continued

GAGAAAGGGGAATTCAGAGAAAACTGGGTGAACGTCATCAGCGAT
TTAAAGAAGATCGAAGATTTAATTCAGTCCATGCATATCGACGCC
ACTTTATACACAGAATCCGACGTGCACCCCTCTTGTAAGGTGACC
GCCATGAAATGTTTTTTACTGGAGCTGCAAGTTATCTCTTTAGAG
AGCGGAGACGCTAGCATCCACGACACCGTGGAGAATTTAATCATT
TTAGCCAATAACTCTTTATCCAGCAACGGCAACGTGACAGAGTCC
GGCTGCAAGGAGTGCGAAGAGCTGGAGGAGAAGAACATCAAGGAG
TTTCTGCAATCCTTTGTGCACATTGTCCAGATGTTCATCAATACC
TCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 201)
MGVKVLFALICIAVAEAQGQDRHMIRMRQLIDIVDQLKNYVNDLVPE
FLPAPEDTVETNCEWSAFSCFQKAQLKSANTGNNERIINVSIKKLKR
KPPSTNAGRRQKHRLCPSCDSYEKKPPKEFLERFKSLLQKMIHQHLS
SRTHGSEDSSGTTNTVAAYNLTWKSTNFKTILEWEPKPVNQVYTVQI
STKSGDWKSKCFYTTDTECDLTDEIVKDVKVKQTYLARVFSYPAGNV
ESTGSAGEPLYENSPEFTPYLETNLGQPTIQSFEQVGTKVNVTVEDE
RTLVRRNNTFLSLRDVFGKDLIYTLYYWKSSSSGKKTAKTNTNEFLI
DVDKGENYCFSVQAVIPSRTVNRKSTDSPVECMGQEKGEFRENWVNV
ISDLKKIEDLIQSMHIDATLYTESDVHPSCKVTAMKCFLLELQVISL
ESGDASIHDTVENLIILANNSLSSNGNVTESGCKECEELEEKNIKEF
LQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 202)
ATGGGAGTGAAAGTTCTTTTTGCCCTTATTTGTATTGCTGTGGC
CGAGGCCCAAGGTCAAGATCGCCACATGATTAGAATGCGTCAACTTAT
AGATATTGTTGATCAGCTGAAAAATTATGTGAATGACTTGGTCCCTGA
ATTTCTGCCAGCTCCAGAAGATGTAGAGACAAACTGTGAGTGGTCAGC
TTTTTCCTGTTTTCAGAAGGCCCAACTAAAGTCAGCAAATACAGGAAA
CAATGAAAGGATAATCAATGTATCAATTAAAAAGCTGAAGAGGAAACC
ACCTTCCACAAATGCAGGGAGAAGACAGAAACACAGACTAACATGCCC
TTCATGTGATTCTTATGAGAAAAAACCACCCAAAGAATTCCTAGAAAG
ATTCAAATCACTTCTCCAAAAGATGATTCATCAGCATCTGTCCTCTAG

-continued

AACACACGGAAGTGAAGATTCCTCAGGCACTACAAATACTGTGGCAGC
ATATAATTTAACTTGGAAATCAACTAATTTCAAGACAATTTTGGAGTG
GGAACCCAAACCCGTCAATCAAGTCTACACTGTTCAAATAAGCACTAA
GTCAGGAGATTGGAAAAGCAAATGCTTTTACACAACAGACACAGAGTG
TGACCTCACCGACGAGATTGTGAAGGATGTGAAGCAGACGTACTTGGC
ACGGGTCTTCTCCTACCCGGCAGGGAATGTGGAGAGCACCGGTTCTGC
TGGGGAGCCTCTGTATGAGAACTCCCCAGAGTTCACACCTTACCTGGA
GACAAACCTCGGACAGCCAACAATTCAGAGTTTTGAACAGGTGGGAAC
AAAAGTGAATGTGACCGTAGAAGATGAACGGACTTTAGTCAGAAGGAA
CAACACTTTCCTAAGCCTCCGGGATGTTTTTGGCAAGGACTTAATTTA
TACACTTTATTATTGGAAATCTTCAAGTTCAGGAAAGAAAACAGCCAA
AACAAACACTAATGAGTTTTTGATTGATGTGGATAAAGGAGAAAACTA
CTGTTTCAGTGTTCAAGCAGTGATTCCCTCCCGAACAGTTAACCGGAA
GAGTACAGACAGCCCGGTAGAGTGTATGGGCCAGGAGAAAGGGGAATT
CAGAGAAAACTGGGTGAACGTCATCAGCGATTTAAAGAAGATCGAAGA
TTTAATTCAGTCCATGCATATCGACGCCACTTTATACACAGAATCCGA
CGTGCACCCCTCTTGTAAGGTGACCGCCATGAAATGTTTTTTACTGGA
GCTGCAAGTTATCTCTTTAGAGAGCGGAGACGCTAGCATCCACGACAC
CGTGGAGAATTTAATCATTTTAGCCAATAACTCTTTATCCAGCAACGG
CAACGTGACAGAGTCCGGCTGCAAGGAGTGCGAAGAGCTGGAGGAGAA
GAACATCAAGGAGTTTCTGCAATCCTTTGTGCACATTGTCCAGATGTT
CATCAATACCTCC

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 203)
DCDIEGKDGKQYESVLMVSIDQLLDSMKEIGSNCLNNENFFKRHIC
DANKEGMFLFRAARKLRQFLKMNSTGDFDLHLLKVSEGTTILLNCT
GQVKGRKPAALGEAQPTKSLEENKSLKEQKKLNDLCFLKRLLQEIK
TCWNKILMGTKEHITCPPPMSVEHADIWVKSYSLYSRERYICNSGF
KRKAGTSSLTECVLNKATNVAHWTTPSLKCIR

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 204)
GATTGTGATATTGAAGGTAAAGATGGCAAACAATATGAGAGTGTTC
TAATGGTCAGCATCGATCAATTATTGGACAGCATGAAAGAAATTGG
TAGCAATTGCCTGAATAATGAATTTAACTTTTTTAAAAGACATATC
TGTGATGCTAATAAGGAAGGTATGTTTTTATTCCGTGCTGCTCGCA
AGTTGAGGCAATTTCTTAAAATGAATAGCACTGGTGATTTTGATCT
CCACTTATTAAAAGTTTCAGAAGGCACAACAATACTGTTGAACTGC
ACTGGCCAGGTTAAAGGAAGAAAACCAGCTGCCCTGGGTGAAGCCC
AACCAACAAAGAGTTTGGAAGAAAATAAATCTTTAAAGGAACAGAA
AAAACTGAATGACTTGTGTTTCCTAAAGAGACTATTACAAGAGATA
AAAACTTGTTGGAATAAAATTTTGATGGGCACTAAAGAACACATCA
CGTGCCCTCCCCCCATGTCCGTGGAACACGCAGACATCTGGGTCAA
GAGCTACAGCTTGTACTCCAGGGAGCGGTACATTTGTAACTCTGGT
TTCAAGCGTAAAGCCGGCACGTCCAGCCTGACGGAGTGCGTGTTGA
ACAAGGCCACGAATGTCGCCCACTGGACAACCCCCAGTCTCAAATG
CATTAGA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 205)
MGVKVLFALICIAVAEADCDIEGKDGKQYESVLMVSIDQLLDSMKEIGS
NCLNNEFNFFKRHICDANKEGMFLFRAARKLRQFLKMNSTGDFDLHLLK
VSEGTTILLNCTGQVKGRKPAALGEAQPTKSLEENKSLKEQKKLNDLCF
LKRLLQEIKTCWNKILMGTKEHITCPPPMSVEHADIWVKSYSLYSRERY
ICNSGFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 206)
ATGGGAGTGAAAGTTCTTTTTGCCCTTATTTGTATTGCTGTGGCCGAG
GCCGATTGTGATATTGAAGGTAAAGATGGCAAACAATATGAGAGTGTT
CTAATGGTCAGCATCGATCAATTATTGGACAGCATGAAAGAAATTGGT
AGCAATTGCCTGAATAATGAATTTAACTTTTTTAAAAGACATATCTGT
GATGCTAATAAGGAAGGTATGTTTTTATTCCGTGCTGCTCGCAAGTTG
AGGCAATTTCTTAAAATGAATAGCACTGGTGATTTTGATCTCCACTTA
TTAAAAGTTTCAGAAGGCACAACAATACTGTTGAACTGCACTGGCCAG
GTTAAAGGAAGAAAACCAGCTGCCCTGGGTGAAGCCCAACCAACAAAG

-continued
AGTTTGGAAGAAAATAAATCTTTAAAGGAACAGAAAAAACTGAATGAC
TTGTGTTTCCTAAAGAGACTATTACAAGAGATAAAAACTTGTTGGAAT
AAAATTTTGATGGGCACTAAAGAACACATCACGTGCCCTCCCCCCATG
TCCGTGGAACACGCAGACATCTGGGTCAAGAGCTACAGCTTGTACTCC
AGGGAGCGGTACATTTGTAACTCTGGTTTCAAGCGTAAAGCCGGCACG
TCCAGCCTGACGGAGTGCGTGTTGAACAAGGCCACGAATGTCGCCCAC
TGGACAACCCCCAGTCTCAAATGCATTAGA.

Exemplary Multi-Chain Chimeric Polypeptides—Type D

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
QGQDRHMIRMRQLIDIVDQLKNYVNDLVPEFLPAPEDVETNCEWSAFS

CLKSANTGNNERIINVSIKKLKRKPPSTNAGRRQKHRLTCPSCDSYEK kPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)
CAAGGTCAAGATCGCCACATGATTAGAATGCGTCAACTTATAGATAT

TGTTGATCAGCTGAAAAATTATGTGAATGACTTGGTCCCTGAATTTC

TGCCAGCTCCAGAAGATGTAGAGACAAACTGTGAGTGGTCAGCTTTT

TCCTGTTTTCAGAAGGCCCAACTAAAGTCAGCAAATACAGGAAACAA

TGAAAGGATAATCAATGTATCAATTAAAAAGCTGAAGAGGAAACCAC

CTTCCACAAATGCAGGGAGAAGACAGAAACACAGACTAACATGCCCT

TCATGTGATTCTTATGAGAAAAAACCACCCAAAGAATTCCTAGAAAG

ATTCAAATCACTTCTCCAAAAGATGATTCATCAGCATCTGTCCTCTA

GAACACACGGAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)
CAGGGCCAGGACAGGCACATGATCCGGATGAGGCAGCTCATCGACAT

CGTCGACCAGCTGAAGAACTACGTGAACGACCTGGTGCCCGAGTTTCTGCC

TGCCCCCGAGGACGTGGAGACCAACTGCGAGTGGTCCGCCTTCTCCTGCTT

TCAGAAGGCCCAGCTGAAGTCCGCCAACACCGGCAACAACGAGCGGATCAT

-continued

CAACGTGAGCATCAAGAAGCTGAAGCGGAAGCCTCCCTCCACAAACGCCGG

CAGGAGGCAGAAGCACAGGCTGACCTGCCCCAGCTGTGACTCCTACGAGAA

GAAGCCCCCCAAGGAGTTCCTGGAGAGGTTCAAGTCCCTGCTGCAGAAGAT

GATCCATCAGCACCTGTCCTCCAGGACCCACGGCTCCGAGGACTCC.

In some embodiments of these multi-chain chimeric polypeptides, the sequence of soluble human IL-7 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
DCDIEGKDGKQYESVLMVSIDQLLDSMKEIGSNCLNNEFNEFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
GATTGTGATATTGAAGGTAAAGATGGCAAACAATATGAGAGTGTTCTAA

TGGTCAGCATCGATCAATTATTGGACAGCATGAAAGAAATTGGTAGCAA

TTGCCTGAATAATGAATTTAACTTTTTTAAAAGACATATCTGTGATGCT

AATAAGGAAGGTATGTTTTTATTCCGTGCTGCTCGCAAGTTGAGGCAAT

TTCTTAAAATGAATAGCACTGGTGATTTTGATCTCCACTTATTAAAAGT

TTCAGAAGGCACAACAATACTGTTGAACTGCACTGGCCAGGTTAAAGGA

AGAAAACCAGCTGCCCTGGGTGAAGCCCAACCAACAAAGAGTTTGGAAG

AAAATAAATCTTTAAAGGAACAGAAAAAACTGAATGACTTGTGTTTCCT

AAAGAGACTATTACAAGAGATAAAAACTTGTTGGAATAAAATTTTGATG

GGCACTAAAGAACAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 207)
DCDIEGKDGKQYESVLMVSIDQLLDSMKEIGSNCLNNEFNEFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

-continued

GTKEHSGTTNTVAAYNLTWKSTNFKTILEWEPKPVNQVYTVQISTKSGD

WKSKCFYTTDTECDLTDEIVKDVKQTYLARVFSYPAGNVESTGSAGEPL

YENSPEFTPYLETNLGQPTIQSFEQVGTKVNVTVEDERTLVRRNNTFLS

LRDVFGKDLIYTLYYWKSSSSGKKTAKTNTNEFLIDVDKGENYCFSVQA

VIPSRTVNRKSTDSPVECMGQEKGEFRENWVNVISDLKKIEDLIQSMHI

DATLYTESDVHPSCKVTAMKCFLLELQVISLESGDASIHDTVENLIILA

NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 208)

GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCATAGCGGCACAACCAACACAGTCGCTGCCTATAACC

TCACTTGGAAGAGCACCAACTTCAAAACCATCCTCGAATGGGAACCCAA

ACCCGTTAACCAAGTTTACACCGTGCAGATCAGCACCAAGTCCGGCGAC

TGGAAGTCCAAATGTTTCTATACCACCGACACCGAGTGCGATCTCACCG

ATGAGATCGTGAAAGATGTGAAACAGACCTACCTCGCCCGGGTGTTTAG

CTACCCCGCCGGCAATGTGGAGAGCACTGGTTCCGCTGGCGAGCCTTTA

TACGAGAACAGCCCCGAATTTACCCCTTACCTCGAGACCAATTTAGGAC

AGCCCACCATCCAAAGCTTTGAGCAAGTTGGCACAAAGGTGAATGTGAC

AGTGGAGGACGAGCGGACTTTAGTGCGGCGGAACAACACCTTTCTCAGC

CTCCGGGATGTGTTCGGCAAAGATTTAATCTACACACTGTATTACTGGA

AGTCCTCTTCCTCCGGCAAGAAGACAGCTAAAACCAACACAAACGAGTT

TTTAATCGACGTGGATAAAGGCGAAAACTACTGTTTCAGCGTGCAAGCT

GTGATCCCCTCCCGGACCGTGAATAGGAAAAGCACCGATAGCCCCGTTG

AGTGCATGGGCCAAGAAAAGGGCGAGTTCCGGGAGAACTGGGTGAACGT

CATCAGCGATTTAAAGAAGATCGAAGATTTAATTCAGTCCATGCATATC

GACGCCACTTTATACACAGAATCCGACGTGCACCCCTCTTGTAAGGTGA

CCGCCATGAAATGTTTTTTACTGGAGCTGCAAGTTATCTCTTTAGAGAG

CGGAGACGCTAGCATCCACGACACCGTGGAGAATTTAATCATTTTAGCC

AATAACTCTTTATCCAGCAACGGCAACGTGACAGAGTCCGGCTGCAAGG

-continued

AGTGCGAAGAGCTGGAGGAGAAGAACATCAAGGAGTTTCTGCAATCCTT

TGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 209)

MKWVTFISLLFLFSSAYSDCDIEGKDGKQYESVLMVSIDQLLDSMKEIG

SNCLNNEFNFFKRHICDANKEGMFLFRAARKLRQFLKMNSTGDFDLHLL

KVSEGTTILLNCTGQVKGRKPAALGEAQPTKSLEENKSLKEQKKLNDLC

FLKRLLQEIKTCWNKILMGTKEHSGTTNTVAAYNLTWKSTNFKTILEWE

PKPVNQVYTVQISTKSGDWKSKCFYTTDTECDLTDEIVKDVKQTYLARV

FSYPAGNVESTGSAGEPLYENSPEFTPYLETNLGQPTIQSFEQVGTKVN

VTVEDERTLVRRNNTFLSLRDVFGKDLIYTLYYWKSSSSGKKTAKTNTN

EFLIDVDKGENYCFSVQAVIPSRTVNRKSTDSPVECMGQEKGEFRENWV

NVISDLKKIEDLIQSMHIDATLYTESDVHPSCKVTAMKCFLLELQVISL

ESGDASIHDTVENLIILANNSLSSNGNVTESGCKECEELEEKNIKEFLQ

SFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 210)

ATGAAGTGGGTGACCTTCATCAGCCTGCTGTTCCTGTTCTCCAGCGCCT

ACTCCGATTGCGACATCGAGGGCAAGGACGGCAAGCAGTACGAGAGCGT

GCTGATGGTGTCCATCGACCAGCTGCTGGACAGCATGAAGGAGATCGGC

TCCAACTGCCTCAACAACGAGTTCAACTTCTTCAAGCGGCACATCTGCG

ACGCCAACAAGGAGGGCATGTTCCTGTTCAGGGCCGCCAGGAAACTGCG

GCAGTTCCTGAAGATGAACTCCACCGGCGACTTCGACCTGCACCTGCTG

AAGGTGTCCGAGGGCACCACCATCCTGCTGAACTGCACCGGACAGGTGA

AGGGCCGGAAACCTGCTGCTCTGGGAGAGGCCCAACCCACCAAGAGCCT

GGAGGAGAACAAGTCCCTGAAGGAGCAGAAGAAGCTGAACGACCTGTGC

TTCCTGAAGAGGCTGCTGCAGGAGATCAAGACCTGCTGGAACAAGATCC

TGATGGGCACCAAGGAGCATAGCGGCACAACCAACACAGTCGCTGCCTA

TAACCTCACTTGGAAGAGCACCAACTTCAAAACCATCCTCGAATGGGAA

CCCAAACCCGTTAACCAAGTTTACACCGTGCAGATCAGCACCAAGTCCG

GCGACTGGAAGTCCAAATGTTTCTATACCACCGACACCGAGTGCGATCT

CACCGATGAGATCGTGAAAGATGTGAAACAGACCTACCTCGCCCGGGTG

-continued

TTTAGCTACCCCGCCGGCAATGTGGAGAGCACTGGTTCCGCTGGCGAGC

CTTTATACGAGAACAGCCCCGAATTTACCCCTTACCTCGAGACCAATTT

AGGACAGCCCACCATCCAAAGCTTTGAGCAAGTTGGCACAAAGGTGAAT

GTGACAGTGGAGGACGAGCGGACTTTAGTGCGGCGGAACAACACCTTTC

TCAGCCTCCGGGATGTGTTCGGCAAAGATTTAATCTACACACTGTATTA

CTGGAAGTCCTCTTCCTCCGGCAAGAAGACAGCTAAAACCAACACAAAC

GAGTTTTTAATCGACGTGGATAAAGGCGAAAACTACTGTTTCAGCGTGC

AAGCTGTGATCCCCTCCCGGACCGTGAATAGGAAAAGCACCGATAGCCC

CGTTGAGTGCATGGGCCAAGAAAAGGGCGAGTTCCGGGAGAACTGGGTG

AACGTCATCAGCGATTTAAAGAAGATCGAAGATTTAATTCAGTCCATGC

ATATCGACGCCACTTTATACACAGAATCCGACGTGCACCCCTCTTGTAA

GGTGACCGCCATGAAATGTTTTTTACTGGAGCTGCAAGTTATCTCTTTA

GAGAGCGGAGACGCTAGCATCCACGACACCGTGGAGAATTTAATCATTT

TAGCCAATAACTCTTTATCCAGCAACGGCAACGTGACAGAGTCCGGCTG

CAAGGAGTGCGAAGAGCTGGAGGAGAAGAACATCAAGGAGTTTCTGCAA

TCCTTTGTGCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 211)

QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDSITCPPPMSVEHADI

WVKSYSLYSRERYICNSGFKRKAGTSSLTECVLNKATNVAHWTTPSLKC

IR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 212)

CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

-continued

GGACTCCATTACATGCCCCCCTCCCATGAGCGTGGAGCACGCCGACATC

TGGGTGAAGAGCTATAGCCTCTACAGCCGGGAGAGGTATATCTGTAACA

GCGGCTTCAAGAGGAAGGCCGGCACCAGCAGCCTCACCGAGTGCGTGCT

GAATAAGGCTACCAACGTGGCTCACTGGACAACACCCTCTTTAAAGTGC

ATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 213)

MKWVTFISLLFLFSSAYSQGQDRHMIRMRQLIDIVDQLKNYVNDLVPEF

LPAPEDVETNCEWSAFSCFQKAQLKSANTGNNERIINVSIKKLKRKPPS

TNAGRRQKHRLTCPSCDSYEKKPPKEFLERFKSLLQKMIHQHLSSRTHG

SEDSITCPPPMSVEHADIWVKSYSLYSRERYICNSGFKRKAGTSSLTEC

VLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 214)

ATGAAGTGGGTGACCTTCATCAGCCTGCTGTTCCTGTTCTCCAGCGCCT

ACTCCCAGGGCCAGGACAGGCACATGATCCGGATGAGGCAGCTCATCGA

CATCGTCGACCAGCTGAAGAACTACGTGAACGACCTGGTGCCCGAGTTT

CTGCCTGCCCCCGAGGACGTGGAGACCAACTGCGAGTGGTCCGCCTTCT

CCTGCTTTCAGAAGGCCCAGCTGAAGTCCGCCAACACCGGCAACAACGA

GCGGATCATCAACGTGAGCATCAAGAAGCTGAAGCGGAAGCCTCCCTCC

ACAAACGCCGGCAGGAGGCAGAAGCACAGGCTGACCTGCCCCAGCTGTG

ACTCCTACGAGAAGAAGCCCCCCAAGGAGTTCCTGGAGAGGTTCAAGTC

CCTGCTGCAGAAGATGATCCATCAGCACCTGTCCTCCAGGACCCACGGC

TCCGAGGACTCCATTACATGCCCCCCTCCCATGAGCGTGGAGCACGCCG

ACATCTGGGTGAAGAGCTATAGCCTCTACAGCCGGGAGAGGTATATCTG

TAACAGCGGCTTCAAGAGGAAGGCCGGCACCAGCAGCCTCACCGAGTGC

GTGCTGAATAAGGCTACCAACGTGGCTCACTGGACAACACCCTCTTTAA

AGTGCATCCGG.

Exemplary Multi-Chain Chimeric Polypeptides—Type E

In some embodiments of any of the multi-chain chimeric polypeptides described herein, the first target-binding domain and the second targeting-binding domain each independently bind specifically to a receptor for IL-18 (e.g., a soluble human IL-18), a receptor for IL-12 (e.g., a soluble human IL-12), or CD16 (e.g., an anti-CD16 scFv). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-12.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12. In some embodiments of these multi-chain chimeric polypeptides, the first target-binding domain binds specifically to CD16, and the second target-binding domain binds specifically to a receptor for IL-18. In some embodiments of these multi-chain chimeric polypeptides, the first target-binding domain binds specifically to a receptor for IL-18, and the second target-binding domain bind specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a soluble IL-18 (e.g., a soluble human IL-18).

In some embodiments of these multi-chain chimeric polypeptides, the soluble human IL-18 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 109)
YFGKLESKLSVIRNLNDQVLFIDQGNRPLFEDMTDSDCRDNAPRTIFIIS
MYKDSQPRGMAVTISVKCEKISTLSCENKIISFKEMNPPDNIKDTKSDII
FFQRSVPGHDNKMQFESSSYEGYFLACEKERDLFKLILKKEDELGDRSIM
FTVQNED.

In some embodiments of these multi-chain chimeric polypeptides, the soluble human IL-18 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 171)
TACTTCGGCAAACTGGAATCCAAGCTGAGCGTGATCCGGAATTTAAACGA
CCAAGTTCTGTTTATCGATCAAGGTAACCGGCCTCTGTTCGAGGACATGA
CCGACTCCGATTGCCGGGACAATGCCCCCCGGACCATCTTCATTATCTCC
ATGTACAAGGACAGCCAGCCCCGGGGCATGGCTGTGACAATTAGCGTGAA
GTGTGAGAAAATCAGCACTTTATCTTGTGAGAACAAGATCATCTCCTTTA
AGGAAATGAACCCCCCCGATAACATCAAGGACACCAAGTCCGATATCATC
TTCTTCCAGCGGTCCGTGCCCGGTCACGATAACAAGATGCAGTTCGAATC
CTCCTCCTACGAGGGCTACTTTTTAGCTTGTGAAAAGGAGAGGGATTTAT
TCAAGCTGATCCTCAAGAAGGAGGACGAGCTGGGCGATCGTTCCATCATG
TTCACCGTCCAAAACGAGGAT.

In some embodiments of these multi-chain chimeric polypeptides, the second target-binding domain includes a soluble IL-12 (e.g., a soluble human IL-12). In some embodiments of these multi-chain chimeric polypeptides, the soluble human IL-15 includes a sequence of soluble human IL-12β (p40) and a sequence of soluble human IL-12α (p35). In some embodiments of these multi-chain chimeric polypeptides, the soluble IL-15 (e.g., soluble human IL-15) further includes a linker sequence (e.g., any of the exemplary linker sequences described herein) between the sequence of soluble IL-120 (p40) and the sequence of soluble human IL-12α (p35). In some examples of these multi-chain chimeric polypeptides, the linker sequence comprises GGGGSGGGGSGGGGS (SEQ ID NO: 102).

In some embodiments of these multi-chain chimeric polypeptides, the sequence of soluble human IL-12β (p40) comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 81)
IWELKKDVYVVELDWYPDAPGEMVVLTCDTPEEDGITWTLDQSSEVLGSG
KTLTIQVKEFGDAGQYTCHKGGEVLSHSLLLLHKKEDGIWSTDILKDQKE
PKNKTFLRCEAKNYSGRFTCWWLTTISTDLTFSVKSSRGSSDPQGVTCGA
ATLSAERVRGDNKEYEYSVECQEDSACPAAEESLPIEVMVDAVHKLKYEN
YTSSFFIRDIIKPDPPKNLQLKPLKNSRQVEVSWEYPDTWSTPHSYFSLT

-continued

FCVQVQGKSKREKKDRVFTDKTSATVICRKNASISVRAQDRYYSSSWSEW
ASVPCS.

In some embodiments of these multi-chain chimeric polypeptides, the soluble human IL-12β (p40) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 172)
ATTTGGGAACTGAAGAAGGACGTCTACGTGGTCGAACTGGACTGGTATCC
CGATGCTCCCGGCGAAATGGTGGTGCTCACTTGTGACACCCCCGAAGAAG
ACGGCATCACTTGGACCCTCGATCAGAGCAGCGAGGTGCTGGGCTCCGGA
AAGACCCTCACAATCCAAGTTAAGGAGTTCGGAGACGCTGGCCAATACAC
ATGCCACAAGGGAGGCGAGGTGCTCAGCCATTCCTTATTATTATTACACA
AGAAGGAAGACGGAATCTGGTCCACCGACATTTTAAAAGATCAGAAGGAG
CCCAAGAATAAGACCTTTTTAAGGTGTGAGGCCAAAAACTACAGCGGTCG
TTTCACTTGTTGGTGGCTGACCACCATTTCCACCGATTTAACCTTCTCCG
TGAAAAGCAGCCGGGGAAGCTCCGACCCTCAAGGTGTGACATGTGGAGCC
GCTACCCTCAGCGCTGAGAGGGTTCGTGGCGATAACAAGGAATACGAGTA
CAGCGTGGAGTGCCAAGAAGATAGCGCTTGTCCCGCTGCCGAAGAATCTT
TACCCATTGAGGTGATGGTGGACGCCGTGCACAAACTCAAGTACGAGAAC
TACACCTCCTCCTTCTTTATCCGGGACATCATTAAGCCCGATCCTCCTAA
GAATTTACAGCTGAAGCCTCTCAAAAATAGCCGGCAAGTTGAGGTCTCTT
GGGAATATCCCGACACTTGGAGCACACCCCACAGCTACTTCTCTTTAACC
TTTTGTGTGCAAGTTCAAGGTAAAAGCAAGCGGGAGAAGAAAGACCGGGT
GTTTACCGACAAAACCAGCGCCACCGTCATCTGTCGGAAGAACGCCTCCA
TCAGCGTGAGGGCTCAAGATCGTTATTACTCCAGCAGCTGGTCCGAGTGG
GCCAGCGTGCCTTGTTCC.

In some embodiments of these multi-chain chimeric polypeptides, the soluble human IL-12α (p35) includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 80)
RNLPVATPDPGMFPCLEIRSQNLLRAVSNMLQKARQTLEFYPCTSEEIDH
EDITKDKTSTVEACLPLELTKNESCLNSRETSFITNGSCLASRKTSFMMA
LCLSSIYEDLKMYQVEFKTMNAKLLMDPKRQIFLDQNMLAVIDELMQALN
FNSETVPQKSSLEEPDFYKTKIKLCILLHAFRIRAVTIDRVMSYLNAS.

In some embodiments of these multi-chain chimeric polypeptides, the soluble human IL-12α (p35) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 173)
CGTAACCTCCCCGTGGCTACCCCCGATCCCGGAATGTTCCCTTGTTTACA

CCACAGCCAGAATTTACTGAGGGCCGTGAGCAACATGCTGCAGAAAGCTA

GGCAGACTTTAGAATTTTACCCTTGCACCAGCGAGGAGATCGACCATGAA

GATATCACCAAGGACAAGACATCCACCGTGGAGGCTTGTTTACCTCTGGA

GCTGACAAAGAACGAGTCTTGTCTCAACTCTCGTGAAACCAGCTTCATCA

CAAATGGCTCTTGTTTAGCTTCCCGGAAGACCTCCTTTATGATGGCTTTA

TGCCTCAGCTCCATCTACGAGGATTTAAAGATGTACCAAGTGGAGTTCAA

GACCATGAACGCCAAGCTGCTCATGGACCCTAAACGGCAGATCTTTTTAG

ACCAGAACATGCTGGCTGTGATTGATGAGCTGATGCAAGCTTTAAACTTC

AACTCCGAGACCGTCCCTCAGAAGTCCTCCCTCGAGGAGCCCGATTTTTA

CAAGACAAAGATCAAACTGTGCATTTTACTCCACGCCTTTAGGATCCGGG

CCGTGACCATTGACCGGGTCATGAGCTATTTAAACGCCAGC.

In some embodiments of these multi-chain chimeric polypeptides, the additional target-binding domain includes an scFv that specifically binds to CD16 (e.g., an anti-CD16 scFv).

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 215)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 216)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

-continued

ACTACTGCAACTCCAGGGACTCCTCCGGCAACCATGTGGTGTTCGGCGGC

GGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 217)
EVQLVESGGGVVRPGGSLRLSCAASGFTFDDYGMSWVRQAPGKGLEWVSG

INWNGGSTGYADSVKGRFTISRDNAKNSLYLQMNSLRAEDTAVYYCARGR

SLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 218)
GAGGTGCAGCTGGTGGAGTCCGGAGGAGGAGTGGTGAGGCCTGGAGGCTC

CCTGAGGCTGAGCTGTGCTGCCTCCGGCTTCACCTTCGACGACTACGGCA

TGTCCTGGGTGAGGCAGGCTCCTGGAAAGGGCCTGGAGTGGGTGTCCGGC

ATCAACTGGAACGGCGGATCCACCGGCTACGCCGATTCCGTGAAGGGCAG

GTTCACCATCAGCAGGGACAACGCCAAGAACTCCCTGTACCTGCAGATGA

ACTCCCTGAGGGCCGAGGACACCGCCGTGTACTACTGCGCCAGGGGCAGG

TCCCTGCTGTTCGACTACTGGGGACAGGGCACCCTGGTGACCGTGTCCAG

G.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 174)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

FFQRSVPGHDNKMQFESSSYEGYFLACEKERDLFKLILKKEDELGDRSIM

FTVQNEDSGTTNTVAAYNLTWKSTNFKTILEWEPKPVNQVYTVQISTKSG

DWKSKCFYTTDTECDLTDEIVKDVKQTYLARVFSYPAGNVESTGSAGEPL

YENSPEFTPYLETNLGQPTIQSFEQVGTKVNVTVEDERTLVRRNNTFLSL

RDVFGKDLIYTLYYWKSSSSGKKTAKTNTNEFLIDVDKGENYCFSVQAVI

-continued

PSRTVNRKSTDSPVECMGQEKGEFRENWVNVISDLKKIEDLIQSMHIDAT

LYTESDVHPSCKVTAMKCFLLELQVISLESGDASIHDTVENLIILANNSL

SSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 175)

TACTTCGGCAAACTGGAATCCAAGCTGAGCGTGATCCGGAATTTAAACGA

CCAAGTTCTGTTTATCGATCAAGGTAACCGGCCTCTGTTCGAGGACATGA

CCGACTCCGATTGCCGGGACAATGCCCCCCGGACCATCTTCATTATCTCC

ATGTACAAGGACAGCCAGCCCCGGGGCATGGCTGTGACAATTAGCGTGAA

GTGTGAGAAAATCAGCACTTTATCTTGTGAGAACAAGATCATCTCCTTTA

AGGAAATGAACCCCCCCGATAACATCAAGGACACCAAGTCCGATATCATC

TTCTTCCAGCGGTCCGTGCCCGGTCACGATAACAAGATGCAGTTCGAATC

CTCCTCCTACGAGGGCTACTTTTTAGCTTGTGAAAAGGAGAGGGATTTAT

TCAAGCTGATCCTCAAGAAGGAGGACGAGCTGGGCGATCGTTCCATCATG

TTCACCGTCCAAAACGAGGATAGCGGCACAACCAACACAGTCGCTGCCTA

TAACCTCACTTGGAAGAGCACCAACTTCAAAACCATCCTCGAATGGGAAC

CCAAACCCGTTAACCAAGTTTACACCGTGCAGATCAGCACCAAGTCCGGC

GACTGGAAGTCCAAATGTTTCTATACCACCGACACCGAGTGCGATCTCAC

CGATGAGATCGTGAAAGATGTGAAACAGACCTACCTCGCCCGGGTGTTTA

GCTACCCCGCCGGCAATGTGGAGAGCACTGGTTCCGCTGGCGAGCCTTTA

TACGAGAACAGCCCCGAATTTACCCCTTACCTCGAGACCAATTTAGGACA

GCCCACCATCCAAAGCTTTGAGCAAGTTGGCACAAAGGTGAATGTGACAG

TGGAGGACGAGCGGACTTTAGTGCGGCGGAACAACACCTTTCTCAGCCTC

CGGGATGTGTTCGGCAAAGATTTAATCTACACACTGTATTACTGGAAGTC

CTCTTCCTCCGGCAAGAAGACAGCTAAAACCAACACAAACGAGTTTTTAA

TCGACGTGGATAAAGGCGAAAACTACTGTTTCAGCGTGCAAGCTGTGATC

CCCTCCCGGACCGTGAATAGGAAAAGCACCGATAGCCCCGTTGAGTGCAT

GGGCCAAGAAAAGGGCGAGTTCCGGGAGAACTGGGTGAACGTCATCAGCG

ATTTAAAGAAGATCGAAGATTTAATTCAGTCCATGCATATCGACGCCACT

TTATACACAGAATCCGACGTGCACCCCTCTTGTAAGGTGACCGCCATGAA

ATGTTTTTTACTGGAGCTGCAAGTTATCTCTTTAGAGAGCGGAGACGCTA

GCATCCACGACACCGTGGAGAATTTAATCATTTTAGCCAATAACTCTTTA

TCCAGCAACGGCAACGTGACAGAGTCCGGCTGCAAGGAGTGCGAAGAGCT

GGAGGAGAAGAACATCAAGGAGTTTCTGCAATCCTTTGTGCACATTGTCC

AGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 176)

MKWVTFISLLFLFSSAYSYFGKLESKLSVIRNLNDQVLFIDQGNRPLFED

MTDSDCRDNAPRTIFIISMYKDSQPRGMAVTISVKCEKISTLSCENKIIS

FKEMNPPDNIKDTKSDIIFFQRSVPGHDNKMQFESSSYEGYFLACEKERD

LFKLILKKEDELGDRSIMFTVQNEDSGTTNTVAAYNLTWKSTNFKTILEW

EPKPVNQVYTVQISTKSGDWKSKCFYTTDTECDLTDEIVKDVKQTYLARV

FSYPAGNVESTGSAGEPLYENSPEFTPYLETNLGQPTIQSFEQVGTKVNV

TVEDERTLVRRNNTFLSLRDVFGKDLIYTLYYWKSSSSGKKTAKTNTNEF

LIDVDKGENYCFSVQAVIPSRTVNRKSTDSPVECMGQEKGEFRENWVNVI

SDLKKIEDLIQSMHIDATLYTESDVHPSCKVTAMKCFLLELQVISLESGD

ASIHDTVENLIILANNSLSSNGNVTESGCKECEELEEKNIKEFLQSFVHI

VQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 177)

ATGAAGTGGGTCACATTTATCTCTTTACTGTTCCTCTTCTCCAGCGCCTA

CAGCTACTTCGGCAAACTGGAATCCAAGCTGAGCGTGATCCGGAATTTAA

ACGACCAAGTTCTGTTTATCGATCAAGGTAACCGGCCTCTGTTCGAGGAC

ATGACCGACTCCGATTGCCGGGACAATGCCCCCCGGACCATCTTCATTAT

CTCCATGTACAAGGACAGCCAGCCCCGGGGCATGGCTGTGACAATTAGCG

TGAAGTGTGAGAAAATCAGCACTTTATCTTGTGAGAACAAGATCATCTCC

TTTAAGGAAATGAACCCCCCCGATAACATCAAGGACACCAAGTCCGATAT

CATCTTCTTCCAGCGGTCCGTGCCCGGTCACGATAACAAGATGCAGTTCG

AATCCTCCTCCTACGAGGGCTACTTTTTAGCTTGTGAAAAGGAGAGGGAT

TTATTCAAGCTGATCCTCAAGAAGGAGGACGAGCTGGGCGATCGTTCCAT

CATGTTCACCGTCCAAAACGAGGATAGCGGCACAACCAACACAGTCGCTG

CCTATAACCTCACTTGGAAGAGCACCAACTTCAAAACCATCCTCGAATGG

GAACCCAAACCCGTTAACCAAGTTTACACCGTGCAGATCAGCACCAAGTC

CGGCGACTGGAAGTCCAAATGTTTCTATACCACCGACACCGAGTGCGATC

TCACCGATGAGATCGTGAAAGATGTGAAACAGACCTACCTCGCCCGGGTG

TTTAGCTACCCCGCCGGCAATGTGGAGAGCACTGGTTCCGCTGGCGAGCC

TTTATACGAGAACAGCCCCGAATTTACCCCTTACCTCGAGACCAATTTAG

GACAGCCCACCATCCAAAGCTTTGAGCAAGTTGGCACAAAGGTGAATGTG

ACAGTGGAGGACGAGCGGACTTTAGTGCGGCGGAACAACACCTTTCTCAG

CCTCCGGGATGTGTTCGGCAAAGATTTAATCTACACACTGTATTACTGGA

-continued

AGTCCTCTTCCTCCGGCAAGAAGACAGCTAAAACCAACACAAACGAGTTT

TTAATCGACGTGGATAAAGGCGAAAACTACTGTTTCAGCGTGCAAGCTGT

GATCCCCTCCCGGACCGTGAATAGGAAAAGCACCGATAGCCCCGTTGAGT

GCATGGGCCAAGAAAAGGGCGAGTTCCGGGAGAACTGGGTGAACGTCATC

AGCGATTTAAAGAAGATCGAAGATTTAATTCAGTCCATGCATATCGACGC

CACTTTATACACAGAATCCGACGTGCACCCCTCTTGTAAGGTGACCGCCA

TGAAATGTTTTTTACTGGAGCTGCAAGTTATCTCTTTAGAGAGCGGAGAC

GCTAGCATCCACGACACCGTGGAGAATTTAATCATTTTAGCCAATAACTC

TTTATCCAGCAACGGCAACGTGACAGAGTCCGGCTGCAAGGAGTGCGAAG

AGCTGGAGGAGAAGAACATCAAGGAGTTTCTGCAATCCTTTGTGCACATT

GTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 223)

IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCSGGGGSGGGGSGGGGSRNLPVATPDPGMFPCLHESQNLLRAVSNM

LQKARQTLEFYPCTSEEIDHEDITKDKTSTVEACLPLELTKNESCLNSRE

TSFITNGSCLASRKTSFMMALCLSSIYEDLKMYQVEFKTMNAKLLMDPKR

QIFLDQNMLAVIDELMQALNFNSETVPQKSSLEEPDFYKTKIKLCILLHA

FRIRAVTIDRVMSYLNASITCPPPMSVEHADIWVKSYSLYSRERYICNSG

FKRKAGTSSLTECVLNKATNVAHWTTPSLKCIRSELTQDPAVSVALGQTV

RITCQGDSLRSYYASWYQQKPGQAPVLVIYGKNNRPSGIPDRFSGSSSGN

TASLTITGAQAEDEADYYCNSRDSSGNHVVFGGGTKLTVGHGGGGSGGGG

SGGGGSEVQLVESGGGVVRPGGSLRLSCAASGFTFDDYGMSWVRQAPGKG

LEWVSGINWNGGSTGYADSVKGRFTISRDNAKNSLYLQMNSLRAEDTAVY

YCARGRSLLFDYWGQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 224)

ATTTGGGAACTGAAGAAGGACGTCTACGTGGTCGAACTGGACTGGTATCC

CGATGCTCCCGGCGAAATGGTGGTGCTCACTTGTGACACCCCCGAAGAAG

ACGGCATCACTTGGACCCTCGATCAGAGCAGCGAGGTGCTGGGCTCCGGA

AAGACCCTCACAATCCAAGTTAAGGAGTTCGGAGACGCTGGCCAATACAC

ATGCCACAAGGGAGGCGAGGTGCTCAGCCATTCCTTATTATTATTACACA

AGAAGGAAGACGGAATCTGGTCCACCGACATTTTAAAAGATCAGAAGGAG

CCCAAGAATAAGACCTTTTTAAGGTGTGAGGCCAAAAACTACAGCGGTCG

TTTCACTTGTTGGTGGCTGACCACCATTTCCACCGATTTAACCTTCTCCG

TGAAAAGCAGCCGGGGAAGCTCCGACCCTCAAGGTGTGACATGTGGAGCC

GCTACCCTCAGCGCTGAGAGGGTTCGTGGCGATAACAAGGAATACGAGTA

CAGCGTGGAGTGCCAAGAAGATAGCGCTTGTCCCGCTGCCGAAGAATCTT

TACCCATTGAGGTGATGGTGGACGCCGTGCACAAACTCAAGTACGAGAAC

TACACCTCCTCCTTCTTTATCCGGGACATCATTAAGCCCGATCCTCCTAA

GAATTTACAGCTGAAGCCTCTCAAAAATAGCCGGCAAGTTGAGGTCTCTT

GGGAATATCCCGACACTTGGAGCACACCCCACAGCTACTTCTCTTTAACC

TTTTGTGTGCAAGTTCAAGGTAAAAGCAAGCGGGAGAAGAAAGACCGGGT

GTTTACCGACAAAACCAGCGCCACCGTCATCTGTCGGAAGAACGCCTCCA

TCAGCGTGAGGGCTCAAGATCGTTATTACTCCAGCAGCTGGTCCGAGTGG

GCCAGCGTGCCTTGTTCCGGCGGTGGAGGATCCGGAGGAGGTGGCTCCGG

CGGCGGAGGATCTCGTAACCTCCCCGTGGCTACCCCCGATCCCGGAATGT

TCCCTTGTTTACACCACAGCCAGAATTTACTGAGGGCCGTGAGCAACATG

CTGCAGAAAGCTAGGCAGACTTTAGAATTTTACCCTTGCACCAGCGAGGA

GATCGACCATGAAGATATCACCAAGGACAAGACATCCACCGTGGAGGCTT

GTTTACCTCTGGAGCTGACAAAGAACGAGTCTTGTCTCAACTCTCGTGAA

ACCAGCTTCATCACAAATGGCTCTTGTTTAGCTTCCCGGAAGACCTCCTT

TATGATGGCTTTATGCCTCAGCTCCATCTACGAGGATTTAAAGATGTACC

AAGTGGAGTTCAAGACCATGAACGCCAAGCTGCTCATGGACCCTAAACGG

CAGATCTTTTTAGACCAGAACATGCTGGCTGTGATTGATGAGCTGATGCA

AGCTTTAAACTTCAACTCCGAGACCGTCCCTCAGAAGTCCTCCCTCGAGG

AGCCCGATTTTTACAAGACAAAGATCAAACTGTGCATTTTACTCCACGCC

TTTAGGATCCGGGCCGTGACCATTGACCGGGTCATGAGCTATTTAAACGC

CAGCATTACATGCCCCCCTCCCATGAGCGTGGAGCACGCCGACATCTGGG

TGAAGAGCTATAGCCTCTACAGCCGGGAGAGGTATATCTGTAACAGCGGC

TTCAAGAGGAAGGCCGGCACCAGCAGCCTCACCGAGTGCGTGCTGAATAA

GGCTACCAACGTGGCTCACTGGACAACACCCTCTTTAAAGTGCATCCGGT

CCGAGCTGACCCAGGACCCTGCTGTGTCCGTGGCTCTGGGCCAGACCGTG

AGGATCACCTGCCAGGGCGACTCCCTGAGGTCCTACTACGCCTCCTGGTA

CCAGCAGAAGCCCGGCCAGGCTCCTGTGCTGGTGATCTACGGCAAGAACA

ACAGGCCCTCCGGCATCCCTGACAGGTTCTCCGGATCCTCCTCCGGCAAC

ACCGCCTCCCTGACCATCACAGGCGCTCAGGCCGAGGACGAGGCTGACTA

CTACTGCAACTCCAGGGACTCCTCCGGCAACCATGTGGTGTTCGGCGGCG

GCACCAAGCTGACCGTGGGCCATGGCGGCGGCGGCTCCGGAGGCGGCGGC

AGCGGCGGAGGAGGATCCGAGGTGCAGCTGGTGGAGTCCGGAGGAGGAGT

GGTGAGGCCTGGAGGCTCCCTGAGGCTGAGCTGTGCTGCCTCCGGCTTCA

CCTTCGACGACTACGGCATGTCCTGGGTGAGGCAGGCTCCTGGAAAGGGC

CTGGAGTGGGTGTCCGGCATCAACTGGAACGGCGGATCCACCGGCTACGC

CGATTCCGTGAAGGGCAGGTTCACCATCAGCAGGGACAACGCCAAGAACT

CCCTGTACCTGCAGATGAACTCCCTGAGGGCCGAGGACACCGCCGTGTAC

TACTGCGCCAGGGGCAGGTCCCTGCTGTTCGACTACTGGGGACAGGGCAC

CCTGGTGACCGTGTCCAGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 225)

MKWVTFISLLFLFSSAYSIWELKKDVYVVELDWYPDAPGEMVVLTCDTPE

EDGITWTLDQSSEVLGSGKTLTIQVKEFGDAGQYTCHKGGEVLSHSLLLL

HKKEDGIWSTDILKDQKEPKNKTFLRCEAKNYSGRFTCWWLTTISTDLTF

SVKSSRGSSDPQGVTCGAATLSAERVRGDNKEYEYSVECQEDSACPAAEE

SLPIEVMVDAVHKLKYENYTSSFFIRDIIKPDPPKNLQLKPLKNSRQVEV

SWEYPDTWSTPHSYFSLTFCVQVQGKSKREKKDRVFTDKTSATVICRKNA

SISVRAQDRYYSSSWSEWASVPCSGGGGSGGGGSGGGGSRNLPVATPDPG

MFPCLHHSQNLLRAVSNMLQKARQTLEFYPCTSEEIDHEDITKDKTSTVE

ACLPLELTKNESCLNSRETSFITNGSCLASRKTSFMMALCLSSIYEDLKM

YQVEFKTMNAKLLMDPKRQIFLDQNMLAVIDELMQALNFNSETVPQKSSL

EEPDFYKTKIKLCILLHAFRIRAVTIDRVMSYLNASITCPPPMSVEHADI

WVKSYSLYSRERYICNSGFKRKAGTSSLTECVLNKATNVAHWTTPSLKCI

RSELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVFG

GGTKLTVGHGGGGSGGGGSGGGGSEVQLVESGGGVVRPGGSLRLSCAASG

FTFDDYGMSWVRQAPGKGLEWVSGINWNGGSTGYADSVKGRFTISRDNAK

NSLYLQMNSLRAEDTAVYYCARGRSLLFDYWGQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 226)

ATGAAATGGGTGACCTTTATTTCTTTACTGTTCCTCTTTAGCAGCGCCTA

CTCCATTTGGGAACTGAAGAAGGACGTCTACGTGGTCGAACTGGACTGGT

ATCCCGATGCTCCCGGCGAAATGGTGGTGCTCACTTGTGACACCCCCGAA

GAAGACGGCATCACTTGGACCCTCGATCAGAGCAGCGAGGTGCTGGGCTC

CGGAAAGACCCTCACAATCCAAGTTAAGGAGTTCGGAGACGCTGGCCAAT

ACACATGCCACAAGGGAGGCGAGGTGCTCAGCCATTCCTTATTATTATTA

CACAAGAAGGAAGACGGAATCTGGTCCACCGACATTTTAAAAGATCAGAA

GGAGCCCAAGAATAAGACCTTTTTAAGGTGTGAGGCCAAAAACTACAGCG

GTCGTTTCACTTGTTGGTGGCTGACCACCATTTCCACCGATTTAACCTTC

TCCGTGAAAAGCAGCCGGGGAAGCTCCGACCCTCAAGGTGTGACATGTGG

AGCCGCTACCCTCAGCGCTGAGAGGGTTCGTGGCGATAACAAGGAATACG

AGTACAGCGTGGAGTGCCAAGAAGATAGCGCTTGTCCCGCTGCCGAAGAA

TCTTTACCCATTGAGGTGATGGTGGACGCCGTGCACAAACTCAAGTACGA

GAACTACACCTCCTCCTTCTTTATCCGGGACATCATTAAGCCCGATCCTC

CTAAGAATTTACAGCTGAAGCCTCTCAAAAATAGCCGGCAAGTTGAGGTC

TCTTGGGAATATCCCGACACTTGGAGCACACCCCACAGCTACTTCTCTTT

AACCTTTTGTGTGCAAGTTCAAGGTAAAAGCAAGCGGGAGAAGAAAGACC

GGGTGTTTACCGACAAAACCAGCGCCACCGTCATCTGTCGGAAGAACGCC

TCCATCAGCGTGAGGGCTCAAGATCGTTATTACTCCAGCAGCTGGTCCGA

GTGGGCCAGCGTGCCTTGTTCCGGCGGTGGAGGATCCGGAGGAGGTGGCT

CCGGCGGCGGAGGATCTCGTAACCTCCCCGTGGCTACCCCCGATCCCGGA

ATGTTCCCTTGTTTACACCACAGCCAGAATTTACTGAGGGCCGTGAGCAA

CATGCTGCAGAAAGCTAGGCAGACTTTAGAATTTTACCCTTGCACCAGCG

AGGAGATCGACCATGAAGATATCACCAAGGACAAGACATCCACCGTGGAG

GCTTGTTTACCTCTGGAGCTGACAAAGAACGAGTCTTGTCTCAACTCTCG

TGAAACCAGCTTCATCACAAATGGCTCTTGTTTAGCTTCCCGGAAGACCT

CCTTTATGATGGCTTTATGCCTCAGCTCCATCTACGAGGATTTAAAGATG

TACCAAGTGGAGTTCAAGACCATGAACGCCAAGCTGCTCATGGACCCTAA

ACGGCAGATCTTTTTAGACCAGAACATGCTGGCTGTGATTGATGAGCTGA

TGCAAGCTTTAAACTTCAACTCCGAGACCGTCCCTCAGAAGTCCTCCCTC

GAGGAGCCCGATTTTTACAAGACAAAGATCAAACTGTGCATTTTACTCCA

CGCCTTTAGGATCCGGGCCGTGACCATTGACCGGGTCATGAGCTATTTAA

ACGCCAGCATTACATGCCCCCCTCCCATGAGCGTGGAGCACGCCGACATC

TGGGTGAAGAGCTATAGCCTCTACAGCCGGGAGAGGTATATCTGTAACAG

CGGCTTCAAGAGGAAGGCCGGCACCAGCAGCCTCACCGAGTGCGTGCTGA

ATAAGGCTACCAACGTGGCTCACTGGACAACACCCTCTTTAAAGTGCATC

CGGTCCGAGCTGACCCAGGACCCTGCTGTGTCCGTGGCTCTGGGCCAGAC

CGTGAGGATCACCTGCCAGGGCGACTCCCTGAGGTCCTACTACGCCTCCT

GGTACCAGCAGAAGCCCGGCCAGGCTCCTGTGCTGGTGATCTACGGCAAG

AACAACAGGCCCTCCGGCATCCCTGACAGGTTCTCCGGATCCTCCTCCGG

CAACACCGCCTCCCTGACCATCACAGGCGCTCAGGCCGAGGACGAGGCTG

ACTACTACTGCAACTCCAGGGACTCCTCCGGCAACCATGTGGTGTTCGGC

-continued

```
GGCGGCACCAAGCTGACCGTGGGCCATGGCGGCGGCGGCTCCGGAGGCGG
CGGCAGCGGCGGAGGAGGATCCGAGGTGCAGCTGGTGGAGTCCGGAGGAG
GAGTGGTGAGGCCTGGAGGCTCCCTGAGGCTGAGCTGTGCTGCCTCCGGC
TTCACCTTCGACGACTACGGCATGTCCTGGGTGAGGCAGGCTCCTGGAAA
GGGCCTGGAGTGGGTGTCCGGCATCAACTGGAACGGCGGATCCACCGGCT
ACGCCGATTCCGTGAAGGGCAGGTTCACCATCAGCAGGGACAACGCCAAG
AACTCCCTGTACCTGCAGATGAACTCCCTGAGGGCCGAGGACACCGCCGT
GTACTACTGCGCCAGGGGCAGGTCCCTGCTGTTCGACTACTGGGGACAGG
GCACCCTGGTGACCGTGTCCAGG.
```

Exemplary Multi-Chain Chimeric Polypeptides—Type F

In some embodiments of any of the multi-chain chimeric polypeptides described herein, the first target-binding domain and the second targeting-binding domain each independently bind specifically to a receptor for IL-7 (e.g., a soluble human IL-7), CD16 (e.g., an anti-CD16 scFv), or a receptor for IL-21 (e.g., a soluble human IL-21). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-21.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of any of the multi-chain chimeric polypeptides described herein, the first target-binding domain binds specifically to a receptor IL-7 and the second target-binding domain binds specifically to CD16 or a receptor for IL-21. In some embodiments of any of the multi-chain chimeric polypeptides described herein, the first target-binding domain includes a soluble IL-7 protein. In some embodiments of any of the multi-chain chimeric polypeptides described herein, the soluble IL-7 protein is a soluble human IL-7. In some embodiments of any of the multi-chain chimeric polypeptides described herein, the second antigen-binding domain includes a target-binding domain that binds specifically to CD16. In some embodiments of any of the multi-chain chimeric polypeptides described herein, the second target-binding domain includes an scFv that binds specifically to CD16. In some embodiments of any of the multi-chain chimeric polypeptides described herein, the second target-binding domain binds specifically to a receptor for IL-21. In some embodiments of any of the multi-chain chimeric polypeptides described herein, the second target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to a receptor for IL-21. In some embodiments of any of the multi-chain chimeric polypeptides described herein, the additional target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a soluble IL-7 (e.g., a soluble human IL-7).

In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
DCDIEGKDGKQYESVLMVSIDQLLDSMKEIGSNCLNNEFNFFKRHICDAN
KEGMFLFRAARKLRQFLKMNSTGDFDLHLLKVSEGTTILLNCTGQVKGRK
PAALGEAQPTKSLEENKSLKEQKKLNDLCFLKRLLQEIKTCWNKILMGTK
EH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
GATTGTGATATTGAAGGTAAAGATGGCAAACAATATGAGAGTGTTCTAAT
GGTCAGCATCGATCAATTATTGGACAGCATGAAAGAAATTGGTAGCAATT
GCCTGAATAATGAATTTAACTTTTTTAAAAGACATATCTGTGATGCTAAT
AAGGAAGGTATGTTTTTATTCCGTGCTGCTCGCAAGTTGAGGCAATTTCT
TAAAATGAATAGCACTGGTGATTTTGATCTCCACTTATTAAAAGTTTCAG
AAGGCACAACAATACTGTTGAACTGCACTGGCCAGGTTAAAGGAAGAAAA
CCAGCTGCCCTGGGTGAAGCCCAACCAACAAAGAGTTTGGAAGAAAATAA
ATCTTTAAAGGAACAGAAAAAACTGAATGACTTGTGTTTCCTAAAGAGAC
TATTACAAGAGATAAAAACTTGTTGGAATAAAATTTTGATGGGCACTAAA
GAACAC.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 227)
GATTGCGACATCGAGGGCAAGGACGGCAAGCAGTACGAGAGCGTGCTGAT
GGTGTCCATCGACCAGCTGCTGGACAGCATGAAGGAGATCGGCTCCAACT
GCCTCAACAACGAGTTCAACTTCTTCAAGCGGCACATCTGCGACGCCAAC
AAGGAGGGCATGTTCCTGTTCAGGGCCGCCAGGAAACTGCGGCAGTTCCT
GAAGATGAACTCCACCGGCGACTTCGACCTGCACCTGCTGAAGGTGTCCG
AGGGCACCACCATCCTGCTGAACTGCACCGGACAGGTGAAGGGCCGGAAA
CCTGCTGCTCTGGGAGAGGCCCAACCCACCAAGAGCCTGGAGGAGAACAA
GTCCCTGAAGGAGCAGAAGAAGCTGAACGACCTGTGCTTCCTGAAGAGGC
TGCTGCAGGAGATCAAGACCTGCTGGAACAAGATCCTGATGGGCACCAAG
GAGCAT.

In some embodiments of these multi-chain chimeric polypeptides, the sequence of soluble human IL-21 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
QGQDRHMIRMRQLIDIVDQLKNYVNDLVPEFLPAPEDVETNCEWSAFSCF
QKAQLKSANTGNNERIINVSIKKLKRKPPSTNAGRRQKHRLTCPSCDSYE
KKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)
CAAGGTCAAGATCGCCACATGATTAGAATGCGTCAACTTATAGATATTGT
TGATCAGCTGAAAAATTATGTGAATGACTTGGTCCCTGAATTTCTGCCAG
CTCCAGAAGATGTAGAGACAAACTGTGAGTGGTCAGCTTTTTCCTGTTTT
CAGAAGGCCCAACTAAAGTCAGCAAATACAGGAAACAATGAAAGGATAAT
CAATGTATCAATTAAAAAGCTGAAGAGGAAACCACCTTCCACAAATGCAG
GGAGAAGACAGAAACACAGACTAACATGCCCTTCATGTGATTCTTATGAG
AAAAAACCACCCAAAGAATTCCTAGAAAGATTCAAATCACTTCTCCAAAA
GATGATTCATCAGCATCTGTCCTCTAGAACACACGGAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC

In some embodiments of these multi-chain chimeric polypeptides, the additional target-binding domain includes an scFv that specifically binds to CD16 (e.g., an anti-CD16 scFv).

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 215)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 216)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 217)
EVQLVESGGGVVRPGGSLRLSCAASGFTFDDYGMSWVRQAPGKGLEWVSG

INWNGGSTGYADSVKGRFTISRDNAKNSLYLQMNSLRAEDTAVYYCARGR

SLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 218)
GAGGTGCAGCTGGTGGAGTCCGGAGGAGGAGTGGTGAGGCCTGGAGGCTC

CCTGAGGCTGAGCTGTGCTGCCTCCGGCTTCACCTTCGACGACTACGGCA

TGTCCTGGGTGAGGCAGGCTCCTGGAAAGGGCCTGGAGTGGGTGTCCGGC

ATCAACTGGAACGGCGGATCCACCGGCTACGCCGATTCCGTGAAGGGCAG

GTTCACCATCAGCAGGGACAACGCCAAGAACTCCCTGTACCTGCAGATGA

ACTCCCTGAGGGCCGAGGACACCGCCGTGTACTACTGCGCCAGGGGCAGG

TCCCTGCTGTTCGACTACTGGGGACAGGGCACCCTGGTGACCGTGTCCAG

G.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 207)
DCDIEGKDGKQYESVLMVSIDQLLDSMKEIGSNCLNNEFNEFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EHSGTTNTVAAYNLTWKSTNFKTILEWEPKPVNQVYTVQISTKSGDWKSK

CFYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVFG

KDLIYTLYYWKSSSSGKKTAKTNTNEFLIDVDKGENYCFSVQAVIPSRTV

NRKSTDSPVECMGQEKGEFRENWVNVISDLKKIEDLIQSMHIDATLYTES

DVHPSCKVTAMKCFLLELQVISLESGDASIHDTVENLIILANNSLSSNGN

VTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 208)
GATTGCGACATCGAGGGCAAGGACGGCAAGCAGTACGAGAGCGTGCTGAT
GGTGTCCATCGACCAGCTGCTGGACAGCATGAAGGAGATCGGCTCCAACT
GCCTCAACAACGAGTTCAACTTCTTCAAGCGGCACATCTGCGACGCCAAC
AAGGAGGGCATGTTCCTGTTCAGGGCCGCCAGGAAACTGCGGCAGTTCCT
GAAGATGAACTCCACCGGCGACTTCGACCTGCACCTGCTGAAGGTGTCCG
AGGGCACCACCATCCTGCTGAACTGCACCGGACAGGTGAAGGGCCGGAAA
CCTGCTGCTCTGGGAGAGGCCCAACCCACCAAGAGCCTGGAGGAGAACAA
GTCCCTGAAGGAGCAGAAGAAGCTGAACGACCTGTGCTTCCTGAAGAGGC
TGCTGCAGGAGATCAAGACCTGCTGGAACAAGATCCTGATGGGCACCAAG
GAGCATAGCGGCACAACCAACACAGTCGCTGCCTATAACCTCACTTGGAA
GAGCACCAACTTCAAAACCATCCTCGAATGGGAACCCAAACCCGTTAACC
AAGTTTACACCGTGCAGATCAGCACCAAGTCCGGCGACTGGAAGTCCAAA
TGTTTCTATACCACCGACACCGAGTGCGATCTCACCGATGAGATCGTGAA
AGATGTGAAACAGACCTACCTCGCCCGGGTGTTTAGCTACCCCGCCGGCA
ATGTGGAGAGCACTGGTTCCGCTGGCGAGCCTTTATACGAGAACAGCCCC
GAATTTACCCCTTACCTCGAGACCAATTTAGGACAGCCCACCATCCAAAG
CTTTGAGCAAGTTGGCACAAAGGTGAATGTGACAGTGGAGGACGAGCGGA
CTTTAGTGCGGCGGAACAACACCTTTCTCAGCCTCCGGGATGTGTTCGGC
AAAGATTTAATCTACACACTGTATTACTGGAAGTCCTCTTCCTCCGGCAA
GAAGACAGCTAAAACCAACACAAACGAGTTTTTAATCGACGTGGATAAAG
GCGAAAACTACTGTTTCAGCGTGCAAGCTGTGATCCCCTCCCGGACCGTG
AATAGGAAAAGCACCGATAGCCCCGTTGAGTGCATGGGCCAAGAAAAGGG
CGAGTTCCGGGAGAACTGGGTGAACGTCATCAGCGATTTAAAGAAGATCG
AAGATTTAATTCAGTCCATGCATATCGACGCCACTTTATACACAGAATCC
GACGTGCACCCCTCTTGTAAGGTGACCGCCATGAAATGTTTTTTACTGGA
GCTGCAAGTTATCTCTTTAGAGAGCGGAGACGCTAGCATCCACGACACCG
TGGAGAATTTAATCATTTTAGCCAATAACTCTTTATCCAGCAACGGCAAC
GTGACAGAGTCCGGCTGCAAGGAGTGCGAAGAGCTGGAGGAGAAGAACAT
CAAGGAGTTTCTGCAATCCTTTGTGCACATTGTCCAGATGTTCATCAATA
CCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 209)
MKWVTFISLLFLFSSAYSDCDIEGKDGKQYESVLMVSIDQLLDSMKEIGS
NCLNNEFNFFKRHICDANKEGMFLFRAARKLRQFLKMNSTGDFDLHLLKV
SEGTTILLNCTGQVKGRKPAALGEAQPTKSLEENKSLKEQKKLNDLCFLK
RLLQEIKTCWNKILMGTKEHSGTTNTVAAYNLTWKSTNFKTILEWEPKPV

-continued

NQVYTVQISTKSGDWKSKCFYTTDTECDLTDEIVKDVKQTYLARVFSYPA
GNVESTGSAGEPLYENSPEFTPYLETNLGQPTIQSFEQVGTKVNVTVEDE
RTLVRRNNTFLSLRDVFGKDLIYTLYYWKSSSSGKKTAKTNTNEFLIDVD
KGENYCFSVQAVIPSRTVNRKSTDSPVECMGQEKGEFRENWVNVISDLKK
IEDLIQSMHIDATLYTESDVHPSCKVTAMKCFLLELQVISLESGDASIHD
TVENLIILANNSLSSNGNVTESGCKECEELEEKNIKEFLQSFVHIVQMFI
NTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 210)
ATGAAGTGGGTGACCTTCATCAGCCTGCTGTTCCTGTTCTCCAGCGCCTA
CTCCGATTGCGACATCGAGGGCAAGGACGGCAAGCAGTACGAGAGCGTGC
TGATGGTGTCCATCGACCAGCTGCTGGACAGCATGAAGGAGATCGGCTCC
AACTGCCTCAACAACGAGTTCAACTTCTTCAAGCGGCACATCTGCGACGC
CAACAAGGAGGGCATGTTCCTGTTCAGGGCCGCCAGGAAACTGCGGCAGT
TCCTGAAGATGAACTCCACCGGCGACTTCGACCTGCACCTGCTGAAGGTG
TCCGAGGGCACCACCATCCTGCTGAACTGCACCGGACAGGTGAAGGGCCG
GAAACCTGCTGCTCTGGGAGAGGCCCAACCCACCAAGAGCCTGGAGGAGA
ACAAGTCCCTGAAGGAGCAGAAGAAGCTGAACGACCTGTGCTTCCTGAAG
AGGCTGCTGCAGGAGATCAAGACCTGCTGGAACAAGATCCTGATGGGCAC
CAAGGAGCATAGCGGCACAACCAACACAGTCGCTGCCTATAACCTCACTT
GGAAGAGCACCAACTTCAAAACCATCCTCGAATGGGAACCCAAACCCGTT
AACCAAGTTTACACCGTGCAGATCAGCACCAAGTCCGGCGACTGGAAGTC
CAAATGTTTCTATACCACCGACACCGAGTGCGATCTCACCGATGAGATCG
TGAAAGATGTGAAACAGACCTACCTCGCCCGGGTGTTTAGCTACCCCGCC
GGCAATGTGGAGAGCACTGGTTCCGCTGGCGAGCCTTTATACGAGAACAG
CCCCGAATTTACCCCTTACCTCGAGACCAATTTAGGACAGCCCACCATCC
AAAGCTTTGAGCAAGTTGGCACAAAGGTGAATGTGACAGTGGAGGACGAG
CGGACTTTAGTGCGGCGGAACAACACCTTTCTCAGCCTCCGGGATGTGTT
CGGCAAAGATTTAATCTACACACTGTATTACTGGAAGTCCTCTTCCTCCG
GCAAGAAGACAGCTAAAACCAACACAAACGAGTTTTTAATCGACGTGGAT
AAAGGCGAAAACTACTGTTTCAGCGTGCAAGCTGTGATCCCCTCCCGGAC
CGTGAATAGGAAAAGCACCGATAGCCCCGTTGAGTGCATGGGCCAAGAAA
AGGGCGAGTTCCGGGAGAACTGGGTGAACGTCATCAGCGATTTAAAGAAG
ATCGAAGATTTAATTCAGTCCATGCATATCGACGCCACTTTATACACAGA
ATCCGACGTGCACCCCTCTTGTAAGGTGACCGCCATGAAATGTTTTTTAC
TGGAGCTGCAAGTTATCTCTTTAGAGAGCGGAGACGCTAGCATCCACGAC
ACCGTGGAGAATTTAATCATTTTAGCCAATAACTCTTTATCCAGCAACGG

-continued

CAACGTGACAGAGTCCGGCTGCAAGGAGTGCGAAGAGCTGGAGGAGAAGA

ACATCAAGGAGTTTCTGCAATCCTTTGTGCACATTGTCCAGATGTTCATC

AATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 232)

SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGHGGGGSGGGGSGGGGSEVQLVESGGGVVRPGGSLRLSCAASGF

TFDDYGMSWVRQAPGKGLEWVSGINWNGGSTGYADSVKGRFTISRDNAKN

SLYLQMNSLRAEDTAVYYCARGRSLLFDYWGQGTLVTVSRITCPPPMSVE

HADIWVKSYSLYSRERYICNSGFKRKAGTSSLTECVLNKATNVAHWTTPS

LKCIRQGQDRHMIRMRQLIDIVDQLKNYVNDLVPEFLPAPEDVETNCEWS

AFSCFQKAQLKSANTGNNERIINVSIKKLKRKPPSTNAGRRQKHRLTCPS

CDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 233)

TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCATGGCGGCGGCGGCTCCGGAGGCGGCGG

CAGCGGCGGAGGAGGATCCGAGGTGCAGCTGGTGGAGTCCGGAGGAGGAG

TGGTGAGGCCTGGAGGCTCCCTGAGGCTGAGCTGTGCTGCCTCCGGCTTC

ACCTTCGACGACTACGGCATGTCCTGGGTGAGGCAGGCTCCTGGAAAGGG

CCTGGAGTGGGTGTCCGGCATCAACTGGAACGGCGGATCCACCGGCTACG

CCGATTCCGTGAAGGGCAGGTTCACCATCAGCAGGGACAACGCCAAGAAC

TCCCTGTACCTGCAGATGAACTCCCTGAGGGCCGAGGACACCGCCGTGTA

CTACTGCGCCAGGGGCAGGTCCCTGCTGTTCGACTACTGGGGACAGGGCA

CCCTGGTGACCGTGTCCAGGATTACATGCCCCCCTCCCATGAGCGTGGAG

CACGCCGACATCTGGGTGAAGAGCTATAGCCTCTACAGCCGGGAGAGGTA

-continued

TATCTGTAACAGCGGCTTCAAGAGGAAGGCCGGCACCAGCAGCCTCACCG

AGTGCGTGCTGAATAAGGCTACCAACGTGGCTCACTGGACAACACCCTCT

TTAAAGTGCATCCGGCAGGGCCAGGACAGGCACATGATCCGGATGAGGCA

GCTCATCGACATCGTCGACCAGCTGAAGAACTACGTGAACGACCTGGTGC

CCGAGTTTCTGCCTGCCCCCGAGGACGTGGAGACCAACTGCGAGTGGTCC

GCCTTCTCCTGCTTTCAGAAGGCCCAGCTGAAGTCCGCCAACACCGGCAA

CAACGAGCGGATCATCAACGTGAGCATCAAGAAGCTGAAGCGGAAGCCTC

CCTCCACAAACGCCGGCAGGAGGCAGAAGCACAGGCTGACCTGCCCCAGC

TGTGACTCCTACGAGAAGAAGCCCCCCAAGGAGTTCCTGGAGAGGTTCAA

GTCCCTGCTGCAGAAGATGATCCATCAGCACCTGTCCTCCAGGACCCACG

GCTCCGAGGACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 234)

MKWVTFISLLFLFSSAYSSELTQDPAVSVALGQTVRITCQGDSLRSYYAS

WYQQKPGQAPVLVIYGKNNRPSGIPDRFSGSSSGNTASLTITGAQAEDEA

DYYCNSRDSSGNHVVFGGGTKLTVGHGGGGSGGGGSGGGGSEVQLVESGG

GVVRPGGSLRLSCAASGFTFDDYGMSWVRQAPGKGLEWVSGINWNGGSTG

YADSVKGRFTISRDNAKNSLYLQMNSLRAEDTAVYYCARGRSLLFDYWGQ

GTLVTVSRITCPPPMSVEHADIWVKSYSLYSRERYICNSGFKRKAGTSSL

TECVLNKATNVAHWTTPSLKCIRQGQDRHMIRMRQLIDIVDQLKNYVNDL

VPEFLPAPEDVETNCEWSAFSCFQKAQLKSANTGNNERIINVSIKKLKRK

PPSTNAGRRQKHRLTCPSCDSYEKKPPKEFLERFKSLLQKMIHQHLSSRT

HGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 235)

ATGAAGTGGGTGACCTTCATCAGCCTGCTGTTCCTGTTCTCCAGCGCCTA

CTCCTCCGAGCTGACCCAGGACCCTGCTGTGTCCGTGGCTCTGGGCCAGA

CCGTGAGGATCACCTGCCAGGGCGACTCCCTGAGGTCCTACTACGCCTCC

TGGTACCAGCAGAAGCCCGGCCAGGCTCCTGTGCTGGTGATCTACGGCAA

GAACAACAGGCCCTCCGGCATCCCTGACAGGTTCTCCGGATCCTCCTCCG

GCAACACCGCCTCCCTGACCATCACAGGCGCTCAGGCCGAGGACGAGGCT

GACTACTACTGCAACTCCAGGGACTCCTCCGGCAACCATGTGGTGTTCGG

CGGCGGCACCAAGCTGACCGTGGGCCATGGCGGCGGCGGCTCCGGAGGCG

-continued

```
GCGGCAGCGGCGGAGGAGGATCCGAGGTGCAGCTGGTGGAGTCCGGAGGA
GGAGTGGTGAGGCCTGGAGGCTCCCTGAGGCTGAGCTGTGCTGCCTCCGG
CTTCACCTTCGACGACTACGGCATGTCCTGGGTGAGGCAGGCTCCTGGAA
AGGGCCTGGAGTGGGTGTCCGGCATCAACTGGAACGGCGGATCCACCGGC
TACGCCGATTCCGTGAAGGGCAGGTTCACCATCAGCAGGGACAACGCCAA
GAACTCCCTGTACCTGCAGATGAACTCCCTGAGGGCCGAGGACACCGCCG
TGTACTACTGCGCCAGGGGCAGGTCCCTGCTGTTCGACTACTGGGGACAG
GGCACCCTGGTGACCGTGTCCAGGATTACATGCCCCCCTCCCATGAGCGT
GGAGCACGCCGACATCTGGGTGAAGAGCTATAGCCTCTACAGCCGGGAGA
GGTATATCTGTAACAGCGGCTTCAAGAGGAAGGCCGGCACCAGCAGCCTC
ACCGAGTGCGTGCTGAATAAGGCTACCAACGTGGCTCACTGGACAACACC
CTCTTTAAAGTGCATCCGGCAGGGCCAGGACAGGCACATGATCCGGATGA
GGCAGCTCATCGACATCGTCGACCAGCTGAAGAACTACGTGAACGACCTG
GTGCCCGAGTTTCTGCCTGCCCCCGAGGACGTGGAGACCAACTGCGAGTG
GTCCGCCTTCTCCTGCTTTCAGAAGGCCCAGCTGAAGTCCGCCAACACCG
GCAACAACGAGCGGATCATCAACGTGAGCATCAAGAAGCTGAAGCGGAAG
CCTCCCTCCACAAACGCCGGCAGGAGGCAGAAGCACAGGCTGACCTGCCC
CAGCTGTGACTCCTACGAGAAGAAGCCCCCCAAGGAGTTCCTGGAGAGGT
TCAAGTCCCTGCTGCAGAAGATGATCCATCAGCACCTGTCCTCCAGGACC
CACGGCTCCGAGGACTCC.
```

Exemplary Multi-Chain Chimeric Polypeptides—Type G

In some embodiments of any of the multi-chain chimeric polypeptides described herein, the first target-binding domain and the second targeting-binding domain each independently bind specifically to TGFβ (e.g., a human TGFβRII receptor), CD16 (e.g., an anti-CD16 scFv), or a receptor for IL-21 (e.g., a soluble human IL-21). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-21.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of any of the multi-chain chimeric polypeptides described herein, the first target-binding domain and the second targeting-binding domain each independently bind specifically to TGF-β, CD16, or a receptor for IL-21. In some embodiments of any of the multi-chain chimeric polypeptides described herein, the first target-binding domain binds specifically to a TGF-β and the second target-binding domain binds specifically to CD16 or a receptor of IL-21. In some embodiments of any of the multi-chain chimeric polypeptides described herein, the first target-binding domain is a soluble TGF-β receptor. In some embodiments of any of the multi-chain chimeric polypeptides described herein, soluble TGF-β receptor is a soluble TGFβRII receptor. In some embodiments of any of the multi-chain chimeric polypeptides described herein, the second target-binding domain binds specifically to CD16. In some embodiments of any of the multi-chain chimeric polypeptides described herein, the second antigen-binding domain includes an antigen-binding domain that binds specifically to CD16. In some embodiments of any of the multi-chain chimeric polypeptides described herein, the second antigen-binding domain includes an scFv that binds specifically to CD16. In some embodiments of any of the multi-chain chimeric polypeptides described herein, the second target-binding domain binds specifically to a receptor for IL-21. In some embodiments of any of the multi-chain chimeric polypeptides described herein, the second target-binding domain includes a soluble IL-21. In some embodiments of any of the multi-chain chimeric polypeptides described herein, the second target-binding domain includes a soluble human IL-21. In some embodiments of any of the multi-chain chimeric polypeptides described herein, the second chimeric polypeptide further includes an additional target-binding domain that binds specifically to a receptor for IL-21. In some embodiments of any of the multi-chain chimeric polypeptides described herein, the additional target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a TGFβRII receptor (e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 183)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 184)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPD.
```

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 185)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT
```

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 186)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG
```

-continued

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)

IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.

In some embodiments of these multi-chain chimeric polypeptides, the soluble human TGFβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)

ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC.

In some embodiments of these multi-chain chimeric polypeptides, the sequence of soluble human IL-21 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)

QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)

CAAGGTCAAGATCGCCACATGATTAGAATGCGTCAACTTATAGATATTGT

TGATCAGCTGAAAAATTATGTGAATGACTTGGTCCCTGAATTTCTGCCAG

CTCCAGAAGATGTAGAGACAAACTGTGAGTGGTCAGCTTTTTCCTGTTTT

CAGAAGGCCCAACTAAAGTCAGCAAATACAGGAAACAATGAAAGGATAAT

CAATGTATCAATTAAAAAGCTGAAGAGGAAACCACCTTCCACAAATGCAG

GGAGAAGACAGAAACACAGACTAACATGCCCTTCATGTGATTCTTATGAG

AAAAAACCACCCAAAGAATTCCTAGAAAGATTCAAATCACTTCTCCAAAA

GATGATTCATCAGCATCTGTCCTCTAGAACACACGGAAGTGAAGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)

CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC.

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 215)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 216)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 217)
EVQLVESGGGVVRPGGSLRLSCAASGFTFDDYGMSWVRQAPGKGLEWVSG

INWNGGSTGYADSVKGRFTISRDNAKNSLYLQMNSLRAEDTAVYYCARGR

SLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 218)
GAGGTGCAGCTGGTGGAGTCCGGAGGAGGAGTGGTGAGGCCTGGAGGCTC

CCTGAGGCTGAGCTGTGCTGCCTCCGGCTTCACCTTCGACGACTACGGCA

TGTCCTGGGTGAGGCAGGCTCCTGGAAAGGGCCTGGAGTGGGTGTCCGGC

ATCAACTGGAACGGCGGATCCACCGGCTACGCCGATTCCGTGAAGGGCAG

GTTCACCATCAGCAGGGACAACGCCAAGAACTCCCTGTACCTGCAGATGA

-continued

ACTCCCTGAGGGCCGAGGACACCGCCGTGTACTACTGCGCCAGGGGCAGG

TCCCTGCTGTTCGACTACTGGGGACAGGGCACCCTGGTGACCGTGTCCAG

G.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 236)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISDLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 237)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

-continued

ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGACAGCGGCACAACCAACACAGTCGCTGCCTATAACCTCACT
TGGAAGAGCACCAACTTCAAAACCATCCTCGAATGGGAACCCAAACCCGT
TAACCAAGTTTACACCGTGCAGATCAGCACCAAGTCCGGCGACTGGAAGT
CCAAATGTTTCTATACCACCGACACCGAGTGCGATCTCACCGATGAGATC
GTGAAAGATGTGAAACAGACCTACCTCGCCCGGGTGTTTAGCTACCCCGC
CGGCAATGTGGAGAGCACTGGTTCCGCTGGCGAGCCTTTATACGAGAACA
GCCCCGAATTTACCCCTTACCTCGAGACCAATTTAGGACAGCCCACCATC
CAAAGCTTTGAGCAAGTTGGCACAAAGGTGAATGTGACAGTGGAGGACGA
GCGGACTTTAGTGCGGCGGAACAACACCTTTCTCAGCCTCCGGGATGTGT
TCGGCAAAGATTTAATCTACACACTGTATTACTGGAAGTCCTCTTCCTCC
GGCAAGAAGACAGCTAAAACCAACACAAACGAGTTTTTAATCGACGTGGA
TAAAGGCGAAAACTACTGTTTCAGCGTGCAAGCTGTGATCCCCTCCCGGA
CCGTGAATAGGAAAAGCACCGATAGCCCCGTTGAGTGCATGGGCCAAGAA
AAGGGCGAGTTCCGGGAGAACTGGGTGAACGTCATCAGCGATTTAAAGAA
GATCGAAGATTTAATTCAGTCCATGCATATCGACGCCACTTTATACACAG
AATCCGACGTGCACCCCTCTTGTAAGGTGACCGCCATGAAATGTTTTTTA
CTGGAGCTGCAAGTTATCTCTTTAGAGAGCGGAGACGCTAGCATCCACGA
CACCGTGGAGAATTTAATCATTTTAGCCAATAACTCTTTATCCAGCAACG
GCAACGTGACAGAGTCCGGCTGCAAGGAGTGCGAAGAGCTGGAGGAGAAG
AACATCAAGGAGTTTCTGCAATCCTTTGTGCACATTGTCCAGATGTTCAT
CAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 238)
MKWVTFISLLFLFSSAYSIPPHVQKSVNNDMIVTDNNGAVKFPQLCKFCD
VRFSTCDNQKSCMSNCSITSICEKPQEVCVAVWRKNDENITLETVCHDPK
LPYHDFILEDAASPKCIMKEKKKPGETFFMCSCSSDECNDNIIFSEEYNT
SNPDGGGGSGGGGSGGGGSIPPHVQKSVNNDMIVTDNNGAVKFPQLCKFC
DVRFSTCDNQKSCMSNCSITSICEKPQEVCVAVWRKNDENITLETVCHDP
KLPYHDFILEDAASPKCIMKEKKKPGETFFMCSCSSDECNDNIIFSEEYN
TSNPDSGTTNTVAAYNLTWKSTNFKTILEWEPKPVNQVYTVQISTKSGDW
KSKCFYTTDTECDLTDEIVKDVKQTYLARVFSYPAGNVESTGSAGEPLYE
NSPEFTPYLETNLGQPTIQSFEQVGTKVNVTVEDERTLVRRNNTFLSLRD

-continued

VFGKDLIYTLYYWKSSSSGKKTAKTNTNEFLIDVDKGENYCFSVQAVIPS
RTVNRKSTDSPVECMGQEKGEFRENWVNVISDLKKIEDLIQSMHIDATLY
TESDVHPSCKVTAMKCFLLELQVISLESGDASIHDTVENLIILANNSLSS
NGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 239)
ATGAAGTGGGTGACCTTCATCAGCCTGCTGTTCCTGTTCTCCAGCGCCTA
CTCCATCCCCCCCCATGTGCAAAAGAGCGTGAACAACGATATGATCGTGA
CCGACAACAACGGCGCCGTGAAGTTTCCCCAGCTCTGCAAGTTCTGCGAT
GTCAGGTTCAGCACCTGCGATAATCAGAAGTCCTGCATGTCCAACTGCAG
CATCACCTCCATCTGCGAGAAGCCCCAAGAAGTGTGCGTGGCCGTGTGGC
GGAAAAATGACGAGAACATCACCCTGGAGACCGTGTGTCACGACCCCAAG
CTCCCTTATCACGACTTCATTCTGGAGGACGCTGCCTCCCCCAAATGCAT
CATGAAGGAGAAGAAGAAGCCCGGAGAGACCTTCTTTATGTGTTCCTGTA
GCAGCGACGAGTGTAACGACAACATCATCTTCAGCGAAGAGTACAACACC
AGCAACCCTGATGGAGGTGGCGGATCCGGAGGTGGAGGTTCTGGTGGAGG
TGGGAGTATTCCTCCCCACGTGCAGAAGAGCGTGAATAATGACATGATCG
TGACCGATAACAATGGCGCCGTGAAATTTCCCCAGCTGTGCAAATTCTGC
GATGTGAGGTTTTCCACCTGCGACAACCAGAAGTCCTGTATGAGCAACTG
CTCCATCACCTCCATCTGTGAGAAGCCTCAGGAGGTGTGCGTGGCTGTCT
GGCGGAAGAATGACGAGAATATCACCCTGGAAACCGTCTGCCACGATCCC
AAGCTGCCCTACCACGATTTCATCCTGGAAGACGCCGCCAGCCCTAAGTG
CATCATGAAAGAGAAAAAGAAGCCTGGCGAGACCTTTTTCATGTGCTCCT
GCAGCAGCGACGAATGCAACGACAATATCATCTTTAGCGAGGAATACAAT
ACCAGCAACCCCGACAGCGGCACAACCAACACAGTCGCTGCCTATAACCT
CACTTGGAAGAGCACCAACTTCAAAACCATCCTCGAATGGGAACCCAAAC
CCGTTAACCAAGTTTACACCGTGCAGATCAGCACCAAGTCCGGCGACTGG
AAGTCCAAATGTTTCTATACCACCGACACCGAGTGCGATCTCACCGATGA
GATCGTGAAAGATGTGAAACAGACCTACCTCGCCCGGGTGTTTAGCTACC
CCGCCGGCAATGTGGAGAGCACTGGTTCCGCTGGCGAGCCTTTATACGAG
AACAGCCCCGAATTTACCCCTTACCTCGAGACCAATTTAGGACAGCCCAC
CATCCAAAGCTTTGAGCAAGTTGGCACAAAGGTGAATGTGACAGTGGAGG
ACGAGCGGACTTTAGTGCGGCGGAACAACACCTTTCTCAGCCTCCGGGAT
GTGTTCGGCAAAGATTTAATCTACACACTGTATTACTGGAAGTCCTCTTC
CTCCGGCAAGAAGACAGCTAAAACCAACACAAACGAGTTTTTAATCGACG
TGGATAAAGGCGAAAACTACTGTTTCAGCGTGCAAGCTGTGATCCCCTCC

-continued

CGGACCGTGAATAGGAAAAGCACCGATAGCCCCGTTGAGTGCATGGGCCA

AGAAAAGGGCGAGTTCCGGGAGAACTGGGTGAACGTCATCAGCGATTTAA

AGAAGATCGAAGATTTAATTCAGTCCATGCATATCGACGCCACTTTATAC

ACAGAATCCGACGTGCACCCCTCTTGTAAGGTGACCGCCATGAAATGTTT

TTTACTGGAGCTGCAAGTTATCTCTTTAGAGAGCGGAGACGCTAGCATCC

ACGACACCGTGGAGAATTTAATCATTTTAGCCAATAACTCTTTATCCAGC

AACGGCAACGTGACAGAGTCCGGCTGCAAGGAGTGCGAAGAGCTGGAGGA

GAAGAACATCAAGGAGTTTCTGCAATCCTTTGTGCACATTGTCCAGATGT

TCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 232)

SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGHGGGGSGGGGSGGGGSEVQLVESGGGVVRPGGSLRLSCAASGF

TFDDYGMSWVRQAPGKGLEWVSGINWNGGSTGYADSVKGRFTISRDNAKN

SLYLQMNSLRAEDTAVYYCARGRSLLFDYWGQGTLVTVSRITCPPPMSVE

HADIWVKSYSLYSRERYICNSGFKRKAGTSSLTECVLNKATNVAHWTTPS

LKCIRQGQDRHMIRMRQLIDIVDQLKNYVNDLVPEFLPAPEDVETNCEWS

AFSCFQKAQLKSANTGNNERIINVSIKKLKRKPPSTNAGRRQKHRLTCPS

CDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 233)

TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCATGGCGGCGGCGGCTCCGGAGGCGGCGG

CAGCGGCGGAGGAGGATCCGAGGTGCAGCTGGTGGAGTCCGGAGGAGGAG

TGGTGAGGCCTGGAGGCTCCCTGAGGCTGAGCTGTGCTGCCTCCGGCTTC

ACCTTCGACGACTACGGCATGTCCTGGGTGAGGCAGGCTCCTGGAAAGGG

CCTGGAGTGGGTGTCCGGCATCAACTGGAACGGCGGATCCACCGGCTACG

-continued

CCGATTCCGTGAAGGGCAGGTTCACCATCAGCAGGGACAACGCCAAGAAC

TCCCTGTACCTGCAGATGAACTCCCTGAGGGCCGAGGACACCGCCGTGTA

CTACTGCGCCAGGGGCAGGTCCCTGCTGTTCGACTACTGGGGACAGGGCA

CCCTGGTGACCGTGTCCAGGATTACATGCCCCCCTCCCATGAGCGTGGAG

CACGCCGACATCTGGGTGAAGAGCTATAGCCTCTACAGCCGGGAGAGGTA

TATCTGTAACAGCGGCTTCAAGAGGAAGGCCGGCACCAGCAGCCTCACCG

AGTGCGTGCTGAATAAGGCTACCAACGTGGCTCACTGGACAACACCCTCT

TTAAAGTGCATCCGGCAGGGCCAGGACAGGCACATGATCCGGATGAGGCA

GCTCATCGACATCGTCGACCAGCTGAAGAACTACGTGAACGACCTGGTGC

CCGAGTTTCTGCCTGCCCCCGAGGACGTGGAGACCAACTGCGAGTGGTCC

GCCTTCTCCTGCTTTCAGAAGGCCCAGCTGAAGTCCGCCAACACCGGCAA

CAACGAGCGGATCATCAACGTGAGCATCAAGAAGCTGAAGCGGAAGCCTC

CCTCCACAAACGCCGGCAGGAGGCAGAAGCACAGGCTGACCTGCCCCAGC

TGTGACTCCTACGAGAAGAAGCCCCCCAAGGAGTTCCTGGAGAGGTTCAA

GTCCCTGCTGCAGAAGATGATCCATCAGCACCTGTCCTCCAGGACCCACG

GCTCCGAGGACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 234)

MKWVTFISLLFLFSSAYSSELTQDPAVSVALGQTVRITCQGDSLRSYYAS

WYQQKPGQAPVLVIYGKNNRPSGIPDRFSGSSSGNTASLTITGAQAEDEA

DYYCNSRDSSGNHVVFGGGTKLTVGHGGGGSGGGGSGGGGSEVQLVESGG

GVVRPGGSLRLSCAASGFTFDDYGMSWVRQAPGKGLEWVSGINWNGGSTG

YADSVKGRFTISRDNAKNSLYLQMNSLRAEDTAVYYCARGRSLLFDYWGQ

GTLVTVSRITCPPPMSVEHADIWVKSYSLYSRERYICNSGFKRKAGTSSL

TECVLNKATNVAHWTTPSLKCIRQGQDRHMIRMRQLIDIVDQLKNYVNDL

VPEFLPAPEDVETNCEWSAFSCFQKAQLKSANTGNNERIINVSIKKLKRK

PPSTNAGRRQKHRLTCPSCDSYEKKPPKEFLERFKSLLQKMIHQHLSSRT

HGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 235)

ATGAAGTGGGTGACCTTCATCAGCCTGCTGTTCCTGTTCTCCAGCGCCTA

CTCCTCCGAGCTGACCCAGGACCCTGCTGTGTCCGTGGCTCTGGGCCAGA

-continued

```
CCGTGAGGATCACCTGCCAGGGCGACTCCCTGAGGTCCTACTACGCCTCC

TGGTACCAGCAGAAGCCCGGCCAGGCTCCTGTGCTGGTGATCTACGGCAA

GAACAACAGGCCCTCCGGCATCCCTGACAGGTTCTCCGGATCCTCCTCCG

GCAACACCGCCTCCCTGACCATCACAGGCGCTCAGGCCGAGGACGAGGCT

GACTACTACTGCAACTCCAGGGACTCCTCCGGCAACCATGTGGTGTTCGG

CGGCGGCACCAAGCTGACCGTGGGCCATGGCGGCGGCGGCTCCGGAGGCG

GCGGCAGCGGCGGAGGAGGATCCGAGGTGCAGCTGGTGGAGTCCGGAGGA

GGAGTGGTGAGGCCTGGAGGCTCCCTGAGGCTGAGCTGTGCTGCCTCCGG

CTTCACCTTCGACGACTACGGCATGTCCTGGGTGAGGCAGGCTCCTGGAA

AGGGCCTGGAGTGGGTGTCCGGCATCAACTGGAACGGCGGATCCACCGGC

TACGCCGATTCCGTGAAGGGCAGGTTCACCATCAGCAGGGACAACGCCAA

GAACTCCCTGTACCTGCAGATGAACTCCCTGAGGGCCGAGGACACCGCCG

TGTACTACTGCGCCAGGGGCAGGTCCCTGCTGTTCGACTACTGGGGACAG

GGCACCCTGGTGACCGTGTCCAGGATTACATGCCCCCCTCCCATGAGCGT

GGAGCACGCCGACATCTGGGTGAAGAGCTATAGCCTCTACAGCCGGGAGA

GGTATATCTGTAACAGCGGCTTCAAGAGGAAGGCCGGCACCAGCAGCCTC

ACCGAGTGCGTGCTGAATAAGGCTACCAACGTGGCTCACTGGACAACACC

CTCTTTAAAGTGCATCCGGCAGGGCCAGGACAGGCACATGATCCGGATGA

GGCAGCTCATCGACATCGTCGACCAGCTGAAGAACTACGTGAACGACCTG

GTGCCCGAGTTTCTGCCTGCCCCCGAGGACGTGGAGACCAACTGCGAGTG

GTCCGCCTTCTCCTGCTTTCAGAAGGCCCAGCTGAAGTCCGCCAACACCG

GCAACAACGAGCGGATCATCAACGTGAGCATCAAGAAGCTGAAGCGGAAG

CCTCCCTCCACAAACGCCGGCAGGAGGCAGAAGCACAGGCTGACCTGCCC

CAGCTGTGACTCCTACGAGAAGAAGCCCCCCAAGGAGTTCCTGGAGAGGT

TCAAGTCCCTGCTGCAGAAGATGATCCATCAGCACCTGTCCTCCAGGACC

CACGGCTCCGAGGACTCC.
```

Exemplary Multi-Chain Chimeric Polypeptides—Type H

In some embodiments of any of the multi-chain chimeric polypeptides described herein, the first target-binding domain and the second targeting-binding domain each independently bind specifically to a receptor of IL-7. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain and the second target-binding domain each independently bind specifically to a receptor for IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain include a soluble IL-7 (e.g., a soluble human IL-7). In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 79)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH.
```

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 227)
GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA
```

-continued

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCAT.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 207)

DCDIEGKDGKQYESVLMVSIDQLLDSMKEIGSNCLNNEFNEFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EHSGTTNTVAAYNLTWKSTNFKTILEWEPKPVNQVYTVQISTKSGDWKSK

CFYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVFG

KDLIYTLYYWKSSSSGKKTAKTNTNEFLIDVDKGENYCFSVQAVIPSRTV

NRKSTDSPVECMGQEKGEFRENWVNVISDLKKIEDLIQSMHIDATLYTES

DVHPSCKVTAMKCFLLELQVISLESGDASIHDTVENLIILANNSLSSNGN

VTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 208)

GATTGCGACATCGAGGGCAAGGACGGCAAGCAGTACGAGAGCGTGCTGAT

GGTGTCCATCGACCAGCTGCTGGACAGCATGAAGGAGATCGGCTCCAACT

GCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCT

GAAGATGAACTCCACCGGCGACTTCGACCTGCACCTGCTGAAGGTGTCCG

AGGGCACCACCATCCTGCTGAACTGCACCGGACAGGTGAAGGGCCGGAAA

CCTGCTGCTCTGGGAGAGGCCCAACCCACCAAGAGCCTGGAGGAGAACAA

GTCCCTGAAGGAGCAGAAGAAGCTGAACGACCTGTGCTTCCTGAAGAGGC

TGCTGCAGGAGATCAAGACCTGCTGGAACAAGATCCTGATGGGCACCAAG

GAGCATAGCGGCACAACCAACACAGTCGCTGCCTATAACCTCACTTGGAA

GAGCACCAACTTCAAAACCATCCTCGAATGGGAACCCAAACCCGTTAACC

AAGTTTACACCGTGCAGATCAGCACCAAGTCCGGCGACTGGAAGTCCAAA

TGTTTCTATACCACCGACACCGAGTGCGATCTCACCGATGAGATCGTGAA

AGATGTGAAACAGACCTACCTCGCCCGGGTGTTTAGCTACCCCGCCGGCA

ATGTGGAGAGCACTGGTTCCGCTGGCGAGCCTTTATACGAGAACAGCCCC

-continued

GAATTTACCCCTTACCTCGAGACCAATTTAGGACAGCCCACCATCCAAAG

CTTTGAGCAAGTTGGCACAAAGGTGAATGTGACAGTGGAGGACGAGCGGA

CTTTAGTGCGGCGGAACAACACCTTTCTCAGCCTCCGGGATGTGTTCGGC

AAAGATTTAATCTACACACTGTATTACTGGAAGTCCTCTTCCTCCGGCAA

GAAGACAGCTAAAACCAACACAAACGAGTTTTTAATCGACGTGGATAAAG

GCGAAAACTACTGTTTCAGCGTGCAAGCTGTGATCCCCTCCCGGACCGTG

AATAGGAAAAGCACCGATAGCCCCGTTGAGTGCATGGGCCAAGAAAAGGG

CGAGTTCCGGGAGAACTGGGTGAACGTCATCAGCGATTTAAAGAAGATCG

AAGATTTAATTCAGTCCATGCATATCGACGCCACTTTATACACAGAATCC

GACGTGCACCCCTCTTGTAAGGTGACCGCCATGAAATGTTTTTTACTGGA

GCTGCAAGTTATCTCTTTAGAGAGCGGAGACGCTAGCATCCACGACACCG

TGGAGAATTTAATCATTTTAGCCAATAACTCTTTATCCAGCAACGGCAAC

GTGACAGAGTCCGGCTGCAAGGAGTGCGAAGAGCTGGAGGAGAAGAACAT

CAAGGAGTTTCTGCAATCCTTTGTGCACATTGTCCAGATGTTCATCAATA

CCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 209)

MKWVTFISLLFLFSSAYSDCDIEGKDGKQYESVLMVSIDQLLDSMKEIGS

NCLNNEFNFFKRHICDANKEGMFLFRAARKLRQFLKMNSTGDFDLHLLKV

SEGTTILLNCTGQVKGRKPAALGEAQPTKSLEENKSLKEQKKLNDLCFLK

RLLQEIKTCWNKILMGTKEHSGTTNTVAAYNLTWKSTNFKTILEWEPKPV

NQVYTVQISTKSGDWKSKCFYTTDTECDLTDEIVKDVKQTYLARVFSYPA

GNVESTGSAGEPLYENSPEFTPYLETNLGQPTIQSFEQVGTKVNVTVEDE

RTLVRRNNTFLSLRDVFGKDLIYTLYYWKSSSSGKKTAKTNTNEFLIDVD

KGENYCFSVQAVIPSRTVNRKSTDSPVECMGQEKGEFRENWVNVISDLKK

IEDLIQSMHIDATLYTESDVHPSCKVTAMKCFLLELQVISLESGDASIHD

TVENLIILANNSLSSNGNVTESGCKECEELEEKNIKEFLQSFVHIVQMFI

NTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 210)

ATGAAGTGGGTGACCTTCATCAGCCTGCTGTTCCTGTTCTCCAGCGCCTA

CTCCGATTGCGACATCGAGGGCAAGGACGGCAAGCAGTACGAGAGCGTGC

-continued

TGATGGTGTCCATCGACCAGCTGCTGGACAGCATGAAGGAGATCGGCTCC

AACTGCCTCAACAACGAGTTCAACTTCTTCAAGCGGCACATCTGCGACGC

CAACAAGGAGGGCATGTTCCTGTTCAGGGCCGCCAGGAAACTGCGGCAGT

TCCTGAAGATGAACTCCACCGGCGACTTCGACCTGCACCTGCTGAAGGTG

TCCGAGGGCACCACCATCCTGCTGAACTGCACCGGACAGGTGAAGGGCCG

GAAACCTGCTGCTCTGGGAGAGGCCCAACCCACCAAGAGCCTGGAGGAGA

ACAAGTCCCTGAAGGAGCAGAAGAAGCTGAACGACCTGTGCTTCCTGAAG

AGGCTGCTGCAGGAGATCAAGACCTGCTGGAACAAGATCCTGATGGGCAC

CAAGGAGCATAGCGGCACAACCAACACAGTCGCTGCCTATAACCTCACTT

GGAAGAGCACCAACTTCAAAACCATCCTCGAATGGGAACCCAAACCCGTT

AACCAAGTTTACACCGTGCAGATCAGCACCAAGTCCGGCGACTGGAAGTC

CAAATGTTTCTATACCACCGACACCGAGTGCGATCTCACCGATGAGATCG

TGAAAGATGTGAAACAGACCTACCTCGCCCGGGTGTTTAGCTACCCCGCC

GGCAATGTGGAGAGCACTGGTTCCGCTGGCGAGCCTTTATACGAGAACAG

CCCCGAATTTACCCCTTACCTCGAGACCAATTTAGGACAGCCCACCATCC

AAAGCTTTGAGCAAGTTGGCACAAAGGTGAATGTGACAGTGGAGGACGAG

CGGACTTTAGTGCGGCGGAACAACACCTTTCTCAGCCTCCGGGATGTGTT

CGGCAAAGATTTAATCTACACACTGTATTACTGGAAGTCCTCTTCCTCCG

GCAAGAAGACAGCTAAAACCAACACAAACGAGTTTTTAATCGACGTGGAT

AAAGGCGAAAACTACTGTTTCAGCGTGCAAGCTGTGATCCCCTCCCGGAC

CGTGAATAGGAAAAGCACCGATAGCCCCGTTGAGTGCATGGGCCAAGAAA

AGGGCGAGTTCCGGGAGAACTGGGTGAACGTCATCAGCGATTTAAAGAAG

ATCGAAGATTTAATTCAGTCCATGCATATCGACGCCACTTTATACACAGA

ATCCGACGTGCACCCCTCTTGTAAGGTGACCGCCATGAAATGTTTTTTAC

TGGAGCTGCAAGTTATCTCTTTAGAGAGCGGAGACGCTAGCATCCACGAC

ACCGTGGAGAATTTAATCATTTTAGCCAATAACTCTTTATCCAGCAACGG

CAACGTGACAGAGTCCGGCTGCAAGGAGTGCGAAGAGCTGGAGGAGAAGA

ACATCAAGGAGTTTCTGCAATCCTTTGTGCACATTGTCCAGATGTTCATC

AATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 203)

DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EHITCPPPMSVEHADIWVKSYSLYSRERYICNSGFKRKAGTSSLTECVLN

KATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 204)

GATTGTGATATTGAAGGTAAAGATGGCAAACAATATGAGAGTGTTCTAAT

GGTCAGCATCGATCAATTATTGGACAGCATGAAAGAAATTGGTAGCAATT

GCCTGAATAATGAATTTAACTTTTTTAAAAGACATATCTGTGATGCTAAT

AAGGAAGGTATGTTTTTATTCCGTGCTGCTCGCAAGTTGAGGCAATTTCT

TAAAATGAATAGCACTGGTGATTTTGATCTCCACTTATTAAAAGTTTCAG

AAGGCACAACAATACTGTTGAACTGCACTGGCCAGGTTAAAGGAAGAAAA

CCAGCTGCCCTGGGTGAAGCCCAACCAACAAAGAGTTTGGAAGAAAATAA

ATCTTTAAAGGAACAGAAAAAACTGAATGACTTGTGTTTCCTAAAGAGAC

TATTACAAGAGATAAAAACTTGTTGGAATAAAATTTTGATGGGCACTAAA

GAACACATCACGTGCCCTCCCCCCATGTCCGTGGAACACGCAGACATCTG

GGTCAAGAGCTACAGCTTGTACTCCAGGGAGCGGTACATTTGTAACTCTG

GTTTCAAGCGTAAAGCCGGCACGTCCAGCCTGACGGAGTGCGTGTTGAAC

AAGGCCACGAATGTCGCCCACTGGACAACCCCCAGTCTCAAATGCATTAG

A.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 250)

MKWVTFISLLFLFSSAYSDCDIEGKDGKQYESVLMVSIDQLLDSMKEIGS

NCLNNEFNFFKRHICDANKEGMFLFRAARKLRQFLKMNSTGDFDLHLLKV

SEGTTILLNCTGQVKGRKPAALGEAQPTKSLEENKSLKEQKKLNDLCFLK

RLLQEIKTCWNKILMGTKEHITCPPPMSVEHADIWVKSYSLYSRERYICN

SGFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 251)

ATGAAGTGGGTGACCTTCATCAGCCTGCTGTTCCTGTTCTCCAGCGCCTA

CTCCGATTGCGACATCGAGGGCAAGGACGGCAAGCAGTACGAGAGCGTGC

TGATGGTGTCCATCGACCAGCTGCTGGACAGCATGAAGGAGATCGGCTCC

AACTGCCTCAACAACGAGTTCAACTTCTTCAAGCGGCACATCTGCGACGC

CAACAAGGAGGGCATGTTCCTGTTCAGGGCCGCCAGGAAACTGCGGCAGT

-continued

```
TCCTGAAGATGAACTCCACCGGCGACTTCGACCTGCACCTGCTGAAGGTG
TCCGAGGGCACCACCATCCTGCTGAACTGCACCGGACAGGTGAAGGGCCG
GAAACCTGCTGCTCTGGGAGAGGCCCAACCCACCAAGAGCCTGGAGGAGA
ACAAGTCCCTGAAGGAGCAGAAGAAGCTGAACGACCTGTGCTTCCTGAAG
AGGCTGCTGCAGGAGATCAAGACCTGCTGGAACAAGATCCTGATGGGCAC
CAAGGAGCATATTACATGCCCCCCTCCCATGAGCGTGGAGCACGCCGACA
TCTGGGTGAAGAGCTATAGCCTCTACAGCCGGGAGAGGTATATCTGTAAC
AGCGGCTTCAAGAGGAAGGCCGGCACCAGCAGCCTCACCGAGTGCGTGCT
GAATAAGGCTACCAACGTGGCTCACTGGACAACACCCTCTTTAAAGTGCA
TCCGG.
```

Exemplary Multi-Chain Chimeric Polypeptides—Type I

In some embodiments of any of the multi-chain chimeric polypeptides described herein, the first target-binding domain and the second targeting-binding domain each independently bind specifically to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain and the second target-binding domain each independently bind specifically to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain is a soluble TGF-β receptor (e.g., a soluble TGFβRII receptor, e.g., a soluble human TGFβRII). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 183)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 184)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPD.
```

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 185)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
```

-continued

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)

ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)

IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)

ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

-continued

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 236)

IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISDLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 237)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACAGCGGCACAACCAACACAGTCGCTGCCTATAACCTCACT

TGGAAGAGCACCAACTTCAAAACCATCCTCGAATGGGAACCCAAACCCGT

TAACCAAGTTTACACCGTGCAGATCAGCACCAAGTCCGGCGACTGGAAGT

CCAAATGTTTCTATACCACCGACACCGAGTGCGATCTCACCGATGAGATC

GTGAAAGATGTGAAACAGACCTACCTCGCCCGGGTGTTTAGCTACCCCGC

CGGCAATGTGGAGAGCACTGGTTCCGCTGGCGAGCCTTTATACGAGAACA

GCCCCGAATTTACCCCTTACCTCGAGACCAATTTAGGACAGCCCACCATC

CAAAGCTTTGAGCAAGTTGGCACAAAGGTGAATGTGACAGTGGAGGACGA

GCGGACTTTAGTGCGGCGGAACAACACCTTTCTCAGCCTCCGGGATGTGT

TCGGCAAAGATTTAATCTACACACTGTATTACTGGAAGTCCTCTTCCTCC

GGCAAGAAGACAGCTAAAACCAACACAAACGAGTTTTTAATCGACGTGGA

TAAAGGCGAAAACTACTGTTTCAGCGTGCAAGCTGTGATCCCCTCCCGGA

CCGTGAATAGGAAAAGCACCGATAGCCCCGTTGAGTGCATGGGCCAAGAA

AAGGGCGAGTTCCGGGAGAACTGGGTGAACGTCATCAGCGATTTAAAGAA

GATCGAAGATTTAATTCAGTCCATGCATATCGACGCCACTTTATACACAG

AATCCGACGTGCACCCCTCTTGTAAGGTGACCGCCATGAAATGTTTTTTA

CTGGAGCTGCAAGTTATCTCTTTAGAGAGCGGAGACGCTAGCATCCACGA

CACCGTGGAGAATTTAATCATTTTAGCCAATAACTCTTTATCCAGCAACG

GCAACGTGACAGAGTCCGGCTGCAAGGAGTGCGAAGAGCTGGAGGAGAAG

AACATCAAGGAGTTTCTGCAATCCTTTGTGCACATTGTCCAGATGTTCAT

CAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 238)
MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDSGTTNTVAAYNLTWKSTNFKTILEWEPKPVNQVYTVQISTKSGDW

KSKCFYTTDTECDLTDEIVKDVKQTYLARVFSYPAGNVESTGSAGEPLYE

NSPEFTPYLETNLGQPTIQSFEQVGTKVNVTVEDERTLVRRNNTFLSLRD

VFGKDLIYTLYYWKSSSSGKKTAKTNTNEFLIDVDKGENYCFSVQAVIPS

RTVNRKSTDSPVECMGQEKGEFRENWVNVISDLKKIEDLIQSMHIDATLY

TESDVHPSCKVTAMKCFLLELQVISLESGDASIHDTVENLIILANNSLSS

NGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 239)
ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACAGCGGCACAACCAACACAGTCGCTGCCTATAACCT

-continued

CACTTGGAAGAGCACCAACTTCAAAACCATCCTCGAATGGGAACCCAAAC
CCGTTAACCAAGTTTACACCGTGCAGATCAGCACCAAGTCCGGCGACTGG
AAGTCCAAATGTTTCTATACCACCGACACCGAGTGCGATCTCACCGATGA
GATCGTGAAAGATGTGAAACAGACCTACCTCGCCCGGGTGTTTAGCTACC
CCGCCGGCAATGTGGAGAGCACTGGTTCCGCTGGCGAGCCTTTATACGAG
AACAGCCCCGAATTTACCCCTTACCTCGAGACCAATTTAGGACAGCCCAC
CATCCAAAGCTTTGAGCAAGTTGGCACAAAGGTGAATGTGACAGTGGAGG
ACGAGCGGACTTTAGTGCGGCGGAACAACACCTTTCTCAGCCTCCGGGAT
GTGTTCGGCAAAGATTTAATCTACACACTGTATTACTGGAAGTCCTCTTC
CTCCGGCAAGAAGACAGCTAAAACCAACACAAACGAGTTTTTAATCGACG
TGGATAAAGGCGAAAACTACTGTTTCAGCGTGCAAGCTGTGATCCCCTCC
CGGACCGTGAATAGGAAAAGCACCGATAGCCCCGTTGAGTGCATGGGCCA
AGAAAAGGGCGAGTTCCGGGAGAACTGGGTGAACGTCATCAGCGATTTAA
AGAAGATCGAAGATTTAATTCAGTCCATGCATATCGACGCCACTTTATAC
ACAGAATCCGACGTGCACCCCTCTTGTAAGGTGACCGCCATGAAATGTTT
TTTACTGGAGCTGCAAGTTATCTCTTTAGAGAGCGGAGACGCTAGCATCC
ACGACACCGTGGAGAATTTAATCATTTTAGCCAATAACTCTTTATCCAGC
AACGGCAACGTGACAGAGTCCGGCTGCAAGGAGTGCGAAGAGCTGGAGGA
GAAGAACATCAAGGAGTTTCTGCAATCCTTTGTGCACATTGTCCAGATGT
TCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 193)
IPPHVQKSVNNDMIVTDNNGAVKFPQLCKFCDVRFSTCDNQKSCMSNCSI
TSICEKPQEVCVAVWRKNDENITLETVCHDPKLPYHDFILEDAASPKCIM
KEKKKPGETFFMCSCSSDECNDNIIFSEEYNTSNPDGGGGSGGGGSGGGG
SIPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKCI
MKEKKKPGETFFMCSCSSDECNDNIIFSEEYNTSNPDITCPPPMSVEHAD
IWVKSYSLYSRERYICNSGFKRKAGTSSLTECVLNKATNVAHWTTPSLKC
IR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 257)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGACATTACATGCCCCCCTCCCATGAGCGTGGAGCACGCCGAC
ATCTGGGTGAAGAGCTATAGCCTCTACAGCCGGGAGAGGTATATCTGTAA
CAGCGGCTTCAAGAGGAAGGCCGGCACCAGCAGCCTCACCGAGTGCGTGC
TGAATAAGGCTACCAACGTGGCTCACTGGACAACACCCTCTTTAAAGTGC
ATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 195)
MKWVTFISLLFLFSSAYSIPPHVQKSVNNDMIVTDNNGAVKFPQLCKFCD
VRFSTCDNQKSCMSNCSITSICEKPQEVCVAVWRKNDENITLETVCHDPK
LPYHDFILEDAASPKCIMKEKKKPGETFFMCSCSSDECNDNIIFSEEYNT
SNPDGGGGSGGGGSGGGGSIPPHVQKSVNNDMIVTDNNGAVKFPQLCKFC
DVRFSTCDNQKSCMSNCSITSICEKPQEVCVAVWRKNDENITLETVCHDP
KLPYHDFILEDAASPKCIMKEKKKPGETFFMCSCSSDECNDNIIFSEEYN
TSNPDITCPPPMSVEHADIWVKSYSLYSRERYICNSGFKRKAGTSSLTEC
VLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 259)
ATGAAGTGGGTGACCTTCATCAGCCTGCTGTTCCTGTTCTCCAGCGCCTA

CTCCATCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACATTACATGCCCCCCTCCCATGAGCGTGGAGCACGC

CGACATCTGGGTGAAGAGCTATAGCCTCTACAGCCGGGAGAGGTATATCT

GTAACAGCGGCTTCAAGAGGAAGGCCGGCACCAGCAGCCTCACCGAGTGC

GTGCTGAATAAGGCTACCAACGTGGCTCACTGGACAACACCCTCTTTAAA

GTGCATCCGG.
```

Exemplary Multi-Chain Chimeric Polypeptides—Type J

In some embodiments of any of the multi-chain chimeric polypeptides described herein, the first target-binding domain and the second targeting-binding domain each independently bind specifically to a receptor of IL-7, a receptor of IL-21, or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a receptor for CD137L (e.g., a soluble CD137L, e.g., a soluble human CD137L).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments, the second chimeric polypeptide can include an additional target-binding domain. In some embodiments, the additional target-binding domain and the In some embodiments of these multi-chain chimeric polypeptides, one or more of the first target-binding domain, the second target-binding domain and the additional target-binding domain is an agonistic antigen-binding domain. In some embodiments of these multi-chain chimeric polypeptides, the first target-binding domain, the second target-binding domain, and the additional target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, the first target-binding domain binds specifically to a receptor for IL-7, and the second target-binding domain binds specifically to a receptor for IL-21 or a receptor for CD137L. In some embodiments, the additional target-binding domain binds specifically to a receptor for IL-21 or a receptor for CD137L.

In some embodiments of these multi-chain chimeric polypeptides, the first target-binding domain is a soluble IL-7

(e.g., a soluble human IL-7). In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
DCDIEGKDGKQYESVLMVSIDQLLDSMKEIGSNCLNNEFNEFKRHICDAN
KEGMFLFRAARKLRQFLKMNSTGDFDLHLLKVSEGTTILLNCTGQVKGRK
PAALGEAQPTKSLEENKSLKEQKKLNDLCFLKRLLQEIKTCWNKILMGTK
EH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 227)
GATTGCGACATCGAGGGCAAGGACGGCAAGCAGTACGAGAGCGTGCTGAT
GGTGTCCATCGACCAGCTGCTGGACAGCATGAAGGAGATCGGCTCCAACT
GCCTCAACAACGAGTTCAACTTCTTCAAGCGGCACATCTGCGACGCCAAC
AAGGAGGGCATGTTCCTGTTCAGGGCCGCCAGGAAACTGCGGCAGTTCCT
GAAGATGAACTCCACCGGCGACTTCGACCTGCACCTGCTGAAGGTGTCCG
AGGGCACCACCATCCTGCTGAACTGCACCGGACAGGTGAAGGGCCGGAAA
CCTGCTGCTCTGGGAGAGGCCCAACCCACCAAGAGCCTGGAGGAGAACAA
GTCCCTGAAGGAGCAGAAGAAGCTGAACGACCTGTGCTTCCTGAAGAGGC
TGCTGCAGGAGATCAAGACCTGCTGGAACAAGATCCTGATGGGCACCAAG
GAGCAT.

In some embodiments of these multi-chain chimeric polypeptides, the second target-binding domain or the additional target-binding domain binds specifically to a receptor for IL-21. In some embodiments of these multi-chain chimeric polypeptides, the second target-binding domain or the additional target-binding domain is a soluble IL-21 (e.g., a soluble human IL-21).

In some embodiments of these multi-chain chimeric polypeptides, a soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
QGQDRHMIRMRQLIDIVDQLKNYVNDLVPEFLPAPEDVETNCEWSAFSCF
QKAQLKSANTGNNERIINVSIKKLKRKPPSTNAGRRQKHRLTCPSCDSYE
KKPPKEFLERFKSLLQKMIHQHLSSRTHGSEDS.

In some embodiments of these multi-chain chimeric polypeptides, a soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)
CAGGGCCAGGACAGGCACATGATCCGGATGAGGCAGCTCATCGACATCGT
CGACCAGCTGAAGAACTACGTGAACGACCTGGTGCCCGAGTTTCTGCCTG
CCCCCGAGGACGTGGAGACCAACTGCGAGTGGTCCGCCTTCTCCTGCTTT
CAGAAGGCCCAGCTGAAGTCCGCCAACACCGGCAACAACGAGCGGATCAT
CAACGTGAGCATCAAGAAGCTGAAGCGGAAGCCTCCCTCCACAAACGCCG
GCAGGAGGCAGAAGCACAGGCTGACCTGCCCCAGCTGTGACTCCTACGAG
AAGAAGCCCCCCAAGGAGTTCCTGGAGAGGTTCAAGTCCCTGCTGCAGAA
GATGATCCATCAGCACCTGTCCTCCAGGACCCACGGCTCCGAGGACTCC.

In some embodiments of these multi-chain chimeric polypeptides, the second target-binding domain binds specifically to a receptor for CD137L. In some embodiments of these multi-chain chimeric polypeptides, the second chimeric polypeptide further comprises an additional target-binding domain that binds specifically to a receptor for CD137L. In some embodiments of these multi-chain chimeric polypeptides, the second target-binding domain and/or the additional target-binding domain is a soluble CD137L (e.g., a soluble human CD137L).

In some embodiments of these multi-chain chimeric polypeptides, a soluble human CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 260)
REGPELSPDDPAGLLDLRQGMFAQLVAQNVLLIDGPLSWYSDPGLAGVSL
TGGLSYKEDTKELVVAKAGVYYVFFQLELRRVVAGEGSGSVSLALHLQPL
RSAAGAAALALTVDLPPASSEARNSAFGFQGRLLHLSAGQRLGVHLHTEA
RARHAWQLTQGATVLGLFRVTPEIPAGLPSPRSE.

In some embodiments of these multi-chain chimeric polypeptides, a soluble human CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 261)
CGCGAGGGTCCCGAGCTTTCGCCCGACGATCCCGCCGGCCTCTTGGACCT
GCGGCAGGGCATGTTTGCGCAGCTGGTGGCCCAAAATGTTCTGCTGATCG
ATGGGCCCCTGAGCTGGTACAGTGACCCAGGCCTGGCAGGCGTGTCCCTG
ACGGGGGGCCTGAGCTACAAAGAGGACACGAAGGAGCTGGTGGTGGCCAA
GGCTGGAGTCTACTATGTCTTCTTTCAACTAGAGCTGCGGCGCGTGGTGG
CCGGCGAGGGCTCAGGCTCCGTTTCACTTGCGCTGCACCTGCAGCCACTG
CGCTCTGCTGCTGGGGCCGCCGCCCTGGCTTTGACCGTGGACCTGCCACC

-continued

CGCCTCCTCCGAGGCTCGGAACTCGGCCTTCGGTTTCCAGGGCCGCTTGC

TGCACCTGAGTGCCGGCCAGCGCCTGGGCGTCCATCTTCACACTGAGGCC

AGGGCACGCCATGCCTGGCAGCTTACCCAGGGCGCCACAGTCTTGGGACT

CTTCCGGGTGACCCCCGAAATCCCAGCCGGACTCCCTTCACCGAGGTCGG

AA.

In some embodiments of these multi-chain chimeric polypeptides, a soluble human CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 262)

DPAGLLDLRQGMFAQLVAQNVLLIDGPLSWYSDPGLAGVSLTGGLSYKED

TKELVVAKAGVYYVFFQLELRRVVAGEGSGSVSLALHLQPLRSAAGAAAL

ALTVDLPPASSEARNSAFGFQGRLLHLSAGQRLGVHLHTEARARHAWQLT

QGATVLGLFRVTPEI.

In some embodiments of these multi-chain chimeric polypeptides, a soluble human CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 263)

GATCCCGCCGGCCTCTTGGACCTGCGGCAGGGCATGTTTGCGCAGCTGGT

GGCCCAAAATGTTCTGCTGATCGATGGGCCCCTGAGCTGGTACAGTGACC

CAGGCCTGGCAGGCGTGTCCCTGACGGGGGGCCTGAGCTACAAAGAGGAC

ACGAAGGAGCTGGTGGTGGCCAAGGCTGGAGTCTACTATGTCTTCTTTCA

ACTAGAGCTGCGGCGCGTGGTGGCCGGCGAGGGCTCAGGCTCCGTTTCAC

TTGCGCTGCACCTGCAGCCACTGCGCTCTGCTGCTGGGGCCGCCGCCCTG

GCTTTGACCGTGGACCTGCCACCCGCCTCCTCCGAGGCTCGGAACTCGGC

CTTCGGTTTCCAGGGCCGCTTGCTGCACCTGAGTGCCGGCCAGCGCCTGG

GCGTCCATCTTCACACTGAGGCCAGGGCACGCCATGCCTGGCAGCTTACC

CAGGGCGCCACAGTCTTGGGACTCTTCCGGGTGACCCCCGAAATC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 207)

DCDIEGKDGKQYESVLMVSIDQLLDSMKEIGSNCLNNEFNEFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

-continued

EHSGTTNTVAAYNLTWKSTNFKTILEWEPKPVNQVYTVQISTKSGDWKSK

CFYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVFG

KDLIYTLYYWKSSSSGKKTAKTNTNEFLIDVDKGENYCFSVQAVIPSRTV

NRKSTDSPVECMGQEKGEFRENWVNVISDLKKIEDLIQSMHIDATLYTES

DVHPSCKVTAMKCFLLELQVISLESGDASIHDTVENLIILANNSLSSNGN

VTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 208)

GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG

GAGGGCATGTTCCTGTTCAGGGCCGCCAGGAAACTGCGGCAGTTCCTGAAG

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCATAGC

GGCACAACCAACACAGTCGCTGCCTATAACCTCACTTGGAAGAGCACCAAC

TTCAAAACCATCCTCGAATGGGAACCCAAACCCGTTAACCAAGTTTACACC

GTGCAGATCAGCACCAAGTCCGGCGACTGGAAGTCCAAATGTTTCTATACC

ACCGACACCGAGTGCGATCTCACCGATGAGATCGTGAAAGATGTGAAACAG

ACCTACCTCGCCCGGGTGTTTAGCTACCCCGCCGGCAATGTGGAGAGCACT

GGTTCCGCTGGCGAGCCTTTATACGAGAACAGCCCCGAATTTACCCCTTAC

CTCGAGACCAATTTAGGACAGCCCACCATCCAAAGCTTTGAGCAAGTTGGC

ACAAAGGTGAATGTGACAGTGGAGGACGAGCGGACTTTAGTGCGGCGGAAC

AACACCTTTCTCAGCCTCCGGGATGTGTTCGGCAAAGATTTAATCTACACA

CTGTATTACTGGAAGTCCTCTTCCTCCGGCAAGAAGACAGCTAAAACCAAC

ACAAACGAGTTTTTAATCGACGTGGATAAAGGCGAAAACTACTGTTTCAGC

GTGCAAGCTGTGATCCCCTCCCGGACCGTGAATAGGAAAAGCACCGATAGC

CCCGTTGAGTGCATGGGCCAAGAAAAGGGCGAGTTCCGGGAGAACTGGGTG

AACGTCATCAGCGATTTAAAGAAGATCGAAGATTTAATTCAGTCCATGCAT

ATCGACGCCACTTTATACACAGAATCCGACGTGCACCCCTCTTGTAAGGTG

ACCGCCATGAAATGTTTTTTACTGGAGCTGCAAGTTATCTCTTTAGAGAGC

GGAGACGCTAGCATCCACGACACCGTGGAGAATTTAATCATTTTAGCCAAT

-continued

AACTCTTTATCCAGCAACGGCAACGTGACAGAGTCCGGCTGCAAGGAGTGC

GAAGAGCTGGAGGAGAAGAACATCAAGGAGTTTCTGCAATCCTTTGTGCAC

ATTGTCCAGATGTTCATCAATACCTCC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 209)

MKWVTFISLLFLFSSAYSDCDIEGKDGKQYESVLMVSIDQLLDSMKEIGSN

CLNNEFNFFKRHICDANKEGMFLFRAARKLRQFLKMNSTGDFDLHLLKVSE

GTTILLNCTGQVKGRKPAALGEAQPTKSLEENKSLKEQKKLNDLCFLKRLL

QEIKTCWNKILMGTKEHSGTTNTVAAYNLTWKSTNFKTILEWEPKPVNQVY

TVQISTKSGDWKSKCFYTTDTECDLTDEIVKDVKQTYLARVFSYPAGNVES

TGSAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENYCF

SVQAVIPSRTVNRKSTDSPVECMGQEKGEFRENWVNVISDLKKIEDLIQSM

HIDATLYTESDVHPSCKVTAMKCFLLELQVISLESGDASIHDTVENLIILA

NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 210)

ATGAAGTGGGTGACCTTCATCAGCCTGCTGTTCCTGTTCTCCAGCGCCTAC

TCCGATTGCGACATCGAGGGCAAGGACGGCAAGCAGTACGAGAGCGTGCTG

ATGGTGTCCATCGACCAGCTGCTGGACAGCATGAAGGAGATCGGCTCCAAC

TGCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCTG

AAGATGAACTCCACCGGCGACTTCGACCTGCACCTGCTGAAGGTGTCCGAG

GGCACCACCATCCTGCTGAACTGCACCGGACAGGTGAAGGGCCGGAAACCT

GCTGCTCTGGGAGAGGCCCAACCCACCAAGAGCCTGGAGGAGAACAAGTCC

CTGAAGGAGCAGAAGAAGCTGAACGACCTGTGCTTCCTGAAGAGGCTGCTG

CAGGAGATCAAGACCTGCTGGAACAAGATCCTGATGGGCACCAAGGAGCAT

AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

-continued

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAGAACTGG

GTGAACGTCATCAGCGATTTAAAGAAGATCGAAGATTTAATTCAGTCCATG

CATATCGACGCCACTTTATACACAGAATCCGACGTGCACCCCTCTTGTAAG

GTGACCGCCATGAAATGTTTTTTACTGGAGCTGCAAGTTATCTCTTTAGAG

AGCGGAGACGCTAGCATCCACGACACCGTGGAGAATTTAATCATTTTAGCC

AATAACTCTTTATCCAGCAACGGCAACGTGACAGAGTCCGGCTGCAAGGAG

TGCGAAGAGCTGGAGGAGAAGAACATCAAGGAGTTTCTGCAATCCTTTGTG

CACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 268)

QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTPSCDSYEKKP

PKEFLERFKSLLQKMIHQHLSSRTHGSEDSITCPPPMSVEHADIWVKSYSL

YSRERYICNSGFKRKAGTSSLTECVLNKATNVAHWTTPSLKCIRGGGGSGG

GGSGGGGSREGPELSPDDPAGLLDLRQGMFAQLVAQNVLLIDGPLSWYSDP

GLAGVSLTGGLSYKEDTKELVVAKAGVYYVFFQLELRRVVAGEGSGSVSLA

LHLQPLRSAAGAAALALTVDLPPASSEARNSAFGFQGRLLHLSAGQRLGVH

LHTEARARHAWQLTQGATVLGLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 269)

CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

-continued

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCCA

TTACATGCCCCCCTCCCATGAGCGTGGAGCACGCCGACATCTGGGTGAAG

AGCTATAGCCTCTACAGCCGGGAGAGGTATATCTGTAACAGCGGCTTCAA

GAGGAAGGCCGGCACCAGCAGCCTCACCGAGTGCGTGCTGAATAAGGCTA

CCAACGTGGCTCACTGGACAACACCCTCTTTAAAGTGCATCCGGGGCGGT

GGAGGATCCGGAGGAGGTGGCTCCGGCGGCGGAGGATCTCGCGAGGGTCC

CGAGCTTTCGCCCGACGATCCCGCCGGCCTCTTGGACCTGCGGCAGGGCA

TGTTTGCGCAGCTGGTGGCCCAAAATGTTCTGCTGATCGATGGGCCCCTG

AGCTGGTACAGTGACCCAGGCCTGGCAGGCGTGTCCCTGACGGGGGGCCT

GAGCTACAAAGAGGACACGAAGGAGCTGGTGGTGGCCAAGGCTGGAGTCT

ACTATGTCTTCTTTCAACTAGAGCTGCGGCGCGTGGTGGCCGGCGAGGGC

TCAGGCTCCGTTTCACTTGCGCTGCACCTGCAGCCACTGCGCTCTGCTGC

TGGGGCCGCCGCCCTGGCTTTGACCGTGGACCTGCCACCCGCCTCCTCCG

AGGCTCGGAACTCGGCCTTCGGTTTCCAGGGCCGCTTGCTGCACCTGAGT

GCCGGCCAGCGCCTGGGCGTCCATCTTCACACTGAGGCCAGGGCACGCCA

TGCCTGGCAGCTTACCCAGGGCGCCACAGTCTTGGGACTCTTCCGGGTGA

CCCCCGAAATCCCAGCCGGACTCCCTTCACCGAGGTCGGAA.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 270)

MKWVTFISLLFLFSSAYSQGQDRHMIRMRQLIDIVDQLKNYVNDLVPEFL

PAPEDVETNCEWSAFSCFQKAQLKSANTGNNERIINVSIKKLKRKPPSTN

AGRRQKHRLTCPSCDSYEKKPPKEFLERFKSLLQKMIHQHLSSRTHGSED

SITCPPPMSVEHADIWVKSYSLYSRERYICNSGFKRKAGTSSLTECVLNK

ATNVAHWTTPSLKCIRGGGGSGGGGSGGGGSREGPELSPDDPAGLLDLRQ

GMFAQLVAQNVLLIDGPLSWYSDPGLAGVSLTGGLSYKEDTKELVVAKAG

VYYVFFQLELRRVVAGEGSGSVSLALHLQPLRSAAGAAALALTVDLPPAS

SEARNSAFGFQGRLLHLSAGQRLGVHLHTEARARHAWQLTQGATVLGLFR

VTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 271)

ATGAAGTGGGTGACCTTCATCAGCCTGCTGTTCCTGTTCTCCAGCGCCTAC

TCCCAGGGCCAGGACAGGCACATGATCCGGATGAGGCAGCTCATCGACATC

GTCGACCAGCTGAAGAACTACGTGAACGACCTGGTGCCCGAGTTTCTGCCT

GCCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCATC

AACGTGAGCATCAAGAAGCTGAAGCGGAAGCCTCCCTCCACAAACGCCGGC

AGGAGGCAGAAGCACAGGCTGACCTGCCCCAGCTGTGACTCCTACGAGAAG

AAGCCCCCCAAGGAGTTCCTGGAGAGGTTCAAGTCCCTGCTGCAGAAGATG

ATCCATCAGCACCTGTCCTCCAGGACCCACGGCTCCGAGGACTCCATTACA

TGCCCCCCTCCCATGAGCGTGGAGCACGCCGACATCTGGGTGAAGAGCTAT

AGCCTCTACAGCCGGGAGAGGTATATCTGTAACAGCGGCTTCAAGAGGAAG

GCCGGCACCAGCAGCCTCACCGAGTGCGTGCTGAATAAGGCTACCAACGTG

GCTCACTGGACAACACCCTCTTTAAAGTGCATCCGGGGCGGTGGAGGATCC

GGAGGAGGTGGCTCCGGCGGCGGAGGATCTCGCGAGGGTCCCGAGCTTTCG

CCCGACGATCCCGCCGGCCTCTTGGACCTGCGGCAGGGCATGTTTGCGCAG

CTGGTGGCCCAAAATGTTCTGCTGATCGATGGGCCCCTGAGCTGGTACAGT

GACCCAGGCCTGGCAGGCGTGTCCCTGACGGGGGGCCTGAGCTACAAAGAG

GACACGAAGGAGCTGGTGGTGGCCAAGGCTGGAGTCTACTATGTCTTCTTT

CAACTAGAGCTGCGGCGCGTGGTGGCCGGCGAGGGCTCAGGCTCCGTTTCA

CTTGCGCTGCACCTGCAGCCACTGCGCTCTGCTGCTGGGGCCGCCGCCCTG

GCTTTGACCGTGGACCTGCCACCCGCCTCCTCCGAGGCTCGGAACTCGGCC

TTCGGTTTCCAGGGCCGCTTGCTGCACCTGAGTGCCGGCCAGCGCCTGGGC

GTCCATCTTCACACTGAGGCCAGGGCACGCCATGCCTGGCAGCTTACCCAG

GGCGCCACAGTCTTGGGACTCTTCCGGGTGACCCCCGAAATCCCAGCCGGA

CTCCCTTCACCGAGGTCGGAA.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 272)

QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDSITCPPPMSVEHADIWVKSYS

LYSRERYICNSGFKRKAGTSSLTECVLNKATNVAHWTTPSLKCIRGGGGSG

GGGSGGGGSDPAGLLDLRQGMFAQLVAQNVLLIDGPLSWYSDPGLAGVSLT

GGLSYKEDTKELVVAKAGVYYVFFQLELRRVVAGEGSGSVSLALHLQPLRS

AAGAAALALTVDLPPASSEARNSAFGFQGRLLHLSAGQRLGVHLHTEARAR

HAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 273)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCCATTACATGC

CCCCCTCCCATGAGCGTGGAGCACGCCGACATCTGGGTGAAGAGCTATAGC

CTCTACAGCCGGGAGAGGTATATCTGTAACAGCGGCTTCAAGAGGAAGGCC

GGCACCAGCAGCCTCACCGAGTGCGTGCTGAATAAGGCTACCAACGTGGCT

CACTGGACAACACCCTCTTTAAAGTGCATCCGGGGCGGTGGAGGATCCGGA

GGAGGTGGCTCCGGCGGCGGAGGATCTGATCCCGCCGGCCTCTTGGACCTG

CGGCAGGGCATGTTTGCGCAGCTGGTGGCCCAAAATGTTCTGCTGATCGAT

GGGCCCCTGAGCTGGTACAGTGACCCAGGCCTGGCAGGCGTGTCCCTGACG

GGGGGCCTGAGCTACAAAGAGGACACGAAGGAGCTGGTGGTGGCCAAGGCT

GGAGTCTACTATGTCTTCTTTCAACTAGAGCTGCGGCGCGTGGTGGCCGGC

GAGGGCTCAGGCTCCGTTTCACTTGCGCTGCACCTGCAGCCACTGCGCTCT

GCTGCTGGGGCCGCCGCCCTGGCTTTGACCGTGGACCTGCCACCCGCCTCC

TCCGAGGCTCGGAACTCGGCCTTCGGTTTCCAGGGCCGCTTGCTGCACCTG

AGTGCCGGCCAGCGCCTGGGCGTCCATCTTCACACTGAGGCCAGGGCACGC

CATGCCTGGCAGCTTACCCAGGGCGCCACAGTCTTGGGACTCTTCCGGGTG

ACCCCCGAAATC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 274)
MKWVTFISLLFLFSSAYSQGQDRHMIRMRQLIDIVDQLKNYVNDLVPEFLP

APEDVETNCEWSAFSCFQKAQLKSANTGNNERIINVSIKKLKRKPPSTNAG

RRQKHRLTCPSCDSYEKKPPKEFLERFKSLLQKMIHQHLSSRTHGSEDSIT

CPPPMSVEHADIWVKSYSLYSRERYICNSGFKRKAGTSSLTECVLNKATNV

AHWTTPSLKCIRGGGGSGGGGSGGGGSDPAGLLDLRQGMFAQLVAQNVLLI

DGPLSWYSDPGLAGVSLTGGLSYKEDTKELVVAKAGVYYVFFQLELRRVVA

GEGSGSVSLALHLQPLRSAAGAAALALTVDLPPASSEARNSAFGFQGRLLH

LSAGQRLGVHLHTEARARHAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 275)
ATGAAGTGGGTGACCTTCATCAGCCTGCTGTTCCTGTTCTCCAGCGCCTAC

TCCCAGGGCCAGGACAGGCACATGATCCGGATGAGGCAGCTCATCGACATC

GTCGACCAGCTGAAGAACTACGTGAACGACCTGGTGCCCGAGTTTCTGCCT

GCCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCATC

AACGTGAGCATCAAGAAGCTGAAGCGGAAGCCTCCCTCCACAAACGCCGGC

AGGAGGCAGAAGCACAGGCTGACCTGCCCCAGCTGTGACTCCTACGAGAAG

AAGCCCCCCAAGGAGTTCCTGGAGAGGTTCAAGTCCCTGCTGCAGAAGATG

ATCCATCAGCACCTGTCCTCCAGGACCCACGGCTCCGAGGACTCCATTACA

TGCCCCCCTCCCATGAGCGTGGAGCACGCCGACATCTGGGTGAAGAGCTAT

AGCCTCTACAGCCGGGAGAGGTATATCTGTAACAGCGGCTTCAAGAGGAAG

GCCGGCACCAGCAGCCTCACCGAGTGCGTGCTGAATAAGGCTACCAACGTG

GCTCACTGGACAACACCCTCTTTAAAGTGCATCCGGGGCGGTGGAGGATCC

GGAGGAGGTGGCTCCGGCGGCGGAGGATCTGATCCCGCCGGCCTCTTGGAC

CTGCGGCAGGGCATGTTTGCGCAGCTGGTGGCCCAAAATGTTCTGCTGATC

GATGGGCCCCTGAGCTGGTACAGTGACCCAGGCCTGGCAGGCGTGTCCCTG

ACGGGGGGCCTGAGCTACAAAGAGGACACGAAGGAGCTGGTGGTGGCCAAG

GCTGGAGTCTACTATGTCTTCTTTCAACTAGAGCTGCGGCGCGTGGTGGCC

GGCGAGGGCTCAGGCTCCGTTTCACTTGCGCTGCACCTGCAGCCACTGCGC

TCTGCTGCTGGGGCCGCCGCCCTGGCTTTGACCGTGGACCTGCCACCCGCC

TCCTCCGAGGCTCGGAACTCGGCCTTCGGTTTCCAGGGCCGCTTGCTGCAC

CTGAGTGCCGGCCAGCGCCTGGGCGTCCATCTTCACACTGAGGCCAGGGCA

CGCCATGCCTGGCAGCTTACCCAGGGCGCCACAGTCTTGGGACTCTTCCGG

GTGACCCCCGAAATC.

Exemplary Multi-Chain Chimeric Polypeptides—Type K

In some embodiments of any of the multi-chain chimeric polypeptides described herein, the first target-binding domain and the second targeting-binding domain each independently bind specifically to a receptor of IL-7 or TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to a receptor for IL-7, and the second target-binding domain binds specifically to TGF-β. In some embodiments of these multi-chain chimeric polypeptides, the first target-binding domain binds specifically to TGF-β, and the second target-binding domain binds specifically to a receptor for IL-7.

In some embodiments of these multi-chain chimeric polypeptides, the first target-binding domain includes a soluble IL-7 protein (e.g., a soluble human IL-7 protein). In some embodiments of these multi-chain chimeric polypeptides, the soluble human IL-7 protein includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 79)
DCDIEGKDGKQYESVLMVSIDQLLDSMKEIGSNCLNNEFNEFKRHICDANK
EGMFLFRAARKLRQFLKMNSTGDFDLHLLKVSEGTTILLNCTGQVKGRKPA
ALGEAQPTKSLEENKSLKEQKKLNDLCFLKRLLQEIKTCWNKILMGTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 227)
GATTGCGACATCGAGGGCAAGGACGGCAAGCAGTACGAGAGCGTGCTGATG
GTGTCCATCGACCAGCTGCTGGACAGCATGAAGGAGATCGGCTCCAACTGC
CTCAACAACGAGTTCAACTTCTTCAAGCGGCACATCTGCGACGCCAACAAG
GAGGGCATGTTCCTGTTCAGGGCCGCCAGGAAACTGCGGCAGTTCCTGAAG
ATGAACTCCACCGGCGACTTCGACCTGCACCTGCTGAAGGTGTCCGAGGGC
ACCACCATCCTGCTGAACTGCACCGGACAGGTGAAGGGCCGGAAACCTGCT
GCTCTGGGAGAGGCCCAACCCACCAAGAGCCTGGAGGAGAACAAGTCCCTG

-continued

AAGGAGCAGAAGAAGCTGAACGACCTGTGCTTCCTGAAGAGGCTGCTGCAG
GAGATCAAGACCTGCTGGAACAAGATCCTGATGGGCACCAAGGAGCAT.

In some embodiments of these multi-chain chimeric polypeptides, the second target-binding domain comprises a target-binding domain that binds specifically to TGF-β. In some embodiments of these multi-chain chimeric polypeptides, the second target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 183)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA

-continued

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)

ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)

IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPDGGGGSGGGGSGGGGSIP

PHVQKSVNNDMIVTDNNGAVKFPQLCKFCDVRFSTCDNQKSCMSNCSITSI

CEKPQEVCVAVWRKNDENITLETVCHDPKLPYHDFILEDAASPKCIMKEKK

KPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)

ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

GGCGCCGTGAAATTTCCCCAGCTGTGCAAATTCTGCGATGTGAGGTTTTCC

ACCTGCGACAACCAGAAGTCCTGTATGAGCAACTGCTCCATCACCTCCATC

TGTGAGAAGCCTCAGGAGGTGTGCGTGGCTGTCTGGCGGAAGAATGACGAG

AATATCACCCTGGAAACCGTCTGCCACGATCCCAAGCTGCCCTACCACGAT

TTCATCCTGGAAGACGCCGCCAGCCCTAAGTGCATCATGAAAGAGAAAAAG

AAGCCTGGCGAGACCTTTTTCATGTGCTCCTGCAGCAGCGACGAATGCAAC

GACAATATCATCTTTAGCGAGGAATACAATACCAGCAACCCCGAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 207)

DCDIEGKDGKQYESVLMVSIDQLLDSMKEIGSNCLNNEFNEFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEHS

GTTNTVAAYNLTWKSTNEKTILEWEPKPVNQVYTVQISTKSGDWKSKCFYT

TDTECDLTDEIVKDVKQTYLARVFSYPAGNVESTGSAGEPLYENSPEFTPY

LETNLGQPTIQSFEQVGTKVNVTVEDERTLVRRNNTFLSLRDVFGKDLIYT

LYYWKSSSSGKKTAKTNTNEFLIDVDKGENYCFSVQAVIPSRTVNRKSTDS

PVECMGQEKGEFRENWVNVISDLKKIEDLIQSMHIDATLYTESDVHPSCKV

TAMKCFLLELQVISLESGDASIHDTVENLIILANNSLSSNGNVTESGCKEC

EELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 208)
GATTGCGACATCGAGGGCAAGGACGGCAAGCAGTACGAGAGCGTGCTGATG
GTGTCCATCGACCAGCTGCTGGACAGCATGAAGGAGATCGGCTCCAACTGC
CTCAACAACGAGTTCAACTTCTTCAAGCGGCACATCTGCGACGCCAACAAG
GAGGGCATGTTCCTGTTCAGGGCCGCCAGGAAACTGCGGCAGTTCCTGAAG
ATGAACTCCACCGGCGACTTCGACCTGCACCTGCTGAAGGTGTCCGAGGGC
ACCACCATCCTGCTGAACTGCACCGGACAGGTGAAGGGCCGGAAACCTGCT
GCTCTGGGAGAGGCCCAACCCACCAAGAGCCTGGAGGAGAACAAGTCCCTG
AAGGAGCAGAAGAAGCTGAACGACCTGTGCTTCCTGAAGAGGCTGCTGCAG
GAGATCAAGACCTGCTGGAACAAGATCCTGATGGGCACCAAGGAGCATAGC
GGCACAACCAACACAGTCGCTGCCTATAACCTCACTTGGAAGAGCACCAAC
TTCAAAACCATCCTCGAATGGGAACCCAAACCCGTTAACCAAGTTTACACC
GTGCAGATCAGCACCAAGTCCGGCGACTGGAAGTCCAAATGTTTCTATACC
ACCGACACCGAGTGCGATCTCACCGATGAGATCGTGAAAGATGTGAAACAG
ACCTACCTCGCCCGGGTGTTTAGCTACCCCGCCGGCAATGTGGAGAGCACT
GGTTCCGCTGGCGAGCCTTTATACGAGAACAGCCCCGAATTTACCCCTTAC
CTCGAGACCAATTTAGGACAGCCCACCATCCAAAGCTTTGAGCAAGTTGGC
ACAAAGGTGAATGTGACAGTGGAGGACGAGCGGACTTTAGTGCGGCGGAAC
AACACCTTTCTCAGCCTCCGGGATGTGTTCGGCAAAGATTTAATCTACACA
CTGTATTACTGGAAGTCCTCTTCCTCCGGCAAGAAGACAGCTAAAACCAAC
ACAAACGAGTTTTTAATCGACGTGGATAAAGGCGAAAACTACTGTTTCAGC
GTGCAAGCTGTGATCCCCTCCCGGACCGTGAATAGGAAAAGCACCGATAGC
CCCGTTGAGTGCATGGGCCAAGAAAAGGGCGAGTTCCGGGAGAACTGGGTG
AACGTCATCAGCGATTTAAAGAAGATCGAAGATTTAATTCAGTCCATGCAT
ATCGACGCCACTTTATACACAGAATCCGACGTGCACCCCTCTTGTAAGGTG
ACCGCCATGAAATGTTTTTTACTGGAGCTGCAAGTTATCTCTTTAGAGAGC
GGAGACGCTAGCATCCACGACACCGTGGAGAATTTAATCATTTTAGCCAAT
AACTCTTTATCCAGCAACGGCAACGTGACAGAGTCCGGCTGCAAGGAGTGC
GAAGAGCTGGAGGAGAAGAACATCAAGGAGTTTCTGCAATCCTTTGTGCAC
ATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 209)
MKWVTFISLLFLFSSAYSDCDIEGKDGKQYESVLMVSIDQLLDSMKEIGSN
CLNNEFNFFKRHICDANKEGMFLFRAARKLRQFLKMNSTGDFDLHLLKVSE
GTTILLNCTGQVKGRKPAALGEAQPTKSLEENKSLKEQKKLNDLCFLKRLL
QEIKTCWNKILMGTKEHSGTTNTVAAYNLTWKSTNFKTILEWEPKPVNQVY
TVQISTKSGDWKSKCFYTTDTECDLTDEIVKDVKQTYLARVFSYPAGNVES

-continued

TGSAGEPLYENSPEFTPYLETNLGQPTIQSFEQVGTKVNVTVEDERTLVRR
NNTFLSLRDVFGKDLIYTLYYWKSSSSGKKTAKTNTNEFLIDVDKGENYCF
SVQAVIPSRTVNRKSTDSPVECMGQEKGEFRENWVNVISDLKKIEDLIQSM
HIDATLYTESDVHPSCKVTAMKCFLLELQVISLESGDASIHDTVENLIILA
NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 210)
ATGAAGTGGGTGACCTTCATCAGCCTGCTGTTCCTGTTCTCCAGCGCCTAC
TCCGATTGCGACATCGAGGGCAAGGACGGCAAGCAGTACGAGAGCGTGCTG
ATGGTGTCCATCGACCAGCTGCTGGACAGCATGAAGGAGATCGGCTCCAAC
TGCCTCAACAACGAGTTCAACTTCTTCAAGCGGCACATCTGCGACGCCAAC
AAGGAGGGCATGTTCCTGTTCAGGGCCGCCAGGAAACTGCGGCAGTTCCTG
AAGATGAACTCCACCGGCGACTTCGACCTGCACCTGCTGAAGGTGTCCGAG
GGCACCACCATCCTGCTGAACTGCACCGGACAGGTGAAGGGCCGGAAACCT
GCTGCTCTGGGAGAGGCCCAACCCACCAAGAGCCTGGAGGAGAACAAGTCC
CTGAAGGAGCAGAAGAAGCTGAACGACCTGTGCTTCCTGAAGAGGCTGCTG
CAGGAGATCAAGACCTGCTGGAACAAGATCCTGATGGGCACCAAGGAGCAT
AGCGGCACAACCAACACAGTCGCTGCCTATAACCTCACTTGGAAGAGCACC
AACTTCAAAACCATCCTCGAATGGGAACCCAAACCCGTTAACCAAGTTTAC
ACCGTGCAGATCAGCACCAAGTCCGGCGACTGGAAGTCCAAATGTTTCTAT
ACCACCGACACCGAGTGCGATCTCACCGATGAGATCGTGAAAGATGTGAAA
CAGACCTACCTCGCCCGGGTGTTTAGCTACCCCGCCGGCAATGTGGAGAGC
ACTGGTTCCGCTGGCGAGCCTTTATACGAGAACAGCCCCGAATTTACCCCT
TACCTCGAGACCAATTTAGGACAGCCCACCATCCAAAGCTTTGAGCAAGTT
GGCACAAAGGTGAATGTGACAGTGGAGGACGAGCGGACTTTAGTGCGGCGG
AACAACACCTTTCTCAGCCTCCGGGATGTGTTCGGCAAAGATTTAATCTAC
ACACTGTATTACTGGAAGTCCTCTTCCTCCGGCAAGAAGACAGCTAAAACC
AACACAAACGAGTTTTTAATCGACGTGGATAAAGGCGAAAACTACTGTTTC
AGCGTGCAAGCTGTGATCCCCTCCCGGACCGTGAATAGGAAAAGCACCGAT
AGCCCCGTTGAGTGCATGGGCCAAGAAAAGGGCGAGTTCCGGGAGAACTGG
GTGAACGTCATCAGCGATTTAAAGAAGATCGAAGATTTAATTCAGTCCATG
CATATCGACGCCACTTTATACACAGAATCCGACGTGCACCCCTCTTGTAAG
GTGACCGCCATGAAATGTTTTTTACTGGAGCTGCAAGTTATCTCTTTAGAG
AGCGGAGACGCTAGCATCCACGACACCGTGGAGAATTTAATCATTTTAGCC
AATAACTCTTTATCCAGCAACGGCAACGTGACAGAGTCCGGCTGCAAGGAG
TGCGAAGAGCTGGAGGAGAAGAACATCAAGGAGTTTCTGCAATCCTTTGTG
CACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 193)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPDGGGGSGGGGSGGGGSIP
PHVQKSVNNDMIVTDNNGAVKFPQLCKFCDVRFSTCDNQKSCMSNCSITSI
CEKPQEVCVAVWRKNDENITLETVCHDPKLPYHDFILEDAASPKCIMKEKK
KPGETFFMCSCSSDECNDNIIFSEEYNTSNPDITCPPPMSVEHADIWVKSY
SLYSRERYICNSGFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 257)
ATCCCCCCCCATGTGCAAAAGAGCGTGAACAACGATATGATCGTGACCGAC
AACAACGGCGCCGTGAAGTTTCCCCAGCTCTGCAAGTTCTGCGATGTCAGG
TTCAGCACCTGCGATAATCAGAAGTCCTGCATGTCCAACTGCAGCATCACC
TCCATCTGCGAGAAGCCCCAAGAAGTGTGCGTGGCCGTGTGGCGGAAAAAT
GACGAGAACATCACCCTGGAGACCGTGTGTCACGACCCCAAGCTCCCTTAT
CACGACTTCATTCTGGAGGACGCTGCCTCCCCCAAATGCATCATGAAGGAG
AAGAAGAAGCCCGGAGAGACCTTCTTTATGTGTTCCTGTAGCAGCGACGAG
TGTAACGACAACATCATCTTCAGCGAAGAGTACAACACCAGCAACCCTGAT
GGAGGTGGCGGATCCGGAGGTGGAGGTTCTGGTGGAGGTGGGAGTATTCCT
CCCCACGTGCAGAAGAGCGTGAATAATGACATGATCGTGACCGATAACAAT
GGCGCCGTGAAATTTCCCCAGCTGTGCAAATTCTGCGATGTGAGGTTTTCC
ACCTGCGACAACCAGAAGTCCTGTATGAGCAACTGCTCCATCACCTCCATC
TGTGAGAAGCCTCAGGAGGTGTGCGTGGCTGTCTGGCGGAAGAATGACGAG
AATATCACCCTGGAAACCGTCTGCCACGATCCCAAGCTGCCCTACCACGAT
TTCATCCTGGAAGACGCCGCCAGCCCTAAGTGCATCATGAAAGAGAAAAAG
AAGCCTGGCGAGACCTTTTTCATGTGCTCCTGCAGCAGCGACGAATGCAAC
GACAATATCATCTTTAGCGAGGAATACAATACCAGCAACCCCGACATTACA
TGCCCCCCTCCCATGAGCGTGGAGCACGCCGACATCTGGGTGAAGAGCTAT
AGCCTCTACAGCCGGGAGAGGTATATCTGTAACAGCGGCTTCAAGAGGAAG
GCCGGCACCAGCAGCCTCACCGAGTGCGTGCTGAATAAGGCTACCAACGTG
GCTCACTGGACAACACCCTCTTTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 195)
MKWVTFISLLFLFSSAYSIPPHVQKSVNNDMIVTDNNGAVKFPQLCKFCDV
RFSTCDNQKSCMSNCSITSICEKPQEVCVAVWRKNDENITLETVCHDPKLP
YHDFILEDAASPKCIMKEKKKPGETFFMCSCSSDECNDNIIFSEEYNTSNP
DGGGGSGGGGSGGGGSIPPHVQKSVNNDMIVTDNNGAVKFPQLCKFCDVRF
STCDNQKSCMSNCSITSICEKPQEVCVAVWRKNDENITLETVCHDPKLPYH
DFILEDAASPKCIMKEKKKPGETFFMCSCSSDECNDNIIFSEEYNTSNPDI
TCPPPMSVEHADIWVKSYSLYSRERYICNSGFKRKAGTSSLTECVLNKATN
VAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 259)
ATGAAGTGGGTGACCTTCATCAGCCTGCTGTTCCTGTTCTCCAGCGCCTAC
TCCATCCCCCCCCATGTGCAAAAGAGCGTGAACAACGATATGATCGTGACC
GACAACAACGGCGCCGTGAAGTTTCCCCAGCTCTGCAAGTTCTGCGATGTC
AGGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAAA
AATGACGAGAACATCACCCTGGAGACCGTGTGTCACGACCCCAAGCTCCCT
TATCACGACTTCATTCTGGAGGACGCTGCCTCCCCCAAATGCATCATGAAG
GAGAAGAAGAAGCCCGGAGAGACCTTCTTTATGTGTTCCTGTAGCAGCGAC
GAGTGTAACGACAACATCATCTTCAGCGAAGAGTACAACACCAGCAACCCT
GATGGAGGTGGCGGATCCGGAGGTGGAGGTTCTGGTGGAGGTGGGAGTATT
CCTCCCCACGTGCAGAAGAGCGTGAATAATGACATGATCGTGACCGATAAC
AATGGCGCCGTGAAATTTCCCCAGCTGTGCAAATTCTGCGATGTGAGGTTT
TCCACCTGCGACAACCAGAAGTCCTGTATGAGCAACTGCTCCATCACCTCC
ATCTGTGAGAAGCCTCAGGAGGTGTGCGTGGCTGTCTGGCGGAAGAATGAC
GAGAATATCACCCTGGAAACCGTCTGCCACGATCCCAAGCTGCCCTACCAC
GATTTCATCCTGGAAGACGCCGCCAGCCCTAAGTGCATCATGAAAGAGAAA
AAGAAGCCTGGCGAGACCTTTTTCATGTGCTCCTGCAGCAGCGACGAATGC
AACGACAATATCATCTTTAGCGAGGAATACAATACCAGCAACCCCGACATT
ACATGCCCCCCTCCCATGAGCGTGGAGCACGCCGACATCTGGGTGAAGAGC
TATAGCCTCTACAGCCGGGAGAGGTATATCTGTAACAGCGGCTTCAAGAGG
AAGGCCGGCACCAGCAGCCTCACCGAGTGCGTGCTGAATAAGGCTACCAAC
GTGGCTCACTGGACAACACCCTCTTTAAAGTGCATCCGG.

Exemplary Multi-Chain Chimeric Polypeptides—Type L

In some embodiments of any of the multi-chain chimeric polypeptides described herein, the first target-binding domain and the second targeting-binding domain each independently bind specifically to TGF-β, a receptor of IL-21, or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a receptor for CD137L (e.g., a soluble CD137L, e.g., a soluble human CD137L).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional target-binding domain is an agonistic antigen-binding domain. In some embodiments of these multi-chain chimeric polypeptides, the first target-binding domain, the second target-binding domain, and the additional target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, the first target-binding domain binds specifically to TGF-β and the second target-binding domain binds specifically to a receptor for IL-21 or a receptor for CD137L.

In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                                    (SEQ ID NO: 183)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPD.
```

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                                    (SEQ ID NO: 184)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPD.
```

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPDGGGGSGGGGSGGGGSIP

PHVQKSVNNDMIVTDNNGAVKFPQLCKFCDVRFSTCDNQKSCMSNCSITSI

CEKPQEVCVAVWRKNDENITLETVCHDPKLPYHDFILEDAASPKCIMKEKK

KPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

GGCGCCGTGAAATTTCCCCAGCTGTGCAAATTCTGCGATGTGAGGTTTTCC

ACCTGCGACAACCAGAAGTCCTGTATGAGCAACTGCTCCATCACCTCCATC

TGTGAGAAGCCTCAGGAGGTGTGCGTGGCTGTCTGGCGGAAGAATGACGAG

AATATCACCCTGGAAACCGTCTGCCACGATCCCAAGCTGCCCTACCACGAT

TTCATCCTGGAAGACGCCGCCAGCCCTAAGTGCATCATGAAAGAGAAAAAG

AAGCCTGGCGAGACCTTTTTCATGTGCTCCTGCAGCAGCGACGAATGCAAC

GACAATATCATCTTTAGCGAGGAATACAATACCAGCAACCCCGAC.

In some embodiments of these multi-chain chimeric polypeptides, the second target-binding domain or the additional target-binding domain binds specifically to a receptor for IL-21. In some embodiments of these multi-chain chimeric polypeptides, the second target-binding domain or the additional target-binding domain includes a soluble IL-21 (e.g., a soluble human IL-21).

In some embodiments of these multi-chain chimeric polypeptides, a soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)
CAGGGCCAGGACAGGCACATGATCCGGATGAGGCAGCTCATCGACATCGTC
GACCAGCTGAAGAACTACGTGAACGACCTGGTGCCCGAGTTTCTGCCTGCC
CCCGAGGACGTGGAGACCAACTGCGAGTGGTCCGCCTTCTCCTGCTTTCAG
AAGGCCCAGCTGAAGTCCGCCAACACCGGCAACAACGAGCGGATCATCAAC
GTGAGCATCAAGAAGCTGAAGCGGAAGCCTCCCTCCACAAACGCCGGCAGG
AGGCAGAAGCACAGGCTGACCTGCCCCAGCTGTGACTCCTACGAGAAGAAG
CCCCCCAAGGAGTTCCTGGAGAGGTTCAAGTCCCTGCTGCAGAAGATGATC
CATCAGCACCTGTCCTCCAGGACCCACGGCTCCGAGGACTCC.

In some embodiments of these multi-chain chimeric polypeptides, the second target-binding domain or the additional target-binding domain binds specifically to a receptor for CD137L. In some embodiments of these multi-chain chimeric polypeptides, the second target-binding domain and/or the additional target-binding domain includes a soluble CD137L (e.g., a soluble human CD137L).

In some embodiments of these multi-chain chimeric polypeptides, a soluble CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 260)
REGPELSPDDPAGLLDLRQGMFAQLVAQNVLLIDGPLSWYSDPGLAGVSLT
GGLSYKEDTKELVVAKAGVYYVFFQLELRRVVAGEGSGSVSLALHLQPLRS
AAGAAALALTVDLPPASSEARNSAFGFQGRLLHLSAGQRLGVHLHTEARAR
HAWQLTQGATVLGLFRVTPEIPAGLPSPRSE.

In some embodiments of these multi-chain chimeric polypeptides, a soluble CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 261)
CGCGAGGGTCCCGAGCTTTCGCCCGACGATCCCGCCGGCCTCTTGGACCTG
CGGCAGGGCATGTTTGCGCAGCTGGTGGCCCAAAATGTTCTGCTGATCGAT
GGGCCCCTGAGCTGGTACAGTGACCCAGGCCTGGCAGGCGTGTCCCTGACG
GGGGGCCTGAGCTACAAAGAGGACACGAAGGAGCTGGTGGTGGCCAAGGCT
GGAGTCTACTATGTCTTCTTTCAACTAGAGCTGCGGCGCGTGGTGGCCGGC
GAGGGCTCAGGCTCCGTTTCACTTGCGCTGCACCTGCAGCCACTGCGCTCT
GCTGCTGGGGCCGCCGCCCTGGCTTTGACCGTGGACCTGCCACCCGCCTCC
TCCGAGGCTCGGAACTCGGCCTTCGGTTTCCAGGGCCGCTTGCTGCACCTG
AGTGCCGGCCAGCGCCTGGGCGTCCATCTTCACACTGAGGCCAGGGCACGC
CATGCCTGGCAGCTTACCCAGGGCGCCACAGTCTTGGGACTCTTCCGGGTG
ACCCCCGAAATCCCAGCCGGACTCCCTTCACCGAGGTCGGAA.

In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 262)
DPAGLLDLRQGMFAQLVAQNVLLIDGPLSWYSDPGLAGVSLTGGLSYKEDT
KELVVAKAGVYYVFFQLELRRVVAGEGSGSVSLALHLQPLRSAAGAAALAL
TVDLPPASSEARNSAFGFQGRLLHLSAGQRLGVHLHTEARARHAWQLTQGA
TVLGLFRVTPEI.

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 263)
GATCCCGCCGGCCTCTTGGACCTGCGGCAGGGCATGTTTGCGCAGCTGGTG
GCCCAAAATGTTCTGCTGATCGATGGGCCCCTGAGCTGGTACAGTGACCCA
GGCCTGGCAGGCGTGTCCCTGACGGGGGGCCTGAGCTACAAAGAGGACACG
AAGGAGCTGGTGGTGGCCAAGGCTGGAGTCTACTATGTCTTCTTTCAACTA
GAGCTGCGGCGCGTGGTGGCCGGCGAGGGCTCAGGCTCCGTTTCACTTGCG
CTGCACCTGCAGCCACTGCGCTCTGCTGCTGGGGCCGCCGCCCTGGCTTTG
ACCGTGGACCTGCCACCCGCCTCCTCCGAGGCTCGGAACTCGGCCTTCGGT
TTCCAGGGCCGCTTGCTGCACCTGAGTGCCGGCCAGCGCCTGGGCGTCCAT
CTTCACACTGAGGCCAGGGCACGCCATGCCTGGCAGCTTACCCAGGGCGCC
ACAGTCTTGGGACTCTTCCGGGTGACCCCCGAAATC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 236)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPDGGGGSGGGGSGGGGSIP
PHVQKSVNNDMIVTDNNGAVKFPQLCKFCDVRFSTCDNQKSCMSNCSITSI
CEKPQEVCVAVWRKNDENITLETVCHDPKLPYHDFILEDAASPKCIMKEKK
KPGETFFMCSCSSDECNDNIIFSEEYNTSNPDSGTTNTVAAYNLTWKSTNF
KTILEWEPKPVNQVYTVQISTKSGDWKSKCFYTTDTECDLTDEIVKDVKQT
YLARVFSYPAGNVESTGSAGEPLYENSPEFTPYLETNLGQPTIQSFEQVGT
KVNVTVEDERTLVRRNNTFLSLRDVFGKDLIYTLYYWKSSSSGKKTAKTNT
NEFLIDVDKGENYCFSVQAVIPSRTVNRKSTDSPVECMGQEKGEFRENWVN
VISDLKKIEDLIQSMHIDATLYTESDVHPSCKVTAMKCFLLELQVISLESG
DASIHDTVENLIIILANNSLSSNGNVTESGCKECEELEEKNIKEFLQSFVHI
VQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 237)
ATCCCCCCCCATGTGCAAAAGAGCGTGAACAACGATATGATCGTGACCGAC
AACAACGGCGCCGTGAAGTTTCCCCAGCTCTGCAAGTTCTGCGATGTCAGG
TTCAGCACCTGCGATAATCAGAAGTCCTGCATGTCCAACTGCAGCATCACC
TCCATCTGCGAGAAGCCCCAAGAAGTGTGCGTGGCCGTGTGGCGGAAAAAT
GACGAGAACATCACCCTGGAGACCGTGTGTCACGACCCCAAGCTCCCTTAT
CACGACTTCATTCTGGAGGACGCTGCCTCCCCCAAATGCATCATGAAGGAG
AAGAAGAAGCCCGGAGAGACCTTCTTTATGTGTTCCTGTAGCAGCGACGAG
TGTAACGACAACATCATCTTCAGCGAAGAGTACAACACCAGCAACCCTGAT
GGAGGTGGCGGATCCGGAGGTGGAGGTTCTGGTGGAGGTGGGAGTATTCCT
CCCCACGTGCAGAAGAGCGTGAATAATGACATGATCGTGACCGATAACAAT
GGCGCCGTGAAATTTCCCCAGCTGTGCAAATTCTGCGATGTGAGGTTTTCC
ACCTGCGACAACCAGAAGTCCTGTATGAGCAACTGCTCCATCACCTCCATC
TGTGAGAAGCCTCAGGAGGTGTGCGTGGCTGTCTGGCGGAAGAATGACGAG
AATATCACCCTGGAAACCGTCTGCCACGATCCCAAGCTGCCCTACCACGAT
TTCATCCTGGAAGACGCCGCCAGCCCTAAGTGCATCATGAAAGAGAAAAAG
AAGCCTGGCGAGACCTTTTTCATGTGCTCCTGCAGCAGCGACGAATGCAAC
GACAATATCATCTTTAGCGAGGAATACAATACCAGCAACCCCGACAGCGGC
ACAACCAACACAGTCGCTGCCTATAACCTCACTTGGAAGAGCACCAACTTC
AAAACCATCCTCGAATGGGAACCCAAACCCGTTAACCAAGTTTACACCGTG
CAGATCAGCACCAAGTCCGGCGACTGGAAGTCCAAATGTTTCTATACCACC
GACACCGAGTGCGATCTCACCGATGAGATCGTGAAAGATGTGAAACAGACC
TACCTCGCCCGGGTGTTTAGCTACCCCGCCGGCAATGTGGAGAGCACTGGT
TCCGCTGGCGAGCCTTTATACGAGAACAGCCCCGAATTTACCCCTTACCTC
GAGACCAATTTAGGACAGCCCACCATCCAAAGCTTTGAGCAAGTTGGCACA
AAGGTGAATGTGACAGTGGAGGACGAGCGGACTTTAGTGCGGCGGAACAAC
ACCTTTCTCAGCCTCCGGGATGTGTTCGGCAAAGATTTAATCTACACACTG
TATTACTGGAAGTCCTCTTCCTCCGGCAAGAAGACAGCTAAAACCAACACA
AACGAGTTTTTAATCGACGTGGATAAAGGCGAAAACTACTGTTTCAGCGTG
CAAGCTGTGATCCCCTCCCGGACCGTGAATAGGAAAAGCACCGATAGCCCC
GTTGAGTGCATGGGCCAAGAAAAGGGCGAGTTCCGGGAGAACTGGGTGAAC
GTCATCAGCGATTTAAAGAAGATCGAAGATTTAATTCAGTCCATGCATATC
GACGCCACTTTATACACAGAATCCGACGTGCACCCCTCTTGTAAGGTGACC
GCCATGAAATGTTTTTTACTGGAGCTGCAAGTTATCTCTTTAGAGAGCGGA
GACGCTAGCATCCACGACACCGTGGAGAATTTAATCATTTTAGCCAATAAC
TCTTTATCCAGCAACGGCAACGTGACAGAGTCCGGCTGCAAGGAGTGCGAA

-continued
GAGCTGGAGGAGAAGAACATCAAGGAGTTTCTGCAATCCTTTGTGCACATT
GTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 238)
MKWVTFISLLFLFSSAYSIPPHVQKSVNNDMIVTDNNGAVKFPQLCKFCDV
RSTCDNQKSCMSNCSITSICEKPQEVCVAVWRKNDENITLETVCHDPKLPY
HDFILEDAASPKCIMKEKKKPGETFFMCSCSSDECNDNIIFSEEYNTSNPD
GGGGSGGGGSGGGGSIPPHVQKSVNNDMIVTDNNGAVKFPQLCKFCDVRFS
TCDNQKSCMSNCSITSICEKPQEVCVAVWRKNDENITLETVCHDPKLPYHD
FILEDAASPKCIMKEKKKPGETFFMCSCSSDECNDNIIFSEEYNTSNPDSG
TTNTVAAYNLTWKSTNFKTILEWEPKPVNQVYTVQISTKSGDWKSKCFYTT
DTECDLTDEIVKDVKQTYLARVFSYPAGNVESTGSAGEPLYENSPEFTPYL
ETNLGQPTIQSFEQVGTKVNVTVEDERTLVRRNNTFLSLRDVFGKDLIYTL
YYWKSSSSGKKTAKTNTNEFLIDVDKGENYCFSVQAVIPSRTVNRKSTDSP
VECMGQEKGEFRENWVNVISDLKKIEDLIQSMHIDATLYTESDVHPSCKVT
AMKCFLLELQVISLESGDASIHDTVENLIILANNSLSSNGNVTESGCKECE
ELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 239)
ATGAAGTGGGTGACCTTCATCAGCCTGCTGTTCCTGTTCTCCAGCGCCTAC
TCCATCCCCCCCCATGTGCAAAAGAGCGTGAACAACGATATGATCGTGACC
GACAACAACGGCGCCGTGAAGTTTCCCCAGCTCTGCAAGTTCTGCGATGTC
AGGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAAA
AATGACGAGAACATCACCCTGGAGACCGTGTGTCACGACCCCAAGCTCCCT
TATCACGACTTCATTCTGGAGGACGCTGCCTCCCCCAAATGCATCATGAAG
GAGAAGAAGAAGCCCGGAGAGACCTTCTTTATGTGTTCCTGTAGCAGCGAC
GAGTGTAACGACAACATCATCTTCAGCGAAGAGTACAACACCAGCAACCCT
GATGGAGGTGGCGGATCCGGAGGTGGAGGTTCTGGTGGAGGTGGGAGTATT
CCTCCCCACGTGCAGAAGAGCGTGAATAATGACATGATCGTGACCGATAAC
AATGGCGCCGTGAAATTTCCCCAGCTGTGCAAATTCTGCGATGTGAGGTTT
TCCACCTGCGACAACCAGAAGTCCTGTATGAGCAACTGCTCCATCACCTCC
ATCTGTGAGAAGCCTCAGGAGGTGTGCGTGGCTGTCTGGCGGAAGAATGAC

-continued

GAGAATATCACCCTGGAAACCGTCTGCCACGATCCCAAGCTGCCCTACCAC

GATTTCATCCTGGAAGACGCCGCCAGCCCTAAGTGCATCATGAAAGAGAAA

AAGAAGCCTGGCGAGACCTTTTTCATGTGCTCCTGCAGCAGCGACGAATGC

AACGACAATATCATCTTTAGCGAGGAATACAATACCAGCAACCCCGACAGC

GGCACAACCAACACAGTCGCTGCCTATAACCTCACTTGGAAGAGCACCAAC

TTCAAAACCATCCTCGAATGGGAACCCAAACCCGTTAACCAAGTTTACACC

GTGCAGATCAGCACCAAGTCCGGCGACTGGAAGTCCAAATGTTTCTATACC

ACCGACACCGAGTGCGATCTCACCGATGAGATCGTGAAAGATGTGAAACAG

ACCTACCTCGCCCGGGTGTTTAGCTACCCCGCCGGCAATGTGGAGAGCACT

GGTTCCGCTGGCGAGCCTTTATACGAGAACAGCCCCGAATTTACCCCTTAC

CTCGAGACCAATTTAGGACAGCCCACCATCCAAAGCTTTGAGCAAGTTGGC

ACAAAGGTGAATGTGACAGTGGAGGACGAGCGGACTTTAGTGCGGCGGAAC

AACACCTTTCTCAGCCTCCGGGATGTGTTCGGCAAAGATTTAATCTACACA

CTGTATTACTGGAAGTCCTCTTCCTCCGGCAAGAAGACAGCTAAAACCAAC

ACAAACGAGTTTTTAATCGACGTGGATAAAGGCGAAAACTACTGTTTCAGC

GTGCAAGCTGTGATCCCCTCCCGGACCGTGAATAGGAAAAGCACCGATAGC

CCCGTTGAGTGCATGGGCCAAGAAAAGGGCGAGTTCCGGGAGAACTGGGTG

AACGTCATCAGCGATTTAAAGAAGATCGAAGATTTAATTCAGTCCATGCAT

ATCGACGCCACTTTATACACAGAATCCGACGTGCACCCCTCTTGTAAGGTG

ACCGCCATGAAATGTTTTTTACTGGAGCTGCAAGTTATCTCTTTAGAGAGC

GGAGACGCTAGCATCCACGACACCGTGGAGAATTTAATCATTTTAGCCAAT

AACTCTTTATCCAGCAACGGCAACGTGACAGAGTCCGGCTGCAAGGAGTGC

GAAGAGCTGGAGGAGAAGAACATCAAGGAGTTTCTGCAATCCTTTGTGCAC

ATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 268)

QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDSITCPPPMSVEHADIWVKSYS

LYSRERYICNSGFKRKAGTSSLTECVLNKATNVAHWTTPSLKCIRGGGGSG

GGGSGGGGSREGPELSPDDPAGLLDLRQGMFAQLVAQNVLLIDGPLSWYSD

PGLAGVSLTGGLSYKEDTKELVVAKAGVYYVFFQLELRRVVAGEGSGSVSL

ALHLQPLRSAAGAAALALTVDLPPASSEARNSAFGFQGRLLHLSAGQRLGV

HLHTEARARHAWQLTQGATVLGLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 269)

CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCCATTACATGC

CCCCCTCCCATGAGCGTGGAGCACGCCGACATCTGGGTGAAGAGCTATAGC

CTCTACAGCCGGGAGAGGTATATCTGTAACAGCGGCTTCAAGAGGAAGGCC

GGCACCAGCAGCCTCACCGAGTGCGTGCTGAATAAGGCTACCAACGTGGCT

CACTGGACAACACCCTCTTTAAAGTGCATCCGGGGCGGTGGAGGATCCGGA

GGAGGTGGCTCCGGCGGCGGAGGATCTCGCGAGGGTCCCGAGCTTTCGCCC

GACGATCCCGCCGGCCTCTTGGACCTGCGGCAGGGCATGTTTGCGCAGCTG

GTGGCCCAAAATGTTCTGCTGATCGATGGGCCCCTGAGCTGGTACAGTGAC

CCAGGCCTGGCAGGCGTGTCCCTGACGGGGGGCCTGAGCTACAAAGAGGAC

ACGAAGGAGCTGGTGGTGGCCAAGGCTGGAGTCTACTATGTCTTCTTTCAA

CTAGAGCTGCGGCGCGTGGTGGCCGGCGAGGGCTCAGGCTCCGTTTCACTT

GCGCTGCACCTGCAGCCACTGCGCTCTGCTGCTGGGGCCGCCGCCCTGGCT

TTGACCGTGGACCTGCCACCCGCCTCCTCCGAGGCTCGGAACTCGGCCTTC

GGTTTCCAGGGCCGCTTGCTGCACCTGAGTGCCGGCCAGCGCCTGGGCGTC

CATCTTCACACTGAGGCCAGGGCACGCCATGCCTGGCAGCTTACCCAGGGC

GCCACAGTCTTGGGACTCTTCCGGGTGACCCCCGAAATCCCAGCCGGACTC

CCTTCACCGAGGTCGGAA

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 270)

MKWVTFISLLFLFSSAYSQGQDRHMIRMRQLIDIVDQLKNYVNDLVP

EFLPAPEDVETNCEWSAFSCFQKAQLKSANTGNNERIINVSIKKLKR

KPPSTNAGRRQKHRLTCPSCDSYEKKPPKEFLERFKSLLQKMIHQHL

SSRTHGSEDSITCPPPMSVEHADIWVKSYSLYSRERYICNSGFKRKA

GTSSLTECVLNKATNVAHWTTPSLKCIRGGGGSGGGGSGGGGSREGP

ELSPDDPAGLLDLRQGMFAQLVAQNVLLIDGPLSWYSDPGLAGVSLT

-continued

GGLSYKEDTKELVVAKAGVYYVFFQLELRRVVAGEGSGSVSLALHLQ

PLRSAAGAAALALTVDLPPASSEARNSAFGFQGRLLHLSAGQRLGVH

LHTEARARHAWQLTQGATVLGLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 271)

ATGAAGTGGGTGACCTTCATCAGCCTGCTGTTCCTGTTCTCCAGCGC

CTACTCCCAGGGCCAGGACAGGCACATGATCCGGATGAGGCAGCTCA

TCGACATCGTCGACCAGCTGAAGAACTACGTGAACGACCTGGTGCCC

GAGTTTCTGCCTGCCCCCGAGGACGTGGAGACCAACTGCGAGTGGTC

CGCCTTCTCCTGCTTTCAGAAGGCCCAGCTGAAGTCCGCCAACACCG

GCAACAACGAGCGGATCATCAACGTGAGCATCAAGAAGCTGAAGCGG

AAGCCTCCCTCCACAAACGCCGGCAGGAGGCAGAAGCACAGGCTGAC

CTGCCCCAGCTGTGACTCCTACGAGAAGAAGCCCCCCAAGGAGTTCC

TGGAGAGGTTCAAGTCCCTGCTGCAGAAGATGATCCATCAGCACCTG

TCCTCCAGGACCCACGGCTCCGAGGACTCCATTACATGCCCCCCTCC

CATGAGCGTGGAGCACGCCGACATCTGGGTGAAGAGCTATAGCCTCT

ACAGCCGGGAGAGGTATATCTGTAACAGCGGCTTCAAGAGGAAGGCC

GGCACCAGCAGCCTCACCGAGTGCGTGCTGAATAAGGCTACCAACGT

GGCTCACTGGACAACACCCTCTTTAAAGTGCATCCGGGGCGGTGGAG

GATCCGGAGGAGGTGGCTCCGGCGGCGGAGGATCTCGCGAGGGTCCC

GAGCTTTCGCCCGACGATCCCGCCGGCCTCTTGGACCTGCGGCAGGG

CATGTTTGCGCAGCTGGTGGCCCAAAATGTTCTGCTGATCGATGGGC

CCCTGAGCTGGTACAGTGACCCAGGCCTGGCAGGCGTGTCCCTGACG

GGGGGCCTGAGCTACAAAGAGGACACGAAGGAGCTGGTGGTGGCCAA

GGCTGGAGTCTACTATGTCTTCTTTCAACTAGAGCTGCGGCGCGTGG

TGGCCGGCGAGGGCTCAGGCTCCGTTTCACTTGCGCTGCACCTGCAG

CCACTGCGCTCTGCTGCTGGGGCCGCCGCCCTGGCTTTGACCGTGGA

CCTGCCACCCGCCTCCTCCGAGGCTCGGAACTCGGCCTTCGGTTTCC

AGGGCCGCTTGCTGCACCTGAGTGCCGGCCAGCGCCTGGGCGTCCAT

CTTCACACTGAGGCCAGGGCACGCCATGCCTGGCAGCTTACCCAGGG

CGCCACAGTCTTGGGACTCTTCCGGGTGACCCCCGAAATCCCAGCCG

GACTCCCTTCACCGAGGTCGGAA

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 272)

QGQDRHMIRMRQLIDIVDQLKNYVNDLVPEFLPAPEDVETNCEWSAFS

CFQKAQLKSANTGNNERIINVSIKKLKRKPPSTNAGRRQKHRLTCPSC

DSYEKKPPKEFLERFKSLLQKMIHQHLSSRTHGSEDSITCPPPMSVEH

ADIWVKSYSLYSRERYICNSGFKRKAGTSSLTECVLNKATNVAHWTTP

SLKCIRGGGGSGGGGSGGGGSDPAGLLDLRQGMFAQLVAQNVLLIDGP

LSWYSDPGLAGVSLTGGLSYKEDTKELVVAKAGVYYVFFQLELRRVVA

GEGSGSVSLALHLQPLRSAAGAAALALTVDLPPASSEARNSAFGFQGR

LLHLSAGQRLGVHLHTEARARHAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 273)

CAGGGCCAGGACAGGCACATGATCCGGATGAGGCAGCTCATCGACATC

GTCGACCAGCTGAAGAACTACGTGAACGACCTGGTGCCCGAGTTTCTG

CCTGCCCCCGAGGACGTGGAGACCAACTGCGAGTGGTCCGCCTTCTCC

TGCTTTCAGAAGGCCCAGCTGAAGTCCGCCAACACCGGCAACAACGAG

CGGATCATCAACGTGAGCATCAAGAAGCTGAAGCGGAAGCCTCCCTCC

ACAAACGCCGGCAGGAGGCAGAAGCACAGGCTGACCTGCCCCAGCTGT

GACTCCTACGAGAAGAAGCCCCCCAAGGAGTTCCTGGAGAGGTTCAAG

TCCCTGCTGCAGAAGATGATCCATCAGCACCTGTCCTCCAGGACCCAC

GGCTCCGAGGACTCCATTACATGCCCCCCTCCCATGAGCGTGGAGCAC

GCCGACATCTGGGTGAAGAGCTATAGCCTCTACAGCCGGGAGAGGTAT

ATCTGTAACAGCGGCTTCAAGAGGAAGGCCGGCACCAGCAGCCTCACC

GAGTGCGTGCTGAATAAGGCTACCAACGTGGCTCACTGGACAACACCC

TCTTTAAAGTGCATCCGGGGCGGTGGAGGATCCGGAGGAGGTGGCTCC

GGCGGCGGAGGATCTGATCCCGCCGGCCTCTTGGACCTGCGGCAGGGC

ATGTTTGCGCAGCTGGTGGCCCAAAATGTTCTGCTGATCGATGGGCCC

CTGAGCTGGTACAGTGACCCAGGCCTGGCAGGCGTGTCCCTGACGGGG

GGCCTGAGCTACAAAGAGGACACGAAGGAGCTGGTGGTGGCCAAGGCT

GGAGTCTACTATGTCTTCTTTCAACTAGAGCTGCGGCGCGTGGTGGCC

GGCGAGGGCTCAGGCTCCGTTTCACTTGCGCTGCACCTGCAGCCACTG

CGCTCTGCTGCTGGGGCCGCCGCCCTGGCTTTGACCGTGGACCTGCCA

CCCGCCTCCTCCGAGGCTCGGAACTCGGCCTTCGGTTTCCAGGGCCGC

TTGCTGCACCTGAGTGCCGGCCAGCGCCTGGGCGTCCATCTTCACACT

GAGGCCAGGGCACGCCATGCCTGGCAGCTTACCCAGGGCGCCACAGTC

TTGGGACTCTTCCGGGTGACCCCCGAAATC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 274)

MKWVTFISLLFLFSSAYSQGQDRHMIRMRQLIDIVDQLKNYVNDLVPEF

LPAPEDVETNCEWSAFSCFQKAQLKSANTGNNERIINVSIKKLKRKPPS

TNAGRRQKHRLTCPSCDSYEKKPPKEFLERFKSLLQKMIHQHLSSRTHG

SEDSITCPPPMSVEHADIWVKSYSLYSRERYICNSGFKRKAGTSSLTEC

VLNKATNVAHWTTPSLKCIRGGGGSGGGGSGGGGSDPAGLLDLRQGMFA

QLVAQNVLLIDGPLSWYSDPGLAGVSLTGGLSYKEDTKELVVAKAGVYY

VFFQLELRRVVAGEGSGSVSLALHLQPLRSAAGAAALALTVDLPPASSE

ARNSAFGFQGRLLHLSAGQRLGVHLHTEARARHAWQLTQGATVLGLFRV

TPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 275)

ATGAAGTGGGTGACCTTCATCAGCCTGCTGTTCCTGTTCTCCAGCGCCT

ACTCCCAGGGCCAGGACAGGCACATGATCCGGATGAGGCAGCTCATCGA

CATCGTCGACCAGCTGAAGAACTACGTGAACGACCTGGTGCCCGAGTTT

CTGCCTGCCCCCGAGGACGTGGAGACCAACTGCGAGTGGTCCGCCTTCT

CCTGCTTTCAGAAGGCCCAGCTGAAGTCCGCCAACACCGGCAACAACGA

GCGGATCATCAACGTGAGCATCAAGAAGCTGAAGCGGAAGCCTCCCTCC

ACAAACGCCGGCAGGAGGCAGAAGCACAGGCTGACCTGCCCCAGCTGTG

ACTCCTACGAGAAGAAGCCCCCCAAGGAGTTCCTGGAGAGGTTCAAGTC

CCTGCTGCAGAAGATGATCCATCAGCACCTGTCCTCCAGGACCCACGGC

TCCGAGGACTCCATTACATGCCCCCCTCCCATGAGCGTGGAGCACGCCG

ACATCTGGGTGAAGAGCTATAGCCTCTACAGCCGGGAGAGGTATATCTG

TAACAGCGGCTTCAAGAGGAAGGCCGGCACCAGCAGCCTCACCGAGTGC

GTGCTGAATAAGGCTACCAACGTGGCTCACTGGACAACACCCTCTTTAA

AGTGCATCCGGGGCGGTGGAGGATCCGGAGGAGGTGGCTCCGGCGGCGG

AGGATCTGATCCCGCCGGCCTCTTGGACCTGCGGCAGGGCATGTTTGCG

CAGCTGGTGGCCCAAAATGTTCTGCTGATCGATGGGCCCCTGAGCTGGT

ACAGTGACCCAGGCCTGGCAGGCGTGTCCCTGACGGGGGGCCTGAGCTA

CAAAGAGGACACGAAGGAGCTGGTGGTGGCCAAGGCTGGAGTCTACTAT

GTCTTCTTTCAACTAGAGCTGCGGCGCGTGGTGGCCGGCGAGGGCTCAG

GCTCCGTTTCACTTGCGCTGCACCTGCAGCCACTGCGCTCTGCTGCTGG

GGCCGCCGCCCTGGCTTTGACCGTGGACCTGCCACCCGCCTCCTCCGAG

GCTCGGAACTCGGCCTTCGGTTTCCAGGGCCGCTTGCTGCACCTGAGTG

CCGGCCAGCGCCTGGGCGTCCATCTTCACACTGAGGCCAGGGCACGCCA

-continued

TGCCTGGCAGCTTACCCAGGGCGCCACAGTCTTGGGACTCTTCCGGGTG

ACCCCCGAAATC.

Exemplary Multi-Chain Chimeric Polypeptides—Type M

In some embodiments of any of the multi-chain chimeric polypeptides described herein, the first target-binding domain and the second targeting-binding domain each independently bind specifically to TGF-β or a receptor of IL-21. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a TGF-β (e.g., a soluble TGF-β receptor, e.g., a soluble TGFβRII receptor).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to TGF-β or a receptor for IL-21. In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 183)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)
ATTCCTCCCCACGTGCAGAAGAGCGTGAATAATGACATGATCGTGACCG
ATAACAATGGCGCCGTGAAATTTCCCCAGCTGTGCAAATTCTGCGATGT
GAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGC
GGAAGAATGACGAGAATATCACCCTGGAAACCGTCTGCCACGATCCCAA
GCTGCCCTACCACGATTTCATCCTGGAAGACGCCGCCAGCCCTAAGTGC
ATCATGAAAGAGAAAAAGAAGCCTGGCGAGACCTTTTTCATGTGCTCCT
GCAGCAGCGACGAATGCAACGACAATATCATCTTTAGCGAGGAATACAA
TACCAGCAACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGAC.

In some embodiments of these multi-chain chimeric polypeptides, the second target-binding domain binds specifically to a receptor for IL-21. In some embodiments of these multi-chain chimeric polypeptides, the second target-binding domain includes a soluble IL-21 (e.g., a human soluble IL-21). In some embodiments of these multi-chain chimeric polypeptides, the soluble IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 83)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS.

In some embodiments of these multi-chain chimeric polypeptides, the soluble IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)
CAGGGCCAGGACAGGCACATGATCGGATGAGGCAGCTCATCGACATCGT
CGACCAGCTGAAGAACTACGTGAACGACCTGGTGCCCGAGTTTCTGCCT

-continued
GCCCCCGAGGACGTGGAGACCAACTGCGAGTGGTCCGCCTTCTCCTGCT
TTCAGAAGGCCCAGCTGAAGTCCGCCAACACCGGCAACAACGAGCGGAT
CATCAACGTGAGCATCAAGAAGCTGAAGCGGAAGCCTCCCTCCACAAAC
GCCGGCAGGAGGCAGAAGCACAGGCTGACCTGCCCCAGCTGTGACTCCT
ACGAGAAGAAGCCCCCCAAGGAGTTCCTGGAGAGGTTCAAGTCCCTGCT
GCAGAAGATGATCCATCAGCACCTGTCCTCCAGGACCCACGGCTCCGAG
GACTCC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 236)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPDSGTTNTV
AAYNLTWKSTNFKTILEWEPKPVNQVYTVQISTKSGDWKSKCFYTTDTE
CDLTDEIVKDVKQTYLARVFSYPAGNVESTGSAGEPLYENSPEFTPYLE
TNLGQPTIQSFEQVGTKVNVTVEDERTLVRRNNTFLSLRDVFGKDLIYT
LYYWKSSSSGKKTAKTNTNEFLIDVDKGENYCFSVQAVIPSRTVNRKST
DSPVECMGQEKGEFRENWVNVISDLKKIEDLIQSMHIDATLYTESDVHP
SCKVTAMKCFLLELQVISLESGDASIHDTVENLIILANNSLSSNGNVTE
SGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 237)
ATCCCCCCCCATGTGCAAAAGAGCGTGAACAACGATATGATCGTGACCGAC
AACAACGGCGCCGTGAAGTTTCCCCAGCTCTGCAAGTTCTGCGATGTCAGG
TTCAGCACCTGCGATAATCAGAAGTCCTGCATGTCCAACTGCAGCATCACC
TCCATCTGCGAGAAGCCCCAAGAAGTGTGCGTGGCCGTGTGGCGGAAAAAT
GACGAGAACATCACCCTGGAGACCGTGTGTCACGACCCCAAGCTCCCTTAT
CACGACTTCATTCTGGAGGACGCTGCCTCCCCCAAATGCATCATGAAGGAG
AAGAAGAAGCCCGGAGAGACCTTCTTTATGTGTTCCTGTAGCAGCGACGAG
TGTAACGACAACATCATCTTCAGCGAAGAGTACAACACCAGCAACCCTGAT

-continued

GGAGGTGGCGGATCCGGAGGTGGAGGTTCTGGTGGAGGTGGGAGTATTCCT
CCCCACGTGCAGAAGAGCGTGAATAATGACATGATCGTGACCGATAACAAT
GGCGCCGTGAAATTTCCCCAGCTGTGCAAATTCTGCGATGTGAGGTTTTCC
ACCTGCGACAACCAGAAGTCCTGTATGAGCAACTGCTCCATCACCTCCATC
TGTGAGAAGCCTCAGGAGGTGTGCGTGGCTGTCTGGCGGAAGAATGACGAG
AATATCACCCTGGAAACCGTCTGCCACGATCCCAAGCTGCCCTACCACGAT
TTCATCCTGGAAGACGCCGCCAGCCCTAAGTGCATCATGAAAGAGAAAAAG
AAGCCTGGCGAGACCTTTTTCATGTGCTCCTGCAGCAGCGACGAATGCAAC
GACAATATCATCTTTAGCGAGGAATACAATACCAGCAACCCCGACAGCGGC
ACAACCAACACAGTCGCTGCCTATAACCTCACTTGGAAGAGCACCAACTTC
AAAACCATCCTCGAATGGGAACCCAAACCCGTTAACCAAGTTTACACCGTG
CAGATCAGCACCAAGTCCGGCGACTGGAAGTCCAAATGTTTCTATACCACC
GACACCGAGTGCGATCTCACCGATGAGATCGTGAAAGATGTGAAACAGACC
TACCTCGCCCGGGTGTTTAGCTACCCCGCCGGCAATGTGGAGAGCACTGGT
TCCGCTGGCGAGCCTTTATACGAGAACAGCCCCGAATTTACCCCTTACCTC
GAGACCAATTTAGGACAGCCCACCATCCAAAGCTTTGAGCAAGTTGGCACA
AAGGTGAATGTGACAGTGGAGGACGAGCGGACTTTAGTGCGGCGGAACAAC
ACCTTTCTCAGCCTCCGGGATGTGTTCGGCAAAGATTTAATCTACACACTG
TATTACTGGAAGTCCTCTTCCTCCGGCAAGAAGACAGCTAAAACCAACACA
AACGAGTTTTTAATCGACGTGGATAAAGGCGAAAACTACTGTTTCAGCGTG
CAAGCTGTGATCCCCTCCCGGACCGTGAATAGGAAAAGCACCGATAGCCCC
GTTGAGTGCATGGGCCAAGAAAAGGGCGAGTTCCGGGAGAACTGGGTGAAC
GTCATCAGCGATTTAAAGAAGATCGAAGATTTAATTCAGTCCATGCATATC
GACGCCACTTTATACACAGAATCCGACGTGCACCCCTCTTGTAAGGTGACC
GCCATGAAATGTTTTTTACTGGAGCTGCAAGTTATCTCTTTAGAGAGCGGA
GACGCTAGCATCCACGACACCGTGGAGAATTTAATCATTTTAGCCAATAAC
TCTTTATCCAGCAACGGCAACGTGACAGAGTCCGGCTGCAAGGAGTGCGAA
GAGCTGGAGGAGAAGAACATCAAGGAGTTTCTGCAATCCTTTGTGCACATT
GTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 238)
MKWVTFISLLFLFSSAYSIPPHVQKSVNNDMIVTDNNGAVKFPQLCKFCDV
RFSTCDNQKSCMSNCSITSICEKPQEVCVAVWRKNDENITLETVCHDPKLP
YHDFILEDAASPKCIMKEKKKPGETFFMCSCSSDECNDNIIFSEEYNTSNP
DGGGGSGGGGSGGGGSIPPHVQKSVNNDMIVTDNNGAVKFPQLCKFCDVRF
STCDNQKSCMSNCSITSICEKPQEVCVAVWRKNDENITLETVCHDPKLPYH
DFILEDAASPKCIMKEKKKPGETFFMCSCSSDECNDNIIFSEEYNTSNPDS

-continued

GTTNTVAAYNLTWKSTNFKTILEWEPKPVNQVYTVQISTKSGDWKSKCFYT
TDTECDLTDEIVKDVKQTYLARVFSYPAGNVESTGSAGEPLYENSPEFTPY
LETNLGQPTIQSFEQVGTKVNVTVEDERTLVRRNNTFLSLRDVFGKDLIYT
LYYWKSSSSGKKTAKTNTNEFLIDVDKGENYCFSVQAVIPSRTVNRKSTDS
PVECMGQEKGEFRENWVNVISDLKKIEDLIQSMHIDATLYTESDVHPSCKV
TAMKCFLLELQVISLESGDASIHDTVENLIILANNSLSSNGNVTESGCKEC
EELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 239)
ATGAAGTGGGTGACCTTCATCAGCCTGCTGTTCCTGTTCTCCAGCGCCTAC
TCCATCCCCCCCCATGTGCAAAAGAGCGTGAACAACGATATGATCGTGACC
GACAACAACGGCGCCGTGAAGTTTCCCCAGCTCTGCAAGTTCTGCGATGTC
AGGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAAA
AATGACGAGAACATCACCCTGGAGACCGTGTGTCACGACCCCAAGCTCCCT
TATCACGACTTCATTCTGGAGGACGCTGCCTCCCCCAAATGCATCATGAAG
GAGAAGAAGAAGCCCGGAGAGACCTTCTTTATGTGTTCCTGTAGCAGCGAC
GAGTGTAACGACAACATCATCTTCAGCGAAGAGTACAACACCAGCAACCCT
GATGGAGGTGGCGGATCCGGAGGTGGAGGTTCTGGTGGAGGTGGGAGTATT
CCTCCCCACGTGCAGAAGAGCGTGAATAATGACATGATCGTGACCGATAAC
AATGGCGCCGTGAAATTTCCCCAGCTGTGCAAATTCTGCGATGTGAGGTTT
TCCACCTGCGACAACCAGAAGTCCTGTATGAGCAACTGCTCCATCACCTCC
ATCTGTGAGAAGCCTCAGGAGGTGTGCGTGGCTGTCTGGCGGAAGAATGAC
GAGAATATCACCCTGGAAACCGTCTGCCACGATCCCAAGCTGCCCTACCAC
GATTTCATCCTGGAAGACGCCGCCAGCCCTAAGTGCATCATGAAAGAGAAA
AAGAAGCCTGGCGAGACCTTTTTCATGTGCTCCTGCAGCAGCGACGAATGC
AACGACAATATCATCTTTAGCGAGGAATACAATACCAGCAACCCCGACAGC
GGCACAACCAACACAGTCGCTGCCTATAACCTCACTTGGAAGAGCACCAAC
TTCAAAACCATCCTCGAATGGGAACCCAAACCCGTTAACCAAGTTTACACC
GTGCAGATCAGCACCAAGTCCGGCGACTGGAAGTCCAAATGTTTCTATACC
ACCGACACCGAGTGCGATCTCACCGATGAGATCGTGAAAGATGTGAAACAG
ACCTACCTCGCCCGGGTGTTTAGCTACCCCGCCGGCAATGTGGAGAGCACT
GGTTCCGCTGGCGAGCCTTTATACGAGAACAGCCCCGAATTTACCCCTTAC
CTCGAGACCAATTTAGGACAGCCCACCATCCAAAGCTTTGAGCAAGTTGGC
ACAAAGGTGAATGTGACAGTGGAGGACGAGCGGACTTTAGTGCGGCGGAAC
AACACCTTTCTCAGCCTCCGGGATGTGTTCGGCAAAGATTTAATCTACACA

-continued

CTGTATTACTGGAAGTCCTCTTCCTCCGGCAAGAAGACAGCTAAAACCAAC
ACAAACGAGTTTTTAATCGACGTGGATAAAGGCGAAAACTACTGTTTCAGC
GTGCAAGCTGTGATCCCCTCCCGGACCGTGAATAGGAAAAGCACCGATAGC
CCCGTTGAGTGCATGGGCCAAGAAAAGGGCGAGTTCCGGGAGAACTGGGTG
AACGTCATCAGCGATTTAAAGAAGATCGAAGATTTAATTCAGTCCATGCAT
ATCGACGCCACTTTATACACAGAATCCGACGTGCACCCCTCTTGTAAGGTG
ACCGCCATGAAATGTTTTTTACTGGAGCTGCAAGTTATCTCTTTAGAGAGC
GGAGACGCTAGCATCCACGACACCGTGGAGAATTTAATCATTTTAGCCAAT
AACTCTTTATCCAGCAACGGCAACGTGACAGAGTCCGGCTGCAAGGAGTGC
GAAGAGCTGGAGGAGAAGAACATCAAGGAGTTTCTGCAATCCTTTGTGCAC
ATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 300)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPDGGGGSGGGGSGGGGSIP
PHVQKSVNNDMIVTDNNGAVKFPQLCKFCDVRFSTCDNQKSCMSNCSITSI
CEKPQEVCVAVWRKNDENITLETVCHDPKLPYHDFILEDAASPKCIMKEKK
KPGETFFMCSCSSDECNDNIIFSEEYNTSNPDITCPPPMSVEHADIWVKSY
SLYSRERYICNSGFKRKAGTSSLTECVLNKATNVAHWTTPSLKCIRQGQDR
HMIRMRQLIDIVDQLKNYVNDLVPEFLPAPEDVETNCEWSAFSCFQKAQLK
SANTGNNERIINVSIKKLKRKPPSTNAGRRQKHRLTCPSCDSYEKKPPKEF
LERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 301)
ATCCCCCCCCATGTGCAAAAGAGCGTGAACAACGATATGATCGTGACCGAC
AACAACGGCGCCGTGAAGTTTCCCCAGCTCTGCAAGTTCTGCGATGTCAGG
TTCAGCACCTGCGATAATCAGAAGTCCTGCATGTCCAACTGCAGCATCACC
TCCATCTGCGAGAAGCCCCAAGAAGTGTGCGTGGCCGTGTGGCGGAAAAAT
GACGAGAACATCACCCTGGAGACCGTGTGTCACGACCCCAAGCTCCCTTAT
CACGACTTCATTCTGGAGGACGCTGCCTCCCCCAAATGCATCATGAAGGAG
AAGAAGAAGCCCGGAGAGACCTTCTTTATGTGTTCCTGTAGCAGCGACGAG
TGTAACGACAACATCATCTTCAGCGAAGAGTACAACACCAGCAACCCTGAT
GGAGGTGGCGGATCCGGAGGTGGAGGTTCTGGTGGAGGTGGGAGTATTCCT
CCCCACGTGCAGAAGAGCGTGAATAATGACATGATCGTGACCGATAACAAT
GGCGCCGTGAAATTTCCCCAGCTGTGCAAATTCTGCGATGTGAGGTTTTCC
ACCTGCGACAACCAGAAGTCCTGTATGAGCAACTGCTCCATCACCTCCATC
TGTGAGAAGCCTCAGGAGGTGTGCGTGGCTGTCTGGCGGAAGAATGACGAG
AATATCACCCTGGAAACCGTCTGCCACGATCCCAAGCTGCCCTACCACGAT
TTCATCCTGGAAGACGCCGCCAGCCCTAAGTGCATCATGAAAGAGAAAAAG
AAGCCTGGCGAGACCTTTTTCATGTGCTCCTGCAGCAGCGACGAATGCAAC
GACAATATCATCTTTAGCGAGGAATACAATACCAGCAACCCCGACATTACA
TGCCCCCCTCCCATGAGCGTGGAGCACGCCGACATCTGGGTGAAGAGCTAT
AGCCTCTACAGCCGGGAGAGGTATATCTGTAACAGCGGCTTCAAGAGGAAG
GCCGGCACCAGCAGCCTCACCGAGTGCGTGCTGAATAAGGCTACCAACGTG
GCTCACTGGACAACACCCTCTTTAAAGTGCATCCGGCAGGGCCAGGACAGG
CACATGATCCGGATGAGGCAGCTCATCGACATCGTCGACCAGCTGAAGAAC
TACGTGAACGACCTGGTGCCCGAGTTTCTGCCTGCCCCCGAGGACGTGGAG
ACCAACTGCGAGTGGTCCGCCTTCTCCTGCTTTCAGAAGGCCCAGCTGAAG
TCCGCCAACACCGGCAACAACGAGCGGATCATCAACGTGAGCATCAAGAAG
CTGAAGCGGAAGCCTCCCTCCACAAACGCCGGCAGGAGGCAGAAGCACAGG
CTGACCTGCCCCAGCTGTGACTCCTACGAGAAGAAGCCCCCCAAGGAGTTC
CTGGAGAGGTTCAAGTCCCTGCTGCAGAAGATGATCCATCAGCACCTGTCC
TCCAGGACCCACGGCTCCGAGGACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 302)
MKWVTFISLLFLFSSAYSIPPHVQKSVNNDMIVTDNNGAVKFPQLCKFCDV
RFSTCDNQKSCMSNCSITSICEKPQEVCVAVWRKNDENITLETVCHDPKLP
YHDFILEDAASPKCIMKEKKKPGETFFMCSCSSDECNDNIIFSEEYNTSNP
DGGGGSGGGGSGGGGSIPPHVQKSVNNDMIVTDNNGAVKFPQLCKFCDVRF
STCDNQKSCMSNCSITSICEKPQEVCVAVWRKNDENITLETVCHDPKLPYH
DFILEDAASPKCIMKEKKKPGETFFMCSCSSDECNDNIIFSEEYNTSNPDI
TCPPPMSVEHADIWVKSYSLYSRERYICNSGFKRKAGTSSLTECVLNKATN
VAHWTTPSLKCIRQGQDRHMIRMRQLIDIVDQLKNYVNDLVPEFLPAPEDV
ETNCEWSAFSCFQKAQLKSANTGNNERIINVSIKKLKRKPPSTNAGRRQKH
RLTCPSCDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                    (SEQ ID NO: 303)
ATGAAGTGGGTGACCTTCATCAGCCTGCTGTTCCTGTTCTCCAGCGCCTAC
TCCATCCCCCCCCATGTGCAAAAGAGCGTGAACAACGATATGATCGTGACC
GACAACAACGGCGCCGTGAAGTTTCCCCAGCTCTGCAAGTTCTGCGATGTC
AGGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAAA
AATGACGAGAACATCACCCTGGAGACCGTGTGTCACGACCCCAAGCTCCCT
TATCACGACTTCATTCTGGAGGACGCTGCCTCCCCCAAATGCATCATGAAG
GAGAAGAAGAAGCCCGGAGAGACCTTCTTTATGTGTTCCTGTAGCAGCGAC
GAGTGTAACGACAACATCATCTTCAGCGAAGAGTACAACACCAGCAACCCT
GATGGAGGTGGCGGATCCGGAGGTGGAGGTTCTGGTGGAGGTGGGAGTATT
CCTCCCCACGTGCAGAAGAGCGTGAATAATGACATGATCGTGACCGATAAC
AATGGCGCCGTGAAATTTCCCCAGCTGTGCAAATTCTGCGATGTGAGGTTT
TCCACCTGCGACAACCAGAAGTCCTGTATGAGCAACTGCTCCATCACCTCC
ATCTGTGAGAAGCCTCAGGAGGTGTGCGTGGCTGTCTGGCGGAAGAATGAC
GAGAATATCACCCTGGAAACCGTCTGCCACGATCCCAAGCTGCCCTACCAC
GATTTCATCCTGGAAGACGCCGCCAGCCCTAAGTGCATCATGAAAGAGAAA
AAGAAGCCTGGCGAGACCTTTTTCATGTGCTCCTGCAGCAGCGACGAATGC
AACGACAATATCATCTTTAGCGAGGAATACAATACCAGCAACCCCGACATT
ACATGCCCCCCTCCCATGAGCGTGGAGCACGCCGACATCTGGGTGAAGAGC
TATAGCCTCTACAGCCGGGAGAGGTATATCTGTAACAGCGGCTTCAAGAGG
AAGGCCGGCACCAGCAGCCTCACCGAGTGCGTGCTGAATAAGGCTACCAAC
GTGGCTCACTGGACAACACCCTCTTTAAAGTGCATCCGGCAGGGCCAGGAC
AGGCACATGATCCGGATGAGGCAGCTCATCGACATCGTCGACCAGCTGAAG
AACTACGTGAACGACCTGGTGCCCGAGTTTCTGCCTGCCCCCGAGGACGTG
GAGACCAACTGCGAGTGGTCCGCCTTCTCCTGCTTTCAGAAGGCCCAGCTG
AAGTCCGCCAACACCGGCAACAACGAGCGGATCATCAACGTGAGCATCAAG
AAGCTGAAGCGGAAGCCTCCCTCCACAAACGCCGGCAGGAGGCAGAAGCAC
AGGCTGACCTGCCCCAGCTGTGACTCCTACGAGAAGAAGCCCCCCAAGGAG
TTCCTGGAGAGGTTCAAGTCCCTGCTGCAGAAGATGATCCATCAGCACCTG
TCCTCCAGGACCCACGGCTCCGAGGACTCC.
```

Exemplary Multi-Chain Chimeric Polypeptides—Type N

In some embodiments of any of the multi-chain chimeric polypeptides described herein, the first target-binding domain and the second targeting-binding domain each independently bind specifically to TGF-β or CD16. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 (e.g., an anti-CD16 scFv) or a TGF-β (e.g., a soluble TGF-β receptor, e.g., a soluble TGFβRII receptor).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to TGF-β or CD16. In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 183)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)
ATTCCTCCCCACGTGCAGAAGAGCGTGAATAATGACATGATCGTGACCGA

TAACAATGGCGCCGTGAAATTTCCCCAGCTGTGCAAATTCTGCGATGTGA

GGTTTTCCACCTGCGACAACCAGAAGTCCTGTATGAGCAACTGCTCCATC

ACCTCCATCTGTGAGAAGCCTCAGGAGGTGTGCGTGGCTGTCTGGCGGAA

GAATGACGAGAATATCACCCTGGAAACCGTCTGCCACGATCCCAAGCTGC

CCTACCACGATTTCATCCTGGAAGACGCCGCCAGCCCTAAGTGCATCATG

AAAGAGAAAAAGAAGCCTGGCGAGACCTTTTTCATGTGCTCCTGCAGCAG

CGACGAATGCAACGACAATATCATCTTTAGCGAGGAATACAATACCAGCA

ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPDGGGGSGGGGSGGGGSIP

PHVQKSVNNDMIVTDNNGAVKFPQLCKFCDVRFSTCDNQKSCMSNCSITSI

CEKPQEVCVAVWRKNDENITLETVCHDPKLPYHDFILEDAASPKCIMKEKK

KPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

-continued

CCCCACGTGCAGAAGAGCGTGAATAATGACATGATCGTGACCGATAACAAT
GGCGCCGTGAAATTTCCCCAGCTGTGCAAATTCTGCGATGTGAGGTTTTCC
ACCTGCGACAACCAGAAGTCCTGTATGAGCAACTGCTCCATCACCTCCATC
TGTGAGAAGCCTCAGGAGGTGTGCGTGGCTGTCTGGCGGAAGAATGACGAG
AATATCACCCTGGAAACCGTCTGCCACGATCCCAAGCTGCCCTACCACGAT
TTCATCCTGGAAGACGCCGCCAGCCCTAAGTGCATCATGAAAGAGAAAAAG
AAGCCTGGCGAGACCTTTTTCATGTGCTCCTGCAGCAGCGACGAATGCAAC
GACAATATCATCTTTAGCGAGGAATACAATACCAGCAACCCCGAC.

In some embodiments of these multi-chain chimeric polypeptides, the second target-binding domain binds specifically to CD16. In some embodiments of these multi-chain chimeric polypeptides, the second target-binding domain includes an anti-CD16 scFv. In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 215)
SELTQDPAVSVALGQTVRITCQGDSLRSYYASWYQQKPGQAPVLVIYGKNN
RPSGIPDRFSGSSSGNTASLTITGAQAEDEADYYCNSRDSSGNHVVFGGGT
KLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 216)
TCCGAGCTGACCCAGGACCCTGCTGTGTCCGTGGCTCTGGGCCAGACCGTG
AGGATCACCTGCCAGGGCGACTCCCTGAGGTCCTACTACGCCTCCTGGTAC
CAGCAGAAGCCCGGCCAGGCTCCTGTGCTGGTGATCTACGGCAAGAACAAC
AGGCCCTCCGGCATCCCTGACAGGTTCTCCGGATCCTCCTCCGGCAACACC
GCCTCCCTGACCATCACAGGCGCTCAGGCCGAGGACGAGGCTGACTACTAC
TGCAACTCCAGGGACTCCTCCGGCAACCATGTGGTGTTCGGCGGCGGCACC
AAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 217)
EVQLVESGGGVVRPGGSLRLSCAASGFTFDDYGMSWVRQAPGKGLEWVSGI
NWNGGSTGYADSVKGRFTISRDNAKNSLYLQMNSLRAEDTAVYYCARGRSL
LFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 218)
GAGGTGCAGCTGGTGGAGTCCGGAGGAGGAGTGGTGAGGCCTGGAGGCTCC
CTGAGGCTGAGCTGTGCTGCCTCCGGCTTCACCTTCGACGACTACGGCATG
TCCTGGGTGAGGCAGGCTCCTGGAAAGGGCCTGGAGTGGGTGTCCGGCATC
AACTGGAACGGCGGATCCACCGGCTACGCCGATTCCGTGAAGGGCAGGTTC
ACCATCAGCAGGGACAACGCCAAGAACTCCCTGTACCTGCAGATGAACTCC
CTGAGGGCCGAGGACACCGCCGTGTACTACTGCGCCAGGGGCAGGTCCCTG
CTGTTCGACTACTGGGGACAGGGCACCCTGGTGACCGTGTCCAGG.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 236)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPDGGGGSGGGGSGGGGSIP
PHVQKSVNNDMIVTDNNGAVKFPQLCKFCDVRFSTCDNQKSCMSNCSITSI
CEKPQEVCVAVWRKNDENITLETVCHDPKLPYHDFILEDAASPKCIMKEKK
KPGETFFMCSCSSDECNDNIIFSEEYNTSNPDSGTTNTVAAYNLTWKSTNF
KTILEWEPKPVNQVYTVQISTKSGDWKSKCFYTTDTECDLTDEIVKDVKQT
YLARVFSYPAGNVESTGSAGEPLYENSPEFTPYLETNLGQPTIQSFEQVGT
KVNVTVEDERTLVRRNNTFLSLRDVFGKDLIYTLYYWKSSSSGKKTAKTNT
NEFLIDVDKGENYCFSVQAVIPSRTVNRKSTDSPVECMGQEKGEFRENWVN
VISDLKKIEDLIQSMHIDATLYTESDVHPSCKVTAMKCFLLELQVISLESG
DASIHDTVENLIIILANNSLSSNGNVTESGCKECEELEEKNIKEFLQSFVHI
VQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 237)

ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

GGCGCCGTGAAATTTCCCCAGCTGTGCAAATTCTGCGATGTGAGGTTTTCC

ACCTGCGACAACCAGAAGTCCTGTATGAGCAACTGCTCCATCACCTCCATC

TGTGAGAAGCCTCAGGAGGTGTGCGTGGCTGTCTGGCGGAAGAATGACGAG

AATATCACCCTGGAAACCGTCTGCCACGATCCCAAGCTGCCCTACCACGAT

TTCATCCTGGAAGACGCCGCCAGCCCTAAGTGCATCATGAAAGAGAAAAAG

AAGCCTGGCGAGACCTTTTTCATGTGCTCCTGCAGCAGCGACGAATGCAAC

GACAATATCATCTTTAGCGAGGAATACAATACCAGCAACCCCGACAGCGGC

ACAACCAACACAGTCGCTGCCTATAACCTCACTTGGAAGAGCACCAACTTC

AAAACCATCCTCGAATGGGAACCCAAACCCGTTAACCAAGTTTACACCGTG

CAGATCAGCACCAAGTCCGGCGACTGGAAGTCCAAATGTTTCTATACCACC

GACACCGAGTGCGATCTCACCGATGAGATCGTGAAAGATGTGAAACAGACC

TACCTCGCCCGGGTGTTTAGCTACCCCGCCGGCAATGTGGAGAGCACTGGT

TCCGCTGGCGAGCCTTTATACGAGAACAGCCCCGAATTTACCCCTTACCTC

GAGACCAATTTAGGACAGCCCACCATCCAAAGCTTTGAGCAAGTTGGCACA

AAGGTGAATGTGACAGTGGAGGACGAGCGGACTTTAGTGCGGCGGAACAAC

ACCTTTCTCAGCCTCCGGGATGTGTTCGGCAAAGATTTAATCTACACACTG

TATTACTGGAAGTCCTCTTCCTCCGGCAAGAAGACAGCTAAAACCAACACA

AACGAGTTTTTAATCGACGTGGATAAAGGCGAAAACTACTGTTTCAGCGTG

CAAGCTGTGATCCCCTCCCGGACCGTGAATAGGAAAAGCACCGATAGCCCC

GTTGAGTGCATGGGCCAAGAAAAGGGCGAGTTCCGGGAGAACTGGGTGAAC

GTCATCAGCGATTTAAAGAAGATCGAAGATTTAATTCAGTCCATGCATATC

GACGCCACTTTATACACAGAATCCGACGTGCACCCCTCTTGTAAGGTGACC

GCCATGAAATGTTTTTTACTGGAGCTGCAAGTTATCTCTTTAGAGAGCGGA

GACGCTAGCATCCACGACACCGTGGAGAATTTAATCATTTTAGCCAATAAC

TCTTTATCCAGCAACGGCAACGTGACAGAGTCCGGCTGCAAGGAGTGCGAA

GAGCTGGAGGAGAAGAACATCAAGGAGTTTCTGCAATCCTTTGTGCACATT

GTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 238)

MKWVTFISLLFLFSSAYSIPPHVQKSVNNDMIVTDNNGAVKFPQLCKFCDV

RFSTCDNQKSCMSNCSITSICEKPQEVCVAVWRKNDENITLETVCHDPKLP

YHDFILEDAASPKCIMKEKKKPGETFFMCSCSSDECNDNIIFSEEYNTSNP

DGGGGSGGGGSGGGGSIPPHVQKSVNNDMIVTDNNGAVKFPQLCKFCDVRF

STCDNQKSCMSNCSITSICEKPQEVCVAVWRKNDENITLETVCHDPKLPYH

DFILEDAASPKCIMKEKKKPGETFFMCSCSSDECNDNIIFSEEYNTSNPDS

GTTNTVAAYNLTWKSTNFKTILEWEPKPVNQVYTVQISTKSGDWKSKCFYT

TDTECDLTDEIVKDVKQTYLARVFSYPAGNVESTGSAGEPLYENSPEFTPY

LETNLGQPTIQSFEQVGTKVNVTVEDERTLVRRNNTFLSLRDVFGKDLIYT

LYYWKSSSSGKKTAKTNTNEFLIDVDKGENYCFSVQAVIPSRTVNRKSTDS

PVECMGQEKGEFRENWVNVISDLKKIEDLIQSMHIDATLYTESDVHPSCKV

TAMKCFLLELQVISLESGDASIHDTVENLIILANNSLSSNGNVTESGCKEC

EELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 239)

ATGAAGTGGGTGACCTTCATCAGCCTGCTGTTCCTGTTCTCCAGCGCCTAC

TCCATCCCCCCCCATGTGCAAAAGAGCGTGAACAACGATATGATCGTGACC

GACAACAACGGCGCCGTGAAGTTTCCCCAGCTCTGCAAGTTCTGCGATGTC

AGGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAAA

AATGACGAGAACATCACCCTGGAGACCGTGTGTCACGACCCCAAGCTCCCT

TATCACGACTTCATTCTGGAGGACGCTGCCTCCCCCAAATGCATCATGAAG

GAGAAGAAGAAGCCCGGAGAGACCTTCTTTATGTGTTCCTGTAGCAGCGAC

GAGTGTAACGACAACATCATCTTCAGCGAAGAGTACAACACCAGCAACCCT

GATGGAGGTGGCGGATCCGGAGGTGGAGGTTCTGGTGGAGGTGGGAGTATT

CCTCCCCACGTGCAGAAGAGCGTGAATAATGACATGATCGTGACCGATAAC

AATGGCGCCGTGAAATTTCCCCAGCTGTGCAAATTCTGCGATGTGAGGTTT

TCCACCTGCGACAACCAGAAGTCCTGTATGAGCAACTGCTCCATCACCTCC

ATCTGTGAGAAGCCTCAGGAGGTGTGCGTGGCTGTCTGGCGGAAGAATGAC

GAGAATATCACCCTGGAAACCGTCTGCCACGATCCCAAGCTGCCCTACCAC

GATTTCATCCTGGAAGACGCCGCCAGCCCTAAGTGCATCATGAAAGAGAAA

AAGAAGCCTGGCGAGACCTTTTTCATGTGCTCCTGCAGCAGCGACGAATGC

AACGACAATATCATCTTTAGCGAGGAATACAATACCAGCAACCCCGACAGC

GGCACAACCAACACAGTCGCTGCCTATAACCTCACTTGGAAGAGCACCAAC

-continued

TTCAAAACCATCCTCGAATGGGAACCCAAACCCGTTAACCAAGTTTACACC
GTGCAGATCAGCACCAAGTCCGGCGACTGGAAGTCCAAATGTTTCTATACC
ACCGACACCGAGTGCGATCTCACCGATGAGATCGTGAAAGATGTGAAACAG
ACCTACCTCGCCCGGGTGTTTAGCTACCCCGCCGGCAATGTGGAGAGCACT
GGTTCCGCTGGCGAGCCTTTATACGAGAACAGCCCCGAATTTACCCCTTAC
CTCGAGACCAATTTAGGACAGCCCACCATCCAAAGCTTTGAGCAAGTTGGC
ACAAAGGTGAATGTGACAGTGGAGGACGAGCGGACTTTAGTGCGGCGGAAC
AACACCTTTCTCAGCCTCCGGGATGTGTTCGGCAAAGATTTAATCTACACA
CTGTATTACTGGAAGTCCTCTTCCTCCGGCAAGAAGACAGCTAAAACCAAC
ACAAACGAGTTTTTAATCGACGTGGATAAAGGCGAAAACTACTGTTTCAGC
GTGCAAGCTGTGATCCCCTCCCGGACCGTGAATAGGAAAAGCACCGATAGC
CCCGTTGAGTGCATGGGCCAAGAAAAGGGCGAGTTCCGGGAGAACTGGGTG
AACGTCATCAGCGATTTAAAGAAGATCGAAGATTTAATTCAGTCCATGCAT
ATCGACGCCACTTTATACACAGAATCCGACGTGCACCCCTCTTGTAAGGTG
ACCGCCATGAAATGTTTTTTACTGGAGCTGCAAGTTATCTCTTTAGAGAGC
GGAGACGCTAGCATCCACGACACCGTGGAGAATTTAATCATTTTAGCCAAT
AACTCTTTATCCAGCAACGGCAACGTGACAGAGTCCGGCTGCAAGGAGTGC
GAAGAGCTGGAGGAGAAGAACATCAAGGAGTTTCTGCAATCCTTTGTGCAC
ATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 308)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPDGGGGSGGGGSGGGGSIP
PHVQKSVNNDMIVTDNNGAVKFPQLCKFCDVRFSTCDNQKSCMSNCSITSI
CEKPQEVCVAVWRKNDENITLETVCHDPKLPYHDFILEDAASPKCIMKEKK
KPGETFFMCSCSSDECNDNIIFSEEYNTSNPDITCPPPMSVEHADIWVKSY
SLYSRERYICNSGFKRKAGTSSLTECVLNKATNVAHWTTPSLKCIRSELTQ
DPAVSVALGQTVRITCQGDSLRSYYASWYQQKPGQAPVLVIYGKNNRPSGI
PDRFSGSSSGNTASLTITGAQAEDEADYYCNSRDSSGNHVVFGGGTKLTVG
HGGGGSGGGGSGGGGSEVQLVESGGGVVRPGGSLRLSCAASGFTFDDYGMS
WVRQAPGKGLEWVSGINWNGGSTGYADSVKGRFTISRDNAKNSLYLQMNSL
RAEDTAVYYCARGRSLLFDYWGQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 309)
ATCCCCCCCCATGTGCAAAAGAGCGTGAACAACGATATGATCGTGACCGAC
AACAACGGCGCCGTGAAGTTTCCCCAGCTCTGCAAGTTCTGCGATGTCAGG
TTCAGCACCTGCGATAATCAGAAGTCCTGCATGTCCAACTGCAGCATCACC
TCCATCTGCGAGAAGCCCCAAGAAGTGTGCGTGGCCGTGTGGCGGAAAAAT
GACGAGAACATCACCCTGGAGACCGTGTGTCACGACCCCAAGCTCCCTTAT
CACGACTTCATTCTGGAGGACGCTGCCTCCCCCAAATGCATCATGAAGGAG
AAGAAGAAGCCCGGAGAGACCTTCTTTATGTGTTCCTGTAGCAGCGACGAG
TGTAACGACAACATCATCTTCAGCGAAGAGTACAACACCAGCAACCCTGAT
GGAGGTGGCGGATCCGGAGGTGGAGGTTCTGGTGGAGGTGGGAGTATTCCT
CCCCACGTGCAGAAGAGCGTGAATAATGACATGATCGTGACCGATAACAAT
GGCGCCGTGAAATTTCCCCAGCTGTGCAAATTCTGCGATGTGAGGTTTTCC
ACCTGCGACAACCAGAAGTCCTGTATGAGCAACTGCTCCATCACCTCCATC
TGTGAGAAGCCTCAGGAGGTGTGCGTGGCTGTCTGGCGGAAGAATGACGAG
AATATCACCCTGGAAACCGTCTGCCACGATCCCAAGCTGCCCTACCACGAT
TTCATCCTGGAAGACGCCGCCAGCCCTAAGTGCATCATGAAAGAGAAAAAG
AAGCCTGGCGAGACCTTTTTCATGTGCTCCTGCAGCAGCGACGAATGCAAC
GACAATATCATCTTTAGCGAGGAATACAATACCAGCAACCCCGACATTACA
TGCCCCCCTCCCATGAGCGTGGAGCACGCCGACATCTGGGTGAAGAGCTAT
AGCCTCTACAGCCGGGAGAGGTATATCTGTAACAGCGGCTTCAAGAGGAAG
GCCGGCACCAGCAGCCTCACCGAGTGCGTGCTGAATAAGGCTACCAACGTG
GCTCACTGGACAACACCCTCTTTAAAGTGCATCCGGTCCGAGCTGACCCAG
GACCCTGCTGTGTCCGTGGCTCTGGGCCAGACCGTGAGGATCACCTGCCAG
GGCGACTCCCTGAGGTCCTACTACGCCTCCTGGTACCAGCAGAAGCCCGGC
CAGGCTCCTGTGCTGGTGATCTACGGCAAGAACAACAGGCCCTCCGGCATC
CCTGACAGGTTCTCCGGATCCTCCTCCGGCAACACCGCCTCCCTGACCATC
ACAGGCGCTCAGGCCGAGGACGAGGCTGACTACTACTGCAACTCCAGGGAC
TCCTCCGGCAACCATGTGGTGTTCGGCGGCGGCACCAAGCTGACCGTGGGC
CATGGCGGCGGCGGCTCCGGAGGCGGCGGCAGCGGCGGAGGAGGATCCGAG
GTGCAGCTGGTGGAGTCCGGAGGAGGAGTGGTGAGGCCTGGAGGCTCCCTG
AGGCTGAGCTGTGCTGCCTCCGGCTTCACCTTCGACGACTACGGCATGTCC
TGGGTGAGGCAGGCTCCTGGAAAGGGCCTGGAGTGGGTGTCCGGCATCAAC
TGGAACGGCGGATCCACCGGCTACGCCGATTCCGTGAAGGGCAGGTTCACC
ATCAGCAGGGACAACGCCAAGAACTCCCTGTACCTGCAGATGAACTCCCTG
AGGGCCGAGGACACCGCCGTGTACTACTGCGCCAGGGGCAGGTCCCTGCTG
TTCGACTACTGGGGACAGGGCACCCTGGTGACCGTGTCCAGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 310)
MKWVTFISLLFLFSSAYSIPPHVQKSVNNDMIVTDNNGAVKFPQLCKFCDV
RFSTCDNQKSCMSNCSITSICEKPQEVCVAVWRKNDENITLETVCHDPKLP
YHDFILEDAASPKCIMKEKKKPGETFFMCSCSSDECNDNIIFSEEYNTSNP
DGGGGSGGGGSGGGGSIPPHVQKSVNNDMIVTDNNGAVKFPQLCKFCDVRF
STCDNQKSCMSNCSITSICEKPQEVCVAVWRKNDENITLETVCHDPKLPYH
DFILEDAASPKCIMKEKKKPGETFFMCSCSSDECNDNIIFSEEYNTSNPDI
TCPPPMSVEHADIWVKSYSLYSRERYICNSGFKRKAGTSSLTECVLNKATN
VAHWTTPSLKCIRSELTQDPAVSVALGQTVRITCQGDSLRSYYASWYQQKP
GQAPVLVIYGKNNRPSGIPDRFSGSSSGNTASLTITGAQAEDEADYYCNSR
DSSGNHVVFGGGTKLTVGHGGGGSGGGGSGGGGSEVQLVESGGGVVRPGGS
LRLSCAASGFTFDDYGMSWVRQAPGKGLEWVSGINWNGGSTGYADSVKGRF
TISRDNAKNSLYLQMNSLRAEDTAVYYCARGRSLLFDYWGQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 311)
ATGAAGTGGGTGACCTTCATCAGCCTGCTGTTCCTGTTCTCCAGCGCCTAC
TCCATCCCCCCCCATGTGCAAAAGAGCGTGAACAACGATATGATCGTGACC
GACAACAACGGCGCCGTGAAGTTTCCCCAGCTCTGCAAGTTCTGCGATGTC
AGGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAAA
AATGACGAGAACATCACCCTGGAGACCGTGTGTCACGACCCCAAGCTCCCT
TATCACGACTTCATTCTGGAGGACGCTGCCTCCCCCAAATGCATCATGAAG
GAGAAGAAGAAGCCCGGAGAGACCTTCTTTATGTGTTCCTGTAGCAGCGAC
GAGTGTAACGACAACATCATCTTCAGCGAAGAGTACAACACCAGCAACCCT
GATGGAGGTGGCGGATCCGGAGGTGGAGGTTCTGGTGGAGGTGGGAGTATT
CCTCCCCACGTGCAGAAGAGCGTGAATAATGACATGATCGTGACCGATAAC
AATGGCGCCGTGAAATTTCCCCAGCTGTGCAAATTCTGCGATGTGAGGTTT
TCCACCTGCGACAACCAGAAGTCCTGTATGAGCAACTGCTCCATCACCTCC
ATCTGTGAGAAGCCTCAGGAGGTGTGCGTGGCTGTCTGGCGGAAGAATGAC
GAGAATATCACCCTGGAAACCGTCTGCCACGATCCCAAGCTGCCCTACCAC
GATTTCATCCTGGAAGACGCCGCCAGCCCTAAGTGCATCATGAAAGAGAAA
AAGAAGCCTGGCGAGACCTTTTTCATGTGCTCCTGCAGCAGCGACGAATGC
AACGACAATATCATCTTTAGCGAGGAATACAATACCAGCAACCCCGACATT
ACATGCCCCCCTCCCATGAGCGTGGAGCACGCCGACATCTGGGTGAAGAGC
TATAGCCTCTACAGCCGGGAGAGGTATATCTGTAACAGCGGCTTCAAGAGG

-continued
AAGGCCGGCACCAGCAGCCTCACCGAGTGCGTGCTGAATAAGGCTACCAAC
GTGGCTCACTGGACAACACCCTCTTTAAAGTGCATCCGGTCCGAGCTGACC
CAGGACCCTGCTGTGTCCGTGGCTCTGGGCCAGACCGTGAGGATCACCTGC
CAGGGCGACTCCCTGAGGTCCTACTACGCCTCCTGGTACCAGCAGAAGCCC
GGCCAGGCTCCTGTGCTGGTGATCTACGGCAAGAACAACAGGCCCTCCGGC
ATCCCTGACAGGTTCTCCGGATCCTCCTCCGGCAACACCGCCTCCCTGACC
ATCACAGGCGCTCAGGCCGAGGACGAGGCTGACTACTACTGCAACTCCAGG
GACTCCTCCGGCAACCATGTGGTGTTCGGCGGCGGCACCAAGCTGACCGTG
GGCCATGGCGGCGGCGGCTCCGGAGGCGGCGGCAGCGGCGGAGGAGGATCC
GAGGTGCAGCTGGTGGAGTCCGGAGGAGGAGTGGTGAGGCCTGGAGGCTCC
CTGAGGCTGAGCTGTGCTGCCTCCGGCTTCACCTTCGACGACTACGGCATG
TCCTGGGTGAGGCAGGCTCCTGGAAAGGGCCTGGAGTGGGTGTCCGGCATC
AACTGGAACGGCGGATCCACCGGCTACGCCGATTCCGTGAAGGGCAGGTTC
ACCATCAGCAGGGACAACGCCAAGAACTCCCTGTACCTGCAGATGAACTCC
CTGAGGGCCGAGGACACCGCCGTGTACTACTGCGCCAGGGGCAGGTCCCTG
CTGTTCGACTACTGGGGACAGGGCACCCTGGTGACCGTGTCCAGG.

Exemplary Multi-Chain Chimeric Polypeptides—Type O

In some embodiments of any of the multi-chain chimeric polypeptides described herein, the first target-binding domain and the second targeting-binding domain each independently bind specifically to TGF-β or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor to TGF-0 (e.g., a soluble TGF-β receptor, e.g., a soluble TGFβRII receptor) or CD137L.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein)

between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to CD137L. In some embodiments of these multi-chain chimeric polypeptides, the first target-binding domain or the additional target-binding domain is a soluble TGF-β receptor (e.g., a soluble TGFβRII receptor, e.g., a soluble human TGFβRII receptor).

In some embodiments of these multi-chain chimeric polypeptides, the soluble human TGFRβRII includes a first sequence of soluble human TGFRβRII and a second sequence of soluble human TGFRβRII. In some embodiments of these multi-chain chimeric polypeptides, the soluble human TGFRβRII includes a linker disposed between the first sequence of soluble human TGFRβRII and the second sequence of soluble human TGFRβRII. In some examples of these multi-chain chimeric polypeptides, the linker includes the sequence GGGGSGGGGSGGGGS (SEQ ID NO: 102).

In some embodiments of these multi-chain chimeric polypeptides, the first sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 183)
IPPHVQKSVNNDMIVTDNNGAVKFPQLCKFCDVRFSTCDNQKSCMNCSITS
ICEKPQEVCVAVWRKNDENITLETVCHDPKLPYHDFILEDAASPKCIMKEK
KKPGETFFMCSCSSDECNDNIIFSEEYNTSNPD.

In some embodiments of these multi-chain chimeric polypeptides, the second sequence of soluble human TGFRβRII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPD.

In some embodiments of these multi-chain chimeric polypeptides, the first sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGAT.

In some embodiments of these multi-chain chimeric polypeptides, the second sequence of soluble human TGFRβRII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)
ATTCCTCCCCACGTGCAGAAGAGCGTGAATAATGACATGATCGTGACCGA
TAACAATGGCGCCGTGAAATTTCCCCAGCTGTGCAAATTCTGCGATGTGA
GGTTTTCCACCTGCGACAACCAGAAGTCCTGTATGAGCAACTGCTCCATC
ACCTCCATCTGTGAGAAGCCTCAGGAGGTGTGCGTGGCTGTCTGGCGGAA
GAATGACGAGAATATCACCCTGGAAACCGTCTGCCACGATCCCAAGCTGC
CCTACCACGATTTCATCCTGGAAGACGCCGCCAGCCCTAAGTGCATCATG
AAAGAGAAAAAGAAGCCTGGCGAGACCTTTTTCATGTGCTCCTGCAGCAG
CGACGAATGCAACGACAATATCATCTTTAGCGAGGAATACAATACCAGCA
ACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPDGGGGSGGGGSGGGGSIP
PHVQKSVNNDMIVTDNNGAVKFPQLCKFCDVRFSTCDNQKSCMSNCSITSI
CEKPQEVCVAVWRKNDENITLETVCHDPKLPYHDFILEDAASPKCIMKEKK
KPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)
ATCCCCCCCCATGTGCAAAAGAGCGTGAACAACGATATGATCGTGACCGA
CAACAACGGCGCCGTGAAGTTTCCCCAGCTCTGCAAGTTCTGCGATGTCA
GGTTCAGCACCTGCGATAATCAGAAGTCCTGCATGTCCAACTGCAGCATC
ACCTCCATCTGCGAGAAGCCCCAAGAAGTGTGCGTGGCCGTGTGGCGGAA
AAATGACGAGAACATCACCCTGGAGACCGTGTGTCACGACCCCAAGCTCC
CTTATCACGACTTCATTCTGGAGGACGCTGCCTCCCCCAAATGCATCATG
AAGGAGAAGAAGAAGCCCGGAGAGACCTTCTTTATGTGTTCCTGTAGCAG
CGACGAGTGTAACGACAACATCATCTTCAGCGAAGAGTACAACACCAGCA
ACCCTGATGGAGGTGGCGGATCCGGAGGTGGAGGTTCTGGTGGAGGTGGG
AGTATTCCTCCCCACGTGCAGAAGAGCGTGAATAATGACATGATCGTGAC
CGATAACAATGGCGCCGTGAAATTTCCCCAGCTGTGCAAATTCTGCGATG
TGAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGCG
GAAGAATGACGAGAATATCACCCTGGAAACCGTCTGCCACGATCCCAAGC
TGCCCTACCACGATTTCATCCTGGAAGACGCCGCCAGCCCTAAGTGCATC
ATGAAAGAGAAAAAGAAGCCTGGCGAGACCTTTTTCATGTGCTCCTGCAG
CAGCGACGAATGCAACGACAATATCATCTTTAGCGAGGAATACAATACCA
GCAACCCCGAC.

In some embodiments of these multi-chain chimeric polypeptides, the second target-binding domain includes a soluble CD137L protein (e.g., a soluble human CD137L protein). In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 260)
REGPELSPDDPAGLLDLRQGMFAQLVAQNVLLIDGPLSWYSDPGLAGVSL
TGGLSYKEDTKELVVAKAGVYYVFFQLELRRVVAGEGSGSVSLALHLQPL
RSAAGAAALALTVDLPPASSEARNSAFGFQGRLLHLSAGQRLGVHLHTEA
RARHAWQLTQGATVLGLFRVTPEIPAGLPSPRSE.

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 261)
CGCGAGGGTCCCGAGCTTTCGCCCGACGATCCCGCCGGCCTCTTGGACCT
GCGGCAGGGCATGTTTGCGCAGCTGGTGGCCCAAAATGTTCTGCTGATCG
ATGGGCCCCTGAGCTGGTACAGTGACCCAGGCCTGGCAGGCGTGTCCCTG
ACGGGGGGCCTGAGCTACAAAGAGGACACGAAGGAGCTGGTGGTGGCCAA
GGCTGGAGTCTACTATGTCTTCTTTCAACTAGAGCTGCGGCGCGTGGTGG
CCGGCGAGGGCTCAGGCTCCGTTTCACTTGCGCTGCACCTGCAGCCACTG
CGCTCTGCTGCTGGGGCCGCCGCCCTGGCTTTGACCGTGGACCTGCCACC
CGCCTCCTCCGAGGCTCGGAACTCGGCCTTCGGTTTCCAGGGCCGCTTGC
TGCACCTGAGTGCCGGCCAGCGCCTGGGCGTCCATCTTCACACTGAGGCC
AGGGCACGCCATGCCTGGCAGCTTACCCAGGGCGCCACAGTCTTGGGACT
CTTCCGGGTGACCCCCGAAATCCCAGCCGGACTCCCTTCACCGAGGTCGG
AA.

In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 262)
DPAGLLDLRQGMFAQLVAQNVLLIDGPLSWYSDPGLAGVSLTGGLSYKED
TKELVVAKAGVYYVFFQLELRRVVAGEGSGSVSLALHLQPLRSAAGAAAL
ALTVDLPPASSEARNSAFGFQGRLLHLSAGQRLGVHLHTEARARHAWQLT
QGATVLGLFRVTPEI.

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 263)
GATCCCGCCGGCCTCTTGGACCTGCGGCAGGGCATGTTTGCGCAGCTGGT
GGCCCAAAATGTTCTGCTGATCGATGGGCCCCTGAGCTGGTACAGTGACC
CAGGCCTGGCAGGCGTGTCCCTGACGGGGGGCCTGAGCTACAAAGAGGAC
ACGAAGGAGCTGGTGGTGGCCAAGGCTGGAGTCTACTATGTCTTCTTTCA
ACTAGAGCTGCGGCGCGTGGTGGCCGGCGAGGGCTCAGGCTCCGTTTCAC
TTGCGCTGCACCTGCAGCCACTGCGCTCTGCTGCTGGGGCCGCCGCCCTG

-continued

GCTTTGACCGTGGACCTGCCACCCGCCTCCTCCGAGGCTCGGAACTCGGC

CTTCGGTTTCCAGGGCCGCTTGCTGCACCTGAGTGCCGGCCAGCGCCTGG

GCGTCCATCTTCACACTGAGGCCAGGGCACGCCATGCCTGGCAGCTTACC

CAGGGCGCCACAGTCTTGGGACTCTTCCGGGTGACCCCCGAAATC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 236)

IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDSGTTNTVAAYNLT

WKSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPTI

QSFEQVGTKVNVTVEDERTLVRRNNTFLSLRDVFGKDLIYTLYYWKSSSS

GKKTAKTNTNEFLIDVDKGENYCFSVQAVIPSRTVNRKSTDSPVECMGQE

KGEFRENWVNVISDLKKIEDLIQSMHIDATLYTESDVHPSCKVTAMKCFL

LELQVISLESGDASIHDTVENLIILANNSLSSNGNVTESGCKECEELEEK

NIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 237)

ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

-continued

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGACAGCGGCACAACCAACACAGTCGCTGCCTATAACCTCACT

TGGAAGAGCACCAACTTCAAAACCATCCTCGAATGGGAACCCAAACCCGT

TAACCAAGTTTACACCGTGCAGATCAGCACCAAGTCCGGCGACTGGAAGT

CCAAATGTTTCTATACCACCGACACCGAGTGCGATCTCACCGATGAGATC

GTGAAAGATGTGAAACAGACCTACCTCGCCCGGGTGTTTAGCTACCCCGC

CGGCAATGTGGAGAGCACTGGTTCCGCTGGCGAGCCTTTATACGAGAACA

GCCCCGAATTTACCCCTTACCTCGAGACCAATTTAGGACAGCCCACCATC

CAAAGCTTTGAGCAAGTTGGCACAAAGGTGAATGTGACAGTGGAGGACGA

GCGGACTTTAGTGCGGCGGAACAACACCTTTCTCAGCCTCCGGGATGTGT

TCGGCAAAGATTTAATCTACACACTGTATTACTGGAAGTCCTCTTCCTCC

GGCAAGAAGACAGCTAAAACCAACACAAACGAGTTTTTAATCGACGTGGA

TAAAGGCGAAAACTACTGTTTCAGCGTGCAAGCTGTGATCCCCTCCCGGA

CCGTGAATAGGAAAAGCACCGATAGCCCCGTTGAGTGCATGGGCCAAGAA

AAGGGCGAGTTCCGGGAGAACTGGGTGAACGTCATCAGCGATTTAAAGAA

GATCGAAGATTTAATTCAGTCCATGCATATCGACGCCACTTTATACACAG

AATCCGACGTGCACCCCTCTTGTAAGGTGACCGCCATGAAATGTTTTTTA

CTGGAGCTGCAAGTTATCTCTTTAGAGAGCGGAGACGCTAGCATCCACGA

CACCGTGGAGAATTTAATCATTTTAGCCAATAACTCTTTATCCAGCAACG

GCAACGTGACAGAGTCCGGCTGCAAGGAGTGCGAAGAGCTGGAGGAGAAG

AACATCAAGGAGTTTCTGCAATCCTTTGTGCACATTGTCCAGATGTTCAT

CAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 238)

MKWVTFISLLFLFSSAYSIPPHVQKSVNNDMIVTDNNGAVKFPQLCKFCD

VRFSTCDNQKSCMSNCSITSICEKPQEVCVAVWRKNDENITLETVCHDPK

LPYHDFILEDAASPKCIMKEKKKPGETFFMCSCSSDECNDNIIFSEEYNT

SNPDGGGGSGGGGSGGGGSIPPHVQKSVNNDMIVTDNNGAVKFPQLCKFC

DVRFSTCDNQKSCMSNCSITSICEKPQEVCVAVWRKNDENITLETVCHDP

KLPYHDFILEDAASPKCIMKEKKKPGETFFMCSCSSDECNDNIIFSEEYN

TSNPDSGTTNTVAAYNLTWKSTNFKTILEWEPKPVNQVYTVQISTKSGDW

KSKCFYTTDTECDLTDEIVKDVKQTYLARVFSYPAGNVESTGSAGEPLYE

-continued

NSPEFTPYLETNLGQPTIQSFEQVGTKVNVTVEDERTLVRRNNTFLSLRD

VFGKDLIYTLYYWKSSSSGKKTAKTNTNEFLIDVDKGENYCFSVQAVIPS

RTVNRKSTDSPVECMGQEKGEFRENWVNVISDLKKIEDLIQSMHIDATLY

TESDVHPSCKVTAMKCFLLELQVISLESGDASIHDTVENLIILANNSLSS

NGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 239)

ATGAAGTGGGTGACCTTCATCAGCCTGCTGTTCCTGTTCTCCAGCGCCTA

CTCCATCCCCCCCCATGTGCAAAAGAGCGTGAACAACGATATGATCGTGA

CCGACAACAACGGCGCCGTGAAGTTTCCCCAGCTCTGCAAGTTCTGCGAT

GTCAGGTTCAGCACCTGCGATAATCAGAAGTCCTGCATGTCCAACTGCAG

CATCACCTCCATCTGCGAGAAGCCCCAAGAAGTGTGCGTGGCCGTGTGGC

GGAAAAATGACGAGAACATCACCCTGGAGACCGTGTGTCACGACCCCAAG

CTCCCTTATCACGACTTCATTCTGGAGGACGCTGCCTCCCCCAAATGCAT

CATGAAGGAGAAGAAGAAGCCCGGAGAGACCTTCTTTATGTGTTCCTGTA

GCAGCGACGAGTGTAACGACAACATCATCTTCAGCGAAGAGTACAACACC

AGCAACCCTGATGGAGGTGGCGGATCCGGAGGTGGAGGTTCTGGTGGAGG

TGGGAGTATTCCTCCCCACGTGCAGAAGAGCGTGAATAATGACATGATCG

TGACCGATAACAATGGCGCCGTGAAATTTCCCCAGCTGTGCAAATTCTGC

GATGTGAGGTTTTCCACCTGCGACAACCAGAAGTCCTGTATGAGCAACTG

CTCCATCACCTCCATCTGTGAGAAGCCTCAGGAGGTGTGCGTGGCTGTCT

GGCGGAAGAATGACGAGAATATCACCCTGGAAACCGTCTGCCACGATCCC

AAGCTGCCCTACCACGATTTCATCCTGGAAGACGCCGCCAGCCCTAAGTG

CATCATGAAAGAGAAAAAGAAGCCTGGCGAGACCTTTTTCATGTGCTCCT

GCAGCAGCGACGAATGCAACGACAATATCATCTTTAGCGAGGAATACAAT

ACCAGCAACCCCGACAGCGGCACAACCAACACAGTCGCTGCCTATAACCT

CACTTGGAAGAGCACCAACTTCAAAACCATCCTCGAATGGGAACCCAAAC

CCGTTAACCAAGTTTACACCGTGCAGATCAGCACCAAGTCCGGCGACTGG

AAGTCCAAATGTTTCTATACCACCGACACCGAGTGCGATCTCACCGATGA

GATCGTGAAAGATGTGAAACAGACCTACCTCGCCCGGGTGTTTAGCTACC

CCGCCGGCAATGTGGAGAGCACTGGTTCCGCTGGCGAGCCTTTATACGAG

AACAGCCCCGAATTTACCCCTTACCTCGAGACCAATTTAGGACAGCCCAC

CATCCAAAGCTTTGAGCAAGTTGGCACAAAGGTGAATGTGACAGTGGAGG

ACGAGCGGACTTTAGTGCGGCGGAACAACACCTTTCTCAGCCTCCGGGAT

GTGTTCGGCAAAGATTTAATCTACACACTGTATTACTGGAAGTCCTCTTC

CTCCGGCAAGAAGACAGCTAAAACCAACACAAACGAGTTTTTAATCGACG

-continued

TGGATAAAGGCGAAAACTACTGTTTCAGCGTGCAAGCTGTGATCCCCTCC

CGGACCGTGAATAGGAAAAGCACCGATAGCCCCGTTGAGTGCATGGGCCA

AGAAAAGGGCGAGTTCCGGGAGAACTGGGTGAACGTCATCAGCGATTTAA

AGAAGATCGAAGATTTAATTCAGTCCATGCATATCGACGCCACTTTATAC

ACAGAATCCGACGTGCACCCCTCTTGTAAGGTGACCGCCATGAAATGTTT

TTTACTGGAGCTGCAAGTTATCTCTTTAGAGAGCGGAGACGCTAGCATCC

ACGACACCGTGGAGAATTTAATCATTTTAGCCAATAACTCTTTATCCAGC

AACGGCAACGTGACAGAGTCCGGCTGCAAGGAGTGCGAAGAGCTGGAGGA

GAAGAACATCAAGGAGTTTCTGCAATCCTTTGTGCACATTGTCCAGATGT

TCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 316)

IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDITCPPPMSVEHAD

IWVKSYSLYSRERYICNSGFKRKAGTSSLTECVLNKATNVAHWTTPSLKC

IRGGGGSGGGGSGGGGSREGPELSPDDPAGLLDLRQGMFAQLVAQNVLLI

DGPLSWYSDPGLAGVSLTGGLSYKEDTKELVVAKAGVYYVFFQLELRRVV

AGEGSGSVSLALHLQPLRSAAGAAALALTVDLPPASSEARNSAFGFQGRL

LHLSAGQRLGVHLHTEARARHAWQLTQGATVLGLFRVTPEIPAGLPSPRS

E.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 317)

ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

-continued

GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGACATTACATGCCCCCCTCCCATG
AGCGTGGAGCACGCCGACATCTGGGTGAAGAGCTATAGCCTCTACAGCC
GGGAGAGGTATATCTGTAACAGCGGCTTCAAGAGGAAGGCCGGCACCAG
CAGCCTCACCGAGTGCGTGCTGAATAAGGCTACCAACGTGGCTCACTGG
ACAACACCCTCTTTAAAGTGCATCCGGGGCGGTGGAGGATCCGGAGGAG
GTGGCTCCGGCGGCGGAGGATCTCGCGAGGGTCCCGAGCTTTCGCCCGA
CGATCCCGCCGGCCTCTTGGACCTGCGGCAGGGCATGTTTGCGCAGCTG
GTGGCCCAAAATGTTCTGCTGATCGATGGGCCCCTGAGCTGGTACAGTG
ACCCAGGCCTGGCAGGCGTGTCCCTGACGGGGGGCCTGAGCTACAAAGA
GGACACGAAGGAGCTGGTGGTGGCCAAGGCTGGAGTCTACTATGTCTTC
TTTCAACTAGAGCTGCGGCGCGTGGTGGCCGGCGAGGGCTCAGGCTCCG
TTTCACTTGCGCTGCACCTGCAGCCACTGCGCTCTGCTGCTGGGGCCGC
CGCCCTGGCTTTGACCGTGGACCTGCCACCCGCCTCCTCCGAGGCTCGG
AACTCGGCCTTCGGTTTCCAGGGCCGCTTGCTGCACCTGAGTGCCGGCC
AGCGCCTGGGCGTCCATCTTCACACTGAGGCCAGGGCACGCCATGCCTG
GCAGCTTACCCAGGGCGCCACAGTCTTGGGACTCTTCCGGGTGACCCCC
GAAATCCCAGCCGGACTCCCTTCACCGAGGTCGGAA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 318)

MKWVTFISLLFLFSSASIPPHVQKSVNNDMIVTDNNGAVKFPQLCKFCD
VRFSTCDNQKSCMSNCSITSICEKPQEVCVAVWRKNDENITLETVCHDP
KLPYHDFILEDAASPKCIMKEKKKPGETFFMCSCSSDECNDNIIFSEEY
NTSNPDGGGGSGGGGSGGGGSIPPHVQKSVNNDMIVTDNNGAVKFPQLC
KFCDVRFSTCDNQKSCMSNCSITSICEKPQEVCVAVWRKNDENITLETV
CHDPKLPYHDFILEDAASPKCIMKEKKKPGETFFMCSCSSDECNDNIIF
SEEYNTSNPDITCPPPMSVEHADIWVKSYSLYSRERYICNSGFKRKAGT

-continued

SSLTECVLNKATNVAHWTTPSLKCIRGGGGSGGGGSGGGGSREGPELSP
DDPAGLLDLRQGMFAQLVAQNVLLIDGPLSWYSDPGLAGVSLTGGLSYK
EDTKELVVAKAGVYYVFFQLELRRVVAGEGSGSVSLALHLQPLRSAAGA
AALALTVDLPPASSEARNSAFGFQGRLLHLSAGQRLGVHLHTEARARHA
WQLTQGATVLGLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 319)

ATGAAGTGGGTGACCTTCATCAGCCTGCTGTTCCTGTTCTCCAGCGCCT
ACTCCATCCCCCCCCATGTGCAAAAGAGCGTGAACAACGATATGATCGT
GACCGACAACAACGGCGCCGTGAAGTTTCCCCAGCTCTGCAAGTTCTGC
GATGTCAGGTTCAGCACCTGCGATAATCAGAAGTCCTGCATGTCCAACT
GCAGCATCACCTCCATCTGCGAGAAGCCCCAAGAAGTGTGCGTGGCCGT
GTGGCGGAAAAAATGACGAGAACATCACCCTGGAGACCGTGTGTCACGAC
CCCAAGCTCCCTTATCACGACTTCATTCTGGAGGACGCTGCCTCCCCCA
AATGCATCATGAAGGAGAAGAAGAAGCCCGGAGAGACCTTCTTTATGTG
TTCCTGTAGCAGCGACGAGTGTAACGACAACATCATCTTCAGCGAAGAG
TACAACACCAGCAACCCTGATGGAGGTGGCGGATCCGGAGGTGGAGGTT
CTGGTGGAGGTGGGAGTATTCCTCCCCACGTGCAGAAGAGCGTGAATAA
TGACATGATCGTGACCGATAACAATGGCGCCGTGAAATTTCCCCAGCTG
TGCAAATTCTGCGATGTGAGGTTTTCCACCTGCGACAACCAGAAGTCCT
GTATGAGCAACTGCTCCATCACCTCCATCTGTGAGAAGCCTCAGGAGGT
GTGCGTGGCTGTCTGGCGGAAGAATGACGAGAATATCACCCTGGAAACC
GTCTGCCACGATCCCAAGCTGCCCTACCACGATTTCATCCTGGAAGACG
CCGCCAGCCCTAAGTGCATCATGAAAGAGAAAAAGAAGCCTGGCGAGAC
CTTTTTCATGTGCTCCTGCAGCAGCGACGAATGCAACGACAATATCATC
TTTAGCGAGGAATACAATACCAGCAACCCCGACATTACATGCCCCCCTC
CCATGAGCGTGGAGCACGCCGACATCTGGGTGAAGAGCTATAGCCTCTA
CAGCCGGGAGAGGTATATCTGTAACAGCGGCTTCAAGAGGAAGGCCGGC
ACCAGCAGCCTCACCGAGTGCGTGCTGAATAAGGCTACCAACGTGGCTC
ACTGGACAACACCCTCTTTAAAGTGCATCCGGGGCGGTGGAGGATCCGG
AGGAGGTGGCTCCGGCGGCGGAGGATCTCGCGAGGGTCCCGAGCTTTCG
CCCGACGATCCCGCCGGCCTCTTGGACCTGCGGCAGGGCATGTTTGCGC
AGCTGGTGGCCCAAAATGTTCTGCTGATCGATGGGCCCCTGAGCTGGTA
CAGTGACCCAGGCCTGGCAGGCGTGTCCCTGACGGGGGGCCTGAGCTAC
AAAGAGGACACGAAGGAGCTGGTGGTGGCCAAGGCTGGAGTCTACTATG
TCTTCTTTCAACTAGAGCTGCGGCGCGTGGTGGCCGGCGAGGGCTCAGG
CTCCGTTTCACTTGCGCTGCACCTGCAGCCACTGCGCTCTGCTGCTGGG

-continued

```
GCCGCCGCCCTGGCTTTGACCGTGGACCTGCCACCCGCCTCCTCCGAGG
CTCGGAACTCGGCCTTCGGTTTCCAGGGCCGCTTGCTGCACCTGAGTGC
CGGCCAGCGCCTGGGCGTCCATCTTCACACTGAGGCCAGGGCACGCCAT
GCCTGGCAGCTTACCCAGGGCGCCACAGTCTTGGGACTCTTCCGGGTGA
CCCCCGAAATCCCAGCCGGACTCCCTTCACCGAGGTCGGAA.
```

Methods of Treating an Aging-Related Disease or Condition

Provided herein are methods of treating an aging-related disease or condition (e.g. any of the exemplary types of aging-related disease or condition described herein or known in the art) in a subject in need thereof that include administering to a subject identified as having an aging-related disease or condition (e.g. any of the exemplary types of aging-related disease or condition described herein or known in the art) a therapeutically effective amount of one or more natural killer (NK) cell activating agent(s) (e.g. any of the natural killer (NK) cell activating agent(s) described herein or known in the art).

Provided herein are methods of treating an aging-related disease or condition (e.g. any of the exemplary types of aging-related disease or condition described herein or known in the art) in a subject in need thereof that include administering to a subject identified as having an aging-related disease or condition (e.g. any of the exemplary types of aging-related disease or condition described herein or known in the art) a therapeutically effective amount of activated NK cells (e.g. any of the activated NK cells described herein or known in the art).

Some embodiments of these methods further include: obtaining a resting NK cell; and contacting the resting NK cell in vitro in a liquid culture medium including one or more NK cell activating agent(s), where the contacting results in the generation of the activated NK cells that are subsequently administered to the subject. In some examples of these methods, the resting NK cell is an autologous NK cell obtained from the subject. In some examples of these methods, the resting NK cell is a haploidentical NK cell obtained from the subject. In some examples of these methods, the resting NK cell is an allogeneic resting NK cell. In some examples of these methods, the resting NK cell is an artificial NK cell. In some examples of any of these methods, the resting NK cell is a genetically-engineered NK cell carrying a chimeric antigen receptor or recombinant T cell receptor.

In some examples of these methods, the liquid culture medium is a serum-free liquid culture medium. In some embodiments of any of the methods described herein, the liquid culture medium is a chemically-defined liquid culture medium. Some examples of these methods further include isolating the activated NK cells (and optionally further administering a therapeutically effective amount of the activated NK cells to a subject, e.g., any of the subjects described herein). In some embodiments of these methods, the contacting step is performed for a period of about 2 hours to about 20 days (or any of the subranges of this range described herein).

In some embodiments of any of the methods described herein, the aging-related disease or condition is selected from the group of: a cancer, an autoimmune disease, a metabolic disease, a neurodegenerative disease, a cardiovascular disease, a skin disease, a progeria disease, and a fragility disease.

Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

A non-limiting example of an autoimmune disease is type-1 diabetes.

Non-limiting examples of metabolic disease include: obesity, a lipodystrophy, and type-2 diabetes mellitus.

Non-limiting examples of neurodegenerative disease include: Alzheimer's disease, Parkinson's disease, and dementia.

Non-limiting examples of cardiovascular disease include: coronary artery disease, atherosclerosis, and pulmonary arterial hypertension.

Non-limiting examples of skin disease include: wound healing, alopecia, wrinkles, senile lentigo, skin thinning, xeroderma pigmentosum, and dyskeratosis congenita.

Non-limiting examples of progeria disease include: progeria and Hutchinson-Gilford Progeria Syndrome.

Non-limiting examples of fragility disease include: frailty, responsiveness to vaccination, osteoporosis, and sarcopenia.

In some embodiments of any of the aging-related disease or condition described herein, the aging-related disease or condition is selected from the group of: age-related macular degeneration, osteoarthritis, adipose atrophy, idiopathic pulmonary fibrosis, kidney transplant failure, liver fibrosis, loss of bone mass, sarcopenia, age-associated loss of lung tissue elasticity, osteoporosis, age-associated renal dysfunction, and chemical-induced renal dysfunction.

In some embodiments of any of the aging-related disease or condition described herein, the aging-related disease or condition is type-2 diabetes or atherosclerosis.

In some embodiments of any of the methods described herein, the subject has been diagnosed or identified as having an aging-related disease or condition (e.g., any of the exemplary aging-related diseases or conditions described herein). Some embodiments of any of the methods described herein can include a step of selecting a subject identified or diagnosed as having an aging-related disease or condition (e.g., any of the exemplary aging-related diseases or conditions described herein).

In some embodiments of these methods, the administering results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 10% decrease to about a 99% decrease, about a 10% decrease to about a 95% decrease, about a 10% decrease to about a 90% decrease, about a 10% decrease to about a 85% decrease, about a 10% decrease to about a 80% decrease, about a 10% decrease to about a 75% decrease, about a 10% decrease to about a 70% decrease, about a 10% decrease to about a 65% decrease, about a 10% decrease to about a 60% decrease, about a 10% decrease to about a 55% decrease, about a 10% decrease to about a 50% decrease, about a 10% decrease to about a 45% decrease, about a 10% decrease to about a 40% decrease, about a 10% decrease to about a 35% decrease, about a 10% decrease to about a 30% decrease, about a 10% decrease to about a 25% decrease, about a 10% decrease to about a 20% decrease, about a 10% decrease to about a 15% decrease, about a 15% decrease to about a 99% decrease, about a 15% decrease to about a 95% decrease, about a 15% decrease to about a 90% decrease, about a 15% decrease to about a 85% decrease, about a 15% decrease to about a 80% decrease, about a 15% decrease to about a 75% decrease, about a 15% decrease to about a 70% decrease, about a 15% decrease to about a 65% decrease, about a 15% decrease to about a 60% decrease, about a 15% decrease to about a 55% decrease, about a 15% decrease to about a 50% decrease, about a 15% decrease to about a 45% decrease, about a 15% decrease to about a 40% decrease, about a 15% decrease to about a 35% decrease, about a 15% decrease to about a 30% decrease, about a 15% decrease to about a 25% decrease, about a 15% decrease to about a 20% decrease, about a 20% decrease to about a 99% decrease, about a 20% decrease to about a 95% decrease, about a 20% decrease to about a 90% decrease, about a 20% decrease to about a 85% decrease, about a 20% decrease to about a 80% decrease, about a 20% decrease to about a 75% decrease, about a 20% decrease to about a 70% decrease, about a 20% decrease to about a 65% decrease, about a 20% decrease to about a 60% decrease, about a 20% decrease to about a 55% decrease, about a 20% decrease to about a 50% decrease, about a 20% decrease to about a 45% decrease, about a 20% decrease to about a 40% decrease, about a 20% decrease to about a 35% decrease, about a 20% decrease to about a 30% decrease, about a 20% decrease to about a 25% decrease, about a 25% decrease to about a 99% decrease, about a 25% decrease to about a 95% decrease, about a 25% decrease to about a 90% decrease, about a 25% decrease to about a 85% decrease, about a 25% decrease to about a 80% decrease, about a 25% decrease to about a 75% decrease, about a 25% decrease to about a 70% decrease, about a 25% decrease to about a 65% decrease, about a 25% decrease to about a 60% decrease, about a 25% decrease to about a 55% decrease, about a 25% decrease to about a 50% decrease, about a 25% decrease to about a 45% decrease, about a 25% decrease to about a 40% decrease, about a 25% decrease to about a 35% decrease, about a 25% decrease to about a 30% decrease, about a 30% decrease to about a 99% decrease, about a 30% decrease to about a 95% decrease, about a 30% decrease to about a 90% decrease, about a 30% decrease to about a 85% decrease, about a 30% decrease to about a 80% decrease, about a 30% decrease to about a 75% decrease, about a 30% decrease to about a 70% decrease, about a 30% decrease to about a 65% decrease, about a 30% decrease to about a 60% decrease, about a 30% decrease to about a 55% decrease, about a 30% decrease to about a 50% decrease, about a 30% decrease to about a 45% decrease, about a 30% decrease to about a 40% decrease, about a 30% decrease to about a 35% decrease, about a 35% decrease to about a 99% decrease, about a 35% decrease to about a 95% decrease, about a 35% decrease to about a 90% decrease, about a 35% decrease to about a 85% decrease, about a 35% decrease to about a 80% decrease, about a 35% decrease to about a 75% decrease, about a 35% decrease to about a 70% decrease, about a 35% decrease to about a 65% decrease, about a 35% decrease to about a 60% decrease, about a 35% decrease to about a 55% decrease, about a 35% decrease to about a 50% decrease, about a 35% decrease to about a 45% decrease, about a 35% decrease to about a 40% decrease, about a 40% decrease to about a 99% decrease, about a 40% decrease to about a 95% decrease, about a 40% decrease to about a 90% decrease, about a 40% decrease to about a 85% decrease, about a 40% decrease to about a 80% decrease, about a 40% decrease to about a 75% decrease, about a 40% decrease to about a 70% decrease, about a 40% decrease to about a 65% decrease, about a 40% decrease to about a 60% decrease, about a 40% decrease to about a 55% decrease, about a 40% decrease to about a 50% decrease, about a 40% decrease to about a 45% decrease, about a 45% decrease to about a 99% decrease, about a 45% decrease to about a 95% decrease, about a 45% decrease to about a 90% decrease, about a 45% decrease to about a 85% decrease, about a 45% decrease to about a 80% decrease, about a 45% decrease to about a 75% decrease, about a 45% decrease to about a 70% decrease, about a 45% decrease to about a 65% decrease, about a 45% decrease to about a 60% decrease, about a 45% decrease to about a 55% decrease, about a 45% decrease to about a 50% decrease, about a 50% decrease to about a 99% decrease, about a 50% decrease to about a 95% decrease, about a 50% decrease to about a 90% decrease, about a 50% decrease to about a 85% decrease, about a 50% decrease to about a 80% decrease, about a 50% decrease to about a 75% decrease, about a 50% decrease to about a 70% decrease, about a 50% decrease to about a 65% decrease, about a 50% decrease to about a 60% decrease, about a 50% decrease to about a 55% decrease, about a 55% decrease to about a 99% decrease, about a 55% decrease to about a 95% decrease, about a 55% decrease to about a 90% decrease, about a 55% decrease to about a 85% decrease, about a 55% decrease to about a 80% decrease, about a 55% decrease to about a 75% decrease, about a 55% decrease to about a 70% decrease, about a 55% decrease to about a 65% decrease, about a 55% decrease to about a 60% decrease, about a 60% decrease to about a 99% decrease, about a 60% decrease to about a 95% decrease, about a 60% decrease to about a 90% decrease, about a 60% decrease to about a 85% decrease, about a 60% decrease to about a 80% decrease, about a 60% decrease to about a 75% decrease, about a 60% decrease to about a 70% decrease, about a 60% decrease to about a 65% decrease, about a 65% decrease to about a 99% decrease, about a 65% decrease to about a 95% decrease, about a 65% decrease to about a 90% decrease, about a 65% decrease to about a 85% decrease, about a 65% decrease to about a 80% decrease, about a 65% decrease to about a 75% decrease, about a 65% decrease to about a 70% decrease, about a 70% decrease to about a 99% decrease, about a 70% decrease to about a 95% decrease, about a 70% decrease to about a 90% decrease, about a 70% decrease to about a 85% decrease, about a 70% decrease to about a 80% decrease, about a 70% decrease to about a 75% decrease, about a 75% decrease to about a 99% decrease, about a 75% decrease to about a 95% decrease, about a 75% decrease to about a 90% decrease, about a 75% decrease to about a 85% decrease, about a 75% decrease to about a 80% decrease, about a 80% decrease to about a 99% decrease, about a 80% decrease to about a 95% decrease, about a 80% decrease to about a 90% decrease, about a 80% decrease to about a 85% decrease, about a 85% decrease to about a 99% decrease, about a 85% decrease to about a 95% decrease, about a 85% decrease to about a 90% decrease, about a 90% decrease to about a 99% decrease, about a 90% decrease to about a 95% decrease, or about a 95% decrease to about a 99% decrease) in the number of senescent cells in a target tissue in the subject, e.g., as compared to the number of senescent cells in the target tissue in the subject prior to treatment.

In some embodiments of these methods, the administering results in an increase (e.g., at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, or at least a 99% increase, or about a 10% increase to about a 500% increase (or any of the subranges of this range described herein) in the levels of IFN-γ, a cytotoxic granule granzyme, and/or perforin in the subject, as compared to the levels in a subject prior to treatment or a similar control subject who has not received a treatment.

In some embodiments, these methods can result in a reduction in the number, severity, or frequency of one or more symptoms of the cancer in the subject (e.g., as compared to the number, severity, or frequency of the one or more symptoms of the cancer in the subject prior to treatment). In some embodiments, these methods can result in a reduction (e.g., about 1% reduction to about 99% reduction, about 1% reduction to about 95% reduction, about 1% reduction to about 90% reduction, about 1% reduction to about 85% reduction, about 1% reduction to about 80% reduction, about 1% reduction to about 75% reduction, about 1% reduction to about 70% reduction, about 1% reduction to about 65% reduction, about 1% reduction to about 60% reduction, about 1% reduction to about 55% reduction, about 1% reduction to about 50% reduction, about 1% reduction to about 45% reduction, about 1% reduction to about 40% reduction, about 1% reduction to about 35% reduction, about 1% reduction to about 30% reduction, about 1% reduction to about 25% reduction, about 1% reduction to about 20% reduction, about 1% reduction to about 15% reduction, about 1% reduction to about 10% reduction, about 1% reduction to about 5% reduction, about 5% reduction to about 99% reduction, about 5% reduction to about 95% reduction, about 5% reduction to about 90% reduction, about 5% reduction to about 85% reduction, about 5% reduction to about 80% reduction, about 5% reduction to about 75% reduction, about 5% reduction to about 70% reduction, about 5% reduction to about 65% reduction, about 5% reduction to about 60% reduction, about 5% reduction to about 55% reduction, about 5% reduction to about 50% reduction, about 5% reduction to about 45% reduction, about 5% reduction to about 40% reduction, about 5% reduction to about 35% reduction, about 5% reduction to about 30% reduction, about 5% reduction to about 25% reduction, about 5% reduction to about 20% reduction, about 5% reduction to about 15% reduction, about 5% reduction to about 10% reduction, about 10% reduction to about 99% reduction, about 10% reduction to about 95% reduction, about 10% reduction to about 90% reduction, about 10% reduction to about 85% reduction, about 10% reduction to about 80% reduction, about 10% reduction to about 75% reduction, about 10% reduction to about 70% reduction, about 10% reduction to about 65% reduction, about 10% reduction to about 60% reduction, about 10% reduction to about 55% reduction, about 10% reduction to about 50% reduction, about 10% reduction to about 45% reduction, about 10% reduction to about 40% reduction, about 10% reduction to about 35% reduction, about 10% reduction to about 30% reduction, about 10% reduction to about 25% reduction, about 10% reduction to about 20% reduction, about 10% reduction to about 15% reduction, about 15% reduction to about 99% reduction, about 15% reduction to about 95% reduction, about 15% reduction to about 90% reduction, about 15% reduction to about 85% reduction, about 15% reduction to about 80% reduction, about 15% reduction to about 75% reduction, about 15% reduction to about 70% reduction, about 15% reduction to about 65% reduction, about 15% reduction to about 60% reduction, about 15% reduction to about 55% reduction, about 15% reduction to about 50% reduction, about 15% reduction to about 45% reduction, about 15% reduction to about 40% reduction, about 15% reduction to about 35% reduction, about 15% reduction to about 30% reduction, about 15% reduction to about 25% reduction, about 15% reduction to about 20% reduction, about 20% reduction to about 99% reduction, about 20% reduction to about 95% reduction, about 20% reduction to about 90% reduction, about 20% reduction to about 85% reduction, about 20% reduction to about 80% reduction, about 20% reduction to about 75% reduction, about 20% reduction to about 70% reduction, about 20% reduction to about 65% reduction, about 20% reduction to about 60% reduction, about 20% reduction to about 55% reduction, about 20% reduction to about 50% reduction, about 20% reduction to about 45% reduction, about 20% reduction to about 40% reduction, about 20% reduction to about 35% reduction, about 20% reduction to about 30% reduction, about 20% reduction to about 25% reduction, about 25% reduction to about 99% reduction, about 25% reduction to about 95% reduction, about 25% reduction to about 90% reduction, about 25% reduction to about 85% reduction, about 25% reduction to about 80% reduction, about 25% reduction to about 75% reduction, about 25% reduction to about 70% reduction, about 25% reduction to about 65% reduction, about 25% reduction to about 60% reduction, about 25% reduction to about 55% reduction, about 25% reduction to about 50% reduction, about 25% reduction to about 45% reduction, about 25% reduction to about 40% reduction, about 25% reduction to about 35% reduction, about 25% reduction to about 30% reduction, about 30% reduction to about 99% reduction, about 30% reduction to about 95% reduction, about 30% reduction to about 90% reduction, about 30% reduction to about 85% reduction, about 30% reduction to about 80% reduction, about 30% reduction to about 75% reduction, about 30% reduction to about 70% reduction, about 30% reduction to about 65% reduction, about 30% reduction to about 60% reduction, about 30% reduction to about 55% reduction, about 30% reduction to about 50% reduction, about 30% reduction to about 45% reduction, about 30% reduction to about 40% reduction, about 30% reduction to about 35% reduction, about 35% reduction to about 99% reduction, about 35% reduction to about 95% reduction, about 35% reduction to about 90% reduction, about 35% reduction to about 85% reduction, about 35% reduction to about 80% reduction, about 35% reduction to about 75% reduction, about 35% reduction to about 70% reduction, about 35% reduction to about 65% reduction, about 35% reduction to about 60% reduction, about 35% reduction to about 55% reduction, about 35% reduction to about 50% reduction, about 35% reduction to about 45% reduction, about 35% reduction to about 40% reduction, about 40% reduction to about 99% reduction, about 40% reduction to about 95% reduction, about 40% reduction to about 90% reduction, about 40% reduction to about 85% reduction, about 40% reduction to about 80% reduction, about 40% reduction to about 75% reduction, about 40% reduction to about 70% reduction, about 40% reduction to about 65% reduction, about 40% reduction to about 60% reduction, about 40% reduction to about 55% reduction, about 40% reduction to about 50% reduction, about 40% reduction to about 45% reduction, about 45% reduction to about 99% reduction, about 45% reduction to about 95% reduction, about 45% reduction to about 90% reduction, about 45% reduction to about 85% reduction, about 45% reduction to about 80% reduction, about 45% reduction to about 75% reduction, about 45% reduction to about 70% reduction, about 45% reduction to about 65% reduction, about 45% reduction to about 60% reduction, about 45% reduction to about 55% reduction, about 45% reduction to about 50% reduction, about 50% reduction to about 99% reduction, about 50% reduction to about 95% reduction, about 50% reduction to about 90% reduction, about 50% reduction to about 85% reduction, about 50% reduction to about 80% reduction, about 50% reduction to about 75% reduction, about 50% reduction to about 70% reduction, about 50% reduction to about 65% reduction, about 50% reduction to about 60% reduction, about 50% reduction to about 55% reduction, about 55% reduction to about 99% reduction, about 55% reduction to about 95% reduction, about 55% reduction to about 90% reduction, about 55% reduction to about 85% reduction, about 55% reduction to about 80% reduction, about 55% reduction to about 75% reduction, about 55% reduction to about 70% reduction, about 55% reduction to about 65% reduction, about 55% reduction to about 60% reduction, about 60% reduction to about 99% reduction, about 60% reduction to about 95% reduction, about 60% reduction to about 90% reduction, about 60% reduction to about 85% reduction, about 60% reduction to about 80% reduction, about 60% reduction to about 75% reduction, about 60% reduction to about 70% reduction, about 60% reduction to about 65% reduction, about 65% reduction to about 99% reduction, about 65% reduction to about 95% reduction, about 65% reduction to about 90% reduction, about 65% reduction to about 85% reduction, about 65% reduction to about 80% reduction, about 65% reduction to about 75% reduction, about 65% reduction to about 70% reduction, about 70% reduction to about 99% reduction, about 70% reduction to about 95% reduction, about 70% reduction to about 90% reduction, about 70% reduction to about 85% reduction, about 70% reduction to about 80% reduction, about 70% reduction to about 75% reduction, about 75% reduction to about 99% reduction, about 75% reduction to about 95% reduction, about 75% reduction to about 90% reduction, about 75% reduction to about 85% reduction, about 75% reduction to about 80% reduction, about 80% reduction to about 99% reduction, about 80% reduction to about 95% reduction, about 80% reduction to about 90% reduction, about 80% reduction to about 85% reduction, about 85% reduction to about 99% reduction, about 85% reduction to about 95% reduction, about 85% reduction to about 90% reduction, about 90% reduction to about 99% reduction, about 90% reduction to about 95% reduction, or about 95% reduction to about 99% reduction) in the volume of one or more solid tumors in the subject (e.g., as compared to the volume of the one or more solid tumors prior to treatment or at the start of treatment). In some embodiments, the these methods can reduce (e.g., about 1% reduction to about 99% reduction, or any of the subranges of this range described herein) the risk of developing a metastasis or developing one or more additional metastasis in a subject (e.g., as compared to the risk of developing a metastasis or developing one or more additional metastasis in a subject prior to treatment or in a similar subject or a population of subjects administered a different treatment).

In some embodiments, these methods can result in treatment of metabolic disease in the subject. In some embodiments, the treatment of metabolic disease can result in, e.g., one or more (e.g., two, three, four, five, or six) improved glucose tolerance, improved glucose utilization, decreased severity or progression of diabetic osteoarthropathy, decreased severity or progression of skin lesions, decreased severity or progression of ketosis, decreased generation of autoantibodies against islet cells, increased insulin sensitivity, decreased mass, and decreased body mass index. The response of a subject to treatment can be monitored by determining fasting glucose or glucose tolerance according to standard techniques. Typically, in accordance with the method, blood glucose is lowered so as to achieve a blood glucose level characterized by a fasting blood glucose of less than 100 mg/dL or a two-hour 75-g oral glucose tolerance test values of less than 140 mg/dL. In some embodiments, response to treatment may include determining other factors relevant to pre-diabetes, new-onset diabetes, or active diabetes including blood pressure, body mass index, PPARγ function, lipid metabolism, glycated hemoglobin (H1c), and renal function.

In some embodiments, these methods can eliminate or reduce the risk, lessen the severity, or delay the outset of the neurodegenerative disease, including biochemical, histologic and/or behavioral symptoms of the disease, its complications and intermediate pathological phenotypes presenting during development of the disease.

In some embodiments, effective treatment of a skin disease can be assessed by any method described herein or known in the art, including inspecting skin conditions that include skin color, moisture, temperature, texture, mobility and turgor, and skin lesions, as compared to the skin conditions prior to treatment.

In some embodiments, effective treatment of an autoimmune disease can be assessed by any method described herein or known in the art, including monitoring full blood count analysis on freshly isolated PBMCs, total Ig levels, and analysis of serum autoantibody titers.

In some embodiments, effective treatment of a fragility disease can be assessed by any method described herein or known in the art, including monitoring bone mineral density, bone architecture and geometry, biomedical markers of bone turnover, vitamin D measurement, Karnofsky performance status and ECOG scores, and responsiveness to vaccination.

Methods of Killing or Reducing the Number of Senescent Cells in a Subject

Provided herein are methods of killing or reducing the number of senescent cells (e.g. any of the exemplary types of senescent cells described herein or known in the art) in a subject in need thereof that include administering to the subject a therapeutically effective amount of one or more NK cell activating agent(s) (e.g. any of the NK cell activating agent(s) described herein or known in the art).

Also provided herein are methods of killing or reducing the number of senescent cells (e.g. any of the exemplary types of senescent cells described herein or known in the art) in a subject in need thereof that include administering to the subject a therapeutically effective amount of activated NK cells (e.g. any of the activated NK cells described herein or known in the art).

Some embodiments of these methods further include: obtaining a resting NK cell; and contacting the resting NK cell in vitro in a liquid culture medium including one or more NK cell activating agent(s), where the contacting results in the generation of the activated NK cells that are subsequently administered to the subject. In some examples of these methods, the resting NK cell is an autologous NK cell obtained from the subject. In some examples of these methods, the resting NK cell is a haploidentical NK cell obtained from the subject. In some examples of these methods, the resting NK cell is an allogeneic resting NK cell. In some examples of these methods, the resting NK cell is an artificial NK cell. In some examples of any of these methods, the resting NK cell is a genetically-engineered NK cell carrying a chimeric antigen receptor or recombinant T cell receptor.

In some examples of these methods, the liquid culture medium is a serum-free liquid culture medium. In some embodiments of any of the methods described herein, the liquid culture medium is a chemically-defined liquid culture medium. Some examples of these methods further include isolating the activated NK cells (and further administering a therapeutically effective amount of the activated NK cells to a subject, e.g., any of the subjects described herein). In some embodiments of these methods, the contacting step is performed for a period of about 2 hours to about 20 days (or any of the subranges of this range described herein).

In some embodiments of these methods, the senescent cells are senescent cancer cells, senescent monocytes, senescent lymphocytes, senescent astrocytes, senescent microglia, senescent neurons, senescent tissue fibroblasts, senescent dermal fibroblasts, senescent keratinocytes, or other differentiated tissue-specific dividing functional cells. In some embodiments of these methods, senescent cancer cells are chemotherapy-induced senescent cells or radiation-induced senescent cells.

In some embodiments of these methods, the subject has been identified or diagnosed as having an aging-related disease or condition (e.g., any of the aging-related diseases or conditions described herein or known in the art). In some embodiments of any of the aging-related disease or condition described herein, the aging-related disease or condition is selected from the group of: a cancer, an autoimmune disease, a metabolic disease, a neurodegenerative disease, a cardiovascular disease, a skin disease, a progeria disease, and a fragility disease.

Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

A non-limiting example of an autoimmune disease is type-1 diabetes.

Non-limiting examples of metabolic disease include: obesity, a lipodystrophy, and type-2 diabetes mellitus.

Non-limiting examples of neurodegenerative disease include: Alzheimer's disease, Parkinson's disease, and dementia.

Non-limiting examples of cardiovascular disease include: coronary artery disease, atherosclerosis, and pulmonary arterial hypertension.

Non-limiting examples of skin disease include: wound healing, alopecia, wrinkles, senile lentigo, skin thinning, xeroderma pigmentosum, and dyskeratosis congenita.

Non-limiting examples of progeria disease include: progeria and Hutchinson-Gilford Progeria Syndrome.

Non-limiting examples of fragility disease include: frailty, responsiveness to vaccination, osteoporosis, and sarcopenia.

In some embodiments of any of the aging-related disease or condition described herein, the aging-related disease or condition is selected from the group of: age-related macular degeneration, osteoarthritis, adipose atrophy, idiopathic pulmonary fibrosis, kidney transplant failure, liver fibrosis, loss of bone mass, sarcopenia, age-associated loss of lung tissue elasticity, osteoporosis, age-associated renal dysfunction, and chemical-induced renal dysfunction.

In some embodiments of any of the aging-related disease or condition described herein, the aging-related disease or condition is type-2 diabetes or atherosclerosis.

In some embodiments of these methods, the administering results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 10% decrease to about a 99% decrease (or any of the subranges of this range described herein)) in the number of senescent cells in a target tissue in the subject, e.g., as compared to the number of senescent cells in the target tissue in the subject prior to treatment. In some embodiments of these methods, the target tissue in the subject can be one or more of an adipose tissue, pancreatic tissue, liver tissue, lung tissue, vasculature, bone tissue, central nervous system (CNS) tissue, eye tissue, skin tissue, muscle tissue, and secondary lympho-organ tissue.

In some embodiments of these methods, the administering results in an increase (e.g., at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, or at least a 99% increase, or about a 10% increase to about a 500% increase (or any of the subranges of this range described herein)) in the levels of IFN-γ, a cytotoxic granule granzyme, and/or perforin in the subject, as compared to the levels in a subject prior to treatment or a similar control subject who has not received a treatment.

In some embodiments of these methods, the number of senescent cells in a target tissue (e.g. any of the target tissues described herein) can be determined by performing immunostaining on a biopsy sample. In some embodiments of these methods, the number of senescent cells in a target tissue (e.g. any of the target tissues described herein) can be observed indirectly through an improvement in one or more symptoms of an aging-related disease or condition (e.g. any of the symptoms of an aging-related disease or condition described herein) in a subject.

Senescent Cells

Senescent cells display important and unique properties which include changes in morphology, chromatin organization, gene expression, and metabolism. There are several biochemical and functional properties associated with cellular senescence, such as (i) increased expression of p16 and p21, inhibitors of cyclin-dependent kinases, (ii) presence of senescence-associated β-galactosidase, a marker of lysosomal activity, (iii) appearance of senescence-associated heterochromatin foci and downregulation of lamin B1 levels, (iv) resistance to apoptosis caused by an increased expression of anti-apoptotic BCL-family protein, and (v) upregulation of CD26 (DPP4), CD36 (Scavenger receptor), forkhead box 4 (FOXO4), and secretory carrier membrane protein 4 (SCAMP4). Senescent cells also express an inflammatory signature, the so-called senescence-associated secretory phenotype (SASP). Through SASP, the senescent cells produce a wide range of inflammatory cytokines (IL-6, IL-8), growth factors (TGF-β), chemokines (CCL-2), and matrix metalloproteinases (MMP-3, MMP-9) that operate in a cell-autonomous manner to reinforce senescence (autocrine effects) and communicate with and modify the microenvironment (paracrine effects). SASP factors can contribute to tumor suppression by triggering senescence surveillance, an immune-mediated clearance of senescent cells. However, chronic inflammation is also a known driver of tumorigenesis, and accumulating evidence indicates that chronic SASP can also boost cancer metastasis and aging-related diseases.

The secretion profile of senescent cells is context dependent. For instance, the mitochondrial dysfunction-associated senescence (MiDAS), induced by different mitochondrial dysfunction in human fibroblasts, led to the appearance of a SASP that was deficient in IL-1-dependent inflammatory factors. A decrease in the NAD+/NADH ratio activated AMPK signaling which induced MiDAS through the activation of p53. As a result, p53 inhibited NF-κB signaling which is a crucial inducer of pro-inflammatory SASP. In contrast, the cellular senescence caused by persistent DNA damage in human cells induced an inflammatory SASP, which was dependent on the activation of ataxia-telangiectasia mutated (ATM) kinase but not on that of p53. In particular, the expression and secretion levels of IL-6 and IL-8 were increased. It was also demonstrated that cellular senescence caused by the ectopic expression p16INK4a and p21CIP1 induced the senescent phenotype in human fibroblasts without an inflammatory SASP indicating that the growth arrest itself did not stimulate SASP.

One of the most defining characteristics of senescence is stable growth arrest. This is achieved by two important pathways, the p16/Rb and the p53/p21, both of which are central in tumor suppression. DNA damage results in: (1) high deposition of γH2Ax (histone coding gene) and 53BP1 (involved in DNA damage response) in chromatin: this leads to activation of a kinase cascade eventually resulting in p53 activation, and (2) activation of p16INK4a and ARF (both encoded by CDKN2A) and P15INK4b (encoded by CDKN2B): p53 induces transcription of cyclin-dependent kinase inhibitor (p21) and along with both p16INK4a and p15INK4b block genes for cell cycle progression (CDK4 and CDK6). This eventually leads to hypophosphorylation of Retinoblastoma protein (Rb) and cell cycle arrest at the G1 phase.

Selectively killing senescent cells has been shown to significantly improve the health span of mice in the context of normal aging and ameliorates the consequences of age-related disease or cancer therapy (Ovadya, J Clin Invest. 128(4):1247-1254, 2018). In nature, the senescent cells are normally removed by the innate immune cells. Induction of senescence not only prevents the potential proliferation and transformation of damaged/altered cells, but also favors tissue repair through the production of SASP factors that function as chemoattractants mainly for Natural Killer (NK) cells (such as IL-15 and CCL2) and macrophages (such as CFS-1 and CCL2). These innate immune cells mediate the immunosurveillance mechanism for eliminating stressed cells. Senescent cells usually up-regulate the NK-cell activating receptor NKG2D and DNAM1 ligands, which belong to a family of stress-inducible ligands: an important component of the frontline immune defense against infectious diseases and malignancies. Upon receptor activation, NK cells can then specifically induce the death of senescent cells through their cytolytic machinery. A role for NK cells in the immune surveillance of senescent cells has been pointed out in liver fibrosis (Sagiv, Oncogene 32(15): 1971-1977, 2013), hepatocellular carcinoma (Iannello, *J Exp Med* 210(10): 2057-2069, 2013), multiple myeloma (Soriani, *Blood* 113 (15): 3503-3511, 2009), and glioma cells stressed by dysfunction of the mevalonate pathway (Ciaglia, *Int J Cancer* 142(1): 176-190, 2018). Endometrial cells undergo acute cellular senescence and do not differentiate into decidual cells. The differentiated decidual cells secrete IL-15 and thereby recruit uterine NK cells to target and eliminate the undifferentiated senescent cells thus helping to re-model and rejuvenate the endometrium (Brighton, *Elife* 6: e31274, 2017). With a similar mechanism, during liver fibrosis, p53-expressing senescent liver satellite cells skewed the polarization of resident Kupfer macrophages and freshly infiltrated macrophages toward the pro-inflammatory M1 phenotype, which display senolytic activity. F4/80+ macrophages have been shown to play a key role in the clearance of mouse uterine senescent cells to maintain postpartum uterine function.

Senescent cells recruit NK cells by mainly upregulating ligands to NKG2D (expressed on NK cells), chemokines, and other SASP factors. In vivo models of liver fibrosis have shown effective clearance of senescent cells by activated NK cells (Krizhanovsky, *Cell* 134(4): 657-667, 2008). Studies have described various models to study senescence including liver fibrosis (Krizhanovsky, *Cell* 134(4): 657-667, 2008), osteoarthritis (Xu, *J Gerontol A Biol Sci Med Sci* 72(6): 780-785, 2017), and Parkinson's disease (Chinta, *Cell Rep* 22(4): 930-940, 2018). Animal models for studying senescent cells are described in: Krizhanovsky, *Cell* 134(4): 657-667, 2008; Baker, *Nature* 479(7372): 232-236, 2011*; Farr, Nat Med* 23(9): 1072-1079, 2017*; Bourgeois, FEBS Lett* 592(12): 2083-2097, 2018*; Xu, Nat Med* 24(8): 1246-1256, 2018).

Methods of Improving the Texture and/or Appearance of Skin and/or Hair

Also provided herein are methods of improving the texture and/or appearance of skin and/or hair in a subject in need thereof over a period of time (e.g. any of the periods of time described herein) that include administering to the subject a therapeutically effective amount of one or more natural killer (NK) cell activating agent(s) (e.g. any of the NK cell activating agent(s) described herein or known in the art).

Also provided herein are methods of improving the texture and/or appearance of skin and/or hair in a subject in need thereof over a period of time (e.g. any of the periods of time described herein) that include administering to the subject a therapeutically effective number of activated NK cells (e.g. any of the activated NK cells described herein or known in the art).

Some embodiments of these methods further include: obtaining a resting NK cell; and contacting the resting NK cell in vitro in a liquid culture medium including one or more NK cell activating agent(s), where the contacting results in the generation of the activated NK cells that are subsequently administered to the subject. In some examples of these methods, the resting NK cell is an autologous NK cell obtained from the subject. In some examples of these methods, the resting NK cell is a haploidentical NK cell obtained from the subject. In some examples of these methods, the resting NK cell is an allogeneic resting NK cell. In some examples of these methods, the resting NK cell is an artificial NK cell. In some examples of any of these methods, the resting NK cell is a genetically-engineered NK cell carrying a chimeric antigen receptor or recombinant T cell receptor.

In some examples of these methods, the liquid culture medium is a serum-free liquid culture medium. In some embodiments of any of the methods described herein, the liquid culture medium is a chemically-defined liquid culture medium. Some examples of these methods further include isolating the activated NK cells (and further administering a therapeutically effective amount of the activated NK cells to a subject, e.g., any of the subjects described herein). In some embodiments of these methods, the contacting step is performed for a period of about 2 hours to about 20 days (or any of the subranges of this range described herein).

In some embodiments of these methods, the method provides for an improvement in the texture and/or appearance of skin of the subject over the period of time (e.g. any of periods of time described herein).

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the rate of formation of wrinkles in the skin of the subject over the period of time (e.g., any of the periods of time described herein), e.g., as compared to the rate of formulation of wrinkles in the subject prior to treatment or the rate of formulation of wrinkles in a similar subject not receiving a treatment.

In some embodiments of these methods, the method results in an improvement in the coloration of skin of the subject over the period of time (e.g. any of the periods of time described herein).

In some embodiments of these methods, the method results in an improvement in the texture of skin of the subject over the period of time (e.g. any of the periods of time described herein).

In some embodiments of these methods, the method provides for an improvement in the texture and/or appearance of hair of the subject over the period of time (e.g. any of the periods of time described herein).

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the rate of formation of gray hair in the subject over the period of time (e.g. any of the range of time period described herein), e.g., as compared to the rate of formulation of gray hair in the subject prior to treatment or the rate of formulation of gray hair in a similar subject not receiving a treatment.

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the number of gray hairs of the subject over the period of time (e.g. any of the periods of time described herein), e.g., as compared to the number of gray hairs in the subject prior to treatment or the rate of formation of gray hairs in a similar subject not receiving a treatment.

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the rate of hair loss in the subject over the period of time (e.g., any of the periods of time described herein), e.g., as compared to the rate of hair loss in the subject prior to treatment or the rate of hair loss in a similar subject not receiving a treatment.

In some embodiments of these methods, the method results in an improvement in the texture of hair of the subject over the period of time (e.g. any of the periods of time described herein).

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the number of senescent dermal fibroblasts in the skin of the subject over the period of time (e.g., any of the periods of time described herein), e.g., as compared to the number of senescent dermal cells in the subject prior to treatment or the number of senescent dermal cells in a similar subject not receiving a treatment.

In some embodiments of these methods, improvement in the texture and/or appearance of skin of the subject over the period of time (e.g. any of the periods of time described herein) can be assessed by any method described herein or known in the art, including inspecting the presence, size and shape of skin lesions, skin color and pigmentation, skin moisture, temperature, elasticity, and vascularity.

In some embodiments of these methods, improvement in the texture and/or appearance of hair of the subject over the period of time (e.g., any of periods of time described herein) can be assessed by any method described herein or known in the art, In some embodiments of these methods, the period of time is, e.g., one month to ten years, one month to nine years, one month to eight years, one month to seven years, one month to six years, one month to five years, one month to four years, one month to three years, one month to two years, one month to eighteen months, one month to twelve months, one month to ten months, one month to eight months, one month to six months, one month to four months, one month to two months, one month to six weeks, six weeks to ten years, six weeks to nine years, six weeks to eight years, six weeks to seven years, six weeks to six years, six weeks to five years, six weeks to four years, six weeks to three years, six weeks to two years, six weeks to eighteen months, six weeks to twelve months, six weeks to ten months, six weeks to eight months, six weeks to six months, six weeks to four months, six weeks to two months, two months to ten years, two months to nine years, two months to eight years, two months to seven years, two months to six years, two months to five years, two months to four years, two months to three years, two months to two years, two months to eighteen months, two months to twelve months, two months to ten months, two months to eight months, two months to six months, two months to four months, four months to ten years, four months to nine years, four months to eight years, four months to seven years, four months to six years, four months to five years, four months to four years, four months to three years, four months to two years, four months to eighteen months, four months to twelve months, four months to ten months, four months to eight months, four months to six months, six months to ten years, six months to nine years, six months to eight years, six months to seven years, six months to six years, six months to five years, six months to four years, six months to three years, six months to two years, six months to eighteen months, six months to twelve months, six months to ten months, six months to eight months, eight months to ten years, eight months to nine years, eight months to eight years, eight months to seven years, eight months to six years, eight months to five years, eight months to four years, eight months to three years, eight months to two years, months to eighteen months, eight months to twelve months, eight months to ten months, ten months to ten years, ten months to nine years, ten months to eight years, ten months to seven years, ten months to six years, ten months to five years, ten months to four years, ten months to three years, ten months to two years, ten months to eighteen months, ten months to twelve months, twelve months to ten years, twelve months to nine years, twelve months to eight years, twelve months to seven years, twelve months to six years, twelve months to five years, twelve months to four years, twelve months to three years, twelve months to two years, twelve months to eighteen months, eighteen months to ten years, eighteen months to nine years, eighteen months to eight years, eighteen months to seven years, eighteen months to six years, eighteen months to five years, eighteen months to four years, eighteen months to three years, eighteen months to two years, two years to ten years, two years to nine years, two years to eight years, two years to seven years, two years to six years, two years to five years, two years to four years, two years to three years, three years to ten years, three years to nine years, three years to eight years, three years to seven years, three years to six years, three years to five years, three years to four years, four years to ten years, four years to nine years, four years to eight years, four years to seven years, four years to six years, four years to five years, five years to ten years, five years to nine years, five years to eight years, five years to seven years, five years to six years, six years to ten years, six years to nine years, six years to eight years, six years to seven years, seven years to ten years, seven years to nine years, seven years to eight years, eight years to ten years, eight years to nine years, or nine years to ten years.

In some embodiments of these methods, the age of the subject is between about to about 35, about 35 to about 40, about 40 to about 45, about 45 to about 50, about 50 to about 55, about 55 to about 60, about 60 to about 65, about 65 to about 70, about 70 to about 75, about 75 to about 80, about 80 to about 85, about 85 to about 90, about 90 to about 95, about 95 to about 100, about 100 to about 105, about 105 to about 110, about 110 to about 115, or about 115 to about 120.

Methods of Assisting in the Treatment of Obesity in a Subject

Provided herein are methods of assisting in the treatment of obesity in a subject in need thereof over a period of time (e.g. any of the range of time period described herein), that include administering to the subject a therapeutically effective amount of one or more natural killer (NK) cell activating agent(s) (e.g. any of the NK cell activating agent(s) described herein or known in the art).

Also provided herein are methods of assisting in the treatment of obesity in a subject in need thereof over a period of time (e.g. any of the range of time period described herein) that include administering to the subject a therapeutically effective number of activated NK cells (e.g. any of the activated NK cells described herein or known in the art).

Some embodiments of these methods further include: obtaining a resting NK cell; and contacting the resting NK cell in vitro in a liquid culture medium including one or more NK cell activating agent(s), where the contacting results in the generation of the activated NK cells that are subsequently administered to the subject. In some examples of these methods, the resting NK cell is an autologous NK cell obtained from the subject. In some examples of these methods, the resting NK cell is a haploidentical NK cell obtained from the subject. In some examples of these methods, the resting NK cell is an allogeneic resting NK cell. In some examples of these methods, the resting NK cell is an artificial NK cell. In some examples of any of these methods, the resting NK cell is a genetically-engineered NK cell carrying a chimeric antigen receptor or recombinant T cell receptor.

In some examples of these methods, the liquid culture medium is a serum-free liquid culture medium. In some embodiments of any of the methods described herein, the liquid culture medium is a chemically-defined liquid culture medium. Some examples of these methods further include isolating the activated NK cells (and further administering a therapeutically effective amount of the activated NK cells to a subject, e.g., any of the subjects described herein). In some embodiments of these methods, the contacting step is performed for a period of about 2 hours to about 20 days (or any of the subranges of this range described herein).

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the mass of the subject over the period of time (e.g. any of the periods of time described herein), e.g., as compared to the mass of the subject prior to treatment.

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the body mass index (BMI) of the subject over the period of time (e.g. any of periods of time described herein), e.g., as compared to the BMI of the subject prior to treatment.

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the rate of progression from pre-diabetes to type 2 diabetes in the subject, e.g., as compared to the rate of progression from pre-diabetes to type 2 diabetes in the subject prior to treatment or the rate of progression from pre-diabetes to type 2 diabetes in a similar subject not receiving a treatment.

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in fasting serum glucose level in the subject, e.g., as compared to the fasting serum glucose level in the subject prior to treatment.

In some embodiments of these methods, the method results in an increase (e.g., at least a 5% increase, at least a 10% increase, at least a 15% increase, at least a 20% increase, at least a 25% increase, at least a 30% increase, at least a 35% increase, at least a 40% increase, at least a 45% increase, at least a 50% increase, at least a 55% increase, at least a 60% increase, at least a 65% increase, at least a 70% increase, at least a 75% increase, at least a 80% increase, at least a 85% increase, at least a 90% increase, at least a 95% increase, or at least a 99% increase, or about a 10% increase to about a 500% increase (or any of the subranges of this range described herein) in insulin sensitivity in the subject, e.g., as compared to the insulin sensitivity in the subject prior to treatment.

In some embodiments of these methods, the method results in a decrease (e.g., at least a 5% decrease, at least a 10% decrease, at least a 15% decrease, at least a 20% decrease, at least a 25% decrease, at least a 30% decrease, at least a 35% decrease, at least a 40% decrease, at least a 45% decrease, at least a 50% decrease, at least a 55% decrease, at least a 60% decrease, at least a 65% decrease, at least a 70% decrease, at least a 75% decrease, at least a 80% decrease, at least a 85% decrease, at least a 90% decrease, or at least a 95% decrease, or about a 5% decrease to about a 99% decrease (or any of the subranges of this range described herein)) in the severity of atherosclerosis in the subject, e.g., as compared to the severity of atherosclerosis in the subject prior to treatment.

In some embodiments of these methods, treatment of obesity in the subject over the period of time (e.g. any of the periods of time described herein) can be assessed by any method described herein or known in the art, including, e.g., measurement of body weight and/or body dimensions, total body fat, total or regional adiposity, and body mass index (BMI).

In some embodiments of these methods, the response of a subject to the treatment can be monitored by determining fasting serum glucose level or glucose tolerance according to standard techniques. In some embodiments of these methods, insulin sensitivity can be measured using any method described herein or known in the art, including hyperinsulinemic euglycemic clamp and intravenous glucose tolerance test, homeostasis model assessment (HOMA), and quantitative insulin sensitivity check index (QUICKI).

In some embodiments of these methods, the severity of atherosclerosis in the subject can be measured using any method described herein or known in the art, including cardiac catheterization, Doppler sonography, blood pressure comparison, MUGA/radionuclide angiography, Thallium/myocardial perfusion scan, and computerized tomography.

In some embodiments of these methods, the period of time is one month to ten years (or any of the subranges of this range described herein).

In some embodiments of these methods, the age range for the subject is between about 1 to about 5, about 5 to about 10, about 10 to about 15, about 15 to about 20, about to about 25, about 25 to about 30, about 30 to about 35, about 35 to about 40, about 40 to about 45, about 45 to about 50, about 50 to about 55, about 55 to about 60, about 60 to about 65, about 65 to about 70, about 70 to about 75, about 75 to about 80, about 80 to about 85, about 85 to about 90, about 90 to about 95, about 95 to about 100, about 100 to about 105, about 105 to about 110, about 110 to about 115, or about 115 to about 120.

Additional Therapeutic Agents

Some embodiments of any of the methods described herein can further include administering to a subject (e.g., any of the subjects described herein) a therapeutically effective amount of one or more additional therapeutic agents. The one or more additional therapeutic agents can be administered to the subject at substantially the same time as the NK cell activating agent(s) or activated NK cells (e.g., administered as a single formulation or two or more formulations to the subject). In some embodiments, one or more additional therapeutic agents can be administered to the subject prior to administration of the NK cell activating agent(s) or activated NK cells. In some embodiments, one or more additional therapeutic agents can be administered to the subject after administration of the NK cell activating agent(s) or activated NK cells to the subject.

Non-limiting examples of additional therapeutic agents include: anti-cancer drugs, activating receptor agonists, immune checkpoint inhibitors, agents for blocking HLA-specific inhibitory receptors, Glucogen Synthase Kinase (GSK) 3 inhibitors, and antibodies.

Non-limiting examples of anticancer drugs include anti-metabolic drugs (e.g., 5-fluorouracil (5-FU), 6-mercaptopurine (6-MP), capecitabine, cytarabine, floxuridine, fludarabine, gemcitabine, hydroxycarbamide, methotrexate, 6-thioguanine, cladribine, nelarabine, pentostatin, or pemetrexed), plant alkaloids (e.g., vinblastine, vincristine, vindesine, camptothecin, 9-methoxycamptothecin, coronaridine, taxol, naucleaorals, diprenylated indole alkaloid, montamine, schischkiniin, protoberberine, berberine, sanguinarine, chelerythrine, chelidonine, liriodenine, clivorine, β-carboline, antofine, tylophorine, cryptolepine, neocryptolepine, corynoline, sampangine, carbazole, crinamine, montanine, ellipticine, paclitaxel, docetaxel, etoposide, tenisopide, irinotecan, topotecan, or acridone alkaloids), proteasome inhibitors (e.g., lactacystin, disulfiram, epigallocatechin-3-gallate, marizomib (salinosporamide A), oprozomib (ONX-0912), delanzomib (CEP-18770), epoxomicin, MG132, beta-hydroxy beta-methylbutyrate, bortezomib, carfilzomib, or ixazomib), antitumor antibiotics (e.g., doxorubicin, daunorubicin, epirubicin, mitoxantrone, idarubicin, actinomycin, plicamycin, mitomycin, or bleomycin), histone deacetylase inhibitors (e.g., vorinostat, panobinostat, belinostat, givinostat, abexinostat, depsipeptide, entinostat, phenyl butyrate, valproic acid, trichostatin A, dacinostat, mocetinostat, pracinostat, nicotinamide, cambinol, tenovin 1, tenovin 6, sirtinol, ricolinostat, tefinostat, kevetrin, quisinostat, resminostat, tacedinaline, chidamide, or selisistat), tyrosine kinase inhibitors (e.g., axitinib, dasatinib, encorafinib, erlotinib, imatinib, nilotinib, pazopanib, and sunitinib), and chemotherapeutic agents (e.g., all-trans retinoic acid, azacitidine, azathioprine, doxifluridine, epothilone, hydroxyurea, imatinib, teniposide, tioguanine, valrubicin, vemurafenib, and lenalidomide). Additional examples of chemotherapeutic agents include alkylating agents, e.g., mechlorethamine, cyclophosphamide, chlorambucil, melphalan, ifosfamide, thiotepa, hexamethylmelamine, busulfan, altretamine, procarbazine, dacarbazine, temozolomide, carmustine, lumustine, streptozocin, carboplatin, cisplatin, and oxaliplatin.

Non-limiting examples of activating receptor agonists include any agonists for activating receptors which activate and enhance the cytotoxicity of NK cells, including anti-CD16 antibodies (e.g., anti-CD16/CD30 bispecific monoclonal antibody (BiMAb)) and Fc-based fusion proteins. Non-limiting examples of checkpoint inhibitors include anti-PD-1 antibodies (e.g., MEDI0680), anti-PD-L1 antibodies (e.g., BCD-135, BGB-A333, CBT-502, CK-301, CS1001, FAZ053, KN035, MDX-1105, MSB2311, SHR-1316, anti-PD-L1/CTLA-4 bispecific antibody KN046, anti-PD-L1/TGFβRII fusion protein M7824, anti-PD-L1/TIM-3 bispecific antibody LY3415244, atezolizumab, or avelumab), anti-TIM3 antibodies (e.g., TSR-022, Sym023, or MBG453) and anti-CTLA-4 antibodies (e.g., AGEN1884, MK-1308, or an anti-CTLA-4/OX40 bispecific antibody ATOR-1015). Non-limiting examples of agents for blocking HLA-specific inhibitory receptors include monalizumab (e.g., an anti-HLA-E NKG2A inhibitory receptor monoclonal antibody). Non-limiting examples of GSK3 inhibitor include tideglusib or CHIR99021. Non-limiting examples of antibodies that can be used as additional therapeutic agents include anti-CD26 antibodies (e.g., YS110), anti-CD36 antibodies, and any other antibody or antibody construct that can bind to and activate an Fc receptor (e.g., CD16) on a NK cell. In some embodiments, an additional therapeutic agent can be insulin or metformin.

EXAMPLES

The invention is further described in the following examples, which do not limit the scope of the invention described in the claims.

Example 1: Immunostimulation in C57BL/6 Mice Using a Multi-Chain Polypeptide Materials and Methods An exemplary multi-chain polypeptide (a type A multi-chain polypeptide described herein) was generated that includes a first polypeptide and a second polypeptide, where the first polypeptide is a soluble fusion of two TGFβRII domains, a human tissue factor 219 fragment, and a human IL-15, and the second polypeptide is a soluble fusion of two TGFβRII domains and the sushi domain of human IL-15Rα chain.

Results

Immunostimulation in C57BL/6 Mice

Figure 1A:
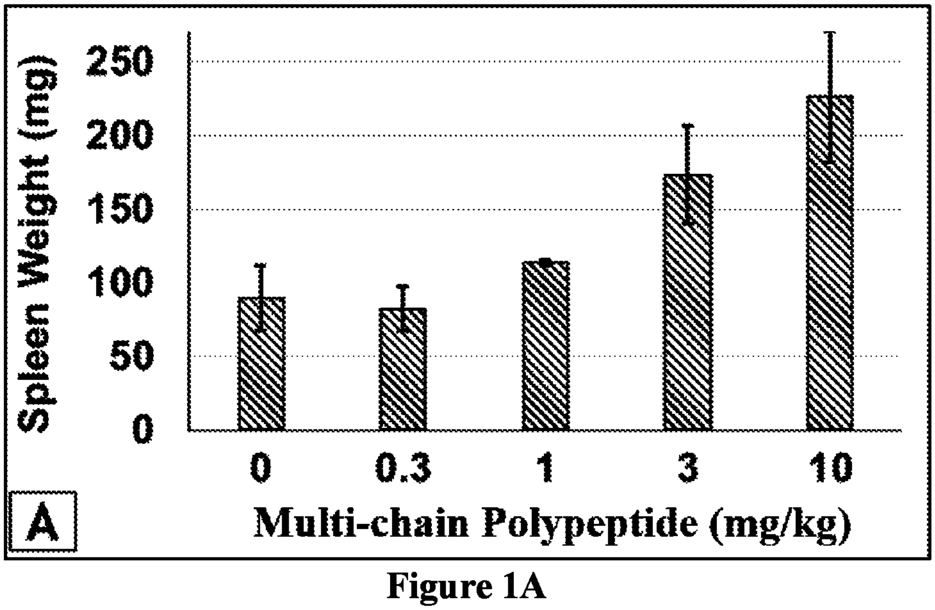
FIGS. 1A-1B show the results of immunostimulation of an exemplary multi-chain polypeptide in C57BL/6 mice.
Figure 1B:
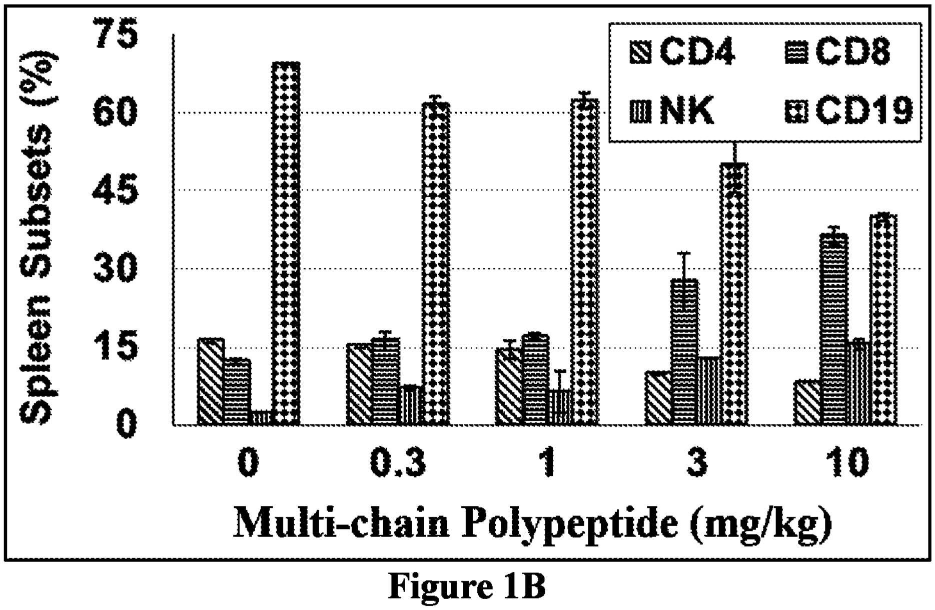

Wild type C57BL/6 mice were treated subcutaneously with either a control PBS solution or with the multi-chain polypeptide at a dosage of 0.3 mg/kg, 1 mg/kg, 3 mg/kg, or 10 mg/kg, respectively. Four days after treatment, spleen weight and the percentages of various immune cell types present in the spleen were evaluated. Specifically, single splenocyte suspensions were generated and stained with fluorochrome-conjugated antibodies including anti-CD4, anti-CD8, anti-NK1.1, and anti-CD19. The percentages of $CD4^+$ T cells, $CD8^+$ T cells, Natural Killer (NK) cells, and $CD19^+$ B cells present in the spleen of mice treated with either the control solution or the multi-chain polypeptide were evaluated using flow cytometry. As shown in FIG. 1A, the spleen weight in mice treated with the multi-chain polypeptide increased with increasing dosage of the multi-chain polypeptide. Moreover, the spleen weight in mice treated with 1 mg/kg, 3 mg/kg, and 10 mg/kg of the multi-chain polypeptide were significantly higher as compared to mice treated with the control solution, respectively. As shown in FIG. 1B, in the spleens of mice treated with the multi-chain polypeptide, the percentages of $CD8^+$ T cells and NK cells both increased with increasing dosage of the multi-chain polypeptide. Specifically, the percentages of $CD8^+$ T cells were higher in mice treated with 0.3 mg/kg, 3 mg/kg, and 10 mg/kg of the multi-chain polypeptide compared to control-treated mice, and the percentages of NK cells were higher in mice treated with 0.3 mg/kg, 1 mg/kg, 3 mg/kg, and 10 mg/kg of the multi-chain polypeptide compared to control-treated mice. These results demonstrate that the exemplary multi-chain polypeptide is able to stimulate immune cells in the spleen, in particular $CD8^+$ T cells and NK cells.

Pharmacokinetics

The pharmacokinetics of the exemplary multi-chain polypeptide were evaluated in wild type C57BL/6 mice. Mice were treated subcutaneously with the multi-chain polypeptide at a dosage of 3 mg/kg. Blood was collected at various time points via tail vein, and serum was prepared. The concentration of the multi-chain polypeptide in the serum was determined with ELISA. Briefly, the multi-chain polypeptide was captured using an anti-human tissue factor antibody, and detected using a biotinylated anti-human TGFβ receptor, a peroxidase conjugated streptavidin, and ABTS substrate. The results showed that the half-life of the exemplary multi-chain polypeptide was 12.66 hours.

Immunostimulation Over Time in C57BL/6 Mice

Figure 2A:
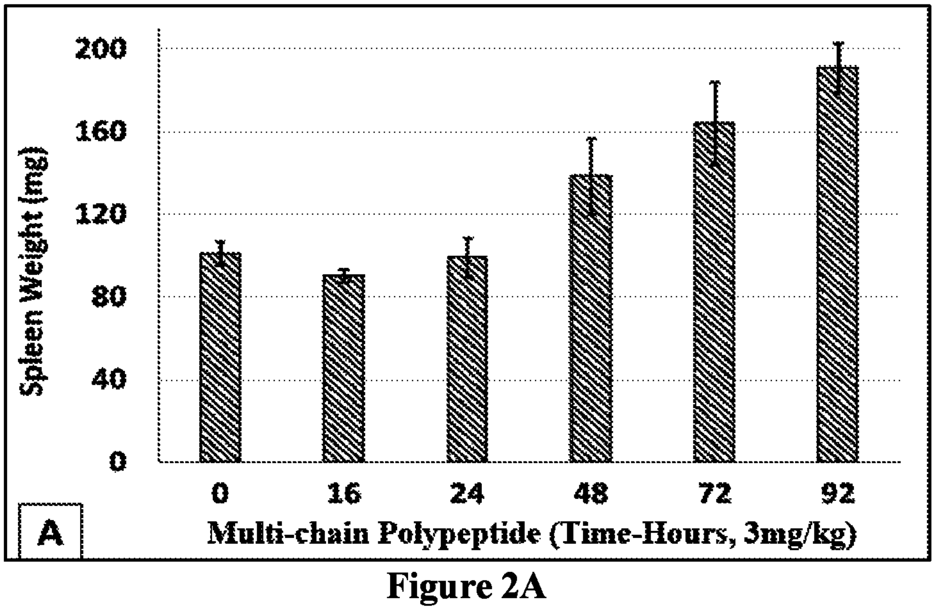
FIGS. 2A-2B show the duration of immunostimulation of an exemplary multi-chain polypeptide in C57BL/6 mice.
Figure 2B:
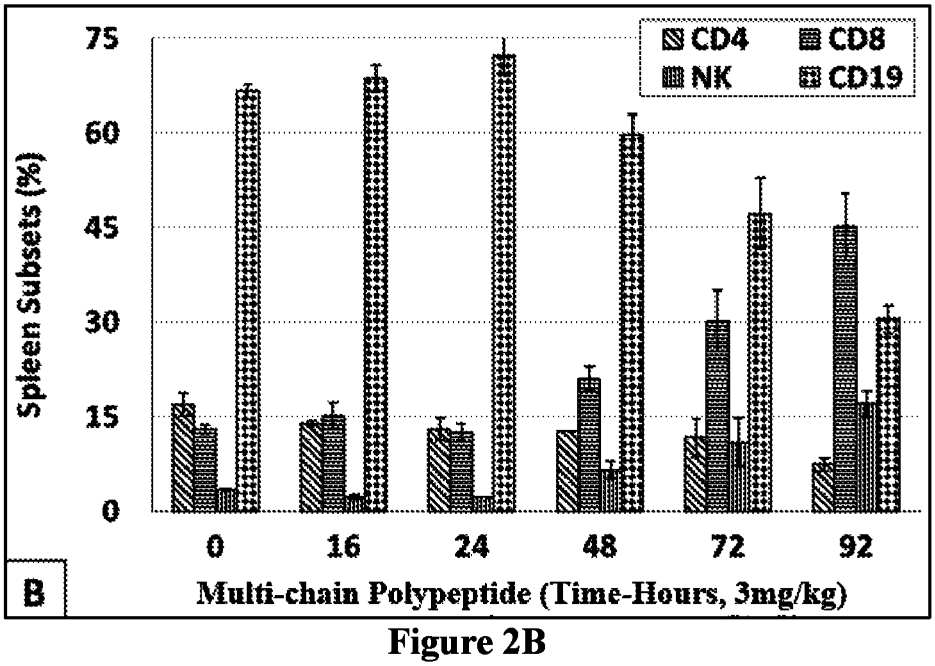

To evaluate the effect of immunostimulation by the multi-chain polypeptide over time, mice were treated with a single dose of the multi-chain polypeptide at 3 mg/kg and the spleen weight and percentages of immune cell types present in the spleen were evaluated immediately upon treatment and at 16, 24, 48, 72, and 92 hours after treatment, using techniques described above. As shown in FIG. 2A, the spleen weight of mice treated with the multi-chain polypeptide increased at 48 hours after treatment, and continued to increase over the next 44 hours. Moreover, as shown in FIG. 2B, in the spleens of mice treated with the multi-chain polypeptide, the percentages of $CD8^+$ T cells and NK cells both increased at 48 hours after treatment and continued to increase over the next 44 hours. These results further demonstrate that the exemplary multi-chain polypeptide is able to stimulate immune cells in the spleen, in particular $CD8^+$ T cells and NK cells, over time.

Figure 3A:
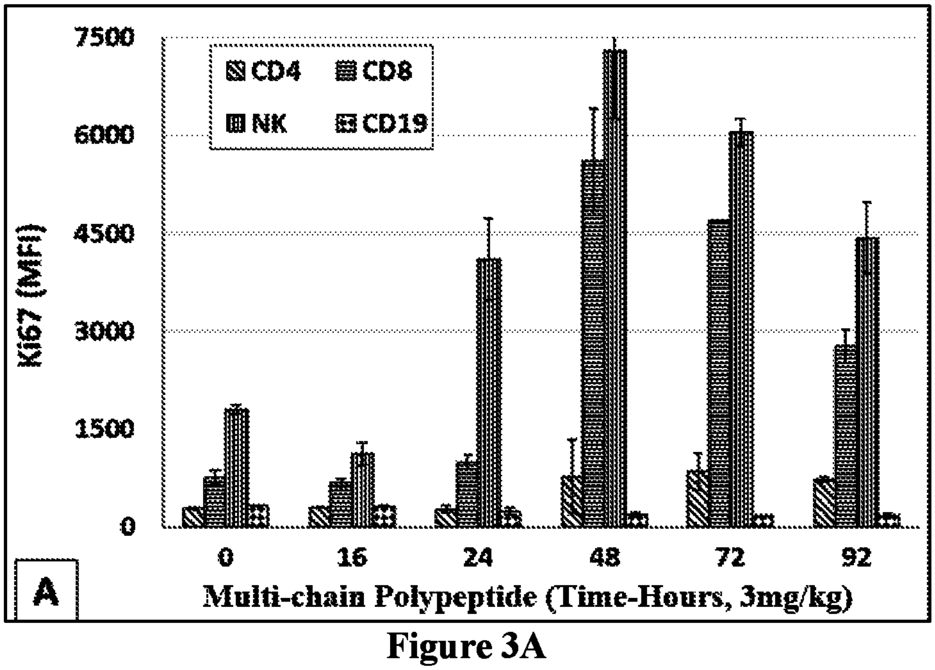
FIGS. 3A-3B show the expression of Ki67 and Granzyme B in immune cells induced by the exemplary multi-chain polypeptide.
Figure 3B:
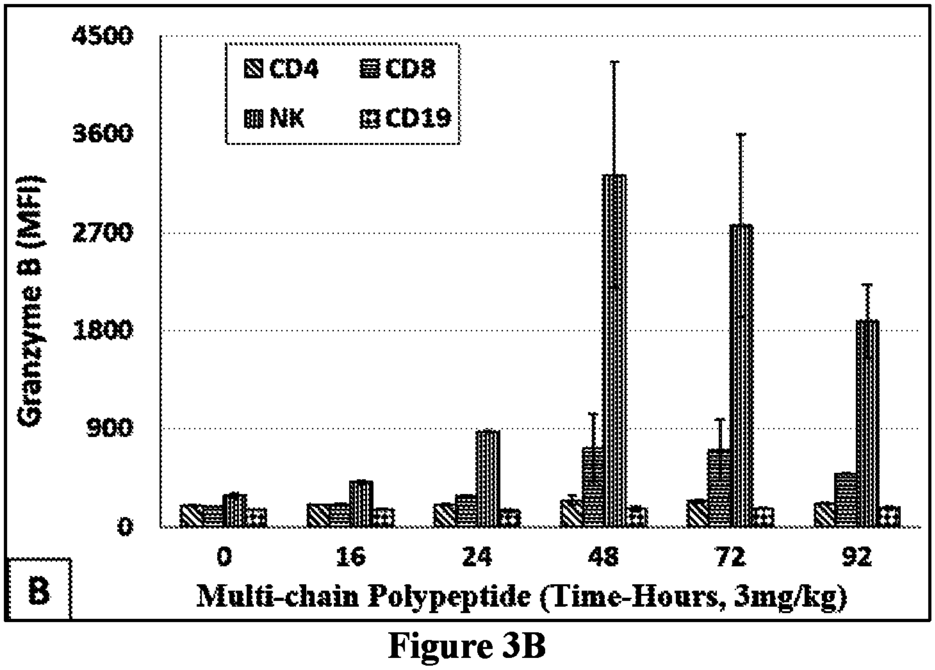

Increased Proliferation and Granzyme B Expression by $CD8^+$ T Cells and NK Cells To evaluate the proliferation and cytotoxic potential of the immune cells induced by the multi-chain polypeptide, mice were treated with a single dose of the multi-chain polypeptide at 3 mg/kg, and the spleens of these mice were evaluated immediately after, and at 16, 24, 48, 72, and 92 hours after treatment. Briefly, single splenocyte suspensions were generated and stained with fluorochrome-conjugated antibodies for the various cell types including anti-CD4, anti-CD8, anti-NK1.1, and anti-CD19, and with an anti-Ki67 antibody (i.e. a cell proliferation marker) and an anti-Granzyme B antibody (i.e. a cytotoxic marker). The mean fluorescent intensity (MFI) of Ki67 and Granzyme B for each immune cell type was analyzed by flow cytometry. As shown in FIGS. 3A and 3B, the expression of Ki67 and Granzyme B by NK cells showed an increase at 24 hours as well as each time point evaluated thereafter as compared to immediately after treatment (0 hours). Moreover, the expression of Ki67 and Granzyme B by $CD8^+$ T cells showed an increase at 48 hours as well as each time point evaluated thereafter as compared to immediately after treatment (0 hours). As such, a single dose of the multi-chain polypeptide resulted in proliferation of $CD8^+$ T cells and NK cells for up to at least 4 days post-treatment.

These results demonstrate that the multi-chain polypeptide not only increased the number of $CD8^+$ T cells and NK cells in the spleen, but also enhanced the proliferation and cytotoxicity of these cells.

Cytotoxicity Against Tumor Cells

Next, the cytotoxicity of the splenocytes activated by the multi-chain polypeptide against tumor cells were evaluated in C57BL/6 mice. Mouse Moloney leukemia cells (Yac-1) were labeled with CellTrace Violet and used as tumor target cells. C57BL/6 mice were treated with a single dose of the multi-chain polypeptide at 3 mg/kg, and splenocytes were prepared at various time points thereafter and used as effector cells. The target tumor cells were mixed with the effector cells at an effector:target (E:T) ratio of 10:1, and incubated at 37 °C for 20 hours. Target cell viability was assessed by analyzing Propidium Iodide (PI)-positive, violet-labeled Yac-1 cells using flow cytometry. The percentage of Yac-1 tumor inhibition was calculated using the formula:

Percentage of Yac-1 tumor inhibition=(1−viable Yac-1 cell number in experimental sample/viable Yac-1 cell number in the sample without splenocytes)×100

Figure 4:
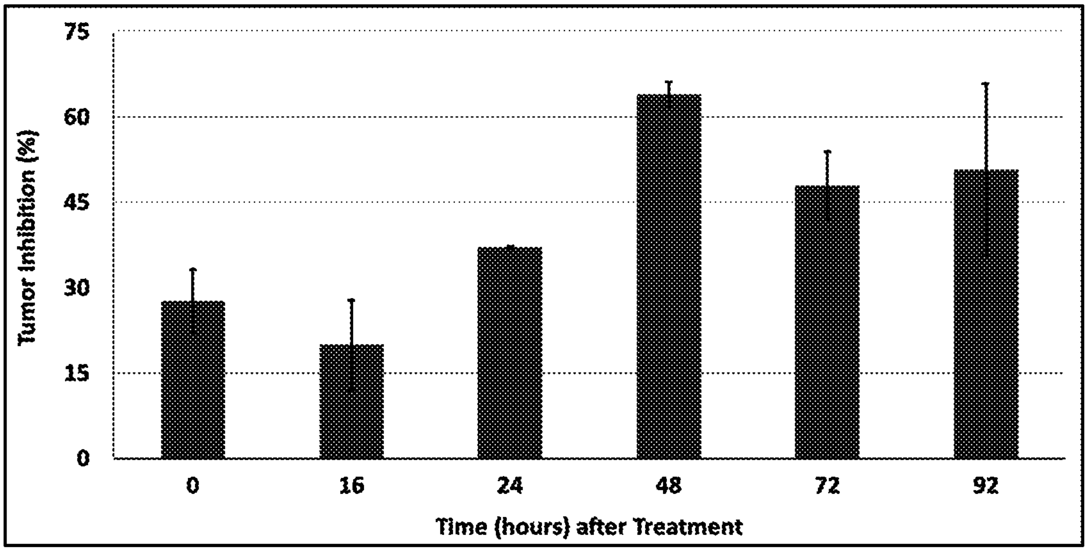
FIG. 4 shows the effect of tumor inhibition by splenocytes prepared from mice treated with an exemplary multi-chain polypeptide at various time points after treatment.

As shown in FIG. 4, splenocytes from mice after 24-hour or more treatment with the multi-chain polypeptide showed increased cytotoxicity against Yac-1 cells as compared to the splenocytes from untreated mice.

Example 2: Immunostimulation in C57BL/6 Mice Using a High Fat Diet-Based Type-2 Diabetes Mouse Model Materials and Methods TGFRt15-TGFRs is a multi-chain chimeric polypeptide (a type A multi-chain chimeric polypeptide described herein) that includes two TGFβ-binding domains which a soluble human TGFβRII dimer (aa24-159). 21t15-TGFRs is a multi-chain chimeric polypeptide (a type A multi-chain chimeric polypeptide described herein) that includes IL-21 and a TGFβ-binding domain. 3t28 is a chimeric polypeptide (a type B chimeric polypeptide described herein) that include two IL-2 polypeptides.

Results

To evaluate the effect of TGFRt15-TGFRs, 2t2, and 21t15-TGFRs in treating Type-2 diabetes, a high fat diet-based Type-2 diabetes mouse model (B6.129P2-ApoE$^{tm1Unc}$/J from The Jackson Laboratory) was used. Mice were fed either a control diet or a high fat diet for 11 weeks. A subset of mice fed with the high fat diet were also treated with TGFRt15-TGFRs, 2t2, or 21t15-TGFRs. Mice fed the control diet, high fat diet, and mice fed with the high fat diet and treated with TGFRt15-TGFRs, 2t2, or 21t15-TGFRs were evaluated 4 days post-treatment. Briefly, single splenocyte suspensions were generated and stained with fluorochrome-conjugated antibodies including anti-CD4, anti-CD8, anti-NK1.1, and anti-CD19. The percentages of $CD4^+$ T cells, $CD8^+$ T cells, Natural Killer (NK) cells, and $CD19^+$ B cells present in the spleen of mice in each group were evaluated using flow cytometry.

Figure 5A:
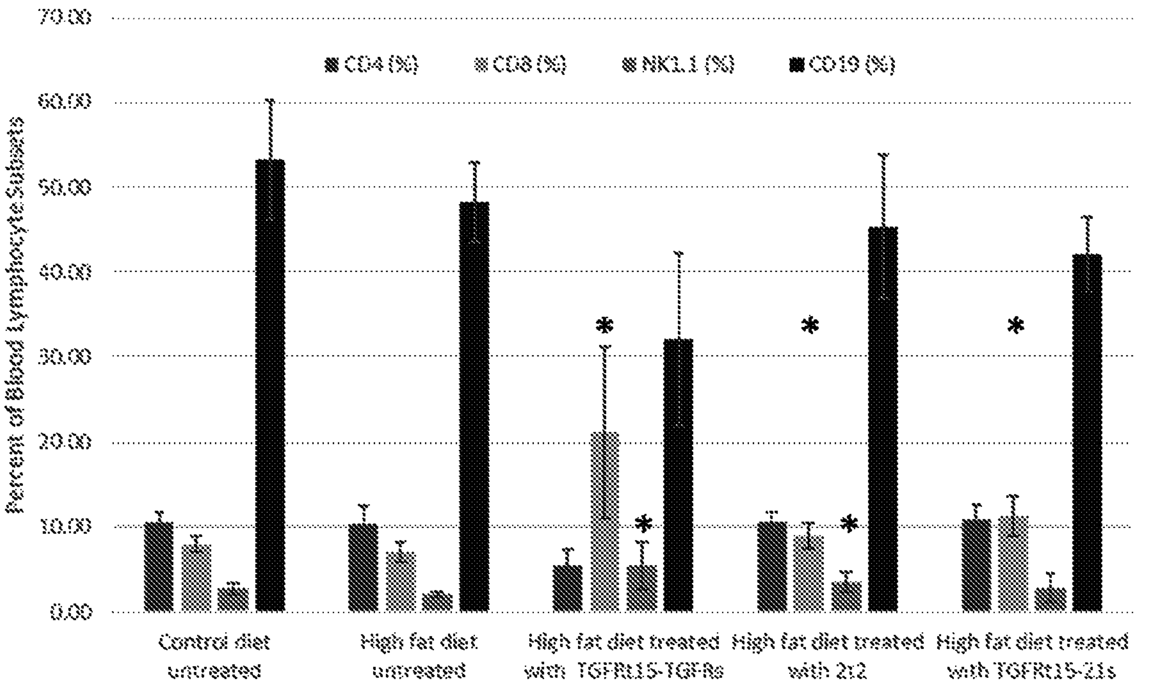
FIGS. 5A-5B show the percentages and the proliferation rate of $CD4^+$ T cells, $CD8^+$ T cells, Natural Killer (NK) cells, and $CD19^+$ B cells in the blood of B6.129P2-ApoE$^{tM1Unc}$/J mice (purchased from The Jackson Laboratory) fed a control diet, a high fat diet and untreated, and mice fed a high fat diet and treated with TGFRt15-TGFRs, 2t2, or 21t15-TGFRs.
Figure 5B:
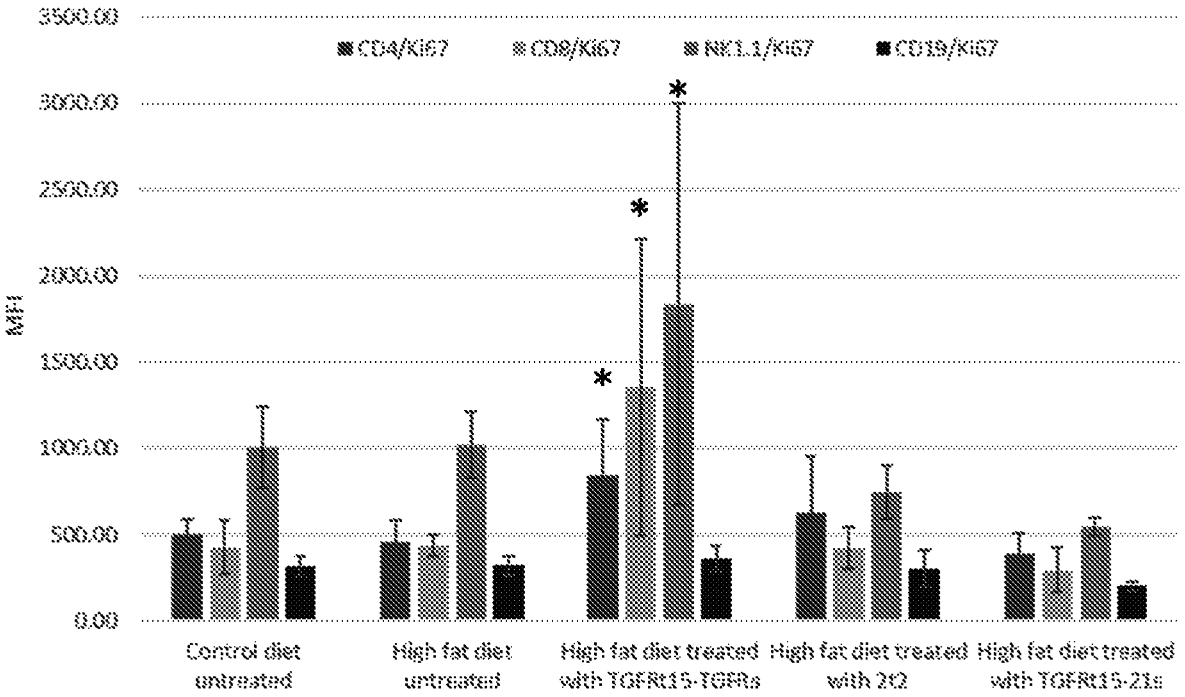

As shown in FIG. 5A, in mice fed a high fat diet, the percentage of NK cells in PBMCs was significantly increased after treatment with TGFRt15-TGFRs or 2t2 compared to untreated mice, but not after treatment with 21t15-TGFRs. Furthermore, the percentage of $CD8^+$ T cells in PBMCs was significantly increased after treatment with TGFRt15-TGFRs, 2t2, or 21t15-TGFRs compared to untreated mice. Moreover, the proliferation of $CD4^+$ T cells, $CD8^+$ T cells, Natural Killer (NK) cells, and $CD19^+$ B cells in PBMCs were also evaluated using an anti-Ki67 antibody. As shown in FIG. 5B, the number of proliferating NK cells, $CD4^+$ T cells, and $CD8^+$ T cells were significantly increased after treatment with TGFRt15-TGFRs, but not after treatment with 2t2 or 21t15-TGFRs.

Figures 6A, 6B, 6C, 6D, 6E:
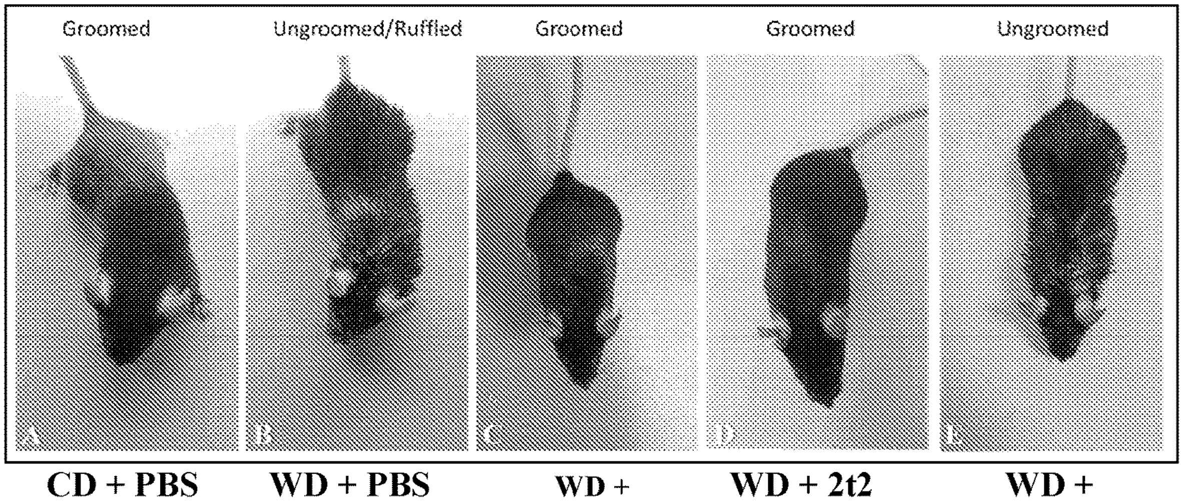
FIGS. 6A-6E show exemplary physical appearance of mice fed either a control or high fat diet and were either untreated or treated with TGFRt15-TGFRs, 2t2, or 21t15-TGFRs.

To examine the effect of TGFRt15-TGFRs, 2t2 and 21t15-TGFRs on the appearance and texture of skin and hair in animals, mice were fed either a control or a high fat diet for 7 weeks, and a subset of the mice fed a high fat diet were also treated with TGFRt15-TGFRs, 2t2 or 21t15-TGFRs. One week post-treatment, the appearance of the mice was evaluated. Mice fed a high fat diet and untreated, or a high diet and treated with 21t15-TGFRs appeared ungroomed and ruffled, and had increased gray hair/hair loss as compared to mice fed a control diet (FIGS. 6A, 6B and 6E). Surprisingly, mice fed a high fat diet that received TGFRt15-TGFRs or 2t2 treatment appeared groomed and healthier (less gray hair/hair loss) (FIGS. 6C and 6D) as compared to mice fed a high fat diet that did not receive TGFRt15-TGFRs or 2t2 treatment (FIG. 6B). Specifically, TGFRt15-TGFRs or 2t2-treated mice showed superior skin and hair appearance and texture as compared to control mice. These results demonstrate that treatment with TGFRt15-TGFRs or 2t2 improves the appearance and texture of skin and hair in mammals.

Figure 7:
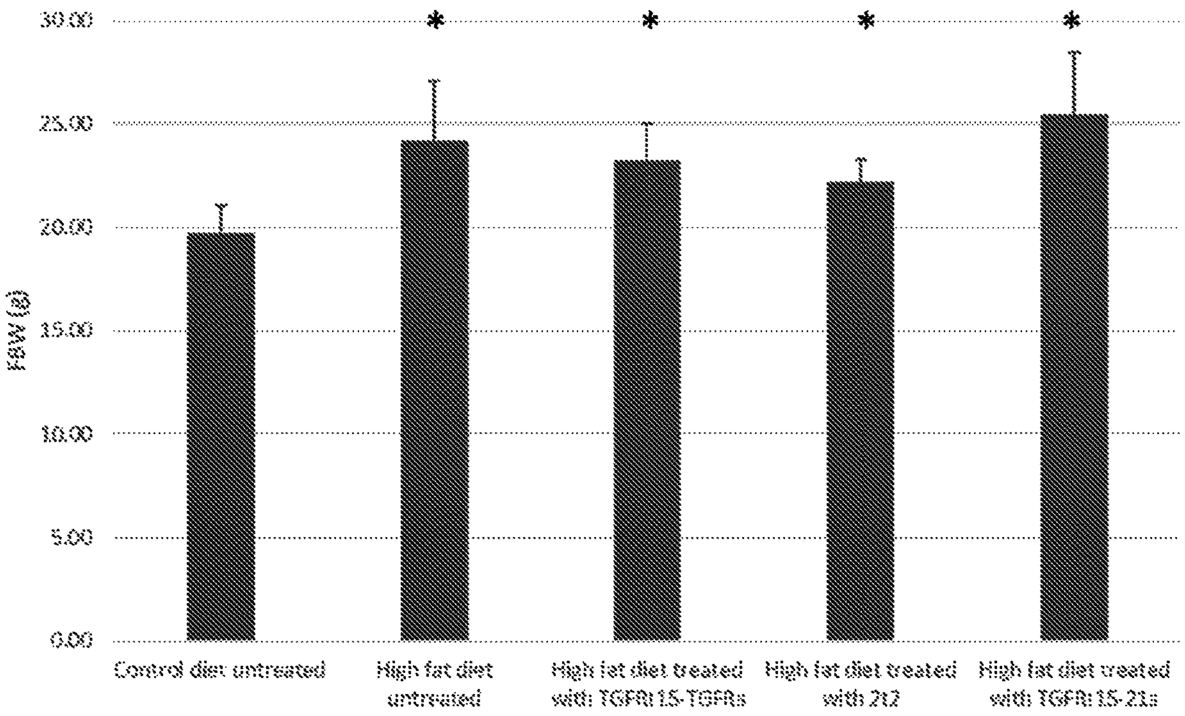
FIG. 7 shows the fasting body weight of mice fed either a control or a high fat diet and were either untreated or treated with TGFRt15-TGFRs, 2t2, or 21t15-TGFRs.

Next, mice were fed either a control or high fat diet for 9 weeks, and a subset of the mice fed a high fat diet were treated with TGFRt15-TGFRs, 2t2, or 21t15-TGFRs. Four days post-treatment, the fasting body weight of mice in each group were measured. The fasting body weight of mice fed with the high fat diet and untreated, as well as mice fed with the high fat diet and treated with 21t15-TGFRs were significantly increased compared to mice fed a control diet. However, the fasting body weight of mice fed a high fat diet and treated with TGFRt15-TGFRs or 2t2 were decreased compared to the other two high fat diet groups mentioned above. The fasting body weight of the mice at the end of the study (9 weeks) is shown in FIG. 7.

Figure 8:
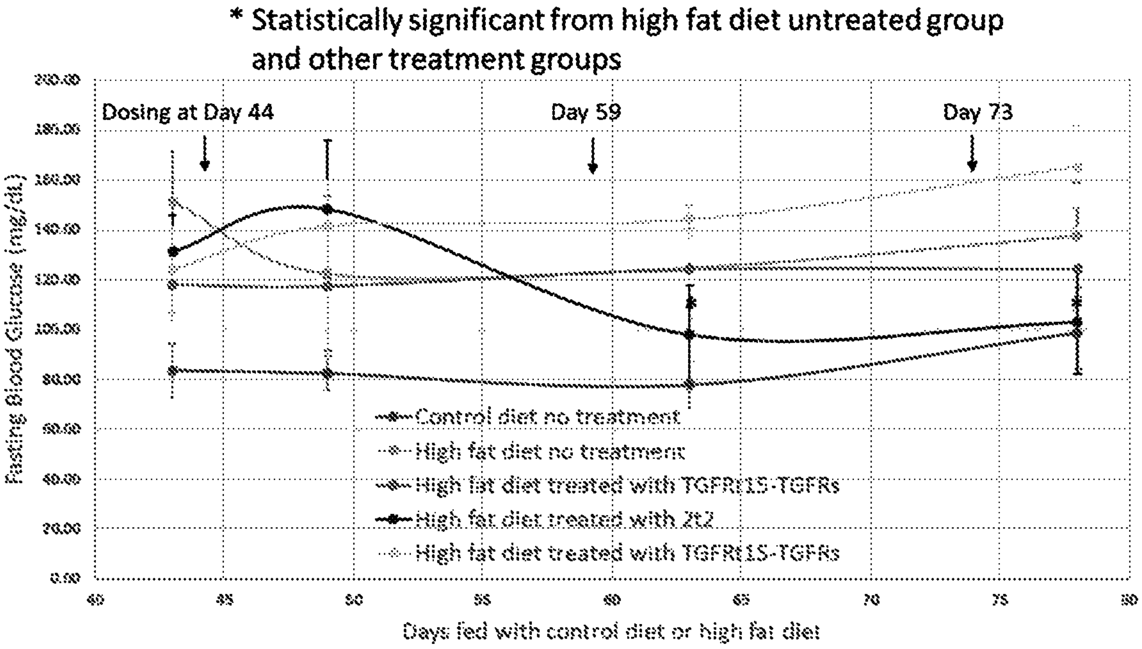
FIG. 8 shows the fasting blood glucose levels of mice fed either a control or a high fat diet and were either untreated or treated with TGFRt15-TGFRs, 2t2, or 21t15-TGFRs.

To evaluate the fasting glucose levels in the mice of each group, mice were fed either a control or a high fat diet and were either untreated or treated with TGFRt15-TGFRs, 2t2, or 21t15-TGFRs on days 44, 59 and 73. The fasting blood glucose in the mice of each group were measured 4 days post-treatment. As shown in FIG. 8, after the second and third doses (on Days 59 and 73, respectively), the fasting blood glucose level was significantly reduced for mice fed a high fat diet and treated with 2t2 (red line) as compared to mice fed a high fat diet but untreated (yellow line). The fasting blood glucose level remained constant for mice fed a high fat diet and treated with TGFRt15-TGFRs (green line), whereas the fasting blood glucose level increased for mice fed a high fat diet and treated with 21t15-TGFRs (blue line).

Example 3: Chemotherapy-Induced Senescent B16F10 Melanoma Cells Express NK Ligands Material and Methods Cellular senescence in B16F10 melanoma cells was induced by treating the cells with docetaxel (7.5 μm, Sigma) for 3 days followed by recovery in complete media for 4 days. Cellular senescence was accessed by staining the cells with senescence-associated β-galactosidase (SA β-gal). Briefly, B16F10 control and senescence cells (B16F10-SNC) were washed once with PBS, fixed with 0.5% glutaraldehyde (PBS (pH 7.2)), for 30 minutes. Cells were stained in X-gal solution (1 mg/mL X-gal, 0.12 mM $K_3Fe[CN]_6$, 0.12 mM $K_4Fe[CN]_6$, and 1 mM $MgCl_2$ in PBS at pH 6.0) overnight at 37 °C, and were imaged using a Nikon optical light microscope.

Results

Figure 9A:
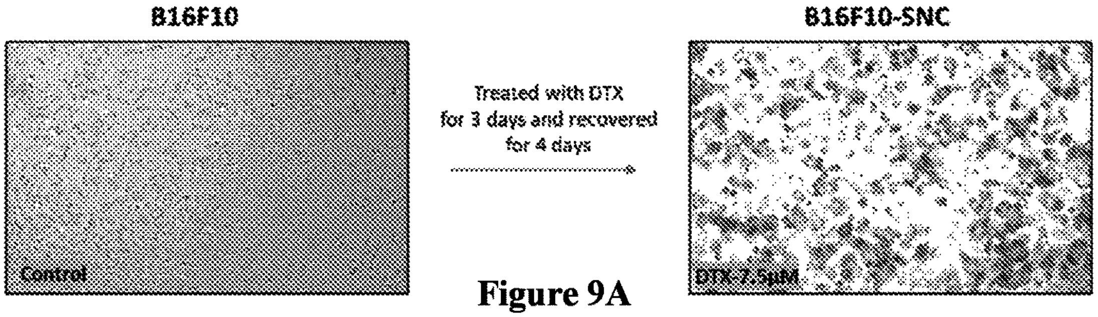
FIGS. 9A-9F show chemotherapy-induced senescent B16F10 cells and expression of senescent genes.
Figure 9B:
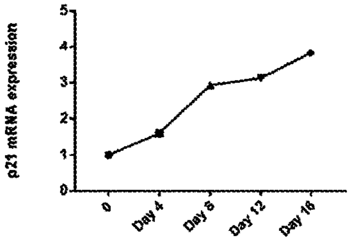
Figure 9C:
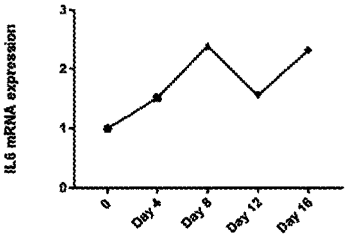
Figure 9D:
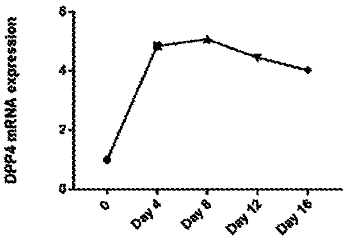
Figure 9E:
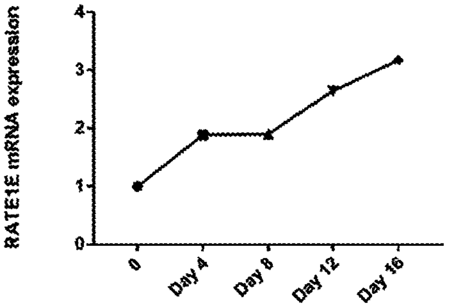
Figure 9F:
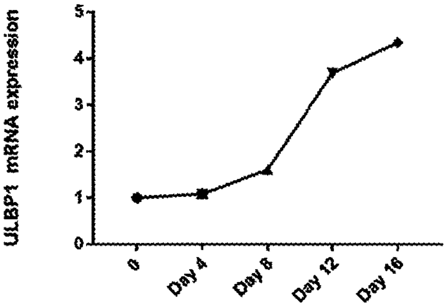

Cellular senescence in B16F10 melanoma cells was induced using chemotherapy as described above. As shown in FIG. 9A, chemotherapy-induced senescent B16F10 cells (B16F10-SNC) were positive for SA β-gal staining, while the control B16F10 cells were not stained. Next, expression of senescence genes was analyzed using RT-qPCR with RNA isolated on day 0 or following senescence induction on days 4, 8, 12 and 16, respectively. The expression levels were normalized to control B16F10 cells. As shown in FIGS. 9B-9D, the expression of p21, IL6 and DPP4 were upregulated in RNA isolated from the senescent cells over the duration of the experiment. Moreover, as shown in FIGS. 9E and 9F, the expression of RATE1E and ULBP1 (NK activating receptor NKG2D ligands) were also induced in senescent cells, with the highest expression level being on day 16. These results demonstrate that the chemotherapy-induced senescent B16F10 cells are subjected to stronger cytotoxicity of activated NK cells than control B16F10 cells.

Figure 10A:
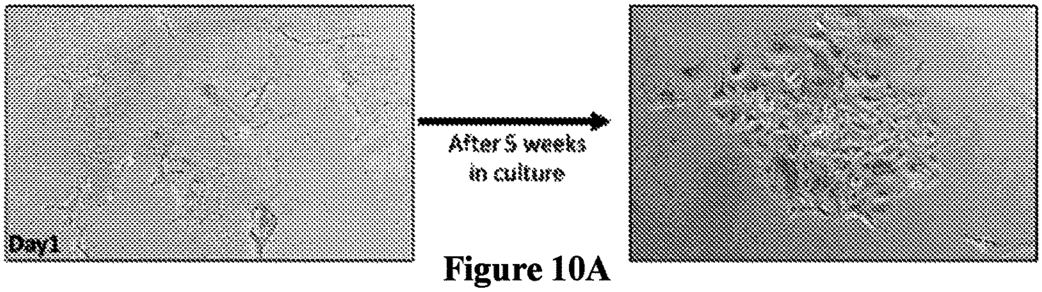
FIGS. 10A-10F show colony formation and expression of stem cell markers by chemotherapy-induced senescent B16F10 cells.
Figure 10B:
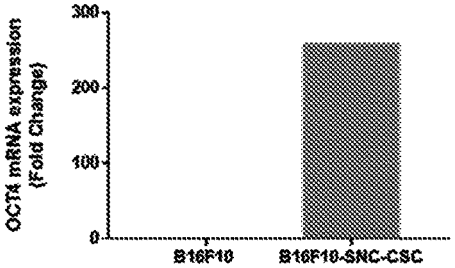
Figure 10C:
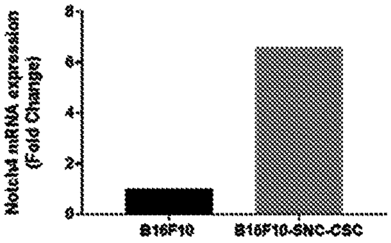
Figure 10D:
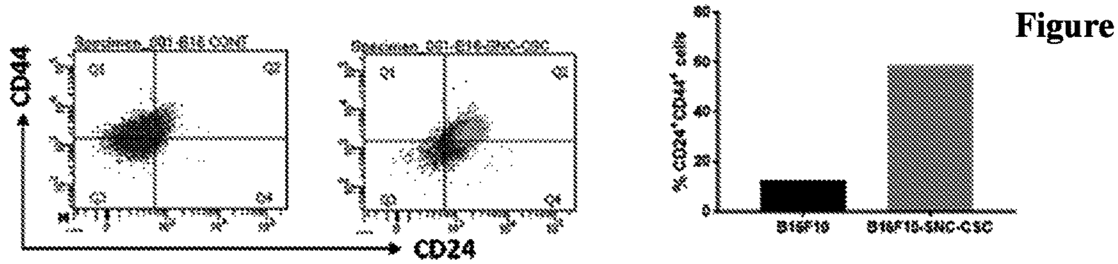
Figure 10E:
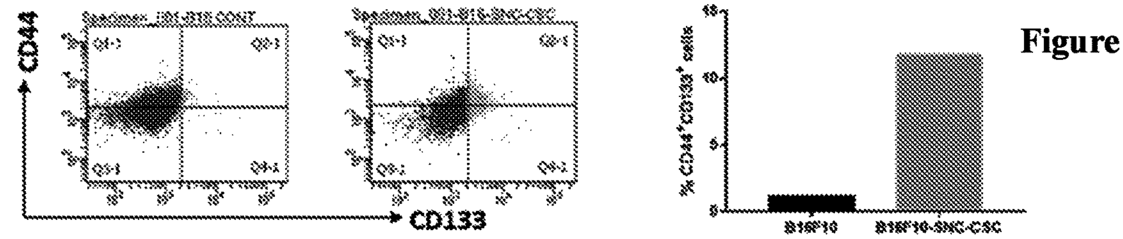
Figure 10F:
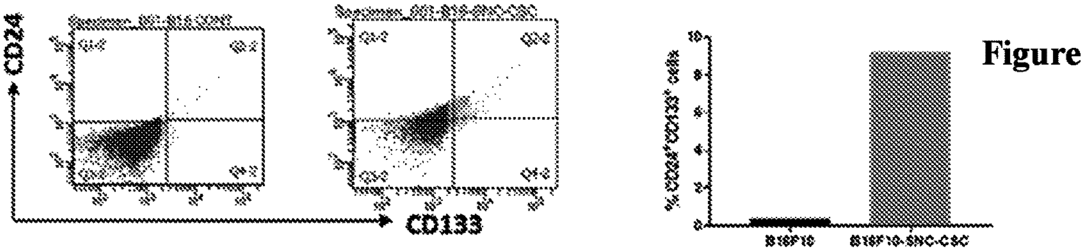

Acquisition of Stem-Cell Properties in Chemotherapy-Induced Senescent B16F10 Melanoma Cells To examine whether chemotherapy-induced senescent B16F10 melanoma cells acquired stem cell properties, a colony formation assay was performed. Briefly, 1000 cells/well were seeded on a six well plate, and the media was changed every third day. As shown in FIG. 10A (images taken at 100× magnification), after 5 weeks in culture the senescent cells were able to form colonies. To evaluate stem cell marker expression by the colonies, RNA was isolated from the colonies and the expression of Oct4 and Notch4 mRNA were determined by RT-qPCR. As compared to control B16F10 cells, chemotherapy-induced senescent B16F10 melanoma cells showed upregulation of Oct4 and Notch 4, which are cancer stem cell markers (FIGS. 10B and 10C). Moreover, cell surface expression of stem cell markers CD44, CD24 and CD133 were evaluated by staining with antibodies against CD44, CD24, and CD133 followed by flow cytometry. As shown in FIGS. 10D-10F, double positive populations ($CD44^+CD24^+$, $CD44^+CD133^+$, and $CD24^+CD133^+$) were increased in the chemotherapy induced senescence stem cells (B16F10-SNC-CSC) compared to control B16F10.

Figure 11A:
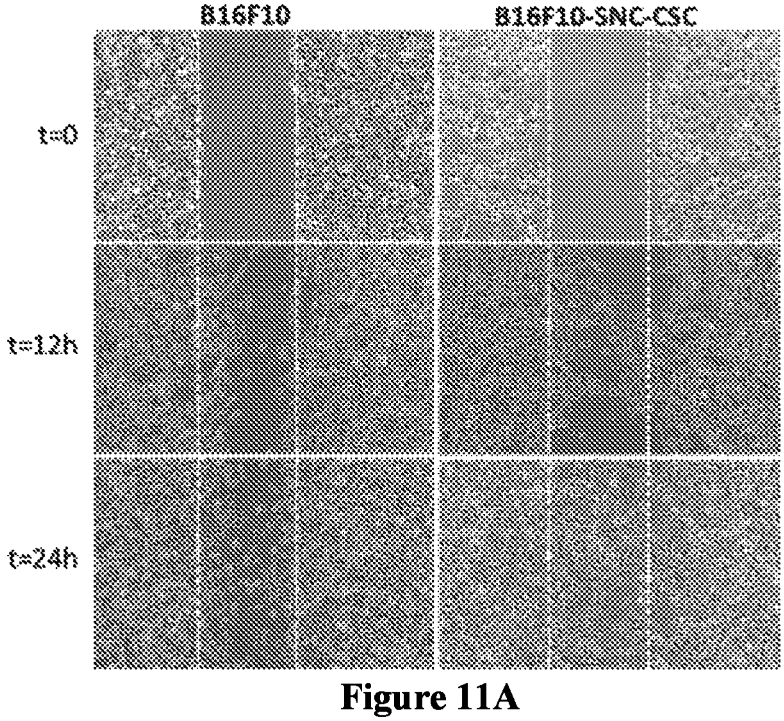
FIGS. 11A-11C show migratory and invasive properties of chemotherapy-induced senescent B16F10 cells.

Chemotherapy-Induced Senescent (CIS) Melanoma Cells with Stem Cell Properties are More “Migratory” and “Invasive” than Control B16F10 Cells The migratory properties of chemotherapy-induced senescent (CIS) melanoma cells with stem cell properties (B16F10-SNC-CSC) were analyzed using a migration assay. Briefly, control B16F10 cells and B16F10-SNC-CSC cells were plated on six well plates and wounded with a p20 pipette tip. Movement of cells were imaged at 0, 12, and 24 hours after. As shown in FIG. 11A, chemotherapy-induced senescent (CIS) melanoma cells with stem cell properties (B16F10-SNC-CSC) were more migratory in the in vitro migration assay, as compared to control B16F10 cells.

Figure 11B:
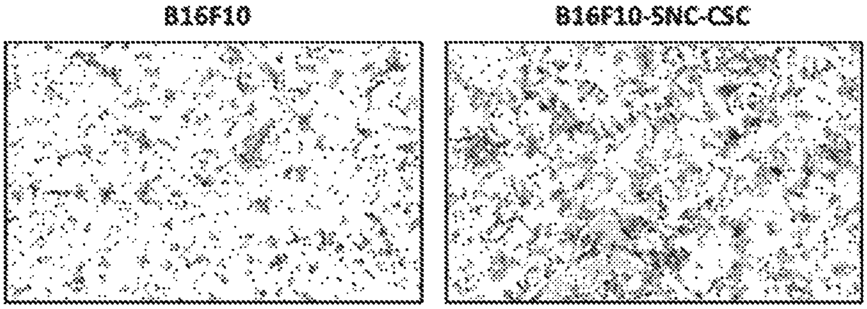
Figure 11C:
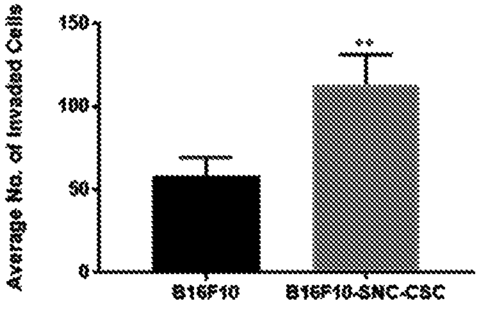

Next, the invasive properties of chemotherapy-induced senescent cells with stem cell properties (B16F10-SNC-CSC) were analyzed using an invasion assay. The invasion assay was carried out on 24-well transwell inserts coated with Matrigel. Briefly, $0.5\times10^6$ control B16F10 cells and B16F10-SNC-CSC cells were seeded in serum-free media onto the upper chamber, and the lower chamber was filled with media supplemented with 10% FBS. After 16 hours of incubation, the cells on the upper surface of the filter were removed, and cells underneath the filter were fixed and stained with a 0.02% crystal violet solution. The number of cells were counted in three fields at 100× magnification. As shown in FIGS. 11B and 11C, chemotherapy-induced senescent cells with stem cell properties were more aggressive in invading the Matrigel coated membrane as compared to control B16F10 cells. These results demonstrate that chemotherapy-induced senescent B16F10 tumor cells are able to regain their proliferation capability, obtain stem-cell features, and have increased migratory abilities and invasiveness for metastasis.

Figure 12A:
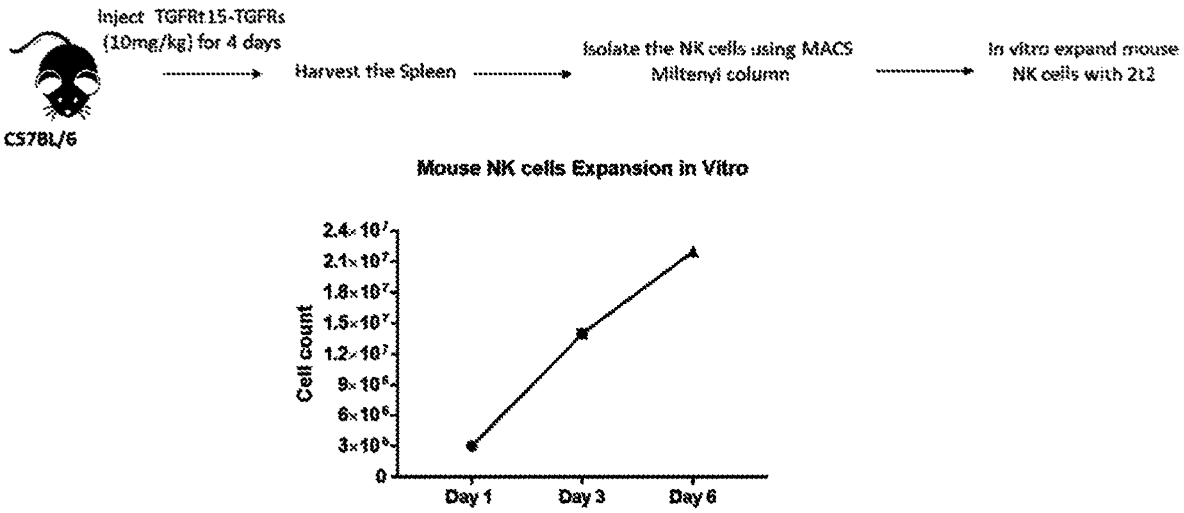
FIGS. 12A and 12B show in vitro expanded NK cells and their cytotoxicity against chemotherapy-induced senescent cells with stem cell properties (B16F10-SNC-CSC) or control B16F10 cells.

Cytotoxic Activity of Mouse NK Cells on Chemotherapy-Induced Senescent Cells with Stem Cell Properties To expand NK cells in vivo, C57BL/6 mice were injected subcutaneously with TGFRt15-TGFRs (10 mg/kg) for 4 days. The spleens from these mice were obtained and NK cells were purified using MACS Miltenyi column. The purified NK cells were then expanded in vitro with 2t2 (FIG. 12A).

Figure 12B:
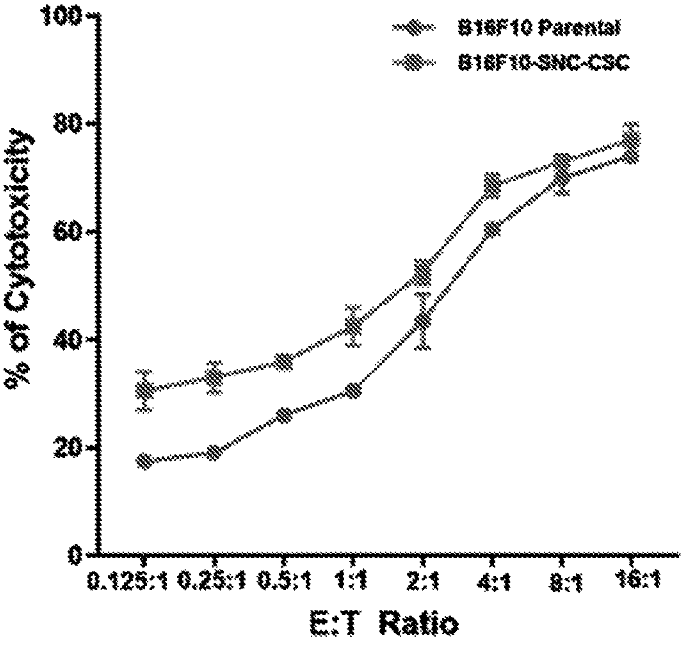

To evaluate the cytotoxicity of the expanded NK cells, chemotherapy-induced senescent stem cells (B16F10-SNC-CSC) or control B16F10 cells were labelled with CellTrace violet and incubated with in vitro activated 2t2 mouse NK cells (isolated from spleen of C57BL/6 mice injected with 10 mg/kg TGFRt15-TGFRs for 4 days) at various E:T ratios for 16 hrs. The B16F10-SNC-CSC and control B16F10 cells were trypsinized, washed and re-suspended in complete media containing a Propidium Iodide (PI) solution, and cytotoxicity was accessed by flow cytometry. As shown in FIG. 12B, NK cells were more effective at killing chemotherapy-induced senescent cells with stem cell properties (B16F10-SNC-CSC), as compared to control B16F10 cells.

Combination Treatment in Melanoma Mouse Model

Figure 13A:
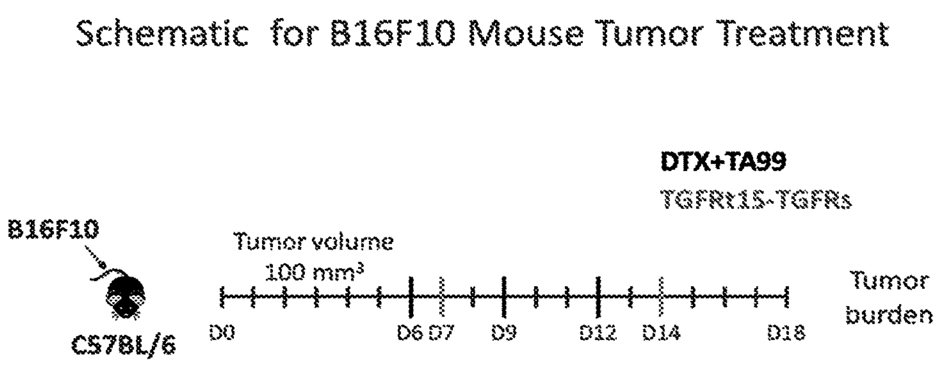
FIGS. 13A-13C show results of combination treatment using a mouse melanoma model.
Figure 13B:
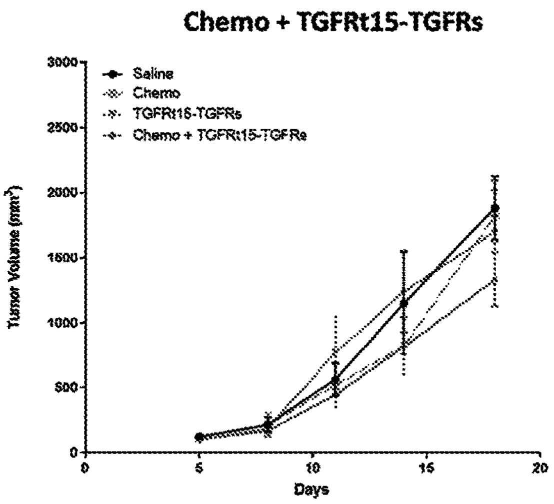
Figure 13C:
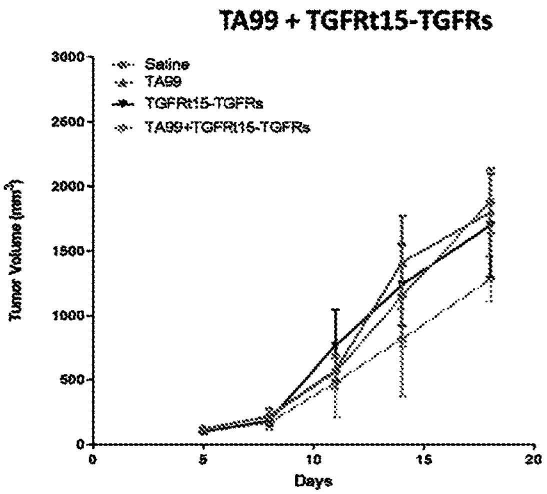

The effect of TGFRt15-TGFRs in treating melanoma was evaluated in a mouse melanoma model. Briefly, $5\times10^5$ B16F10 cells were injected subcutaneously into C57BL/6 mice. When the tumor volume reached ~100 $mm^3$, mice were treated with docetaxel (chemotherapy) (5 mg/kg) or TA99 (200 μg) either as a single agent or in combination every third day, and TGFRt15-TGFRs (3 mg/kg) was given once a week (FIG. 13A). Mice that received saline, docetaxel (chemotherapy)/TA99 alone, or TGFRt15-TGFRs alone were used as controls. Five mice were tested in each experimental and control group. Tumor volume was measured every third day. As shown in FIGS. 13B and 13C, combinations of TGFRt15-TGFRs with either chemotherapy or TA99 slowed down tumor progression as compared to mice treated with saline or mice treated with chemotherapy or TA99 alone in the syngeneic melanoma mouse model.

Example 4: Chemotherapeutic Induction of Senescence in Human Pancreatic Cell Line SW1990

Materials and Methods

β-galactosidase staining: Confirmation of chemotherapy induced senescence was carried out by standard β-galactosidase staining at pH 6.0 using commercially available kit (Cell Signaling Technology) according to manufacturer's instructions. The following day, the staining solution was removed, and cells were washed with phosphate buffered saline, and 70% glycerol was added to the wells. The β-galactosidase positive cells will be stained blue, while control untreated cells will not stain.

Flow cytometry: One million control and senescent cells were obtained and stained using commercially available antibodies to surface markers of stem cells such as anti-CD44 and anti-CD24 antibodies (Biolegend) according to manufacturers' instructions. The cells were then washed and analyzed using the BD Celesta flow cytometer. Cells showing stem cell-like properties will be doubly positive for both CD44 and CD24.

Gene expression assay: One million control and senescent cells were obtained and lysed using Trizol (Thermofisher), followed by RNA purification using an RNA isolation kit (Qiagen). The RNA was quantified and converted to cDNA using a Qiagen cDNA QUANTITECT® kit (kit for cDNA synthesis with integrated removal of genomic DNA contamination). The cDNA was then used as a template for standard Taqman gene expression assays (Thermofisher) to quantify the relative abundance of senescent, stem cell markers as well as NK ligands.

NK cell cytotoxicity assay: NK cells were isolated from healthy human donors (n=2) using a commercially available NK isolation kit (Stem Cell), and were activated overnight using the cytokine fusion molecule 18t15-12s (100 nM). On the following day, NK cells were washed to remove cytokine molecules and mixed with either CELLTRACE™ Violet (cell proliferation kit for flow cytometry)-labelled control untreated tumor cells or chemotherapy-induced senescent tumor cells at an E:T ratio of 4:1 for 20 hours. On the following day, cells were trypsinized, and complete contents of each well were analyzed using flow cytometry and percent inhibition of cells was analyzed.

Results

Figure 14:
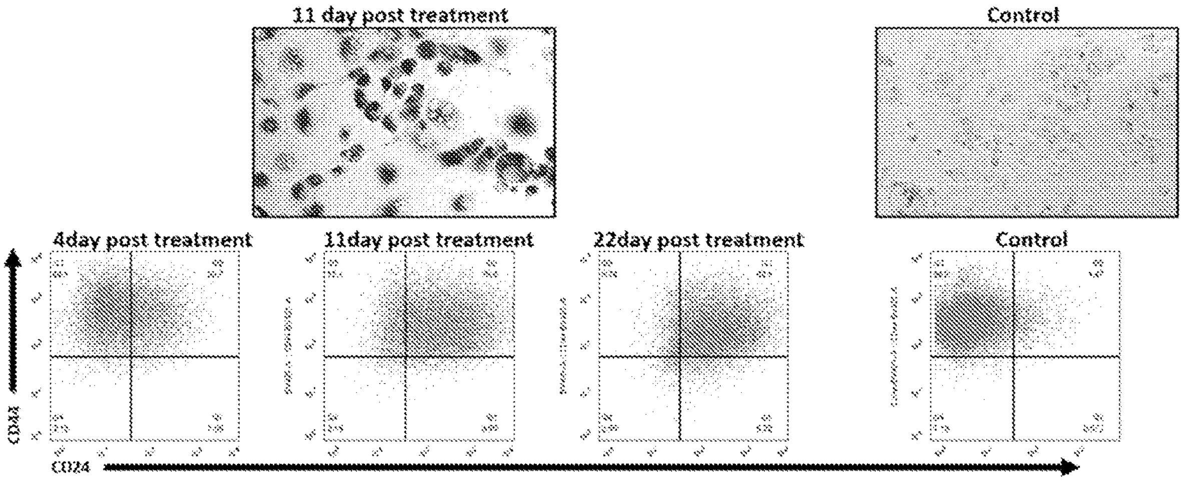
FIG. 14 shows induction of senescence in the human pancreatic tumor cell line SW1990 and expression of CD44 and CD24 in senescent SW1990 cells as compared to control SW1990 cells.
Figure 15:
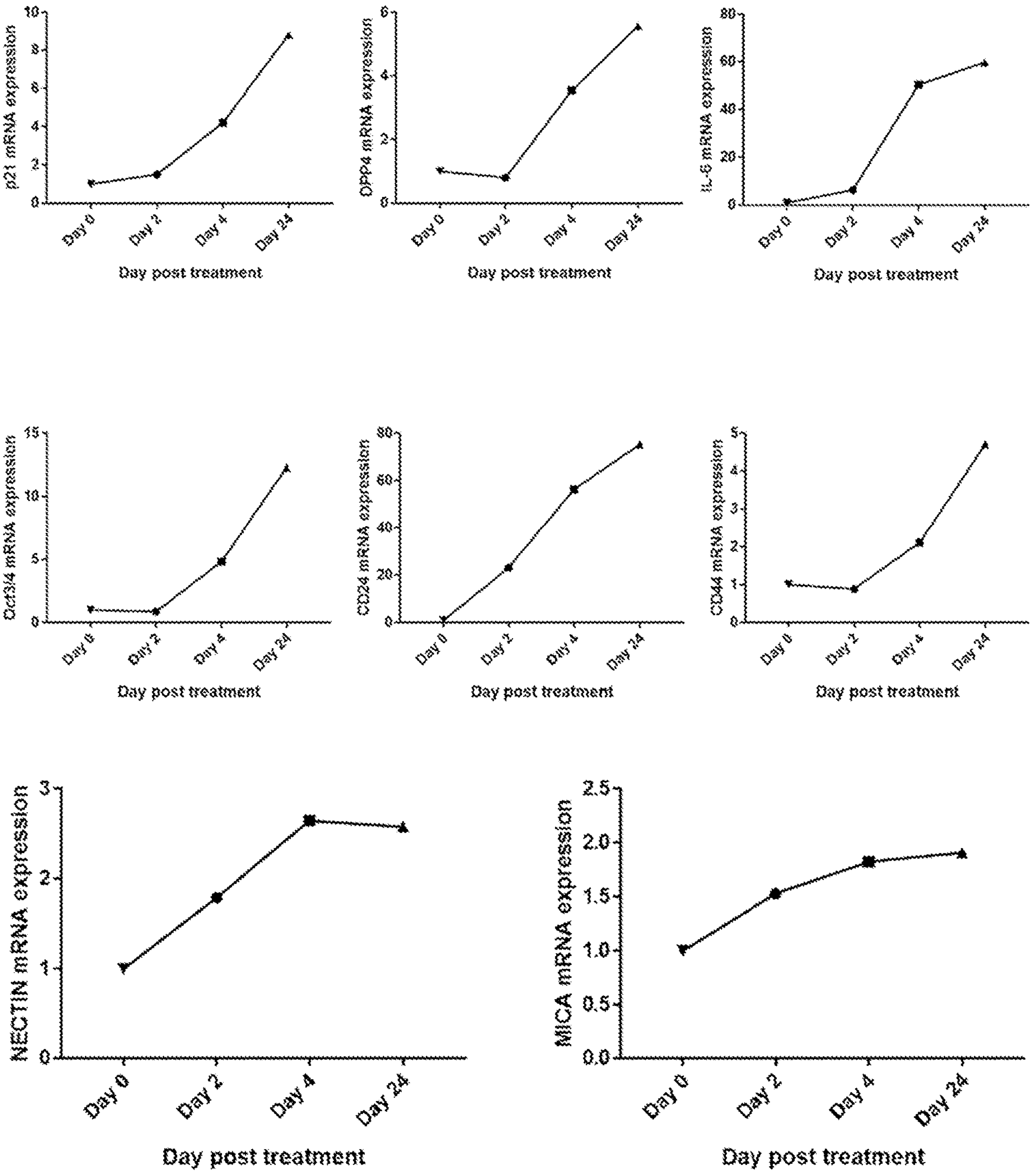
FIG. 15 shows expression of senescent markers by chemotherapy-induced senescent SW1990 cells.

Senescence in the human pancreatic tumor cell line SW1990 was induced through treatment with chemotherapeutic drugs Abraxane (Celgene) and Gemcitabine (Sigma Aldrich) for 3 days at 2.5 μm and 6.25 μm, respectively. SW1990 cells that were untreated were used as controls. Media was changed after 3 days and cells were allowed to rest in the culture media for 4 days. As shown in FIG. 14, senescent cells treated with the chemotherapeutic drugs were positive for β-galactosidase staining (blue), while control cells were not stained. Senescent cells and control cells were evaluated for their expression of senescence and stem cell markers at 4 days, 11 days, and 22 days post-treatment. As shown in FIG. 14, senescent cells showed increased double positive staining for CD44 and CD24 over time as compared to the control cells. Moreover, the chemotherapy-induced senescent SW1990 cells were also analyzed for their expression of senescent markers including DPP4, IL6, and p21, stem cell markers including Oct3/4, CD24, and CD44, and NK ligands including Nectin and MICA, on day 0, and days 2, 4, and 24 post-treatment using the gene expression assay described above. As shown in FIG. 15, the expression of all of the markers mentioned showed an increase over time.

Cytotoxicity of In Vitro Activated Human NK Cells

Figure 16:
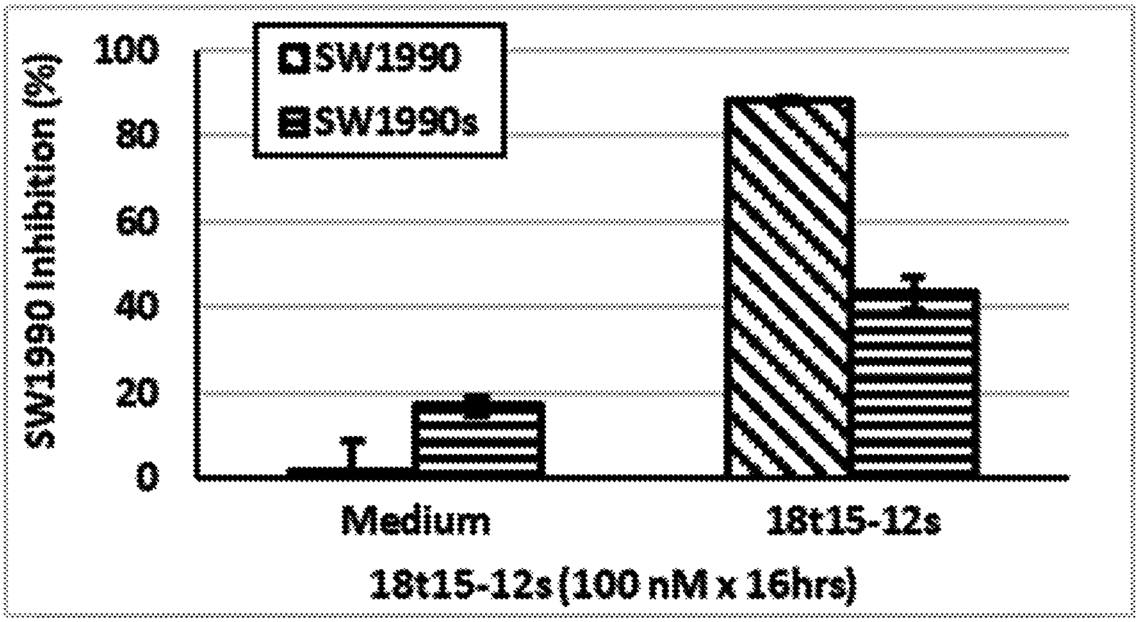
FIG. 16 shows the cytotoxicity of in vitro activated human NK cells against chemotherapy-induced senescent SW1990 cells or control SW1990 cells.

To evaluate the cytotoxicity of in vitro activated human NK Cells (treated with 18t15-12s), senescence in the human pancreatic tumor cell line SW1990 was induced through treatment with chemotherapeutic drugs Abraxane (Celgene) and Gemcitabine (Sigma Aldrich) for 3 days at 2.5 μm and 6.25 μm, respectively. SW1990 cells that were untreated were used as controls. Media was changed after 3 days and cells were allowed to rest in the culture media for 30 days. The culture media was changed every 4 days. Activated NK cells were obtained and their cytotoxicity for chemotherapy-induced senescent tumor cells and untreated control tumor cells were evaluated using the NK cell cytotoxicity assay described above. As shown in FIG. 16, activated NK cells showed increased cytotoxicity against both control SW1990 cells (SW1990) and senescent SW1990 cells (SW1990s).

Example 5: Creation of an IL-12/IL-15RαSu DNA Construct

Figure 17:
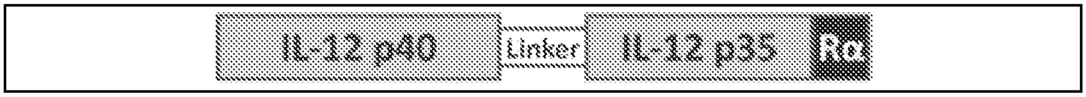
FIG. 17 shows a schematic diagram of an exemplary IL-12/IL-15RαSu DNA construct.

In a non-limiting example, an IL-12/IL-15RαSu DNA construct was created (FIG. 17). The human IL-12 subunit sequences, human IL-15RαSu sequence, human IL-15 sequence, human tissue factor 219 sequence, and human IL-18 sequence were obtained from the UniProt website and DNA for these sequences was synthesized by Genewiz. A DNA construct was made linking the IL-12 subunit beta (p40) to IL-12 subunit alpha (p35) with a GS (3) linker to generate a single chain version of IL-12 and then directly linking the IL-12 sequence to the IL-15RαSu sequence. The final IL-12/IL-15RαSu DNA construct sequence was synthesized by Genewiz.

The nucleic acid sequence of the IL12/IL-15RαSu construct (including signal peptide sequence) is as follows (SEQ ID NO: 181):

```
(Signal peptide)
ATGAAATGGGTGACCTTTATTTCTTTACTGTTCCTCTTTAGCAGCGCCT

ACTCC

(Human IL-12 subunit beta (p40))
ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC

GGAAAGACCCTCACAATCCAAGTTAAGGAGTTCGGAGACGCTGGCCAAT

ACACATGCCACAAGGGAGGCGAGGTGCTCAGCCATTCCTTATTATTATT

ACACAAGAAGGAAGACGGAATCTGGTCCACCGACATTTTAAAAGATCAG

AAGGAGCCCAAGAATAAGACCTTTTTAAGGTGTGAGGCCAAAAACTACA

GCGGTCGTTTCACTTGTTGGTGGCTGACCACCATTTCCACCGATTTAAC

CTTCTCCGTGAAAAGCAGCCGGGGAAGCTCCGACCCTCAAGGTGTGACA

TGTGGAGCCGCTACCCTCAGCGCTGAGAGGGTTCGTGGCGATAACAAGG

AATACGAGTACAGCGTGGAGTGCCAAGAAGATAGCGCTTGTCCCGCTGC

CGAAGAATCTTTACCCATTGAGGTGATGGTGGACGCCGTGCACAAACTC

AAGTACGAGAACTACACCTCCTCCTTCTTTATCCGGGACATCATTAAGC

CCGATCCTCCTAAGAATTTACAGCTGAAGCCTCTCAAAAATAGCCGGCA

AGTTGAGGTCTCTTGGGAATATCCCGACACTTGGAGCACACCCCACAGC

TACTTCTCTTTAACCTTTTGTGTGCAAGTTCAAGGTAAAAGCAAGCGGG

AGAAGAAAGACCGGTGTTTACCGACAAAACCAGCGCCACCGTCATCTGT

CGGAAGAACGCCTCCATCAGCGTGAGGGCTCAAGATCGTTATTACTCCA

GCAGCTGGTCCGAGTGGGCCAGCGTGCCTTGTTCC

(Linker)
GGCGGTGGAGGATCCGGAGGAGGTGGCTCCGGCGGCGGAGGATCT

(Human IL-12 subunit alpha (p35))
CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC
```

-continued

```
CCGATTTTTACAAGACAAAGATCAAACTGTGCATTTTACTCCACGCCTT

TAGGATCCGGGCCGTGACCATTGACCGGGTCATGAGCTATTTAAACGCC

AGC

(Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG
```

Example 6: Creation of an IL-18/TF/IL-15 DNA Construct

Figure 18:
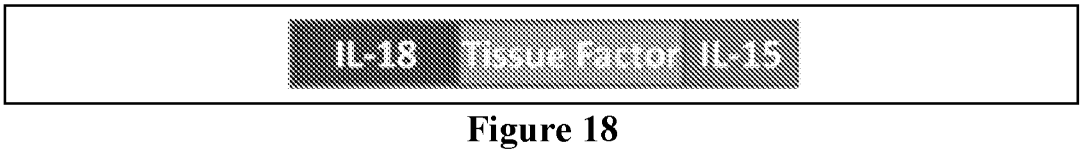
FIG. 18 shows a schematic diagram of an exemplary IL-18/TF/IL-15 DNA construct.

In a non-limiting example, an IL-18/TF/IL-15 construct was made (FIG. 18) linking the IL-18 sequence to the N-terminus coding region of tissue factor 219, and further linking the IL-18/TF construct with the N-terminus coding region of IL-15. The nucleic acid sequence of the IL-18/TF/IL-15 construct (including leader sequence), synthesized by Genewiz, is as follows (SEQ ID NO: 177):

```
(Signal peptide)
ATGAAGTGGGTCACATTTATCTCTTTACTGTTCCTCTTCTCCAGCGCCT

ACAGC

(Human IL-18)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGAT

(Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA
```

-continued

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

Example 7: Secretion of IL-12/IL-15RαSu and IL-18/TF/IL-15 Fusion Proteins

Figure 19:
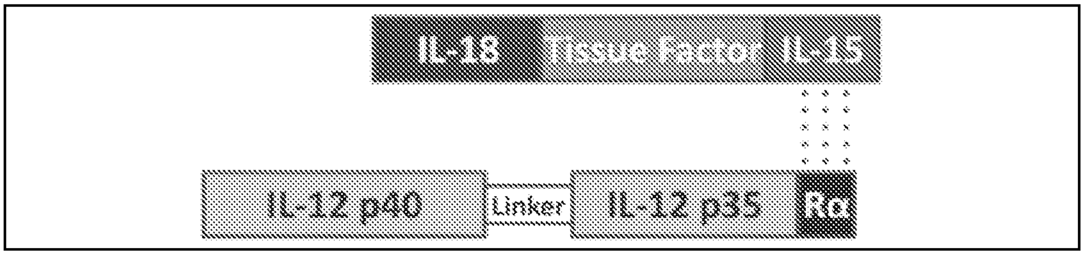
FIG. 19 shows a schematic diagram of the interaction between the exemplary IL-12/IL-15RαSu and IL-18/TF/IL-15 DNA constructs.
Figure 20:
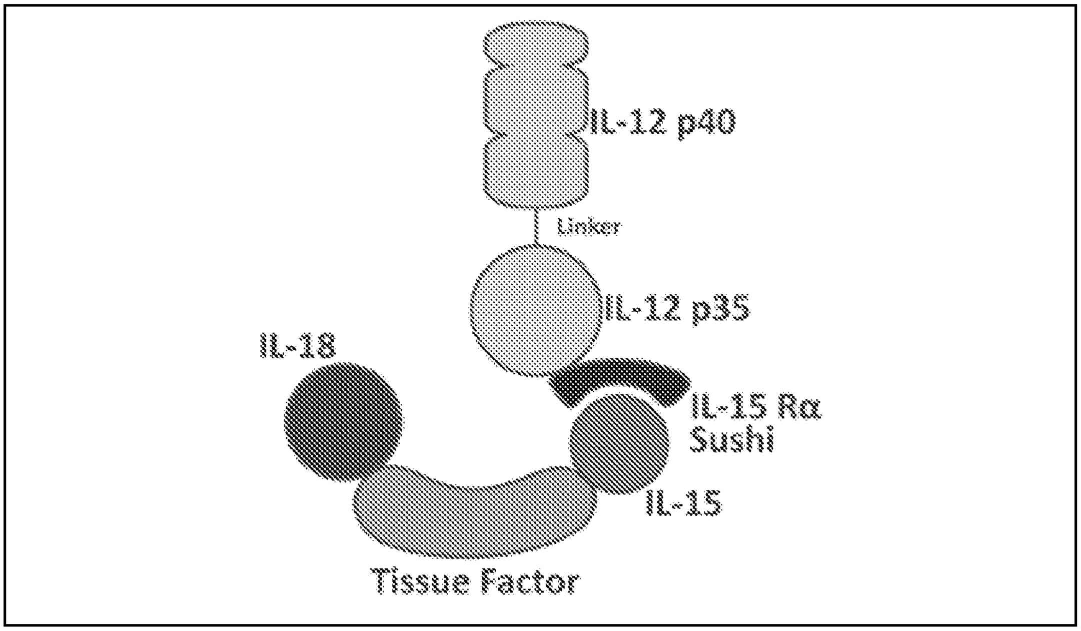
FIG. 20 shows a schematic diagram of the interaction between the exemplary IL-12/IL-15RαSu and IL-18/TF/IL-15 fusion proteins resulting in IL-18/TF/IL-15:IL-12/IL-15RαSu complex (18t15-12s).

The IL-12/IL-15RαSu and IL-18/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-18/TF/IL-15:IL-12/IL-15RαSu protein complex (referred to as 18t15-12s; FIG. 19 and FIG. 20). The 18t15-12s protein was purified from CHO-K1 cell culture supernatant using anti-TF antibody affinity chromatography and size exclusion chromatography resulting in soluble (non-aggregated) protein complexes consisting of IL-12/IL-15RαSu and IL-18/TF/IL-15 fusion proteins.

The amino acid sequence of the IL12/IL-15RαSu fusion protein (including signal peptide sequence) is as follows (SEQ ID NO: 180):

(Signal peptide)
MHWVTFISLLFLFSSAYS (Human IL-12 subunit beta (p40))
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS (Linker)
GGGGSGGGGSGGGGS (Human IL-12 subunit alpha (p35))
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS

-continued (Human IL-15R α sushi domain)
ITCPPPMSVEHADIWVKSYSLYSRERYICNSGFKRKAGTSSLTECVLNKA

TNVAHWTTPSLKCIR

The amino acid sequence of the IL-18/TF/IL-15 fusion protein (including signal peptide sequence) is as follows (SEQ ID NO: 176):

(Signal peptide)
MKWVTFISLLFLFSSAYS (Human IL-18)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

FFQRSVPGHDNKMQFESSSYEGYFLACEKERDLFKLILKKEDELGDRSIM

FTVQNED (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

In some cases, the leader (signal sequence) peptide is cleaved from the intact polypeptide to generate the mature form that may be soluble or secreted.

Example 8: Purification of 18t15-12s by Immunoaffinity Chromatography

An anti-TF antibody affinity column was connected to a GE Healthcare™ AKTA Avant protein purification system. The flow rate was 4 mL/min for all steps except the elution step, which was 2 mL/min.

Figure 21:
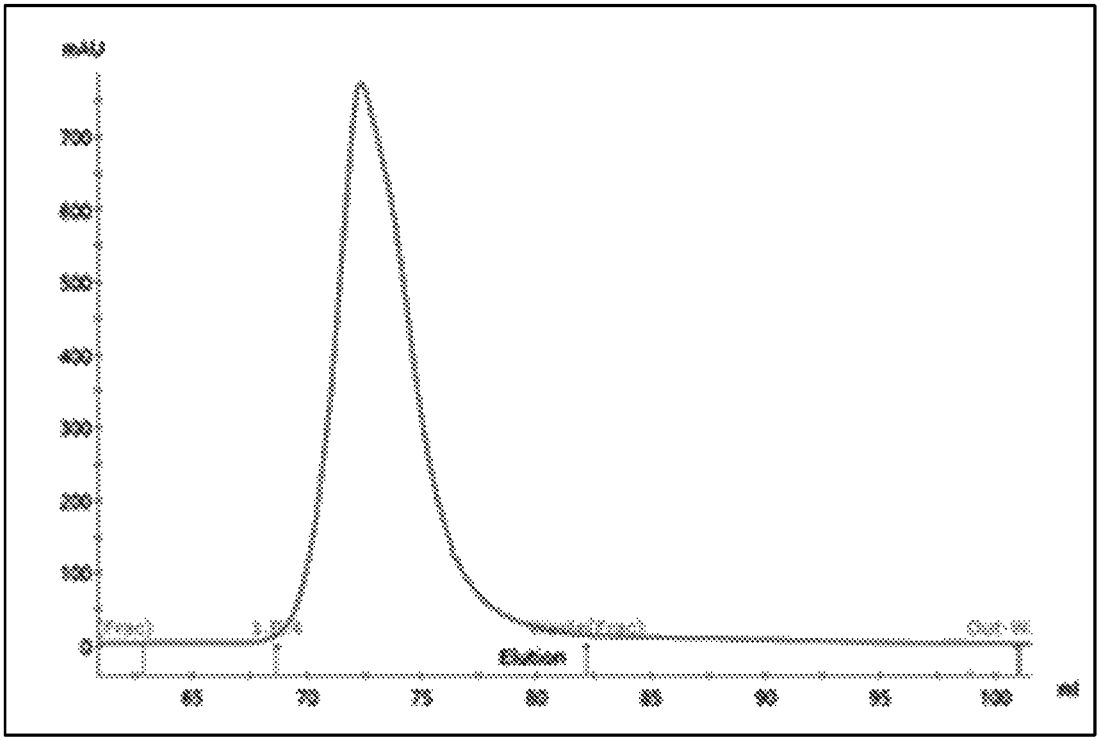
FIG. 21 shows a chromatograph of 18t15-12s purification elution from an anti-TF antibody affinity column.

Cell culture harvest of 18t15-12s was adjusted to pH 7.4 with 1 M Tris base and loaded onto the anti-TF antibody affinity column equilibrated with 5 column volumes of PBS. After loading the sample, the column was washed with 5 column volumes PBS, followed by elution with 6 column volumes 0.1 M acetic acid, pH 2.9. Absorbance at 280 nm was collected and then the sample was neutralized to pH 7.5-8.0 by adding 1 M Tris base. The neutralized sample was then buffer exchanged into PBS using Amicon® centrifugal filters with a 30 KDa molecular weight cutoff. FIG. 21 shows that the 18t15-12s complex binds the anti-TF antibody affinity column, wherein TF is an 18t15-12s binding partner. The buffer-exchanged protein sample is stored at 2-8 °C for further biochemical analysis and biological activity testing.

After each elution, the anti-TF antibody affinity column was then stripped using 6 column volumes 0.1 M glycine, pH 2.5. The column was then neutralized using 10 column volumes PBS, 0.05% sodium azide and stored at 2-8 °C.

Example 9: Size Exclusion Chromatography of 18t15-12s

Figure 22:
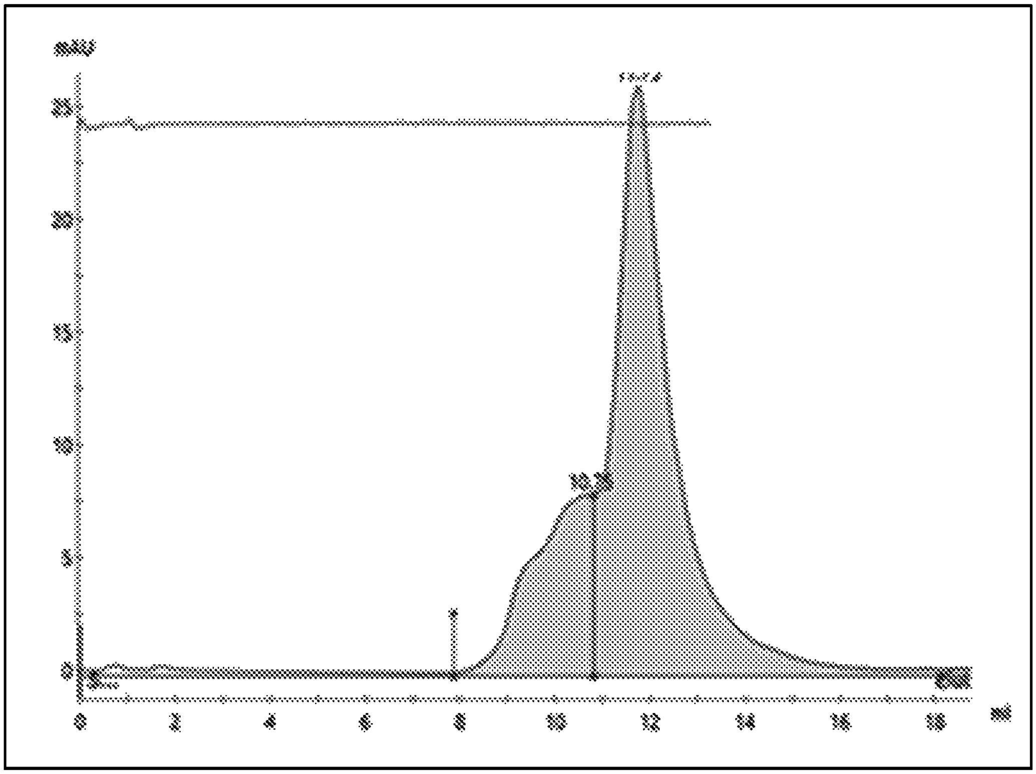
FIG. 22 shows an exemplary chromatographic profile of anti-TF Ab/SEC-purified 18t15-12s protein following elution on an analytical size exclusion column, demonstrating separation of monomeric multiprotein 18t15-12s complexes from protein aggregates.

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.8 mL/min. A capillary loop was used to inject 200 μL, of 1 mg/mL of 18t15-12s complex onto the column. The injection was chased with 1.25 column volumes of PBS. The SEC chromatograph is shown in FIG. 22. There is a main 18t15-12s protein peak with a minor high molecular weight peak, likely due to differing degrees of glycosylation of 18t15-12s dimers or aggregates.

Example 10: SDS-PAGE of 18t15-12s

Figure 23:
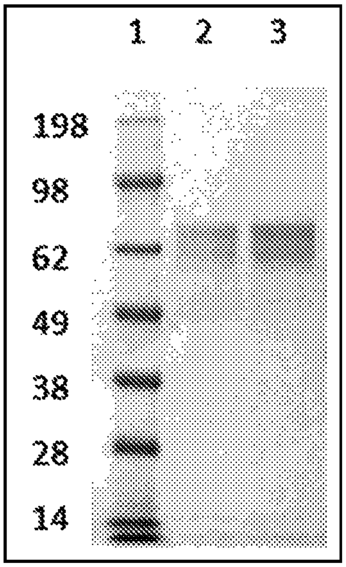
FIG. 23 shows an example of a 4-12% SDS-PAGE of the 18t15-12s complex following disulfide bond reduction. Lane 1: SeeBlue Plus2 marker; Lane 2: anti-TF Ab-purified 18t15-12s (0.5 μg); Lane 3: anti-TF Ab-purified 18t15-12s (1 μg).

To determine the purity and protein molecular weight, the purified 18t15-12s protein sample was analyzed using 4-12% NuPage Bis-Tris protein gel SDS-PAGE. The gel was stained with InstantBlue™ for about 30 min, followed by destaining overnight in purified water. FIG. 23 shows an example SDS gel of anti-TF antibody affinity purified 18t15-12s, with bands at the expected molecular weights (66 kDa and 56 kDa).

Example 11: Glycosylation of 18t15-12s in CHO-K1 Cells

Figure 24:
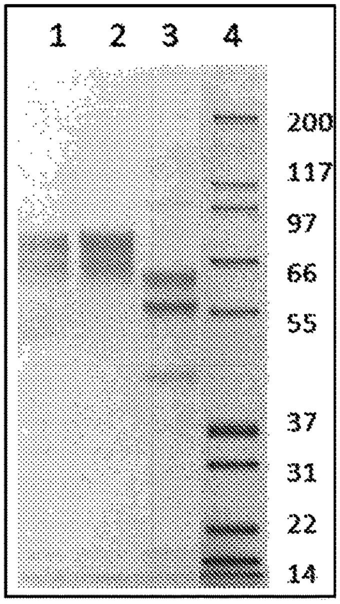
FIG. 24 shows SDS PAGE analysis of deglycosylated and non-deglycosylated 18t15-12s. Lane 1: anti-TF Ab-purified 18t15-12s (0.5 μg), non-deglycosylated; Lane 2: anti-TF Ab-purified 18t15-12s (1 μg), non-deglycosylated; Lane 3: 18t15-12s (1 μg), deglycosylated, Lane 4: Mark12 unstained maker.
Figure 25:
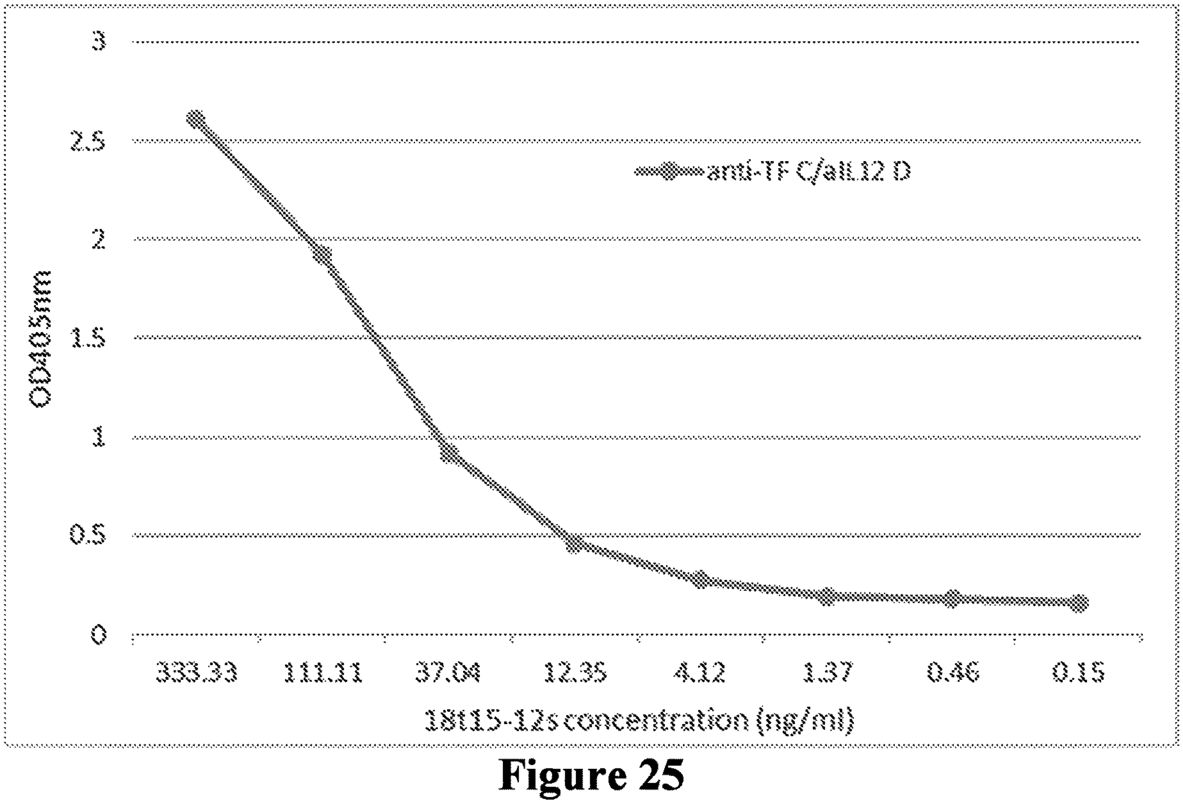
FIG. 25 shows a sandwich ELISA for the 18t15-12s complex, comprising an anti-human tissue factor antibody capture and a biotinylated anti-human IL-12 detection antibody (BAF 219).
Figure 26:
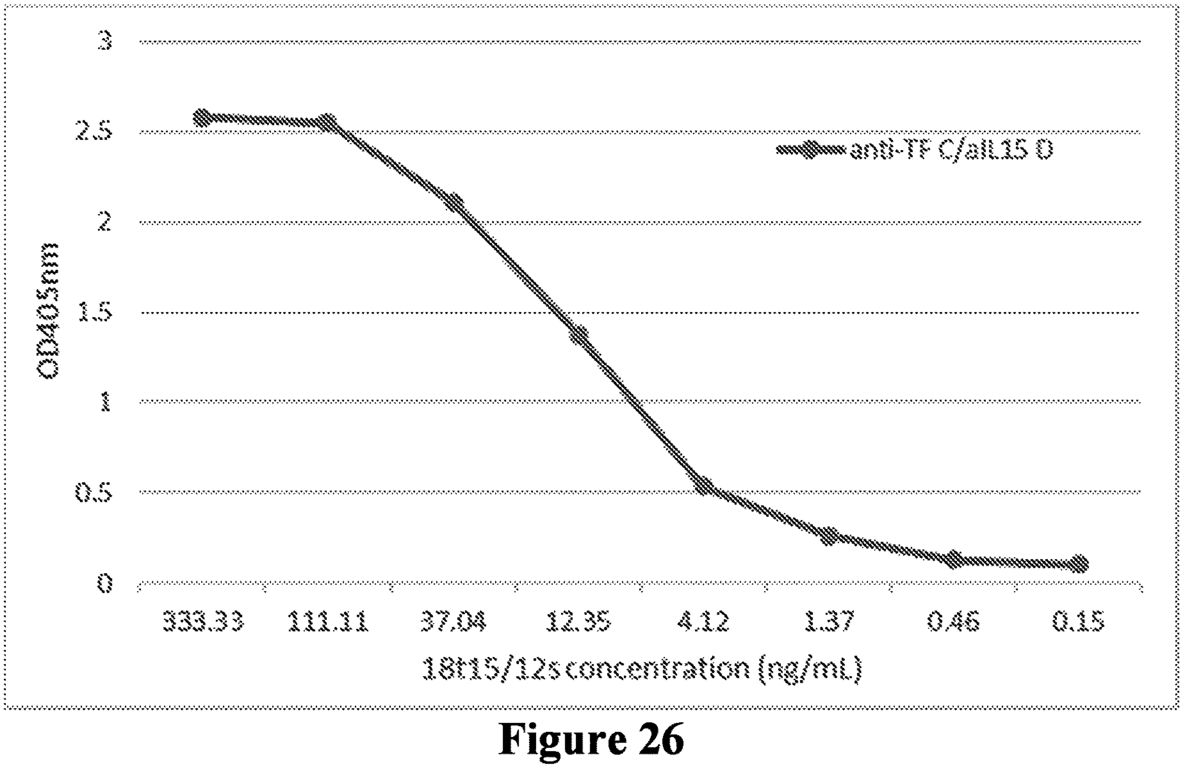
FIG. 26 shows a sandwich ELISA for the 18t15-12s complex, comprising an anti-human tissue factor antibody capture and a biotinylated anti-human IL-15 detection antibody (BAM 247).
Figure 27:
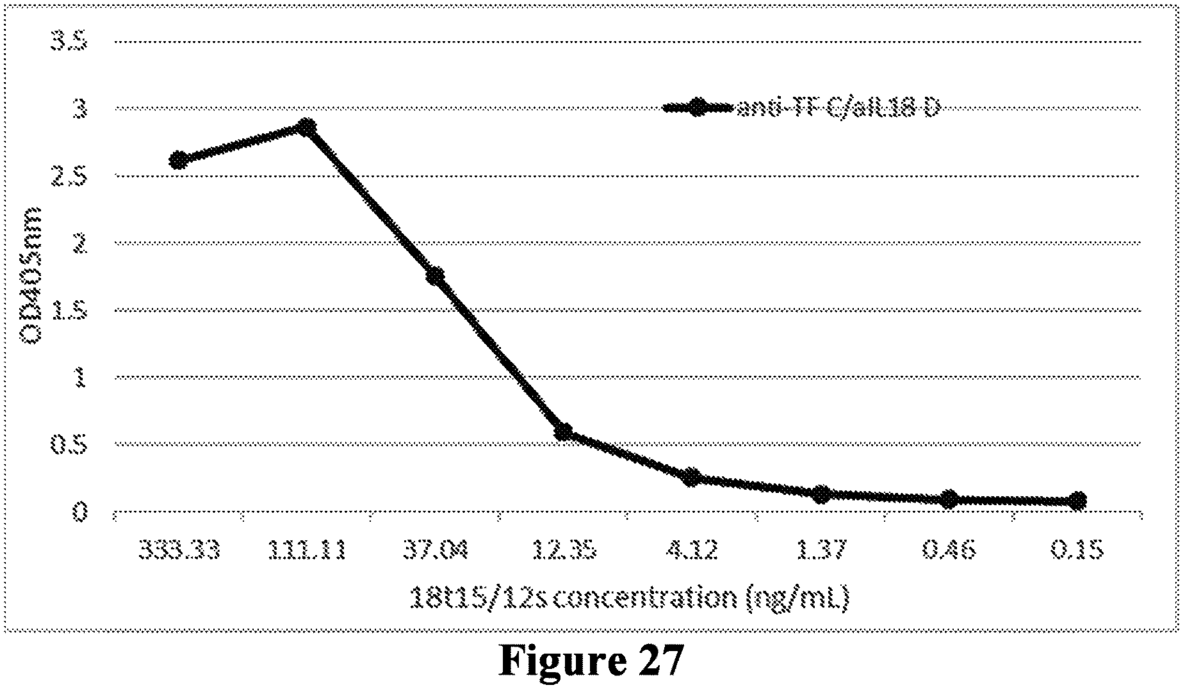
FIG. 27 shows a sandwich ELISA for the 18t15-12s complex, comprising an anti-human tissue factor antibody capture and a biotinylated anti-human IL-18 detection antibody (D045-6).
Figure 28:
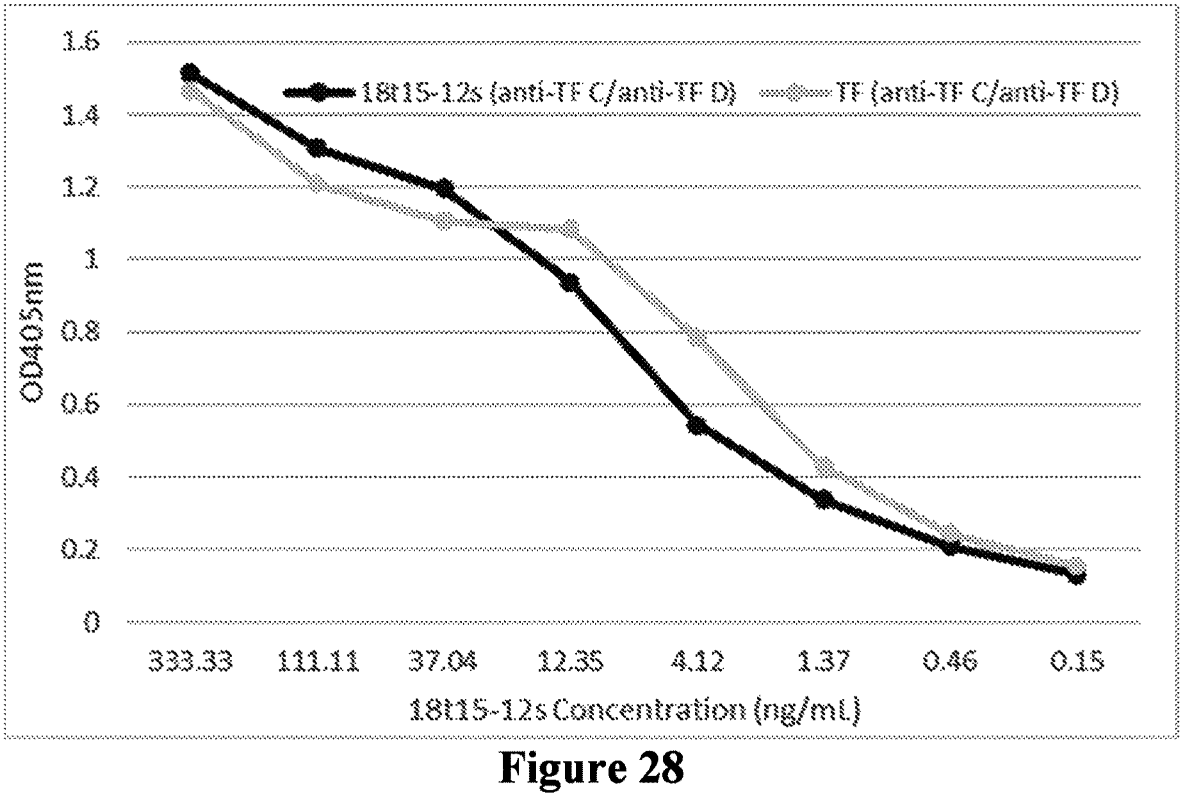
FIG. 28 shows a sandwich ELISA for the 18t15-12s complex, comprising an anti-human tissue factor (I43) capture antibody and an anti-human tissue factor detection antibody.
Figure 29:
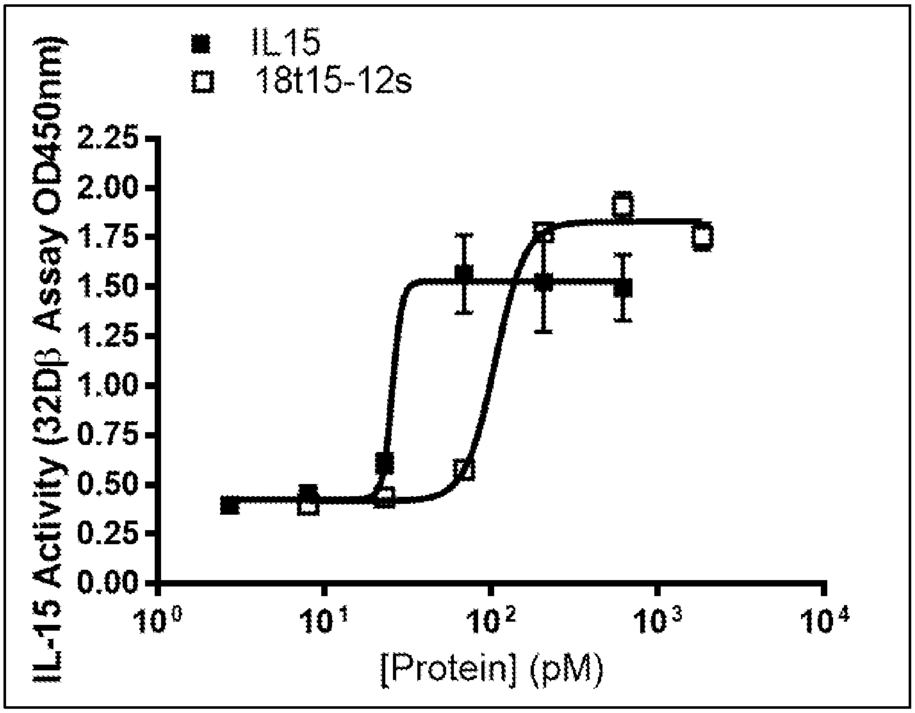
FIG. 29 shows proliferation of IL-15-dependent 32D13 cells mediated by the 18t15-12s complex (open squares) and recombinant IL-15 (black squares).

Glycosylation of 18t15-12s in CHO-K1 cells was confirmed using the Protein Deglycosylation Mix II kit (New England Biolabs), according to the manufacturer's instructions. FIG. 24 shows an example SDS PAGE of deglycosylated and non-deglycosylated 18t15-12s. Deglycosylation reduces the molecular weight of 18t15-12s as seen in FIG. 24, lane 4.

Example 12: Recombinant Protein Quantitation of 18t15-12s Complexes

The 18t15-12s complex was detected and quantified using standard sandwich ELISA methods (FIGS. 25-28). Anti-human tissue factor antibody served as the capture antibody and biotinylated anti-human IL-12, IL-15, or IL-18 antibody (BAF 219, BAM 247, D045-6, all R&D Systems) served as the detection antibody. Tissue factor in purified 18t15-12s protein complexes was also detected using an anti-human tissue factor capture antibody (I43), and anti-human tissue factor antibody detection. The I43/anti-TF antibody ELISA was compared to purified tissue factor at similar concentrations.

Example 13: Immunostimulatory Capacity of the 18t15-12s Complex

To assess the IL-15 immunostimulatory activity of the 18t15-12s complex, increasing concentrations of 18t15-12s was added to 32D13 cells (104 cell/well) in 200 μL IMDM: 10% FBS media. The 32D13 cells were incubated for 3 days at 37 °C. On the fourth day, WST-1 proliferation reagent (10 μL/well) was added and after 4 hours, absorbance was measured at 450 nm to determine cell proliferation based on cleavage of WST-1 to a soluble formazan dye. Bioactivity of human recombinant IL-15 was assessed as a positive control. As shown in FIG. 29, 18t15-12s demonstrated IL-15-dependent cell proliferation of 32D13 cells. The 18t15-12s complex demonstrated reduced activity compared to human recombinant IL-15, possibly due to the linkage of IL-18 and tissue factor to the IL-15 domain.

Figure 30:
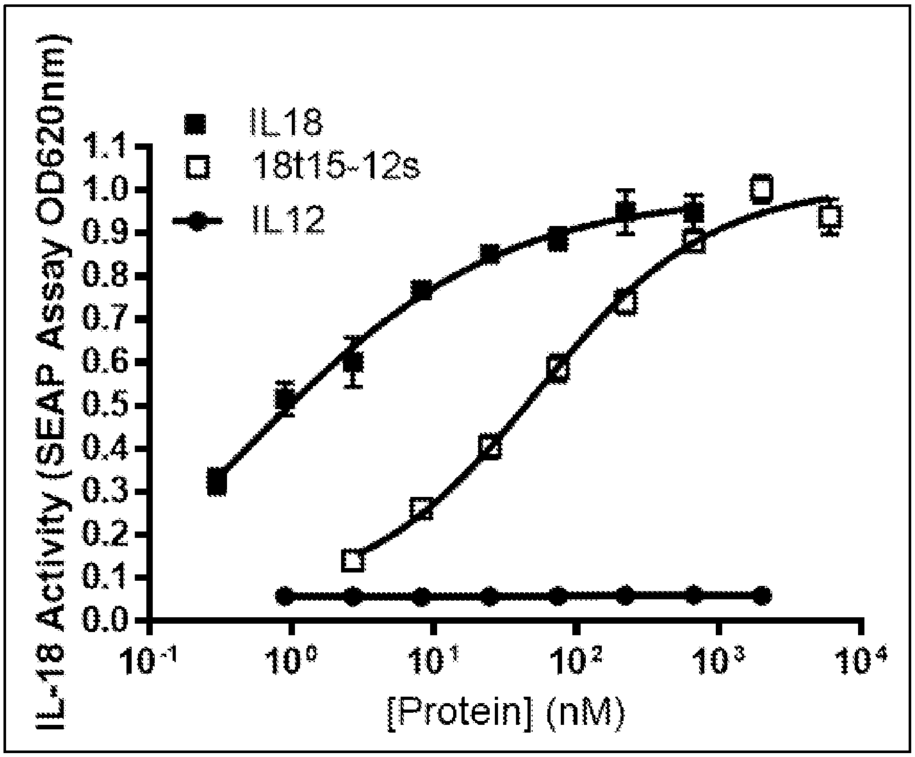
FIG. 30 shows biological activity of IL-18 within the 18t15-12s complex (open squares), where recombinant IL-18 (black squares) and recombinant IL-12 (black circles) serve as positive and negative controls, respectively.
Figure 31:
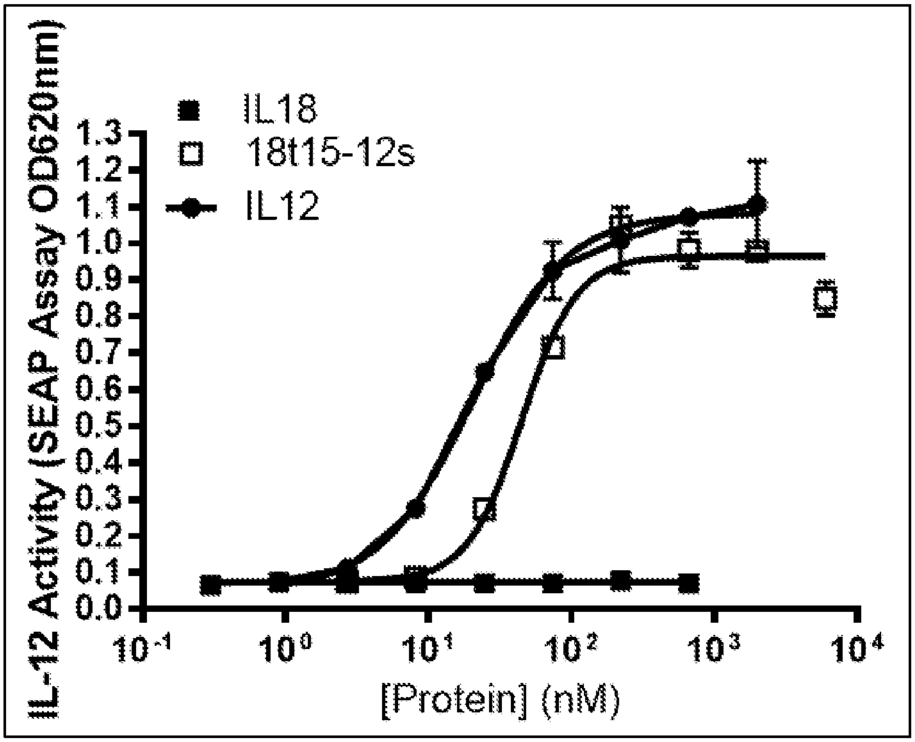
FIG. 31 shows biological activity of IL-12 within the 18t15-12s complex (open squares), where recombinant IL-12 (black circles) and recombinant IL-18 (open squares) serve as positive and negative controls, respectively.

In order to assess the individual activities of IL-12 and IL-18 in the 18t15-12s complex, 18t15-12s was added to HEK-Blue IL-12 and HEK-Blue IL-18 reporter cells ($5\times10^4$ cell/well; hkb-il12 and hkb-hmil 18, InvivoGen) in 200 μL IMDM:10% heat-inactivated FBS media. Cells were incubated for overnight at 37 °C 20 μl of induced HEK-Blue IL-12 and HEK-Blue IL-18 reporter cell supernatant was added to 180 μl of QUANTI-Blue (InvivoGen), and incubated for 1-3 hours at 37 °C. IL-12 or IL-18 activity was assessed by measuring absorbance at 620 nm. Human recombinant IL-12 or IL-18 was assessed as a positive or negative control. As shown in FIG. 30 and FIG. 31, each of the cytokine domains of the 18t15-12s complex retain specific biological activity. The activity of 18t15-12s was reduced compared to that of human recombinant IL-18 or IL-12, possibly due to linkage of IL-15 and tissue factor to the IL-18 domain and linkage of IL-12 to the IL-15Rα sushi domain.

Example 14: Induction of Cytokine-Induced Memory-Like NK Cells by the 18t15-12s Complex Cytokine-induced memory-like NK cells can be induced ex vivo following overnight stimulation of purified NK cells with saturating amounts of IL-12 (10 ng/mL), IL-15 (50 ng/mL), and IL-18 (50 ng/mL). These memory-like properties have been measured through expression of IL-2 receptor α (IL-2Rα, CD25), CD69 (and other activation markers), and increased IFN-γ production. To evaluate the ability of 18t15-12s complexes to promote generation of cytokine-induced memory-like NK cells, purified human NK cells (>95% CD56+) were stimulated for 14-18 hours with 0.01 nM to 10000 nM of the 18t15-12s complex or a combination of individual cytokines (recombinant IL-12 (10 ng/ml), IL-18 (50 ng/ml), and IL-15 (50 ng/ml)). Cell-surface CD25 and CD 69 expression and intracellular IFN-γ levels were assessed by antibody-staining and flow cytometry.

Figure 32A:
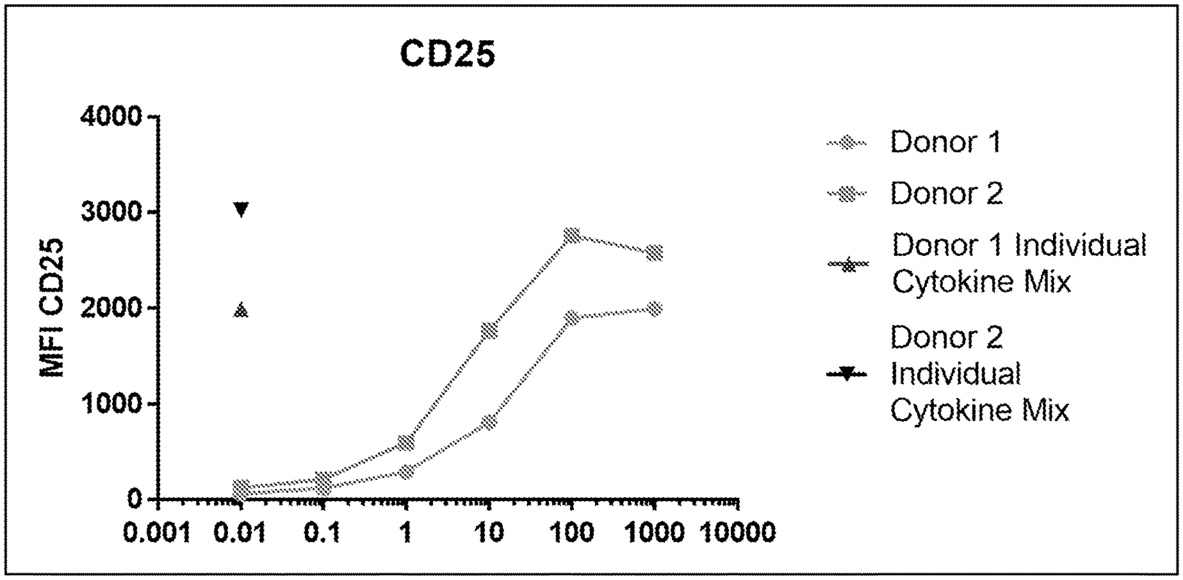
FIGS. 32A and 32B show cell-surface expression of CD25 on NK cells induced by the 18t15-12s complex and cell-surface CD69 expression of NK cells induced by the 18t15-12s complex.
Figure 32B:
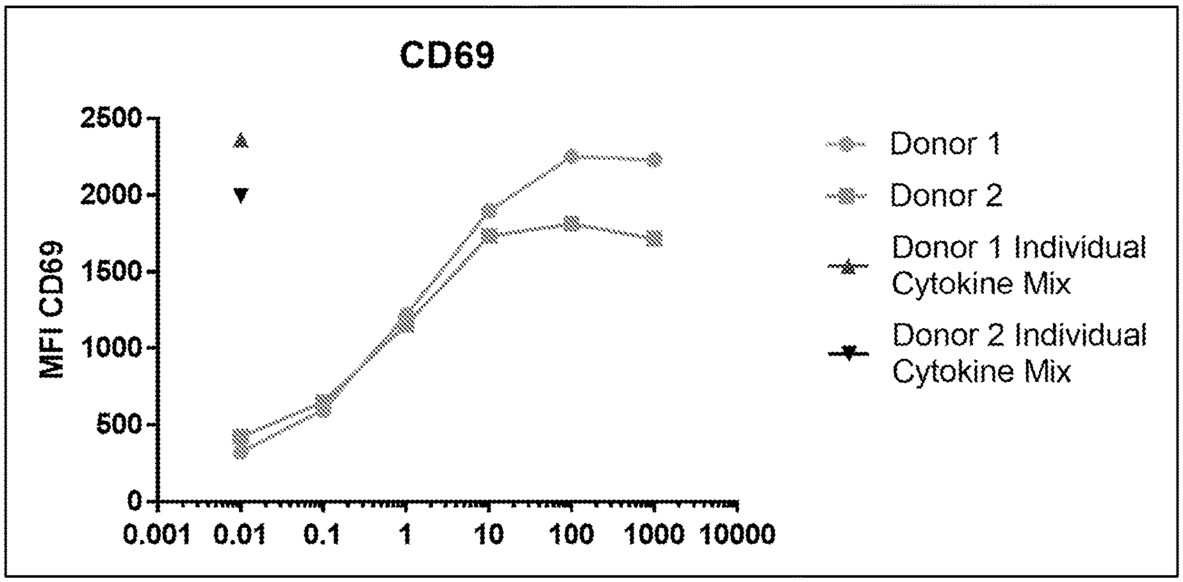

Fresh human leukocytes were obtained from a blood bank and CD56+NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in $0.2\times10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either a mixture of cytokines hIL-12 (10 ng/mL) (Biolegend), hIL-18 (50 ng/mL) (R&D Systems) and hIL-(50 ng/mL) (NCI) or with 0.01 nM to 10000 nM of the 18t15-12s at 37 °C, 5% $CO_2$ for 14-18 hrs. The cells were then harvested and surface stained for CD56-BV421, CD16-BV510, CD25-PE, CD69-APCFire750 specific antibodies (BioLegend) for 30 minutes. After staining, cells were washed (1500 RPM for 5 minutes at room temperature) in FACS buffer (1×PBS (Hyclone), with 0.5% BSA (EMD Millipore) and 0.001% sodium azide (Sigma)). After two washes, cells were analyzed using a BD FACS-Celesta™ flow cytometer (Plotted Data-Mean Fluorescence Intensity; FIG. 32A and FIG. 32B).

Figure 33:
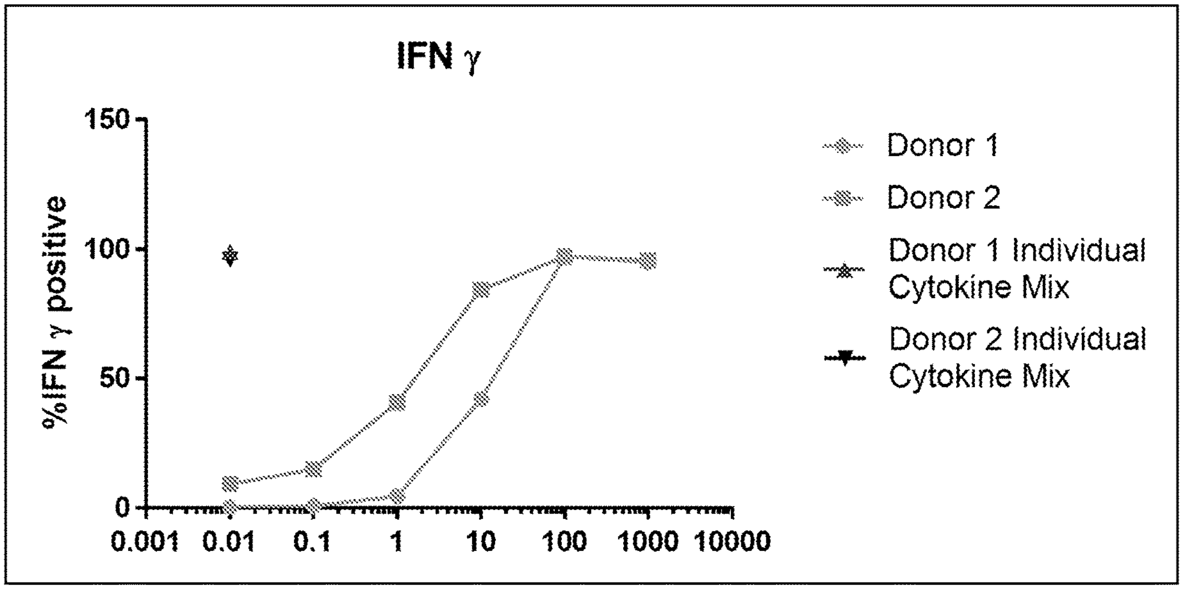
FIG. 33 shows a flow cytometry graph of intracellular IFN-γ expression of NK cells induced by the 18t15-12s complex.

Fresh human leukocytes were obtained from a blood bank and CD56+NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in $0.2\times10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either a cytokine mix of hIL-12 (10 ng/mL) (Biolegend), hIL-18 (50 ng/mL) (R&D), and hIL-15 (50 ng/mL) (NCI), or 0.01 nM to 10000 nM of the 18t15-12s complex at 37 °C, 5% $CO_2$ for 14-18 hrs. The cells were then treated with 10 μg/mL of Brefeldin A (Sigma) and 1× of Monensin (eBioscience) for 4 hrs before harvesting and staining for CD56-BV421, CD16-BV510, CD25-PE, CD69-APCFire750 specific antibodies for 30 minutes. After staining, cells were washed (1500 RPM for 5 minutes in room temperature) in FACS buffer (1×PBS (Hyclone), with 0.5% BSA (EMD Millipore) and 0.001% sodium azide (Sigma)) and fixed for 10 minutes at room temperature. After fixation, cells were washed (1500 RPM for 5 minutes in room temperature) in 1× permeabilized buffer (eBioscience) and stained with IFN-γ-PE (Biolegend) for 30 minutes at room temperature. Cells were washed once again with 1× permeabilized buffer and then washed with FACS buffer. Cell pellets were resuspended in 300 μls of FACS buffer and analyzed using a BD FACSCelesta™ flow cytometer (Plotted % of IFN-γ Positive Cells; FIG. 33).

Example 15: In Vitro Cytotoxicity of NK Cells Against Human Tumor Cells

Figure 34:
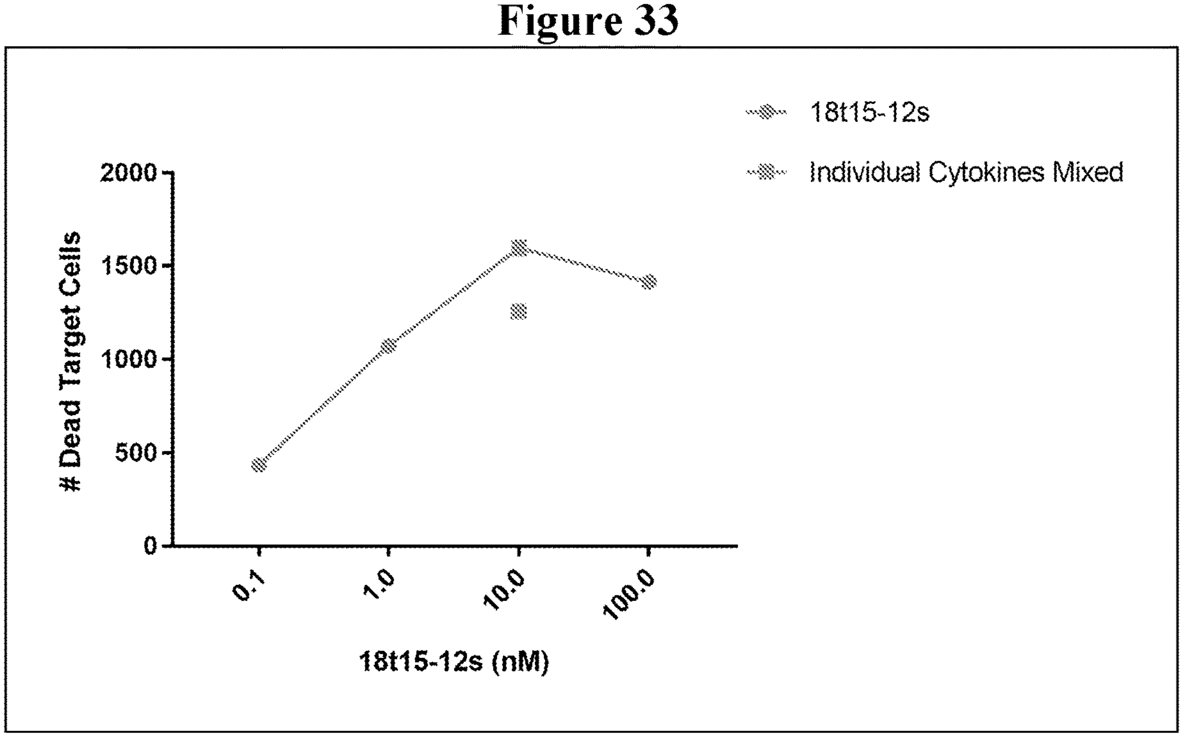
FIG. 34 shows cytotoxicity of 18t15-12s induced human NK cells against K562 cells.

Human myelogenous leukemia cells, K562 (CellTrace violet labelled), were incubated with purified human NK cells in the presence of increasing concentrations of the 18t15-12s complex or a mixture of cytokines as a control. After 20 hours, the cultures were harvested, stained with propidium iodide (PI), and assessed by flow cytometry. As shown in FIG. 34, the 18t15-12s complex induced human NK cytotoxicity against K562, at levels similar or greater than the cytokine mixture, wherein both the 18t15-12s complex and the cytokine mixture induced greater cytotoxicity than the medium control.

Figure 35:
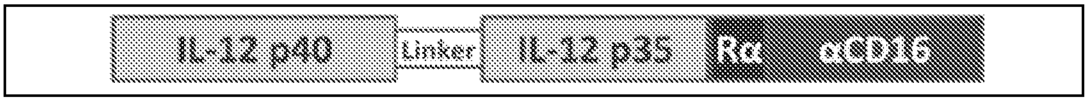
FIG. 35 shows a schematic diagram of an exemplary IL-12/IL-15RαSu/αCD16 DNA construct.
Figure 36:
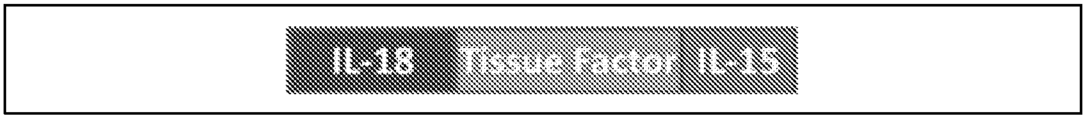
FIG. 36 shows a schematic diagram of an exemplary IL-18/TF/IL-15 DNA construct.

Example 16: Creation of IL-12/IL-15RαSu/aCD16scFv and IL-18/TF/IL-15 DNA Constructs In a non-limiting example, IL-12/IL-15RαSu/aCD16scFv and IL-18/TF/IL-15 DNA constructs were created (FIG. 35 and FIG. 36). The human IL-12 subunit sequences, human IL-15RαSu sequence, human IL-15 sequence, human tissue factor 219 sequence, and human IL-18 sequence were synthesized by Genewiz. A DNA construct was made linking the IL-12 subunit beta (p40) to IL-12 subunit alpha (p35) with a GS (3) linker to generate a single chain version of IL-12, directly linking the IL-12 sequence to the IL-15RαSu sequence, and directly linking the IL-12/IL-15RαSu construct to the N-terminus coding region of aCD16scFv.

The nucleic acid sequence of the IL-12/IL-15RαSu/aCD16scFv construct is as follows (SEQ ID NO: 226):

```
(Signal peptide)
ATGAAATGGGTGACCTTTATTTCTTTACTGTTCCTCTTTAGCAGCGCCTAC

TCC
```

-continued

```
(Human IL-12 subunit beta (p40))
ATTTGGGAACTGAAGAAGGACGTCTACGTGGTCGAACTGGACTGGTATCCC

TGCTCCCGGCGAAATGGTGGTGCTCACTTGTGACACCCCCGAAGAAGGAAC

GGCATCACTTGGACCCTCGATCAGAGCAGCGAGGTGCTGGGCTCCGGAAAG

ACCCTCACAATCCAAGTTAAGGAGTTCGGAGACGCTGGCCAATACACATGC

CACAAGGGAGGCGAGGTGCTCAGCCATTCCTTATTATTATTACACAAGAAG

GAAGACGGAATCTGGTCCACCGACATTTTAAAAGATCAGAAGGAGCCCAAG

AATAAGACCTTTTTAAGGTGTGAGGCCAAAAACTACAGCGGTCGTTTCACT

TGTTGGTGGCTGACCACCATTTCCACCGATTTAACCTTCTCCGTGAAAAGC

AGCCGGGGAAGCTCCGACCCTCAAGGTGTGACATGTGGAGCCGCTACCCTC

AGCGCTGAGAGGGTTCGTGGCGATAACAAGGAATACGAGTACAGCGTGGAG

TGCCAAGAAGATAGCGCTTGTCCCGCTGCCGAAGAATCTTTACCCATTGAG

GTGATGGTGGACGCCGTGCACAAACTCAAGTACGAGAACTACACCTCCTCC

TTCTTTATCCGGGACATCATTAAGCCCGATCCTCCTAAGAATTTACAGCTG

AAGCCTCTCAAAAATAGCCGGCAAGTTGAGGTCTCTTGGGAATATCCCGAC

ACTTGGAGCACACCCCACAGCTACTTCTCTTTAACCTTTTGTGTGCAAGTT

CAAGGTAAAAGCAAGCGGGAGAAGAAAGACCGGGTGTTTACCGACAAAACC

AGCGCCACCGTCATCTGTCGGAAGAACGCCTCCATCAGCGTGAGGGCTCAA

GATCGTTATTACTCCAGCAGCTGGTCCGAGTGGGCCAGCGTGCCTTGTTCC

(Linker)
GGCGGTGGAGGATCCGGAGGAGGTGGCTCCGGCGGCGGAGGATCT

(Human IL-12 subunit alpha (p35))
CGTAACCTCCCCGTGGCTACCCCCGATCCCGGAATGTTCCCTTGTTTACAC

CACAGCCAGAATTTACTGAGGGCCGTGAGCAACATGCTGCAGAAAGCTAGG

CAGACTTTAGAATTTTACCCTTGCACCAGCGAGGAGATCGACCATGAAGAT

ATCACCAAGGACAAGACATCCACCGTGGAGGCTTGTTTACCTCTGGAGCTG

ACAAAGAACGAGTCTTGTCTCAACTCTCGTGAAACCAGCTTCATCACAAAT

GGCTCTTGTTTAGCTTCCCGGAAGACCTCCTTTATGATGGCTTTATGCCTC

AGCTCCATCTACGAGGATTTAAAGATGTACCAAGTGGAGTTCAAGACCATG

AACGCCAAGCTGCTCATGGACCCTAAACGGCAGATCTTTTTAGACCAGAAC

ATGCTGGCTGTGATTGATGAGCTGATGCAAGCTTTAAACTTCAACTCCGAG

ACCGTCCCTCAGAAGTCCTCCCTCGAGGAGCCCGATTTTTACAAGACAAAG

ATCAAACTGTGCATTTTACTCCACGCCTTTAGGATCCGGGCCGTGACCATT

GACCGGGTCATGAGCTATTTAAACGCCAGC

(Human IL-15R α sushi domain)
ATTACATGCCCCCCTCCCATGAGCGTGGAGCACGCCGACATCTGGGTGAAG

GACTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG

(anti-Human CD16 light chain variable domain)
TCCGAGCTGACCCAGGACCCTGCTGTGTCCGTGGCTCTGGGCCAGACCGTG

AGGATCACCTGCCAGGGCGACTCCCTGAGGTCCTACTACGCCTCCTGGTAC

CAGCAGAAGCCCGGCCAGGCTCCTGTGCTGGTGATCTACGGCAAGAACAAC
```

-continued

AGGCCCTCCGGCATCCCTGACAGGTTCTCCGGATCCTCCTCCGGCAACACC

GCCTCCCTGACCATCACAGGCGCTCAGGCCGAGGACGAGGCTGACTACTAC

TGCAACTCCAGGGACTCCTCCGGCAACCATGTGGTGTTCGGCGGCGGCACC

AAGCTGACCGTGGGCCAT (Linker)
GGCGGCGGCGGCTCCGGAGGCGGCGGCAGCGGCGGAGGAGGATCC (anti-Human CD16 heavy chain variable domain)
GAGGTGCAGCTGGTGGAGTCCGGAGGAGGAGTGGTGAGGCCTGGAGGCTCC

CTGAGGCTGAGCTGTGCTGCCTCCGGCTTCACCTTCGACGACTACGGCATG

TCCTGGGTGAGGCAGGCTCCTGGAAAGGGCCTGGAGTGGGTGTCCGGCATC

AACTGGAACGGCGGATCCACCGGCTACGCCGATTCCGTGAAGGGCAGGTTC

ACCATCAGCAGGGACAACGCCAAGAACTCCCTGTACCTGCAGATGAACTCC

CTGAGGGCCGAGGACACCGCCGTGTACTACTGCGCCAGGGGCAGGTCCCTG

CTGTTCGACTACTGGGGACAGGGCACCCTGGTGACCGTGTCCAGG

Constructs were also made linking the IL-18 sequence to the N-terminus coding region of tissue factor 219, and linking the IL-18/TF construct with the N-terminus coding region of IL-15 (FIG. 36). The nucleic acid sequence of the IL-18/TF/IL-15 construct (including leader sequence) is as follows (SEQ ID NO: 177):

(Signal peptide)
ATGAAGTGGGTCACATTTATCTCTTTACTGTTCCTCTTCTCCAGCGCCTAC

AGC (Human IL-18)
TACTTCGGCAAACTGGAATCCAAGCTGAGCGTGATCCGGAATTTAAACGAC

CAAGTTCTGTTTATCGATCAAGGTAACCGGCCTCTGTTCGAGGACATGACC

GACTCCGATTGCCGGGACAATGCCCCCCGGACCATCTTCATTATCTCCATG

TACAAGGACAGCCAGCCCCGGGGCATGGCTGTGACAATTAGCGTGAAGTGT

GAGAAAATCAGCACTTTATCTTGTGAGAACAAGATCATCTCCTTTAAGGAA

ATGAACCCCCCCGATAACATCAAGGACACCAAGTCCGATATCATCTTCTTC

CAGCGGTCCGTGCCCGGTCACGATAACAAGATGCAGTTCGAATCCTCCTCC

TACGAGGGCTACTTTTTAGCTTGTGAAAAGGAGAGGGATTTATTCAAGCTG

ATCCTCAAGAAGGAGGACGAGCTGGGCGATCGTTCCATCATGTTCACCGTC

CAAAACGAGGAT (Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

-continued

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC

Figure 37:
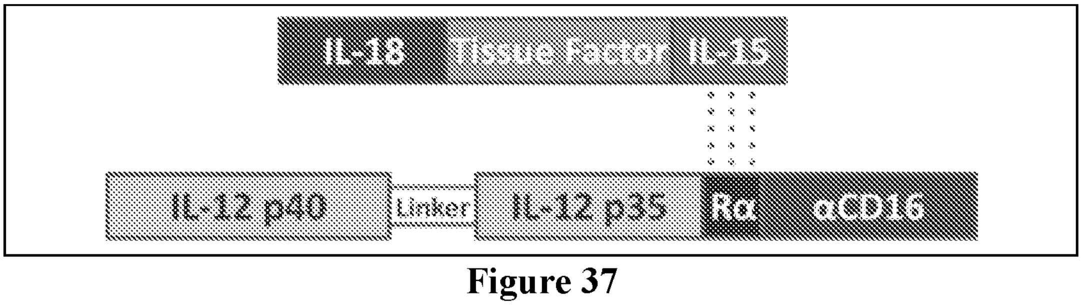
FIG. 37 shows a schematic diagram of the interaction between the exemplary IL-12/IL-15RαSu/αCD16scFv and IL-18/TF/IL-15 DNA constructs.
Figure 38:
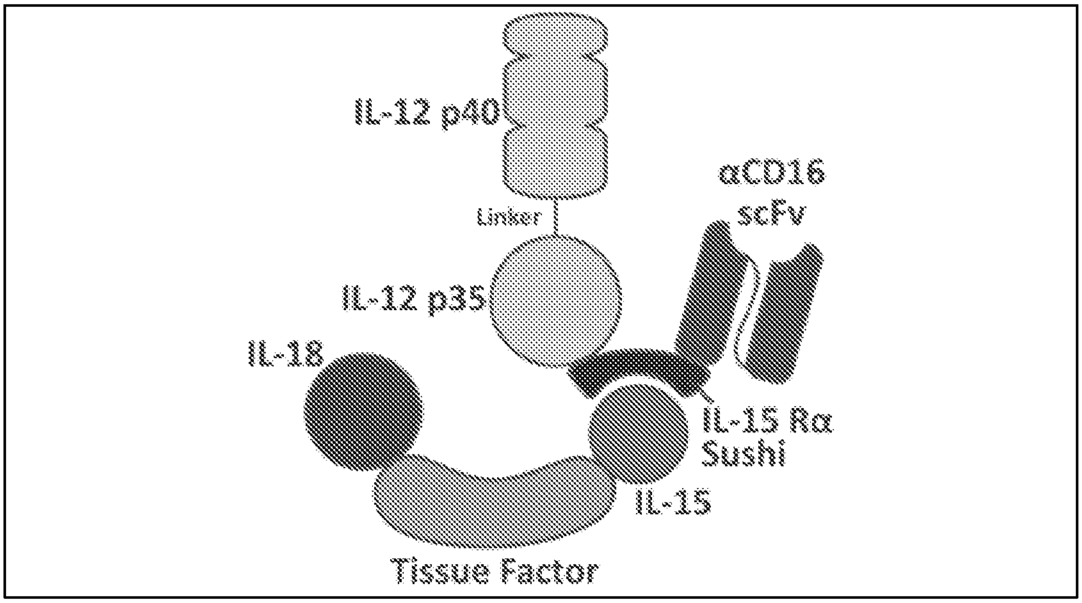
FIG. 38 shows a schematic diagram of an exemplary 18t15-12s/αCD16 protein complex.

Example 17: Secretion of IL-12/IL-15RαSu/aCD16scFv and IL-18/TF/IL-15 Fusion Proteins The IL-12/IL-15RαSu/aCD16scFv and IL-18/TF/IL-15 constructs were cloned into a pMSGV-1 modified retrovirus expression vector (Hughes, *Hum Gene Ther* 16:457-72, 2005, herein incorporated by reference), and the expression vector was transfected into CHO-K1 cells. Co-expression of the two constructs in CHO-K1 cells resulted in secretion of a soluble IL-18/TF/IL-15:IL-12/IL-15RαSu/aCD16scFv protein complex (referred to as 18t15-12s/aCD16; FIG. 37 and FIG. 38). Co-expression of the two constructs in CHO-K1 cells resulted in secretion of the soluble IL-18/TF/IL-15:IL-12/IL-15RαSu/aCD16scFv protein complex (referred to as 18t15-12s/aCD16; FIG. 37 and FIG. 38), which can be purified by anti-TF Ab affinity and other chromatography methods. In some cases, the signal peptide is cleaved from the intact polypeptide to generate the mature form.

The amino acid sequence of the IL-12/IL-15RαSu/aCD16scFv fusion protein (including signal peptide sequence) is as follows (SEQ ID NO: 225):

(Signal peptide)
MKWVTFISLLFLFSSAYS (Human IL-12 subunit beta (p40))
IWELKKDVYVVELDWYPDAPGEMVVLTCDTPEEDGITWTLDQSSEVLGSG

KTLTIQVKEFGDAGQYTCHKGGEVLSHSLLLLHKKEDGIWSTDILKDQKE

PKNKTFLRCEAKNYSGRFTCWWLTTISTDLTFSVKSSRGSSDPQGVTCGA

ATLSAERVRGDNKEYEYSVECQEDSACPAAEESLPIEVMVDAVHKLKYEN

YTSSFFIRDIIKPDPPKNLQLKPLKNSRQVEVSWEYPDTWSTPHSYFSLT

FCVQVQGKSKREKKDRVFTDKTSATVICRKNASISVRAQDRYYSSSWSEW

ASVPCS

-continued (Linker)
GGGGSGGGGSGGGGS (Human IL-12 subunit alpha (p35))
RNLPVATPDPGMFPCLHHSQNLLRAVSNMLQKARQTLEFYPCTSEEIDHE

DITKDKTSTVEACLPLELTKNESCLNSRETSFITNGSCLASRKTSFMMAL

CLSSIYEDLKMYQVEFKTMNAKLLMDPKRQIFLDQNMLAVIDELMQALNF

NSETVPQKSSLEEPDFYKTKIKLCILLHAFRIRAVTIDRVMSYLNAS (Human IL-15R α sushi domain)
ITCPPPMSVEHADIWVKSYSLYSRERYICNSGFKRKAGTSSLTECVLNKA

TNVAHWTTPSLKCIR (anti-Human CD16 light chain variable domain)
SELTQDPAVSVALGQTVRITCQGDSLRSYYASWYQQKPGQAPVLVIYGKN

NRPSGIPDRFSGSSSGNTASLTITGAQAEDEADYYCNSRDSSGNHVVFGG

GTKLTVGH (Linker)
GGGGSGGGGSGGGGS (anti-Human CD16 heavy chain variable domain)
EVQLVESGGGVVRPGGSLRLSCAASGFTFDDYGMSWVRQAPGKGLEWVSG

INWNGGSTGYADSVKGRFTISRDNAKNSLYLQMNSLRAEDTAVYYCARGR

SLLFDYWGQGTLVTVSR

The amino acid sequence of the IL-18/TF/IL-15 fusion protein (including leader sequence) is as follows (SEQ ID NO: 221):

(Signal peptide)
MKWVTFISLLFLFSSAYS (Human IL-18)
YFGKLESKLSVIRNLNDQVLFIDQGNRPLFEDMTDSDCRDNAPRTIFIIS

MYKDSQPRGMAVTISVKCEKISTLSCENKIISFKEMNPPDNIKDTKSDII

FFQRSVPGHDNKMQFESSSYEGYFLACEKERDLFKLILKKEDELGDRSIM

FTVQNED (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVIS

LESGDASIHDTVENLIIILANNSLSSNGNVTESGCKECEELEEKNIKEFLQS

FVHIVQMFINTS

Example 18: Creation of IL-18/IL-15RαSu and IL-12/TF/IL-15 DNA Constructs

In a non-limiting example, IL-18/IL-15RαSu and IL-12/TF/IL-15 DNA constructs were created. The human IL-18 subunit sequences, human IL-15RαSu sequence, human IL-12 sequence, human tissue factor 219 sequence, and human IL-15 sequence were synthesized by Genewiz. A DNA construct was made linking IL-18 directly to IL-15RαSu. An additional construct was also made linking IL-12 sequence to the N-terminus coding region of human tissue factor 219 form, and further linking the IL-12/TF construct to the N-terminus coding region of IL-15. As described above, a single-chain version of IL-12 (p40-linker-p35) was used.

The nucleic acid sequence of the IL-18/IL-15RαSu construct (including signal peptide sequence) is as follows (SEQ ID NO: 320):

(Signal peptide)
ATGAAGTGGGTCACATTTATCTCTTTACTGTTCCTCTTCTCCAGCGCCTA

CAGC (Human IL-18)
TACTTCGGCAAACTGGAATCCAAGCTGAGCGTGATCCGGAATTTAAACGA

CCAAGTTCTGTTTATCGATCAAGGTAACCGGCCTCTGTTCGAGGACATGA

CCGACTCCGATTGCCGGGACAATGCCCCCCGGACCATCTTCATTATCTCC

ATGTACAAGGACAGCCAGCCCCGGGGCATGGCTGTGACAATTAGCGTGAA

GTGTGAGAAAATCAGCACTTTATCTTGTGAGAACAAGATCATCTCCTTTA

AGGAAATGAACCCCCCCGATAACATCAAGGACACCAAGTCCGATATCATC

TTCTTCCAGCGGTCCGTGCCCGGTCACGATAACAAGATGCAGTTCGAATC

CTCCTCCTACGAGGGCTACTTTTTAGCTTGTGAAAAGGAGAGGGATTTAT

TCAAGCTGATCCTCAAGAAGGAGGACGAGCTGGGCGATCGTTCCATCATG

TTCACCGTCCAAAACGAGGAT (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG

The nucleic acid sequence of the IL-12/TF/IL-15 construct (including leader sequence) is as follows (SEQ ID NO: 321):

(Signal peptide)
ATGAAATGGGTGACCTTTATTTCTTTACTGTTCCTCTTTAGCAGCGCCTA

CTCC (Human IL-12 subunit beta (p40))
ATTTGGGAACTGAAGAAGGACGTCTACGTGGTCGAACTGGACTGGTATCC

CGATGCTCCCGGCGAAATGGTGGTGCTCACTTGTGACACCCCCGAAGAAG

ACGGCATCACTTGGACCCTCGATCAGAGCAGCGAGGTGCTGGGCTCCGGA

AAGACCCTCACAATCCAAGTTAAGGAGTTCGGAGACGCTGGCCAATACAC

ATGCCACAAGGGAGGCGAGGTGCTCAGCCATTCCTTATTATTATTACACA

AGAAGGAAGACGGAATCTGGTCCACCGACATTTTAAAAGATCAGAAGGAG

CCCAAGAATAAGACCTTTTTAAGGTGTGAGGCCAAAAACTACAGCGGTCG

TTTCACTTGTTGGTGGCTGACCACCATTTCCACCGATTTAACCTTCTCCG

TGAAAAGCAGCCGGGGAAGCTCCGACCCTCAAGGTGTGACATGTGGAGCC

GCTACCCTCAGCGCTGAGAGGGTTCGTGGCGATAACAAGGAATACGAGTA

-continued

CAGCGTGGAGTGCCAAGAAGATAGCGCTTGTCCCGCTGCCGAAGAATCTT

TACCCATTGAGGTGATGGTGGACGCCGTGCACAAACTCAAGTACGAGAAC

TACACCTCCTCCTTCTTTATCCGGGACATCATTAAGCCCGATCCTCCTAA

GAATTTACAGCTGAAGCCTCTCAAAAATAGCCGGCAAGTTGAGGTCTCTT

GGGAATATCCCGACACTTGGAGCACACCCCACAGCTACTTCTCTTTAACC

TTTTGTGTGCAAGTTCAAGGTAAAAGCAAGCGGGAGAAGAAAGACCGGGT

GTTTACCGACAAAACCAGCGCCACCGTCATCTGTCGGAAGAACGCCTCCA

TCAGCGTGAGGGCTCAAGATCGTTATTACTCCAGCAGCTGGTCCGAGTGG

GCCAGCGTGCCTTGTTCC (Linker)
GGCGGTGGAGGATCCGGAGGAGGTGGCTCCGGCGGCGGAGGATCT (Human IL-12 subunit alpha (p35))
CGTAACCTCCCCGTGGCTACCCCCGATCCCGGAATGTTCCCTTGTTTACA

CCACAGCCAGAATTTACTGAGGGCCGTGAGCAACATGCTGCAGAAAGCTA

GGCAGACTTTAGAATTTTACCCTTGCACCAGCGAGGAGATCGACCATGAA

GATATCACCAAGGACAAGACATCCACCGTGGAGGCTTGTTTACCTCTGGA

GCTGACAAAGAACGAGTCTTGTCTCAACTCTCGTGAAACCAGCTTCATCA

CAAATGGCTCTTGTTTAGCTTCCCGGAAGACCTCCTTTATGATGGCTTTA

TGCCTCAGCTCCATCTACGAGGATTTAAAGATGTACCAAGTGGAGTTCAA

GACCATGAACGCCAAGCTGCTCATGGACCCTAAACGGCAGATCTTTTTAG

ACCAGAACATGCTGGCTGTGATTGATGAGCTGATGCAAGCTTTAAACTTC

AACTCCGAGACCGTCCCTCAGAAGTCCTCCCTCGAGGAGCCCGATTTTTA

CAAGACAAAGATCAAACTGTGCATTTTACTCCACGCCTTTAGGATCCGGG

CCGTGACCATTGACCGGGTCATGAGCTATTTAAACGCCAGC (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

-continued

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

Example 19: Secretion of IL-18/IL-15RαSu and IL-12/TF/IL-15 Fusion Proteins

The IL-18/IL-15RαSu and IL-12/TF/IL-15 constructs were cloned into a pMSGV-1 modified retrovirus expression vector (Hughes, *Hum Gene Ther* 16:457-72, 2005 herein incorporated by reference), and the expression vector was transfected into CHO-K1 cells. Co-expression of the two constructs in CHO-K1 cells resulted in secretion of a soluble IL-12/TF/IL-15:IL-18/IL-15RαSu protein complex (referred to as 12t15/s18), which can be purified by anti-TF Ab affinity and other chromatography methods.

The amino acid sequence of the IL-18/IL-15RαSu fusion protein (including signal peptide sequence) is as follows (SEQ ID NO: 322):

(Signal peptide)
MKWVTFISLLFLFSSAYS (Human IL-18)
YFGKLESKLSVIRNLNDQVLFIDQGNRPLFEDMTDSDCRDNAPRTIFIISM

YKDSQPRGMAVTISVKCEKISTLSCENKIISFKEMNPPDNIKDTKSDIIFF

QRSVPGHDNKMQFESSSYEGYFLACEKERDLFKLILKKEDELGDRSIMFTV

QNED (Human IL-15R α sushi domain)
ITCPPPMSVEHADIWVKSYSLYSRERYICNSGFKRKAGTSSLTECVLNKAT

NVAHWTTPLKCIR

The amino acid sequence of the IL-12/TF/IL-15 fusion protein (including leader sequence) is as follows (SEQ ID NO: 323):

(Signal peptide)
MKWVTFISLLFLFSSAYS (Human IL-12 subunit beta (p40))
IWELKKDVYVVELDWYPDAPGEMVVLTCDTPEEDGITWTLDQSSEVLGSGK

TLTIQVKEFGDAGQYTCHKGGEVLSHSLLLLHKKEDGIWSTDILKDQKEPK

NKTFLRCEAKNYSGRFTCWWLTTISTDLTFSVKSSRGSSDPQGVTCGAATL

SAERVRGDNKEYEYSVECQEDSACPAAEESLPIEVMVDAVHKLKYENYTSS

FFIRDIIKPDPPKNLQLKPLKNSRQVEVSWEYPDTWSTPHSYFSLTFCVQV

QGKSKREKKDRVFTDKTSATVICRKNASISVRAQDRYYSSSWSEWASVPCS (Linker)
GGGGSGGGGSGGGGS (Human IL-12 subunit alpha (p35))
RNLPVATPDPGMFPCLHHSQNLLRAVSNMLQKARQTLEFYPCTSEEIDHED

ITKDKTSTVEACLPLELTKNESCLNSRETSFITNGSCLASRKTSFMMALCL

SSIYEDLKMYQVEFKTMNAKLLMDPKRQIFLDQNMLAVIDELMQALNFNSE

TVPQKSSLEEPDFYKTKIKLCILLHAFRIRAVTIDRVMSYLNAS

-continued (Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

In some cases, the leader peptide is cleaved from the intact polypeptide to generate the mature form that may be soluble or secreted.

Example 20: Recombinant Protein Quantitation of the 18t15-12s16 Complex

Figure 39:
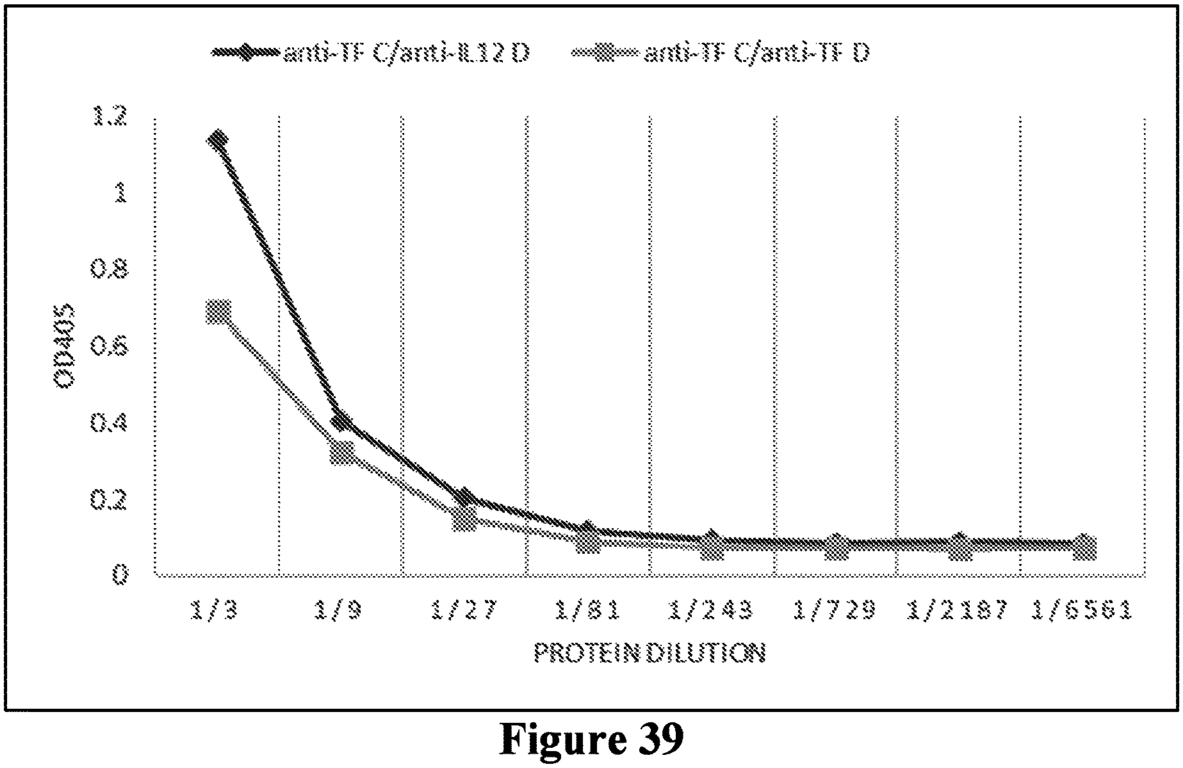
FIG. 39 shows a sandwich ELISA for the 18t15-12s16 complex, comprising an anti-human tissue factor antibody capture antibody and a biotinylated anti-human IL-12 (BAF 219) (dark line) or an anti-human tissue factor detection antibody (light line).

The 18t15-12s16 complex (comprising IL-12/IL-15RαSu/aCD16scFv; IL-18/TF/IL-15) was detected and quantified using standard sandwich ELISA methods (FIG. 39). Anti-human tissue factorantibody/IL-2 or anti-TF Ab/IL-18 served as the capture antibody and biotinylated anti-human IL-12 or IL-18 antibody (BAF 219, D045-6, both R&D Systems) served as the detection antibody. Tissue factor was also detected using an anti-human tissue factor antibody (I43), and anti-human tissue factor antibody detection.

Example 21: Creation of TGFβRII/IL-15RαSu and IL-21/TF/IL-15 DNA Constructs

Figure 40:
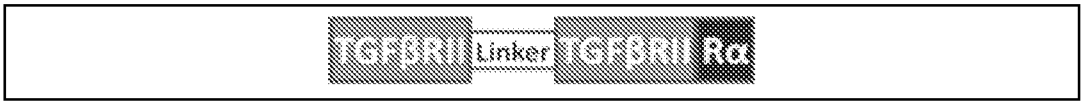
FIG. 40 shows a schematic diagram of an exemplary TGFβRII/IL-15RαSu DNA construct.

In a non-limiting example, a TGFβRII/IL-15RαSu DNA construct was created (FIG. 40). The human TGFβRII dimer and human IL-21 sequences were obtained from the UniProt website and DNA for these sequences was synthesized by Genewiz. A DNA construct was made linking the TGFβRII to another TGFβRII with a linker to generate a single chain version of TGFβRII and then directly linking the TGFβRII single chain dimer sequence to the N-terminal coding region of IL-15RαSu.

The nucleic acid sequences of the TGFβRII/IL-15RαSu construct (including signal sequence) is as follows (SEQ ID NO: 196):

(Signal peptide)
ATGAAGTGGGTGACCTTCATCAGCCTGCTGTTCCTGTTCTCCAGCGCCTAC

TCC (Human TGFβRII-1$^{st}$ fragment)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCACGATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

-continued

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT (Linker)
GGAGGTGGCGGATCCGGAGGTGGAGGTTCTGGTGGAGGTGGGAGT (Human TGFβRII-2$^{nd}$ fragment)
ATTCCTCCCCACGTGCAGAAGAGCGTGAATAATGACATGATCGTGACCGAT

AACAATGGCGCCGTGAAATTTCCCCAGCTGTGCAAATTCTGCGATGTGAGG

TTTTCCACCTGCGACAACCAGAAGTCCTGTATGAGCAACTGCACAATCACC

TCCATCTGTGAGAAGCCTCAGGAGGTGTGCGTGGCTGTCTGGCGGAAGAAT

GACGAGAATATCACCCTGGAAACCGTCTGCCACGATCCCAAGCTGCCCTAC

CACGATTTCATCCTGGAAGACGCCGCCAGCCCTAAGTGCATCATGAAAGAG

AAAAAGAAGCCTGGCGAGACCTTTTTCATGTGCTCCTGCAGCAGCGACGAA

TGCAACGACAATATCATCTTTAGCGAGGAATACAATACCAGCAACCCCGAC (Human IL-15R α sushi domain)
ATCACGTGTCCTCCTCCTATGTCCGTGGAACACGCAGACATCTGGGTCAAG

AGCTACAGCTTGTACTCCAGGGAGCGGTACATTTGTAACTCTGGTTTCAAG

CGTAAAGCCGGCACGTCCAGCCTGACGGAGTGCGTGTTGAACAAGGCCACG

AATGTCGCCCACTGGACAACCCCCAGTCTCAAATGTATTAGA

Figure 41:
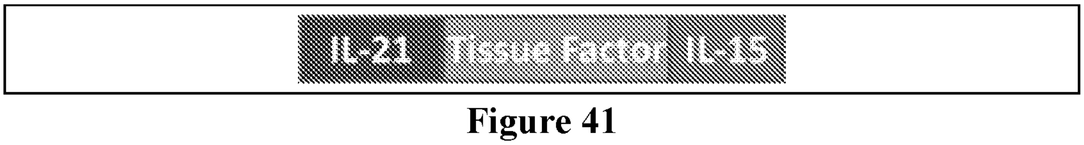
FIG. 41 shows a schematic diagram of an exemplary IL-21/TF/IL-15 construct.

Additionally, an IL-21/TF/IL-15 construct was made linking the IL-21 sequence to the N-terminus coding region of tissue factor 219, and further linking the IL-21/TF construct to the N-terminus coding region of IL-15 (FIG. 41). The nucleic acid sequence of the IL-21/TF/IL-15 construct (including leader sequence) is as follows (SEQ ID NO: 192):

(Signal peptide)
ATGAAGTGGGTGACCTTCATCAGCCTGCTGTTCCTGTTCTCCAGCGCCTAC

TCC (Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC (Human Tissue Factor 219)
TCCGGCACCACCAATACCGTGGCCGCTTATAACCTCACATGGAAGAGCACC

AACTTCAAGACAATTCTGGAATGGGAACCCAAGCCCGTCAATCAAGTTTAC

ACCGTGCAGATCTCCACCAAATCCGGAGACTGGAAGAGCAAGTGCTTCTAC

ACAACAGACACCGAGTGTGATTTAACCGACGAAATCGTCAAGGACGTCAAG

CAAACCTATCTGGCTCGGGTCTTTTCCTACCCCGCTGGCAATGTCGAGTCC

ACCGGCTCCGCTGGCGAGCCTCTCTACGAGAATTCCCCCGAATTCACCCCT

TATTTAGAGACCAATTTAGGCCAGCCTACCATCCAGAGCTTCGAGCAAGTT

GGCACCAAGGTGAACGTCACCGTCGAGGATGAAAGGACTTTAGTGCGGCGG

-continued

AATAACACATTTTTATCCCTCCGGGATGTGTTCGGCAAAGACCTCATCTAC

ACACTGTACTATTGGAAGTCCAGCTCCTCCGGCAAAAAGACCGCTAAGACC

AACACCAACGAGTTTTTAATTGACGTGGACAAAGGCGAGAACTACTGCTTC

AGCGTGCAAGCCGTGATCCCTTCTCGTACCGTCAACCGGAAGAGCACAGAT

TCCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC

Figure 42:
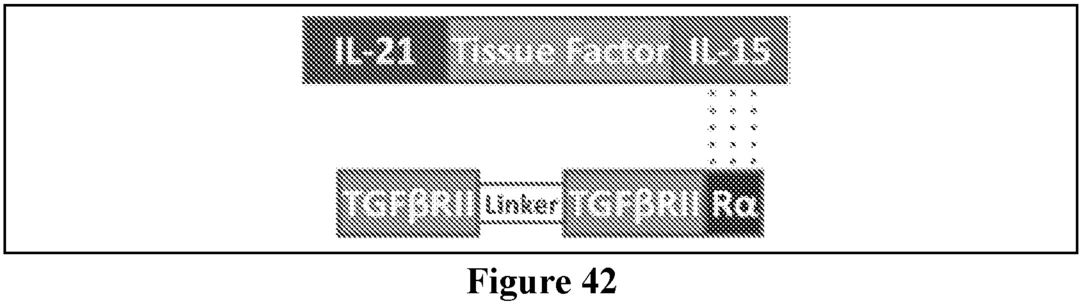
FIG. 42 shows a schematic diagram of the interaction between the exemplary IL-IL-21/TF/IL-15 and TGFβRII/IL-15RαSu constructs.
Figure 43:
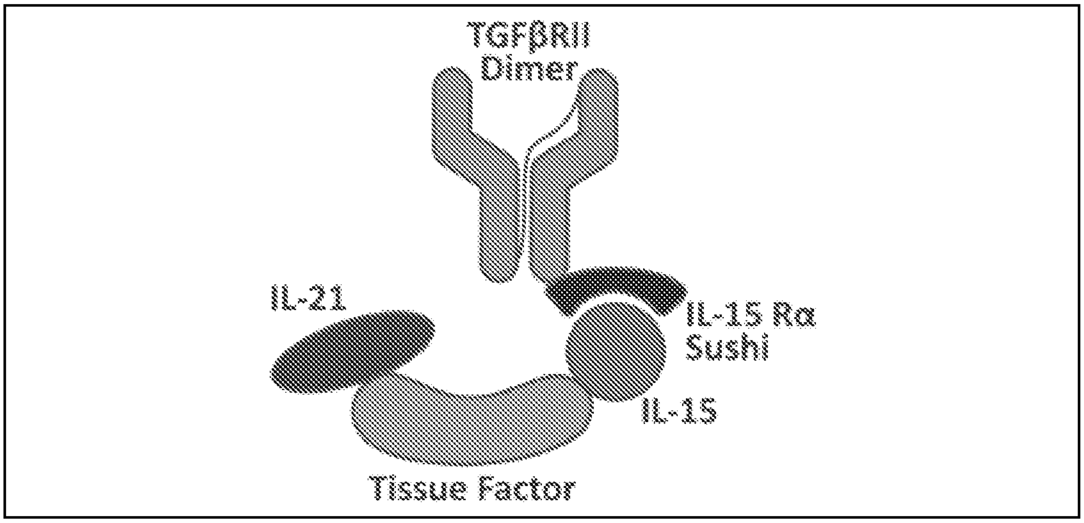
FIG. 43 shows a schematic diagram of the interaction between the exemplary TGFβRII/IL-15RαSu and IL-21/TF/IL-15 fusion proteins, resulting in an IL-21/TF/IL-15/TGFβRII/IL-15RαSu complex (21t15-TGFRs).

Example 22: Secretion of TGFβRII/IL-15RαSu and IL-21/TF/IL-15 Fusion Proteins The TGFβRII/IL-15RαSu and IL-21/TF/IL-15 DNA constructs were cloned into a pMSGV-1 modified retrovirus expression vector (as described in Hughes et al., *Hum Gene Ther* 16:457-72, 2005, herein incorporated by reference), and the expression vector was transfected into CHO-K1 cells. Co-expression of the two constructs in CHO-K1 cells resulted in secretion of the soluble IL-21/TF/IL-15: TGFβRII/IL-15RαSu protein complex (referred to as 21t15-TGFRs; FIG. 42 and FIG. 43). The 21t15-TGFRs complex was purified from CHO-K1 cell culture supernatant using anti-TF antibody affinity chromatography and other chromatography methods.

The amino acid sequence of the TGFβRII/IL-15RαSu construct (including signal peptide sequence) is as follows (SEQ ID NO: 195):

(Signal peptide)
MKWVTFISLLFLFSSAYS (Human TGFβRII-1st fragment)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPD (Linker)
GGGGSGGGGSGGGGS (Human TGFβRII-2nd fragment)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNKAT

NVAHWTTPSLKCIR

The amino acid sequence of the mature IL-21/TF/IL-15 fusion protein (including signal peptide sequence) is as follows (SEQ ID NO: 191):

(Signal peptide)
MKWVTFISLLFLFSSAYS (Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS (Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

In some cases, the leader peptide is cleaved from the intact polypeptide to generate a mature form that may be soluble or secreted.

Example 23: Purification of 21t15-TGFRs by Immunoaffinity Chromatography

An anti-TF antibody affinity column was connected to a GE Healthcare AKTA™ Avant protein purification system. The flow rate was 4 mL/min for all steps except the elution step, which was 2 mL/min.

Figure 44:
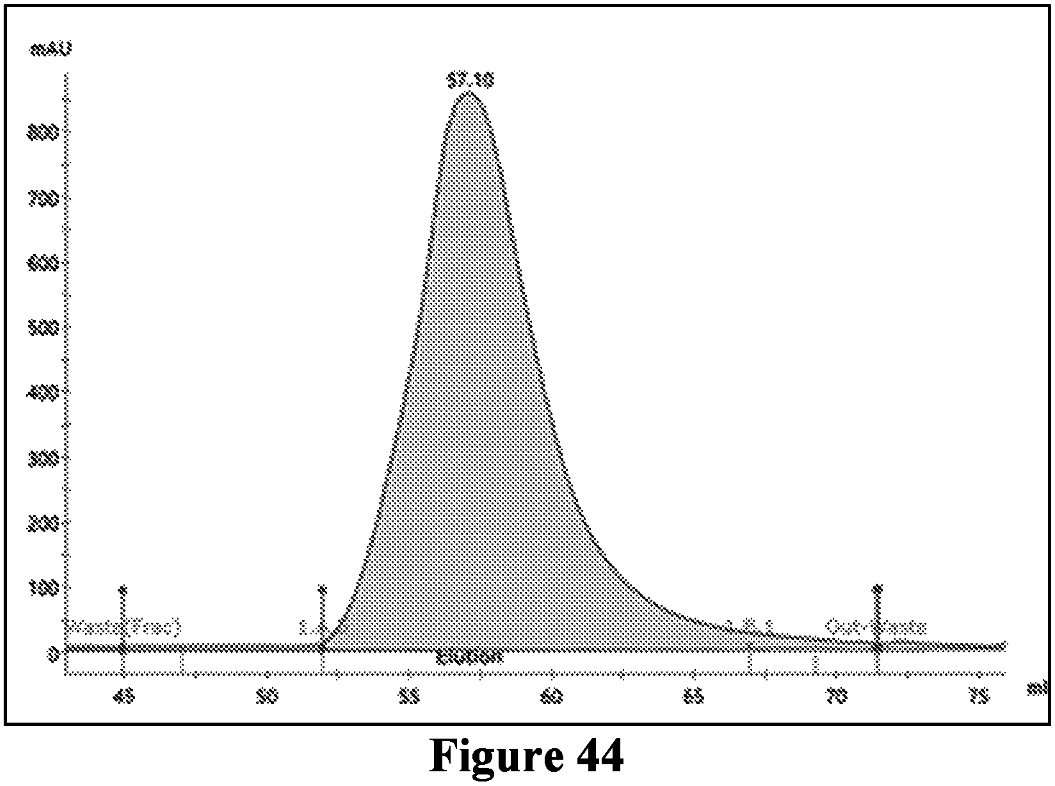
FIG. 44 shows a chromatograph of 21t15-TGFRs purification elution from an anti-TF antibody affinity column.

Cell culture harvest of 21t15-TGFRs was adjusted to pH 7.4 with 1 M Tris base and loaded onto the anti-TF antibody affinity column equilibrated with 5 column volumes of PBS. After loading the sample, the column was washed with 5 column volumes PBS, followed by elution with 6 column volumes 0.1 M acetic acid, pH 2.9. Absorbance at 280 nm was collected and then the sample was then neutralized to pH 7.5-8.0 by adding 1 M Tris base. The neutralized sample was then buffer exchanged into PBS using Amicon® centrifugal filters with a 30 KDa molecular weight cutoff. FIG. 44 shows that the 21t15-TGFRs complex binds anti-TF antibody affinity column, wherein TF is a 21t15-TGFRs binding partner. The buffer-exchanged protein sample is stored at 2-8 °C for further biochemical analysis and biological activity testing.

After each elution, the anti-TF antibody affinity column was then stripped using 6 column volumes 0.1 M glycine, pH 2.5. The column was then neutralized using 10 column volumes PBS, 0.05% sodium azide, and stored at 2-8 °C.

Example 24: Size Exclusion Chromatography of 21t15-TGFRs

Figure 45:
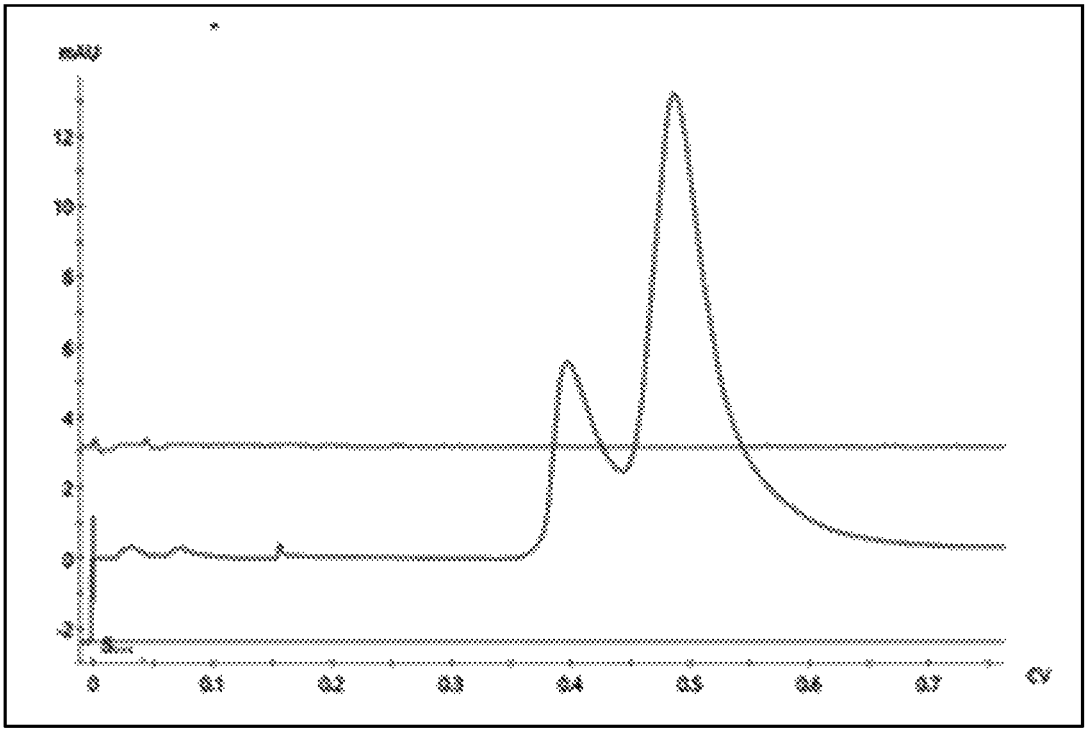
FIG. 45 shows an exemplary 21t15-TGFRs size exclusion chromatograph showing a main protein peak and a high molecular weight peak

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.8 mL/min. A capillary loop was used to inject 2004, of 1 mg/mL of 21t15-TGFRs complex onto the column. The injection was then chased with 1.25 column volumes of PBS. The SEC chromatograph was shown in FIG. 45. There were two protein peaks, likely representing a monomer and dimer forms of 21t15-TGFRs.

Example 25: SDS-PAGE of 21t15-TGFRs

Figure 46:
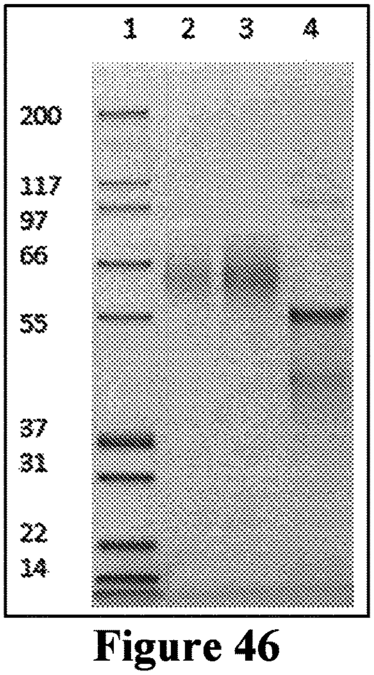
FIG. 46 shows an example of a 4-12% SDS-PAGE of the 21t15-TGFRs complex following disulfide bond reduction. Lane 1: Mark12 unstained marker (numbers on the left side indicate molecular weights in kDa); Lane 2: 21t15-TGFRs (0.5 μg); Lane 3: 21t15-TGFRs (1 μg); Lane 4: 21t15-TGFRs, deglycosylated (1 μg), wherein the MW was the expected size of 53 kDa and 39.08 kDa.
Figure 47:
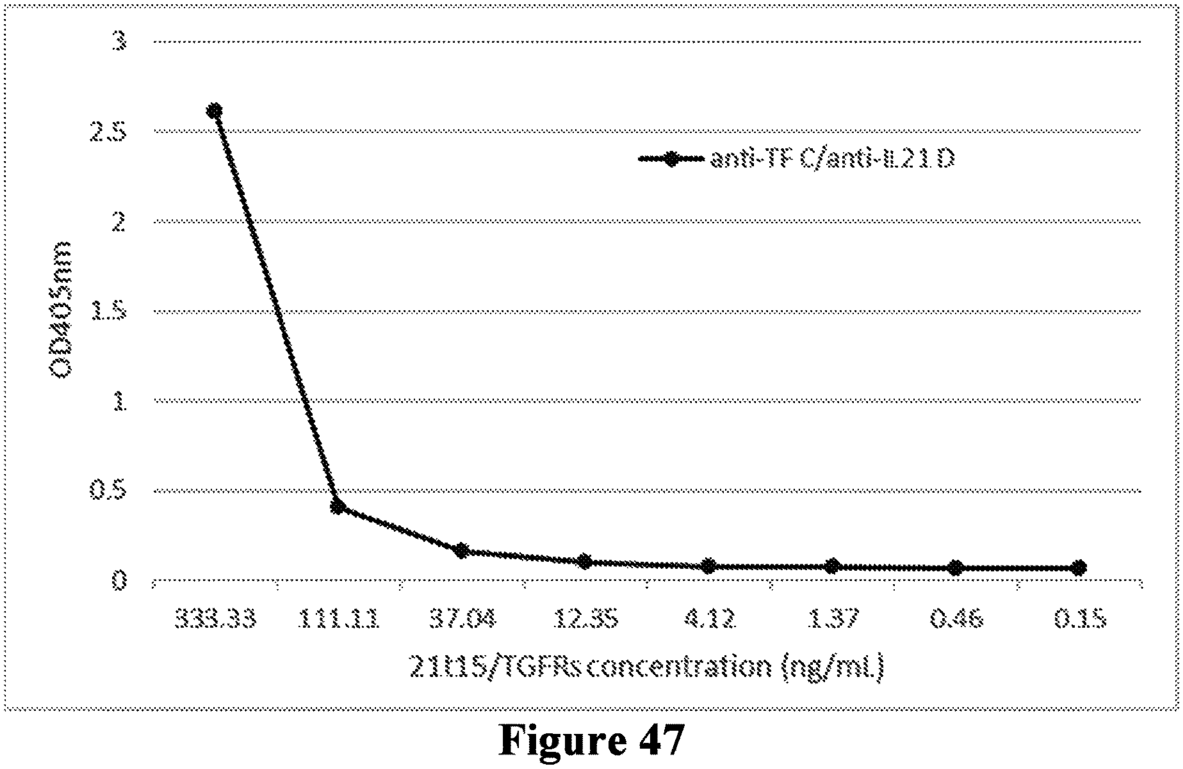
FIG. 47 shows a sandwich ELISA for the 21t15-TGFRs complex, comprising an anti-human tissue factor capture and a biotinylated anti-human IL-21 detection antibody (13-7218-81, BioLegend).
Figure 48:
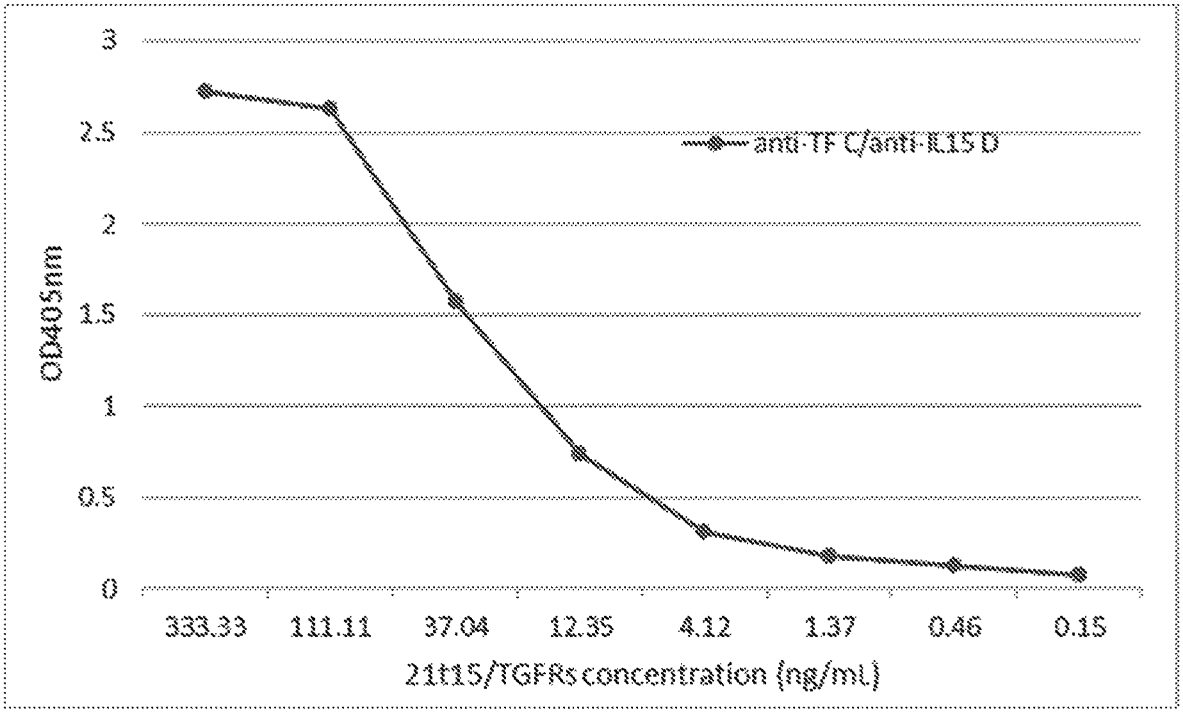
FIG. 48 shows a sandwich ELISA for the 21t15-TGFRs complex, comprising an anti-human tissue factor antibody capture and a biotinylated anti-human IL-15 detection antibody (BAM 247, R&D Systems).
Figure 49:
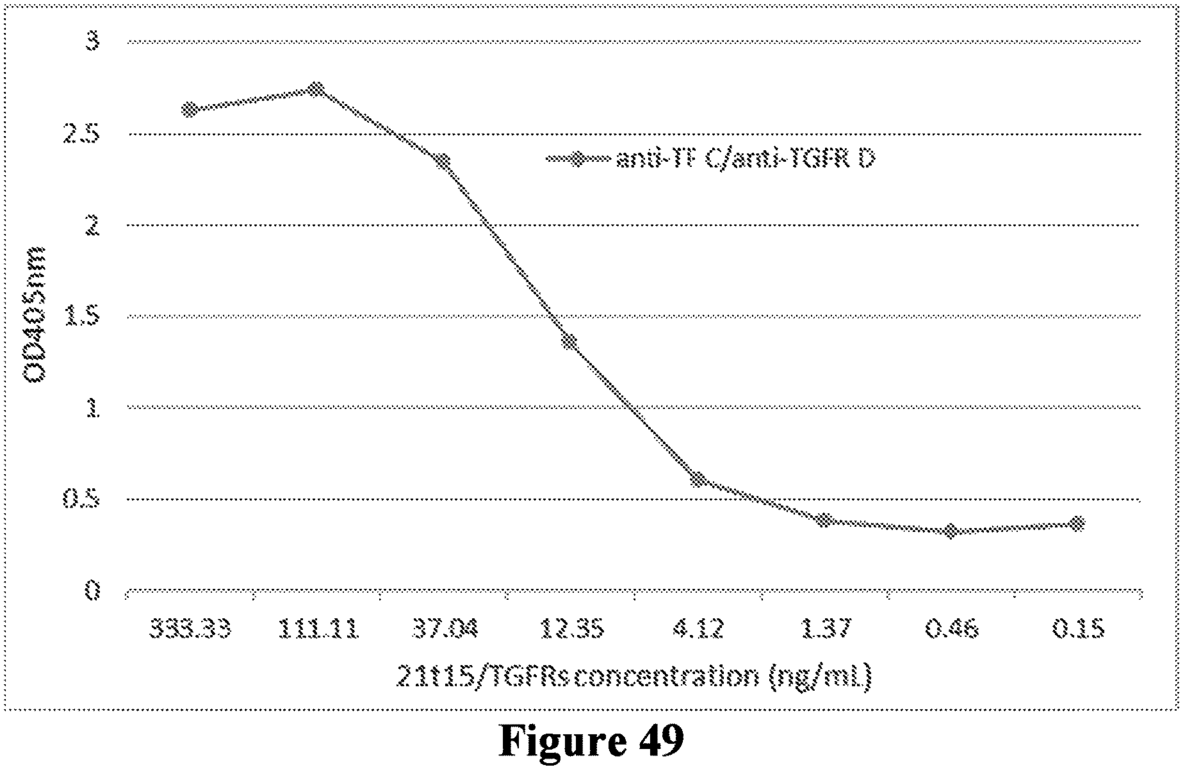
FIG. 49 shows a sandwich ELISA for the 21t15-TGFRs complex, comprising an anti-human tissue factor antibody capture and a biotinylated anti-human TGFβRII detection antibody (BAF241, R&D Systems).
Figure 50:
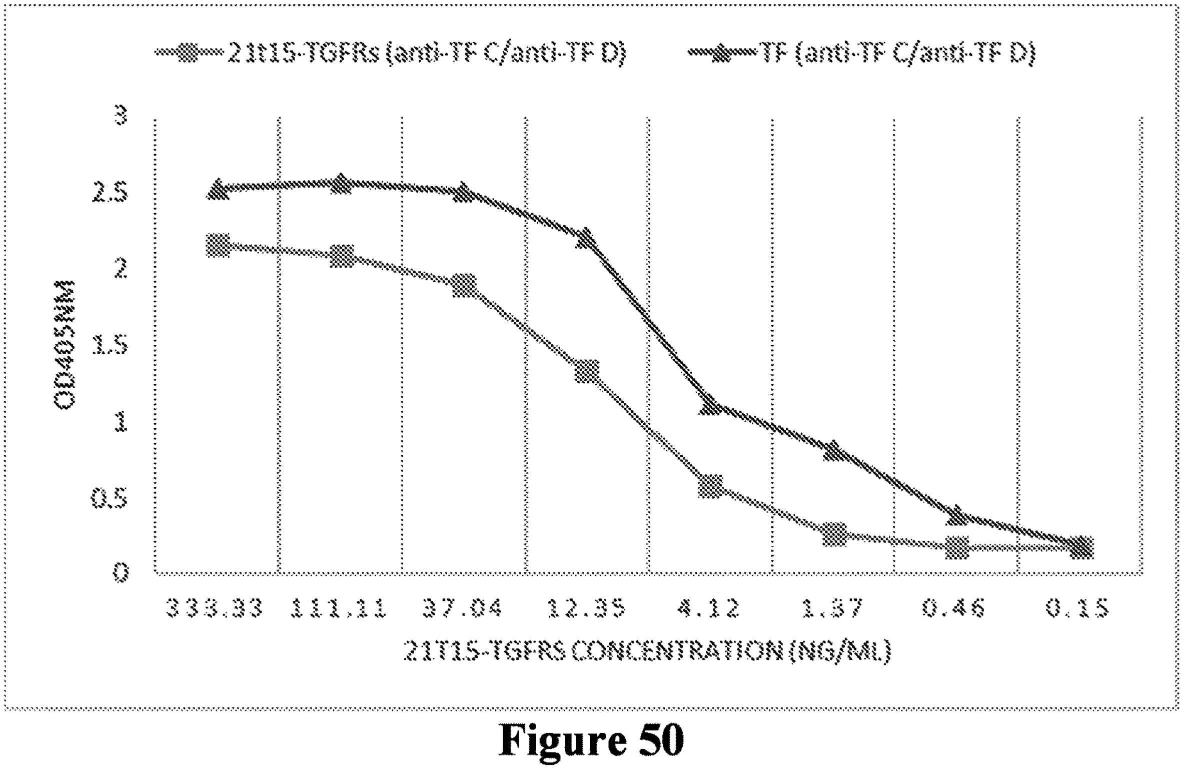
FIG. 50 shows a sandwich ELISA for the 21t15-TGFRs complex, comprising an anti-human tissue factor (I43) capture antibody and an anti-human tissue factor detection antibody.

To determine the purity and protein molecular weight, the purified 21t15-TGFRs complex protein sample was analyzed using 4-12% NuPage Bis-Tris protein gel SDS-PAGE under reduced conditions. The gel was stained with InstantBlue™ for about 30 min, followed by destaining overnight in purified water. FIG. 46 shows an example SDS gel of anti-TF antibody affinity purified 21t15-TGFRs, with bands at 39.08 kDa and 53 kDa. Glycosylation of 21t15-TGFRs in CHO cells was confirmed using the Protein Deglycosylation Mix II kit (New England Biolabs) and the manufacturer's instructions. Deglycosylation reduces the molecular weight of 21t15-TGFRs, as seen in lane 4 of FIG. 46.

Example 26: Recombinant Protein Quantitation of 21t15-TGFRs Complexes

The 21t15-TGFRs complex was detected and quantified using standard sandwich ELISA methods (FIGS. 47-50). Anti-human tissue factor antibody served as the capture antibody and biotinylated anti-human IL-21, IL-15, or TGFβRII served as the detection antibody. Tissue factor was also detected using an anti-human tissue factor capture antibody (I43), and anti-human tissue factor antibody detection. The I43/anti-TF antibody ELISA was compared to purified tissue factor at similar concentrations.

Example 27: Immunostimulatory Capacity of the 21t15-TGFRs Complex

Figure 51:
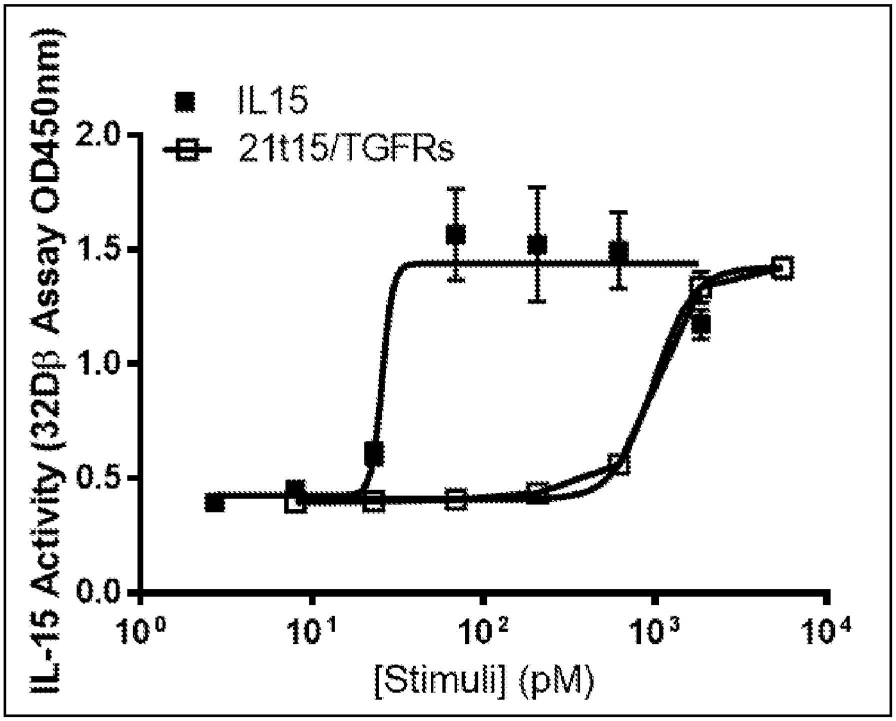
FIG. 51 shows IL-15-dependent proliferation of 32D13 cells mediated by the 21t15-TGFRs complex (open squares) compared to IL-15 (black squares).

To assess the IL-15 immunostimulatory activity of the 21t15-TGFRs complexes, increasing concentrations of 21t15-TGFRs was added to 32D13 cells ($10^4$ cell/well) in 200 μL IMDM:10% FBS media and cells were incubated for 3 days at 37 °C. On the fourth day, WST-1 proliferation reagent (10 μL/well) then was added and after 4 hours, absorbance was measured at 450 nm to determine cell proliferation based on cleavage of WST-1 to a soluble formazan dye. Bioactivity of the human recombinant IL-15 was assessed as a positive control. As shown in FIG. 51, 21t15-TGFRs demonstrated IL-15-dependent 32Dβ cell proliferation. The 21t15-TGFRs complex was reduced compared to that of human recombinant IL-15, possibly due to the linkage of IL-21 and tissue factor to the IL-15 domain.

Figure 52:
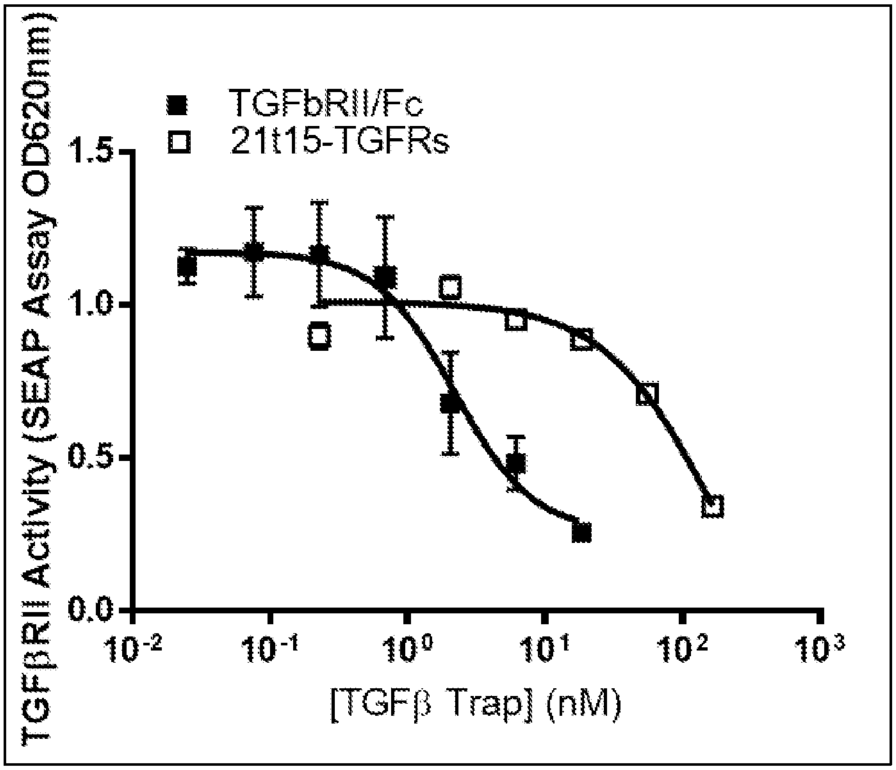
FIG. 52 shows biological activity of the TGFβRII domain within the 21t15-TGFRs complex (open squares). TGFβRII/Fc (black squares) served as a positive control.

Additionally, HEK-Blue TGFβ reporter cells (hkb-tgfb, InvivoGen) were used to measure the ability of 21t15-TGFRs to block TGFβ1 activity (FIG. 52). Increasing concentrations of 21t15-TGFRs were mixed with 0.1 nM of TGFβ1 and added to HEK-Blue TGFβ reporter cells ($2.5\times10^4$ cell/well) in 200 μL IMDM:10% heat-inactivated FBS media. Cells were incubated overnight at 37 °C. The next day, 20 μl of induced HEK-Blue TGFβ reporter cell supernatant was added to 180 μl of QUANTI-Blue (InvivoGen) and incubated for 1-3 hours at 37 °C 21t15-TGFRs activity was assessed by measuring absorbance at 620 nm. Human recombinant TGFβRII/Fc activity was assessed as a positive control.

These results demonstrate that TGFβRII domain of the 21t15-TGFRs complex retains its ability to trap TGFβ1. The ability of 21t15-TGFRs to block TGFβ1 activity was reduced compared to that of human recombinant TGFβRII/Fc, possibly due to the linkage of TGFβRII to the IL-15Rα sushi domain.

Example 28: Induction of Cytokine-Induced Memory-Like NK Cells by the 21t15-TGFRs Complex Cytokine-induced memory-like NK cells can be induced ex vivo following overnight stimulation of purified NK cells with saturating amounts of cytokines. These memory-like properties can be measured through expression of IL-2 receptor α (IL-2Rα, CD25), CD69 (and other activation markers), and increased IFN-γ production. To evaluate the ability of 21t15-TGFRs complexes to promote generation of cytokine-induced memory-like NK cells, purified human NK cells (>95% CD56+) were stimulated for 14-18 hours with 1 nM to 100 nM of the 21t15-TGFRs complex. Cell-surface CD25 and CD 69 expression and intracellular IFN-γ levels were assessed by antibody-staining and flow cytometry.

Figure 53:
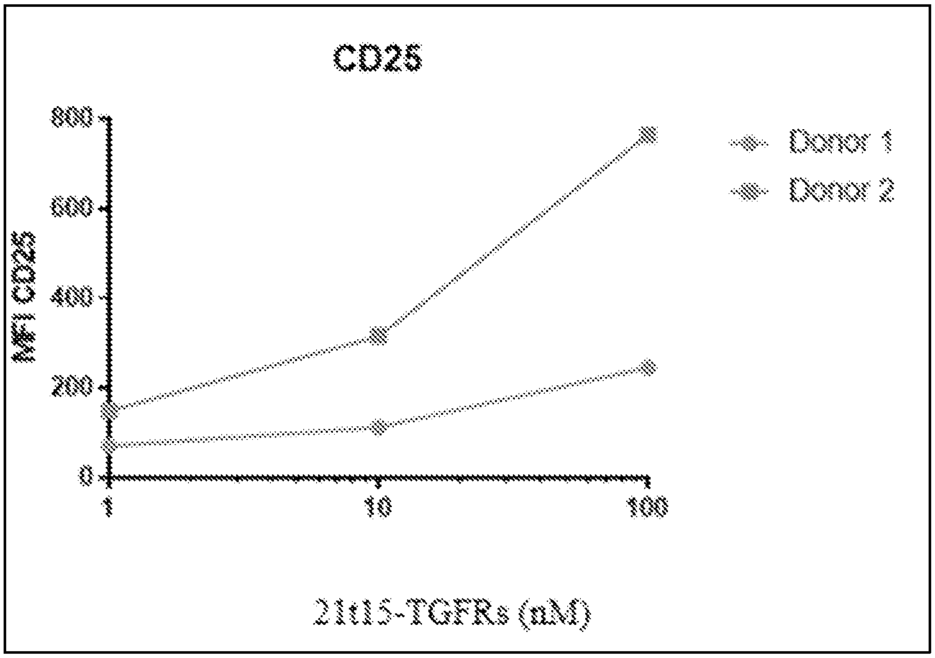
FIG. 53 shows a flow cytometry graph of cell-surface CD25 expression of NK cells induced by the 21t15-TGFRs complex.
Figure 54:
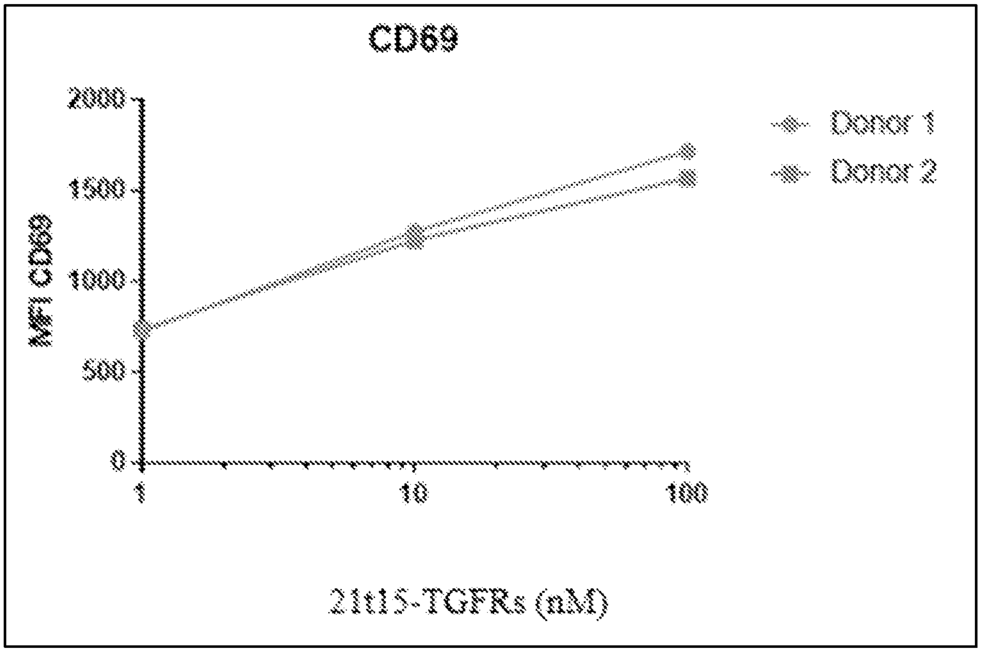
FIG. 54 shows a flow cytometry graph of cell-surface CD69 expression of NK cells induced by the 21t15-TGFRs complex.

Fresh human leukocytes were obtained from a blood bank and CD56+NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in $0.2\times10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-21 (50 ng/ml) (Biolegend) and hIL-15 (50 ng/ml) (NCI) or with 1 nM, nM, or 100 nM 21t15-TGFRs complex overnight at 37 °C, 5% $CO_2$ for 14-18 hrs. The cells were then harvested and surface stained for CD56-BV421, CD16-BV510, CD25-PE, CD69-APCFire750 specific antibodies for 30 minutes. After staining, cells were washed (1500 RPM for 5 minutes at room temperature) in FACS buffer (1×PBS (Hyclone) with 0.5% BSA (EMD Millipore) and 0.001% sodium azide (Sigma)). After two washes, cells were analyzed using a BD FACSCelesta™ flow cytometer. (Plotted Data-Mean Fluorescence Intensity; FIG. 53 and FIG. 54).

Figure 55:
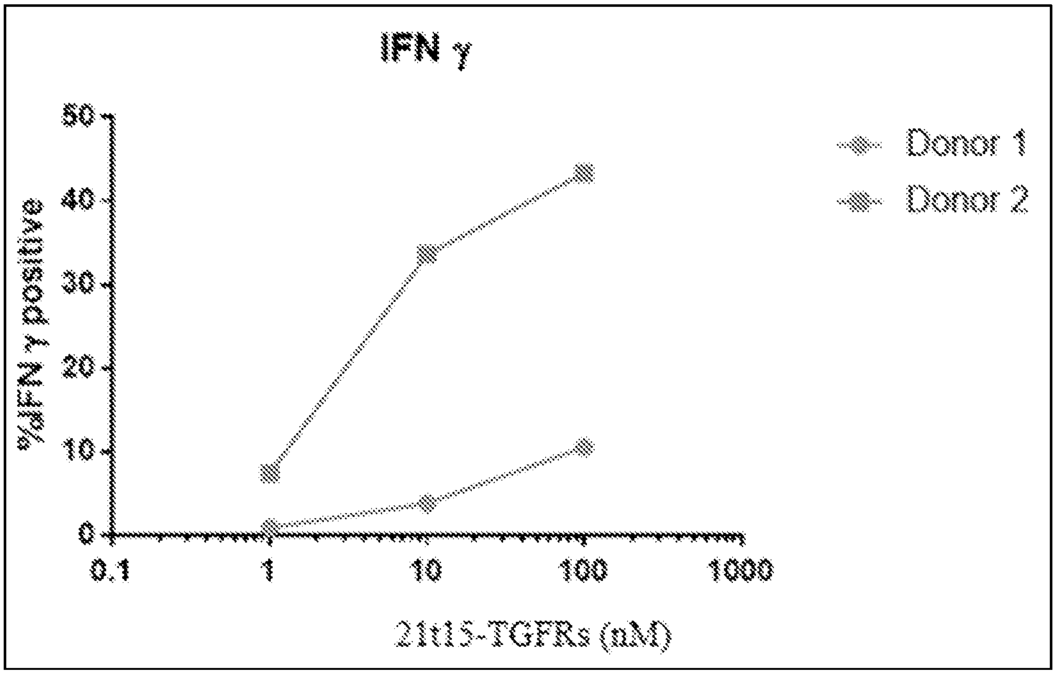
FIG. 55 shows a flow cytometry graph of intracellular IFN-γ expression of NK cells induced by the 21t15-TGFRs complex.

Fresh human leukocytes were obtained from a blood bank and CD56+NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in 0.2×106/ml in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-21 (50 ng/ml) (Biolegend) and hIL-15 (50 ng/ml) (NCI) or with 1 nM, nM, or 100 nM 21t15-TGFRs complex overnight at 37 °C, 5% $CO_2$ for 14-18 hrs. The cells were then treated with 10 μg/ml of Brefeldin A (Sigma) and 1× of Monensin (eBioscience) for 4 hrs. Cells were harvested and surface stained for CD56-BV421, CD16-BV510, CD25-PE, CD69-APCFire750 specific antibodies for 30 minutes. After staining, cells were washed (1500 RPM for 5 minutes at room temperature) in FACS buffer (1×PBS (Hyclone) with 0.5% BSA (EMD Millipore) and 0.001% sodium azide (Sigma)) and fixed for 10 minutes at room temperature. After fixation, cells were washed (1500 RPM for 5 minutes at room temperature) with 1× permeabilized buffer (eBioscience) and stained for intracellular IFN-γ-PE (Biolegend) for 30 minutes at room temperature. Cells were washed once again with 1× permeabilized buffer and then washed with FACS buffer. Cell pellets were resuspended in 300 μls of FACS Buffer and analyzed using a BD FACSCelesta™ flow cytometer. (Plotted % of IFN-γ Positive Cells; FIG. 55).

Example 29: In Vitro Cytotoxicity of NK Cells Against Human Tumor Cells

Figure 56:
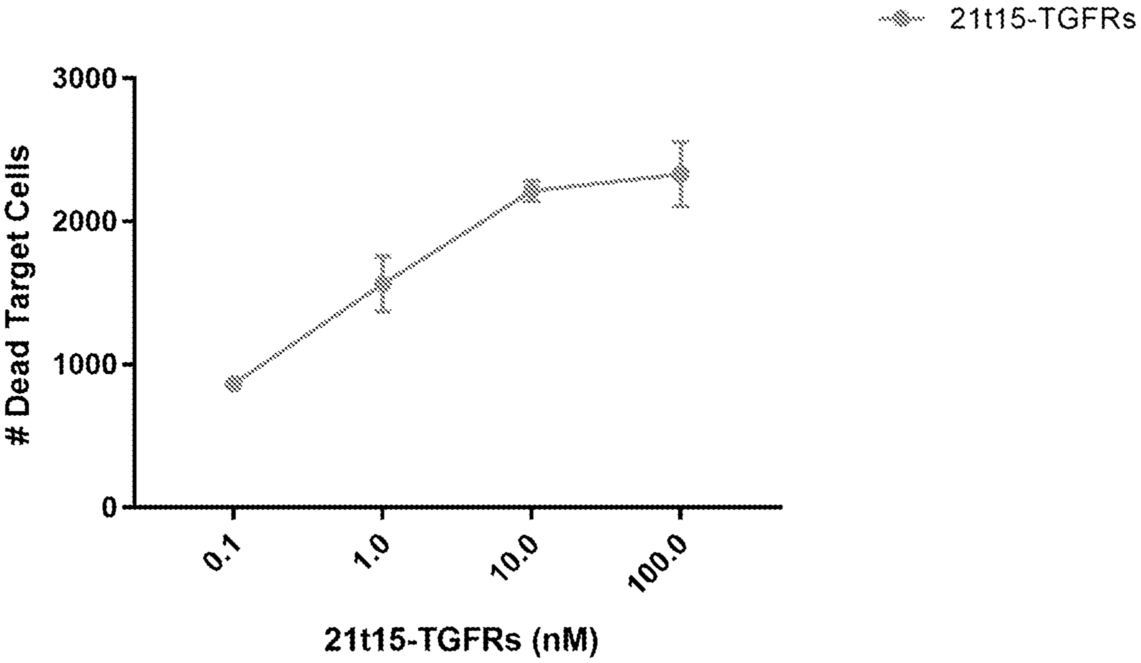
FIG. 56 shows cytotoxicity of 21t15-TGFRs-induced human NK cells against K562 cells.

K562 (CellTrace violet labelled), human myelogenous leukemia cells, were incubated with purified human NK cells (using StemCell human NK cell purification kit (E:T ratio; 2:1)) in the presence of increasing concentrations of the 21t15-TGFRs complex. After 20 hours, the cultures were harvested, stained with propidium iodide (PI), and assessed by flow cytometry. As shown in FIG. 56, the 21t15-TGFRs complex induced human NK cytotoxicity against K562, as compared to control.

Example 30: Creation of an IL-21/TF Mutant/IL-15 DNA Construct and Resulting Fusion Protein Complex with TGFβRII/IL-15RαSu In a non-limiting example, an IL-21/TF mutant/IL-15 DNA construct was made by linking IL-21 directly to the N-terminus coding region of a tissue factor 219 mutant, and further linking the IL-21/TF mutant to the N-terminus coding region of IL-15.

The nucleic acid sequence of the IL-21/TF mutant/IL-15 construct (including signal peptide sequence) is as follows (SEQ ID NO: 324, bold nucleotides are mutant and the mutant codons are in italics):

(Signal sequence)
ATGAAGTGGGTGACCTTCATCAGCCTGCTGTTCCTGTTCTCCAGCGCCTAC

TCC (Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC (Human Tissue Factor 219 mutants)
TCCGGCACCACCAATACCGTGGCCGCTTATAACCTCACATGGAAGAGCACC

AACTTC*__GC__G*ACA*__GCT__CT*GGAATGGGAACCCAAGCCCGTCAATCAAGTTTAC

ACCGTGCAGATCTCCACCAAATCCGGAGACTGGAAGAGCAAGTGCTTCTAC

ACAACAGACACCGAGTGTGCTTTAACCGACGAAATCGTCAAGGACGTCAAG

CAAACCTATCTGGCTCGGGTCTTTTCCTACCCCGCTGGCAATGTCGAGTCC

ACCGGCTCCGCTGGCGAGCCTCTCTACGAGAATTCCCCCGAATTCACCCCT

TATTTAGAGACCAATTTAGGCCAGCCTACCATCCAGAGCTTCGAGCAAGTT

-continued

GGCACCAAGGTGAACGTCACCGTCGAGGATGAAAGGACTTTAGTG*__GC__G*CGG

AATAACACA*__GCT__*TTATCCCTCCGGGATGTGTTCGGCAAAGACCTCATCTAC

ACACTGTACTATTGGAAGTCCAGCTCCTCCGGCAAAAAGACCGCTAAGACC

AACACCAACGAGTTTTTAATTGACGTGGACAAAGGCGAGAACTACTGCTTC

AGCGTGCAAGCCGTGATCCCTTCTCGTACCGTCAACCGGAAGAGCACAGAT

TCCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC

The amino acid sequence of the IL-21/TF mutant/IL-15 construct (including signal peptide sequence) is as follows (SEQ ID NO: 325, substituted residues are shaded):

(Signal peptide)
MKWVTFISLLFLFSSAYS (Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS (Human Tissue Factor 219)
SGTTNTVAAYNLTWKSTNFATALEWEPKPVNQVYTVQISTKSGDWKSKCFY

TTDTECALTDEIVKDVKQTYLARVFSYPAGNVESTGSAGEPLYENSPEFTP

YLETNLGQPTIQSFEQVGTKVNVTVEDERTLVARNNTALSLRDVFGKDLIY

TLYYWKSSSSGKKTAKTNTNEFLIDVDKGENYCFSVQAVIPSRTVNRKSTD

SPVECMGQEKGEFRE (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

In some cases, the leader peptide is cleaved from the intact polypeptide to generate a mature form that may be soluble or secreted.

In some embodiments, the IL-21/TF mutant/IL-15 DNA construct may be combined with an TGFβRII/IL-15RαSu DNA construct, transfected into cells using a retroviral vector as described above, and expressed as IL-21/TF mutant/IL-15 and TGFβRII/IL-15RαSu fusion proteins. The IL-15RαSu domain of the TGFβRII/IL-15RαSu fusion protein binds to the IL-15 domain of the IL-21/TF mutant/IL-15 fusion protein to create an IL-21/TF mutant/IL-15: TGFβRII/IL-15RαSu complex.

Example 31: Creation of IL-21/IL-15RαSu and TGFβRII/TF/IL-15 DNA Constructs and the Resulting Fusion Protein Complex In a non-limiting example, an IL-21/IL-15RαSu DNA construct was made by linking IL-21 directly to the IL-15RαSu subunit sequence. The nucleic acid sequence of the IL-21/IL-15RαSu construct (including signal sequence) is as follows (SEQ ID NO: 214):

```
(Signal sequence)
ATGAAGTGGGTGACCTTCATCAGCCTGCTGTTCCTGTTCTCCAGCGCCTAC

TCC

(Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC

(Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG
```

The amino acid sequence of the IL-21/IL-15RαSu construct (including signal peptide sequence) is as follows (SEQ ID NO: 213):

```
(Signal peptide)
MKWVTFISLLFLFSSAYS

(Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS

(Human IL-15R α sushi domain)
ITCPPPMSVEHADIWVKSYSLYSRERYICNSGFKRKAGTSSLTECVLNKAT

NVAHWTTPSLKCIR
```

In some cases, the leader peptide is cleaved from the intact polypeptide to generate a mature form that may be soluble or secreted.

In some embodiments, the IL-21/IL-15RαSu DNA construct may be combined with a TGFβRII/TF/IL-15 DNA construct, transfected into a retroviral vector as described above, and expressed as IL-21/IL-15RαSu and TGFβRII/TF/IL-15 fusion proteins. The IL-15RαSu domain of the IL-21/IL-15RαSu fusion protein binds to the IL-domain of the TGFβRII/TF/IL-15 fusion protein to create a TGFβRII/TF/IL-15:IL-21/IL-15RαSu complex.

The TGFβRII/TF/IL-15RαSu DNA construct was created by linking the TGFβRII sequence to the N-terminus coding region of human tissue factor 219 form, and then linking the TGFβRII/TF construct to the N-terminus coding region of IL-15. As described above, a single-chain version of TGFβRII (TGFβRII-linker-TGFβRII) was used. The nucleic acid sequence of the TGFβRII/TF/IL-15 construct (including leader sequence) is as follows (SEQ ID NO: 239):

```
(Signal peptide)
ATGAAGTGGGTGACCTTCATCAGCCTGCTGTTCCTGTTCTCCAGCGCCTAC

TCC

(Human TGFβII-1st fragment)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCACGATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

(Linker)
GGAGGTGGCGGATCCGGAGGTGGAGGTTCTGGTGGAGGTGGGAGT

(Human TGFβRII-2nd fragment)
ATTCCTCCCCACGTGCAGAAGAGCGTGAATAATGACATGATCGTGACCGAT

AACAATGGCGCCGTGAAATTTCCCCAGCTGTGCAAATTCTGCGATGTGAGG

TTTTCCACCTGCGACAACCAGAAGTCCTGTATGAGCAACTGCACAATCACC

TCCATCTGTGAGAAGCCTCAGGAGGTGTGCGTGGCTGTCTGGCGGAAGAAT

GACGAGAATATCACCCTGGAAACCGTCTGCCACGATCCCAAGCTGCCCTAC

CACGATTTCATCCTGGAAGACGCCGCCAGCCCTAAGTGCATCATGAAAGAG

AAAAAGAAGCCTGGCGAGACCTTTTTCATGTGCTCCTGCAGCAGCGACGAA

TGCAACGACAATATCATCTTTAGCGAGGAATACAATACCAGCAACCCCGAC

(Human Tissue Factor 219)
TCCGGCACCACCAATACCGTGGCCGCTTATAACCTCACATGGAAGAGCACC

AACTTCAAGACAATTCTGGAATGGGAACCCAAGCCCGTCAATCAAGTTTAC

ACCGTGCAGATCTCCACCAAATCCGGAGACTGGAAGAGCAAGTGCTTCTAC

ACAACAGACACCGAGTGTGATTTAACCGACGAAATCGTCAAGGACGTCAAG

CAAACCTATCTGGCTCGGGTCTTTTCCTACCCCGCTGGCAATGTCGAGTCC

ACCGGCTCCGCTGGCGAGCCTCTCTACGAGAATTCCCCCGAATTCACCCCT

TATTTAGAGACCAATTTAGGCCAGCCTACCATCCAGAGCTTCGAGCAAGTT

GGCACCAAGGTGAACGTCACCGTCGAGGATGAAAGGACTTTAGTGCGGCGG

AATAACACATTTTTATCCCTCCGGGATGTGTTCGGCAAAGACCTCATCTAC

ACACTGTACTATTGGAAGTCCAGCTCCTCCGGCAAAAAGACCGCTAAGACC

AACACCAACGAGTTTTTAATTGACGTGGACAAAGGCGAGAACTACTGCTTC

AGCGTGCAAGCCGTGATCCCTTCTCGTACCGTCAACCGGAAGAGCACAGAT

TCCCCCGTTGAGTGCATGGGCCAAGAAAAGGGCGAGTTCCGGGAG

(Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT
```

-continued

TGTAAGGTGACCGCCATGAAATGTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC

The amino acid sequence of the TGFβRII/TF/IL-15 fusion protein (including signal peptide) is as follows (SEQ ID NO: 238):

(Signal peptide)
MKWVTFISLLFLFSSAYS (Human TGFβII-1$^{st}$ fragment)
IPPHVQKSVNNDMIVTDNNGAVKFPQLCKFCDVRFSTCDNQKSCMSNCSTI

SICEKPQEVCVAVWRKNDENITLETVCHDPKLPYHDFILEDAASPKCIMKE

KKKPGETFFMCSCSSDECNDNIIFSEEYNTSNPD (Linker)
GGGGSGGGGSGGGGS (Human TGFβRII-2$^{nd}$ fragment)
IPPHVQKSVNNDMIVTDNNGAVKFPQLCKFCDVRFSTCDNQKSCMSNCSTI

SICEKPQEVCVAVWRKNDENITLETVCHDPKLPYHDFILEDAASPKCIMKE

KKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

Example 32. Production of an Exemplary Single-Chain Chimeric Polypeptides

Figure 57:
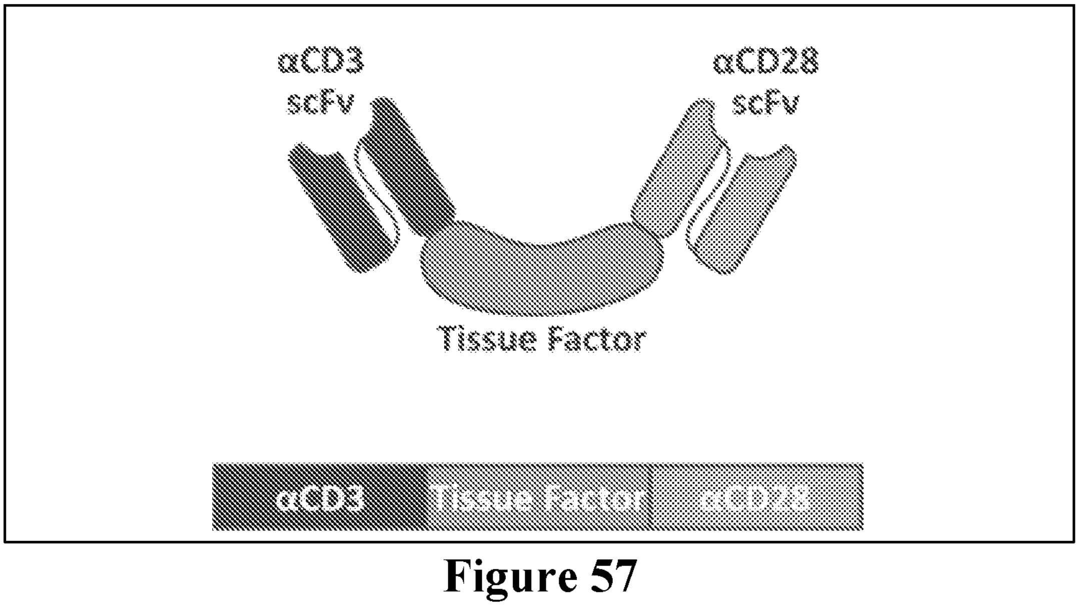
FIG. 57 are schematic diagrams of an exemplary αCD3scFv/TF/αCD28scFv single-chain chimeric polypeptide.

An exemplary single-chain chimeric polypeptide including a first target-binding domain that is an anti-CD3 scFv, a soluble human tissue factor domain, and a second target-binding domain that is an anti-CD28 scFv was generated (aCD3scFv/TF/aCD28scFv) (FIG. 57). The nucleic acid and amino acid sequences of this single-chain chimeric polypeptide are shown below.

Nucleic Acid Encoding Exemplary Single-Chain Chimeric Polypeptide (αCD3scFv/TF/αCD28scFv) (SEQ ID NO: 158)

(Signal peptide)
ATGAAGTGGGTGACCTTCATCAGCTTATTATTTTTATTCAGCTCCGCCTAT

TCC

-continued (αCD3 light chain variable region)
CAGATCGTGCTGACCCAAAGCCCCGCCATCATGAGCGCTAGCCCCGGTGAG

AAGGTGACCATGACATGCTCCGCTTCCAGCTCCGTGTCCTACATGAACTGG

TATCAGCAGAAAAGCGGAACCAGCCCCAAAAGGTGGATCTACGACACCAGC

AAGCTGGCCTCCGGAGTGCCCGCTCATTTCCGGGGCTCTGGATCCGGCACC

AGCTACTCTTTAACCATTTCCGGCATGGAAGCTGAAGACGCTGCCACCTAC

TATTGCCAGCAATGGAGCAGCAACCCCTTCACATTCGGATCTGGCACCAAG

CTCGAAATCAATCGT (Linker)
GGAGGAGGTGGCAGCGGCGGCGGTGGATCCGGCGGAGGAGGAAGC (αCD3 heavy chain variable region)
CAAGTTCAACTCCAGCAGAGCGGCGCTGAACTGGCCCGGCCCGGCGC

CTCCGTCAAGATGAGCTGCAAGGCTTCCGGCTATACATTTACTCGTTACAC

AATGCATTGGGTCAAGCAGAGGCCCGGTCAAGGTTTAGAGTGGATCGGATA

TATCAACCCTTCCCGGGGCTACACCAACTATAACCAAAAGTTCAAGGATAA

AGCCACTTTAACCACTGACAAGAGCTCCTCCACCGCCTACATGCAGCTGTC

CTCTTTAACCAGCGAGGACTCCGCTGTTTACTACTGCGCTAGGTATTACGA

CGACCACTACTGTTTAGACTATTGGGGACAAGGTACCACTTTAACCGTCAG

CAGC (Human tissue factor 219 form)
TCCGGCACCACCAATACCGTGGCCGCTTATAACCTCACATGGAAGAGCACC

AACTTCAAGACAATTCTGGAATGGGAACCCAAGCCCGTCAATCAAGTTTAC

ACCGTGCAGATCTCCACCAAATCCGGAGACTGGAAGAGCAAGTGCTTCTAC

ACAACAGACACCGAGTGTGATTTAACCGACGAAATCGTCAAGGACGTCAAG

CAAACCTATCTGGCTCGGGTCTTTTCCTACCCCGCTGGCAATGTCGAGTCC

ACCGGCTCCGCTGGCGAGCCTCTCTACGAGAATTCCCCCGAATTCACCCCT

TATTTAGAGACCAATTTAGGCCAGCCTACCATCCAGAGCTTCGAGCAAGTT

GGCACCAAGGTGAACGTCACCGTCGAGGATGAAAGGACTTTAGTGCGGCGG

AATAACACATTTTTATCCCTCCGGGATGTGTTCGGCAAAGACCTCATCTAC

ACACTGTACTATTGGAAGTCCAGCTCCTCCGGCAAAAAGACCGCTAAGACC

AACACCAACGAGTTTTTAATTGACGTGGACAAAGGCGAGAACTACTGCTTC

AGCGTGCAAGCCGTGATCCCTTCTCGTACCGTCAACCGGAAGAGCACAGAT

TCCCCCGTTGAGTGCATGGGCCAAGAAAAGGGCGAGTTCCGGGAG (αCD28 light chain variable region)
GTCCAGCTGCAGCAGAGCGGACCCGAACTCGTGAAACCCGGTGCTTCCGTG

AAAATGTCTTGTAAGGCCAGCGGATACACCTTCACCTCCTATGTGATCCAG

TGGGTCAAACAGAAGCCCGGACAAGGTCTCGAGTGGATCGGCAGCATCAAC

CCTTACAACGACTATACCAAATACAACGAGAAGTTTAAGGGAAAGGCTACT

TTAACCTCCGACAAAAGCTCCATCACAGCCTACATGGAGTTCAGCTCTTTA

ACATCCGAGGACAGCGCTCTGTACTATTGCGCCCGGTGGGGCGACGGCAAT

TACTGGGGACGGGGCACAACACTGACCGTGAGCAGC

-continued (Linker)
GGAGGCGGAGGCTCCGGCGGAGGCGGATCTGGCGGTGGCGGCTCC (αCD28 light chain variable region)
GACATCGAGATGACCCAGTCCCCCGCTATCATGTCCGCCTCTTTAGGCGAG

CGGGTCACAATGACTTGTACAGCCTCCTCCAGCGTCTCCTCCTCCTACTTC

CATTGGTACCAACAGAAACCCGGAAGCTCCCCTAAACTGTGCATCTACAGC

ACCAGCAATCTCGCCAGCGGCGTGCCCCCTAGGTTTTCCGGAAGCGGAAGC

ACCAGCTACTCTTTAACCATCTCCTCCATGGAGGCTGAGGATGCCGCCACC

TACTTTTGTCACCAGTACCACCGGTCCCCCACCTTCGGAGGCGGCACCAAA

CTGGAGACAAAGAGG

Exemplary Single-Chain Chimeric Polypeptide (αCD3scFv/TF/αCD28scFv) (SEQ ID NO: 157)

(Signal peptide)
MKWVTFISLLFLFSSAYS (αCD3 light chain variable region)
QIVLTQSPAIMSASPGEKVTMTCSASSSVSYMNWYQQKSGTSPKRWIYDTS

KLASGVPAHFRGSGSGTSYSLTISGMEAEDAATYYCQQWSSNPFTFGSGTK

LEINR (Linker)
GGGGSGGGGSGGGGS (αCD3 heavy chain variable region)
QVQLQQSGAELARPGASVKMSCKASGYTFTRYTMHWVKQRPGQGLEWIGYI

NPSRGYTNYNQKFKDKATLTTDKSSSTAYMQLSSLTSEDSAVYYCARYYDD

HYCLDYWGQGTTLTVSS (Human tissue factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE (αCD28 light chain variable region)
VQLQQSGPELVKPGASVKMSCKASGYTFTSYVIQWVKQKPGQGLEWIGSIN

PYNDYTKYNEKFKGKATLTSDKSSITAYMEFSSLTSEDSALYYCARWGDGN

YWGRGTTLTVSS (Linker)
GGGGSGGGGSGGGGS (αCD28 heavy chain variable region)
DIEMTQSPAIMSASLGERVTMTCTASSSVSSSYFHWYQQKPGSSPKLCIYS

TSNLASGVPPRFSGSGSGTSYSLTISSMEAEDAATYFCHQYHRSPTFGGGTK

LETKR

A second exemplary single-chain chimeric polypeptide including a first target-domain that is an anti-CD28 scFv, a soluble human tissue factor domain, and a second target-binding domain that is an anti-CD3 scFv was generated (aCD28scFv/TF/aCD3scFv) (FIG. 57). The nucleic acid and amino acid sequences of this single-chain chimeric polypeptide are shown below.

Nucleic Acid Encoding Exemplary Single-Chain Chimeric Polypeptide (αCD28scFv/TF/αCD3scFv) (SEQ ID NO: 326)

(Signal peptide)
ATGAAATGGGTCACCTTCATCTCTTTACTGTTTTTATTTAGCAGCGCCTAC

AGC (αCD28 light chain variable region)
GTGCAGCTGCAGCAGTCCGGACCCGAACTGGTCAAGCCCGGTGCCTCCGTG

AAAATGTCTTGTAAGGCTTCTGGCTACACCTTTACCTCCTACGTCATCCAA

TGGGTGAAGCAGAAGCCCGGTCAAGGTCTCGAGTGGATCGGCAGCATCAAT

CCCTACAACGATTACACCAAGTATAACGAAAAGTTTAAGGGCAAGGCCACT

CTGACAAGCGACAAGAGCTCCATTACCGCCTACATGGAGTTTTCCTCTTTA

ACTTCTGAGGACTCCGCTTTATACTATTGCGCTCGTTGGGGCGATGGCAAT

TATTGGGGCCGGGGAACTACTTTAACAGTGAGCTCC (Linker)
GGCGGCGGCGGAAGCGGAGGTGGAGGATCTGGCGGTGGAGGCAGC (αCD28 heavy chain variable region)
GACATCGAGATGACACAGTCCCCCGCTATCATGAGCGCCTCTTTAGGAGAA

CGTGTGACCATGACTTGTACAGCTTCCTCCAGCGTGAGCAGCTCCTATTTC

CACTGGTACCAGCAGAAACCCGGCTCCTCCCCTAAACTGTGTATCTACTCC

ACAAGCAATTTAGCTAGCGGCGTGCCTCCTCGTTTTAGCGGCTCCGGCAGC

ACCTCTTACTCTTTAACCATTAGCTCTATGGAGGCCGAAGATGCCGCCACA

TACTTTTGCCATCAGTACCACCGGTCCCCTACCTTTGGCGGAGGCACAAAG

CTGGAGACCAAGCGG (Human tissue factor 219 form)
AGCGGCACCACCAACACAGTGGCCGCCTACAATCTGACTTGGAAATCCACC

AACTTCAAGACCATCCTCGAGTGGGAGCCCAAGCCCGTTAATCAAGTTTAT

ACCGTGCAGATTTCCACCAAGAGCGGCGACTGGAAATCCAAGTGCTTCTAT

ACCACAGACACCGAGTGCGATCTCACCGACGAGATCGTCAAAGACGTGAAG

CAGACATATTTAGCTAGGGTGTTCTCCTACCCCGCTGGAAACGTGGAGAGC

ACCGGATCCGCTGGAGAGCCTTTATACGAGAACTCCCCCGAATTCACCCCC

TATCTGGAAACCAATTTAGGCCAGCCCACCATCCAGAGCTTCGAACAAGTT

GGCACAAAGGTGAACGTCACCGTCGAAGATGAGAGGACTTTAGTGCGGAGG

AACAATACATTTTTATCCTTACGTGACGTCTTCGGCAAGGATTTAATCTAC

ACACTGTATTACTGGAAGTCTAGCTCCTCCGGCAAGAAGACCGCCAAGACC

AATACCAACGAATTTTTAATTGACGTGGACAAGGGCGAGAACTACTGCTTC

TCCGTGCAAGCTGTGATCCCCTCCCGGACAGTGAACCGGAAGTCCACCGAC

TCCCCCGTGGAGTGCATGGGCCAAGAGAAGGGAGAGTTTCGTGAG (αCD3 light chain variable region)
CAGATCGTGCTGACCCAGTCCCCCGCTATTATGAGCGCTAGCCCCGGTGAA

AAGGTGACTATGACATGCAGCGCCAGCTCTTCCGTGAGCTACATGAACTGG

TATCAGCAGAAGTCCGGCACCAGCCCTAAAAGGTGGATCTACGACACCAGC

AAGCTGGCCAGCGGCGTCCCCGCTCACTTTCGGGGCTCCGGCTCCGGAACA

AGCTACTCTCTGACCATCAGCGGCATGGAAGCCGAGGATGCCGCTACCTAT

-continued

TACTGTCAGCAGTGGAGCTCCAACCCCTTCACCTTTGGATCCGGCACCAAG

CTCGAGATTAATCGT (Linker)
GGAGGCGGAGGTAGCGGAGGAGGCGGATCCGGCGGTGGAGGTAGC (αCD3 heavy chain variable region)
CAAGTTCAGCTCCAGCAAAGCGGCGCCGAACTCGCTCGGCCCGGCGCTTCC

GTGAAGATGTCTTGTAAGGCCTCCGGCTATACCTTCACCCGGTACACAATG

CACTGGGTCAAGCAACGGCCCGGTCAAGGTTTAGAGTGGATTGGCTATATC

AACCCCTCCCGGGGCTATACCAACTACAACCAGAAGTTCAAGGACAAAGCC

ACCCTCACCACCGACAAGTCCAGCAGCACCGCTTACATGCAGCTGAGCTCT

TTAACATCCGAGGATTCCGCCGTGTACTACTGCGCTCGGTACTACGACGAT

CATTACTGCCTCGATTACTGGGGCCAAGGTACCACCTTAACAGTCTCCTCC

Exemplary Single-Chain Chimeric Polypeptide (αCD28scFv/TF/αCD3scFv) (SEQ ID NO: 327)

(Signal peptide)
MKWVTFISLLFLFSSAYS (αCD28 light chain variable region)
VQLQQSGPELVKPGASVKMSCKASGYTFTSYVIQWVKQKPGQGLEWIGSIN

PYNDYTKYNEKFKGKATLTSDKSSITAYMEFSSLTSEDSALYYCARWGDGN

YWGRGTTLTVSS (Linker)
GGGGSGGGGSGGGGS (αCD28 heavy chain variable region)
DIEMTQSPAIMSASLGERVTMTCTASSSVSSSYFHWYQQKPGSSPKLCIYS

TSNLASGVPPRFSGSGSTSYSLTISSMEAEDAATYFCHQYHRSPTFGGGTK

LETKR (Human tissue factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE (αCD3 light chain variable region)
QIVLTQSPAIIVISASPGEKVTMTCSASSSVSYMNWYQQKSGTSPKRWIYD

TSKLASGVPAHFRGSGSGTSYSLTISGMEAEDAATYYCQQWSSNPFTFGSG

TKLEINR (Linker)
GGGGSGGGGSGGGGS (αCD3 heavy chain variable region)
QVQLQQSGAELARPGASVKMSCKASGYTFTRYTMHWVKQRPGQGLEWIGYI

NPSRGYTNYNQKFKDKATLTTDKSSSTAYMQLSSLTSEDSAVYYCARYYDD

HYCLDYWGQGTTLTVSS

The nucleic acid encoding aCD3scFv/TF/aCD28scFv was cloned into a modified retrovirus expression vectors as described previously (Hughes et al., *Hum Gene Ther* 16:457-72, 2005). The expression vector encoding aCD3scFv/TF/aCD28scFv was transfected into CHO-K1 cells. Expression of the expression vector in CHO-K1 cells allowed for secretion of the soluble aCD3scFv/TF/aCD28scFv single-chain chimeric polypeptide (referred to as 3t28), which can be purified by anti-TF Ab affinity and other chromatography methods.

An anti-tissue factor affinity column was used to purify the aCD3scFv/TF/αCD28scFv single-chain chimeric polypeptide. The anti-tissue factor affinity column was connected to a GE Healthcare AKTA Avant system. A flow rate of 4 mL/min was used for all steps except the elution step, which was 2 mL/min.

Figure 58:
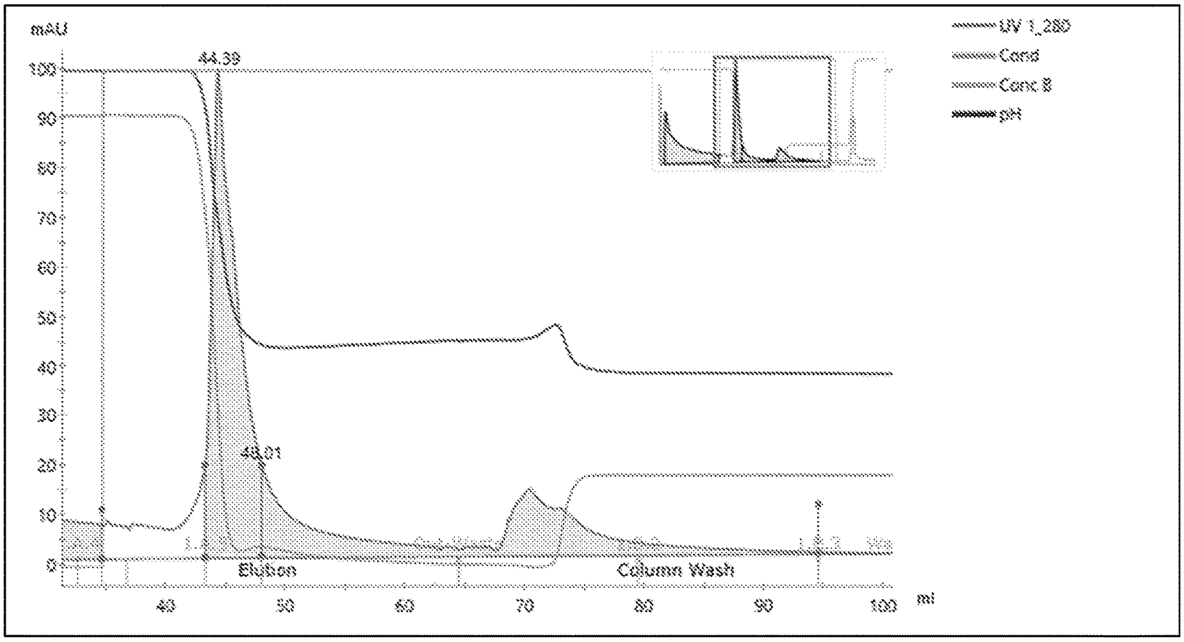
FIG. 58 is a chromatograph showing the elution of an exemplary αCD3scFv/TF/αCD28scFv single-chain chimeric polypeptide from an anti-tissue factor affinity column.

Cell culture harvest including aCD3scFv/TF/αCD28scFv single-chain chimeric polypeptide was adjusted to pH 7.4 with 1 M Tris base and loaded onto the anti-TF antibody affinity column (described above) which was equilibrated with 5 column volumes of PBS. After sample loading, the column was washed with 5 column volumes PBS, followed by elution with 6 column volumes 0.1 M acetic acid, pH 2.9. An A280 elution peak was collected and then neutralized to pH 7.5-8.0 by adding 1 M Tris base. The neutralized sample was then buffer exchanged into PBS using Amicon centrifugal filters with a 30 kDa molecular weight cutoff. The data in FIG. 58 show that the anti-tissue factor affinity column can bind the aCD3scFv/TF/αCD28scFv single-chain chimeric polypeptide, which contains a human soluble tissue factor domain. The buffer-exchanged protein sample was stored at 2-8 °C for further biochemical analysis and biological activity testing.

After each elution, the anti-tissue factor affinity column was stripped using 6 column volumes of 0.1 M glycine, pH 2.5. The column was then neutralized using 10 column volumes of PBS, 0.05% $NaN_3$, and stored at 2-8 °C.

Figure 59:
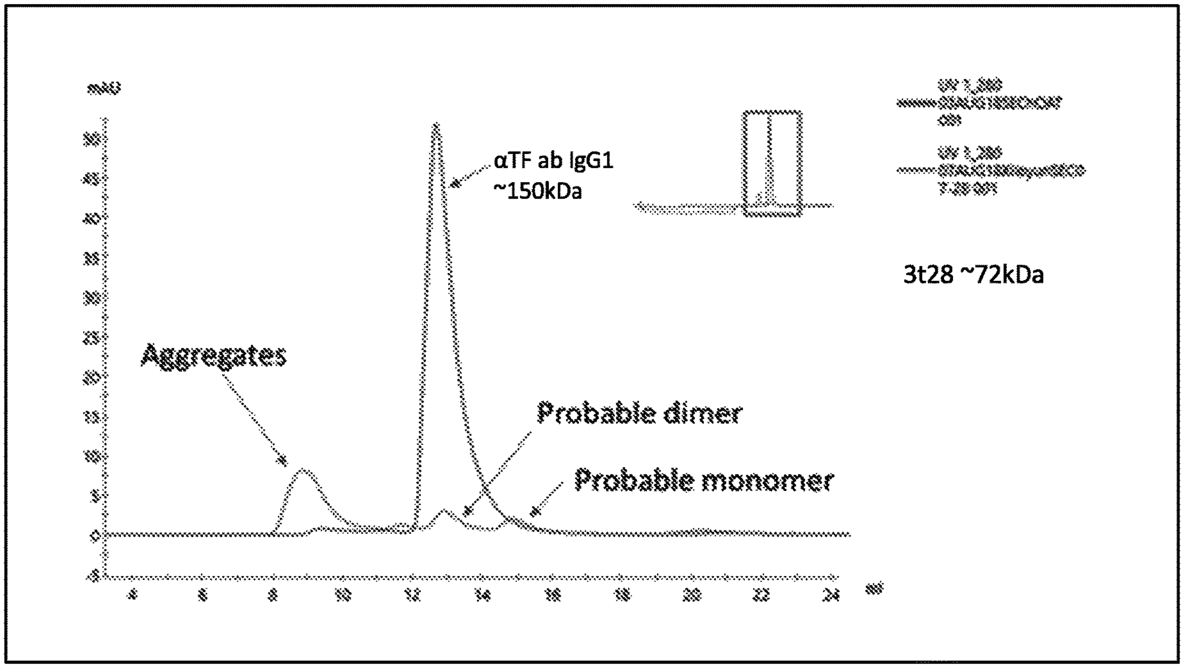
FIG. 59 is a chromatograph showing the elution of a Superdex 200 Increase 10/300 GL gel filtration column loaded with an exemplary αCD3scFv/TF/αCD28scFv single-chain chimeric polypeptide.

Analytical size exclusion chromatography (SEC) was performed on the αCD3scFv/TF/αCD28scFv single-chain chimeric polypeptide using a Superdex 200 Increase 10/300 GL gel filtration column (from GE Healthcare) connected to an AKTA Avant system (from GE Healthcare). The column was equilibrated with 2 column volumes of PBS. A flow rate of 0.8 mL/min was used. Two hundred μL of αCD3scFv/TF/αCD28scFv single-chain chimeric polypeptide (1 mg/mL) was injected onto the column using a capillary loop. After injection of the single-chain chimeric polypeptide, 1.25 column volumes of PBS were flowed into the column. The SEC chromatograph is shown in FIG. 59. The data show that there are 3 protein peaks, likely representing a monomer and dimer or other different forms of the αCD3scFv/TF/αCD28scFv single-chain chimeric polypeptide.

Figure 60:
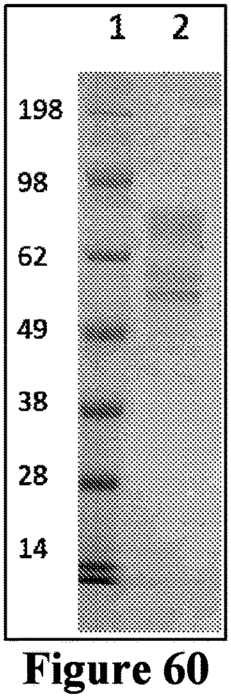
FIG. 60 is a sodium dodecyl sulfate polyacrylamide gel (4-12% NuPage Bis-Tris gel) of an exemplary αCD3scFv/TF/αCD28scFv single-chain chimeric polypeptide purified using an anti-tissue factor affinity column.

To determine the purity and protein molecular weight of the αCD3scFv/TF/αCD28scFv single-chain chimeric polypeptide, the purified αCD3scFv/TF/αCD28scFv protein sample from anti-tissue factor affinity column was analyzed by standard sodium dodecyl sulfate polyacrylamide gel (4-12% NuPage Bis-Tris gel) electrophoresis (SDS-PAGE) method under reduced conditions. The gel was stained with InstantBlue for about 30 minutes and destained overnight with purified water. FIG. 60 shows the SDS gel of the αCD3scFv/TF/αCD28scFv single-chain chimeric polypeptide purified using an anti-tissue factor affinity column. The results show that the purified αCD3scFv/TF/αCD28scFv single-chain chimeric polypeptide has the expected molecular weight (72 kDa) in reduced SDS gel.

Figure 61:
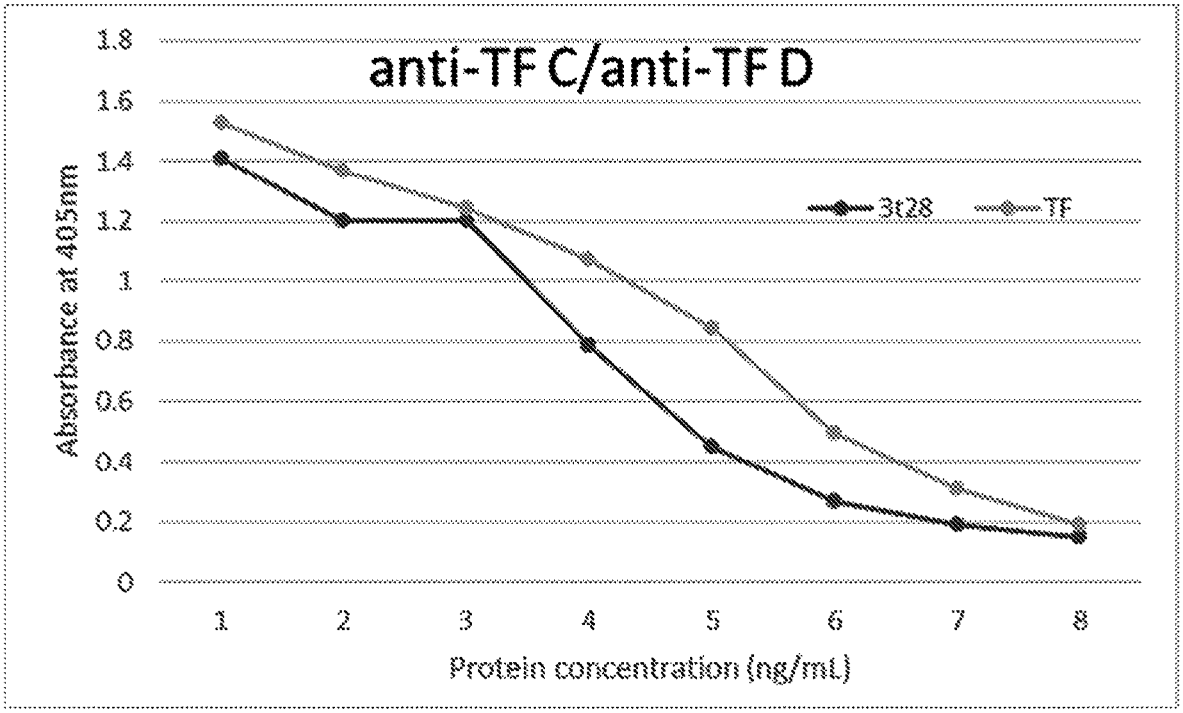
FIG. 61 is a graph showing the ELISA quantitation of an exemplary αCD3scFv/TF/αCD28scFv single-chain chimeric polypeptide performed using the methods described in Example 1. Purified tissue factor was used as the control.

Example 33. Functional Characterization of αCD3scFv/TF/αCD28scFv Single-Chain Chimeric Polypeptide ELISA-based methods confirmed the formation of the αCD3scFv/TF/αCD28scFv single-chain chimeric polypeptide. The αCD3scFv/TF/αCD28scFv single-chain chimeric polypeptide was detected using an anti-TF antibody (I43)/anti-TF antibody-specific ELISA with a capture antibody, anti-human tissue factor antibody (I43), and a detection antibody, anti-TF antibody(FIG. 61). A purified tissue factor protein with a similar concentration was used as a control.

Figure 62:
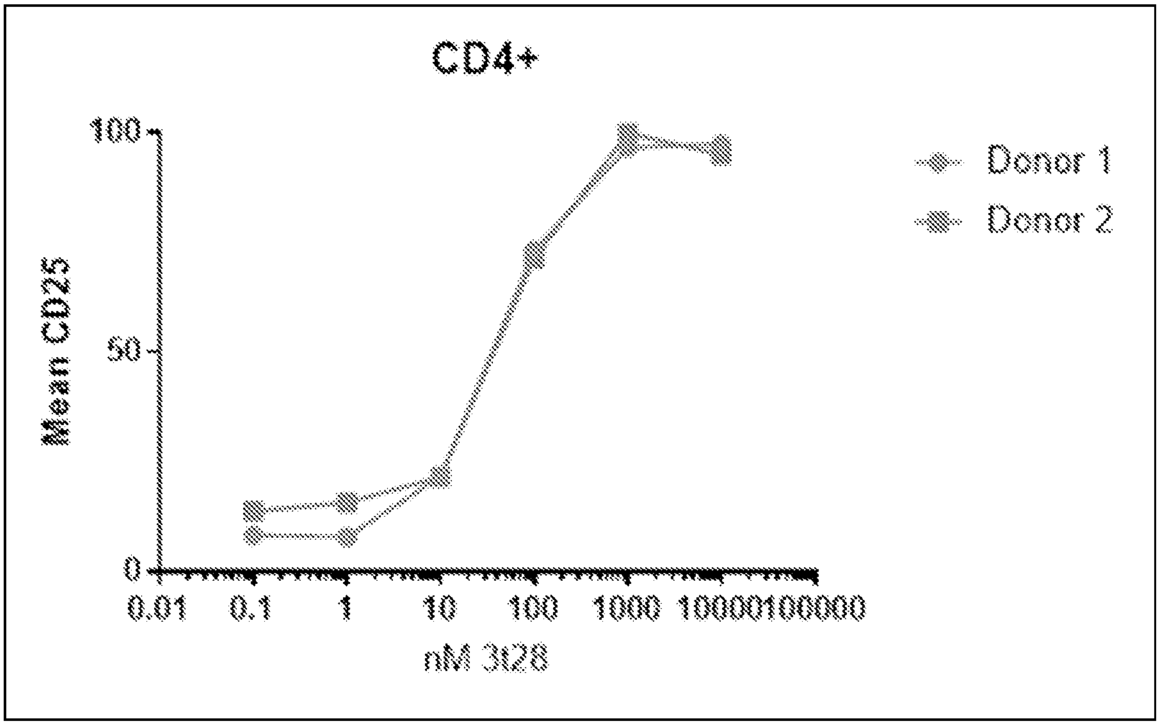
FIG. 62 is a graph showing the ability of an exemplary αCD3scFv/TF/αCD28scFv single-chain chimeric polypeptide to stimulate CD25 expression in $CD4^+$ T-cells isolated from blood from two donors. The experiments were performed as described in Example 2.
Figure 63:
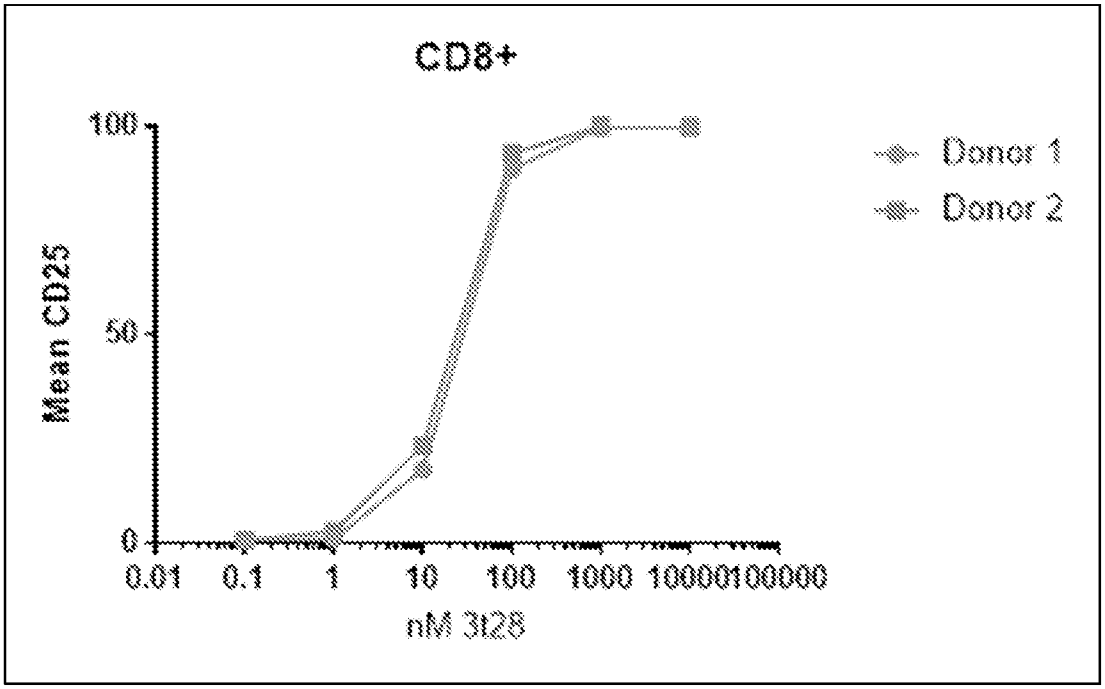
FIG. 63 is a graph showing the ability of an exemplary αCD3scFv/TF/αCD28scFv single-chain chimeric polypeptide to stimulate CD25 expression in $CD8^+$ T-cells isolated from blood from two donors. The experiments were performed as described in Example 2.
Figure 64:
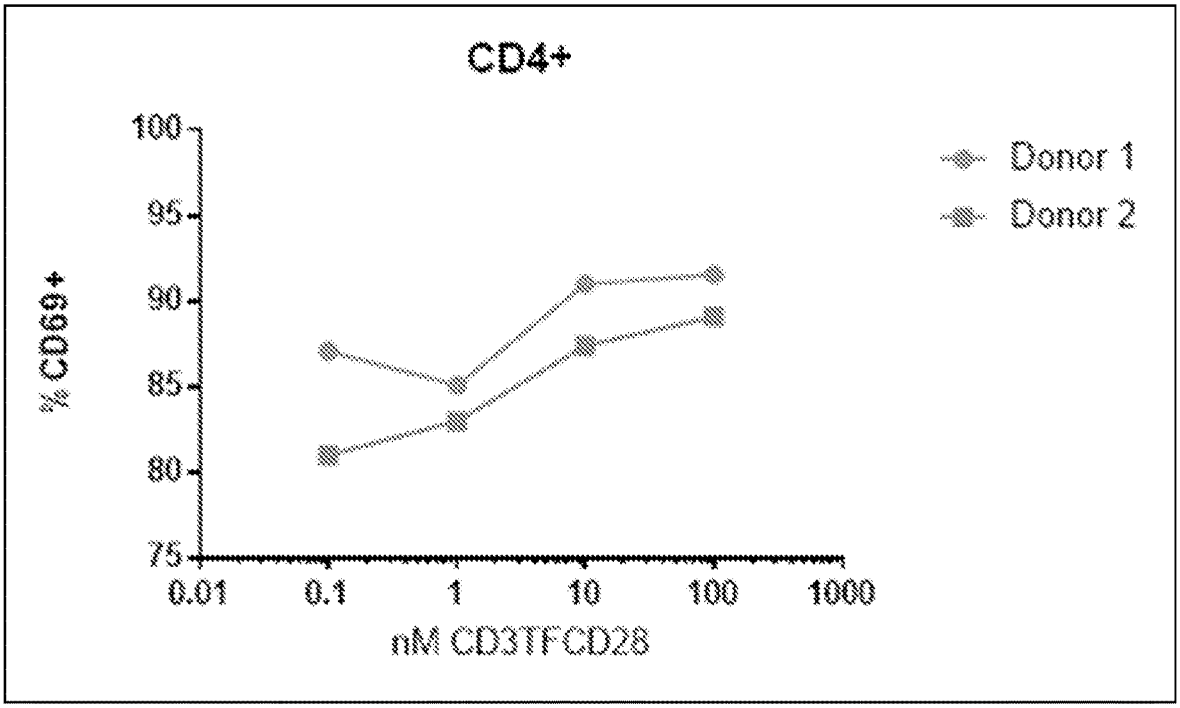
FIG. 64 is a graph showing the ability of an exemplary αCD3scFv/TF/αCD28scFv single-chain chimeric polypeptide to stimulate CD69 expression in $CD4^+$ T-cells isolated from blood from two donors. The experiments were performed as described in Example 2.

A further in vitro experiment was performed to determine whether the αCD3scFv/TF/αCD28scFv single-chain chimeric polypeptide is capable of activating human peripheral blood mononuclear cells (PBMCs). Fresh human leukocytes were obtained from the blood bank and peripheral blood mononuclear cells (PBMC) were isolated using density gradient Histopaque (Sigma). The cells were counted and resuspended in $0.2\times10^6$/mL in a 96-well flat bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with αCD3scFv/TF/αCD28scFv single-chain chimeric polypeptide from 0.01 nM to 1000 nM for 3 days at 37 °C, 5% $CO_2$. After 72 hours, the cells were harvested and surface stained for CD4-488, CD8-PerCP Cy5.5, CD25-BV421,CD69-APCFire750, CD62L-PE Cy7, and CD44-PE specific antibodies (Biolegend) for 30 minutes. After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were resuspended in 300 μL of FACS buffer and analyzed by Flow Cytometry (Celesta-BD Bioscience). The data in FIGS. 62 and 63 show that the αCD3scFv/TF/αCD28scFv single-chain chimeric polypeptide is able to stimulate both $CD8^+$ and $CD4^+$ T-cells. A further experiment was performed, in which PBMCs isolated from blood using Histopaque (Sigma) were counted and resuspended in $0.2\times10^6$/mL in a 96-well flat bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were then stimulated with the αCD3scFv/TF/αCD28scFv single-chain chimeric polypeptide from 0.01 nM to 1000 nM for 3 days at 37 °C, 5% $CO_2$. After 72 hours, the cells were harvested and surface stained for CD4-488, CD8-PerCP Cy5.5, CD25-BV421, CD69-APCFire750, CD62L-PE Cy7, and CD44-PE (Biolegend) for 30 minutes. After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were resuspended in 300 μL of FACS buffer and analyzed by Flow Cytometry (Celesta-BD Bioscience). The data again show that the αCD3scFv/TF/αCD28scFv single-chain chimeric polypeptide was able to stimulate activation of $CD4^+$ T cells (FIG. 64).

Example 34: Creation of an IL-7/IL-15RαSu DNA Construct

Figure 65:
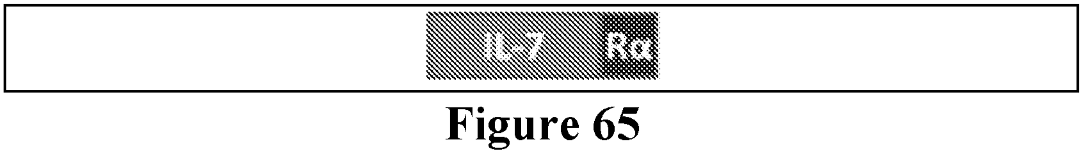
FIG. 65 shows a schematic diagram of an exemplary IL-7/IL-15RαSu DNA construct.

In a non-limiting example, an IL-7/IL-15RαSu DNA construct was created (see FIG. 65). The human IL-7 sequence, human IL-15RαSu sequence, human IL-15 sequence, and human tissue factor 219 sequence were obtained from the UniProt website and DNA for these sequences was synthesized by Genewiz. A DNA construct was made linking the IL-7 sequence to the IL-15RαSu sequence. The final IL-7/IL-15RαSu DNA construct sequence was synthesized by Genewiz.

The nucleic acid sequence encoding the second chimeric polypeptide of IL-7/IL-15RαSu construct (including signal peptide sequence) is as follows (SEQ ID NO: 206):

```
(Signal peptide)
ATGGGAGTGAAAGTTCTTTTTGCCCTTATTTGTATTGCTGTGGCCGAGGCC

(Human IL-7)
GATTGTGATATTGAAGGTAAAGATGGCAAACAATATGAGAGTGTTCTAATG

GTCAGCATCGATCAATTATTGGACAGCATGAAAGAAATTGGTAGCAATTGC

CTGAATAATGAATTTAACTTTTTAAAAGACATATCTGTGATGCTAATAAG

GAAGGTATGTTTTTATTCCGTGCTGCTCGCAAGTTGAGGCAATTTCTTAAA

ATGAATAGCACTGGTGATTTTGATCTCCACTTATTAAAAGTTTCAGAAGGC

ACAACAATACTGTTGAACTGCACTGGCCAGGTTAAAGGAAGAAAACCAGCT

GCCCTGGGTGAAGCCCAACCAACAAAGAGTTTGGAAGAAAATAAATCTTTA

AAGGAACAGAAAAAACTGAATGACTTGTGTTTCCTAAAGAGACTATTACAA

GAGATAAAAACTTGTTGGAATAAAATTTTGATGGGCACTAAAGAACAC

(Human IL-15R α sushi domain)
ATCACGTGCCCTCCCCCCATGTCCGTGGAACACGCAGACATCTGGGTCAAG

AGCTACAGCTTGTACTCCAGGGAGCGGTACATTTGTAACTCTGGTTTCAAG

CGTAAAGCCGGCACGTCCAGCCTGACGGAGTGCGTGTTGAACAAGGCCACG

AATGTCGCCCACTGGACAACCCCCAGTCTCAAATGCATTAGA
```

The second chimeric polypeptide of IL-7/IL-15RαSu construct (including signal peptide sequence) is as follows (SEQ ID NO: 205):

```
(Signal peptide)
MKWVTFISLLFLFSSAYS

(Human IL-7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE

(Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS
```

Example 35: Creation of an IL-21/TF/IL-15 DNA Construct

Figure 66:
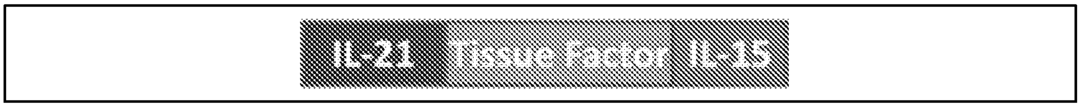
FIG. 66 shows a schematic diagram of an exemplary IL-21/TF/IL-15 DNA construct.

In a non-limiting example, an IL-21/TF/IL-15 construct was made (FIG. 66) by linking the IL-21 sequence to the N-terminus coding region of tissue factor 219, and further linking the IL-21/TF construct with the N-terminus coding region of IL-15.

The nucleic acid sequence encoding the first chimeric polypeptide of IL-21/TF/IL-15 construct (including leader sequence), synthesized by Genewiz, is as follows (SEQ ID NO: 202):

```
(Signal peptide)
ATGGGAGTGAAAGTTCTTTTTGCCCTTATTTGTATTGCTGTGGCCGAGGCC

(Human IL-21 fragment)
CAAGGTCAAGATCGCCACATGATTAGAATGCGTCAACTTATAGATATTGTT

GATCAGCTGAAAAATTATGTGAATGACTTGGTCCCTGAATTTCTGCCAGCT

CCAGAAGATGTAGAGACAAACTGTGAGTGGTCAGCTTTTTCCTGTTTTCAG

AAGGCCCAACTAAAGTCAGCAAATACAGGAAACAATGAAAGGATAATCAAT

GTATCAATTAAAAAGCTGAAGAGGAAACCACCTTCCACAAATGCAGGGAGA

AGACAGAAACACAGACTAACATGCCCTTCATGTGATTCTTATGAGAAAAAA

CCACCCAAAGAATTCCTAGAAAGATTCAAATCACTTCTCCAAAAGATGATT

CATCAGCATCTGTCCTCTAGAACACACGGAAGTGAAGATTCC

(Human Tissue Factor 219)
TCAGGCACTACAAATACTGTGGCAGCATATAATTTAACTTGGAAATCAACT

AATTTCAAGACAATTTTGGAGTGGGAACCCAAACCCGTCAATCAAGTCTAC

ACTGTTCAAATAAGCACTAAGTCAGGAGATTGGAAAAGCAAATGCTTTTAC

ACAACAGACACAGAGTGTGACCTCACCGACGAGATTGTGAAGGATGTGAAG

CAGACGTACTTGGCACGGGTCTTCTCCTACCCGGCAGGGAATGTGGAGAGC

ACCGGTTCTGCTGGGGAGCCTCTGTATGAGAACTCCCCAGAGTTCACACCT

TACCTGGAGACAAACCTCGGACAGCCAACAATTCAGAGTTTTGAACAGGTG

GGAACAAAAGTGAATGTGACCGTAGAAGATGAACGGACTTTAGTCAGAAGG

AACAACACTTTCCTAAGCCTCCGGGATGTTTTTGGCAAGGACTTAATTTAT

ACACTTTATTATTGGAAATCTTCAAGTTCAGGAAAGAAAACAGCCAAAACA

AACACTAATGAGTTTTTGATTGATGTGGATAAAGGAGAAAACTACTGTTTC

AGTGTTCAAGCAGTGATTCCCTCCCGAACAGTTAACCGGAAGAGTACAGAC

AGCCCGGTAGAGTGTATGGGCCAGGAGAAAGGGGAATTCAGAGAA

(Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC
```

The first chimeric polypeptide of IL-21/TF/IL-15 construct including leader sequence is SEQ ID NO: 201:

```
(Signal peptide)
                                        (SEQ ID NO: 328)
MGVKVLFALICIAVAEA

(Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE

(Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS
```

Example 36: Secretion of IL-7/IL-15RαSu and IL-21/TF/IL-15 Fusion Proteins

Figure 67:
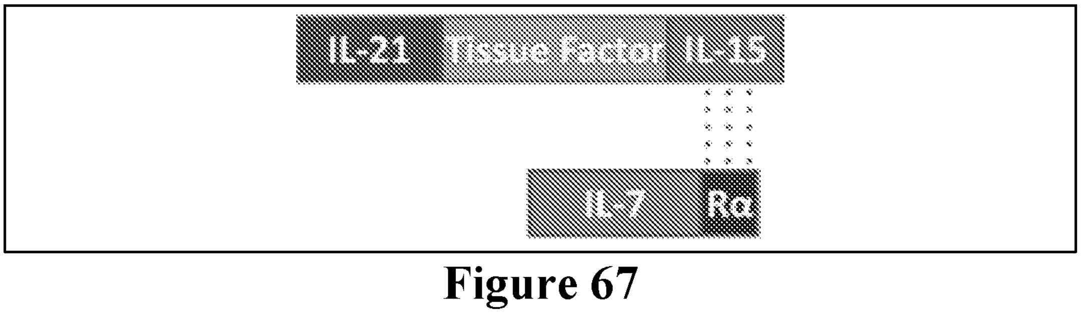
FIG. 67 shows a schematic diagram of the interaction between the exemplary IL-7/IL-15RαSu and IL-21/TF/IL-15 DNA constructs.
Figure 68:
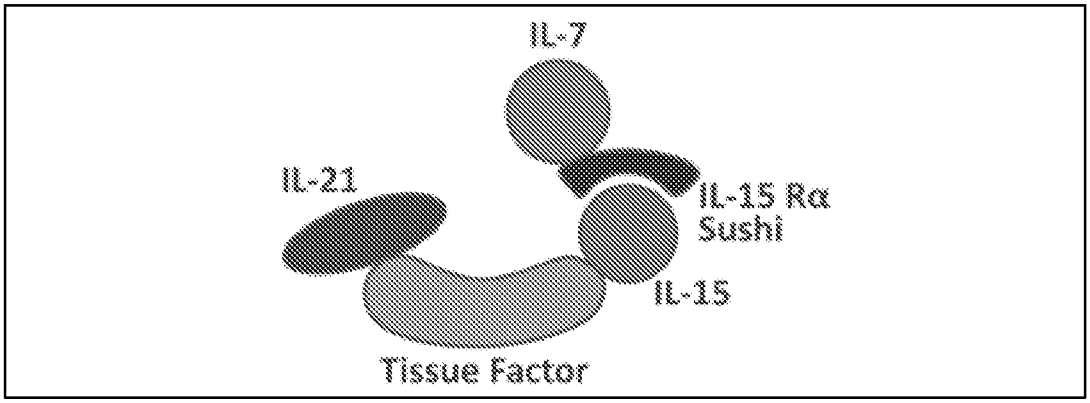
FIG. 68 shows a schematic diagram of the interaction between the exemplary IL-7/IL-15RαSu and IL-21/TF/IL-15 fusion proteins resulting in an IL-21/TF/IL-15:IL-7/IL-15RαSu complex (21t15-7s).

The IL-7/IL-15RαSu and IL-21/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-21/TF/IL-15:IL-7/IL-15RαSu protein complex (referred to as 21t15-7s; FIG. 67 and FIG. 68). The 21t15-7s protein was purified from CHO-K1 cell culture supernatant using anti-TF antibody affinity chromatography and size exclusion chromatography resulting in soluble (non-aggregated) protein complexes consisting of IL-7/IL-15RαSu and IL-21/TF/IL-15 fusion proteins.

In some cases, the leader (signal sequence) peptide is cleaved from the intact polypeptide to generate the mature form that may be soluble or secreted.

Example 37: Purification of 21t15-7s by Immunoaffinity Chromatography

An anti-TF antibody affinity column was connected to a GE Healthcare™ AKTA Avant protein purification system. The flow rate was 4 mL/min for all steps except the elution step, which was 2 mL/min.

Cell culture harvest of 21t15-7s was adjusted to pH 7.4 with 1 M Tris base and loaded onto the anti-TF antibody affinity column equilibrated with 5 column volumes of PBS. After loading the sample, the column was washed with 5 column volumes PBS, followed by elution with 6 column volumes 0.1 M acetic acid, pH 2.9. Absorbance at 280 nm was collected and then the sample was neutralized to pH 7.5-8.0 by adding 1 M Tris base. The neutralized sample was then buffer exchanged into PBS using Amicon® centrifugal filters with a 30 KDa molecular weight cutoff. The buffer-exchanged protein sample was stored at 2-8 °C for further biochemical analysis and biological activity testing.

After each elution, the anti-TF antibody affinity column was then stripped using 6 column volumes 0.1 M glycine, pH 2.5. The column was then neutralized using 10 column volumes PBS, 0.05% sodium azide and stored at 2-8 °C.

Example 38: Size Exclusion Chromatography

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.7 mL/min. A capillary loop was used to inject 2004, of 1 mg/mL of 7t15-21s complex onto the column. The injection was chased with 1.25 column volumes of PBS.

Example 39: SDS-PAGE of 21t15-7s and 21t15-TGFRs

To determine the purity and protein molecular weight, the purified 21t15-7s or 21t15-TGFRs protein sample were analyzed using 4-12% NuPage Bis-Tris protein gel SDS-PAGE. The gel will be stained with InstantBlue™ for about 30 min, followed by destaining overnight in purified water.

Example 40: Glycosylation of 21t15-7s and 21t15-TGFRs in CHO-K1 Cells

Glycosylation of 21t15-7s in CHO-K1 cells or 21t15-TGFRs in CHO-K1 cells were confirmed using the Protein Deglycosylation Mix II kit (New England Biolabs), according to the manufacturer's instructions.

Example 41: Recombinant Protein Quantitation of 21t15-7s and 21t15-TGFRs Complexes The 21t15-7s complex or the 21t15-TGFRs complex were detected and quantified using standard sandwich ELISA methods. Anti-human tissue factor antibody (IgG1) served as the capture antibody and biotinylated anti-human IL-21, IL-15, or IL-7 antibody (21t15-7s) or biotinylated anti-human IL-21, IL-15, or TGF-βRII antibody (21t15-TGFRs) served as the detection antibody. Tissue factor in purified 21t15-7s or 21t15-TGFRs protein complexes was detected using an anti-human tissue factor capture antibody, and anti-human tissue factor antibody (IgG1) detection antibody. The anti-TF antibody ELISA will be compared to purified tissue factor at similar concentrations.

Example 42: Creation of an IL-21/IL-15RαSu DNA Construct

Figure 69:
FIG. 69 shows a schematic diagram of an exemplary IL-21/IL-15RαSu DNA construct.

In a non-limiting example, an IL-21/IL-15RαSu DNA construct was created. The human IL-21 sequence and human IL-15RαSu sequence were obtained from the UniProt website and DNA for these sequences was synthesized by Genewiz. A DNA construct was made linking the IL-21 sequence to the IL-15RαSu sequence. The final IL-21/IL-15RαSu DNA construct sequence was synthesized by Genewiz. See FIG. 69.

Example 43: Creation of an IL-7/TF/IL-15 DNA Construct

Figure 70:
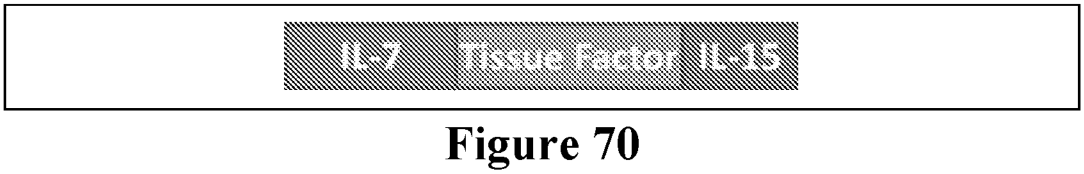
FIG. 70 shows a schematic diagram of an exemplary IL-7/TF/IL-15 DNA construct.

In a non-limiting example, an IL-7/TF/IL-15 construct was made by linking the IL-7 sequence to the N-terminus coding region of tissue factor 219, and further linking the IL-7/TF construct with the N-terminus coding region of IL-15. See FIG. 70.

Example 44: Creation of an IL-21/IL-15Rα Sushi DNA Construct

In a non-limiting example, a second chimeric polypeptide of IL-21/IL-15RαSu was generated. The human IL-21 and human IL-15Rα sushi sequences were obtained from the UniProt website and DNA for these sequences was synthesized by Genewiz. A DNA construct was made linking the IL-21 sequence to the IL-15Rα sushi sequence. The final IL-21/IL-15RαSu DNA construct sequence was synthesized by Genewiz.

The nucleic acid sequence encoding the second chimeric polypeptide of IL-21/IL-15RαSu domain (including leader sequence), synthesized by Genewiz, is as follows (SEQ ID NO: 214):

```
(Signal peptide)
ATGAAGTGGGTGACCTTCATCAGCCTGCTGTTCCTGTTCTCCAGCGCCTAC

TCC

(Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC

(Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG
```

The second chimeric polypeptide of IL-21/IL-15Rα sushi domain (including leader sequence) is as follows (SEQ ID NO: 213):

```
(Signal Sequence)
MKWVTFISLLFLFSSAYS

(Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS

(Human IL-15Rα sushi domain)
ITCPPPMSVEHADIWVKSYSLYSRERYICNSGFKRKAGTSSLTECVLNKAT

NVAHWTTPSLKCIR
```

Example 45: Creation of an IL-7/TF/IL-15 DNA Construct

In a non-limiting example, an exemplary first chimeric polypeptide of IL-7/TF/IL-15 was made by linking the IL-7 sequence to the N-terminus coding region of tissue factor 219, and further linking the IL-7/TF construct with the N-terminus coding region of IL-15. The nucleic acid sequence encoding the first chimeric polypeptide of IL-7/TF/IL-15 (including leader sequence), synthesized by Genewiz, is as follows (SEQ ID NO: 210):

```
(Signal peptide)
ATGAAGTGGGTGACCTTCATCAGCCTGCTGTTCCTGTTCTCCAGCGCCTAC

TCC

(Human IL-7 fragment)
GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG

GAGGGCATGTTCCTGTTCAGGGCCGCCAGGAAACTGCGGCAGTTCCTGAAG

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCAT

(Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG

(Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC
```

The first chimeric polypeptide of IL-7/TF/IL-15 (including leader sequence), is as follows (SEQ ID NO: 209):

```
(Signal peptide)
MKWVTFISLLFLFSSAYS

(Human IL-7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE

(Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS
```

Example 46: Secretion of IL-21/IL-15RαSu and IL-7/TF/IL-15 Fusion Proteins

Figure 71:
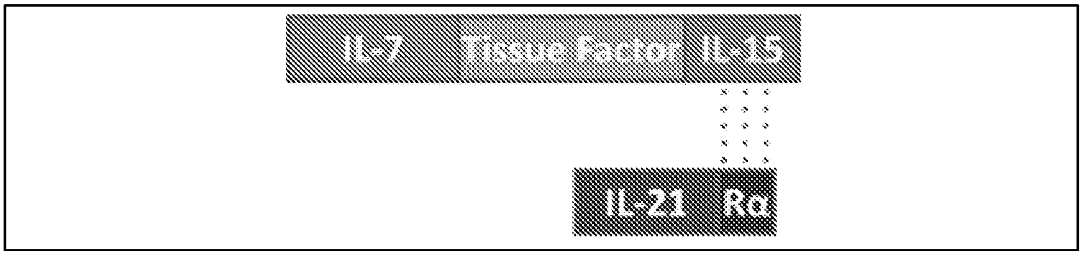
FIG. 71 shows a schematic diagram of the interaction between the exemplary IL-21/IL-15RαSu and IL-7/TF/IL-15 DNA constructs.
Figure 72:
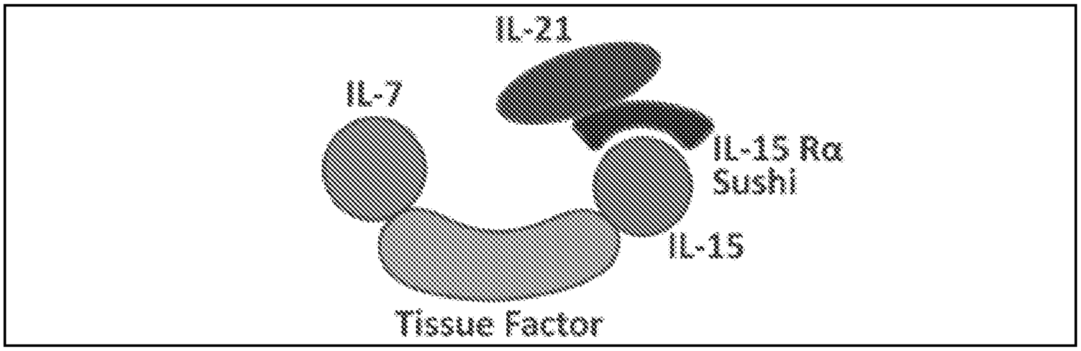
FIG. 72 shows a schematic diagram of the interaction between the exemplary IL-21/IL-15RαSu and IL-7/TF/IL-15 fusion proteins resulting in an IL-7/TF/IL-15:IL-21/IL-15RαSU complex (7t15-21s).

The IL-21/IL-15RαSu and IL-7/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-7/TF/IL-15:IL-21/IL-15RαSu protein complex (referred to as 7t15-21s). The 7t15-21s protein was purified from CHO-K1 cell culture supernatant using anti-TF antibody (IgG1) affinity chromatography and size exclusion chromatography resulting in soluble (non-aggregated) protein complexes consisting of IL-21/IL-15RαSu and IL-7/TF/IL-15 fusion proteins. See FIGS. 71 and FIG. 72.

Example 47: Expansion Capacity of Primary Natural Killer (NK) Cells by 7t15-21s Complex+Anti-TF IgG1 Antibody To assess the 7t15-21s complex's ability to expand primary natural killer (NK) cells, 7t15-21s complex and 7t15-21s complex+anti-TF IgG1 antibody are added to NK cells obtained from samples of fresh human leukocytes. Cells are stimulated with 50 nM of 7t15-21s complex with or without 25 nM of anti-TF IgG1 or anti-TF IgG4 antibody at 37° and 5% $CO_2$. Cells are maintained at concentration at $0.5\times10^6$/mL not exceeding $2.0\times10^6$/mL by counting every 48-72 hours and media is replenished with fresh stimulator. Cells stimulated with 7t15-21s complex or anti-TF IgG1 antibody or anti-TFIgG4 antibody or anti-TF IgG4+7t15-21s complex are maintained up to day 5. Expansion of primary NK cells upon incubation with 21t15-7s complex+anti-TF IgG1 antibody is observed.

Example 48: Activation of Expanded NK Cells by the 7t15-21s Complex+Anti-TF IgG1 Antibody Primary NK cells are induced ex vivo following overnight stimulation of purified NK cells with 7t15-21s complex+ anti-TF IgG1 antibody. Fresh human leukocytes are obtained from a blood bank and CD56+NK cells are isolated with the RosetteSep/human NK cell reagent (StemCell Technologies). The purity of NK cells is >80% and is confirmed by staining with CD56-BV421 and CD16-BV510 specific antibodies (BioLegend). Cells are counted and resuspended in $1\times10^6$/mL in a 24 well flat bottom plate in 1 mL of complete media (RPMI 1640 (Gibco), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). Cells are stimulated with 50 nM of 7t15-21s with or without 25 nM of anti-TF IgG1 antibody at 37° and 5% $CO_2$. Cells are counted every 48-72 hours and maintained at a concentration of $0.5\times10^6$/mL to $2.0\times10^6$/mL until day 14. Media is periodically replenished with fresh stimulator. Cells are harvested and surface stained at day 3 for CD56-BV421, CD16-BV510, CD25-PE, CD69-APCFire750 specific antibodies (Biolegend and analyzed by Flow Cytometry-Celeste-BD Bioscience). The activation marker CD25 MFI are observed to increase with 7t15-21s complex+anti-TF IgG1 antibody stimulation, but not 7t15-21s complex stimulation. The activation marker CD69 MFI is observed to increase with both 7t15-21s complex+anti-TF IgG1 antibody and with 7t15-21s complex, alone.

Example 49: Increase in Glucose Metabolism in NK Cells Using 18t15-12s

A set of experiments was performed to determine the effect of the construct of 18t15-12s on oxygen consumption rate and extracellular acidification rate (ECAR) on NK cells purified from human blood.

In these experiments, fresh human leukocytes were obtained from the blood bank from two different human donors and NK cells were isolated via negative selection using the RosetteSep/human NK cell reagent (StemCell Technologies). The purity of NK cells was >80% and confirmed by staining with CD56-BV421 and CD16-BV510 specific antibodies (BioLegend). The cells were counted and resuspended in $2\times10^6$/mL in 24-well, flat-bottom plates in 1 mL of complete media (RPMI 1640 (Gibco) supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies) and 10% FBS (Hyclone)). The cells were stimulated with either (1) media alone, (2) 100 nM 18t15-12s, or (3) mixture of single cytokines recombinant human IL-12 (0.25 μg), recombinant human IL-15 (1.25 μg), and recombinant human IL-18 (1.25 μg) overnight at 37 °C, 5% $CO_2$. On the next day, the cells were harvested and extracellular flux assays on expanded NK cells were performed using a XFp Analyzer (Seahorse Bioscience). The harvested cells washed and plated $2.0\times10^5$ cells/well in at least duplicate for extracellular flux analysis of OCR (Oxygen Consumption Rate) and ECAR (Extracellular Acidification Rate). The glycolysis stress tests were performed in Seahorse Media contain 2 mM of glutamine. The following were used during the assay: 10 mM glucose; 100 nM oligomycin; and 100 mM 2-deoxy-D-glycose (2DG).

Figure 73:
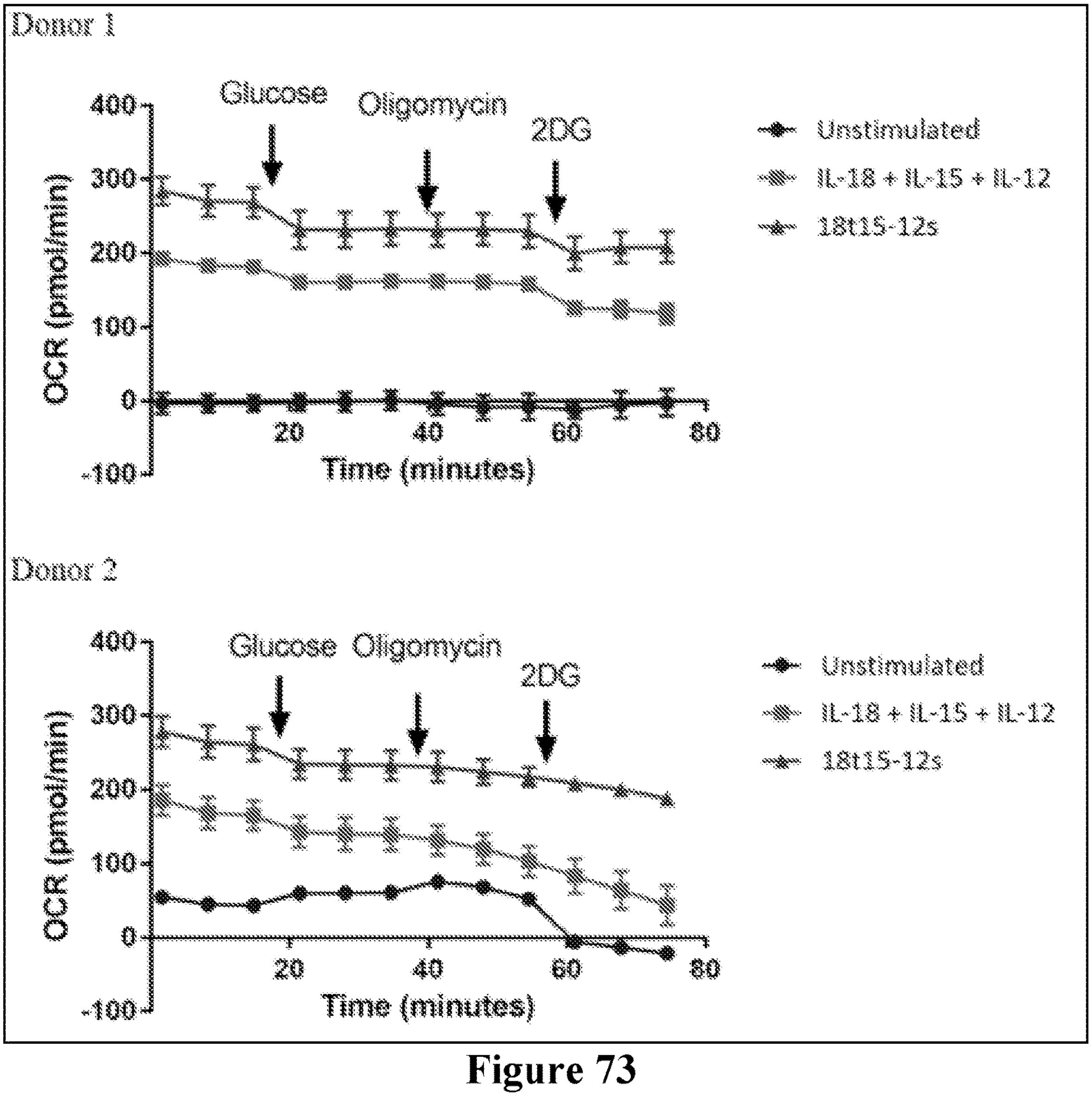
FIG. 73 shows the oxygen consumption rate (OCR) in pmoles/min for human NK cells isolated from blood ($2\times10^6$ cells/mL) of two different donors.
Figure 74:
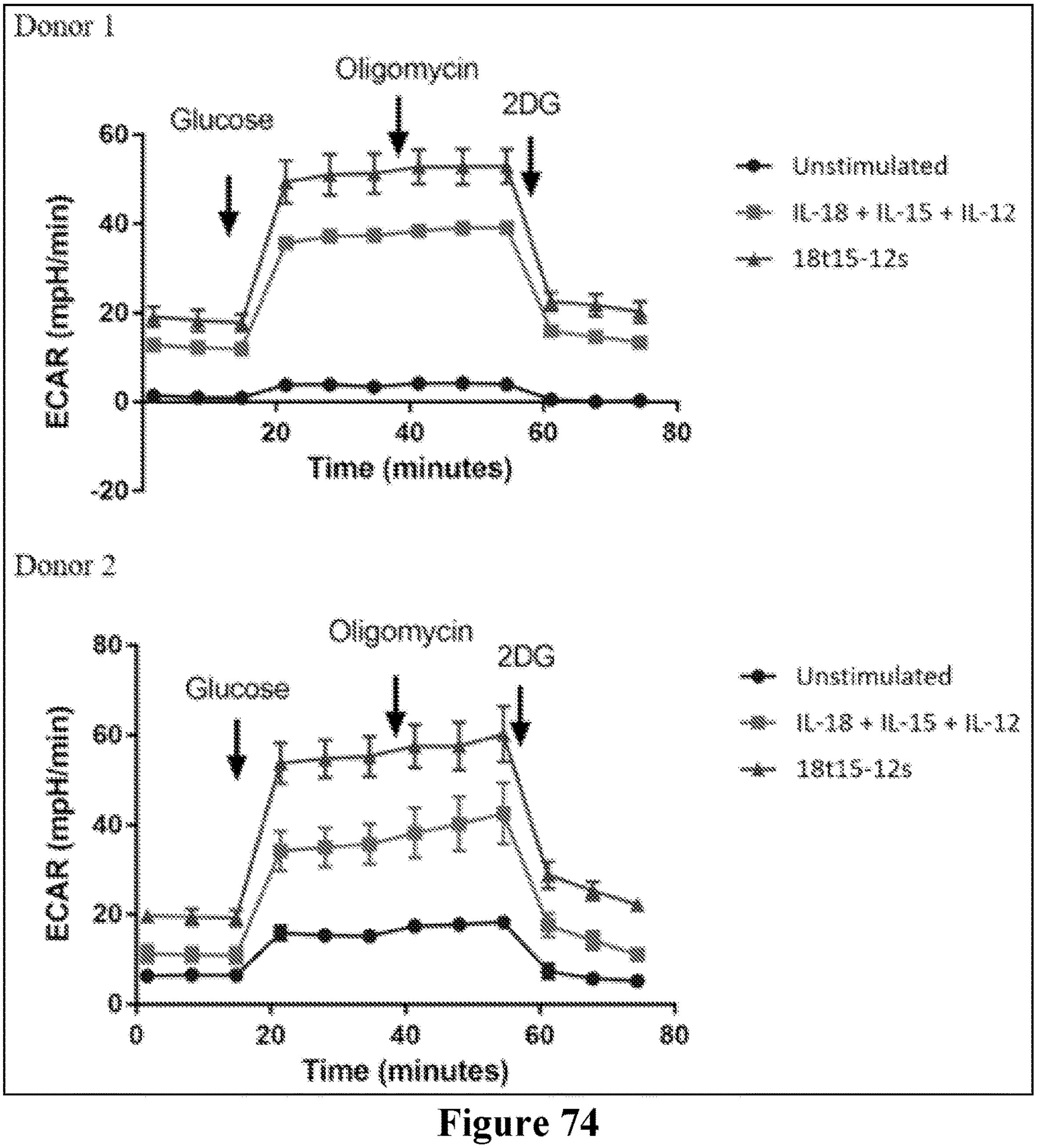
FIG. 74 shows the extracellular acidification rate (ECAR) in mpH/minute for human NK cells isolated from blood ($2\times10^6$ cells/mL) of two different donors.

The data show that the 18t15-12s results in significantly increased oxygen consumption rate (FIG. 73) and extracellular acidification rate (ECAR) as compared to the same cells activated with a combination of recombinant human IL-12, recombinant human IL-15, and recombinant human IL-18 (FIG. 74).

Example 50: 7t15-16s21 Fusion Protein Generation and Characterization

A fusion protein complex was generated comprising of anti-CD16scFv/IL-15RαSu/IL-21 and IL-7/TF/IL-15 fusion proteins. The human IL-7 and IL-21 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15.

The nucleic acid and protein sequences of a construct comprising IL-7 linked to the N-terminus of tissue factor 219 following with the N-terminus of IL-15 are shown below.

The nucleic acid sequence of the IL-7/TF/IL-15 construct (including signal peptide sequence) is as follows:

```
(Signal peptide)
ATGAAGTGGGTGACCTTCATCAGCCTGCTGTTCCTGTTCTCCAGCGCCTAC

TCC

(Human IL-7)
GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG

GAGGGCATGTTCCTGTTCAGGGCCGCCAGGAAACTGCGGCAGTTCCTGAAG

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCAT

(Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG
```

-continued

```
(Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC
```

The amino acid sequence of IL-7/TF/IL-15 fusion protein (including the leader sequence) is as follows:

```
(Signal peptide)
MKWVTFISLLFLFSSAYS

(Human IL-7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE

(Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS
```

Constructs were also made by linking the anti-CD16scFv sequence to the N-terminus coding region of IL-15RαSu chain followed by the N-terminus coding region of IL-21 which was synthesized by Genewiz. The nucleic acid and protein sequences of a construct comprising the anti-CD16scFv linked to the N-terminus of IL-15RαSu chain followed by the N-terminus coding region of IL-21 are shown below.

The nucleic acid sequence of the anti-CD16SscFv/IL-15 RαSu/IL-21 construct (including signal peptide sequence) is as follows:

```
(Signal peptide)
ATGAAGTGGGTGACCTTCATCAGCCTGCTGTTCCTGTTCTCCAGCGCCTAC

TCC

((Anti-human CD16scFv)
TCCGAGCTGACCCAGGACCCTGCTGTGTCCGTGGCTCTGGGCCAGACCGTG

AGGATCACCTGCCAGGGCGACTCCCTGAGGTCCTACTACGCCTCCTGGTAC

CAGCAGAAGCCCGGCCAGGCTCCTGTGCTGGTGATCTACGGCAAGAACAAC

AGGCCCTCCGGCATCCCTGACAGGTTCTCCGGATCCTCCTCCGGCAACACC

GCCTCCCTGACCATCACAGGCGCTCAGGCCGAGGACGAGGCTGACTACTAC
```

-continued

```
TGCAACTCCAGGGACTCCTCCGGCAACCATGTGGTGTTCGGCGGCGGCACC

AAGCTGACCGTGGGCCATGGCGGCGGCGGCTCCGGAGGCGGCGGCAGCGGC

GGAGGAGGATCCGAGGTGCAGCTGGTGGAGTCCGGAGGAGGAGTGGTGAGG

CCTGGAGGCTCCCTGAGGCTGAGCTGTGCTGCCTCCGGCTTCACCTTCGAC

GACTACGGCATGTCCTGGGTGAGGCAGGCTCCTGGAAAGGGCCTGGAGTGG

GTGTCCGGCATCAACTGGAACGGCGGATCCACCGGCTACGCCGATTCCGTG

AAGGGCAGGTTCACCATCAGCAGGGACAACGCCAAGAACTCCCTGTACCTG

CAGATGAACTCCCTGAGGGCCGAGGACACCGCCGTGTACTACTGCGCCAGG

GGCAGGTCCCTGCTGTTCGACTACTGGGGACAGGGCACCCTGGTGACCGTG

TCCAGG

(Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG

(Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC
```

The amino acid sequence of the anti-CD16scFv/IL-15RαSu/IL-21 construct (including signal peptide sequence) is as follows:

```
(Signal peptide)
MKWVTFISLLFLFSSAYS

(Anti-human CD16scFv)
SELTQDPAVSVALGQTVRITCQGDSLRSYYASWYQQKPGQAPVLVIYGKNN

RPSGIPDRFSGSSSGNTASLTITGAQAEDEADYYCNSRDSSGNHVVFGGGT

KLTVGHGGGGSGGGGSGGGGSEVQLVESGGGVVRPGGSLRLSCAASGFTFD

DYGMSWVRQAPGKGLEWVSGINWNGGSTGYADSVKGRFTISRDNAKNSLYL

QMNSLRAEDTAVYYCARGRSLLFDYWGQGTLVTVSR

(Human IL-15R α sushi domain)
ITCPPPMSVEHADIWVKSYSLYSRERYICNSGFKRKAGTSSLTECVLNKAT

NVAHWTTPSLKCIR

(Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS
```

In some cases, the leader peptide is cleaved from the intact polypeptide to generate the mature form that may be soluble or secreted.

Figure 75:
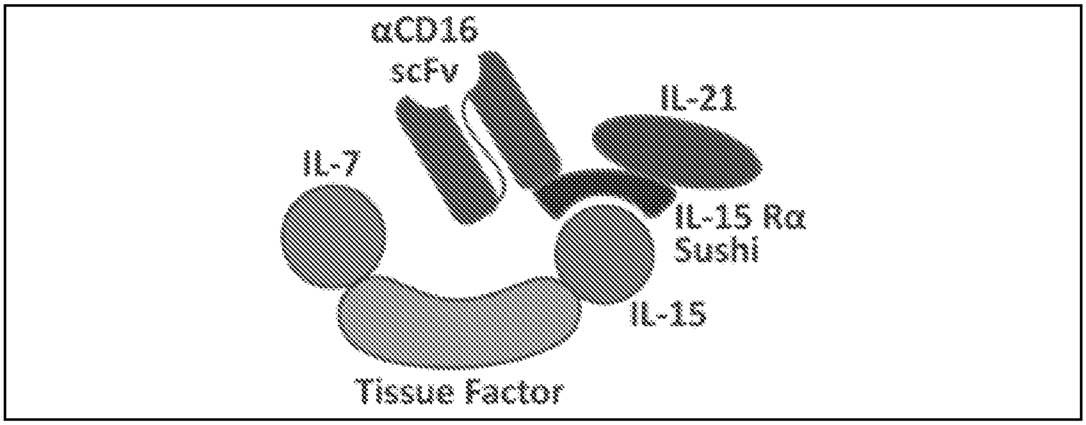
FIG. 75 shows a schematic of the 7t15-16s21 construct.
Figure 76:
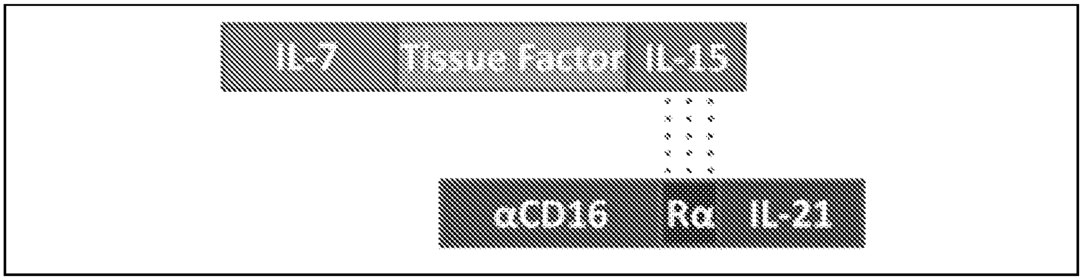
FIG. 76 shows an additional schematic of the 7t15-16s21 construct.

The anti-CD16scFv/IL-15RαSu/IL-21 and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15:anti-CD16scFv/IL-15RαSu/IL-21 protein complex (referred to as 7t15-16s21; FIG. 75 and FIG. 76), which can be purified by anti-TF IgG1 antibody-based affinity and other chromatography methods.

Binding of 7t15-16s21 to CHO Cells Expressing Human CD16b

Figure 77A:
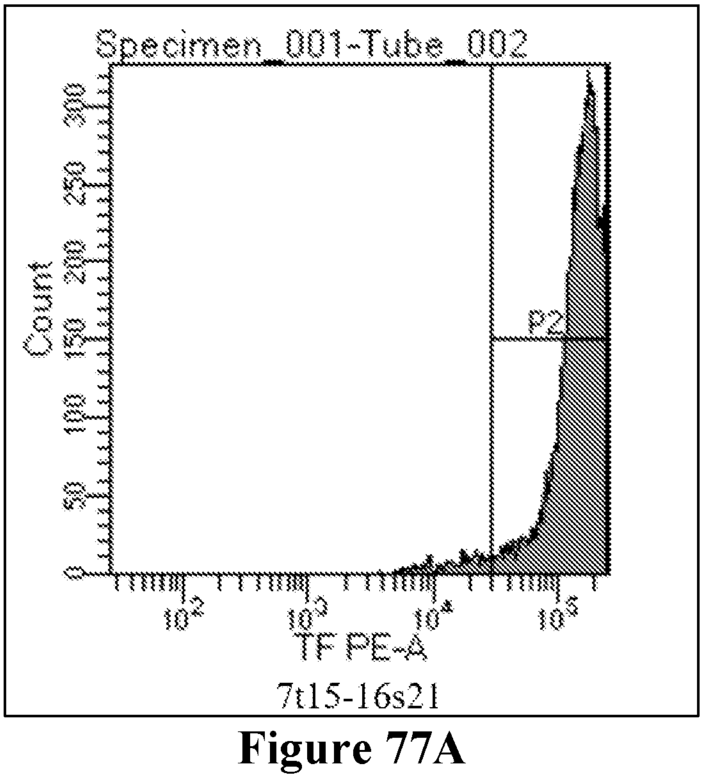
FIGS. 77A and 77B show binding of 7t15-16s21 to CHO cells expressing human CD16b as compared to a control protein.
Figure 77B:
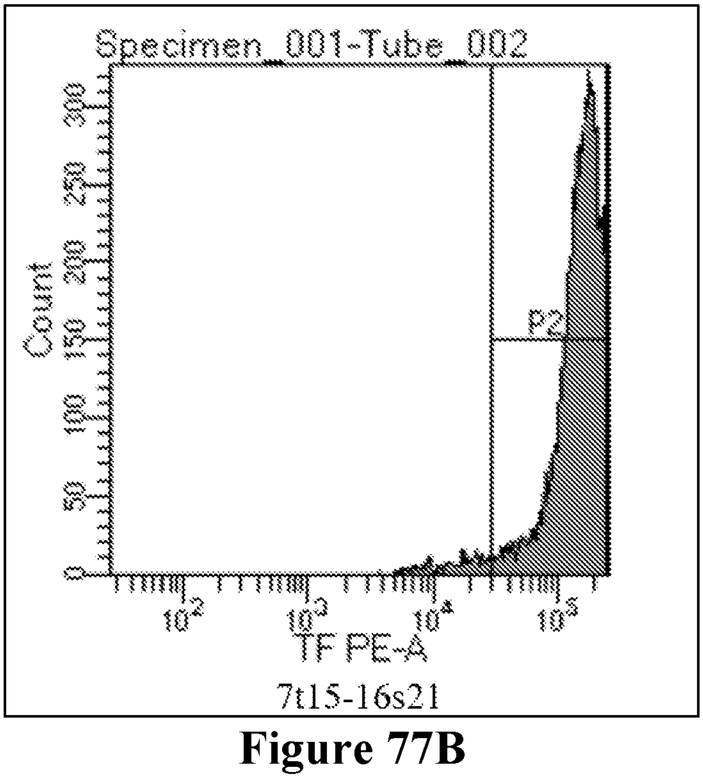

CHO cells were transfected with human CD16b in a pMC plasmid and selected with 10 μg/mL of blasticidin for 10 days. The CHO cells stably expressing CD16b were stained with 1.2 μg/mL of 7t15-16s21, containing anti-human CD16 scFv or 18t15-12s, which does not contain anti-human CD16 scFv, as a negative control, and then stained with biotinylated anti-human tissue factor and PE conjugated streptavidin. Only anti-human CD16scFv containing 7t15-16s21 stained the cells as shown in FIG. 77A. 18t15-12s did not stain the CHO cells expressing human CD16b as showed in FIG. 77B.

Detection of IL-15, IL-21, and IL-7 in 7t15-16s21 Using ELISA

Figure 78A:
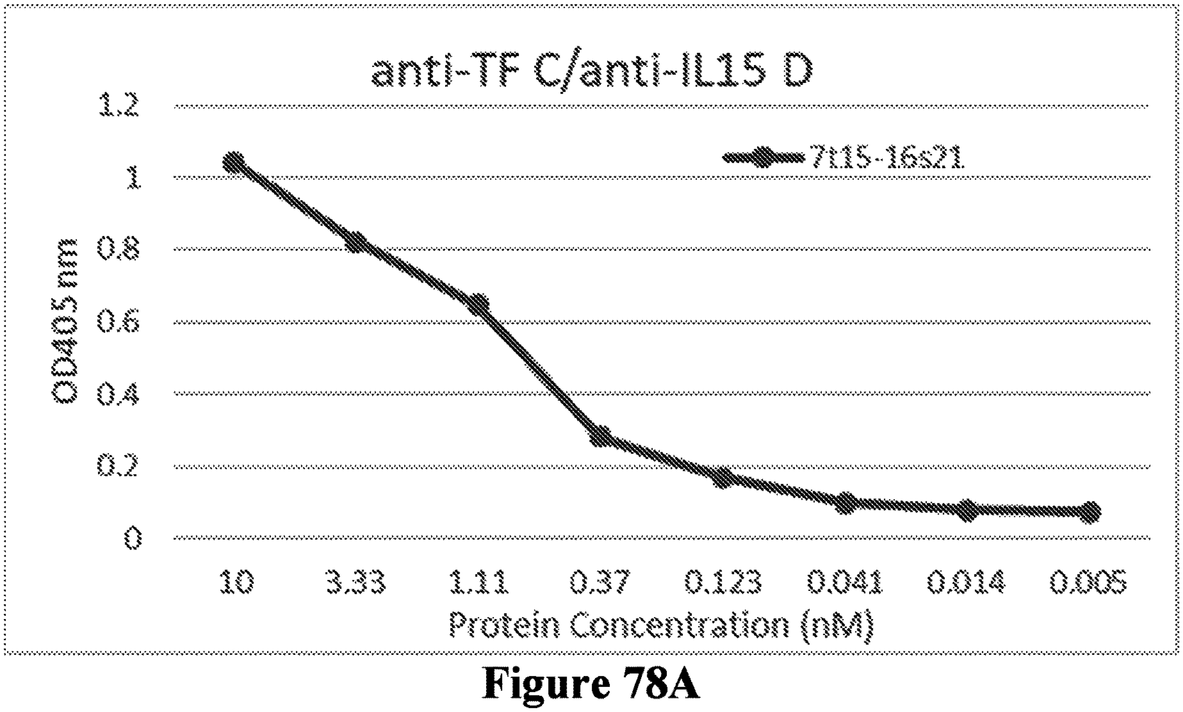
FIGS. 78A-78C are results from ELISA experiments using antibodies against IL-15, IL-21, and IL-7 in detecting 7t15-16s21.
Figure 78B:
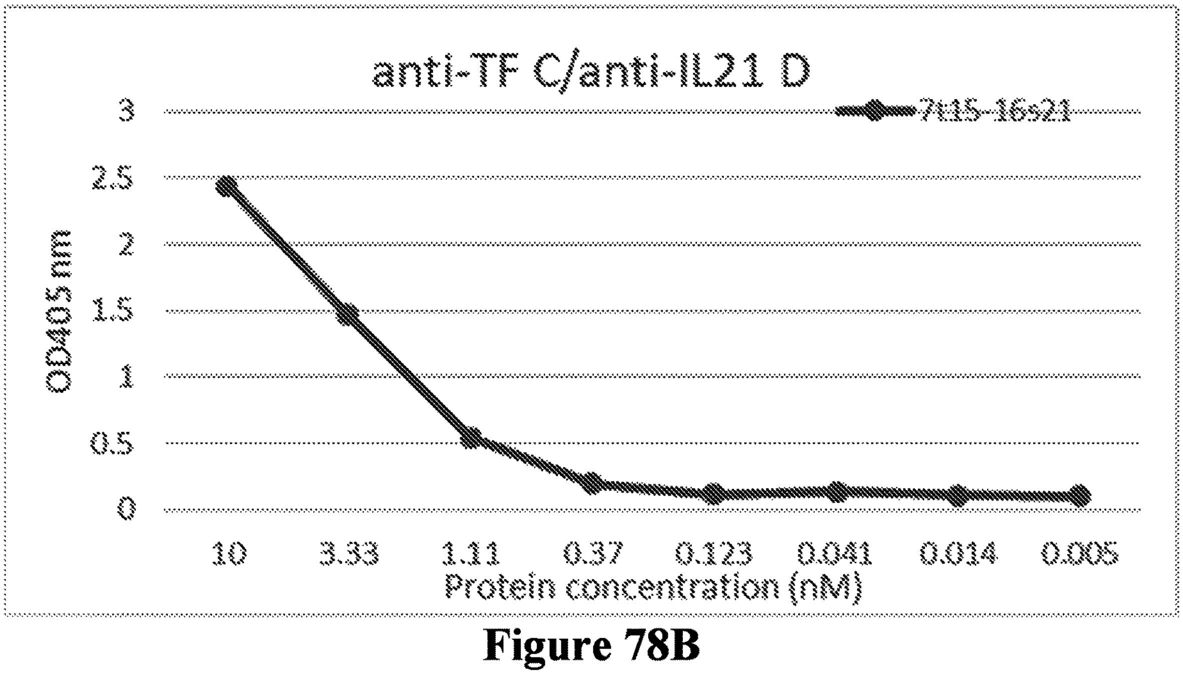
Figure 78C:
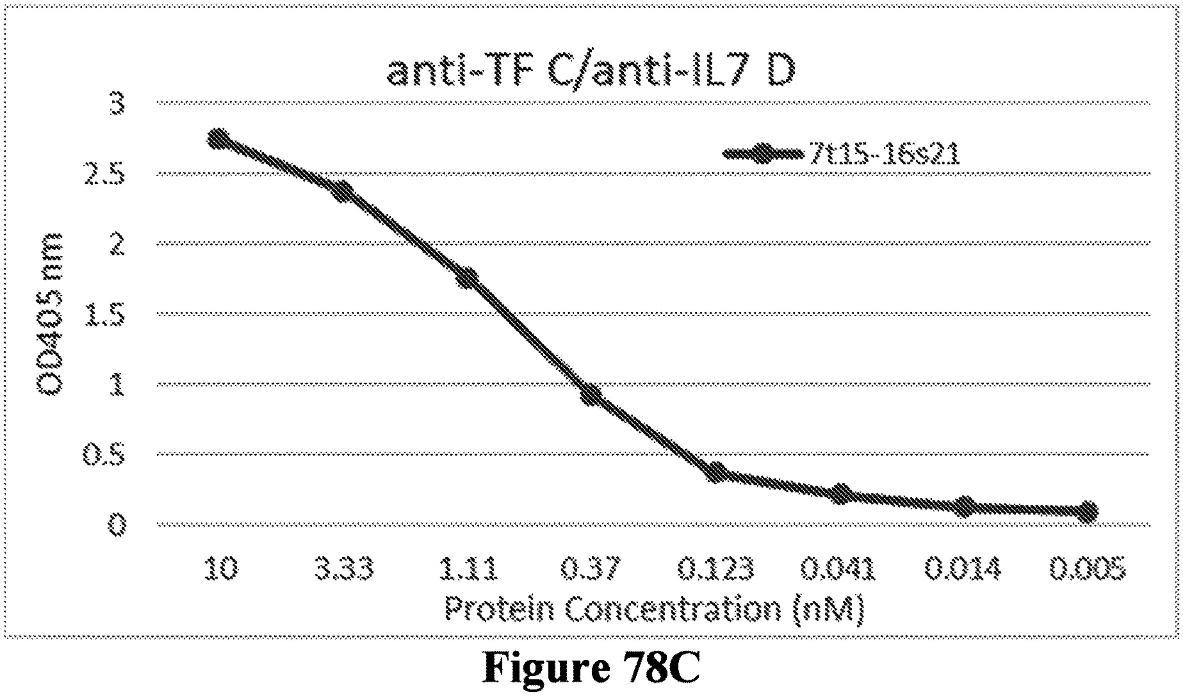

A 96-well plate was coated with 100 μL (8 μg/mL) of anti-TF IgG1 in R5 (coating buffer) and incubated at room temperature (RT) for 2 hrs. The plates were washed 3 times and blocked with 100 μL of 1% BSA in PBS. Serial dilution of 7t15-16s21 (at a 1:3 ratio) were added to the wells, and incubated at RT for 60 min. Following 3 washes, 50 ng/mL of biotinylated-anti-IL-15 antibody (BAM247, R&D Systems), 500 ng/mL of biotinylated-anti-IL-21 antibody (13-7218-81, R&D Systems), or 500 ng/mL of biotinylated-anti-IL-7 antibody (506602, R&D Systems) was added to the wells and incubated at RT for 60 min. The plate was washed 3 times, and incubated with 0.25 μg/mL of HRP-SA (Jackson ImmunoResearch) at 100 μL per well for 30 min at RT, followed by 4 washes and incubation with 100 μl of ABTS for 2 mins at RT. Absorbance was read at 405 nm. As shown in FIGS. 78A-78C, the IL-15, IL-21, and IL-7 domains in 7t15-16s21 were detected by the individual antibodies.

Figure 79:
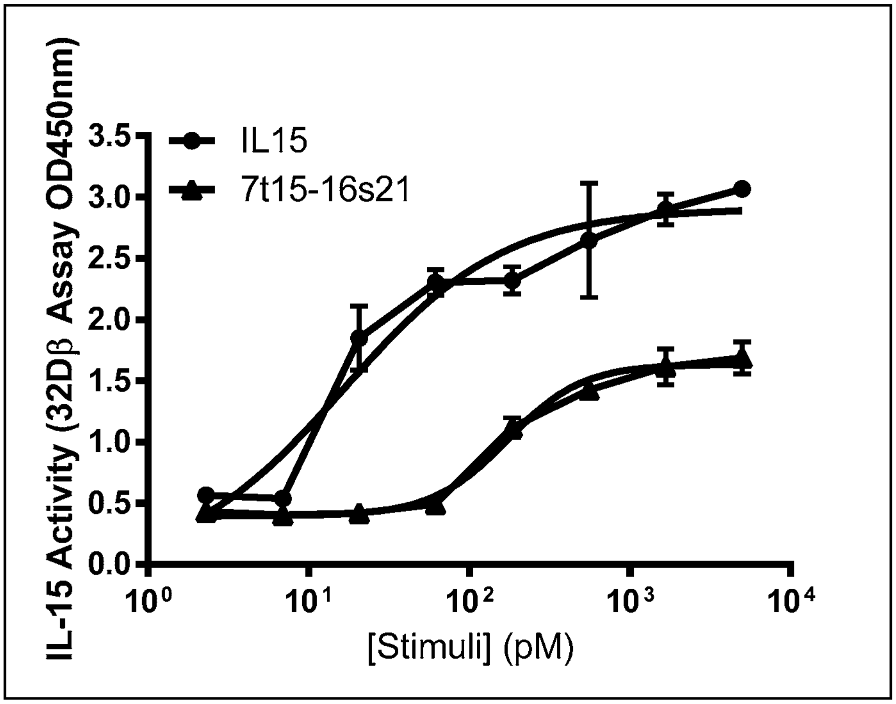
FIG. 79 shows results of the 32Dβ cell proliferation assay with 7t15-16s21 or recombinant IL-15.

The IL-15 in 7t15-16s21 Promotes IL-2Rβ and Common γ Chain Containing 32Dβ Cell Proliferation To analyze the activity of IL-15 in 7t15-16s21, the IL-15 activity of 7t15-16s21 was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted 7t15-16s21 or IL-15 were added to the cells (FIG. 79). Cells were incubated in a $CO_2$ incubator at 37 °C for 3 days. Cell proliferation was detected by adding 10 μl of WST1 to each well on day 3 and incubating for an additional 3 hours in a $CO_2$ incubator at 37 °C. The absorbance at 450 nm was measured by analyzing the amount of formazan dye produced. As shown in FIG. 79, 7t15-16s21 and IL-1.5 promoted 32143 cell proliferation, with the $EC_{50}$ of 7t15-16s21 and IL-15 being 172.2 pM. and 16.63 pM, respectively.

Figure 80:
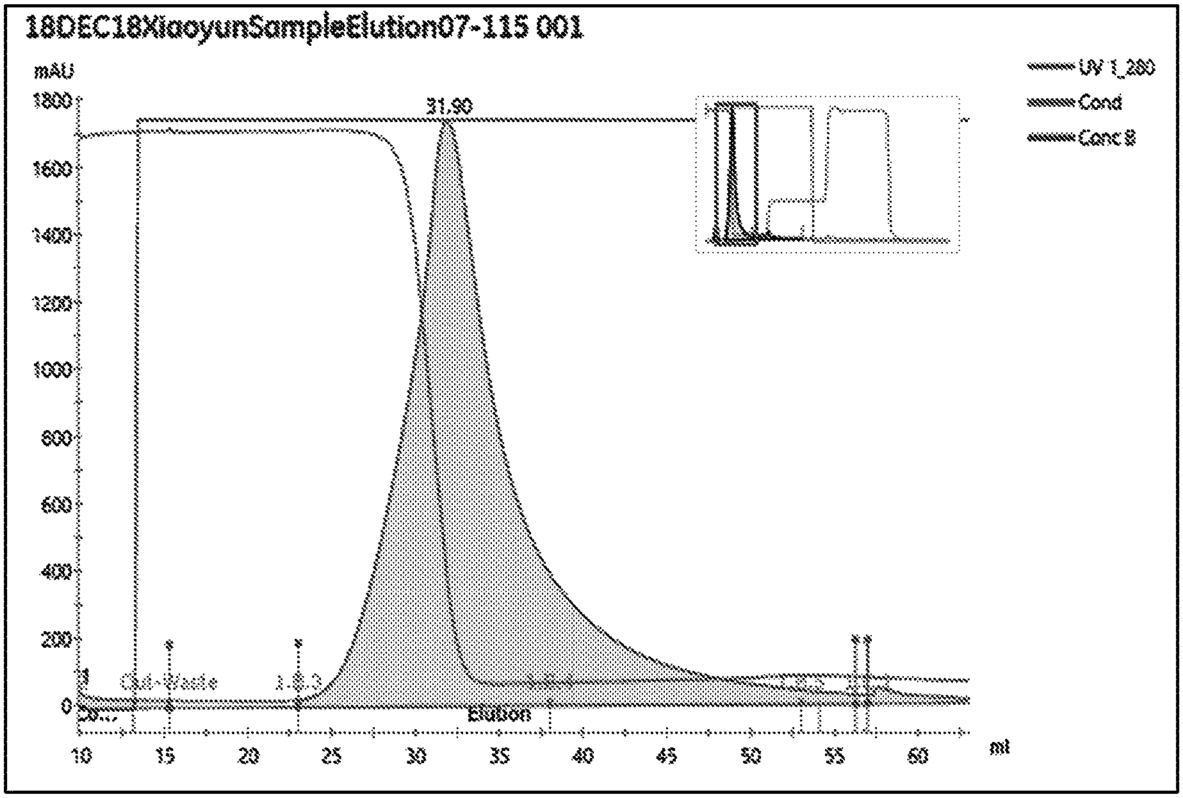
FIG. 80 shows the chromatographic profile of 7t15-16s21 protein containing cell culture supernatant following binding and elution on anti-TF antibody resin.

Purification Elution Chromatograph of 7t15-16s21 from Anti-TF Antibody Affinity Column 7t15-16s21 harvested from cell culture was loaded onto the anti-TF antibody affinity column equilibrated with 5 column volumes of PBS. The column was then washed with 5 column volumes of PBS, followed by elution with 6 column volumes of 0.1 M acetic acid (pH 2.9). A280 elution peak was collected and neutralized to pH 7.5-8.0 with 1 M Tris base. The neutralized sample was buffer exchanged into PBS using Amicon centrifugal filters with a 30 KDa molecular weight cutoff. FIG. 80 is a line graph showing the chromatographic profile of 7t15-16s21 protein containing cell culture supernatant following binding and elution on anti-TF antibody resin. As shown in FIG. 80, the anti-TF antibody affinity column bound 7t15-16s21 which contains TF. The buffer-exchanged protein sample was stored at 2-8 °C for further biochemical analyses and biological activity tests. After each elution, the anti-TF antibody affinity column was stripped using 6 column volumes of 0.1 M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of 7t15-16s21

Figure 81:
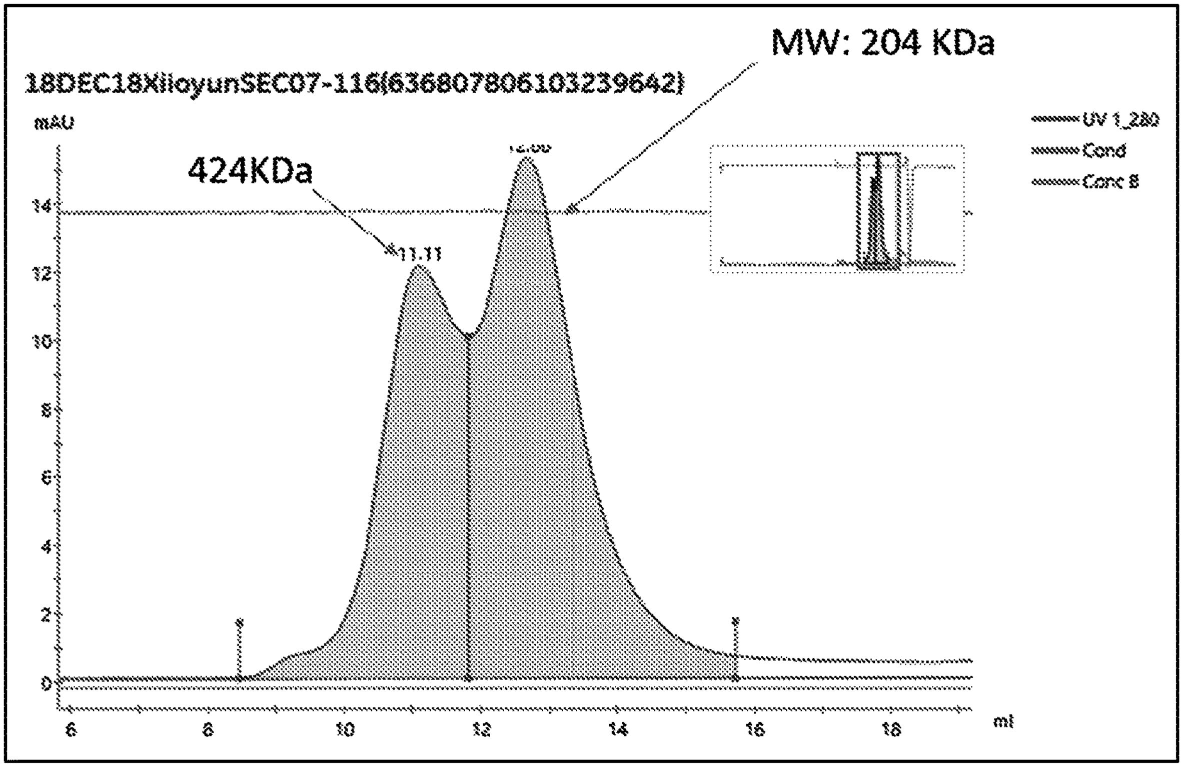
FIG. 81 shows the analytical SEC Profile of 7t15-16s21.

To perform size exclusion chromatography (SEC) analysis for 7t15-16s21, a Superdex 200 Increase 10/300 GL gel filtration column (GE Healthcare) connected to an AKTA Avant system (GE Healthcare) was used. The column was equilibrated with 2 column volumes of PBS. The flow rate was 0.7 mL/min. A sample containing 7t15-16s21 in PBS was injected into the Superdex 200 column using a capillary loop, and analyzed by SEC. As shown in FIG. 81, the SEC results showed two protein peaks for 7t15-16s21.

Example 51: TGFRt15-16s21 Fusion Protein Generation and Characterization

Figure 82:
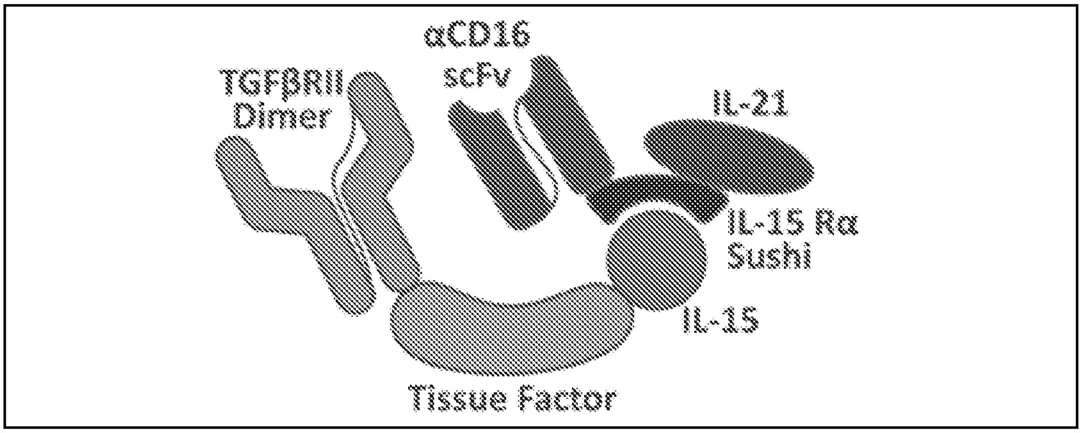
FIG. 82 shows a schematic of the TGFRt15-16s21 construct.
Figure 83:
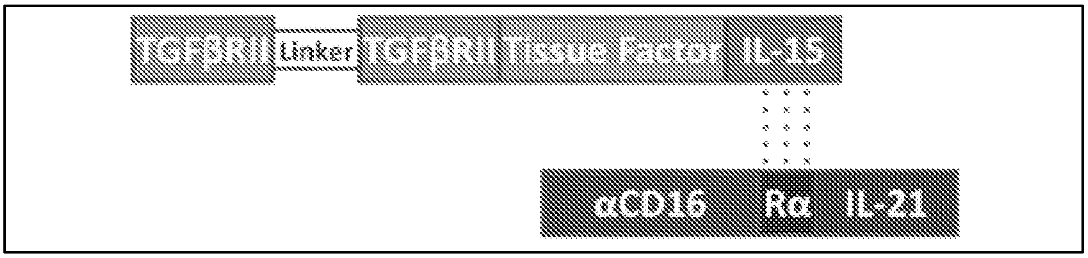
FIG. 83 shows an additional schematic of the TGFRt15-16s21 construct.

A fusion protein complex was generated comprising anti-human CD16scFv/IL-15RαSu/IL21 and TGFβ Receptor II/TF/IL-15 fusion proteins (FIGS. 82 and 83). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the two TGFβ Receptor II/TF/IL-15 construct (including signal peptide sequence) is as follows:

```
(Signal peptide)
ATGAAGTGGGTGACCTTCATCAGCCTGCTGTTCCTGTTCTCCAGCGCCTAC

TCC

(Two Human TGFβ Receptor II fragments)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG
```

-continued

TTCAGCACCTGCGATAATCAGAAGTCCTGCATGTCCAACTGCAGCATCACC
TCCATCTGCGAGAAGCCCCAAGAAGTGTGCGTGGCCGTGTGGCGGAAAAAT
GACGAGAACATCACCCTGGAGACCGTGTGTCACGACCCCAAGCTCCCTTAT
CACGACTTCATTCTGGAGGACGCTGCCTCCCCCAAATGCATCATGAAGGAG
AAGAAGAAGCCCGGAGAGACCTTCTTTATGTGTTCCTGTAGCAGCGACGAG
TGTAACGACAACATCATCTTCAGCGAAGAGTACAACACCAGCAACCCTGAT
GGAGGTGGCGGATCCGGAGGTGGAGGTTCTGGTGGAGGTGGGAGTATTCCT
CCCCACGTGCAGAAGAGCGTGAATAATGACATGATCGTGACCGATAACAAT
GGCGCCGTGAAATTTCCCCAGCTGTGCAAATTCTGCGATGTGAGGTTTTCC
ACCTGCGACAACCAGAAGTCCTGTATGAGCAACTGCTCCATCACCTCCATC
TGTGAGAAGCCTCAGGAGGTGTGCGTGGCTGTCTGGCGGAAGAATGACGAG
AATATCACCCTGGAAACCGTCTGCCACGATCCCAAGCTGCCCTACCACGAT
TTCATCCTGGAAGACGCCGCCAGCCCTAAGTGCATCATGAAAGAGAAAAAG
AAGCCTGGCGAGACCTTTTTCATGTGCTCCTGCAGCAGCGACGAATGCAAC
GACAATATCATCTTTAGCGAGGAATACAATACCAGCAACCCCGAC (Human Tissue Factor 219)
AGCGGCACAACCAACACAGTCGCTGCCTATAACCTCACTTGGAAGAGCACC
AACTTCAAAACCATCCTCGAATGGGAACCCAAACCCGTTAACCAAGTTTAC
ACCGTGCAGATCAGCACCAAGTCCGGCGACTGGAAGTCCAAATGTTTCTAT
ACCACCGACACCGAGTGCGATCTCACCGATGAGATCGTGAAAGATGTGAAA
CAGACCTACCTCGCCCGGGTGTTTAGCTACCCCGCCGGCAATGTGGAGAGC
ACTGGTTCCGCTGGCGAGCCTTTATACGAGAACAGCCCCGAATTTACCCCT
TACCTCGAGACCAATTTAGGACAGCCCACCATCCAAAGCTTTGAGCAAGTT
GGCACAAAGGTGAATGTGACAGTGGAGGACGAGCGGACTTTAGTGCGGCGG
AACAACACCTTTCTCAGCCTCCGGGATGTGTTCGGCAAAGATTTAATCTAC
ACACTGTATTACTGGAAGTCCTCTTCCTCCGGCAAGAAGACAGCTAAAACC
AACACAAACGAGTTTTTAATCGACGTGGATAAAGGCGAAAACTACTGTTTC
AGCGTGCAAGCTGTGATCCCCTCCCGGACCGTGAATAGGAAAAGCACCGAT
AGCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAATTCAG
TCCATGCATATCGACGCCACTTTATACACAGAATCCGACGTGCACCCCTCT
TGTAAGGTGACCGCCATGAAATGTTTTTTACTGGAGCTGCAAGTTATCTCT
TTAGAGAGCGGAGACGCTAGCATCCACGACACCGTGGAGAATTTAATCATT
TTAGCCAATAACTCTTTATCCAGCAACGGCAACGTGACAGAGTCCGGCTGC
AAGGAGTGCGAAGAGCTGGAGGAGAAGAACATCAAGGAGTTTCTGCAATCC
TTTGTGCACATTGTCCAGATGTTCATCAATACCTCC The amino acid sequence of TGFβ Receptor II/TF/IL-15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSIT
SICEKPQEVCVAVWRKNDENITLETVCHDPKLPYHDFILEDAASPKCIMKE
KKKPGETFFMCSCSSDECNDNIIFSEEYNTSNPDGGGGSGGGGSGGGGSIP
PHVQKSVNNDMIVTDNNGAVKFPQLCKFCDVRFSTCDNQKSCMSNCSITSI
CEKPQEVCVAVWRKNDENITLETVCHDPKLPYHDFILEDAASPKCIMKEKK
KPGETFFMCSCSSDECNDNIIFSEEYNTSNPD (Human Tissue Factor 219)
SGTTNTVAAYNLTWKSTNFKTILEWEPKPVNQVYTVQISTKSGDWKSKCFY
TTDTECDLTDEIVKDVKQTYLARVFSYPAGNVESTGSAGEPLYENSPEFTP
YLETNLGQPTIQSFEQVGTKVNVTVEDERTLVRRNNTFLSLRDVFGKDLIY
TLYYWKSSSSGKKTAKTNTNEFLIDVDKGENYCFSVQAVIPSRTVNRKSTD
SPVECMGQEKGEFRE (Human IL-15)
NWVNVISDLKKIEDLIQSMHIDATLYTESDVHPSCKVTAMKCFLLELQVIS
LESGDASIHDTVENLIILANNSLSSNGNVTESGCKECEELEEKNIKEFLQS
FVHIVQMFINTS Constructs were also made by attaching anti-human CD16scFv directly linking to the N-terminus coding region of IL-15RαSu chain followed by the N-terminus coding region of IL-21 which was synthesized by Genewiz. The nucleic acid and protein sequences of a construct comprising the anti-human CD16scFv linked to the N-terminus of IL-15RαSu followed by the N-terminus coding region of IL-21 are shown below.

The nucleic acid sequence of the anti-CD16scFv/IL-15 RαSu/IL-21 construct (including signal peptide sequence) is as follows:

(Signal peptide)
ATGAAGTGGGTGACCTTCATCAGCCTGCTGTTCCTGTTCTCCAGCGCCTAC
TCC (Anti-human CD16scFv)
TCCGAGCTGACCCAGGACCCTGCTGTGTCCGTGGCTCTGGGCCAGACCGTG
AGGATCACCTGCCAGGGCGACTCCCTGAGGTCCTACTACGCCTCCTGGTAC
CAGCAGAAGCCCGGCCAGGCTCCTGTGCTGGTGATCTACGGCAAGAACAAC
AGGCCCTCCGGCATCCCTGACAGGTTCTCCGGATCCTCCTCCGGCAACACC
GCCTCCCTGACCATCACAGGCGCTCAGGCCGAGGACGAGGCTGACTACTAC
TGCAACTCCAGGGACTCCTCCGGCAACCATGTGGTGTTCGGCGGCGGCACC
AAGCTGACCGTGGGCCATGGCGGCGGCGGCTCCGGAGGCGGCGGCAGCGGC
GGAGGAGGATCCGAGGTGCAGCTGGTGGAGTCCGGAGGAGGAGTGGTGAGG
CCTGGAGGCTCCCTGAGGCTGAGCTGTGCTGCCTCCGGCTTCACCTTCGAC
GACTACGGCATGTCCTGGGTGAGGCAGGCTCCTGGAAAGGGCCTGGAGTGG
GTGTCCGGCATCAACTGGAACGGCGGATCCACCGGCTACGCCGATTCCGTG -continued

```
AAGGGCAGGTTCACCATCAGCAGGGACAACGCCAAGAACTCCCTGTACCTG

CAGATGAACTCCCTGAGGGCCGAGGACACCGCCGTGTACTACTGCGCCAGG

GGCAGGTCCCTGCTGTTCGACTACTGGGGACAGGGCACCCTGGTGACCGTG

TCCAGG

(Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG

(Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC
```

The amino acid sequence of the anti-CD16scFv/IL-15RαSu/IL-21 construct (including signal peptide sequence) is as follows:

```
(Signal peptide)
MKWVTFISLLFLFSSAYS

(Anti-human CD16scFv)
SELTQDPAVSVALGQTVRITCQGDSLRSYYASWYQQKPGQAPVLVIYGKNN

RPSGIPDRFSGSSSGNTASLTITGAQAEDEADYYCNSRDSSGNHVVFGGGT

KLTVGHGGGGSGGGGSGGGGSEVQLVESGGGVVRPGGSLRLSCAASGFTFD

DYGMSWVRQAPGKGLEWVSGINWNGGSTGYADSVKGRFTISRDNAKNSLYL

QMNSLRAEDTAVYYCARGRSLLFDYWGQGTLVTVSR

(Human IL-15R α sushi domain)
ITCPPPMSVEHADIWVKSYSLYSRERYICNSGFKRKAGTSSLTECVLNKAT

NVAHWTTPSLKCIR

(Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS
```

In some cases, the leader peptide is cleaved from the intact polypeptide to generate the mature form that may be soluble or secreted.

The anti-CD16scFv/IL-15RαSu/IL-21 and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:CD16scFv/IL-15RαSu/IL-21 protein complex (referred to as TGFRt15-16s21), which can be purified by anti-TF IgG1-based affinity and other chromatography methods.

Interaction Between TGFRt15-16s21 and CHO Cells Expressing Human CD16b

Figure 84A:
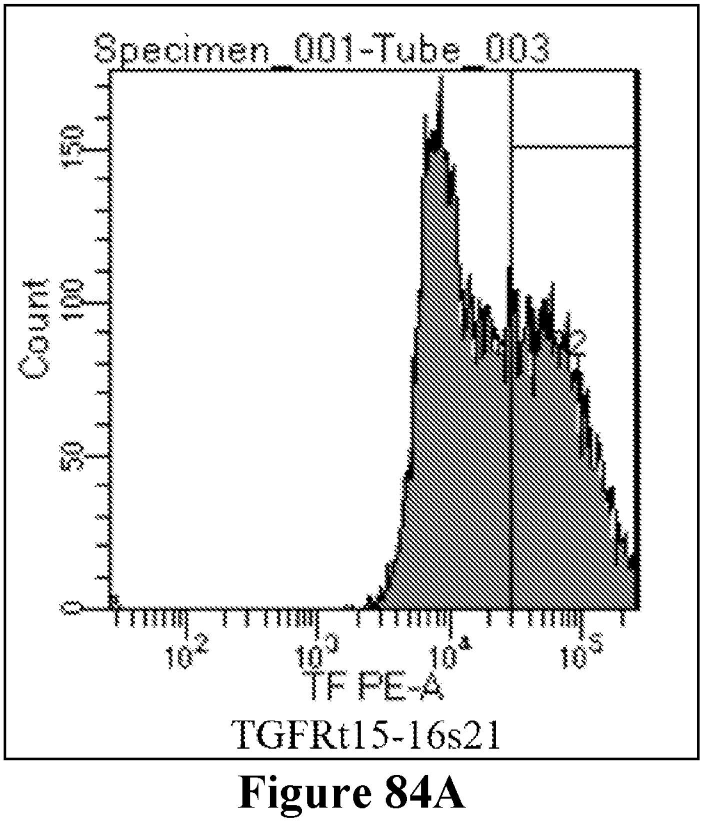
FIGS. 84A and 84B show binding affinity of TGFRT15-16S21 and 7t15-21s with CHO cells expressing human CD16b.
Figure 84B:
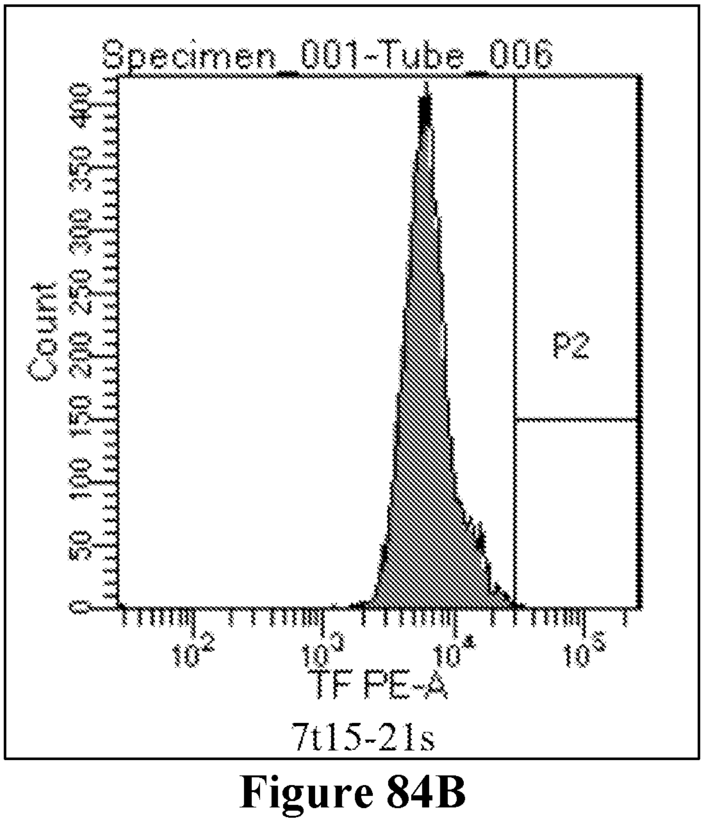

CHO cells were transfected with human CD16b in a pMC plasmid and selected with 10 μg/mL of blasticidin for 10 days. Cells stably expressing CD16b were stained with 1.2 μg/mL of TGFRt15-16s21, containing anti-human CD16 scFv, or 7t15-21s, not containing anti-human CD16 scFv, as a negative control, and with biotinylated anti-human tissue factor antibody and PE conjugated streptavidin. As shown in FIGS. 84A and 84B, TGFRt15-16s21, which contains anti-human CD16scFv, showed positive binding, while 7t15-21s did not show binding.

Effect of TGFRt15-16s21 on TGFβ1 Activity in HEK-Blue TGFβ Cells

To evaluate the activity of TGFβRII in TGFRt15-16s21, the effect of TGFRt15-16s21 on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, 50 μl cells were added to each well ($2.5\times10^4$ cells/well) and followed with 50 μL 0.1 nM TGFβ1 (R&D systems). TGFRt15-16s21 or TGFR-Fc (R&D Systems) prepared at a 1:3 serial dilution was then added to the plate to reach a total volume of 200 μL. After 24 hrs of incubation at 37 °C, 40 μL of induced HEK-Blue TGFβ cell supernatant was added to 160 μL pre-warmed QUANTI-Blue (Invivogen) in a flat-bottom 96-well plate, and incubated at 37 °C for 1-3 hrs. The OD values were then determined using a plate reader (Multiscan Sky) at 620-655 nM. The $IC_{50}$ of each protein sample was calculated with GraphPad Prism 7.04. The $IC_{50}$ of TGFRt15-16s21 and TGFR-Fc were 9127 pM and 460.6 pM respectively. These results showed that the TGFβRII domain in TGFRt15-16s21 was able to block the activity of TGFβ-1 in HEK-Blue TGFβ cells.

Figure 85:
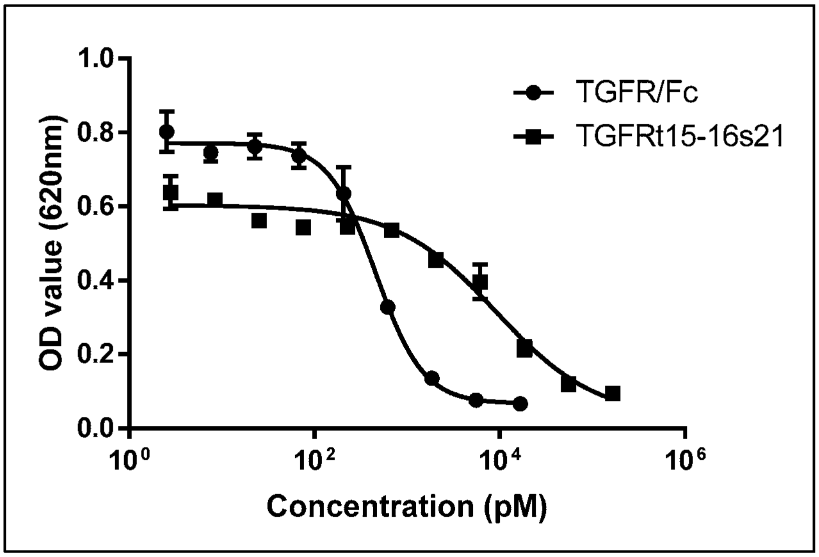
FIG. 85 shows results of TGFβ1 inhibition by TGFRt15-16s21 and TGFR-Fc.
Figure 86:
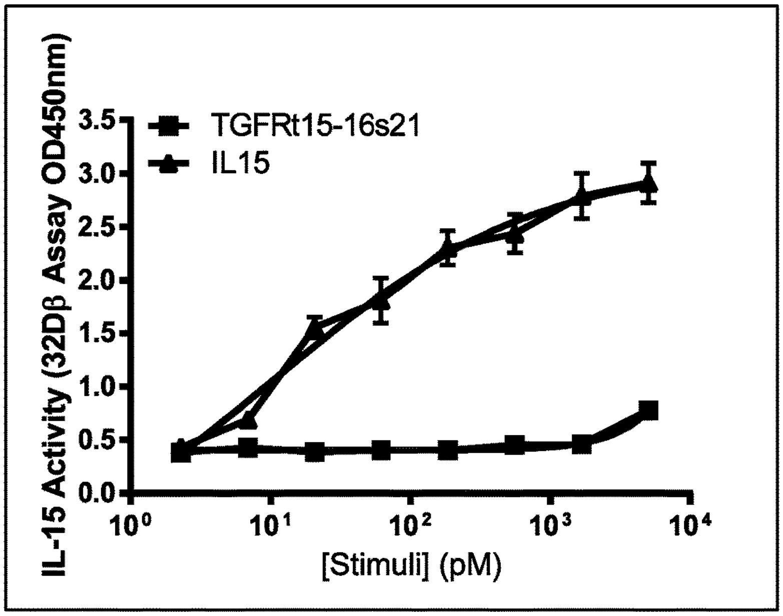
FIG. 86 shows results of 32Dβ cell proliferation assay with TGFRt15-16s21 or recombinant IL-15.

The IL-15 in TGFRt15-16s21 Promotes IL-2Rβ and Common γ Chain Containing 32Dβ Cell Proliferation To analyze the activity of IL-15 in TGFRt15-16s21, the IL-15 activity of TGFRt15-16s21 was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted TGFRt15-16s21 or IL-15 were added to the cells (FIG. 86). Cells were incubated in a $CO_2$ incubator at 37 °C for 3 days. Cell proliferation was detected by adding 10 μL of WST1 to each well on day 3 and incubating for an additional 3 hours in a $CO_2$ incubator at 37 °C. The absorbance at 450 nm was measured by analyzing the amount of formazan dye produced. The data are shown in FIG. 85. As shown in FIG. 86, TGFRt15-16s21 and IL-15 promoted 32Dβ cell proliferation, with the $EC_{50}$ of TGFRt15-16s21 and IL-15 being 51298 pM and 10.63 pM, respectively.

Detection of IL-15, IL-21, and TGFβRII in TGFRt15-16s21 Using ELISA

Figure 87A:
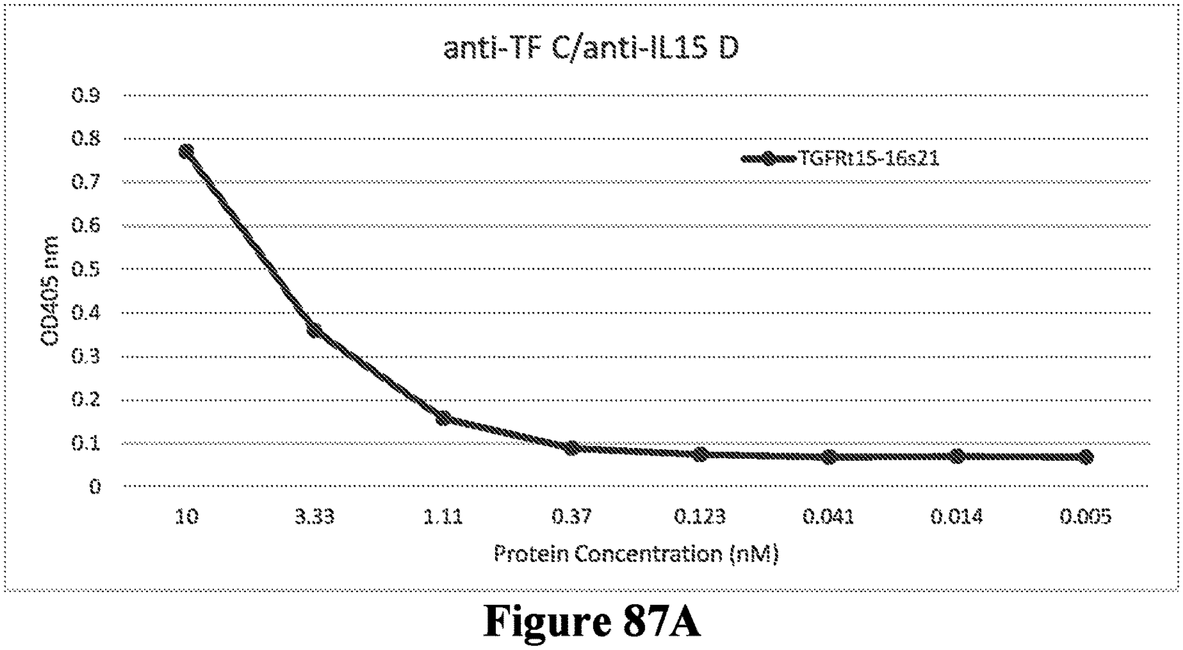
FIGS. 87A-87C show results of detecting IL-15, IL-21, and TGFβRII in TGFRt15-16s21 with corresponding antibodies using ELISA.
Figure 87B:
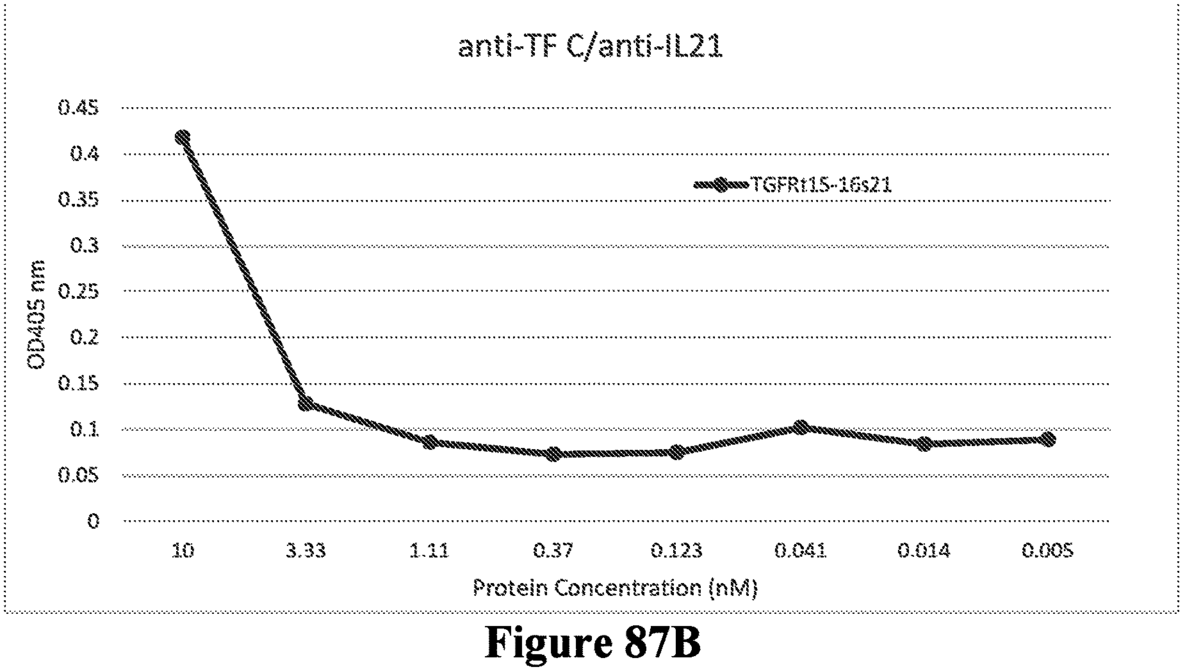
Figure 87C:
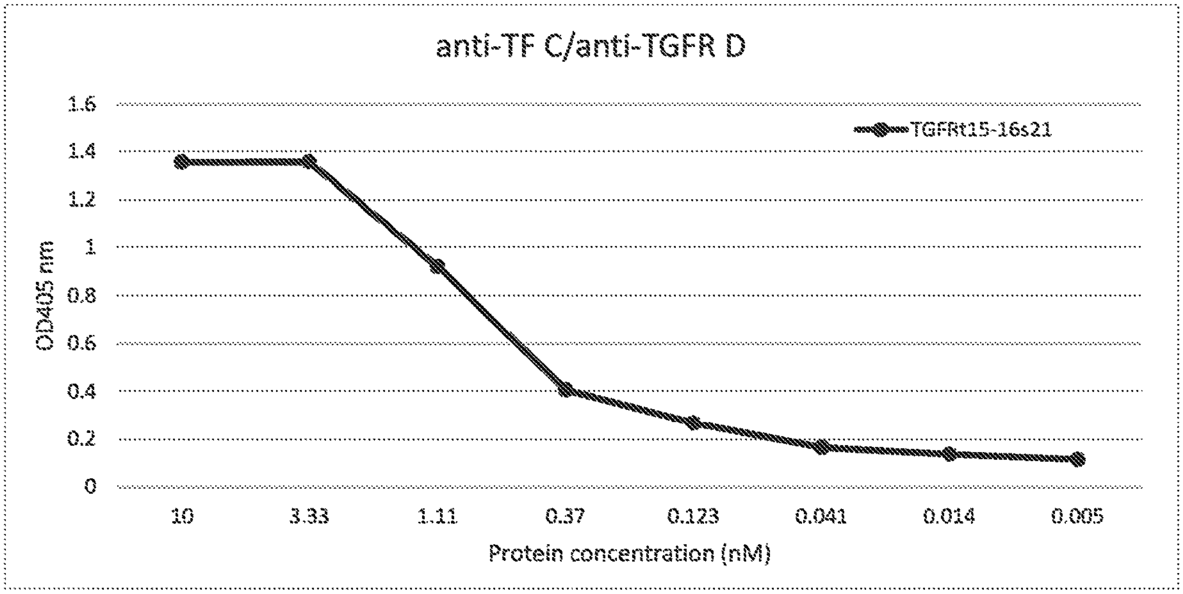

A 96-well plate was coated with 100 μL (8 pg/mL) of anti-TF IgG1 in R5 (coating buffer) and incubated at room temperature (RT) for 2 hrs. The plates were washed 3 times and blocked with 100 μL of 1% BSA in PBS. TGFRt15-16s21 serially diluted at a 1:3 ratio was added and incubated at RT for 60 min. Following three washes, 50 ng/mL of biotinylated-anti-IL-15 antibody (BAM247, R&D Systems), 500 ng/mL of biotinylated-anti-IL-21 antibody (13-7218-81, R&D Systems), or 200 ng/mL of biotinylated-anti-TGFβRII antibody (BAF241, R&D Systems) was applied per well, and incubated at RT for 60 min. Following three washes, incubation with 0.25 μg/mL of HRP-SA (Jackson ImmunoResearch at 100 μL per well for 30 min at RT was carried out, followed by 4 washes and incubation with 100 μL of ABTS for 2 mins at RT. Absorbance was read at 405 nm. As shown in FIGS. 87A-87C, the IL-15, IL-21, and TGFβRII domains in TGFRt15-16s21 were detected by the respective antibodies.

Figure 88:
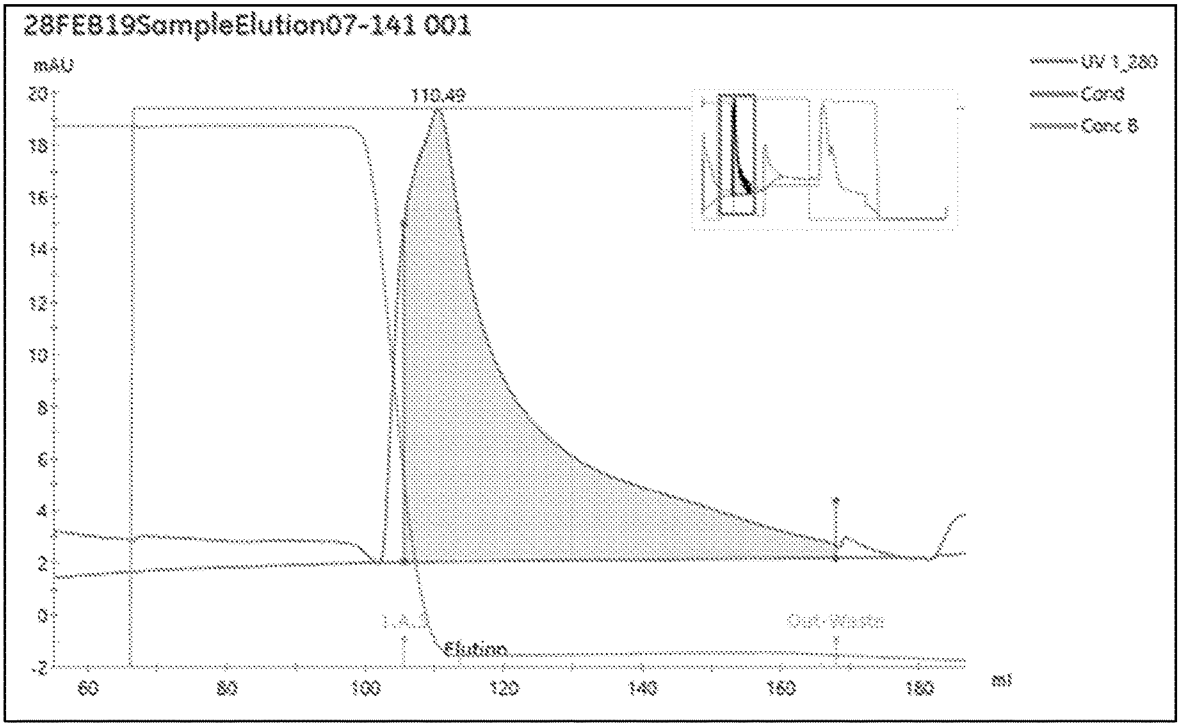
FIG. 88 shows the chromatographic profile of TGFRt15-16s21 protein containing cell culture supernatant following binding and elution on anti-TF antibody resin.

Purification Elution Chromatograph of TGFRt15-16s21 Using Anti-TF Antibody Affinity Column TGFRt15-16s21 harvested from cell culture was loaded onto the anti-TF antibody affinity column equilibrated with 5 column volumes of PBS. After sample loading, the column was washed with 5 column volumes of PBS, followed by elution with 6 column volumes of 0.1 M acetic acid (pH 2.9). A280 elution peak was collected and then neutralized to pH 7.5-8.0 with 1 M Tris base. The neutralized sample was then buffer exchanged into PBS using Amicon centrifugal filters with a 30 KDa molecular weight cutoff. As shown in FIG. 88, the anti-TF antibody affinity column bound to TGFRt15-16s21, which contains tissue factor as a fusion partner. The buffer-exchanged protein sample was stored at 2-8 °C for further biochemical analyses and biological activity tests. After each elution, the anti-TF antibody affinity column was stripped using 6 column volumes of 0.1 M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE of TGFRt15-16s21

To determine the purity and molecular weight of the TGFRt15-16s21 protein, protein sample purified with anti-TF antibody affinity column was analyzed by sodium dodecyl sulfate polyacrylamide gel (4-12% NuPage Bis-Tris gel) electrophoresis (SDS-PAGE) under reduced condition. After electrophoresis, the gel was stained with InstantBlue for about 30 min, followed by destaining overnight in purified water.

Figure 89:
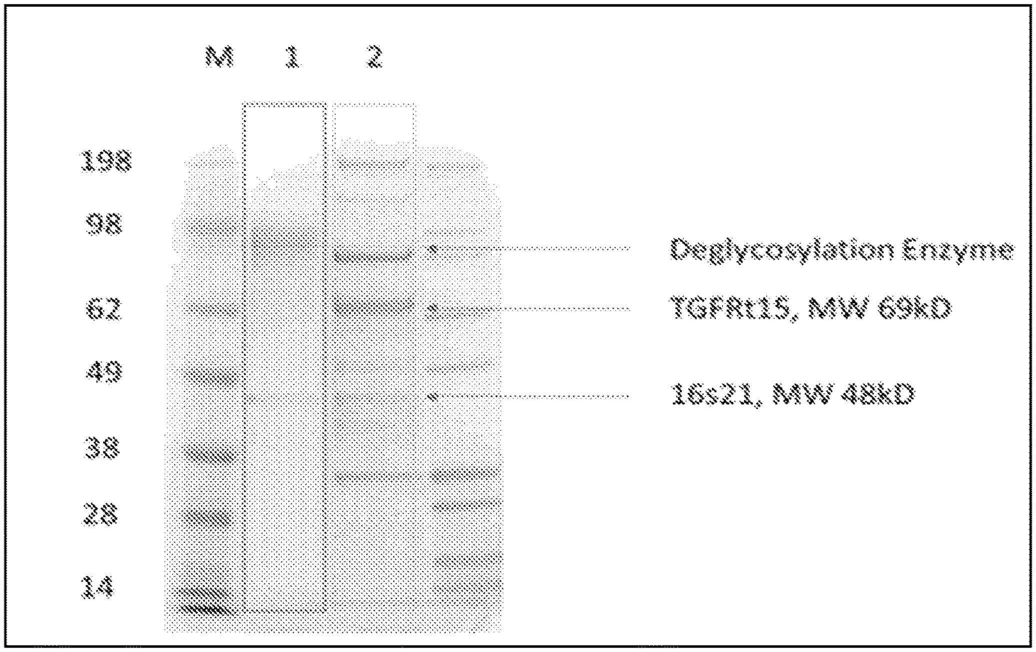
FIG. 89 shows results of a reduced SDS-PAGE analysis of TGFRt15-16s21.

To verify that the TGFRt15-16s21 protein undergoes glycosylation after translation in CHO cells, a deglycosylation experiment was conducted using the Protein Deglycosylation Mix II kit from New England Biolabs according to the manufacturer's instructions. FIG. 89 shows results from the reduced SDS-PAGE analysis of the sample in non-deglycosylated (lane 1 in red outline) and deglycosylated (lane 2 in yellow outline) state. The results showed that the TGFRt15-16s21 protein is glycosylated when expressed in CHO cells. After deglycosylation, the purified sample showed expected molecular weights (69 kDa and 48 kDa) in the reduced SDS gel. Lane M was loaded with 104, of SeeBlue Plus2 Prestained Standard.

Example 52: 7t15-7s Fusion Protein Generation and Characterization

Figure 90:
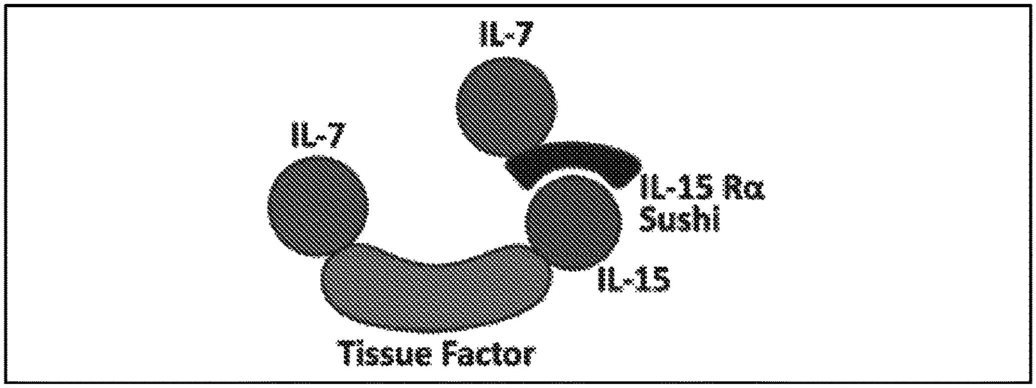
FIG. 90 shows a schematic of the 7t15-7s construct.
Figure 91:
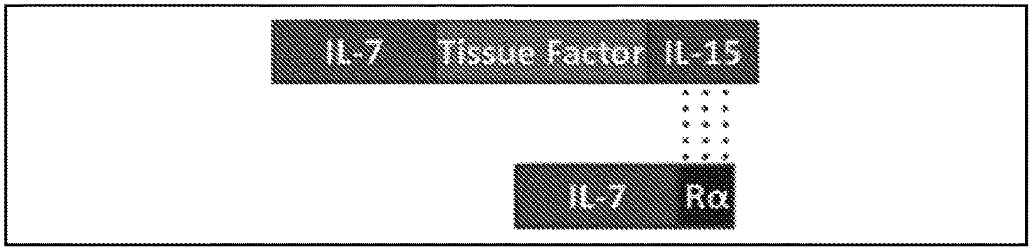
FIG. 91 shows an additional schematic of the 7t15-7s construct.

A fusion protein complex was generated comprising IL-7/TF/IL-15 and IL-7/IL-15RαSu fusion proteins (FIG. 90 and FIG. 91). The human IL-7, tissue factor 219, and IL-15 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15.

The nucleic acid and protein sequences of a construct comprising IL-7 linked to the N-terminus of tissue factor 219 following with the N-terminus of IL-15 are shown below.

The nucleic acid sequence of 7t15 construct (including signal peptide sequence) is as follows:

```
(Signal peptide)
ATGAAGTGGGTGACCTTCATCAGCCTGCTGTTCCTGTTCTCCAGCGCCTAC

TCC

(Human IL7)
GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG

GAGGGCATGTTCCTGTTCAGGGCCGCCAGGAAACTGCGGCAGTTCCTGAAG

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCAT

(Human Tissue Factor 219)
AGCGGCACAACCAACACAGTCGCTGCCTATAACCTCACTTGGAAGAG

CACCAACTTCAAAACCATCCTCGAATGGGAACCCAAACCCGTTAACCAAGT

TTACACCGTGCAGATCAGCACCAAGTCCGGCGACTGGAAGTCCAAATGTTT

CTATACCACCGACACCGAGTGCGATCTCACCGATGAGATCGTGAAAGATGT

GAAACAGACCTACCTCGCCCGGGTGTTTAGCTACCCCGCCGGCAATGTGGA

GAGCACTGGTTCCGCTGGCGAGCCTTTATACGAGAACAGCCCCGAATTTAC

CCCTTACCTCGAGACCAATTTAGGACAGCCCACCATCCAAAGCTTTGAGCA

AGTTGGCACAAAGGTGAATGTGACAGTGGAGGACGAGCGGACTTTAGTGCG

GCGGAACAACACCTTTCTCAGCCTCCGGGATGTGTTCGGCAAAGATTTAAT

CTACACACTGTATTACTGGAAGTCCTCTTCCTCCGGCAAGAAGACAGCTAA

AACCAACACAAACGAGTTTTTAATCGACGTGGATAAAGGCGAAAACTACTG

TTTCAGCGTGCAAGCTGTGATCCCCTCCCGGACCGTGAATAGGAAAAGCAC

CGATAGCCCCGTTGAGTGCATGGGCCAAGAAAAGGGCGAGTTCCGGGAG

(Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC
```

The amino acid sequence of 7t15 fusion protein (including the leader sequence) is as follows:

```
(Signal peptide)
MKWVTFISLLFLFSSAYS

(Human IL7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQ SFEQVGTKVNVTVEDERTLVRRNNTFLSLRDVFGKDL

IYTLYYWKSSSSGKKTAKTNTNEFLIDVDKGENYCFSVQAVIPSRTVNRKS

TDSPVECMGQEKGEFRE

(Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS
```

Constructs were also made by linking the IL-7 sequence to the N-terminus coding region of IL-15RαSu chain which was synthesized by Genewiz. The nucleic acid and protein sequences of a construct comprising the IL-7 linked to the N-terminus of IL-15RαSu chain are shown below.

The nucleic acid sequence of 7s construct (including signal peptide sequence) is as follows:

```
(Signal peptide)
ATGAAGTGGGTGACCTTCATCAGCCTGCTGTTCCTGTTCTCCAGCGCCTAC

TTCC

(Human IL7)
GATTGCGACATCGAGGGCAAGGACGGCAAGCAGTACGAGAGCGTGCTGATG

ATGGTGTCCATCGACCAGCTGCTGGACAGCATGAAGGAGATCGGCTCCAAC

TGCCTCAACAACGAGTTCAACTTCTTCAAGCGGCACATCTGCGACGCCAAC

AAGGAGGGCATGTTCCTGTTCAGGGCCGCCAGGAAACTGCGGCAGTTCCTG

AAGATGAACTCCACCGGCGACTTCGACCTGCACCTGCTGAAGGTGTCCGAG

GGCACCACCATCCTGCTGAACTGCACCGGACAGGTGAAGGGCCGGAAACCT

GCTGCTCTGGGAGAGGCCCAACCCACCAAGAGCCTGGAGGAGAACAAGTCC

CTGAAGGAGCAGAAGAAGCTGAACGACCTGTGCTTCCTGAAGAGGCTGCTG

CAGGAGATCAAGACCTGCTGGAACAAGATCCTGATGGGCACCAAGGAGCAT

(Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

SGAAGGCCGGCACCAGCAGCCTCACCGAGTGCGTGCTGAATAAGGCTACCA

ACGTGGCTCACTGGACAACACCCTCTTTAAAGTGCATCCGG
```

-continued

```
The amino acid sequence of 7s fusion protein
(including the leader sequence) is as follows:
(Signal peptide)
MKWVTFISLLFLFSSAYS

(Human IL7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH

(Human IL-15R α sushi domain)
ITCPPPMSVEHADIWVKSYSLYSRERYICNSGFKRKAGTSSLTECVLNKAT

NVAHWTTPSLKCIR
```

The IL-7/TF/IL-15 and IL-7/IL-15RαSu constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15:IL-7/IL-15RαSu protein complex referred to as 7t15-7s, which can be purified by anti-TF antibody IgG1 affinity and other chromatography methods.

Figure 92:
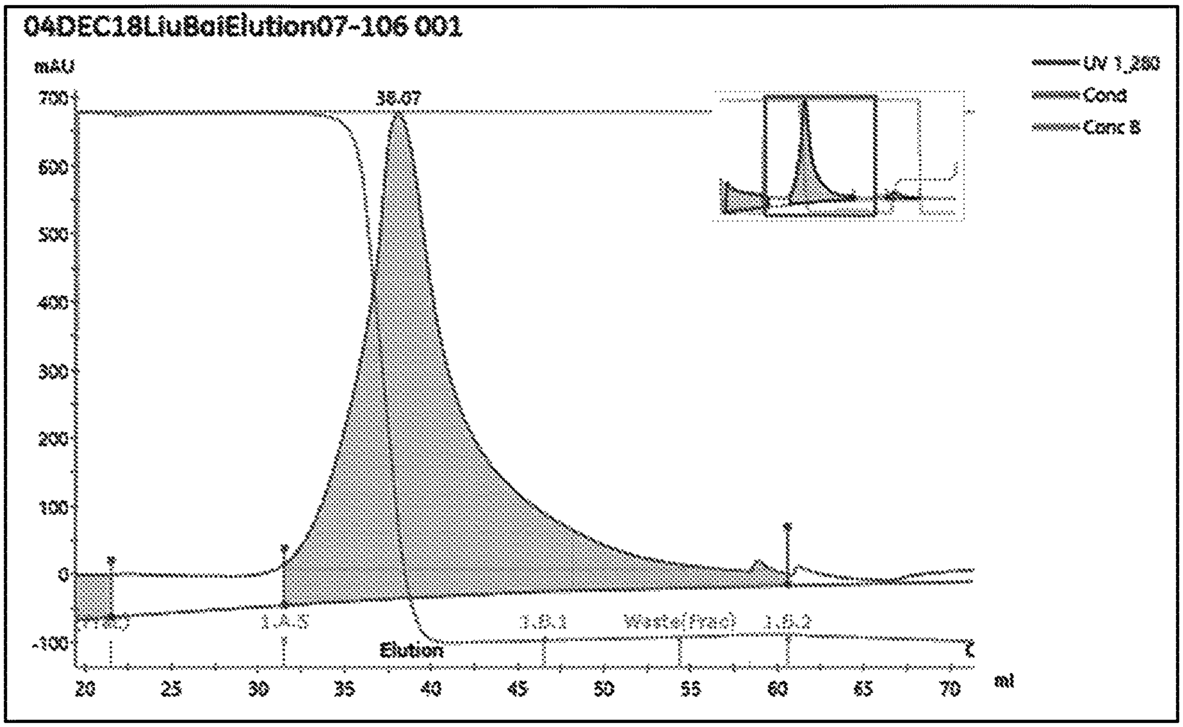
FIG. 92 shows the chromatographic profile of 7t15-7s protein containing cell culture supernatant following binding and elution on anti-TF antibody resin.

Purification Elution Chromatograph of 7t15-7s Using Anti-TF Antibody Affinity Column 7t15-7s harvested from cell culture was loaded onto the anti-TF antibody affinity column equilibrated with 5 column volumes of PBS. After sample loading, the column was washed with 5 column volumes of PBS, followed by elution with 6 column volumes of 0.1 M acetic acid (pH 2.9). A280 elution peak was collected and then neutralized to pH 7.5-8.0 with 1 M Tris base. The neutralized sample was then buffer exchanged into PBS using Amicon centrifugal filters with a 30 KDa molecular weight cutoff. As shown in FIG. 92, the anti-TF antibody affinity column bound to 7t15-7s which contains tissue factor (TF) as a fusion partner. The buffer-exchanged protein sample was stored at 2-8 °C for further biochemical analyses and biological activity tests. After each elution, the anti-TF antibody affinity column was stripped using 6 column volumes of 0.1 M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except the elution step, which was 2 mL/min.

Immunostimulation of 7t15-7s in C57BL/6 Mice

7t15-7s is a multi-chain polypeptide (a type A multi-chain polypeptide described herein) that includes the first polypeptide that is a soluble fusion of human IL-7, human tissue factor 219 fragment and human IL-15 (7t15), and the second polypeptide that is a soluble fusion of human IL-7 and sushi domain of human IL-15 receptor alpha chain (7s).

Figure 93:
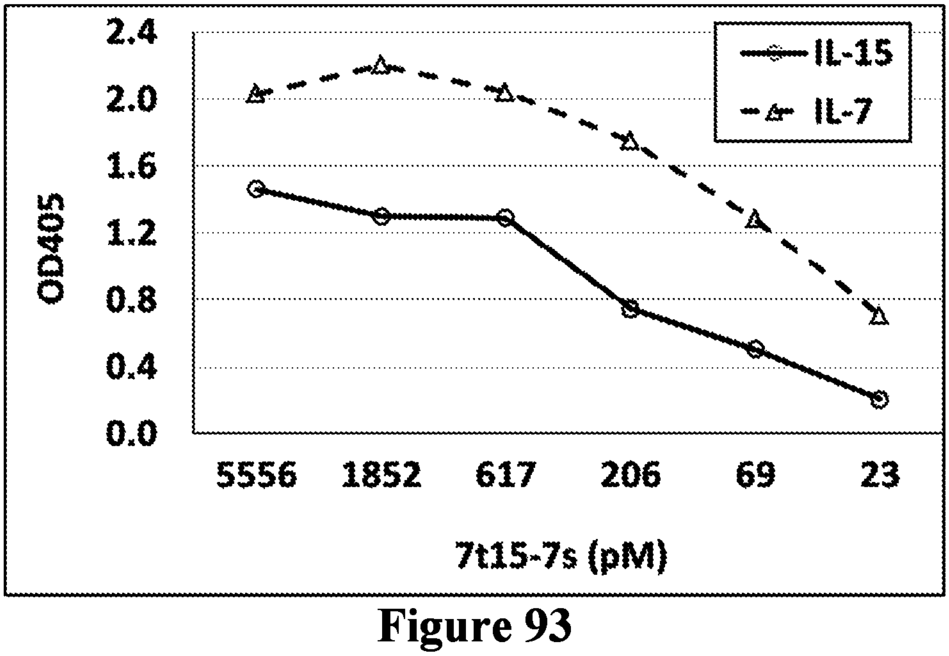
FIG. 93 shows detection of TF, IL-15 and IL-7 in 7t15-7s using ELISA.

CHO cells were co-transfected with the IL7-TF-IL-15 (7t15) and IL7-IL-15Rα sushi domain (7s) vectors. The 7t15-7s complex was purified from the transfected CHO cell culture supernatant. The IL-7, IL-15 and tissue factor (TF) components were demonstrated in the complex by ELISA as shown in FIG. 93. A humanized anti-TF antibody monoclonal antibody (anti-TF IgG1) was used as the capture antibody to determine TF in 7t15-7s, and biotinylated anti-human IL-15 antibody (R&D systems) and biotinylated anti-human IL-7 antibody (R&D Systems) were used as the detection antibodies to respectively detect IL-15 and IL-7 in 7t15-7s, followed by peroxidase conjugated streptavidin (Jackson ImmunoResearch Lab) and ABTS substrate (Surmodics IVD, Inc.).

Figure 94A:
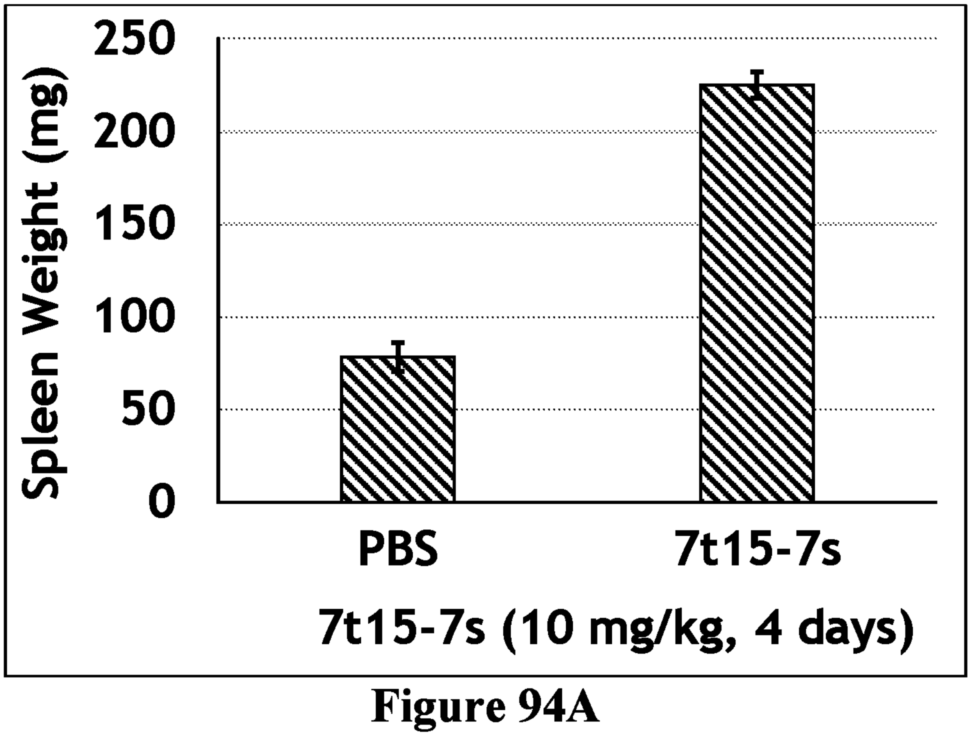
FIGS. 94A and 94B show spleen weight and the percentages of immune cell types in 7t15-7s-treated and control-treated mice.
Figure 94B:
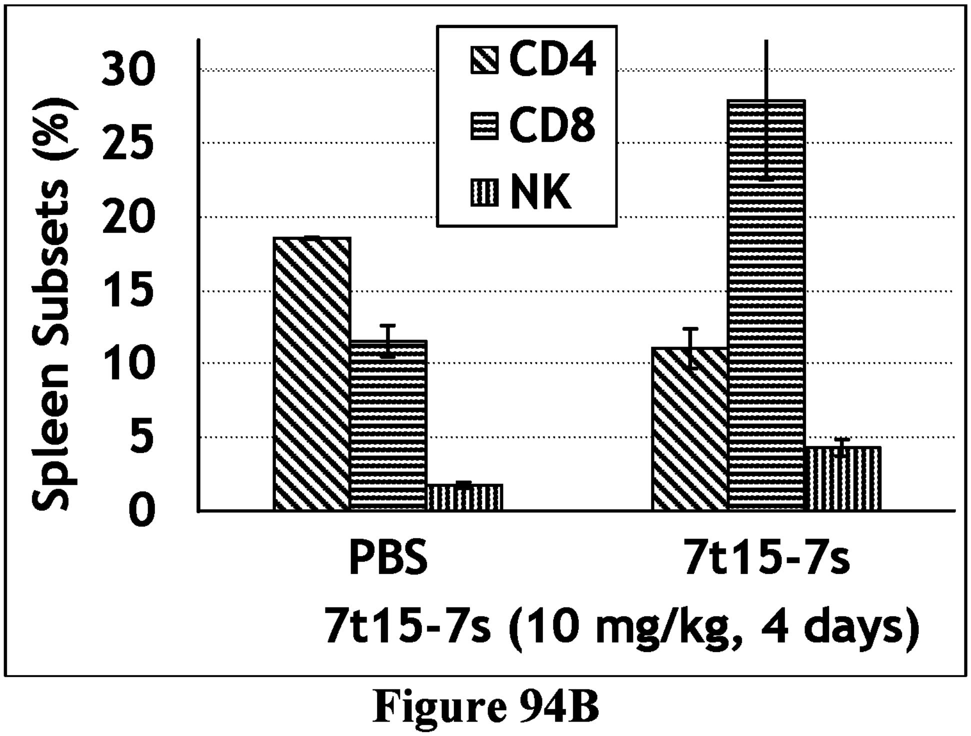

7t15-7s was subcutaneously injected into C57BL/6 mice at 10 mg/kg to determine the immunostimulatory activity of 7t15-7s in vivo. C57BL/6 mice subcutaneously treated with PBS were used as control. The mouse spleens were collected and weighed day 4 post treatment. Single splenocytes suspensions were prepared, and with fluorochrome-conjugated anti-CD4, anti-CD8, and anti-NK1.1 antibodies and the percentage of $CD4^+$ T cells, $CD8^+$ T cells, and NK cells was analyzed by flow cytometry. The results showed that 7t15-7s was effective at expanding splenocytes based on spleen weight (FIG. 94A) and specifically, the percentages of $CD8^+$ T cells and NK cells were higher compared to control-treated mice (FIG. 94B).

Example 53: TGFRt15-TGFRs Fusion Protein Generation and Characterization

Figure 95:
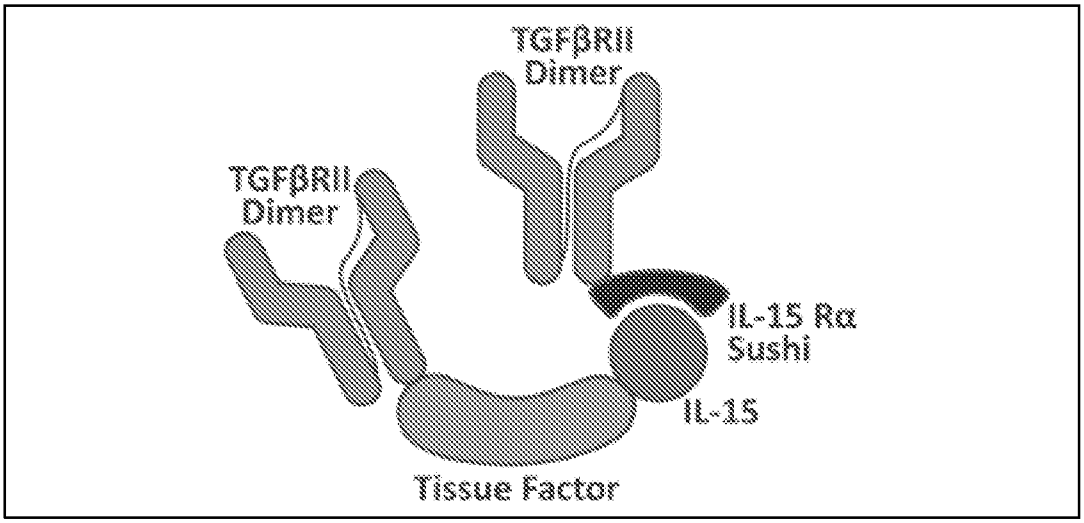
FIG. 95 shows a schematic of the TGFRt15-TGFRs construct.
Figure 96:
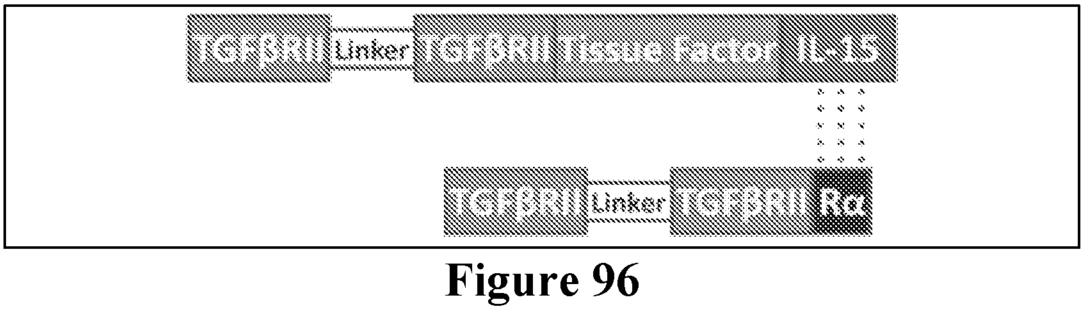
FIG. 96 shows an additional schematic of the TGFRt15-TGFRs construct.

A fusion protein complex was generated comprising of TGFβ Receptor II/IL-15RαSu and TGFβ Receptor II/TF/IL-15 fusion proteins (FIG. 95 and FIG. 96). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the two TGFβ Receptor II/TF/IL-15 construct (including signal peptide sequence) is as follows:

```
(Signal peptide)
ATGAAGTGGGTGACCTTCATCAGCCTGCTGTTCCTGTTCTCCAGCGCCACT

TCC

(Two Human TGFβ Receptor II fragments)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

GGCGCCGTGAAATTTCCCCAGCTGTGCAAATTCTGCGATGTGAGGTTTTCC

ACCTGCGACAACCAGAAGTCCTGTATGAGCAACTGCTCCATCACCTCCATC

TGTGAGAAGCCTCAGGAGGTGTGCGTGGCTGTCTGGCGGAAGAATGACGAG
```

-continued

```
AATATCACCCTGGAAACCGTCTGCCACGATCCCAAGCTGCCCTACCACGAT

TTCATCCTGGAAGACGCCGCCAGCCCTAAGTGCATCATGAAAGAGAAAAAG

AAGCCTGGCGAGACCTTTTTCATGTGCTCCTGCAGCAGCGACGAATGCAAC

GACAATATCATCTTTAGCGAGGAATACAATACCAGCAACCCCGAC

(Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG

(Human IL-15)
AACTGGGTGAACGTCATCAGCGATTTAAAGAAGATCGAAGATTTAATCAGT

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC
```

The amino acid sequence of TGFβ Receptor II/TF/IL-15 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRSTCDNQKSCMSNCSITS

ICEKPQEVCVAVWRKNDENITLETVCHDPKLPYHDFILEDAASPKCIMKEK

KKPGETFFMCSCSSDECNDNIIFSEEYNTSNPDGGGGSGGGGSGGGGSIPP

HVQKSVNNDMIVTDNNGAVKFPQLCKFCDVRFSTCDNQKSCMSNCSITSIC

EKPQEVCVAVWRKNDENITLETVCHDPKLPYHDFILEDAASPKCIMKEKKK

PGETFFMCSCSSDECNDNIIFSEEYNTSNPD

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE
```

-continued (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

Constructs were also made by attaching two TGFβ Receptor II directly to the IL-15RαSu chain which was synthesized by Genewiz. The nucleic acid and protein sequences of a construct comprising the TGFβ Receptor II linked to the N-terminus of IL-15RαSu are shown below.

The nucleic acid sequence of the TGFβ Receptor II/IL-15 RαSu construct (including signal peptide sequence) is as follows:

(Signal peptide)
ATGAAGTGGGTGACCTTCATCAGCCTGCTGTTCCTGTTCTCCAGCGCCTAC

TCC (Two human TGFβ Receptor II fragments)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

GGCGCCGTGAAATTTCCCCAGCTGTGCAAATTCTGCGATGTGAGGTTTTCC

ACCTGCGACAACCAGAAGTCCTGTATGAGCAACTGCTCCATCACCTCCATC

TGTGAGAAGCCTCAGGAGGTGTGCGTGGCTGTCTGGCGGAAGAATGACGAG

AATATCACCCTGGAAACCGTCTGCCACGATCCCAAGCTGCCCTACCACGAT

TTCATCCTGGAAGACGCCGCCAGCCCTAAGTGCATCATGAAAGAGAAAAAG

AAGCCTGGCGAGACCTTTTTCATGTGCTCCTGCAGCAGCGACGAATGCAAC

GACAATATCATCTTTAGCGAGGAATACAATACCAGCAACCCCGAC (Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG

The amino acid sequence of the two TGFβ Receptor II/IL-15RαSu construct (including signal peptide sequence) is as follows:

(Signal peptide)
MKWVTFISLLFLFSSAYS (Two human TGFβ Receptor II extra-cellular domains)
IPPHVQKSVNNDMIVTDNNGAVKFPQLCKFCDVRFSTCDNQKSCMSNCSIT -continued

SICEKPQEVCVAVWRKNDENITLETVCHDPKLPYHDFILEDAASPKCIMKE

KKKPGETFFMCSCSSDECNDNIIFSEEYNTSNPDGGGGSGGGGSGGGGSIP

PHVQKSVNNDMIVTDNNGAVKFPQLCKFCDVRFSTCDNQKSCMSNCSITSI

CEKPQEVCVAVWRKNDENITLETVCHDPKLPYHDFILEDAASPKCIMKEKK

KPGETFFMCSCSSDECNDNIIFSEEYNTSNPD (Human IL-15R α sushi domain)
ITCPPPMSVEHADIWVKSYSLYSRERYICNSGFKRKAGTSLTECVLNKAT

NVAHWTTPSLKCIR

In some cases, the leader peptide is cleaved from the intact polypeptide to generate the mature form that may be soluble or secreted.

The TGFβR/IL-15RαSu and TGFβR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFβR/TF/IL-15:TGFβR/IL-15RαSu protein complex (referred to as TGFRt15-TGFRs), which can be purified by anti-TF IgG1 affinity and other chromatography methods.

Effect of TGFRt15-TGFRs on TGFβ1 Activity in HEK-Blue TGFβ Cells

Figure 97:
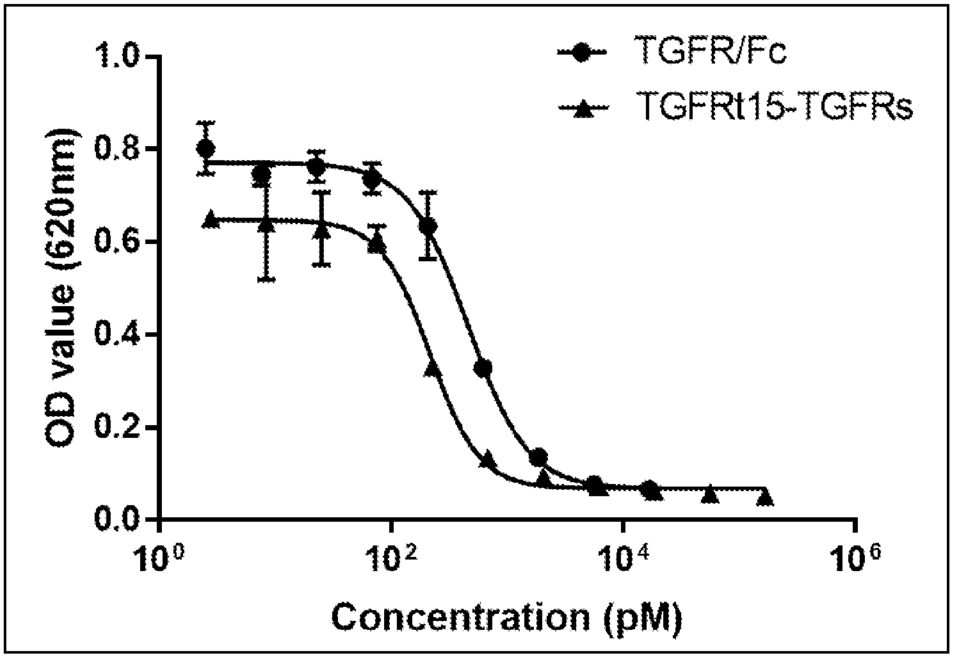
FIG. 97 shows results of TGFβ1 inhibition by TGFRt15-TGFRs and TGFR-Fc.

To evaluate the activity of TGFβRII in TGFRt15-TGFRs, the effect of TGFRt15-16s21 on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, 50 μL cells were added to each well ($2.5\times10^4$ cells/well) and followed with 50 μL 0.1 nM TGFβ1 (R&D systems). TGFRt15-16s21 or TGFR-Fc (R&D Systems) prepared at a 1:3 serial dilution was then added to the plate to reach a total volume of 200 μL. After 24 hrs of incubation at 37 °C, 40 μL of induced HEK-Blue TGFβ cell supernatant was added to 160 μL pre-warmed QUANTI-Blue (Invivogen) in a flat-bottom 96-well plate, and incubated at 37 °C for 1-3 hrs. The OD values were then determined using a plate reader (Multiscan Sky) at 620-655 nM (FIG. 97). The $IC_{50}$ of each protein sample was calculated with GraphPad Prism 7.04. The $IC_{50}$ of TGFRt15-TGFRs and TGFR-Fc were 216.9 pM and 460.6 pM respectively. These results showed that the TGFβRII domain in TGFRt15-TGFRs was able to block the activity of TGFβ1 in HEK-Blue TGFβ cells.

Figure 98:
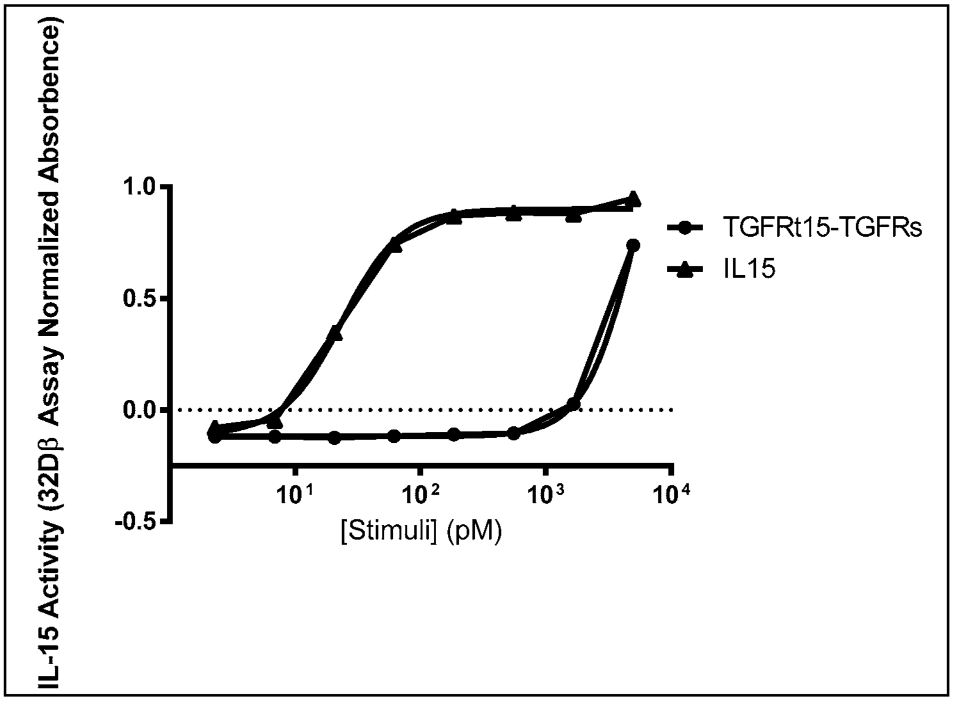
FIG. 98 shows results of 32Dβ cell proliferation assay with TGFRt15-TGFRs or recombinant IL-15

The IL-15 in TGFRt15-TGFRs Promotes IL-2Rβ and Common γ Chain Containing 32D Cell Proliferation To evaluate the activity of IL-15 in TGFRt15-TGFRs, the IL-15 activity of TGFRt15-TGFRs was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted TGFRt15-TGFRs or IL-15 were added to the cells (FIG. 98). Cells were incubated in a $CO_2$ incubator at 37 °C for 3 days. Cell proliferation was detected by adding 10 μL of WST1 to each well on day 3 and incubating for an additional 3 hours in a $CO_2$ incubator at 37 °C. The absorbance at 450 nm was measured by analyzing the amount of formazan dye produced. As shown in FIG. 98, TGFRt15-TGFRs and IL-15 promoted 32Dβ cell proliferation, with the $EC_{50}$ of TGFRt15-16s21 and IL-15 being 1901 pM and 10.63 pM, respectively.

Figure 99A:
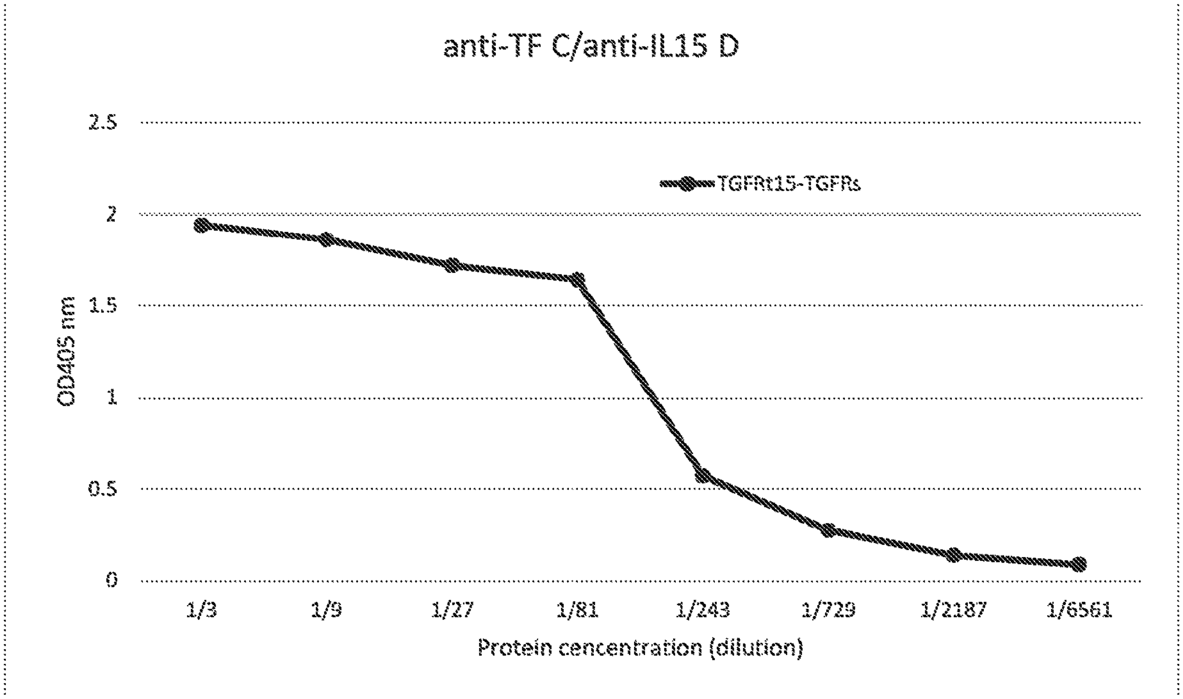
FIGS. 99A and 99B show results of detecting IL-15 and TGFβRII in TGFRt15-TGFRs with corresponding antibodies using ELISA.
Figure 99B:
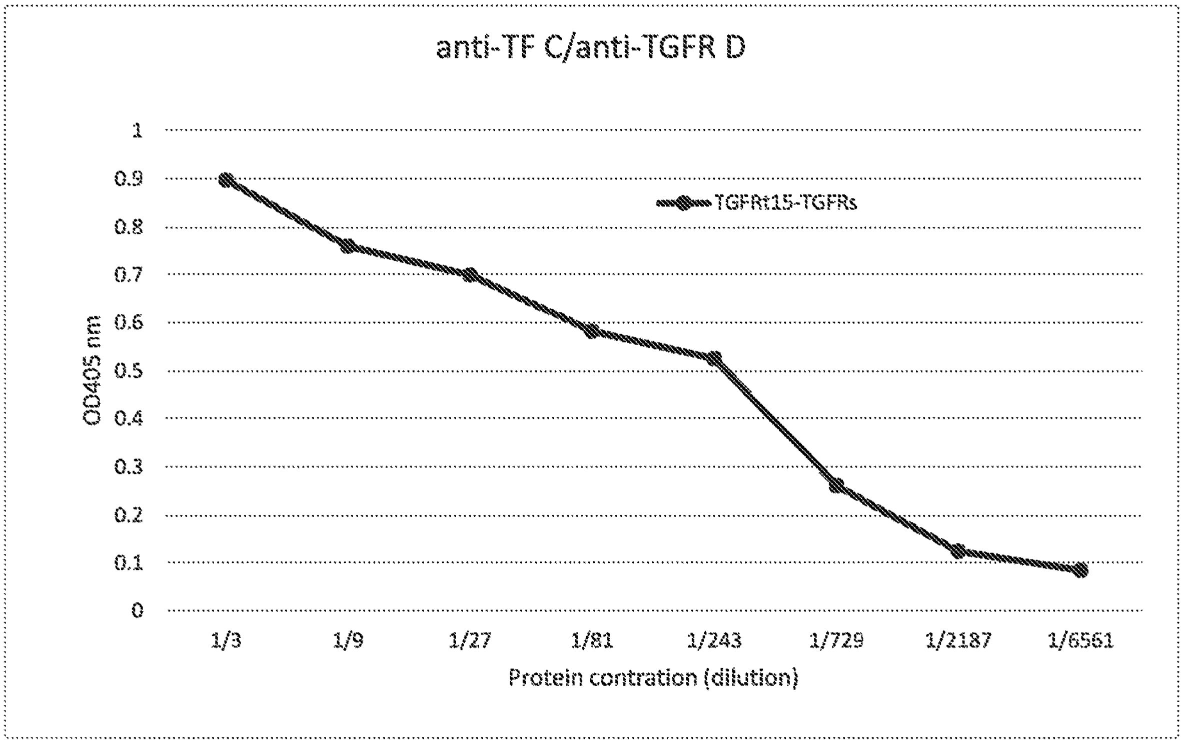

Detection of IL-15 and TGFβRII Domains in TGFRt15-TGFRs with Corresponding Antibodies Using ELISA A 96-well plate was coated with 100 μL (8 pg/mL) of anti-TF IgG1 in R5 (coating buffer) and incubated at room temperature (RT) for 2 hrs. The plates were washed 3 times and blocked with 100 μL of 1% BSA in PBS. TGFRt15-TGFRs was added at a 1:3 serial dilution, and incubated at RT for 60 min. After 3 washes, 50 ng/mL of biotinylated-anti-IL-15 antibody (BAM247, R&D Systems), or 200 ng/mL of biotinylated-anti-TGFbRII antibody (BAF241, R&D Systems) was added to the wells and incubated at RT for 60 min. Next the plates were washed 3 times, and 0.25 μg/mL of HRP-SA (Jackson ImmunoResearch) at 100 μL per well was added and incubated for 30 min at RT, followed by 4 washes and incubation with 100 μL of ABTS for 2 mins at RT. Absorbance at 405 nm was read. As shown in FIGS. 99A and 99B, the IL-15 and TGFβRII domains in TGFRt15-TGFRs were detected by the individual antibodies.

Figure 100:
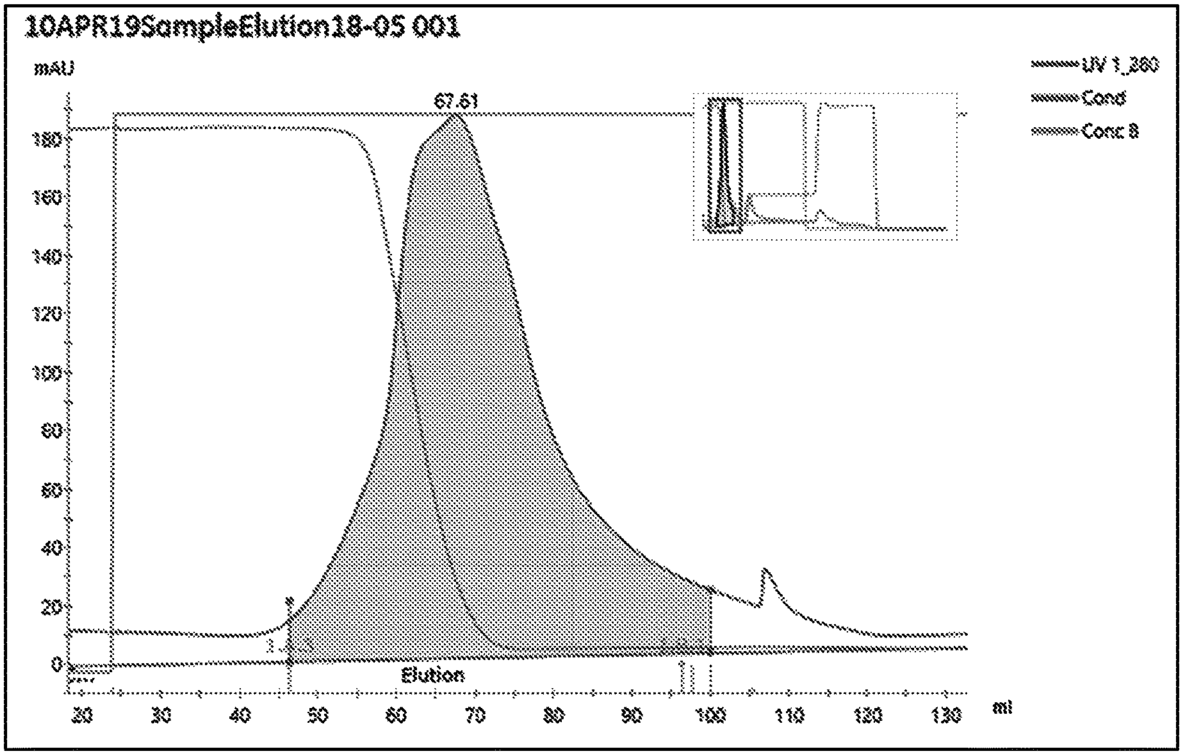
FIG. 100 is a line graph showing the chromatographic profile of TGFRt15-TGFRs protein containing cell culture supernatant following binding and elution on anti-TF antibody resin.

Purification Elution Chromatograph of TGFRt15-TGFRs from Anti-TF Antibody Affinity Column TGFRt15-TGFRs harvested from cell culture was loaded onto the anti-TF antibody affinity column equilibrated with 5 column volumes of PBS. After sample loading, the column was washed with 5 column volumes of PBS, followed by elution with 6 column volumes of 0.1 M acetic acid (pH 2.9). A280 elution peak was collected and then neutralized to pH 7.5-8.0 with 1 M Tris base. The neutralized sample was then buffer exchanged into PBS using Amicon centrifugal filters with a 30 KDa molecular weight cutoff. As shown in FIG. 100, the anti-TF antibody affinity column bound to TGFRt15-TGFRs which contains TF as a fusion partner. The buffer-exchanged protein sample was stored at 2-8 °C for further biochemical analyses and biological activity tests. After each elution, the anti-TF antibody affinity column was stripped using 6 column volumes of 0.1 M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of TGFRt15-TGFRs

Figure 101:
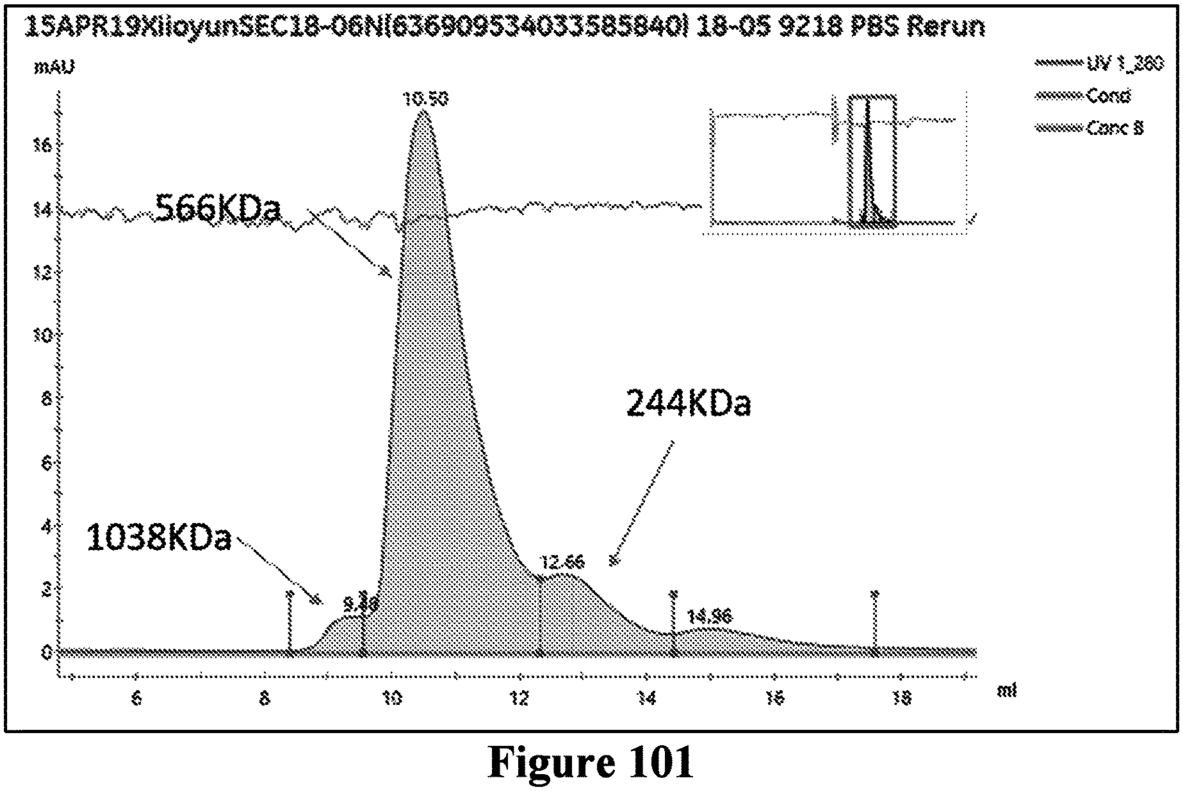
FIG. 101 shows the analytical SEC profile of TGFRt15-TGFRs.

A Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. A sample containing TGFRt15-TGFRs in PBS was injected into the Superdex 200 column using a capillary loop, and analyzed by SEC. The SEC chromatograph of the sample is shown in FIG. 101. The SEC results showed four protein peaks for TGFRt15-TGFRs.

Reduced SDS PAGE Analysis of TGFRt15-TGFRs

To determine the purity and molecular weight of the TGFRt15-TGFRs protein, protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

Figure 102:
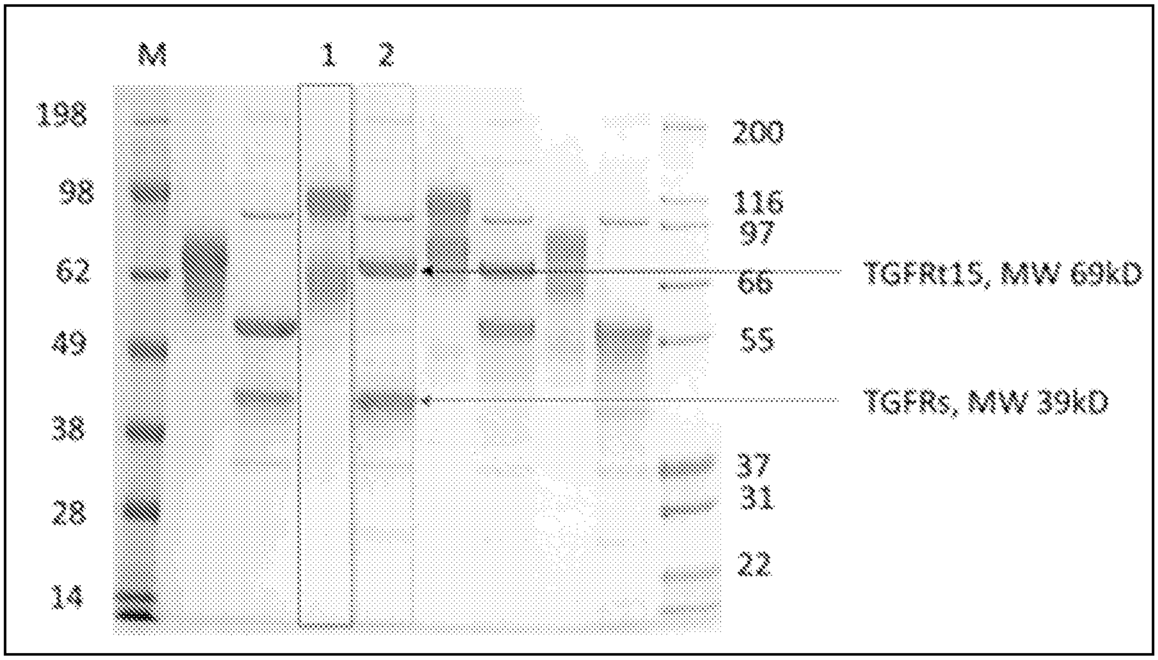
FIG. 102 shows TGFRt15-TGFRs before and after deglycosylation on as analyzed by reduced SDS-PAGE.

To verify that the TGFRt15-TGFRs protein undergoes glycosylation after translation in CHO cells, a deglycosylation experiment was conducted using the Protein Deglycosylation. Mix II kit from New England Biolabs and the manufacturer's instructions. FIG. 102 shows the reduced SDS-PAGE analysis of the sample in non-deglycosylated (lane tin red outline) and deglycosylated (lane 2 in yellow outline) state. The results showed that the TGFRt15-TGFRs protein is glycosylated when expressed in CHO cells. After deglycosylation, the purified sample showed expected molecular weights (69 kDa and 39 kDa) in the reduced SDS gel. Lane M was loaded with 10 ul of SeeBlue Plus2 Prestained Standard.

Immunostimulatory Activity of TGFRt15-TGFRs in C57BL/6 Mice

TGFRt15-TGFRs is a multi-chain polypeptide (a type A multi-chain polypeptide described herein) that includes a first polypeptide that is a soluble fusion of two TGFβRII domains, human tissue factor 219 fragment and human IL-15, and the second polypeptide that is a soluble fusion of two TGFβRII domains and sushi domain of human IL-15 receptor alpha chain.

Figure 103A:
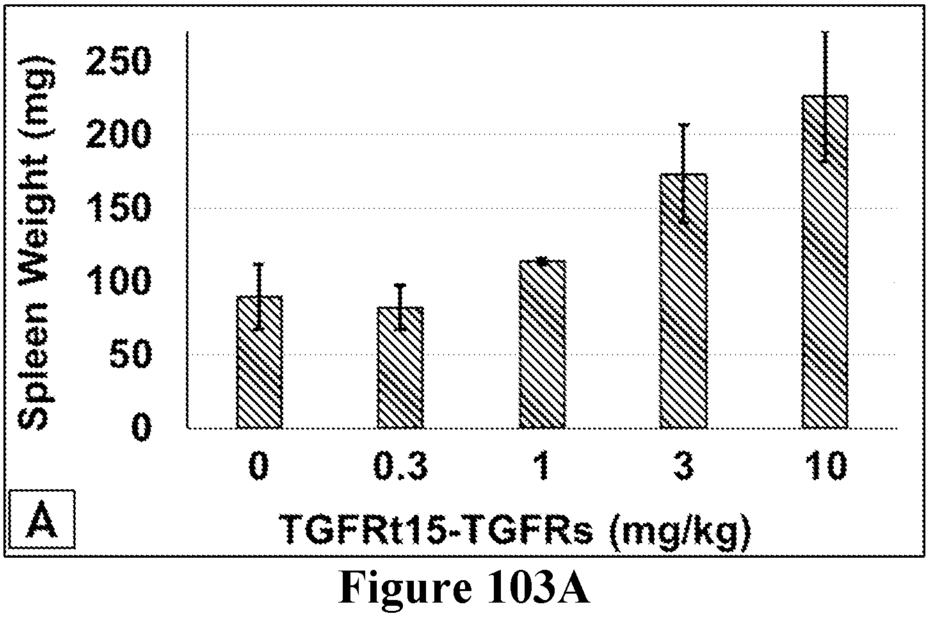
FIGS. 103A and 103B show spleen weight and the percentages of immune cell types in TGFRt15-TGFRs-treated and control-treated mice.
Figure 103B:
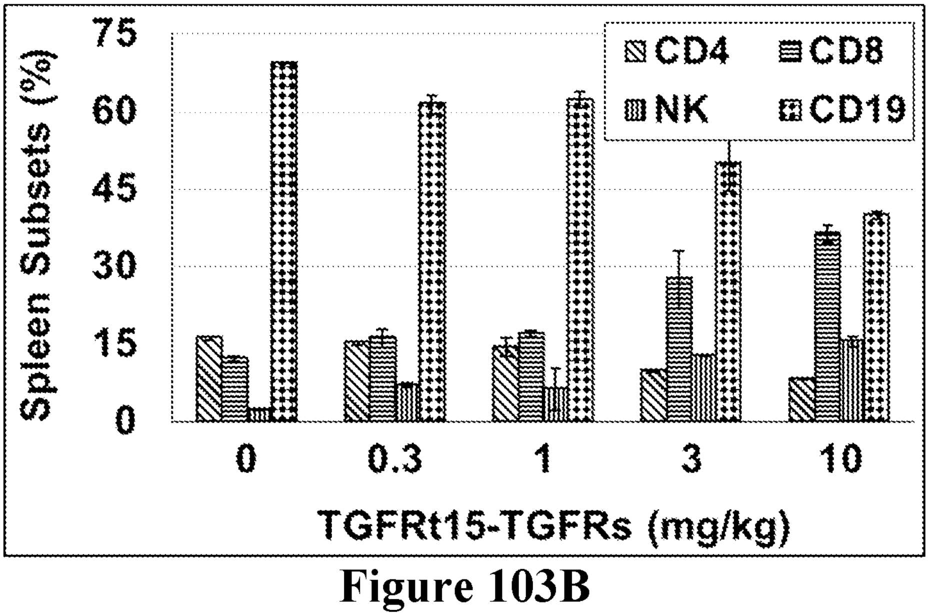

Wild type C57BL/6 mice were treated subcutaneously with either control solution or with TGFRt15-TGFRs at a dosage of 0.3 mg/kg, 1 mg/kg, 3 mg/kg, or 10 mg/kg. Four days after treatment, spleen weight and the percentages of various immune cell types present in the spleen were evaluated. As shown in FIG. 103A, the spleen weight in mice treated with TGFRt15-TGFRs increased with increasing dosage of TGFRt15-TGFRs. Moreover, the spleen weight in mice treated with 1 mg/kg, 3 mg/kg, and 10 mg/kg of TGFRt15-TGFRs were higher as compared to mice treated with the control solution, respectively. In addition, the percentages of $CD4^+$ T cells, $CD8^+$ T cells, NK cells, and $CD19^+$ B cells present in the spleen of control-treated and TGFRt15-TGFRs-treated mice were evaluated. As shown in FIG. 103B, in the spleens of mice treated with TGFRt15-TGFRs, the percentages of $CD8^+$ T cells and NK cells both increased with increasing dosage of TGFRt15-TGFRs. Specifically, the percentages of $CD8^+$ T cells were higher in mice treated with 0.3 mg/kg, 3 mg/kg, and 10 mg/kg of TGFRt15-TGFRs compared to control-treated mice, and the percentages of NK cells were higher in mice treated with 0.3 mg/kg, 1 mg/kg, 3 mg/kg, and 10 mg/kg of TGFRt15-TGFRs compared to control-treated mice. These results demonstrate that TGFRt15-TGFRs is able to stimulate immune cells in the spleen, in particular $CD8^+$ T cells and NK cells.

The pharmacokinetics of TGFRt15-TGFRs molecules were evaluated in wild type C57BL/6 mice. The mice were treated subcutaneously with TGFRt15-TGFRs at a dosage of 3 mg/kg. The mouse blood was drained from tail vein at various time points and the serum was prepared. The TGFRt15-TGFRs concentrations in mouse serum was determined with ELISA (capture: anti-human tissue factor antibody; detection: biotinylated anti-human TGFβ receptor antibody and followed by peroxidase conjugated streptavidin and ABTS substrate). The results showed that the half-life of TGFRt15-TGFRs was 12.66 hours in C57BL/6 mice.

Figure 104A:
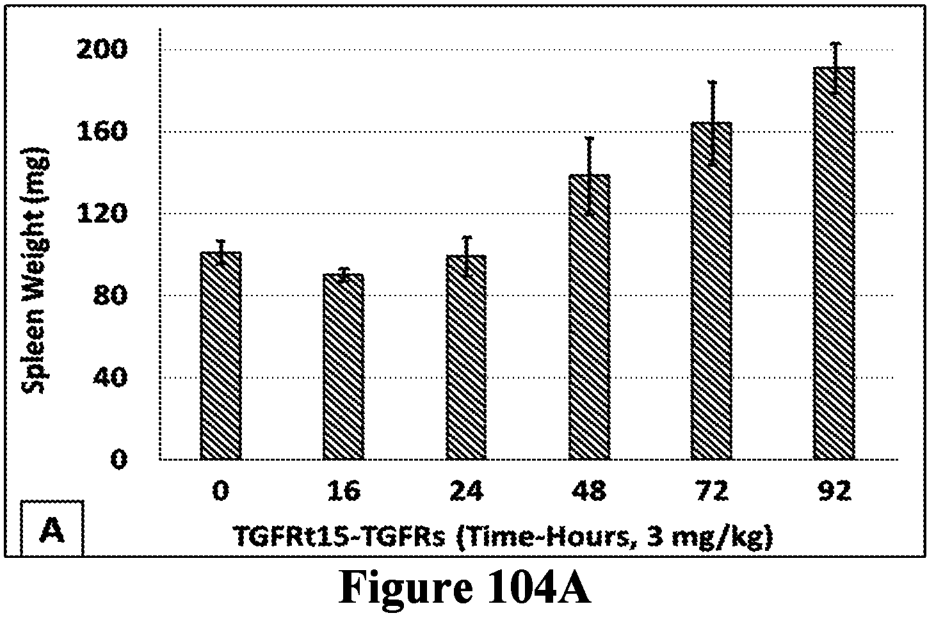
FIGS. 104A and 104B show the spleen weight and immunostimulation over 92 hours in mice treated with TGFRt15-TGFRs.
Figure 104B:
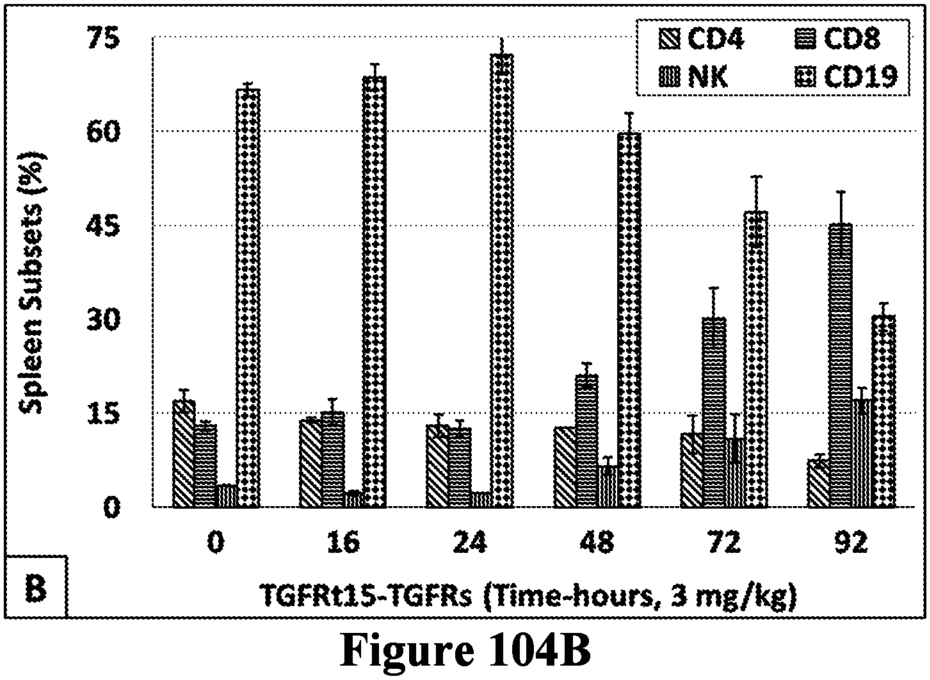

The mouse splenocytes were prepared in order to evaluate the immunostimulatory activity of TGFRt15-TGFRs over time in mice. As shown in FIG. 104A, the spleen weight in mice treated with TGFRt15-TGFRs increased 48 hours posttreatment and continued to increase over time. In addition, the percentages of $CD4^+$ T cells, $CD8^+$ T cells, NK cells, and $CD19^+$ B cells present in the spleen of control-treated and TGFRt15-TGFRs-treated mice were evaluated. As shown in FIG. 104B, in the spleens of mice treated with TGFRt15-TGFRs, the percentages of $CD8^+$ T cells and NK cells both increased at 48 hours after treatment and were higher and higher overtime after the single dose treatment. These results further demonstrate that TGFRt15-TGFRs is able to stimulate immune cells in the spleen, in particular $CD8^+$ T cells and NK cells.

Figure 105A:
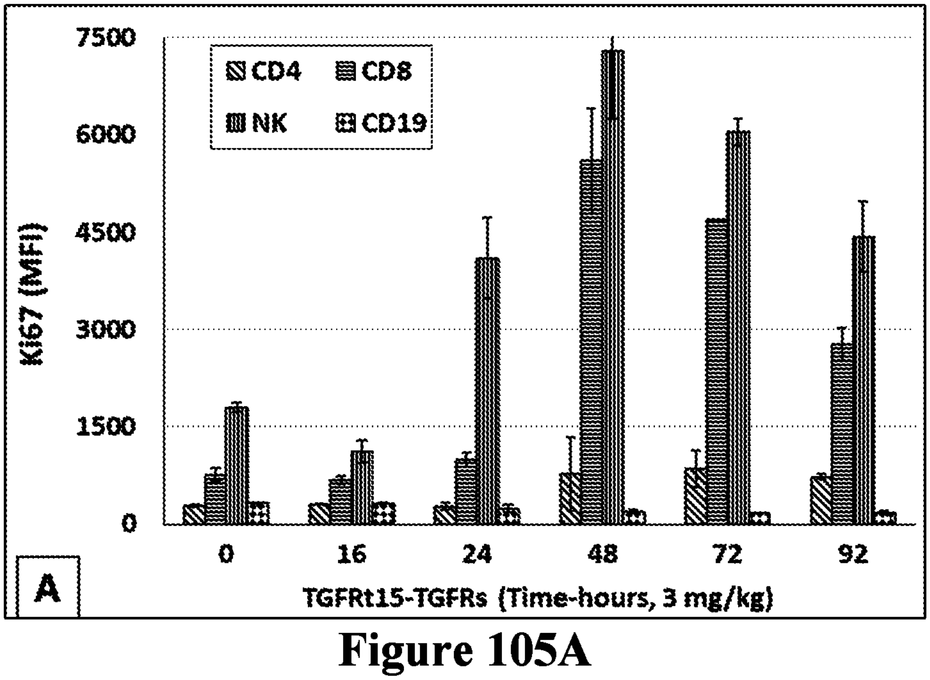
FIGS. 105A and 105B show Ki67 and Granzyme B expression in mice treated with TGFRt15-TGFRs over time.
Figure 105B:
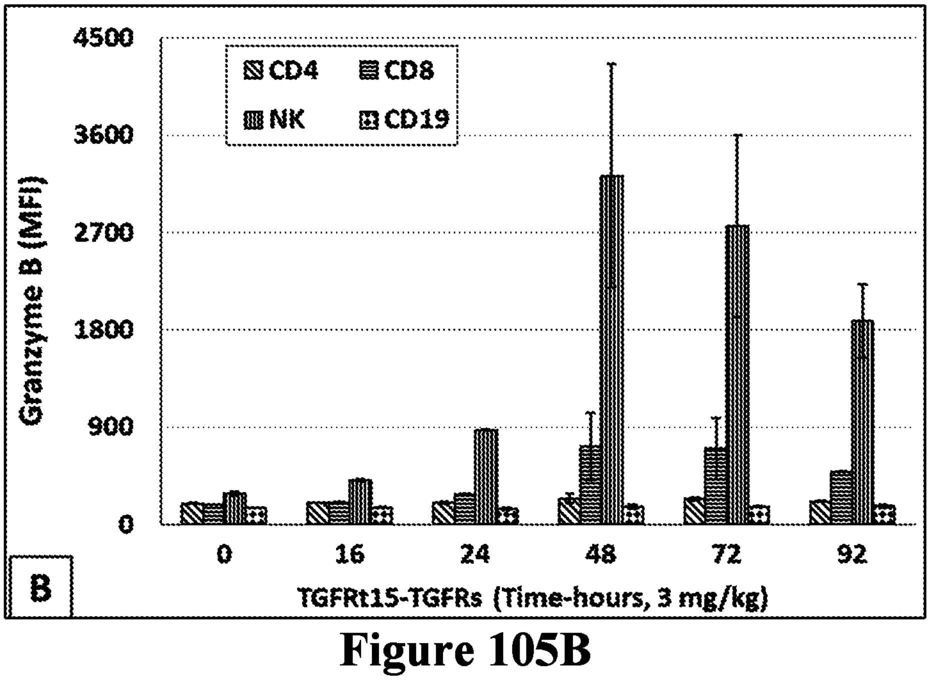

Furthermore, the dynamic proliferation of immune cells based on Ki67 expression of splenocytes and cytotoxicity potential based on granzyme B expression were evaluated in splenocytes isolated from mice following a single dose (3 mg/kg) of TGFRt15-TGFRs. As shown in FIGS. 105A and 105B, in the spleens of mice treated with TGFRt15-TGFRs, the expression of Ki67 and granzyme B by NK cells increased at 24 hours after treatment and its expression of $CD8^+$ T cells and NK cells both increased at 48 hours and later time points after the single dose treatment. These results demonstrate that TGFRt15-TGFRs not only increases the numbers of $CD8^+$ T cells and NK cells but also enhance the cytotoxicity of these cells. The single dose treatment of TGFRt15-TGFRs led $CD8^+$ T cells and NK cells to proliferate for at least 4 days.

Figure 106:
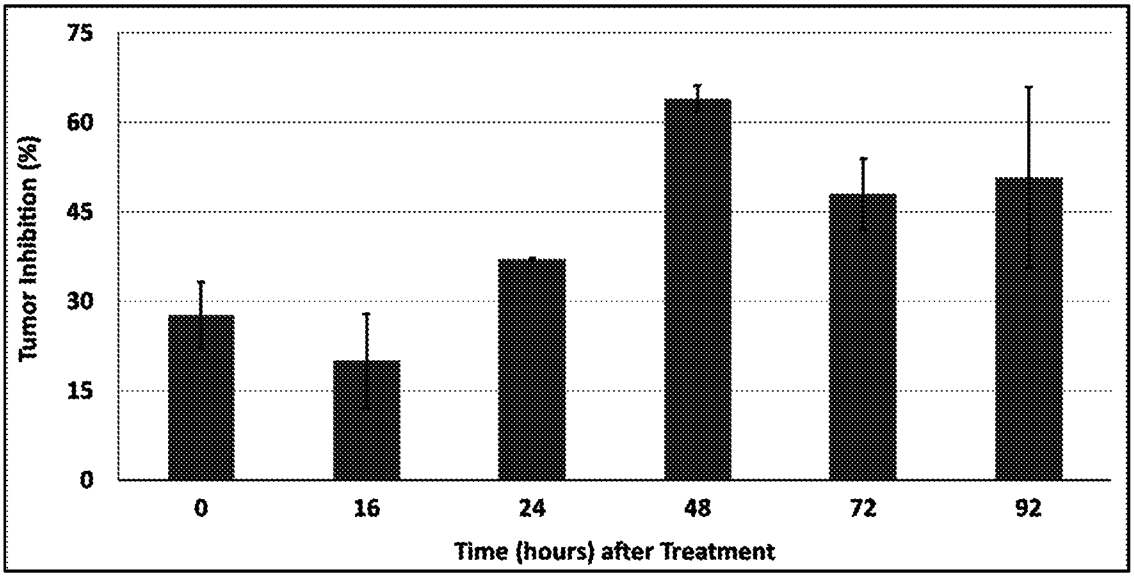
FIG. 106 shows enhancement of cytotoxicity of splenocytes by TGFRt15-TGFRs in C57BL/6 Mice.

The cytotoxicity of the splenocytes from TGFRt15-TGFRs-treated mice against tumor cells was also evaluated. Mouse Moloney leukemia cells (Yac-1) were labeled with CellTrace Violet and were used as tumor target cells. Splenocytes were prepared from TGFRt15-TGFRs (3 mg/kg)-treated mouse spleens at various time points post treatment and were used as effector cells. The target cells were mixed with effector cells at an E:T ratio=10:1 and incubated at 37 °C for 20 hours. Target cell viability was assessed by analysis of propidium iodide positive, violet-labeled Yac-1 cells using flow cytometry. Percentage of Yac-1 tumor inhibition was calculated using the formula, (1-[viable Yac-1 cell number in experimental sample]/[viable Yac-1 cell number in the sample without splenocytes])×100. As shown in FIG. 106, splenocytes from TGFRt15-TGFRs-treated mice had stronger cytotoxicity against Yac-1 cells than the control mouse splenocytes.

Tumor Size Analysis in Response to Chemotherapy and/or TGFRt15-TGFRs

Figure 107:
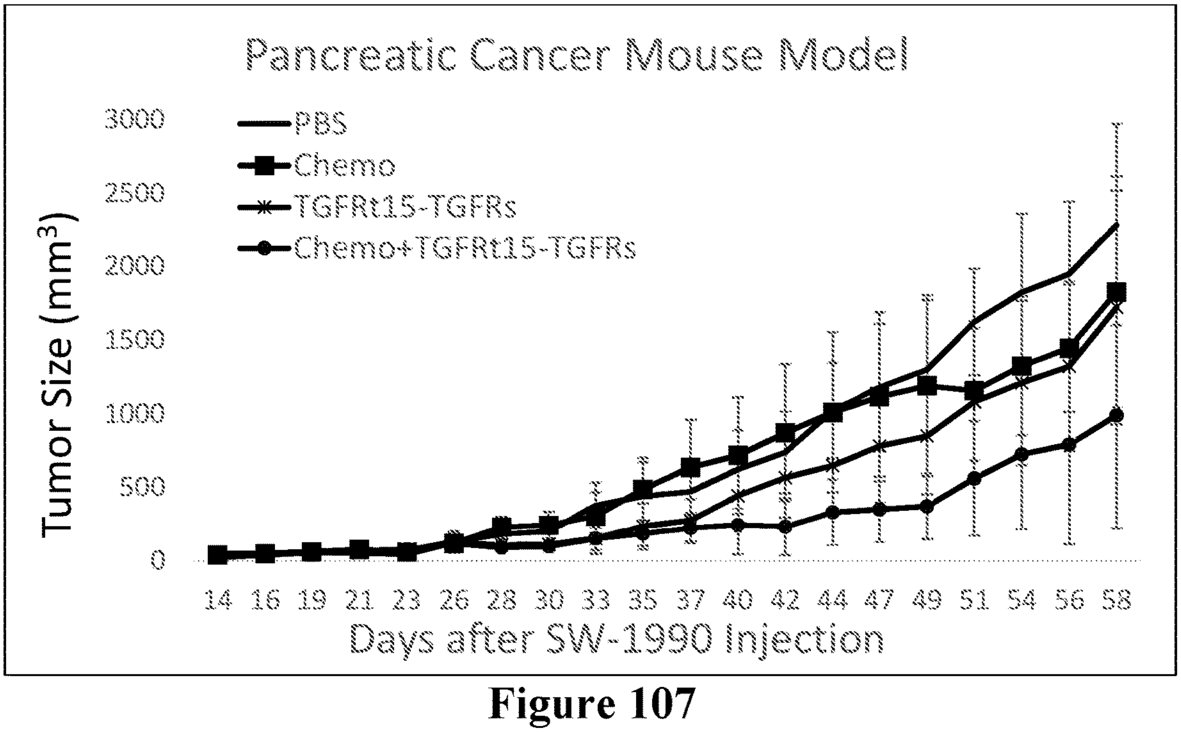
FIG. 107 shows changes in tumor size in response to PBS treatment, chemotherapy alone, TGFRt15-TGFRs alone, or chemotherapy and TGFRt15-TGFRs combination, in a pancreatic cancer mouse model.

Pancreatic cancer cells (SW1990, ATCC® CRL-2172) were subcutaneously (s.c.) injected into C57BL/6 scid mice (The Jackson Laboratory, 001913, $2\times10^6$ cells/mouse, in 100 μL HBSS) to establish the pancreatic cancer mouse model. Two weeks after tumor cell injection, chemotherapy was initiated in these mice intraperitoneally with a combination of Abraxane (Celgene, 68817-134, 5 mg/kg, i.p.) and Gemcitabine (Sigma Aldrich, G6423, 40 mg/kg, i.p.), followed by immunotherapy with TGFRt15-TGFRs (3 mg/kg, s.c.) in 2 days. The procedure above was considered one treatment cycle and was repeated for another 3 cycles (1 cycle/week). Control groups were set up as the SW1990-injected mice that received PBS, chemotherapy (Gemcitabine and Abraxane), or TGFRt15-TGFRs alone. Along with the treatment cycles, tumor size of each animal was measured and recorded every other day, until the termination of the experiment 2 months after the SW1990 cells were injected. Measurement of the tumor volumes were analyzed by group and the results indicated that the animals receiving a combination of chemotherapy and TGFRt15-TGFRs had significantly smaller tumors comparing to the PBS group, whereas neither chemotherapy nor TGFRt15-TGFRs therapy alone work as sufficiently as the combination (FIG. 107).

In Vitro Senescent B16F10 Melanoma Model

Figure 108:
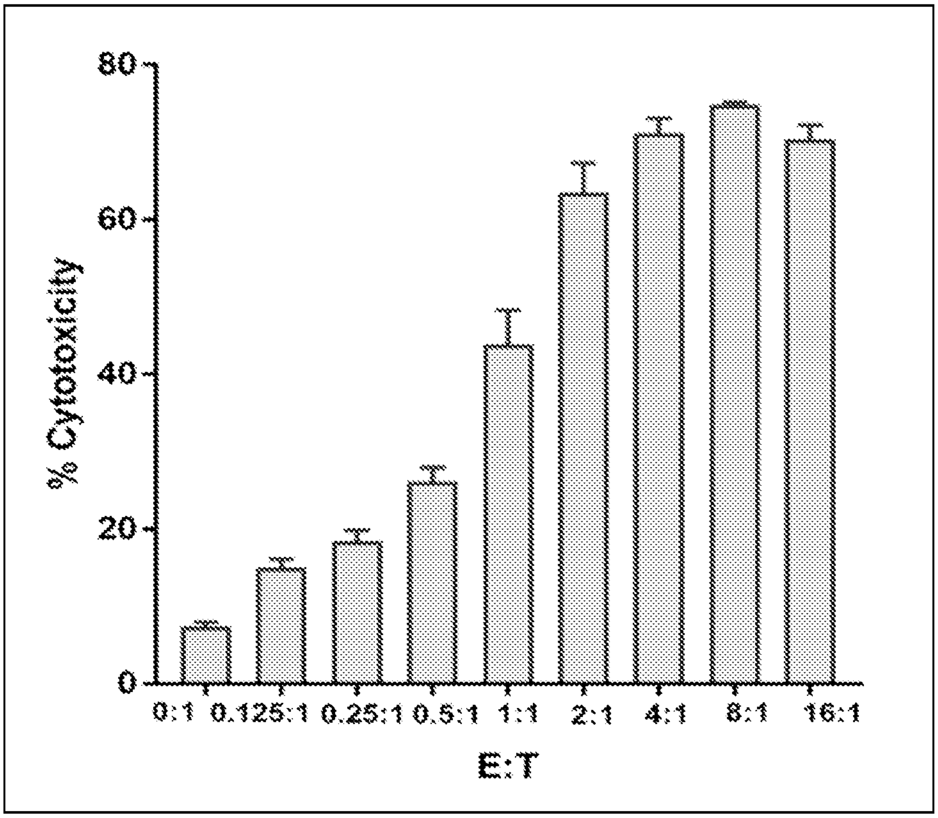
FIG. 108 shows the cytotoxicity of NK cells isolated from mice treated with TGFRt15-TGFRs.

Next, in vitro killing of senescent B16F10 melanoma cells by activated mouse NK cells was evaluated. B16F10 senescence cells (B16F10-SNC) cells were labelled with CellTrace violet and incubated for 16 hrs with different E:T ratio of in vitro 2t2-activated mouse NK cells (isolated from spleen of C57BL/6 mice injected with TGFRt15-TGFRs10 mg/kg for 4 days). The cells were trypsinized, washed and resuspended in complete media containing propidium iodide (PI) solution. The cytotoxicity was assessed by flow cytometry (FIG. 108).

Figure 109:
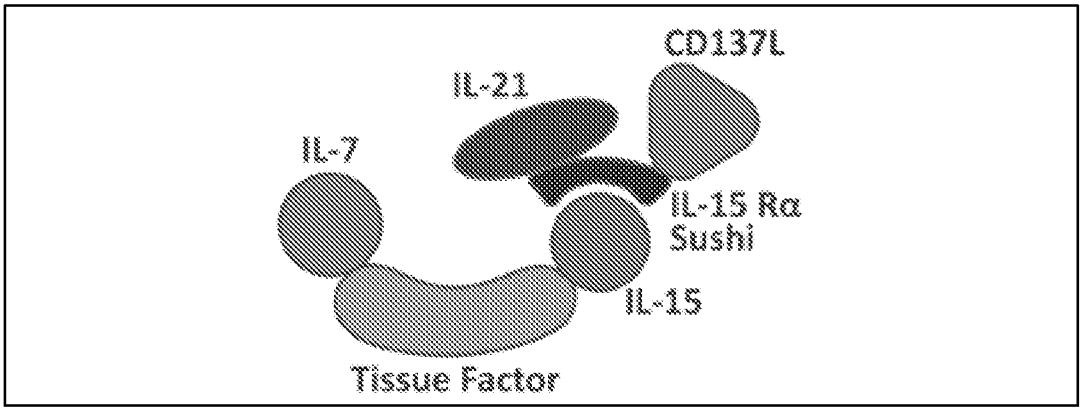
FIG. 109 shows a schematic of the 7t15-21s137L (long version) construct.
Figure 110:
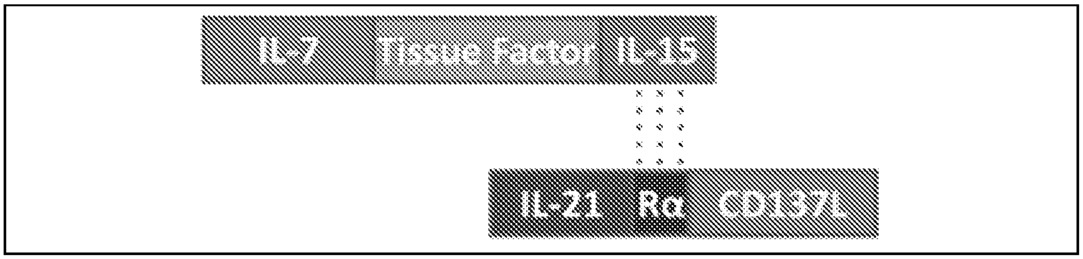
FIG. 110 shows an additional schematic of the 7t15-21s137L (long version) construct.

Example 54: 7t15-21s137L (Long Version) Fusion Protein Creation and Characterization A fusion protein complex was generated comprising of IL-21/IL-15RαSu/CD137L and IL-7/TF/IL-15 fusion proteins (FIG. 109 and FIG. 110). Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of the 7t15 construct (including signal peptide sequence) is as follows:

```
(Signal peptide)
ATGAAGTGGGTGACCTTCATCAGCCTGCTGTTCCTGTTCTCCAGCGCCTAC

TCC

(Human IL7)
GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG

GAGGGCATGTTCCTGTTCAGGGCCGCCAGGAAACTGCGGCAGTTCCTGAAG

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCAT

(Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG
```

-continued (Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC

The amino acid sequence of 7t15 fusion protein (including the leader sequence) is as follows:

(Signal peptide)
MKWVTFISLLFLFSSAYS (Human IL7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH (Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

The nucleic acid and protein sequences of the 21s137L are shown below. The nucleic acid sequence of the 21s137L construct (including signal peptide sequence) is as follows:

(Signal peptide)
ATGAAGTGGGTGACCTTCATCAGCCTGCTGTTCCTGTTCTCCAGCGCCTAC

TCC (Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC (Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

-continued

AGGAAGGCCGGCACCAGCAGCCTCACCGAGTGCGTGCTGAATAAGGCTACC

AACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGACCTG

CGGCAGGGCATGTTTGCGCAGCTGGTGGCCCAAAATGTTCTGCTGATCGAT

GGGCCCCTGAGCTGGTACAGTGACCCAGGCCTGGCAGGCGTGTCCCTGACG

GGGGGCCTGAGCTACAAAGAGGACACGAAGGAGCTGGTGGTGGCCAAGGCT

GGAGTCTACTATGTCTTCTTTCAACTAGAGCTGCGGCGCGTGGTGGCCGGC

GAGGGCTCAGGCTCCGTTTCACTTGCGCTGCACCTGCAGCCACTGCGCTCT

GCTGCTGGGGCCGCCGCCCTGGCTTTGACCGTGGACCTGCCACCCGCCTCC

TCCGAGGCTCGGAACTCGGCCTTCGGTTTCCAGGGCCGCTTGCTGCACCTG

AGTGCCGGCCAGCGCCTGGGCGTCCATCTTCACACTGAGGCCAGGGCACGC

CATGCCTGGCAGCTTACCCAGGGCGCCACAGTCTTGGGACTCTTCCGGGTG

ACCCCCGAAATCCCAGCCGGACTCCCTTCACCGAGGTCGGAA

The amino acid sequence of 21s137L fusion protein (including the leader sequence) is as follows:

(Signal peptide)
MKWVTFISLLFLFSSAYS (Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS (Human IL-15R α sushi domain)
ITCPPPMSVEHADIWVKSYSLYSRERYICNSGFKRKAGTSSLTECVLNKAT

NVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGVSLT

GGLSYKEDTKELVVAKAGVYYVFFQLELRRVVAGEGSGSVSLALHLQPLRS

AAGAAALALTVDLPPASSEARNSAFGFQGRLLHLSAGQRLGVHLHTEARAR

HAWQLTQGATVLGLFRVTPEIPAGLPSPRSE

In some cases, the leader peptide is cleaved from the intact polypeptide to generate the mature form that may be soluble or secreted.

The IL-21/IL-15RαSu/CD137L and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15: IL-21/IL-15RαSu/CD137L protein complex (referred to as 7t15-21s137L), which can be purified by anti-TF antibody IgG1 affinity and other chromatography methods.

Figure 111:
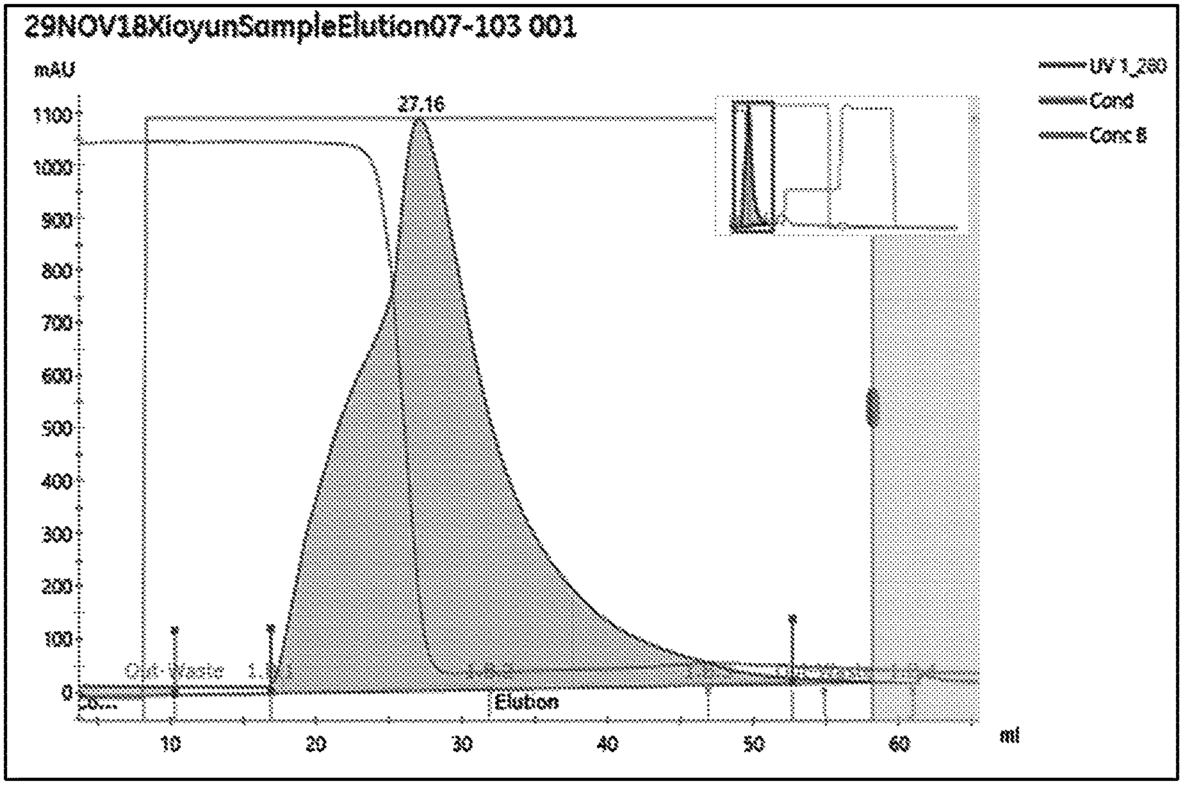
FIG. 111 is a line graph showing the chromatographic profile of 7t15-21s137L (long version) protein containing cell culture supernatant following binding and elution on anti-TF antibody resin.
Figure 112:
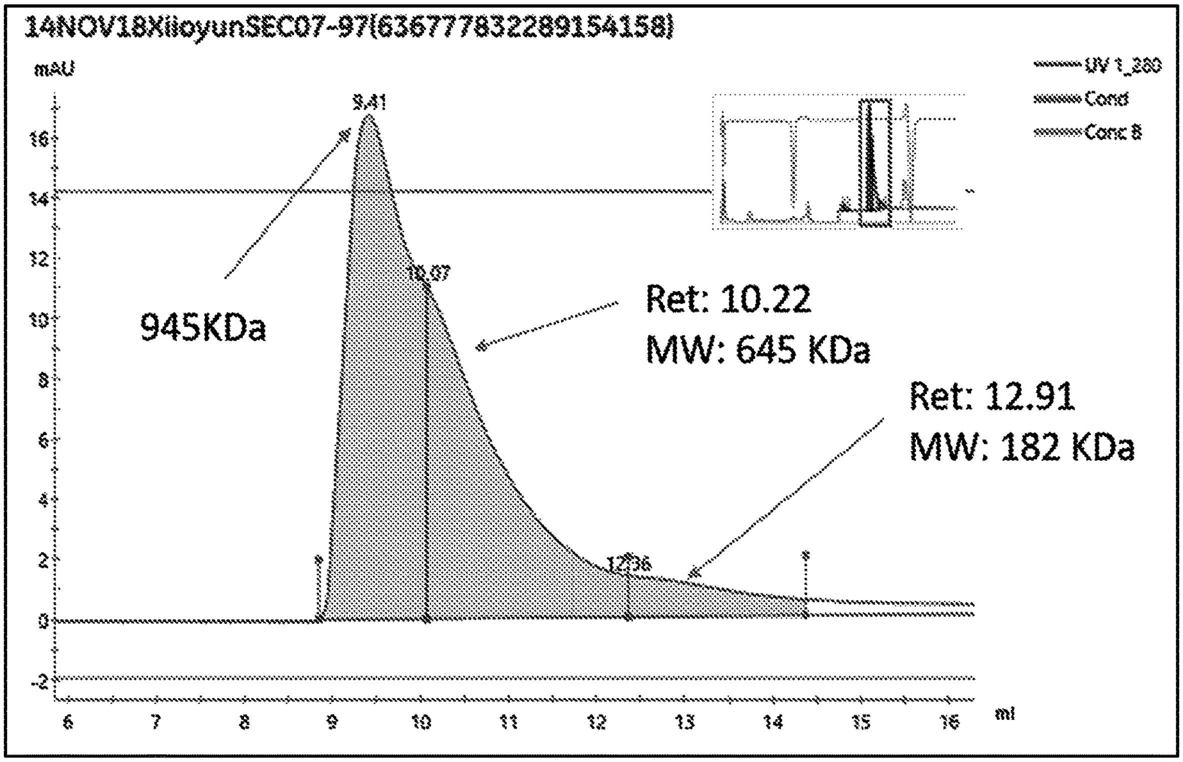
FIG. 112 shows the analytical SEC profile of 7t15-21s137L (long version).
Figure 113:
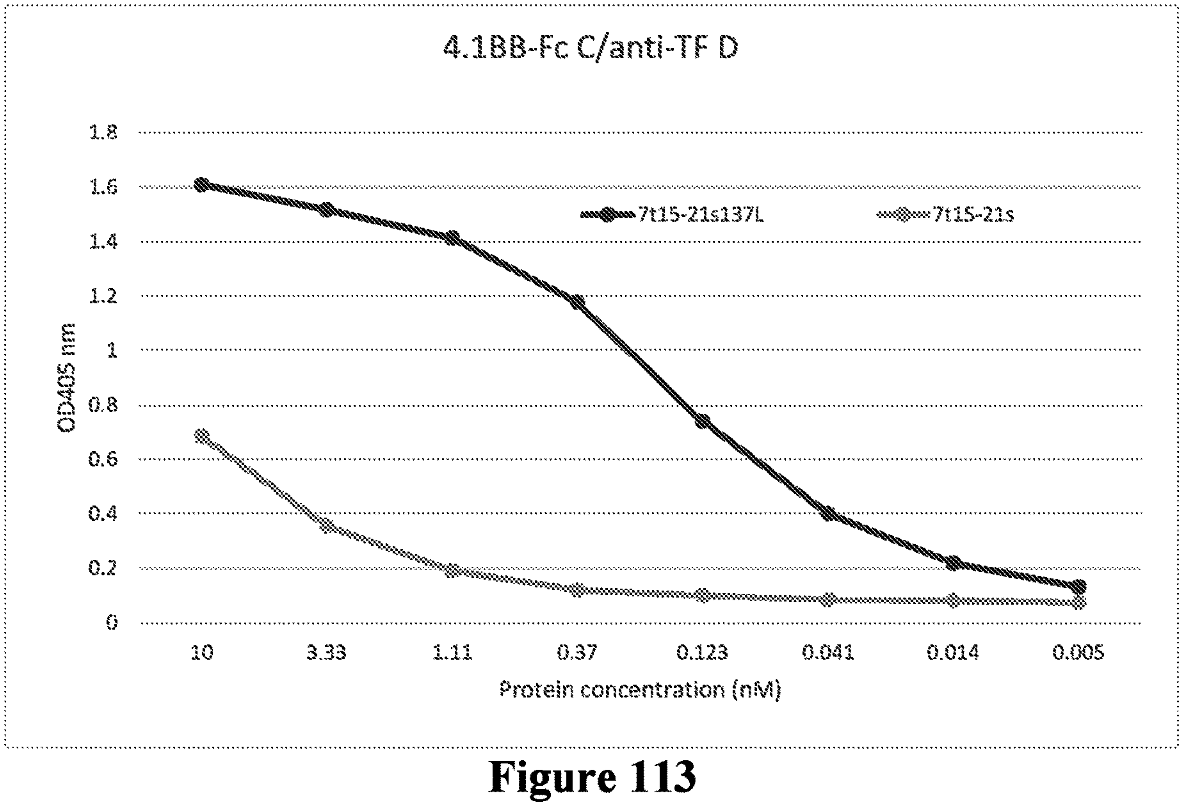
FIG. 113 shows binding of 7t15-21s137L (short version) to CD137L (4.1BBL)

Purification Elution Chromatograph of 7t15-21s137L Using Anti-TF Antibody Affinity Column 7t15-21s137L harvested from cell culture was loaded onto the anti-TF antibody affinity column equilibrated with 5 column volumes of PBS. After sample loading, the column was washed with 5 column volumes of PBS, followed by elution with 6 column volumes of 0.1 M acetic acid (pH 2.9). A280 elution peak was collected and then neutralized to pH 7.5-8.0 with 1 M Tris base. The neutralized sample was then buffer exchanged into PBS using Amicon centrifugal filters with a 30 KDa molecular weight cutoff. As shown in FIG. 111, the anti-TF antibody affinity column bound to 7t15-21s137L which contains TF as a fusion partner. The buffer-exchanged protein sample was stored at 2-8 °C for further biochemical analyses and biological activity tests. After each elution, the anti-TF antibody affinity column was stripped using 6 column volumes of 0.1 M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min. FIG. 112 shows the analytical SEC profile of 7t15-21s137L.

Example 55: 7t15-21s137L (Short Version) Fusion Protein Generation and Characterization A fusion protein complex was generated comprising of IL-21/IL-15RαSu/CD137L and IL-7/TF/IL-15 fusion proteins. Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of 7t15 construct (including signal peptide sequence) is as follows:

```
(Signal peptide)
ATGAAGTGGGTGACCTTCATCAGCCTGCTGTTCCTGTTCTCCAGCGCCTAC

TCC

(Human IL7)
GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG

GAGGGCATGTTCCTGTTCAGGGCCGCCAGGAAACTGCGGCAGTTCCTGAAG

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCAT

(Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA
```

-continued

```
CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG

(Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC
```

The amino acid sequence of 7t15 fusion protein (including the leader sequence) is as follows:

```
(Signal peptide)
MKWVTFISLLFLFSSAYS

(Human IL7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE

(Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS
```

The nucleic acid and protein sequences of the 21s137L (short version) are shown below. The nucleic acid sequence of 21s137L (short version) construct (including signal peptide sequence) is as follows:

```
(Signal peptide)
ATGAAGTGGGTGACCTTCATCAGCCTGCTGTTCCTGTTCTCCAGCGCCTAC

TCC

(Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC

(Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG

((G4S)3 linker)
GGCGGTGGAGGATCCGGAGGAGGTGGCTCCGGCGGCGGAGGATCT

(Human CD137 Ligand short version)
GATCCCGCCGGCCTCTTGGACCTGCGGCAGGGCATGTTTGCGCAGCTGGTG

GCCCAAAATGTTCTGCTGATCGATGGGCCCCTGAGCTGGTACAGTGACCCA

GGCCTGGCAGGCGTGTCCCTGACGGGGGGCCTGAGCTACAAAGAGGACACG

AAGGAGCTGGTGGTGGCCAAGGCTGGAGTCTACTATGTCTTCTTTCAACTA

GAGCTGCGGCGCGTGGTGGCCGGCGAGGGCTCAGGCTCCGTTTCACTTGCG

CTGCACCTGCAGCCACTGCGCTCTGCTGCTGGGGCCGCCGCCCTGGCTTTG

ACCGTGGACCTGCCACCCGCCTCCTCCGAGGCTCGGAACTCGGCCTTCGGT

TTCCAGGGCCGCTTGCTGCACCTGAGTGCCGGCCAGCGCCTGGGCGTCCAT

CTTCACACTGAGGCCAGGGCACGCCATGCCTGGCAGCTTACCCAGGGCGCC

ACAGTCTTGGGACTCTTCCGGGTGACCCCCGAAATC
```

The amino acid sequence of the 21s137L (short version) construct (including signal peptide sequence) is as follows:

```
(Signal peptide)
MKWVTFISLLFLFSSAYS

(Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS
```

-continued

```
(Human IL-15R α sushi domain)
ITCPPPMSVEHADIWVKSYSLYSRERYICNSGFKRKAGTSSLTECVLNKAT

NVAHWTTPSLKCIR

((G4S)3 linker)
GGGGSGGGGSGGGGS

(Human CD137 Ligand short version)
DPAGLLDLRQGMFAQLVAQNVLLIDGPLSWYSDPGLAGVSLTGGLSYKEDT

KELVVAKAGVYYVFFQLELRRVVAGEGSGSVSLALHLQPLRSAAGAAALAL

TVDLPPASSEARNSAFGFQGRLLHLSAGQRLGVHLHTEARARHAWQLTQGA

TVLGLFRVTPEI
```

The IL-21/IL-15RαSu/CD137L (short version) and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15: IL-21/IL-15RαSu/CD137L protein complex (referred to as 7t15-21s137L (short version)), which can be purified by anti-TF antibody IgG1 affinity and other chromatography methods.

Binding of 7t15-21s137L (Short Version) to CD137 (4.1BB)

On day 1, a 96-well plate was coated with 100 μL (2.5 μg/mL) of GAH IgG Fc (G-102-C, R&D Systems) in R5 (coating buffer) or R5 only and incubated at 4 °C, overnight. On day 2, the plates were washed three times and blocked with 300 μL of 1% BSA in PBS at 37 °C for 2 hrs. 10 ng/mL of 4.1BB/Fc (838-4B, R&D Systems) was added at 100 μL/well and incubated for 2 hrs at RT. After three washes, the 7t15-21s137L or 7t15-21s serially diluted at a 1/3 ratio (starting at 10 nM), and incubated at 4 °C overnight. On day 3, following 3 washes, 300 ng/mL of biotinylated-anti-hTF antibody (BAF2339, R&D Systems) was added at 100 μL per well and incubated at RT for 2 hrs. The plate was then washed three times and incubated with 0.25 μg/mL of HRP-SA (Jackson ImmuneResearch) at 100 μL per well for 30 min, followed by 3 washes and incubation with 100 μL of ABTS for 2 mins at RT. Absorbance was read at 405 nm. As shown in FIG. 113, 7t15-21s137L (short version) showed significant interaction with 4.1BB/Fc (blue line) as compared to 7t15-21s.

Detection of IL-15, IL-21, and IL-7 in 7t15-21s137L (Short Version) with ELISA

Figure 114A:
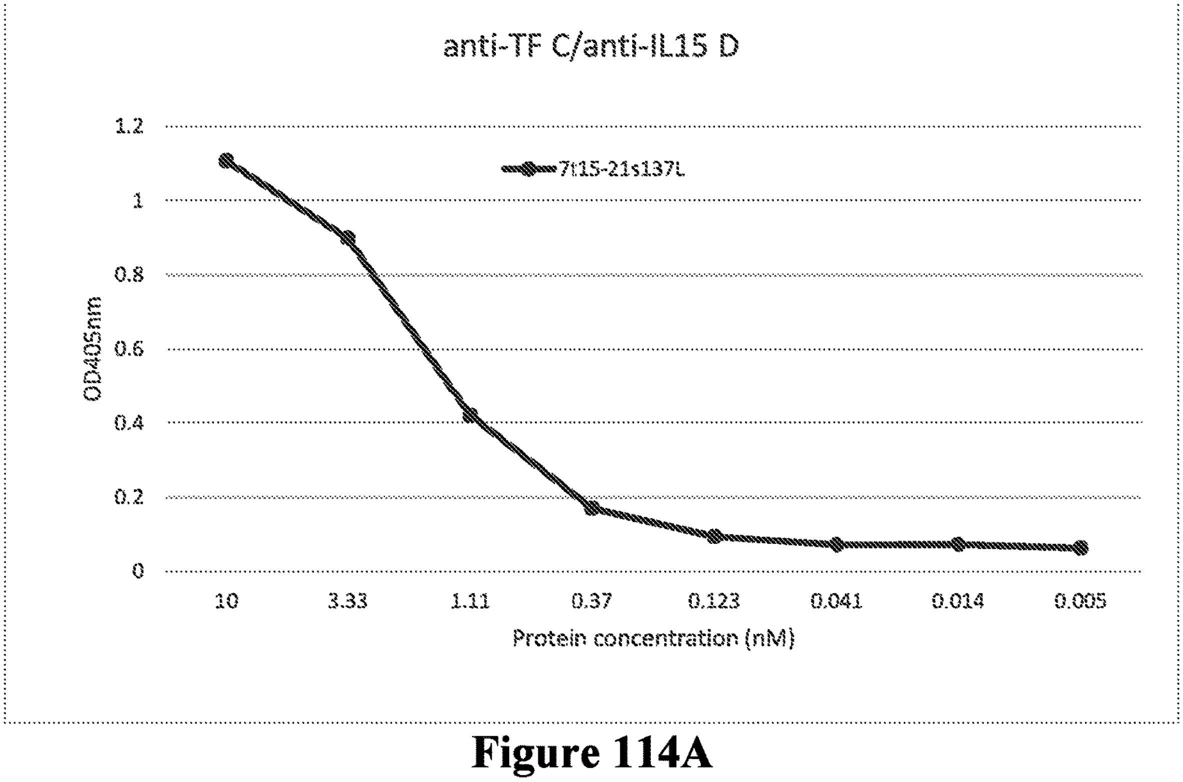
FIGS. 114A-114C show detection of IL-15, IL21, and IL7 in 7t15-21s137L (short version) with ELISA.
Figure 114B:
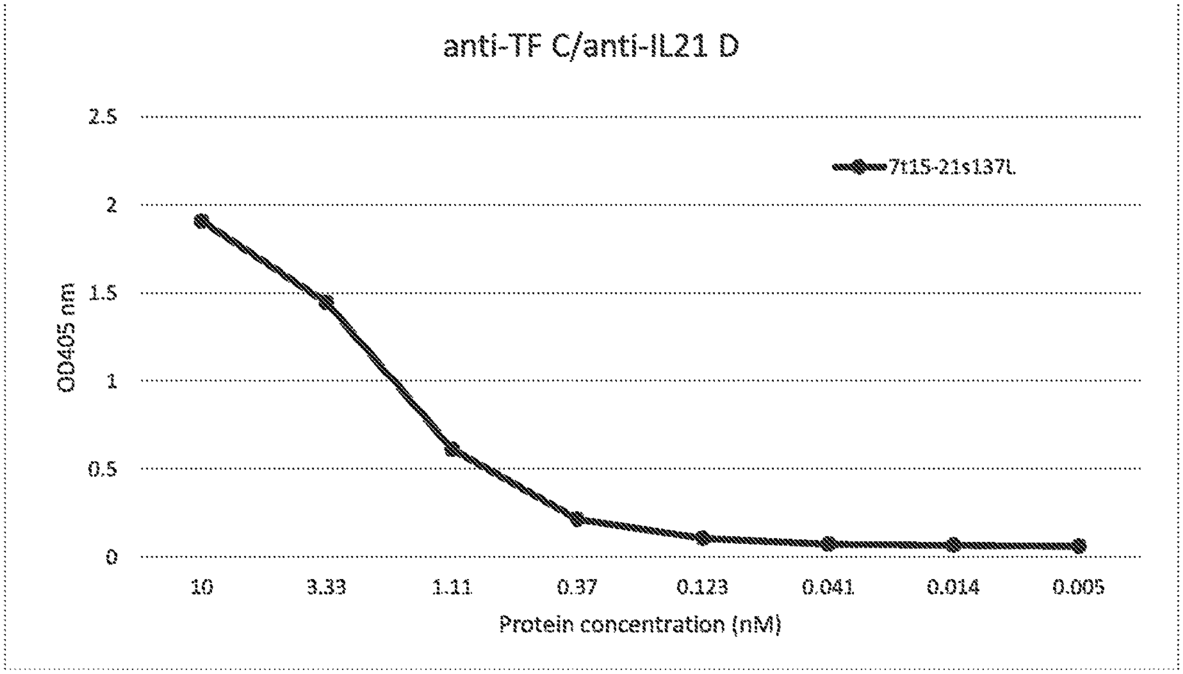
Figure 114C:
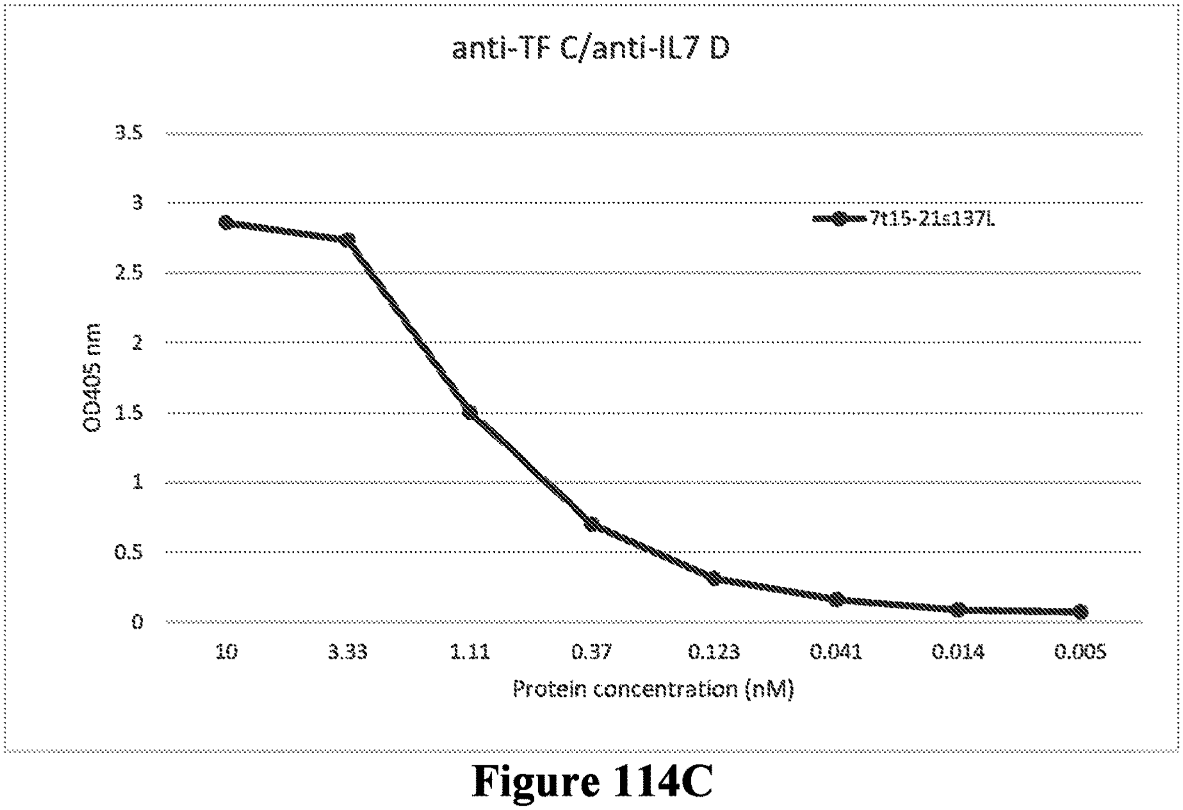

A 96-well plate was coated with 100 μL (8 μg/mL) of anti-TF antibody IgG1 in R5 (coating buffer) and incubated at RT for 2 hrs. The plates were washed 3 times and blocked with 100 μL of 1% BSA in PBS. 7t15-21s137L (short version), serially diluted at a 1:3 ratio was added, and incubated at RT for 60 min. After three washes, 50 ng/mL of biotinylated-anti-IL-15 antibody (BAM247, R&D Systems), 500 ng/mL of biotinylated-anti-IL21 antibody (13-7218-81, R&D Systems), or 500 ng/mL of biotinylated-anti-IL7 antibody (506602, R&D Systems) was added to the wells and incubated at RT for 60 min. After three washes and incubation with 0.25 μg/mL of HRP-SA (Jackson ImmunoResearch) at 100 μL per well was carried out for 30 min at RT, followed by four washes and incubation with 100 μL of ABTS for 2 mins at RT. Absorbance was read at 405 nm. As shown in FIGS. 114A-114C, the IL-15, IL-21, and IL-7 domains in 7t15-21s137L (short version) were detected by the respective antibodies.

Figure 115:
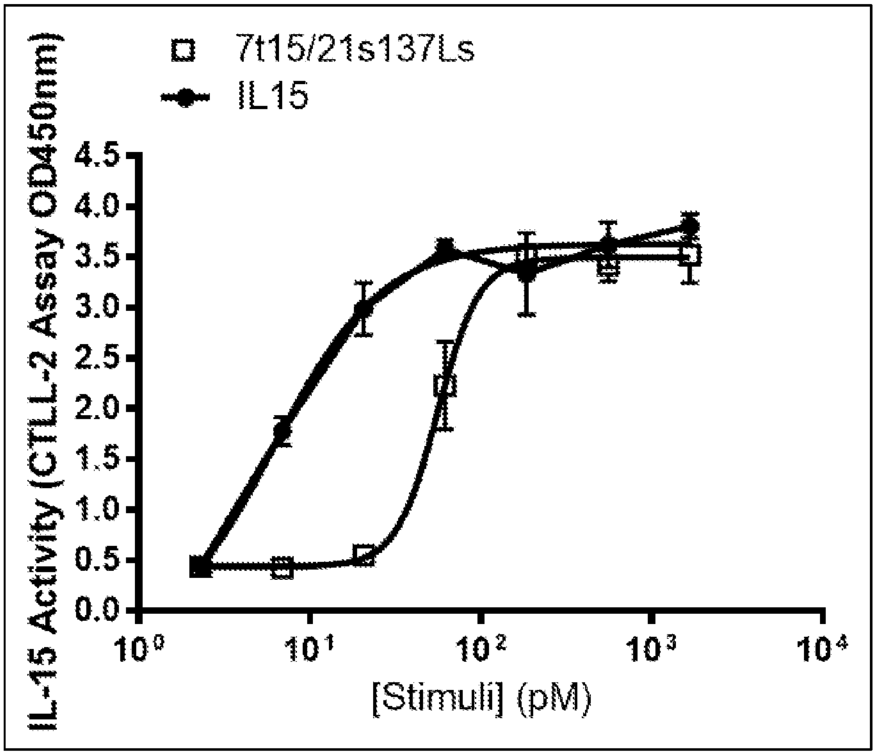
FIG. 115 shows results from a CTLL-2 cell proliferation assay.

The IL-15 in 7t15-1s137L (Short Version) Promotes IL2Raβγ Containing CTLL2 Cell Proliferation To evaluate the IL-15 activity of 7t15-21s137L (short version), 7t15-21s137L (short version) was compared with recombinant IL-15 in promoting proliferation of IL2Raβγ expressing CTLL2 cells. IL-15-dependent CTLL2 cells were washed 5 times with IMDM-10% FBS and seeded to the wells at $2\times10^4$ cells/well. Serially diluted 7t15-21s137L (short version) or IL-15 were added to the cells (FIG. 115). Cells were incubated in a $CO_2$ incubator at 37 °C for 3 days. Cell proliferation was detected by adding 10 μL of WST1 to each well on day 3 and incubated for an additional 3 hours in a $CO_2$ incubator at 37 °C. The amount of formazan dye produced was analyzed by measuring the absorbance at 450 nm. As shown in FIG. 115, 7t15-21s137L (short version) and IL-15 promoted CTLL2 cell proliferation. The $EC_{50}$ of 7t15-21s137L (short version) and IL-15 was 55.91 pM and 6.22 pM. respectively.

Figure 116:
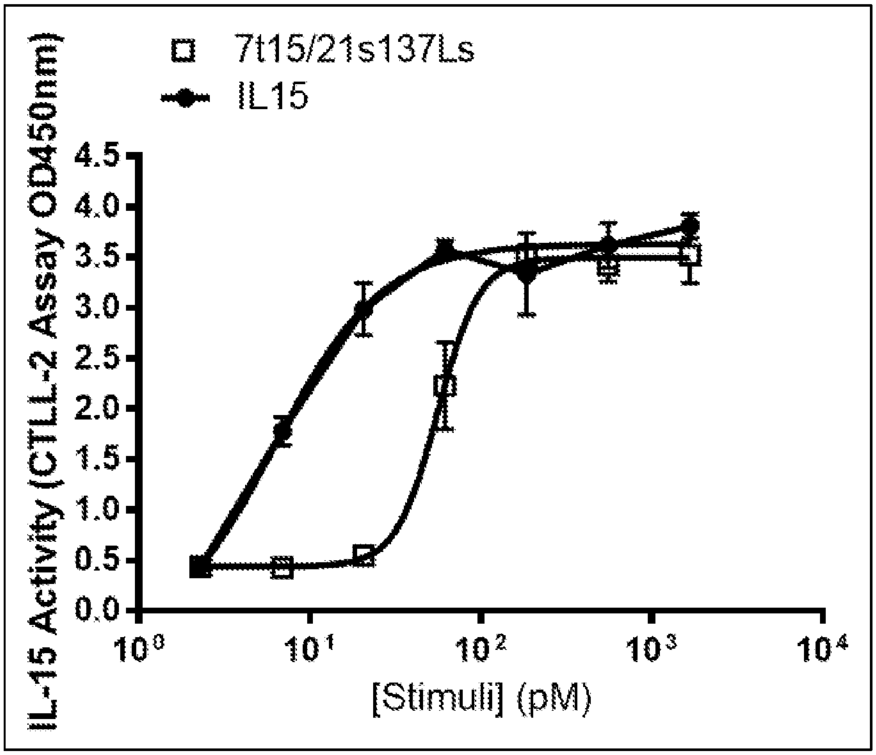
FIG. 116 shows the activity of 7t15-1s137L (short version) in promoting IL21R containing B9 cell proliferation.

The IL-21 in 7t15-1s137L (Short Version) Promotes IL21R Containing B9 Cell Proliferation To evaluate the IL-21 activity of 7t15-21s137L (short version), 7t15-21s137L (short version) was compared with recombinant IL-21 in promoting proliferation of IL-21R expressing B9 cells. IL-21R containing B9 cells were washed 5 times with RPMI-10% FBS and seeded to the wells at $1\times10^4$ cells/well. Serially diluted 7t15-21s137L (short version) or IL-21 were added to the cells (FIG. 116). Cells were incubated in a $CO_2$ incubator at 37 °C for 5 days. Cell proliferation was detected by adding 10 μL of WST1 to each well on day 5 and incubated for an additional 4 hours in a $CO_2$ incubator at 37 °C. The amount of formazan dye produced was analyzed by measuring the absorbance at 450 nm. As shown in FIG. 116, 7t15-21s137L (short version) and IL-21 promoted B9 cell proliferation, The $EC_{50}$ of 7t15-21s137L (short version) and IL-21 was 104.1 nM and 72.55 nM. respectively.

Example 56: 7t15-TGFRs Fusion Protein Generation and Characterization

Figure 117:
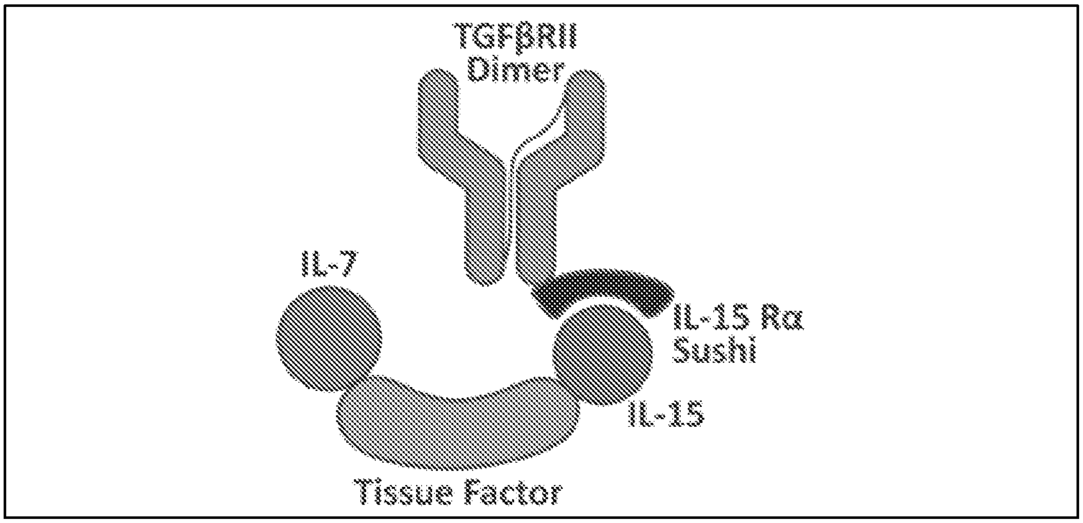
FIG. 117 shows a schematic of the 7t15-TGFRs construct.
Figure 118:
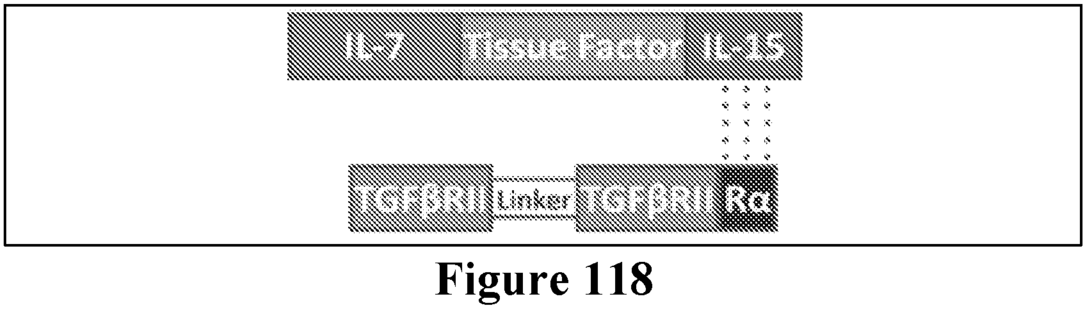
FIG. 118 shows an additional schematic of the 7t15-TGFRs construct.

A fusion protein complex was generated comprising of TGFβ Receptor II/IL-15RαSu and IL-7/TF/IL-15 fusion proteins (FIG. 117 and FIG. 118). The human TGFβ Receptor II (Ile24-Asp159), tissue factor 219, IL-15, and IL-7 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of the 7t15 construct (including signal peptide sequence) is as follows:

```
(Signal peptide)
ATGAAGTGGGTGACCTTCATCAGCCTGCTGTTCCTGTTCTCCAGCGCCTAC

TCC

(Human IL7)
GATTGCGACATCGAGGGCAAGGACGGCAAGCAGTACGAGAGCGTGCTGATG

GTGTCCATCGACCAGCTGCTGGACAGCATGAAGGAGATCGGCTCCAACTGC

CTCAACAACGAGTTCAACTTCTTCAAGCGGCACATCTGCGACGCCAACAAG

GAGGGCATGTTCCTGTTCAGGGCCGCCAGGAAACTGCGGCAGTTCCTGAAG

ATGAACTCCACCGGCGACTTCGACCTGCACCTGCTGAAGGTGTCCGAGGGC

ACCACCATCCTGCTGAACTGCACCGGACAGGTGAAGGGCCGGAAACCTGCT

GCTCTGGGAGAGGCCCAACCCACCAAGAGCCTGGAGGAGAACAAGTCCCTG

AAGGAGCAGAAGAAGCTGAACGACCTGTGCTTCCTGAAGAGGCTGCTGCAG

GAGATCAAGACCTGCTGGAACAAGATCCTGATGGGCACCAAGGAGCAT

(Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG

(Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC
```

The amino acid sequence of 7t15 fusion protein (including the leader sequence) is as follows:

```
(Signal peptide)
MKWVTFISLLFLFSSAYS

(Human IL7)
DCDIEGKDGKQYESVLMVSIDQLLDSMKEIGSNCLNNEFNFFKRHICDANK

EGMFLFRAARKLRQFLKMNSTGDFDLHLLKVSEGTTILLNCTGQVKGRKPA

ALGEAQPTKSLEENKSLKEQKKLNDLCFLKRLLQEIKTCWNKILMGTKEH

(Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE

(Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS
```

Constructs were also made by attaching two TGFβ Receptor II directly to the IL-15RαSu chain which was synthesized by Genewiz. The nucleic acid and protein sequences of a construct comprising the TGFβ Receptor II linked to the N-terminus of IL-15RαSu are shown below.

The nucleic acid sequence of the TGFRs construct (including signal peptide sequence) is as follows:

```
(Signal peptide)
ATGAAGTGGGTGACCTTCATCAGCCTGCTGTTCCTGTTCTCCAGCGCCT

ACTCC

(Human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGATGT

CAGGTTCAGCACCTGCGATAATCAGAAGTCCTGCATGTCCAACTGCAGCA

TCACCTCCATCTGCGAGAAGCCCCAAGAAGTGTGCGTGGCCGTGTGGCGG

AAAAATGACGAGAACATCACCCTGGAGACCGTGTGTCACGACCCCAAGCT

CCCTTATCACGACTTCATTCTGGAGGACGCTGCCTCCCCCAAATGCATCA

TGAAGGAGAAGAAGAAGCCCGGAGAGACCTTCTTTATGTGTTCCTGTAGC

AGCGACGAGTGTAACGACAACATCATCTTCAGCGAAGAGTACAACACCAG

CAACCCTGATGGAGGTGGCGGATCCGGAGGTGGAGGTTCTGGTGGAGGTG

GGAGTATTCCTCCCCACGTGCAGAAGAGCGTGAATAATGACATGATCGTG

ACCGATAACAATGGCGCCGTGAAATTTCCCCAGCTGTGCAAATTCTGCGA

TGTGAGGTTTTCCACCTGCGACAACCAGAAGTCCTGTATGAGCAACTGCT

CCATCACCTCCATCTGTGAGAAGCCTCAGGAGGTGTGCGTGGCTGTCTGG

CGGAAGAATGACGAGAATATCACCCTGGAAACCGTCTGCCACGATCCCAA

GCTGCCCTACCACGATTTCATCCTGGAAGACGCCGCCAGCCCTAAGTGCA

TCATGAAAGAGAAAAAGAAGCCTGGCGAGACCTTTTTCATGTGCTCCTGC
```

-continued

```
AGCAGCGACGAATGCAACGACAATATCATCTTTAGCGAGGAATACAATAC

CAGCAACCCCGAC

(Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG
```

The amino acid sequence of TGFRs fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD

(Human IL-15R α sushi domain)
ITCPPPMSVEHADIWVKSYSLYSRERYICNSGFKRKAGTSSLTECVLNKA

TNVAHWTTPSLKCIR
```

Effect of 7t15-TGFRs on TGFβ1 Activity in HEK-Blue TGFβ Cells

Figure 119:
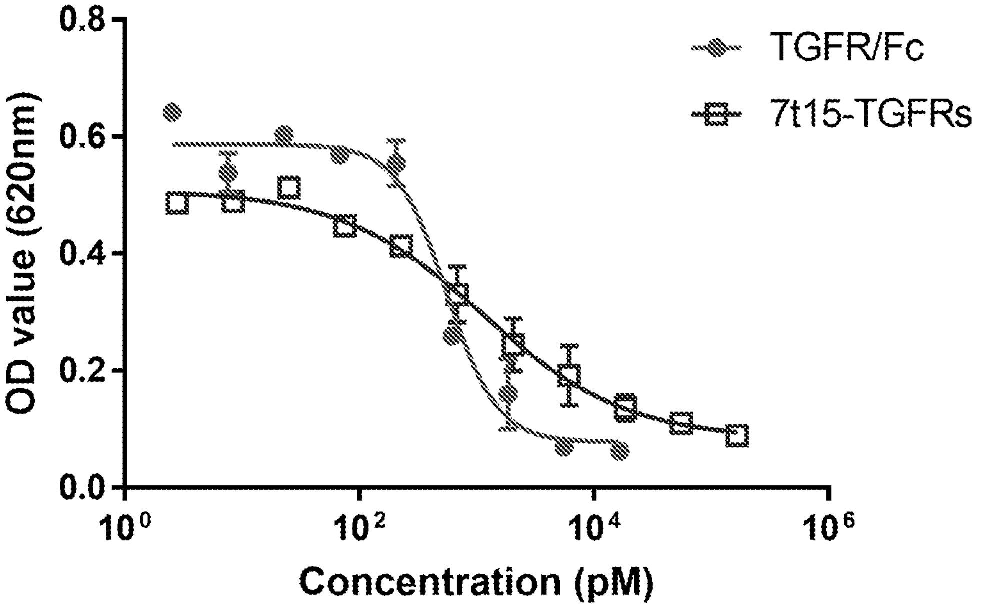
FIG. 119 shows results of TGFβ1 inhibition by 7t15-TGFRs and TGFR-Fc.

To evaluate the activity of TGFβR in 7t15-TGFRs, the effect of 7t15-TGFRs on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, 50 μL cells were added to each well ($2.5\times10^4$ cells/well) and followed with 50 μL 0.1 nM TGFβ1 (R&D systems). 7t15-TGFRs or TGFR-Fc (R&D Systems) prepared at a 1:3 serial dilution was then added to the plate to reach a total volume of 200 μL. After 24 hrs of incubation at 37 °C, 40 μL of induced HEK-Blue TGFβ cell supernatant was added to 160 μL pre-warmed QUANTI-Blue (Invivogen) in a flat-bottom 96-well plate, and incubated at 37 °C for 1-3 hrs. The OD values were then determined using a plate reader (Multiscan Sky) at 620-655 nM. The data are shown in FIG. 119. The $IC_{50}$ of each protein sample was calculated with GraphPad Prism 7.04. The $IC_{50}$ of 7t15-TGFRs and TGFR-Fc were 1142 pM and 558.6 pM respectively. These results showed that the TGFβR in 7t15-TGFRs was able to block the activity of TGFβ1 in HEK-Blue TGFβ cells.

Detection of IL-15, TGFβRII, and IL-7 in 7t15-TGFRs with ELISA

Figure 120A:
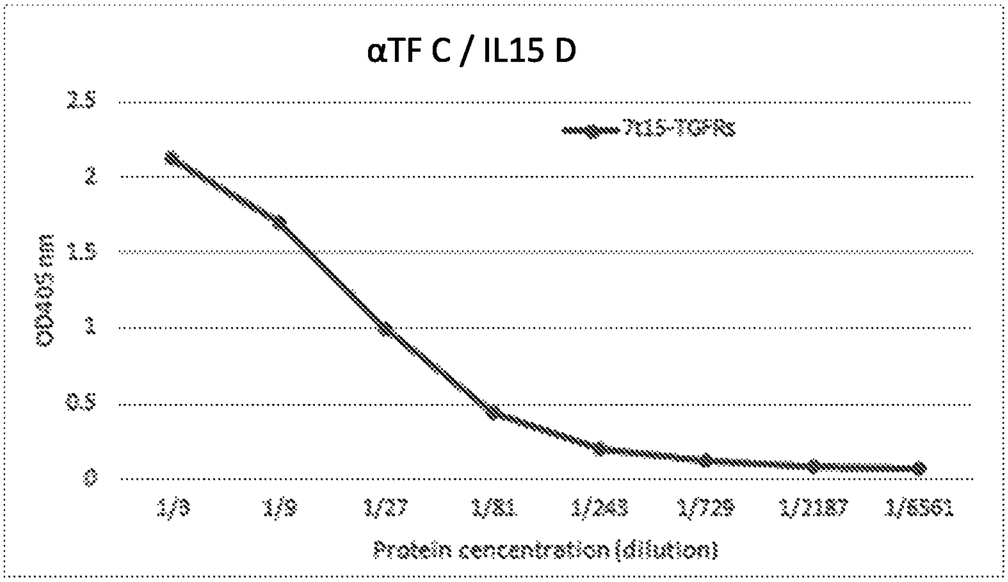
FIGS. 120A-120C show detection of IL-15, TGFβRII, and IL-7 in 7t15-TGFRs with ELISA.
Figure 120B:
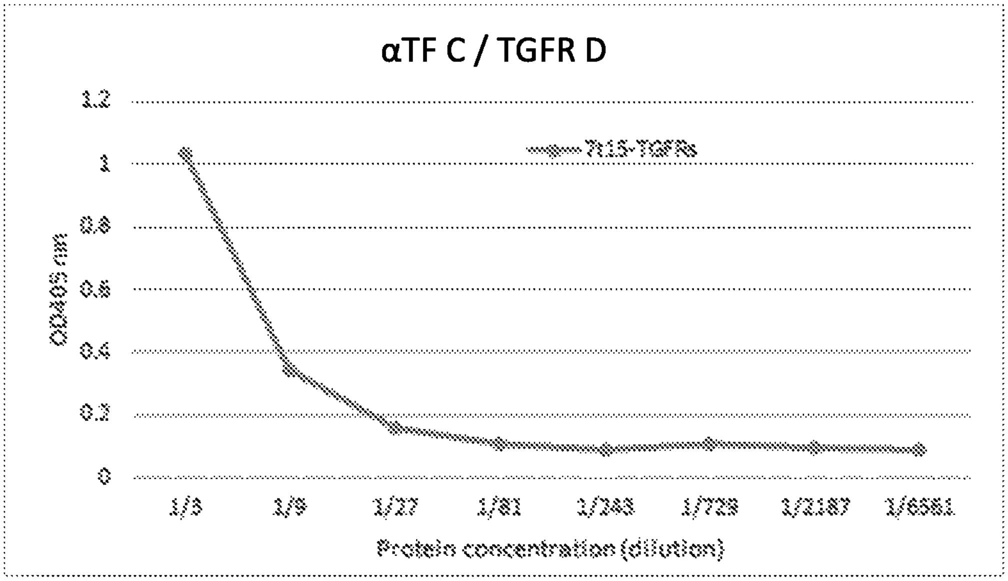
Figure 120C:
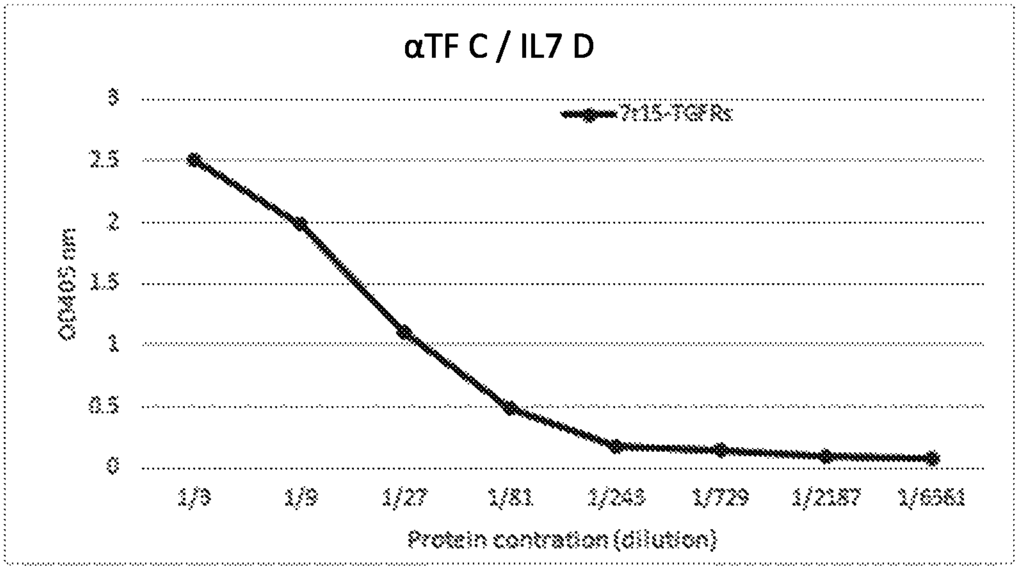

A 96-well plate was coated with 100 μL (8 μg/mL) of anti-TF antibody IgG1 in R5 (coating buffer) and incubated at room temperature (RT) for 2 hrs. The plates were washed three times and blocked with 100 μL of 1% BSA in PBS. Serial dilution of 7t15-TGFRs (1:3 ratio) was added, and incubated at RT for 60 mins. After 3 washes, 50 ng/mL of biotinylated-anti-IL-15 antibody (BAM247, R&D Systems), 200 ng/mL of biotinylated-anti-TGFbRII antibody (BAF241, R&D Systems), or 500 ng/mL of biotinylated-anti-IL-7 antibody (506602, R&D Systems) was added and incubated at RT for 60 min. Following three washes, incubation with 0.25 μg/mL of HRP-SA (Jackson ImmunoResearch) at 100 μL per well was carried out for 30 min at RT, followed by 4 washes and incubation with 100 μL of ABTS for 2 mins at RT. Absorbance was read at 405 nm. As shown in FIGS. 120A-120C, the IL-15, TGFR, and IL-7 in 7t15-TGFRs were detected by the respective antibodies.

Figure 121:
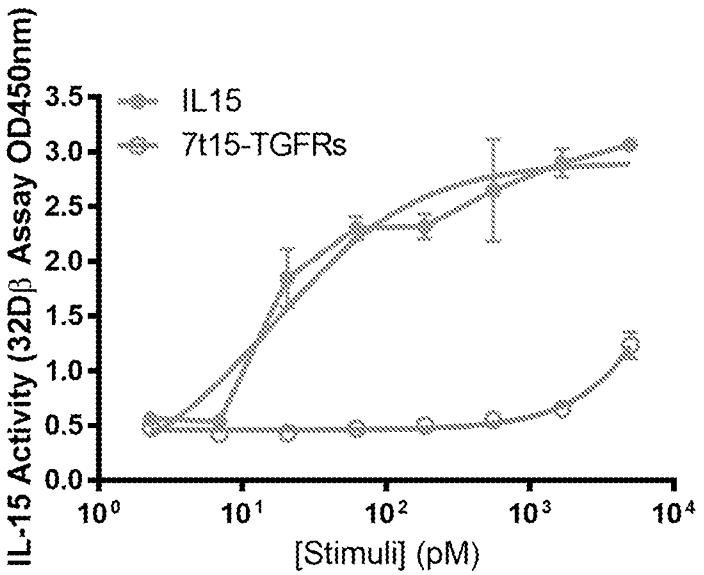

The IL-15 in 7t15-TGFRs Promotes IL-2Rβ and Common γ Chain Containing 32Dβ Cell Proliferation To evaluate the activity of IL-15 in 7t15-TGFRs, 7t15-TGFRs was compared to recombinant IL-15 using 32Dβ cells that express IL2Rβ and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted 7t15-TGFRs or IL-15 were added to the cells (FIG. 121). Cells were incubated in a $CO_2$ incubator at 37 °C for 3 days. Cell proliferation was detected by adding 10 μL of WST1 to each well on day 3 and incubating for an additional 3 hours in a $CO_2$ incubator at 37 °C. The amount of formazan dye produced was analyzed by measuring the absorbance at 450 nm. As shown in FIG. 121, 7t15-TGFRs and IL-15 promoted 32Dβ cell proliferation, with the $EC_{50}$ of 7t15-TGFRs and IL-15 being 126 nM and 16.63 pM, respectively.

Figure 122:
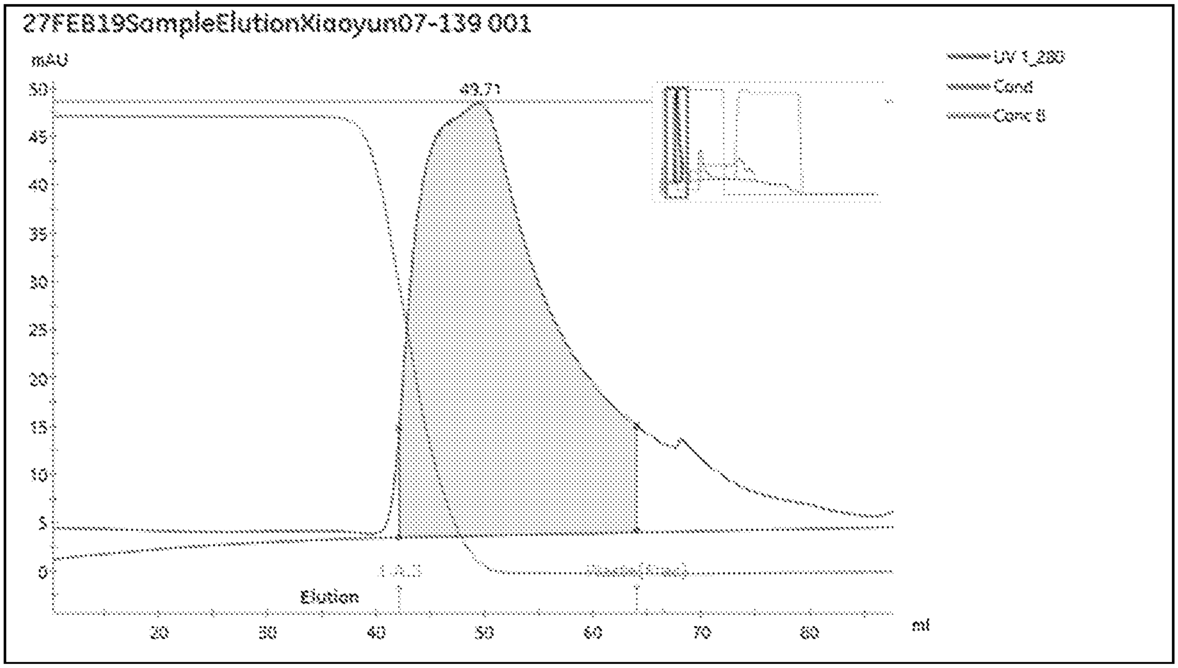

Purification Elution Chromatograph of 7t15-TGFRs Using Anti-TF Antibody Affinity Column 7t15-TGFRs harvested from cell culture was loaded onto the anti-TF antibody affinity column equilibrated with 5 column volumes of PBS. After sample loading, the column was washed with 5 column volumes of PBS, followed by elution with 6 column volumes of 0.1 M acetic acid (pH 2.9). A280 elution peak was collected and then neutralized to pH 7.5-8.0 with 1 M Tris base. The neutralized sample was then buffer exchanged into PBS using Amicon centrifugal filters with a 30 KDa molecular weight cutoff. As shown in FIG. 122, the anti-TF antibody affinity column can bind 7t15-TGFRs which contains TF as a fusion partner of 7t15-TGFRs. The buffer-exchanged protein sample was stored at 2-8 °C for further biochemical analyses and biological activity tests. After each elution, the anti-TF antibody affinity column was stripped using 6 column volumes of 0.1 M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE Analysis of 7t15-TGFRs

To determine the purity and molecular weight of the protein, 7t15-TGFRs protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

Figure 123:
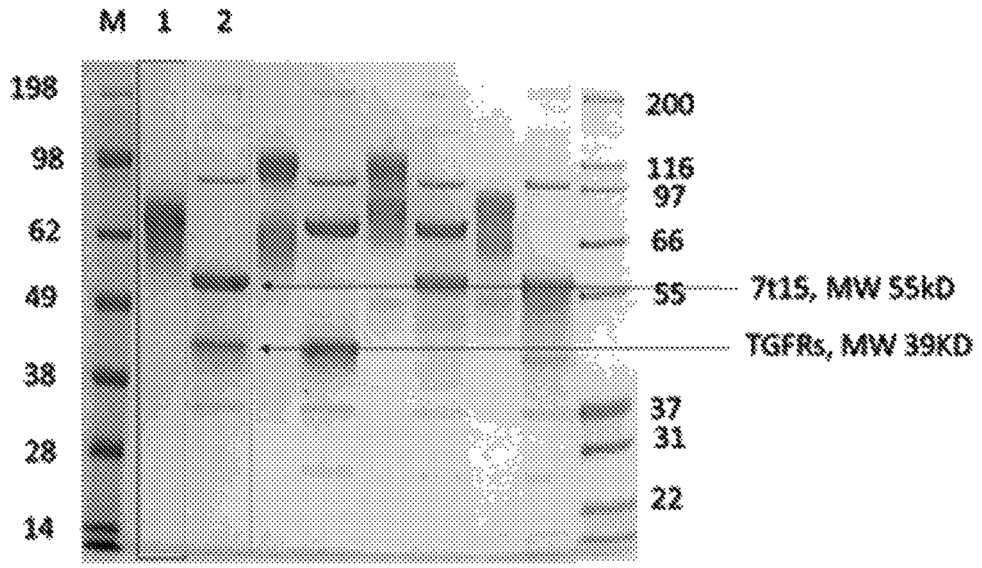

To verify that the 7t15-TGFRs protein undergoes glycosylation after translation in CHO cells, a deglycosylation experiment was conducted using the Protein Deglycosylation Mix II kit from New England Biolabs and the manufacturer's instructions. FIG. 123 shows reduced SDS-PAGE analysis of the sample in non-deglycosylated (lane 1 in red outline) and deglycosylated (lane 2 in yellow outline) state. These results showed that the protein is glycosylated when it is expressed in CHO cells. After deglycosylation, the purified sample showed expected molecular weights (55 kDa and 39 kDa) in reduced SDS gel. Lane M was loaded with 10 ul of SeeBlue Plus2 Prestained Standard.

Characterization of 7t15-TGFRs

7t15-TGFRs is a multi-chain polypeptide (a type A multi-chain polypeptide described herein) that includes the first polypeptide that is a soluble fusion of human IL-7, human tissue factor 219 fragment and human IL-15 (7t15), and the second polypeptide that is a soluble fusion of single chain two TGFβRII domains and sushi domain of human IL-15 receptor alpha chain (TGFRs).

Figure 124:
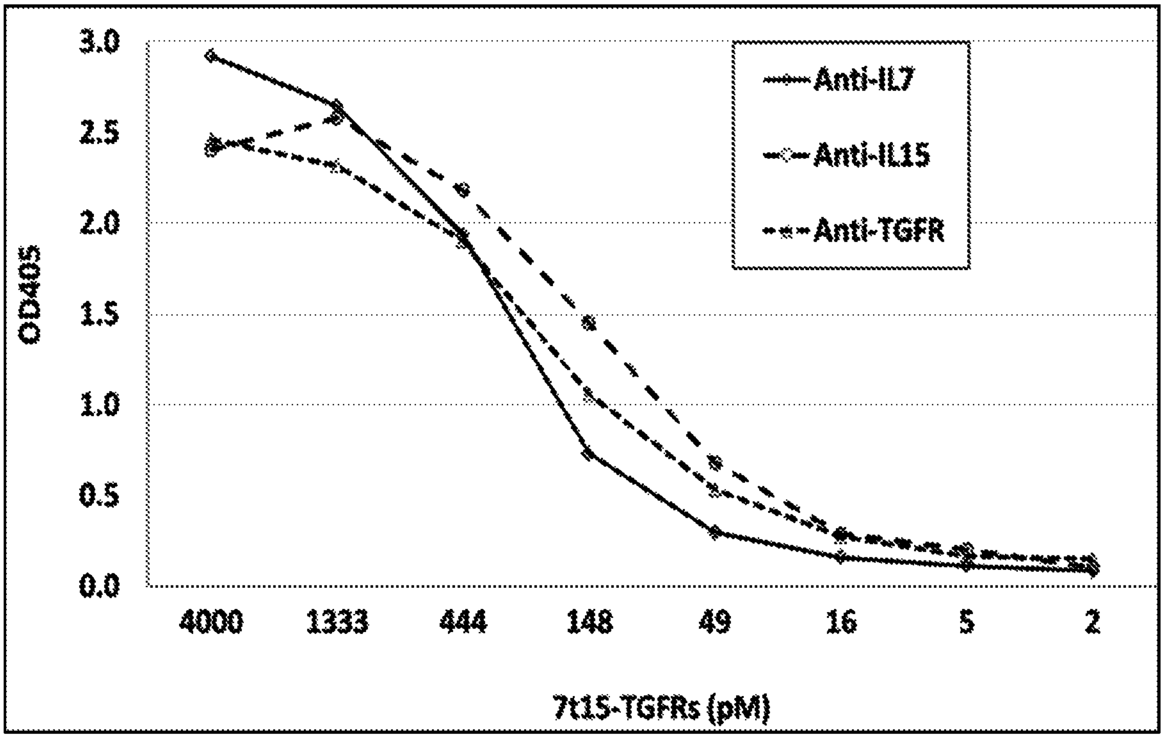

CHO cells were co-transfected with 7t15 and TGFRs vectors. The 7t15-TGFRs complex was purified from the transfected CHO cell culture supernatant. The IL-7, IL-15, TGFβ receptor and tissue factor (TF) components were demonstrated in the complex by ELISA as shown in FIG. 124. A humanized anti-TF antibody monoclonal antibody (anti-TF antibody IgG1) was used as the capture antibody to determine TF in 7t15-TGFRs, and biotinylated antibodies against human IL-15 (R&D systems), human IL-7 (Biolegend), anti-TGFβ receptor (R&D Systems) were used as the detection antibodies to respectively determine IL-7, IL-15 and TGFβ receptor in 7t15-TGFRs. Peroxidase conjugated streptavidin (Jackson ImmunoResearch Lab) and ABTS substrate (Surmodics IVD, Inc.) were then used to detect the bound biotinylated antibodies. The results were analyzed by ELISA (FIG. 124).

In Vivo Characterization of 7t15-TGFRs in C57BL/6 Mice

To determine the immunostimulatory activity of 7t15-TGFRs in vivo, C57BL/6 mice were subcutaneously treated with control solution (PBS) or 7t15-TGFRs at 0.3, 1, 3 and 10 mg/kg. The treated mice were euthanized. The mouse spleens were collected and weighed day 4 post treatment. Single splenocyte suspensions were prepared and stained with fluorochrome-conjugated anti-CD4, anti-CD8, and anti-NK1.1 antibodies and the percentage of $CD4^+$ T cells, $CD8^+$ T cells, and NK cells was analyzed by flow cytometry. The results showed that 7t15-TGFRs was effective at expanding splenocytes based on spleen weight (FIG. 125A), especially at 1-10 mg/kg. The percentages of $CD8^+$ T cells and NK cells were higher compared to control-treated mice (FIG. 125B) at all doses tested.

$CD44$ Expression of $CD4^+$ and $CD8^+$ T Cells

It has been known that IL-15 induces CD44 expression on T cells and development of memory T cells. CD44 expression of $CD4^+$ and $CD8^+$ T cells in the 7t15-TGFRs treated mice were assessed. C57BL/6 mice were subcutaneously treated with 7t15-TGFRs. The splenocytes were stained with fluorochrome-conjugated anti-CD4, anti-CD8 and anti-CD44 monoclonal antibodies for immunocyte subsets. The percentages of $CD4^+CD44^{high}$ T cells of total CD4+ T cells and $CD8^+CD44^{high}$ T cells of total $CD8^+$ T cells were analyzed by flow cytometry. As shown in FIGS. 126A and 126B, 7t15-TGFRs significantly activated $CD4^+$ and $CD8^+$ T cells to differentiate into memory T cells.

Furthermore, the dynamic proliferation of immune cells based on Ki67 expression of splenocytes and cytotoxicity potential based on granzyme B expression of the splenocytes induced by 7t15-TGFRs after the single dose treatment of mouse were also evaluated. C57BL/6 mice were subcutaneously treated with 7t15-TGFRs at 3 mg/kg. The treated mice were euthanized and the splenocytes were prepared. The prepared splenocytes were stained with fluorochrome-conjugated anti-CD4, anti-CD8, and anti-NK1.1 (NK) antibodies for immunocyte subsets and then intracellularly stained with anti-Ki67 antibody for cell proliferation and anti-granzyme B antibody for cytotoxic marker. The mean fluorescent intensity (MFI) of Ki67 and granzyme B of corresponding immunocyte subsets was analyzed by flow cytometry. As shown in FIGS. 127A and 127B, in the spleens of mice treated with 7t15-TGFRs, the expression of Ki67 and granzyme B by $CD8^+$ T cells and NK cells increased compared with PBS control treatment. These results demonstrate that 7t15-TGFRs is not only to increase numbers of $CD8^+$ T cells and NK cells but also enhance potential cytotoxicity of these cells.

Additionally, cytotoxicity of the mouse splenocytes against tumor cells was also evaluated. Mouse Yac-1 cells were labeled with CELLTRACE™ Violet (cell proliferation kit for flow cytometry) and used as tumor target cells. The splenocytes were prepared from 7t15-TGFRs-treated mice and used as effector cells. The target cells were mixed with effector cells at E:T ratio=10:1 in RPMI-10 medium with or without 7t15-TGFRs at 100 nM and incubated at 37 °C for 20 hours. Target Yac-1 cell inhibition was assessed by analysis of viable violet-labeled Yac-1 cells using flow cytometry. Percentage of Yac-1 inhibition was calculated using a formula, (1-viable Yac-1 cell number in experimental sample/viable Yac-1 cell number in the sample without splenocytes)×100. As shown in FIG. 128, 7t15-TGFRs-treated mouse splenocytes had stronger cytotoxicity against Yac-1 cells than the control mouse splenocytes and addition of 7t15-TGFRs during cytotoxic assay further enhanced cytotoxicity of splenocytes against Yac-1 target cells.

Example 57: TGFRt15-21s137L Fusion Protein Generation and Characterization

A fusion protein complex was generated comprising IL-21/IL-15RαSu/CD137L and TGFβ Receptor II/TF/IL-15 fusion proteins (FIG. 129 and FIG. 130). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGCCTAC

TCC

(Human TGFβ Receptor II fragments)
ATCCCCCCCCATGTGCAAAAGAGCGTGAACAACGATATGATCGTGACCGAC

AACAACGGCGCCGTGAAGTTTCCCCAGCTCTGCAAGTTCTGCGATGTCAGG

TTCAGCACCTGCGATAATCAGAAGTCCTGCATGTCCAACTGCAGCATCACC

TCCATCTGCGAGAAGCCCCAAGAAGTGTGCGTGGCCGTGTGGCGGAAAAAT

GACGAGAACATCACCCTGGAGACCGTGTGTCACGACCCCAAGCTCCCTTAT

CACGACTTCATTCTGGAGGACGCTGCCTCCCCCAAATGCATCATGAAGGAG

AAGAAGAAGCCCGGAGAGACCTTCTTTATGTGTTCCTGTAGCAGCGACGAG

TGTAACGACAACATCATCTTCAGCGAAGAGTACAACACCAGCAACCCTGAT

GGAGGTGGCGGATCCGGAGGTGGAGGTTCTGGTGGAGGTGGGAGTATTCCT

CCCCACGTGCAGAAGAGCGTGAATAATGACATGATCGTGACCGATAACAAT

GGCGCCGTGAAATTTCCCCAGCTGTGCAAATTCTGCGATGTGAGGTTTTCC

ACCTGCGACAACCAGAAGTCCTGTATGAGCAACTGCTCCATCACCTCCATC

TGTGAGAAGCCTCAGGAGGTGTGCGTGGCTGTCTGGCGGAAGAATGACGAG

AATATCACCCTGGAAACCGTCTGCCACGATCCCAAGCTGCCCTACCACGAT

TTCATCCTGGAAGACGCCGCCAGCCCTAAGTGCATCATGAAAGAGAAAAAG

AAGCCTGGCGAGACCTTTTTCATGTGCTCCTGCAGCAGCGACGAATGCAAC

GACAATATCATCTTTAGCGAGGAATACAATACCAGCAACCCCGAC

(Human Tissue Factor 219)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG

(Human IL-15)
AACTGGGTGAACGTCATCAGCGATTTAAAGAAGATCGAAGATTTAATTCAG

TCCATGCATATCGACGCCACTTTATACACAGAATCCGACGTGCACCCCTCT

TGTAAGGTGACCGCCATGAAATGTTTTTTACTGGAGCTGCAAGTTATCTCT

TTAGAGAGCGGAGACGCTAGCATCCACGACACCGTGGAGAATTTAATCATT

TTAGCCAATAACTCTTTATCCAGCAACGGCAACGTGACAGAGTCCGGCTGC

AAGGAGTGCGAAGAGCTGGAGGAGAAGAACATCAAGGAGTTTCTGCAATCC

TTTGTGCACATTGTCCAGATGTTCATCAATACCTCC
```

The amino acid sequence of TGFRt15 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSNCSIT

SICEKPQEVCVAVWRKNDENITLETVCHDPKLPYHDFILEDAASPKCIMKE

KKKPGETFFMCSCSSDECNDNIIFSEEYNTSNPDGGGGSGGGGSGGGGSIP

PHVQKSVNNDMIVTDNNGAVKFPQLCKFCDVRFSTCDNQKSCMSNCSITSI

CEKPQEVCVAVWRKNDENITLETVCHDPKLPYHDFILEDAASPKCIMKEKK

KPGETFFMCSCSSDECNDNIIFSEEYNTSNPD
```

-continued (Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE (Human IL-15)
NWVNVISDLKKIEDLIQSMHIDATLYTESDVHPSCKVTAMKCFLLELQVIS

LESGDASIHDTVENLIILANNSLSSNGNVTESGCKECEELEEKNIKEFLQS

FVHIVQMFINTS

The nucleic acid and protein sequences of the 21s137L are shown below. The nucleic acid sequence of the 21s137L construct (including signal peptide sequence) is as follows:

(Signal peptide)
ATGAAGTGGGTGACCTTCATCAGCCTGCTGTTCCTGTTCTCCAGCGCCTAC

TCC (Human IL-21)
CAGGGCCAGGACAGGCACATGATCCGGATGAGGCAGCTCATCGACATCGTC

GACCAGCTGAAGAACTACGTGAACGACCTGGTGCCCGAGTTTCTGCCTGCC

CCCGAGGACGTGGAGACCAACTGCGAGTGGTCCGCCTTCTCCTGCTTTCAG

AAGGCCCAGCTGAAGTCCGCCAACACCGGCAACAACGAGCGGATCATCAAC

GTGAGCATCAAGAAGCTGAAGCGGAAGCCTCCCTCCACAAACGCCGGCAGG

AGGCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGATC

CATCAGCACCTGTCCTCCAGGACCCACGGCTCCGAGGACTCC (Human IL-15R α sushi domain)
ATTACATGCCCCCCTCCCATGAGCGTGGAGCACGCCGACATCTGGGTGAAG

AGCTATAGCCTCTACAGCCGGGAGAGGTATATCTGTAACAGCGGCTTCAAG

AGGAAGGCCGGCACCAGCAGCCTCACCGAGTGCGTGCTGAATAAGGCTACC

AACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGACCTG

CGGCAGGGCATGTTTGCGCAGCTGGTGGCCCAAAATGTTCTGCTGATCGAT

GGGCCCCTGAGCTGGTACAGTGACCCAGGCCTGGCAGGCGTGTCCCTGACG

GGGGGCCTGAGCTACAAAGAGGACACGAAGGAGCTGGTGGTGGCCAAGGCT

GGAGTCTACTATGTCTTCTTTCAACTAGAGCTGCGGCGCGTGGTGGCCGGC

GAGGGCTCAGGCTCCGTTTCACTTGCGCTGCACCTGCAGCCACTGCGCTCT

GCTGCTGGGGCCGCCGCCCTGGCTTTGACCGTGGACCTGCCACCCGCCTCC

TCCGAGGCTCGGAACTCGGCCTTCGGTTTCCAGGGCCGCTTGCTGCACCTG

AGTGCCGGCCAGCGCCTGGGCGTCCATCTTCACACTGAGGCCAGGGCACGC

CATGCCTGGCAGCTTACCCAGGGCGCCACAGTCTTGGGACTCTTCCGGGTG

ACCCCCGAAATCCCAGCCGGACTCCCTTCACCGAGGTCGGAA

The amino acid sequence of 21s137L fusion protein (including the leader sequence) is as follows:

(Signal peptide)
MKWVTFISLLFLFSSAYS (Human IL-21)
QGQDRHMIRMRQLIDIVDQLKNYVNDLVPEFLPAPEDVETNCEWSAFSCF

QKAQLKSANTGNNERIINVSIKKLKRKPPSTNAGRRQKHRLTCPSCDSYE

KKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLNKA

TNVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGVS

LTGGLSYKEDTKELVVAKAGVYYVFFQLELRRVVAGEGSGSVSLALHLQ

PLRSAAGAAALALTVDLPPASSEARNSAFGFQGRLLHLSAGQRLGVHLH

TEARARHAWQLTQGATVLGLFRVTPEIPAGLPSPRSE

In some cases, the leader peptide is cleaved from the intact polypeptide to generate the mature form that may be soluble or secreted.

The IL-21/IL-15RαSu/CD137L and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15: IL-21/IL-15RαSu/CD137L protein complex (referred to as TGFRt15-21s137L), which can be purified by anti-TF antibody IgG1 affinity and other chromatography methods.

Purification Elution Chromatograph of TGFRt15-21s137L Using Anti-TF Antibody Affinity Column TGFRt15-21s137L harvest from cell culture was loaded onto the anti-TF antibody affinity column equilibrated with 5 column volumes of PBS. After sample loading, the column was washed with 5 column volumes of PBS, followed by elution with 6 column volumes of 0.1 M acetic acid (pH 2.9). A280 elution peak was collected and then neutralized to pH 7.5-8.0 with 1 M Tris base. The neutralized sample was then buffer exchanged into PBS using Amicon centrifugal filters with a 30 KDa molecular weight cutoff. As shown in FIG. 131, the anti-TF antibody affinity column bound to TGFRt15-21s137L which contains TF as a fusion partner of TGFRt15-21s137L. The buffer-exchanged protein sample was stored at 2-8 °C for further biochemical analyses and biological activity tests. After each elution, the anti-TF antibody affinity column was stripped using 6 column volumes of 0.1 M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Example 58: TGFRt15-TGFRs21 Fusion Protein Generation and Characterization

A fusion protein complex was generated comprising of TGFβ Receptor II/IL-15RαSu/IL-21 and TGFβ Receptor II/TF/IL-15 fusion proteins (FIG. 132 and FIG. 133). The human TGFβ Receptor II (Ile24-Asp159), tissue factor 219, IL-21, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGCCT

ACTCC

(Human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

AGCATCACCTCCATCTGCGAGAAGCCCCAAGAAGTGTGCGTGGCCGTG

TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

GGTTCTGGTGGAGGTGGGAGTATTCCTCCCCACGTGCAGAAGAGCGTG

AATAATGACATGATCGTGACCGATAACAATGGCGCCGTGAAATTTCCC

CAGCTGTGCAAATTCTGCGATGTGAGGTTTTCCACCTGCGACAACCAG

AAGTCCTGTATGAGCAACTGCTCCATCACCTCCATCTGTGAGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGAC

(Human Tissue Factor 219)
AGCGGCACAACCAACACAGTCGCTGCCTATAACCTCACTTGGAAGAGC

ACCAACTTCAAAACCATCCTCGAATGGGAACCCAAACCCGTTAACCAA

GTTTACACCGTGCAGATCAGCACCAAGTCCGGCGACTGGAAGTCCAAA

TGTTTCTATACCACCGACACCGAGTGCGATCTCACCGATGAGATCGTG

AAAGATGTGAAACAGACCTACCTCGCCCGGGTGTTTAGCTACCCCGCC
```

-continued

```
GGCAATGTGGAGAGCACTGGTTCCGCTGGCGAGCCTTTATACGAGAAC

AGCCCCGAATTTACCCCTTACCTCGAGACCAATTTAGGACAGCCCACC

ATCCAAAGCTTTGAGCAAGTTGGCACAAAGGTGAATGTGACAGTGGAG

GACGAGCGGACTTTAGTGCGGCGGAACAACACCTTTCTCAGCCTCCGG

GATGTGTTCGGCAAAGATTTAATCTACACACTGTATTACTGGAAGTCC

TCTTCCTCCGGCAAGAAGACAGCTAAAACCAACACAAACGAGTTTTTA

ATCGACGTGGATAAAGGCGAAAACTACTGTTTCAGCGTGCAAGCTGTG

ATCCCCTCCCGGACCGTGAATAGGAAAAGCACCGATAGCCCCGTTGAG

TGCATGGGCCAAGAAAAGGGCGAGTTCCGGGAG

(Human IL-15)
AACTGGGTGAACGTCATCAGCGATTTAAAGAAGATCGAAGATTTAATT

CAGTCCATGCATATCGACGCCACTTTATACACAGAATCCGACGTGCAC

CCCTCTTGTAAGGTGACCGCCATGAAATGTTTTTTACTGGAGCTGCAA

GTTATCTCTTTAGAGAGCGGAGACGCTAGCATCCACGACACCGTGGAG

AATTTAATCATTTTAGCCAATAACTCTTTATCCAGCAACGGCAACGTG

ACAGAGTCCGGCTGCAAGGAGTGCGAAGAGCTGGAGGAGAAGAACATC

CAAGGAGTTTCTGCAATCCTTTGTGACATTGTCCAGATGTTCATCAAT

ACCTCC
```

The amino acid sequence of TGFRt15 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD

(Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSPE

FTPYLETNLGQPTIQSFEQVGTKVNVTVEDERTLVRRNNTFLSLRDVFGK

DLIYTLYYWKSSSSGKKTAKTNTNEFLIDVDKGENYCFSVQAVIPSRTVN

RKSTDSPVECMGQEKGEFRE

(Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

Constructs were also made by attaching two TGFβ Receptor II directly to the IL-15RαSu chain, followed by the N-terminus coding region of IL-21, which was synthesized by Genewiz. The nucleic acid and protein sequences of a construct comprising the TGFβ Receptor II linked to the N-terminus of IL-15RαSu following with the N-terminus of IL-21 are shown below.

The nucleic acid sequence of the TGFRs21 construct (including signal peptide sequence) is as follows:

```
(Signal peptide)
ATGAAGTGGGTGACCTTCATCAGCCTGCTGTTCCTGTTCTCCAGCGCCT

ACTCC

(Human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

AGCATCACCTCCATCTGCGAGAAGCCCCAAGAAGTGTGCGTGGCCGTG

TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

GGTTCTGGTGGAGGTGGGAGTATTCCTCCCCACGTGCAGAAGAGCGTG

AATAATGACATGATCGTGACCGATAACAATGGCGCCGTGAAATTTCCC

CAGCTGTGCAAATTCTGCGATGTGAGGTTTTCCACCTGCGACAACCAG

AAGTCCTGTATGAGCAACTGCTCCATCACCTCCATCTGTGAGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGAC

(Human IL-15R α sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGC

TTCAAGAGGAAGGCCGGCACCAGCAGCCTCACCGAGTGCGTGCTGAAT

AAGGCTACCAACGTGGCTCACTGGACAACACCCTCTTTAAAGTGCATC

CGG

(Human IL-21)
CAGGGCCAGGACAGGCACATGATCCGGATGAGGCAGCTCATCGACATC

GTCGACCAGCTGAAGAACTACGTGAACGACCTGGTGCCCGAGTTTCTG

CCTGCCCCCGAGGACGTGGAGACCAACTGCGAGTGGTCCGCCTTCTCC

TGCTTTCAGAAGGCCCAGCTGAAGTCCGCCAACACCGGCAACAACGAG

CGGATCATCAACGTGAGCATCAAGAAGCTGAAGCGGAAGCCTCCCTCC

ACAAACGCCGGCAGGAGGCAGAAGCACAGGCTGACCTGCCCCAGCTGT

GACTCCTACGAGAAGAAGCCCCCCAAGGAGTTCCTGGAGAGGTTCAAG

TCCCTGCTGCAGAAGATGATCCATCAGCACCTGTCCTCCAGGACCCAC

GGCTCCGAGGACTCC
```

The amino acid sequence of TGFRs21 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIMK

EKKKPGETFFMCSCSSDECNDNIIFSEEYNTSNPDGGGGSGGGGSGGGGSI

PPHVQKSVNNDMIVTDNNGAVKFPQLCKFCDVRFSTCDNQKSCMSNCSITS

ICEKPQEVCVAVWRKNDENITLETVCHDPKLPYHDFILEDAASPKCIMKEK

KKPGETFFMCSCSSDECNDNIIFSEEYNTSNPD

(Human IL-15R α sushi domain)
ITCPPPMSVEHADIWVKSYSLYSRERYICNSGFKRKAGTSSLTECVLNKAT

NVAHWTTPSLKCIR

(Human IL-21)
QGQDRHMIRMRQLIDIVDQLKNYVNDLVPEFLPAPEDVETNCEWSAFSCFQ

KAQLKSANTGNNERIINVSIKKLKRKPPSTNAGRRQKHRLTCPSCDSYEKK

PPKEFLERFKSLLQKMIHQHLSSRTHGSEDS
```

In some cases, the leader peptide is cleaved from the intact polypeptide to generate the mature form that may be soluble or secreted.

The TGFR/IL-15RαSu/IL-21 and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/IL-21 protein complex (referred to as TGFRt15-TGFRs21), which can be purified by anti-TF antibody IgG1 affinity and other chromatography methods.

Purification Elution Chromatograph of TGFRt15-TGFRs21 Using Anti-TF Antibody Affinity Column TGFRt15-TGFRs21 harvested from cell culture was loaded onto the anti-TF antibody affinity column equilibrated with 5 column volumes of PBS. After sample loading, the column was washed with 5 column volumes of PBS, followed by elution with 6 column volumes of 0.1 M acetic acid (pH 2.9). A280 elution peak was collected and then neutralized to pH 7.5-8.0 with 1 M Tris base. The neutralized sample was then buffer exchanged into PBS using Amicon centrifugal filters with a 30 KDa molecular weight cutoff. As shown in FIG. 134, the anti-TF antibody affinity column bound to TGFRt15-TGFRs21 which contains TF as a fusion partner. The buffer-exchanged protein sample was stored at 2-8 °C for further biochemical analyses and biological activity tests. After each elution, the anti-TF antibody affinity column was stripped using 6 column volumes of 0.1 M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS PAGE Analysis of TGFRt15-TGFRs21

To determine the purity and molecular weight of the protein, TGFRt15-TGFRs21 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

To verify that the TGFRt15-TGFRs21 protein undergoes glycosylation after translation in CHO cells, a deglycosylation experiment was conducted using the Protein Deglycosylation Mix II kit from New England Biolabs and the manufacturer's instructions. FIG. 135 shows the reduced SDS-PAGE analysis of the sample in non-deglycosylated (lane 1 in red outline) and deglycosylated (lane 2 in yellow outline) state. It is clear that the protein is glycosylated when it is expressed in CHO cells. After deglycosylation, the purified sample showed expected molecular weights (69 kDa and 55 kDa) in reduced SDS gel. Lane M was loaded with 10 ul of SeeBlue Plus2 Prestained Standard.

Immunostimulation of TGFRt15-TGFRs21 in C57BL/6 Mice

TGFRt15-TGFRs21 is a multi-chain polypeptide (a type A multi-chain polypeptide described herein) that includes the first polypeptide that is a soluble fusion of single chain two TGFβRII domains, human tissue factor 219 fragment and human IL-15 (TGFRt15), and the second polypeptide that is a soluble fusion of single chain two TGFβRII domains, sushi domain of human IL-15 receptor alpha chain and human IL-21 (TGFRs21).

CHO cells were co-transfected with TGFRt15 and TGFRs21 vectors. The TGFRt15-TGFRs21 complex was purified from the transfected CHO cell culture supernatant. The TGFβ receptor, IL-15, IL-21 and tissue factor (TF) components were demonstrated in the complex by ELISA as shown in FIG. 136. A humanized anti-TF monoclonal antibody (anti-TF IgG1) was used as the capture antibody to determine TF in TGFRt15-TGFRs21, biotinylated anti-human IL-15 antibody (R&D systems), biotinylated anti-human TGFβ receptor antibody (R&D systems, and biotinylated anti-human IL-21 antibody (R&D Systems) were used as the detection antibodies to respectively determine IL-15, TGFβ receptor, and IL-21 in TGFRt15-TGFRs21. For detection, peroxidase conjugated streptavidin (Jackson ImmunoResearch Lab) and ABTS were used.

Wild type C57BL/6 mice were treated subcutaneously with either control solution (PBS) or with TGFRt15-TGFRs21 at 3 mg/kg. Four days after treatment, spleen weight and the percentages of various immune cell types present in the spleen were evaluated. As shown in FIG. 137A, the percentages of $CD4^+$ T cells, $CD8^+$ T cells, and NK cells present in the spleen of control-treated and TGFRt15-TGFRs21-treated mice were evaluated. The dynamic proliferation of immune cells based on Ki67 expression after TGFRt15-TGFRs21 treatment was also evaluated. The splenocytes were stained with fluorochrome-conjugated anti-CD4, anti-CD8, and anti-NK1.1 (NK) antibodies and then intracellularly stained with anti-Ki67 antibody. The percentage of $CD4^+$ T cells, $CD8^+$ T cells, and NK cells and the mean fluorescent intensity (MFI) of Ki67 of corresponding immunocyte subsets were analyzed by flow cytometry (FIGS. 137A and 137B). Furthermore, cytotoxicity potential based on granzyme B expression of the splenocytes induced by TGFRt15-TGFRs21 after the single dose treatment of mouse was also evaluated. As shown in FIG. 138, in the spleens of mice treated with TGFRt15-TGFRs21, the expression of granzyme B by NK cells increased after treatment. The splenocytes from TGFRt15-TGFRs21-treated mice were stained with fluorochrome-conjugated anti-CD4, anti-CD8, and anti-NK1.1 (NK) antibodies and then intracellularly stained with anti-granzyme B antibody. The mean fluorescent intensity (MFI) of granzyme B of corresponding immunocyte subsets was analyzed by flow cytometry (FIG. 138).

As shown in FIG. 137A, in the spleens of mice treated with TGFRt15-TGFRs21, the percentages of $CD8^+$ T cells and NK cells both increased on day 4 after a single TGFRt15-TGFRs21 treatment. These results demonstrate that TGFRt15-TGFRs21 is able to induce immune cells to proliferate in mouse spleen, in particular $CD8^+$ T cells and NK cells.

Additionally, cytotoxicity of the mouse splenocytes against tumor cells was also evaluated. Mouse Yac-1 cells were labeled with CELLTRACE™ Violet (cell proliferation kit for flow cytometry) and used as tumor target cells. The splenocytes were prepared from TGFRt15-TGFRs21-treated mice and used as effector cells. The target cells were mixed with effector cells at E:T ratio=10:1 in RPMI-10 medium with or without TGFRt15-TGFRs21 at 100 nM and incubated at 37 °C for 24 hours. Target Yac-1 cell inhibition was assessed by analysis of viable violet-labeled Yac-1 cells using flow cytometry. Percentage of Yac-1 inhibition was calculated using a formula, (1-[viable Yac-1 cell number in experimental sample]/[viable Yac-1 cell number in the sample without splenocytes])×100. As shown in FIG. 139, TGFRt15-TGFRs21-treated mouse splenocytes had stronger cytotoxicity against Yac-1 cells than the control mouse cells in the presence of TGFRt15-TGFRs21 during cytotoxic assay (FIG. 139).

Example 59: TGFRt15-TGFRs16 Fusion Protein Generation

A fusion protein complex was generated comprising of TGFβ Receptor II/IL-15RαSu/anti-CD16scFv and TGFβ Receptor II/TF/IL-15 fusion proteins (FIG. 140 and FIG. 141). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGCCT

ACTCC

(Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACTCCATCTGCGAGAAGCCCCAAGAAGTGTGCGTGGCCGTGTGGCGGAAA

AATGACGAGAACATCACCCTGGAGACCGTGTGTCACGACCCCAAGCTCCC
```

-continued

```
TTATCACGACTTCATTCTGGAGGACGCTGCCTCCCCCAAATGCATCATGA

AGGAGAAGAAGAAGCCCGGAGAGACCTTCTTTATGTGTTCCTGTAGCAGC

GACGAGTGTAACGACAACATCATCTTCAGCGAAGAGTACAACACCAGCAA

CCCTGATGGAGGTGGCGGATCCGGAGGTGGAGGTTCTGGTGGAGGTGGGA

GTATTCCTCCCCACGTGCAGAAGAGCGTGAATAATGACATGATCGTGACC

GATAACAATGGCGCCGTGAAATTTCCCCAGCTGTGCAAATTCTGCGATGT

GAGGTTTTCCACCTGCGACAACCAGAAGTCCTGTATGAGCAACTGCTCCA

TCACCTCCATCTGTGAGAAGCCTCAGGAGGTGTGCGTGGCTGTCTGGCGG

AAGAATGACGAGAATATCACCCTGGAAACCGTCTGCCACGATCCCAAGCT

GCCCTACCACGATTTCATCCTGGAAGACGCCGCCAGCCCTAAGTGCATCA

TGAAAGAGAAAAAGAAGCCTGGCGAGACCTTTTTCATGTGCTCCTGCAGC

AGCGACGAATGCAACGACAATATCATCTTTAGCGAGGAATACAATACCAG

CAACCCCGAC
```

```
(Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG
```

```
(Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC
```

The amino acid sequence of TGFRt15 fusion protein (including the leader sequence) is as follows:

```
(Signal peptide)
MKWVTFISLLFLFSSAYS
```

```
(Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD
```

```
(Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE
```

```
(Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS
```

Constructs were also made by attaching two TGFβ Receptor II directly to the IL-15RαSu chain, followed by the anti-CD16scFv sequence, which was synthesized by Genewiz. The nucleic acid and protein sequences of a construct comprising the TGFβ Receptor II linked to the N-terminus of IL-15RαSu following with the anti-CD16scFv sequence are shown below.

The nucleic acid sequence of the TGFRs16 construct (including signal peptide sequence) is as follows:

```
(Signal peptide)
ATGAAGTGGGTGACCTTCATCAGCCTGCTGTTCCTGTTCTCCAGCGCCTA

CTCC
```

```
(Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC
```

-continued

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG (Anti-human CD16scFv)
TCCGAGCTGACCCAGGACCCTGCTGTGTCCGTGGCTCTGGGCCAGACCGT

GAGGATCACCTGCCAGGGCGACTCCCTGAGGTCCTACTACGCCTCCTGGT

ACCAGCAGAAGCCCGGCCAGGCTCCTGTGCTGGTGATCTACGGCAAGAAC

AACAGGCCCTCCGGCATCCCTGACAGGTTCTCCGGATCCTCCTCCGGCAA

CACCGCCTCCCTGACCATCACAGGCGCTCAGGCCGAGGACGAGGCTGACT

ACTACTGCAACTCCAGGGACTCCTCCGGCAACCATGTGGTGTTCGGCGGC

GGCACCAAGCTGACCGTGGGCCATGGCGGCGGCGGCTCCGGAGGCGGCGG

CAGCGGCGGAGGAGGATCCGAGGTGCAGCTGGTGGAGTCCGGAGGAGGAG

TGGTGAGGCCTGGAGGCTCCCTGAGGCTGAGCTGTGCTGCCTCCGGCTTC

ACCTTCGACGACTACGGCATGTCCTGGGTGAGGCAGGCTCCTGGAAAGGG

CCTGGAGTGGGTGTCCGGCATCAACTGGAACGGCGGATCCACCGGCTACG

CCGATTCCGTGAAGGGCAGGTTCACCATCAGCAGGGACAACGCCAAGAAC

TCCCTGTACCTGCAGATGAACTCCCTGAGGGCCGAGGACACCGCCGTGTA

CTACTGCGCCAGGGGCAGGTCCCTGCTGTTCGACTACTGGGGACAGGGCA

CCCTGGTGACCGTGTCCAGG

The amino acid sequence of TGFRs16 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNKAT

NVAHWTTPSLKCIR

-continued (Anti-human CD16scFv)
SELTQDPAVSVALGQTVRITCQGDSLRSYYASWYQQKPGQAPVLVIYGKNN

RPSGIPDRFSGSSSGNTASLTITGAQAEDEADYYCNSRDSSGNHVVFGGT

KLTVGHGGGGSGGGGSGGGGSEVQLVESGGGVVRPGGSLRLSCAASGFTFD

DYGMSWVRQAPGKGLEWVSGINWNGGSTGYADSVKGRFTISRDNAKNSLYL

QMNSLRAEDTAVYYCARGRSLLFDYWGQGTLVTVSR

In some cases, the leader peptide is cleaved from the intact polypeptide to generate the mature form that may be soluble or secreted.

The TGFR/IL-15RαSu/anti-CD16scFv and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/anti-CD16scFv protein complex (referred to as TGFRt15-TGFRs16), which can be purified by anti-TF IgG1 affinity and other chromatography methods.

Example 60: The TGFRt15-TGFRs137L Fusion Protein Generation

A fusion protein complex was generated comprising of TGFβ Receptor II/IL-15RαSu/CD137L and TGFβ Receptor II/TF/IL-15 fusion proteins (FIG. 142 and FIG. 143). The human TGFβ Receptor II (Ile24-Asp159), tissue factor 219, CD137L, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

(Signal peptide)
ATGAAGTGGGTGACCTTCATCAGCCTGCTGTTCCTGTTCTCCAGCGCCTA

CTCC (Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

-continued

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC (Human Tissue Factor 219)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC

AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG (Human IL-15)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC

The amino acid sequence of TGFRt15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

-continued

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKCF

YTTDTECDLTDEIVKDVKQTYLARVFSYPAGNVESTGSAGEPLYENSPEF

TPYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVNR

KSTDSPVECMGQEKGEFRE (Human IL-15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

Constructs were also made by attaching two TGFβ Receptor II directly to the IL-15RαSu chain, followed by a (G4S)3 linker and the CD137L sequence, which was synthesized by Genewiz. The nucleic acid and protein sequences of a construct comprising the TGFβ Receptor II linked to the N-terminus of IL-15RαSu following with a (G4S)3 linker and the CD137L sequence are shown below.

The nucleic acid sequence of the TGFRs137L construct (including signal peptide sequence) is as follows:

(Signal peptide)
ATGAAGTGGGTGACCTTCATCAGCCTGCTGTTCCTGTTCTCCAGCGCCTA

CTCC (Human TGFβ Receptor II fragments)
ATCCCCCCCCATGTGCAAAAGAGCGTGAACAACGATATGATCGTGACCGA

CAACAACGGCGCCGTGAAGTTTCCCCAGCTCTGCAAGTTCTGCGATGTCA

GGTTCAGCACCTGCGATAATCAGAAGTCCTGCATGTCCAACTGCAGCATC

ACCTCCATCTGCGAGAAGCCCCAAGAAGTGTGCGTGGCCGTGTGGCGGAA

AAATGACGAGAACATCACCCTGGAGACCGTGTGTCACGACCCCAAGCTCC

CTTATCACGACTTCATTCTGGAGGACGCTGCCTCCCCCAAATGCATCATG

AAGGAGAAGAAGAAGCCCGGAGAGACCTTCTTTATGTGTTCCTGTAGCAG

CGACGAGTGTAACGACAACATCATCTTCAGCGAAGAGTACAACACCAGCA

ACCCTGATGGAGGTGGCGGATCCGGAGGTGGAGGTTCTGGTGGAGGTGGG

AGTATTCCTCCCCACGTGCAGAAGAGCGTGAATAATGACATGATCGTGAC

CGATAACAATGGCGCCGTGAAATTTCCCCAGCTGTGCAAATTCTGCGATG

TGAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGCG

GAAGAATGACGAGAATATCACCCTGGAAACCGTCTGCCACGATCCCAAGC

TGCCCTACCACGATTTCATCCTGGAAGACGCCGCCAGCCCTAAGTGCATC

ATGAAAGAGAAAAAGAAGCCTGGCGAGACCTTTTTCATGTGCTCCTGCAG

CAGCGACGAATGCAACGACAATATCATCTTTAGCGAGGAATACAATACCA

GCAACCCCGAC

-continued (Human IL-15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGACCT

GCGGCAGGGCATGTTTGCGCAGCTGGTGGCCCAAAATGTTCTGCTGATCG

ATGGGCCCCTGAGCTGGTACAGTGACCCAGGCCTGGCAGGCGTGTCCCTG

ACGGGGGGCCTGAGCTACAAAGAGGACACGAAGGAGCTGGTGGTGGCCAA

GGCTGGAGTCTACTATGTCTTCTTTCAACTAGAGCTGCGGCGCGTGGTGG

CCGGCGAGGGCTCAGGCTCCGTTTCACTTGCGCTGCACCTGCAGCCACTG

CGCTCTGCTGCTGGGGCCGCCGCCCTGGCTTTGACCGTGGACCTGCCACC

CGCCTCCTCCGAGGCTCGGAACTCGGCCTTCGGTTTCCAGGGCCGCTTGC

TGCACCTGAGTGCCGGCCAGCGCCTGGGCGTCCATCTTCACACTGAGGCC

AGGGCACGCCATGCCTGGCAGCTTACCCAGGGCGCCACAGTCTTGGGACT

CTTCCGGGTGACCCCCGAAATCCCAGCCGGACTCCCTTCACCGAGGTCGG

AA

The amino acid sequence of TGFRs137L fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCSI

TSICEKPQEVCVAVWRKNDENITLETVCHDPKLPYHDFILEDAASPKCIM

KEKKKPGETFFMCSCSSDECNDNIIFSEEYNTSNPDGGGGSGGGGSGGGG

SIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSDECNDNIIFSEEYNTSNPD (Human IL-15R α sushi domain)
ITCPPPMSVEHADIWVKSYSLYSRERYICNSGFKRKAGTSSLTECVLNKAT

NVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGVSLT

GGLSYKEDTKELVVAKAGVYYVFFQLELRRVVAGEGSGSVSLALHLQPLRS

AAGAAALALTVDLPPASSEARNSAFGFQGRLLHLSAGQRLGVHLHTEARAR

HAWQLTQGATVLGLFRVTPEIPAGLPSPRSE

In some cases, the leader peptide is cleaved from the intact polypeptide to generate the mature form that may be soluble or secreted.

The TGFR/IL-15RαSu/CD137L and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/CD137L protein complex (referred to as TGFRt15-TGFRs137L), which can be purified by anti-TF IgG1 affinity and other chromatography methods.

Example 61. Production and Characterization of the Exemplary Single-Chain Chimeric Polypeptide 2t2

An exemplary single-chain chimeric polypeptide including a first target-binding domain that binds to an IL-2 receptor, a soluble human tissue factor domain, and a second target-binding domain that binds to an IL-2 receptor was generated (IL-2/TF/IL-2; referred to as 2t2) (FIG. 144). The nucleic acid and amino acid sequences of this single-chain chimeric polypeptide are shown below.

Nucleic Acid Encoding Exemplary Single-Chain Chimeric Polypeptide (IL-2/TF/IL-2) (SEQ ID NO: 164)

(Signal peptide)
ATGAAGTGGGTGACCTTCATCAGCCTGCTGTTCCTGTTCTCCAGCGCCTAC

TCC (First IL-2 fragment)
GCCCCCACCTCCTCCTCCACCAAGAAGACCCAGCTGCAGCTGGAGCATTTA

CTGCTGGATTTACAGATGATTTTAAACGGCATCAACAACTACAAGAACCCC

AAGCTGACTCGTATGCTGACCTTCAAGTTCTACATGCCCAAGAAGGCCACC

GAGCTGAAGCATTTACAGTGTTTAGAGGAGGAGCTGAAGCCCCTCGAGGAG

GTGCTGAATTTAGCCCAGTCCAAGAATTTCCATTTAAGGCCCCGGGATTTA

ATCAGCAACATCAACGTGATCGTTTTAGAGCTGAAGGGCTCCGAGACCACC

TTCATGTGCGAGTACGCCGACGAGACCGCCACCATCGTGGAGTTTTTAAAT

CGTTGGATCACCTTCTGCCAGTCCATCATCTCCACTTTAACC (Human tissue factor 219 form)
AGCGGCACAACCAACACAGTCGCTGCCTATAACCTCACTTGGAAGAGCACC

AACTTCAAAACCATCCTCGAATGGGAACCCAAACCCGTTAACCAAGTTTAC

ACCGTGCAGATCAGCACCAAGTCCGGCGACTGGAAGTCCAAATGTTTCTAT

ACCACCGACACCGAGTGCGATCTCACCGATGAGATCGTGAAAGATGTGAAA

CAGACCTACCTCGCCCGGGTGTTTAGCTACCCCGCCGGCAATGTGGAGAGC

ACTGGTTCCGCTGGCGAGCCTTTATACGAGAACAGCCCCGAATTTACCCCT

TACCTCGAGACCAATTTAGGACAGCCCACCATCCAAAGCTTTGAGCAAGTT

GGCACAAAGGTGAATGTGACAGTGGAGGACGAGCGGACTTTAGTGCGGCGG

AACAACACCTTTCTCAGCCTCCGGGATGTGTTCGGCAAAGATTTAATCTAC

ACACTGTATTACTGGAAGTCCTCTTCCTCCGGCAAGAAGACAGCTAAAACC

AACACAAACGAGTTTTTAATCGACGTGGATAAAGGCGAAAACTACTGTTTC

AGCGTGCAAGCTGTGATCCCCTCCCGGACCGTGAATAGGAAAAGCACCGAT

AGCCCCGTTGAGTGCATGGGCCAAGAAAAGGGCGAGTTCCGGGAG

-continued (Second IL-2 fragment)
GCACCTACTTCAAGTTCTACAAAGAAAACACAGCTACAACTGGAGCATTA

CTGCTGGATTTACAGATGATTTTGAATGGAATTAATAATTACAAGAATCCC

AAACTCACCAGGATGCTCACATTTAAGTTTTACATGCCCAAGAAGGCCACA

GAACTGAAACATCTTCAGTGTCTAGAAGAAGAACTCAAACCTCTGGAGGAA

GTGCTAAATTTAGCTCAAAGCAAAAACTTTCACTTAAGACCCAGGGACTTA

ATCAGCAATATCAACGTAATAGTTCTGGAACTAAAGGGATCTGAAACAACA

TTCATGTGTGAATATGCTGATGAGACAGCAACCATTGTAGAATTTCTGAAC

AGATGGATTACCTTTTGTCAAAGCATCATCTCAACACTAACT

Exemplary Single-Chain Chimeric Polypeptide (IL-2/TF/IL-2) (SEQ ID NO: 163)

(Signal peptide)
MKWVTFISLLFLFSSAYS (Human IL-2)
APTSSSTKKTQLQLEHLLLDLQMILNGINNYKNPKLTRMLTFKFYMPKKAT

ELKHLQCLEEELKPLEEVLNLAQSKNFHLRPRDLISNINVIVLELKGSETT

FMCEYADETATIVEFLNRWITFCQSIISTLT (Human Tissue Factor 219)
SGTTNTVAAYNLTWKSTNFKTILEWEPKPVNQVYTVQISTKSGDWKSKCFY

TTDTECDLTDEIVKDVKQTYLARVFSYPAGNVESTGSAGEPLYENSPEFTP

YLETNLGQPTIQSFEQVGTKVNVTVEDERTLVRRNNTFLSLRDVFGKDLIY

TLYYWKSSSSGKKTAKTNTNEFLIDVDKGENYCFSVQAVIPSRTVNRKSTD

SPVECMGQEKGEFRE (Human IL-2)
APTSSSTKKTQLQLEHLLLDLQMILNGINNYKNPKLTRMLTFKFYMPKKAT

ELKHLQCLEEELKPLEEVLNLAQSKNFHLRPRDLISNINVIVLELKGSETT

FMCEYADETATIVEFLNRWITFCQSIISTLT

The nucleic acid encoding IL-2/TF/IL-2 was cloned into a modified retrovirus expression vector as described previously (Hughes et al., *Hum Gene Ther* 16:457-72, 2005). The expression vector encoding IL-2/TF/IL-2 was transfected into CHO-K1 cells. Expression of the expression vector in CHO-K1 cells allowed for secretion of the soluble IL-2/TF/IL-2 single-chain chimeric polypeptide (referred to as 2t2), which can be purified by anti-TF antibody affinity and other chromatography methods.

IL-2 and 2t2 Promoted IL-2Rβ and Common γ Chain Containing 32Dβ Cell Proliferation in a Similar Manner To evaluate the IL-2 activity of 2t2, 2t2 was compared with recombinant IL-2 for promoting proliferation of 32Dβ cells that express IL-2Rβ and common γ chain. IL-2 dependent 32Dβ cells were washed 5 times with IMDM-10% FBS and seeded to the wells at $2\times10^4$ cells/well. Serial dilutions of 2t2 or IL-2 were added to the cells (FIG. 145). Cells were incubated in a $CO_2$ incubator at 37 °C for 3 days. Cell proliferation was detected by adding 10 μl of WST1 to each well on day 3 and incubating for an additional 3 hours in a $CO_2$ incubator at 37 °C. The amount of formazan dye produced was analyzed by measuring the absorbance at 450 nm. As shown in FIG. 145. 2t2 and IL-2 activated 32Dβ cells in a similar manner. The $EC_{50}$ of 2t2 and IL-2 was 158.1 pM and 140 pM. respectively.

2t2 Showed Improved Ability to Promote IL-2Rαβγ Containing CTLL-2 Cell Proliferation as Compared to IL-2

To evaluate the IL-2 activity of 2t2, 2t2 was compared with recombinant IL-2 for promoting proliferation of CTLL-2 cells that express IL-2Rα, IL-2Rβ and common γ chain. IL-2 dependent CTLL-2 cells were washed 5 times with IMDM-10% FBS and seeded to the wells at $2\times10^4$ cells/well. Serial dilutions of 2t2 or IL-2 were added to the cells (FIG. 146). Cells were incubated in a $CO_2$ incubator at 37 °C for 3 days. Cell proliferation was detected by adding 10 μl of WST1 to each well in the day 3 and incubating for an additional 3 hours in a $CO_2$ incubator at 37 °C. The amount of formazan dye produced was analyzed by measuring the absorbance at 450 nm. As shown in FIG. 146, 2t2 promoted CTLL-2 cell proliferation 4-5-fold stronger than IL-2. The $EC_{50}$ of 2t2 was 123.2 pM and IL-2 was 548.2 pM.

2t2 Suppressed the Increase of the High Fat-Induced Hyperglycemia in $ApoE^{-/-}$ Mice Six-week-old female $ApoE^{-/-}$ mice (Jackson Lab) were fed with standard chow diet or high diet fat containing 21% fat, 0.15% cholesterol, 34.1% sucrose, 19.5% casein, and 15% starch (TD88137, Harlan Laboratories) and maintained in the standard conditions. At week 7, mice fed with high fat diet were randomly assigned into the control group and treatment group. Mice then received either 2t2 (treatment group) or PBS (chow diet group and control group) per subcutaneous injection at a dosage of 3 mg/kg. Three days post dosing, the mice were fasted overnight, and blood samples were collected through retro-orbital venous plexus puncture. Overnight fasting glucose levels were measured using a OneTouch Glucometer. As shown in FIG. 147, the results showed that 2t2 injection effectively suppresses the increase of glucose levels in $ApoE^{-/-}$ mice.

2t2 Significantly Upregulate the Ratio of $CD4^+CD25^+$ $FoxP3^+$ T Regulatory (Treg) Cells in Blood Lymphocytes Six-week-old female $ApoE^{-/-}$ mice (Jackson Lab) were fed with standard chow diet or high diet fat containing 21% fat, 0.15% cholesterol, 34.1% sucrose, 19.5% casein, and 15% starch (TD88137, Harlan Laboratories) and maintained in the standard conditions. At week 7, mice fed with the high fat diet were randomly assigned into control group and treatment group. Mice then received either 2t2 (treatment group) or PBS (chow diet group and control group) per subcutaneous injection at a dosage of 3 mg/kg. Three days after the dosing, overnight fasting blood samples were collected through retro-orbital venous plexus puncture and incubated with ACK lysing buffer (Thermo Fisher Scientific) at 37 °C for 5 minutes. Samples were then resuspended in FACS buffer (1×PBS (Hyclone) with 0.5% BSA (EMD Millipore) and 0.001% sodium azide (Sigma)) and surface stained with FITC-anti-CD4 and APC-anti-CD25 antibodies (BioLegend) for 30 minutes. Surface-stained samples were further fixed and premetallized with Fix/Perm buffer (BioLegend) and intracellular stained with PE-anti-Foxp3 antibody (BioLegend). After staining, cells were washed twice with FACs buffer followed by centrifugation at 1500 RPM for 5 minutes at room temperature. The cells were analyzed by flow cytometry (Celesta-BD Bioscience). As shown in FIG. 148, 2t2 treatment significantly increased Treg populations in blood lymphocytes (3.5%±0.32) compared to the untreated groups (0.4%±0.16 for chow diet group and 0.46%±0.09 for high fat diet group).

Purification Elution Chromatograph of 2t2 from Anti-TF Antibody Affinity Column

2t2 harvested from cell culture was loaded onto the anti-TF antibody affinity column equilibrated with 5 column volumes of PBS. After sample loading, the column was washed with 5 column volumes of PBS, followed by elution with 6 column volumes of 0.1 M acetic acid, pH 2.9. A280 elution peak was collected and then neutralized to pH 7.5-8.0 with 1 M Tris base. The neutralized sample was then buffer exchanged into PBS using Amicon centrifugal filters with a 30 kDa molecular weight cutoff. As shown in FIG. 149, the anti-TF antibody affinity column bound to 2t2 which contains TF as a fusion domain. The buffer-exchanged protein sample was stored at 2-8 °C for further biochemical analyses and biological activity tests. After each elution, the anti-TF antibody affinity column was stripped using 6 column volumes of 0.1 M glycine, pH 2.5. The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of 2t2

To analyze 2t2 using analytical size exclusion chromatography (SEC), a Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. A sample containing 2t2 in PBS was injected into the Superdex 200 column using a capillary loop, and analyzed by SEC. The SEC chromatograph of the sample is shown in FIG. 150. The SEC results indicated two protein peaks for 2t2.

Reduced SDS-PAGE of 2t2

To determine the purity and molecular weight of the protein, 2t2 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

To verify that the 2t2 protein undergoes glycosylation after translation in CHO cells, a deglycosylation experiment was conducted using the Protein Deglycosylation Mix II kit from New England Biolabs according to the manufacturer's instructions. FIGS. 151A and 151B show the reduced SDS-PAGE analysis of the sample in non-deglycosylated (lane 1 in red outline) and deglycosylated (lane 2 in yellow outline) state. The results show that the 2t2 protein is glycosylated when expressed in CHO cells. After deglycosylation, the purified sample ran with expected molecular weights (56 kDa) in reduced SDS gel. Lane M was loaded with 10 μL of SeeBlue Plus2 Prestained Standard.

In Vivo Characterization of 2t2

2t2 was subcutaneously injected into C57BL/6 mice at various doses to determine the immunostimulatory activity of 2t2 in vivo. Mice were subcutaneously treated with control solution (PBS) or 2t2 at 0.1, 0.4, 2 and 10 mg/kg. The treated mice were euthanized day 3 post treatment. The mouse spleens were collected and weighed day 3 post treatment. Single splenocyte suspensions were prepared, and the prepared splenocytes were stained for $CD4^+$ T cells, $CD8^+$ T cells and NK cells (with fluorochrome-conjugated anti-CD4, -CD8, and —NK1.1 antibodies), and analyzed by flow cytometry. The results showed that 2t2 was effective at expanding splenocytes based on spleen weight (FIG. 152A) especially at 0.1-10 mg/kg. The percentage of $CD8^+$ T cells were higher compared to control-treated mice (FIG. 152B) at 2 and 10 mg/kg. The percentage of NK cells were higher compared to control-treated mice (FIG. 152B) at all doses tested.

It has been known that IL-2 upregulates CD25 expression by immunocytes. We therefore accessed CD25 expression of $CD4^+$ T cells, $CD8^+$ T cells and NK cells in the 2t2 treated mice. C57BL/6 mice were subcutaneously treated with 2t2 as described in the paragraph above. The splenocytes were stained with fluorochrome-conjugated anti-CD4, -CD8, CD25 and NK1.1 monoclonal antibodies. The CD25 expression (MFI) of splenocyte subsets was analyzed by flow cytometry. As shown in FIG. 153, at the doses and time points tested, 2t2 significantly upregulated CD25 expression by $CD4^+$ T cells but not CD8+ T cells or NK cells.

The pharmacokinetics of 2t2 in C57BL/6 mice were also investigated. 2t2 was subcutaneously injected into C57BL/6 mice at 1 mg/kg. The mouse blood was drawn from tail vein at various time points as shown in FIG. 154 and the serum was prepared. 2t2 concentrations were determined with ELISA (Capture: anti-tissue factor antibody; Detection: biotinylated anti-human IL-2 antibody followed by SA-HRP and ABTS substrate). The half-life of 2t2 was 1.83 hours calculated with PK Solutions 2.0 (Summit Research Services).

2t2 Attenuated the Formation of High Fat-Induced Atherosclerotic Plaques in $ApoE^{-/-}$ Mice Six-week-old female $ApoE^{-/-}$ mice (The Jackson Laboratory) were fed with standard chow diet or high diet fat (21% fat, 0.15% cholesterol, 34.1% sucrose, 19.5% casein, and 15% starch) (TD88137, Harlan Laboratories) and maintained in the standard conditions. At week 7, mice fed with high fat diet (HFD) were randomly assigned into control group and treatment group. Mice were then administrated either 2t2 (treatment group) or PBS (chow diet group and control group) subcutaneously at a dosage of 3 mg/kg weekly for 4 weeks. At week 12, all mice were euthanized by isoflurane. Aortas were collected, opened longitudinally and stained with Sudan IV solution (0.5%) using en face method. The percentage of plaque area (red color as shown in FIG. 155A) relative to total aorta area was then quantified with Image J software. FIG. 155A shows a representative view of atherosclerotic plaques from each group. FIG. 155B shows the results of quantitative analysis of atherosclerotic plaques of each group. The percentage of plaque areas in control group (HF Diet) was much higher than the treatment group (HFD+2t2), being 10.28% vs 4.68%.

2t2 Suppresses the Progression of Type 2 Diabetes.

Male BKS.Cg-$Dock7^{m}$+/+ $Lepr^{db}$/J (db/db (Jackson Lab)) mice were fed with standard chow diet and received drinking water ad libitum. At the age of six weeks, mice were randomly assigned into control group and treatment group. The treatment group received 2t2 by subcutaneous injection at 3 mg/kg bi-weekly, while control group received vehicle (PBS) only. Overnight fasting glucose levels were measure weekly using a OneTouch Glucometer. The results showed that 2t2 effectively suppressed the increase of glucose levels in BKS.Cg-$Dock7^{m}$+/+ $Lepr^{db}$/J mice (FIG. 156).

2t2 Significantly Upregulates the Ratio of $CD4^+CD25^+$ $FoxP3^+$ T Regulatory Cells in Blood Lymphocytes after the First Injection Male BKS.Cg-$Dock7^{m}$+/+ $Lepr^{db}$/J (db/db) (The Jackson Laboratory) mice were fed with standard chow diet and received drinking water ad libitum. At the age of six weeks, mice were randomly assigned into control group and treatment group. The treatment group received 2t2 by subcutaneous injection at 3 mg/kg bi-weekly, while the control group received vehicle (PBS) only. Four days after the first drug injection, overnight fasting blood samples were collected and incubated with ACK lysing buffer (Thermo Fisher Scientific) at 37 °C for 5 minutes. Samples were then resuspended in FACS buffer (1×PBS (Hyclone) with 0.5% BSA (EMD Millipore) and 0.001% sodium azide (Sigma)) and surface stained with FITC-anti-CD4 and APC-anti-CD25 antibodies (BioLegend) for 30 minutes. Surface-stained samples were further fixed and premetallized with Fix/Perm buffer (BioLegend) and intracellular stained with PE-anti-Foxp3 antibody (BioLegend). After staining, cells were washed twice with FACs buffer and were analyzed by flow cytometry (Celesta-BD Bioscience). The percentage of $CD4^+CD25^+FoxP3^+$ Tregs in blood lymphocytes were measured. As shown in FIG. 157, the results showed that 2t2 significantly upregulated the ratio of Tregs in blood lymphocytes (*p<0.05).

Example 62. Production and Characterization of the Exemplary Single-Chain Chimeric Polypeptide 15t15

A second exemplary single-chain chimeric polypeptide including a first target-binding domain that binds to an IL-15 receptor, a soluble human tissue factor domain, and a second target-binding domain that binds to an IL-15 receptor was generated (IL-15/TF/IL-15; referred to at 15t15) (FIG. 158). The nucleic acid and amino acid sequences of this single-chain chimeric polypeptide are shown below.

Nucleic Acid Encoding Exemplary Single-Chain Chimeric Polypeptide (IL-15/TF/IL-15) (SEQ ID NO: 170)

```
(Signal peptide)
ATGAAGTGGGTGACCTTCATCAGCCTGCTGTTCCTGTTCTCCAGCGCCT

ACTCC

(First IL-15 fragment)
AACTGGGTGAACGTGATCAGCGATTTAAAGAAGATCGAGGATTTAATCCA

GAGCATGCACATCGACGCCACTCTGTACACTGAGAGCGACGTGCACCCTA

GCTGCAAGGTGACTGCCATGAAGTGCTTTTTACTGGAGCTGCAAGTTATC

TCTTTAGAGAGCGGCGATGCCAGCATCCACGACACTGTGGAGAATTTAAT

CATTTTAGCCAACAACTCTTTAAGCAGCAACGGCAACGTGACAGAGAGCG

GCTGCAAGGAGTGCGAGGAGCTGGAGGAGAAGAACATCAAGGAGTTTTTA

CAGAGCTTCGTGCACATCGTGCAGATGTTCATCAACACTAGC

(Human tissue factor 219 form)
AGCGGCACAACCAACACAGTCGCTGCCTATAACCTCACTTGGAAGAGCAC

CAACTTCAAAACCATCCTCGAATGGGAACCCAAACCCGTTAACCAAGTTT

ACACCGTGCAGATCAGCACCAAGTCCGGCGACTGGAAGTCCAAATGTTTC

TATACCACCGACACCGAGTGCGATCTCACCGATGAGATCGTGAAAGATGT

GAAACAGACCTACCTCGCCCGGGTGTTTAGCTACCCCGCCGGCAATGTGG

AGAGCACTGGTTCCGCTGGCGAGCCTTTATACGAGAACAGCCCCGAATTT

ACCCCTTACCTCGAGACCAATTTAGGACAGCCCACCATCCAAAGCTTTGA

GCAAGTTGGCACAAAGGTGAATGTGACAGTGGAGGACGAGCGGACTTTAG

TGCGGCGGAACAACACCTTTCTCAGCCTCCGGGATGTGTTCGGCAAAGAT

TTAATCTACACACTGTATTACTGGAAGTCCTCTTCCTCCGGCAAGAAGAC
```

-continued

```
AGCTAAAACCAACACAAACGAGTTTTTAATCGACGTGGATAAAGGCGAAA

ACTACTGTTTCAGCGTGCAAGCTGTGATCCCCTCCCGGACCGTGAATAGG

AAAAGCACCGATAGCCCCGTTGAGTGCATGGGCCAAGAAAAGGGCGAGTT

CCGGGAG

(Second IL-15 fragment)
AACTGGGTGAACGTCATCAGCGATTTAAAGAAGATCGAAGATTTAATTCA

GTCCATGCATATCGACGCCACTTTATACACAGAATCCGACGTGCACCCCT

CTTGTAAGGTGACCGCCATGAAATGTTTTTTACTGGAGCTGCAAGTTATC

TCTTTAGAGAGCGGAGACGCTAGCATCCACGACACCGTGGAGAATTTAAT

CATTTTAGCCAATAACTCTTTATCCAGCAACGGCAACGTGACAGAGTCCG

GCTGCAAGGAGTGCGAAGAGCTGGAGGAGAAGAACATCAAGGAGTTTCTG

CAATCCTTTGTGCACATTGTCCAGATGTTCATCAATACCTCC
```

Exemplary Single-Chain Chimeric Polypeptide (IL-15/TF/IL-15) (SEQ ID NO: 169)

```
(Signal peptide)
MKWVTFISLLFLFSSAYS

(Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

(Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE

(Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQNIFINTS
```

The nucleic acid encoding IL-15/TF/IL-15 was cloned into a modified retrovirus expression vector as described previously (Hughes et al., *Hum Gene Ther* 16:457-72, 2005). The expression vector encoding IL-15/TF/IL-15 was transfected into CHO-K1 cells. Expression of the expression vector in CHO-K1 cells allowed for secretion of the soluble IL-15/TF/IL-15 single-chain chimeric polypeptide (referred to as 15t15), which can be purified by anti-TF antibody affinity and other chromatography methods.

15t15 Promotes IL-2Rβ and Common γ Chain Containing 32D/3 Cell Proliferation

IL-15 activity of 15t15 was compared with recombinant IL-15 in IL2Rβ and common γ chain expressed 321313 cells. IL-15 dependent 321313 cells were washed five times with IMDM-10% FBS and seeded to the wells at $2\times10^4$ cells/well. Serial dilutions of 15t15 or IL-15 were added to the cells (FIG. 159). Cells were incubated in a $CO_2$ incubator at 37 °C for 3 days. Cell proliferation was detected by adding 10 μl of WST1 to each well in the day 3 and incubating for an additional 3 hours in a $CO_2$ incubator at 37 °C. The amount of formazan dye produced was analyzed by measuring the absorbance at 450 nm. As shown in FIG. 159, 15t15 promoted 32Dβ cell proliferation less efficiently as compared to IL-15. The $EC_{50}$ of 15t15 and IL-15 was 161.4 pM and 1.6 pM. respectively.

Purification Elution Chromatograph of 15t15 from Anti-TF Antibody Affinity Column 15t15 harvested from cell culture was loaded onto the anti-TF antibody affinity column equilibrated with 5 column volumes of PBS. After sample loading, the column was washed with 5 column volumes of PBS, followed by elution with 6 column volumes of 0.1 M acetic acid, pH 2.9. A280 elution peak was collected and then neutralized to pH 7.5-8.0 with 1 M Tris base. The neutralized sample was then buffer exchanged into PBS using Amicon centrifugal filters with a 30 kDa molecular weight cutoff. As shown in FIG. 160, the anti-TF antibody affinity column bound to 15t15 which contains TF as a fusion domain. The buffer-exchanged protein sample was stored at 2-8 °C for further biochemical analyses and biological activity tests. After each elution, the anti-TF antibody affinity column was stripped using 6 column volumes of 0.1 M glycine, pH 2.5. The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE of 15t15

To determine the purity and molecular weight of the protein, 15t15 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

To verify that the 15t15 protein undergoes glycosylation after translation in CHO cells, a deglycosylation experiment was conducted using the Protein Deglycosylation Mix II kit from New England Biolabs and the manufacturer's instructions. FIGS. 161A and 161B show the reduced SDS-PAGE analysis of the sample in non-deglycosylated (lane 1 in red outline) and deglycosylated (lane 2 in yellow outline) state. The results showed that the 15t15 protein is glycosylated when expressed in CHO cells. After deglycosylation, the purified sample ran with expected molecular weights (50 kDa) in reduced SDS gel. Lane M was loaded with 10 μL of SeeBlue Plus2 Prestained Standard.

Example 63: Stimulation of NK Cells In Vitro

A set of experiments was performed to assess the changes in surface phenotype of NK cells after stimulation with 18t15-12s, 18t15-12s16, and 7t15-21s+anti-TF antibody. In these experiments, fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended at $0.2\times10^6$/mL in a 96-well flat-bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 18t15-12s (100 nM); 18t15-12s16 (100 nM); a mixture of single cytokines rhIL-15 (50 ng/mL) (Miltenyi), rhIL18 (50 ng/mL) (Invivogen), and rhIL-12 (10 ng/mL) (Peprotech); 7t15-21s+anti-TF antibody (100 nM-50 nM); 7t15-21s (100 nM); or anti-TF antibody (50 nM) at 37 °C and 5% $CO_2$ for 16 hours. The next day, the cells were harvested and surface stained for 30 minutes with CD56, CD16, CD25, CD69, CD27, CD62L, NKp30, and NKp44 specific antibodies. After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). FIGS. 162A and 162B shows that overnight incubation of purified NK cells with 18t15-12s, 18t15-12s16, and 7t15-21s+anti-TF antibody resulted in an increase in the percentage of cells expressing CD25, CD69, NKp44, and NKp30 activation markers and a decrease in the percentage of cells expressing CD62L. All activation marker data is from $CD56^+$ gated lymphocytes.

A set of experiments was performed to assess changes in the surface phenotype of lymphocyte populations after stimulation with 18t15-12s, 18t15-12s16, and 7t15-21s. In these experiments, fresh human leukocytes were obtained from the blood bank. Peripheral blood lymphocytes were isolated with the Ficoll-PAQUE Plus (GE Healthcare) density gradient media. The cells were counted and resuspended at $0.2\times10^6$/mL in a 96-well flat-bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 18t15-12s (100 nM); 18t15-12s16 (100 nM), a mixture of single cytokines rhIL-15 (50 ng/mL) (Miltenyi), rhIL18 (50 ng/mL) (Invivogen), and rhIL-12 (10 ng/mL) (Peprotech); 7t15-21s (100 nM)+anti-TF antibody (50 nM); 7t15-21s (100 nM); or anti-TF antibody (50 nM) at 37 °C and 5% $CO_2$ for 16 hours. The next day, the cells were harvested and surface stained for 30 minutes for CD4 or CD8, CD62L, and CD69 specific antibodies. After surface staining, cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). FIG. 163 shows that overnight incubation of purified lymphocyte populations (CD4 and CD8 T cells) with 18t15-12s, 18t15-12s16, or 7t15-21s+anti-TF antibody resulted in an increase in the percentage of CD8 and CD4 T cells expressing CD69. Additionally, incubation with 7t15-21s+anti-TF antibody resulted in an increase in the percentage of CD8 and CD4 T cells expressing CD62L (FIG. 163).

A set of experiments was performed to determine the effect of 18t15-12s on the extracellular acidification rate (ECAR) of NK cells purified from human blood. ECAR can be used to measure glycolysis. Glycolysis is the intracellular biochemical conversion of one molecule of glucose into two molecules of pyruvate with the concurrent generation of two molecules of ATP. An increase in glycolysis was indicated by an increase in ECAR measured by a Seahorse XF96 Analyzer. In these experiments, fresh human leukocytes were obtained from the blood bank and $CD56^+$ NK cells were isolated with the RosetteSep/human NK cell reagent (StemCell Technologies). The purity of NK cells was >70% and confirmed by staining for CD56-BV421, CD16-BV510, CD25-PE, and CD69-APCFire750 antibodies (BioLegend). The cells were counted and resuspended in $0.2\times10^6$/mL in a 96-well flat-bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with either a mixture of single cytokines hIL-12 (10 ng/mL) (Biolegend), hIL-18 (50 ng/mL) (R&D), and hIL-15 (50 ng/mL) (NCI) or 18t15-12s (100 nM) at 37 °C and 5% $CO_2$ for 14-18 hours. The next day, the cells were harvested and washed two times in Seahorse media. The cells ($2\times10^5$ cells/well) were seeded in 96-well flux plates that were coated with 10 μL of poly-L-lysine (Sigma). NK cells were adhered to plates for 30 minutes prior to the assay. Glucose, oligomycin, and 2DG solutions were prepared at 10× concentration in buffered Seahorse medium and injected in port A, B, and C of the calibration plate. ECAR readings were taken every 6.5-7 minutes and ECAR results represent the average readings over 80 minutes or average readings at each timepoint. FIG. 164 shows overnight stimulation of NK cells with 18t15-12s resulted in increased basal ECAR levels. The addition of glucose and oligomycin further showed enhanced glycolysis and glycolytic capacity, respectively, of NK cells stimulated with 18t15-12s overnight (FIG. 164). NK cells treated overnight with media alone or a mixture of IL12, IL18, and IL-15 were used for comparison (FIG. 164).

A set of experiments was performed to determine the increase in phospho-STAT4 and phospho-STAT5 levels in NK cells after stimulation with 18t15-12s. In these experiments, fresh human leukocytes were obtained from the blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, and CD69-APCFire750 specific antibodies (BioLegend). The cells were counted and resuspended in $0.05\times10^6$/mL in a 96-well flat-bottom plate in 0.1 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with hIL-12 (10 ng/mL) (Biolegend) or hIL-15 (50 ng/mL) (NCI) (Single cytokines), or 18t15-12s (100 nM) at 37 °C and 5% $CO_2$ for 90 minutes. Unstimulated NK cells (US) were used as a control. The cells were harvested and fixed in paraformaldehyde (Sigma) to a final concentration of 1.6%. Plates were incubated in the dark at room temperature for 10 minutes. FACS buffer (1×PBS (Hyclone) with 0.5% BSA (EMD Millipore) and 0.001% sodium azide (Sigma)) (100 μL) was added and cells were transferred to 96-well "V" bottom plate. The cells were washed for 1500 RPM for 5 minutes at room temperature. The cell pellet was mixed with 100 μL chilled methanol by gently pipetting up and down, and cells were incubated for 30 minutes at 4 °C. The cells were mixed with 100 mL of FACS buffer and washed for 1500 RPM for 5 minutes at room temperature. The cell pellets were mixed with 50 mL of FACS buffer containing 4 mL of pSTAT4 (BD Bioscience) and pSTAT5 antibodies (BD Bioscience) followed by incubation for 30 minutes at room temperature in the dark. The cells were mixed with 100 mL of FACS buffer and washed for 1500 RPM for 5 minutes at room temperature. The cell pellets were mixed with 50 mL of FACS buffer and cells were analyzed by flow cytometry (Celesta-BD Bioscience). FIG. 165 shows that incubation of NK cells with 18t15-12s induced an increase in pSTAT4 and pSTAT5 (plotted data, normalized fold-change).

A set of experiments was performed to determine the effect of 18t15-12s or a mixture of cytokines (e.g., IL12, IL18, and IL-15) on oxygen consumption rate (OCR) and extracellular acidification rate (ECAR) on NK cells purified from human blood. OCR and ECAR were measured by a Seahorse XF96 Analyzer. In these experiments, fresh human NK cells were isolated from human leukocytes via negative selection using the RosetteSep/human NK cell reagent (StemCell Technologies). Freshly purified NK cells were stimulated overnight (16 h) with either 18t15-12s (100 nM) or a mixture of rhIL12 (10 ng/mL), rhIL18 (50 ng/mL), and rhIL-15 (50 ng/mL) cytokines as a control. The next day, the cells were washed, counted, and equal numbers of cells were plated in buffered Seahorse media. Glucose, oligomycin, and 2DG solutions were prepared at 10× concentration in buffered Seahorse medium and injected in port A, B, and C of the calibration plate. FIG. 166 shows OCR (left) and ECAR (right) data from two individual donors. Overnight stimulation of NK cells with 18t15-12s resulted in an increase in basal ECAR and OCR levels. Addition of glucose and oligomycin further showed enhanced glycolysis and glycolytic capacity, respectively, of NK cells stimulated with 18t15-12s overnight. NK cells treated overnight with media alone or a mixture of IL12, IL18, and IL-15 were used for comparison.

Example 64: Stimulation of NK Cells In Vivo by 2t2 and/or TGFRt15-TGFRs

A set of experiments was performed to determine the effect of the 2t2 construct on immune stimulation in C57BL/6 mice. In these experiments, C57BL/6 mice were subcutaneously treated with control solution (PBS) or 2t2 at 0.1, 0.4, 2, and 10 mg/kg. Treated mice were euthanized 3 days post-treatment. Spleen weight was measured and single splenocyte suspensions were prepared. Splenocytes suspensions were stained with conjugated anti-CD4, anti-CD8, and anti-NK1.1 (NK) antibodies. The percentage of $CD4^+$ T cells, $CD8^+$ T cells, and NK cells, and CD25 expression on lymphocyte subsets were analyzed by flow cytometry. FIG. 167A shows that 2t2 was effective at expanding splenocytes based on spleen weight especially at a dose level of 0.1-10 mg/kg. Following treatment, the percentage of $CD8^+$ T cells were higher in 2t2-treated mice compared to control-treated mice at 2 and 10 mg/kg (FIG. 167B). The percentage of NK cells were also higher in 2t2-treated mice compared to control-treated mice at all doses of 2t2 tested (FIG. 167B). Additionally, 2t2 significantly upregulated CD25 expression by $CD4^+$ T cells, but not $CD8^+$ T cells and NK cells following treatment at 0.4 to 10 mg/kg (FIG. 167C).

A set of experiments was performed to determine the effect of the TGFRt15-TGFRs construct on immune stimulation in C57BL/6 mice. In these experiments, C57BL/6 mice were subcutaneously treated with control solution (PBS) or TGFRt15-TGFRs at 0.3, 1, 3, and 10 mg/kg. The treated mice were euthanized 4 days post-treatment. Spleen weight was measured and single splenocyte suspensions were prepared. The splenocytes suspensions were stained with conjugated anti-CD4, anti-CD8, and anti-NK1.1 (NK) antibodies. The percentage of $CD4^+$ T cells, $CD8^+$ T cells, and NK cells were analyzed by flow cytometry. FIG. 168A shows that spleen weight in mice treated with TGFRt15-TGFRs increased with increasing dosage of TGFRt15-TGFRs. Additionally, spleen weight in mice treated with 1 mg/kg, 3 mg/kg, and 10 mg/kg of TGFRt15-TGFRs were higher as compared to mice treated with the control solution. FIG. 168B shows that the percentages of $CD8^+$ T cells and NK cells both increased with increasing dosage of TGFRt15-TGFRs. Specifically, the percentages of $CD8^+$ T cells were higher in mice treated with 0.3 mg/kg, 3 mg/kg, and 10 mg/kg of TGFRt15-TGFRs compared to control-treated mice, and the percentages of NK cells were higher in mice treated with 0.3 mg/kg, 1 mg/kg, 3 mg/kg, and 10 mg/kg of TGFRt15-TGFRs compared to control-treated mice.

A set of experiments was performed to determine the effect of the TGFRt15-TGFRs construct or 2t2 construct on immune stimulation in $ApoE^{-/-}$ mice fed with a Western diet. In these experiments, 6-week old female B6.129P2-$ApoE^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-weeks of the Western diet, the mice were injected subcutaneously with TGFRt15-TGFRs or 2t2 at 3 mg/kg. Three days post treatment, mice were fasted for 16 hours and then blood samples were collected through retro-orbital venous plexus puncture. The blood was mixed with 10 μL 0.5 M EDTA, and 20 μL blood was taken for lymphocyte subsets analysis. The red blood cells were lysed with ACK (0.15 M $NH_4Cl$, 1.0 mM $KHCO_3$, 0.1 mM $Na_2EDTA$, pH 7.4) and the lymphocytes were stained with anti-mouse CD8a and anti-mouse NK1.1 antibodies for 30 minutes at 4 °C in FACS staining buffer (1% BSA in PBS). The cells were washed once and analyzed with a BD FACS Celesta. For Treg staining, ACK treated blood lymphocytes were stained with anti-mouse CD4 and anti-mouse CD25 antibodies for 30 minutes at 4 °C in FACS staining buffer. The cells were washed once and resuspended in fixation/permeabilization working solution and incubated at room temperature for 60 minutes. The cells were washed once and resuspended in permeabilization buffer. The samples were centrifuged at 300-400×g for 5 minutes at room temperature and the supernatant was then discarded. The cell pellet was resuspended in residual volume and the volume adjusted to about 100 μL with 1× permeabilization buffer. Anti-Foxp3 antibody was added to the cells, and the cells were incubated for 30 minutes at room temperature. Permeabilization buffer (200 μL) was added to the cells, and the cells were centrifuged at 300-400×g for 5 minutes at room temperature. The cells were resuspended in flow cytometry staining buffer and analyzed on a flow cytometer. FIGS. 169B-169C show that treatment with TGFRt15-TGFRs and 2t2 increased the percentage of NK cells and $CD8^+$ T cells in $ApoE^{-/-}$ mice fed with Western diet. FIG. 169A shows that treatment with 2t2 also increased the percentage of Treg cells.

Example 65: Induction of Proliferation of Immune Cells In Vivo

A set of experiments was performed to determine the effect of the 2t2 construct on immune cell stimulation in C57BL/6 mice. In these experiments, C57BL/6 mice were subcutaneously treated with control solution (PBS) or 2t2 at 0.1, 0.4, 2, and 10 mg/kg. Treated mice were euthanized 3 days post-treatment. Spleen weight was measured and single splenocyte suspensions were prepared. The splenocyte suspensions were stained with conjugated anti-CD4, anti-CD8, and anti-NK1.1 (NK) antibodies. The percentage of $CD4^+$ T cells, $CD8^+$ T cells, and NK cells were analyzed by flow cytometry. FIG. 170A shows that 2t2 treatment was effective at expanding splenocytes based on spleen weight especially at 0.1-10 mg/kg. The percentage of $CD8^+$ T cells was higher compared to control-treated mice at 2 and 10 mg/kg (FIG. 170B). Additionally, the percentage of NK cells was higher compared to control-treated mice at all doses of 2t2 tested (FIG. 170B). These results demonstrate that 2t2 treatment was able to induce proliferation of $CD8^+$ T cells and NK cells in C57BL/6 mice.

A set of experiments was performed to determine the effect of the TGFRt15-TGFRs construct on immune stimulation in C57BL/6 mice. In these experiments, C57BL/6 mice were subcutaneously treated with control solution (PBS) or TGFRt15-TGFRs at 0.1, 0.3, 1, 3, and 10 mg/kg. The treated mice were euthanized 4 days post-treatment. Spleen weight was measured and splenocyte suspensions were prepared. The splenocyte suspensions were stained with conjugated anti-CD4, anti-CD8, and anti-NK1.1 (NK) antibodies. The cells were additionally stained for proliferation marker Ki67. FIG. 171A shows that spleen weight in mice treated with TGFRt15-TGFRs increased with increasing dosage of TGFRt15-TGFRs. Additionally, spleen weight in mice treated with 1 mg/kg, 3 mg/kg, and 10 mg/kg of TGFRt15-TGFRs was higher as compared to mice treated with just the control solution. The percentages of $CD8^+$ T cells and NK cells both increased with increasing dosage of TGFRt15-TGFRs (FIG. 171B). Finally, TGFRt15-TGFRs significantly upregulated expression of cell proliferation marker Ki67 in both $CD8^+$ T cells and NK cells at all doses of TGFRt15-TGFRs tested. These results demonstrate that TGFRt15-TGFRs treatment induced proliferation of both $CD8^+$ T cells and NK cells in C57BL/6 mice.

A set of experiments was performed to determine the effect of the TGFRt15-TGFRs construct or the 2t2 construct on immune stimulation in $ApoE^{-/-}$ mice fed with a Western diet. In these experiments, 6-week old female B6.129P2-$ApoE^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-week of the Western diet, the mice were injected subcutaneously with TGFRt15-TGFRs or 2t2 at 3 mg/kg. Three days post-treatment, the mice were fasted for 16 hours and then blood samples were collected through retro-orbital venous plexus puncture. The blood was mixed with 10 μL 0.5 M EDTA and 20 μL blood was taken for lymphocyte subsets analysis. The red blood cells were lysed with ACK (0.15 M $NH_4Cl$, 1.0 mM $KHCO_3$, 0.1 mM $Na_2EDTA$, pH 7.4) and the lymphocytes were stained with anti-mouse CD8a and anti-mouse NK1.1 antibodies for 30 minutes at 4 °C in FACS staining buffer (1% BSA in PBS). The cells were washed once and resuspended in Fixation Buffer (BioLegend Cat #420801) for 20 minutes at room temperature. The cells were centrifuged at 350×g for 5 minutes, the fixed cells were resuspended in Intracellular Staining Permeabilization Wash Buffer (BioLegend Cat #421002) and then centrifuged at 350×g for 5 minutes. The cells were then stained with anti-Ki67 antibody for 20 minutes at RT. The cells were washed twice with Intracellular Staining Permeabilization Wash Buffer and centrifuged at 350×g for 5 minutes. The cells were then resuspended in FACS staining buffer. Lymphocyte subsets were analyzed with a BD FACS Celesta. As described in FIG. 172A, treatment of $ApoE^{-/-}$ mice with TGFRt15-TGFRs induced proliferation (Ki67-positive staining) in NK and $CD8^+$ T cells. Additionally, FIG. 172B shows treatment of $ApoE^{-/-}$ mice with 2t2 also induced proliferation (Ki67-positive staining) in NK and $CD8^+$ T cells.

A set of experiments was performed to determine the effect 7t15-21s+anti-TF antibody-expanded NK cells in NSG mice following treatment with 7t15-21s, TGFRt15-TGFRs, and 2t2. In these experiments, fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended in $2\times10^6$/mL in a 24-well flat-bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 7t15-21s (100 nM) and anti-TF antibody (50 nM) for 15 days. After every 2 days, the cells were resuspended at $2\times10^6$/mL with fresh media containing 100 nM 7t15-21s and 50 nM of anti-TF antibody. As the volume of the cultures increased, the cells were transferred to higher volume flasks. The cells were counted using trypan blue to access the fold-expansion. 7t15-21s+anti-TF antibody-expanded NK cells were washed three times in warm HBSS Buffer (Hyclone) at 1000 RPM for 10 minutes at room temperature. The 7t15-21s+anti-TF antibody-expanded-NK cells were resuspended in $10\times10^6$/0.2 mL HBSS buffer and injected intravenously into the tail vein of NSG mice (NOD scid gamma mouse) (Jackson Laboratories). The transferred NK cells were supported every 48 hours with either 7t15-21s (10 ng/dose, i.p.), TGFRt15-TGFRs (10 ng/dose, i.p.) or 2t2 (10 ng/dose, i.p.) for up to 21 days. Engraftment and persistence of the human 7t15-21s+anti-TF antibody-expanded NK cells were measured every week in blood staining for hCD45, mCD45, hCD56, hCD3, and hCD16 antibodies by flow cytometry (Celesta-BD Bioscience) (Data represent 3 mice per group). FIG. 173 indicates that treatment of mice bearing adoptively-transferred 7t15-21s+ anti-TF antibody-expanded NK cells with 7t15-21s-, TGFRt15-TGFRs-, or 2t2-induced expansion and persistence of the adoptively transferred NK cells compared to control treated mice.

Example 66: NK-Mediated Cytotoxicity Following Treatment with Single-Chain Constructs or Multi-Chain Constructs A set of experiments was performed to determine if treatment of NK cells with TGFRt15-TGFRs enhanced cytotoxicity of NK cells. In these experiments, Human Daudi B lymphoma cells were labeled with CELLTRACE™ Violet (CTV) (cell proliferation kit for flow cytometry) and used as tumor target cells. Mouse NK effector cells were isolated with NK1.1-positive selection using a magnetic cell sorting method (Miltenyi Biotec) of C57BL/6 female mouse spleens 4 days post TGFRt15-TGFRs subcutaneous treatment at 3 mg/kg. Human NK effector cells were isolated from peripheral blood mononuclear cells derived from human blood buffy coats with the RosetteSep/human NK cell reagent (Stemcell Technologies). The target cells (Human Daudi B lymphoma cells) were mixed with effector cells (either mouse NK effector cells or human NK effector cells) in the presence of 50 nM TGFRt15-TGFRs or in the absence of TGFRt15-TGFRs (control) and incubated at 37 °C for 44 hours for mouse NK cells and for 20 hours for human NK cells. Target cell (Daudi) viability was assessed by analysis of propidium iodide-positive, CTV-labeled cells using flow cytometry. The percentage of Daudi inhibition was calculated using the formula (1-viable tumor cell number in experimental sample/viable tumor cell number in the sample without NK cells)×100. FIG. 174 shows that mouse (FIG. 174A) and human (FIG. 174B) NK cells had significantly stronger cytotoxicity against Daudi B cells following NK cell activation with TGFRt15-TGFRs than in the absence of TGFRt15-TGFRs activation.

A set of experiments was performed to determine antibody-dependent cellular cytotoxicity (ADCC) of mouse and human NK cells following treatment with TGFRt15-TGFRs. In these experiments, human Daudi B lymphoma cells were labeled with CellTrace Violet (CTV) and used as tumor target cells. Mouse NK effector cells were isolated with NK1.1-positive selection using a magnetic cell sorting method (Miltenyi Biotec) of C57BL/6 female mouse spleens 4 days post-TGFRt15-TGFRs subcutaneous treatment at 3 mg/kg. Human NK effector cells were isolated from peripheral blood mononuclear cells derived from human blood buffy coats with the RosetteSep/human NK cell reagent (Stemcell Technologies). The target cells (Daudi B cells) were mixed with effector cells (either mouse NK effector cells or human NK effector cells) in the presence of anti-CD20 antibody (10 nM Rituximab, Genentech) and in the presence of 50 nM TGFRt15-TGFRs, or in the absence of TGFRt15-TGFRs (control) and incubated at 37 °C for 44 hours for mouse NK cells and for 20 hours for human NK cells. The Daudi B cells express the CD20 targets for the anti-CD20 antibody. Target cell viability was assessed after incubation by analysis of propidium iodide-positive, CTV-labeled target cells using flow cytometry. The percentage of Daudi inhibition was calculated using the formula (1-viable tumor cell number in experimental sample/viable tumor cell number in the sample without NK cells)×100. FIG. 175 shows that mouse NK cells (FIG. 175A) and human NK cells (FIG. 175B) had stronger ADCC activity against Daudi B cells following NK cell activation with TGFRt15-TGFRs than in the absence of TGFRt15-TGFRs activation.

A set of experiments was performed to determine cytotoxicity of TGFRt15-TGFRs-activated mouse NK cells towards senescent B16F10 melanoma cells. In these experiments, mouse NK cells were activated in vivo by injecting C57BL/6 mice with 10 mg/kg of TGFRt15-TGFRs for 4 days followed by isolation of splenic NK cells. The NK cells were then expanded in vitro for 7 days in the presence of 100 nM 2t2. The B16F10 senescent target cells (B16F10-SNC) were labelled with CellTrace Violet (CTV) and incubated at different Effector:Target (E:T) ratios with the activated mouse NK effector cells for 16 hours. The cells were trypsinized, washed, and resuspended in complete media containing propidium iodide (PI) solution. The cytotoxicity of the TGFRt15-TGFRs/2t2-activated NK cells against the senescent cell targets was accessed by flow cytometry based on PI staining of the CTV-labeled cells. The findings demonstrate that in vivo activation of NK cells with TGFRt15-TGFRs followed by in vitro expansion and activation with 2t2 resulted in increased killing of senescent melanoma tumor cells by the NK cells (FIG. 176).

Example 67: Treatment of Cancer, Diabetes, and Atherosclerosis

Figure 177A:
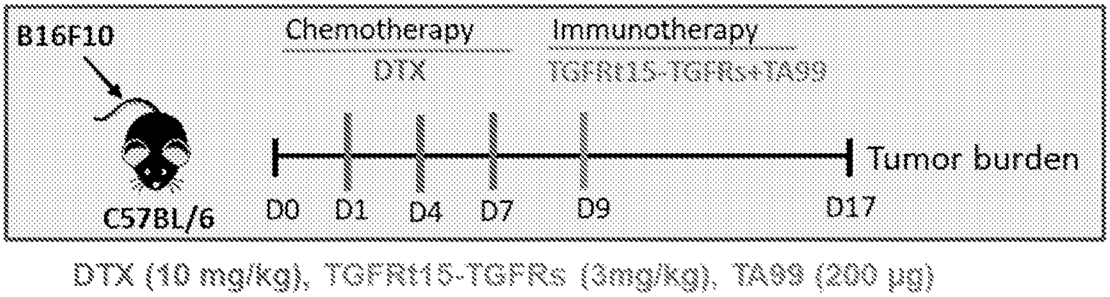
Figure 177B:
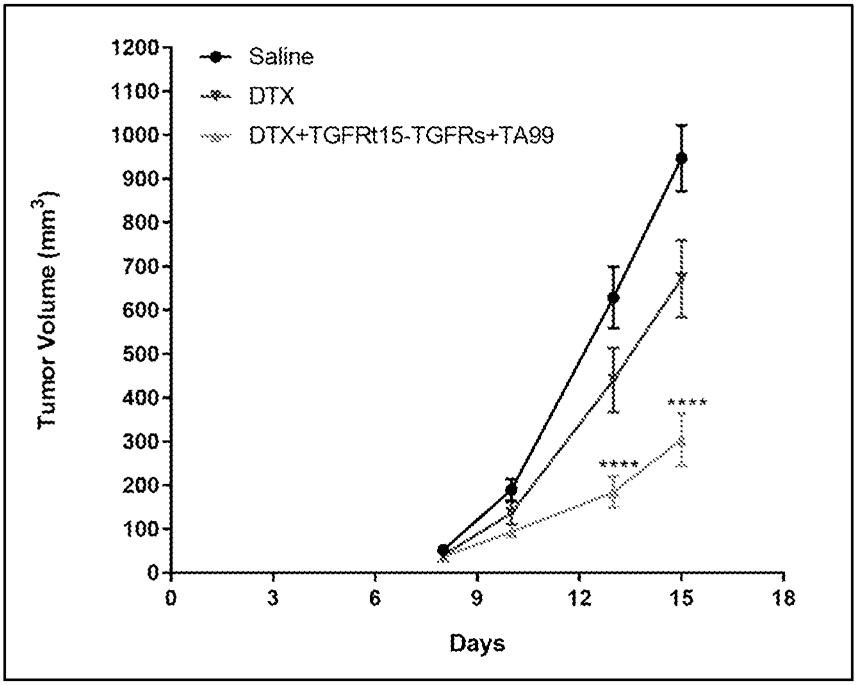

A set of experiments was performed to assess antitumor activity of TGFRt15-TGFRs plus anti-TRP1 antibody (TA99) in combination with chemotherapy in a melanoma mouse model. In these experiments, C57BL/6 mice were subcutaneously injected with $0.5\times10^6$ B16F10 melanoma cells. The mice were treated with three doses of chemotherapy docetaxel (10 mg/kg) (DTX) on day 1, day 4, and day 7, followed by treatment with single dose of combination immunotherapy TGFRt15-TGFRs (3 mg/kg)+anti-TRP1 antibody TA99 (200 µg) on day 9. FIG. 177A shows a schematic of the treatment regimen. Tumor growth was monitored by caliper measurement, and tumor volume was calculated using the formula $V=(L\times W^2)/2$, where L is the largest tumor diameter and W is the perpendicular tumor diameter. FIG. 177B shows that treatment with DTX+TGFRt15-TGFRs+TA99 significantly reduced tumor growth compared to saline control and DTX treatment groups (N=10, ****p<0.001, Multiple t test analyses).

Figure 177C:
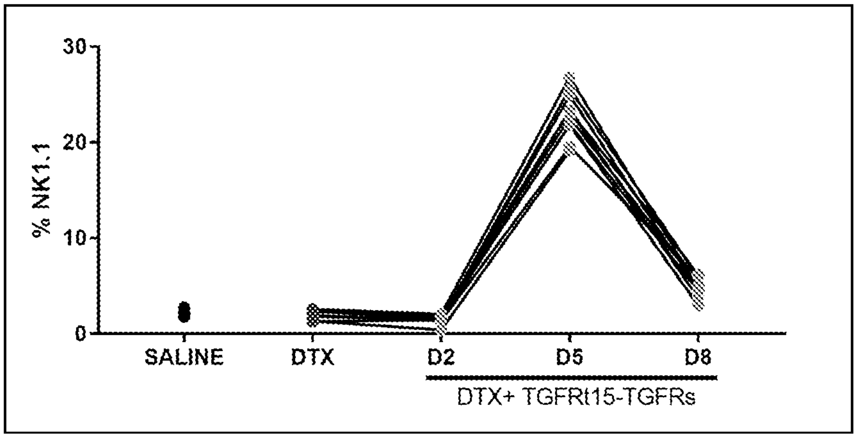
Figure 177D:
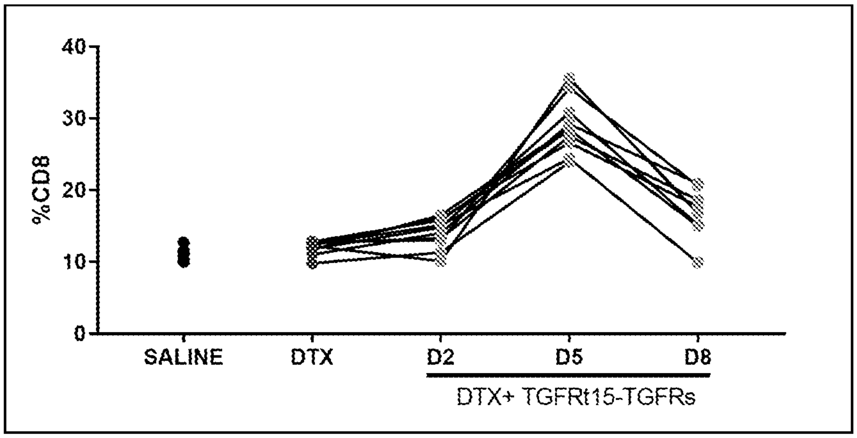
Figure 177E:
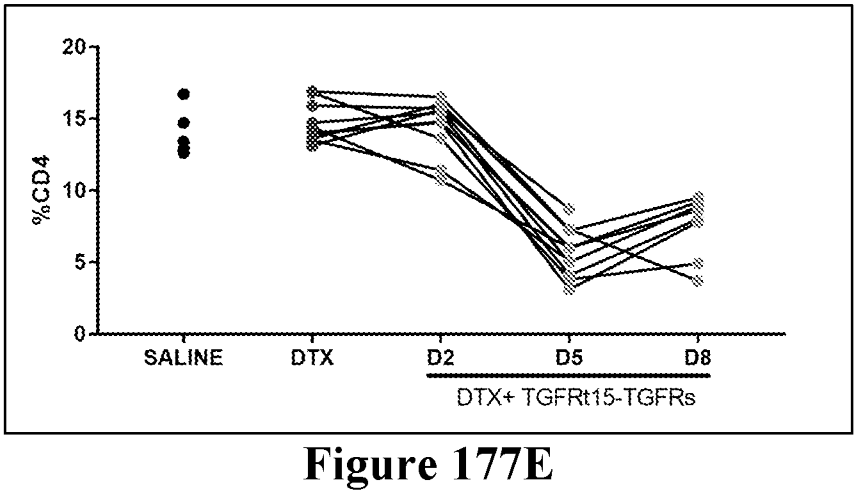

To assess immune cell subsets in the B16F10 tumor model, peripheral blood analysis was performed. In these experiments, C57BL/6 mice were injected with B16F10 cells and treated with DTX, DTX+TGFRt15-TGFRs+TA99, or saline. Blood was drawn from the submandibular vein of B16F10 tumor-bearing mice on days 2, 5, and 8 post-immunotherapy for the DTX+TGFRt15-TGFRs+TA99 group and day 11 post-tumor injection for the DTX and saline groups. RBCs were lysed in ACK lysis buffer and the lymphocytes were washed and stained with anti-NK1.1, anti-CD8, and anti-CD4 antibodies. The cells were analyzed by flow cytometry (Celesta-BD Bioscience). FIGS. 177C-177E show that DTX+TGFRt15-TGFRs+TA99 treatment induced an increase in the percentage of NK cells and $CD8^+$ T cells in the tumors compared to the saline and DTX treatment groups.

Figure 177F:
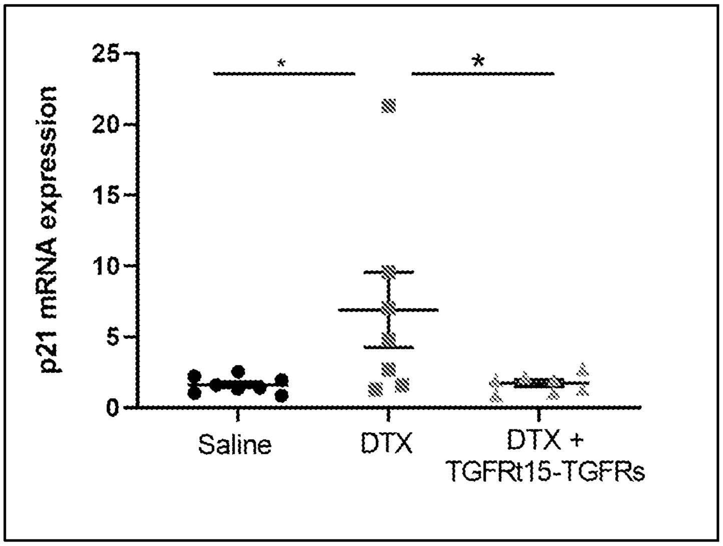
Figure 177G:
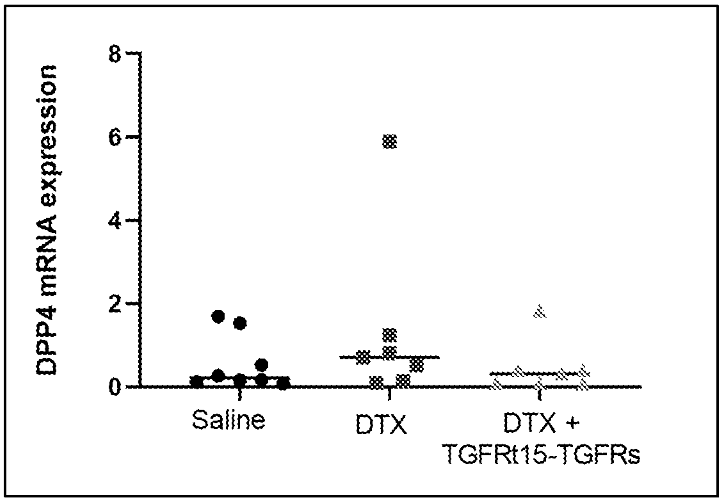
Figure 177H:
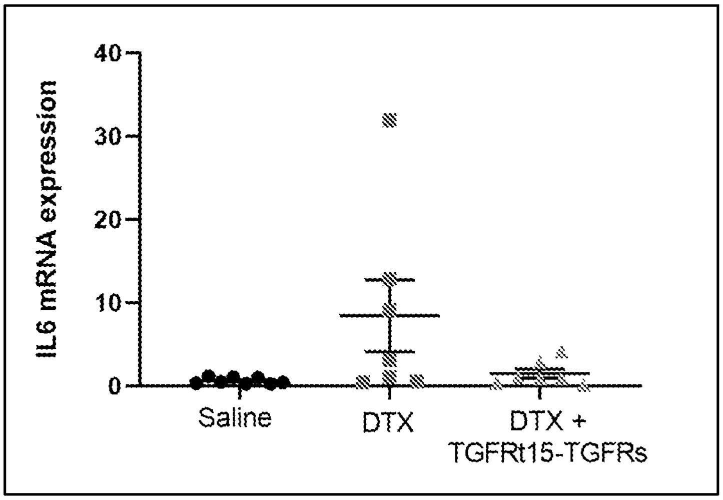

On day 17, total RNA was extracted from tumors of mice treated with saline, DTX or DTX TGFRt15+TGFRs TA99 using Trizol. Total RNA (1 μg) was used for cDNA synthesis using the QUANTITECT® Reverse Transcription Kit (Qiagen)(kit for cDNA synthesis with integrated removal of genomic DNA contamination). Real-time PCR was carried out with CFX96 Detection System (Bio-Rad) using FAM-labeled predesigned primers for senescence cell markers, (F) p21 (G) DPP4 and (H) IL6. The housekeeping gene 18S ribosomal RNA was used as an internal control to normalize the variability in expression levels. The expression of each target mRNA relative to 18S rRNA was calculated based on Ct as $2^{-\Delta(\Delta Ct)}$, in which $\Delta Ct=Ct_{target}-Ct_{18S}$. The data is presented as fold-change as compared to saline control. FIG. 177F-177H show that DTX treatment induced an increase in senescent tumor cells that were subsequently reduced following treatment with TGFRt15-TGFRs+TA99 immunotherapy.

A set of experiments was performed to investigate amelioration of Western diet-induced hyperglycemia in $ApoE^{-/-}$ mice by 2t2. In these experiments, 6-week old female B6.129P2-$ApoE^{tm1Unc}$/J mice (Jackson Laboratory) were fed with a Western diet containing 21% fat, 0.15% cholesterol, 34.1% sucrose, 19.5% casein, and 15% starch (TD88137, Envigo Laboratories). After 8-weeks of the Western diet, the mice were injected subcutaneously with TGFRt15-TGFRs or 2t2 at 3 mg/kg. Three days post-treatment, the mice were fasted for 16 hours and then blood samples were collected through retro-orbital venous plexus puncture. Blood glucose was detected with a glucose meter (OneTouch UltraMini) and GenUltimated test strips using a drop of fresh blood. As shown in FIG. 178A, 2t2 treatment significantly reduced hyperglycemia induced by the Western diet (p<0.04). The plasma insulin and resistin levels were analyzed with Mouse Rat Metabolic Array by Eve Technologies. HOMA-IR was calculated using the following formula: homeostatic model assessment-insulin resistance=Glucose (mg/dL)*Insulin (mU/mL)/405. As shown in FIG. 178B, both 2t2 and TGFRt15-TGFRs treatment reduced insulin resistance compared to the untreated group. Both 2t2 (p<0.02) and TGFRt15-TGFRs (p<0.05) reduced resistin levels significantly compared to the untreated group as shown in FIG. 178C, which may relate to the reduced insulin resistance induced by 2t2 and TGFRt15-TGFRs (Figure F3B).

Example 68: Induction of Differentiation of NK Cells into Cytokine-Induced Memory Like NK Cells A set of experiments was performed to assess the differentiation of NK cells into cytokine-induced memory like NK Cells (CIMK-NK Cells) after stimulation with 18t15-12s. In these experiments, fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended in $2\times10^6$/mL in a 24-well flat-bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were unstimulated ("No Spike") or stimulated with 18t15-12s (100 nM) or a mixture of single cytokines including rhIL-15 (50 ng/mL) (Miltenyi), rhIL18 (50 ng/mL) (Invivogen), and rhIL-12 (10 ng/mL) (Peprotech) ("single cytokines") at 37 °C and 5% $CO_2$ for 16 hrs. The next day, the cells were harvested, and washed two times with warm complete media at 1000 RPM for 10 minutes at room temperature. The cells were resuspended at $2\times10^6$/mL in a 24-well flat-bottom plate in 2 mL of complete media with rhIL-15 (1 ng/mL). After every 2 days, half of the medium was replaced with fresh complete media containing rhIL-15.

To assess the change in memory phenotype of NK cells at day 7, the cells were stained with antibodies to cell-surface CD56, CD16, CD27, CD62L, NKp30, and NKp44 (BioLegend). After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). FIG. 179 shows that incubation of NK cells with 18t15-12s resulted in an increase in the percentage of $CD16^+CD56^+$ NK cells expressing CD27, CD62L, and NKp44, and an increase in the levels (MFI) of NKp30 in $CD16^+CD56^+$ NK cells.

Example 69. Upregulation of CD44 Memory T Cells

C57BL/6 mice were subcutaneously treated with TGFRt15-TGFRs or 2t2. The treated mice were euthanized and the single splenocyte suspensions were prepared 4 days (TGFRt15-TGFRs) or 3 days (2t2) following the treatment. The prepared splenocytes were stained with fluorochrome-conjugated anti-CD4, anti-CD8 and anti-CD44 antibodies and the percentages of $CD44^{high}$ T cells in $CD4^+$ T cells or $CD8^+$ T cells were analyzed by flow cytometry. The results show that TGFRt15-TGFRs and 2t2 upregulated expression of the memory marker CD44 on CD4+ and CD8+ T cells (FIG. 180). These findings indicate that TGFRt15-TGFRs and 2t2 molecules were able to induce mouse T cells to differentiate into memory T cells.

Example 70: Improvement of the Texture and/or Appearance and/or Hair

To examine the effect of 2t2 on hair regrowth, dorsal hair of C57BL6/J mice (Jackson Laboratory) was first shortened with clippers followed by application of depilatory cream (Nair) to the shaved region for a period of 30 seconds before wiping clean. After 4 hours, 2t2 (3 mg/kg, single dose), low dose recombinant IL-2 (25000 IU, 5 consecutive days, 1 dose/day), or PBS were administered subcutaneously. The mice were monitored for skin pigmentation related to hair regrowth and pictures were taken and analyzed using the Image J software. FIG. 181A shows skin pigmentation 10 days after depilation in PBS-, 2t2-, or IL-2-treated mice. FIG. 181B shows the percent pigmentation in each group of mice 10 days post-treatment as analyzed using the Image J software. The results showed that treatment of mice with 2t2 or IL-2 promoted hair regrowth following depilation compared to PBS-treated mice.

Dorsal hair of C57BL6/J mice (Jackson Laboratory) was first shortened with clippers before applying depilatory cream (Nair) to the shaved region for a period of exactly 30 seconds before wiping clean. After 4 hours, 2t2 (3 mg/kg, single dose), low dose recombinant IL-2 (25000 IU, 5 consecutive days, 1 dose/day) or PBS were administered subcutaneously. The mice were monitored for skin pigmentation related to hair regrowth and pictures were taken and analyzed using Image J software. FIG. 182 shows skin pigmentation 14 days after depilation in PBS-, 2t2-, or IL-2-treated mice. The results showed that treatment of mice with 2t2 or IL-2 promoted hair regrowth following depilation compared to the PBS-treated mice.

Example 71: Tissue Factor Coagulation Assays Following Treatment with Single-Chain or Multi-Chain Chimeric Polypeptides A set of experiments was performed to assess blood coagulation following treatment with single-chain or multi-chain chimeric polypeptides. To initiate the blood coagulation cascade pathway, tissue factor (TF) binds to Factor VIIa (FVIIa) to form a TF/FVIIa complex. The TF/FVIIa complex then binds Factor X (FX) and converts FX to FXa.

Factor VIIa (FVIIa) Activity Assay

One assay to measure blood coagulation involves measuring Factor VIIa (FVIIa) activity. This type of assay requires the presence of tissue factor and calcium. The TF/FVIIa complex activity can be measured by a small substrate or by a natural protein substrate, for example, Factor X (FX). When FX is used as a substrate, phospholipids are also required for TF/FVIIa activity. In this assay, FVIIa activity is determined with FVIIa-specific chromogenic substrate S-2288 (Diapharma, West Chester, OH). The color change of the S-2288 substrate can be measured spectrophotometrically and is proportional to the proteolytic activity of FVIIa (e.g., the TF/FVIIa complex).

In these experiments, the FVIIa activity of the following groups were compared: the 219-amino acid extracellular domain of tissue factor domain ($TF_{219}$), a multi-chain chimeric polypeptide with a wild-type tissue factor domain, and a multi-chain chimeric polypeptide with a mutant tissue factor domain. The chimeric polypeptides containing mutant tissue factor molecules were constructed with mutations to the TF domain at amino acid sites: Lys20, Ile22, Asp58, Arg135, and Phe140.

In order to assess activity of FVIIa, FVIIa, and $TF_{219}$ or a $TF_{219}$-containing multi-chain chimeric polypeptide were mixed at an equal molar concentration (10 nM) in all wells of a 96-well ELISA plate in a total volume of 70 μL. After incubation for 10 minutes at 37 °C, 10 μL of 8 mM S-2288 substrate was added to start the reaction. The incubation was then kept at 37 °C for 20 minutes. Finally, color change was monitored by reading absorbance at 405 nm. The OD values of different TF/VIIa complexes are shown in Table 1 and Table 2. Table 1 shows a comparison of $TF_{219}$, 21t15-21s wild-type (WT) and 21t15-21s mutant (Mut). Table 2 shows a comparison of $TF_{219}$, 21t15-TGFRs wild-type (WT), and 21t15-TGFRs mutant (Mut). These data show that $TF_{219}$-containing multi-chain chimeric polypeptides (e.g., 21t15-21s-WT, 21t15-21s-Mut, 21t15-TGFRS-WT, and 21t15-TGFRS-Mut) have lower FVIIa activity than $TF_{219}$ when the chromogenic S-2288 was used as a substrate. Notably, the multi-chain chimeric polypeptides containing $TF_{219}$ mutations showed much lower FVIIa activity when compared to multi-chain chimeric polypeptides containing wild type $TF_{219}$.

TABLE 1

| FVIIa activity | |
|---|---|
| Molecule | OD value at 405 nm |
| $TF_{219}$ | 0.307 |
| 21t15/21S-WT | 0.136 |
| 21t15/21S-Mut | 0.095 |

WT: wild type of $TF_{219}$, Mut: $TF_{219}$ containing mutations.

TABLE 2

| FVIIa activity | |
|---|---|
| Molecule | OD value at 405 nm |
| $TF_{219}$ | 0.345 |
| 21t15/TGFRS-WT | 0.227 |
| 21t15/TGFRS-Mut | 0.100 |

WT: wild type of $TF_{219}$, Mut: $TF_{219}$ containing mutations.

Factor X (FX) Activation Assay

An additional assay to measure blood coagulation involves measuring activation of Factor X (FX). Briefly, TF/VIIa activates blood coagulation Factor X (FX) to Factor Xa (FXa) in the presence of calcium and phospholipids. $TF_{243}$, which contains the transmembrane domain of TF, has much higher activity in activating FX to FXa than $TF_{219}$, which does not contain the transmembrane domain. TF/VIIa dependent activation of FX is determined by measuring FXa activity using an FXa-specific chromogenic substrate S-2765 (Diapharma, West Chester, OH). The color change of S-2765 can be monitored spectrophotometrically and is proportional to the proteolytic activity of FXa.

In these experiments, FX activation with a multi-chain chimeric polypeptide (18t15-12s, mouse (m)21t15, 21t15-TGFRs, and 21t15-7s) was compared with a positive control (Innovin) or $TF_{219}$. $TF_{219}$ (or $TF_{219}$-containing multi-chain chimeric polypeptides)/FVIIa complexes were mixed at an equal molar concentration (0.1 nM each) in a volume of 50 μL in round bottom wells of a 96-well ELISA plate, after which 10 μL of 180 nM FX was added. After 15 minutes of incubation at 37 °C, during which time FX was converted to FXa, 8 μL of 0.5 M EDTA (which chelates calcium and thus terminates FX activation by TF/VIIa) was added to each well to stop FX activation. Next, 10 μL of 3.2 mM S-2765 substrate was added to the reaction mixture. Immediately, the plate absorbance was measured at 405 nm and was recorded as the absorbance at time 0. The plate was then incubated for 10-20 minutes at 37 °C. The color change was monitored by reading absorbance at 405 nm following the incubation. Results of FX activation as measured by FXa activity using chromogenic substrate S-2765 are shown in FIG. 183. In this experiment, Innovin, which is a commercial prothrombin reagent containing lipidated recombinant human $TF_{243}$, was used as a positive control for FX activation. Innovin was reconstituted with purified water to about nM of $TF_{243}$. Next, 0.1 nM TF/VIIa complex was made by mixing an equal volume of 0.2 nM of FVIIa with 0.2 nM of Innovin. Innovin demonstrated very potent FX activation activity, while $TF_{219}$ and $TF_{219}$-containing multi-chain chimeric polypeptides had very low FX activation activity, confirming that $TF_{219}$ is not active in a TF/FVIIa complex for activating natural substrate FX in vivo.

Prothrombin Time Test

A third assay to measure blood coagulation is the prothrombin time (PT) test, which measures blood clotting activity. Here, the PT test was performed using commercially available normal human plasma (Ci-Trol Coagulation Control, Level I). For a standard PT test, clot reactions were initiated by addition of Innovin, a lipidated recombinant human $TF_{243}$, in the presence of calcium. Clotting time was monitored and reported by STart PT analyzer (Diagnostica Stago, Parsippany, N.J.). PT assays were started by injecting 0.2 mL of various dilutions of Innovin diluted in PT assay buffer (50 mM Tris-HCl, pH 7.5, 14.6 mM $CaCl_2$), 0.1% BSA) into cuvettes containing 0.1 mL of normal human plasma prewarmed at 37 °C. In the PT assay, shorter PT time (clotting time) indicates a higher TF-dependent clotting activity while longer PT (clotting time) means lower TF-dependent clotting activity.

As seen in FIG. 184, addition of different amounts of Innovin (e.g., Innovin reconstituted with purified water equivalent to 10 nM of lipidated recombinant human $TF_{243}$ was considered to be 100% Innovin) to the PT assay demonstrated a dose-response relationship, where lower concentrations of $TF_{243}$ resulted in a longer PT time (lower clotting activity). For example, 0.001% Innovin had a PT time greater than 110 seconds, which was almost the same as buffer alone.

In another experiment, the PT test was conducted on $TF_{219}$ and multi-chain chimeric polypeptides including: 18t15-12s, 7t15-21s, 21t15-TGFRs-WT, and 21t15-TGFRs-Mut. FIG. 185 show that $TF_{219}$ and $TF_{219}$-containing multi-chain chimeric polypeptides (at a concentration of 100 nM) had prolonged PT times indicating extremely low or no clotting activity.

Studies were also conducted to evaluate whether incubating the multi-chain chimeric polypeptides in the presence of other cells carrying receptors for the cytokine components of the multi-chain chimeric polypeptide (32Dβ or human PBMCs) would affect the clotting time in the PT assay. To examine whether cells that express IL-15 receptor (32Dβ cells) or IL-15 and IL-21 receptors (PBMCs) would bind IL-15-containing multi-chain chimeric polypeptides to mimic natural TF as a cellular FVIIa receptor, $TF_{219}$-containing multi-chain chimeric polypeptides (at a concentration of 100 nM for each molecule) were diluted in the PT assay buffer and preincubated with 32Dβ cells (at $2\times10^5$ cells/mL) or PBMC (at $1\times10^5$ cells/mL) for 20-30 minutes at room temperature. The PT assay was then conducted as described above. FIGS. 186 and 187 shows that $TF_{219}$ and $TF_{219}$-containing multi-chain chimeric polypeptides mixed with 32Dβ cells (FIG. 186) or PBMC (FIG. 187) at a final concentration of 100 nM had prolonged PT times similar to 0.001-0.01% Innovin (equivalent to 0.1 pM to 1.0 pM of $TF_{243}$). Expressed in percentage of relative $TF_{243}$ activity, $TF_{219}$-containing multi-chain chimeric polypeptides had 100,000 to 1,000,000 times lower TF dependent clotting activity when compared to Innovin. This demonstrated that $TF_{219}$-containing multi-chain chimeric polypeptides had extremely low or no TF-dependent clotting activity, even while the molecules were bound to an intact cell membrane surface, such as 32Dβ or PBMCs.

Example 72: Characterization of 7t15-21s137L (Long Version)

The nucleic acid sequence of the 7t15 construct (including signal peptide sequence) is as follows (SEQ ID NO: 210):

```
(Signal peptide)
ATGAAGTGGGTGACCTTCATCAGCCTGCTGTTCCTGTTCTCCAGCGCCT

ACTCC

(Human IL7)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT

(Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG

(Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA
```

-continued

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

The amino acid sequence of 7t15 fusion protein (including the leader sequence) is as follows (SEQ ID NO: 209):

(Signal peptide)
MKWVTFISLLFLFSSAYS (Human IL7)
DCDIEGKDGKQYESVLMVSIDQLLDSMKEIGSNCLNNEFNFFKRHICDAN

KEGMFLFRAARKLRQFLKMNSTGDFDLHLLKVSEGTTILLNCTGQVKGRK

PAALGEAQPTKSLEENKSLKEQKKLNDLCFLKRLLQEIKTCWNKILMGTK

EH (Human Tissue Factor 219)
SGTTNTVAAYNLTWKSTNFKTILEWEPKPVNQVYTVQISTKLSGDWKSKC

FYTTDTECDLTDEIVKDVKQTYLARVFSYPAGNVESTGSAGEPLYENSPE

FTPYLETNLGQPTIQSFEQVGTKVNVTVEDERTLVRRNNTFLSLRDVFGK

DLIYTLYYWKSSSSGKKTAKTNTNEFLIDVDKGENYCFSVQAVIPSRTVN

RKSTDSPVECMGQEKGEFRE (Human IL 15)
NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMEFINTS

The nucleic acid sequence of the 21s137L construct (including signal peptide sequence) is as follows (SEQ ID NO: 331):

(Signal peptide)
ATGAAGTGGGTGACCTTCATCAGCCTGCTGTTCCTGTTCTCCAGCGCCTA

CTCC (Human IL 21)
CAGGGCCAGGACAGGCACATGATCCGGATGAGGCAGCTCATCGACATCGT

CGACCAGCTGAAGAACTACGTGAACGACCTGGTGCCCGAGTTTCTGCCTG

CCCCCGAGGACGTGGAGACCAACTGCGAGTGGTCCGCCTTCTCCTGCTTT

CAGAAGGCCCAGCTGAAGTCCGCCAACACCGGCAACAACGAGCGGATCAT

CAACGTGAGCATCAAGAAGCTGAAGCGGAAGCCTCCCTCCACAAACGCCG

GCAGGAGGCAGAAGCACAGGCTGACCTGCCCCAGCTGTGACTCCTACGAG

AAGAAGCCCCCCAAGGAGTTCCTGGAGAGGTTCAAGTCCCTGCTGCAGAA

GATGATCCATCAGCACCTGTCCTCCAGGACCCACGGCTCCGAGGACTCC (Human IL 15R α sushi domain)
ATTACATGCCCCCCTCCCATGAGCGTGGAGCACGCCGACATCTGGGTGAA

GAGCTATAGCCTCTACAGCCGGGAGAGGTATATCTGTAACAGCGGCTTCA

AGAGGAAGGCCGGCACCAGCAGCCTCACCGAGTGCGTGCTGAATAAGGCT

ACCAACGTGGCTCACTGGACAACACCCTCTTTAAAGTGCATCCGG

-continued ((G48)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGACCT

GCGGCAGGGCATGTTTGCGCAGCTGGTGGCCCAAAATGTTCTGCTGATCG

ATGGGCCCCTGAGCTGGTACAGTGACCCAGGCCTGGCAGGCGTGTCCCTG

ACGGGGGGCCTGAGCTACAAAGAGGACACGAAGGAGCTGGTGGTGGCCAA

GGCTGGAGTCTACTATGTCTTCTTTCAACTAGAGCTGCGGCGCGTGGTGG

CCGGCGAGGGCTCAGGCTCCGTTTCACTTGCGCTGCACCTGCAGCCACTG

CGCTCTGCTGCTGGGGCCGCCGCCCTGGCTTTGACCGTGGACCTGCCACC

CGCCTCCTCCGAGGCTCGGAACTCGGCCTTCGGTTTCCAGGGCCGCTTGC

TGCACCTGAGTGCCGGCCAGCGCCTGGGCGTCCATCTTCACACTGAGGCC

AGGGCACGCCATGCCTGGCAGCTTACCCAGGGCGCCACAGTCTTGGGACT

CTTCCGGGTGACCCCCGAAATCCCAGCCGGACTCCCTTCACCGAGGTCGG

AA

The amino acid sequence of 21s137L fusion protein (including the leader sequence) is as follows (SEQ ID NO: 332):

(Signal peptide)
MKWVTFISLLFLFSSAYS (Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLNK

ATNVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGVS

LTGGLSYKEDTKELVVAKAGVYYVFFQLELRRVVAGEGSGSVSLALHLQ

PLRSAAGAAALALTVDLPPASSEARNSAFGFQGRLLHLSAGQRLGVHLH

TEARARHAWQLTQGATVLGLFRVTPEIPAGLPSPRSE

The following experiment was conducted to evaluate whether the CD137L portion in 7t15-21s137L was intact to bind to CD137 (4.1BB). On day 1, a 96-well plate was coated with 100 μL (2.5 μg/mL) of GAH IgG Fc (G-102-C, R&D Systems) in R5 (coating buffer), overnight. On day 2, the plates were washed three times and blocked with 300 μL of 1% BSA in PBS at 37 °C for 2 hrs. 10 ng/ml of 4.1BB/Fc (838-4B, R&D Systems) was added at 100 μl/well for 2 hrs at room temperature. Following three washes, 7t15-21s137L (long version) or 7t15-21s137Ls (short version) was added starting at 10 nM, or recombinant human 4.1BBL starting at 180 ng/mL, with 1/3 dilution, followed by incubation at 4 °C overnight. On day 3, the plates were washed three times, and 500 ng/mL of biotinylate-goat anti-human 4.1BBL (BAF2295, R&D Systems) was applied at 100 μL per well, followed by incubation at RT for 2 hrs. The plates were washed three times, and incubated with 0.25 μg/mL of HRP-SA (Jackson ImmuneResearch) at 100 μL per well for 30 min. The plates were then washed three times, and incubated with 100 μL of ABTS for 2 mins at RT. The results were read at 405 nm. As shown in FIG. 188, both 7t15-21s137L (long version) and 7t15-21s137L (short version) could interact with 4.1BB/Fc (dark diamond and gray square) compared to the recombinant human 4.1BB ligand (rhCD137L, light gray star). 7t15-21s137L (long version) (dark diamond) interacted better with 4.1BB/Fc as compared to 7t15-21s137L (short version) (gray square).

The following experiments were conducted to evaluate whether the components IL7, IL21, IL15, and 4.1BBL in 7t15-21s137L (long version) were intact to be detected by the individual antibody using ELISA. A 96-well plate was coated with 100 μL (4 μg/mL) of anti-TF (human IgG1) in R5 (coating buffer) and incubated at RT for 2 hrs. The plates were washed three times, and blocked with 100 μL of 1% BSA in PBS. Purified 7t15-21s137L (long version) was added starting at 10 nM, and at 1/3 dilution, followed by incubation at RT for 60 min. The plates were washed three times, and 500 ng/mL of biotinylate-anti-IL7 (506602, R&D Systems), 500 ng/mL of biotinylate-anti-IL21 (13-7218-81, R&D Systems), 50 ng/mL of biotinylate-anti-IL15 (BAM247, R&D Systems), or 500 ng/ml of biotinylate-goat anti-human 4.1BBL (BAF2295, R&D Systems) was added per well and incubated at room temperature for 60 min. The plates were washed three times and incubated with 0.25 μg/mL of HRP-SA (Jackson ImmunoResearch) at 100 μL per well for 30 min at RT. The plates were washed four times, and incubated with 100 μL of ABTS for 2 mins at room temperature. The absorbance results were read at 405 nm. As shown in FIG. 189A-189D, the components including IL7, IL21, IL15, and 4.1BBL in 7t15-21s137L (long version) were detected by the individual antibodies.

The following experiment was conducted to evaluate the activity of IL15 in 7t15-21s137L (long version) and 7t15-21s137L (short version). The ability of 7t15-21s137L (long version) and 7t15-21s137L (short version) to promote proliferation of IL2Rαβγ-expressing CTLL2 cells was compared with that of recombinant IL15. IL15 dependent CTLL2 cells were washed five times with IMDM-10% FBS and seeded to the wells at $2\times10^4$ cells/well. Serially diluted 7t15-21s137L (long version), 7t15-21s137L (short version), or IL15 were added to the cells. Cells were incubated in a $CO_2$ incubator at 37 °C for 3 days. Cell proliferation was detected by adding 20 μL of PrestoBlue (A13261, ThermoFisher) to each well on day 3 and incubated for an additional 4 hours in a $CO_2$ incubator at 37 °C. Raw absorbance at 570-610 nm was read in a micro-titer plate reader. As shown in FIG. 190, 7t15-21s137L (long version), 7t15-21s137L (short version), and IL15 all promoted CTLL2 cell proliferation. The $EC_{50}$, of 7t15-21s137L (long version), 7t15-21s137L (short version), and IL15 is 51.19 pM, 55.75 pM, and 4.947 pM, respectively.

Example 73: Induction of Treg Cells by 2t2

The peripheral blood mononuclear cells (PBMC) of a heathy donor (Donor 163) were isolated from 5 mL of whole blood buffy coats by Ficoll Paque Plus (GE17144003). The PBMC were then lysed with ACK to remove red blood cells. Cells were washed with IMDM-10% FBS and counted. $1.8\times10^6$ cells (100 μL/tube) were seeded to the flow tubes and incubated with 50 μL of descending 2t2 or IL2 (15000, 1500, 150, 15, 1.5, 0.15, or 0 pM) and 50 μL of pre-staining antibodies (anti-CD8-BV605 and anti-CD127-AF647). Cells were incubated for 30 min at 37 °C in water bath. 200 μL of pre-warmed BD Phosflow Fix Buffer I (Cat #557870, Becton Dickinson Biosciences) was added for 10 min at 37 °C in water bath to stop the stimulation. Cells ($4.5\times10^5$ cells/100 μL) were transferred to a V-shape 96-well plate and were spun down followed by permeabilization with 100 μL of −20 °C pre-cooled BD Phosflow Perm Buffer III (Cat #BD Biosciences) for 30 min on ice. The cells were then extensively washed x2 with 200 μL of FACS buffer and stained with a panel of fluorescent antibodies (anti-CD25-PE, CD4-PerCP-Cy5.5, CD56-BV421, CD45RA-PE-Cy7 and pSTAT5a-AF488) to distinguish between different lymphocyte subpopulations and evaluate the pSTAT5a status. Cells were spun down and resuspended in 200 μL of FACS buffer for FACSCelesta analysis. As shown in FIG. 191A, 6 pM of 2t2 was sufficient to induce the phosphorylation of Stat5a in $CD4^+CD25$ $T_{reg}$ cells while 43.11 pM of IL-2 was required to induce phosphorylation of Stat5a in the same population of lymphocytes. In contrast, 2t2 was less active (FIG. 191B) or equally active (FIG. 191C) as compared to IL2 in inducing phosphorylation of Stat5a in $CD4^+CD25^-$ $T_{con}$ and $CD8^+T_{con}$, cells. These results suggest that 2t2 is superior as compared to IL2 in activating $T_{reg}$ in human PBMC, and that 2t2 demonstrates increased $T_{reg}$ selectivity compared to IL-2 in human blood lymphocyte pStat5a responses.

Example 74. Improvement in Hair Growth Using a Single-Chain Chimeric Polypeptide The dorsal hair of 7-week-old C57BL6/J mice was shaved and depilated using commercial depilatory cream. The mice were injected on the same day subcutaneously with a single dose of 2t2 or low dose commercially available recombinant IL-2, followed by daily dosing for four additional days. Untreated mice served as controls. On day 10, the mice were sacrificed and skin sections of the shaved areas were prepared. Representative H&E staining of skin sections from C57BL6J mice on day 10 following depilation are shown in FIGS. 192A-192E. FIG. 192A shows control mice—only depilation done after hair was shaved, FIG. 192B shows mice where depilation was followed by low dose IL-2 (1 mg/kg) administration, and FIGS. 192C-192E shows mice where depilation was followed by 2t2 administered at 0.3 mg/kg (FIG. 192C), 1 mg/kg (FIG. 192D), and 3 mg/kg (FIG. 192E). Black arrows indicate anagen-phase hair follicles that will later extend into dermis and facilitate hair growth. FIG. 194 shows the total number of anagen phase hair follicles counted per 10 fields for each treatment group. In summary, the data show that the 2t2 molecule resulted in increased numbers of anagen-phase hair follicles compared to depilation alone. This effect was also dose-dependent.

Example 75: Differentiation of the Immune Cell into a Memory-Like Immune Cell

Fresh human leukocytes were obtained from the blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 (BioLegend). The cells were counted and resuspended at a density of $2\times10^6$ cells/mL in RPMI 1640 medium (Gibco) supplemented with 2 mM L-glutamine (Thermo Life Technologies), antibiotics (penicillin, 10,000 units/mL; streptomycin, 10,000 μg/mL; Thermo Life Technologies), and 10% FBS (Hyclone). The cells (1 mL) were transferred into a 24-well flat bottom plate, and subjected to either: no treatment, or expanded with 7t15-21s+anti-tissue factor (TF)-antibody (IgG1) (50 nM) for 14 days with medium. The cells were replenished with fresh 7t15-21s+anti-TF-antibody (IgG1) (50 nM) to keep the cell density at approximately $1\times10^6$ cells/mL.

Unexpanded NK cells to treatment groups were used as positive controls for full DNA methylation levels (Data not shown). NK cells were pelleted ($1\times10^6$), and genomic DNA (nDNA) isolated using the QIAamp UCP DNA Micro Kit (Qiagen). 500 ng of purified nDNA was subjected to sodium bisulfite treatment using the EZ DNA Methylation-Direct kit (Zymo Research) according to the manufacturer's protocol. Bisulfite treatment introduces methylation-dependent changes in the DNA with demethylated cytosines being converted into uracil, whereas methylated cytosines remain unchanged. The bisulfite-treated nDNA (10-50 ng) was used as template to PCR amplify a 228 bp region of the IFNγ promoter containing two CpG sites (CpG-186 and CpG-54, position relative to the transcription start site, TSS), known to be heavily regulated by DNA methylation in T cells, using the Pyromark PCR kit (Qiagen) with the forward primer IFNG127F (5'-ATGGTATAGGTGGGTATAATGG-3') and the biotinylated reverse primer IFNG355R-bio (biotin-5'-CAATATACTACACCTCCTCTAACTAC-3') (GENEWIZ). The PCR conditions were 15 minutes at 95 °C, 48 cycles of 30 seconds at 95 °C, 30 seconds at 56 °C, 60 seconds at 72 °C followed by 10 minutes at 72 °C. The integrity and quality of the PCR amplified products were visualized on a 1.2% TAE agarose gel. The DNA methylation status of these two CpG sites was determined by pyrosequencing, which is the gold standard technique to quantitatively measure DNA methylation at single CpG-site. Pyrosequencing reactions were performed at Johns Hopkins University Genetic Resources Core Facility using the DNA sequencing primers C186-IFNG135F (5'-GGTGGGTATAATGGG-3') (SEQ ID NO: 333) and C54-IFNG261F (5'-ATTATTTTATTT-TAAAAAATTTGTG-3') (SEQ ID NO: 334), specific to the CpG sites −186 and −54, respectively. Commercially available non-methylated and methylated DNA (Zymo Research) were used as controls for DNA methylation. The methylation percentages of the two CpG sites (−186 and −54) were pooled for each treatment. The percent difference in DNA methylation was calculated relative to the levels of DNA methylation at the two CpG sites observed in unexposed NK cells.

Analysis of the DNA methylation status of these two IFNγ CpG sites revealed higher levels of DNA demethylation in NK cells supported by 7t15-21s+anti-TF-antibody compared to unexposed NK cells (FIG. 194). These 7t15-21s+anti-TF-antibody supported NK cells exhibited 47.70%±11.76 difference in DNA methylation (i.e., demethylation) compared to unexposed NK cells. The DNA methylation levels of these two IFNγ CpG sites correlated with increased expression of IFNγ following treatment with 7t15-21s+anti-TF-antibody. These data suggest that long-term exposure of NK cells (14 days expansion in culture) with a combination regimen of 7t15-21s+anti-TF-antibody is able to induce DNA demethylation of the two hypomethylated IFNγ CpG sites (−186 and −54) and that 7t15-21s+anti-TF-antibody (IgG1) can epigenetically reprogram gene expression of IFNγ via DNA demethylation of CpG sites leading to interconversion of NK cells into innate immune memory NK cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

EXEMPLARY EMBODIMENTS

Embodiment A1. A single-chain chimeric polypeptide comprising:
(i) a first target-binding domain;
(ii) a soluble tissue factor domain; and
(iii) a second target-binding domain.

Embodiment A2. The single-chain chimeric polypeptide of embodiment A1, wherein the first target-binding domain and the soluble tissue factor domain directly abut each other.

Embodiment A3. The single-chain chimeric polypeptide of embodiment A1, wherein the single-chain chimeric polypeptide further comprises a linker sequence between the first target-binding domain and the soluble tissue factor domain.

Embodiment A4. The single-chain chimeric polypeptide of any one of embodiments A1-A3, wherein the soluble tissue factor domain and the second target-binding domain directly abut each other.

Embodiment A5. The single-chain chimeric polypeptide of any one of embodiments A1-A3, wherein the single-chain chimeric polypeptide further comprises a linker sequence between the soluble tissue factor domain and the second target-binding domain.

Embodiment A6. The single-chain chimeric polypeptide of embodiment A1, wherein the first target-binding domain and the second target-binding domain directly abut each other.

Embodiment A7. The single-chain chimeric polypeptide of embodiment A1, wherein the single-chain chimeric polypeptide further comprises a linker sequence between the first target-binding domain and the second target-binding domain.

Embodiment A8. The single-chain chimeric polypeptide of embodiment A6 or A7, wherein the second target-binding domain and the soluble tissue factor domain directly abut each other.

Embodiment A9. The single-chain chimeric polypeptide of embodiment A6 or A7, wherein the single-chain chimeric polypeptide further comprises a linker sequence between the second target-binding domain and the soluble tissue factor domain.

Embodiment A10. The single-chain chimeric polypeptide of any one of embodiments A1-A9, wherein the first target-binding domain and the second target-binding domain bind specifically to the same antigen.

Embodiment A11. The single-chain chimeric polypeptide of embodiment A10, wherein the first target-binding domain and the second target-binding domain bind specifically to the same epitope.

Embodiment A12. The single-chain chimeric polypeptide of embodiment A11, wherein the first target-binding domain and the second target-binding domain comprise the same amino acid sequence.

Embodiment A13. The single-chain chimeric polypeptide of any one of embodiments A1-A9, wherein the first target-binding domain and the second target-binding domain bind specifically to different antigens.

Embodiment A14. The single-chain chimeric polypeptide of any one of embodiments A1-A13, wherein one or both of the first target-binding domain and the second target-binding domain is an antigen-binding domain.

Embodiment A15. The single-chain chimeric polypeptide of embodiment A14, wherein the first target-binding domain and the second target-binding domain are each an antigen-binding domain.

Embodiment A16. The single-chain chimeric polypeptide of embodiment A13, wherein antigen-binding domain comprises a scFv or a single domain antibody.

Embodiment A17. The single-chain chimeric polypeptide of any one of embodiments A1-A16, wherein one or both of the first target-binding domain and the second target-binding domain bind to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-D, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment A18. The single-chain chimeric polypeptide of any one of embodiments A1-A16, wherein one or both of the first target-binding domain and the second target-binding domain is a soluble interleukin or cytokine protein.

Embodiment A19. The single-chain chimeric polypeptide of embodiment A18, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-D, and SCF, FLT3L, MICA, MICB, and a ULP16-binding protein.

Embodiment A20. The single-chain chimeric polypeptide of any one of embodiments A1-A16, wherein one or both of the first target-binding domain and the second target-binding domain is a soluble interleukin or cytokine receptor.

Embodiment A21. The single-chain chimeric polypeptide of embodiment A20, wherein the soluble interleukin or cytokine receptor is a soluble TGF-β receptor II (TGF-βRII), a soluble TGF-βRIII, a soluble NKG2D, a soluble NKp30, a soluble NKp44, a soluble NKp46, a soluble DNAM1, a scMHCI, a scMHCII, a scTCR, a soluble CD155, or a soluble CD28.

Embodiment A22. The single-chain chimeric polypeptide of any one of embodiments A1-A21, wherein the soluble tissue factor domain is a soluble human tissue factor domain.

Embodiment A23. The single-chain chimeric polypeptide of embodiment A22, wherein the soluble human tissue factor domain comprises a sequence that is at least 80% identical to SEQ ID NO: 93.

Embodiment A24. The single-chain chimeric polypeptide of embodiment A23, wherein the soluble human tissue factor domain comprises a sequence that is at least 90% identical to SEQ ID NO: 93.

Embodiment A25. The single-chain chimeric polypeptide of embodiment A24, wherein the soluble human tissue factor domain comprises a sequence that is at least 95% identical to SEQ ID NO: 93.

Embodiment A26. The single-chain chimeric polypeptide of any one of embodiments A22-A25, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment A27. The single-chain chimeric polypeptide of embodiment A26, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment A28. The single-chain chimeric polypeptide of any one of embodiments A1-A27, wherein the soluble tissue factor domain is not capable of binding Factor VIIa.

Embodiment A29. The single-chain chimeric polypeptide of any one of embodiments A1-A28, wherein the soluble tissue factor domain does not convert inactive Factor X into Factor Xa.

Embodiment A30. The single-chain chimeric polypeptide of any one of embodiments A1-A29, wherein the single-chain chimeric polypeptide does not stimulate blood coagulation in a mammal.

Embodiment A31. The single-chain chimeric polypeptide of any one of embodiments A1-A30, wherein the single-chain chimeric polypeptide further comprises one or more additional target-binding domains at its N- and/or C-terminus.

Embodiment A32. The single-chain chimeric polypeptide of embodiment A31, wherein the single-chain chimeric polypeptide comprises one or more additional target-binding domains at its N-terminus.

Embodiment A33. The single-chain chimeric polypeptide of embodiment A32, wherein one or more additional target-binding domains directly abuts the first target-binding domain, the second target-binding domain, or the soluble tissue factor domain.

Embodiment A34. The single-chain chimeric polypeptide of embodiment A33, wherein the single-chain chimeric polypeptide further comprises a linker sequence between one of the at least one additional target-binding domains and the first target-binding domain, the second target-binding domain, or the soluble tissue factor domain.

Embodiment A35. The single-chain chimeric polypeptide of embodiment A31, wherein the single-chain chimeric polypeptide comprises one or more additional target-binding domains at its C-terminus.

Embodiment A36. The single-chain chimeric polypeptide of embodiment A35, wherein one of the one or more additional target-binding domains directly abuts the first target-binding domain, the second target-binding domain, or the soluble tissue factor domain.

Embodiment A37. The single-chain chimeric polypeptide of embodiment A35, wherein the single-chain chimeric polypeptide further comprises a linker sequence between one of the at least one additional target-binding domains and the first target-binding domain, the second target-binding domain, or the soluble tissue factor domain.

Embodiment A38. The single-chain chimeric polypeptide of embodiment A31, wherein the single-chain chimeric polypeptide comprises one or more additional target binding domains at its N-terminus and the C-terminus.

Embodiment A39. The single-chain chimeric polypeptide of embodiment A38, wherein one of the one or more additional antigen binding domains at the N-terminus directly abuts the first target-binding domain, the second target-binding domain, or the soluble tissue factor domain.

Embodiment A40. The single-chain chimeric polypeptide of embodiment A38, wherein the single-chain chimeric polypeptide further comprises a linker sequence between one of the one or more additional antigen-binding domains at the N-terminus and the first target-binding domain, the second target-binding domain, or the soluble tissue factor domain.

Embodiment A41. The single-chain chimeric polypeptide of embodiment A38, wherein one of the one or more additional antigen binding domains at the C-terminus directly abuts the first target-binding domain, the second target-binding domain, or the soluble tissue factor domain.

Embodiment A42. The single-chain chimeric polypeptide of embodiment A38, wherein the single-chain chimeric polypeptide further comprises a linker sequence between one of the one or more additional antigen-binding domains at the C-terminus and the first target-binding domain, the second target-binding domain, or the soluble tissue factor domain.

Embodiment A43. The single-chain chimeric polypeptide of any one of embodiments A31-A42, wherein two or more of the first target-binding domain, the second target-binding domain, and the one or more additional target-binding domains bind specifically to the same antigen.

Embodiment A44. The single-chain chimeric polypeptide of embodiment A43, wherein two or more of the first target-binding domain, the second target-binding domain, and the one or more additional target-binding domains bind specifically to the same epitope.

Embodiment A45. The single-chain chimeric polypeptide of embodiment A44, wherein two or more of the first target-binding domain, the second target-binding domain, and the one or more additional target-binding domains comprise the same amino acid sequence.

Embodiment A46. The single-chain chimeric polypeptide of embodiment A43, wherein the first target-binding domain, the second target-binding domain, and the one or more additional target-binding domains each bind specifically to the same antigen.

Embodiment A47. The single-chain chimeric polypeptide of embodiment A46, wherein the first target-binding domain, the second target-binding domain, and the one or more additional target-binding domains each bind specifically to the same epitope.

Embodiment A48. The single-chain chimeric polypeptide of embodiment A47, wherein the first target-binding domain, the second target-binding domain, and the one or more additional target-binding domains each comprise the same amino acid sequence.

Embodiment A49. The single-chain chimeric polypeptide of any one of embodiments A31-A42, wherein the first target-binding domain, the second target-binding domain, and the one or more additional target-binding domains bind specifically to different antigens.

Embodiment A50. The single-chain chimeric polypeptide of any one of embodiments A31-A49, wherein one or more of the first target-binding domain, the second target-binding domain, and the one or more target-binding domains is an antigen-binding domain.

Embodiment A51. The single-chain chimeric polypeptide of embodiment A50, wherein the first target-binding domain, the second target-binding domain, and the one or more additional target-binding domains are each an antigen-binding domain.

Embodiment A52. The single-chain chimeric polypeptide of embodiment A51, wherein antigen-binding domain comprises a scFv or a single domain antibody.

Embodiment A53. The single-chain chimeric polypeptide of any one of embodiments A31-A52, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-D, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment A54. The single-chain chimeric polypeptide of any one of embodiments A31-A52, wherein one or more of the first target-binding domain, the second target-binding domain, and the one or more additional target-binding domains is a soluble interleukin or cytokine protein.

Embodiment A55. The single-chain chimeric polypeptide of embodiment A54, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-D, and SCF, FLT3L, MICA, MICB, and a ULP16-binding protein.

Embodiment A56. The single-chain chimeric polypeptide of any one of embodiments A31-A52, wherein one or more of the first target-binding domain, the second target-binding domain, and the one or more additional target-binding domains is a soluble interleukin or cytokine receptor.

Embodiment A57. The single-chain chimeric polypeptide of embodiment A56, wherein the soluble receptor is a soluble TGF-β receptor II (TGF-βRII), a soluble TGF-βRIII, a soluble NKG2D, a soluble NKp30, a soluble NKp44, a soluble NKp46, a soluble DNAM1, a scMHCI, a scMHCII, a scTCR, a soluble CD155, a soluble CD122, a soluble CD3, or a soluble CD28.

Embodiment A58. The single-chain chimeric polypeptide of any one of embodiments A1-A57, wherein the single-chain chimeric polypeptide further comprises a signal sequence at its N-terminal end.

Embodiment A59. The single-chain chimeric polypeptide of any one of embodiments A1-A58, wherein the single-chain chimeric polypeptide further comprises a peptide tag positioned at the N-terminal end or the C-terminal end of the single-chain chimeric polypeptide.

Embodiment A60. A composition comprising any of the single-chain chimeric polypeptides of embodiments A1-A59.

Embodiment A61. The composition of embodiment A60, wherein the composition is a pharmaceutical composition.

Embodiment A62. A kit comprising at least one dose of the composition of embodiment A60 or A61.

Embodiment A63. Nucleic acid encoding any of the single-chain chimeric polypeptides of any one of embodiments A1-A59.

Embodiment A64. A vector comprising the nucleic acid of embodiment A63.

Embodiment A65. The vector of embodiment A64, wherein the vector is an expression vector.

Embodiment A66. A cell comprising the nucleic acid of embodiment A63 or the vector of embodiment A64 or A65.

Embodiment A67. A method of producing a single-chain chimeric polypeptide, the method comprising:

culturing the cell of embodiment A66 in a culture medium under conditions sufficient to result in the production of the single-chain chimeric polypeptide; and recovering the single-chain chimeric polypeptide from the cell and/or the culture medium.

Embodiment A68. A single-chain chimeric polypeptide produced by the method of embodiment A67.

Embodiment A69. The single-chain chimeric polypeptide of embodiment A26, wherein the soluble human tissue factor domain comprises a sequence that is at least 80% identical to SEQ ID NO: 97.

Embodiment A70. The single-chain chimeric polypeptide of embodiment A69, wherein the soluble human tissue factor domain comprises a sequence that is at least 90% identical to SEQ ID NO: 97.

Embodiment A71. The single-chain chimeric polypeptide of embodiment A70, wherein the soluble human tissue factor domain comprises a sequence that is at least 95% identical to SEQ ID NO: 97.

Embodiment A72. The single-chain chimeric polypeptide of embodiment A71, wherein the soluble human tissue factor domain comprises a sequence that is 100% identical to SEQ ID NO: 97.

Embodiment A73. The single-chain chimeric polypeptide of embodiment A26, wherein the soluble human tissue factor domain comprises a sequence that is at least 80% identical to SEQ ID NO: 98.

Embodiment A74. The single-chain chimeric polypeptide of embodiment A73, wherein the soluble human tissue factor domain comprises a sequence that is at least 90% identical to SEQ ID NO: 98.

Embodiment A75. The single-chain chimeric polypeptide of embodiment A74, wherein the soluble human tissue factor domain comprises a sequence that is at least 95% identical to SEQ ID NO: 98.

Embodiment A76. The single-chain chimeric polypeptide of embodiment A75, wherein the soluble human tissue factor domain comprises a sequence that is 100% identical to SEQ ID NO: 98.

Embodiment B1. A single-chain chimeric polypeptide comprising:

(i) a first target-binding domain;

(ii) a soluble tissue factor domain; and (iii) a second target-binding domain, wherein:

the first target-binding domain and the second target-binding domain each specifically bind to an IL-2 receptor; or the first target-binding domain and the second target-binding domain each specifically bind to an IL-15 receptor.

Embodiment B2. The single-chain chimeric polypeptide of embodiment B1, wherein the first target-binding domain and the soluble tissue factor domain directly abut each other.

Embodiment B3. The single-chain chimeric polypeptide of embodiment B1, wherein the single-chain chimeric polypeptide further comprises a linker sequence between the first target-binding domain and the soluble tissue factor domain.

Embodiment B4. The single-chain chimeric polypeptide of any one of embodiments B1-B3, wherein the soluble tissue factor domain and the second target-binding domain directly abut each other.

Embodiment B5. The single-chain chimeric polypeptide of any one of embodiments B1-B3, wherein the single-chain chimeric polypeptide further comprises a linker sequence between the soluble tissue factor domain and the second target-binding domain.

Embodiment B6. The single-chain chimeric polypeptide of embodiment B1, wherein the first target-binding domain and the second target-binding domain directly abut each other.

Embodiment B7. The single-chain chimeric polypeptide of embodiment B1, wherein the single-chain chimeric polypeptide further comprises a linker sequence between the first target-binding domain and the second target-binding domain.

Embodiment B8. The single-chain chimeric polypeptide of embodiment B6 or B7, wherein the second target-binding domain and the soluble tissue factor domain directly abut each other.

Embodiment B9. The single-chain chimeric polypeptide of embodiment B6 or B7, wherein the single-chain chimeric polypeptide further comprises a linker sequence between the second target-binding domain and the soluble tissue factor domain.

Embodiment B10. The single-chain chimeric polypeptide of any one of embodiments B1-B9, wherein both the first target-binding domain and the second target-binding domain is a soluble interleukin protein.

Embodiment B11. The single-chain chimeric polypeptide of embodiment B10, wherein the first target-binding domain and the second target-binding domain is a soluble IL-2 protein.

Embodiment B12. The single-chain chimeric polypeptide of embodiment B11, wherein the soluble IL-2 protein is a soluble human IL-2 protein.

Embodiment B13. The single-chain chimeric polypeptide of embodiment B12, wherein the soluble human IL-2 protein comprises SEQ ID NO: 78.

Embodiment B14. The single-chain chimeric polypeptide of embodiment B10, wherein the first target-binding domain and the second target-binding domain is a soluble IL-15 protein.

Embodiment B15. The single-chain chimeric polypeptide of embodiment B14, wherein the soluble IL-15 protein is a soluble human IL-15 protein.

Embodiment B16. The single-chain chimeric polypeptide of embodiment B15, wherein the soluble human IL-15 protein comprises SEQ ID NO: 82.

Embodiment B17. The single-chain chimeric polypeptide of any one of embodiments B1-B16, wherein the soluble tissue factor domain is a soluble human tissue factor domain.

Embodiment B18. The single-chain chimeric polypeptide of embodiment B17, wherein the soluble human tissue factor domain comprises a sequence that is at least 80% identical to SEQ ID NO: 93.

Embodiment B19. The single-chain chimeric polypeptide of embodiment B18, wherein the soluble human tissue factor domain comprises a sequence that is at least 90% identical to SEQ ID NO: 93.

Embodiment B20. The single-chain chimeric polypeptide of embodiment B19, wherein the soluble human tissue factor domain comprises a sequence that is at least 95% identical to SEQ ID NO: 93.

Embodiment B21. The single-chain chimeric polypeptide of any one of embodiments B17-B20, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment B22. The single-chain chimeric polypeptide of embodiment B21, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment B23. The single-chain chimeric polypeptide of any one of embodiments B1-B22, wherein the soluble tissue factor domain is not capable of binding Factor VIIa.

Embodiment B24. The single-chain chimeric polypeptide of any one of embodiments B1-B23, wherein the soluble tissue factor domain does not convert inactive Factor X into Factor Xa.

Embodiment B25. The single-chain chimeric polypeptide of any one of embodiments B1-B24, wherein the single-chain chimeric polypeptide does not stimulate blood coagulation in a mammal.

Embodiment B26. The single-chain chimeric polypeptide of any one of embodiments B1-B25, wherein the single-chain chimeric polypeptide further comprises one or more additional target-binding domains at its N- and/or C-terminus.

Embodiment B27. The single-chain chimeric polypeptide of embodiment B26, wherein the single-chain chimeric polypeptide comprises one or more additional target-binding domains at its N-terminus.

Embodiment B28. The single-chain chimeric polypeptide of embodiment B27, wherein one or more additional target-binding domains directly abuts the first target-binding domain, the second target-binding domain, or the soluble tissue factor domain.

Embodiment B29. The single-chain chimeric polypeptide of embodiment B28, wherein the single-chain chimeric polypeptide further comprises a linker sequence between one of the at least one additional target-binding domains and the first target-binding domain, the second target-binding domain, or the soluble tissue factor domain.

Embodiment B30. The single-chain chimeric polypeptide of embodiment B26, wherein the single-chain chimeric polypeptide comprises one or more additional target-binding domains at its C-terminus.

Embodiment B31. The single-chain chimeric polypeptide of embodiment B30, wherein one of the one or more additional target-binding domains directly abuts the first target-binding domain, the second target-binding domain, or the soluble tissue factor domain.

Embodiment B32. The single-chain chimeric polypeptide of embodiment B30, wherein the single-chain chimeric polypeptide further comprises a linker sequence between one of the at least one additional target-binding domains and the first target-binding domain, the second target-binding domain, or the soluble tissue factor domain.

Embodiment B33. The single-chain chimeric polypeptide of embodiment B26, wherein the single-chain chimeric polypeptide comprises one or more additional target binding domains at its N-terminus and the C-terminus.

Embodiment B34. The single-chain chimeric polypeptide of embodiment B33, wherein one of the one or more additional antigen binding domains at the N-terminus directly abuts the first target-binding domain, the second target-binding domain, or the soluble tissue factor domain.

Embodiment B35. The single-chain chimeric polypeptide of embodiment B33, wherein the single-chain chimeric polypeptide further comprises a linker sequence between one of the one or more additional antigen-binding domains at the N-terminus and the first target-binding domain, the second target-binding domain, or the soluble tissue factor domain.

Embodiment B36. The single-chain chimeric polypeptide of embodiment B33, wherein one of the one or more additional antigen binding domains at the C-terminus directly abuts the first target-binding domain, the second target-binding domain, or the soluble tissue factor domain.

Embodiment B37. The single-chain chimeric polypeptide of embodiment B33, wherein the single-chain chimeric polypeptide further comprises a linker sequence between one of the one or more additional antigen-binding domains at the C-terminus and the first target-binding domain, the second target-binding domain, or the soluble tissue factor domain.

Embodiment B38. The single-chain chimeric polypeptide of any one of embodiments B26-B37, wherein each of the first target-binding domain, the second target-binding domain, and the one or more additional target-binding domains bind specifically to an IL-2 receptor or an IL-15 receptor.

Embodiment B39. The single-chain chimeric polypeptide of embodiment B38, wherein each of the first target-binding domain, the second target-binding domain, and the one or more additional target-binding domains comprise the same amino acid sequence.

Embodiment B40. The single-chain chimeric polypeptide of any one of embodiments B26-B37, wherein the one or more additional target-binding domains is an antigen-binding domain.

Embodiment B41. The single-chain chimeric polypeptide of embodiment B40, wherein the antigen-binding domain comprises a scFv or a single domain antibody.

Embodiment B42. The single-chain chimeric polypeptide of any one of embodiments B26-B37, B40, and B41, wherein the one or more additional target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment B43. The single-chain chimeric polypeptide of any one of embodiments B6-B37, B40, and B41, wherein the one or more additional target-binding domains is a soluble interleukin or cytokine protein.

Embodiment B44. The single-chain chimeric polypeptide of embodiment B43, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment B45. The single-chain chimeric polypeptide of any one of embodiments B6-B37, B40, and B41, wherein the one or more additional target-binding domains is a soluble interleukin or cytokine receptor.

Embodiment B46. The single-chain chimeric polypeptide of embodiment B45, wherein the soluble receptor is a soluble TGF-β receptor II (TGF-βRII) and a soluble TGF-βRIII.

Embodiment B47. The single-chain chimeric polypeptide of any one of embodiments B1-B46, wherein the single-chain chimeric polypeptide further comprises a signal sequence at its N-terminal end.

Embodiment B48. The single-chain chimeric polypeptide of any one of embodiments B1-B47, wherein the single-chain chimeric polypeptide further comprises a peptide tag positioned at the N-terminal end or the C-terminal end of the single-chain chimeric polypeptide.

Embodiment B49. A composition comprising any of the single-chain chimeric polypeptides of embodiments B1-B48.

Embodiment B50. The composition of embodiment B49, wherein the composition is a pharmaceutical composition.

Embodiment B51. A kit comprising at least one dose of the composition of embodiment B49 or B50.

Embodiment B52. A nucleic acid encoding any of the single-chain chimeric polypeptides of any one of embodiments B1-B48.

Embodiment B53. A vector comprising the nucleic acid of embodiment B52.

Embodiment B54. The vector of embodiment B53, wherein the vector is an expression vector.

Embodiment B55. A cell comprising the nucleic acid of embodiment B52 or the vector of embodiment B53 or B54.

Embodiment B56. A method of producing a single-chain chimeric polypeptide, the method comprising:

culturing the cell of embodiment B55 in a culture medium under conditions sufficient to result in the production of the single-chain chimeric polypeptide; and recovering the single-chain chimeric polypeptide from the cell and/or the culture medium.

Embodiment B57. A single-chain chimeric polypeptide produced by the method of embodiment B56.

Embodiment B58. The single-chain chimeric polypeptide of embodiment B21, wherein the soluble human tissue factor domain comprises a sequence that is at least 80% identical to SEQ ID NO: 97.

Embodiment B59. The single-chain chimeric polypeptide of embodiment B58, wherein the soluble human tissue factor domain comprises a sequence that is at least 90% identical to SEQ ID NO: 97.

Embodiment B60. The single-chain chimeric polypeptide of embodiment B59, wherein the soluble human tissue factor domain comprises a sequence that is at least 95% identical to SEQ ID NO: 97.

Embodiment B61. The single-chain chimeric polypeptide of embodiment B60, wherein the soluble human tissue factor domain comprises a sequence that is 100% identical to SEQ ID NO: 97.

Embodiment B62. The single-chain chimeric polypeptide of embodiment B21, wherein the soluble human tissue factor domain comprises a sequence that is at least 80% identical to SEQ ID NO: 98.

Embodiment B63. The single-chain chimeric polypeptide of embodiment B62, wherein the soluble human tissue factor domain comprises a sequence that is at least 90% identical to SEQ ID NO: 98.

Embodiment B64. The single-chain chimeric polypeptide of embodiment B63, wherein the soluble human tissue factor domain comprises a sequence that is at least 95% identical to SEQ ID NO: 98.

Embodiment B65. The single-chain chimeric polypeptide of embodiment B64, wherein the soluble human tissue factor domain comprises a sequence that is 100% identical to SEQ ID NO: 98.

Embodiment C1. A multi-chain chimeric polypeptide comprising:

(a) a first chimeric polypeptide comprising:
  (i) a first target-binding domain;
  (ii) a soluble tissue factor domain; and
  (iii) a first domain of a pair of affinity domains;

(b) a second chimeric polypeptide comprising:
  (i) a second domain of a pair of affinity domains; and
  (ii) a second target-binding domain, wherein the first chimeric polypeptide and the second chimeric polypeptide associate through the binding of the first domain and the second domain of the pair of affinity domains.

Embodiment C2. The multi-chain chimeric polypeptide of embodiment C1, wherein the first target-binding domain and the soluble tissue factor domain directly abut each other in the first chimeric polypeptide.

Embodiment C3. The multi-chain chimeric polypeptide of embodiment C1, wherein the first chimeric polypeptide further comprises a linker sequence between the first target-binding domain and the soluble tissue factor domain in the first chimeric polypeptide.

Embodiment C4. The multi-chain chimeric polypeptide of any one of embodiments C1-C3, wherein the soluble tissue factor domain and the first domain of the pair of affinity domains directly abut each other in the first chimeric polypeptide.

Embodiment C5. The multi-chain chimeric polypeptide of any one of embodiments C1-C3, wherein the first chimeric polypeptide further comprises a linker sequence between the soluble tissue factor domain and the first domain of the pair of affinity domains in the first chimeric polypeptide.

Embodiment C6. The multi-chain chimeric polypeptide of any one of embodiments C1-C5, wherein the second domain of the pair of affinity domains and the second target-binding domain directly abut each other in the second chimeric polypeptide.

Embodiment C7. The multi-chain chimeric polypeptide of any one of embodiments C1-C5, wherein second chimeric polypeptide further comprises a linker sequence between the second domain of the pair of affinity domains and the second target-binding domain in the second chimeric polypeptide.

Embodiment C8. The multi-chain chimeric polypeptide of any one of embodiments C1-C7, wherein the first target-binding domain and the second target-binding domain bind specifically to the same antigen.

Embodiment C9. The multi-chain chimeric polypeptide of embodiment C8, wherein the first target-binding domain and the second target-binding domain bind specifically to the same epitope.

Embodiment C10. The multi-chain chimeric polypeptide of embodiment C9, wherein the first target-binding domain and the second target-binding domain comprise the same amino acid sequence.

Embodiment C11. The multi-chain chimeric polypeptide of any one of embodiments C1-C7, wherein the first target-binding domain and the second target-binding domain bind specifically to different antigens.

Embodiment C12. The multi-chain chimeric polypeptide of any one of embodiments C1-C11, wherein one or both of the first target-binding domain and the second target-binding domain is an antigen-binding domain.

Embodiment C13. The multi-chain chimeric polypeptide of embodiment C12, wherein the first target-binding domain and the second target-binding domain are each antigen-binding domains.

Embodiment C14. The multi-chain chimeric polypeptide of embodiment C12 or C13, wherein antigen-binding domain comprises a scFv or a single domain antibody.

Embodiment C15. The multi-chain chimeric polypeptide of any one of embodiments C1-C14, wherein one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment C16. The multi-chain chimeric polypeptide of any one of embodiments C1-C14, wherein one or both of the first target-binding domain and the second target-binding domain is a soluble interleukin or cytokine protein.

Embodiment C17. The multi-chain chimeric polypeptide of embodiment C16, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment C18. The multi-chain chimeric polypeptide of any one of embodiments C1-C14, wherein one or both of the first target-binding domain and the second target-binding domain is a soluble interleukin or cytokine receptor.

Embodiment C19. The multi-chain chimeric polypeptide of embodiment C18, wherein the soluble receptor is a soluble TGF-β receptor II (TGF-β MI), a soluble TGF-βRIII, a soluble NKG2D, a soluble NKp30, a soluble NKp44, a soluble NKp46, a soluble DNAM1, a scMHCI, a scMHCII, a scTCR, a soluble CD155, or a soluble CD28.

Embodiment C20. The multi-chain chimeric polypeptide of any one of embodiments C1-C19, wherein the first chimeric polypeptide further comprises one or more additional target-binding domain(s), where at least one of the one or more additional antigen-binding domain (s) is positioned between the soluble tissue factor domain and the first domain of the pair of affinity domains.

Embodiment C21. The multi-chain chimeric polypeptide of embodiment C20, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment C22. The multi-chain chimeric polypeptide of any one of embodiments C1-C19, wherein the first chimeric polypeptide further comprises one or more additional target-binding domains at the N-terminal and/or C-terminal end of the first chimeric polypeptide.

Embodiment C23. The multi-chain chimeric polypeptide of embodiment C22, wherein at least one of the one or more additional target-binding domains directly abuts the first domain of the pair of affinity domains in the first chimeric polypeptide.

Embodiment C24. The multi-chain chimeric polypeptide of embodiment C22, wherein the first chimeric polypeptide further comprises a linker sequence between the at least one of the one or more additional target-binding domains and the first domain of the pair of affinity domains.

Embodiment C25. The multi-chain chimeric polypeptide of embodiment C22, wherein the at least one of the one or more additional target-binding domains directly abuts the first target-binding domain in the first chimeric polypeptide.

Embodiment C26. The multi-chain chimeric polypeptide of embodiment C22, wherein the first chimeric polypeptide further comprises a linker sequence between the at least one of the one or more additional target-binding domains and the first target-binding domain.

Embodiment C27. The multi-chain chimeric polypeptide of embodiment C22, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment C28. The multi-chain chimeric polypeptide of embodiment C27, wherein the at least one additional target-binding domain of the one or more additional target-binding domains disposed at the N-terminus directly abuts the first target-binding domain or the first domain of the pair of affinity domains in the first chimeric polypeptide.

Embodiment C29. The multi-chain chimeric polypeptide of embodiment C27, wherein the first chimeric polypeptide further comprises a linker sequence disposed between the at least one additional target-binding domain and the first target-binding domain or the first domain of the pair of affinity domains in the first chimeric polypeptide.

Embodiment C30. The multi-chain chimeric polypeptide of embodiment C27, wherein the at least one additional target-binding domain of the one or more additional target-binding domains disposed at the C-terminus directly abuts the first target-binding domain or the first domain of the pair of affinity domains in the first chimeric polypeptide.

Embodiment C31. The multi-chain chimeric polypeptide of embodiment C27, wherein the first chimeric polypeptide further comprises a linker sequence disposed between the at least one additional target-binding domain and the first target-binding domain or the first domain of the pair of affinity domains in the first chimeric polypeptide.

Embodiment C32. The multi-chain chimeric polypeptide of embodiment C27, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment C33. The multi-chain chimeric polypeptide of embodiment C27, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment C34. The multi-chain chimeric polypeptide of any one of embodiments C1-C33, wherein the second chimeric polypeptide further comprises one or more additional target-binding domains at the N-terminal end or the C-terminal end of the second chimeric polypeptide.

Embodiment C35. The multi-chain chimeric polypeptide of embodiment C34, wherein at least one of the one or more additional target-binding domains directly abuts the second domain of the pair of affinity domains in the second chimeric polypeptide.

Embodiment C36. The multi-chain chimeric polypeptide of embodiment C34, wherein the second chimeric polypeptide further comprises a linker sequence between at least one of the one or more additional target-binding domains and the second domain of the pair of affinity domains in the second chimeric polypeptide.

Embodiment C37. The multi-chain chimeric polypeptide of embodiment C34, wherein at least one of the one or more additional target-binding domains directly abuts the second target-binding domain in the second chimeric polypeptide.

Embodiment C38. The multi-chain chimeric polypeptide of embodiment C34, wherein the second chimeric polypeptide further comprises a linker sequence between at least one of the one or more additional target-binding domains and the second target-binding domain in the second chimeric polypeptide.

Embodiment C39. The multi-chain chimeric polypeptide of any one of embodiments C20-C38, wherein two or more of the first target-binding domain, the second target-binding domain, and the one or more additional target-binding domains bind specifically to the same antigen.

Embodiment C40. The multi-chain chimeric polypeptide of embodiment C39, wherein two or more of the first target-binding domain, the second target-binding domain, and the one or more additional target-binding domains bind specifically to the same epitope.

Embodiment C41. The multi-chain chimeric polypeptide of embodiment C40, wherein two or more of the first target-binding domain, the second target-binding domain, and the one or more additional target-binding domains comprise the same amino acid sequence.

Embodiment C42. The multi-chain chimeric polypeptide of embodiment C39, wherein the first target-binding domain, the second target-binding domain, and the one or more additional target-binding domains each bind specifically to the same antigen.

Embodiment C43. The multi-chain chimeric polypeptide of embodiment C42, wherein the first target-binding domain, the second target-binding domain, and the one or more additional target-binding domains each bind specifically to the same epitope.

Embodiment C44. The multi-chain chimeric polypeptide of embodiment C43, wherein the first target-binding domain, the second target-binding domain, and the one or more additional target-binding domains each comprise the same amino acid sequence.

Embodiment C45. The multi-chain chimeric polypeptide of any one of embodiments C20-C38, wherein the first target-binding domain, the second target-binding domain, and the one or more additional target-binding domains bind specifically to different antigens.

Embodiment C46. The multi-chain chimeric polypeptide of any one of embodiments C20-C45, wherein one or more of the first target-binding domain, the second target-binding domain, and the one or more target-binding domains is an antigen-binding domain.

Embodiment C47. The multi-chain chimeric polypeptide of embodiment C46, wherein the first target-binding domain, the second target-binding domain, and the one or more additional target-binding domains are each an antigen-binding domain.

Embodiment C48. The multi-chain chimeric polypeptide of embodiment C47, wherein antigen-binding domain comprises a scFv.

Embodiment C49. The multi-chain chimeric polypeptide of any one of embodiments C20-C48, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

Embodiment C50. The multi-chain chimeric polypeptide of any one of embodiments C20-C48, wherein one or more of the first target-binding domain, the second target-binding domain, and the one or more additional target-binding domains is a soluble interleukin or cytokine protein.

Embodiment C51. The multi-chain chimeric polypeptide of embodiment C50, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, and SCF, FLT3L, MICA, MICB, and a ULP16-binding protein.

Embodiment C52. The multi-chain chimeric polypeptide of any one of embodiments C20-C48, wherein one or more of the first target-binding domain, the second target-binding domain, and the one or more additional target-binding domains is a soluble interleukin or cytokine receptor.

Embodiment C53. The multi-chain chimeric polypeptide of embodiment C52, wherein the soluble receptor is a soluble TGF-β receptor II (TGF-β MI), a soluble TGF-βRIII, a soluble NKG2D, a soluble NKp30, a soluble NKp44, a soluble NKp46, a soluble DNAM1, a scMHCI, a scMHCII, a scTCR, a soluble CD155, a soluble CD122, a soluble CD3, or a soluble CD28.

Embodiment C54. The multi-chain chimeric polypeptide of any one of embodiments C1-C53, wherein the first chimeric polypeptide further comprises a peptide tag at the N-terminal end or the C-terminal end of the first chimeric polypeptide.

Embodiment C55. The multi-chain chimeric polypeptide of any one of embodiments C1-C53, wherein the second chimeric polypeptide further comprises a peptide tag at the N-terminal end or the C-terminal end of the second chimeric polypeptide.

Embodiment C56. The multi-chain chimeric polypeptide of any one of embodiments C1-C55, wherein the soluble tissue factor domain is a soluble human tissue factor domain.

Embodiment C57. The multi-chain chimeric polypeptide of embodiment C56, wherein the soluble human tissue factor domain comprises a sequence that is at least 80% identical to SEQ ID NO: 93.

Embodiment C58. The multi-chain chimeric polypeptide of embodiment C57, wherein the soluble human tissue factor domain comprises a sequence that is at least 90% identical to SEQ ID NO: 93.

Embodiment C59. The multi-chain chimeric polypeptide of embodiment C58, wherein the soluble human tissue factor domain comprises a sequence that is at least 95% identical to SEQ ID NO: 93.

Embodiment C60. The multi-chain chimeric polypeptide of any one of embodiments C56-059, wherein the soluble human tissue factor domain does not comprise one or more of: a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment C61. The multi-chain chimeric polypeptide of embodiment C60, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment C62. The multi-chain chimeric polypeptide of any one of embodiments C1-C61, wherein the soluble tissue factor domain is not capable of binding to Factor VIIa.

Embodiment C63. The multi-chain chimeric polypeptide of any one of embodiments C1-C62, wherein the soluble tissue factor domain does not convert inactive Factor X into Factor Xa.

Embodiment C64. The multi-chain chimeric polypeptide of any one of embodiments C1-C63, wherein the multi-chain chimeric polypeptide does not stimulate blood coagulation in a mammal.

Embodiment C65. The multi-chain chimeric polypeptide of any one of embodiments C1-C64, wherein the pair of affinity domains is a sushi domain from an alpha chain of human IL-15 receptor (IL-15Rα) and a soluble IL-15.

Embodiment C66. The multi-chain chimeric polypeptide of embodiment C65, wherein the soluble IL-15 has a D8N or D8A amino acid substitution.

Embodiment C67. The multi-chain chimeric polypeptide of embodiment C65 or C66, wherein the human IL-15Rα is a mature full-length IL-15Rα.

Embodiment C68. The multi-chain chimeric polypeptide of any one of embodiments C1-C64, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment C69. The multi-chain chimeric polypeptide of any one of embodiments C1-C68, wherein the first chimeric polypeptide and/or the second chimeric polypeptide further comprises a signal sequence at its N-terminal end.

Embodiment C70. A composition comprising any of the multi-chain chimeric polypeptides of embodiments C1-C69.

Embodiment C71. The composition of embodiment C70, wherein the composition is a pharmaceutical composition.

Embodiment C72. A kit comprising at least one dose of the composition of embodiment C70 or C71.

Embodiment C73. Nucleic acid encoding any of the multi-chain chimeric polypeptides of any one of embodiments C1-C69.

Embodiment C74. A vector comprising the nucleic acid of embodiment C73.

Embodiment C75. The vector of embodiment C74, wherein the vector is an expression vector.

Embodiment C76. A cell comprising the nucleic acid of embodiment C73 or the vector of embodiment C74 or C75.

Embodiment C77. A method of producing a multi-chain chimeric polypeptide, the method comprising:

culturing the cell of embodiment C76 in a culture medium under conditions sufficient to result in the production of the multi-chain chimeric polypeptide; and recovering the multi-chain chimeric polypeptide from the cell and/or the culture medium.

Embodiment C78. A multi-chain chimeric polypeptide produced by the method of embodiment C77.

Embodiment C79. The multi-chain chimeric polypeptide of embodiment A56, wherein the soluble human tissue factor domain comprises a sequence that is at least 80% identical to SEQ ID NO: 97.

Embodiment C80. The multi-chain chimeric polypeptide of embodiment C79, wherein the soluble human tissue factor domain comprises a sequence that is at least 90% identical to SEQ ID NO: 97.

Embodiment C81. The multi-chain chimeric polypeptide of embodiment C80, wherein the soluble human tissue factor domain comprises a sequence that is at least 95% identical to SEQ ID NO: 97.

Embodiment C82. The multi-chain chimeric polypeptide of embodiment C81, wherein the soluble human tissue factor domain comprises a sequence that is 100% identical to SEQ ID NO: 97.

Embodiment C83. The multi-chain chimeric polypeptide of embodiment C56, wherein the soluble human tissue factor domain comprises a sequence that is at least 80% identical to SEQ ID NO: 98.

Embodiment C84. The multi-chain chimeric polypeptide of embodiment C83, wherein the soluble human tissue factor domain comprises a sequence that is at least 90% identical to SEQ ID NO: 98.

Embodiment C85. The multi-chain chimeric polypeptide of embodiment C84, wherein the soluble human tissue factor domain comprises a sequence that is at least 95% identical to SEQ ID NO: 98.

Embodiment C86. The multi-chain chimeric polypeptide of embodiment C85, wherein the soluble human tissue factor domain comprises a sequence that is 100% identical to SEQ ID NO: 98.

Embodiment D1. A multi-chain chimeric polypeptide comprising:

(a) a first chimeric polypeptide comprising:
  (i) a first target-binding domain;
  (ii) a soluble tissue factor domain; and
  (iii) a first domain of a pair of affinity domains;

(b) a second chimeric polypeptide comprising:
  (i) a second domain of a pair of affinity domains; and
  (ii) a second target-binding domain, wherein:

the first chimeric polypeptide and the second chimeric polypeptide associate through the binding of the first domain and the second domain of the pair of affinity domains;

the first target-binding domain and the second targeting-binding domain each independently bind specifically to a receptor of IL-18 or a receptor of IL-12.

Embodiment D2. The multi-chain chimeric polypeptide of embodiment D1, wherein the first target-binding domain and the soluble tissue factor domain directly abut each other in the first chimeric polypeptide.

Embodiment D3. The multi-chain chimeric polypeptide of embodiment D1, wherein the first chimeric polypeptide further comprises a linker sequence between the first target-binding domain and the soluble tissue factor domain in the first chimeric polypeptide.

Embodiment D4. The multi-chain chimeric polypeptide of any one of embodiments D1-D3, wherein the soluble tissue factor domain and the first domain of the pair of affinity domains directly abut each other in the first chimeric polypeptide.

Embodiment D5. The multi-chain chimeric polypeptide of any one of embodiments D1-D3, wherein the first chimeric polypeptide further comprises a linker sequence between the soluble tissue factor domain and the first domain of the pair of affinity domains in the first chimeric polypeptide.

Embodiment D6. The multi-chain chimeric polypeptide of any one of embodiments D1-D5, wherein the second domain of the pair of affinity domains and the second target-binding domain directly abut each other in the second chimeric polypeptide.

Embodiment D7. The multi-chain chimeric polypeptide of any one of embodiments D1-D5, wherein second chimeric polypeptide further comprises a linker sequence between the second domain of the pair of affinity domains and the second target-binding domain in the second chimeric polypeptide.

Embodiment D8. The multi-chain chimeric polypeptide of any one of embodiments D1-D7, wherein the soluble tissue factor domain is a soluble human tissue factor domain.

Embodiment D9. The multi-chain chimeric polypeptide of embodiment D8, wherein the soluble human tissue factor domain comprises a sequence that is at least 80% identical to SEQ ID NO: 93.

Embodiment D10. The multi-chain chimeric polypeptide of embodiment D9, wherein the soluble human tissue factor domain comprises a sequence that is at least 90% identical to SEQ ID NO: 93.

Embodiment D11. The multi-chain chimeric polypeptide of embodiment D10, wherein the soluble human tissue factor domain comprises a sequence that is at least 95% identical to SEQ ID NO: 93.

Embodiment D12. The multi-chain chimeric polypeptide of any one of embodiments D8-D11, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment D13. The multi-chain chimeric polypeptide of embodiment D12, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment D14. The multi-chain chimeric polypeptide of any one of embodiments D1-D13, wherein the soluble tissue factor domain is not capable of binding to Factor VIIa.

Embodiment D15. The multi-chain chimeric polypeptide of any one of embodiments D1-D14, wherein the soluble tissue factor domain does not convert inactive Factor X into Factor Xa.

Embodiment D16. The multi-chain chimeric polypeptide of any one of embodiments D1-D15, wherein the multi-chain chimeric polypeptide does not stimulate blood coagulation in a mammal.

Embodiment D17. The multi-chain chimeric polypeptide of any one of embodiments D1-D16, wherein the first chimeric polypeptide further comprises a peptide tag at the N-terminal end or the C-terminal end of the first chimeric polypeptide.

Embodiment D18. The multi-chain chimeric polypeptide of any one of embodiments D1-D17, wherein the second chimeric polypeptide further comprises a peptide tag at the N-terminal end or the C-terminal end of the second chimeric polypeptide.

Embodiment D19. The multi-chain chimeric polypeptide of any one of embodiments D1-D18, wherein the first chimeric polypeptide and/or the second chimeric polypeptide further comprises a signal sequence at its N-terminal end.

Embodiment D20. The multi-chain chimeric polypeptide of embodiment D19, wherein the signal sequence comprises SEQ ID NO: 117.

Embodiment D21. The multi-chain chimeric polypeptide of embodiment D20, wherein the signal sequence is SEQ ID NO: 117.

Embodiment D22. The multi-chain chimeric polypeptide of any one of embodiments D1-D21, wherein the pair of affinity domains is a sushi domain from an alpha chain of human IL-15 receptor (IL-15Rα) and a soluble IL-15.

Embodiment D23. The multi-chain chimeric polypeptide of embodiment D22, wherein the soluble IL-15 has a D8N or D8A amino acid substitution.

Embodiment D24. The multi-chain chimeric polypeptide of embodiment D22, wherein the soluble IL-15 comprises a sequence that is 80% identical to SEQ ID NO: 82.

Embodiment D25. The multi-chain chimeric polypeptide of embodiment D24, wherein the soluble IL-15 comprises a sequence that is 90% identical to SEQ ID NO: 82.

Embodiment D26. The multi-chain chimeric polypeptide of embodiment D25, wherein the soluble IL-15 comprises a sequence that is 95% identical to SEQ ID NO: 82.

Embodiment D27. The multi-chain chimeric polypeptide of embodiment D26, wherein the soluble IL-15 comprises SEQ ID NO: 82.

Embodiment D28. The multi-chain chimeric polypeptide of any one of embodiments D22-D27, wherein the sushi domain of IL-15Rα comprises a sushi domain from human IL-15Rα.

Embodiment D29. The multi-chain chimeric polypeptide of embodiment D28, wherein the sushi domain from human IL-15Rα comprises a sequence that is 80% identical to SEQ ID NO: 113.

Embodiment D30. The multi-chain chimeric polypeptide of embodiment D29, wherein the sushi domain from human IL-15Rα comprises a sequence that is 90% identical to SEQ ID NO: 113.

Embodiment D31. The multi-chain chimeric polypeptide of embodiment D30, wherein the sushi domain from human IL-15Rα comprises a sequence that is 95% identical to SEQ ID NO: 113.

Embodiment D32. The multi-chain chimeric polypeptide of embodiment D31, wherein the sushi domain from human IL-15Rα comprises SEQ ID NO: 113.

Embodiment D33. The multi-chain chimeric polypeptide of embodiment D28, wherein the sushi domain from human IL-15Rα is a mature full-length IL-15Rα.

Embodiment D34. The multi-chain chimeric polypeptide of any one of embodiments D1-D21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment D35. The multi-chain chimeric polypeptide of any one of embodiments D1-D34, wherein one or both of the first target-binding domain and the second target-binding domain is an agonistic antigen-binding domain.

Embodiment D36. The multi-chain chimeric polypeptide of embodiment D35, wherein the first target-binding domain and the second target-binding domain are each agonistic antigen-binding domains.

Embodiment D37. The multi-chain chimeric polypeptide of embodiment D35 or D36, wherein antigen-binding domain comprises a scFv or single-domain antibody.

Embodiment D38. The multi-chain chimeric polypeptide of any one of embodiments D1-D34, wherein one or both of the first target-binding domain and the second target-binding domain is a soluble IL-15 or a soluble IL-18.

Embodiment D39. The multi-chain chimeric polypeptide of embodiment D38, wherein the first target-binding domain and the second target-binding domain are each independently a soluble IL-15 or a soluble IL-18.

Embodiment D40. The multi-chain chimeric polypeptide of any one of embodiments D1-D39, wherein the first target-binding domain and the second target-binding domain both bind specifically to a receptor of IL-18 or a receptor of IL-12.

Embodiment D41. The multi-chain chimeric polypeptide of embodiment B40, wherein the first target-binding domain and the second target-binding domain bind specifically to the same epitope.

Embodiment D42. The multi-chain chimeric polypeptide of embodiment D41, wherein the first target-binding domain and the second target-binding domain comprise the same amino acid sequence.

Embodiment D43. The multi-chain chimeric polypeptide of any one of embodiments D1-D39, wherein the first target-binding domain binds specifically to a receptor for IL-12, and the second target-binding domain binds specifically to a receptor for IL-18.

Embodiment D44. The multi-chain chimeric polypeptide of any one of embodiments D1-D39, wherein the first target-binding domain binds specifically to a receptor for IL-18, and the second target-binding domain bind specifically to a receptor for IL-12.

Embodiment D45. The multi-chain chimeric polypeptide of embodiment D44, wherein the first target-binding domain comprises a soluble IL-18.

Embodiment D46. The multi-chain chimeric polypeptide of embodiment D45, wherein the soluble IL-18 is a soluble human IL-18.

Embodiment D47. The multi-chain chimeric polypeptide of embodiment D46, wherein the soluble human IL-18 comprises a sequence at least 80% identical to SEQ ID NO: 109.

Embodiment D48. The multi-chain chimeric polypeptide of embodiment D47, wherein the soluble human IL-18 comprises a sequence at least 90% identical to SEQ ID NO: 109.

Embodiment D49. The multi-chain chimeric polypeptide of embodiment D48, wherein the soluble human IL-18 comprises a sequence at least 95% identical to SEQ ID NO: 109.

Embodiment D50. The multi-chain chimeric polypeptide of embodiment D49, wherein the soluble human IL-18 comprises a sequence of SEQ ID NO: 109.

Embodiment D51. The multi-chain chimeric polypeptide of any one of embodiments D44-D50, wherein the second target-binding domain comprises a soluble IL-12.

Embodiment D52. The multi-chain chimeric polypeptide of embodiment D51, wherein the soluble IL-18 is a soluble human IL-12.

Embodiment D53. The multi-chain chimeric polypeptide of embodiment D52, wherein the soluble human IL-15 comprises a sequence of soluble human IL-120 (p40) and a sequence of soluble human IL-12a (p35).

Embodiment D54. The multi-chain chimeric polypeptide of embodiment D53, wherein the soluble human IL-15 further comprises a linker sequence between the sequence of soluble IL-120 (p40) and the sequence of soluble human IL-12a (p35).

Embodiment D55. The multi-chain chimeric polypeptide of embodiment D54, wherein the linker sequence comprises SEQ ID NO: 102.

Embodiment D56. The multi-chain chimeric polypeptide of any one of embodiments D53-D55, wherein the sequence of soluble human IL-120 (p40) comprises a sequence that is at least 80% identical to SEQ ID NO: 81.

Embodiment D57. The multi-chain chimeric polypeptide of embodiment D56, wherein the sequence of soluble human IL-120 (p40) comprises a sequence that is at least 90% identical to SEQ ID NO: 81.

Embodiment D58. The multi-chain chimeric polypeptide of embodiment D57, wherein the sequence of soluble human IL-120 (p40) comprises a sequence that is at least 95% identical to SEQ ID NO: 81.

Embodiment D59. The multi-chain chimeric polypeptide of embodiment D58, wherein the sequence of soluble human IL-120 (p40) comprises SEQ ID NO: 81.

Embodiment D60. The multi-chain chimeric polypeptide of any one of embodiments D53-D59, wherein the sequence of soluble human IL-12a (p35) comprises a sequence that is at least 80% identical to SEQ ID NO: 80.

Embodiment D61. The multi-chain chimeric polypeptide of embodiment D60, wherein the sequence of soluble human IL-12a (p35) comprises a sequence that is at least 90% identical to SEQ ID NO: 80.

Embodiment D62. The mule-chain chimeric polypeptide of embodiment D61, wherein the sequence of soluble human IL-12a (p35) comprises a sequence that is at least 95% identical to SEQ ID NO: 80.

Embodiment D63. The multi-chain chimeric polypeptide of embodiment D62, wherein the sequence of soluble human IL-12a (p35) comprises SEQ ID NO: 80.

Embodiment D64. The multi-chain chimeric polypeptide of embodiment D1, wherein the first chimeric polypeptide comprises a sequence that is at least 80% identical to SEQ ID NO: 174.

Embodiment D65. The multi-chain chimeric polypeptide of embodiment D64, wherein the first chimeric polypeptide comprises a sequence that is at least 90% identical to SEQ ID NO: 174.

Embodiment D66. The multi-chain chimeric polypeptide of embodiment D65, wherein the first chimeric polypeptide comprises a sequence that is at least 95% identical to SEQ ID NO: 174.

Embodiment D67. The multi-chain chimeric polypeptide of embodiment D66, wherein the first chimeric polypeptide comprises SEQ ID NO: 174.

Embodiment D68. The multi-chain chimeric polypeptide of embodiment D67, wherein the first chimeric polypeptide comprises SEQ ID NO: 176.

Embodiment D69. The multi-chain chimeric polypeptide of any one of embodiments D1 and D64-D68, wherein the second chimeric polypeptide comprises a sequence that is at least 80% identical to SEQ ID NO: 178.

Embodiment D70. The multi-chain chimeric polypeptide of embodiment D69, wherein the second chimeric polypeptide comprises a sequence that is at least 90% identical to SEQ ID NO: 178.

Embodiment D71. The multi-chain chimeric polypeptide of embodiment D70, wherein the second chimeric polypeptide comprises a sequence that is at least 95% identical to SEQ ID NO: 178.

Embodiment D72. The multi-chain chimeric polypeptide of embodiment D71, wherein the second chimeric polypeptide comprises SEQ ID NO: 178.

Embodiment D73. The multi-chain chimeric polypeptide of embodiment D72, wherein the second chimeric polypeptide comprises SEQ ID NO: 180.

Embodiment D74. The multi-chain chimeric polypeptide of any one of embodiments D1-D63, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment D75. The multi-chain chimeric polypeptide of embodiment D74, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment D76. The multi-chain chimeric polypeptide of any one of embodiments D1-D63, wherein the first chimeric polypeptide further comprises one or more additional target-binding domains at the N-terminal and/or C-terminal end of the first chimeric polypeptide.

Embodiment D77. The multi-chain chimeric polypeptide of embodiment D76, wherein at least one of the one or more additional target-binding domains directly abuts the first domain of the pair of affinity domains in the first chimeric polypeptide.

Embodiment D78. The multi-chain chimeric polypeptide of embodiment D76, wherein the first chimeric polypeptide further comprises a linker sequence between the at least one of the one or more additional target-binding domains and the first domain of the pair of affinity domains.

Embodiment D79. The multi-chain chimeric polypeptide of embodiment D76, wherein the at least one of the one or more additional target-binding domains directly abuts the first target-binding domain in the first chimeric polypeptide.

Embodiment D80. The multi-chain chimeric polypeptide of embodiment D76, wherein the first chimeric polypeptide further comprises a linker sequence between the at least one of the one or more additional target-binding domains and the first target-binding domain.

Embodiment D81. The multi-chain chimeric polypeptide of embodiment D76, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment D82. The multi-chain chimeric polypeptide of embodiment D81, wherein the at least one additional target-binding domain of the one or more additional target-binding domains disposed at the N-terminus directly abuts the first target-binding domain or the first domain of the pair of affinity domains in the first chimeric polypeptide.

Embodiment D83. The multi-chain chimeric polypeptide of embodiment D81, wherein the first chimeric polypeptide further comprises a linker sequence disposed between the at least one additional target-binding domain and the first target-binding domain or the first domain of the pair of affinity domains in the first chimeric polypeptide.

Embodiment D84. The multi-chain chimeric polypeptide of embodiment D81, wherein the at least one additional target-binding domain of the one or more additional target-binding domains disposed at the C-terminus directly abuts the first target-binding domain or the first domain of the pair of affinity domains in the first chimeric polypeptide.

Embodiment D85. The multi-chain chimeric polypeptide of embodiment D81, wherein the first chimeric polypeptide further comprises a linker sequence disposed between the at least one additional target-binding domain and the first target-binding domain or the first domain of the pair of affinity domains in the first chimeric polypeptide.

Embodiment D86. The multi-chain chimeric polypeptide of embodiment D81, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment D87. The multi-chain chimeric polypeptide of embodiment D81, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment D88. The multi-chain chimeric polypeptide of any one of embodiments D1-D63 and D74-D87, wherein the second chimeric polypeptide further comprises one or more additional target-binding domains at the N-terminal end or the C-terminal end of the second chimeric polypeptide.

Embodiment D89. The multi-chain chimeric polypeptide of embodiment D88, wherein at least one of the one or more additional target-binding domains directly abuts the second domain of the pair of affinity domains in the second chimeric polypeptide.

Embodiment D90. The multi-chain chimeric polypeptide of embodiment D88, wherein the second chimeric polypeptide further comprises a linker sequence between at least one of the one or more additional target-binding domains and the second domain of the pair of affinity domains in the second chimeric polypeptide.

Embodiment D91. The multi-chain chimeric polypeptide of embodiment D88, wherein at least one of the one or more additional target-binding domains directly abuts the second target-binding domain in the second chimeric polypeptide.

Embodiment D92. The multi-chain chimeric polypeptide of embodiment D88, wherein the second chimeric polypeptide further comprises a linker sequence between at least one of the one or more additional target-binding domains and the second target-binding domain in the second chimeric polypeptide.

Embodiment D93. The multi-chain chimeric polypeptide of any one of embodiments D74-D92, wherein two or more of the first target-binding domain, the second target-binding domain, and the one or more additional target-binding domains bind specifically to the same antigen.

Embodiment D94. The multi-chain chimeric polypeptide of embodiment B93, wherein two or more of the first target-binding domain, the second target-binding domain, and the one or more additional target-binding domains bind specifically to the same epitope.

Embodiment D95. The multi-chain chimeric polypeptide of embodiment B94, wherein two or more of the first target-binding domain, the second target-binding domain, and the one or more additional target-binding domains comprise the same amino acid sequence.

Embodiment D96. The multi-chain chimeric polypeptide of any one of embodiments D74-D92, wherein the first target-binding domain, the second target-binding domain, and the one or more additional target-binding domains bind specifically to different antigens.

Embodiment D97. The multi-chain chimeric polypeptide of any one of embodiments D74-D96, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment D98. The multi-chain chimeric polypeptide of any one of embodiments D74-D96, wherein the one or more additional target-binding domains is a soluble interleukin or cytokine protein.

Embodiment D99. The multi-chain chimeric polypeptide of embodiment B98, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment D100. The multi-chain chimeric polypeptide of any one of embodiments D74-D96, wherein the one or more additional target-binding domains is a soluble interleukin or cytokine receptor.

Embodiment D101. The multi-chain chimeric polypeptide of embodiment B100, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM1, a scMHCI, a scMHCII, a scTCR, a soluble CD155, a soluble CD122, or a soluble CD28.

Embodiment D102. A composition comprising any of the multi-chain chimeric polypeptides of embodiments D1-D101.

Embodiment D103. The composition of embodiment D102, wherein the composition is a pharmaceutical composition.

Embodiment D104. A kit comprising at least one dose of the composition of embodiment D102 or D103.

Embodiment D105. Nucleic acid encoding any of the multi-chain chimeric polypeptides of any one of embodiments D1-D101.

Embodiment D106. A vector comprising the nucleic acid of embodiment D105. Embodiment D107. The vector of embodiment D106, wherein the vector is an expression vector.

Embodiment D108. A cell comprising the nucleic acid of embodiment D105 or the vector of embodiment D106 or D107.

Embodiment D109. A method of producing a multi-chain chimeric polypeptide, the method comprising:

culturing the cell of embodiment D108 in a culture medium under conditions sufficient to result in the production of the multi-chain chimeric polypeptide; and recovering the multi-chain chimeric polypeptide from the cell and/or the culture medium.

Embodiment D110. A multi-chain chimeric polypeptide produced by the method of embodiment D109.

Embodiment D111. The multi-chain chimeric polypeptide of embodiment D8, wherein the soluble human tissue factor domain comprises a sequence that is at least 80% identical to SEQ ID NO: 97.

Embodiment D112. The multi-chain chimeric polypeptide of embodiment D111, wherein the soluble human tissue factor domain comprises a sequence that is at least 90% identical to SEQ ID NO: 97.

Embodiment D113. The multi-chain chimeric polypeptide of embodiment D112, wherein the soluble human tissue factor domain comprises a sequence that is at least 95% identical to SEQ ID NO: 97.

Embodiment D114. The multi-chain chimeric polypeptide of embodiment D113, wherein the soluble human tissue factor domain comprises a sequence that is 100% identical to SEQ ID NO: 97.

Embodiment D115. The multi-chain chimeric polypeptide of embodiment D8, wherein the soluble human tissue factor domain comprises a sequence that is at least 80% identical to SEQ ID NO: 98.

Embodiment D116. The multi-chain chimeric polypeptide of embodiment D115, wherein the soluble human tissue factor domain comprises a sequence that is at least 90% identical to SEQ ID NO: 98.

Embodiment D117. The multi-chain chimeric polypeptide of embodiment D116, wherein the soluble human tissue factor domain comprises a sequence that is at least 95% identical to SEQ ID NO: 98.

Embodiment D118. The multi-chain chimeric polypeptide of embodiment D117, wherein the soluble human tissue factor domain comprises a sequence that is 100% identical to SEQ ID NO: 98.

Embodiment E1. A multi-chain chimeric polypeptide comprising:

(a) a first chimeric polypeptide comprising:

(i) a first target-binding domain;

(ii) a soluble tissue factor domain; and (iii) a first domain of a pair of affinity domains;

(b) a second chimeric polypeptide comprising:

(i) a second domain of a pair of affinity domains; and (ii) a second target-binding domain, wherein:

the first chimeric polypeptide and the second chimeric polypeptide associate through the binding of the first domain and the second domain of the pair of affinity domains; and the first target-binding domain and the second targeting-binding domain each independently bind specifically to a receptor of IL-21 or a ligand of tumor growth factor receptor βII (TGFβRII).

Embodiment E2. The multi-chain chimeric polypeptide of embodiment E1, wherein the first target-binding domain and the soluble tissue factor domain directly abut each other in the first chimeric polypeptide.

Embodiment E3. The multi-chain chimeric polypeptide of embodiments E1, wherein the first chimeric polypeptide further comprises a linker sequence between the first target-binding domain and the soluble tissue factor domain in the first chimeric polypeptide.

Embodiment E4. The multi-chain chimeric polypeptide of any one of embodiments E1-E3, wherein the soluble tissue factor domain and the first domain of the pair of affinity domains directly abut each other in the first chimeric polypeptide.

Embodiment E5. The multi-chain chimeric polypeptide of any one of embodiments E1-E3, wherein the first chimeric polypeptide further comprises a linker sequence between the soluble tissue factor domain and the first domain of the pair of affinity domains in the first chimeric polypeptide.

Embodiment E6. The multi-chain chimeric polypeptide of any one of embodiments E1-E5, wherein the second domain of the pair of affinity domains and the second target-binding domain directly abut each other in the second chimeric polypeptide.

Embodiment E7. The multi-chain chimeric polypeptide of any one of embodiments E1-E5, wherein second chimeric polypeptide further comprises a linker sequence between the second domain of the pair of affinity domains and the second target-binding domain in the second chimeric polypeptide.

Embodiment E8. The multi-chain chimeric polypeptide of any one of embodiments E1-E7, wherein the soluble tissue factor domain is a soluble human tissue factor domain.

Embodiment E9. The multi-chain chimeric polypeptide of embodiment E8, wherein the soluble human tissue factor domain comprises a sequence that is at least 80% identical to SEQ ID NO: 93.

Embodiment E10. The multi-chain chimeric polypeptide of embodiment E9, wherein the soluble human tissue factor domain comprises a sequence that is at least 90% identical to SEQ ID NO: 93.

Embodiment E11. The multi-chain chimeric polypeptide of embodiment E10, wherein the soluble human tissue factor domain comprises a sequence that is at least 95% identical to SEQ ID NO: 93.

Embodiment E12. The multi-chain chimeric polypeptide of any one of embodiments E8-E11, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment E13. The multi-chain chimeric polypeptide of embodiment E12, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment E14. The multi-chain chimeric polypeptide of any one of embodiments E1-E13, wherein the soluble tissue factor domain is not capable of binding to Factor VIIa.

Embodiment E15. The multi-chain chimeric polypeptide of any one of embodiments E1-E14, wherein the soluble tissue factor domain does not convert inactive Factor X into Factor Xa.

Embodiment E16. The multi-chain chimeric polypeptide of any one of embodiments E1-E15, wherein the multi-chain chimeric polypeptide does not stimulate blood coagulation in a mammal.

Embodiment E17. The multi-chain chimeric polypeptide of any one of embodiments E1-E16, wherein the first chimeric polypeptide further comprises a peptide tag at the N-terminal end or the C-terminal end of the first chimeric polypeptide.

Embodiment E18. The multi-chain chimeric polypeptide of any one of embodiments E1-E17, wherein the second chimeric polypeptide further comprises a peptide tag at the N-terminal end or the C-terminal end of the second chimeric polypeptide.

Embodiment E19. The multi-chain chimeric polypeptide of any one of embodiments E1-E18, wherein the first chimeric polypeptide and/or the second chimeric polypeptide further comprises a signal sequence at its N-terminal end.

Embodiment E20. The multi-chain chimeric polypeptide of embodiment E19, wherein the signal sequence comprises SEQ ID NO: 117.

Embodiment E21. The multi-chain chimeric polypeptide of embodiment E20, wherein the signal sequence is SEQ ID NO: 117.

Embodiment E22. The multi-chain chimeric polypeptide of any one of embodiments E1-E21, wherein the pair of affinity domains is a sushi domain from an alpha chain of human IL-15 receptor (IL-15Rα and a soluble IL-15.

Embodiment E23. The multi-chain chimeric polypeptide of embodiment E22, wherein the soluble IL-15 has a D8N or D8A amino acid substitution.

Embodiment E24. The multi-chain chimeric polypeptide of embodiment E22, wherein the soluble IL-15 comprises a sequence that is 80% identical to SEQ ID NO: 82.

Embodiment E25. The multi-chain chimeric polypeptide of embodiment E24, wherein the soluble IL-15 comprises a sequence that is 90% identical to SEQ ID NO: 82.

Embodiment E26. The multi-chain chimeric polypeptide of embodiment E25, wherein the soluble IL-15 comprises a sequence that is 95% identical to SEQ ID NO: 82.

Embodiment E27. The multi-chain chimeric polypeptide of embodiment E26, wherein the soluble IL-15 comprises SEQ ID NO: 82.

Embodiment E28. The multi-chain chimeric polypeptide of any one of embodiments E22-E27, wherein the sushi domain of IL-15Rα comprises a sushi domain from human IL-15Rα.

Embodiment E29. The multi-chain chimeric polypeptide of embodiment E28, wherein the sushi domain from human IL-15Rα comprises a sequence that is 80% identical to SEQ ID NO: 113.

Embodiment E30. The multi-chain chimeric polypeptide of embodiment E29, wherein the sushi domain from human IL-15Rα comprises a sequence that is 90% identical to SEQ ID NO: 113.

Embodiment E31. The multi-chain chimeric polypeptide of embodiment E30, wherein the sushi domain from human IL-15Rα comprises a sequence that is 95% identical to SEQ ID NO: 113.

Embodiment E32. The multi-chain chimeric polypeptide of embodiment E31, wherein the sushi domain from human IL-15Rα comprises SEQ ID NO: 113.

Embodiment E33. The multi-chain chimeric polypeptide of embodiment E28, wherein the sushi domain from human IL-15Rα is a mature full-length IL-15Rα.

Embodiment E34. The multi-chain chimeric polypeptide of any one of embodiments E1-E21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment E35. The multi-chain chimeric polypeptide of any one of embodiments E1-E34, wherein one or both of the first target-binding domain and the second target-binding domain is an antigen-binding domain.

Embodiment E36. The multi-chain chimeric polypeptide of embodiment E35, wherein the first target-binding domain and the second target-binding domain are antigen-binding domains.

Embodiment E37. The multi-chain chimeric polypeptide of embodiment E35 or E36, wherein antigen-binding domain comprises a scFv or single-domain antibody.

Embodiment E38. The multi-chain chimeric polypeptide of any one of embodiments E1-E34, wherein one or both of the first target-binding domain and the second target-binding domain is a soluble IL-21 or a soluble TGFβRII.

Embodiment E39. The multi-chain chimeric polypeptide of any one of embodiments E1-E38, wherein the first target-binding domain and the second target-binding domain both bind specifically to a receptor of IL-21 or a ligand of TGFβRII.

Embodiment E40. The multi-chain chimeric polypeptide of embodiment E39, wherein the first target-binding domain and the second target-binding domain bind specifically to the same epitope.

Embodiment E41. The multi-chain chimeric polypeptide of embodiment E40, wherein the first target-binding domain and the second target-binding domain comprise the same amino acid sequence.

Embodiment E42. The multi-chain chimeric polypeptide of any one of embodiments E1-E38, wherein the first target-binding domain binds specifically to a ligand of TGFβRII, and the second target-binding domain binds specifically to a receptor for IL-21.

Embodiment E43. The multi-chain chimeric polypeptide of any one of embodiments E1-E38, wherein the first target-binding domain binds specifically to a receptor for IL-21, and the second target-binding domain bind specifically to a ligand of TGFβRII.

Embodiment E44. The multi-chain chimeric polypeptide of embodiment E43, wherein the first target-binding domain comprises a soluble IL-21.

Embodiment E45. The multi-chain chimeric polypeptide of embodiment E44, wherein the soluble IL-21 is a soluble human IL-21.

Embodiment E46. The multi-chain chimeric polypeptide of embodiment E45, wherein the soluble human IL-21 comprises a sequence at least 80% identical to SEQ ID NO: 83.

Embodiment E47. The multi-chain chimeric polypeptide of embodiment E46, wherein the soluble human IL-21 comprises a sequence at least 90% identical to SEQ ID NO: 83.

Embodiment E48. The multi-chain chimeric polypeptide of embodiment E47, wherein the soluble human IL-21 comprises a sequence at least 95% identical to SEQ ID NO: 83.

Embodiment E49. The multi-chain chimeric polypeptide of embodiment E48, wherein the soluble human IL-21 comprises a sequence of SEQ ID NO: 83.

Embodiment E50. The multi-chain chimeric polypeptide of any one of embodiments E43-E49, wherein the second target-binding domain comprises a soluble TGFβRII.

Embodiment E51. The multi-chain chimeric polypeptide of embodiment E50, wherein the soluble TGFβRII is a soluble human TGFβRII.

Embodiment E52. The multi-chain chimeric polypeptide of embodiment E51, wherein the soluble human TGFβRII comprises a first sequence of soluble human TGFβRII and a second sequence of soluble human TGFβRII.

Embodiment E53. The multi-chain chimeric polypeptide of embodiment E52, wherein the soluble human TGFβRII further comprises a linker sequence between the first sequence of soluble human TGFβRII and the second sequence of soluble human TGFβRII.

Embodiment E54. The multi-chain chimeric polypeptide of embodiment E53, wherein the linker sequence comprises SEQ ID NO: 102.

Embodiment E55. The multi-chain chimeric polypeptide of any one of embodiments E52-E54, wherein the first sequence of soluble human TGFβRII comprises a sequence that is at least 80% identical to SEQ ID NO: 183.

Embodiment E56. The multi-chain chimeric polypeptide of embodiment E55, wherein the first sequence of soluble human TGFβRII comprises a sequence that is at least 90% identical to SEQ ID NO: 183.

Embodiment E57. The multi-chain chimeric polypeptide of embodiment E56, wherein the first sequence of soluble human TGFβRII comprises a sequence that is at least 95% identical to SEQ ID NO: 183.

Embodiment E58. The multi-chain chimeric polypeptide of embodiment E57, wherein the first sequence of soluble human TGFβRII comprises SEQ ID NO: 183.

Embodiment E59. The multi-chain chimeric polypeptide of any one of embodiments E52-E58, wherein the second sequence of soluble human TGFβRII comprises a sequence that is at least 80% identical to SEQ ID NO: 184.

Embodiment E60. The multi-chain chimeric polypeptide of embodiment E59, wherein the second sequence of soluble human TGFβRII comprises a sequence that is at least 90% identical to SEQ ID NO: 184.

Embodiment E61. The mule-chain chimeric polypeptide of embodiment E60, wherein the second sequence of soluble human TGFβRII comprises a sequence that is at least 95% identical to SEQ ID NO: 184.

Embodiment E62. The multi-chain chimeric polypeptide of embodiment E61, wherein the second sequence of soluble human TGFβRII comprises SEQ ID NO: 184.

Embodiment E63. The multi-chain chimeric polypeptide of embodiment E1, wherein the first chimeric polypeptide comprises a sequence that is at least 80% identical to SEQ ID NO: 189.

Embodiment E64. The multi-chain chimeric polypeptide of embodiment E63, wherein the first chimeric polypeptide comprises a sequence that is at least 90% identical to SEQ ID NO: 189.

Embodiment E65. The multi-chain chimeric polypeptide of embodiment E64, wherein the first chimeric polypeptide comprises a sequence that is at least 95% identical to SEQ ID NO: 189.

Embodiment E66. The multi-chain chimeric polypeptide of embodiment E65, wherein the first chimeric polypeptide comprises SEQ ID NO: 189.

Embodiment E67. The multi-chain chimeric polypeptide of embodiment E66, wherein the first chimeric polypeptide comprises SEQ ID NO: 191.

Embodiment E68. The multi-chain chimeric polypeptide of any one of embodiments E1 and E63-E67, wherein the second chimeric polypeptide comprises a sequence that is at least 80% identical to SEQ ID NO: 193.

Embodiment E69. The multi-chain chimeric polypeptide of embodiment E68, wherein the second chimeric polypeptide comprises a sequence that is at least 90% identical to SEQ ID NO: 193.

Embodiment E70. The multi-chain chimeric polypeptide of embodiment E69, wherein the second chimeric polypeptide comprises a sequence that is at least 95% identical to SEQ ID NO: 193.

Embodiment E71. The multi-chain chimeric polypeptide of embodiment E70, wherein the second chimeric polypeptide comprises SEQ ID NO: 193.

Embodiment E72. The multi-chain chimeric polypeptide of embodiment E71, wherein the second chimeric polypeptide comprises SEQ ID NO: 195.

Embodiment E73. The multi-chain chimeric polypeptide of any one of embodiments E1-E62, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment E74. The multi-chain chimeric polypeptide of embodiment E73, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment E75. The multi-chain chimeric polypeptide of any one of embodiments E1-E62, wherein the first chimeric polypeptide further comprises one or more additional target-binding domains at the N-terminal and/or C-terminal end of the first chimeric polypeptide.

Embodiment E76. The multi-chain chimeric polypeptide of embodiment E75, wherein at least one of the one or more additional target-binding domains directly abuts the first domain of the pair of affinity domains in the first chimeric polypeptide.

Embodiment E77. The multi-chain chimeric polypeptide of embodiment E75, wherein the first chimeric polypeptide further comprises a linker sequence between the at least one of the one or more additional target-binding domains and the first domain of the pair of affinity domains.

Embodiment E78. The multi-chain chimeric polypeptide of embodiment E75, wherein the at least one of the one or more additional target-binding domains directly abuts the first target-binding domain in the first chimeric polypeptide.

Embodiment E79. The multi-chain chimeric polypeptide of embodiment E75, wherein the first chimeric polypeptide further comprises a linker sequence between the at least one of the one or more additional target-binding domains and the first target-binding domain.

Embodiment E80. The multi-chain chimeric polypeptide of embodiment E75, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment E81. The multi-chain chimeric polypeptide of embodiment E80, wherein the at least one additional target-binding domain of the one or more additional target-binding domains disposed at the N-terminus directly abuts the first target-binding domain or the first domain of the pair of affinity domains in the first chimeric polypeptide.

Embodiment E82. The multi-chain chimeric polypeptide of embodiment E80, wherein the first chimeric polypeptide further comprises a linker sequence disposed between the at least one additional target-binding domain and the first target-binding domain or the first domain of the pair of affinity domains in the first chimeric polypeptide.

Embodiment E83. The multi-chain chimeric polypeptide of embodiment E80, wherein the at least one additional target-binding domain of the one or more additional target-binding domains disposed at the C-terminus directly abuts the first target-binding domain or the first domain of the pair of affinity domains in the first chimeric polypeptide.

Embodiment E84. The multi-chain chimeric polypeptide of embodiment E80, wherein the first chimeric polypeptide further comprises a linker sequence disposed between the at least one additional target-binding domain and the first target-binding domain or the first domain of the pair of affinity domains in the first chimeric polypeptide.

Embodiment E85. The multi-chain chimeric polypeptide of embodiment E80, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment E86. The multi-chain chimeric polypeptide of embodiment E80, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment E87. The multi-chain chimeric polypeptide of any one of embodiments E1-E62 and E73-E86, wherein the second chimeric polypeptide further comprises one or more additional target-binding domains at the N-terminal end or the C-terminal end of the second chimeric polypeptide.

Embodiment E88. The multi-chain chimeric polypeptide of embodiment E87, wherein at least one of the one or more additional target-binding domains directly abuts the second domain of the pair of affinity domains in the second chimeric polypeptide.

Embodiment E89. The multi-chain chimeric polypeptide of embodiment E87, wherein the second chimeric polypeptide further comprises a linker sequence between at least one of the one or more additional target-binding domains and the second domain of the pair of affinity domains in the second chimeric polypeptide.

Embodiment E90. The multi-chain chimeric polypeptide of embodiment E87, wherein at least one of the one or more additional target-binding domains directly abuts the second target-binding domain in the second chimeric polypeptide.

Embodiment E91. The multi-chain chimeric polypeptide of embodiment E87, wherein the second chimeric polypeptide further comprises a linker sequence between at least one of the one or more additional target-binding domains and the second target-binding domain in the second chimeric polypeptide.

Embodiment E92. The multi-chain chimeric polypeptide of any one of embodiments E73-E91, wherein two or more of the first target-binding domain, the second target-binding domain, and the one or more additional target-binding domains bind specifically to the same antigen.

Embodiment E93. The multi-chain chimeric polypeptide of embodiment E92, wherein two or more of the first target-binding domain, the second target-binding domain, and the one or more additional target-binding domains bind specifically to the same epitope.

Embodiment E94. The multi-chain chimeric polypeptide of embodiment E93, wherein two or more of the first target-binding domain, the second target-binding domain, and the one or more additional target-binding domains comprise the same amino acid sequence.

Embodiment E95. The multi-chain chimeric polypeptide of any one of embodiments E73-E91, wherein the first target-binding domain, the second target-binding domain, and the one or more additional target-binding domains bind specifically to different antigens.

Embodiment E96. The multi-chain chimeric polypeptide of any one of embodiments E73-E95, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-D, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment E97. The multi-chain chimeric polypeptide of any one of embodiments E73-E95, wherein the one or more additional target-binding domains is a soluble interleukin or cytokine protein.

Embodiment E98. The multi-chain chimeric polypeptide of embodiment E97, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment E99. The multi-chain chimeric polypeptide of any one of embodiments E73-E95, wherein the one or more additional target-binding domains is a soluble interleukin or cytokine receptor.

Embodiment E100. The multi-chain chimeric polypeptide of embodiment E99, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM1, a scMHCI, a scMHCII, a scTCR, a soluble CD155, or a soluble CD28.

Embodiment E101. A composition comprising any of the multi-chain chimeric polypeptides of embodiments E1-E100.

Embodiment E102. The composition of embodiment E101, wherein the composition is a pharmaceutical composition.

Embodiment E103. A kit comprising at least one dose of the composition of embodiment E101 or E102.

Embodiment E104. Nucleic acid encoding any of the multi-chain chimeric polypeptides of any one of embodiments E1-E100.

Embodiment E105. A vector comprising the nucleic acid of embodiment E104.

Embodiment E106. The vector of embodiment E105, wherein the vector is an expression vector.

Embodiment E107. A cell comprising the nucleic acid of embodiment C104 or the vector of embodiment E105 or E106.

Embodiment E108. A method of producing a multi-chain chimeric polypeptide, the method comprising:

culturing the cell of embodiment E107 in a culture medium under conditions sufficient to result in the production of the multi-chain chimeric polypeptide; and recovering the multi-chain chimeric polypeptide from the cell and/or the culture medium.

Embodiment E109. A multi-chain chimeric polypeptide produced by the method of embodiment E108.

Embodiment E110. The multi-chain chimeric polypeptide of embodiment E12, wherein the soluble human tissue factor domain comprises a sequence that is at least 80% identical to SEQ ID NO: 97.

Embodiment E111. The multi-chain chimeric polypeptide of embodiment E110, wherein the soluble human tissue factor domain comprises a sequence that is at least 90% identical to SEQ ID NO: 97.

Embodiment E112. The multi-chain chimeric polypeptide of embodiment E111, wherein the soluble human tissue factor domain comprises a sequence that is at least 95% identical to SEQ ID NO: 97.

Embodiment E113. The multi-chain chimeric polypeptide of embodiment E112, wherein the soluble human tissue factor domain comprises a sequence that is 100% identical to SEQ ID NO: 97.

Embodiment E114. The multi-chain chimeric polypeptide of embodiment E12, wherein the soluble human tissue factor domain comprises a sequence that is at least 80% identical to SEQ ID NO: 98.

Embodiment E115. The multi-chain chimeric polypeptide of embodiment E114, wherein the soluble human tissue factor domain comprises a sequence that is at least 90% identical to SEQ ID NO: 98.

Embodiment E116. The multi-chain chimeric polypeptide of embodiment E115, wherein the soluble human tissue factor domain comprises a sequence that is at least 95% identical to SEQ ID NO: 98.

Embodiment E117. The multi-chain chimeric polypeptide of embodiment E116, wherein the soluble human tissue factor domain comprises a sequence that is 100% identical to SEQ ID NO: 98.

Embodiment F1. A multi-chain chimeric polypeptide comprising:

(c) a first chimeric polypeptide comprising:
  (i) a first target-binding domain;
  (ii) a soluble tissue factor domain; and
  (iii) a first domain of a pair of affinity domains;
(d) a second chimeric polypeptide comprising:
  (i) a second domain of a pair of affinity domains; and
  (ii) a second target-binding domain, wherein:

the first chimeric polypeptide and the second chimeric polypeptide associate through the binding of the first domain and the second domain of the pair of affinity domains;

the first target-binding domain and the second targeting-binding domain each independently bind specifically to a receptor of IL-21 or a receptor of IL-7.

Embodiment F2. The multi-chain chimeric polypeptide of embodiment F1, wherein the first target-binding domain and the soluble tissue factor domain directly abut each other in the first chimeric polypeptide.

Embodiment F3. The multi-chain chimeric polypeptide of embodiment F1, wherein the first chimeric polypeptide further comprises a linker sequence between the first target-binding domain and the soluble tissue factor domain in the first chimeric polypeptide.

Embodiment F4. The multi-chain chimeric polypeptide of any one of embodiments F1-F3, wherein the soluble tissue factor domain and the first domain of the pair of affinity domains directly abut each other in the first chimeric polypeptide.

Embodiment F5. The multi-chain chimeric polypeptide of any one of embodiments F1-F3, wherein the first chimeric polypeptide further comprises a linker sequence between the soluble tissue factor domain and the first domain of the pair of affinity domains in the first chimeric polypeptide.

Embodiment F6. The multi-chain chimeric polypeptide of any one of embodiments F1-F5, wherein the second domain of the pair of affinity domains and the second target-binding domain directly abut each other in the second chimeric polypeptide.

Embodiment F7. The multi-chain chimeric polypeptide of any one of embodiments F1-F5, wherein second chimeric polypeptide further comprises a linker sequence between the second domain of the pair of affinity domains and the second target-binding domain in the second chimeric polypeptide.

Embodiment F8. The multi-chain chimeric polypeptide of any one of embodiments F1-F7, wherein the soluble tissue factor domain is a soluble human tissue factor domain.

Embodiment F9. The multi-chain chimeric polypeptide of embodiment F8, wherein the soluble human tissue factor domain comprises a sequence that is at least 80% identical to SEQ ID NO: 93.

Embodiment F10. The multi-chain chimeric polypeptide of embodiment F9, wherein the soluble human tissue factor domain comprises a sequence that is at least 90% identical to SEQ ID NO: 93.

Embodiment F11. The multi-chain chimeric polypeptide of embodiment F10, wherein the soluble human tissue factor domain comprises a sequence that is at least 95% identical to SEQ ID NO: 93.

Embodiment F12. The multi-chain chimeric polypeptide of embodiment F11, wherein the soluble human tissue factor domain comprises SEQ ID NO: 93.

Embodiment F13. The multi-chain chimeric polypeptide of embodiment F8, wherein the soluble human tissue factor domain comprises a sequence that is at least 80% identical to SEQ ID NO: 97.

Embodiment F14. The multi-chain chimeric polypeptide of embodiment F13, wherein the soluble human tissue factor domain comprises a sequence that is at least 90% identical to SEQ ID NO: 97.

Embodiment F15. The multi-chain chimeric polypeptide of embodiment F14, wherein the soluble human tissue factor domain comprises a sequence that is at least 95% identical to SEQ ID NO: 97.

Embodiment F16. The multi-chain chimeric polypeptide of embodiment F15, wherein the soluble human tissue factor domain comprises SEQ ID NO: 97.

Embodiment F17. The multi-chain chimeric polypeptide of embodiment F8, wherein the soluble human tissue factor domain comprises a sequence that is at least 80% identical to SEQ ID NO: 98.

Embodiment F18. The multi-chain chimeric polypeptide of embodiment F17, wherein the soluble human tissue factor domain comprises a sequence that is at least 90% identical to SEQ ID NO: 98.

Embodiment F19. The multi-chain chimeric polypeptide of embodiment F18, wherein the soluble human tissue factor domain comprises a sequence that is at least 95% identical to SEQ ID NO: 98.

Embodiment F20. The multi-chain chimeric polypeptide of embodiment F19, wherein the soluble human tissue factor domain comprises SEQ ID NO: 98.

Embodiment F21. The multi-chain chimeric polypeptide of any one of embodiments F8-F11, F13-F15, and F17-F19, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment F22. The multi-chain chimeric polypeptide of embodiment F21, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment F23. The multi-chain chimeric polypeptide of any one of embodiments F1-F22, wherein the soluble tissue factor domain is not capable of binding to Factor VIIa.

Embodiment F24. The multi-chain chimeric polypeptide of any one of embodiments F1-F23, wherein the soluble tissue factor domain does not convert inactive Factor X into Factor Xa.

Embodiment F25. The multi-chain chimeric polypeptide of any one of embodiments F1-F24, wherein the multi-chain chimeric polypeptide does not stimulate blood coagulation in a mammal.

Embodiment F26. The multi-chain chimeric polypeptide of any one of embodiments F1-F25, wherein the first chimeric polypeptide further comprises a peptide tag at the N-terminal end or the C-terminal end of the first chimeric polypeptide.

Embodiment F27. The multi-chain chimeric polypeptide of any one of embodiments F1-F26, wherein the second chimeric polypeptide further comprises a peptide tag at the N-terminal end or the C-terminal end of the second chimeric polypeptide.

Embodiment F28. The multi-chain chimeric polypeptide of any one of embodiments F1-F27, wherein the first chimeric polypeptide and/or the second chimeric polypeptide further comprises a signal sequence at its N-terminal end.

Embodiment F29. The multi-chain chimeric polypeptide of embodiment F28, wherein the signal sequence comprises SEQ ID NO: 117.

Embodiment F30. The multi-chain chimeric polypeptide of embodiment F28, wherein the signal sequence is SEQ ID NO: 328.

Embodiment F31. The multi-chain chimeric polypeptide of any one of embodiments F1-F30, wherein the pair of affinity domains is a sushi domain from an alpha chain of human IL-15 receptor (IL-15R$\alpha$) and a soluble IL-15.

Embodiment F32. The multi-chain chimeric polypeptide of embodiment F31, wherein the soluble IL-15 has a D8N or D8A amino acid substitution.

Embodiment F33. The multi-chain chimeric polypeptide of embodiment F31, wherein the soluble IL-15 comprises a sequence that is at least 80% identical to SEQ ID NO: 82.

Embodiment F34. The multi-chain chimeric polypeptide of embodiment F33, wherein the soluble IL-15 comprises a sequence that is at least 90% identical to SEQ ID NO: 82.

Embodiment F35. The multi-chain chimeric polypeptide of embodiment F34, wherein the soluble IL-15 comprises a sequence that is at least 95% identical to SEQ ID NO: 82.

Embodiment F36. The multi-chain chimeric polypeptide of embodiment F35, wherein the soluble IL-15 comprises SEQ ID NO: 82.

Embodiment F37. The multi-chain chimeric polypeptide of any one of embodiments F31-F36, wherein the sushi domain of IL-15Rα comprises a sushi domain from human IL-15Rα.

Embodiment F38. The multi-chain chimeric polypeptide of embodiment F37, wherein the sushi domain from human IL-15Rα comprises a sequence that is at least 80% identical to SEQ ID NO: 113.

Embodiment F39. The multi-chain chimeric polypeptide of embodiment F38, wherein the sushi domain from human IL-15Rα comprises a sequence that is at least 90% identical to SEQ ID NO: 113.

Embodiment F40. The multi-chain chimeric polypeptide of embodiment F39, wherein the sushi domain from human IL-15Rα comprises a sequence that is at least 95% identical to SEQ ID NO: 113.

Embodiment F41. The multi-chain chimeric polypeptide of embodiment F40, wherein the sushi domain from human IL-15Rα comprises SEQ ID NO: 113.

Embodiment F42. The multi-chain chimeric polypeptide of embodiment F37, wherein the sushi domain from human IL-15Rα is a mature full-length IL-15Rα.

Embodiment F43. The multi-chain chimeric polypeptide of any one of embodiments F1-F30, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment F44. The multi-chain chimeric polypeptide of any one of embodiments F1-F43, wherein one or both of the first target-binding domain and the second target-binding domain is an agonistic antigen-binding domain.

Embodiment F45. The multi-chain chimeric polypeptide of embodiment F44, wherein the first target-binding domain and the second target-binding domain are each agonistic antigen-binding domains.

Embodiment F46. The multi-chain chimeric polypeptide of embodiment F44 or F45, wherein antigen-binding domain comprises a scFv or single-domain antibody.

Embodiment F47. The multi-chain chimeric polypeptide of any one of embodiments F1-F43, wherein one or both of the first target-binding domain and the second target-binding domain is a soluble IL-21 or a soluble IL-7.

Embodiment F48. The multi-chain chimeric polypeptide of embodiment F47, wherein the first target-binding domain and the second target-binding domain are each independently a soluble IL-21 or a soluble IL-7.

Embodiment F49. The multi-chain chimeric polypeptide of any one of embodiments F1-F48, wherein the first target-binding domain and the second target-binding domain both bind specifically to a receptor of IL-21 or a receptor of IL-7.

Embodiment F50. The multi-chain chimeric polypeptide of embodiment F49, wherein the first target-binding domain and the second target-binding domain bind specifically to the same epitope.

Embodiment F51. The multi-chain chimeric polypeptide of embodiment F50, wherein the first target-binding domain and the second target-binding domain comprise the same amino acid sequence.

Embodiment F52. The multi-chain chimeric polypeptide of any one of embodiments F1-F48, wherein the first target-binding domain binds specifically to a receptor for IL-21, and the second target-binding domain binds specifically to a receptor for IL-7.

Embodiment F53. The multi-chain chimeric polypeptide of any one of embodiments F1-F48, wherein the first target-binding domain binds specifically to a receptor for IL-7, and the second target-binding domain bind specifically to a receptor for IL-21.

Embodiment F54. The multi-chain chimeric polypeptide of embodiment F53, wherein the first target-binding domain comprises a soluble IL-21.

Embodiment F55. The multi-chain chimeric polypeptide of embodiment F54, wherein the soluble IL-21 is a soluble human IL-21.

Embodiment F56. The multi-chain chimeric polypeptide of embodiment F55, wherein the soluble human IL-21 comprises a sequence at least 80% identical to SEQ ID NO: 83.

Embodiment F57. The multi-chain chimeric polypeptide of embodiment F56, wherein the soluble human IL-21 comprises a sequence at least 90% identical to SEQ ID NO: 83.

Embodiment F58. The multi-chain chimeric polypeptide of embodiment F57, wherein the soluble human IL-21 comprises a sequence at least 95% identical to SEQ ID NO: 83.

Embodiment F59. The multi-chain chimeric polypeptide of embodiment F58, wherein the soluble human IL-21 comprises a sequence of SEQ ID NO: 83.

Embodiment F60. The multi-chain chimeric polypeptide of any one of embodiments F53-F59, wherein the second target-binding domain comprises a soluble IL-7.

Embodiment F61. The multi-chain chimeric polypeptide of embodiment F60, wherein the soluble IL-7 is a soluble human IL-7.

Embodiment F62. The multi-chain chimeric polypeptide of embodiment F61, wherein the soluble human IL-7 comprises a sequence at least 80% identical to SEQ ID NO: 79.

Embodiment F63. The multi-chain chimeric polypeptide of embodiment F62, wherein the soluble human IL-7 comprises a sequence at least 90% identical to SEQ ID NO: 79.

Embodiment F64. The multi-chain chimeric polypeptide of embodiment F63, wherein the soluble human IL-7 comprises a sequence at least 95% identical to SEQ ID NO: 79.

Embodiment F65. The multi-chain chimeric polypeptide of embodiment F64, wherein the soluble human IL-7 comprises a sequence of SEQ ID NO: 79.

Embodiment F66. The multi-chain chimeric polypeptide of embodiment F1, wherein the first chimeric polypeptide comprises a sequence that is at least 80% identical to SEQ ID NO: 207.

Embodiment F67. The multi-chain chimeric polypeptide of embodiment F66, wherein the first chimeric polypeptide comprises a sequence that is at least 90% identical to SEQ ID NO: 207.

Embodiment F68. The multi-chain chimeric polypeptide of embodiment F67, wherein the first chimeric polypeptide comprises a sequence that is at least 95% identical to SEQ ID NO: 207.

Embodiment F69. The multi-chain chimeric polypeptide of embodiment F68, wherein the first chimeric polypeptide comprises SEQ ID NO: 207.

Embodiment F70. The multi-chain chimeric polypeptide of embodiment F69, wherein the first chimeric polypeptide comprises SEQ ID NO: 209.

Embodiment F71. The multi-chain chimeric polypeptide of any one of embodiments F1 and F66-F70, wherein the second chimeric polypeptide comprises a sequence that is at least 80% identical to SEQ ID NO: 211.

Embodiment F72. The multi-chain chimeric polypeptide of embodiment F71, wherein the second chimeric polypeptide comprises a sequence that is at least 90% identical to SEQ ID NO: 211.

Embodiment F73. The multi-chain chimeric polypeptide of embodiment F72, wherein the second chimeric polypeptide comprises a sequence that is at least 95% identical to SEQ ID NO: 211.

Embodiment F74. The multi-chain chimeric polypeptide of embodiment F73, wherein the second chimeric polypeptide comprises SEQ ID NO: 211.

Embodiment F75. The multi-chain chimeric polypeptide of embodiment F74, wherein the second chimeric polypeptide comprises SEQ ID NO: 213.

Embodiment F76. The multi-chain chimeric polypeptide of embodiment F1, wherein the first chimeric polypeptide comprises a sequence that is at least 80% identical to SEQ ID NO: 199.

Embodiment F77. The multi-chain chimeric polypeptide of embodiment F76, wherein the first chimeric polypeptide comprises a sequence that is at least 90% identical to SEQ ID NO: 199.

Embodiment F78. The multi-chain chimeric polypeptide of embodiment F77, wherein the first chimeric polypeptide comprises a sequence that is at least 95% identical to SEQ ID NO: 199.

Embodiment F79. The multi-chain chimeric polypeptide of embodiment F68, wherein the first chimeric polypeptide comprises SEQ ID NO: 199.

Embodiment F80. The multi-chain chimeric polypeptide of embodiment F69, wherein the first chimeric polypeptide comprises SEQ ID NO: 201.

Embodiment F81. The multi-chain chimeric polypeptide of any one of embodiments F1 and F76-F80, wherein the second chimeric polypeptide comprises a sequence that is at least 80% identical to SEQ ID NO: 203.

Embodiment F82. The multi-chain chimeric polypeptide of embodiment F81, wherein the second chimeric polypeptide comprises a sequence that is at least 90% identical to SEQ ID NO: 203.

Embodiment F83. The multi-chain chimeric polypeptide of embodiment F82, wherein the second chimeric polypeptide comprises a sequence that is at least 95% identical to SEQ ID NO: 203.

Embodiment F84. The multi-chain chimeric polypeptide of embodiment F83, wherein the second chimeric polypeptide comprises SEQ ID NO: 203.

Embodiment F85. The multi-chain chimeric polypeptide of embodiment F84, wherein the second chimeric polypeptide comprises SEQ ID NO: 209.

Embodiment F86. The multi-chain chimeric polypeptide of any one of embodiments F1-F65, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment F87. The multi-chain chimeric polypeptide of embodiment F86, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment F88. The multi-chain chimeric polypeptide of any one of embodiments F1-F65, wherein the first chimeric polypeptide further comprises one or more additional target-binding domains at the N-terminal and/or C-terminal end of the first chimeric polypeptide.

Embodiment F89. The multi-chain chimeric polypeptide of embodiment F88, wherein at least one of the one or more additional target-binding domains directly abuts the first domain of the pair of affinity domains in the first chimeric polypeptide.

Embodiment F90. The multi-chain chimeric polypeptide of embodiment F88, wherein the first chimeric polypeptide further comprises a linker sequence between the at least one of the one or more additional target-binding domains and the first domain of the pair of affinity domains.

Embodiment F91. The multi-chain chimeric polypeptide of embodiment F88, wherein the at least one of the one or more additional target-binding domains directly abuts the first target-binding domain in the first chimeric polypeptide.

Embodiment F92. The multi-chain chimeric polypeptide of embodiment F88, wherein the first chimeric polypeptide further comprises a linker sequence between the at least one of the one or more additional target-binding domains and the first target-binding domain.

Embodiment F93. The multi-chain chimeric polypeptide of embodiment F88, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment F94. The multi-chain chimeric polypeptide of embodiment F93, wherein the at least one additional target-binding domain of the one or more additional target-binding domains disposed at the N-terminus directly abuts the first target-binding domain or the first domain of the pair of affinity domains in the first chimeric polypeptide.

Embodiment F95. The multi-chain chimeric polypeptide of embodiment F93, wherein the first chimeric polypeptide further comprises a linker sequence disposed between the at least one additional target-binding domain and the first target-binding domain or the first domain of the pair of affinity domains in the first chimeric polypeptide.

Embodiment F96. The multi-chain chimeric polypeptide of embodiment F93, wherein the at least one additional target-binding domain of the one or more additional target-binding domains disposed at the C-terminus directly abuts the first target-binding domain or the first domain of the pair of affinity domains in the first chimeric polypeptide.

Embodiment F97. The multi-chain chimeric polypeptide of embodiment F93, wherein the first chimeric polypeptide further comprises a linker sequence disposed between the at least one additional target-binding domain and the first target-binding domain or the first domain of the pair of affinity domains in the first chimeric polypeptide.

Embodiment F98. The multi-chain chimeric polypeptide of embodiment F93, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment F99. The multi-chain chimeric polypeptide of embodiment F93, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment F100. The multi-chain chimeric polypeptide of any one of embodiments F1-F65 and F86-F99, wherein the second chimeric polypeptide further comprises one or more additional target-binding domains at the N-terminal end or the C-terminal end of the second chimeric polypeptide.

Embodiment F101. The multi-chain chimeric polypeptide of embodiment F100, wherein at least one of the one or more additional target-binding domains directly abuts the second domain of the pair of affinity domains in the second chimeric polypeptide.

Embodiment F102. The multi-chain chimeric polypeptide of embodiment F100, wherein the second chimeric polypeptide further comprises a linker sequence between at least one of the one or more additional target-binding domains and the second domain of the pair of affinity domains in the second chimeric polypeptide.

Embodiment F103. The multi-chain chimeric polypeptide of embodiment F100, wherein at least one of the one or more additional target-binding domains directly abuts the second target-binding domain in the second chimeric polypeptide.

Embodiment F104. The multi-chain chimeric polypeptide of embodiment F100, wherein the second chimeric polypeptide further comprises a linker sequence between at least one of the one or more additional target-binding domains and the second target-binding domain in the second chimeric polypeptide.

Embodiment F105. The multi-chain chimeric polypeptide of any one of embodiments F86-F104, wherein two or more of the first target-binding domain, the second target-binding domain, and the one or more additional target-binding domains bind specifically to the same antigen.

Embodiment F106. The multi-chain chimeric polypeptide of embodiment F105, wherein two or more of the first target-binding domain, the second target-binding domain, and the one or more additional target-binding domains bind specifically to the same epitope.

Embodiment F107. The multi-chain chimeric polypeptide of embodiment F106, wherein two or more of the first target-binding domain, the second target-binding domain, and the one or more additional target-binding domains comprise the same amino acid sequence.

Embodiment F108. The multi-chain chimeric polypeptide of any one of embodiments F86-F104, wherein the first target-binding domain, the second target-binding domain, and the one or more additional target-binding domains bind specifically to different antigens.

Embodiment F109. The multi-chain chimeric polypeptide of any one of embodiments F86-F108, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment F110. The multi-chain chimeric polypeptide of any one of embodiments F86-F108, wherein the one or more additional target-binding domains is a soluble interleukin or cytokine protein.

Embodiment F111. The multi-chain chimeric polypeptide of embodiment F110, wherein the soluble interleukin, cytokine, or ligand protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment F112. The multi-chain chimeric polypeptide of any one of embodiments F86-F108, wherein the one or more additional target-binding domains is a soluble interleukin or cytokine receptor.

Embodiment F113. The multi-chain chimeric polypeptide of embodiment F112, wherein the soluble receptor is a soluble TGF-β receptor II (TGF-βRII), a soluble TGF-βRIII, a soluble NKG2D, a soluble NKp30, a soluble NKp44, a soluble NKp46, a soluble DNAM1, a scMHCI, a scMHCII, a scTCR, a soluble CD155, a soluble CD122, or a soluble CD28.

Embodiment F114. A composition comprising any of the multi-chain chimeric polypeptides of embodiments F1-F113.

Embodiment F115. The composition of embodiment F114, wherein the composition is a pharmaceutical composition.

Embodiment F116. A kit comprising at least one dose of the composition of embodiment F114 or F115.

Embodiment F117. Nucleic acid encoding any of the multi-chain chimeric polypeptides of any one of embodiments F1-F113.

Embodiment F118. A vector comprising the nucleic acid of embodiment F117.

Embodiment F119. The vector of embodiment F118, wherein the vector is an expression vector.

Embodiment F120. A cell comprising the nucleic acid of embodiment F117 or the vector of embodiment F118 or F119.

Embodiment F121. A method of producing a multi-chain chimeric polypeptide, the method comprising:

culturing the cell of embodiment F120 in a culture medium under conditions sufficient to result in the production of the multi-chain chimeric polypeptide; and recovering the multi-chain chimeric polypeptide from the cell and/or the culture medium.

Embodiment F122. A multi-chain chimeric polypeptide produced by the method of embodiment F121.

Embodiment G1. A multi-chain chimeric polypeptide comprising:

(e) a first chimeric polypeptide comprising:

(i) a first target-binding domain;

(ii) a soluble tissue factor domain; and (iii) a first domain of a pair of affinity domains;

(f) a second chimeric polypeptide comprising:

(i) a second domain of a pair of affinity domains; and (ii) a second target-binding domain, wherein:

the first chimeric polypeptide and the second chimeric polypeptide associate through the binding of the first domain and the second domain of the pair of affinity domains; and the first target-binding domain and the second targeting-binding domain each independently bind specifically to: a receptor for IL-7, CD16, a receptor for IL-21, TGF-β, or a receptor for CD137L.

Embodiment G2. The multi-chain chimeric polypeptide of embodiment G1, wherein the first target-binding domain and the soluble tissue factor domain directly abut each other in the first chimeric polypeptide.

Embodiment G3. The multi-chain chimeric polypeptide of embodiment G1, wherein the first chimeric polypeptide further comprises a linker sequence between the first target-binding domain and the soluble tissue factor domain in the first chimeric polypeptide.

Embodiment G4. The multi-chain chimeric polypeptide of any one of embodiments G1-G3, wherein the soluble tissue factor domain and the first domain of the pair of affinity domains directly abut each other in the first chimeric polypeptide.

Embodiment G5. The multi-chain chimeric polypeptide of any one of embodiments G1-G3, wherein the first chimeric polypeptide further comprises a linker sequence between the soluble tissue factor domain and the first domain of the pair of affinity domains in the first chimeric polypeptide.

Embodiment G6. The multi-chain chimeric polypeptide of any one of embodiments G1-G5, wherein the second domain of the pair of affinity domains and the second target-binding domain directly abut each other in the second chimeric polypeptide.

Embodiment G7. The multi-chain chimeric polypeptide of any one of embodiments G1-G5, wherein second chimeric polypeptide further comprises a linker sequence between the second domain of the pair of affinity domains and the second target-binding domain in the second chimeric polypeptide.

Embodiment G8. The multi-chain chimeric polypeptide of any one of embodiments G1-G7, wherein the soluble tissue factor domain is a soluble human tissue factor domain.

Embodiment G9. The multi-chain chimeric polypeptide of embodiment G8, wherein the soluble human tissue factor domain comprises a sequence that is at least 80% identical to SEQ ID NO: 93.

Embodiment G10. The multi-chain chimeric polypeptide of embodiment G9, wherein the soluble human tissue factor domain comprises a sequence that is at least 90% identical to SEQ ID NO: 93.

Embodiment G11. The multi-chain chimeric polypeptide of embodiment G10, wherein the soluble human tissue factor domain comprises a sequence that is at least 95% identical to SEQ ID NO: 93.

Embodiment G12. The multi-chain chimeric polypeptide of any one of embodiments G8-G11, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment G13. The multi-chain chimeric polypeptide of embodiment G12, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment G14. The multi-chain chimeric polypeptide of any one of embodiments G1-G13, wherein the soluble tissue factor domain is not capable of binding to Factor VIIa.

Embodiment G15. The multi-chain chimeric polypeptide of any one of embodiments G1-G14, wherein the soluble tissue factor domain does not convert inactive Factor X into Factor Xa.

Embodiment G16. The multi-chain chimeric polypeptide of any one of embodiments G1-G15, wherein the multi-chain chimeric polypeptide does not stimulate blood coagulation in a mammal.

Embodiment G17. The multi-chain chimeric polypeptide of any one of embodiments G1-G16, wherein the first chimeric polypeptide further comprises a peptide tag at the N-terminal end or the C-terminal end of the first chimeric polypeptide.

Embodiment G18. The multi-chain chimeric polypeptide of any one of embodiments G1-G17, wherein the second chimeric polypeptide further comprises a peptide tag at the N-terminal end or the C-terminal end of the second chimeric polypeptide.

Embodiment G19. The multi-chain chimeric polypeptide of any one of embodiments G1-G18, wherein the first chimeric polypeptide and/or the second chimeric polypeptide further comprises a signal sequence at its N-terminal end.

Embodiment G20. The multi-chain chimeric polypeptide of embodiment G19, wherein the signal sequence comprises SEQ ID NO: 117.

Embodiment G21. The multi-chain chimeric polypeptide of embodiment G20, wherein the signal sequence is SEQ ID NO: 117.

Embodiment G22. The multi-chain chimeric polypeptide of any one of embodiments G1-G21, wherein the pair of affinity domains is a sushi domain from an alpha chain of human IL-15 receptor (IL-15Rα) and a soluble IL-15.

Embodiment G23. The multi-chain chimeric polypeptide of embodiment G22, wherein the soluble IL-15 has a D8N or D8A amino acid substitution.

Embodiment G24. The multi-chain chimeric polypeptide of embodiment G22, wherein the soluble IL-15 comprises a sequence that is 80% identical to SEQ ID NO: 82.

Embodiment G25. The multi-chain chimeric polypeptide of embodiment G24, wherein the soluble IL-15 comprises a sequence that is 90% identical to SEQ ID NO: 82.

Embodiment G26. The multi-chain chimeric polypeptide of embodiment G25, wherein the soluble IL-15 comprises a sequence that is 95% identical to SEQ ID NO: 82.

Embodiment G27. The multi-chain chimeric polypeptide of embodiment G26, wherein the soluble IL-15 comprises SEQ ID NO: 82.

Embodiment G28. The multi-chain chimeric polypeptide of any one of embodiments G22-G27, wherein the sushi domain of IL-15Rα comprises a sushi domain from human IL-15Rα.

Embodiment G29. The multi-chain chimeric polypeptide of embodiment G28, wherein the sushi domain from human IL-15Rα comprises a sequence that is 80% identical to SEQ ID NO: 113.

Embodiment G30. The multi-chain chimeric polypeptide of embodiment G29, wherein the sushi domain from human IL-15Rα comprises a sequence that is 90% identical to SEQ ID NO: 113.

Embodiment G31. The multi-chain chimeric polypeptide of embodiment G30, wherein the sushi domain from human IL-15Rα comprises a sequence that is 95% identical to SEQ ID NO: 113.

Embodiment G32. The multi-chain chimeric polypeptide of embodiment G31, wherein the sushi domain from human IL-15Rα comprises SEQ ID NO: 113.

Embodiment G33. The multi-chain chimeric polypeptide of embodiment G28, wherein the sushi domain from human IL-15Rα is a mature full-length IL-15Rα.

Embodiment G34. The multi-chain chimeric polypeptide of any one of embodiments G1-G21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment G35. The multi-chain chimeric polypeptide of any one of embodiments G1-G34, wherein the first target-binding domain and the second targeting-binding domain each independently bind specifically to a receptor for IL-7, CD16, or a receptor for IL-21.

Embodiment G36. The multi-chain chimeric polypeptide of embodiment G35, wherein the first target-binding domain binds specifically to a receptor IL-7 and the second target-binding domain binds specifically to CD16 or a receptor for IL-21.

Embodiment G37. The multi-chain chimeric polypeptide of embodiment G36, wherein the first target-binding domain comprises a soluble IL-7 protein.

Embodiment G38. The multi-chain chimeric polypeptide of embodiment G37, wherein the soluble IL-7 protein is a soluble human IL-7.

Embodiment G39. The multi-chain chimeric polypeptide of any one of embodiments G36-G38, wherein the second antigen-binding domain comprises an antigen-binding domain that binds specifically to CD16.

Embodiment G40. The multi-chain chimeric polypeptide of embodiment G39, wherein the second antigen-binding domain comprises an scFv that binds specifically to CD16.

Embodiment G41. The multi-chain chimeric polypeptide of any one of embodiments G36-G38, wherein the second antigen-binding domain bind specifically to a receptor for IL-21.

Embodiment G42. The multi-chain chimeric polypeptide of embodiment G41, wherein the second antigen-binding domain comprises a soluble IL-21.

Embodiment G43. The multi-chain chimeric polypeptide of embodiment G42, wherein the soluble IL-21 is a soluble human IL-21.

Embodiment G44. The multi-chain chimeric polypeptide of any one of embodiments G36-G40, wherein the second chimeric polypeptide further comprises an additional target-binding domain that binds specifically to a receptor for IL-21.

Embodiment G45. The multi-chain chimeric polypeptide of embodiment G44, wherein the additional target-binding domain comprises a soluble IL-21.

Embodiment G46. The multi-chain chimeric polypeptide of embodiment G45, wherein the soluble IL-21 is a soluble human IL-12.

Embodiment G47. The multi-chain chimeric polypeptide of any one of embodiments G1-G34, wherein the first target-binding domain and the second targeting-binding domain each independently bind specifically to TGF-β, CD16, or a receptor for IL-21.

Embodiment G48. The multi-chain chimeric polypeptide of embodiment G47, wherein the first target-binding domain binds specifically to a TGF-β and the second target-binding domain binds specifically to CD16 or a receptor of IL-21.

Embodiment G49. The multi-specific chimeric polypeptide of embodiment G48, wherein the first target-binding domain is a soluble TGF-β receptor.

Embodiment G50. The multi-specific chimeric polypeptide of embodiment G49, wherein soluble TGF-β receptor is a soluble TGFβRII receptor.

Embodiment G51. The multi-specific chimeric polypeptide of any one of embodiments G48-G50, wherein the second target-binding domain binds specifically to CD16.

Embodiment G52. The multi-specific chimeric polypeptide of embodiment G51, wherein the second antigen-binding domain comprises an antigen-binding domain that binds specifically to CD16.

Embodiment G53. The multi-chain chimeric polypeptide of embodiment G52, wherein the second antigen-binding domain comprises an scFv that binds specifically to CD16.

Embodiment G54. The multi-chain chimeric polypeptide of any one of embodiments G48-G50, wherein the second target-binding domain binds specifically to a receptor for IL-21.

Embodiment G55. The multi-chain chimeric polypeptide of embodiment G54, wherein the second target-binding domain comprises a soluble IL-21.

Embodiment G56. The multi-chain chimeric polypeptide of embodiment G55, wherein the second target-binding domain comprises a soluble human IL-21.

Embodiment G57. The multi-chain chimeric polypeptide of any one of embodiments G48-G53, wherein the second chimeric polypeptide further comprises an additional target-binding domain that binds specifically to a receptor for IL-21.

Embodiment G58. The multi-chain chimeric polypeptide of embodiment G57, wherein the additional target-binding domain comprises a soluble IL-21.

Embodiment G59. The multi-chain chimeric polypeptide of embodiment G58, wherein the soluble IL-21 is a soluble human IL-21.

Embodiment G60. The multi-chain chimeric polypeptide of any one of embodiments G1-G34, wherein the first target-binding domain and the second target-binding domain each independently bind specifically to a receptor for IL-7.

Embodiment G61. The multi-chain chimeric polypeptide of embodiment G60, wherein the first target-binding domain and the second target-binding domain include a soluble IL-7.

Embodiment G62. The multi-chain chimeric polypeptide of embodiment G61, wherein the soluble IL-7 is a soluble human IL-7.

Embodiment G63. The multi-chain chimeric polypeptide of any one of embodiments G1-G34, wherein the first target-binding domain and the second target-binding domain each independently bind specifically to TGF-β.

Embodiment G64. The multi-specific chimeric polypeptide of embodiment G63, wherein the first target-binding domain and the second target-binding domain is a soluble TGF-β receptor.

Embodiment G65. The multi-specific chimeric polypeptide of embodiment G64, wherein the soluble TGF-β receptor is a soluble TGFβRII receptor.

Embodiment G66. The multi-specific chimeric polypeptide of any one of embodiments G1-G34, wherein the first target-binding domain and the second targeting-binding domain each independently bind specifically to a receptor for IL-7, a receptor for IL-21, or a receptor for CD137L.

Embodiment G67. The multi-chain chimeric polypeptide of embodiment G66, wherein the first target-binding domain binds specifically to a receptor for IL-7 and the second target-binding domain binds specifically to a receptor for IL-21 or a receptor for CD137L.

Embodiment G68. The multi-specific chimeric polypeptide of embodiment G67, wherein the first target-binding domain is a soluble IL-7.

Embodiment G69. The multi-specific chimeric polypeptide of embodiment G68, wherein the soluble IL-7 is a soluble human IL-7.

Embodiment G70. The multi-chain chimeric polypeptide of any one of embodiments G67-G69, wherein the second target-binding domain binds specifically to a receptor for IL-21.

Embodiment G71. The multi-chain chimeric polypeptide of embodiment G70, wherein the second target-binding domain is a soluble IL-21.

Embodiment G72. The multi-chain chimeric polypeptide of embodiment G71, wherein the soluble IL-21 is a soluble human IL-21.

Embodiment G73. The multi-chain chimeric polypeptide of any one of embodiments G67-G69, wherein the second antigen-binding domain binds specifically to a receptor for CD137L.

Embodiment G74. The multi-chain chimeric polypeptide of embodiment G73, wherein the second antigen-binding domain is a soluble CD137L.

Embodiment G75. The multi-chain chimeric polypeptide of embodiment G74, wherein the soluble CD137L is a soluble human CD137L.

Embodiment G76. The multi-chain chimeric polypeptide of any one of embodiments G67-G72, wherein the second chimeric polypeptide further comprises an additional target-binding domain that binds specifically to a receptor for CD137L.

Embodiment G77. The multi-chain chimeric polypeptide of embodiment G76, wherein the additional target-binding domain comprises a soluble CD137L.

Embodiment G78. The multi-chain chimeric polypeptide of embodiment G77, wherein the soluble CD137L is a soluble human CD137L.

Embodiment G79. The multi-chain chimeric polypeptide of any one of embodiments G1-G34, wherein the first target-binding domain and the second targeting-binding domain each independently bind specifically to a receptor for IL-7 or TGF-β.

Embodiment G80. The multi-chain chimeric polypeptide of embodiment G79, wherein the first target-binding domain binds specifically to a receptor IL-7 and the second target-binding domain binds specifically to TGF-β.

Embodiment G81. The multi-chain chimeric polypeptide of embodiment G80, wherein the first target-binding domain comprises a soluble IL-7 protein.

Embodiment G82. The multi-chain chimeric polypeptide of embodiment G81, wherein the soluble IL-7 protein is a soluble human IL-7.

Embodiment G83. The multi-chain chimeric polypeptide of any one of embodiments G80-G82, wherein the second antigen-binding domain comprises an antigen-binding domain that binds specifically to TGF-β.

Embodiment G84. The multi-specific chimeric polypeptide of embodiment G83, wherein the second target-binding domain is a soluble TGF-β receptor.

Embodiment G85. The multi-specific chimeric polypeptide of embodiment G84, wherein the soluble TGF-β receptor is a soluble TGFβRII receptor.

Embodiment G86. The multi-chain chimeric polypeptide of any one of embodiments G1-G34, wherein the first target-binding domain and the second targeting-binding domain each independently bind specifically to TGF-β, a receptor for IL-21, or a receptor for CD137L.

Embodiment G87. The multi-chain chimeric polypeptide of embodiment G86, wherein the first target-binding domain binds specifically to a TGF-β and the second target-binding domain binds specifically to a receptor for IL-21 or a receptor for CD137L.

Embodiment G88. The multi-specific chimeric polypeptide of embodiment G87, wherein the first target-binding domain is a soluble TGF-β receptor.

Embodiment G89. The multi-specific chimeric polypeptide of embodiment G88, wherein the soluble TGF-β receptor is a soluble TGFβRII receptor.

Embodiment G90. The multi-specific chimeric polypeptide of any one of embodiments G87-G89, wherein the second target-binding domain binds specifically to a receptor for IL-21.

Embodiment G91. The multi-chain chimeric polypeptide of embodiment G90, wherein the second target-binding domain comprises a soluble IL-21.

Embodiment G92. The multi-chain chimeric polypeptide of embodiment G91, wherein the second target-binding domain comprises a soluble human IL-21.

Embodiment G93. The multi-specific chimeric polypeptide of any one of embodiments G87-G89, wherein the second target-binding domain binds specifically to a receptor for CD137L.

Embodiment G94. The multi-chain chimeric polypeptide of embodiment G93, wherein the second target-binding domain comprises a soluble CD137L.

Embodiment G95. The multi-chain chimeric polypeptide of embodiment G94, wherein the second target-binding domain comprises a soluble human CD137L.

Embodiment G96. The multi-chain chimeric polypeptide of any one of embodiments G87-G92, wherein the second chimeric polypeptide further comprises an additional target-binding domain that binds specifically to a receptor for CD137L.

Embodiment G97. The multi-chain chimeric polypeptide of embodiment G96, wherein the additional target-binding domain comprises a soluble CD137L.

Embodiment G98. The multi-chain chimeric polypeptide of embodiment G97, wherein the soluble CD137L is a soluble human CD137L.

Embodiment G99. The multi-chain chimeric polypeptide of any one of embodiments G1-G34, wherein the first target-binding domain and the second targeting-binding domain each independently bind specifically to TGF-β or a receptor for IL-21.

Embodiment G100. The multi-chain chimeric polypeptide of embodiment G99, wherein the first target-binding domain binds specifically to a TGF-β and the second target-binding domain binds specifically to TGF-β or a receptor for IL-21.

Embodiment G101. The multi-specific chimeric polypeptide of embodiment G100, wherein the first target-binding domain is a soluble TGF-β receptor.

Embodiment G102. The multi-specific chimeric polypeptide of embodiment G101, wherein the soluble TGF-β receptor is a soluble TGFβRII receptor.

Embodiment G103. The multi-specific chimeric polypeptide of any one of embodiments G100-G102, wherein the second target-binding domain binds specifically to a receptor for IL-21.

Embodiment G104. The multi-chain chimeric polypeptide of embodiment G103, wherein the second target-binding domain comprises a soluble IL-21.

Embodiment G105. The multi-chain chimeric polypeptide of embodiment G104, wherein the second target-binding domain comprises a soluble human IL-21.

Embodiment G106. The multi-specific chimeric polypeptide of any one of embodiments G100-G102, wherein the second target-binding domain binds specifically to TGF-β.

Embodiment G107. The multi-specific chimeric polypeptide of embodiment G106, wherein the first target-binding domain is a soluble TGF-β receptor.

Embodiment G108. The multi-specific chimeric polypeptide of embodiment G107, wherein the soluble TGF-β receptor is a soluble TGFβRII receptor.

Embodiment G109. The multi-specific chimeric polypeptide of any one of embodiments G100-G105, wherein the second polypeptide further comprises an additional target-binding domain that binds specifically to TGF-β.

Embodiment G110. The multi-specific chimeric polypeptide of embodiment G109, wherein the first target-binding domain is a soluble TGF-β receptor.

Embodiment G111. The multi-specific chimeric polypeptide of embodiment G110, wherein the soluble TGF-β receptor is a soluble TGFβRII receptor.

Embodiment G112. The multi-chain chimeric polypeptide of any one of embodiments G1-G34, wherein the first target-binding domain and the second targeting-binding domain each independently bind specifically to TGF-β or IL-16.

Embodiment G113. The multi-chain chimeric polypeptide of embodiment G112, wherein the first target-binding domain binds specifically to a TGF-β and the second target-binding domain binds specifically to TGF-β or IL-16.

Embodiment G114. The multi-specific chimeric polypeptide of embodiment G113, wherein the first target-binding domain is a soluble TGF-β receptor.

Embodiment G115. The multi-specific chimeric polypeptide of embodiment G114, wherein the soluble TGF-β receptor is a soluble TGFβRII receptor.

Embodiment G116. The multi-specific chimeric polypeptide of any one of embodiments G113-G115, wherein the second target-binding domain binds specifically to IL-16.

Embodiment G117. The multi-specific chimeric polypeptide of embodiment G116, wherein the second antigen-binding domain comprises an antigen-binding domain that binds specifically to CD16.

Embodiment G118. The multi-chain chimeric polypeptide of embodiment G117, wherein the second antigen-binding domain comprises an scFv that binds specifically to CD16.

Embodiment G119. The multi-specific chimeric polypeptide of any one of embodiments G113-G115, wherein the second target-binding domain binds specifically to TGF-β.

Embodiment G120. The multi-specific chimeric polypeptide of embodiment G119, wherein the first target-binding domain is a soluble TGF-β receptor.

Embodiment G121. The multi-specific chimeric polypeptide of embodiment G120, wherein the soluble TGF-β receptor is a soluble TGFβRII receptor.

Embodiment G122. The multi-specific chimeric polypeptide of any one of embodiments G113-G118, wherein the second chimeric polypeptide further comprises an additional target-binding domain that binds specifically to TGF-β.

Embodiment G123. The multi-specific chimeric polypeptide of embodiment G122, wherein the first target-binding domain is a soluble TGF-β receptor.

Embodiment G124. The multi-specific chimeric polypeptide of embodiment G123, wherein the soluble TGF-β receptor is a soluble TGFβRII receptor.

Embodiment G125. The multi-chain chimeric polypeptide of any one of embodiments G1-G34, wherein the first target-binding domain and the second targeting-binding domain each independently bind specifically to a TGF-β or a receptor for CD137L.

Embodiment G126. The multi-chain chimeric polypeptide of embodiment G125, wherein the first target-binding domain binds specifically to TGF-β and the second target-binding domain binds specifically to a receptor for CD137L.

Embodiment G127. The multi-specific chimeric polypeptide of embodiment G126, wherein the first target-binding domain is a soluble TGF-β receptor.

Embodiment G128. The multi-specific chimeric polypeptide of embodiment G127, wherein the soluble TGF-β receptor is a soluble TGFβRII receptor.

Embodiment G129. The multi-chain chimeric polypeptide of embodiment G128, wherein the second target-binding domain comprises a soluble CD137L protein.

Embodiment G130. The multi-chain chimeric polypeptide of embodiment G129, wherein the soluble CD137L protein is a soluble human CD137L.

Embodiment G131. The multi-chain chimeric polypeptide of any one of embodiments G126-G130, wherein the second chimeric polypeptide further comprises an additional target-binding domain that binds specifically to TGF-β.

Embodiment G132. The multi-specific chimeric polypeptide of embodiment G131, wherein the additional target-binding domain is a soluble TGF-β receptor.

Embodiment G133. The multi-specific chimeric polypeptide of embodiment G132, wherein the soluble TGF-β receptor is a soluble TGFβRII receptor.

Embodiment G134. The multi-chain chimeric polypeptide of embodiment G1, wherein the first chimeric polypeptide comprises a sequence that is at least 80% identical to SEQ ID NO: 207.

Embodiment G135. The multi-chain chimeric polypeptide of embodiment G134, wherein the first chimeric polypeptide comprises a sequence that is at least 90% identical to SEQ ID NO: 207.

Embodiment G136. The multi-chain chimeric polypeptide of embodiment G135, wherein the first chimeric polypeptide comprises a sequence that is at least 95% identical to SEQ ID NO: 207.

Embodiment G137. The multi-chain chimeric polypeptide of embodiment G136, wherein the first chimeric polypeptide comprises SEQ ID NO: 207.

Embodiment G138. The multi-chain chimeric polypeptide of embodiment G137, wherein the first chimeric polypeptide comprises SEQ ID NO: 209.

Embodiment G139. The multi-chain chimeric polypeptide of any one of embodiments G1 and G134-G138, wherein the second chimeric polypeptide comprises a sequence that is at least 80% identical to SEQ ID NO: 232.

Embodiment G140. The multi-chain chimeric polypeptide of embodiment G139, wherein the second chimeric polypeptide comprises a sequence that is at least 90% identical to SEQ ID NO: 232.

Embodiment G141. The multi-chain chimeric polypeptide of embodiment G140, wherein the second chimeric polypeptide comprises a sequence that is at least 95% identical to SEQ ID NO: 232.

Embodiment G142. The multi-chain chimeric polypeptide of embodiment G141, wherein the second chimeric polypeptide comprises SEQ ID NO: 232.

Embodiment G143. The multi-chain chimeric polypeptide of embodiment G142, wherein the second chimeric polypeptide comprises SEQ ID NO: 234.

Embodiment G144. The multi-chain chimeric polypeptide of embodiment G1, wherein the first chimeric polypeptide comprises a sequence that is at least 80% identical to SEQ ID NO: 236.

Embodiment G145. The multi-chain chimeric polypeptide of embodiment G144, wherein the first chimeric polypeptide comprises a sequence that is at least 90% identical to SEQ ID NO: 236.

Embodiment G146. The multi-chain chimeric polypeptide of embodiment G145, wherein the first chimeric polypeptide comprises a sequence that is at least 95% identical to SEQ ID NO: 236.

Embodiment G147. The multi-chain chimeric polypeptide of embodiment G146, wherein the first chimeric polypeptide comprises SEQ ID NO: 236.

Embodiment G148. The multi-chain chimeric polypeptide of embodiment G147, wherein the first chimeric polypeptide comprises SEQ ID NO: 238.

Embodiment G149. The multi-chain chimeric polypeptide of any one of embodiments G1 and G144-G148, wherein the second chimeric polypeptide comprises a sequence that is at least 80% identical to SEQ ID NO: 232.

Embodiment G150. The multi-chain chimeric polypeptide of embodiment G149, wherein the second chimeric polypeptide comprises a sequence that is at least 90% identical to SEQ ID NO: 232.

Embodiment G151. The multi-chain chimeric polypeptide of embodiment G150, wherein the second chimeric polypeptide comprises a sequence that is at least 95% identical to SEQ ID NO: 232.

Embodiment G152. The multi-chain chimeric polypeptide of embodiment G151, wherein the second chimeric polypeptide comprises SEQ ID NO: 232.

Embodiment G153. The multi-chain chimeric polypeptide of embodiment G152, wherein the second chimeric polypeptide comprises SEQ ID NO: 234.

Embodiment G154. The multi-chain chimeric polypeptide of embodiment G1, wherein the first chimeric polypeptide comprises a sequence that is at least 80% identical to SEQ ID NO: 207.

Embodiment G155. The multi-chain chimeric polypeptide of embodiment G154, wherein the first chimeric polypeptide comprises a sequence that is at least 90% identical to SEQ ID NO: 207.

Embodiment G156. The multi-chain chimeric polypeptide of embodiment G155, wherein the first chimeric polypeptide comprises a sequence that is at least 95% identical to SEQ ID NO: 207.

Embodiment G157. The multi-chain chimeric polypeptide of embodiment G156, wherein the first chimeric polypeptide comprises SEQ ID NO: 207.

Embodiment G158. The multi-chain chimeric polypeptide of embodiment G157, wherein the first chimeric polypeptide comprises SEQ ID NO: 209.

Embodiment G159. The multi-chain chimeric polypeptide of any one of embodiments G1 and G154-G158, wherein the second chimeric polypeptide comprises a sequence that is at least 80% identical to SEQ ID NO: 203.

Embodiment G160. The multi-chain chimeric polypeptide of embodiment G159, wherein the second chimeric polypeptide comprises a sequence that is at least 90% identical to SEQ ID NO: 203.

Embodiment G161. The multi-chain chimeric polypeptide of embodiment G160, wherein the second chimeric polypeptide comprises a sequence that is at least 95% identical to SEQ ID NO: 203.

Embodiment G162. The multi-chain chimeric polypeptide of embodiment G161, wherein the second chimeric polypeptide comprises SEQ ID NO: 203.

Embodiment G163. The multi-chain chimeric polypeptide of embodiment G162, wherein the second chimeric polypeptide comprises SEQ ID NO: 250.

Embodiment G164. The multi-chain chimeric polypeptide of embodiment G1, wherein the first chimeric polypeptide comprises a sequence that is at least 80% identical to SEQ ID NO: 236.

Embodiment G165. The multi-chain chimeric polypeptide of embodiment G164, wherein the first chimeric polypeptide comprises a sequence that is at least 90% identical to SEQ ID NO: 236.

Embodiment G166. The multi-chain chimeric polypeptide of embodiment G165, wherein the first chimeric polypeptide comprises a sequence that is at least 95% identical to SEQ ID NO: 236.

Embodiment G167. The multi-chain chimeric polypeptide of embodiment G166, wherein the first chimeric polypeptide comprises SEQ ID NO: 236.

Embodiment G168. The multi-chain chimeric polypeptide of embodiment G167, wherein the first chimeric polypeptide comprises SEQ ID NO: 238.

Embodiment G169. The multi-chain chimeric polypeptide of any one of embodiments G1 and G164-G168, wherein the second chimeric polypeptide comprises a sequence that is at least 80% identical to SEQ ID NO: 193.

Embodiment G170. The multi-chain chimeric polypeptide of embodiment G169, wherein the second chimeric polypeptide comprises a sequence that is at least 90% identical to SEQ ID NO: 193.

Embodiment G171. The multi-chain chimeric polypeptide of embodiment G170, wherein the second chimeric polypeptide comprises a sequence that is at least 95% identical to SEQ ID NO: 193.

Embodiment G172. The multi-chain chimeric polypeptide of embodiment G171, wherein the second chimeric polypeptide comprises SEQ ID NO: 193.

Embodiment G173. The multi-chain chimeric polypeptide of embodiment G172, wherein the second chimeric polypeptide comprises SEQ ID NO: 195.

Embodiment G174. The multi-chain chimeric polypeptide of embodiment G1, wherein the first chimeric polypeptide comprises a sequence that is at least 80% identical to SEQ ID NO: 207.

Embodiment G175. The multi-chain chimeric polypeptide of embodiment G174, wherein the first chimeric polypeptide comprises a sequence that is at least 90% identical to SEQ ID NO: 207.

Embodiment G176. The multi-chain chimeric polypeptide of embodiment G175, wherein the first chimeric polypeptide comprises a sequence that is at least 95% identical to SEQ ID NO: 207.

Embodiment G177. The multi-chain chimeric polypeptide of embodiment G176, wherein the first chimeric polypeptide comprises SEQ ID NO: 207.

Embodiment G178. The multi-chain chimeric polypeptide of embodiment G177, wherein the first chimeric polypeptide comprises SEQ ID NO: 209.

Embodiment G179. The multi-chain chimeric polypeptide of any one of embodiments G1 and G174-G178, wherein the second chimeric polypeptide comprises a sequence that is at least 80% identical to SEQ ID NO: 268.

Embodiment G180. The multi-chain chimeric polypeptide of embodiment G179, wherein the second chimeric polypeptide comprises a sequence that is at least 90% identical to SEQ ID NO: 268.

Embodiment G181. The multi-chain chimeric polypeptide of embodiment G180, wherein the second chimeric polypeptide comprises a sequence that is at least 95% identical to SEQ ID NO: 268.

Embodiment G182. The multi-chain chimeric polypeptide of embodiment G181, wherein the second chimeric polypeptide comprises SEQ ID NO: 268.

Embodiment G183. The multi-chain chimeric polypeptide of embodiment G182, wherein the second chimeric polypeptide comprises SEQ ID NO: 270.

Embodiment G184. The multi-chain chimeric polypeptide of embodiment G1, wherein the first chimeric polypeptide comprises a sequence that is at least 80% identical to SEQ ID NO: 207.

Embodiment G185. The multi-chain chimeric polypeptide of embodiment G184, wherein the first chimeric polypeptide comprises a sequence that is at least 90% identical to SEQ ID NO: 207.

Embodiment G186. The multi-chain chimeric polypeptide of embodiment G185, wherein the first chimeric polypeptide comprises a sequence that is at least 95% identical to SEQ ID NO: 207.

Embodiment G187. The multi-chain chimeric polypeptide of embodiment G186, wherein the first chimeric polypeptide comprises SEQ ID NO: 207.

Embodiment G188. The multi-chain chimeric polypeptide of embodiment G187, wherein the first chimeric polypeptide comprises SEQ ID NO: 209.

Embodiment G189. The multi-chain chimeric polypeptide of any one of embodiments G1 and G184-G188, wherein the second chimeric polypeptide comprises a sequence that is at least 80% identical to SEQ ID NO: 272.

Embodiment G190. The multi-chain chimeric polypeptide of embodiment G189, wherein the second chimeric polypeptide comprises a sequence that is at least 90% identical to SEQ ID NO: 272.

Embodiment G191. The multi-chain chimeric polypeptide of embodiment G190, wherein the second chimeric polypeptide comprises a sequence that is at least 95% identical to SEQ ID NO: 272.

Embodiment G192. The multi-chain chimeric polypeptide of embodiment G191, wherein the second chimeric polypeptide comprises SEQ ID NO: 272.

Embodiment G193. The multi-chain chimeric polypeptide of embodiment G192, wherein the second chimeric polypeptide comprises SEQ ID NO: 272.

Embodiment G194. The multi-chain chimeric polypeptide of embodiment G1, wherein the first chimeric polypeptide comprises a sequence that is at least 80% identical to SEQ ID NO: 207.

Embodiment G195. The multi-chain chimeric polypeptide of embodiment G194, wherein the first chimeric polypeptide comprises a sequence that is at least 90% identical to SEQ ID NO: 207.

Embodiment G196. The multi-chain chimeric polypeptide of embodiment G195, wherein the first chimeric polypeptide comprises a sequence that is at least 95% identical to SEQ ID NO: 207.

Embodiment G197. The multi-chain chimeric polypeptide of embodiment G196, wherein the first chimeric polypeptide comprises SEQ ID NO: 207.

Embodiment G198. The multi-chain chimeric polypeptide of embodiment G197, wherein the first chimeric polypeptide comprises SEQ ID NO: 209.

Embodiment G199. The multi-chain chimeric polypeptide of any one of embodiments G1 and G194-G198, wherein the second chimeric polypeptide comprises a sequence that is at least 80% identical to SEQ ID NO: 193.

Embodiment G200. The multi-chain chimeric polypeptide of embodiment G199, wherein the second chimeric polypeptide comprises a sequence that is at least 90% identical to SEQ ID NO: 193.

Embodiment G201. The multi-chain chimeric polypeptide of embodiment G200, wherein the second chimeric polypeptide comprises a sequence that is at least 95% identical to SEQ ID NO: 193.

Embodiment G202. The multi-chain chimeric polypeptide of embodiment G201, wherein the second chimeric polypeptide comprises SEQ ID NO: 193.

Embodiment G203. The multi-chain chimeric polypeptide of embodiment G202, wherein the second chimeric polypeptide comprises SEQ ID NO: 195.

Embodiment G204. The multi-chain chimeric polypeptide of embodiment G1, wherein the first chimeric polypeptide comprises a sequence that is at least 80% identical to SEQ ID NO: 236.

Embodiment G205. The multi-chain chimeric polypeptide of embodiment G204, wherein the first chimeric polypeptide comprises a sequence that is at least 90% identical to SEQ ID NO: 236.

Embodiment G206. The multi-chain chimeric polypeptide of embodiment G205, wherein the first chimeric polypeptide comprises a sequence that is at least 95% identical to SEQ ID NO: 236.

Embodiment G207. The multi-chain chimeric polypeptide of embodiment G206, wherein the first chimeric polypeptide comprises SEQ ID NO: 236.

Embodiment G208. The multi-chain chimeric polypeptide of embodiment G207, wherein the first chimeric polypeptide comprises SEQ ID NO: 238.

Embodiment G209. The multi-chain chimeric polypeptide of any one of embodiments G1 and G204-G208, wherein the second chimeric polypeptide comprises a sequence that is at least 80% identical to SEQ ID NO: 268.

Embodiment G210. The multi-chain chimeric polypeptide of embodiment G209, wherein the second chimeric polypeptide comprises a sequence that is at least 90% identical to SEQ ID NO: 268.

Embodiment G211. The multi-chain chimeric polypeptide of embodiment G210, wherein the second chimeric polypeptide comprises a sequence that is at least 95% identical to SEQ ID NO: 268.

Embodiment G212. The multi-chain chimeric polypeptide of embodiment G211, wherein the second chimeric polypeptide comprises SEQ ID NO: 268.

Embodiment G213. The multi-chain chimeric polypeptide of embodiment G212, wherein the second chimeric polypeptide comprises SEQ ID NO: 270.

Embodiment G214. The multi-chain chimeric polypeptide of embodiment G1, wherein the first chimeric polypeptide comprises a sequence that is at least 80% identical to SEQ ID NO: 236.

Embodiment G215. The multi-chain chimeric polypeptide of embodiment G214, wherein the first chimeric polypeptide comprises a sequence that is at least 90% identical to SEQ ID NO: 236.

Embodiment G216. The multi-chain chimeric polypeptide of embodiment G215, wherein the first chimeric polypeptide comprises a sequence that is at least 95% identical to SEQ ID NO: 236.

Embodiment G217. The multi-chain chimeric polypeptide of embodiment G216, wherein the first chimeric polypeptide comprises SEQ ID NO: 236.

Embodiment G218. The multi-chain chimeric polypeptide of embodiment G217, wherein the first chimeric polypeptide comprises SEQ ID NO: 238.

Embodiment G219. The multi-chain chimeric polypeptide of any one of embodiments G1 and G214-G218, wherein the second chimeric polypeptide comprises a sequence that is at least 80% identical to SEQ ID NO: 300.

Embodiment G220. The multi-chain chimeric polypeptide of embodiment G219, wherein the second chimeric polypeptide comprises a sequence that is at least 90% identical to SEQ ID NO: 300.

Embodiment G221. The multi-chain chimeric polypeptide of embodiment G220, wherein the second chimeric polypeptide comprises a sequence that is at least 95% identical to SEQ ID NO: 300.

Embodiment G222. The multi-chain chimeric polypeptide of embodiment G221, wherein the second chimeric polypeptide comprises SEQ ID NO: 300.

Embodiment G223. The multi-chain chimeric polypeptide of embodiment G222, wherein the second chimeric polypeptide comprises SEQ ID NO: 302.

Embodiment G224. The multi-chain chimeric polypeptide of embodiment G1, wherein the first chimeric polypeptide comprises a sequence that is at least 80% identical to SEQ ID NO: 236.

Embodiment G225. The multi-chain chimeric polypeptide of embodiment G224, wherein the first chimeric polypeptide comprises a sequence that is at least 90% identical to SEQ ID NO: 236.

Embodiment G226. The multi-chain chimeric polypeptide of embodiment G225, wherein the first chimeric polypeptide comprises a sequence that is at least 95% identical to SEQ ID NO: 236.

Embodiment G227. The multi-chain chimeric polypeptide of embodiment G226, wherein the first chimeric polypeptide comprises SEQ ID NO: 236.

Embodiment G228. The multi-chain chimeric polypeptide of embodiment G227, wherein the first chimeric polypeptide comprises SEQ ID NO: 238.

Embodiment G229. The multi-chain chimeric polypeptide of any one of embodiments G1 and G224-G228, wherein the second chimeric polypeptide comprises a sequence that is at least 80% identical to SEQ ID NO: 308.

Embodiment G230. The multi-chain chimeric polypeptide of embodiment G229, wherein the second chimeric polypeptide comprises a sequence that is at least 90% identical to SEQ ID NO: 308.

Embodiment G231. The multi-chain chimeric polypeptide of embodiment G230, wherein the second chimeric polypeptide comprises a sequence that is at least 95% identical to SEQ ID NO: 308.

Embodiment G232. The multi-chain chimeric polypeptide of embodiment G231, wherein the second chimeric polypeptide comprises SEQ ID NO: 308.

Embodiment G233. The multi-chain chimeric polypeptide of embodiment G232, wherein the second chimeric polypeptide comprises SEQ ID NO: 310.

Embodiment G234. The multi-chain chimeric polypeptide of embodiment G1, wherein the first chimeric polypeptide comprises a sequence that is at least 80% identical to SEQ ID NO: 236.

Embodiment G235. The multi-chain chimeric polypeptide of embodiment G234, wherein the first chimeric polypeptide comprises a sequence that is at least 90% identical to SEQ ID NO: 236.

Embodiment G236. The multi-chain chimeric polypeptide of embodiment G235, wherein the first chimeric polypeptide comprises a sequence that is at least 95% identical to SEQ ID NO: 236.

Embodiment G237. The multi-chain chimeric polypeptide of embodiment G236, wherein the first chimeric polypeptide comprises SEQ ID NO: 236.

Embodiment G238. The multi-chain chimeric polypeptide of embodiment G237, wherein the first chimeric polypeptide comprises SEQ ID NO: 238.

Embodiment G239. The multi-chain chimeric polypeptide of any one of embodiments G1 and G234-G238, wherein the second chimeric polypeptide comprises a sequence that is at least 80% identical to SEQ ID NO: 316.

Embodiment G240. The multi-chain chimeric polypeptide of embodiment G239, wherein the second chimeric polypeptide comprises a sequence that is at least 90% identical to SEQ ID NO: 316.

Embodiment G241. The multi-chain chimeric polypeptide of embodiment G240, wherein the second chimeric polypeptide comprises a sequence that is at least 95% identical to SEQ ID NO: 316.

Embodiment G242. The multi-chain chimeric polypeptide of embodiment G241, wherein the second chimeric polypeptide comprises SEQ ID NO: 316.

Embodiment G243. The multi-chain chimeric polypeptide of embodiment G242, wherein the second chimeric polypeptide comprises SEQ ID NO: 318.

Embodiment G244. The multi-chain chimeric polypeptide of any one of embodiments G1-G133, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment G245. The multi-chain chimeric polypeptide of embodiment G244, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment G246. The multi-chain chimeric polypeptide of any one of embodiments G1-G133, wherein the first chimeric polypeptide further comprises one or more additional target-binding domains at the N-terminal and/or C-terminal end of the first chimeric polypeptide.

Embodiment G247. The multi-chain chimeric polypeptide of embodiment G246, wherein at least one of the one or more additional target-binding domains directly abuts the first domain of the pair of affinity domains in the first chimeric polypeptide.

Embodiment G248. The multi-chain chimeric polypeptide of embodiment G246, wherein the first chimeric polypeptide further comprises a linker sequence between the at least one of the one or more additional target-binding domains and the first domain of the pair of affinity domains.

Embodiment G249. The multi-chain chimeric polypeptide of embodiment G246, wherein the at least one of the one or more additional target-binding domains directly abuts the first target-binding domain in the first chimeric polypeptide.

Embodiment G250. The multi-chain chimeric polypeptide of embodiment G246, wherein the first chimeric polypeptide further comprises a linker sequence between the at least one of the one or more additional target-binding domains and the first target-binding domain.

Embodiment G251. The multi-chain chimeric polypeptide of embodiment G246, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment G252. The multi-chain chimeric polypeptide of embodiment G251, wherein the at least one additional target-binding domain of the one or more additional target-binding domains disposed at the N-terminus directly abuts the first target-binding domain or the first domain of the pair of affinity domains in the first chimeric polypeptide.

Embodiment G253. The multi-chain chimeric polypeptide of embodiment G251, wherein the first chimeric polypeptide further comprises a linker sequence disposed between the at least one additional target-binding domain and the first target-binding domain or the first domain of the pair of affinity domains in the first chimeric polypeptide.

Embodiment G254. The multi-chain chimeric polypeptide of embodiment G251, wherein the at least one additional target-binding domain of the one or more additional target-binding domains disposed at the C-terminus directly abuts the first target-binding domain or the first domain of the pair of affinity domains in the first chimeric polypeptide.

Embodiment G255. The multi-chain chimeric polypeptide of embodiment G251, wherein the first chimeric polypeptide further comprises a linker sequence disposed between the at least one additional target-binding domain and the first target-binding domain or the first domain of the pair of affinity domains in the first chimeric polypeptide.

Embodiment G256. The multi-chain chimeric polypeptide of embodiment G251, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment G257. The multi-chain chimeric polypeptide of embodiment G251, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment G258. The multi-chain chimeric polypeptide of any one of embodiments G44-G46, G57-G59, G76-G78, G96-G98, G109-G111, G122-G124, and G131-G133, wherein the second chimeric polypeptide further comprises the additional target-binding domain at the N-terminal end or the C-terminal end of the second chimeric polypeptide.

Embodiment G259. The multi-chain chimeric polypeptide of embodiment G258, wherein the additional target-binding domain directly abuts the second domain of the pair of affinity domains in the second chimeric polypeptide.

Embodiment G260. The multi-chain chimeric polypeptide of embodiment G258, wherein the second chimeric polypeptide further comprises a linker sequence between the additional target-binding domain and the second domain of the pair of affinity domains in the second chimeric polypeptide.

Embodiment G261. The multi-chain chimeric polypeptide of embodiment G258, wherein the additional target-binding domain directly abuts the second target-binding domain in the second chimeric polypeptide.

Embodiment G262. The multi-chain chimeric polypeptide of embodiment G258, wherein the second chimeric polypeptide further comprises a linker sequence between the additional target-binding domain and the second target-binding domain in the second chimeric polypeptide.

Embodiment G263. A composition comprising any of the multi-chain chimeric polypeptides of embodiments G1-G262.

Embodiment G264. The composition of embodiment G263, wherein the composition is a pharmaceutical composition.

Embodiment G265. A kit comprising at least one dose of the composition of embodiment G263 or G264.

Embodiment G266. Nucleic acid encoding any of the multi-chain chimeric polypeptides of any one of embodiments G1-G262.

Embodiment G267. A vector comprising the nucleic acid of embodiment G266.

Embodiment G268. The vector of embodiment G267, wherein the vector is an expression vector.

Embodiment G269. A cell comprising the nucleic acid of embodiment G323 or the vector of embodiment G267 or G268.

Embodiment G270. A method of producing a multi-chain chimeric polypeptide, the method comprising: culturing the cell of embodiment G269 in a culture medium under conditions sufficient to result in the production of the multi-chain chimeric polypeptide; and recovering the multi-chain chimeric polypeptide from the cell and/or the culture medium.

Embodiment G271. A multi-chain chimeric polypeptide produced by the method of embodiment G270.

Embodiment G272. The multi-chain chimeric polypeptide of embodiment G8, wherein the soluble human tissue factor domain comprises a sequence that is at least 80% identical to SEQ ID NO: 97.

Embodiment G273. The multi-chain chimeric polypeptide of embodiment G272, wherein the soluble human tissue factor domain comprises a sequence that is at least 90% identical to SEQ ID NO: 97.

Embodiment G274. The multi-chain chimeric polypeptide of embodiment G273, wherein the soluble human tissue factor domain comprises a sequence that is at least 95% identical to SEQ ID NO: 97.

Embodiment G275. The multi-chain chimeric polypeptide of embodiment G274, wherein the soluble human tissue factor domain comprises a sequence that is 100% identical to SEQ ID NO: 97.

Embodiment G276. The multi-chain chimeric polypeptide of embodiment G8, wherein the soluble human tissue factor domain comprises a sequence that is at least 80% identical to SEQ ID NO: 98.

Embodiment G277. The multi-chain chimeric polypeptide of embodiment G276, wherein the soluble human tissue factor domain comprises a sequence that is at least 90% identical to SEQ ID NO: 98.

Embodiment G278. The multi-chain chimeric polypeptide of embodiment G277, wherein the soluble human tissue factor domain comprises a sequence that is at least 95% identical to SEQ ID NO: 98.

Embodiment G279. The multi-chain chimeric polypeptide of embodiment G278, wherein the soluble human tissue factor domain comprises a sequence that is 100% identical to SEQ ID NO: 98.

Embodiment H1. A method of treating an aging-related disease or condition in a subject in need thereof, the method comprising administering to a subject identified as having an aging-related disease or condition a therapeutically effective amount of one or more natural killer (NK) cell activating agent(s).

Embodiment H2. A method of killing or reducing the number of senescent cells in a subject in need thereof, the method comprising administering to the subject a therapeutically effective amount of one or more NK cell activating agent(s).

Embodiment H3. The method of embodiment H2, wherein the senescent cells are senescent cancer cells, senescent monocytes, senescent lymphocytes, senescent astrocytes, senescent microglia, senescent neurons, senescent tissue fibroblasts, senescent dermal fibroblasts, senescent keratinocytes, or other differentiated tissue-specific dividing functional cells.

Embodiment H4. The method of embodiment H3, wherein the senescent cancer cells are chemotherapy-induced senescent cells or radiation-induced senescent cells.

Embodiment H5. The method of embodiment H2, wherein the subject has been identified or diagnosed as having an aging-related disease or condition.

Embodiment H6. The method of embodiment H1 or H5, wherein the aging-related disease or condition is selected from the group consisting of: a cancer, an autoimmune disease, a metabolic disease, a neurodegenerative disease, a cardiovascular disease, a skin disease, a progeria disease, and a fragility disease.

Embodiment H7. The method of embodiment H6, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H8. The method of embodiment H6, wherein the autoimmune disease is type-1 diabetes.

Embodiment H9. The method of embodiment H6, wherein the metabolic disease is selected from the group consisting of: obesity, a lipodystrophy, and type 2 diabetes mellitus.

Embodiment H10. The method of embodiment H6, wherein the neurodegenerative disease is selected from the group consisting of: Alzheimer's disease, Parkinson's disease, and dementia.

Embodiment H11. The method of embodiment H6, wherein the cardiovascular disease is selected from the group consisting of: coronary artery disease, atherosclerosis, and pulmonary arterial hypertension.

Embodiment H12. The method of embodiment H6, wherein the skin disease is selected from the group consisting of: wound healing, alopecia, wrinkles, senile lentigo, skin thinning, xeroderma pigmentosum, and dyskeratosis congenita.

Embodiment H13. The method of embodiment H6, wherein the progeria disease is selected from the group consisting of: progeria and Hutchinson-Gilford Progeria Syndrome.

Embodiment H14. The method of embodiment H6, wherein the fragility disease is selected from the group consisting of: frailty, responsiveness to vaccination, osteoporosis, and sarcopenia.

Embodiment H15. The method of embodiment H1 or H5, wherein the aging-related disease or condition is selected from the group of: age-related macular degeneration, osteoarthritis, adipose atrophy, idiopathic pulmonary fibrosis, kidney transplant failure, liver fibrosis, loss of bone mass, sarcopenia, age-associated loss of lung tissue elasticity, osteoporosis, age-associated renal dysfunction, and chemical-induced renal dysfunction.

Embodiment H16. The method of embodiment H1 or H5, wherein the aging-related disease or condition is type 2 diabetes or atherosclerosis.

Embodiment H17. The method of any one of embodiments H1-H16, wherein the administering results in a decrease in the number of senescent cells in a target tissue in the subject.

Embodiment H18. The method of embodiment H17, wherein the target tissue is selected from the group consisting of: adipose tissue, pancreatic tissue, liver tissue, lung tissue, vasculature, bone tissue, central nervous system (CNS) tissue, eye tissue, skin tissue, muscle tissue, and secondary lympho-organ tissue.

Embodiment H19. The method of any one of embodiments H1-H18, wherein the administering results in an increase in the expression levels of CD25, CD69, MTOR-C1, SREBP1, IFN-γ, and granzyme B in activated NK cells.

Embodiment H20. A method of treating an aging-related disease or condition in a subject in need thereof, the method comprising administering to a subject identified as having an aging-related disease or condition a therapeutically effective number of activated NK cells.

Embodiment H21. A method of killing or reducing the number of senescent cells in a subject in need thereof, the method comprising administering to the subject a therapeutically effective number of activated NK cells.

Embodiment H22. The method of embodiment H21, wherein the senescent cells are senescent cancer cells, senescent monocytes, senescent lymphocytes, senescent astrocytes, senescent microglia, senescent neurons, senescent tissue fibroblasts, senescent dermal fibroblasts, senescent keratinocytes, or other differentiated tissue-specific dividing functional cells.

Embodiment H23. The method of embodiment H22, wherein the senescent cancer cells are chemotherapy-induced senescent cells or radiation-induced senescent cells.

Embodiment H24. The method of embodiment H21, wherein the subject has been identified or diagnosed as having an aging-related disease or condition.

Embodiment H25. The method of embodiment H20 or H24, wherein the aging-related disease or condition is selected from the group consisting of: a cancer, an autoimmune disease, a metabolic disease, a neurodegenerative disease, a cardiovascular disease, a skin disease, a progeria disease, and a fragility disease.

Embodiment H26. The method of embodiment H25, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H27. The method of embodiment H25, wherein the autoimmune disease is type-1 diabetes.

Embodiment H28. The method of embodiment H25, wherein the metabolic disease is selected from the group consisting of: obesity, a lipodystrophy, and type 2 diabetes mellitus.

Embodiment H29. The method of embodiment H25, wherein the neurodegenerative disease is selected from the group consisting of: Alzheimer's disease, Parkinson's disease, and dementia.

Embodiment H30. The method of embodiment H25, wherein the cardiovascular disease is selected from the group consisting of: coronary artery disease, atherosclerosis, and pulmonary arterial hypertension.

Embodiment H31. The method of embodiment H25, wherein the skin disease is selected from the group consisting of: wound healing, alopecia, wrinkles, senile lentigo, skin thinning, xeroderma pigmentosum, and dyskeratosis congenita.

Embodiment H32. The method of embodiment H25, wherein the progeria disease is selected from the group consisting of: progeria and Hutchinson-Gilford Progeria Syndrome.

Embodiment H33. The method of embodiment H25, wherein the fragility disease is selected from the group consisting of: frailty, responsiveness to vaccination, osteoporosis, and sarcopenia.

Embodiment H34. The method of embodiment H20 or H24, wherein the aging-related disease or condition is selected from the group consisting of: age-related macular degeneration, osteoarthritis, adipose atrophy, idiopathic pulmonary fibrosis, kidney transplant failure, liver fibrosis, loss of bone mass, sarcopenia, age-associated loss of lung tissue elasticity, osteoporosis, age-associated renal dysfunction, and chemical-induced renal dysfunction.

Embodiment H35. The method of any one of embodiments H20-H34, wherein the method further comprises:

obtaining a resting NK cell; and contacting the resting NK cell in vitro in a liquid culture medium comprising one or more NK cell activating agent(s), wherein the contacting results in the generation of the activated NK cells that are subsequently administered to the subject.

Embodiment H36. The method of embodiment H35, wherein the resting NK cell is an autologous NK cell obtained from the subject.

Embodiment H37. The method of embodiment H35, wherein the resting NK cell is an allogeneic resting NK cell.

Embodiment H38. The method of embodiment H35, wherein the resting NK cell is an artificial NK cell.

Embodiment H39. The method of embodiment H35, wherein the resting NK cell is a haploidentical resting NK cell.

Embodiment H40. The method of any one of embodiments H35-H39, wherein the resting NK cell is a genetically-engineered NK cell carrying a chimeric antigen receptor or recombinant T cell receptor.

Embodiment H41. The method of any one of embodiments H35-H40, wherein the method further comprises isolating the activated NK cells before the activated NK cells are administered to the subject.

Embodiment H42. A method of improving the texture and/or appearance of skin and/or hair in a subject in need thereof over a period of time, the method comprising administering to the subject a therapeutically effective amount of one or more natural killer (NK) cell activating agent(s).

Embodiment H43. A method of improving the texture and/or appearance of skin and/or hair in a subject in need thereof over a period of time, the method comprising administering to the subject a therapeutically effective number of activated NK cells.

Embodiment H44. The method of embodiment H43, wherein the method further comprises:

obtaining a resting NK cell; and contacting the resting NK cell in vitro in a liquid culture medium comprising one or more NK cell activating agent(s), wherein the contacting results in the generation of the activated NK cells that are subsequently administered to the subject.

Embodiment H45. The method of embodiment H44, wherein the resting NK cell is an autologous NK cell obtained from the subject.

Embodiment H46. The method of embodiment H44, wherein the resting NK cell is an allogeneic resting NK cell.

Embodiment H47. The method of embodiment H44, wherein the resting NK cell is an artificial NK cell.

Embodiment H48. The method of embodiment H44, wherein the resting NK cell is a haploidentical resting NK cell.

Embodiment H49. The method of any one of embodiments H44-H48, wherein the resting NK cell is a genetically-engineered NK cell carrying a chimeric antigen receptor or recombinant T cell receptor.

Embodiment H50. The method of any one of embodiments H44-H49, wherein the method further comprises isolating the activated NK cells before the activated NK cells are administered to the subject.

Embodiment H51. The method of any one of embodiments H42-H50, wherein the method provides for an improvement in the texture and/or appearance of skin of the subject over the period of time.

Embodiment H52. The method of embodiment H51, wherein the method results in a decrease in the rate of formation of wrinkles in the skin of the subject over the period of time.

Embodiment H53. The method of embodiment H51 or H52, wherein the method results in an improvement in the coloration of skin of the subject over the period of time.

Embodiment H54. The method of any one of embodiments H51-H53, wherein the method results in an improvement in the texture of skin of the subject over the period of time.

Embodiment H55. The method of any one of embodiments H42-H50, wherein the method provides for an improvement in the texture and/or appearance of hair of the subject over the period of time.

Embodiment H56. The method of embodiment H55, wherein the method results in a decrease in the rate of formation of gray hair in the subject over the period of time.

Embodiment H57. The method of embodiment H55 or H56, wherein the method results in a decrease in the number of gray hairs of the subject over the period of time.

Embodiment H58. The method of any one of embodiments H55-H57, wherein the method results in a decrease in the rate of hair loss in the subject over time.

Embodiment H59. The method of any one of embodiments H55-H58, wherein the method results in an improvement in the texture of hair of the subject over the period of time.

Embodiment H60. The method of any one of embodiments H42-H59, wherein the period of time is between about one month and about 10 years.

Embodiment H61. The method of any one of embodiments H42-H60, wherein the method results in a decrease in the number of senescent dermal fibroblasts in the skin of the subject over the period of time.

Embodiment H62. A method of assisting in the treatment of obesity in a subject in need thereof over a period of time, the method comprising administering to the subject a therapeutically effective amount of one or more natural killer (NK) cell activating agent(s).

Embodiment H63. A method of assisting in the treatment of obesity in a subject in need thereof over a period of time, the method comprising administering to the subject a therapeutically effective number of activated NK cells.

Embodiment H64. The method of embodiment H63, wherein the method further comprises:

obtaining a resting NK cell; and contacting the resting NK cell in vitro in a liquid culture medium comprising one or more NK cell activating agent(s), wherein the contacting results in the generation of the activated NK cells that are subsequently administered to the subject.

Embodiment H65. The method of embodiment H64, wherein the resting NK cell is an autologous NK cell obtained from the subject.

Embodiment H66. The method of embodiment H64, wherein the resting NK cell is an allogeneic resting NK cell.

Embodiment H67. The method of embodiment H64, wherein the resting NK cell is an artificial NK cell.

Embodiment H68. The method of embodiment H64, wherein the resting NK cell is a haploidentical resting NK cell.

Embodiment H69. The method of any one of embodiments H64-H68, wherein the resting NK cell is a genetically-engineered NK cell carrying a chimeric antigen receptor or recombinant T cell receptor.

Embodiment H70. The method of any one of embodiments H64-H69, wherein the method further comprises isolating the activated NK cells before the activated NK cells are administered to the subject.

Embodiment H71. The method of any one of embodiments H62-H70, wherein the method results in a decrease in the mass of the subject over the period of time.

Embodiment H72. The method of any one of embodiments H62-H71, wherein the method results in a decrease in the body mass index (BMI) of the subject over the period of time.

Embodiment H73. The method of any one of embodiments H62-H70, wherein the method results in a decrease in the rate of progression from pre-diabetes to type 2 diabetes in the subject.

Embodiment H74. The method of any one of embodiments H62-H70, wherein the method results in a decrease in fasting serum glucose level in the subject.

Embodiment H75. The method of any one of embodiments H62-H70, wherein the method results in an increase in insulin sensitivity in the subject.

Embodiment H76. The method of any one of embodiments H62-H70, wherein the method results in a decrease in the severity of atherosclerosis in the subject.

Embodiment H77. The method of any one of embodiments H62-H76, wherein the period of time is between about two weeks and about 10 years.

Embodiment H78. The method of any one of embodiments H1-H19, H35-H42, H44-H62, and H64-H77, wherein at least one of the one or more NK cell activating agent(s) results in activation of one or more of: a receptor for IL-2, a receptor for IL-7, a receptor for IL-12, a receptor for IL-15, a receptor for IL-18, a receptor for IL-21, a receptor for IL-33, CD16, CD69, CD25, CD36, CD59, CD352, NKp80, DNAM-1, 2B4, NKp30, NKp44, NKp46, NKG2D, KIR2DS1, KIR2Ds2/3, KIR2DL4, KIR2DS4, KIR2DS5, and KIR3DS1.

Embodiment H79. The method of embodiment H78, wherein the at least one of the one or more NK cell activating agent(s) that results in activation of a receptor for IL-2 is a soluble IL-2 or an agonistic antibody that binds specifically to an IL-2 receptor.

Embodiment H80. The method of embodiment H78, wherein the at least one of the one or more NK cell activating agent(s) that results in activation of a receptor for IL-7 is a soluble IL-7 or an agonistic antibody that binds specifically to an IL-7 receptor.

Embodiment H81. The method of embodiment H78, wherein the at least one of the one or more NK cell activating agent(s) that results in activation of a receptor for IL-12 is a soluble IL-12 or an agonistic antibody that binds specifically to an IL-12 receptor.

Embodiment H82. The method of embodiment H78, wherein the at least one of the one or more NK cell activating agent(s) that results in activation of a receptor for IL-15 is a soluble IL-15 or an agonistic antibody that binds specifically to an IL-15 receptor.

Embodiment H83. The method of embodiment H78, wherein the at least one of the one or more NK cell activating agent(s) that results in activation of a receptor for IL-21 is a soluble IL-21 or an agonistic antibody that binds specifically to an IL-21 receptor.

Embodiment H84. The method of embodiment H78, wherein the at least one of the one or more NK cell activating agent(s) that results in activation of a receptor for IL-33 is a soluble IL-33 or an agonistic antibody that binds specifically to an IL-33 receptor.

Embodiment H85. The method of embodiment H78, wherein the at least one of the one or more NK cell activating agent(s) that results in activation of a receptor for CD16 is an agonistic antibody that binds specifically to a CD16.

Embodiment H86. The method of embodiment H78, wherein the at least one of the one or more NK cell activating agent(s) that results in activation of a receptor for CD69 is an agonistic antibody that binds specifically to a CD69.

Embodiment H87. The method of embodiment H78, wherein the at least one of the one or more NK cell activating agent(s) that results in activation of a receptor for CD25, CD36, CD59 is an agonistic antibody that binds specifically to a CD25, CD6, CD59.

Embodiment H88. The method of embodiment H78, wherein the at least one of the one or more NK cell activating agent(s) that results in activation of a receptor for CD352 is an agonistic antibody that binds specifically to a CD352.

Embodiment H89. The method of embodiment H78, wherein the at least one of the one or more NK cell activating agent(s) that results in activation of a receptor for NKp80 is an agonistic antibody that binds specifically to an NKp80.

Embodiment H90. The method of embodiment H78, wherein the at least one of the one or more NK cell activating agent(s) that results in activation of a receptor for DNAM-1 is an agonistic antibody that binds specifically to a DNAM-1.

Embodiment H91. The method of embodiment H78, wherein the at least one of the one or more NK cell activating agent(s) that results in activation of a receptor for 2B4 is an agonistic antibody that binds specifically to a 2B4.

Embodiment H92. The method of embodiment H78, wherein the at least one of the one or more NK cell activating agent(s) that results in activation of a receptor for NKp30 is an agonistic antibody that binds specifically to an NKp30.

Embodiment H93. The method of embodiment H78, wherein the at least one of the one or more NK cell activating agent(s) that results in activation of a receptor for NKp44 is an agonistic antibody that binds specifically to an NKp44.

Embodiment H94. The method of embodiment H78, wherein the at least one of the one or more NK cell activating agent(s) that results in activation of a receptor for NKp46 is an agonistic antibody that binds specifically to an NKp46.

Embodiment H95. The method of embodiment H78, wherein the at least one of the one or more NK cell activating agent(s) that results in activation of a receptor for NKG2D is an agonistic antibody that binds specifically to an NKG2D.

Embodiment H96. The method of embodiment H78, wherein the at least one of the one or more NK cell activating agent(s) that results in activation of a receptor for KIR2DS1 is an agonistic antibody that binds specifically to a KIR2DS1.

Embodiment H97. The method of embodiment H78, wherein the at least one of the one or more NK cell activating agent(s) that results in activation of a receptor for KIR2DS2/3 is an agonistic antibody that binds specifically to a KIR2DS2/3.

Embodiment H98. The method of embodiment H78, wherein the at least one of the one or more NK cell activating agent(s) that results in activation of a receptor for KIR2DL4 is an agonistic antibody that binds specifically to a KIR2DL4.

Embodiment H99. The method of embodiment H78, wherein the at least one of the one or more NK cell activating agent(s) that results in activation of a receptor for KIR2DS4 is an agonistic antibody that binds specifically to a KIR2DS4.

Embodiment H100. The method of embodiment H78, wherein the at least one of the one or more NK cell activating agent(s) that results in activation of a receptor for KIR2DS5 is an agonistic antibody that binds specifically to a KIR2DS5.

Embodiment H101. The method of embodiment H78, wherein the at least one of the one or more NK cell activating agent(s) that results in activation of a receptor for KIR3DS1 is an agonistic antibody that binds specifically to a KIR3DS1.

Embodiment H102. The method of any one of embodiments H1-H19, H35-H42, H44-H62, and H64-H101, wherein at least one of the one or more NK cell activating agent(s) results in a decrease in the activation of one or more of: PD-1, a TGF-β receptor, TIGIT, CD1, TIM-3, Siglec-7, IRP60, Tactile, IL1R8, NKG2A/KLRD1, KIR2DL1, KIR2DL2/3, KIR2DL5, KIR3DL1, KIR3DL2, ILT2/LIR-1, and LAG-2.

Embodiment H103. The method of embodiment H102, wherein the at least one of the one or more NK cell activating agent(s) that results in a decrease in the activation of PD-1 is an antagonistic antibody that binds specifically to PD-1, a soluble PD-1, a soluble PD-L1, or an antibody that binds specifically to PD-L1.

Embodiment H104. The method of embodiment H102, wherein at least one of the one or more NK cell activating agent(s) that results in a decrease in the activation of a TGF-β receptor is a soluble TGF-β receptor, an antibody that binds specifically to TGF-β, or an antagonistic antibody that binds specifically to a TGF-β receptor.

Embodiment H105. The method of embodiment H102, wherein at least one of the one or more NK cell activating agent(s) that results in a decrease in the activation of TIGIT is an antagonistic antibody that binds specifically to TIGIT, a soluble TIGIT, or an antibody that binds specifically to a ligand of TIGIT.

Embodiment H106. The method of embodiment H102, wherein at least one of the one or more NK cell activating agent(s) that results in a decrease in the activation of CD1 is an antagonistic antibody that binds specifically to CD1, a soluble CD1, or an antibody that binds specifically to a ligand of CD1.

Embodiment H107. The method of embodiment H102, wherein at least one of the one or more NK cell activating agent(s) that results in a decrease in the activation of TIM-3 is an antagonistic antibody that binds specifically to TIM-3, a soluble TIM-3, or an antibody that binds specifically to a ligand of TIM-3.

Embodiment H108. The method of embodiment H102, wherein at least one of the one or more NK cell activating agent(s) that results in a decrease in the activation of Siglec-7 is an antagonistic antibody that binds specifically to Siglec-7 or an antibody that binds specifically to a ligand of Siglec-7.

Embodiment H109. The method of embodiment H102, wherein at least one of the one or more NK cell activating agent(s) that results in a decrease in the activation of IRP60 is an antagonistic antibody that binds specifically to IRP60 or an antibody that binds specifically to a ligand of IRP60.

Embodiment H110. The method of embodiment H102, wherein at least one of the one or more NK cell activating agent(s) that results in a decrease in the activation of Tactile is an antagonistic antibody that binds specifically to Tactile or an antibody that binds specifically to a ligand of Tactile.

Embodiment H111. The method of embodiment H102, wherein at least one of the one or more NK cell activating agent(s) that results in a decrease in the activation of IL1R8 is an antagonistic antibody that binds specifically to IL1R8 or an antibody that binds specifically to a ligand of IL1R8.

Embodiment H112. The method of embodiment H102, wherein at least one of the one or more NK cell activating agent(s) that results in a decrease in the activation of NKG2A/KLRD1 is an antagonistic antibody that binds specifically to NKG2A/KLRD1 or an antibody that binds specifically to a ligand of NKG2A/KLRD1.

Embodiment H113. The method of embodiment H102, wherein at least one of the one or more NK cell activating agent(s) that results in a decrease in the activation of KIR2DL1 is an antagonistic antibody that binds specifically to KIR2DL1 or an antibody that binds specifically to a ligand of KIR2DL1.

Embodiment H114. The method of embodiment H102, wherein at least one of the one or more NK cell activating agent(s) that results in a decrease in the activation of KIR2DL2/3 is an antagonistic antibody that binds specifically to KIR2DL2/3 or an antibody that binds specifically to a ligand of KIR2DL2/3.

Embodiment H115. The method of embodiment H102, wherein at least one of the one or more NK cell activating agent(s) that results in a decrease in the activation of KIR2DL5 is an antagonistic antibody that binds specifically to KIR2DL5 or an antibody that binds specifically to a ligand of KIR2DL5.

Embodiment H116. The method of embodiment H102, wherein at least one of the one or more NK cell activating agent(s) that results in a decrease in the activation of KIR3DL1 is an antagonistic antibody that binds specifically to KIR3DL1 or an antibody that binds specifically to a ligand of KIR3DL1.

Embodiment H117. The method of embodiment H102, wherein at least one of the one or more NK cell activating agent(s) that results in a decrease in the activation of KIR3DL2 is an antagonistic antibody that binds specifically to KIR3DL2 or an antibody that binds specifically to a ligand of KIR3DL2.

Embodiment H118. The method of embodiment H102, wherein at least one of the one or more NK cell activating agent(s) that results in a decrease in the activation of ILT2/LIR-1 is an antagonistic antibody that binds specifically to ILT2/LIR-1 or an antibody that binds specifically to a ligand of ILT2/LIR-1.

Embodiment H119. The method of embodiment H102, wherein at least one of the one or more NK cell activating agent(s) that results in a decrease in the activation of LAG-2 is an antagonistic antibody that binds specifically to LAG-2 or an antibody that binds specifically to a ligand of LAG-2.

Embodiment H120. The method of any one of embodiments H1-H19, H35-H42, H44-H62, and H64-H77, wherein at least one of the one or more NK cell activating agent(s) is a single-chain chimeric polypeptide comprising:

(i) a first target-binding domain;

(ii) a soluble tissue factor domain; and (iii) a second target-binding domain.

Embodiment H121. The method of embodiment H120, wherein the first target-binding domain and the soluble tissue factor domain directly abut each other.

Embodiment H122. The method of embodiment H120, wherein the single-chain chimeric polypeptide further comprises a linker sequence between the first target-binding domain and the soluble tissue factor domain.

Embodiment H123. The method of any one of embodiments H120-H122, wherein the soluble tissue factor domain and the second target-binding domain directly abut each other.

Embodiment H124. The method of any one of embodiments H120-H122, wherein the single-chain chimeric polypeptide further comprises a linker sequence between the soluble tissue factor domain and the second target-binding domain.

Embodiment H125. The method of embodiment H120, wherein the first target-binding domain and the second target-binding domain directly abut each other.

Embodiment H126. The method of embodiment H120, wherein the single-chain chimeric polypeptide further comprises a linker sequence between the first target-binding domain and the second target-binding domain.

Embodiment H127. The method of embodiment H125 or H126, wherein the second target-binding domain and the soluble tissue factor domain directly abut each other.

Embodiment H128. The method of embodiment H125 or H126, wherein the single-chain chimeric polypeptide further comprises a linker sequence between the second target-binding domain and the soluble tissue factor domain.

Embodiment H129. The method of any one of embodiments H120-H128, wherein the first target-binding domain and the second target-binding domain bind specifically to the same antigen.

Embodiment H130. The method of embodiment H129, wherein the first target-binding domain and the second target-binding domain bind specifically to the same epitope.

Embodiment H131. The method of embodiment H130, wherein the first target-binding domain and the second target-binding domain comprise the same amino acid sequence.

Embodiment H132. The method of any one of embodiments H120-H128, wherein the first target-binding domain and the second target-binding domain bind specifically to different antigens.

Embodiment H133. The method of any one of embodiments H120-H132, wherein one or both of the first target-binding domain and the second target-binding domain is an antigen-binding domain.

Embodiment H134. The method of embodiment H133, wherein the first target-binding domain and the second target-binding domain are each an antigen-binding domain.

Embodiment H135. The method of embodiment H134, wherein antigen-binding domain comprises a scFv or a single domain antibody.

Embodiment H136. The method of any one of embodiments H120-H135, wherein one or both of the first target-binding domain and the second target-binding domain bind to a target selected from the group consisting of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKP30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

Embodiment H137. The method of any one of embodiments H120-H128, wherein one or both of the first target-binding domain and the second target-binding domain is a soluble interleukin or cytokine protein.

Embodiment H138. The method of embodiment H137, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment H139. The method of any one of embodiments H120-H128, wherein one or both of the first target-binding domain and the second target-binding domain is a soluble interleukin or cytokine receptor.

Embodiment H140. The method of embodiment H139, wherein the soluble interleukin or cytokine receptor is a soluble TGF-β receptor II (TGF-βRII) a soluble TGF-βRIII, a soluble receptor for TNFα, a soluble receptor for IL-4, or a soluble receptor for IL-10.

Embodiment H141. The method of any one of embodiments H120-H140, wherein the soluble tissue factor domain is a soluble human tissue factor domain.

Embodiment H142. The method of embodiment H141, wherein the soluble human tissue factor domain comprises a sequence that is at least 80% identical to SEQ ID NO: 93.

Embodiment H143. The method of embodiment H142, wherein the soluble human tissue factor domain comprises a sequence that is at least 90% identical to SEQ ID NO: 93.

Embodiment H144. The method of embodiment H143, wherein the soluble human tissue factor domain comprises a sequence that is at least 95% identical to SEQ ID NO: 93.

Embodiment H145. The method of any one of embodiments H141-H144, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H146. The method of embodiment H145, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H147. The method of any one of embodiments H120-H146, wherein the soluble tissue factor domain is not capable of binding Factor VIIa.

Embodiment H148. The method of any one of embodiments H120-H147, wherein the soluble tissue factor domain does not convert inactive Factor X into Factor Xa.

Embodiment H149. The method of any one of embodiments H120-H148, wherein the single-chain chimeric polypeptide does not stimulate blood coagulation in a mammal.

Embodiment H150. The method of any one of embodiments H120-H149, wherein the single-chain chimeric polypeptide further comprises one or more additional target-binding domains at its N- and/or C-terminus.

Embodiment H151. The method of embodiment H150, wherein the single-chain chimeric polypeptide comprises one or more additional target-binding domains at its N-terminus.

Embodiment H152. The method of embodiment H151, wherein one or more additional target-binding domains directly abuts the first target-binding domain, the second target-binding domain, or the soluble tissue factor domain.

Embodiment H153. The method of embodiment H152, wherein the single-chain chimeric polypeptide further comprises a linker sequence between one of the at least one additional target-binding domains and the first target-binding domain, the second target-binding domain, or the soluble tissue factor domain.

Embodiment H154. The method of embodiment H150, wherein the single-chain chimeric polypeptide comprises one or more additional target-binding domains at its C-terminus.

Embodiment H155. The method of embodiment H154, wherein one of the one or more additional target-binding domains directly abuts the first target-binding domain, the second target-binding domain, or the soluble tissue factor domain.

Embodiment H156. The method of embodiment H154, wherein the single-chain chimeric polypeptide further comprises a linker sequence between one of the at least one additional target-binding domains and the first target-binding domain, the second target-binding domain, or the soluble tissue factor domain.

Embodiment H157. The method of embodiment H150, wherein the single-chain chimeric polypeptide comprises one or more additional target binding domains at its N-terminus and the C-terminus.

Embodiment H158. The method of embodiment H157, wherein one of the one or more additional antigen binding domains at the N-terminus directly abuts the first target-binding domain, the second target-binding domain, or the soluble tissue factor domain.

Embodiment H159. The method of embodiment H157, wherein the single-chain chimeric polypeptide further comprises a linker sequence between one of the one or more additional antigen-binding domains at the N-terminus and the first target-binding domain, the second target-binding domain, or the soluble tissue factor domain.

Embodiment H160. The method of embodiment H157, wherein one of the one or more additional antigen binding domains at the C-terminus directly abuts the first target-binding domain, the second target-binding domain, or the soluble tissue factor domain.

Embodiment H161. The method of embodiment H157, wherein the single-chain chimeric polypeptide further comprises a linker sequence between one of the one or more additional antigen-binding domains at the C-terminus and the first target-binding domain, the second target-binding domain, or the soluble tissue factor domain.

Embodiment H162. The method of any one of embodiments H150-H161, wherein two or more of the first target-binding domain, the second target-binding domain, and the one or more additional target-binding domains bind specifically to the same antigen.

Embodiment H163. The method of embodiment H162, wherein two or more of the first target-binding domain, the second target-binding domain, and the one or more additional target-binding domains bind specifically to the same epitope.

Embodiment H164. The method of embodiment H163, wherein two or more of the first target-binding domain, the second target-binding domain, and the one or more additional target-binding domains comprise the same amino acid sequence.

Embodiment H165. The method of embodiment H162, wherein the first target-binding domain, the second target-binding domain, and the one or more additional target-binding domains each bind specifically to the same antigen.

Embodiment H166. The method of embodiment H165, wherein the first target-binding domain, the second target-binding domain, and the one or more additional target-binding domains each bind specifically to the same epitope.

Embodiment H167. The method of embodiment H166, wherein the first target-binding domain, the second target-binding domain, and the one or more additional target-binding domains each comprise the same amino acid sequence.

Embodiment H168. The method of any one of embodiments H150-H161, wherein the first target-binding domain, the second target-binding domain, and the one or more additional target-binding domains bind specifically to different antigens.

Embodiment H169. The method of any one of embodiments H150-H168, wherein one or more of the first target-binding domain, the second target-binding domain, and the one or more target-binding domains is an antigen-binding domain.

Embodiment H170. The method of embodiment H169, wherein the first target-binding domain, the second target-binding domain, and the one or more additional target-binding domains are each an antigen-binding domain.

Embodiment H171. The method of embodiment H170, wherein antigen-binding domain comprises a scFv or a single domain antibody.

Embodiment H172. The method of any one of embodiments H150-H171, wherein one or more of the first target-binding domain, the second target-binding domain, and the one or more target-binding domains bind specifically to a target selected from the group consisting of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKP30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

Embodiment H173. The method of any one of embodiments H150-H161, wherein one or more of the first target-binding domain, the second target-binding domain, and the one or more additional target-binding domains is a soluble interleukin or cytokine protein.

Embodiment H174. The method of embodiment H173, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment H175. The method of any one of embodiments H150-H161, wherein one or more of the first target-binding domain, the second target-binding domain, and the one or more additional target-binding domains is a soluble interleukin or cytokine receptor.

Embodiment H176. The method of embodiment H175, wherein the soluble receptor is a soluble TGF-β receptor II (TGF-βRII) a soluble TGF-βRIII, a soluble receptor for TNFα, a soluble receptor for IL-4, or a soluble receptor for IL-10.

Embodiment H177. The method of any one of embodiments H1-H19, H35-H42, H44-H62, and H64-H77, wherein at least one of the one or more NK cell activating agent(s) is a multi-chain chimeric polypeptide comprising:

(c) a first chimeric polypeptide comprising:
  (i) a first target-binding domain;
  (ii) a soluble tissue factor domain; and
  (iii) a first domain of a pair of affinity domains;
(d) a second chimeric polypeptide comprising:
  (i) a second domain of a pair of affinity domains; and
  (ii) a second target-binding domain, wherein the first chimeric polypeptide and the second chimeric polypeptide associate through the binding of the first domain and the second domain of the pair of affinity domains.

Embodiment H178. The method of embodiment H177, wherein the first target-binding domain and the soluble tissue factor domain directly abut each other in the first chimeric polypeptide.

Embodiment H179. The method of embodiment H177, wherein the first chimeric polypeptide further comprises a linker sequence between the first target-binding domain and the soluble tissue factor domain in the first chimeric polypeptide.

Embodiment H180. The method of any one of embodiments H177-H179, wherein the soluble tissue factor domain and the first domain of the pair of affinity domains directly abut each other in the first chimeric polypeptide.

Embodiment H181. The method of any one of embodiments H177-H179, wherein the first chimeric polypeptide further comprises a linker sequence between the soluble tissue factor domain and the first domain of the pair of affinity domains in the first chimeric polypeptide.

Embodiment H182. The method of any one of embodiments H177-H181, wherein the second domain of the pair of affinity domains and the second target-binding domain directly abut each other in the second chimeric polypeptide.

Embodiment H183. The method of any one of embodiments H177-H181, wherein second chimeric polypeptide further comprises a linker sequence between the second domain of the pair of affinity domains and the second target-binding domain in the second chimeric polypeptide.

Embodiment H184. The method of any one of embodiments H177-H183, wherein the first target-binding domain and the second target-binding domain bind specifically to the same antigen.

Embodiment H185. The method of embodiment H184, wherein the first target-binding domain and the second target-binding domain bind specifically to the same epitope.

Embodiment H186. The method of embodiment H185, wherein the first target-binding domain and the second target-binding domain comprise the same amino acid sequence.

Embodiment H187. The method of any one of embodiments H177-H183, wherein the first target-binding domain and the second target-binding domain bind specifically to different antigens.

Embodiment H188. The method of any one of embodiments H177-H187, wherein one or both of the first target-binding domain and the second target-binding domain is an antigen-binding domain.

Embodiment H189. The method of embodiment H188, wherein the first target-binding domain and the second target-binding domain are each antigen-binding domains.

Embodiment H190. The method of embodiment H188 or H189, wherein antigen-binding domain comprises a scFv or a single domain antibody.

Embodiment H191. The method of any one of embodiments H177-H190, wherein one or both of the first target-binding domain and the second target-binding domain bind specifically to a target selected from the group consisting of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKP30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

Embodiment H192. The method of any one of embodiments H177-H183, wherein one or both of the first target-binding domain and the second target-binding domain is a soluble interleukin or cytokine protein.

Embodiment H193. The method of embodiment H192, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment H194. The method of any one of embodiments H177-H183, wherein one or both of the first target-binding domain and the second target-binding domain is a soluble interleukin or cytokine receptor.

Embodiment H195. The method of embodiment H194, wherein the soluble receptor is a soluble TGF-β receptor II (TGF-βRII) a soluble TGF-βRIII, a soluble receptor for TNFα, a soluble receptor for IL-4, or a soluble receptor for IL-10.

Embodiment H196. The method of any one of embodiments H177-H195, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment H197. The method of embodiment H196, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment H198. The method of any one of embodiments H177-H195, wherein the first chimeric polypeptide further comprises one or more additional target-binding domains at the N-terminal and/or C-terminal end of the first chimeric polypeptide.

Embodiment H199. The method of embodiment H198, wherein at least one of the one or more additional target-binding domains directly abuts the first domain of the pair of affinity domains in the first chimeric polypeptide.

Embodiment H200. The method of embodiment H198, wherein the first chimeric polypeptide further comprises a linker sequence between the at least one of the one or more additional target-binding domains and the first domain of the pair of affinity domains.

Embodiment H201. The method of embodiment H198, wherein the at least one of the one or more additional target-binding domains directly abuts the first target-binding domain in the first chimeric polypeptide.

Embodiment H202. The method of embodiment H198, wherein the first chimeric polypeptide further comprises a linker sequence between the at least one of the one or more additional target-binding domains and the first target-binding domain.

Embodiment H203. The method of embodiment H198, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment H204. The method of embodiment H203, wherein the at least one additional target-binding domain of the one or more additional target-binding domains disposed at the N-terminus directly abuts the first target-binding domain or the first domain of the pair of affinity domains in the first chimeric polypeptide.

Embodiment H205. The method of embodiment H203, wherein the first chimeric polypeptide further comprises a linker sequence disposed between the at least one additional target-binding domain and the first target-binding domain or the first domain of the pair of affinity domains in the first chimeric polypeptide.

Embodiment H206. The method of embodiment H203, wherein the at least one additional target-binding domain of the one or more additional target-binding domains disposed at the C-terminus directly abuts the first target-binding domain or the first domain of the pair of affinity domains in the first chimeric polypeptide.

Embodiment H207. The method of embodiment H203, wherein the first chimeric polypeptide further comprises a linker sequence disposed between the at least one additional target-binding domain and the first target-binding domain or the first domain of the pair of affinity domains in the first chimeric polypeptide.

Embodiment H208. The method of embodiment H203, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment H209. The method of embodiment H203, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment H210. The method of any one of embodiments H177-H209, wherein the second chimeric polypeptide further comprises one or more additional target-binding domains at the N-terminal end or the C-terminal end of the second chimeric polypeptide.

Embodiment H211. The method of embodiment H210, wherein at least one of the one or more additional target-binding domains directly abuts the second domain of the pair of affinity domains in the second chimeric polypeptide.

Embodiment H212. The method of embodiment H210, wherein the second chimeric polypeptide further comprises a linker sequence between at least one of the one or more additional target-binding domains and the second domain of the pair of affinity domains in the second chimeric polypeptide.

Embodiment H213. The method of embodiment H210, wherein at least one of the one or more additional target-binding domains directly abuts the second target-binding domain in the second chimeric polypeptide.

Embodiment H214. The method of embodiment H210, wherein the second chimeric polypeptide further comprises a linker sequence between at least one of the one or more additional target-binding domains and the second target-binding domain in the second chimeric polypeptide.

Embodiment H215. The method of any one of embodiments H196-H214, wherein two or more of the first target-binding domain, the second target-binding domain, and the one or more additional target-binding domains bind specifically to the same antigen.

Embodiment H216. The method of embodiment H215, wherein two or more of the first target-binding domain, the second target-binding domain, and the one or more additional target-binding domains bind specifically to the same epitope.

Embodiment H217. The method of embodiment H216, wherein two or more of the first target-binding domain, the second target-binding domain, and the one or more additional target-binding domains comprise the same amino acid sequence.

Embodiment H218. The method of embodiment H215, wherein the first target-binding domain, the second target-binding domain, and the one or more additional target-binding domains each bind specifically to the same antigen.

Embodiment H219. The method of embodiment H218, wherein the first target-binding domain, the second target-binding domain, and the one or more additional target-binding domains each bind specifically to the same epitope.

Embodiment H220. The method of embodiment H219, wherein the first target-binding domain, the second target-binding domain, and the one or more additional target-binding domains each comprise the same amino acid sequence.

Embodiment H221. The method of any one of embodiments H196-H214, wherein the first target-binding domain, the second target-binding domain, and the one or more additional target-binding domains bind specifically to different antigens.

Embodiment H222. The method of any one of embodiments H196-H221, wherein one or more of the first target-binding domain, the second target-binding domain, and the one or more target-binding domains is an antigen-binding domain.

Embodiment H223. The method of embodiment H222, wherein the first target-binding domain, the second target-binding domain, and the one or more additional target-binding domains are each an antigen-binding domain.

Embodiment H224. The method of embodiment H223, wherein antigen-binding domain comprises a scFv.

Embodiment H225. The method of any one of embodiments H196-H224, wherein one or more of the first target-binding domain, the second target-binding domain, and the one or more target-binding domains bind specifically to a target selected from the group consisting of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

Embodiment H226. The method of any one of embodiments H196-H214, wherein one or more of the first target-binding domain, the second target-binding domain, and the one or more additional target-binding domains is a soluble interleukin or cytokine protein.

Embodiment H227. The method of embodiment H226, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment H228. The method of any one of embodiments H196-H214, wherein one or more of the first target-binding domain, the second target-binding domain, and the one or more additional target-binding domains is a soluble interleukin or cytokine receptor.

Embodiment H229. The method of embodiment H228, wherein the soluble receptor α soluble TGF-β receptor II (TGF-βRII) a soluble TGF-βRIII, a soluble receptor for TNFα, a soluble receptor for IL-4, or a soluble receptor for IL-10.

Embodiment H230. The method of any one of embodiments H196-H229, wherein the soluble tissue factor domain is a soluble human tissue factor domain.

Embodiment H231. The method of embodiment H230, wherein the soluble human tissue factor domain comprises a sequence that is at least 80% identical to SEQ ID NO: 93.

Embodiment H232. The method of embodiment H231, wherein the soluble human tissue factor domain comprises a sequence that is at least 90% identical to SEQ ID NO: 93.

Embodiment H233. The method of embodiment H232, wherein the soluble human tissue factor domain comprises a sequence that is at least 95% identical to SEQ ID NO: 93.

Embodiment H234. The method of any one of embodiments H230-H233, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H235. The method of embodiment H234, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H236. The method of any one of embodiments H196-H235, wherein the soluble tissue factor domain is not capable of binding to Factor VIIa.

Embodiment H237. The method of any one of embodiments H196-H236, wherein the soluble tissue factor domain does not convert inactive Factor X into Factor Xa.

Embodiment H238. The method of any one of embodiments H196-H237, wherein the multi-chain chimeric polypeptide does not stimulate blood coagulation in a mammal.

Embodiment H239. The method of any one of embodiments H196-H238, wherein the pair of affinity domains is a sushi domain from an alpha chain of human IL-15 receptor (IL-15Rα) and a soluble IL-15.

Embodiment H240. The method of embodiment H239, wherein the soluble IL-15 has a D8N or D8A amino acid substitution.

Embodiment H241. The method of embodiment H239 or H240, wherein the human IL-15Rα is a mature full-length IL-15Rα.

Embodiment H242. The method of any one of embodiments H196-H238, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment H243. The method of any one of embodiments H1-H19, H35-H42, H44-H62, and H64-H77, wherein at least one of the one or more NK cell activating agent(s) is a multi-chain chimeric polypeptide comprising:

(a) a first and second chimeric polypeptides, wherein each comprises:
  (i) a first target-binding domain;
  (ii) a Fc domain; and
  (iii) a first domain of a pair of affinity domains;

(b) a third and fourth chimeric polypeptide, wherein each comprises:
  (i) a second domain of a pair of affinity domains; and
  (ii) a second target-binding domain, wherein the first and second chimeric polypeptides and the third and fourth chimeric polypeptides associate through the binding of the first domain and the second domain of the pair of affinity domains, and the first and second chimeric polypeptides associate through their Fc domains.

Embodiment H244. The method of embodiment H243, wherein the first target-binding domain and the Fc domain directly abut each other in the first and second chimeric polypeptides.

Embodiment H245. The method of embodiment H243, wherein the first and second chimeric polypeptides further comprise a linker sequence between the first target-binding domain and the Fc domain in the first and second chimeric polypeptides.

Embodiment H246. The method of any one of embodiments H243-H245, wherein the Fc domain and the first domain of the pair of affinity domains directly abut each other in the first and second chimeric polypeptides.

Embodiment H247. The method of any one of embodiments H243-H245, wherein the first chimeric polypeptide further comprises a linker sequence between the Fc domain and the first domain of the pair of affinity domains in the first and second chimeric polypeptides.

Embodiment H248. The method of any one of embodiments H243-H247, wherein the second domain of the pair of affinity domains and the second target-binding domain directly abut each other in the third and fourth chimeric polypeptides.

Embodiment H249. The method of any one of embodiments H243-H247, wherein third and fourth chimeric polypeptides further comprise a linker sequence between the second domain of the pair of affinity domains and the second target-binding domain in the third and fourth chimeric polypeptides.

Embodiment H250. The method of any one of embodiments H243-H249, wherein the first target-binding domain and the second target-binding domain bind specifically to the same antigen.

Embodiment H251. The method of embodiment H250, wherein the first target-binding domain and the second target-binding domain bind specifically to the same epitope.

Embodiment H252. The method of embodiment H251, wherein the first target-binding domain and the second target-binding domain comprise the same amino acid sequence.

Embodiment H253. The method of any one of embodiments H243-H249, wherein the first target-binding domain and the second target-binding domain bind specifically to different antigens.

Embodiment H254. The method of any one of embodiments H243-H253, wherein one or both of the first target-binding domain and the second target-binding domain is an antigen-binding domain.

Embodiment H255. The method of embodiment H254, wherein the first target-binding domain and the second target-binding domain are each antigen-binding domains.

Embodiment H256. The method of embodiment H254 or H255, wherein antigen-binding domain comprises a scFv or a single domain antibody.

Embodiment H257. The method of any one of embodiments H243-H256, wherein one or both of the first target-binding domain and the second target-binding domain bind specifically to a target selected from the group consisting of: CD16a, CD33, CD20, CD19, CD22, CD123, PDL-1, TIGIT, PD-1, TIM3, CTLA4, MICA, MICB, IL-6, IL-8, TNFα, CD26, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM1, a ligand of NKp46, a ligand of NKp44, a ligand of NKG2D, a ligand of NKp30, a ligand for a scMHCI, a ligand for a scMHCII, a ligand for a scTCR, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD122.

Embodiment H258. The method of any one of embodiments H243-H256, wherein one or both of the first target-binding domain and the second target-binding domain is a soluble interleukin or cytokine protein.

Embodiment H259. The method of embodiment H258, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment H260. The method of any one of embodiments H243-H256, wherein one or both of the first target-binding domain and the second target-binding domain is a soluble interleukin or cytokine receptor.

Embodiment H261. The method of embodiment H260, wherein the soluble receptor is a soluble TGF-β receptor II (TGF-βRII) a soluble TGF-βRIII, a soluble receptor for TNFα, a soluble receptor for IL-4, or a soluble receptor for IL-10.

---

What is claimed is:

1. A method of treating liver fibrosis in a subject, the method comprising administering to the subject a therapeutically effective amount of a multi-chain chimeric polypeptide comprising:
   (a) a first chimeric polypeptide comprising:
      (i) a first target-binding domain comprising a sequence that is at least 80% identical to SEQ ID NO: 188;
      (ii) a soluble tissue factor domain comprising a sequence that is at least 80% identical to SEQ ID NO: 93; and
      (iii) a first domain of a pair of affinity domains, wherein the first domain of the pair of the affinity domains comprises a sequence that is at least 80% identical to SEQ ID NO: 115; and
   (b) a second chimeric polypeptide comprising:
      (i) a second domain of the pair of affinity domains, wherein the second domain of the pair of affinity domains comprises a sequence that is at least 80% identical to SEQ ID NO: 113; and
      (ii) a second target-binding domain comprising a sequence that is at least 80% identical to SEQ ID NO: 188,
   wherein the first chimeric polypeptide and the second chimeric polypeptide associate through the binding of the first domain and the second domain of the pair of affinity domains.

2. The method of claim 1, wherein the multi-chain chimeric polypeptide results in a decrease in the activation of a TGF-β receptor.

3. The method of claim 1, wherein the first target-binding domain and the soluble tissue factor domain directly abut each other in the first chimeric polypeptide.

4. The method of claim 1, wherein the first chimeric polypeptide further comprises a linker sequence between the first target-binding domain and the soluble tissue factor domain in the first chimeric polypeptide.

5. The method of claim 1, wherein the soluble tissue factor domain and the first domain of the pair of affinity domains directly abut each other in the first chimeric polypeptide.

6. The method of claim 1, wherein the first chimeric polypeptide further comprises a linker sequence between the soluble tissue factor domain and the first domain of the pair of affinity domains in the first chimeric polypeptide.

7. The method of claim 1, wherein the second domain of the pair of affinity domains and the second target-binding domain directly abut each other in the second chimeric polypeptide.

8. The method of claim 1, wherein the second chimeric polypeptide further comprises a linker sequence between the second domain of the pair of affinity domains and the second target-binding domain in the second chimeric polypeptide.

9. The method of claim 1, wherein the soluble tissue factor domain does not stimulate blood coagulation.

10. The method of claim 1, wherein the soluble tissue factor domain comprises or consists of a sequence from a wildtype soluble human tissue factor.

11. The method of claim 1, wherein:
   the first target-binding domain comprises a sequence that is at least 90% identical to SEQ ID NO: 188;
   the soluble tissue factor domain comprises a sequence that is at least 90% identical to SEQ ID NO: 93;
   the first domain of the pair of affinity domains comprises a sequence that is at least 90% identical to SEQ ID NO: 115;
   the second domain of the pair of affinity domains comprises a sequence that is at least 90% identical to SEQ ID NO: 113; and
   the second target-binding domain comprises a sequence that is at least 90% identical to SEQ ID NO: 188.

12. The method of claim 1, wherein:
   the first target-binding domain comprises a sequence that is at least 95% identical to SEQ ID NO: 188;

the soluble tissue factor domain comprises a sequence that is at least 95% identical to SEQ ID NO: 93;

the first domain of the pair of affinity domains comprises a sequence that is at least 95% identical to SEQ ID NO: 115;

the second domain of the pair of affinity domains comprises a sequence that is at least 95% identical to SEQ ID NO: 113; and the second target-binding domain comprises a sequence that is at least 95% identical to SEQ ID NO: 188.

13. The method of claim 1, wherein:

the first target-binding domain comprises SEQ ID NO: 188;

the soluble tissue factor domain comprises SEQ ID NO: 93;

the first domain of the pair of affinity domains comprises SEQ ID NO: 115;

the second domain of the pair of affinity domains comprises SEQ ID NO: 113; and the second target-binding domain comprises SEQ ID NO: 188.

14. The method of claim 1, wherein:

the first chimeric polypeptide comprises a sequence that is at least 80% identical to SEQ ID NO: 236; and the second chimeric polypeptide comprises a sequence that is at least 80% identical to SEQ ID NO: 193.

15. The method of claim 1, wherein:

the first chimeric polypeptide comprises a sequence that is at least 90% identical to SEQ ID NO: 236; and the second chimeric polypeptide comprises a sequence that is at least 90% identical to SEQ ID NO: 193.

16. The method of claim 1, wherein:

the first chimeric polypeptide comprises a sequence that is at least 95% identical to SEQ ID NO: 236; and the second chimeric polypeptide comprises a sequence that is at least 95% identical to SEQ ID NO: 193.

17. The method of claim 1, wherein:

the first chimeric polypeptide comprises SEQ ID NO: 236; and the second chimeric polypeptide comprises SEQ ID NO: 193.

18. A method of killing or reducing the number of senescent cells in a subject having liver fibrosis, the method comprising administering to the subject a therapeutically effective amount of a multi-chain chimeric polypeptide comprising:

(a) a first chimeric polypeptide comprising:

(i) a first target-binding domain comprising a sequence that is at least 80% identical to SEQ ID NO: 188;

(ii) a soluble tissue factor domain comprising a sequence that is at least 80% identical to SEQ ID NO: 93; and (iii) a first domain of a pair of affinity domains, wherein the first domain of the pair of the affinity domains comprises a sequence that is at least 80% identical to SEQ ID NO: 115; and (b) a second chimeric polypeptide comprising:

(i) a second domain of the pair of affinity domains, wherein the second domain of the pair of affinity domains comprises a sequence that is at least 80% identical to SEQ ID NO: 113; and (ii) a second target-binding domain comprising a sequence that is at least 80% identical to SEQ ID NO: 188, wherein the first chimeric polypeptide and the second chimeric polypeptide associate through the binding of the first domain and the second domain of the pair of affinity domains.

19. The method of claim 18, wherein the multi-chain chimeric polypeptide results in a decrease in the activation of a TGF-β receptor.

20. The method of claim 18, wherein the first target-binding domain and the soluble tissue factor domain directly abut each other in the first chimeric polypeptide.

21. The method of claim 18, wherein the first chimeric polypeptide further comprises a linker sequence between the first target-binding domain and the soluble tissue factor domain in the first chimeric polypeptide.

22. The method of claim 18, wherein the soluble tissue factor domain and the first domain of the pair of affinity domains directly abut each other in the first chimeric polypeptide.

23. The method of claim 18, wherein the first chimeric polypeptide further comprises a linker sequence between the soluble tissue factor domain and the first domain of the pair of affinity domains in the first chimeric polypeptide.

24. The method of claim 18, wherein the second domain of the pair of affinity domains and the second target-binding domain directly abut each other in the second chimeric polypeptide.

25. The method of claim 18, wherein the second chimeric polypeptide further comprises a linker sequence between the second domain of the pair of affinity domains and the second target-binding domain in the second chimeric polypeptide.

26. The method of claim 18, wherein the soluble tissue factor domain does not stimulate blood coagulation.

27. The method of claim 18, wherein the soluble tissue factor domain comprises or consists of a sequence from a wildtype soluble human tissue factor.

28. The method of claim 18, wherein:

the first target-binding domain comprises a sequence that is at least 90% identical to SEQ ID NO: 188;

the soluble tissue factor domain comprises a sequence that is at least 90% identical to SEQ ID NO: 93;

the first domain of the pair of affinity domains comprises a sequence that is at least 90% identical to SEQ ID NO: 115;

the second domain of the pair of affinity domains comprises a sequence that is at least 90% identical to SEQ ID NO: 113; and the second target-binding domain comprises a sequence that is at least 90% identical to SEQ ID NO: 188.

29. The method of claim 18, wherein:

the first target-binding domain comprises a sequence that is at least 95% identical to SEQ ID NO: 188;

the soluble tissue factor domain comprises a sequence that is at least 95% identical to SEQ ID NO: 93;

the first domain of the pair of affinity domains comprises a sequence that is at least 95% identical to SEQ ID NO: 115;

the second domain of the pair of affinity domains comprises a sequence that is at least 95% identical to SEQ ID NO: 113; and the second target-binding domain comprises a sequence that is at least 95% identical to SEQ ID NO: 188.

30. The method of claim 18, wherein:

the first target-binding domain comprises SEQ ID NO: 188;

the soluble tissue factor domain comprises SEQ ID NO: 93;

the first domain of the pair of affinity domains comprises SEQ ID NO: 115;

the second domain of the pair of affinity domains comprises SEQ ID NO: 113; and the second target-binding domain comprises SEQ ID NO: 188.

31. The method of claim 18, wherein:

the first chimeric polypeptide comprises a sequence that is at least 80% identical to SEQ ID NO: 236; and the second chimeric polypeptide comprises a sequence that is at least 80% identical to SEQ ID NO: 193.

32. The method of claim 18, wherein:

the first chimeric polypeptide comprises a sequence that is at least 90% identical to SEQ ID NO: 236; and the second chimeric polypeptide comprises a sequence that is at least 90% identical to SEQ ID NO: 193.

33. The method of claim 18, wherein:

the first chimeric polypeptide comprises a sequence that is at least 95% identical to SEQ ID NO: 236; and the second chimeric polypeptide comprises a sequence that is at least 95% identical to SEQ ID NO: 193.

34. The method of claim 18, wherein:

the first chimeric polypeptide comprises SEQ ID NO: 236; and the second chimeric polypeptide comprises SEQ ID NO: 193.

* * * * *